(12) United States Patent
Ju et al.

(10) Patent No.: US 11,959,137 B2
(45) Date of Patent: Apr. 16, 2024

(54) SYNTHESIS OF NOVEL DISULFIDE LINKER BASED NUCLEOTIDES AS REVERSIBLE TERMINATORS FOR DNA SEQUENCING BY SYNTHESIS

(71) Applicant: The Trustees of Columbia University in the City of New York, New York, NY (US)

(72) Inventors: Jingyue Ju, Englewood Cliffs, NJ (US); Xiaoxu Li, New York, NY (US); Xin Chen, New York, NY (US); Zengmin Li, Flushing, NY (US); Shiv Kumar, Belle Meade, NJ (US); Shundi Shi, Ozone Park, NY (US); Cheng Guo, Brooklyn, NY (US); Jianyi Ren, New York, NY (US); Min-Kang Hsieh, New York, NY (US); Minchen Chien, Tenafly, NJ (US); Chuanjuan Tao, Fort Lee, NJ (US); Ece Erturk, New York, NY (US); Sergey Kalachikov, Bronx, NY (US); James J. Russo, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 17/818,705

(22) Filed: Aug. 9, 2022

(65) Prior Publication Data

US 2023/0160000 A1    May 25, 2023

Related U.S. Application Data

(63) Continuation of application No. 17/816,555, filed on Aug. 1, 2022, which is a continuation of application No. 17/373,295, filed on Jul. 12, 2021, which is a continuation of application No. 15/763,364, filed as application No. PCT/US2016/054236 on Sep. 28, 2016, now Pat. No. 11,085,076.

(60) Provisional application No. 62/257,102, filed on Nov. 18, 2015, provisional application No. 62/233,950, filed on Sep. 28, 2015.

(51) Int. Cl.
| | |
|---|---|
| *C12Q 1/68* | (2018.01) |
| *C07H 19/10* | (2006.01) |
| *C07H 19/14* | (2006.01) |
| *C07H 19/20* | (2006.01) |
| *C12Q 1/6869* | (2018.01) |

(52) U.S. Cl.
CPC ........... *C12Q 1/6869* (2013.01); *C07H 19/10* (2013.01); *C07H 19/14* (2013.01); *C07H 19/20* (2013.01)

(58) Field of Classification Search
CPC ...... C12Q 1/6869; C07H 19/10; C07H 19/14; C07H 19/20
See application file for complete search history.

(56) References Cited

U.S. PATENT DOCUMENTS

| | | | |
|---|---|---|---|
| 5,034,036 A | 7/1991 | Summerton | |
| 5,235,033 A | 8/1993 | Summerton | |
| 5,547,839 A * | 8/1996 | Dower ................ | B01J 19/0046 435/6.12 |
| 5,804,386 A | 9/1998 | Ju | |
| 5,814,454 A | 9/1998 | Ju | |
| 5,876,936 A | 3/1999 | Ju | |
| 5,952,180 A | 9/1999 | Ju | |
| 6,046,005 A | 4/2000 | Ju et al. | |
| 6,485,944 B1 | 11/2002 | Church | |
| 6,627,748 B1 | 9/2003 | Ju et al. | |
| 6,664,079 B2 | 12/2003 | Ju et al. | |
| 7,074,597 B2 | 7/2006 | Ju | |
| 7,279,563 B2 | 10/2007 | Kwiatkowski | |
| 7,345,159 B2 | 3/2008 | Ju et al. | |
| 7,414,116 B2 | 8/2008 | Milton | |
| 7,541,444 B2 | 6/2009 | Milton | |
| 7,566,537 B2 | 7/2009 | Barnes | |
| 7,622,279 B2 | 11/2009 | Ju | |
| 7,635,578 B2 | 12/2009 | Ju et al. | |
| 7,713,698 B2 | 5/2010 | Ju et al. | |
| 7,771,973 B2 | 8/2010 | Milton | |
| 7,790,869 B2 | 9/2010 | Ju et al. | |
| 7,883,869 B2 | 2/2011 | Ju et al. | |
| 7,982,029 B2 | 7/2011 | Ju et al. | |
| 8,071,739 B2 | 12/2011 | Milton | |
| 8,088,575 B2 | 1/2012 | Ju et al. | |
| 8,114,973 B2 | 2/2012 | Siddiqi | |
| 8,298,792 B2 | 10/2012 | Ju et al. | |
| 8,399,188 B2 | 3/2013 | Zhao | |
| 8,597,881 B2 | 12/2013 | Milton | |
| 8,796,432 B2 | 8/2014 | Ju et al. | |

(Continued)

FOREIGN PATENT DOCUMENTS

| | | |
|---|---|---|
| CN | 109476694 A | 3/2019 |
| EP | 2876166 | 5/2015 |

(Continued)

OTHER PUBLICATIONS

Response to Dec. 30, 2020 Office Action, filed May 14, 2021 in connection with counterpart Chinese Application No. 201680069556. 3, including English language draft thereof.

(Continued)

*Primary Examiner* — Jezia Riley
(74) *Attorney, Agent, or Firm* — Gary J. Gershik

(57) ABSTRACT

Disclosed herein, inter alia, are compounds, compositions, and methods of use thereof in the sequencing of a nucleic acid.

20 Claims, 83 Drawing Sheets

Specification includes a Sequence Listing.

(56) References Cited

U.S. PATENT DOCUMENTS

| | | |
|---|---|---|
| 8,889,348 B2 | 11/2014 | Ju |
| 8,900,810 B2 | 12/2014 | Gordon et al. |
| 9,115,163 B2 | 8/2015 | Ju et al. |
| 9,121,060 B2 | 9/2015 | Milton |
| 9,121,062 B2 | 9/2015 | Balasubramanian |
| 9,133,511 B2 | 9/2015 | Ju et al. |
| 9,169,510 B2 | 10/2015 | Ju et al. |
| 9,175,342 B2 | 11/2015 | Ju et al. |
| 9,255,292 B2 | 2/2016 | Ju et al. |
| 9,297,042 B2 | 3/2016 | Ju et al. |
| 9,388,464 B2 | 7/2016 | Milton |
| 9,410,200 B2 | 8/2016 | Balasubramanian |
| 9,453,258 B2 | 9/2016 | Kain |
| 9,528,151 B2 | 12/2016 | Ju et al. |
| 9,593,373 B2 | 3/2017 | Liu |
| 9,624,539 B2 | 4/2017 | Ju et al. |
| 9,670,539 B2 | 6/2017 | Ju et al. |
| 9,708,358 B2 | 7/2017 | Ju et al. |
| 9,718,852 B2 | 8/2017 | Ju et al. |
| 9,719,139 B2 | 8/2017 | Ju et al. |
| 9,725,480 B2 | 8/2017 | Ju et al. |
| 9,868,985 B2 | 1/2018 | Ju et al. |
| 9,890,426 B2 | 2/2018 | Ju et al. |
| 10,000,801 B2 | 6/2018 | Ju et al. |
| 10,144,961 B2 | 12/2018 | Ju et al. |
| 10,190,157 B2 | 1/2019 | Wu |
| 10,240,195 B2 | 3/2019 | Fuller et al. |
| 10,246,479 B2 | 4/2019 | Ju et al. |
| 10,260,094 B2 | 4/2019 | Ju et al. |
| 10,273,539 B2 | 4/2019 | Marma et al. |
| 10,301,346 B2 | 5/2019 | Marma |
| 10,336,785 B2 | 7/2019 | Marma et al. |
| 11,085,076 B2 | 8/2021 | Ju |
| 11,089,353 B1 | 8/2021 | Ju |
| 2002/0015961 A1 | 2/2002 | Kwiatkowski |
| 2003/0027140 A1 | 2/2003 | Ju et al. |
| 2006/0003383 A1 | 1/2006 | Graham |
| 2006/0057565 A1 | 3/2006 | Ju et al. |
| 2006/0188901 A1 | 8/2006 | Barnes et al. |
| 2006/0252038 A1 | 11/2006 | Ju |
| 2007/0009980 A1 | 1/2007 | Graham |
| 2007/0219367 A1 | 9/2007 | Shchepinov |
| 2009/0047699 A1 | 2/2009 | Graham |
| 2009/0312188 A1* | 12/2009 | Duer ............... B01L 3/502715 506/38 |
| 2010/0311144 A1* | 12/2010 | Peris ............. C12Y 207/07007 435/235.1 |
| 2011/0014611 A1 | 1/2011 | Ju |
| 2012/0142006 A1 | 6/2012 | Ju et al. |
| 2012/0156671 A1 | 6/2012 | Liu |
| 2012/0156680 A1 | 6/2012 | Ju et al. |
| 2013/0264207 A1 | 10/2013 | Ju et al. |
| 2013/0280700 A1 | 10/2013 | Ju et al. |
| 2014/0113281 A1* | 4/2014 | Hubbell ............... G16B 30/00 435/6.1 |
| 2015/0037788 A1 | 2/2015 | Ju |
| 2015/0080232 A1 | 3/2015 | Ju |
| 2015/0111759 A1* | 4/2015 | Ju ............................ C12Q 1/42 536/26.22 |
| 2015/0140561 A1 | 5/2015 | Bergmann et al. |
| 2015/0197800 A1 | 7/2015 | Ju et al. |
| 2015/0368710 A1 | 12/2015 | Fuller |
| 2016/0002721 A1 | 1/2016 | Liu |
| 2016/0024570 A1 | 1/2016 | Ju et al. |
| 2016/0041179 A1 | 2/2016 | Ju et al. |
| 2016/0108382 A1 | 4/2016 | Efcavitch |
| 2016/0208313 A1 | 7/2016 | Ju et al. |
| 2016/0264612 A1 | 9/2016 | Ju et al. |
| 2016/0265048 A1 | 9/2016 | Ju et al. |
| 2016/0355541 A1 | 12/2016 | Jain |
| 2016/0369336 A1 | 12/2016 | Stupi |
| 2017/0002407 A1 | 1/2017 | Balasubramanian et al. |
| 2017/0058335 A1 | 3/2017 | Tao et al. |
| 2017/0137869 A1 | 5/2017 | Marma et al. |
| 2017/0166961 A1 | 6/2017 | Liu |
| 2017/0211134 A1 | 7/2017 | Marma et al. |
| 2017/0283451 A1 | 10/2017 | Ju et al. |
| 2018/0073071 A1 | 3/2018 | Ju et al. |
| 2018/0112257 A1 | 4/2018 | Ju et al. |
| 2018/0201642 A1 | 7/2018 | Ju et al. |
| 2018/0208774 A1 | 7/2018 | Marma et al. |
| 2018/0274024 A1 | 9/2018 | Ju |
| 2018/0274025 A1 | 9/2018 | Marma et al. |
| 2018/0327828 A1 | 11/2018 | Ju et al. |
| 2019/0031704 A1 | 1/2019 | Ju et al. |
| 2019/0031705 A1 | 1/2019 | Ju et al. |
| 2019/0031706 A1 | 1/2019 | Ju et al. |
| 2019/0085014 A1 | 3/2019 | Ju et al. |
| 2019/0085015 A1 | 3/2019 | Ju et al. |
| 2019/0085016 A1 | 3/2019 | Ju et al. |
| 2019/0085388 A1 | 3/2019 | Ju et al. |
| 2019/0092805 A1 | 3/2019 | Ju et al. |
| 2019/0092806 A1 | 3/2019 | Ju et al. |
| 2019/0112650 A1 | 4/2019 | Ju et al. |
| 2019/0135850 A1 | 5/2019 | Ju et al. |
| 2019/0135851 A1 | 5/2019 | Ju et al. |
| 2019/0136308 A1 | 5/2019 | Ju et al. |
| 2019/0153527 A1 | 5/2019 | Ju et al. |
| 2019/0330693 A1 | 10/2019 | Liu |
| 2021/0381043 A1 | 12/2021 | Ju |

FOREIGN PATENT DOCUMENTS

| | | |
|---|---|---|
| EP | 3356381 | 8/2018 |
| EP | 3356381 A4 | 5/2019 |
| WO | WO 2002/022883 | 3/2002 |
| WO | WO 2002/029003 | 4/2002 |
| WO | WO 2008/037568 A2 | 3/2008 |
| WO | WO 2008/144315 A1 | 11/2008 |
| WO | WO 2009/054922 | 4/2009 |
| WO | WO 2012/083249 | 6/2012 |
| WO | WO 2012/162429 | 11/2012 |
| WO | WO 2013/154999 | 10/2013 |
| WO | WO 2013/191793 | 12/2013 |
| WO | WO 2014/144883 | 9/2014 |
| WO | WO 2014/144898 | 9/2014 |
| WO | WO 2015/123430 | 8/2015 |
| WO | WO 2015/148402 | 10/2015 |
| WO | WO 2016/063059 A1 | 4/2016 |
| WO | WO 2016/144973 | 9/2016 |
| WO | WO 2016/154215 | 9/2016 |
| WO | WO 2017/058953 A1 | 4/2017 |
| WO | WO 2017/079498 | 5/2017 |
| WO | WO 2017/087887 | 5/2017 |
| WO | WO 2017/176677 | 10/2017 |
| WO | WO 2017/176679 | 10/2017 |
| WO | WO 2017/205336 | 11/2017 |
| WO | WO 2018/183538 | 10/2018 |
| WO | WO 2019/105421 A1 | 6/2019 |

OTHER PUBLICATIONS

Sep. 24, 2021 Office Action issued in connection with counterpart Chinese Application No. 201680069556.3, including English Summary thereof.

Response to Sep. 24, 2021 Office Action, filed Dec. 9, 2021 in connection with counterpart Chinese Application No. 201680069556.3, including English language draft thereof.

Response to Feb. 10, 2021 Communication pursuant to Article 94(3) EPC, filed Aug. 20, 2021 in connection with counterpart European Patent Application No. EP 16852516.0.

Qiu C, Kumar S, Guo J, Yu L, Guo W, Shi S, Russo JJ, Ju J. Design and synthesis of cleavable biotinylated dideoxynucleotides for DNA sequencing by matrix-assisted laser desorption/ionization time-of-flight mass spectrometry. Anal Biochem. Aug. 15, 2012;427(2):193-201. doi: 10.1016/j.ab.2012.04.021. Epub Apr. 25, 2012. PMID: 22543091.

Communication pursuant to Article 94(3) EPC dated Feb. 10, 2021 by the European Patent Office in connection with EP 16852516.0.

Dec. 30, 2020 Office Action issued in connection with Chinese Application No. 201680069556.3.

(56) References Cited

OTHER PUBLICATIONS

International Search Report dated Dec. 29, 2016 in connection with PCT International Application No. PCT/US2016/054236.
May 10, 2019 Extended European Search Report issued in connection with European Patent Application No. EP16852516.0, which is a foreign counterpart of the subject application.
PubChem Compound Summary for CID 121486816 (Aug. 16, 2016). Located at <https://pubchem.ncbi.nlm.nih.gov/compound/121486816> last visited Apr. 22, 2019, 7 pages.
PubChem Compound Summary for CID 69188114 (Nov. 30, 2012). Located at <https://pubchem.ncbi.nlm.nih.gov/compound/69188114> last visited Apr. 22, 2019, 7 pages.
Written Opinion (form PCT/ISA/237) dated Dec. 29, 2016 in connection with PCT International Application No. PCT/US2016/054236.
Bentley, D.R. et al. (Nov. 6, 2008). "Accurate whole humangenome sequencing using reversible terminator chemistry," Nature 456(7218):53-59.
Bergen, K. et al. (Jun. 17, 2013, e-published Jun. 3, 2013). "Structures of KOD and 9°N DNA polymerases complexed with primer template duplex, " Chembiochem 14(9):1058-1062.
Bergseid, M. et al. (Nov. 2000). "Small molecule-based chemical affinity system for the purification of proteins, " BioTechniques 29(5):1126-1133.
Binauld, S. et al. (Mar. 14, 2013). "Acid-degradable polymers fordrug delivery: a decade of innovation," Chem Commun 49(21):2082-2102.
Blackman, M.L. et al. (Oct. 15, 2008, e-published Sep. 18, 2008). "The Tetrazine ligation: fast bioconjugation based on inverse-electron-demand Diels-Alder reactivity," J Am Chem Soc 130(41):13518-13519.
Debets, M.F. et al. (Oct. 14, 2013, e-published Aug. 23, 2013). "Bioorthogonal labelling of biomolecules: new functional handles and ligation methods," Org Biomol Chem 11(38):6439-6455.
Fuller, C.W. et al. (May 10, 2016, e-published Apr. 18, 2016). "Real-time single-molecule electronic DNA sequencing by synthesis using polymer-tagged nucleotides on a nanopore array, " PNAS USA 113(19):5233-5238.
Guillier, F. et al. (Jun. 14, 2000). "Linkers and cleavage strategies in solid-phase organic synthesis and combinatorial chemistry," Chem Rev 100(6):2091-2158.
Guo, J. et al. (Jul. 8, 2008, e-published Jun. 30, 2008). "Four-color DNA sequencing with 3'-O-modified nucleotide reversible terminators and chemically cleavable fluorescent dideoxynucleotides," PNAS USA 105(27):9145-9150.
Hutter, D. et al. (Nov. 2010). "Labeled nucleosidetriphosphates with reversibly terminating aminoalkoxyl groups," Nucleosides Nucleotides Nucleic Acids 29(11):879-895.
Inoue, T. et al. (Nov. 2015). "Synthesis of trifluoromethyl ethers and difluoro (methylthio) methyl ethers by the reaction of dithiocarbonates with IF5-pyridine-HF," Journal of Fluorine Chemistry 179:48-52.
Jewett, J.C. et al. (Mar. 24, 2010). "Rapid Cu-free clickchemistry with readily synthesized biarylazacyclooctynones," J Am Chem Soc 132(11):3688-3690.
Ju, J. et al. (Dec. 26, 2006, e-published Dec. 14, 2006). "Four-color DNA sequencing by synthesis using cleavable fluorescent nucleotide reversible terminators," PNAS USA 103(52):19635-19640.
Kumar, S. et al. (2012, e-published Sep. 21, 2012). "PEG-labeled nucleotides and nanopore detection for single molecule DNA sequencing by synthesis," Sci Rep 2:684.

Leicher, T. et al. (Dec. 25, 1998). "Coexpression of the KCNA3B gene product with Kv1.5 leads to a novel A-type potassium channel," J Biol Chem 273(52):35095-35101.
Leriche, G. et al. (Jul. 2010). "Optimization of the Azobenzene Scaffold for Reductive Cleavage by Dithionite Development of an Azobenzene Cleavable Linker for Proteomic Applications, " Eur J Org Chem 2010(23):4360-4364.
Marcus-Sekura, C.J. et al. (Aug. 1, 1988). "Techniques for using antisense oligodeoxyribonucleotides to study gene expression," Anal Biochem 172(2):289-295.
Needleman, S.B . et al. (Mar. 1970). "A general method applicable to the search for similarities in the amino acid sequence of two proteins," J Mol Biol 48(3):443-453.
Pearson, W.R. et al. (Apr. 1988). "Improved tools for biological sequence comparison," PNAS USA 85(8):2444-2448.
Rathod, K.M. et al. (2013). "Synthesis and Antimicrobial Activity of Azo Compounds Containing m-Cresol Moiety," Chem Sci Trans 2(1):25-28.
Rosenblum, B.B. et al. (Nov. 15, 1997). "New dye-labeled terminators for improved DNA sequencing patterns," Nucleic Acids Res 25(22):4500-4504.
Ruparel, H. et al. (Apr. 26, 2005, e-published Apr. 13, 2005). "Design and synthesis of a 3'-O-allyl photocleavable fluorescent nucleotide as a reversible terminator for DNA sequencing by synthesis," PNAS USA 102(17):5932-5937.
Shenoi, R.A. et al. (Sep. 12, 2012, e-published Aug. 30, 2012). "Branched multifunctional polyether polyketals: variation of ketal group structure enables unprecedented control over polymer degradation in solution and within cells," J Am Chem Soc 134(36):14945-14957.
Smith T.F. et al. (Dec. 1981). "Comparison of biosequences," Adv Appl Math 2(4):482-489.
Southworth, M.W. et al. (May 28, 1996). "Cloning of thermostable DNA polymerases from hyperthermophilic marine Archaea with emphasis on *Thermococcus* sp. 9°N-7 and mutations affecting 3'-5' exonuclease activity," PNAS USA 93(11):5281-5285.
Svagera, Z., Hanzlikova, D., Simek, P., and Husek, P. (2012) Study of disulfide reduction and alkyl chloroformate derivatization of plasma sulfur amino acids using gas chromatography-mass spectrometry. Anal. Bioanal. Chem. 402: 2953-2963.
Tang et al. Synthesis and Application of Four Fluorescence Labeled Nucleotides Through Disulfide as Reversible Terminators in DNA Sequencing by Synthesis. Chem. J. Chinese U. Nov. 2014 35(11):2346-52, including an English language abstract.
Uhlmann, E. et al. (Jun. 1990). "Antisense oligonucleotides: a new therapeutic principle," Chemical Reviews 90(4):543-584.
Weintraub, H.M. (Jan. 1990). "Antisense RNA and DNA, " Sci Am 262(1):40-46.
Wolfram Schumacher, Christof Holliger, Alexander J.B Zehnder, Wilfred R Hagen, Redox chemistry of cobalamin and iron-sulfur cofactors in the tetrachloroethene reductase of Dehalobacter restrictus, FEBS Letters, vol. 409, Issue 3, 1997, pp. 421-425, ISSN 0014-5793.
Wu, J. et al. (Oct. 16, 2007, e-published Oct. 8, 2007). "3'-O-modified nucleotides as reversible terminators for pyrosequencing," PNAS USA 104(42):16462-16467.
Zhu, Z. et al. (Aug. 25, 1994). "Directly labeled DNA probes using fluorescent nucleotides with different length linkers," Nucleic Acids Res 22(16):3418-3422.

* cited by examiner

EXHIBIT B

3'-O-DTM-dATP-7-SS-Biotin

3'-O-DTM-dCTP-5-SS-Biotin

3'-O-DTM-dGTP-7-SS-Biotin

3'-O-DTM-dUTP-5-SS-Biotin

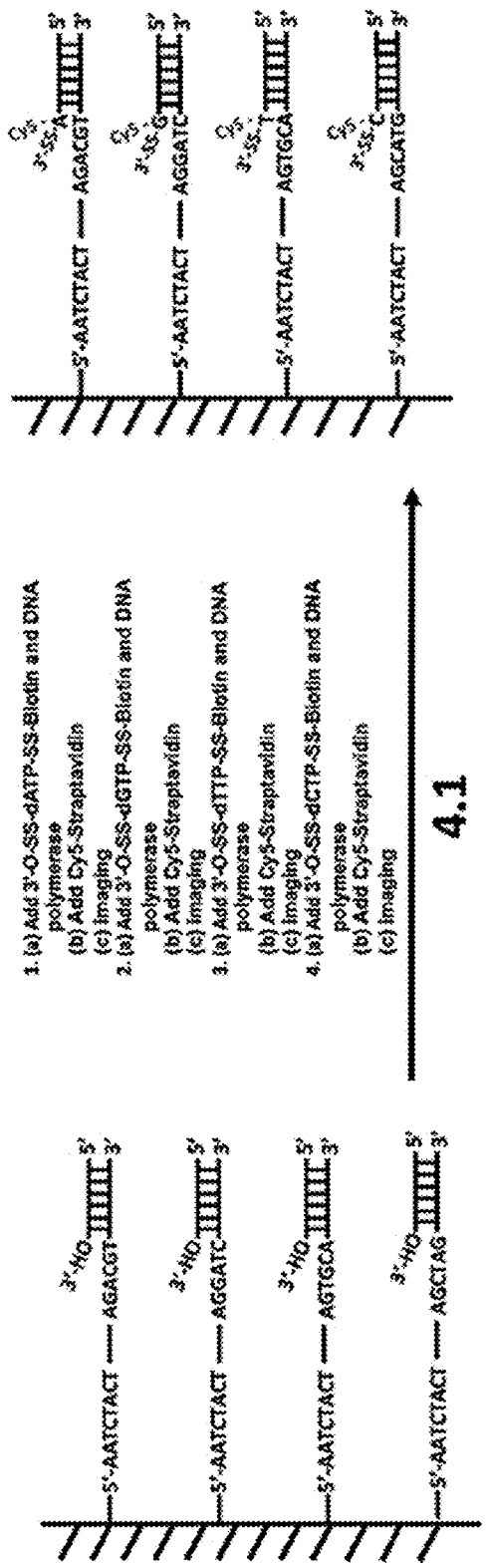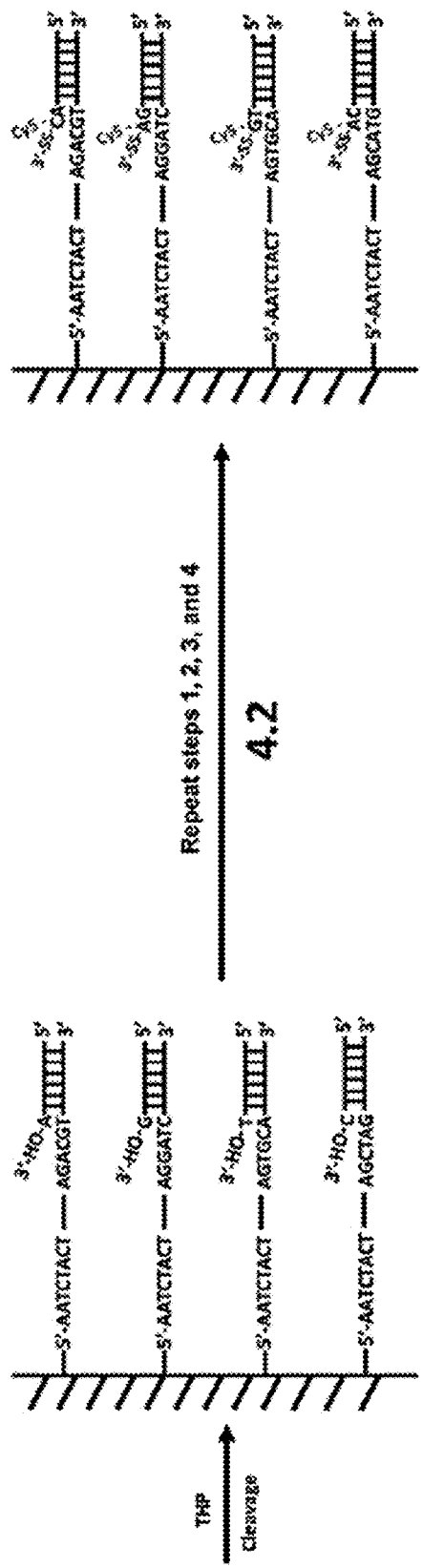
FIG. 4A
FIG. 4B

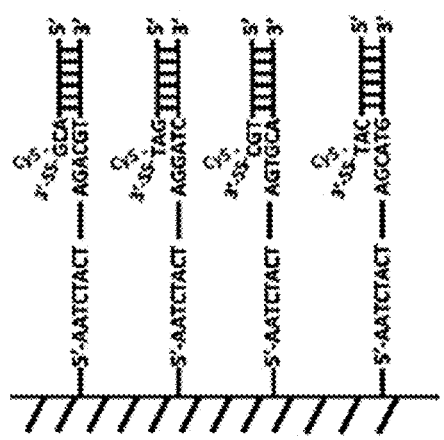
FIG. 4C
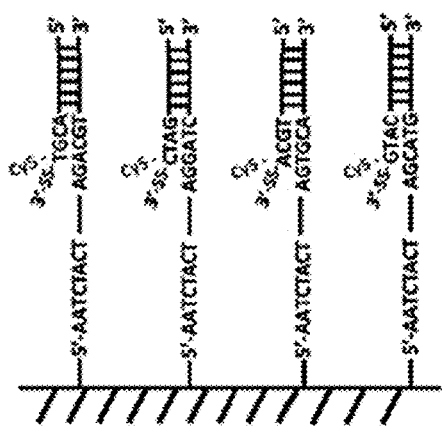
FIG. 4D
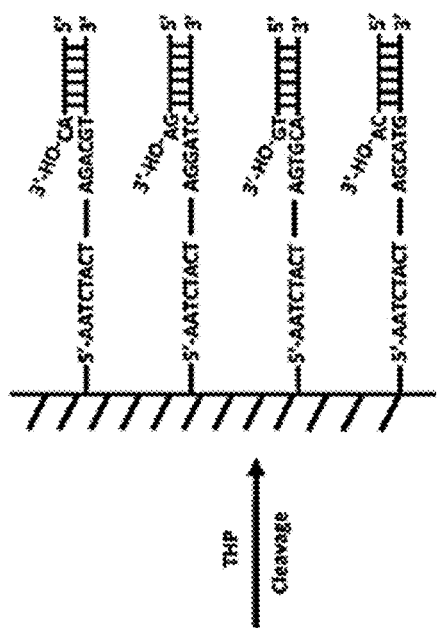

FIG. 6
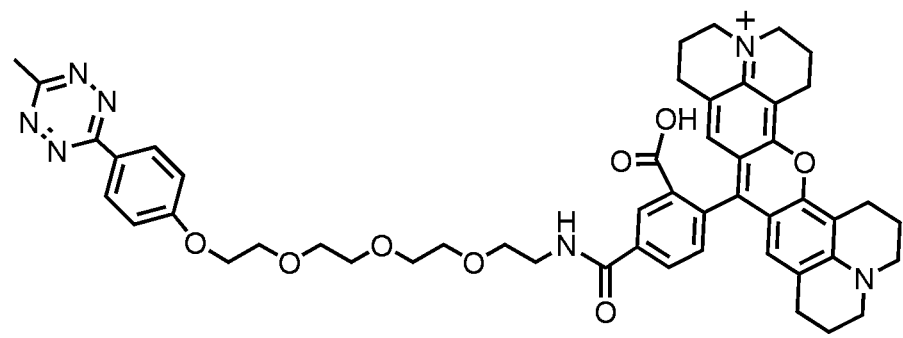
Rox Labeled Tetrazine
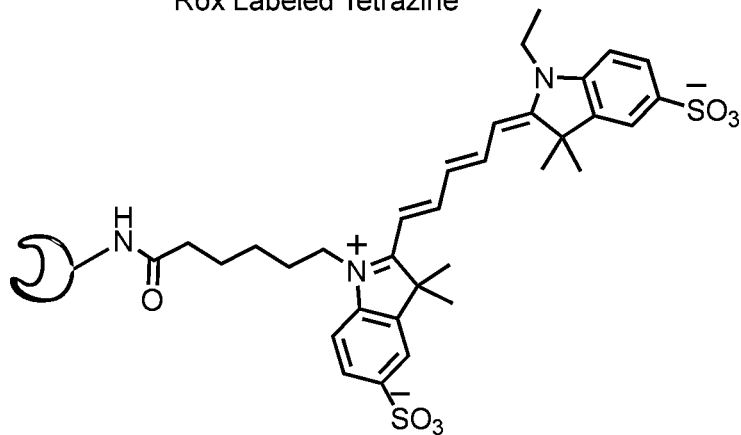
Cy5 Labeled Streptavidin
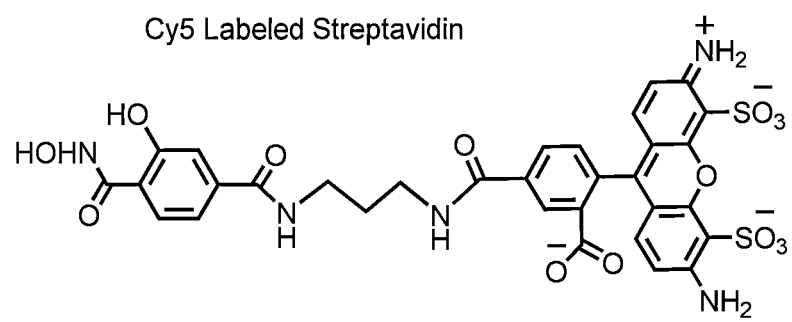
Alexa488 Labeled SHA
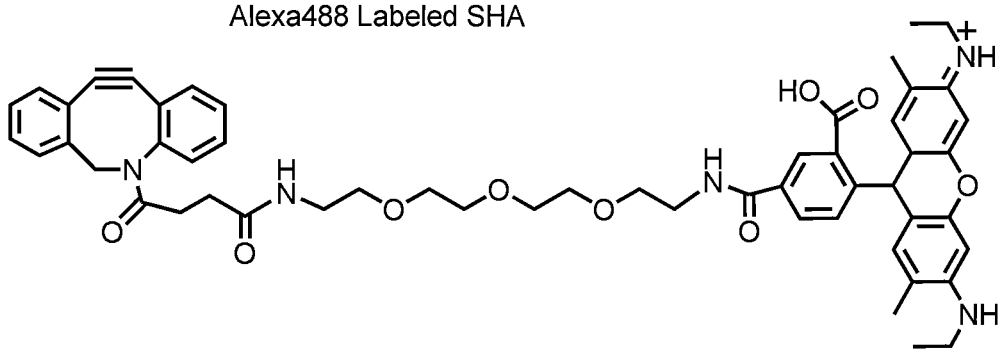
R6G Labeled Dibenzocyclooctyne(DBCO)

3'-O-DTM-dNTP-SS-TCO

Long-distance FRET cassette labeled SHA

Rox-7-Cy5

3'-O-DTM-dATP-7-SS-ROX

3'-O-DTM-dCTP-5-SS-Alexa488

3'-O-DTM-dGTP-7-SS-TCO

Rox Labeled Tetrazine

3'-O-DTM-dUTP-5-SS-N3

Alexa 488 Labeled Dibenzocyclooctyne

3'-O-DTM-dUTP-SS-Azo-N₃

3'-O-DTM-dATP-SS-Azo-Rox

3'-O-DTM-dNTP-SS-Allyl-Dye(Anchor,Rox as example)

3'-O-DTM-dNTP-SS-Nitrobenzyl-Dye(Anchor, Rox as example)

3'-O-DTM-dGTP

DBCO- Azo(-N=N-Linker)-Rox

Streptavidin-Rox

Cleavage III with THP
Washing, Imaging

5

Repeat Steps 1, 2, 3, 4, 5
For Subsequent Cycles
of Sequencing

3'-O-DTM(SS)-dCTP-5-SS-Alexa488

3'-O-DTM(SS)-dUTP-5-SS-R6G

3'-O-DTM(SS)-dATP-7-SS-Rox

FIG. 24B
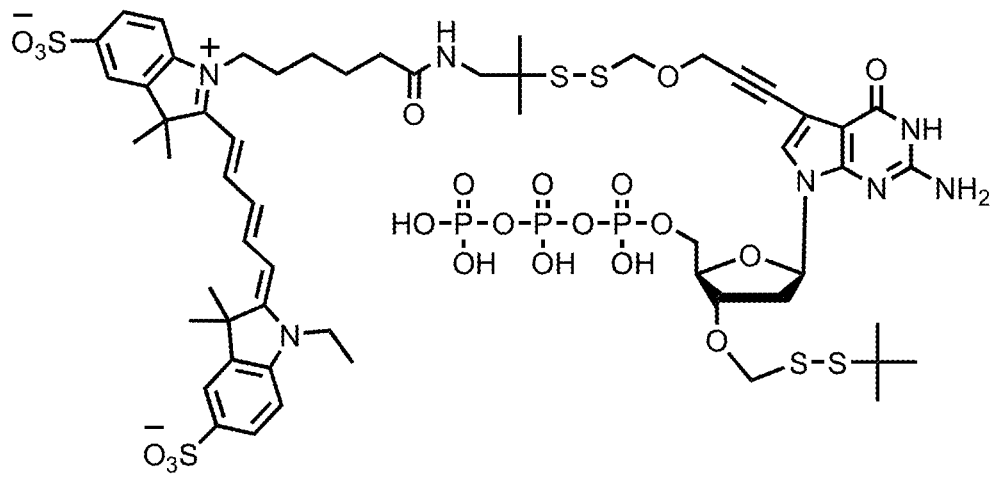
3'-O-DTM(SS)-dGTP-7-SS-Cy5
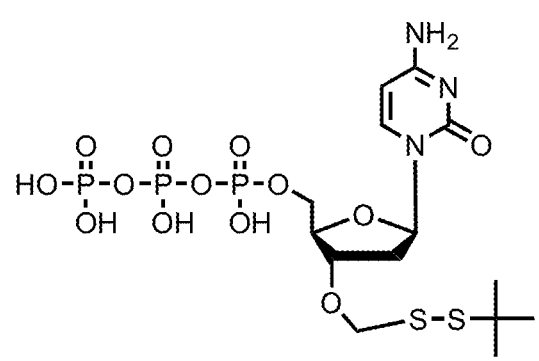
3'-O-DTM(SS)-dCTP
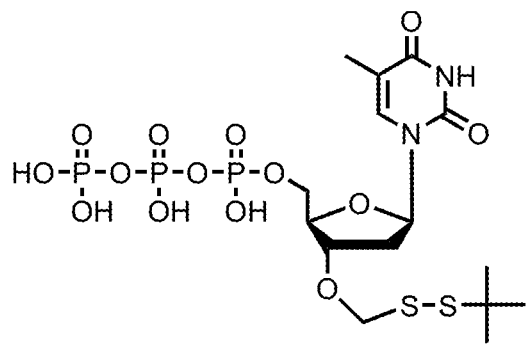
3'-O-DTM(SS)-dTTP
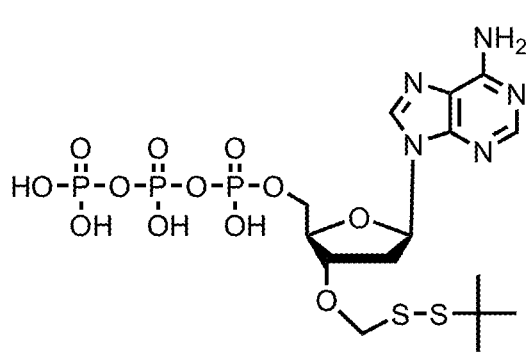
3'-O-DTM(SS)-dATP
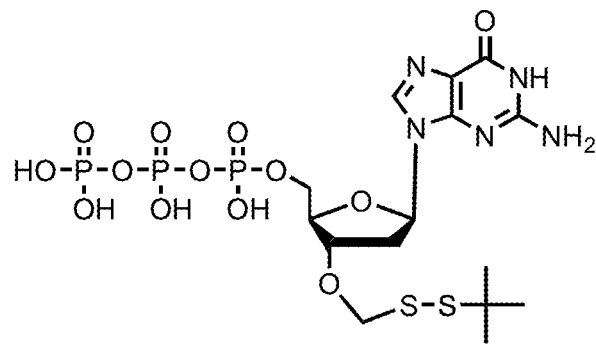
3'-O-DTM(SS)-dGTP Step 4
Cleavage: THP
Washing Repeat steps 1, 2, 3, and 4
For Subsequent Cycles
of Sequencing Extension Product Using 3'-SS-dATP-SS-Rox Cleavage Product Extension Product Using 3'-SS-dCTP-SS-Alexa488

FIG. 30C
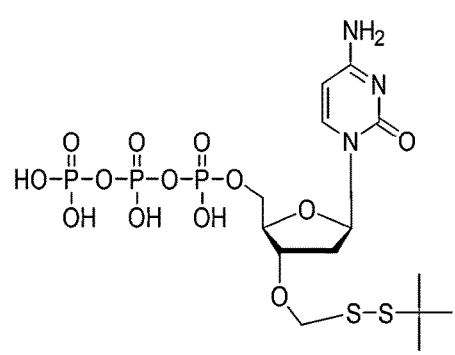
3'-O-*t*-butyldithio-dCTP(3'-O-DTM-dCTP)
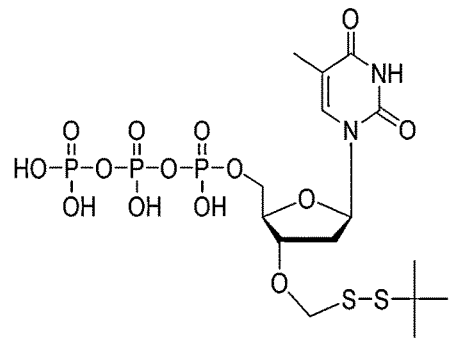
3'-O-*t*-butyldithio-dTTP(3'-O-DTM-dTTP)
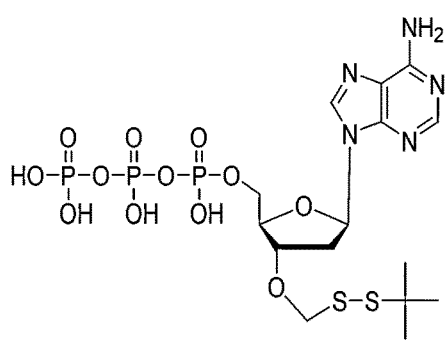
3'-O-*t*-butyldithio-dATP(3'-O-DTM-dATP)
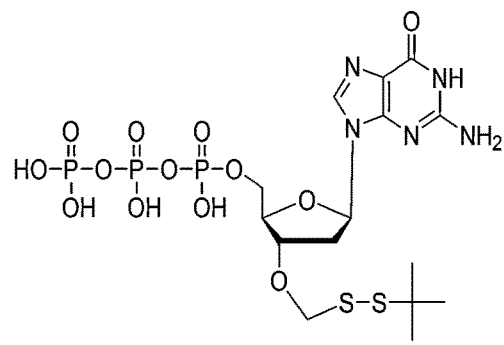
3'-O-*t*-butyldithio-dGTP(3'-O-DTM-dGTP $R_1, R_2, R_3, R_4, R_5$ = H, D, methyl, ethyl, propyl, isopropyl, t-butyl, or phenyl

X= O, S, NH $R_1$, $R_2$, $R_3$, $R_4$, $R_5$ = H, D, methyl, ethyl, propyl, isopropyl, t-butyl, or phenyl 3'-O-alkyldithiomethyl-dCTP-5-SS-Alexa488
(3'-O-DTM-dCTP-5-SS-Alexa488)

3'-O-alkyldithiomethyl-dUTP-5-SS-R6G
(3'-O-DTM-dUTP-5-SS-R6G)

3'-O-alkyldithiomethyl-dATP-7-SS-ROX
(3'-O-DTM-dATP-7-SS-ROX)

3'-O-alkyldithiomethyl-dGTP-7-SS-Cy5
(3'-O-DTM-dGTP-7-SS-Cy5)
R= methyl, ethyl, propyl, isopropyl, t-Butyl, phenyl
m= 1-4

3'-O-alkyldithiomethyl-dCTP-5-SS-Alexa488
(3'-O-DTM-dCTP-5-SS-Alexa488)

3'-O-alkyldithiomethyl-dUTP-5-SS-R6G
(3'-O-DTM-dUTP-5-SS-R6G)

3'-O-alkyldithiomethyl-dATP-7-SS-ROX
(3'-O-DTM-dATP-7-SS-ROX)

3'-O-alkyldithiomethyl-dGTP-7-SS-Cy5
(3'-O-DTM-dGTP-7-SS-Cy5)

$R_1, R_2$ = H, D, methyl, ethyl, propyl, isopropyl, *t*-Butyl, phenyl
$R_3, R_4, R_5$ = methyl, ethyl, propyl, isopropyl, *t*-Butyl, phenyl
m= 1-4

R₁, R₂ = H, D, methyl, ethyl, propyl, isopropyl, *t*-Butyl, phenyl
R₃, R₄, R₅ = methyl, ethyl, propyl, isopropyl, *t*-Butyl, phenyl
X = O, S, N
m = 1-4

FIG. 44
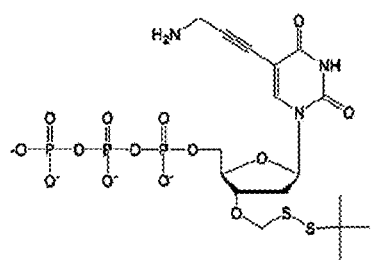
5-(3-aminopropynyl)-3'-O-tert-butyldithiomethyl-dTTP
(5PA-DTM-TTP)
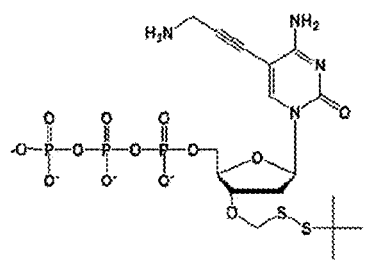
5-(3-aminopropynyl)-3'-O-tert-butyldithiomethyl-dCTP
(5PA-DTM-dCTP)
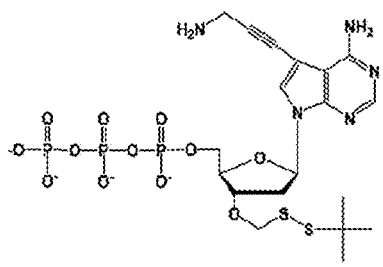
7-(3-aminopropynyl)-3'-O-tert-butyldithiomethyl-7-deaza-dATP
(7PA-DTM-dATP)
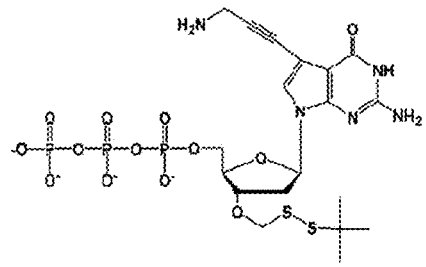
7-(3-aminopropynyl)-3'-O-tert-butyldithiomethyl-7-deaza-dGTP
(7PA-DTM-dGTP)

FIG. 46
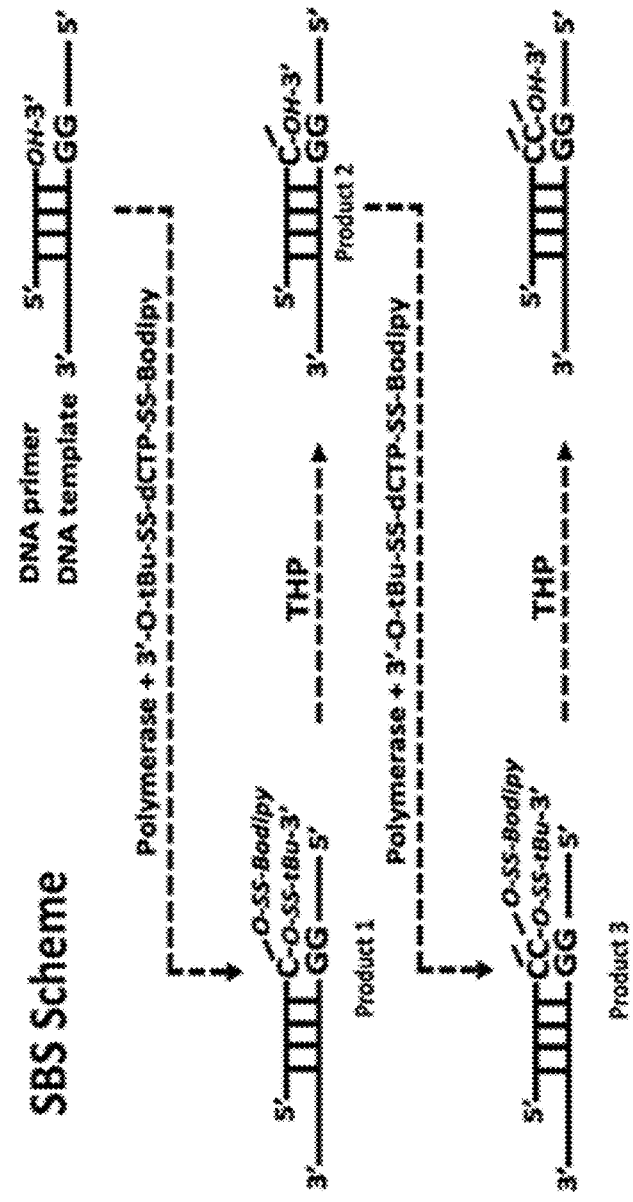
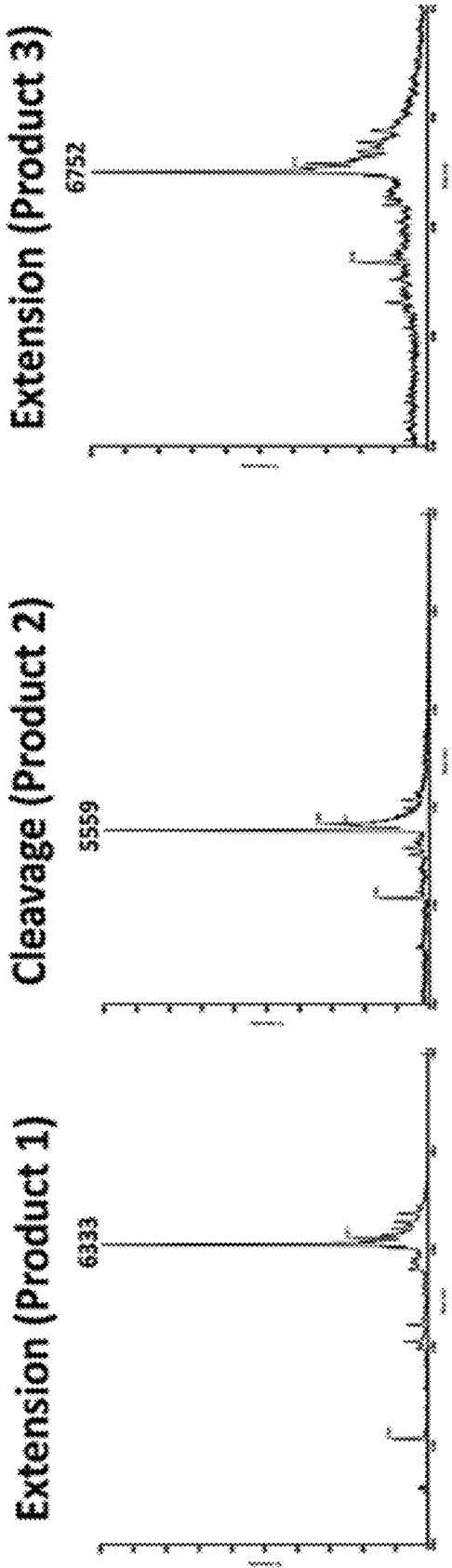

SYNTHESIS OF NOVEL DISULFIDE LINKER BASED NUCLEOTIDES AS REVERSIBLE TERMINATORS FOR DNA SEQUENCING BY SYNTHESIS

CROSS-REFERENCES TO RELATED APPLICATIONS

This application is a continuation of U.S. application Ser. No. 17/816,555, filed Aug. 1, 2022, which is a continuation of U.S. application Ser. No. 17/373,295, filed Jul. 12, 2021, which is a continuation of U.S. application Ser. No. 15/763,364, filed Mar. 26, 2018, now U.S. Pat. No. 11,080,076, issued Aug. 10, 2021, which is a § 371 national stage of PCT International Application No. PCT/US2016/054236, filed Sep. 28, 2016, claiming the benefit of U.S. Provisional Applications Nos. 62/257,102, filed Nov. 18, 2015, and 62/233,950, filed Sep. 28, 2015, the contents of each of which are hereby incorporated by reference into the application.

STATEMENT REGARDING FEDERALLY SPONSORED RESEARCH OR DEVELOPMENT

This invention was made with government support under grants HG003582 and HG005109 awarded by the National Institutes of Health. The government has certain rights in the invention.

REFERENCE TO SEQUENCE LISTING

This application incorporates-by-reference nucleotide and/or amino acid sequences which are present in the file named "2022-08-09 88050-AAAA-PCT-US Sequence Listing YX.xml", which is 14 kilobytes in size, and which was created Aug. 9, 2022 in the IBM-PC machine format, having an operating system compatibility with MS-Windows, which is contained in the xml file filed Aug. 9, 2022 as part of this application.

BACKGROUND

DNA sequencing is a fundamental tool in biological and medical research, and is especially important for the paradigm of personalized medicine. Various new DNA sequencing methods have been investigated with the aim of eventually realizing the goal of the $1,000 genome; the dominant method is sequencing by synthesis (SBS) an approach that determines DNA sequences during the polymerase reaction. The currently widely used high-throughput SBS technology (Bentley D R, et al. Nature, 2008, 456, 53-59) uses cleavable fluorescent nucleotide reversible terminator (NRT) sequencing chemistry that we developed previously (Ju J et al, 2003, U.S. Pat. No. 6,664,079; Ju J et al. Proc Natl Acad Sci USA, 2006, 103, 19635-19640). These cleavable fluorescent NRTs were designed based on the following rationale: each of the four nucleotides (A, C, G, T) is modified by attaching a unique cleavable fluorophore to the specific location of the base and capping the 3'OH group with a small reversible moiety so that they are still recognized by DNA polymerase as substrates. Thus the cleavable fluorescent. NRTs involve two site modifications (Ju J et al, 2003, U.S. Pat. No. 6,664,079; Ju J et al. Proc Natl Acad Sci USA, 2006, 103, 19635-19640): a fluorescent dye to serve as a reporter group on the base and a small chemical moiety to cap the 3'-OH group to temporarily terminate the polymerase reaction after nucleotide incorporation for sequence determination. After incorporation and signal detection, the fluorophore is cleaved and the 3'-OH capping moiety removed to resume the polymerase reaction in the next cycle. These cleavable fluorescent NRTs have proved to be good substrates for reengineered polymerases and have been used extensively in next generation DNA sequencing systems (Ju J et al. Proc Natl Acad Sci USA, 2006, 103, 19635-19640; Bentley D R, et al, Nature, 2008, 456, 53-59). Moreover, they enable accurate determination of homopolymer sequences, since only one base is identified in each cycle.

To achieve long read length in the SBS strategy it is essential that the cleavable linker be stable during the sequencing reactions, and that there are few manipulations and that a long tail is not left on the base after the cleavage reaction.

BRIEF SUMMARY OF THE INVENTION

A compound of the formula:

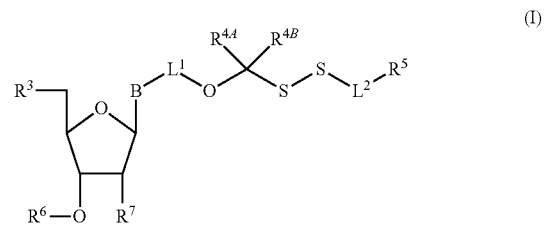

wherein
B is a base;
$L^1$ is covalent linker;
$L^2$ is covalent linker;
$R^3$ is —OH, monophosphate, polyphosphate or a nucleic acid;
$R^{4A}$ is hydrogen, —$CH_3$, —$CX^1_3$, —$CHX^1_2$, —$CH_2X^1$, —CN, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{4B}$ is hydrogen, —$CH_3$, —$CX^2_3$, —$CHX^2_2$, —$CH_2X^2$, —CN, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^5$ is a detectable label or anchor moiety;
$R^6$ is hydrogen or a polymerase-compatible cleavable moiety;
$R^7$ is hydrogen or —$OR^{7A}$, wherein $R^{7A}$ is hydrogen or a polymerase-compatible cleavable moiety; and
$X^1$ and $X^2$ are independently halogen.

BRIEF DESCRIPTION OF THE DRAWINGS

FIG. 1B: SBS using 3'-O—SS(DTM)-dNTP-SS-"anchors" and corresponding labeled binding molecules. (STEP 1) Addition of a DNA polymerase to the primed template moiety (only the primer strand is shown above) leads to the incorporation of a complementary 3'-O-SS(DTM)-dNTPs-SS (DTM)-"anchor" to the 3' end of a primer with high efficiency and specificity. (STEP 2) Addition of labeled binding molecules to the corresponding primer extension product leads to orthogonal binding of the labeled binding molecules with the corresponding "anchor" moiety on the base of the primer extension product; after washing away the unbound labeled molecule, the detection of the unique label attached to the primer extension product determines the identity of the incorporated nucleotide. (STEP 3) Addition of TCEP or THP results in the cleavage of the disulfide bond, and therefore to the removal of the label on the primer extension product and the regeneration of the 3'-OH on the primer extension product. The repetition of STEP 1 through STEP 3 allows for continuous DNA sequence determination. The "Anchor" moiety and the labeled binding molecule include any specifically reactive pair that can form a covalent bond or a stable noncovalent bond. The label can be a fluorescent molecule, a FRET cassette or fluorescent dendrimers.

FIGS. 4A-4D. One-color SBS using 3'-O-DTM-dNTP-SS-Biotins and Cy5 Labeled Streptavidin. A DNA polymerase incorporation reaction is conducted by using one of the four 3' DTM-dNTP-SS-Biotins (FIGS. 3A-3E), followed by the addition of Cy5 labeled streptavidin and imaging to determine DNA sequences as described in STEP 1 through STEP 4 (as shown in FIG. 4A Step 1 and repeated in FIGS. 4A-4D steps 2 to 4). Each step consists of three parts: (PART a) Add polymerase and one of the four 3'-O-DTM-dNTP-SS-Biotins followed by washing; if the added nucleotide is complementary to the nucleotide on the template immediately next to the 3' end of the primer, then the added nucleotide will incorporate into the primer to produce a DNA extension product that has a Biotin. (PART b) Add Cy5 Labeled Streptavidin, which will bind to the Biotin on the the DNA extension product. (PART c) After washing away the unbound Cy5 labeled streptavidin, perform imaging to detect the Cy5 signal for the identification of the incorporated nucleotide. Following STEP 4, addition of THP to the DNA extension products will cleave the disulfide bond and regenerate a free 3'-OH group on the 3' end of the DNA extension products. Sequential repetition of the process, consisting of STEP 1 through STEP 4, followed by THP cleavage, allows continuing sequence determination.

FIG. 6. Structures of four-color labeled orthogonal binding molecules (Rox-Labeled Tetrazine, Alexa488-Labeled SHA, Cy5-Labeled Streptavidin, and R6G-Labeled Dibenzocyclooctyne) that bond specifically with the four "anchor" moieties in the nucleotide analogues (3'-O-t-Butyldithiomethyl-dATP-7-SS-TCO, 3'-O-t-Butyldithiomethyl-dCTP-5-SS-PBA, 3'-O-t-Butyldithiomethyl-dGTP-7-SS-Biotin, 3'-O-t-Butyldithiomethyl-dTTP-5-SS-N$_3$) listed in FIG. 4, as follows: Rox is attached to the Tetrazine (which specifically reacts with TCO); Alexa488 is attached to the SHA (which forms a stable complex with PBA); Cy5 is attached to the Streptavidin (which forms a stable complex with Biotin); and R6G is attached to the Dibenzocyclooctyne (DBCO, which quickly forms a Triazole moiety with an N$_3$ group). Thus, each nucleotide analogue listed in FIG. 5 can be labeled by a unique fluorescent dye.

Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'''-O-SS-nucleotide analogue to the growing DNA strands that were not extended with one of the dye labeled 3'-O-t-Butyldithiomethyl(SS)-dNTP in step 1. The growing DNA strands are terminated with one of the four nucleotide analogues (A, C, G, T) with the four distinct fluorescent dyes or the same one of the four nucleotide analogues (A, C, G, T) without dye. After washing away the unincorporated nucleotide analogues (Step 3), detection of the unique fluorescence signal from each of the fluorescent dyes on the DNA products allows for the identification of the incorporated nucleotide for sequence determination (Step 4). Next, in Step 5, treatment of the DNA products with THP cleaves the SS linker, leading to the removal of the fluorescent dye and the regeneration of a free 3'-OH group on the DNA extension product, which is ready for the next cycle of the DNA sequencing reaction.

FIGS. 26A-26F. Four color SBS without chasing. SBS using 3'-O-SS(DTM)-dNTP-SS-Dye (3'-O-t-Butyldithiomethyl(SS)-dATP-SS-Rox, 3'-O-t-Butyldithiomethyl(SS)-dCTP-SS-Alexa488, 3'-O-t-Butyldithiomethyl(SS)-dGTP-SS-Cy5, 3'-O-t-Butyldithiomethyl(SS)-dUTP-SS-R6G) (FIG. 24) Step 1, addition of the DNA polymerase and the four 3'-O-SS(DTM)-dNTP-SS-Dye (3'-O-t-Butyldithiomethyl(SS)-dATP-SS-Rox, 3'-O-t-Butyldithiomethyl(SS)-dCTP-SS-Alexa488, 3'-O-t-Butyldithiomethyl(SS)-dGTP-SS-Cy5, 3'-O-t-Butyldithiomethyl(SS)-dUTP-SS-R6G) to the immobilized primed DNA template enables the incorporation of the complementary nucleotide analogue to the growing DNA strand. The growing DNA strand is terminated with each of the four nucleotide analogues (A, C, G, T) with the four distinct fluorescent dyes. After washing (Step 2) to remove unincorporated dye labeled nucleotide analogues, detection of the unique fluorescence signal (Step 3) from each of the fluorescent dyes on the DNA products allows for the identification of the incorporated nucleotide. Next, in Step 4, treatment of the DNA products with THP cleaves the SS linker, leading to the removal of the fluorescent dye and the regeneration of a free 3'-OH group on the DNA extension product, which is ready for the next cycle of the DNA sequencing reaction.

Figure 27A:
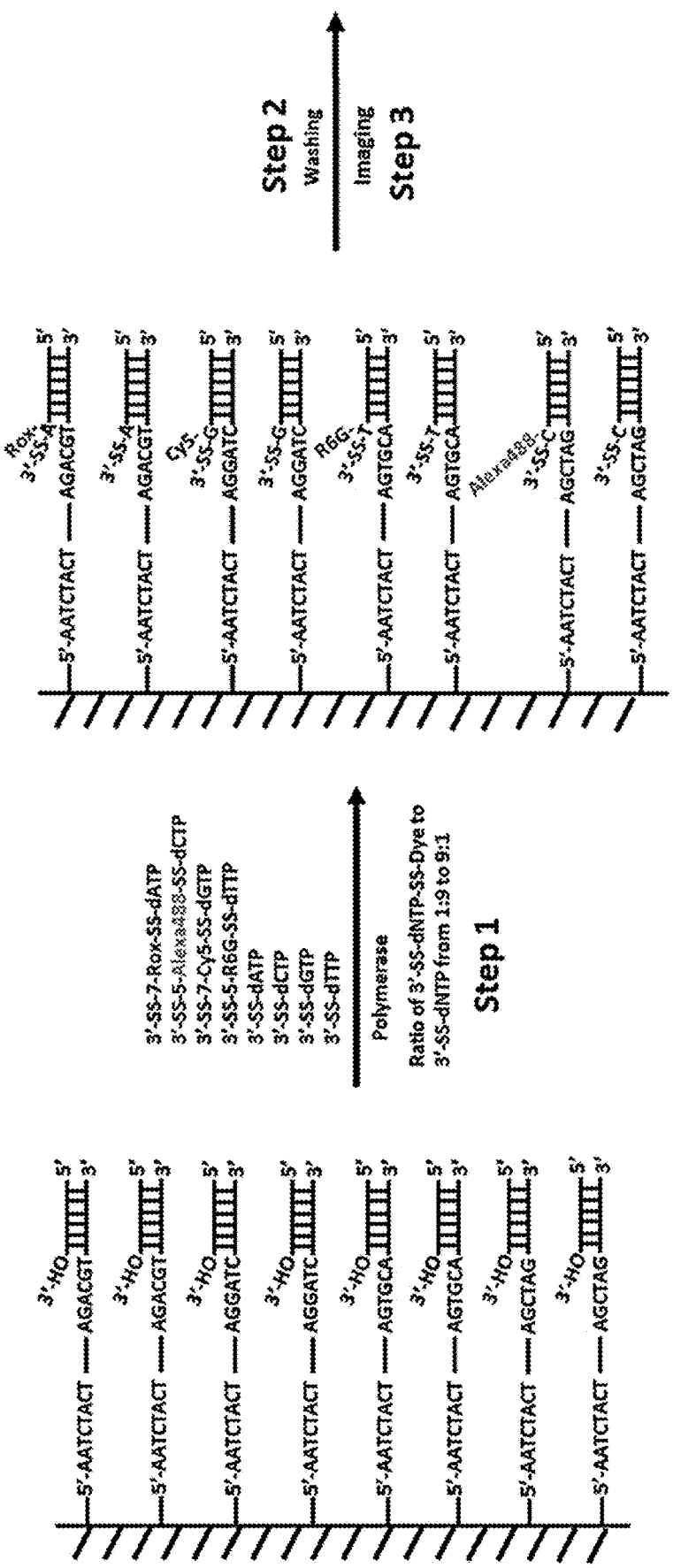
Figure 27B:
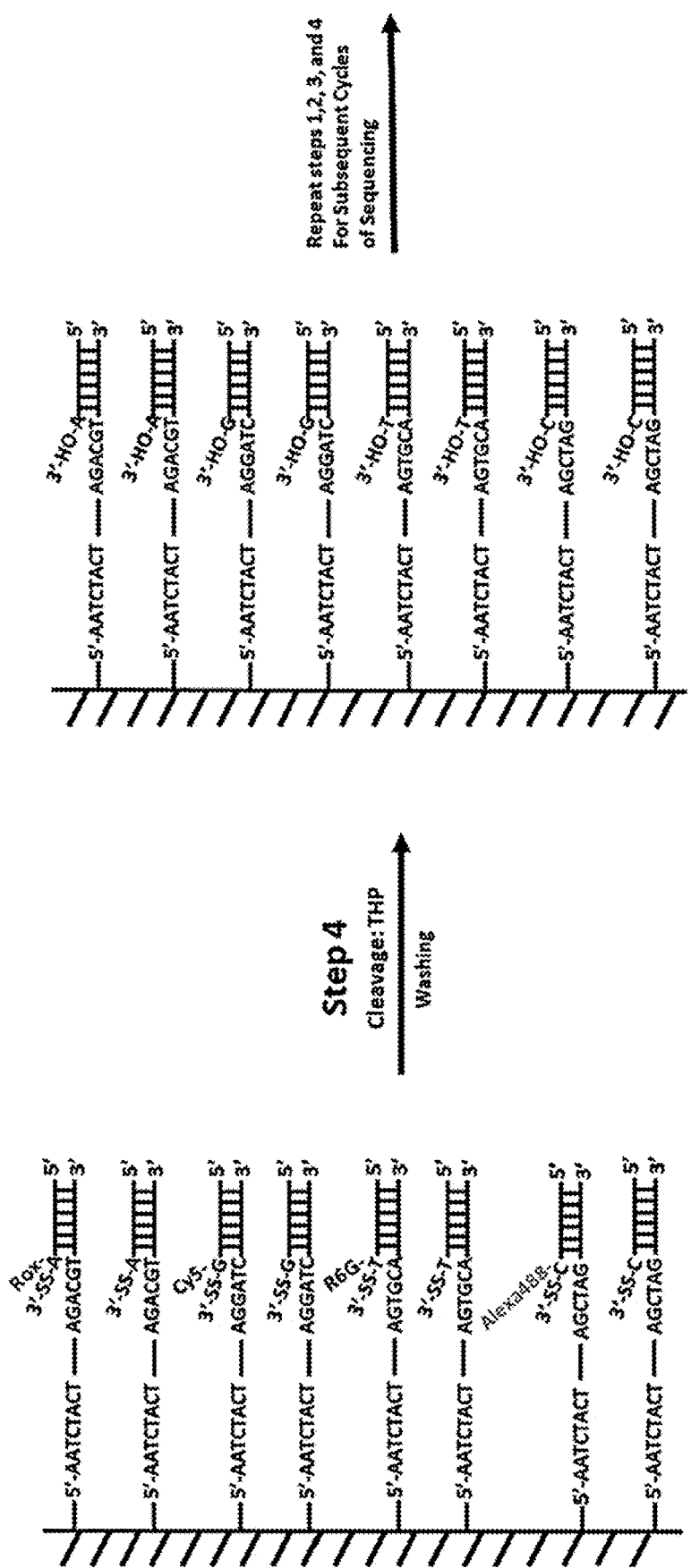

FIGS. 27A-27B. Four color SBS with a mixture of labeled and unlabeled reversible terminators. SBS using 3'-O-SS (DTM)-dNTP-SS-Dye (3'-O-t-Butyldithiomethyl(SS)-dATP-SS-Rox, 3'-O-t-Butyldithiomethyl(SS)-dCTP-SS-Alexa488, 3'-O-t-Butyldithiomethyl(SS)-dGTP-SS-Cy5, 3'-O-t-Butyldithiomethyl(SS)-dUTP-SS-R6G) (FIG. 24) and four 3'-O-t-Butyldithiomethyl(SS)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) (FIG. 24). Step 1, Addition of the DNA polymerase, the four 3'-O-SS(DTM)-dNTP-SS-Dye ((3'-O-t-Butyldithiomethyl(SS)-dATP-SS-Rox, 3'-O-t-Butyldithiomethyl(SS)-dCTP-SS-Alexa488, 3'-O-t-Butyldithiomethyl(SS)-dGTP-SS-Cy5, 3'-O-t-Butyldithiomethyl(SS)-dUTP-SS-R6G) and four 3'-O-t-Butyldithiomethyl(SS)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary nucleotide analogue to the growing DNA strand, The growing DNA strand is terminated with each of the four nucleotide analogues (A, C, G, T) with the four distinct fluorescent dyes or without dye labeling. After washing away (Step 2) the unincorporated nucleotide analogues, detection of the unique fluorescence signal (Step 3) from each of the fluorescent dyes on the DNA products allows for the identification of the incorporated nucleotide. Next, in Step 4, treatment of the DNA products with THP cleaves the SS linker, leading to the removal of the fluorescent dye and the regeneration of a free 3'-OH group on the DNA extension product, which is ready for the next cycle of DNA sequencing.

Figure 28A:
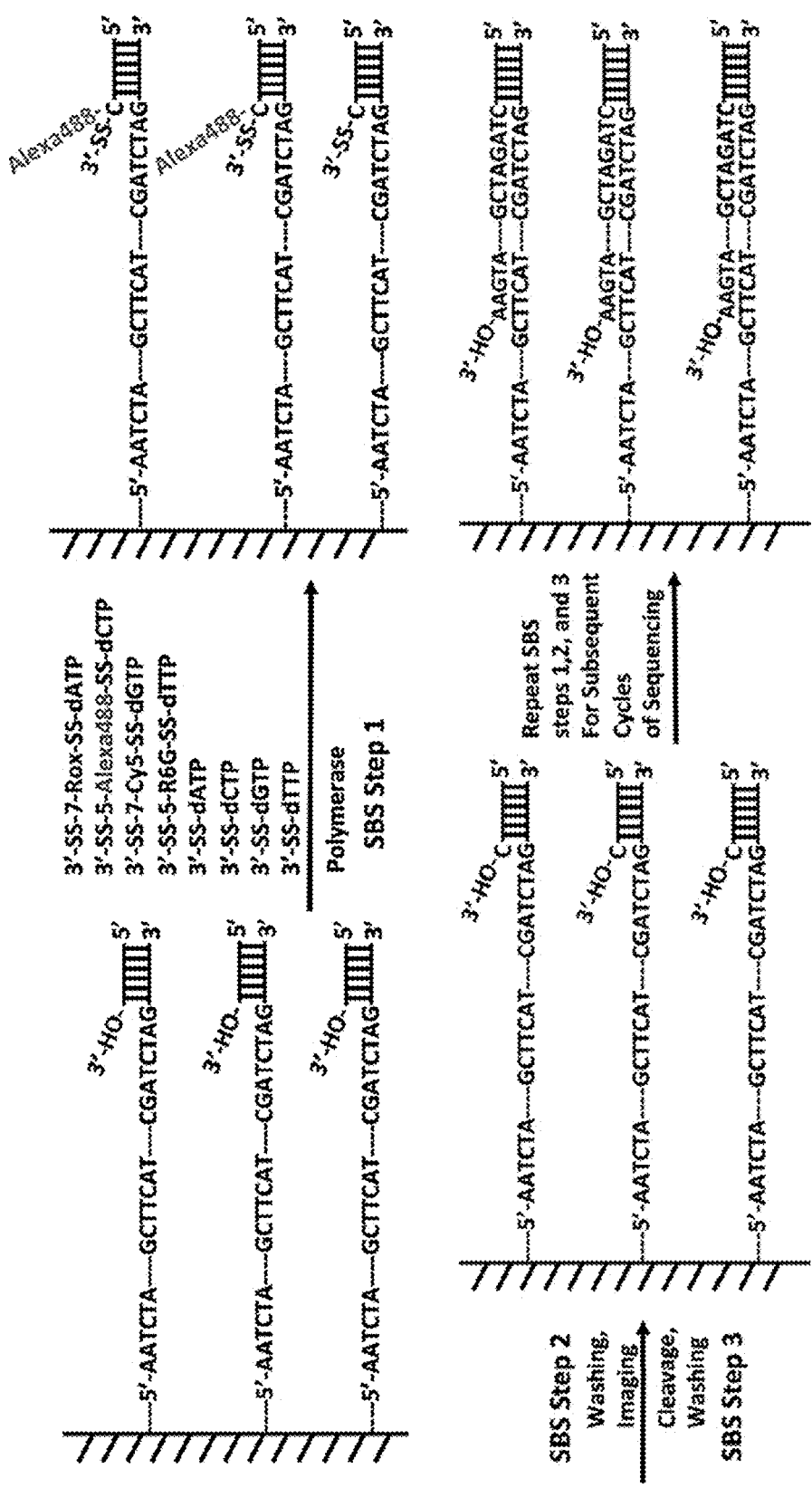
Figure 28B:
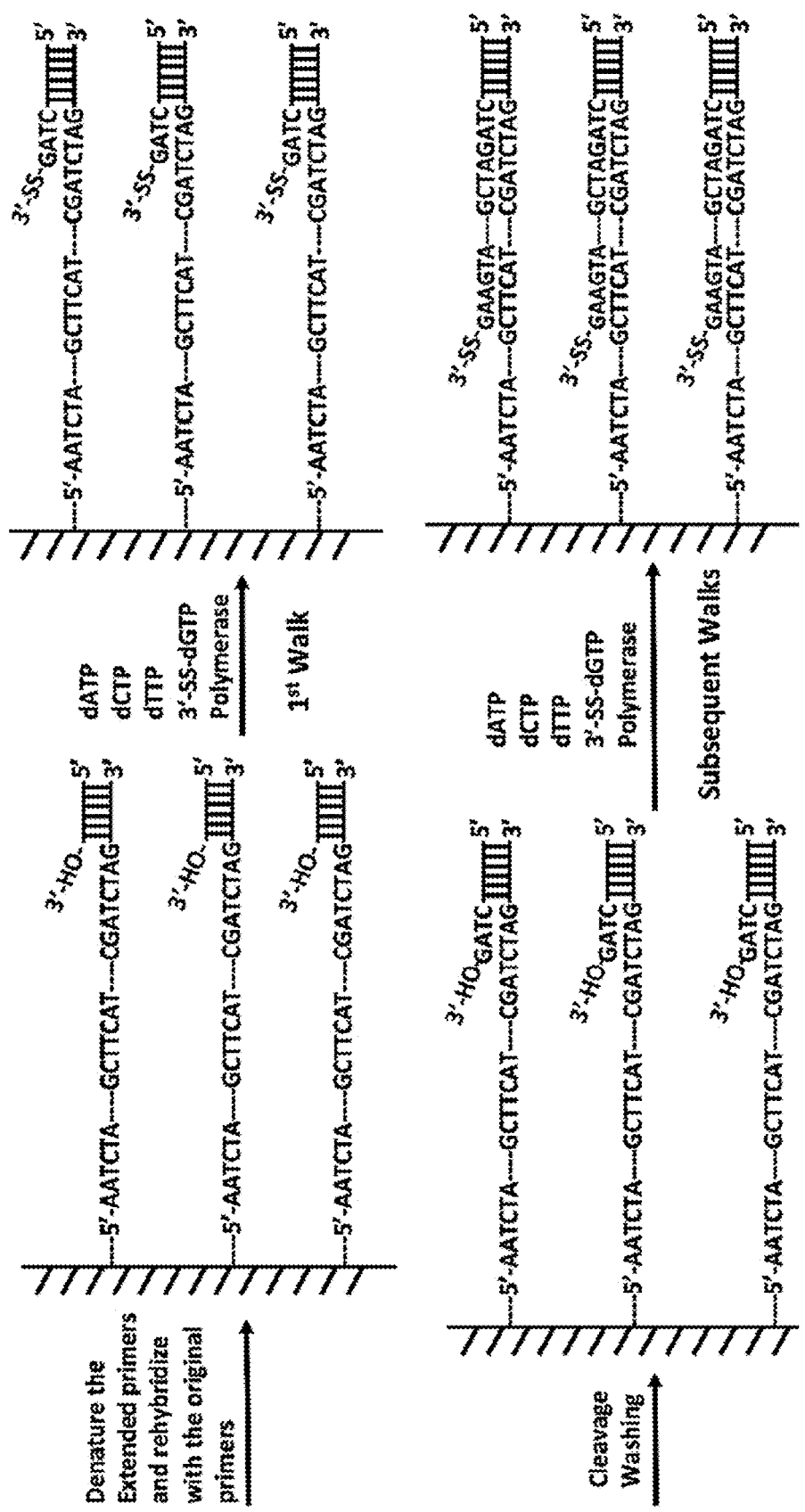
Figure 29A:
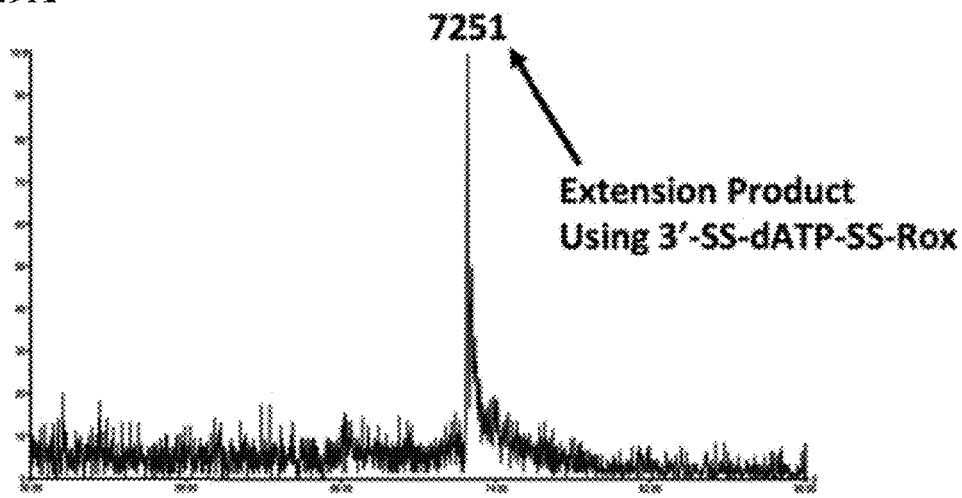
Figure 29B:
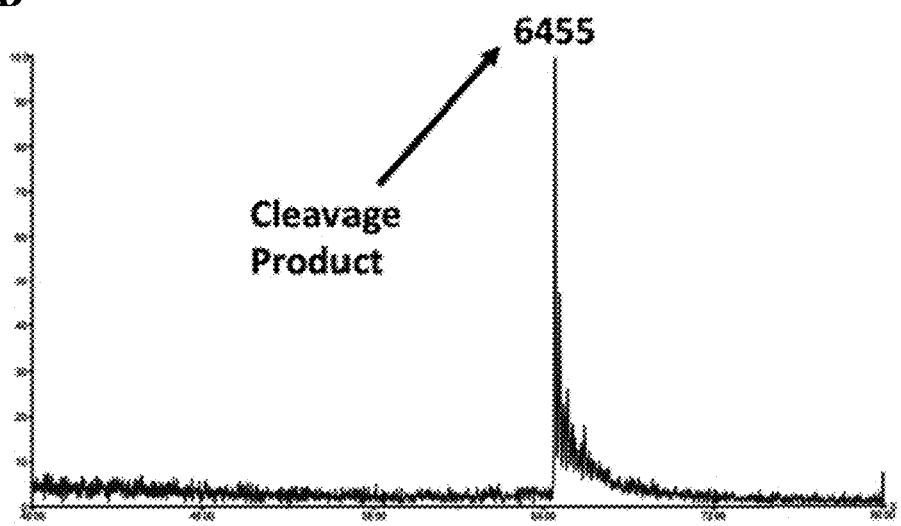
Figure 29C:
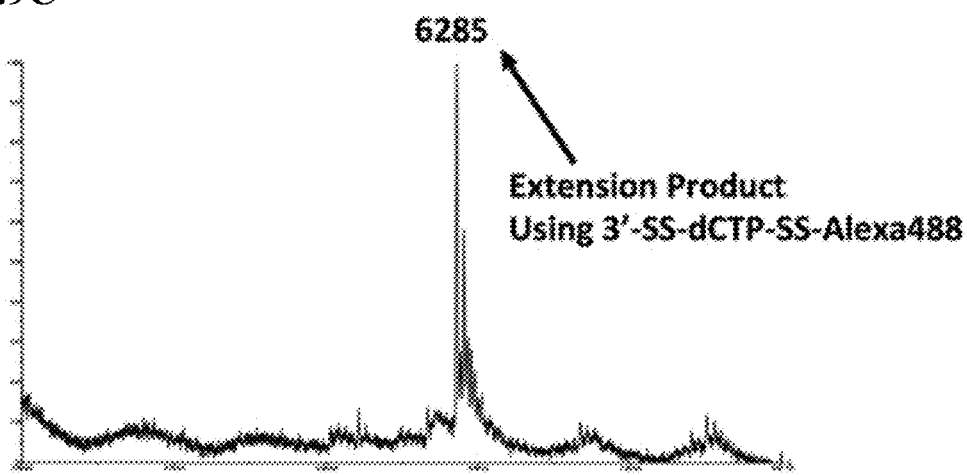
Figure 29D:
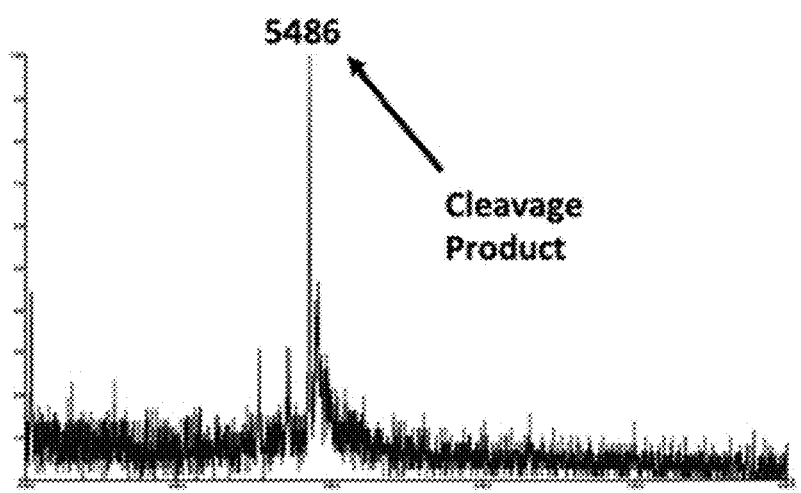
Figure 29E:
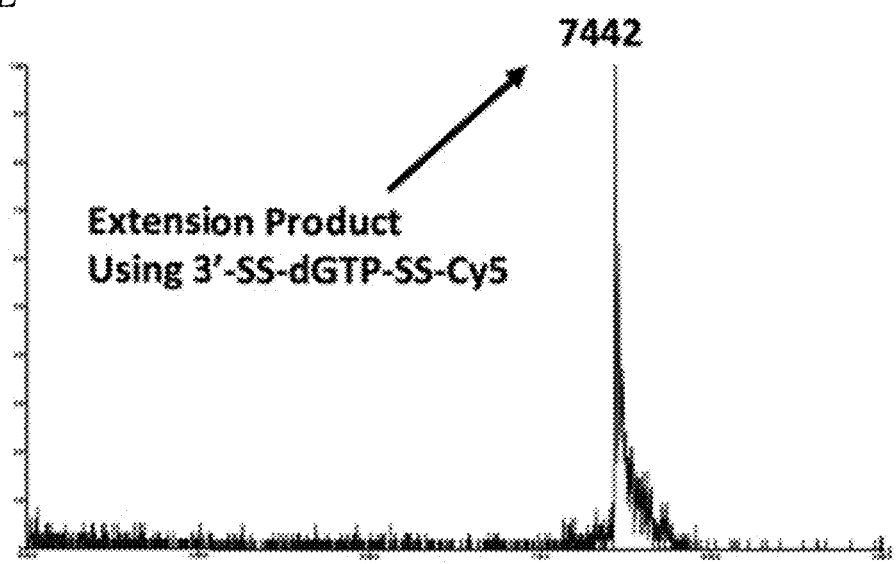
Figure 29F:
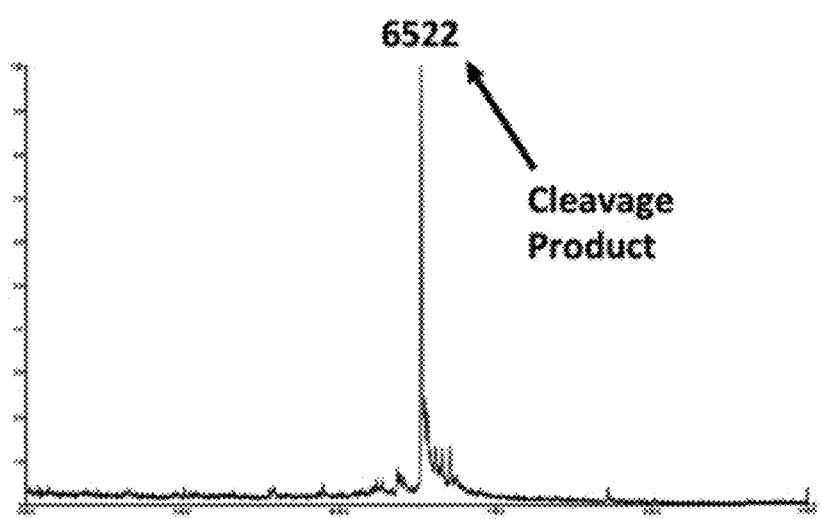
Figure 29G:
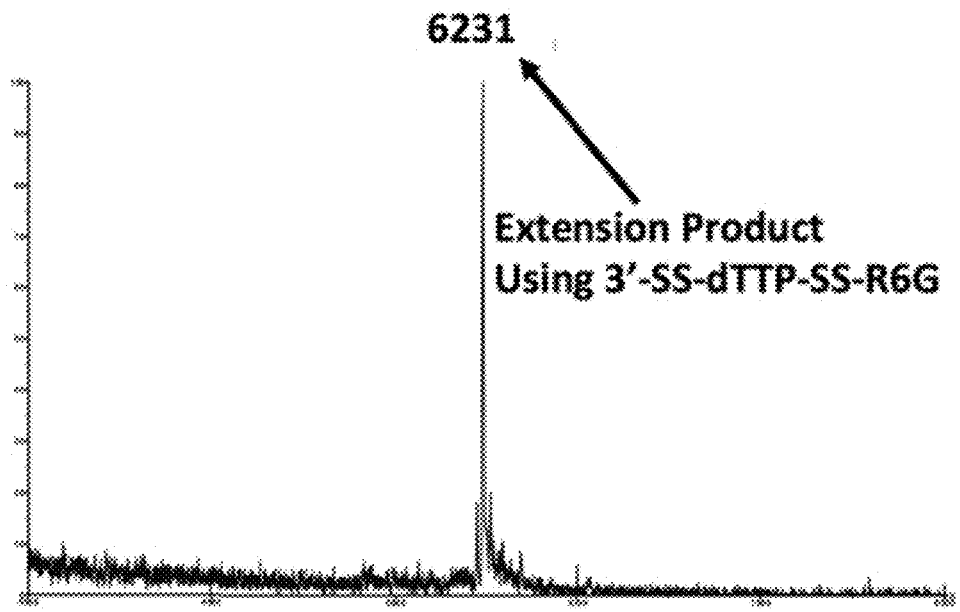
Figure 29H:
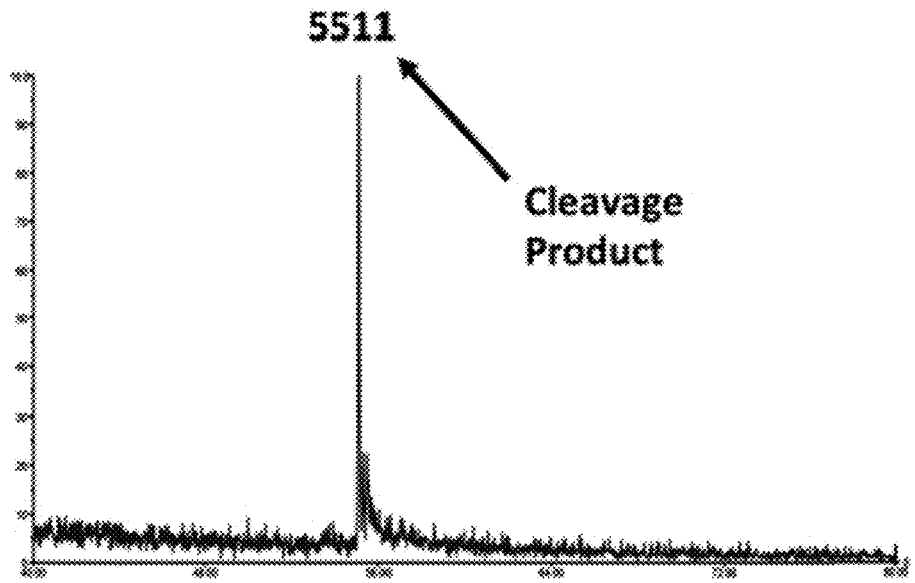

FIGS. 28A-28B. Four color SBS with chasing and walking. In this example, the four fluorescent nucleotide analogues with 3'-O-blocking groups as well as the four unlabeled blocked nucleotides are added together to obtain sequencing as in the previous example (FIG. 27). Next, the DNA is denatured to strip off the extended primer. The original primer is reannealed to the DNA template. After this, three natural nucleotides and one 3'-O-blocked nucleotide, all unlabeled, are added to the original primed template to carry out extension to the position complementary to the next occurrence of the single 3'-O-blocked nucleotide. This is repeated a sufficient number of times to rapidly walk to approximately the position where the prior sequencing run had ended (the number of steps in the walk will be determined by the expected base frequencies in the genome of interest). At this point the four labeled and four unlabeled 3'-O-blocked nucleotides are added to produce a new sequence read that extends from where the previous read left off. The sequence-denature-walk protocol can be repeated several times to obtain much longer sequences than could be obtained without walking.

FIGS. 29A-29H. MALDI-TOF MS spectra showing single base extension and cleavage products using 3'-SS-dATP-SS-Rox (M.W. 1344), 3'-SS-dCTP-SS-Alexa488 (M.W.1319), 3'-SS-dGTP-SS-Cy5 (M.W. 1482), and 3'-SS-dUTP-SS-R6G (M.W. 1233) (structures shown in FIG. 24), respectively. The masses of the expected extension products are 7253, 6288, 7438, and 6221 Daltons, respectively. The masses of the expected cleavage products are 6451, 5488, 6515, and 5508 Daltons. The y axis shows the percent intensity, while the x axis shows mass (m/z).

Figure 30A:
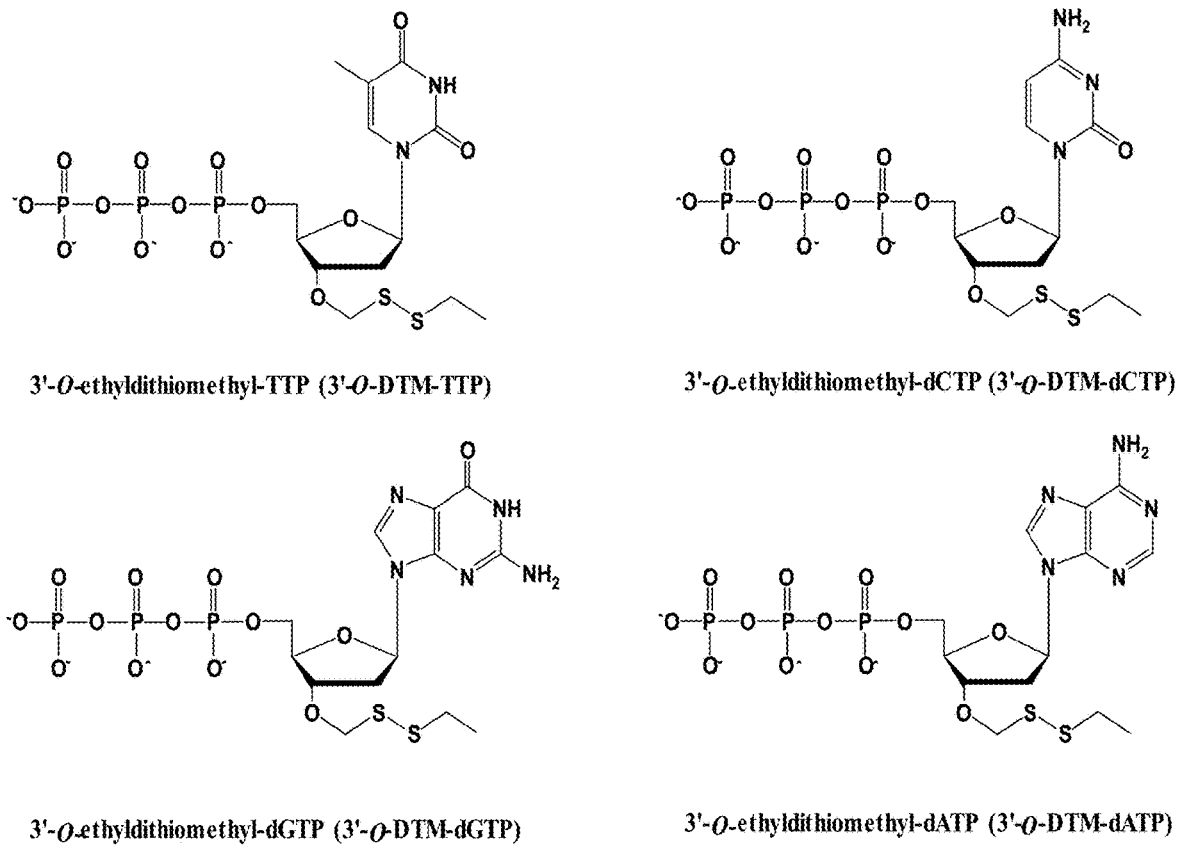
Figure 30B:
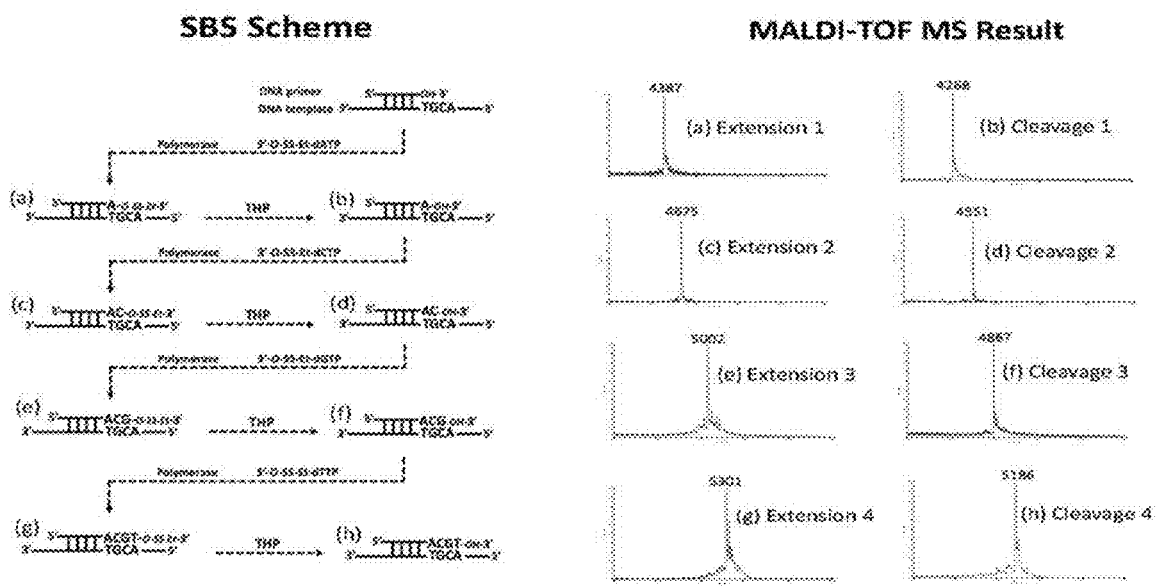

FIGS. 30A-30D. Example structures and Experimental scheme of continuous DNA sequencing by synthesis (left) using four 3'-O-Et-dithiomethyl-dNTPs reversible terminators (3'-O-SS-Et-dNTPs or 3'-O-DTM-dNTPs) and MALDI-TOF MS spectra (right) obtained from each step of extension and cleavage. THP=(tris(hydroxypropyl)phosphine). The masses of the expected extension products are 4381, 4670, 4995, and 5295 Da respectively. The masses of the expected cleavage products are 4272, 4561, 4888, and 5186 Da. The measured masses shown in FIG. 30B are within the resolution of MALDI-TOF MS. Experimental scheme of continuous DNA sequencing by synthesis (left) using four 3'-O-t-Bu-SS-dNTPs reversible terminators (FIG. 30C) and MALDI-TOF MS spectra Fig.D) obtained from each step of extension and cleavage. The masses of the expected extension products are 4404, 4697, 5024, and 5328 Daltons respectively. The masses of the expected cleavage products are 4272, 4563, 4888, and 5199 Daltons.

Figure 31:
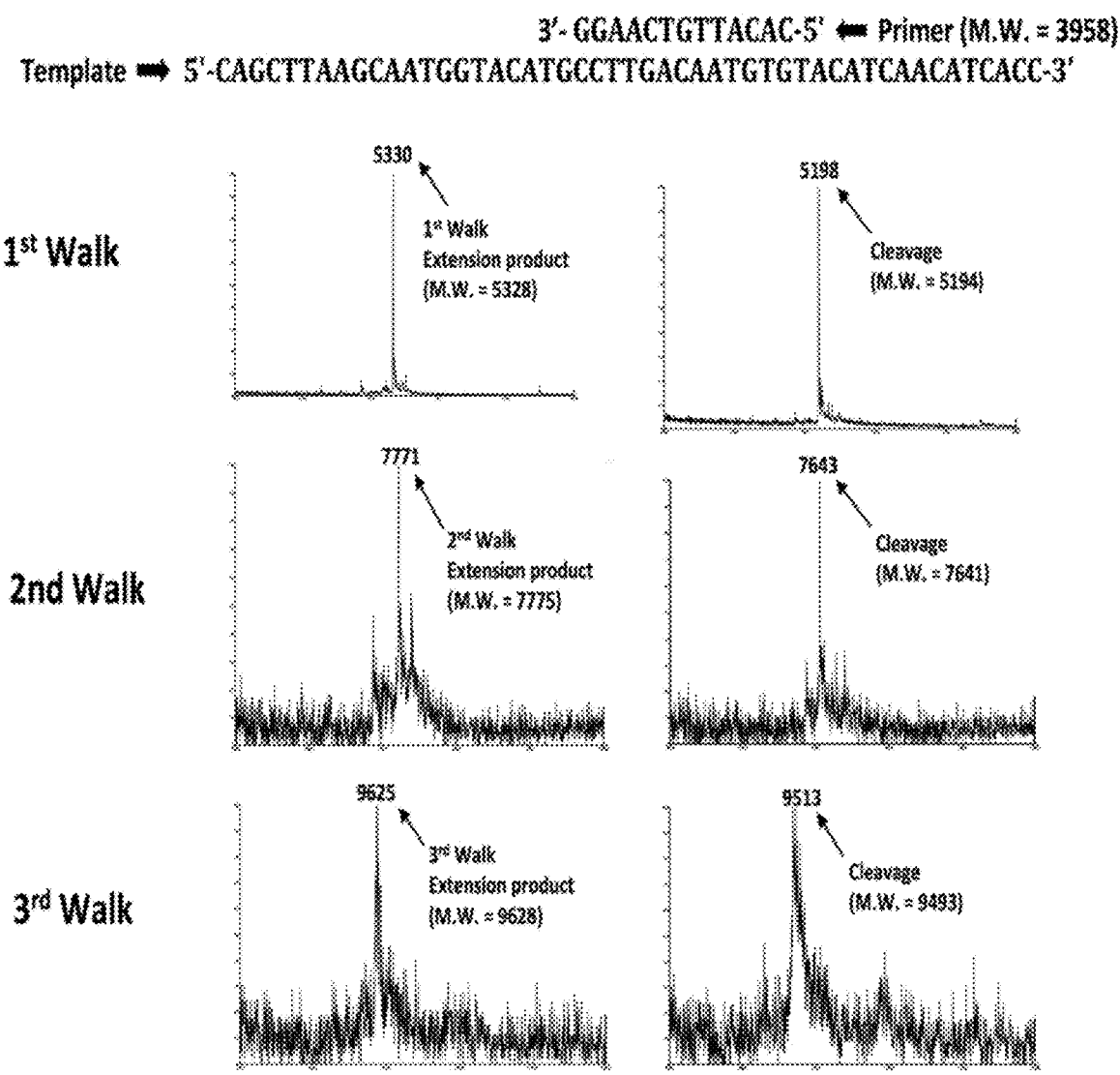

FIG. 31. Demonstration of walking strategy. The DNA template (SEQ ID NO:1) and primer (SEQ ID NO:2) shown above were used (the portion of the template shown in green is the primer binding region) and incubation was carried out using Therminator IX DNA polymerase, dATP, dCTP, dTTP and 3'-O-t-butyl-SS-dGTP. After the first walk, the primer was extended to the point of the next C in the template (rightmost C highlighted in red in the template strand). The size of the extension product was 5330 Daltons (5328 Da expected) as shown in the top left MALDI-TOF MS trace.

After cleavage with THP, the 5198 Da product shown at the top right was observed (5194 Da expected). A second walk was performed with Therminator IX DNA polymerase, dATP, dCTP, dTTP and 3'-O-t-butyl-SS-dGTP to obtain the product shown in the middle left trace (7771 Da observed, 7775 Da expected to reach the middle C highlighted in red). After cleavage, a product of 7643 Da was obtained (expected 7641 Da). Finally a third walk and cleavage were performed, giving products of 9625 Da (9628 Da expected for the leftmost red highlighted C) and 9513 Da (9493 Da expected), respectively. This demonstrates the ability to use the 3'-O-t-butyl-SS-nucleotide as a terminator for walking reactions. These can be incorporated into a combined sequencing/walking scheme such as the one depicted in FIG. 27.

Figure 32:
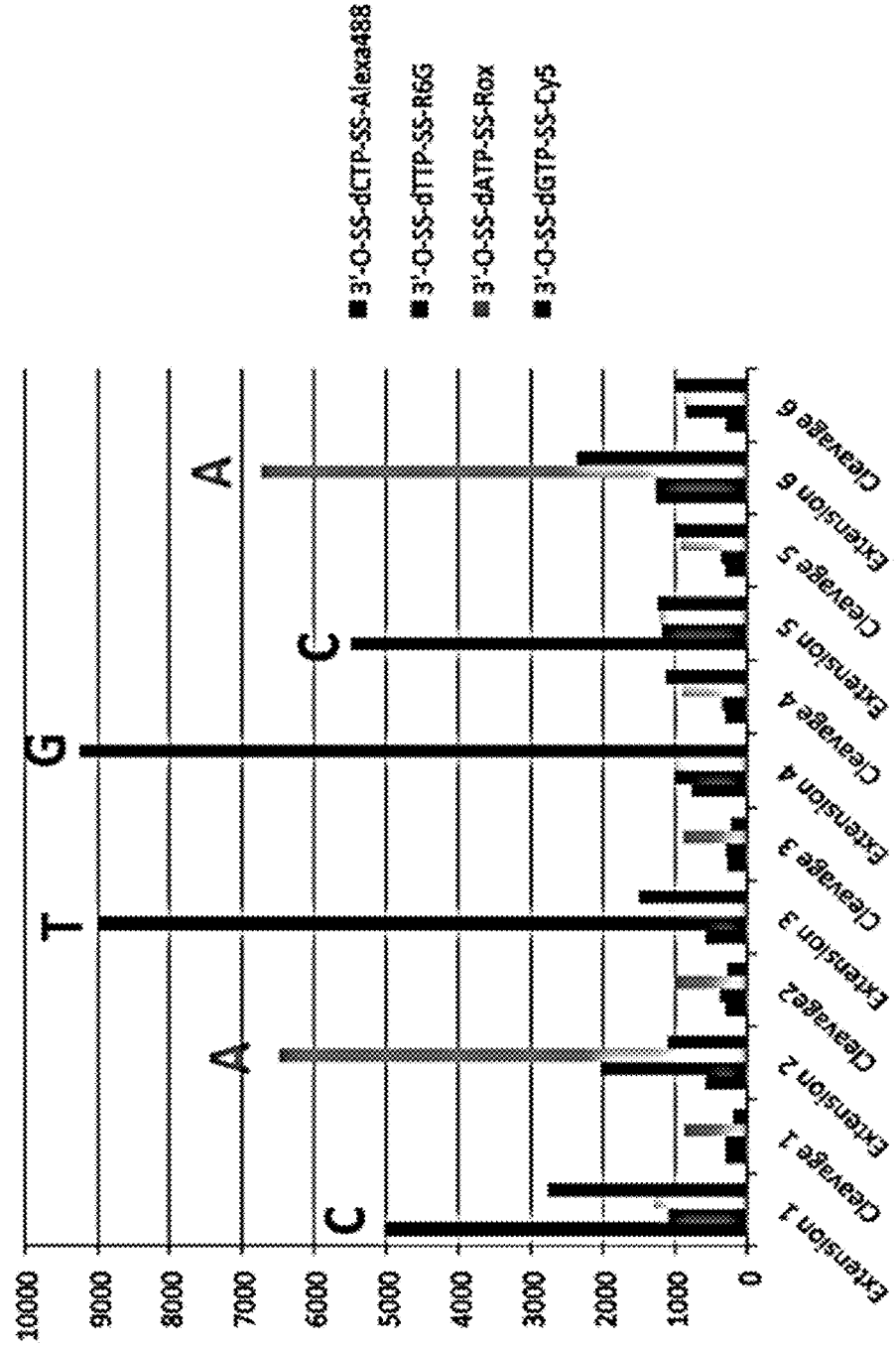

FIG. 32. Four Color SBS Data on a Solid Surface. A four-color sequencing data plot of raw fluorescence emission intensity obtained by using a mixture of 3'-SS-dATP-SS-Rox, 3'-SS-dCTP-SS-Alexa488, 3'-SS-dGTP-SS-Cy5, and 3'-SS-dTTP-SS-R6G for each sequencing cycle using the self-priming DNA template shown above covalently attached to a glass slide.

Figure 33:
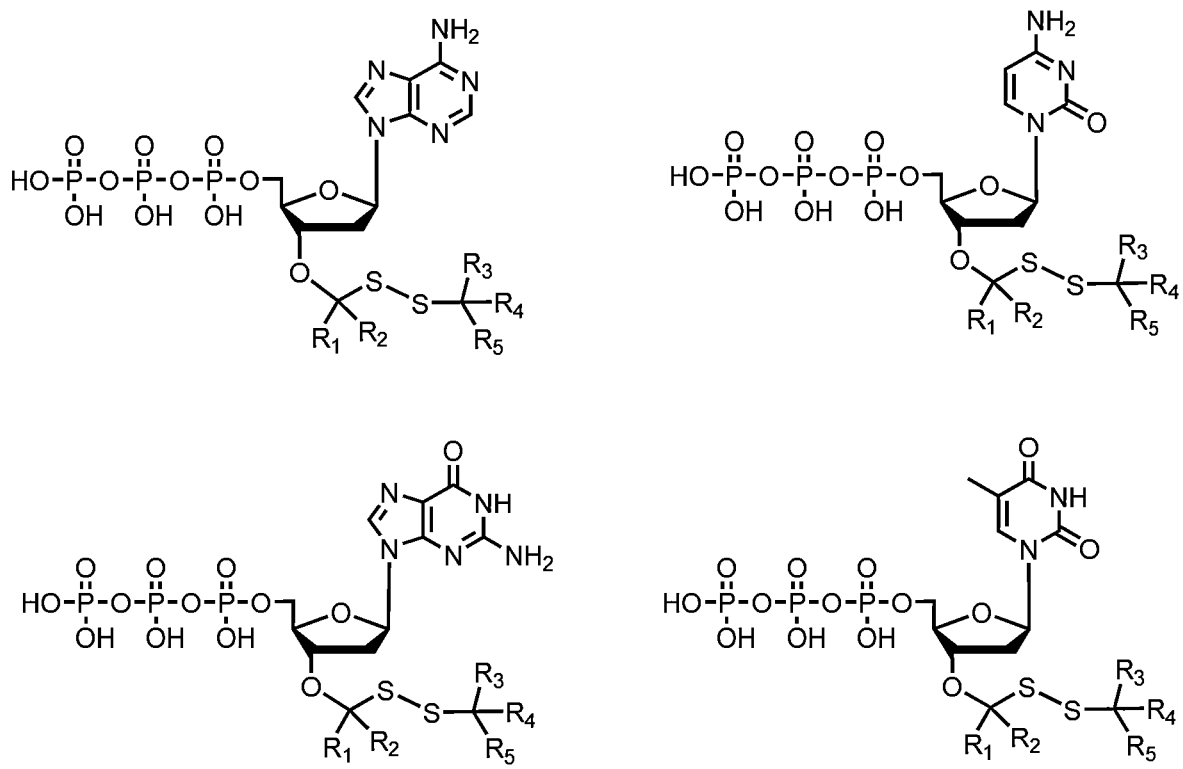

FIG. 33. General structures of derivatives of 3'-O-SS-dNTPs.

Figure 34:
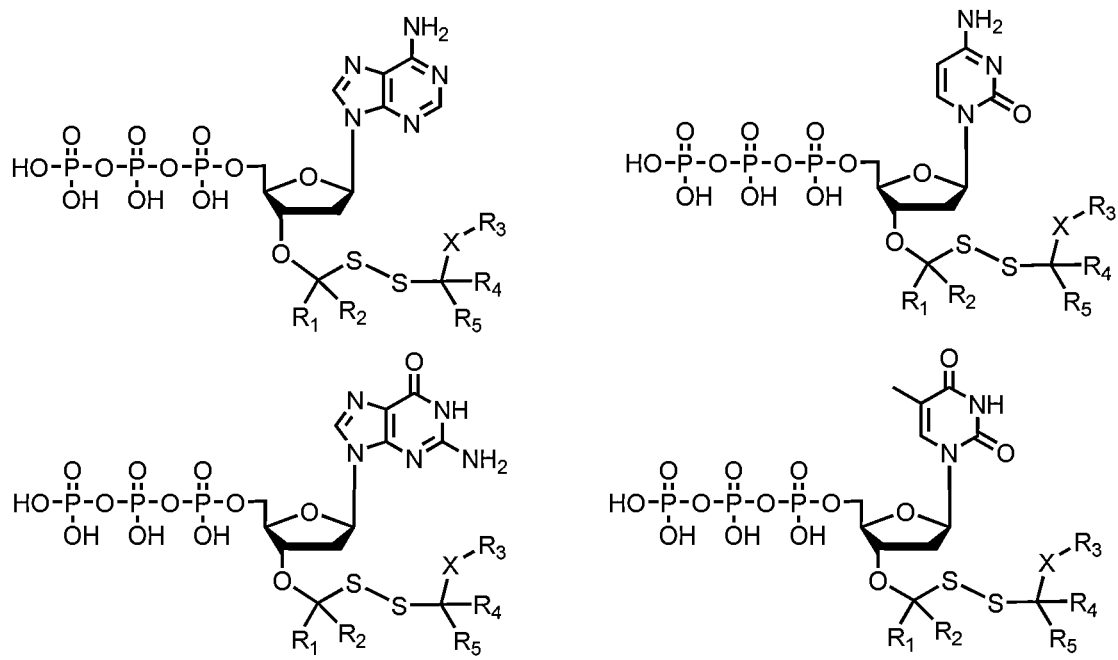

FIG. 34. General Structures of derivatives of 3'-O-SS-dNTPs.

Figure 35A:
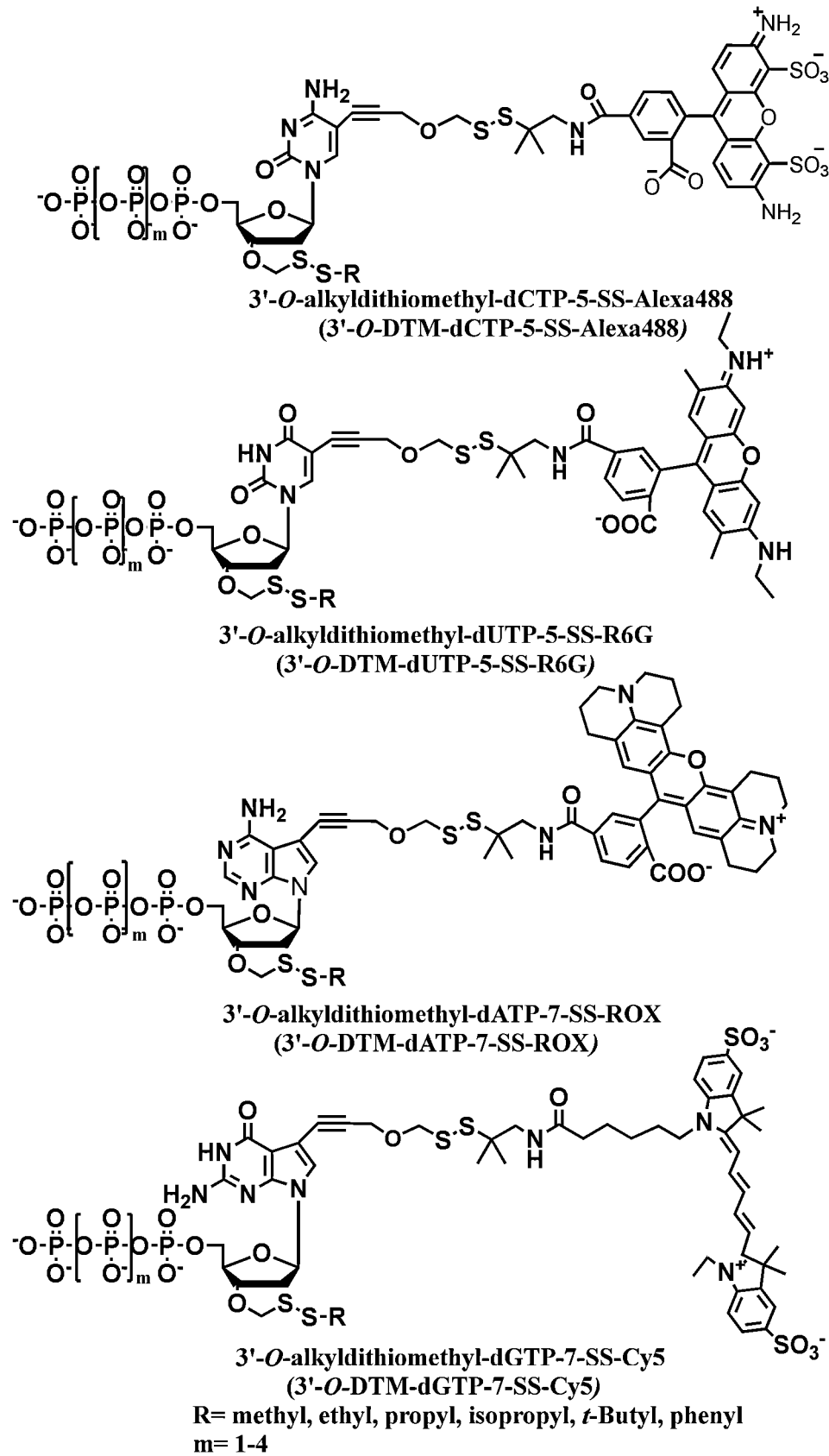
Figure 35B:
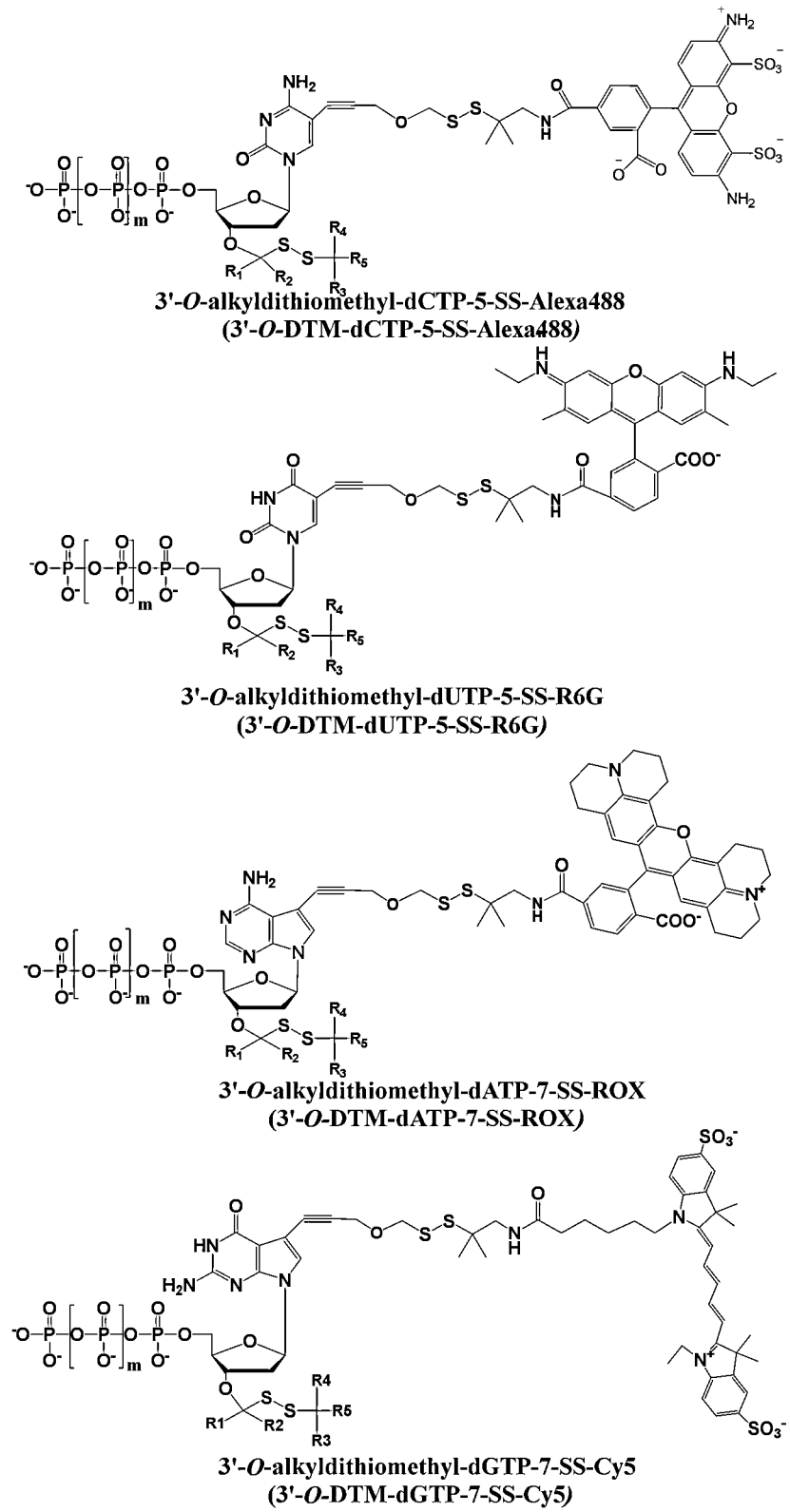
Figure 35C:
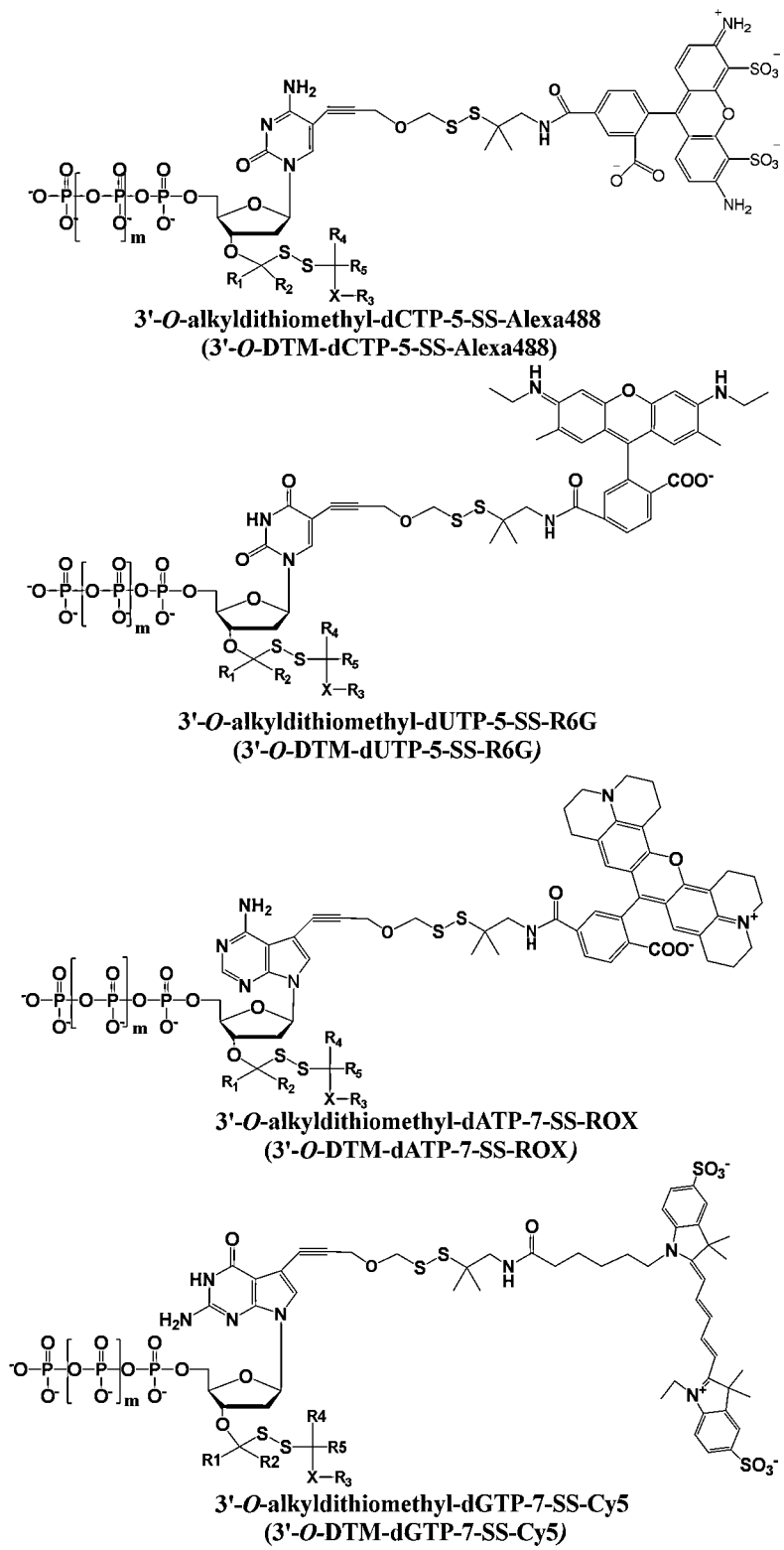

FIG. 35A-35C. Base-Labeled Reversible Terminators with different blocking group modifications.

Figure 36:
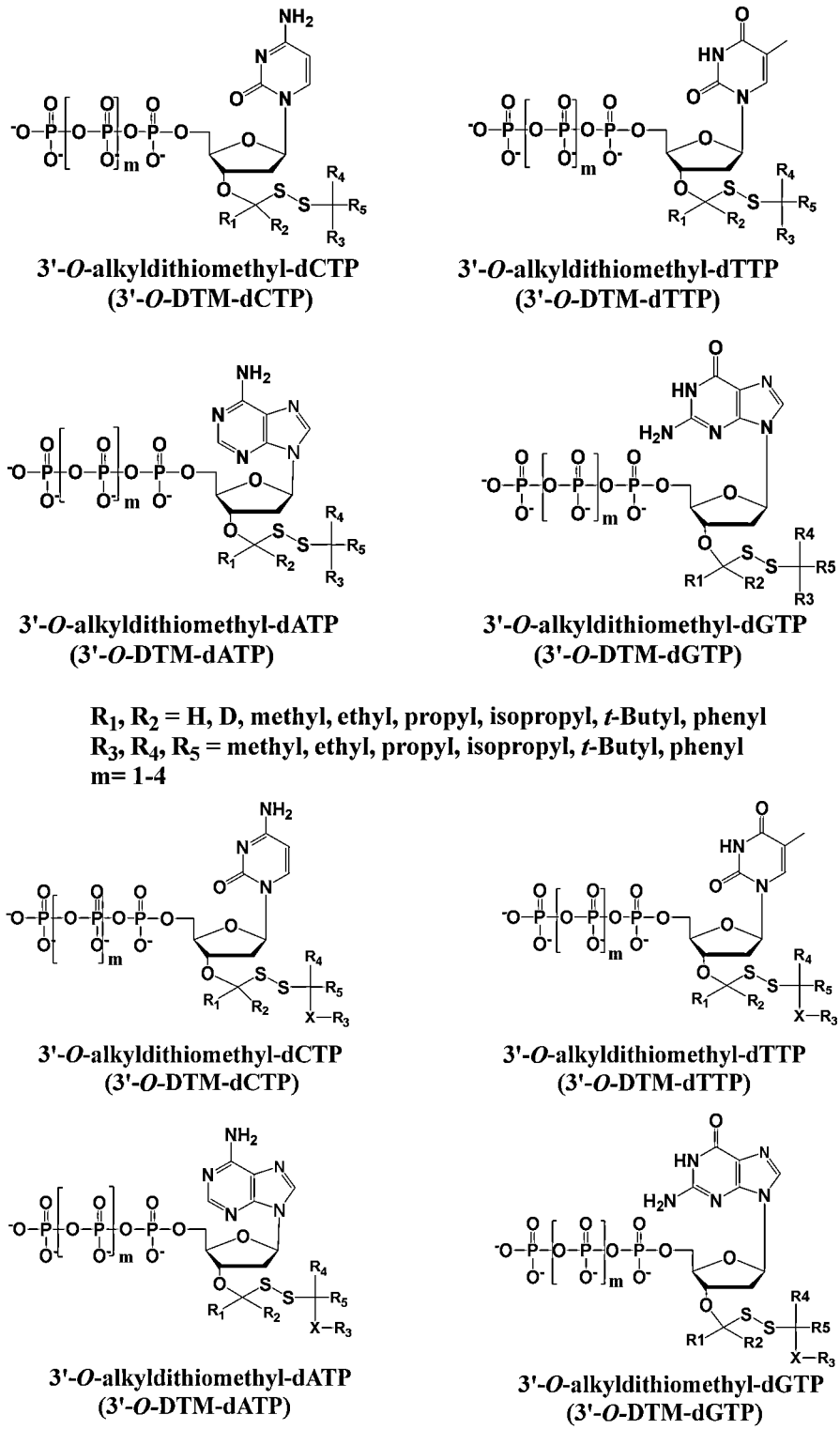

FIG. 36. Unlabeled Reversible Terminators with different blocking group modifications at 3'-O position (used for sequencing, chasing and walking).

Figure 37:
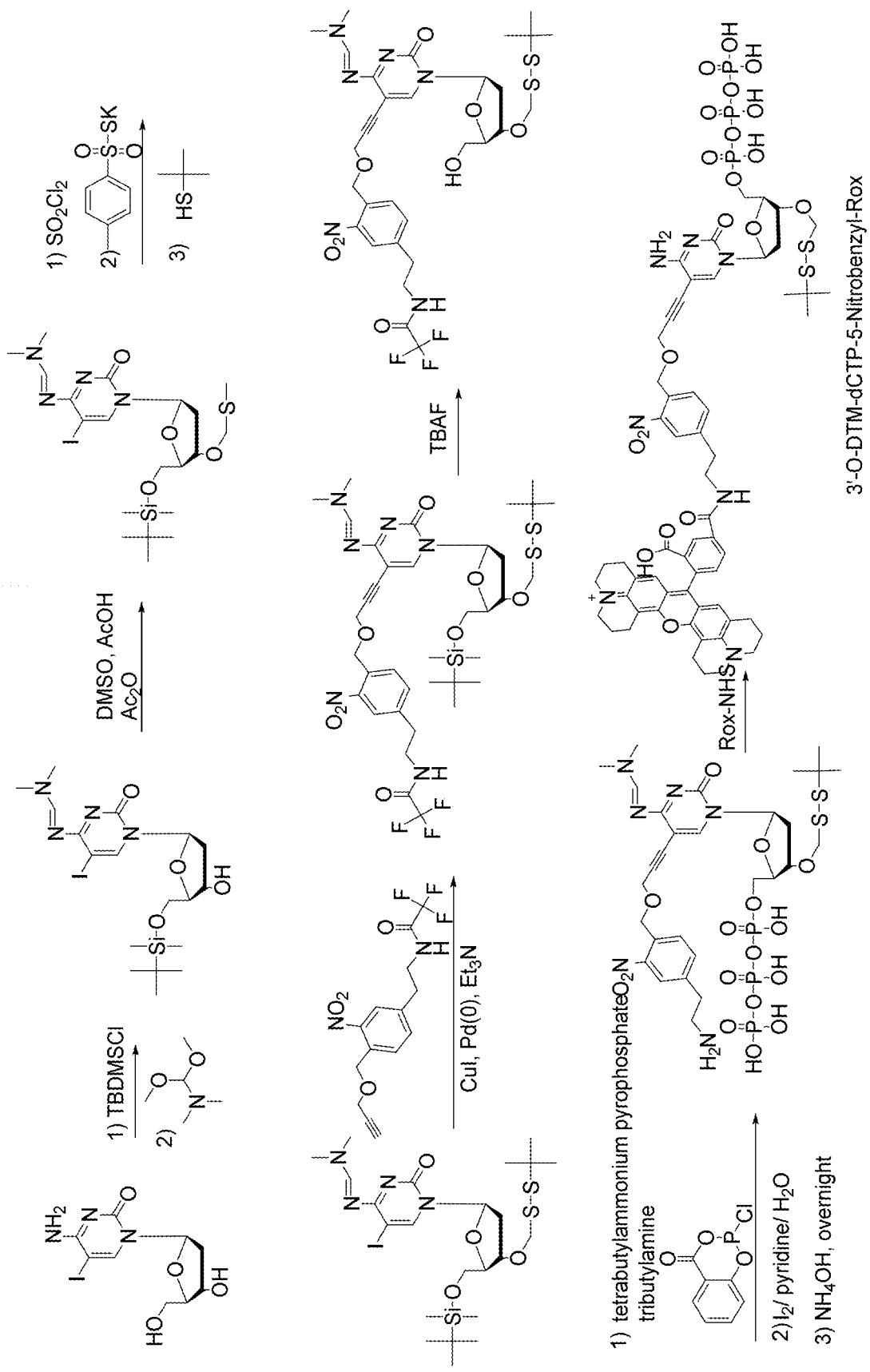

FIG. 37. Synthesis of 3'-O-DTM-dCTP-5-Nitrobenzyl-Rox.

Figure 38:
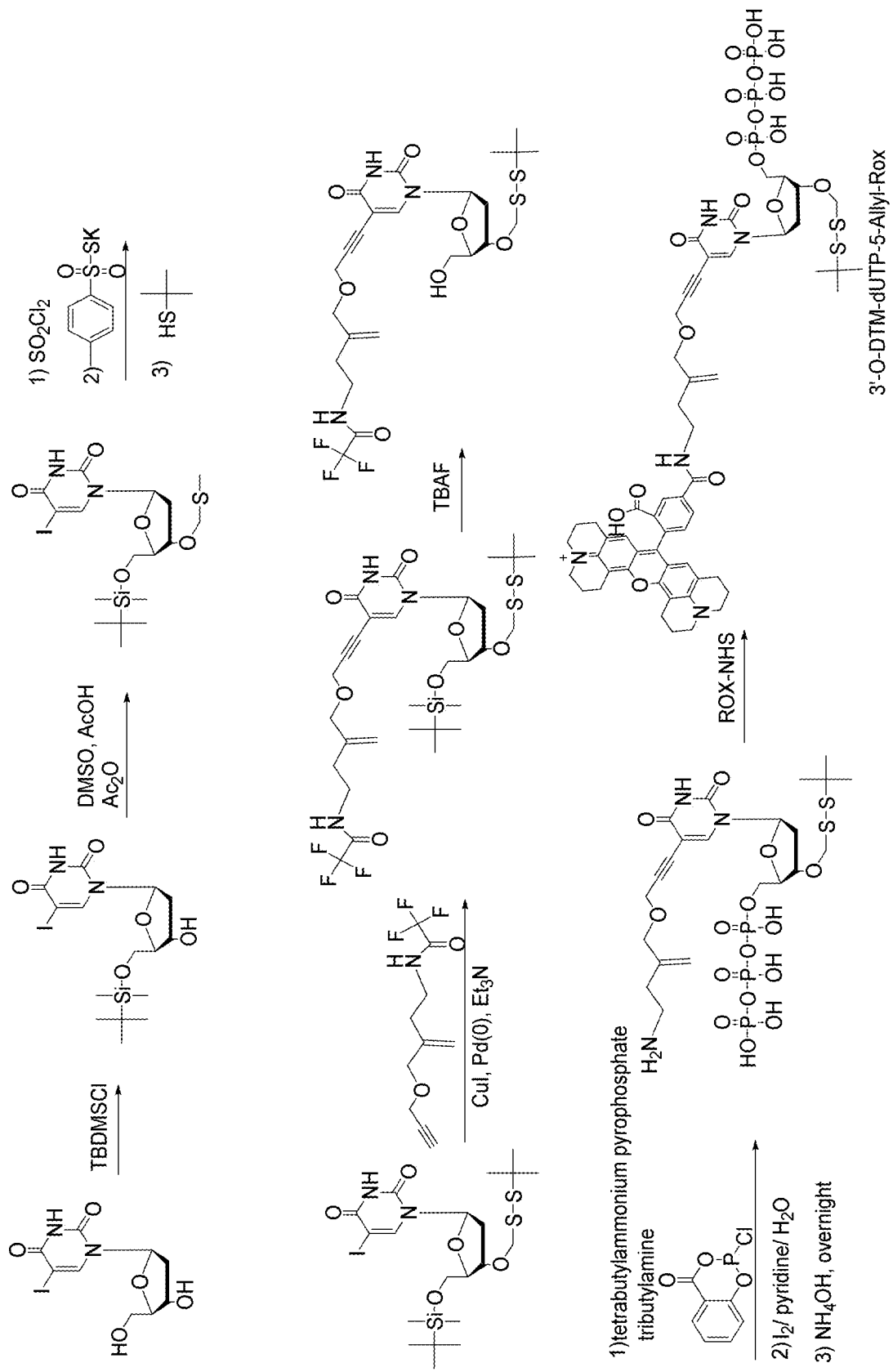

FIG. 38. Synthesis of 3'-O-DTM-dUTP-S-Allyl-Rox.

Figure 39:
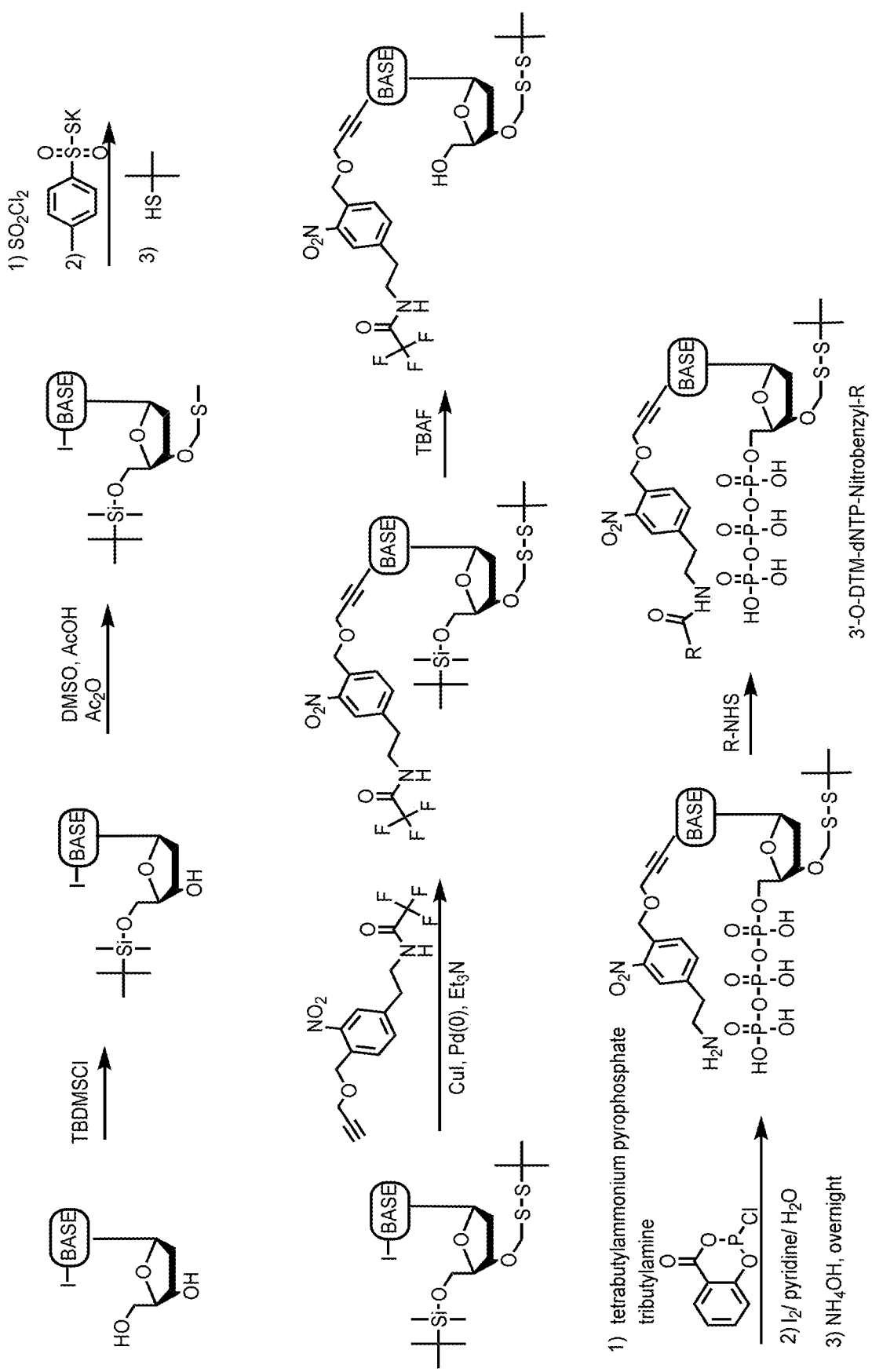

FIG. 39. Synthesis of 3'O-DTM-dNTP-Nitrobenzyl-R; R refers to Dye or "Anchor" molecule.

Figure 40:
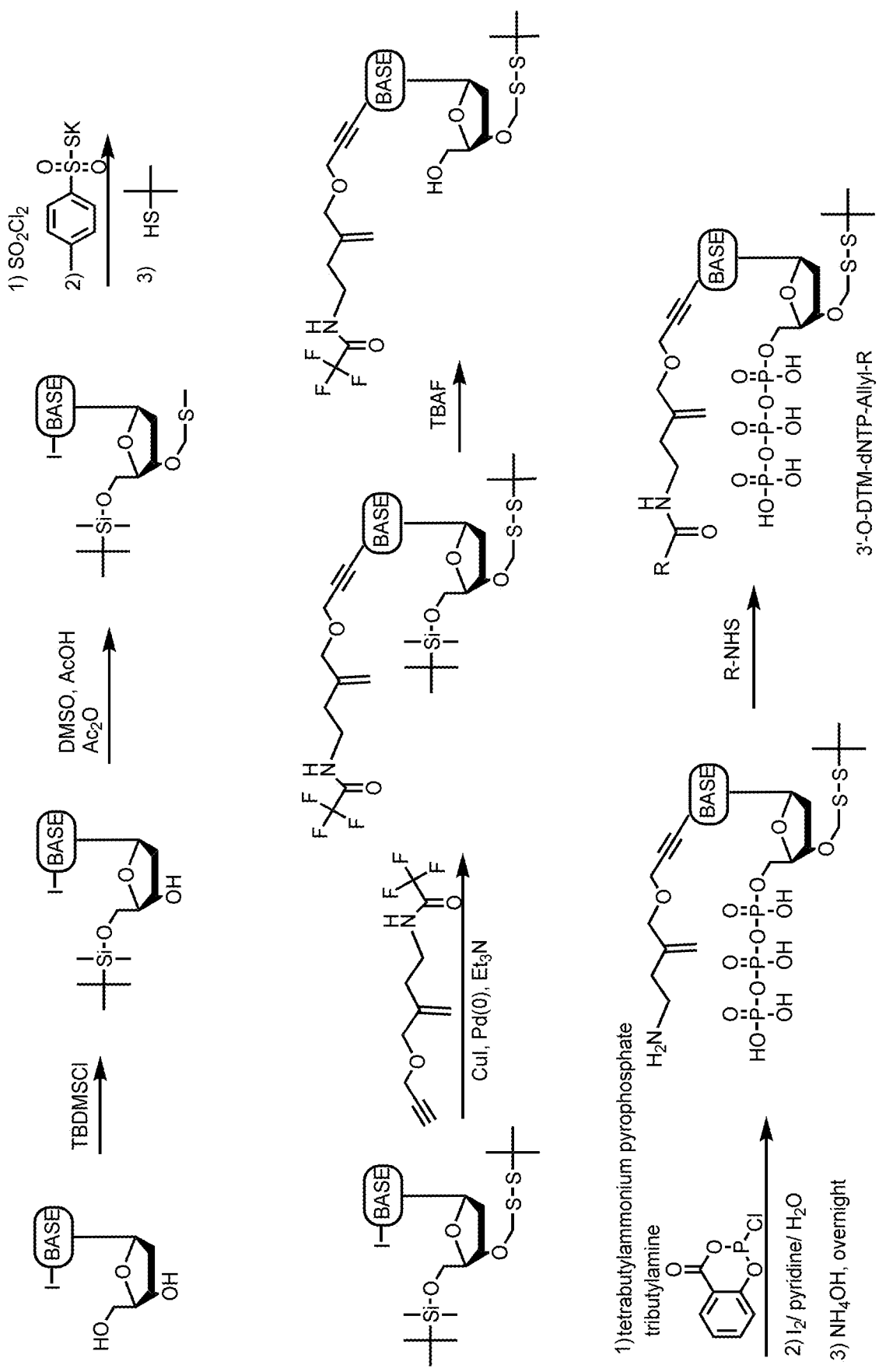

FIG. 40. Synthesis of 3'-O-DTM-dNTP-Allyl-R; R refers to Dye or "Anchor" molecule.

Figure 41:
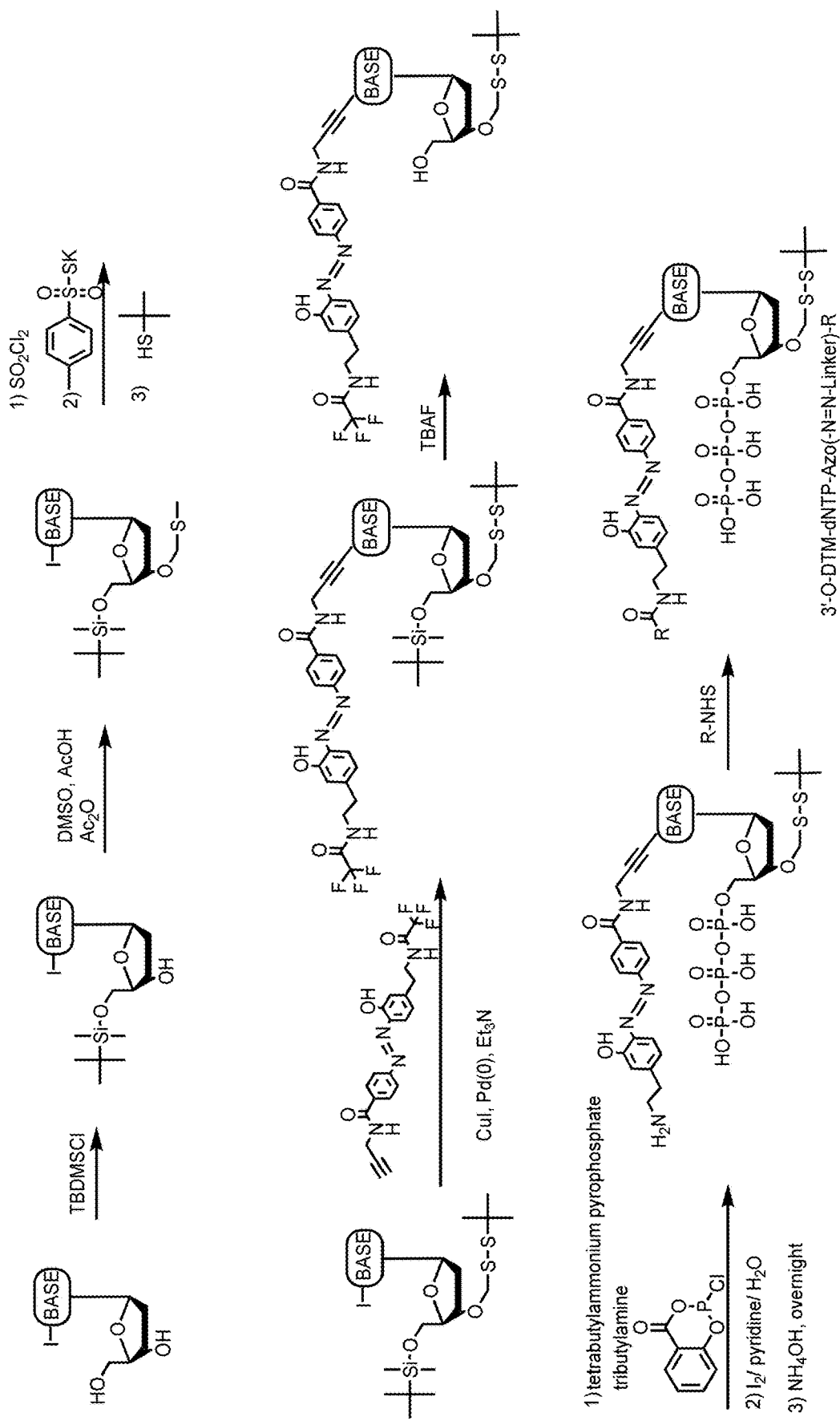

FIG. 41. Synthesis of 3'-O-DTM-dNTP-Azo(—N=N-Linker)-R; R refers to Dye or "Anchor" molecule.

Figure 42:
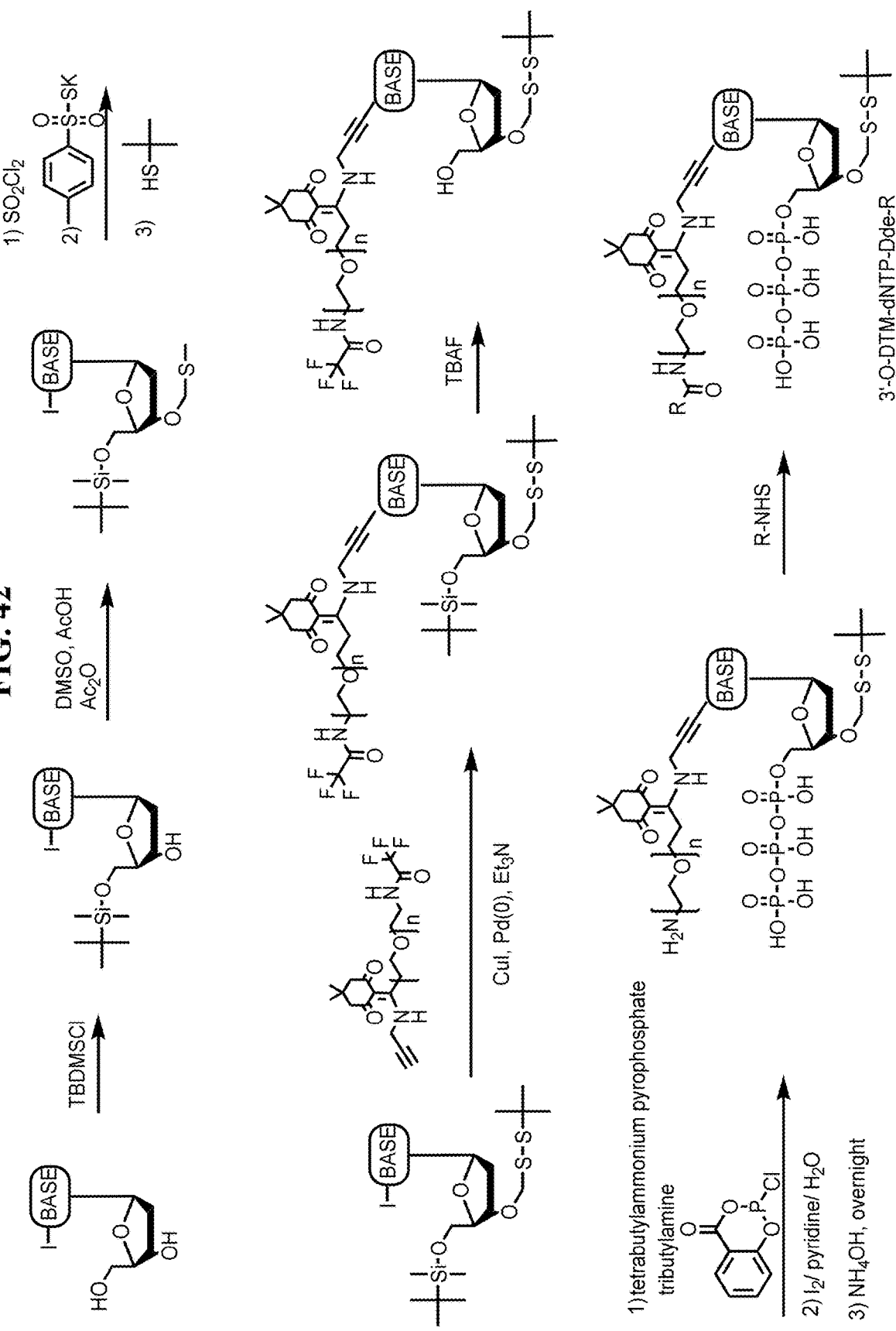

FIG. 42. Synthesis of 3'-O-DTM-dNTP-Dde Linker-R; R refers to Dye or "Anchor" molecule.

Figure 43:
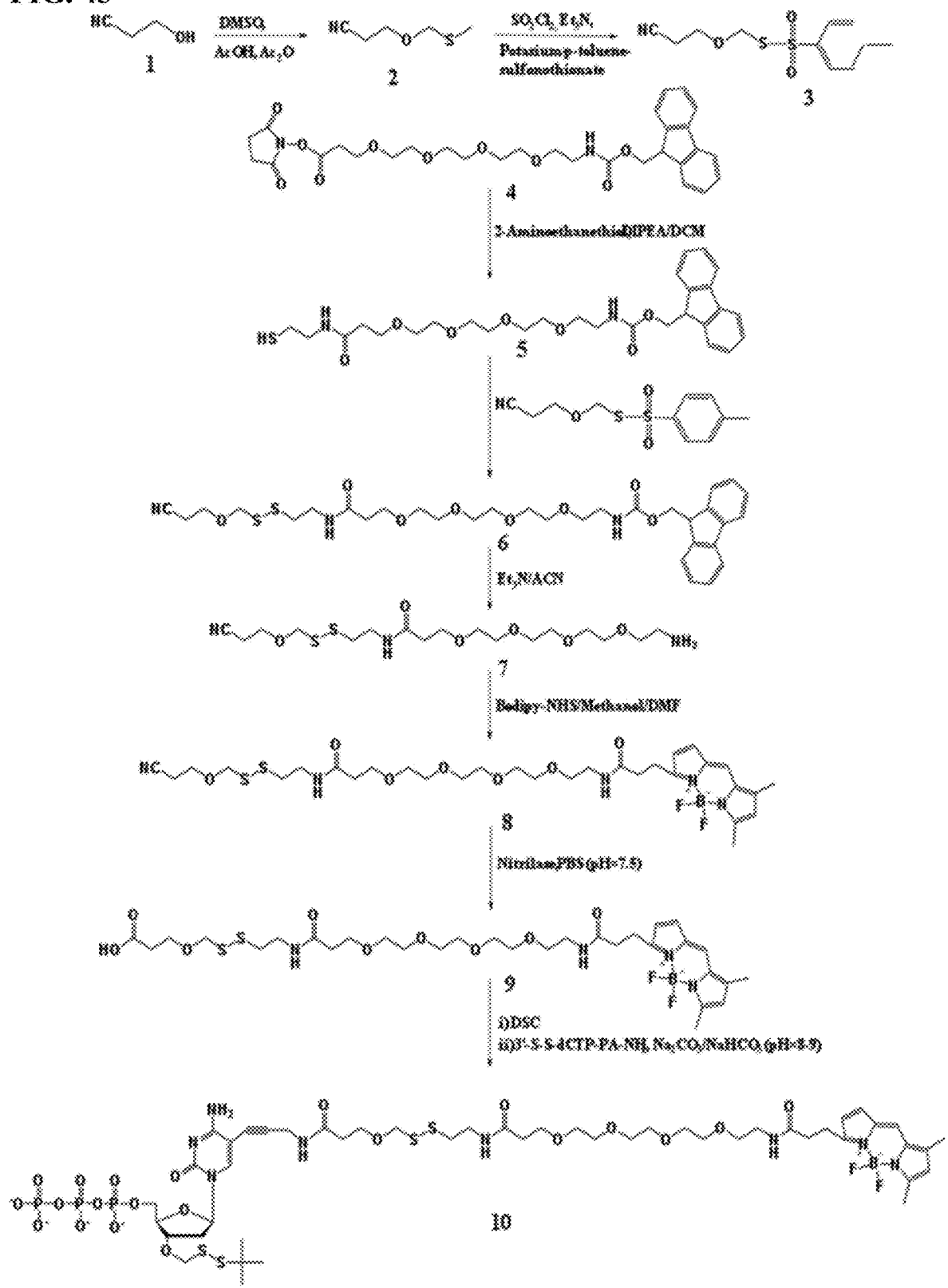

FIG. 43. Synthetic scheme for the preparation of 3'-O-DTM-dNTPs-SS-Dye.

FIG. 44. Structures of four 5(7)-aminopropynyl-3'-O-tBu-dithiomethyl-dNTPs (PA-3' DTM-dNTPs).

Figure 45:
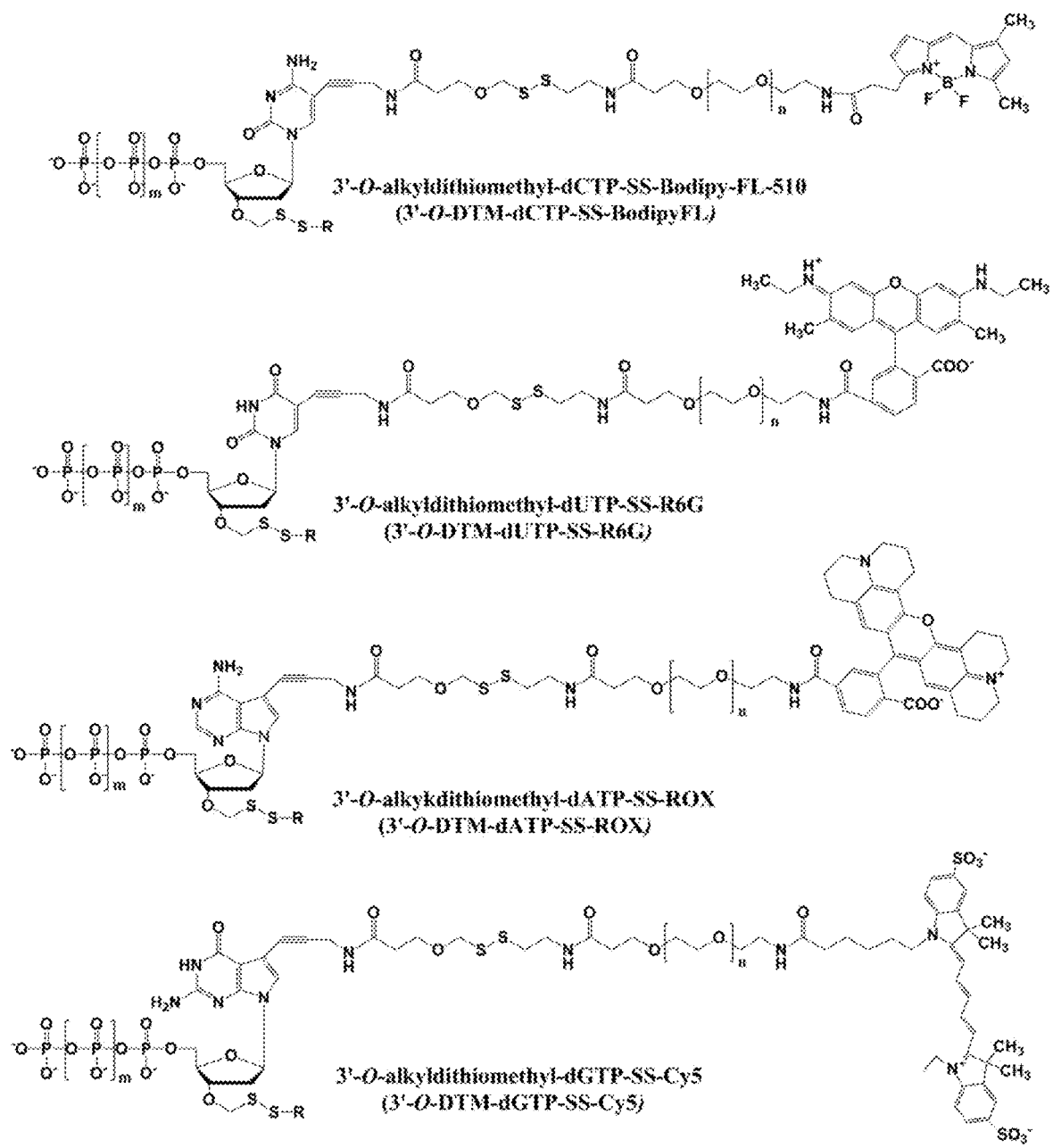

FIG. 45. Structures of four 3'-O-alkyldithiomethyl-dNTPs-SS-Linker-Dye (3'-O-DTM-dNTPs-SS-Dye).

FIG. 46. Experimental scheme of consecutive extensions (Top) using 3'-O-t-Bu-SS-dCTP-SS-BodipyFL reversible terminator and MALDI-TOF MS spectra of the first extension product (Product 1, left, expected MW. 6334), the first cleavage product (Product 2, middle, expected MW. 5556), and the second extension product (Product 3, right, expected MW. 6746).

Figure 47:
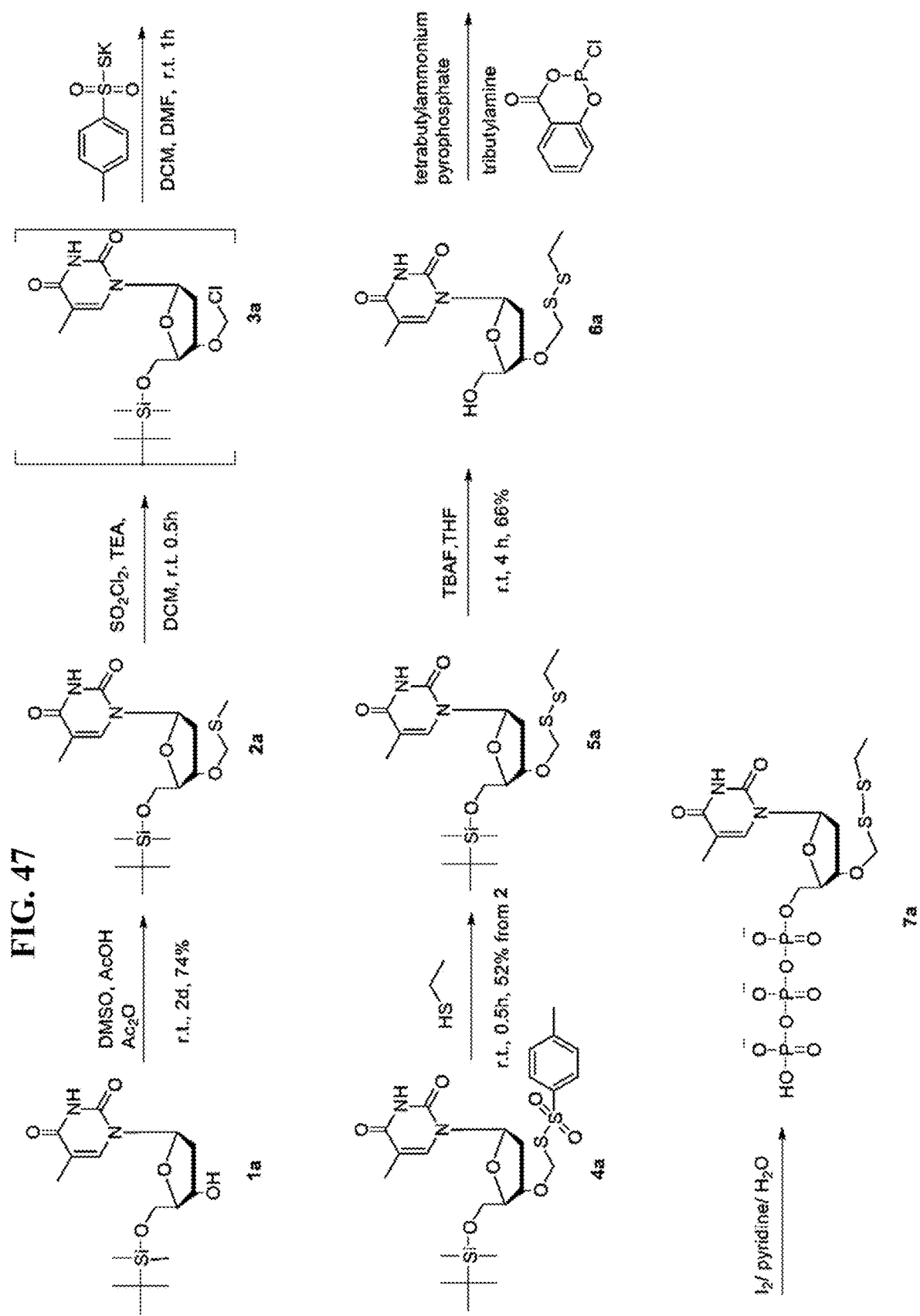

FIG. 47. Scheme for synthesis of 3'-O-ethyldithiomethyl-dTTP (7a).

Figure 48:
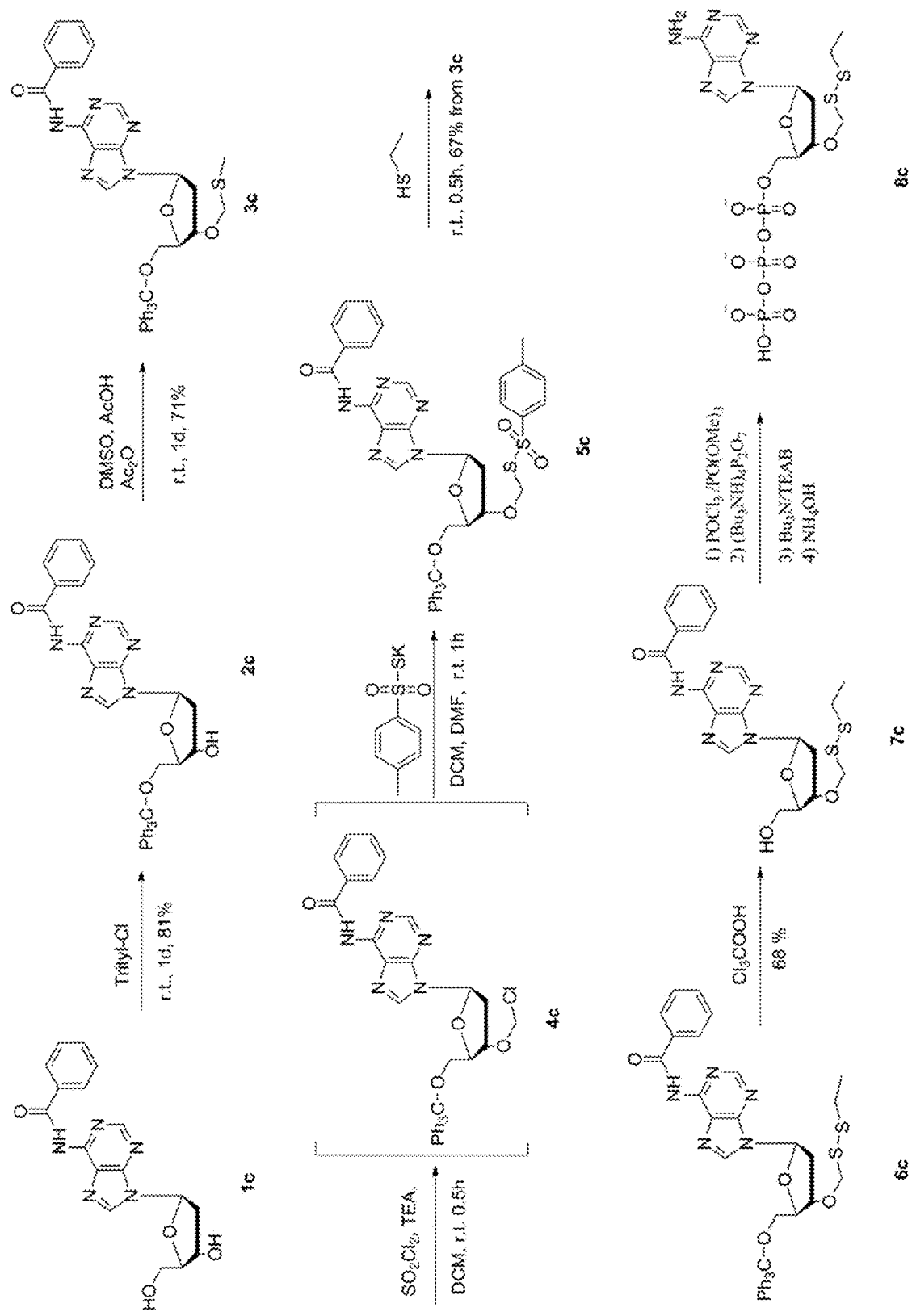

FIG. 48. Scheme for synthesis of 3'-O-ethyldithiomethyl-dATP (8c).

Figure 49:
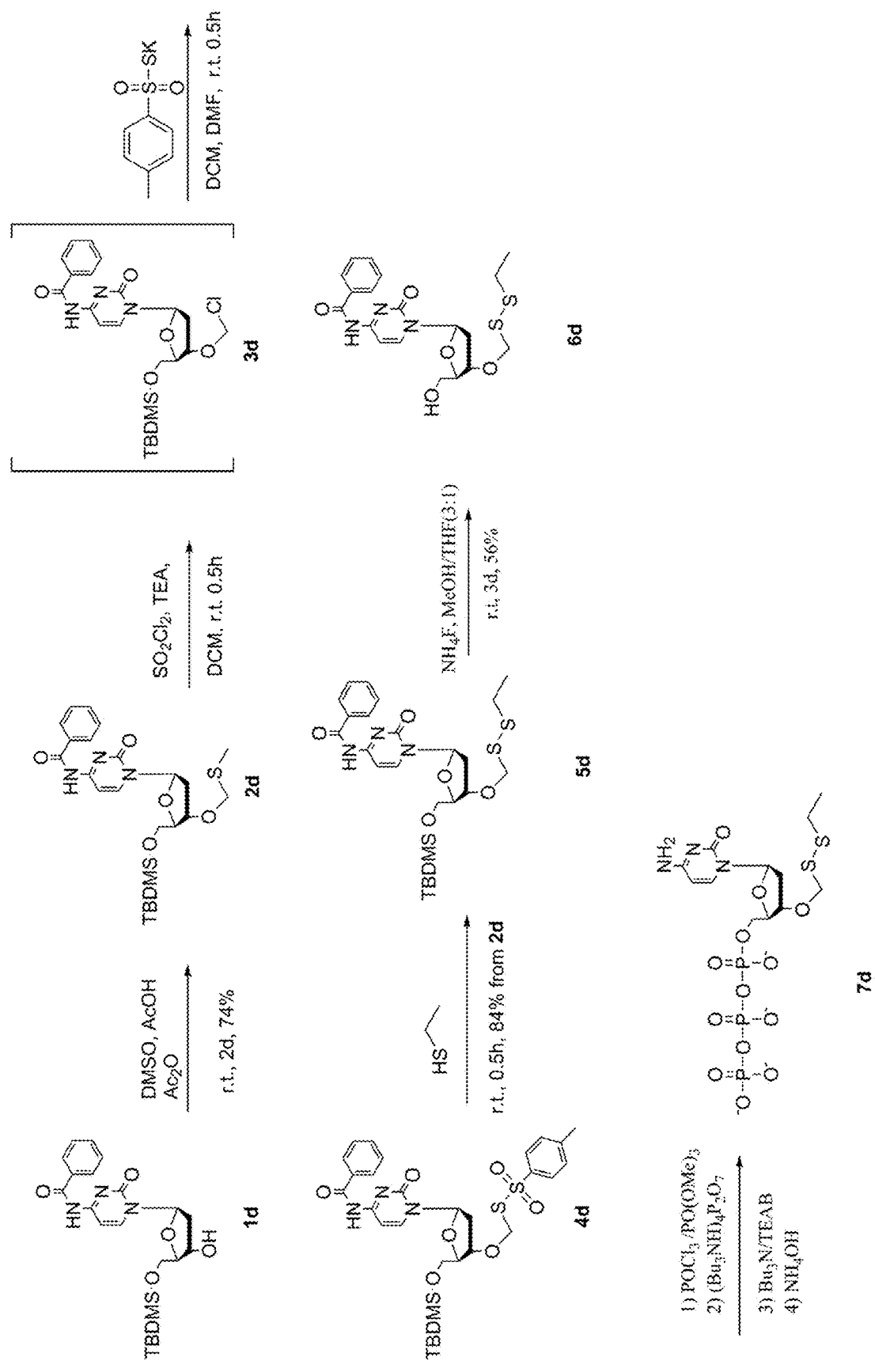

FIG. 49. Scheme for synthesis of 3'-O-ethyldithiomethyl-dCTP (3'-O-DTM-dCTP 7d).

Figure 50:
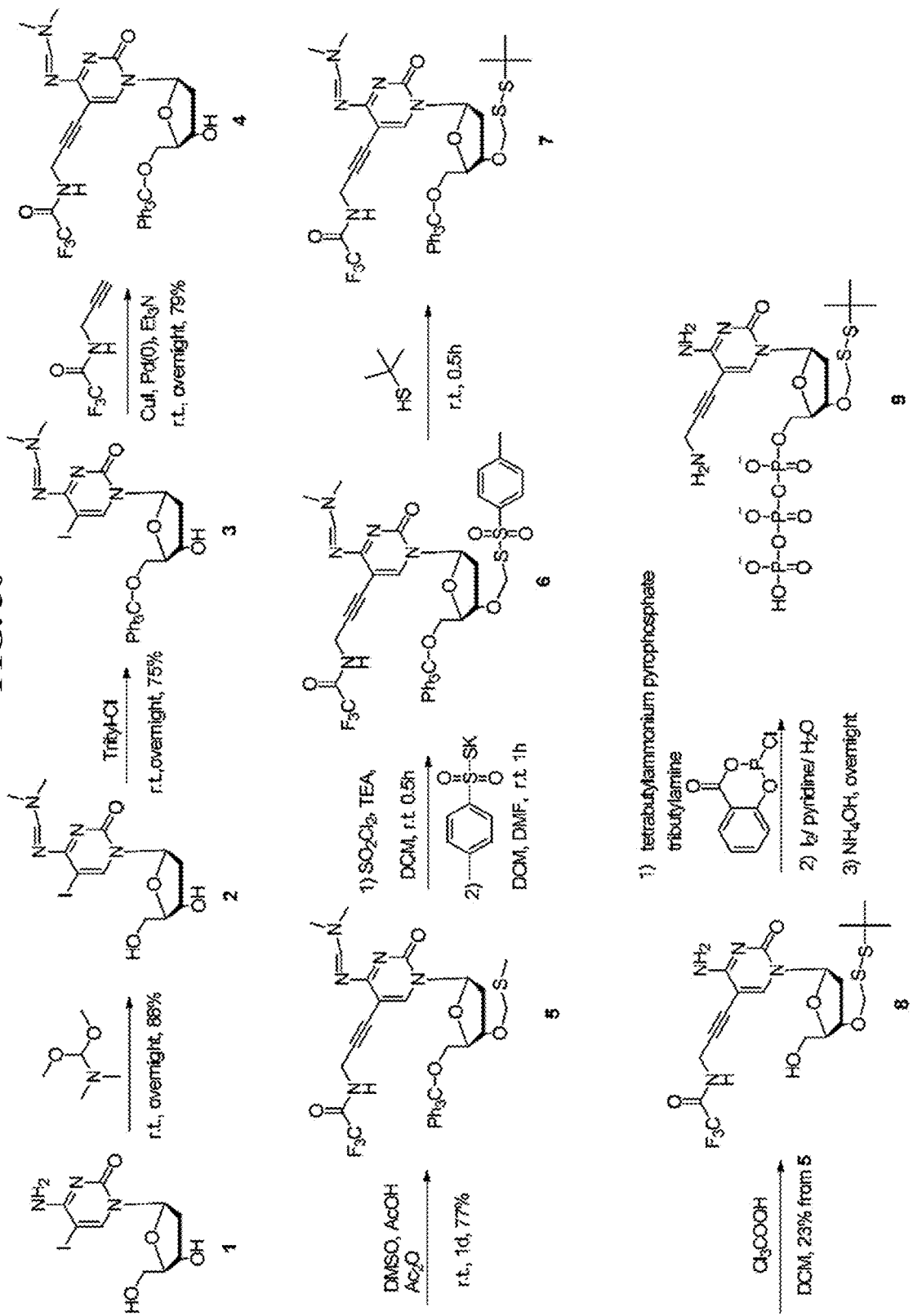

FIG. 50. Scheme for synthesis of 5-(3-aminopropynyl)-3'-O-t-butyldithiomethyl-dCTP (5-PA-3'-O-DTM-dCTP).

DETAILED DESCRIPTION

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl and an unsaturated alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene (e.g., alkylene, alkenylene, or alkynylene) group, generally having eight or fewer carbon atoms. The term "alkenylene," by itself or as part of another substituent, means, unless otherwise stated, a divalent radical derived from an alkene. The term "alkynylene" by itself or as part of another substituent, means, unless otherwise stated, a divalent radical derived from an alkyne.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl" by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkenylene groups, heteroatoms can also occupy either or both of the chain termini (e.g., alkyleneoxy, alkylenedioxy, alkyleneamino, alkylenediamino, and the like). Still further, for alkelyene (e.g., alkylene, alkenylene, or alkynylene) and heteroalkelyene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl; substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkelyene and individual rings within a spirocyclic ring group may be any of the immediately previous list, including having all rings of one type (e.g. all rings being substituted heterocycloalkelyene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "~" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkelyene (e.g., alkylene, alkenylene, or alkynylene) moiety (also referred to herein as an alkelyene). In embodiments, the alkylarylene group has the formula:

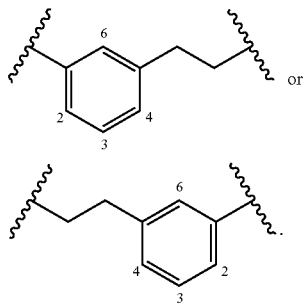

or

An alkylarylene moiety may be substituted (e.g., with a substituent group) on the alkelyene (e.g., alkylene, alkenylene, or alkynylene) moiety or the arylene linker (e.g. at carbons 2, 3, 4, or 6) with halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2CH_3$—$SO_3H$, —$OSO_3H$, —$SO_2NH_2$, —$NHNH_2$, —$ONH_2$, —NHC(O) $NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR, -halogen, —SiR'R"R'", —OC(O)R, —C(O)R, —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"'NR'"R", —CN, —NO$_2$, —NR'SO$_2$R", —NRC(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents; one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R, —COX, —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)K, —S(O)$_2$R', —S(O)$_2$NR'R", —NRSO$_2$R', —NR'NR"R'", —ONR'R", —NR'C(O)NR"NR'"R", —CN, —NO$_2$, —R', —$N_3$, —CH(Ph)$_2$, fluoro($C_1$-$C_4$)alkoxy, and fluoro($C_1$-$C_4$)alkyl, —NR'SO$_2$R", —NRC(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl; substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R"')$_d$—, where s and d are independently integers of from 0 to 3, and X' is —O—, —NR'—, —S—, —S(O)—, —S(O)$_2$—, or —S(O)$_2$NR'—. The substituents R, R', R", and R"' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include boron (B), oxygen (O), nitrogen (N), sulfur (S), phosphorus (P), and silicon (Si).

A "substituent" or "substituent group," as used herein, means a group selected from the following moieties:

(A) oxo, halogen, —CF$_3$, —CHF$_2$, —CH$_2$F, —C(halogen)$_3$, —CH(halogen)$_2$, —CH$_2$(halogen), —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O) OH, —NHOH, —OCF$_3$, —OCHF$_2$, —OCH$_2$F, —OCF$_3$, —OCHF$_2$, —OCH$_2$F, —OC(halogen)$_3$, —OCH(halogen)$_2$, —OCH$_2$(halogen), unsubstituted alkyl unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:
(i) oxo, halogen, —CF$_3$, —CHF$_2$, —CH$_2$F, —C(halogen)$_3$, —CH(halogen)$_2$, —CH$_2$(halogen), —CN. —OH, —NH$_2$. —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, —OCH$_2$F, —OCF$_3$, —OCHF$_2$, —OCH$_2$F, —OC(halogen)$_3$, —OCH(halogen)$_2$, —OCH$_2$(halogen), unsubstituted alkyl, unsubstituted heteroalkyl, unsubstituted cycloalkyl, un substituted heterocycloalkyl, un substituted aryl, un substituted heteroaryl, and
(ii) alkyl, heteroalkyl, cycloalkyl, heterocycloalkyl, aryl, heteroaryl, substituted with at least one substituent selected from:
(a) oxo, halogen, —CF$_3$, —CHF$_2$. —CH$_2$F, —C(halogen)$_3$, —CH(halogen)$_2$, —CH$_2$(halogen), —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCHF$_2$, —OCH$_2$F, —OCF$_3$, —OCHF$_2$, —OCH$_2$F, —OC(halogen)$_3$, —OCH(halogen)$_2$, —OCH$_2$(halogen), unsubstituted alkyl, unsubstituted heteroalkyl, unsubstituted cycloalkyl, unsubstituted heterocycloalkyl, unsubstituted aryl, unsubstituted heteroaryl, and
(b) alkyl, heteroalkyl, cycloalkyl, heterocycloalkyl, aryl, heteroaryl, substituted with at least one substituent selected from: oxo, halogen, —CF$_3$—CHF$_2$, —CH$_2$F, —C(halogen)$_3$, —CH(halogen)$_2$, —CH$_2$(halogen), —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, NHC(O)OH, —NHOH, —OCF$_3$, —OCHF$_2$, —OCH$_2$F, —OCF$_3$, —OCHF$_2$, —OCH$_2$F, —OC(halogen)$_3$, —OCH(halogen)$_2$, —OCH$_2$(halogen), unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkelyene (e.g., alkylene, alkenylene, or alkynylene) is a substituted or unsubstituted $C_1$-$C_{20}$ alkylene, each substituted or unsubstituted heteroalkelyene is a substituted or unsubstituted 2 to 20 membered heteroalkylene, each substituted or unsubstituted cycloalkelyene is a substituted or unsubstituted $C_3$-$C_8$ cycloalkylene, each substituted or unsubstituted heterocycloalkelyene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkelyene (e.g., alkylene, alkenylene, or alkynylene) is a substituted or unsubstituted $C_1$-$C_8$ alkylene, each substituted or unsubstituted heteroalkelyene is a substituted or unsubstituted 2 to 8 membered heteroalkylene, each substituted or unsubstituted cycloalkelyene is a substituted or unsubstituted $C_3$-$C_7$ cycloalkylene, each substituted or unsubstituted heterocycloalkelyene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

Certain compounds of the present invention possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C) All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{70}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple RP substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "detectable agent" or "detectable compound" or "detectable label" or "detectable moiety" is a composition detectable by spectroscopic, photochemical, biochemical, immunochemical, chemical, magnetic resonance imaging, or other physical means. For example, detectable agents include $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ca, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorophore (e.g. fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monocrystalline iron oxide nanoparticles, monocrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable. e.g., by incorporating a radiolabel into a peptide or antibody specifically reactive with a target peptide.

Radioactive substances (e.g., radioisotopes) that may be used as detectable, imaging and/or labeling agents in accordance with the embodiments described herein include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ca, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, and $^{225}$Ac. Paramagnetic ions that may be used as additional imaging agents in accordance with the embodiments of the disclosure include, but are not limited to, ions of transition and lanthanide metals (e.g. metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Examples of detectable agents include imaging agents, including fluorescent and luminescent substances, including, but not limited to, a variety of organic or inorganic small molecules commonly referred to as "dyes," "labels," or "indicators." Examples include fluorescein, rhodamine, acridine dyes, Alexa dyes, and cyanine dyes. In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescein isothiocyanate moiety, tetramethyl-rhodamine-5-(and 6)-isothiocyanate moiety, Cy2 moiety, Cy3 moiety, Cy5 moiety, Cy7 moiety, 4',6-diamidino-2-phenylindole moiety, Hoechst 33258 moiety, Hoechst 33342 moiety, Hoechst 34580 moiety, propidium-iodide moiety, or acridine orange moiety. In embodiments, the detectable moiety is a Indo-1, Ca saturated moiety, Indo-1 Ca2+ moiety, Cascade Blue BSA pH 7.0 moiety, Cascade Blue moiety, LysoTracker Blue moiety, Alexa 405 moiety, LysoSensor Blue pH 5.0 moiety, LysoSensor Blue moiety, DyLight 405 moiety, DyLight 350 moiety, BFP (Blue Fluorescent Protein) moiety, Alexa 350 moiety, 7-Amino-4-methylcoumarin pH 7.0 moiety, Amino Coumarin moiety, AMCA conjugate moiety, Coumarin moiety, 7-Hydroxy-4-methylcoumarin moiety, 7-Hydroxy-4-methylcoumarin pH 9.0 moiety, 6,8-Difluoro-7-hydroxy-4-methylcoumarin pH 9.0 moiety, Hoechst 33342 moiety, Pacific Blue moiety, Hoechst 33258 moiety, Hoechst 33258-DNA moiety, Pacific Blue antibody conjugate pH 8.0 moiety, PO-PRO-1 moiety, PO-PRO-1-DNA moiety, POPO-1 moiety, POPO-1-DNA moiety, DAPI-DNA moiety, DAPI moiety, Marina Blue moiety, SYTOX Blue-DNA moiety, CFP (Cyan Fluorescent Protein) moiety, eCFP (Enhanced Cyan Fluorescent Protein) moiety, 1-Anilinonaphthalene-8-sulfonic acid (1,8-ANS) moiety, Indo-1, Ca free moiety, 1,8-ANS (1-Anilinonaphthalene-8-sulfonic acid) moiety, BO-PRO-1-DNA moiety, BOPRO-1 moiety, BOBO-1-DNA moiety, SYTO 45-DNA moiety, evoglow-Pp1 moiety, evoglow-Bs1 moiety, evoglow-Bs2 moiety, Auramine O moiety, DiO moiety, LysoSensor Green pH 5.0 moiety, Cy 2 moiety, LysoSensor Green moiety, Fura-2, high Ca moiety, Fura-2 Ca2+sup> moiety, SYTO 13-DNA moiety, YO-PRO-1-DNA moiety, YOYO-1-DNA moiety, eGFP (Enhanced Green Fluorescent Protein) moiety, LysoTracker Green moiety, GFP (S65T) moiety, BODIPY FL. MeOH moiety, Sapphire moiety, BODIPY FL conjugate moiety, MitoTracker Green moiety, MitoTracker Green FM, MeOH moiety, Fluorescein 0.1 M NaOH moiety, Calcein pH 9.0 moiety, Fluorescein pH 9.0 moiety, Calcein moiety, Fura-2, no Ca moiety, Fluo-4 moiety, FDA moiety, DTAF moiety, Fluorescein moiety, CFDA moiety, FITC moiety, Alexa Fluor 488 hydrazide-water moiety, DyLight 488 moiety, 5-FAM pH 9.0 moiety, Alexa 488 moiety, Rhodamine 110 moiety, Rhodamine 110 pH 7.0 moiety, Acridine Orange moiety, BCECF pH 5.5 moiety, PicoGreendsDNA quantitation reagent moiety, SYBR Green I moiety, Rhodaminen Green pH 7.0 moiety, CyQUANT GR-DNA moiety, NeuroTrace 500/525, green fluorescent Nissl stain-RNA moiety, DansylCadaverine moiety, Fluoro-Emerald moiety, Nissl moiety, Fluorescein dextran pH 8.0 moiety, Rhodamine Green moiety, 5-(and -6)-Carboxy-2',7'-dichlorofluorescein pH 9.0 moiety, DansylCadaverine, MeOH moiety, eYFP (Enhanced Yellow Fluorescent Protein) moiety, Oregon Green 488 moiety, Fluo-3 moiety, BCECF pH 9.0 moiety, SBFI-Na+ moiety, Fluo-3 Ca2+ moiety, Rhodamine 123 MeOH moiety, FlAsH moiety, Calcium Green-1 Ca2+ moiety, Magnesium Green moiety, DM-NERF pH 4.0 moiety, Calcium Green moiety, Citrine moiety, LysoSensor Yellow pH 9.0 moiety, TO-PRO-1-DNA moiety, Magnesium Green Mg2+ moiety, Sodium Green Na+ moiety, TOTO-1-DNA moiety, Oregon Green 514 moiety, Oregon Green 514 antibody conjugate pH 8.0 moiety, NBD-X moiety, DM-NERF pH 7.0 moiety, NBD-X, MeOH moiety. CI-NERF pH 6.0 moiety, Alexa 430 moiety, CI-NERF pH 2.5 moiety, Lucifer Yellow, CH moiety, LysoSensor Yellow pH 3.0 moiety, 6-TET, SE pH 9.0 moiety, Eosin antibody conjugate pH 8.0 moiety, Eosin moiety, 6-Carboxyrhodamine 6G pH 7.0 moiety, 6-Carboxyrhodamine 6G, hydrochloride moiety, Bodipy R6G SE moiety, BODIPY R6G MeOH moiety, 6 JOE moiety, Cascade Yellow moiety, mBanana moiety, Alexa 532 moiety, Erythrosin-5-isothiocyanate pH 9.0 moiety, 6-HEX, SE pH 9.0 moiety, mOrange moiety, mHoneydew moiety, Cy 3 moiety, Rhodamine B moiety, DiI moiety, 5-TAMRA-MeOH moiety, Alexa 555 moiety, DyLight 549 moiety, BODIPY TMR-X, SE moiety, BODIPY TMR-X MeOH moiety, PO-PRO-3-DNA moiety, PO-PRO-3 moiety, Rhodamine moiety, POPO-3 moiety, Alexa 546 moiety, Calcium Orange Ca2+ moiety, TRITC moiety, Calcium Orange moiety, Rhodaminephalloidin pH 7.0 moiety, MitoTracker Orange moiety, MitoTracker Orange MeOH moiety, Phycoerythrin moiety, Magnesium Orange moiety, R-Phycoerythrin pH 7.5 moiety, 5-TAMRA pH 7.0 moiety, 5-TAMRA moiety, Rhod-2 moiety, FM 1-43 moiety, Rhod-2 Ca2+ moiety, FM 1-43 lipid moiety, LOLO-1-DNA moiety, dTomato moiety, DsRed moiety, Dapoxyl (2-aminoethyl) sulfonamide moiety, Tetramethylrhodamine dextran pH 7.0 moiety, Fluor-Ruby moiety, Resorufin moiety, Resorufin pH 9.0 moiety, mTangerine moiety, LysoTracker Red moiety, Lissaminerhodamine moiety, Cy 3.5 moiety, Rhodamine Red-X antibody conjugate pH 8.0 moiety, Sulforhodamine 101 EtOH moiety, JC-1 pH 8.2 moiety, JC-1 moiety, mStrawberry moiety, MitoTracker Red moiety, MitoTracker Red, MeOH moiety, X-Rhod-1 Ca2+ moiety, Alexa 568 moiety, 5-ROX pH 7.0 moiety, 5-ROX (5-Carboxy-X-rhodamine, triethylammonium salt) moiety, BO-PRO-3-DNA moiety, BOPRO-3 moiety, BOBO-3-DNA moiety, Ethidium Bromide moiety, ReAsH moiety, Calcium Crimson moiety, Calcium Crimson Ca2+ moiety, mRFP moiety, mCherry moiety, HcRed moiety, DyLight 594 moiety, Ethidium homodimer-1-DNA moiety, Ethidiumhomodimer moiety, Propidium Iodide moiety, SYPRO Ruby moiety, Propidium Iodide-DNA moiety, Alexa 594 moiety, BODIPY TR-X, SE moiety, BODIPY TR-X, MeOH moiety, BODIPY TR-X phallacidin pH 7.0 moiety, Alexa Fluor 610 R-phycoerythrin streptavidin pH 7.2 moiety, YO-PRO-3-DNA moiety, Di-8 ANEPPS moiety, Di-8-ANEPPS-lipid moiety, YOYO-3-DNA moiety, Nile Red-lipid moiety, Nile Red moiety, DyLight 633 moiety, mPlum moiety, TO-PRO-3-DNA moiety, DDAO pH 9.0 moiety, Fura Red high Ca moiety, Allophycocyanin pH 7.5 moiety, APC (allophycocyanin) moiety, Nile Blue, EtOH moiety, TOTO-3-DNA moiety, Cy 5 moiety, BODIPY 650/665-X, MeOH moiety, Alexa Fluor 647 R-phycoerythrin streptavidin pH 7.2 moiety, DyLight 649 moiety, Alexa 647 moiety, Fura Red Ca2+ moiety, Atto 647 moiety, Fura Red, low Ca moiety, Carboxynaphthofluorescein pH 10.0 moiety, Alexa 660 moiety, Cy 5.5 moiety, Alexa 680 moiety, DyLight 680 moiety, Alexa 700 moiety, FM 4-64, 2% CHAPS moiety, or FM 4-64 moiety.

In embodiments, the dectable moiety is a moiety of 1,1-Diethyl-4,4-carbocyanine iodide, 1,2-Diphenylacetylene. 1,4-Diphenylbutadiene, 1,4-Diphenylbutadiyne, 1,6-Diphenylhexatriene, 1,6-Diphenylhexatriene, 1-anilinonaphthalene-8-sulfonic acid, 2,7-Dichlorofluorescein, 2,5-DIPHENYLOXAZOLE, 2-Di-1-ASP, 2-dodecylresorufin, 2-Methylbenzoxazole, 3,3-Diethylthiadicarbocyanine iodide, 4-Dimethylamino-4-Nitrostilbene, 5(6)-Carboxyfluorescein, 5(6)-Carboxynaphtofluorescein, 5(6)-Carboxytetramethylrhodamine B, 5-(and -6)-carboxy-2',7'-dichlorofluorescein, 5-(and -6)-carboxy-2,7-dichlorofluorescein, 5-(N-hexadecanoyl)aminoeosin, 5-(N-hexadecanoyl)aminoeosin, 5-chloromethylfluorescein, 5-FAM, 5-ROX, 5-TAMRA, 5-TAMRA, 6,8-difluoro-7-hydroxy-4-methylcoumarin, 6,8-difluoro-7-hydroxy-4-methylcoumarin, 6-carboxyrhodamine 6G, 6-HEX, 6-JOE, 6-JOE, 6-TET, 7-aminoactinomycin D, 7-Benzylamino-4-Nitrobenz-2-Oxa-1,3-Diazole, 7-Methoxycoumarin-4-Acetic Acid, 8-Benzyloxy-5,7-diphenylquinoline, 8-Benzyloxy-5,7-diphenylquinoline, 9,10-Bis(Phenylethynyl) Anthracene, 9,10-Diphenylanthracene, 9-METHYLCARBAZOLE, (CS)2Ir(µ-Cl)2Ir(CS)2, AAA, Acridine Orange, Acridine Orange, Acridine Yellow, Acridine Yellow, Adams Apple Red 680, Adirondack Green 520, Alexa Fluor 350, Alexa Fluor 405, Alexa Fluor 430, Alexa Fluor 430, Alexa Fluor 480, Alexa Fluor 488, Alexa Fluor 488, Alexa Fluor 488 hydrazide, Alexa Fluor 500, Alexa Fluor 514, Alexa Fluor 532, Alexa Fluor 546, Alexa Fluor 546, Alexa Fluor 555, Alexa Fluor 555, Alexa Fluor 568, Alexa Fluor 594, Alexa Fluor 594, Alexa Fluor 594, Alexa Fluor 610, Alexa Fluor 610-R-PE, Alexa Fluor 633, Alexa Fluor 635, Alexa Fluor 647, Alexa Fluor 647, Alexa Fluor 647-R-PE, Alexa Fluor 660, Alexa Fluor 680, Alexa Fluor 680-APC, Alexa Fluor 680-R-PE, Alexa Fluor 700, Alexa Fluor 750, Alexa Fluor 790, Allophycocyanin, AmCyan1, Aminomethylcoumarin, Amplex Gold (product), Amplex Red Reagent, Amplex UltraRed, Anthracene, APC, APC-Seta-750, AsRed2, ATTO 390, ATTO 425, ATTO 430LS, ATTO 465, ATTO 488, ATTO 490LS, ATTO 495, ATTO 514, ATTO 520, ATTO 532, ATTO 550, ATTO 565, ATTO 590, ATTO 594, ATTO 610, ATTO 620, ATTO 633, ATTO 635, ATTO 647, ATTO 647N, ATTO 655, ATTO 665, ATTO 680, ATTO 700, ATTO 725, ATTO 740, ATTO Oxa12, ATTO Rho3B, ATTO Rho6G, ATTO Rho11, ATTO Rho 12, ATTO Rho 13, ATTO Rho 14, ATTO Rho 101, ATTO Thio12, Auramine O, Azami Green, Azami Green monomeric, B-phycoerythrin, BCECF, BCECF, Bex1, Biphenyl, Birch Yellow 580, Blue-green algae, BO-PRO-1, BO-PRO-3, BOBO-1, BOBO-3, BODIPY 630 650-X, BODIPY 650/665-X, BODIPY FL, BODIPY FL, BODIPY R6G, BODIPY TMR-X, BODIPY TR-X, BODIPY TR-X Ph 7.0, BODIPY TR-X phallacidin, BODIPY-DiMe, BODIPY-Phenyl, BODIPY-TMSCC, C3-Indocyanine, C3-Indocyanine, C3-Oxacyanine, C3-Thiacyanine Dye (EtOH), C3-Thiacyanine Dye (PrOH), C5-Indocyanine, C5-Oxacyanine, C5-Thiacyanine, C7-Indocyanine, C7-Oxacyanine, C545T, C-Phycocyanin, Calcein, Calcein red-orange, Calcium Crimson, Calcium Green-1, Calcium Orange, Calcofluor white 2MR, Carboxy SNARF-1 pH 6.0, Carboxy SNARF-1 pH 9.0, Carboxynaphthofluorescein, Cascade Blue, Cascade Yellow, Catskill Green 540, CBQCA, CellMask Orange, CellTrace BODIPY TR methyl ester, CellTrace calcein violet, CellTrace™ Far Red, CellTracker Blue, CellTracker Red CMTPX, CellTracker Violet BMQC, CF405M, CF405S, CF488A, CF543, CF555, CFP, CFSE, CF™ 350, CF™ 485, Chlorophyll A, Chlorophyll B, Chromeo 488, Chromeo 494, Chromeo 505, Chromeo 546, Chromeo 642, Citrine, Citrine, ClOH butoxy aza-BODIPY, ClOH C12 aza-BODIPY, CM-H2DCFDA, Coumarin 1, Coumarin 6, Coumarin 6, Coumarin 30, Coumarin 314, Coumarin 334, Coumarin 343, Coumarin 545T, Cresyl Violet Perchlorate, Crypt® Light $CF_1$, CryptoLight $CF_2$, CryptoLight $CF_3$, CryptoLight $CF_4$, CryptoLight CF5, CryptoLight $CF_6$, Crystal Violet, Cumarin153, Cy2, Cy3, Cy3, Cy3.5, Cy3B, Cy3B, Cy3Cy5 ET, Cy5, Cy5, Cy5.5, Cy7, Cyanine3 NHS ester, Cyanine5 carboxylic acid, Cyanine5 NHS ester, Cyclotella meneghiniana Kützing, CypHer5, CypHer5 pH 9.15, CyQUANT GR, CyTrak Orange, Dabcyl SE, DAF-FM, DAMC (Weiss), dansyl cadaverine, Dansyl Glycine (Dioxane), DAPI, DAPI, DAPI, DAPI, DAPI (DMSO), DAPI (H2O), Dapoxyl (2-aminoethyl)sulfonamide, DCI, DCM, DCM, DCM (acetonitrile), DCM (MeOH), DDAO, Deep Purple, di-8-ANEPPS, DiA, Dichlorotris(1,10-phenanthroline) ruthenium(II), DiClOH C12 aza-BODIPY, DiClOHbutoxy aza-BODIPY, DiD, DiI, DiIC18(3), DiO, DiR, Diversa Cyan-FP, Diversa Green-FP, DM-NERF pH 4.0, DOCI, Doxorubicin, DPP pH-Probe 590-7.5, DPP pH-Probe 590-9.0, DPP pH-Probe 590-11.0, DPP pH-Probe 590-11.0, Dragon Green, DRAQS, DsRed, DsRed, DsRed, DsRed-Express, DsRed-Express2, DsRed-Express T1, dTomato, DY-350XL, DY-480, DY-480XL MegaStokes, DY-485, DY-485XL MegaStokes, DY-490, DY-490XL MegaStokes, DY-500, DY-500XL MegaStokes, DY-520, DY-520XL MegaStokes, DY-547, DY-549P1, DY-549P1, DY-554, DY-555, DY-557, DY-557, DY-590, DY-590, DY-615, DY-630, DY-631, DY-633, DY-635, DY-636, DY-647, DY-649P1, DY-649P1, DY-650, DY-651, DY-656, DY-673, DY-675, DY-676, DY-680, DY-681, DY-700, DY-701, DY-730, DY-731, DY-750, DY-751, DY-776, DY-782, Dye-28, Dye-33, Dye-45, Dye-304, Dye-1041, DyLight 488, DyLight 549, DyLight 594, DyLight 633, DyLight 649, DyLight 680, E2-Crimson, E2-Orange, E2-Red/Green, EBFP, ECF, ECFP, ECL Plus, eGFP, ELF 97, Emerald, Envy Green, Eosin, Eosin Y, epicocconone, EqFP611, Erythrosin-5-isothiocyanate, Ethidium bromide, ethidium homodimer-1, Ethyl Eosin, Ethyl Eosin, Ethyl Nile Blue A, Ethyl-p-Dimethylaminobenzoate, Ethyl-p-Dimethylaminobenzoate, Eu203 nanoparticles, Eu (Soini), Eu(tta) 3DEADIT, EvaGreen, EVOblue-30, EYFP, FAD, FITC, FITC, FlAsH (Adams), Flash Red EX, FlAsH-CCPGCC, FlAsH-CCXXCC, Fluo-3, Fluo-4, Fluo-5F, Fluorescein, Fluorescein 0.1 NaOH, Fluorescein-Dibase, fluoro-emerald, Fluorol 5G, FluoSpheres blue, FluoSpheres crimson, FluoSpheres dark red, FluoSpheres orange, FluoSpheres red, FluoSpheres yellow-green, FM4-64 in CTC, FM4-64 in SDS, FM 1-43, FM 4-64, Fort Orange 600, Fura Red, Fura Red Ca free, fura-2, Fura-2 Ca free, Gadodiamide, Gd-Dtpa-Bma, Gadodiamide, Gd-Dtpa-Bma, GelGreen™, GelRed™, H9-40, HcRed1, Hemo Red 720, HiLyte Fluor 488, HiLyte Fluor 555, HiLyte Fluor 647, HiLyte Fluor 680, HiLyte Fluor 750, HiLyte Plus 555, HiLyte Plus 647, HiLyte Plus 750, HmGFP, Hoechst 33258, Hoechst 33342, Hoechst-33258, Hoechst-33258, Hops Yellow 560, HPTS, HPTS, HPTS, HPTS, HPTS, indo-1, Indo-1 Ca free, Ir(Cn)2(acac), Ir(Cs)2(acac), IR-775 chloride, IR-806, Ir-OEP-CO-Cl, IRDye® 650 Alkyne, IRDye® 650 Azide, IRDye® 650 Carboxylate, IRDye® 650 DBCO, IRDye® 650 Maleimide, IRDye® 650 NHS Ester, IRDye® 680LT Carboxylate, IRDye® 680LT Maleimide, IRDye® 680LT NHS Ester, IRDye® 680RD Alkyne, IRDye® 680RD Azide, IRDye® 680RD Carboxylate, IRDye® 680RD DBCO, IRDye® 680RD Maleimide, IRDye® 680RD NHS Ester, IRDye® 700 phosphoramidite, IRDye® 700DX, IRDye® 700DX, IRDye® 700DX Carboxylate, IRDye® 700DX NHS Ester, IRDye® 750 Carboxylate, IRDye® 750 Maleimide, IRDye® 750 NHS Ester, IRDye® 800 phosphoramidite, IRDye® 800CW, IRDye® 800CW Alkyne, IRDye® 800CW Azide, IRDye® 800CW Carboxylate, IRDye® 800CW DBCO, IRDye® 800CW Maleimide, IRDye® 800CW NHS Ester, IRDye® 800RS, 800RS Carboxylate, IRDye® 800RS NHS Ester, IRDye® QC-1 Carboxylate, IRDye® QC-1 NHS Ester, Isochrysis galbana-Parke, JC-1, JC-1, JOJO-1, Jonamac Red Evitag T2, Kaede Green, Kaede Red, kusabira orange, Lake Placid 490, LDS 751, Lissamine Rhodamine (Weiss), LOLO-1, lucifer yellow CH, Lucifer Yellow CH, lucifer yellow CH, Lucifer Yellow CH Dilitium salt, Lumio Green, Lumio Red, Lumogen F Orange, Lumogen Red F300, Lumogen Red F300, LysoSensor Blue DND-192, LysoSensor Green DND-153, LysoSensor Green DND-153, LysoSensor Yellow/Blue DND-160 pH 3, LysoSensor YellowBlue DND-160, LysoTracker Blue DND-22, LysoTracker Blue DND-22, LysoTracker Green DND-26, LysoTracker Red DND-99, LysoTracker Yellow HCK-123, Macoun Red Evitag T2, Macrolex Fluorescence Red G, Macrolex Fluorescence Yellow 10GN, Macrolex Fluorescence Yellow 10GN, Magnesium Green, Magnesium Octaethylporphyrin Magnesium Orange, Magnesium Phthalocyanine, Magnesium Phthalocyanine, Magnesium Tetramesitylporphyrin, Magnesium Tetraphenylporphyrin, malachite green isothiocyanate, Maple Red-Orange 620, Marina Blue, mBanana, mBBr, mCherry Merocyanine 540, Methyl green, Methyl green, Methyl green, Methylene Blue, Methylene Blue, mHoneyDew, MitoTracker Deep Red 633, MitoTracker Green FM, MitoTracker Orange CMTMRos, MitoTracker Red CMXRos, monobromobimane, Monochlorobimane, Monoraphidium, mOrange, mOrange2, mPlum, mRaspberry, mRFP, mRFP1, mRFP1.2 (Wang), mStrawberry (Shaner), mTangerine (Shaner), N,N-Bis(2,4, 6-trimethylphenyl)-3,4:9,10-perylenebis(dicarboximide), NADH, Naphthalene, Naphthalene, Naphthofluorescein, Naphthofluorescein, NBD-X, NeuroTrace 500525, Nilblau perchlorate, nile blue, Nile Blue, Nile Blue (EtOH), nile red, Nile Red, Nile Red, Nile red, Nileblue A, NIR1, NIR2, NIR3, NIR4, NIR820, Octaethylporphyrin, OH butoxy aza-BODIPY, OHC12 aza-BODIPY, Orange Fluorescent Protein, Oregon Green 488, Oregon Green 488 DHPE, Oregon Green 514, Oxazin1, Oxazin 750, Oxazine 1, Oxazine 170, P4-3, P-Quaterphenyl, P-Terphenyl, PA-GFP (post-activation), PA-GFP (pre-activation), Pacific Orange, Palladium (II) meso-tetraphenyl-tetrabenzoporphyrin, PdOEPK, PdTFPP, PerCP-Cy5.5, Perylene, Perylene, Perylene bisimide pH-Probe 550-5.0, Perylene bisimide pH-Probe 550-5.5, Perylene bisimide pH-Probe 550-6.5, Perylene Green pH-Probe 720-5.5, Perylene Green Tag pH-Probe 720-6.0, Perylene Orange pH-Probe 550-2.0, Perylene Orange Tag 550. Perylene Red pH-Probe 600-5.5, Perylenediimid, Perylne Green pH-Probe 740-5.5, Phenol, Phenylalanine, pHrodo, succinimidyl ester, Phthalocyanine, PicoGreen dsDNA quantitation reagent, Pinacyanol-Iodide, Piroxicam, Platinum(II) tetraphenyltetrabenzoporphyrin, Plum Purple, PO-PRO-1, PO-PRO-3, POPO-1, POPO-3, POPOP, Porphin, PPO, Proflavin, PromoFluor-350, PromoFluor-405

PromoFluor-415, PromoFluor-488, PromoFluor-488 Premium, PromoFluor-488LSS PromoFluor-500LSS, PromoFluor-505, PromoFluor-510LSS, PromoFluor-514LSS, PromoFluor-520LSS, PromoFluor-532, PromoFluor-546, PromoFluor-555, PromoFluor-590, PromoFluor-610, PromoFluor-633, PromoFluor-647, PromoFluor-670, PromoFluor-680, PromoFluor-700, PromoFluor-750, PromoFluor-770, PromoFluor-780, PromoFluor-840, propidium iodide, Protoporphyrin IX, PTIR475/UF, PTIR545/UF, PtOEP, PtOEPK, PtTFPP, Pyrene, QD525, QD565, QD585, QD605, QD655, QD705, QD800, QD903, QD PbS 950, QDot 525, QDot 545, QDot 565, Qdot 585, Qdot 605, Qdot 625, Qdot 655, Qdot 705, Qdot 800, QpyMe2, QSY 7, QSY 7, QSY 9, QSY 21, QSY 35, quinine, Quinine Sulfate, Quinine sulfate, R-phycoerythrin, R-phycoerythrin, ReAsH-CCPGCC, ReAsH-CCXXCC, Red Beads (Weiss), Redmond Red, Resorufin, resorufin, rhod-2, Rhodamin 700 perchlorate, rhodamine, Rhodamine 6G, Rhodamine 6G, Rhodamine 101, rhodamine 110, Rhodamine 123, rhodamine 123, Rhodamine B, Rhodamine B, Rhodamine Green, Rhodamine pH-Probe 585-7.0, Rhodamine pH-Probe 585-7.5, Rhodamine phalloidin, Rhodamine Red-X, Rhodamine Red-X, Rhodamine Tag pH-Probe 585-7.0, Rhodol Green, Riboflavin, Rose Bengal, Sapphire, SBFI, SBFI Zero Na, Scenedesmus sp., SensiLight PBXL-1, SensiLight PBXL-3, Seta 633-NHS, Seta-633-NHS, SeTau-380-NHS, SeTau-647-NHS, Snake-Eye Red 900, SNIR1, SNIR2, SNIR3, SNIR4, Sodium Green, Solophenyl flavine 7GFE 500, Spectrum Aqua, Spectrum Blue, Spectrum FRed, Spectrum Gold, Spectrum Green, Spectrum Orange, Spectrum Red, Squarylium dye III, Stains A11, Stilben derivate, Stilbene, Styryl8 perchlorate, Sulfo-Cyanine3 carboxylic acid, Sulfo-Cyanine3 carboxylic acid, Sulfo-Cyanine3 NHS ester, Sulfo-Cyanine5 carboxylic acid, Sulforhodamine 101, sulforhodamine 101, Sulforhodamine B, Sulforhodamine G, Suncoast Yellow, SuperGlo BFP, SuperGlo GFP, Surf Green EX, SYBR Gold nucleic acid gel stain, SYBR Green I, SYPRO Ruby, SYTO 9, SYTO 11, SYTO 13, SYTO 16, SYTO 17, SYTO 45, SYTO 59, SYTO 60, SYTO 61, SYTO 62, SYTO 82, SYTO RNASelect, SYTO RNASelect, SYTOX Blue, SYTOX Green, SYTOX Orange, SYTOX Red, T-Sapphire, Tb (Soini), tCO, tdTomato, Terrylen, Tcrrylcndiimid, testdye, Tetra-t-Butylazaporphine, Tetra-t-Butylnaphthalocyanine, Tetracen, Tetrakis(o-Aminophenyl)Porphyrin, Tetramesitylporphyrin, Tetramethylrhodamine, tetramethylrhodamine, Tetraphenylporphyrin, Tetraphenylporphyrin, Texas Red, Texas Red DHPE, Texas Red-X, ThiolTracker Violet, Thionin acetate, TMRE, TO-PRO-1, TO-PRO-3, Toluene, Topaz (Tsien1998), TOTO-1, TOTO-3, Tris(2,2-Bipyridyl)Ruthenium(II) chloride, Tris(4,4-diphenyl-2,2-bipyridine) ruthenium(II) chloride, Tris(4,7-diphenyl-1,10-phenanthroline) ruthenium(II) TMS, TRITC (Weiss), TRITC Dextran (Weiss), Tryptophan, Tyrosine, Vex1, Vybrant DyeCycle Green stain, Vybrant DyeCycle Orange stain, Vybrant DyeCycle Violet stain, WEGFP (post-activation), WellRED D2, WellRED D3, WellRED D4, WtGFP, WtGFP (Tsien1998), X-rhod-1, Yakima Yellow, YFP, YO-PRO-1, YO-PRO-3, YOYO-1, YoYo-1, YoYo-1 dsDNA, YoYo-1 ssDNA, YOYO-3, Zinc Octaethylporphyrin, Zinc Phthalocyanine, Zinc Tetramesitylporphyrin, Zinc Tetraphenylporphyrin, ZsGreen1, or ZsYellow1.

In embodiments, the detectable label is a fluorescent dye. In embodiments, the detectable label is a fluorescent dye capable of exchanging energy with another fluorescent dye (e.g., fluorescence resonance energy transfer (FRET) chromophores).

In embodiments, the detectable moiety is a moiety of a derivative of one of the detectable moieties described immediately above, wherein the derivative differs from one of the detectable moieties immediately above by a modification resulting from the conjugation of the detectable moiety to a compound described herein.

The term "cyanine" or "cyanine moiety" as described herein refers to a compound containing two nitrogen groups separated by a polymethine chain. In embodiments, the cyanine moiety has 3 methine structures (i.e. cyanine 3 or Cy3). In embodiments, the cyanine moiety has 5 methine structures (i.e. cyanine 5 or Cy5). In embodiments, the cyanine moiety has 7 methine structures (i.e. cyanine 7 or Cy7).

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromide s, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Hybridize" shall mean the annealing of one single-stranded nucleic acid (such as a primer) to another nucleic acid based on the well-understood principle of sequence complementarity. In an embodiment the other nucleic acid is a single-stranded nucleic acid. The propensity for hybridization between nucleic acids depends on the temperature and ionic strength of their miliu, the length of the nucleic acids and the degree of complementarity. The effect of these parameters on hybridization is described in, for example, Sambrook J, Fritsch E F, Maniatis T., Molecular cloning: a laboratory manual, Cold Spring Harbor Laboratory Press, New York (1989). As used herein, hybridization of a primer, or of a DNA extension product, respectively, is extendable by creation of a phosphodiester bond with an available nucleotide or nucleotide analogue capable of forming a phosphodiester bond, therewith.

"Primer" as used herein (a primer sequence) is a short, usually chemically synthesized oligonucleotide, of appropriate length, for example about 18-24 bases, sufficient to hybridize to a target nucleic acid (e.g. a single stranded nucleic acid) and permit the addition of a nucleotide residue thereto, or oligonucleotide or polynucleotide synthesis therefrom, under suitable conditions well-known in the art. In an embodiment the primer is a DNA primer, i.e. a primer consisting of, or largely consisting of, deoxyribonucleotide residues. The primers are designed to have a sequence that is the complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product. In another embodiment the primer is an RNA primer.

"Nucleoside," as used herein, refers to a glycosyl compound consisting of a nucleobase and a 5-membered ring sugar (either ribose or deoxyribose). Nucleosides may comprise bases such as A, C, G, T, U, or analogues thereof. Nucleotides may be modified at the base and/or and the sugar. In an embodiment, the nucleoside is a deoxyribonucleoside. In another embodiment, the nucleoside is a ribonucleoside.

"Nucleotide," as used herein, refers to a nucleoside-5'-polyphosphate compound, or a structural analog thereof, which can be incorporated by a nucleic acid polymerase to extend a growing nucleic acid chain (such as a primer). Nucleotides may comprise bases such as A, C, G, T, U, or analogues thereof, and may comprise 2, 3, 4, 5, 6, 7, 8, or more phosphates in the phosphate group. Nucleotides may be modified at one or more of the base, sugar, or phosphate group. A nucleotide may have a label or tag attached (a "labeled nucleotide" or "tagged nucleotide"). In an embodiment, the nucleotide is a deoxyribonucleotide. In another embodiment, the nucleotide is a ribonucleotide.

"Polymerase," as used herein, refers to any natural or non-naturally occurring enzyme or other catalyst that is capable of catalyzing a polymerization reaction, such as the polymerization of nucleotide monomers to form a nucleic acid polymer. Exemplary types of polymerases that may be used in the compositions and methods of the present disclosure include the nucleic acid polymerases such as DNA polymerase, DNA- or RNA-dependent RNA polymerase, and reverse transcriptase. In some cases, the DNA polymerase is 9° N polymerase or a variant thereof, *E. Coli* DNA polymerase I, Bacteriophage T4 DNA polymerase, Sequenase, Taq DNA polymerase, DNA polymerase from *Bacillus stearothermophilus*, Bst 2.0 DNA polymerase, 9° N polymerase, 9° N polymerase (exo-)A485L/Y409V, Phi29 DNA Polymerase (φ29 DNA Polymerase), T7 DNA polymerase, DNA polymerase II, DNA polymerase III holoenzyme, DNA polymerase IV, DNA polymerase V, VentR DNA polymerase, Therminator™ II DNA Polymerase, Therminator™ III DNA Polymerase, or or Therminator™ IX DNA Polymerase.

"Solid substrate" shall mean any suitable medium present in the solid phase to which a nucleic acid or an agent may be affixed. Non-limiting examples include chips, beads and columns.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "activation", "activate", "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The terms "streptavidin" and "" refer to a tetrameric protein (including homologs, isoforms, and functional fragments thereof) capable of binding biotin. The term includes any recombinant or naturally-occurring form of streptavidin variants thereof that maintain streptavidin activity (e.g. within at least 30%, 40%, 50%, 60%, 70%, 80%, 90%, 95%, or 100% activity compared to wildtype streptavidin).

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *Spodoptera*) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "aberrant" as used herein refers to different from normal. When used to describe enzymatic activity or protein function, aberrant refers to activity or function that is greater or less than a normal control or the average of normal non-diseased control samples.

"Nucleic acid" or "oligonucleotide" or "polynucleotide" or grammatical equivalents used herein means at least two nucleotides covalently linked together. The term "nucleic acid" includes single-, double-, or multiple-stranded DNA, RNA and analogs (derivatives) thereof. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. In certain embodiments the nucleic acids herein contain phosphodiester bonds. In other embodiments, nucleic acid analogs are included that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. A residue of a nucleic acid, as referred to herein, is a monomer of the nucleic acid (e.g., a nucleotide).

A particular nucleic acid sequence also encompasses "splice variants." Similarly, a particular protein encoded by a nucleic acid encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095-35101 (1998).

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated.

Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 10 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., *Current Protocols in Molecular Biology* (Ausubel et al., eds. 1995 supplement)).

As used herein, the term "bioconjugate" or "bioconjugate linker" refers to the resulting association between atoms or molecules of bioconjugate reactive groups. The association can be direct or indirect. For example, a conjugate between a first bioconjugate reactive group (e.g. —$NH_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments a bioconjugate is a click chemistry reactant moiety when the association between atoms or molecules of bioconjugate reactive groups is direct (e.g., covalent bond, linker).

In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g. a sulfhydryl). In embodiments, the first bioconjugate reactive group (e.g., haloacetyl moiety) is covalently attached to the second bioconjugate reactive group (e.g. a sulfhydryl). In embodiments, the first bioconjugate reactive group (e.g., pyridyl moiety) is covalently attached to the second bioconjugate reactive group (e.g. a sulfhydryl). In embodiments, the first bioconjugate reactive group (e.g., —N-hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g. a sulfhydryl). In embodiments, the first bioconjugate reactive group (e.g., -sulfo-N-hydroxysuccinimide moiety) is covalently attached to the second bioconjugate reactive group (e.g. an amine).

Useful bioconjugate reactive groups used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkenyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido or maleimide groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold, or react with maleimides;

(h) amine or sulfhydryl groups (e.g., present in cysteine), which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;

(l) metal silicon oxide bonding; and (m) metal bonding to reactive phosphorus groups (e.g. phosphines) to form, for example, phosphate diester bonds.

(n) azides coupled to alkynes using copper catalyzed cycloaddition click chemistry.

(o) biotin conjugate can react with avidin or strepavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

The terms "monophosphate" is used in accordance with its ordinary meaning in the arts and refers to a moiety having the formula:

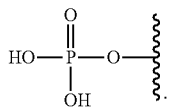

The term "polyphosphate" refers to at least two phosphate groups, having the formula:

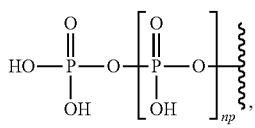

wherein np is an integer of 1 or greater. In embodiments, np is an integer from 0 to 5. In embodiments, np is an integer from 0 to 2. In embodiments, np is 2.

The term "base" as used herein refers to a divalent purine or pyrimidine compound or a derivative thereof, that may be a constituent of nucleic acid (i.e. DNA or RNA, or a derivative thereof). In embodiments, the base is a derivative of a naturally occurring DNA or RNA base (e.g., a base analogue). In embodiments the base is a hybridizing base. In embodiments the base hybridizes to a complementary base. In embodiments, the base is capable of forming at least one hydrogen bond with a complementary base (e.g., adenine hydrogen bonds with thymine, adenine hydrogen bonds with uracil, guanine pairs with cytosine). Non-limiting examples of a base includes cytosine or a derivative thereof (e.g., cytosine analogue), guanine or a derivative thereof (e.g., guanine analogue), adenine or a derivative thereof (e.g., adenine analogue), thymine or a derivative thereof (e.g., thymine analogue), uracil or a derivative thereof (e.g., uracil analogue), hypoxanthine or a derivative thereof (e.g., hypoxanthine analogue), xanthine or a derivative thereof (e.g., xanthine analogue), 7-methylguanine or a derivative thereof (e.g., 7-methylguanine analogue), deaza-adenine or a derivative thereof (e.g., deaza-adenine analogue), deaza-guanine or a derivative thereof (e.g., deaza-guanine), deaza-hypoxanthine or a derivative thereof, 5,6-dihydrouracil or a derivative thereof (e.g., 5,6-dihydrouracil analogue), 5-methylcytosine or a derivative thereof (e.g., 5-methylcytosine analogue), or 5-hydroxymethylcytosine or a derivative thereof (e.g., 5-hydroxymethylcytosine analogue) moieties. In embodiments, the base is adenine, guanine, hypoxanthine, xanthine, theobromine, caffeine, uric acid, or isoguanine. In embodiments, the base is

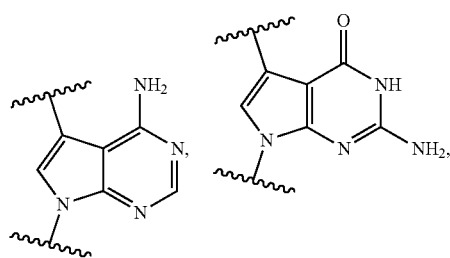

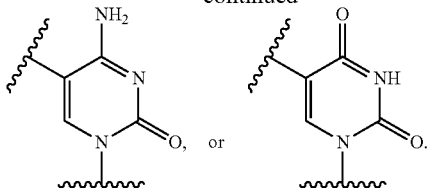

The term "non-covalent linker" is used in accordance with its ordinary meaning and refers to a divalent moiety which includes at least two molecules that are not covalently linked to each other but do interact with each other via a non-covalent bond (e.g. electrostatic interactions (e.g. ionic bond, hydrogen bond, halogen bond) or van der Waals interactions (e.g. dipole-dipole, dipole-induced dipole, London dispersion).

The term "anchor moiety" as used herein refers to a chemical moiety capable of interacting (e.g., covalently or non-covalently) with a second, optionally different, chemical moiety (e.g., complementary anchor moiety binder). In embodiments, the anchor moiety is a bioconjugate reactive group capable of interacting (e.g., covalently) with a complementary bioconjugate reactive group (e.g., complementary anchor moiety reactive group). In embodiments, an anchor moiety is a click chemistry reactant moiety. In embodiments, the anchor moiety (an "affinity anchor moiety") is capable of non-covalently interacting with a second chemical moiety (e.g., complementary affinity anchor moiety binder). Non-limiting examples of an anchor moiety include biotin, azide, trans-cyclooctene (TCO) (Melissa L, et al. *J. Am. Chem. Soc.*, 2008, 130, 13518-13519; Marjoke F. et al. *Org. Biomol. Chem.*, 2013, 11, 6439-6455) and phenyl boric acid (PBA) (Bergseid M, et al. *BioTechniques*, 2000, 29, 1126-1133). In embodiments, an affinity anchor moiety (e.g., biotin moiety) interacts non-covalently with a complementary affinity anchor moiety binder (e.g., streptavidin moiety). In embodiments, an anchor moiety (e.g., azide moiety, trans-cyclooctene (TCO) moiety, phenyl boric acid (PBA) moiety) covalently binds a complementary anchor moiety binder (e.g., dibenzocyclooctyne (DBCO) moiety (Jewett J C and Bertozzi C R *J. Am. Chem. Soc.*, 2010, 132, 3688-3690), tetrazine (TZ) moiety, salicylhydroxamic acid (SHA) moiety).

The terms "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. A cleavable linker is cleavable (e.g., specifically cleavable) in response to external stimuli (e.g., enzymes, nucleophilic/basic reagents, reducing agents, photo-irradiation, electrophilic/acidic reagents, organometallic and metal reagents, or oxidizing reagents). A chemically cleavable linker refers to a linker which is capable of being split in response to the presence of a chemical (e.g., acid, base, oxidizing agent, reducing agent, Pd(O), tris-(2-carboxyethyl)phosphine, dilute nitrous acid, fluoride, tris(3-hydroxypropyl)phosphine), sodium dithionite ($Na_2S_2O_4$), hydrazine ($N_2H_4$)). A chemically cleavable linker is non-enzymatically cleavable. In embodiments, the cleavable linker is cleaved by contacting the cleavable linker with a cleaving agent. In embodiments, the cleaving agent is sodium dithionite ($Na_2S_2O_4$), weak acid, hydrazine ($N_2H_4$), Pd(O), or light-irradiation (e.g., ultraviolet radiation).

A photocleavable linker (e.g., including or consisting of a o-nitrobenzyl group) refers to a linker which is capable of being split in response to photo-irradiation (e.g., ultraviolet radiation). An acid-cleavable linker refers to a linker which is capable of being split in response to a change in the pH (e.g., increased acidity). A base-cleavable linker refers to a linker which is capable of being split in response to a change in the pH (e.g., decreased acidity). An oxidant-cleavable linker refers to a linker which is capable of being split in response to the presence of an oxidizing agent. A reductant-cleavable linker refers to a linker which is capable of being split in response to the presence of an reducing agent (e.g., Tris(3-hydroxypropyl)phosphine). In embodiments, the cleavable linker is a dialkylketal linker (Binaulda S, et al. *Chem. Commun.*, 2013, 49, 2082-2102; Shenoi R A, et al. *J. Am. Chem. Soc.*, 2012, 134, 14945-14957), an azo linker (Rathod, K M, et al. *Chem. Sci. Tran.*, 2013, 2, 25-28; Leriche G, et al. *Eur. J. Org. Chem.*, 2010, 23, 4360-64), an allyl linker, a cyanoethyl linker, a 1-(4,4-dimethyl-2,6-dioxocyclohex-1-ylidene)ethyl linker, or a nitrobenzyl linker. The term "orthogonally cleavable linker" or "orthogonal cleavable linker" as used herein refers to a cleavable linker that is cleaved by a first cleaving agent (e.g., enzyme, nucleophilic/basic reagent, reducing agent, photo-irradiation, electrophilic/acidic reagent, organometallic and metal reagent, oxidizing reagent) in a mixture of two or more different cleaving agents and is not cleaved by any other different cleaving agent in the mixture of two or more cleaving agents. For example, two different cleavable linkers are both orthogonal cleavable linkers when a mixture of the two different cleavable linkers are reacted with two different cleaving agents and each cleavable linker is cleaved by only one of the cleaving agents and not the other cleaving agent. In embodiments, an orthogonally is a cleavable linker that following cleavage the two separated entities (e.g., fluorescent dye, bioconjugate reactive group) do not further react and form a new orthogonally cleavable linker.

The term "orthogonal binding group" or "orthogonal binding molecule" as used herein refer to a binding group (e.g. anchor moiety or complementary anchor moiety binder) that is capable of binding a first complementary binding group (e.g., complementary anchor moiety binder or anchor moiety) in a mixture of two or more different complementary binding groups and is unable to bind any other different complementary binding group in the mixture of two or more complementary binding groups. For example, two different binding groups are both orthogonal binding groups when a mixture of the two different binding groups are reacted with two complementary binding groups and each binding group binds only one of the complementary binding groups and not the other complementary binding group. An example of a set of four orthogonal binding groups and a set of orthogonal complementary binding groups are the binding groups biotin, azide, trans-cyclooctene (TCO) and phenyl boric acid (PBA), which specifically and efficiently bind or react with the complementary binding groups streptavidin, dibenzocyclooctyne (DBCO), tetrazine (TZ) and salicylhydroxamic acid (SHA) respectively.

The term "orthogonal detectable label" or "orthogonal detectable moiety" as used herein refer to a detectable label (e.g. fluorescent dye or detectable dye) that is capable of being detected and identified (e.g., by use of a detection means (e.g., emission wavelength, physical characteristic measurement)) in a mixture or a panel (collection of separate samples) of two or more different detectable labels. For example, two different detectable labels that are fluorescent dyes are both orthogonal detectable labels when a panel of the two different fluorescent dyes is subjected to a wavelength of light that is absorbed by one fluorescent dye but not the other and results in emission of light from the fluorescent dye that absorbed the light but not the other fluorescent dye. Orthogonal detectable labels may be separately identified by different absorbance or emission intensities of the orthogonal detectable labels compared to each other and not only be the absolute presence of absence of a signal. An example of a set of four orthogonal detectable labels is the set of Rox-Labeled Tetrazine, Alexa488-Labeled SHA, Cy5-Labeled Streptavidin, and R6G-Labeled Dibenzocyclooctyne.

The term "polymerase-compatible cleavable moiety" as used herein refers a cleavable moiety which does not interfere with the function of a polymerase (e.g., DNA polymerase, modified DNA polymerase). Methods for determining the function of a polymerase contemplated herein are described in B. Rosenblum et al. (Nucleic Acids Res. 1997 Nov. 15; 25(22): 4500-4504); and Z. Zhu et al. (Nucleic Acids Res. 1994 Aug. 25; 22(16): 3418-3422), which are incorporated by reference herein in their entirety for all purposes. In embodiments the polymerase-compatible cleavable moiety does not decrease the function of a polymerase relative to the absence of the polymerase-compatible cleavable moiety. In embodiments, the polymerase-compatible cleavable moiety does not negatively affect DNA polymerase recognition. In embodiments, the polymerase-compatible cleavable moiety does not negatively affect (e.g., limit) the read length of the DNA polymerase. Additional examples of a polymerase-compatible cleavable moiety may be found in U.S. Pat. No. 6,664,079, Ju J. et al. (2006) *Proc Natl Acad Sci USA* 103(52):19635-19640; Ruparel H. et al. (2005) *Proc Natl Acad Sci USA* 102(17):5932-5937; Wu J. et al. (2007) *Proc Natl Acad Sci USA* 104(104):16462-16467; Guo J. et al. (2008) *Proc Natl Acad Sci USA* 105(27): 9145-9150 Bentley D. R. et al. (2008) *Nature* 456(7218): 53-59; or Hutter D. et al. (2010) *Nucleosides Nucleotides & Nucleic Acids* 29:879-895, which are incorporated herein by reference in their entirety for all purposes. In embodiments, a polymerase-compatible cleavable moiety includes an azido moiety or a dithiol linking moiety. In embodiments, the polymerase-compatible cleavable moiety is $-NH_2$, $-CN$, $-CH_3$, $C_2$-$C_6$ allyl (e.g., $-CH_2-CH=CH_2$), methoxyalkyl (e.g., $-CH_2-O-CH_3$), or $-CH_2N_3$. In embodiments, the polymerase-compatible cleavable moiety is:

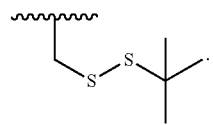 [SMILES: *CSSC(C)(C)C]

The term "allyl" as described herein refers to an unsubstituted methylene attached to a vinyl group (i.e. $-CH=CH_2$), having the formula

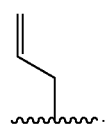 [SMILES: *CC=C]

An "allyl linker" refers to a divalent unsubstituted methylene attached to a vinyl group, having the formula

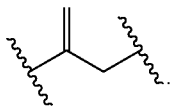 [SMILES: *CC(*)=C]

Where a range of values is provided, it is understood that each intervening value, to the tenth of the unit (if appropriate) of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Certain Embodiments

II. Compounds

In an aspect is provided a compound of the formula:

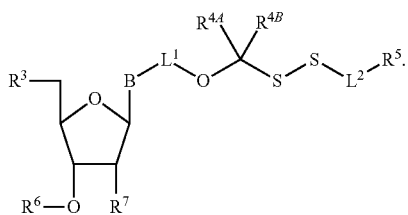

(I)

B is a base. $L^1$ is covalent linker. $L^2$ is covalent linker. $R^3$ is —OH, monophosphate, diphosphate, triphosphate, polyphosphate or a nucleic acid. $R^{4A}$ is hydrogen, —$CX^1_3$, —$CHX^1_2$, —$CH_2X^1$, —$OCH_2X^1$, —$OCHX^1_2$, —CN, —OH, —SH, —$NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. $R^{4B}$ is hydrogen, —$CX^2_3$, —$CHX^2_2$, —$CH_2X^2$, —$OCX^2_3$, —$OCH_2X^2$, —$OCHX^2_2$, —CN, —OH, —SH, —$NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. $R^5$ is a detectable label or anchor moiety. $R^6$ is hydrogen or a polymerase-compatible cleavable moiety. $R^7$ is hydrogen or —$OR^{7A}$, wherein $R^{7A}$ is hydrogen or the polymerase-compatible cleavable moiety. The symbols $X^1$ and $X^2$ are independently halogen.

In an aspect is provided a compound of the formula:

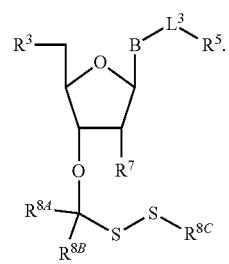

(II)

B is a base. $L^3$ is a cleavable linker. $R^3$ is —OH, monophosphate, polyphosphate or a nucleic acid. $R^5$ is a detectable label or anchor moiety. $R^7$ is hydrogen or —$OR^{7A}$, wherein $R^{7A}$ is hydrogen or

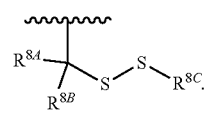

$R^{8A}$ is independently hydrogen, —$CH_3$, —$CX^3_3$, —$CHX^3_2$, —$CH_2X^3$, —$OCX^3_3$, —$OCH_2X^3$, —$OCHX^3_2$, —CN, —OH, —SH, —$NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. $R^{8B}$ is independently hydrogen, $CH_3$, —$CX^4_3$, —$CHX^4_2$, —$CH_2X^4$, —$OCX^4_3$, —$OCH_2X^4$, —$OCHX^4_2$, —CN, —OH, —SH, —$NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. $R^{8C}$ is independently hydrogen, $CH_3$, $-CX^{8C}_3$, $-CHX^{8C}_2$, $-CH_2X^{8C}$, $-OCX^{8C}_3$, $-OCH_2X^{8C}$, $-OCHX^{8C}_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. The symbols $X^3$, $X^4$, and $X^{8C}$ are independently halogen. In embodiments, $R^{8C}$ is independently unsubstituted phenyl.

In an aspect is provided a compound of the formulae

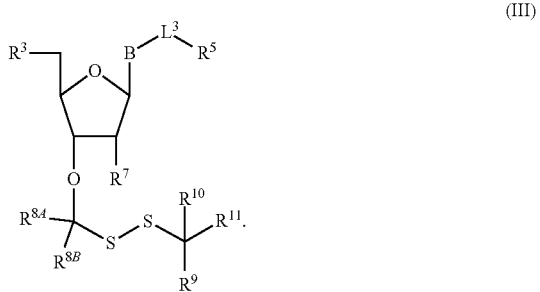

(III)

B is a base. $L^3$ is a cleavable linker. $R^3$ is $-OH$, monophosphate, polyphosphate or a nucleic acid. $R^5$ is a detectable label or anchor moiety. $R^7$ is hydrogen or $-OR^{7A}$, wherein $R^{7A}$ is hydrogen or

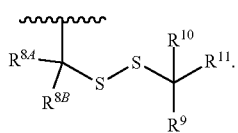

$R^{8A}$ is hydrogen, $CH_3$, $-CX^3_3$, $-CHX^3_2$, $-CH_2X^3$, $-OCX^3_3$, $-OCH_2X^3$, $-OCHX^3_2$, $-CN$, CN, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. $R^{8B}$ is hydrogen, $CH_3$, $-CX^4_3$, $-CHX^4_2$, $-CH_2X^4$, $-OCX^4_3$, $-OCH_2X^4$, $-OCHX^4_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. $R^9$ is hydrogen, $CH_3$, $-CX^5_3$, $-CHX^5_2$, $-CH_2X^5$, $-OCX^5_3$, $-OCH_2X^5$, $-OCHX^5_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. $R^{10}$ is hydrogen, $-CX^6_3$, $-CHX^6_2$, $-CH_2X^6$, $-OCX^6_3$, $-OCH_2X^6$, $-OCHX^6_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. $R^{11}$ is hydrogen, $CH_3$, $-CX^7_3$, $-CHX^7_2$, $-CH_2X^7$, $-OCX^7_3$, $-OCH_2X^7$, $-OCHX^7_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. The symbols $X^3$, $X^4$, $X^5$, $X^6$ and $X^7$ are independently halogen.

In another aspect is provided a compound of the formula:

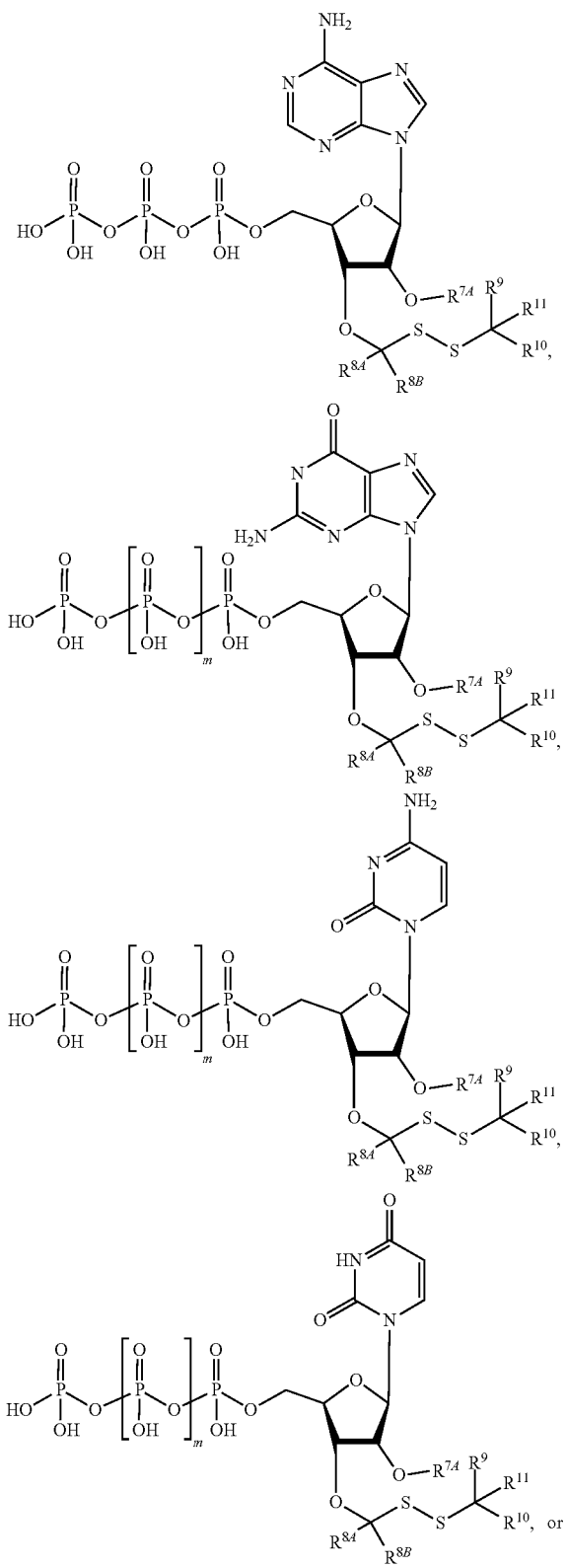

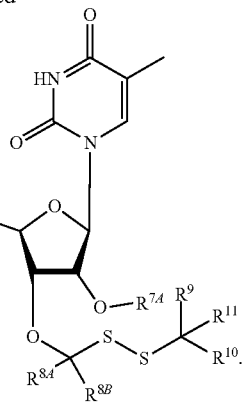

$R^{7A}$ is hydrogen or a polymerase-compatible cleavable moiety; $R^{8A}$ is independently hydrogen, $CH_3$, $-CX^3_3$, $-CHX^3_2$, $-CH_2X^3$, $-OCX^3_3$, $-OCH_2X^3$, $-OCHX^3_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. $R^{8B}$ is independently hydrogen, $CH_3$, $-CX^4_3$, $-CHX^4_2$, $-CH_2X^4$, $-OCX^4_3$, $-OCH_2X^4$, $-OCHX^4_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl; or substituted (e.g., substituted with a substituent group, size-limited substituent group, or lower substituent group) or unsubstituted heteroaryl. $R^9$ is independently hydrogen, $CH_3$, $-CX^5_3$, $-CHX^5_2$, $-CH_2X^5$, $-OCX^5_3$, $-OCH_2X^5$, $-OCHX^5_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. $R^{10}$ is independently hydrogen, —$CX^6_3$, —$CHX^6_2$, —$CH_2X^6$, —$OCX^6_3$, —$OCH_2X^6$, —$OCHX^6_2$, —CN, —OH, —SH, —$NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. $R^{11}$ is independently hydrogen, $CH_3$, —$CX^7_3$, —$CHX^1_2$, —$CH_2X^7$, —$OCX^7_3$, —$OCH_2X^1$, —$OCHX^7_2$, —CN, —OH, —SH, —$NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. The symbols $X^3$, $X^4$, $X^5$, $X^6$ and $X^7$ are independently halogen. The symbol m is independently an integer from 1 to 4.

In an aspect is provided a compound of the formula:

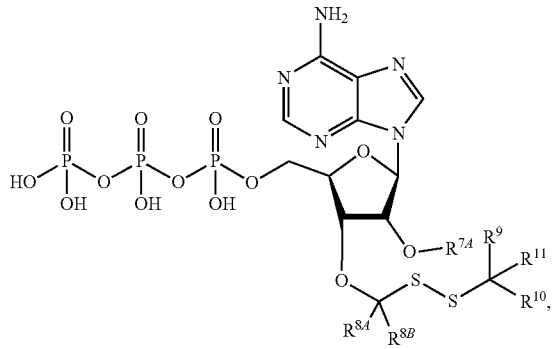

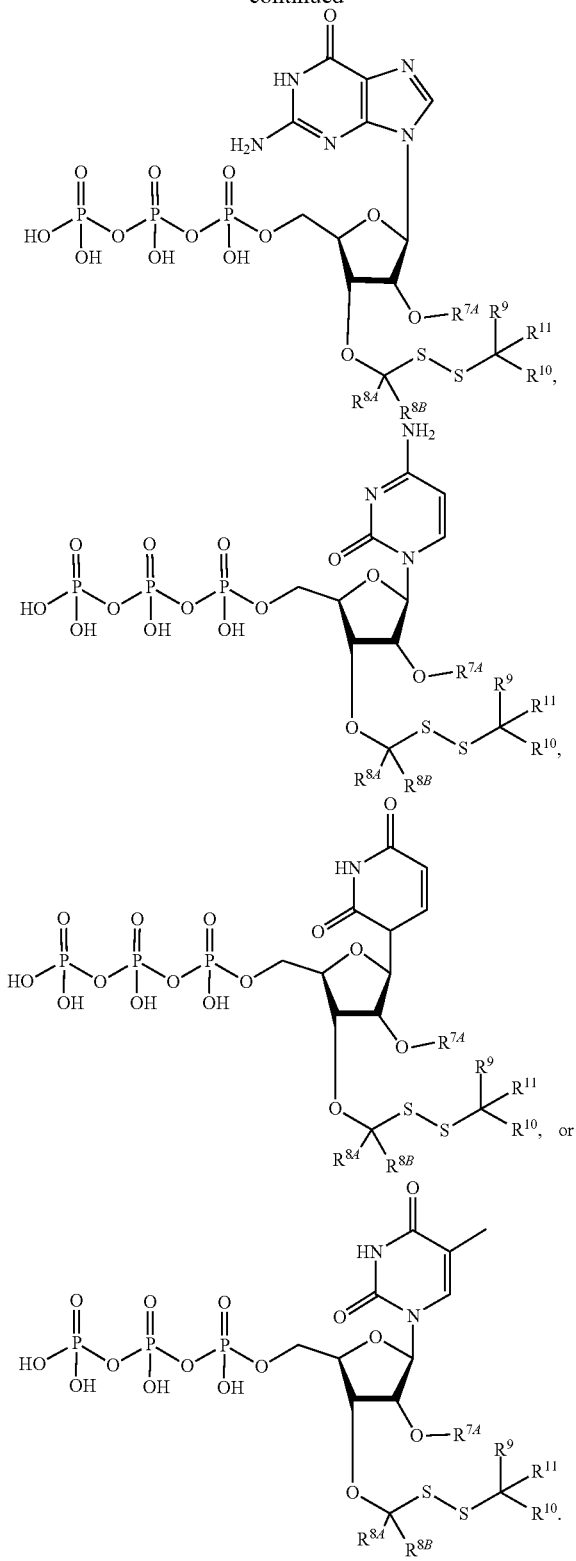

$R^{7A}$ is hydrogen or a polymerase-compatible cleavable moiety; $R^{8A}$ is independently hydrogen, $CH_3$, —$CX^3_3$, —$CHX^3_2$, —$CH_2X^3$, —$OCX^3_3$, —$OCH_2X^3$, —$OCHX^3_2$, —CN, —OH, —SH, —$NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. $R^{8B}$ is independently hydrogen, $CH_3$, $-CX^4_3$, $-CHX^4_2$, $-CH_2X^4$, $-OCX^4_3$, $-OCH_2X^4$, $-OCHX^4_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl $R^9$ is independently hydrogen, $CH_3$, $-CX^5_3$, $-CHX^5_2$, $-CH_2X^5$, $-OCX^5_3$, $-OCH_2X^5$, $-OCHX^5_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. $R^{10}$ is independently hydrogen, $CH_3$, $-CX^6_3$, $-CHX^6_2$, $-OCX^6_3$, $-OCH_2X^6$, $-OCHX^6_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl is independently hydrogen, $CH_3$, $-CX^7_3$, $-CHX^7_2$, $-CH_2X^7$, $-OCX^7_3$, $-OCH_2X^7$, $-OCHX^7_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. The symbols $X^3$, $X^4$, $X^5$, $X^6$ and $X^7$ are independently halogen.

In an aspect is provided a the formula:

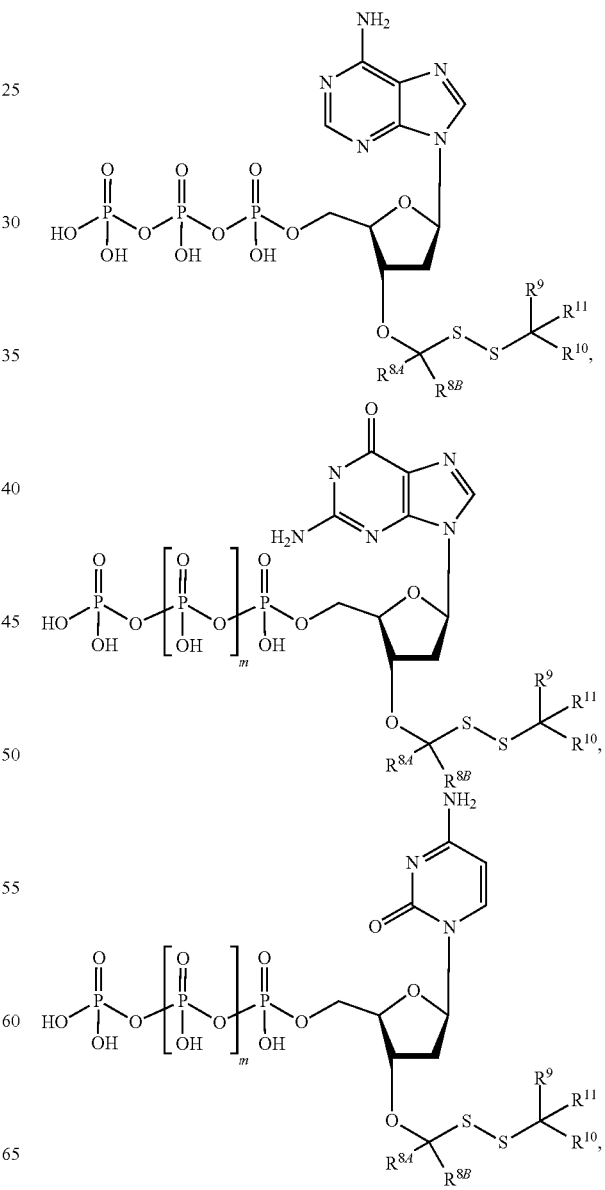

-continued

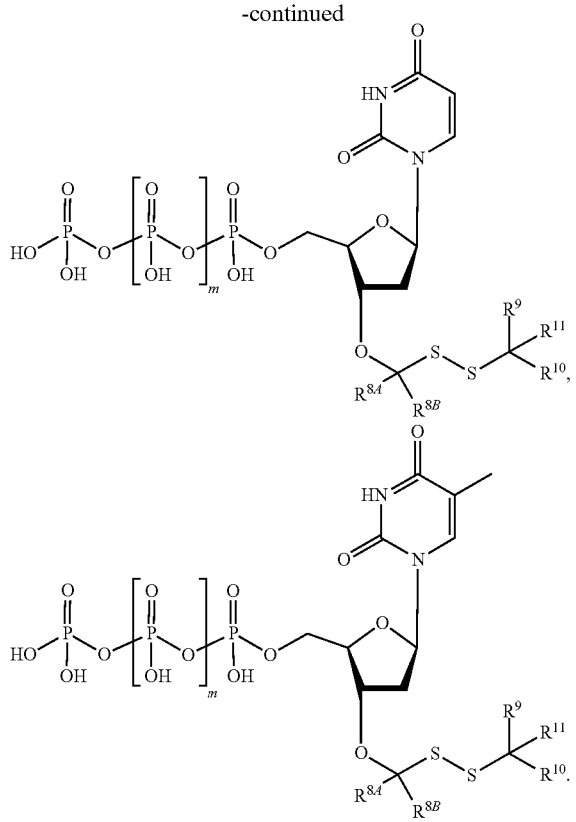

$R^{8A}$ is hydrogen, $CH_3$, —$CX^3_3$, —$CHX^3_2$, —$CH_2X^3$, —$OCX^3_3$, —$OCH_2X^3$, —$OCHX^3_2$, —OH, —SH, —$NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. $R^{8B}$ is independently hydrogen, $CH_3$, —$CX^4_3$, —$CHX^4_2$, —$CH_2X^4$, —$OCX^4_3$, —$OCH_2X^4$, —$OCHX^4_2$, —CN, —OH, —SH, —$NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. $R^9$ is independently hydrogen, $CH_3$, —$CX^5_3$, —$CHX^5_2$, —$CH_2X^5$, —$OCX^5_3$, —$OCH_2X^5$, —$OCHX^5_2$, —CN, —OH, —SH, —$NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. $R^{10}$ is independently hydrogen, $CH_3$, —$CX^6_3$, —$CHX^6_2$, —$OCX^6_3$, —$OCH_2X^6$, —CN, —OH, —SH, —$NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. $R^{11}$ is independently hydrogen, $CH_3$, —$CX^7_3$, —$CHX^7_2$, —$CH_2X^7$, —$OCX^7_3$, —$OCH_2X^7$, —$OCHX^7_2$, —CN, —OH, —SH, —$NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. The symbols $X^3$, $X^4$, $X^5$, $X^6$ and $X^7$ are independently halogen. The symbol m is independently an integer from 1 to 4.

In an aspect is a compound of the formula:

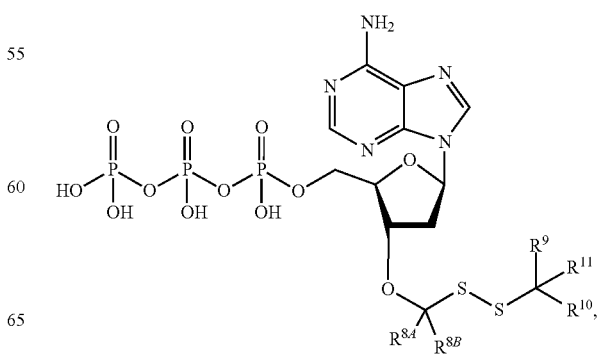

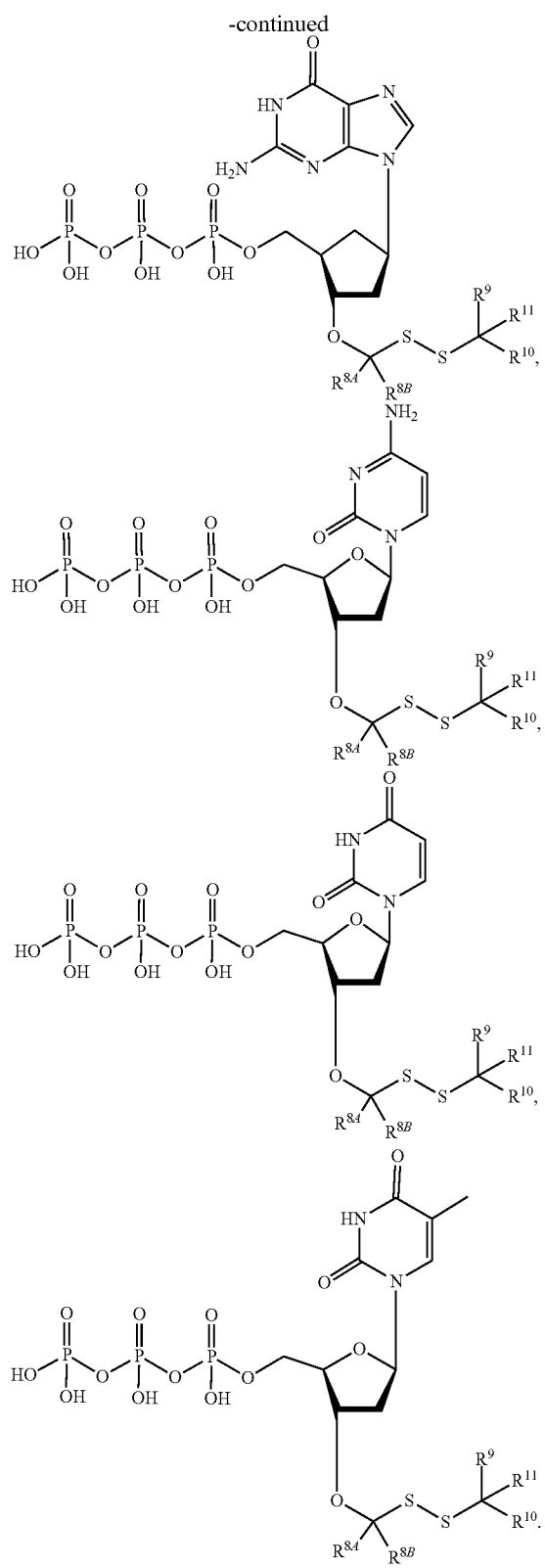

substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. $R^{8B}$ is independently hydrogen, $CH_3$, $-CX^4_3$, $-CHX^4_2$, $-CH_2X^4$, $-OCX^4_3$, $-OCH_2X^4$, $-OCHX^4_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. $R^9$ is independently hydrogen, $CH_3$, $-CX^5_3$, $-CHX^5_2$, $-CH_2X^5$, $-OCX^5_3$, $-OCH_2X^5$, $-OCHX^5_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. $R^{10}$ is independently hydrogen, $CH_3$, $-CX^6_3$, $-CHX^6_2$, $-CH_2X^6$, $-OCX^6_3$, $-OCH_2X^6$, $-OCHX^6_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. $R^{11}$ is independently hydrogen, $CH_3$, $-CX^7_3$, $-CHX^7_2$, $-CH_2X^7$, $-OCX^7_3$, $-OCH_2X^7$, $-OCHX^7_2$, $-CN$, $-OH$, $-SH$, $-NH_2$, substituted (e.g., substituted with a substituent group, size-limited substituent group, or lower substituent group) or unsubstituted alkyl, substituted (e.g., $R^{8A}$ is independently hydrogen, $CH_3$, $-CX^3_3$, $-CHX^3_2$, $-CH_2X^3$, $-OCX^3_3$, $-OCH_2X^3$, $-OCHX^3_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or un substituted heteroaryl. The symbols $X^3$, $X^4$, $X^5$, $X^6$ and $X^7$ are independently halogen.

In another aspect is provided a composition of the formula:

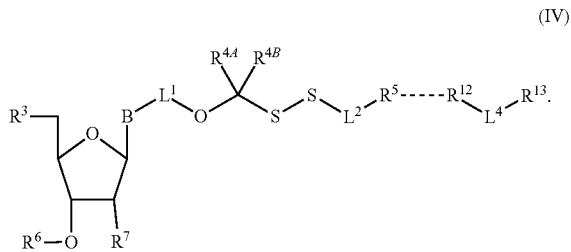

(IV)

The symbol "---" is a non-covalent bond. B is a base. $L^1$ is covalent linker. $L^2$ is covalent linker. $L^4$ is a covalent linker. $R^3$ is —OH, monophosphate, polyphosphate or a nucleic acid. $R^{4A}$ is hydrogen, $CH_3$, —$CX^1_3$, —$CHX^1_2$, —$CH_2X^1$, —$OCX^1_3$, —$OCH_2X^1$, —$OCHX^1_2$, —CN, —OH, —SH, —$NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. $R^{4B}$ is hydrogen, $CH_3$, —$CX^2_3$, —$CHX^2_2$, —$CH_2X^2$, —$OCX^2_3$, —$OCH_2X^2$, —$OCHX^2_2$, —CN, —OH, —SH, —$NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. $R^5$ is an affinity anchor moiety. $R^6$ is hydrogen or a polymerase-compatible cleavable moiety. $R^7$ is hydrogen or —$OR^{7A}$, wherein $R^{7A}$ is hydrogen or a polymerase-compatible cleavable moiety. $R^{12}$ is a complementary affinity anchor moiety binder. $R^{13}$ is a detectable label. The symbols $X^1$ and $X^2$ are independently halogen.

In embodiments, b is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, deaza-adenine or a derivative thereof, deaza-guanine or a derivative thereof, deaza-hypoxanthine or a derivative thereof divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof.

In embodiments, B is a divalent cytosine, divalent guanine, divalent adenine, divalent thymine, divalent uracil, divalent hypoxanthine, divalent xanthine, deaza-adenine, deaza-guanine, deaza-hypoxanthine or a derivative thereof divalent 7-methylguanine, divalent 5,6-dihydrouracil, divalent 5-methylcytosine, or divalent 5-hydroxymethylcytosine. In embodiments, B is a divalent cytosine. In embodiments, B is a divalent guanine. In embodiments, B is a divalent adenine. In embodiments, B is a divalent thymine. In embodiments, B is a divalent uracil. In embodiments, B is a divalent hypoxanthine. In embodiments, B is a divalent xanthine. In embodiments, B is a deaza-adenine. In embodiments, B is a deaza-guanine. In embodiments, B is a deaza-hypoxanthine or a derivative thereof divalent 7-methylguanine. In embodiments, B is a divalent 5,6-dihydrouracil. In embodiments, B is a divalent 5-methylcytosine. In embodiments, B is a divalent 5-hydroxymethylcytosine.

In embodiments, B is a divalent cytosine or a derivative thereof. In embodiments, B is a divalent guanine or a derivative thereof. In embodiments, B is a divalent adenine or a derivative thereof. In embodiments, B is a divalent thymine or a derivative thereof. In embodiments, B is a divalent uracil or a derivative thereof. In embodiments, B is a divalent hypoxanthine or a derivative thereof. In embodiments, B is a divalent xanthine or a derivative thereof. In embodiments, B is a deaza-adenine or a derivative thereof. In embodiments, B is a deaza-guanine or a derivative thereof. In embodiments, B is a deaza-hypoxanthine or a derivative thereof divalent 7-methylguanine or a derivative thereof. In embodiments, B is a divalent 5,6-dihydrouracil or a derivative thereof. In embodiments, B is a divalent 5-methylcytosine or a derivative thereof. In embodiments, B is a divalent 5-hydroxymethylcytosine or a derivative thereof.

In embodiments, B is

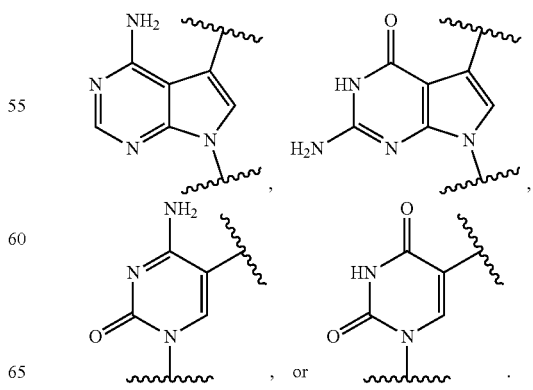

, or .

In embodiments, B is

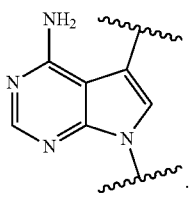

In embodiments, B is

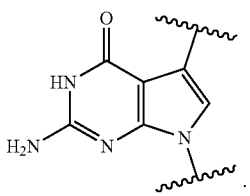 [SMILES: *c1cn(*)c2nc(N)[nH]c(=O)c12]

In embodiments, B is

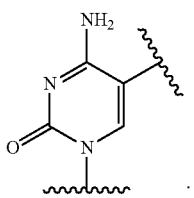 [SMILES: *c1cn(*)c(=O)nc1N]

In embodiments, B is

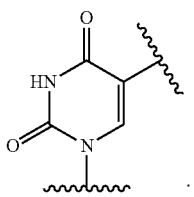 [SMILES: *c1cn(*)c(=O)[nH]c1=O]

In embodiments, $L^1$ is $L^{1A}$-$L^{1B}$-$L^{1C}$-$L^{1D}$-$L^{1E}$; and $L^{1A}$, $L^{1B}$, $L^{1C}$, $L^{1D}$ and $L^{1E}$ are independently a bond, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{1A}$, $L^{1B}$, $L^{1C}$, $L^{1D}$ and $L^{1E}$ is not a bond.

In embodiments, $L^1$ is $L^{1A}$-$L^{1B}$-$L^{1C}$-$L^{1D}$-$L^{1E}$; and $L^{1A}$, $L^{1B}$, $L^{1C}$, $L^{1D}$ and $L^{1E}$ are independently a bond, substituted (e.g., substituted with a substituent group, size-limited substituent group, or lower substituent group) or unsubstituted $C_1$-$C_8$ alkylene (e.g., alkylene, alkenylene, or alkynylene), substituted (e.g., substituted with a substituent group, size-limited substituent group, or lower substituent group) or unsubstituted 2 to 8 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene; wherein at least one of $L^{1A}$, $L^{1B}$, $L^{1C}$, $L^{1D}$ and $L^{1E}$ is not a bond.

In embodiments, $L^1$ is $L^{1A}$-$L^{1B}$-$L^{1C}$-$L^{1D}$-$L^{1E}$; and $L^{1A}$, $L^{1B}$, $L^{1C}$, $L^{1D}$ and $L^{1E}$ are independently a bond, substituted (e.g., substituted with a substituent group, size-limited substituent group, or lower substituent group) or unsubstituted $C_1$-$C_6$ alkylene (e.g., alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene; wherein at least one of $L^{1A}$, $L^{1B}$, $L^{1C}$, $L^{1D}$ and $L^{1E}$ is not a bond.

In embodiments, $L^1$ is a bond, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene.

In embodiments, $L^1$ is a bond, substituted (e.g., substituted with a substituent group, size-limited substituent group, or lower substituent group) or unsubstituted $C_1$-$C_8$ alkylene (e.g., alkylene, alkenylene, or alkynylene), substituted (e.g., substituted with a substituent group, size-limited substituent group, or lower substituent group) or unsubstituted 2 to 8 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene.

In embodiments, $L^1$ is a bond, substituted (e.g., substituted with a substituent group, size-limited substituent group, or lower substituent group) or unsubstituted $C_1$-$C_6$ alkylene (e.g., alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene.

In embodiments, $L^1$ is $L^{1A}$-$L^{1B}$-$L^{1C}$-$L^{1D}$-$L^{1E}$; and $L^{1A}$, $L^{1B}$, $L^{1C}$, $L^{1D}$ and $L^{1E}$ are independently a bond, substituted (e.g., substituted with a substituent group, size-limited substituent group, or lower substituent group) or unsubstituted alkenylene (e.g., substituted with a substituent group, or substituted with size-limited substituent group), substituted (e.g., substituted with a substituent group, size-limited substituent group, or lower substituent group) or unsubstituted heteroalkenylene; wherein at least one of $L^{1A}$, $L^{1B}$, $L^{1C}$, $L^{1D}$ and $L^{1E}$ is not a bond.

In embodiments, $L^1$ is $L^{1A}$-$L^{1B}$-$L^{1C}$-$L^{1D}$-$L^{1E}$; and $L^{1A}$, $L^{1B}$, $L^{1C}$, $L^{1D}$ and $L^{1E}$ are independently a bond, substituted (e.g., substituted with a substituent group, size-limited substituent group, or lower substituent group) or unsubstituted $C_1$-$C_8$ alkenylene, or substituted (e.g., substituted with a substituent group, size-limited substituent group, or lower substituent group) or unsubstituted 2 to 8 membered heteroalkenylene; wherein at least one of $L^{1A}$, $L^{1B}$, $L^{1C}$, $L^{1D}$ and $L^{1E}$ is not a bond. In embodiments, $L^1$ is $L^1$ is $L^{1A}$-$L^{1B}$-$L^{1C}$-$L^{1D}$-$L^{1E}$; and $L^{1A}$, $L^{1B}$, $L^{1C}$, $L^{1D}$ and $L^{1E}$ are independently a bond, substituted (e.g., substituted with a substituent group, size-limited substituent group, or lower substituent group) or unsubstituted $C_1$-$C_6$ alkenylene, or substituted (e.g., substituted with a substituent group, size-limited substituent group, or lower substituent group) or unsubstituted 2 to 6 membered heteroalkenylene; wherein at least one of $L^{1A}$, $L^{1B}$, $L^{1C}$, $L^{1D}$ and $L^{1E}$ is not a bond.

In embodiments, $L^1$ is a bond, substituted (e.g., substituted with a substituent group, size-limited substituent group, or lower substituent group) or unsubstituted alkenylene, or substituted (e.g., substituted with a substituent group, size-limited substituent group, or lower substituent group) or unsubstituted heteroalkenylene. In embodiments, $L^1$ is a bond, substituted (e.g., substituted with a substituent group, size-limited substituent group, or lower substituent group) or unsubstituted $C_2$-$C_8$ alkenylene, or substituted (e.g., substituted with a substituent group, size-limited substituent group, or lower substituent group) or unsubstituted 3 to 8 membered heteroalkenylene. In embodiments, $L^1$ is a bond, substituted (e.g., substituted with a substituent group, size-limited substituent group, or lower substituent group) or unsubstituted $C_2$-$C_6$ alkenylene, or substituted (e.g., substituted with a substituent group, size-limited substituent group, or lower substituent group) or unsubstituted 3 to 6 membered heteroalkenylene.

In embodiments, $L^1$ is $L^{1A}$-$L^{1B}$-$L^{1C}$-$L^{1D}$-$L^{1E}$; and $L^{1A}$, $L^{1B}$, $L^{1C}$, $L^{1D}$ and $L^{1E}$ are independently a bond, substituted (e.g., substituted with a substituent group, size-limited substituent group, or lower substituent group) or unsubstituted alkynylene, substituted (e.g., substituted with a substituent group, size-limited substituent group, or lower substituent group) or unsubstituted heteroalkynylene: wherein at least one of $L^{1A}$, $L^{1B}$, $L^{1C}$, $L^{1D}$ and $L^{1E}$ is not a bond.

In embodiments, $L^1$ is $L^{1A}$-$L^{1B}$-$L^{1C}$-$L^{1D}$-$L^{1E}$; and $L^{1A}$, $L^{1B}$, $L^{1C}$, $L^{1D}$ and $L^{1E}$ are independently a bond, substituted (e.g., substituted with a substituent group, size-limited substituent group, or lower substituent group) or unsubstituted $C_1$-$C_5$ alkynylene, or substituted (e.g., substituted with a substituent group, size-limited substituent group, or lower substituent group) or unsubstituted 2 to 8 membered heteroalkynylene; wherein at least one of $L^{1A}$, $L^{1B}$, $L^{1C}$, $L^{1D}$ and $L^{1E}$ is not a bond. In embodiments, $L^1$ is $L^1$ is $L^{1A}$-$L^{1B}$-$L^{1C}$-$L^{1D}$-$L^{1E}$; and $L^{1A}$, $L^{1B}$, $L^{1C}$, $L^{1D}$ and $L^{1E}$ are independently a bond, substituted (e.g., substituted with a substituent group, size-limited substituent group, or lower substituent group) or unsubstituted $C_1$-$C_6$ alkynylene, or substituted (e.g., substituted with a substituent group, size-limited substituent group, or lower substituent group) or unsubstituted 2 to 6 membered heteroalkynylene; wherein at least one of $L^{1A}$, $L^{1B}$, $L^{1C}$, $L^{1D}$ and $L^{1E}$ is not a bond.

In embodiments, $L^1$ is a bond, substituted (e.g., substituted with a substituent group, size-limited substituent group, or lower substituent group) or unsubstituted alkynylene, or substituted (e.g., substituted with a substituent group, size-limited substituent group, or lower substituent group) or unsubstituted heteroalkynylene. In embodiments, $L^1$ is a bond, substituted (e.g., substituted with a substituent group, size-limited substituent group, or lower substituent group) or unsubstituted $C_2$-$C_8$ alkynylene, or substituted (e.g., substituted with a substituent group, size-limited substituent group, or lower substituent group) or unsubstituted 3 to 8 membered heteroalkynylene. In embodiments, $L^1$ is a bond, substituted (e.g., substituted with a substituent group, size-limited substituent group, or lower substituent group) or unsubstituted $C_2$-$C_6$ alkynylene, or substituted (e.g., substituted with a substituent group, size-limited substituent group, or lower substituent group) or unsubstituted 3 to 6 membered heteroalkynylene.

In embodiments, $L^1$ is a substituted (e.g., substituted with a substituent group, size-limited substituent group, or lower substituent group) or unsubstituted $C_1$-$C_6$ alkelyene (e.g., alkylene (e.g., alkylene, alkenylene, or alkynylene), alkenylene, or alkynylene) or substituted (e.g., substituted with a substituent group, size-limited substituent group, or lower substituent group) or unsubstituted 2 to 6 membered heteroalkylene (e.g., heteroalkylene, heteroalkynylene, or heteroalkynylene). In embodiments, $L^1$ is an unsubstituted alkylene (e.g., alkylene, alkenylene, or alkynylene). In embodiments, $L^1$ is —C≡C—CH$_2$—.

In embodiments; $L^1$ is a polymer. The term "polymer" refers to a molecule including repeating subunits (e.g., polymerized monomers). For example, polymeric molecules may be based upon polyethylene glycol (PEG), tetraethylene glycol (TEG), polyvinylpyrrolidone (PVP), poly(xylene), or poly(p-xylylene). The term "polymerizable monomer" is used in accordance with its meaning in the art of polymer chemistry and refers to a compound that may covalently bind chemically to other monomer molecules (such as other polymerizable monomers that are the same or different) to form a polymer.

In embodiments, $L^2$ is a cleavable linker. In embodiments, $L^2$ is a chemically cleavable linker. In embodiments, $L^2$ is a photocleavable linker, an acid-cleavable linker, a base-cleavable linker, an oxidant-cleavable linker, a reductant-cleavable linker, or a fluoride-cleavable linker. In embodiments, $L^2$ is a photocleavable linker. In embodiments, $L^2$ is an acid-cleavable linker. In embodiments, $L^2$ is a base-cleavable linker. In embodiments, $L^2$ is an oxidant-cleavable linker. In embodiments, $L^2$ is a reductant-cleavable linker. In embodiments, $L^2$ is a fluoride-cleavable linker.

In embodiments, $L^2$ includes a cleavable linker. In embodiments, $L^2$ includes a chemically cleavable linker. In embodiments, $L^2$ includes a photocleavable linker, an acid-cleavable linker; a base-cleavable linker, an oxidant-cleavable linker, a reductant-cleavable linker, or a fluoride-cleavable linker. In embodiments, $L^2$ includes a photocleavable linker. In embodiments, $L^2$ includes an acid-cleavable linker. In embodiments, $L^2$ includes a base-cleavable linker. In embodiments, $L^2$ includes an oxidant-cleavable linker. In embodiments, $L^2$ includes a reductant-cleavable linker. In embodiments, $L^2$ includes a fluoride-cleavable linker.

In embodiments, $L^2$ is a cleavable linker including a dialkylketal linker, an azo linker, an allyl linker, a cyanoethyl linker, a 1-(4,4-dimethyl-2,6-dioxocyclohex-1-ylidene)ethyl linker, or a nitrobenzyl linker. In embodiments, $L^2$ is a cleavable linker including a dialkylketal linker, In embodiments, $L^2$ is a cleavable linker including an azo linker. In embodiments, $L^2$ is a cleavable linker including an allyl linker. In embodiments, $L^2$ is a cleavable linker including a cyanoethyl linker. In embodiments, $L^2$ is a cleavable linker including a 1-(4,4-dimethyl-2,6-dioxocyclohex-1-ylidene)ethyl linker. In embodiments, $L^2$ is a cleavable linker including a nitrobenzyl linker.

In embodiments; $L^2$ is $L^{2A}$-$L^{2B}$-$L^{2C}$-$L^{2D}$-$L^{2E}$; and $L^{2A}$, $L^{2B}$, $L^{2C}$, $L^{2D}$ and $L^{2E}$ are independently a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{2A}$, $L^{2B}$, $L^{2C}$, $L^{2D}$ and $L^{2E}$ is not a bond.

In embodiments, $L^2$ is $L^{2A}$-$L^{2B}$-$L^{2C}$-$L^{2D}$-$L^{2E}$; and $L^{2A}$, $L^{2B}$, $L^{2C}$, $L^{2D}$ and $L^{2E}$ are independently a bond, —NN—, —NHC(O)—, —C(O)NH—, substituted (e.g., substituted with a substituent group, size-limited substituent group, or lower substituent group) or unsubstituted $C_1$-$C_{20}$ alkylene (e.g., alkylene, alkenylene, or alkynylene), substituted (e.g., substituted with a substituent group, size-limited substituent group, or lower substituent group) or unsubstituted 2 to 20 membered heteroalkylene (e.g., heteroalkylene, heteroalkenylene, or heteroalkynylene), substituted (e.g.; substituted with a substituent group, size-limited substituent group, or lower substituent group) or unsubstituted $C_3$-$C_{20}$ cycloalkylene, substituted (e.g., substituted with a substituent group, size-limited substituent group, or lower substituent group) or unsubstituted 3 to 20 membered heterocycloalkylene, substituted (e.g., substituted with a substituent group, size-limited substituent group, or lower substituent group) or unsubstituted $C_6$-$C_{20}$ arylene, or substituted (e.g., substituted with a substituent group, size-limited substituent group, or lower substituent group) or unsubstituted 5 to 20 membered heteroarylene; wherein at least one of $L^{2A}$, $L^{2B}$, $L^{2C}$, $L^{2D}$ and $L^{2E}$ is not a bond.

In embodiments, $L^2$ is $L^{2A}$-$L^{2B}$-$L^{2C}$-$L^{2D}$-$L^{2E}$; and $L^{2A}$, $L^{2B}$, $L^{2C}$, $L^{2D}$ and $L^{2E}$ are independently a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted 2 to 10 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene; wherein at least one of $L^{2A}$, $L^{2B}$, $L^{2C}$, $L^{2D}$ and $L^{2E}$ is not a bond.

In embodiments, $L^2$ is $L^{2A}$-$L^{2B}$-$L^{2C}$-$L^{2D}$-$L^{2E}$; and $L^{2A}$, $L^{2B}$, $L^{2C}$, $L^{2D}$ and $L^{2E}$ are independently a bond, —NN—, —NHC(O)—, —C(O)NH—, substituted (e.g., substituted with a substituent group, size-limited substituent group, or lower substituent group) or unsubstituted $C_1$-$C_6$ alkylene (e.g., alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene; wherein at least one of $L^{2A}$, $L^{2B}$, $L^{2C}$, $L^{2D}$ and $L^{2E}$ is not a bond.

In embodiments, $L^2$ is $L^{2A}$-$L^{2B}$-$L^{2C}$-$L^{2D}$-$L^{2E}$; $L^{2A}$ is a bond, substituted (e.g., substituted with a substituent group, size-limited substituent group, or lower substituent group) or unsubstituted alkylene (e.g., alkylene, alkynylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene). $L^{2B}$ is a bond, substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene; $L^{2C}$ is a bond, substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene; $L^{2D}$ is a bond, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene); and $L^{2E}$ is a bond, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{2A}$, $L^{2B}$, $L^{2C}$, $L^{2D}$ and $L^{2E}$ is not a bond.

In embodiments, $L^2$ is a bond, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene. In embodiments, $L^2$ is a bond, substituted (e.g., substituted with a substituent group, size-limited substituent group, or lower substituent group) or unsubstituted $C_1$-$C_{20}$ alkylene (e.g., alkylene, alkenylene, or alkynylene), substituted (e.g., substituted with a substituent group, size-limited substituent group, or lower substituent group) or unsubstituted 2 to 20 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_{20}$ cycloalkylene, substituted (e.g., substituted with a substituent group, size-limited substituent group, or lower substituent group) or unsubstituted 3 to 20 membered heterocycloalkylene, substituted (e.g., substituted with a substituent group, size-limited substituent group, or lower substituent group) or unsubstituted $C_6$-$C_{20}$ arylene, or substituted (e.g., substituted with a substituent group, size-limited substituent group, or lower substituent group) or unsubstituted 5 to 20 membered heteroarylene. In embodiments, $L^2$ is a bond, substituted (e.g., substituted with a substituent group, size-limited substituent group, or lower substituent group) or unsubstituted $C_1$-$C_8$ alkylene (e.g., alkylene, alkenylene, or alkynylene), substituted (e.g., substituted with a substituent group, size-limited substituent group, or lower substituent group) or unsubstituted 2 to 8 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_5$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene. In embodiments, $L^2$ is a bond, substituted (e.g., substituted with a substituent group, size-limited substituent group, or lower substituent group) or unsubstituted $C_1$-$C_6$ alkylene (e.g., alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene.

In embodiments, $L^2$ is a substituted (e.g., substituted with a substituent group, size-limited substituent group, or lower substituent group) or unsubstituted 4 to 10 membered heteroalkylene (e.g., heteroalkylene, heteroalkenylene, or heteroalkynylene). In embodiments, $L^2$ is a substituted (e.g., substituted with a substituent group, size-limited substituent group, or lower substituent group) or unsubstituted 4 to 8 membered heteroalkylene (e.g., heteroalkylene, heteroalkenylene, or heteroalkynylene). In embodiments, $L^2$ is a substituted (e.g., substituted with a substituent group, size-limited substituent group, or lower substituent group) or unsubstituted 4 to 6 membered heteroalkylene (e.g., heteroalkylene, heteroalkenylene, or heteroalkynylene).

In embodiments, $L^3$ is an orthogonally cleavable linker. In embodiments, $L^3$ is a cleavable linker. In embodiments, $L^3$ is a chemically cleavable linker. In embodiments, $L^3$ is a photocleavable linker, an acid-cleavable linker, a base-cleavable linker, an oxidant-cleavable linker, a reductant-cleavable linker, or a fluoride-cleavable linker. In embodiments, $L^3$ is a photocleavable linker. In embodiments, $L^3$ is an acid-cleavable linker. In embodiments, $L^3$ is a base-cleavable linker. In embodiments, $L^3$ is an oxidant-cleavable linker. In embodiments, $L^3$ is a reductant-cleavable linker. In embodiments, $L^3$ is a fluoride-cleavable linker. In embodiments, $L^3$ is a cleavable linker including a dialkylketal linker, an azo linker, an allyl linker, a cyanoethyl linker, a 1-(4,4-dimethyl-2,6-dioxocyclohex-1-ylidene)ethyl linker, or a nitrobenzyl linker. In embodiments, $L^3$ is a cleavable linker including a dialkylketal linker. In embodiments, $L^3$ is an azo linker. In embodiments, $L^3$ is an allyl linker. In embodiments, $L^3$ is a cyanoethyl linker. In embodiments, $L^3$ is a 1-(4,4-dimethyl-2,6-dioxocyclohex-1-ylidene)ethyl linker, or a nitrobenzyl linker.

In embodiments, $L^3$ includes an orthogonally cleavable linker. In embodiments, $L^3$ includes a cleavable linker. In embodiments, $L^3$ includes a chemically cleavable linker. In embodiments, $L^3$ includes a photocleavable linker, an acid-cleavable linker, a base-cleavable linker, an oxidant-cleavable linker, a reductant-cleavable linker, or a fluoride-cleavable linker. In embodiments, $L^3$ includes a photocleavable linker. In embodiments, $L^3$ includes an acid-cleavable linker. In embodiments, $L^3$ includes a base-cleavable linker. In embodiments, $L^3$ includes an oxidant-cleavable linker. In embodiments, $L^3$ includes a reductant-cleavable linker. In embodiments, $L^3$ includes a fluoride-cleavable linker. In embodiments, $L^3$ includes a dialkylketal linker, an azo linker, an allyl linker, a cyanoethyl linker, a 1-(4,4-dimethyl-2,6-dioxocyclohex-1-ylidene)ethyl linker, or a nitrobenzyl linker. In embodiments, $L^3$ includes a dialkylketal linker. In embodiments, $L^3$ includes an azo linker. In embodiments, $L^3$ includes an allyl linker. In embodiments, $L^3$ includes a cyanoethyl linker. In embodiments, $L^3$ includes a 1-(4,4-dimethyl-2,6-dioxocyclohex-1-ylidene)ethyl linker. In embodiments, $L^3$ includes a nitrobenzyl linker.

In embodiments, $L^3$ is $L^{3A}\text{-}L^{3B}\text{-}L^{3C}\text{-}L^{3D}\text{-}L^{3E}$; and $L^{3A}$, $L^{3B}$, $L^{3C}$, $L^{3D}$ and $L^{3E}$ are independently a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{3A}$, $L^{3B}$, $L^{3C}$, $L^{3D}$, and $L^{3E}$ is not a bond.

In embodiments, $L^3$ is $L^{3A}\text{-}L^{3B}\text{-}L^{3C}\text{-}L^{3D}\text{-}L^{3E}$; and $L^{3A}$, $L^{3B}$, $L^{3C}$, $L^{3D}$ and $L^{3E}$ are independently a bond, —NN—, —NHC(O)—, —C(O)NH—, substituted (e.g., substituted with a substituent group, size-limited substituent group, or lower substituent group) or unsubstituted $C_1$-$C_{20}$ alkylene (e.g., alkylene, alkenylene, or alkynylene), substituted (e.g., substituted with a substituent group, size-limited substituent group, or lower substituent group) or unsubstituted 2 to 20 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_{20}$ cycloalkylene, substituted (e.g., substituted with a substituent group, size-limited substituent group, or lower substituent group) or unsubstituted 3 to 20 membered heterocycloalkylene, substituted (e.g., substituted with a substituent group, size-limited substituent group, or lower substituent group) or unsubstituted $C_6$-$C_{20}$ arylene, or substituted (e.g., substituted with a substituent group, size-limited substituent group, or lower substituent group) or unsubstituted 5 to 20 membered heteroarylene; wherein at least one of $L^{3A}$, $L^{3B}$, $L^{3C}$, $L^{3D}$, and $L^{3E}$ is not a bond.

In embodiments, $L^3$ is $L^{3A}\text{-}L^{3B}\text{-}L^{3C}\text{-}L^{3D}\text{-}L^{3E}$; and $L^{3A}$, $L^{3B}$, $L^{3C}$, $L^{3D}$ and $L^{3E}$ are independently a bond, —NN—, —NHC(O)—, —C(O)NH—, substituted (e.g., substituted with a substituent group, size-limited substituent group, or lower substituent group) or unsubstituted $C_1$-$C_{10}$ alkylene (e.g., alkylene, alkenylene, or alkynylene), substituted (e.g., substituted with a substituent group, size-limited substituent group, or lower substituent group) or unsubstituted 2 to 10 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene; wherein at least one of $L^{3A}$, $L^{3B}$, $L^{3C}$, $L^{3D}$, and $L^{3E}$ is not a bond.

In embodiments, $L^3$ is $L^{3A}\text{-}L^{3B}\text{-}L^{3C}\text{-}L^{3D}\text{-}L^{3E}$; and $L^{3A}$, $L^{3B}$, $L^{3C}$, $L^{3D}$ and $L^{3E}$ are independently a bond, —NN—, —NHC(O)—, —C(O)NH—, substituted (e.g., substituted with a substituent group, size-limited substituent group, or lower substituent group) or unsubstituted $C_1$-$C_6$ alkylene (e.g., alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene; wherein at least one of $L^{3A}$, $L^{3B}$, $L^{3C}$, $L^{3D}$, and $L^{3E}$ is not a bond.

In embodiments, $L^3$ is $L^{3A}\text{-}L^{3B}\text{-}L^{3C}\text{-}L^{3D}\text{-}L^{3E}$; wherein $L^{3A}$ is a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene); $L^{3B}$ is a bond, —NN—, —NHC(O)—, —C(O)NH—, substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene; $L^{3C}$ is a bond, —NN—, —NHC(O)—, —C(O)NH—, substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene; $L^{3D}$ is a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene); and $L^{3E}$ is a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{3A}$, $L^{3B}$, $L^{3C}$, $L^{3D}$, and $L^{3E}$ is not a bond.

In embodiments, $L^3$ is a bond, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene.

In embodiments, $L^3$ is a bond, substituted (e.g., substituted with a substituent group, size-limited substituent group, or lower substituent group) or unsubstituted $C_1$-$C_{20}$ alkylene (e.g., alkylene, alkenylene, or alkynylene), substituted (e.g., substituted with a substituent group, size-limited substituent group, or lower substituent group) or unsubstituted 2 to 20 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_{20}$ cycloalkylene, substituted (e.g., substituted with a substituent group, size-limited substituent group, or lower substituent group) or unsubstituted 3 to 20 membered heterocycloalkylene, substituted (e.g., substituted with a substituent group, size-limited substituent group, or lower substituent group) or unsubstituted $C_6$-$C_{20}$ arylene, or substituted (e.g., substituted with a substituent group, size-limited substituent group, or lower substituent group) or unsubstituted 5 to 20 membered heteroarylene.

In embodiments, $L^3$ is a bond, substituted (e.g., substituted with a substituent group, size-limited substituent group, or lower substituent group) or unsubstituted $C_1$-$C_8$ alkylene (e.g., alkylene, alkenylene, or alkynylene), substituted (e.g., substituted with a substituent group, size-limited substituent group, or lower substituent group) or unsubstituted 2 to 8 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene.

In embodiments, $L^3$ is a bond, substituted (e.g., substituted with a substituent group, size-limited substituent group, or lower substituent group) or unsubstituted $C_1$-$C_6$ alkylene (e.g., alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene.

In embodiments, $L^3$ is a substituted (e.g., substituted with a substituent group, size-limited substituent group, or lower substituent group) or unsubstituted 3 to 10 membered heteroalkylene (e.g., heteroalkylene, heteroalkenylene, or heteroalkynylene). In embodiments, $L^3$ is a substituted (e.g., substituted with a substituent group, size-limited substituent group, or lower substituent group) or unsubstituted 3 to 8 membered heteroalkylene (e.g., heteroalkylene, heteroalkenylene, or heteroalkynylene). In embodiments, L³ is a substituted (e.g., substituted with a substituent group, size-limited substituent group, or lower substituent group) or unsubstituted 3 to 6 membered heteroalkylene (e.g., heteroalkylene, heteroalkenylene, or heteroalkynylene).

In embodiments, L³ is

,

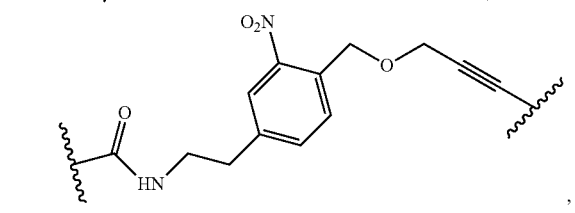,

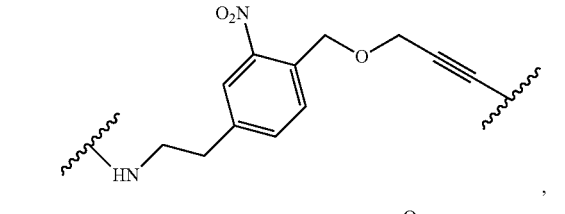,

,

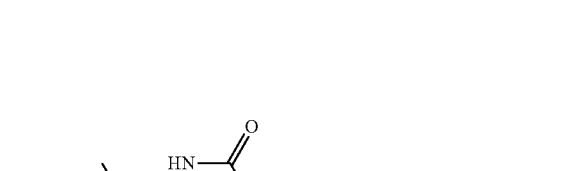,

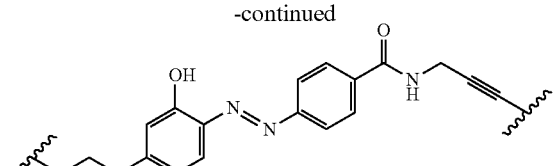,

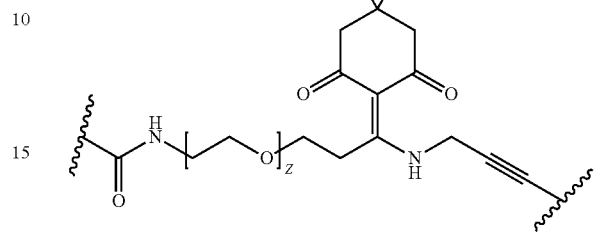

wherein Z is an integer from 0 to 20, or

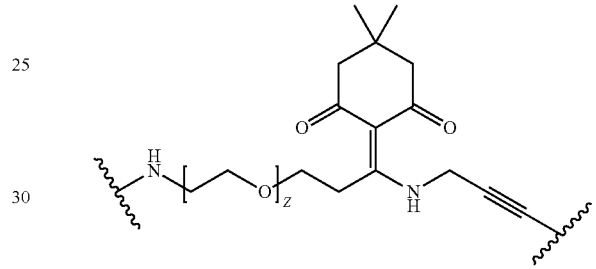

wherein Z is an integer from 0 to 20.

In embodiments, L²-C(CH₃)₂CH₂NHC(O)—.

In embodiments. L² is an orthogonally cleavable linker or a non-covalent linker. In embodiments, L² includes an orthogonally cleavable linker or a non-covalent linker. In embodiments, L² is an orthogonally cleavable linker. In embodiments, L² is a non-covalent linker.

In embodiments, -L²-R⁵ is

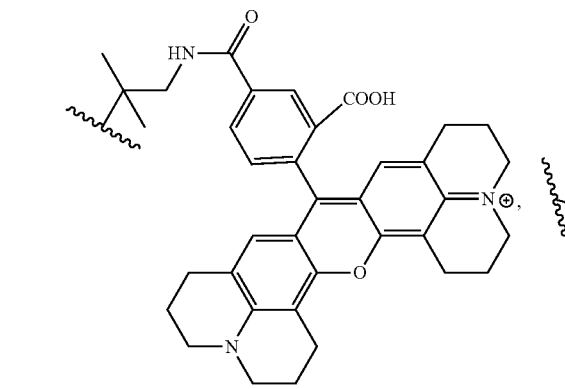

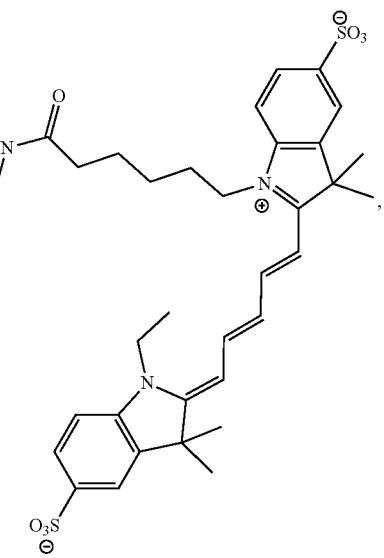

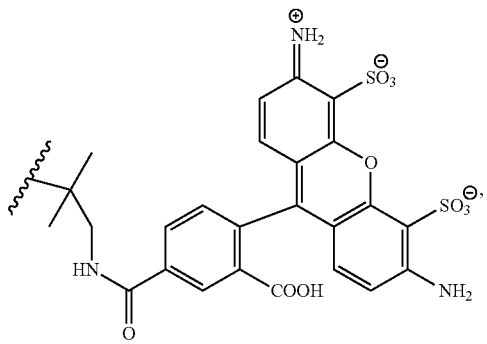
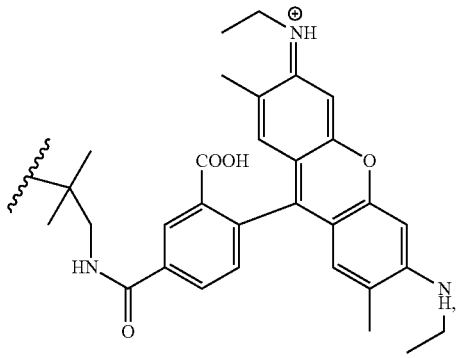
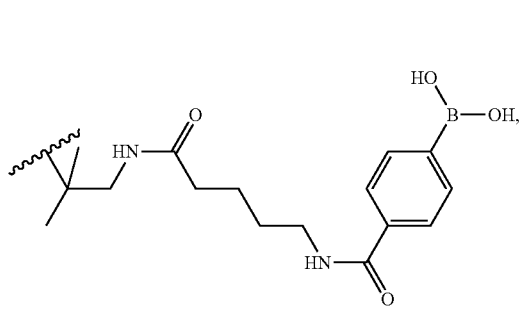
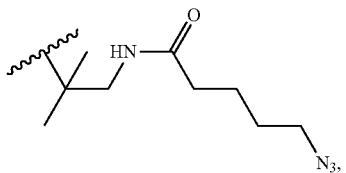
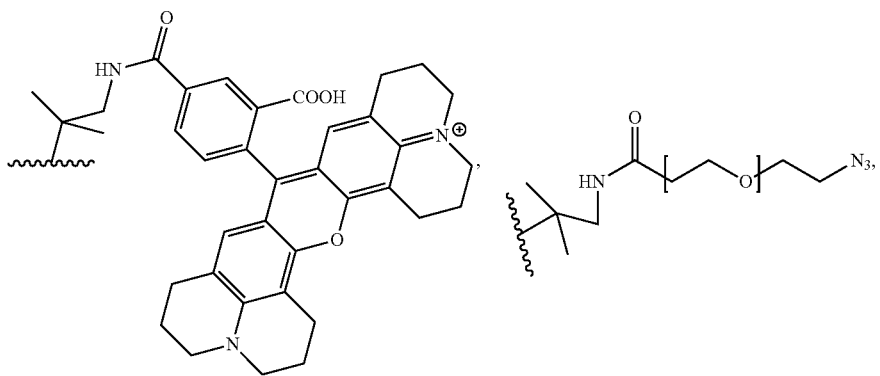
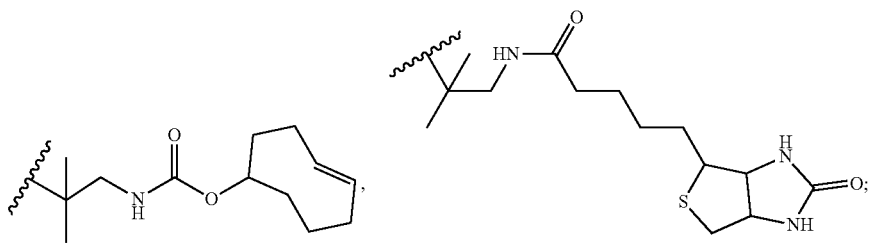

75
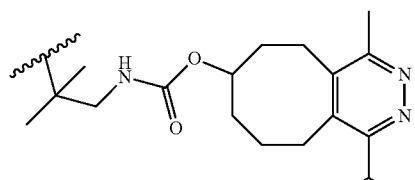
76
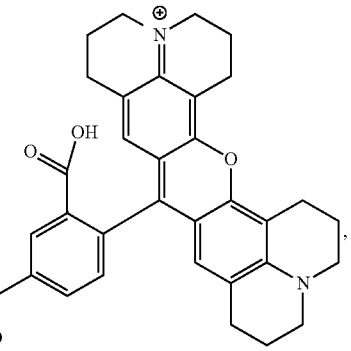
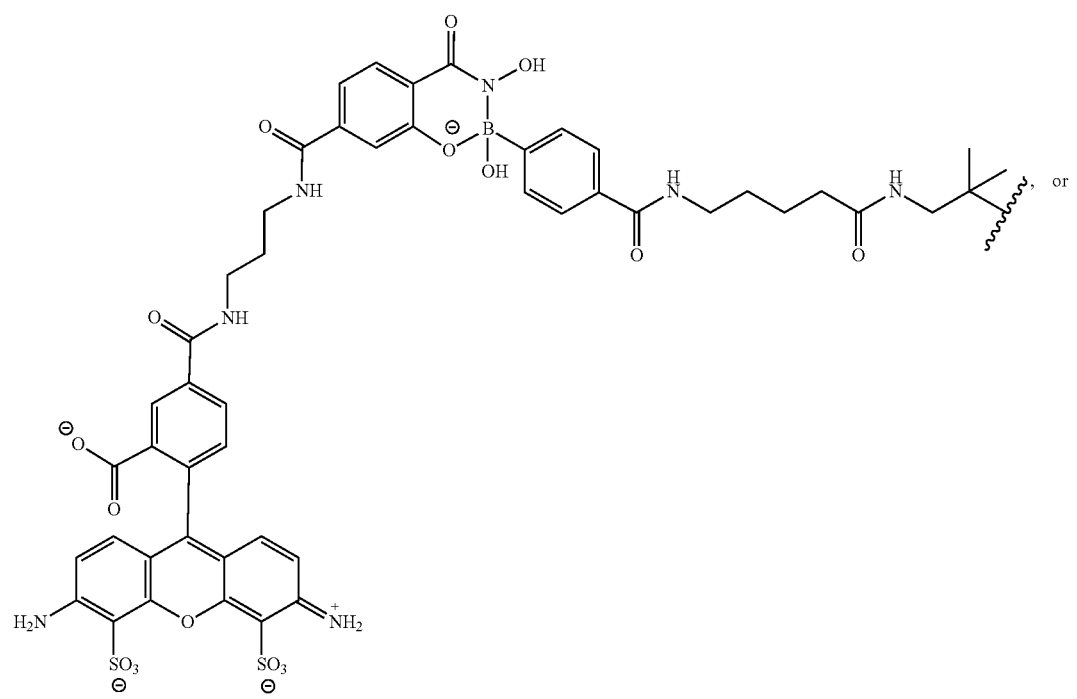

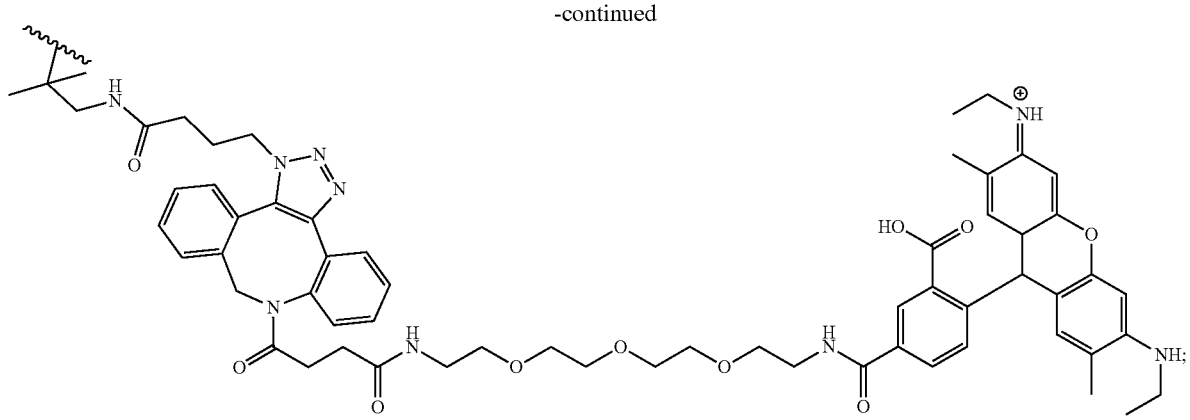
and z is an integer from 0 to 10.
In embodiments, -L²-R⁵ is
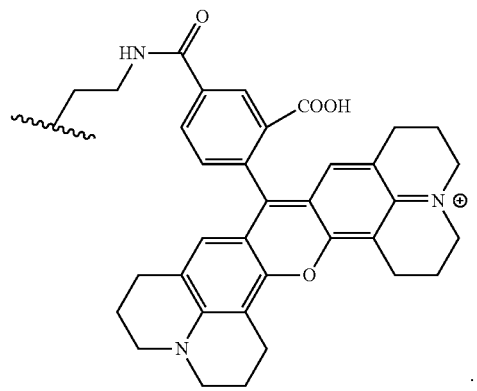 [SMILES: *CCNC(=O)c1ccc(C2=c3cc4c5c(c3Oc3c2cc2c6c3CCCN6CCC2)CCC[N+]=5CCC4)c(C(=O)O)c1]
In embodiments, -L²-R⁵ is
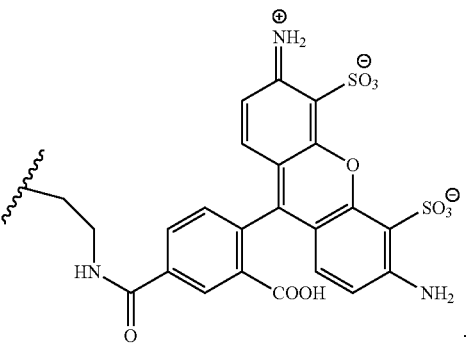
In embodiments, -L²-R⁵ is
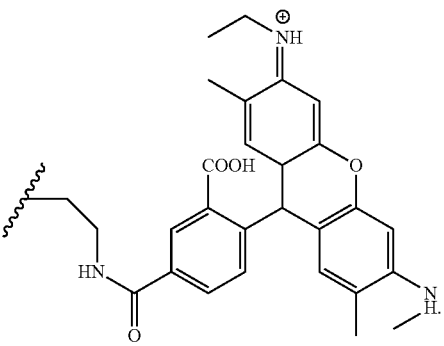 [SMILES: *CCNC(=O)c1ccc(C2c3cc(C)c(NC)cc3OC3=C/C(=[NH+]/CC)C(C)=CC32)c(C(=O)O)c1]
In embodiments, -L²-R⁵ is
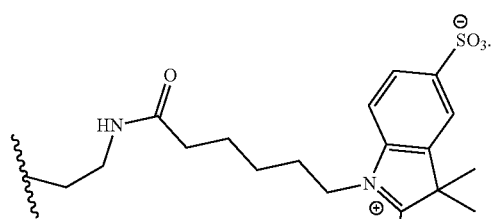
In embodiments, -L²-R⁵ is
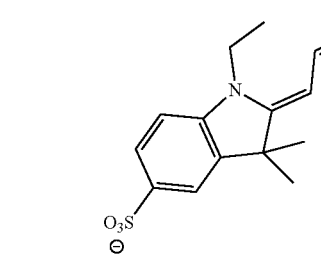
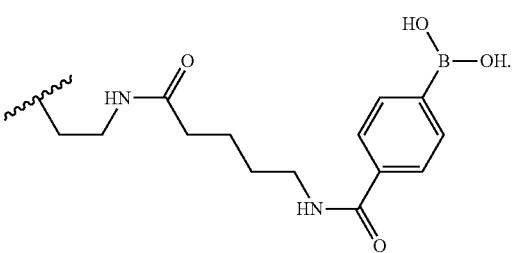 [SMILES: *CCNC(=O)CCCCNC(=O)c1ccc(B(O)O)cc1]

In embodiments, -L²-R⁵ is
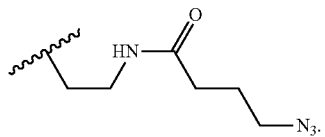 [SMILES: *CCNC(=O)CCCN=[N+]=[N-]]
In embodiments, -L²-R⁵ is
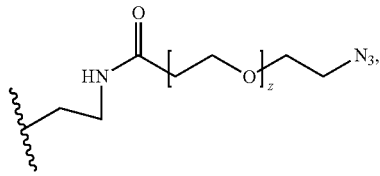
wherein z is an integer from 0 to 10. In embodiments, -L²-R⁵ is
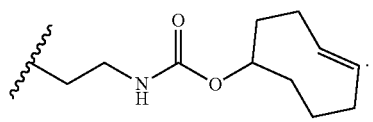 [SMILES: *CCNC(=O)OC1CC/C=C/CCC1]
In embodiments, -L²-R⁵ is
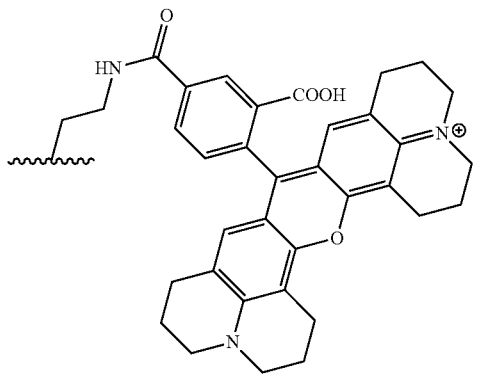
In embodiments, -L²-R⁵ is
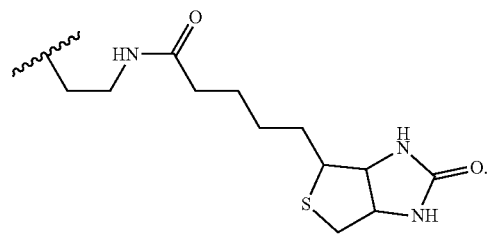 [SMILES: *CCNC(=O)CCCCC1SCC2NC(=O)NC21]
In embodiments, -L²-R⁵ is
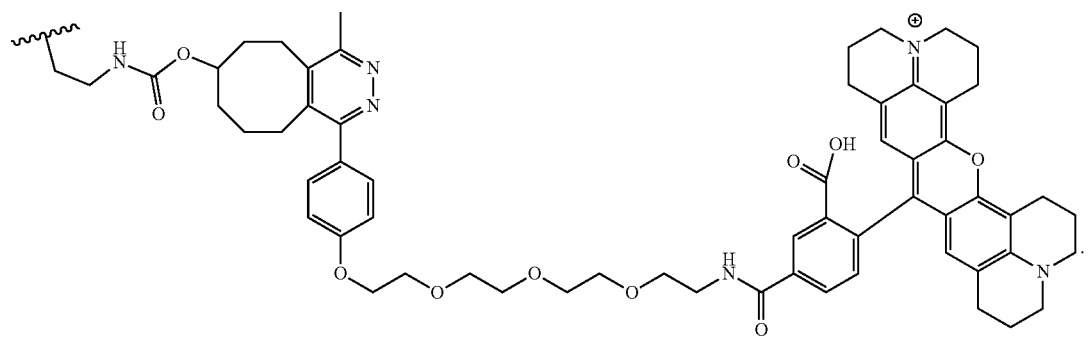 [SMILES: *CCNC(=O)OC1CCCc2c(-c3ccc(OCCOCCOCCOCCNC(=O)c4ccc(C5=c6cc7c8c(c6Oc6c5cc5c9c6CCCN9CCC5)CCC[N+]=8CCC7)c(C(=O)O)c4)cc3)nnc(C)c2CC1]

In embodiments, -L²-R⁵ is

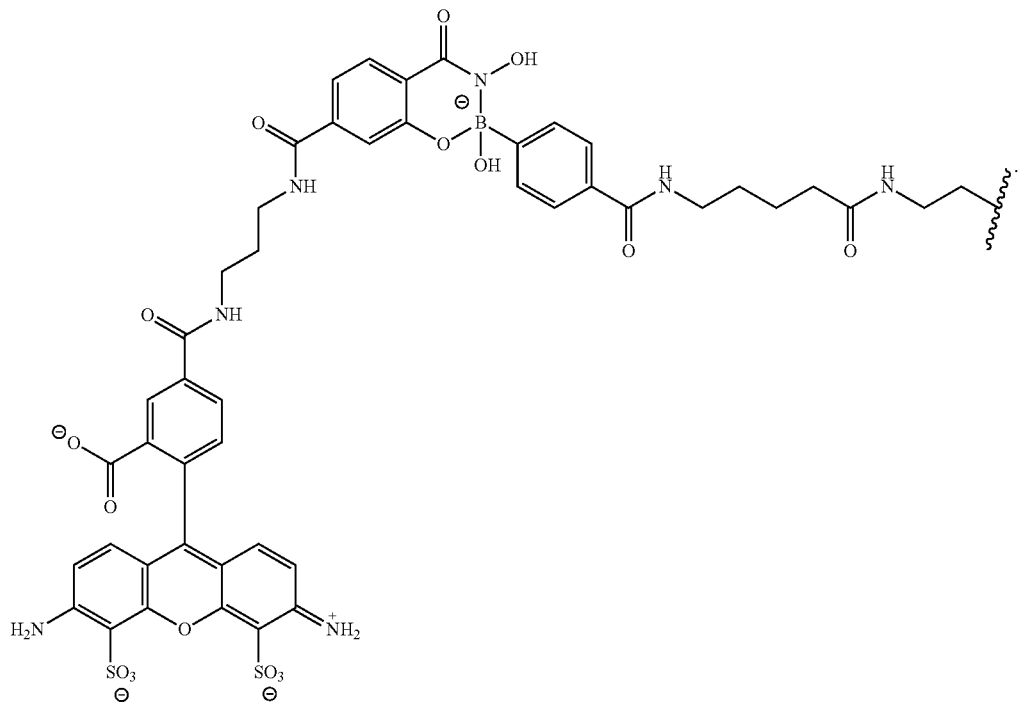

In embodiments, -L²-R⁵ is

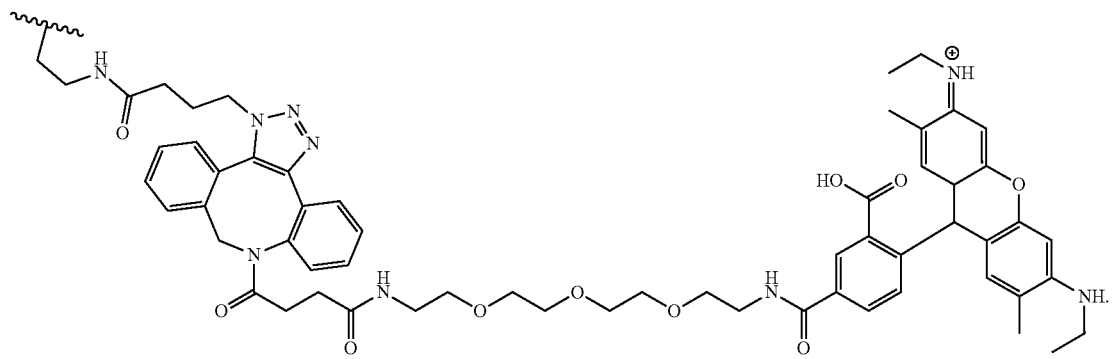 [SMILES: *CCNC(=O)CCCn1nnc2c1-c1ccccc1CN(C(=O)CCC(=O)NCCOCCOCCOCCNC(=O)c1ccc(C3c4cc(C)c(NCC)cc4OC4=C/C(=[NH+]/CC)C(C)=CC43)c(C(=O)O)c1)c1ccccc1-2]

In embodiments, L³ is

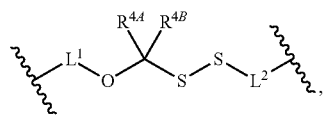

wherein L¹ is a bond, substituted (e.g., substituted with a substituent group, size-limited substituent group, or lower substituent group) or unsubstituted a substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene: L² is a bond, substituted (e.g., substituted with a substituent group, size-limited substituent group, or lower substituent group) or unsubstituted a substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene, a cleavable linker, an orthogonally cleavable linker, non-covalent linker, or $L^{2A}$-$L^{2B}$-$L^{2C}$-$L^{2D}$-, wherein $L^{2A}$ is a bond, substituted (e.g., substituted with a substituent group, size-limited substituent group, or lower substituent group) or unsubstituted a substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene); $L^{2B}$ is a bond substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene; $L^{2C}$ is a bond substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene; and $L^{2D}$ is a bond, substituted (e.g., substituted with a substituent group, size-limited substituent group, or lower substituent group) or unsubstituted a substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), wherein at least one of $L^{2A}$, $L^{2B}$, $L^{2C}$, $L^{2D}$ is not a bond; $R^{4A}$ is hydrogen, $CH_3$, $-CX^1_3$, $-CHX^1_2$, $-CH_2X^1$, $-OCX^1_3$, $-OCH_2X^1$, $-OCHX^1_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl; $R^{4B}$ is hydrogen, $CH_3$, $-CX^2_3$, $-CHX^2_2$, $-CH_2X^2$, $-OCX^2_3$, $-OCH_2X^2$, $-OCHX^2_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl; and $X^1$ and $X^2$ are independently halogen.

In embodiments, $L^3$ is

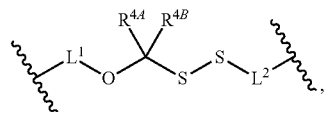

wherein $L^1$ is covalent linker; $L^2$ is covalent linker; $R^{4A}$ is hydrogen, $CH_3$, $-CX^1_3$, $-CHX^1_2$, $-CH_2X^1$, $-OCX^1_3$, $-OCH_2X^1$, $-OCHX^1_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl; $R^{4B}$ is hydrogen, $CH_3$, $-CX^2_3$, $-CHX^2_2$, $-CH_2X^2$, $-OCX^2_3$, $-OCH_2X^2$, $-OCHX^2_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl; and $X^1$ and $X^2$ are independently halogen In embodiments, $L^4$ is an orthogonally cleavable linker. In embodiments, $L^4$ is a cleavable linker. In embodiments, $L^4$ is a chemically cleavable linker. In embodiments, $L^4$ is a photocleavable linker, an acid-cleavable linker, a base-cleavable linker, an oxidant-cleavable linker, a reductant-cleavable linker, or a fluoride-cleavable linker. In embodiments, $L^4$ is a photocleavable linker. In embodiments, $L^4$ is an acid-cleavable linker. In embodiments, $L^4$ is a base-cleavable linker. In embodiments, $L^4$ is an oxidant-cleavable linker. In embodiments, $L^4$ is a reductant-cleavable linker. In embodiments, $L^4$ is a fluoride-cleavable linker. In embodiments, $L^4$ is a cleavable linker including a dialkylketal linker, an azo linker, an allyl linker, a cyanoethyl linker, a 1-(4,4-dimethyl-2,6-dioxocyclohex-1-ylidene)ethyl linker, or a nitrobenzyl linker. In embodiments, $L^4$ is a cleavable linker including a dialkylketal linker. In embodiments, $L^4$ is an azo linker. In embodiments, $L^4$ is an allyl linker. In embodiments, $L^4$ is a cyanoethyl linker. In embodiments, $L^4$ is a 1-(4,4-dimethyl-2,6-dioxocyclohex-1-ylidene)ethyl linker, or a nitrobenzyl linker.

In embodiments, $L^4$ includes an orthogonally cleavable linker. In embodiments, $L^4$ includes a cleavable linker. In embodiments, $L^4$ includes a chemically cleavable linker. In embodiments, $L^4$ includes a photocleavable linker, an acid-cleavable linker, a base-cleavable linker, an oxidant-cleavable linker, a reductant-cleavable linker, or a fluoride-cleavable linker. In embodiments. $L^4$ includes a photocleavable linker. In embodiments, $L^4$ includes an acid-cleavable linker. In embodiments, $L^4$ includes a base-cleavable linker. In embodiments, $L^4$ includes an oxidant-cleavable linker. In embodiments, $L^4$ includes a reductant-cleavable linker. In embodiments, $L^4$ includes a fluoride-cleavable linker. In embodiments, $L^4$ includes a dialkylketal linker, an azo linker, an allyl linker, a cyanoethyl linker, a 1-(4,4-dimethyl-2,6-dioxocyclohex-1-ylidene)ethyl linker, or a nitrobenzyl linker. In embodiments, $L^4$ includes a dialkylketal linker. In embodiments, $L^4$ includes an azo linker. In embodiments, $L^4$ includes an allyl linker. In embodiments, $L^4$ includes a cyanoethyl linker. In embodiments, $L^4$ includes a 1-(4,4-dimethyl-2,6-dioxocyclohex-1-ylidene)ethyl linker. In embodiments. $L^4$ includes a nitrobenzyl linker.

In embodiments, $L^4$ is $L^{4A}$-$L^{4B}$-$L^{4C}$-$L^{4D}$-$L^{4E}$; and $L^{4A}$, $L^{4B}$, $L^{4C}$, $L^{4D}$ and $L^{4E}$ are independently a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{4A}$, $L^{4B}$, $L^{4C}$, $L^{4D}$, and $L^{4E}$ is not a bond.

In embodiments, $L^4$ is $L^{4A}$-$L^{4B}$-$L^{4C}$-$L^{4D}$-$L^{4E}$; and $L^{4A}$, $L^{4B}$, $L^{4C}$, $L^{4D}$ and $L^{4E}$ are independently a bond, —NN—, —NHC(O)—, —C(O)NH—, substituted (e.g., substituted with a substituent group, size-limited substituent group, or lower substituent group) or unsubstituted $C_1$-$C_{20}$ alkylene (e.g., alkylene, alkenylene, or alkynylene), substituted (e.g., substituted with a substituent group, size-limited substituent group, or lower substituent group) or unsubstituted 2 to 20 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_{20}$ cycloalkylene, substituted (e.g., substituted with a substituent group, size-limited substituent group, or lower substituent group) or unsubstituted 3 to 20 membered heterocycloalkylene, substituted (e.g., substituted with a substituent group, size-limited substituent group, or lower substituent group) or unsubstituted $C_6$-$C_{20}$ arylene, or substituted (e.g., substituted with a substituent group, size-limited substituent group, or lower substituent group) or unsubstituted 5 to 20 membered heteroarylene; wherein at least one of $L^{4A}$, $L^{4B}$, $L^{4C}$, $L^{4D}$ and $L^{4E}$ is not a bond.

In embodiments, $L^4$ is $L^{4A}$-$L^{4B}$-$L^{4C}$-$L^{4D}$-$L^{4E}$; and $L^{4A}$, $L^{4B}$, $L^{4C}$, $L^{4D}$ and $L^{4E}$ are independently a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted 2 to 10 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or un substituted $C_6$-$C_{10}$ arylene, or substituted (e.g., substituted with a substituent group, size-limited substituent group, or lower substituent group) or unsubstituted 5 to 10 membered heteroarylene; wherein at least one of $L^{4A}$, $L^{4B}$, $L^{4C}$, $L^{4D}$ and $L^{4E}$ is not a bond.

In embodiments, $L^4$ is $L^{4A}$-$L^{4B}$-$L^{4C}$-$L^{4D}$-$L^{4E}$; and $L^{4A}$, $L^{4B}$, $L^{4C}$, $L^{4D}$ and $L^{4E}$ are independently a bond, —NN—, —NHC(O)—, —C(O)NH—, substituted (e.g., substituted with a substituent group, size-limited substituent group, or lower substituent group) or unsubstituted $C_1$-$C_6$ alkylene (e.g., alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene; wherein at least one of $L^{4A}$, $L^{4B}$, $L^{4C}$, $L^{4D}$ and $L^{4E}$ is not a bond.

In embodiments, $L^4$ is $L^{4A}$-$L^{4B}$-$L^{4C}$-$L^{4D}$-$L^{4E}$; wherein $L^{4A}$ is a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene); $L^{4B}$ is a bond, —NN—, —NHC(O)—, —C(O)NH—, substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene; $L^{4C}$ is a bond, —NN—, —NHC(O)—, —C(O)NH—, substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene; $L^{4D}$ is a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene); and $L^{4E}$ is a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{4A}$, $L^{4B}$, $L^{4C}$, $L^{4D}$, and $L^{4E}$ is not a bond.

In embodiments, $L^4$ is a bond, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene.

In embodiments, $L^4$ is a bond, substituted (e.g., substituted with a substituent group, size-limited substituent group, or lower substituent group) or unsubstituted $C_1$-$C_{20}$ alkylene (e.g., alkylene, alkenylene, or alkynylene), substituted (e.g., substituted with a substituent group, size-limited substituent group, or lower substituent group) or unsubstituted 2 to 20 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_{20}$ cycloalkylene, substituted (e.g., substituted with a substituent group, size-limited substituent group, or lower substituent group) or unsubstituted 3 to 20 membered heterocycloalkylene, substituted (e.g., substituted with a substituent group, size-limited substituent group, or lower substituent group) or unsubstituted $C_6$-$C_{20}$ arylene, or substituted (e.g., substituted with a substituent group, size-limited substituent group, or lower substituent group) or unsubstituted 5 to 20 membered heteroarylene.

In embodiments, $L^4$ is a bond, substituted (e.g., substituted with a substituent group, size-limited substituent group, or lower substituent group) or unsubstituted $C_1$-$C_8$ alkylene (e.g., alkylene, alkenylene, or alkynylene), substituted (e.g., substituted with a substituent group, size-limited substituent group, or lower substituent group) or unsubstituted 2 to 8 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or un substituted $C_6$-$C_{10}$ arylene, or substituted (e.g., substituted with a substituent group, size-limited substituent group, or lower substituent group) or unsubstituted 5 to 10 membered heteroarylene.

In embodiments, $L^4$ is a bond, substituted (e.g., substituted with a substituent group, size-limited substituent group, or lower substituent group) or unsubstituted $C_1$-$C_6$ alkylene (e.g., alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene.

In embodiments, $L^4$ is a substituted (e.g., substituted with a substituent group, size-limited substituent group, or lower substituent group) or unsubstituted 3 to 10 membered heteroalkylene (e.g., heteroalkylene, heteroalkenylene, or heteroalkynylene). In embodiments, $L^4$ is a substituted (e.g., substituted with a substituent group, size-limited substituent group, or lower substituent group) or unsubstituted 3 to 8 membered heteroalkylene (e.g., heteroalkylene, heteroalkenylene, or heteroalkynylene). In embodiments, $L^4$ is a substituted (e.g., substituted with a substituent group, size-limited substituent group, or lower substituent group) or unsubstituted 3 to 6 membered heteroalkylene (e.g., heteroalkylene, heteroalkenylene, or heteroalkynylene).

In embodiments, $L^{4z}$ is an orthogonally cleavable linker. In embodiments, $L^{4z}$ is a cleavable linker. In embodiments, $L^{1z}$ is a chemically cleavable linker. In embodiments, $L^{4z}$ is a photocleavable linker, an acid-cleavable linker, a base-cleavable linker, an oxidant-cleavable linker, a reductant-cleavable linker, or a fluoride-cleavable linker. In embodiments, $L^{4z}$ is a photocleavable linker. In embodiments, $L^{4z}$ is an acid-cleavable linker. In embodiments, $L^{4z}$ is a base-cleavable linker. In embodiments, $L^{4z}$ is an oxidant-cleavable linker. In embodiments, $L^{4z}$ is a reductant-cleavable linker. In embodiments, $L^{4z}$ is a cleavable linker including a dialkylketal linker, an azo linker, an allyl linker, a cyanoethyl linker, a 1-(4,4-dimethyl-2,6-dioxocyclohex-1-ylidene)ethyl linker, or a nitrobenzyl linker.

In embodiments, $L^{4z}$ includes an orthogonally cleavable linker. In embodiments, $L^{4z}$ includes a cleavable linker. In embodiments, $L^{4z}$ includes a chemically cleavable linker. In embodiments, $L^{4z}$ includes a photocleavable linker, an acid-cleavable linker, a base-cleavable linker, an oxidant-cleavable linker, a reductant-cleavable linker, or a fluoride-cleavable linker. In embodiments, $L^{4z}$ includes a photocleavable linker. In embodiments, $L^{4z}$ includes an acid-cleavable linker. In embodiments, $L^{4z}$ includes a base-cleavable linker. In embodiments, $L^{4z}$ includes an oxidant-cleavable linker. In embodiments, $L^{4z}$ includes a reductant-cleavable linker. In embodiments, $L^{4z}$ includes a cleavable linker including a dialkylketal linker, an azo linker, an allyl linker, a cyanoethyl linker, a 1-(4,4-dimethyl-2,6-dioxocyclohex-1-ylidene)ethyl linker, or a nitrobenzyl linker.

In embodiments, $L^{4z}$ is $L^{4zA}$-$L^{4zB}$-$L^{4zC}$-$L^{4zD}$-$L^{4zE}$; and $L^{4zA}$, $L^{4zB}$, $L^{4zC}$, $L^{4zD}$ and $L^{4zE}$ are independently a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{4zA}$, $L^{4zB}$, $L^{4zC}$, $L^{4zD}$ and $L^{4zE}$ is not a bond.

In embodiments, $L^{4z}$ is $L^{4zA}$-$L^{4zB}$-$L^{4zC}$-$L^{4zD}$-$L^{4zE}$; and $L^{4zA}$, $L^{4zB}$, $L^{4zC}$, $L^{4zD}$ and $L^{4zE}$ are independently a bond, —NN—, —NHC(O)—, —C(O)NH—, substituted (e.g., substituted with a substituent group, size-limited substituent group, or lower substituent group) or unsubstituted $C_1$-$C_{20}$ alkylene (e.g., alkylene, alkenylene, or alkynylene), substituted (e.g., substituted with a substituent group, size-limited substituent group, or lower substituent group) or unsubstituted 2 to 20 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_{20}$ cycloalkylene, substituted (e.g., substituted with a substituent group, size-limited substituent group, or lower substituent group) or unsubstituted 3 to 20 membered heterocycloalkylene, substituted (e.g., substituted with a substituent group, size-limited substituent group, or lower substituent group) or unsubstituted $C_6$-$C_{20}$ arylene, or substituted (e.g., substituted with a substituent group, size-limited substituent group, or lower substituent group) or unsubstituted 5 to 20 membered heteroarylene; wherein at least one of $L^{4zA}$, $L^{4zB}$, $L^{4zC}$, $L^{4zD}$ and $L^{4zE}$ is not a bond.

In embodiments, $L^{4z}$ is $L^{4zA}$-$L^{4zB}$-$L^{4zC}$-$L^{4zD}$-$L^{4zE}$; and $L^{4zA}$, $L^{4zB}$, $L^{4zC}$, $L^{4zD}$ and $L^{4zE}$ are independently a bond, —NN—, —NHC(O)—, —C(O)NH—, substituted (e.g., substituted with a substituent group, size-limited substituent group, or lower substituent group) or unsubstituted $C_1$-$C_{10}$ alkylene (e.g., alkylene, alkenylene, or alkynylene), substituted (e.g., substituted with a substituent group, size-limited substituent group, or lower substituent group) or unsubstituted 2 to 10 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene; wherein at least one of $L^{4zA}$, $L^{4zB}$, $L^{4zC}$, $L^{4zD}$ and $L^{4zE}$ is not a bond.

In embodiments, $L^{4z}$ is $L^{4zA}$-$L^{4zB}$-$L^{4zC}$-$L^{4zD}$-$L^{4zE}$; and $L^{4zA}$, $L^{4zB}$, $L^{4zC}$, $L^{4zD}$ and $L^{4zE}$ are independently a bond, —NN—, —NHC(O)—, —C(O)NH—, substituted (e.g., substituted with a substituent group, size-limited substituent group, or lower substituent group) or unsubstituted $C_1$-$C_6$ alkylene (e.g., alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g.; substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group; or lower substituent group) or unsubstituted phenyl, or substituted (e.g., substituted with a substituent group, size-limited substituent group, or lower substituent group) or unsubstituted 5 to 6 membered heteroarylene; wherein at least one of $L^{4zA}$, $L^{4zB}$, $L^{4zC}$, $L^{4zD}$ and $L^{4zE}$ is not a bond.

In embodiments, $L^{4z}$ is $L^{4zA}$-$L^{4zB}$-$L^{4zC}$-$L^{4zD}$-$L^{4zE}$; wherein $L^{4zA}$ is a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene); $L^{4zB}$ is a bond, —NN—, —NHC(O)—, —C(O)NH—, substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene; $L^{4zC}$ is a bond, —NN—, —NHC(O)—, —C(O)NH—, substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, substituted (e.g., substituted with a substituent group, size-limited substituent group, or lower substituent group) or unsubstituted heteroarylene; $L^{4zD}$ is a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene); and $L^{4zE}$ is a bond, —NN—, —NHC(O)—, —C(O)NH—, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{4zA}$, $L^{4zB}$, $L^{4zC}$, $L^{4zD}$ and $L^{4zE}$ is not a bond.

In embodiments, $L^{4z}$ is a bond, substituted (e.g., substituted with a substituent group, size-limited substituent group, or lower substituent group) or unsubstituted alkylene (e.g., alkylene, alkenylene, or alkynylene), substituted (e.g., substituted with a substituent group, size-limited substituent group, or lower substituent group) or unsubstituted heteroalkylene (e.g., heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene.

In embodiments, $L^{4z}$ is a bond, substituted (e.g., substituted with a substituent group, size-limited substituent group, or lower substituent group) or unsubstituted $C_1$-$C_{20}$ alkylene (e.g., alkylene, alkenylene, or alkynylene), substituted (e.g., substituted with a substituent group, size-limited substituent group, or lower substituent group) or unsubstituted 2 to 20 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_{20}$ cycloalkylene, substituted (e.g., substituted with a substituent group, size-limited substituent group, or lower substituent group) or unsubstituted 3 to 20 membered heterocycloalkylene, substituted (e.g., substituted with a substituent group, size-limited substituent group, or lower substituent group) or unsubstituted $C_6$-$C_{20}$ arylene, or substituted (e.g., substituted with a substituent group, size-limited substituent group, or lower substituent group) or unsubstituted 5 to 20 membered heteroarylene.

In embodiments, $L^{4z}$ is a bond, substituted (e.g., substituted with a substituent group, size-limited substituent group, or lower substituent group) or unsubstituted $C_1$-$C_8$ alkylene (e.g., alkylene, alkenylene, or alkynylene), substituted (e.g., substituted with a substituent group, size-limited substituent group, or lower substituent group) or unsubstituted 2 to 8 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_8$ cycloalkylene, substituted (e.g., substituted with a substituent group, size-limited substituent group, or lower substituent group) or unsubstituted 3 to 8 membered heterocycloalkylene, substituted (e.g., substituted with a substituent group, size-limited substituent group, or lower substituent group) or unsubstituted $C_6$-$C_{10}$ arylene, or substituted (e.g., substituted with a substituent group, size-limited substituent group, or lower substituent group) or unsubstituted 5 to 10 membered heteroarylene.

In embodiments, $L^{4z}$ is a bond, substituted (e.g., substituted with a substituent group, size-limited substituent group, or lower substituent group) or unsubstituted $C_1$-$C_6$ alkylene (e.g., alkylene, alkenylene, or alkynylene), substituted (e.g., substituted with a substituent group, size-limited substituent group, or lower substituent group) or unsubstituted 2 to 6 membered heteroalkylene (e.g., heteroalkylene, heteroalkenylene, or heteroalkynylene), substituted (e.g., substituted with a substituent group, size-limited substituent group, or lower substituent group) or unsubstituted $C_3$-$C_6$ cycloalkylene, substituted (e.g., substituted with a substituent group, size-limited substituent group, or lower substituent group) or unsubstituted 3 to 6 membered heterocycloalkylene, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroarylene.

In embodiments, $L^{4z}$ is a substituted (e.g., substituted with a substituent group, size-limited substituent group, or lower substituent group) or unsubstituted 3 to 10 membered heteroalkylene (e.g., heteroalkylene, heteroalkenylene, or heteroalkynylene). In embodiments, $L^{1z}$ is a substituted (e.g., substituted with a substituent group, size-limited substituent group, or lower substituent group) or unsubstituted 3 to 8 membered heteroalkylene (e.g., heteroalkylene, heteroalkenylene, or heteroalkynylene). In embodiments, $L^{4z}$ is a substituted (e.g., substituted with a substituent group, size-limited substituent group, or lower substituent group) or unsubstituted 3 to 6 membered heteroalkylene (e.g., heteroalkylene, heteroalkenylene, or heteroalkynylene).

In embodiments, $R^3$ is —OH. In embodiments, $R^3$ is a monophosphate. In embodiments, $R^3$ is a diphosphate. In embodiments, $R^3$ is triphosphate. In embodiments, $R^3$ is a polyphosphate. In embodiments, $R^3$ is monophosphate, diphosphate, triphosphate, tetraphosphate, pentaphosphate, or hexaphosphate. In embodiments, $R^3$ is tetraphosphate, pentaphosphate, or hexaphosphate. In embodiments, $R^3$ is tetraphosphate. In embodiments, $R^3$ is pentaphosphate. In embodiments, $R^3$ is hexaphosphate.

In embodiments, $R^3$ is a nucleic acid. In embodiments, $R^3$ is a residue of a nucleic acid. In embodiments, $R^3$ is a base of 10 to 10,000 base of a nucleic acid. In embodiments, $R^3$ is a 100 to 10,000 base of a nucleic acid. In embodiments, $R^3$ is a 1000 to 10,000 base of a nucleic acid. In embodiments, $R^3$ is a 10 to 8,000 base of a nucleic acid. In embodiments, $R^3$ is a 10 to 9,000 base of a nucleic acid. In embodiments, $R^3$ is a 10 to 7,000 base of a nucleic acid. In embodiments, $R^3$ is a 10 to 6,000 base of a nucleic acid. In embodiments, $R^3$ is a 10 to 5,000 base of a nucleic acid. In embodiments, $R^3$ is a 10 to 4,000 base of a nucleic acid. In embodiments, $R^3$ is a 10 to 3,000 base of a nucleic acid. In embodiments, $R^3$ is a 10 to 2,000 base of a nucleic acid. In embodiments, $R^3$ is a 10 to 1,000 base of a nucleic acid. In embodiments, $R^3$ is a 10 to 900 base of a nucleic acid. In embodiments, $R^3$ is a 10 to 800 base of a nucleic acid. In embodiments, $R^3$ is a 10 to 700 base of a nucleic acid. In embodiments, $R^3$ is a 10 to 600 base of a nucleic acid. In embodiments, $R^3$ is a 10 to 500 base of a nucleic acid. In embodiments, $R^3$ is a 10 to 400 base of a nucleic acid. In embodiments, $R^3$ is a 10 to 300 base of a nucleic acid. In embodiments, $R^3$ is a 10 to 200 base of a nucleic acid. In embodiments, $R^3$ is a 10 to 90 base of a nucleic acid. In embodiments, $R^3$ is a 10 to 75 base of a nucleic acid.

In embodiments, $R^3$ is a 5 to 25 base nucleic acid. In embodiments, $R^3$ is a 10 to 25 base nucleic acid. In embodiments, $R^3$ is a 10 to 20 base nucleic acid. In embodiments, $R^3$ is a 10 to 15 base nucleic acid. In embodiments, $R^3$ is a 10 to 1000 base nucleic acid. In embodiments, $R^3$ is a 100 to 600 base nucleic acid. In embodiments, $R^3$ is a 10 to 500 base nucleic acid. In embodiments, $R^3$ is a 10 to 250 base nucleic acid. In embodiments, $R^3$ is a 10 to 100 base nucleic acid. In embodiments, $R^3$ is a 10 to 50 base nucleic acid.

In embodiments, $R^3$ is a nucleobase of a nucleic acid. In embodiments, $R^3$ is a nucleotide of a nucleic acid. In embodiments, $R^3$ is a nucleoside of a nucleic acid. In embodiments, $R^3$ is a base of a nucleic acid 10 to 10,000 nucleotides in length. In embodiments, $R^3$ is a base of a nucleic acid 100 to 10,000 nucleotides in length. In embodiments, $R^3$ is a base of a nucleic acid 1000 to 10,000 nucleotides in length. In embodiments, $R^3$ is a base of a nucleic acid 10 to 8,000 nucleotides in length. In embodiments, $R^3$ is a base of a nucleic acid 10 to 9,000 nucleotides in length. In embodiments, $R^3$ is a base of a nucleic acid 10 to 7,000 nucleotides in length. In embodiments, $R^3$ is a base of a nucleic acid 10 to 6,000 nucleotides in length. In embodiments, $R^3$ is a base of a nucleic acid 10 to 5,000 nucleotides in length. In embodiments, $R^3$ is a base of a nucleic acid 10 to 4,000 base of a nucleic acid. In embodiments, $R^3$ is a base of a nucleic acid 10 to 3,000 nucleotides in length. In embodiments, $R^3$ is a base of a nucleic acid 10 to 2,000 nucleotides in length. In embodiments, $R^3$ is a base of a nucleic acid 10 to 1,000 nucleotides in length. In embodiments, $R^3$ is a base of a nucleic acid 10 to 900 nucleotides in length. In embodiments, $R^3$ is a base of a nucleic acid 10 to 800 nucleotides in length. In embodiments, $R^3$ is a base of a nucleic acid 10 to 700 nucleotides in length. In embodiments, $R^3$ is a base of a nucleic acid 10 to 600 base of a nucleic acid. In embodiments, $R^3$ is a base of a nucleic acid 10 to 500 nucleotides in length. In embodiments, $R^3$ is a base of a nucleic acid 10 to 400 nucleotides in length. In embodiments, $R^3$ is a base of a nucleic acid 10 to 300 nucleotides in length. In embodiments, $R^3$ is a base of a nucleic acid 10 to 200 nucleotides in length. In embodiments, $R^3$ is a base of a nucleic acid 10 to 90 nucleotides in length. In embodiments, $R^3$ is a base of a nucleic acid 10 to 75 nucleotides in length.

In embodiments, $R^{4A}$ is hydrogen, $CH_3$, $-CX^1_3$, $-CHX^1_2$, $-CH_2X^1$, $-OCX^1_3$, $-OCH_2X^1$, $-OCHX^1_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. In embodiments, $R^{4A}$ is hydrogen, $CH_3$, $-CX^1_3$, $-CHX^1_2$, $-CH_2X^1$, $-OCX^1_3$, $-OCH_2X^1$, $-OCHX^1_2$, $-CN$, $-OH$, $-SH$, $-NH_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl. In embodiments, $R^{4A}$ is hydrogen.

In embodiments, $R^{4A}$ is hydrogen, $-CH_3$, $-CHX^1_2$, $-CH_2X^1$, $-CN$, -Ph, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

In embodiments, $R^{4B}$ is hydrogen, $CH_3$, $-CX^2_3$, $-CHX^2_2$, $-CH_2X^2$, $-OCX^2_3$, $-OCH_2X^2$, $-OCHX^2_2$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. In embodiments, $R^{4B}$ is hydrogen, $CH_3$, $-CX^2{}_3$, $-CHX^2{}_2$, $-CH_2X^2$, $-OCX^2{}_3$, $-OCH_2X^2$, $-OCHX^2{}_2$, $-CN$, $-OH$, $-SH$, $-NH_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl. In embodiments, $R^{4B}$ is hydrogen.

In embodiments, $R^{4B}$ is hydrogen, $-CH_3$, $-CHX^2{}_2$, $-CH_2X^2$, $-CN$, -Ph, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

In embodiments, $R^{4A}$ is hydrogen, $-CH_3$, $-CX^1{}_3$, $-CHX^1{}_2$, $-CH_2X^1$, $-CN$, -Ph, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

In embodiments, $R^{4A}$ is hydrogen, $-CH_3$, $-CX^1{}_3$, $-CHX^1{}_2$, $-CH_2X^1$, $-CN$, -Ph, substituted (e.g., substituted with a substituent group, size-limited substituent group, or lower substituent group) or unsubstituted (e.g., substituted with a substituent group, size-limited substituent group, or lower substituent group) $C_1$-$C_6$ alkyl, substituted (e.g., substituted with a substituent group, size-limited substituent group, or lower substituent group) or unsubstituted (e.g., substituted with a substituent group, size-limited substituent group, or lower substituent group) 2 to 6 membered heteroalkyl, substituted (e.g., substituted with a substituent group, size-limited substituent group, or lower substituent group) or unsubstituted (e.g., substituted with a substituent group, size-limited substituent group, or lower substituent group) $C_3$-$C_6$ cycloalkyl, substituted (e.g., substituted with a substituent group, size-limited substituent group, or lower substituent group) or unsubstituted (e.g., substituted with a substituent group, size-limited substituent group, or lower substituent group) 3 to 6 membered heterocycloalkyl, substituted (e.g., substituted with a substituent group, size-limited substituent group, or lower substituent group) or unsubstituted (e.g., substituted with a substituent group, size-limited substituent group, or lower substituent group) phenyl, or substituted (e.g., substituted with a substituent group, size-limited substituent group, or lower substituent group) or unsubstituted (e.g., substituted with a substituent group, size-limited substituent group, or lower substituent group) 5 to 6 membered heteroaryl.

In embodiments, $R^{4B}$ is hydrogen, $-CH_3$, $-CX^2{}_3$, $-CHX^2{}_2$, $-CN$, -Ph, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

In embodiments, $R^{4B}$ is hydrogen, $-CH_3$, $-CX^2{}_3$, $-CHX^2{}_2$, $-CH_2X^2$, $-CN$, -Ph, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl.

In embodiments, $R^5$ is a detectable label. In embodiments, $R^5$ is a fluorescent dye. In embodiments, $R^5$ is an anchor moiety. In embodiments, $R^5$ is a click chemistry reactant moiety. In embodiments, $R^5$ is a trans-cyclooctene moiety or azide moiety. In embodiments, $R^5$ is an affinity anchor moiety. In embodiments, $R^5$ is a biotin moiety. In embodiments, $R^5$ is a reactant for a bioconjugate reaction that forms a covalent bond between $R^5$ and a second bioconjugate reaction reactant.

In embodiments, $R^5$ is a fluorescent dye. In embodiments $R^5$ is a Alexa Fluor® 350 moiety, Alexa Fluor® 405 moiety, Alexa Fluor® 430 moiety, Alexa Fluor® 488 moiety, Alexa Fluor® 532 moiety, Alexa Fluor® 546 moiety, Alexa Fluor® 555 moiety, Alexa Fluor® 568 moiety, Alexa Fluor® 594 moiety, Alexa Fluor® 610 moiety, Alexa Fluor® 633 moiety, Alexa Fluor® 635 moiety, Alexa Fluor® 647 moiety, Alexa Fluor® 660 moiety, Alexa Fluor® 680 moiety, Alexa Fluor® 700 moiety, Alexa Fluor® 750 moiety, or Alexa Fluor® 790 moiety. In embodiments the detectable moiety is a Alexa Fluor® 488 moiety, Rhodamine 6G (R6G) moiety, ROX Reference Dye (ROX) moiety, or Cy5 moiety.

In embodiments $R^5$ is a FAM™ moiety, TET™ moiety, JOE™ moiety, VIC® moiety, HEX™ moiety, NED™ moiety, PET® moiety, ROX™ moiety, TAMRA™ moiety, TET™ moiety, Texas Red® moiety, Alexa Fluor® 488 moiety, Rhodamine 6G (R6G) moiety, ROX Reference Dye (ROX) moiety, Sulfo-Cy5, or Cy5 moiety. In embodiments $R^5$ is a Rhodamine 6G (R6G) moiety, ROX Reference Dye (ROX) moiety, Sulfo-Cy5, or Cy5 moiety.

In embodiments $R^5$ is a FAM™ moiety. In embodiments $R^5$ is a TET™ moiety. In embodiments $R^5$ is a JOE™ moiety. In embodiments $R^5$ is a VIC® moiety. In embodiments $R^5$ is a HEX™ moiety. In embodiments $R^5$ is a NED™ moiety. In embodiments $R^5$ is a PET® moiety. In embodiments $R^5$ is a ROX™ moiety. In embodiments $R^5$ is a TAMRA™ moiety. In embodiments $R^5$ is a TET™ moiety. In embodiments $R^5$ is a Texas Red® moiety. In embodiments $R^5$ is an Alexa Fluor® 488 moiety. In embodiments $R^5$ is a Rhodamine 6G (R6G) moiety. In embodiments $R^5$ is a ROX Reference Dye (ROX) moiety. In embodiments $R^5$ is a Sulfo-Cy5. In embodiments $R^5$ is a Cy5 moiety.

In embodiments, $R^5$ is a biotin moiety. In embodiments, $R^5$ is a biotin moiety and $R^{12}$ is a streptavidin moiety.

In embodiments, $R^5$ is

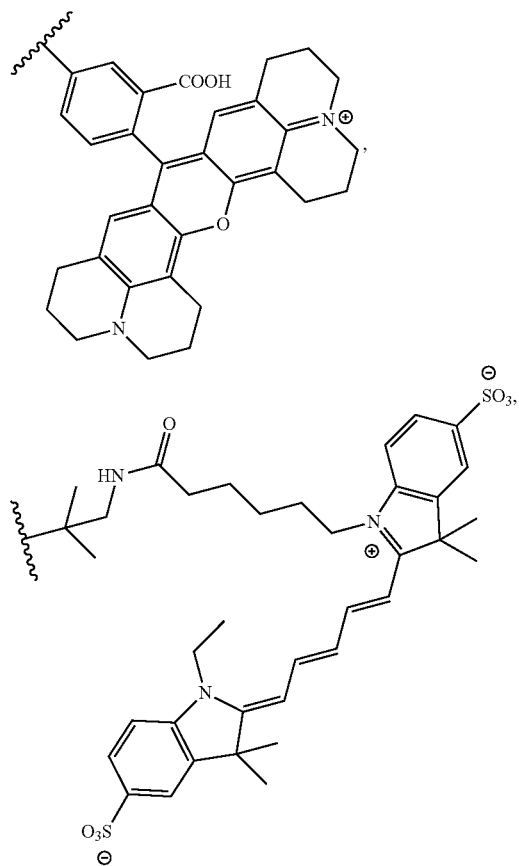

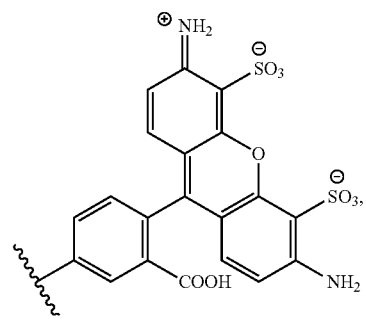

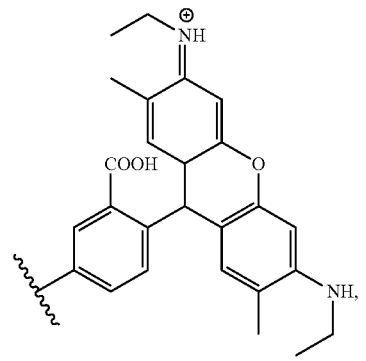

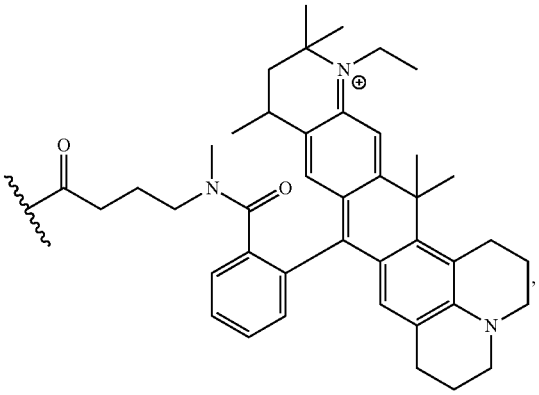

-continued
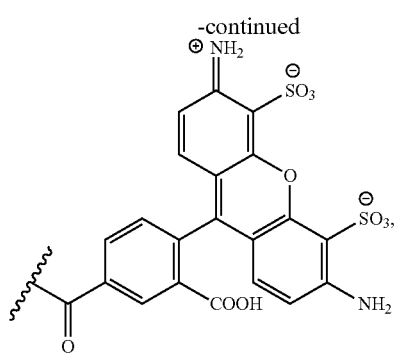
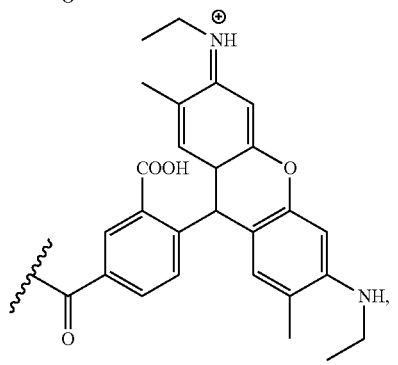
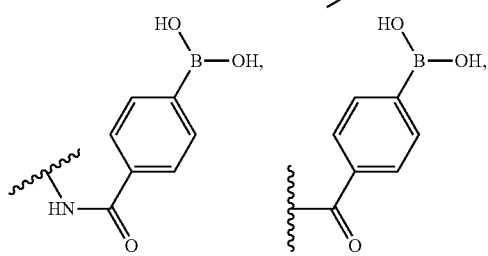
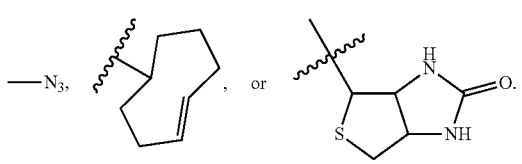
In embodiments, R⁵ is
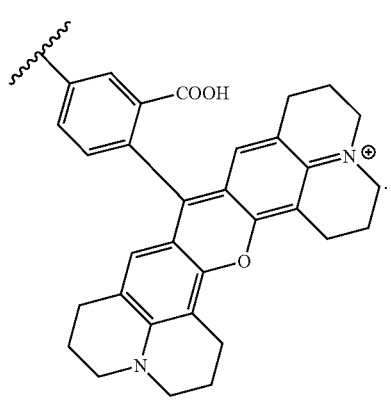 [SMILES: *c1ccc(C2=c3cc4c5c(c3Oc3c2cc2c6c3CCCN6CCC2)CCC[N+]=5CCC4)c(C(=O)O)c1]
In embodiments, R⁵ is
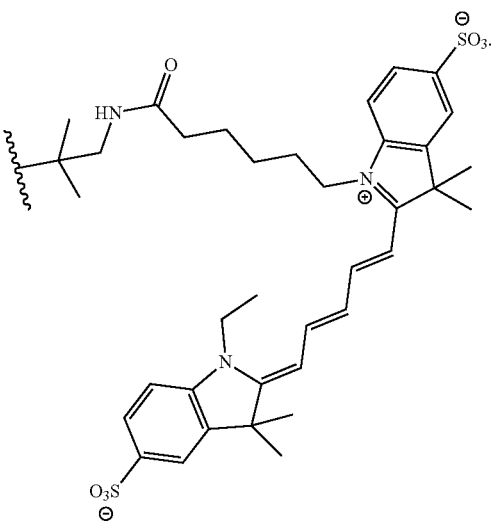
In embodiments, R⁵ is
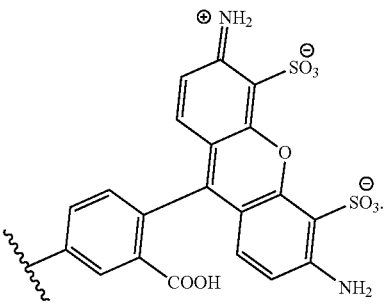
In embodiments, R⁵ is
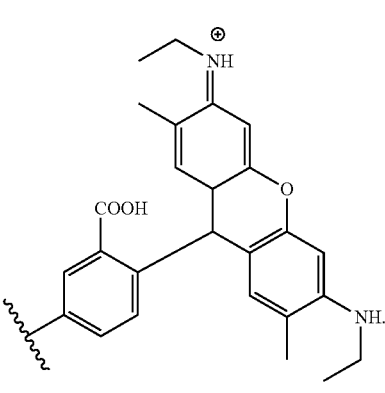 [SMILES: *c1ccc(C2c3cc(C)c(NCC)cc3OC3=C/C(=[NH+]/CC)C(C)=CC32)c(C(=O)O)c1]

In embodiments, R⁵ is
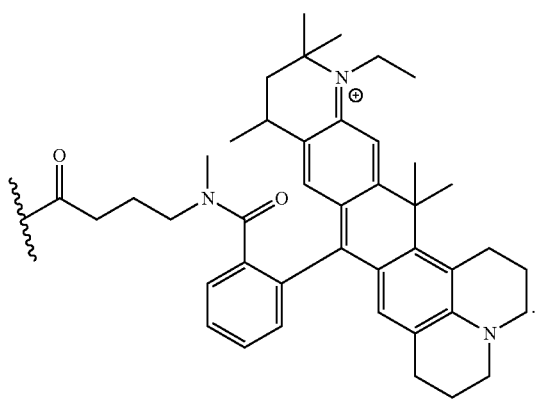 [SMILES: *C(=O)CCCN(C)C(=O)c1ccccc1C1=c2cc3c(cc2C(C)(C)c2c1cc1c4c2CCCN4CCC1)=[N+](CC)C(C)(C)CC3C]
In embodiments, R⁵ is
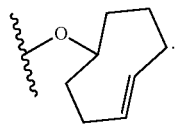
In embodiments, R⁵ is
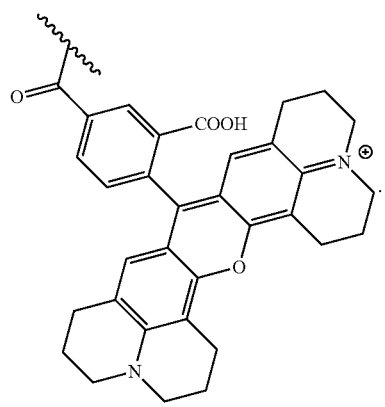 [SMILES: *C(=O)c1ccc(C2=c3cc4c5c(c3Oc3c2cc2c6c3CCCN6CCC2)CCC[N+]=5CCC4)c(C(=O)O)c1]
In embodiments, R⁵ is
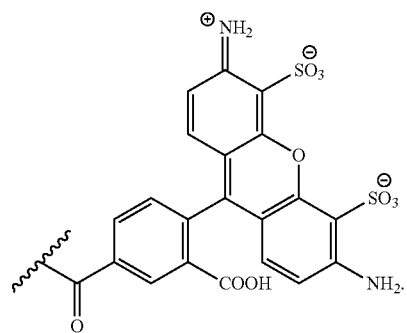
In embodiments, R⁵ is
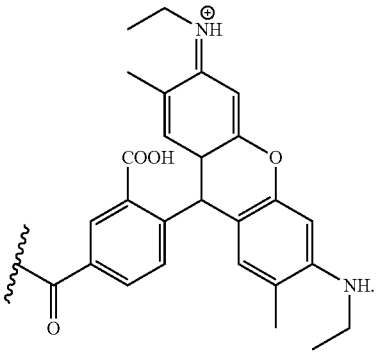 [SMILES: *C(=O)c1ccc(C2c3cc(C)c(NCC)cc3OC3=C/C(=[NH+]/CC)C(C)=CC32)c(C(=O)O)c1]
In embodiments, R⁵ is
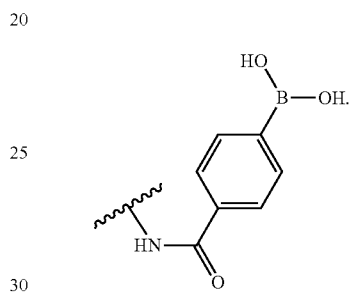
In embodiments, R⁵ is
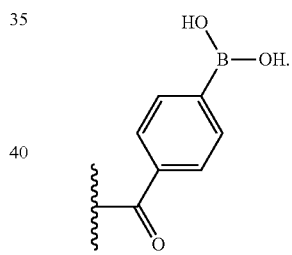
In embodiments, R⁵ is —N₃. In embodiments, R⁵ is
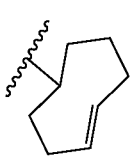
In embodiments, R⁵ is
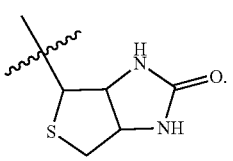 [SMILES: *C1SCC2NC(=O)NC21]
In embodiments, R⁶ is hydrogen. In embodiments, R⁶ is a polymerase-compatible cleavable moiety. In embodiments, $R^6$ is a polymerase-compatible cleavable moiety including an azido moiety. In embodiments, $R^6$ is a polymerase-compatible cleavable moiety including a dithiol linker. In embodiments, $R^6$ is a polymerase-compatible cleavable moiety; and the polymerase-compatible cleavable moiety is $-CH_2N_3$. In embodiments, the polymerase-compatible cleavable moiety is $-NH_2$, $-CN$, $-CH_3$, $C_2$-$C_6$ allyl (e.g., $-CH_2-CH=CH_2$), methoxyalkyl (e.g., $-CH_2-O-CH_3$), or $-CH_2N_3$. In embodiments, $R^6$ is $-NH_2$. In embodiments, $R^6$ is $-CH_2N_3$. In embodiments, $R^6$ is

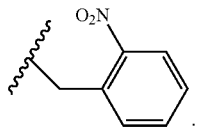

In embodiments, $R^6$ is

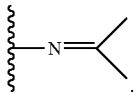

In embodiments, $R^6$ is

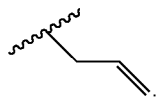 [SMILES: *CC=C]

In embodiments, $R^6$ is $-CH_2-O-CH_3$. In embodiments, $R^6$ is $-NH_2$, $-CH_2N_3$,

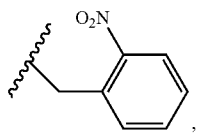

or $-CH_2-O-CH_3$. In embodiments, $L^3$ includes a dithiol linker and $R^6$ is $-NH_2$, $-CH_2N_3$,

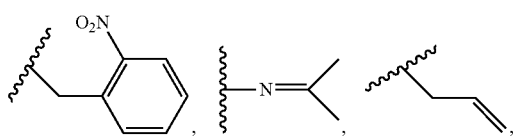

or $-CH_2-O-CH_3$. In embodiments, $L^3$ is

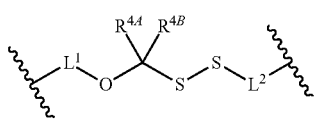

and $R^6$ is $-NH_2$, $-CH_2N_3$,

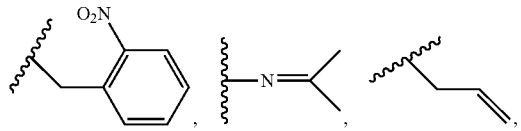

or $-CH_2-O-CH_3$.

In embodiments, $R^6$ is a polymerase-compatible cleavable moiety; and the polymerase-compatible cleavable moiety is

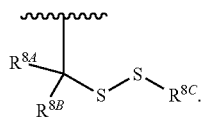

$R^{8C}$ is hydrogen, $CH_3$, $-CX^{8C}_3$, $-CHX^{8C}_2$, $-CH_2X^{8C}$, $-OCX^{8C}_3$, $-OCH_2X^{8C}$, $-OCHX^{8C}_2$, $-CN$, $-OH$, $-SH$, $-NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol $X^{8C}$ is independently halogen. In embodiments, $R^{8C}$ is independently unsubstituted phenyl.

In embodiments $R^6$ is a polymerase-compatible cleavable moiety; and the polymerase-compatible cleavable moiety is:

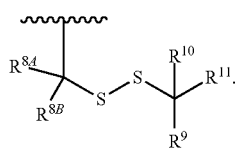

$R^{8A}$ is independently hydrogen, $CH_3$, $-CX^3_3$, $-CHX^3_2$, $-CH_2X^3$, $-OCX^3_3$, $-OCH_2X^3$, $-OCHX^3_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. In embodiments, $R^{8A}$ is independently hydrogen, $CH_3$, $-CX^3_3$, $-CHX^3_2$, $-CH_2X^3$, $-OCX^3_3$, $-OCH_2X^3$, $-OCHX^3_2$, $-CN$, $-OH$, $-SH$, $-NH_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl. $R^{8B}$ is independently hydrogen, $CH_3$, $-CX^4_3$, $-CHX^4_2$, $-OCX^4_3$, $-OCH_2X^4$, $-OCHX^4_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. In embodiments, $R^{8B}$ is independently hydrogen, $CH_3$, $-CX^4_3$, $-CHX^4_2$, $-CH_2X^4$, $-OCX^4_3$, $-OCH_2X^4$, $-OCHX^4_2$, $-CN$, $-OH$, $-SH$, $-NH_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl. $R^9$ is independently hydrogen, $CH_3$, $-CX^5_3$, $-CHX^5_2$, $-CH_2X^5$, $-OCX^5_3$, $-OCH_2X^5$, $-OCHX^5_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. In embodiments, $R^9$ is independently hydrogen, $-CX^5_3$, $-CHX^5_2$, $-CH_2X^5$, $-OCX^5_3$, $-OCH_2X^5$, $-OCHX^5_2$, $-CN$, $-OH$, $-SH$, $-NH_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl. $R^{10}$ is independently hydrogen, $CH_3$, $-CX^6_3$, $-CHX^6_2$, $-CH_2X^6$, $-OCX^6_3$, $-OCH_2X^6$, $-OCHX^6_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. In embodiments, $R^{10}$ is independently hydrogen, $CH_3$, $-CX^6_3$, $-CHX^6_2$, $-CH_2X^6$, $-OCX^6_3$, $-OCH_2X^6$, $-OCHX^6_2$, $-CN$, $-OH$, $-SH$, $-NH_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl. $R^{11}$ is independently hydrogen, $CH_3$, $-CX^7_3$, $-CHX^7_2$, $-CH_2X^7$, $-OCX^7_3$, $-OCH_2X^7$, $-OCHX^7_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. In embodiments, $R^{11}$ is independently hydrogen, $CH_3$, $-CX^7_3$, $-CHX^7_2$, $-CH_2X^7$, $-OCX^7_3$, $-OCH_2X^7$, $-OCHX^7_2$, $-CN$, $-OH$, $-SH$, $-NH_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl. The symbols $X^3$, $X^4$, $X^5$, $X^6$ and $X^7$ are independently halogen.

In embodiments, $R^6$ is a polymerase-compatible cleavable moiety; and the polymerase-compatible cleavable moiety is

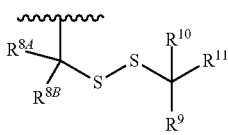

wherein, $R^{8A}$ is independently hydrogen, $CH_3$, —$CX^3_3$, —$CHX^3_2$, —$CH_2X^3$, —$OCX^3_3$, —$OCH_2X^3$, —$OCHX^3_2$, —CN, —OH, —SH, —$NH_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl; $R^{8B}$ is independently hydrogen, $CH_3$, —$CX^4_3$, —$CHX^4_2$, —$OCX^4_3$, —$OCH_2X^4$, —$OCHX^4_2$, —CN, —OH, —SH, —$NH_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl; $R^9$ is independently hydrogen, $CH_3$, —$CX^5_3$, —$CHX^5_2$, —$CH_2X^5$, —$OCX^5_3$, —$OCH_2X^5$, —$OCHX^5_2$, —CN, —OH, —SH, —$NH_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl; $R^{10}$ is independently hydrogen, —$CX^6_3$, —$CHX^6_2$, —$CH_2X^6$, —$OCX^6_3$, —$OCH_2X^6$, —$OCHX^6_2$, —CN, —OH, —SH, —$NH_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl; $R^{11}$ is independently hydrogen, $CH_3$, —$CX^7_3$, —$CHX^7_2$, —$CH_2X^7$, —$OCX^7_3$, —$OCH_2X^7$, —$OCHX^7_2$, —CN, —OH, —SH, —$NH_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl; and $X^3$, $X^4$, $X^5$, $X^6$ and $X^7$ are independently halogen.

In embodiments, $R^6$ is a polymerase-compatible cleavable moiety; and the polymerase-compatible cleavable moiety is:

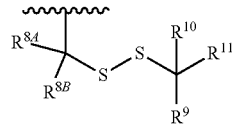

wherein $R^{8A}$ and $R^{8B}$ are independently hydrogen or unsubstituted alkyl; $R^9$, $R^{10}$, and $R^{11}$ are independently unsubstituted alkyl or unsubstituted heteroalkyl. In embodiments, $R^6$ is a polymerase-compatible cleavable moiety; and the polymerase-compatible cleavable moiety is:

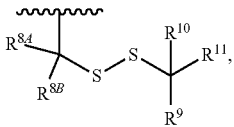

wherein $R^{8A}$ and $R^{8B}$ are independently hydrogen or unsubstituted $C_1$-$C_4$ alkyl; and $R^9$, $R^{10}$, and $R^{11}$ are independently unsubstituted $C_1$-$C_6$ alkyl or unsubstituted 2 to 4 membered heteroalkyl. In embodiments, $R^6$ is a polymerase-compatible cleavable moiety; and the polymerase-compatible cleavable moiety is:

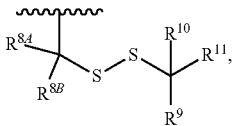

wherein $R^{8A}$ and $R^{8B}$ are independently hydrogen; and $R^9$, $R^{10}$ and $R^{11}$ are independently unsubstituted $C_1$-$C_6$ alkyl or unsubstituted 2 to 4 membered heteroalkyl. In embodiments, $R^6$ is a polymerase-compatible cleavable moiety; and the polymerase-compatible cleavable moiety is:

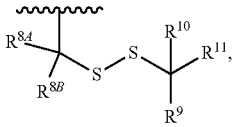

$R^{8A}$ and $R^{8B}$ are independently hydrogen; and $R^9$, $R^{10}$, and $R^{11}$ are independently unsubstituted methyl or unsubstituted methoxy. In embodiments, $R^6$ is a polymerase-compatible cleavable moiety; and the polymerase-compatible cleavable moiety is:

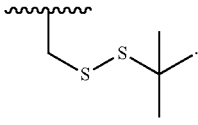

In embodiments, $R^7$ is hydrogen. In embodiments, $R^7$ is $-OR^{7A}$; and $R^{7A}$ is hydrogen. In embodiments, $R^7$ is $-OR^{7A}$; and $R^{7A}$ is a polymerase-compatible cleavable moiety. In embodiments, $R^7$ is $-OR^{7A}$; and $R^{7A}$ is a polymerase-compatible cleavable moiety including an azido moiety. In embodiments, $R^7$ is $-OR^{7A}$; and $R^{7A}$ is a polymerase-compatible cleavable moiety including a dithiol linker. In embodiments, $R^7$ is $-OR^{7A}$; $R^{7A}$ is a polymerase-compatible cleavable moiety; and the polymerase-compatible cleavable moiety is $-CH_2N_3$. In embodiments, $R^7$ is $-OR^{7A}$; and $R^{7A}$ is a polymerase-compatible cleavable moiety comprising a dithiol linker, an allyl group, or a 2-nitrobenzyl group. In embodiments, $R^7$ is $-NH_2$, $-CH_2N_3$,

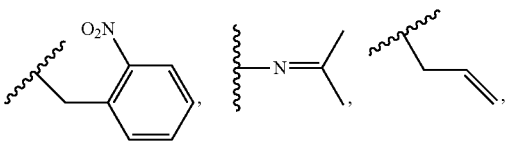

or $-CH_2-O-CH_3$.

In embodiments, $R^7$ is $-OR^{7A}$; $R^{7A}$ is a polymerase-compatible cleavable moiety; and the polymerase-compatible cleavable moiety is:

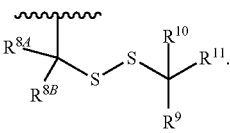

In embodiments, $R^{7A}$ is

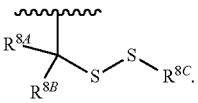

$R^{8C}$ is hydrogen, $CH_3$, $-CX^{8C}_3$, $-CHX^{8C}_2$, $-CH_2X^{8C}$, $-OCX^{8C}_3$, $-OCH_2X^{8C}$, $-OCHX^{8C}_2$, $-CN$, $-OH$, $-SH$, $-NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol $X^{8C}$ is independently halogen. In embodiments, $R^{8C}$ is independently unsubstituted phenyl.

In embodiments, $R^{8A}$, is independently hydrogen, $CH_3$, $-CX^3_3$, $-CHX^3_2$, $-CH_2X^3$, $-OCX^3_3$, $-OCH_2X^3$, $-OCHX^3_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. In embodiments $R^{8A}$ is independently hydrogen, $CH_3$, $-CX^3_3$, $-CHX^3_2$, $-CH_2X^3$, $-OCX^3_3$, $-OCH_2X^3$, $-OCHX^3_2$, $-CN$, $-OH$, $-SH$, $-NH_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl. In embodiments, $R^{8A}$ is independently hydrogen, deuterium, —C(CH$_3$)$_3$, —CH(CH$_3$)$_2$, —CH$_2$CH$_2$CH$_3$, —CH$_2$CH$_3$, —CH$_3$, —CX$^3_3$, —CHX$^3_2$, —CH$_2$X$^3$. —CN, or -Ph. In embodiments, $R^{8B}$ is independently hydrogen, deuterium, —C(CH$_3$)$_3$, —CH(CH$_3$)$_2$, —CH$_2$CH$_2$CH$_3$, —CH$_2$CH$_3$, —CH$_3$, —CX$^4_3$, —CHX$^4_2$, —CH$_2$X$^4$, —CN, or -Ph.

$R^{8B}$ is independently hydrogen, CH$_3$, —CX$^4_3$, —CHX$^4_2$, —CH$_2$X$^4$, —OCX$^4_3$, —OCH$_2$X$^4$, —OCHX$^4_2$, —CN, —OH, —SH, —NH$_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. In embodiments, $R^{8B}$ is independently hydrogen, CH$_3$, —CX$^4_3$, —CHX$^4_2$, —CH$_2$X$^4$, —OCX$^4_3$, —OCH$_2$X$^4$, —OCHX$^4_2$, —CN, —OH, —SH, —NH$_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl.

In embodiments, $R^{8A}$ is independently hydrogen, —CH$_3$, —CX$^3_3$, —CHX$^3_2$, —CH$_2$X$^3$, —CN, -Ph, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. In embodiments, $R^{8B}$ is independently hydrogen, —CH$_3$, —CX$^4_3$, —CHX$^4_2$, —CH$_2$X$^4$, —CN, -Ph, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

In embodiments, $R^{8A}$ and $R^{8B}$ are independently hydrogen or unsubstituted alkyl. In embodiments, $R^{8A}$ and $R^{8B}$ are independently hydrogen or unsubstituted $C_1$-$C_4$ alkyl. In embodiments, $R^{8A}$ and $R^{8B}$ are independently hydrogen.

In embodiments; $R^9$ is independently hydrogen, CH$_3$, —CX$^5_3$, —CHX$^5_2$, —CH$_2$X$^5$, —OCX$^5_3$, —OCH$_2$X$^5$, —OCHX$^5_2$, —CN, —OH, —SH, —NH$_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. In embodiments, $R^9$ is independently hydrogen, CH$_3$, —CX$^5_3$, —CHX$^5_2$, —CH$_2$X$^5$, —OCX$^5_3$, —OCH$_2$X$^5$, —OCHX$^5_2$, —CN, —OH, —SH, —NH$_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl.

In embodiments, $R^{10}$ is independently hydrogen, CH$_3$, —CX$^6_3$, —CHX$^6_2$, —CH$_2$X$^6$, —OCX$^6_3$, —OCH$_2$X$^6$, —OCHX$^6_2$, —CN, —OH, —SH, —NH$_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. In embodiments, $R^{10}$ is independently hydrogen, $CH_3$, $-CX^6{}_3$, $-CHX^6{}_2$, $-CH_2X^6$, $-OCX^6{}_3$, $-OCH_2X^6$, $-OCHX^6{}_2$, $-CN$, $-OH$, $-SH$, $-NH_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl.

In embodiments, $R^9$ is independently hydrogen, $CH_3$, $-CX^5{}_3$, $-CHX^5{}_2$, $-CH_2X^5$, $-OCH_3$, $-NHCH_3$, $-CN$, -Ph, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl; $R^{10}$ is independently hydrogen, $CH_3$, $-CX^6{}_3$, $-OCH_3$, $-SCH_3$, $-NHCH_3$, $-CN$, -Ph, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

In embodiments $R^{11}$ is independently hydrogen, $CH_3$, $-CX^7{}_3$, $-CHX^1{}_2$, $-CH_2X^7$, $-OCX^7{}_3$, $-OCH_2X^1$, $-OCHX^7{}_2$, $-CN$, $-OH$, $-SH$, $-NH_2$, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl. In embodiments, $R^{11}$ is independently hydrogen, $-CX^7{}_3$, $-CHX^7{}_2$, $-CH_2X^7$, $-OCX^7{}_3$, $-OCH_2X^7$, $-OCHX^7{}_2$, $-CN$, $-OH$, $-SH$, $-NH_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl. The symbols $X^3$, $X^4$, $X^5$, $X^6$ and $X^7$ are independently halogen.

In embodiments, $R^{11}$ is independently hydrogen, $CH_3$, $-CX^1{}_3$, $-CHX^7{}_2$, $-CH_2X^7$, $-OCH_3$, $-SCH_3$, $-NHCH_3$, $-CN$, -Ph substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

In embodiments, $R^9$, $R^{10}$, and $R^{11}$ are independently unsubstituted alkyl or unsubstituted heteroalkyl. In embodiments, $R^9$, $R^{10}$, and $R^{11}$ are independently unsubstituted $C_1$-$C_6$ alkyl or unsubstituted 2 to 4 membered heteroalkyl. In embodiments, $R^9$, $R^{10}$, and $R^{11}$ are independently unsubstituted $C_1$-$C_6$ alkyl or unsubstituted 2 to 4 membered heteroalkyl. In embodiments, $R^9$, $R^{10}$, and $R^{11}$ are independently unsubstituted methyl or unsubstituted methoxy. In embodiments, $R^{8A}$, $R^{8B}$, $R^9$, $R^{10}$, and $R^{11}$ are independently hydrogen or unsubstituted methyl. In embodiments, $R^{8A}$ and $R^{8B}$ are hydrogen and $R^9$, $R^{10}$, and $R^{11}$ are unsubstituted methyl.

In embodiments, $R^7$ is $-OR^{7A}$; $R^{7A}$ is a polymerase-compatible cleavable moiety; and the polymerase-compatible cleavable moiety is:

wherein $R^{8A}$ is hydrogen, $-CX^3{}_3$, $-CHX^3{}_2$, $-CH_2X^3$, $-OCX^3{}_3$, $-OCH_2X^3$, $-OCHX^3{}_2$, $-CN$, $-OH$, $-SH$, $-NH_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl; $R^{8B}$ is independently hydrogen, $CH_3$, $-CX^4{}_3$, $-CHX^4{}_2$, $-CH_2X^4$, $-OCX^4{}_3$, $-OCH_2X^4$, $-OCHX^4{}_2$, $-CN$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl; or substituted (e.g., substituted with a substituent group, size-limited substituent group, or lower substituent group) or unsubstituted 5 to 6 membered heteroaryl; $R^9$ is independently hydrogen, $CH_3$, $-CX^5{}_3$; $-CHX^5{}_2$, $-CH_2X^5$, $-OCX^5{}_3$, $-OCH_2X^5$, $-OCHX^5{}_2$, $-CN$, $-OH$, $-SH$, $-NH_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl; or substituted (e.g., substituted with a substituent group, size-limited substituent group, or lower substituent group) or unsubstituted 5 to 6 membered heteroaryl; $R^{11}$ is independently hydrogen, $CH_3$, $-CX^6{}_3$; $-CHX^6{}_2$, $-CH_2X^6$, $-OCX^6{}_3$, $-OCH_2X^6$; $-OCHX^6{}_2$, $-CN$, $-OH$, $-SH$, $-NH_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl; $R^{11}$ is independently hydrogen, $CH_3$, $-CX^7{}_3$, $-CHX^7{}_2$, $-CH_2X^7$, $-OCX^7{}_3$, $-OCH_2X^7$, $-OCHX^7{}_2$, $-CN$, $-OH$, $-SH$, $-NH_2$, substituted (e.g., substituted with a substituent group, size-limited substituent group, or lower substituent group) or unsubstituted $C_1$-$C_6$ alkyl, substituted (e.g., substituted with a substituent group, size-limited substituent group, or lower substituent group) or unsubstituted 2 to 6 membered heteroalkyl, substituted (e.g., substituted with a substituent group, size-limited substituent group, or lower substituent group) or unsubstituted $C_3$-$C_6$ cycloalkyl, substituted (e.g., substituted with a substituent group, size-limited substituent group, or lower substituent group) or unsubstituted 3 to 6 membered heterocycloalkyl, substituted (e.g., substituted with a substituent group, size-limited substituent group, or lower substituent group) or unsubstituted phenyl, or substituted (e.g., substituted with a substituent group, size-limited substituent group, or lower substituent group) or unsubstituted 5 to 6 membered heteroaryl; and $X^3$, $X^4$, $X^5$, $X^6$ and $X^7$ are independently halogen.

In embodiments, $R^7$ is $-OR^{7A}$; $R^{7A}$ is a polymerase-compatible cleavable moiety; and the polymerase-compatible cleavable moiety is:

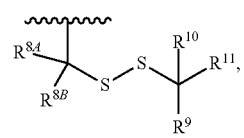

wherein $R^{8A}$, $R^{8B}$, $R^9$, $R^{10}$, and $R^{11}$ are independently hydrogen or unsubstituted methyl. In embodiments, $R^7$ is $-OR^{7A}$; $R^{7A}$ is a polymerase-compatible cleavable moiety; and the polymerase-compatible cleavable moiety is:

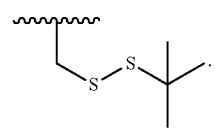 [SMILES: *CSSC(C)(C)C]

In embodiments, $R^{7A}$ is hydrogen. In embodiments, $R^{7A}$ is

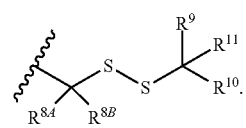

In embodiments, $R^{7A}$ is

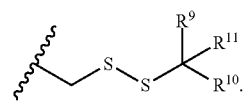

In embodiments, $R^{7A}$ is

[structure: -CH_2-S-S-C(CH_3)_3]

In embodiments, $R^{8A}$ is independently hydrogen, deuterium, —C(CH$_3$)$_3$, —CH(CH$_3$)$_2$, —CH$_2$CH$_2$CH$_3$, —CH$_2$CH$_3$, —CH$_3$, —OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, —CN, or -Ph. In embodiments, $R^{8A}$ is independently hydrogen, —CH$_3$, —CX$^3{}_3$, —CN, -Ph, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or un substituted heteroaryl.

In embodiments, $R^{8A}$ is independently hydrogen, —C(CH$_3$)$_3$, —CH(CH$_3$)$_2$, —CH$_2$CH$_2$CH$_3$, —CH$_2$CH$_3$, —CH$_3$, —OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, —CN, or -Ph.

In embodiments, $R^{8B}$ is independently hydrogen, deuterium, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, —CN, or -Ph. In embodiments, $R^{8B}$ is hydrogen, —CH$_3$, —CX$^4{}_3$, —CHX$^4{}_2$, —CN, -Ph, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

In embodiments, $R^{8B}$ is independently hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, —CN, or -Ph.

In embodiments, —CR$^9$R$^{10}$R$^{11}$ is unsubstituted methyl, unsubstituted ethyl, unsubstituted propyl, unsubstituted isopropyl, unsubstituted butyl, or unsubstituted tert-butyl.

In embodiments; $R^9$ is independently hydrogen, —C(CH$_3$)$_3$, —CH(CH$_3$)$_2$, —CH$_2$CH$_2$CH$_3$, —CH$_2$CH$_3$, —CH$_3$, —OC(CH$_3$)$_3$; —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, or -Ph. In embodiments, $R^9$ is hydrogen, —CX$^5{}_3$, —CHX$^5{}_2$, —OCH$_3$, —SCH$_3$, —NHCH$_3$, —CN, -Ph, substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g.; substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

In embodiments, is independently hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —CH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$; —NHCH(CH$_3$)$_2$, —NHCH$_2$CH$_2$CH$_3$, —NHCH$_2$CH$_3$, —NHCH$_3$, or -Ph. $R^{10}$ is hydrogen, —CX$^6{}_3$, —CHX$^6{}_2$, —CH$_2$X$^6$, —OCH$_3$, —SCH$_3$, —NHCH$_3$, —CN, -Ph, substituted (e.g.; substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl;

In embodiments, $R^{11}$ is independently hydrogen, —C(CH$_3$)$_3$, —CH(CH$_3$)$_2$, —CH$_2$CH$_2$CH$_3$; —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, or -Ph. In embodiments, R$^{11}$ is hydrogen, —CX$^7_3$, —CHX$^7_2$, —CH$_2$X$^7$, —OCH$_3$, —SCH$_3$, —NHCH$_3$, —CN, -Ph substituted (e.g., substituted with a substituent group, size-limited substituent group, or lower substituent group) or unsubstituted alkyl, substituted (e.g., substituted with a substituent group, size-limited substituent group, or lower substituent group) or unsubstituted heteroalkyl, substituted (e.g., substituted with a substituent group, size-limited substituent group, or lower substituent group) or unsubstituted cycloalkyl, substituted (e.g., substituted with a substituent group, size-limited substituent group, or lower substituent group) or unsubstituted heterocycloalkyl, substituted (e.g., substituted with a substituent group, size-limited substituent group, or lower substituent group) or unsubstituted aryl, or substituted (e.g., substituted with a substituent group, size-limited substituent group, or lower substituent group) or unsubstituted heteroaryl.

In embodiments, R$^{13}$ is a fluorescent dye. In embodiments R$^{13}$ is a Alexa Fluor® 350 moiety, Alexa Fluor® 405 moiety, Alexa Fluor® 430 moiety, Alexa Fluor® 488 moiety, Alexa Fluor® 532 moiety, Alexa Fluor® 546 moiety, Alexa Fluor® 555 moiety, Alexa Fluor® 568 moiety, Alexa Fluor® 594 moiety, Alexa Fluor® 610 moiety, Alexa Fluor® 633 moiety, Alexa Fluor® 635 moiety, Alexa Fluor® 647 moiety, Alexa Fluor® 660 moiety, Alexa Fluor® 680 moiety, Alexa Fluor® 700 moiety, Alexa Fluor® 750 moiety, or Alexa Fluor® 790 moiety. In embodiments the detectable moiety is a Alexa Fluor® 488 moiety, Rhodamine 6G (R6G) moiety, ROX Reference Dye (ROX) moiety, or Cy5 moiety.

In embodiments R$^{13}$ is a FAM™ moiety, TET™ moiety, JOE™ moiety, VIC® moiety, HEX™ moiety, NED™ moiety, PET® moiety, ROX™ moiety, TAMRA™ moiety, TET™ moiety, Texas Red® moiety, Alexa Fluor® 488 moiety, Rhodamine 6G (R6G) moiety, ROX Reference Dye (ROX) moiety, Sulfo-Cy5, or Cy5 moiety. In embodiments R$^{13}$ is a Rhodamine 6G (R6G) moiety, ROX Reference Dye (ROX) moiety, Sulfo-Cy5, or Cy5 moiety.

In embodiments, X$^1$ is independently —F. In embodiments, X$^1$ is independently —Cl. In embodiments, X$^1$ is independently —Br. In embodiments, X$^1$ is independently —I. In embodiments, X$^2$ is independently —F. In embodiments, X$^2$ is independently —Cl. In embodiments, X$^2$ is independently —Br. In embodiments, X$^2$ is independently —I. In embodiments, X$^3$ is independently —F. In embodiments, X$^3$ is independently —Cl. In embodiments, X$^3$ is independently —Br. In embodiments, X$^3$ is independently —I. In embodiments, X$^4$ is independently —F. In embodiments, X$^4$ is independently —Cl. In embodiments, X$^4$ is independently —Br. In embodiments, X$^4$ is independently —I. In embodiments, X$^5$ is independently —F. In embodiments, X$^5$ is independently —Cl. In embodiments, X$^5$ is independently —Br. In embodiments, X$^5$ is independently —I. In embodiments, X$^6$ is independently —F. In embodiments, X$^6$ is independently —Cl. In embodiments, X$^6$ is independently —Br. In embodiments, X$^6$ is independently —I. In embodiments, X$^7$ is independently —F. In embodiments, X$^7$ is independently —Cl. In embodiments, X$^7$ is independently —Br. In embodiments, X$^7$ is independently —I.

In embodiments, z is an integer from 0 to 20. In embodiments, z is an integer from 0 to 10. In embodiments, z is an integer from 0 to 15. In embodiments, z is an integer from 5 to 10. In embodiments, z is 0. In embodiments, z is 1. In embodiments, z is 2. In embodiments, z is 3. In embodiments, z is 4. In embodiments, z is 5. In embodiments, z is 6. In embodiments, z is 7. In embodiments, z is 8. In embodiments, z is 9. In embodiments, z is 10. In embodiments, z is 11. In embodiments, z is 12. In embodiments, z is 13. In embodiments, z is 14. In embodiments, z is 15. In embodiments, z is 16. In embodiments, z is 17. In embodiments, z is 18. In embodiments, z is 19. In embodiments, z is 20.

In embodiments, m is an integer from 1 to 4. In embodiments, m is 1. In embodiments, m is 2. In embodiments, m is 3. In embodiments, m is 4.

In embodiments, the compound has the formula:

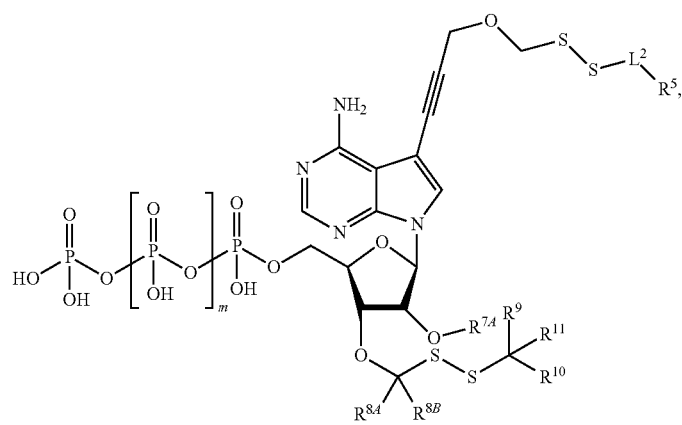

-continued
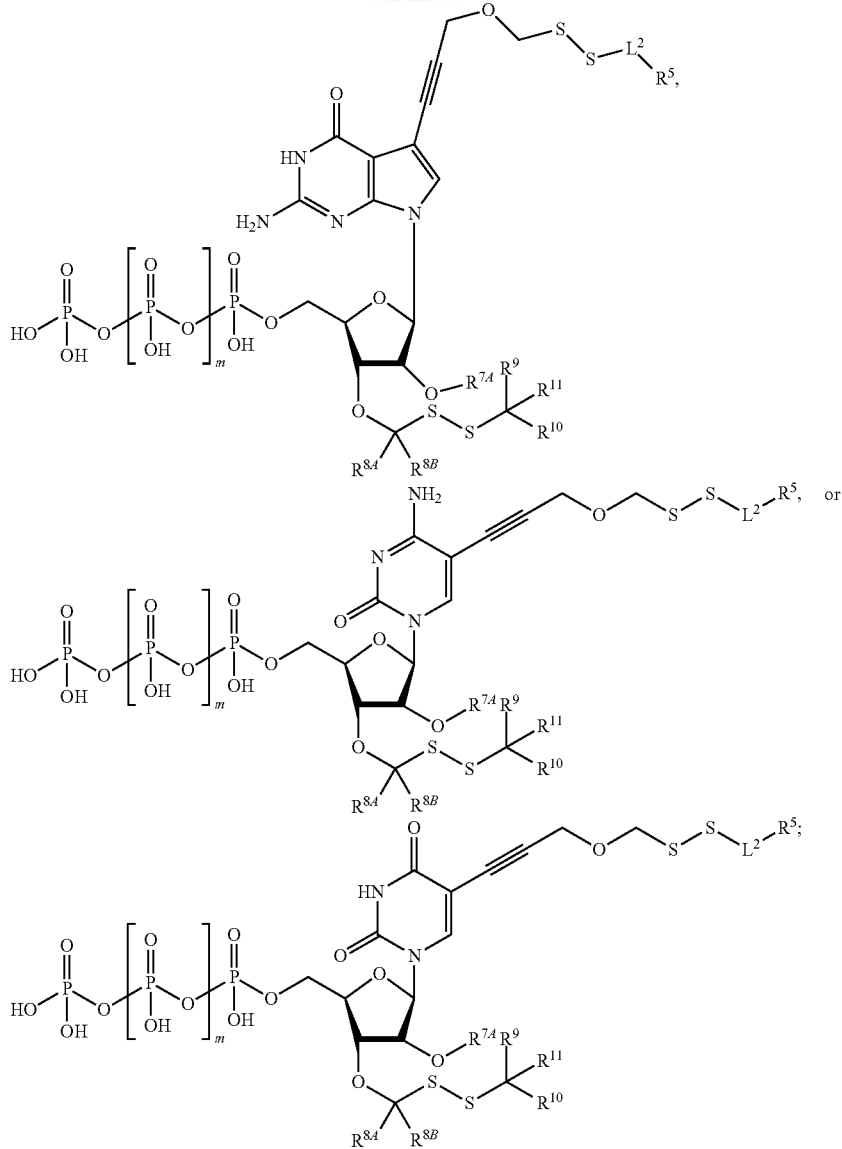
wherein $L^2$, $R^5$, $R^{7A}$, $R^{8A}$, $R^{8B}$, $R^9$, $R^{10}$, and $R^{11}$ are as described herein, and m is an integer from 1 to 4.
In embodiments, the compound has the formula:
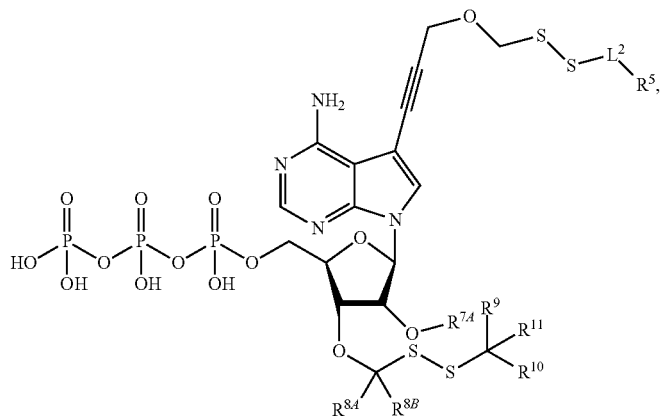

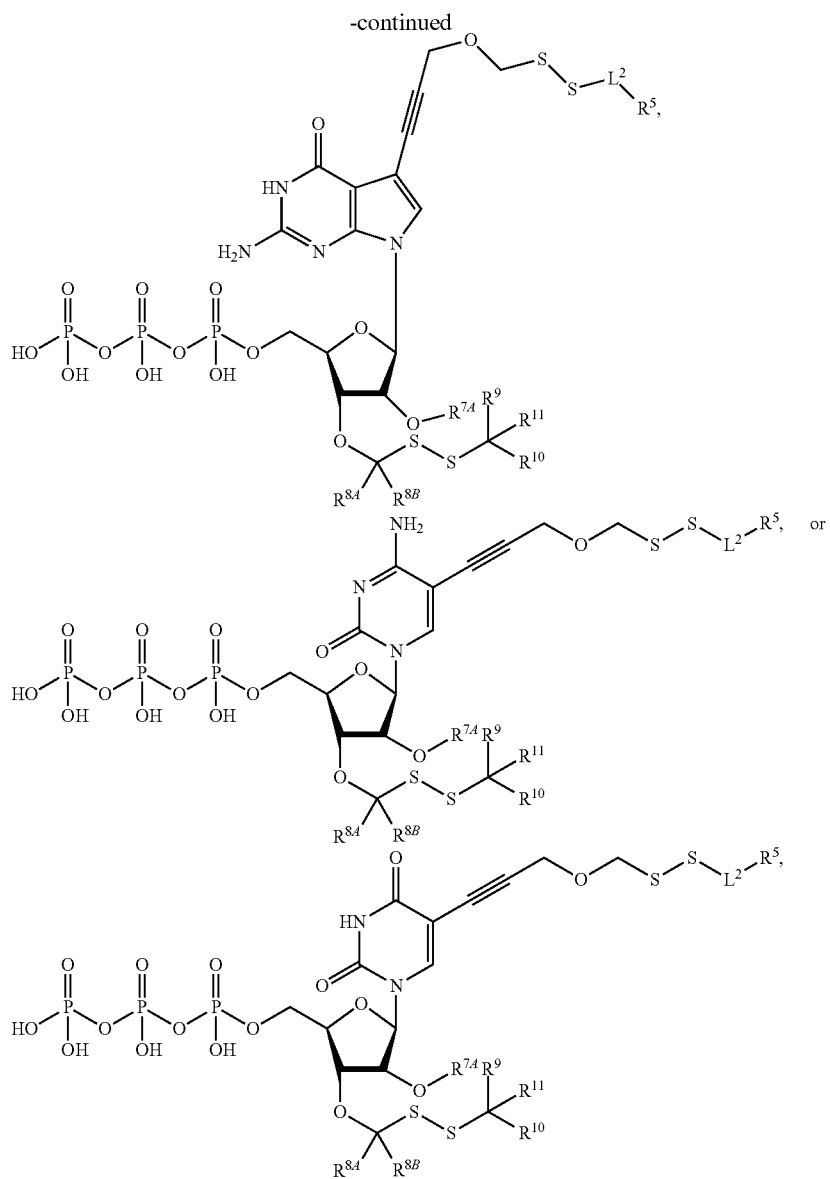
wherein $L^2$, $R^5$, $R_{7A}$, $R^{8A}$, $R^{8B}$, $R^9$, $R^{10}$, and $R^{11}$ are as described herein are as described herein.
In embodiments, the compound has the formula:
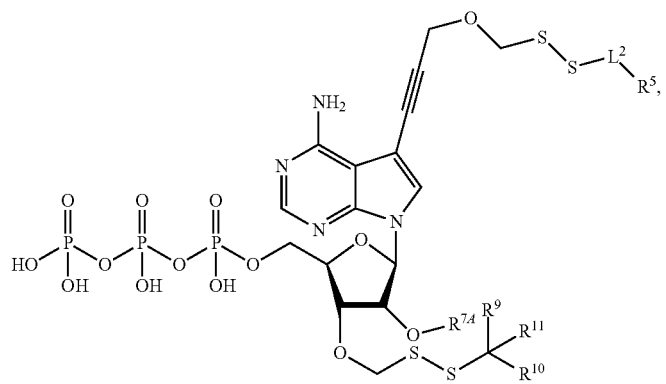

-continued
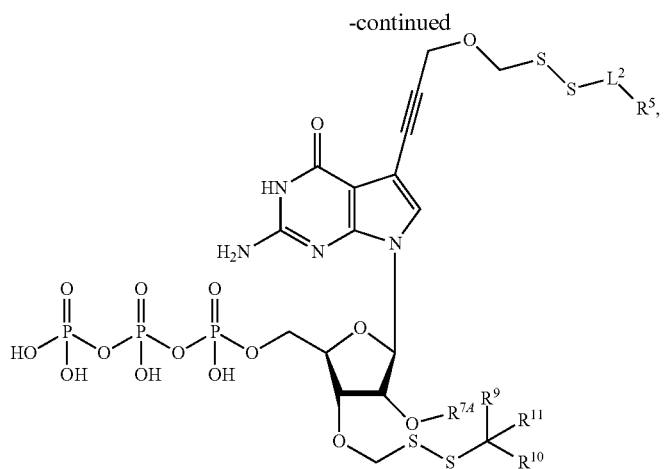
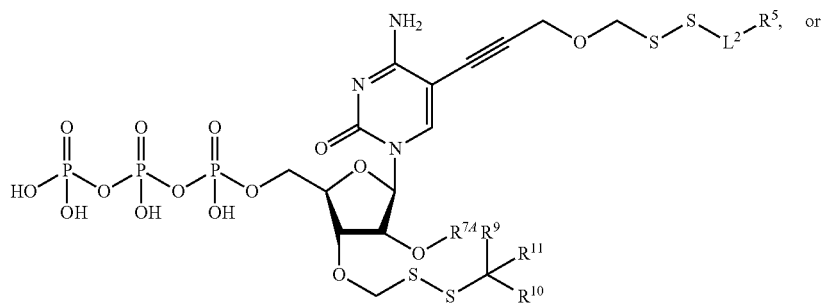
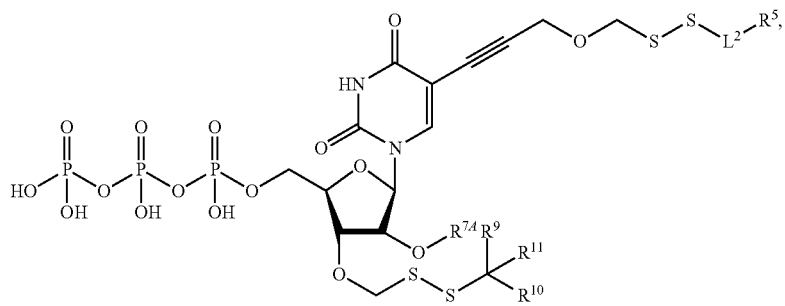
wherein $L^2$, $R^5$, $R_{7A}$, $R^9$, $R^{10}$, and $R^{11}$ are as described herein are as described herein.
In embodiments, the compound has the formula:
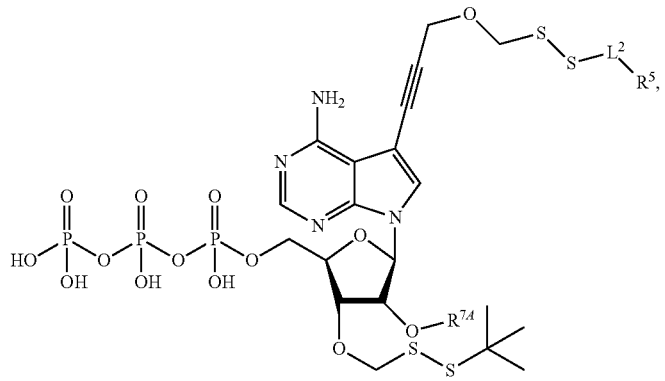

-continued
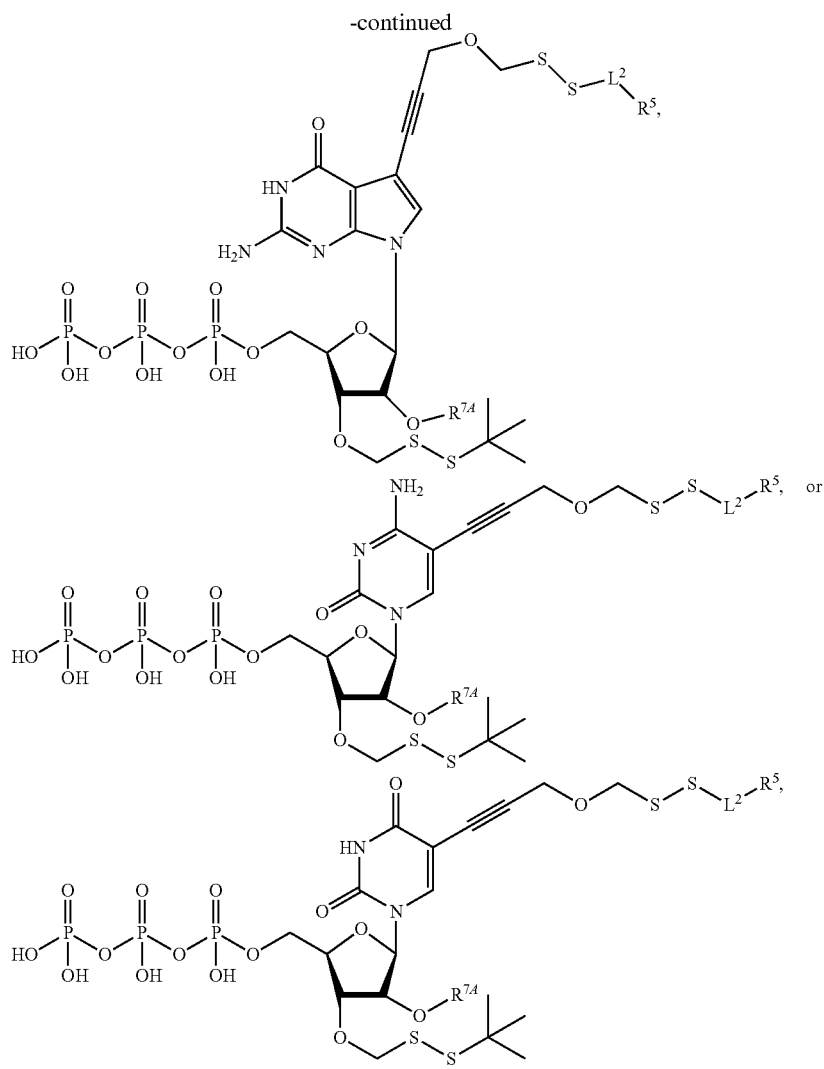
wherein $L^2$, $R^5$, and $R^{7A}$ are as described herein are as described herein.
In embodiments, the compound has the formula:
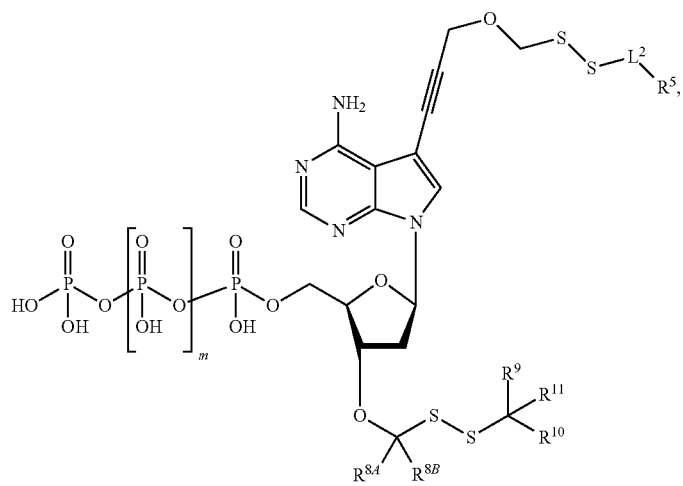

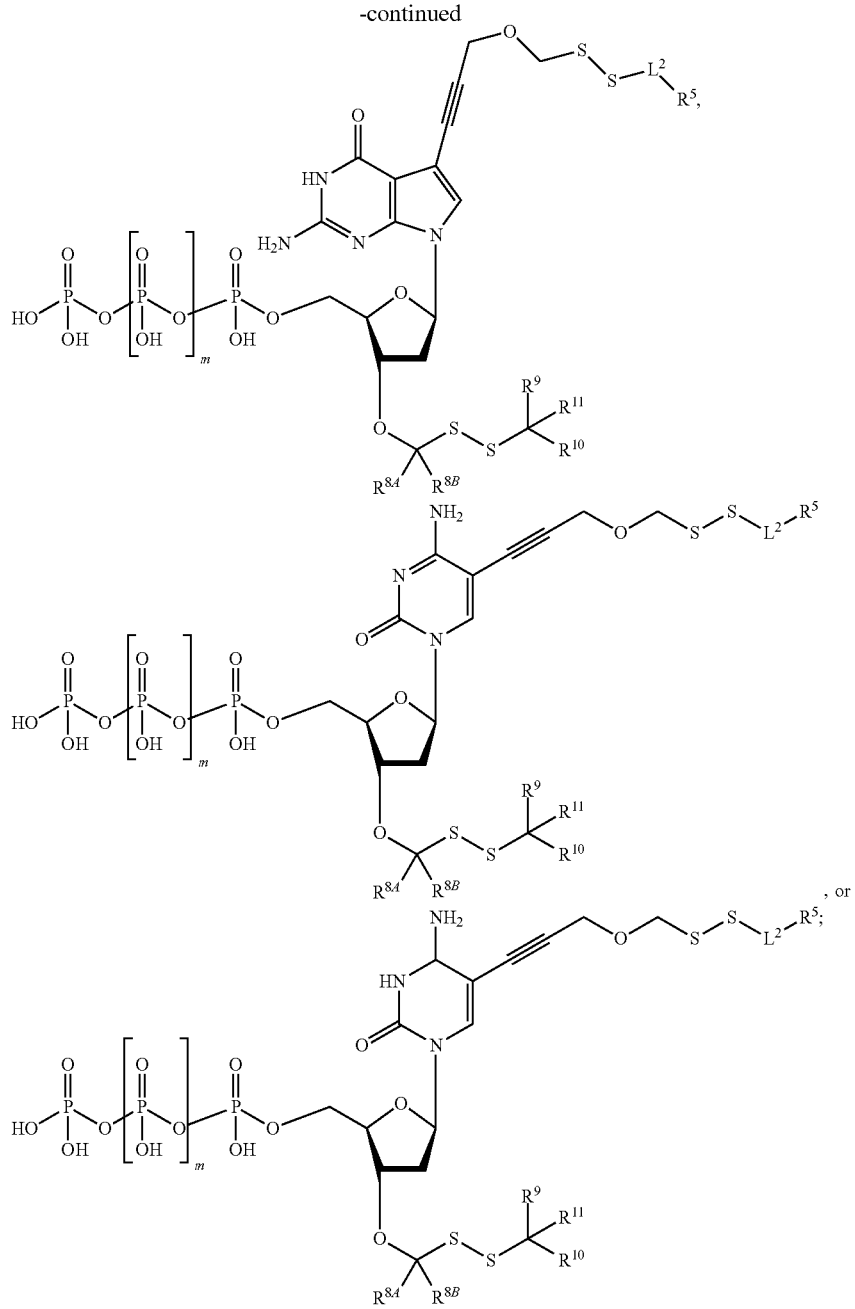

wherein $L^2$, $R^5$, $R^{8A}$, $R^{8B}$, $R^9$, $R^{10}$, and $R^{11}$ are as described herein are as described herein and m is an integer from 1 to 4. In embodiments, $R^{8A}$ is hydrogen, deuterium, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, —CN, or -Ph. In embodiments, $R^{8A}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, $R^{8B}$ is hydrogen, deuterium, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, —CN, or -Ph. In embodiments, $R^{8B}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$. —NHCH(CH$_3$)$_2$, —NHCH$_2$CH$_2$CH$_3$, —NHCH$_2$CH$_3$, —NHCH$_3$—CN, or -Ph. In embodiments, —CR$^9$R$^{10}$R$^{11}$ is unsubstituted methyl, unsubstituted ethyl, unsubstituted propyl, unsubstituted isopropyl, unsubstituted butyl, or unsubstituted tert-butyl. In embodiments, $R^9$ is hydrogen, —C(CH₃)₃, —CH(CH₃)₂, —CH₂CH₂CH₃, —CH₂CH₃, —CH₃, —OC(CH₃)₃, —OCH(CH₃)₂, —OCH₂CH₂CH₃, —OCH₂CH₃, —OCH₃, —SC(CH₃)₃, —SCH(CH₃)₂, —SCH₂CH₂CH₃, —SCH₂CH₃, —SCH₃, —NHC(CH₃)₃, —NHCH(CH₃)₂, —NHCH₂CH₃, —NHCH₂CH₃, —NHCH₃, or -Ph. In embodiments, $R^{10}$ is hydrogen, —C(CH₃)₃, —CH(CH₃)₂, —CH₂CH₂CH₃, —CH₂CH₃, —CH₃, OC(CH₃)₃, —OCH(CH₃)₂, —OCH₂CH₂CH₃, —OCH₂CH₃, —OCH₃, —SC(CH₃)₃, —SCH(CH₃)₂, —SCH₂CH₂CH₃, —SCH₂CH₃, —SCH₃, —NHC(CH₃)₃, —NHCH(CH₃)₂, —NHCH₂CH₃, —NHCH₂CH₃, —NHCH₃, or -Ph. In embodiments, $R^{11}$ is hydrogen, —C(CH₃)₃, —CH(CH₃)₂, —CH₂CH₂CH₃, —CH₂CH₃, —CH₃, —OC(CH₃)₃, —OCH(CH₃)₂, —OCH₂CH₂CH₃, —OCH₂CH₃, —OCH₃, —SC(CH₃)₃, —SCH(CH₃)₂, —SCH₂CH₂CH₃, —SCH₂CH₃, —SCH₃, —NHC(CH₃)₃, —NHCH(CH₃)₂, —NHCH₂CH₃, —NHCH₂CH₃, —NHCH₃, or -Ph.

In embodiments, the compound has the formula:

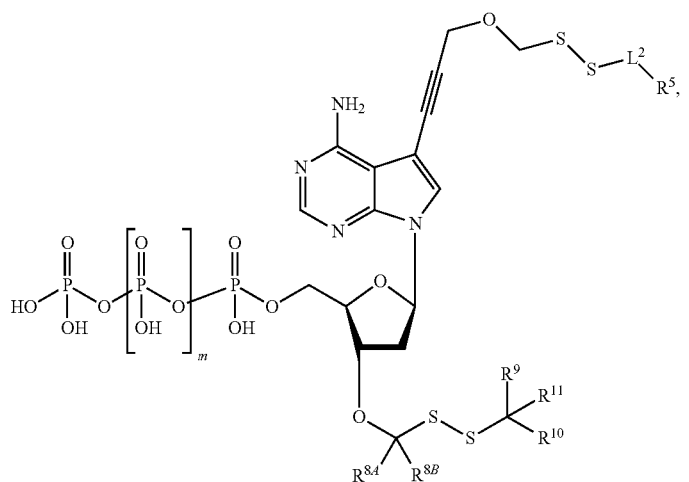

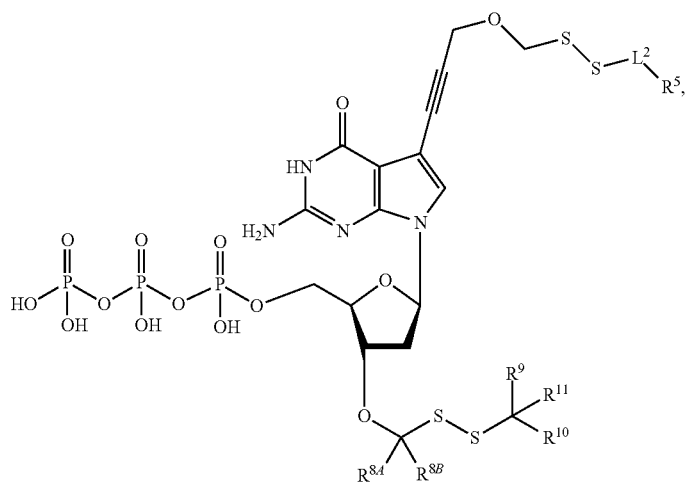

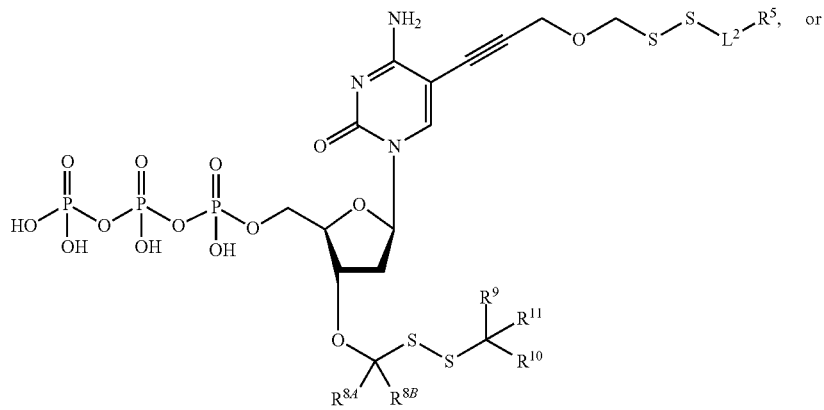

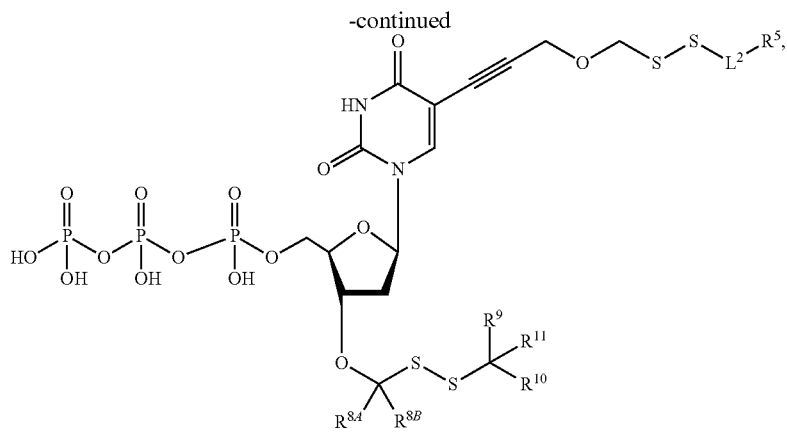

wherein $L^2$, $R^5$, $R^{8A}$, $R^{8B}$, $R^9$, $R^{10}$, and $R^{11}$ are as described herein. In embodiments, $R^{8A}$ is hydrogen, deuterium, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, $R^{8A}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$. —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, $R^{8B}$ is hydrogen, deuterium, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, $R^{8B}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, —CR$^9$R$^{10}$R$^{11}$ is unsubstituted methyl, unsubstituted ethyl, unsubstituted propyl, unsubstituted isopropyl, unsubstituted butyl, or unsubstituted tert-butyl. In embodiments, $R^9$ is hydrogen, —C(CH$_3$)$_3$, —CH(CH$_3$)$_2$, —CH$_2$CH$_2$CH$_3$, —CH$_2$CH$_3$, —CH$_3$, —OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, —CN, or -Ph. In embodiments, $R^{10}$ is hydrogen, —C(CH$_3$)$_3$, —CH(CH$_3$)$_2$, —CH$_2$CH$_2$CH$_3$, —CH$_2$CH$_3$, —CH$_3$, —OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$. —NHCH$_3$, CN, or -Ph. In embodiments, $R^{11}$ is hydrogen, —C(CH$_3$)$_3$, —CH(CH$_3$)$_2$, —CH$_2$CH$_2$CH$_3$, —CH$_2$CH$_3$, —CH$_3$, —OC(CH$_3$)$_3$, —OCH(CH$_3$)$_2$, —OCH$_2$CH$_2$CH$_3$, —OCH$_2$CH$_3$, —OCH$_3$, C(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, —CN, or -Ph.

In embodiments, the compound has the formula:

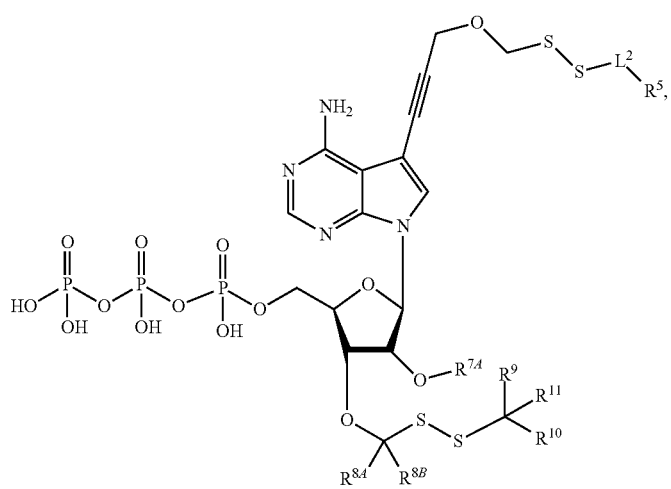

-continued
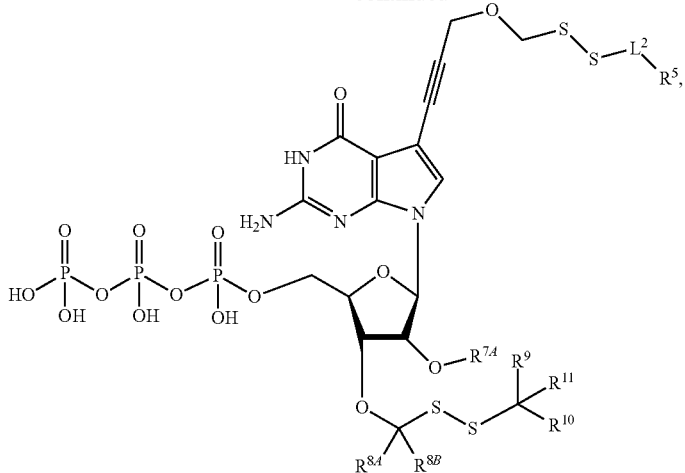
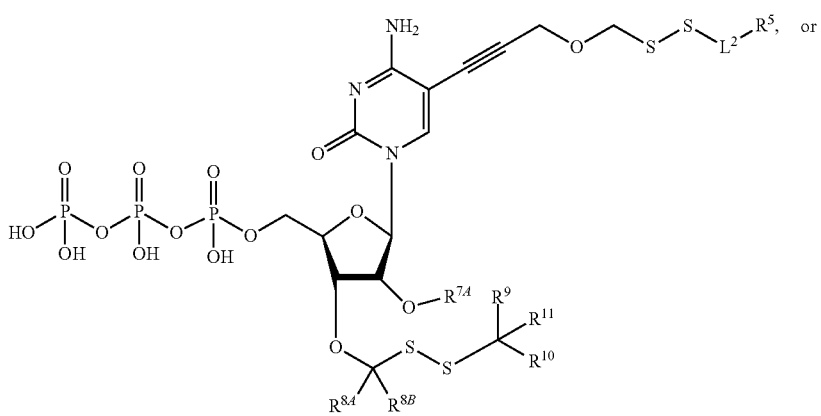
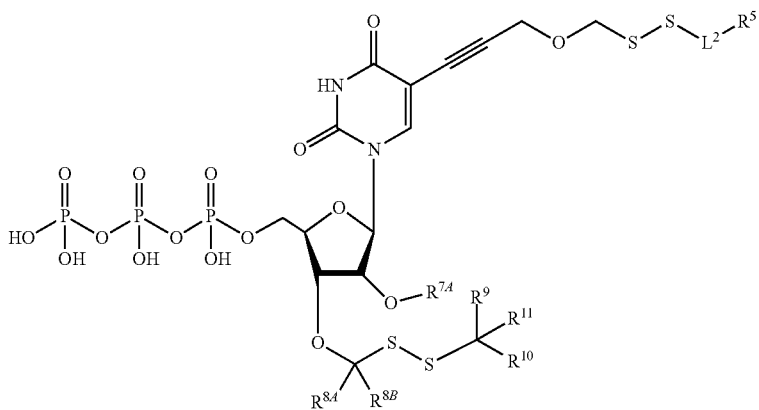
wherein $L^2$, $R^5$, $R^{7A}$, $R^{8A}$, $R^{8B}$, $R^9$, $R^{10}$, and $R^{11}$ are as described herein are as described herein.

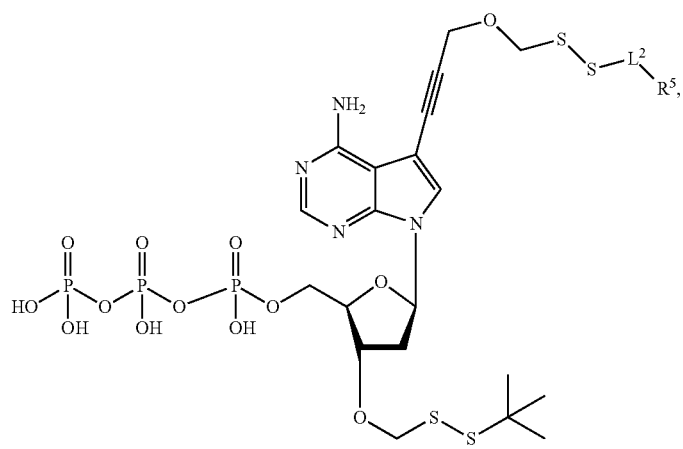
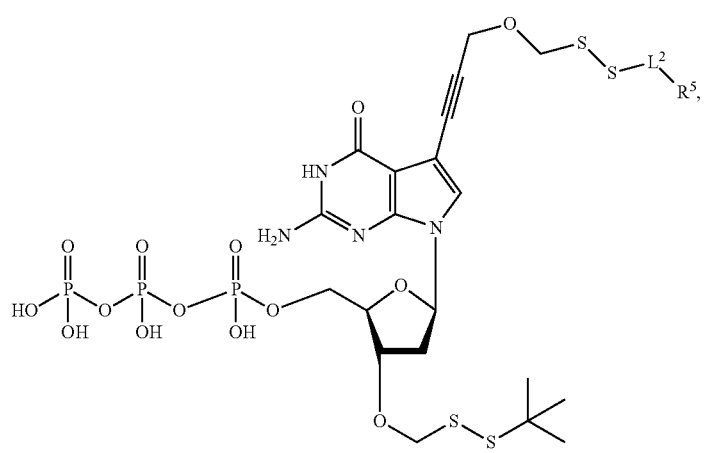
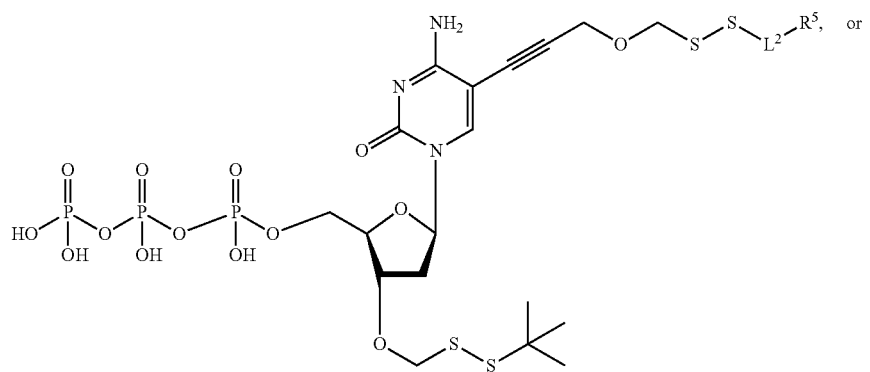

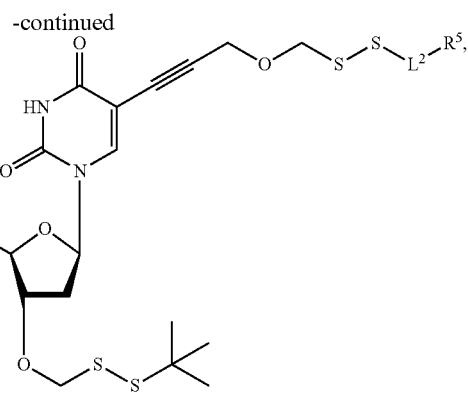
wherein L² and R⁵ is as described herein.
In embodiments, the compound has formula:
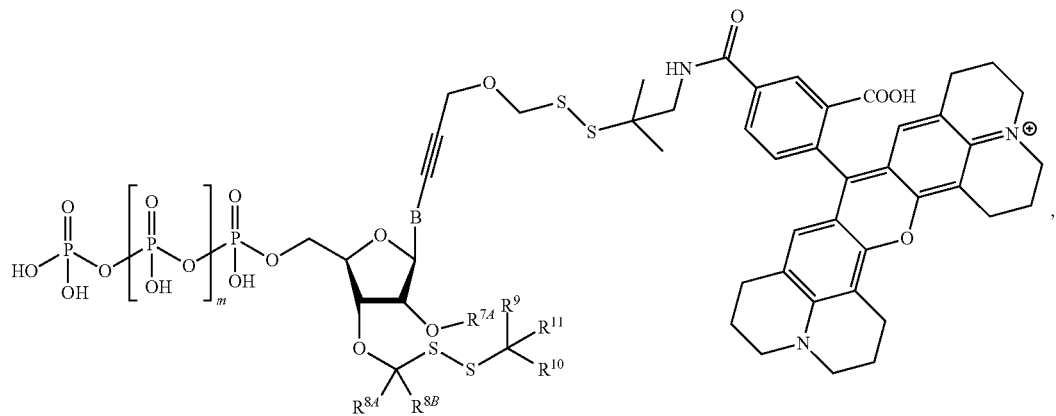
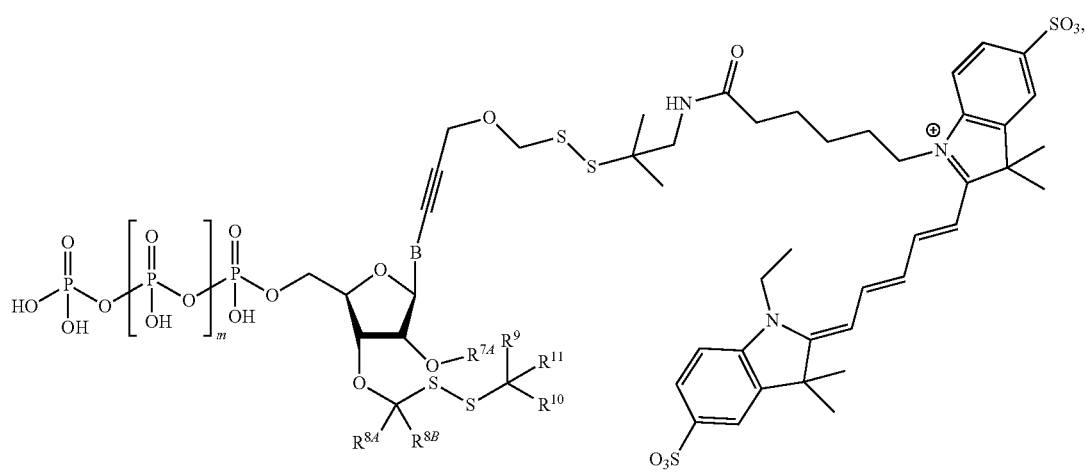

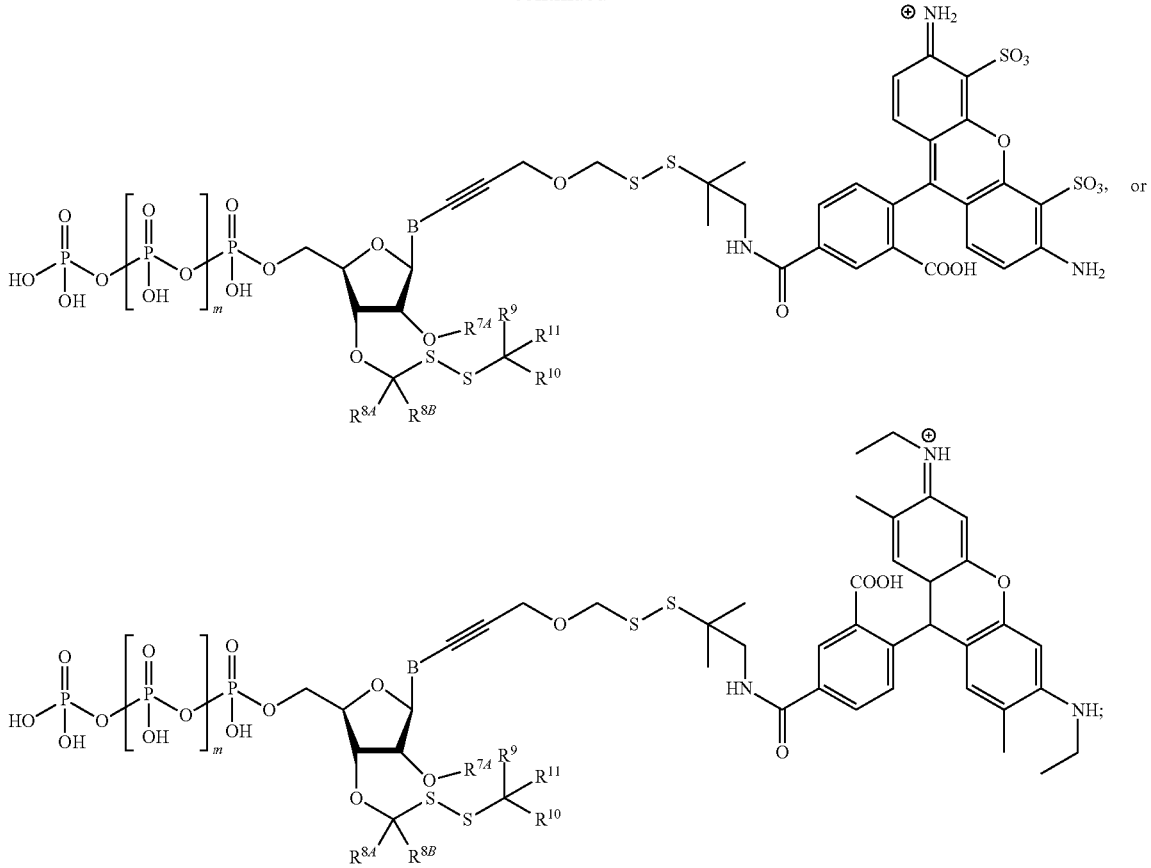

wherein B, $R^{7A}$, $R^{8A}$, $R^{8B}$, $R^9$, $R^{10}$, and $R^{11}$ are as described herein and in is an integer from 1 to 4. In embodiments, $R^{8A}$ is hydrogen, deuterium, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, $R^{8A}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, $R^{8B}$ is hydrogen, deuterium, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, $R^{8B}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, —CR$^9$R$^{10}$R$^{11}$ is unsubstituted methyl, unsubstituted ethyl, unsubstituted propyl, unsubstituted isopropyl, unsubstituted butyl, or unsubstituted tert-butyl. In embodiments, $R^9$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, —CN, or -Ph. In embodiments, $R^{10}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, CN, or - Ph. In embodiments, $R^{11}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, CN, or - Ph.

In embodiments, $R^{7A}$ is hydrogen. In embodiments $R^{7A}$ is

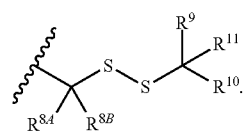

In embodiments, —R$^{7A}$ is
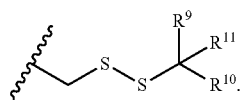
In embodiments, R$^{7A}$ is
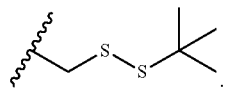 [SMILES: *CSSC(C)(C)C]
In embodiments, B is
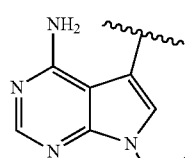
In embodiments, B is
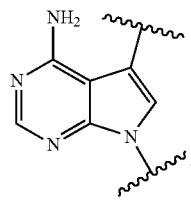
In embodiments, B is
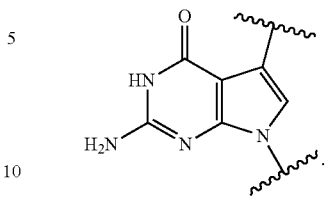
In embodiments, B is
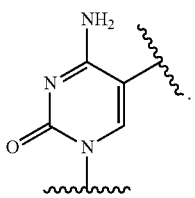 [SMILES: *c1cn(*)c(=O)nc1N]
In embodiments, B is
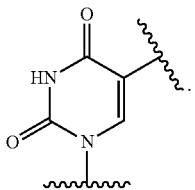
In embodiments, the compound has the formula:
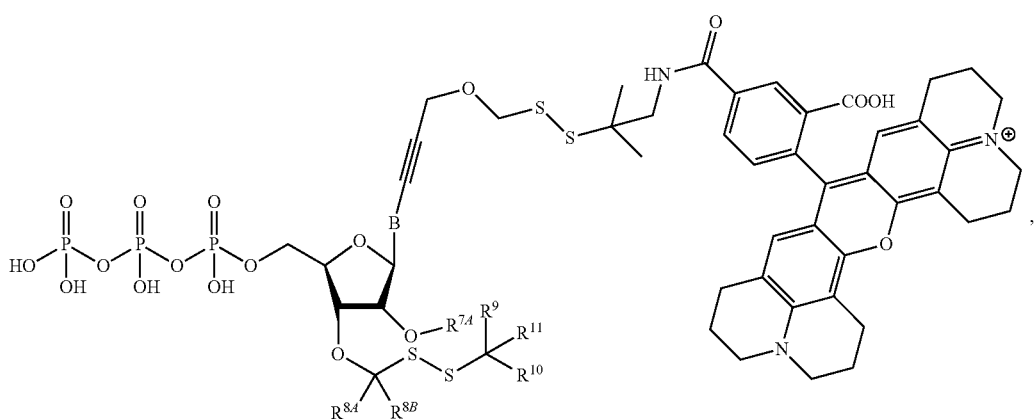

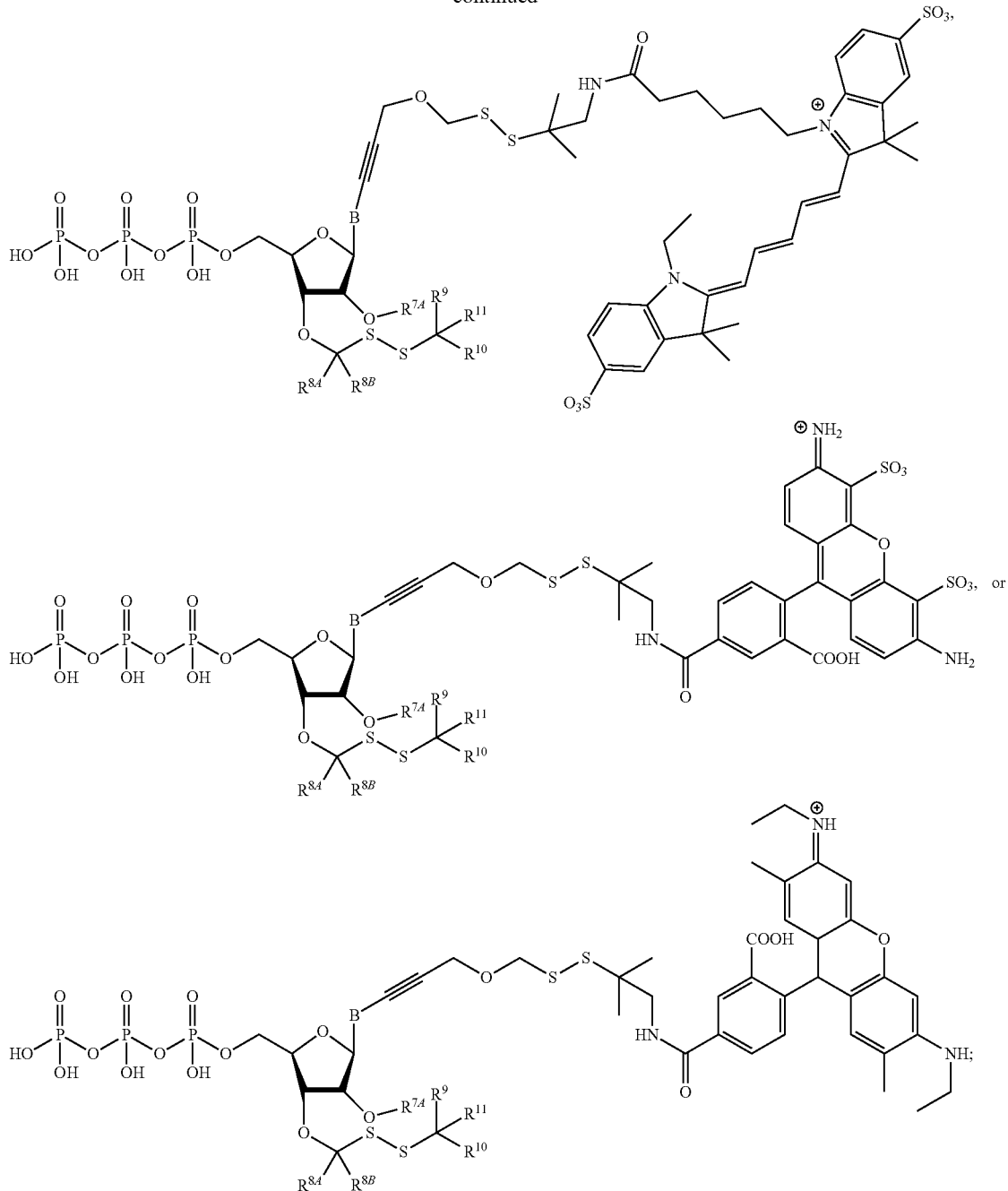

wherein B, $R^{7A}$, $R^{8A}$, $R^{8B}$, $R^9$, $R^{10}$, and $R^{11}$ are as described herein In embodiments, $R^{8A}$ is hydrogen, deuterium, —C(CH$_3$)$_3$, —CH(CH$_3$)$_2$, —CH$_2$CH$_2$CH$_3$, —CH$_2$CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, $R^{8A}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_3$, —NHCH$_3$—CN, or -Ph. In embodiments, $R^{8B}$ is hydrogen, deuterium, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, $R^{8B}$ is hydrogen, —C(CH$_3$)$_3$,—CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, —CR⁹R¹⁰R¹¹ is unsubstituted methyl, unsubstituted ethyl, unsubstituted propyl, unsubstituted isopropyl, unsubstituted butyl, or unsubstituted tert-butyl. In embodiments, R⁹ is hydrogen, —C(CH₃)₃, —CH(CH₃)₂, —CH₂CH₂CH₃, —CH₂CH₃, —CH₃, —OC(CH₃)₃, —OCH(CH₃)₂, —OCH₂CH₂CH₃, —OCH₂CH₃, —OCH₃, —SC(CH₃)₃, —SCH(CH₃)₂, —SCH₂CH₂CH₃, —SCH₂CH₃, —SCH₃, —NHC(CH₃)₃, —NHCH(CH₃)₂, —NHCH₂CH₂CH₃, —NHCH₂CH₃, —NHCH₃, —CN, or -Ph. In embodiments, R¹⁰ is hydrogen, —C(CH₃)₃, —CH(CH₃)₂, —CH₂CH₂CH₃, —CH₂CH₃, —CH₃, OC(CH₃)₃, —OCH(CH₃)₂, —OCH₂CH₂CH₃, —OCH₂CH₃, —OCH₃, —SC(CH₃)₃, —SCH(CH₃)₂, —SCH₂CH₂CH₃, —SCH₂CH₃, —SCH₃, —NHC(CH₃)₃, —NHCH(CH₃)₂, —NHCH₂CH₂CH₃, —NHCH₂CH₃, —NHCH₃, —CN, or -Ph. In embodiments, R¹¹ is hydrogen, —C(CH₃)₃, —CH(CH₃)₂, —CH₂CH₂CH₃, —CH₂CH₃, —CH₃, OC(CH₃)₃, —OCH(CH₃)₂, —OCH₂CH₂CH₃, —OCH₂CH₃, —OCH₃, —SC(CH₃)₃, —SCH(CH₃)₂, —SCH₂CH₂CH₃, —SCH₂CH₃, —SCH₃, —NHC(CH₃)₃, —NHCH(CH₃)₂, —NHCH₂CH₂CH₃, —NHCH₂CH₃, —NHCH₃, —CN, or -Ph. In embodiments, R⁷ᴬ is hydrogen. In embodiments R⁷ᴬ is

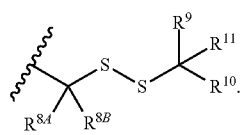

In embodiments, —R⁷ᴬ is

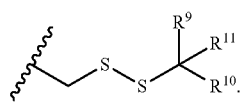

In embodiments, R⁷ᴬ is

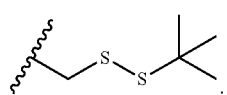 [SMILES: *CSSC(C)(C)C]

In embodiments, B is

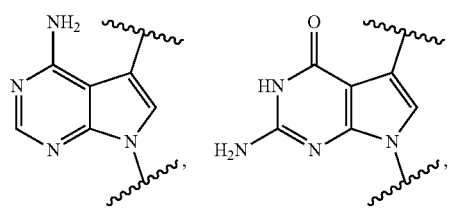

In embodiments, B is

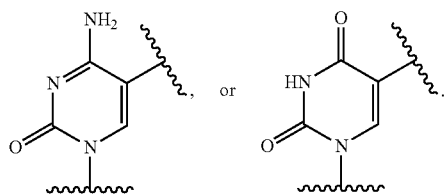

In embodiments, B is

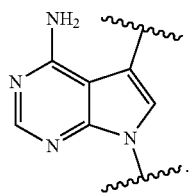 [SMILES: *c1cn(*)c2ncnc(N)c12]

In embodiments, B is

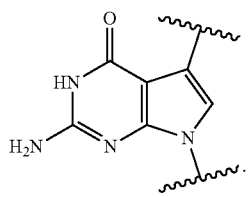

In embodiments, B is

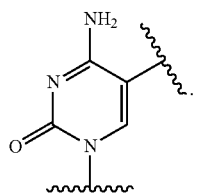 [SMILES: *c1cn(*)c(=O)nc1N]

In embodiments, B is

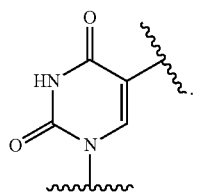 [SMILES: *c1cn(*)c(=O)[nH]c1=O]

In embodiments, the compound has the formula:
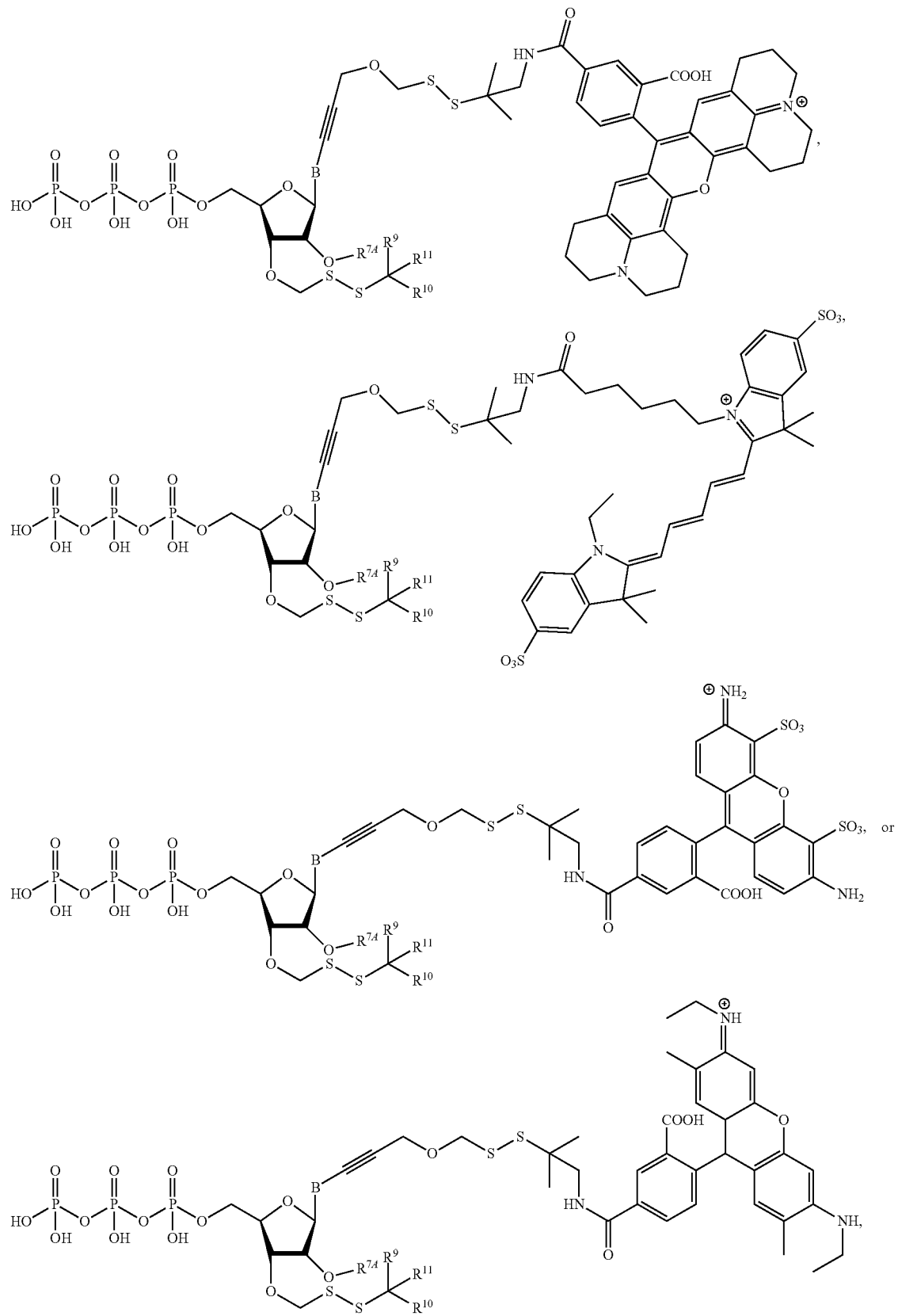

wherein B, $R^{7A}$, $R^9$, $R^{10}$, and $R^{11}$ are as described herein is are as described herein.
In embodiments, the compound has the formula:
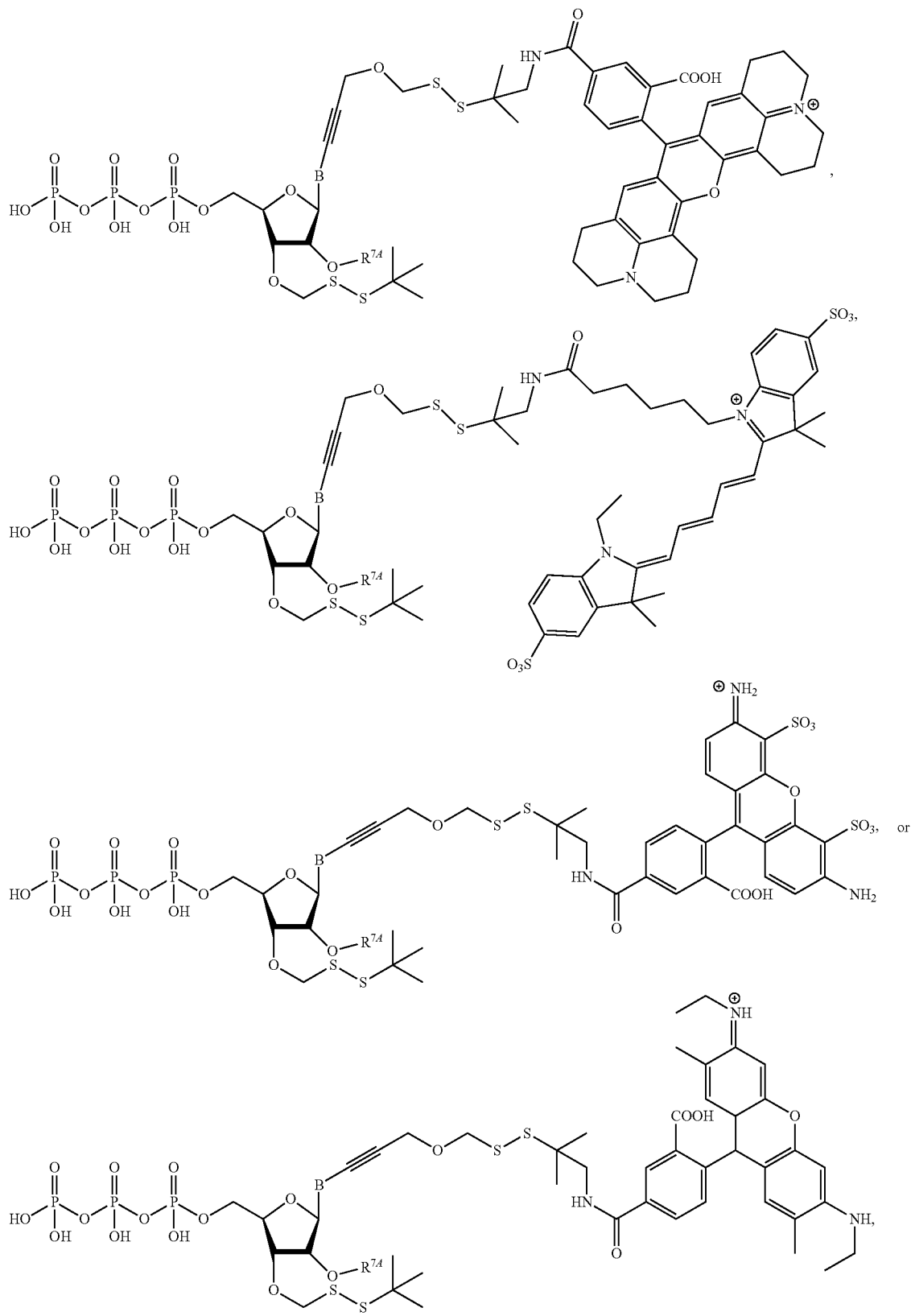

wherein B and $R^{7A}$ are as described herein are as described herein.
In embodiments, the compound has the formula:
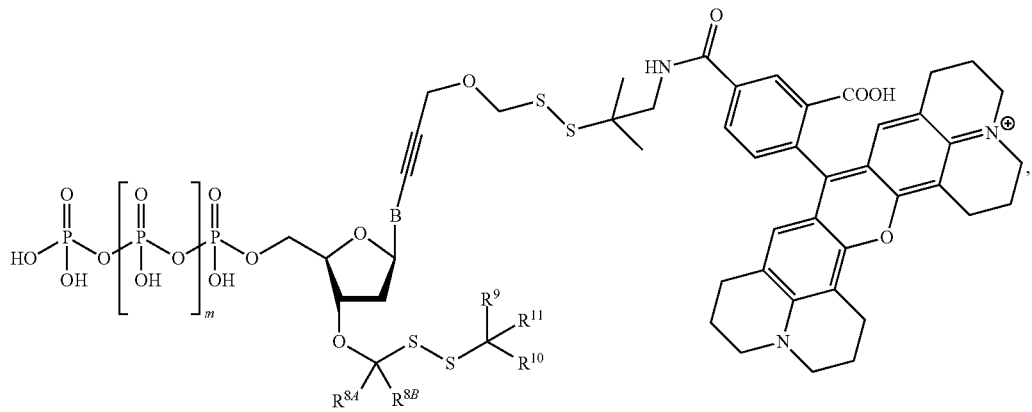
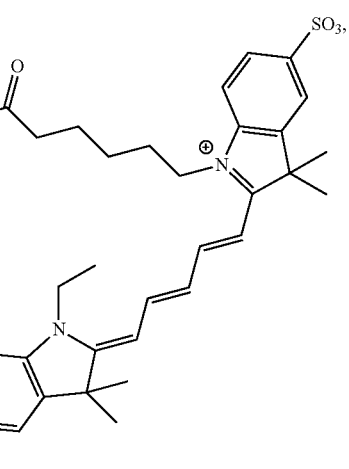
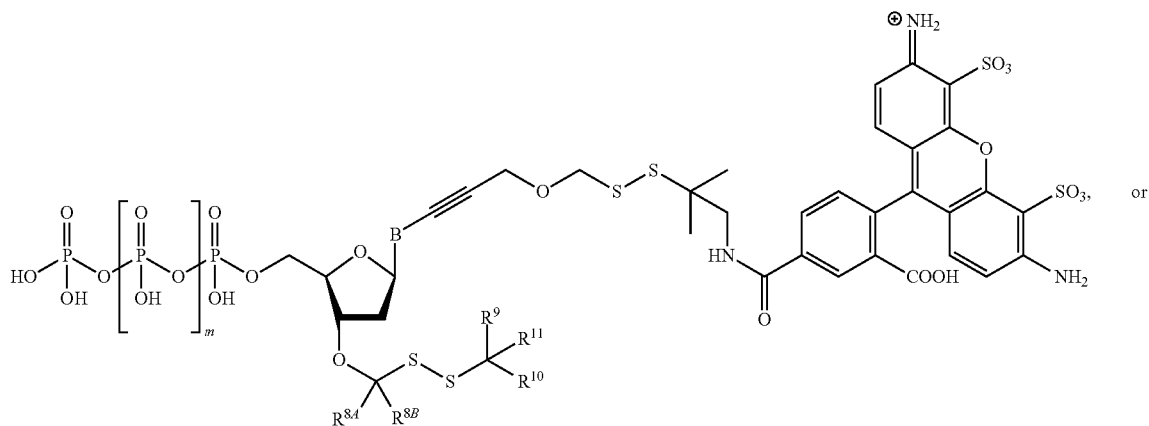
or

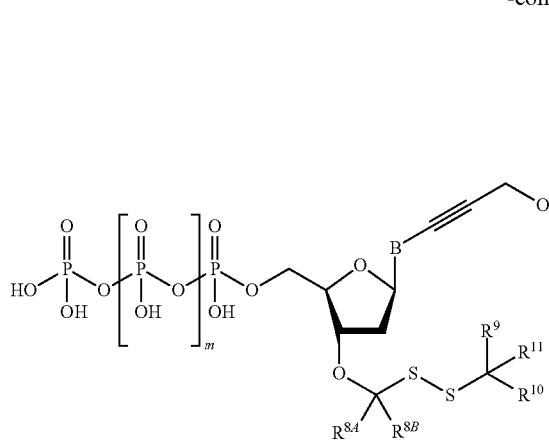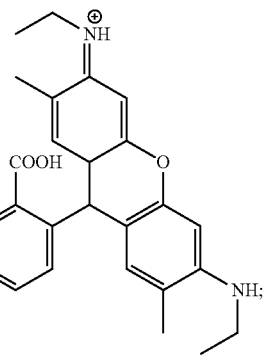

wherein B, $R^{8A}$, $R^{8B}$, $R^9$, $R^{10}$, and $R^{11}$ are as described herein and m is an integer from 1 to 4. In embodiments, $R^{8A}$ is hydrogen, deuterium, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, R" is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, $R^{8B}$ is hydrogen, deuterium, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, $R^{8B}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, —CR$^9$R$^{10}$R$^{11}$ is unsubstituted methyl, unsubstituted ethyl, unsubstituted propyl, unsubstituted isopropyl, unsubstituted butyl, or unsubstituted ten-butyl. In embodiments, $R^9$ is hydrogen, C(CH$_3$)$_3$, —CH(CH$_3$)$_2$, —CH$_2$CH$_2$CH$_3$, —CH$_2$CH$_3$, —CH$_3$, —OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, —CN, or -Ph. In embodiments, $R^{10}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, or -Ph. In embodiments, $R^{11}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, —CN, or -Ph. In embodiments, B is

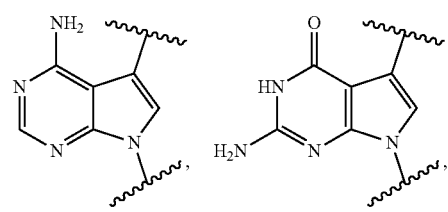

In embodiments, B is

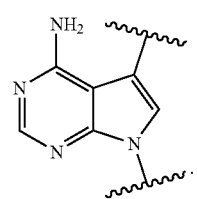

In embodiments, B is

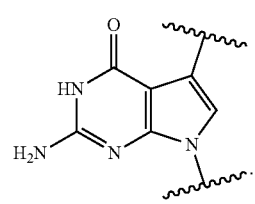 [SMILES: *c1cn(*)c2nc(N)[nH]c(=O)c12]

In embodiments, B is
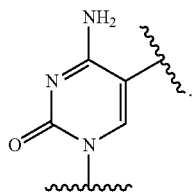 [SMILES: *c1cn(*)c(=O)nc1N]
In embodiments, B is
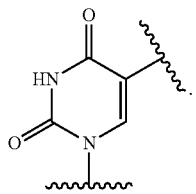
In embodiments, the compound has the formula:
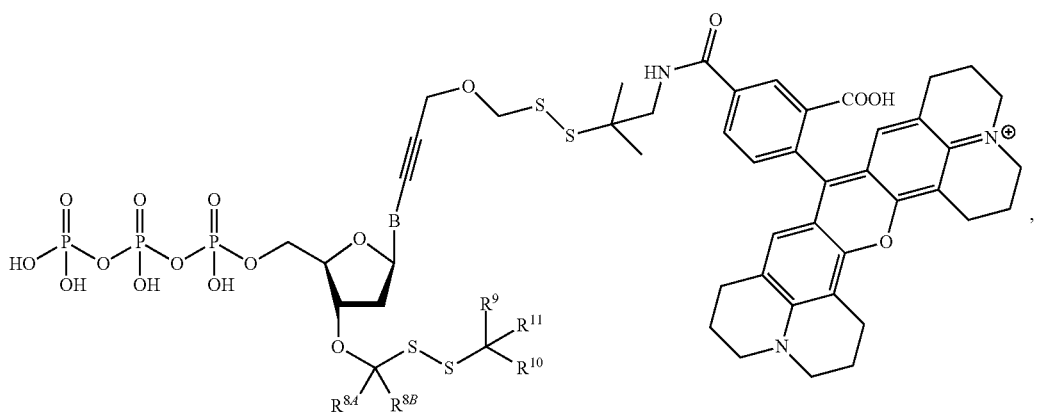
,
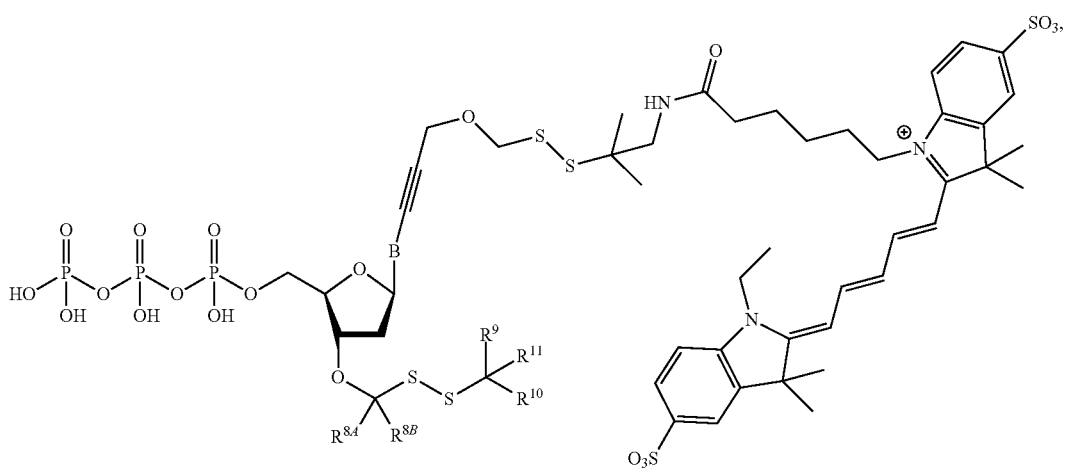
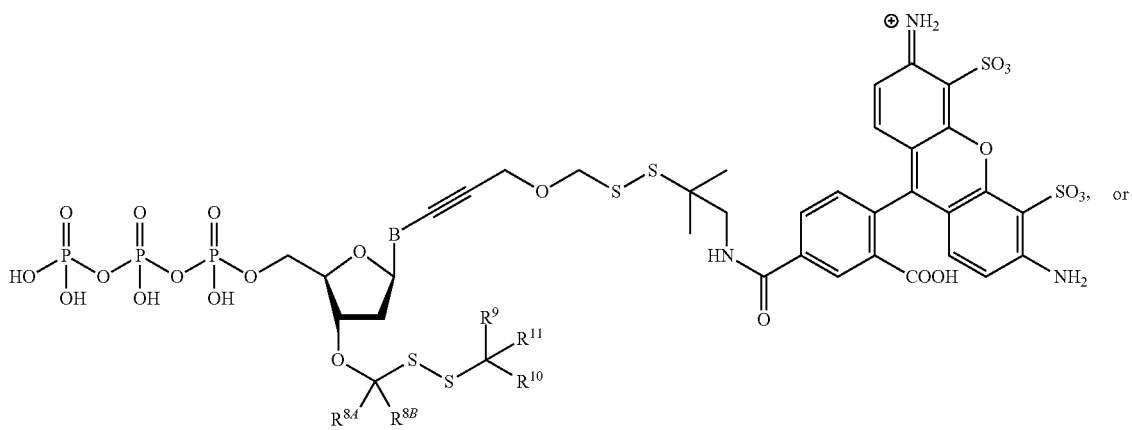
or -continued

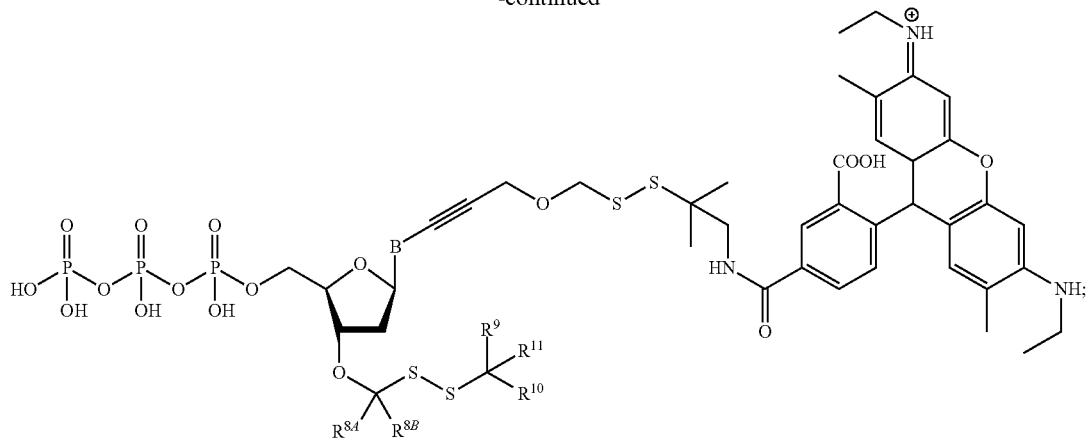

wherein B, $R^{8A}$, $R^{8B}$, $R^9$, $R^{10}$, and $R^{11}$ are as described herein. In embodiments, $R^{8A}$ is hydrogen, deuterium, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, or -Ph. In embodiments, $R^{8A}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, $R^{8B}$ is hydrogen, deuterium, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$. —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, $R^{8B}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, —CR$^9$R$^{10}$R$^{11}$ is unsubstituted methyl, unsubstituted ethyl, unsubstituted propyl, unsubstituted isopropyl, unsubstituted butyl, or unsubstituted tert-butyl. In embodiments, $R^9$ is hydrogen, —C(CH$_3$)$_3$, —CH(CH$_3$)$_2$, —CH$_2$CH$_2$CH$_3$, —CH$_2$CH$_3$, —CH$_3$, —OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$. —CN, or -Ph. In embodiments, $R^{10}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, —CN, or -Ph. In embodiments, $R^{11}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, —CN, or -Ph. In embodiments, B is

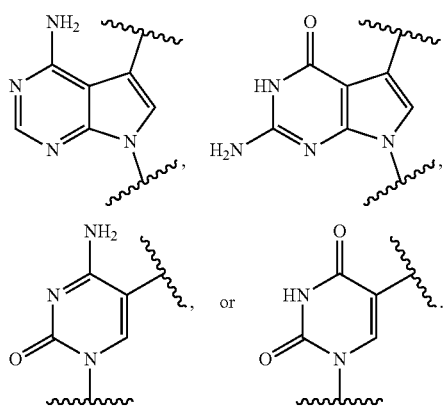

In embodiments, B is

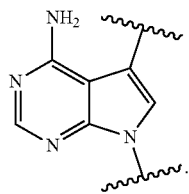

In embodiments, B is

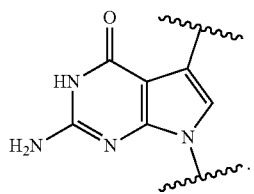

In embodiments, B is
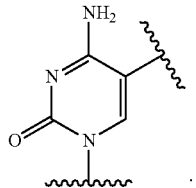
In embodiments, B is
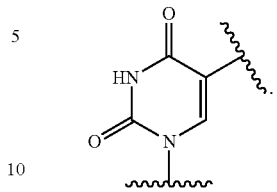
In embodiments, the compound has the formula:
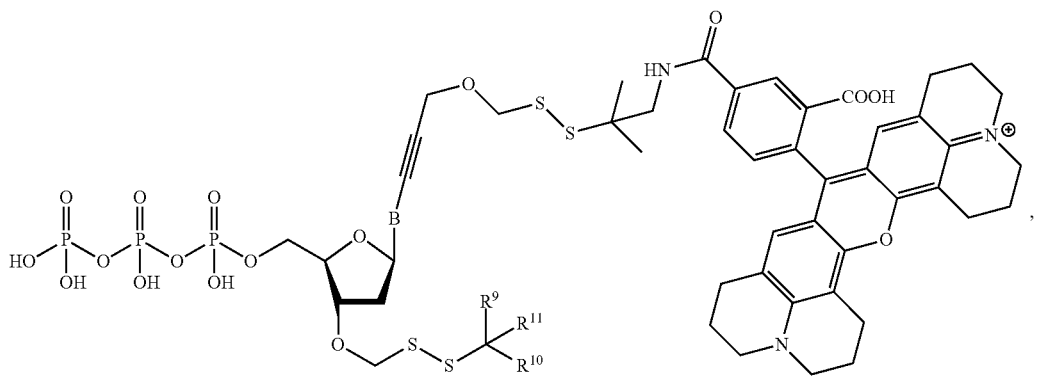
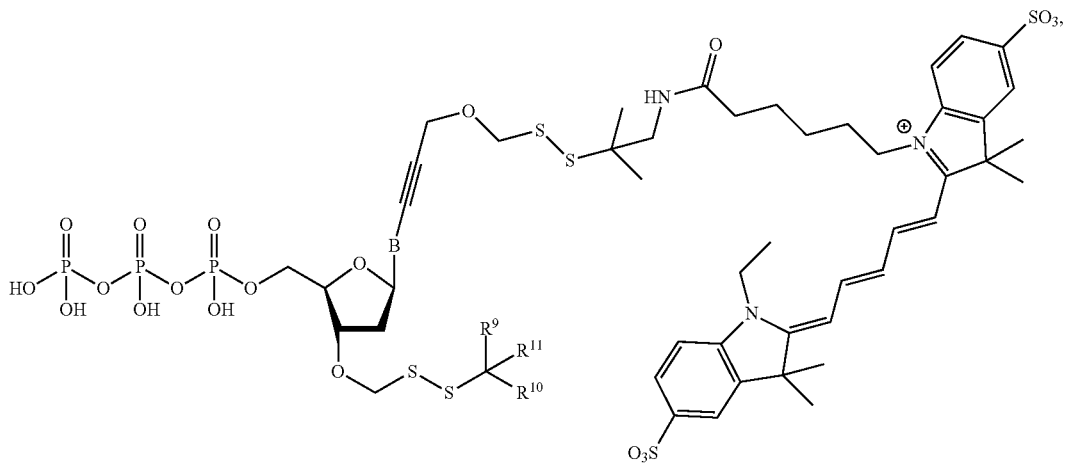
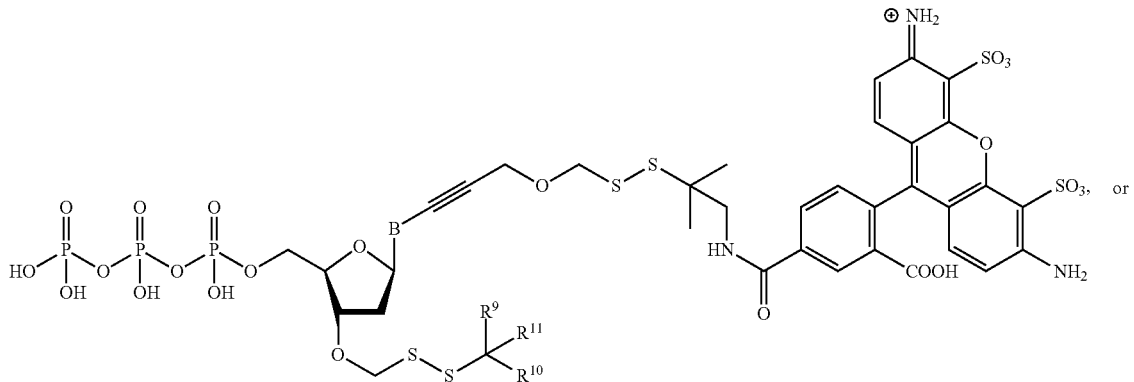

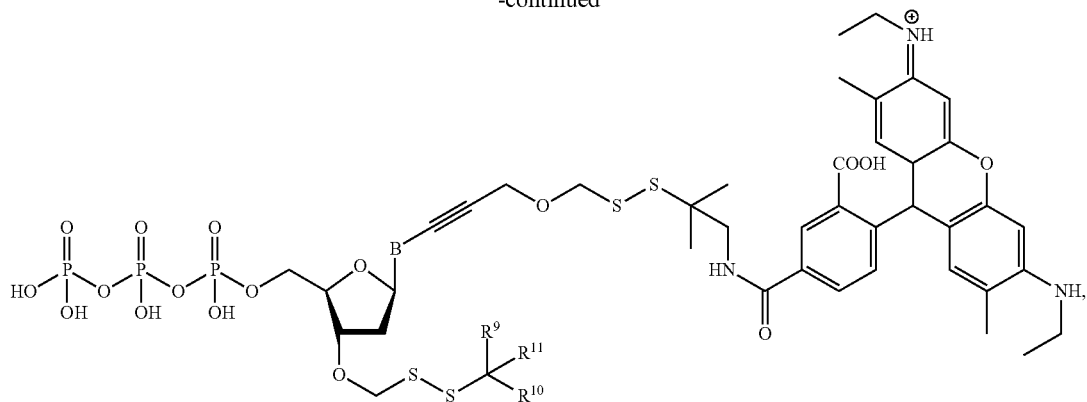
wherein B, $R^9$, $R^{10}$, and $R^{11}$ are as described herein are as described herein. In embodiments, B is
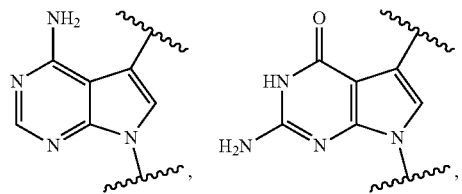
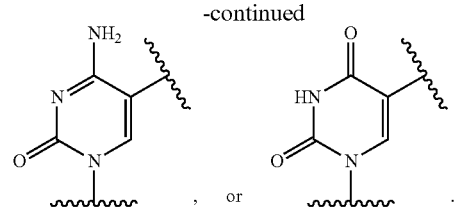
In embodiments, the compound has the formula:
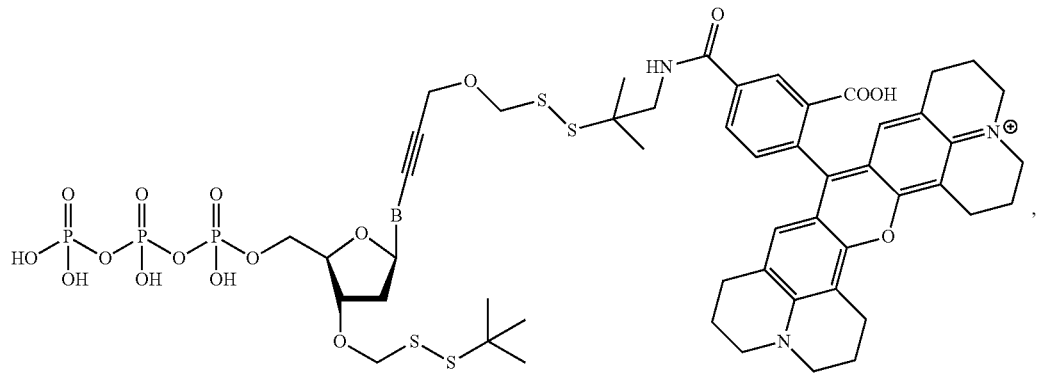
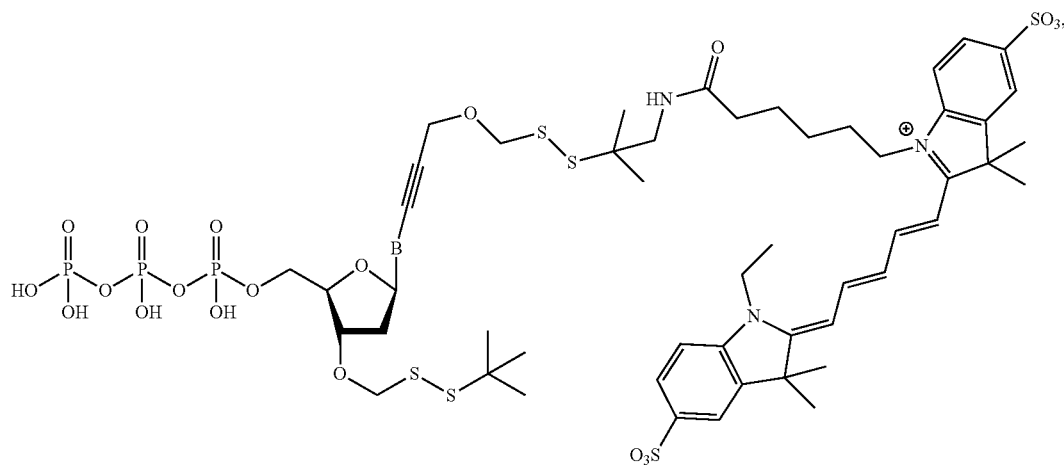

-continued
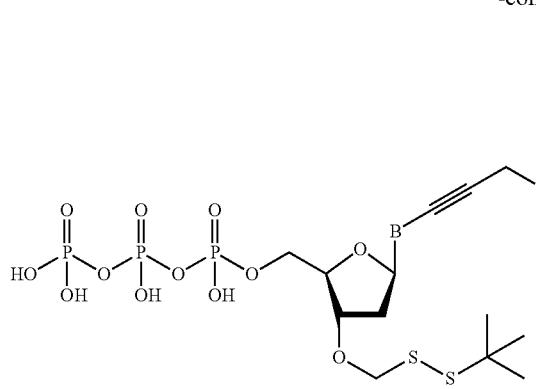 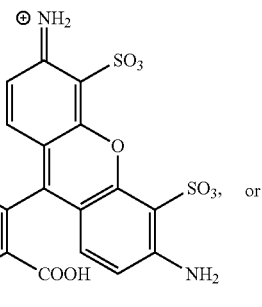 or
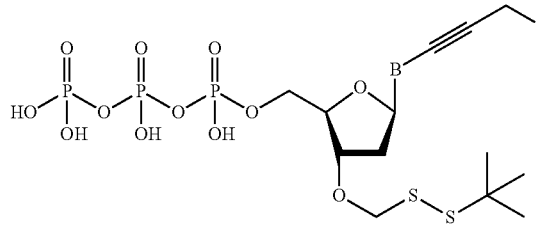 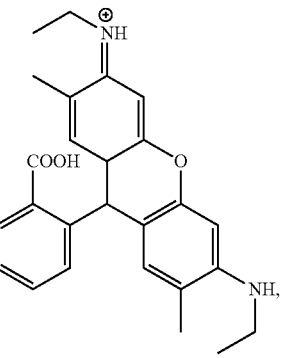
wherein B is as described herein. In embodiments, B is
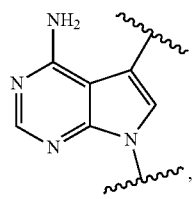 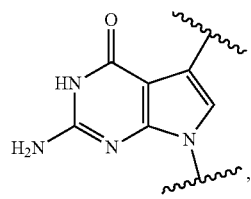,
In embodiments, B is
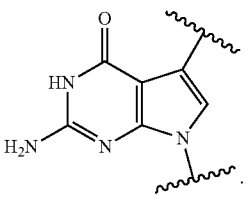.
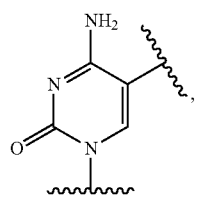, or 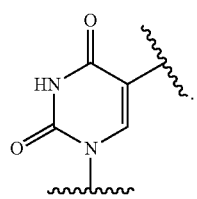 [SMILES: *c1cn(*)c(=O)[nH]c1=O].
In embodiments, B is
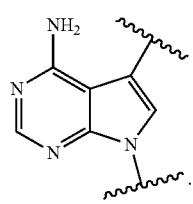.
In embodiments, B is
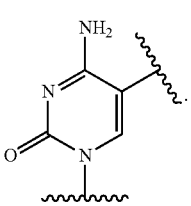 [SMILES: *c1cn(*)c(=O)nc1N].

In embodiments, B is
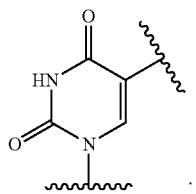 [SMILES: *c1cn(*)c(=O)[nH]c1=O]
In embodiments, the compound has the formula:
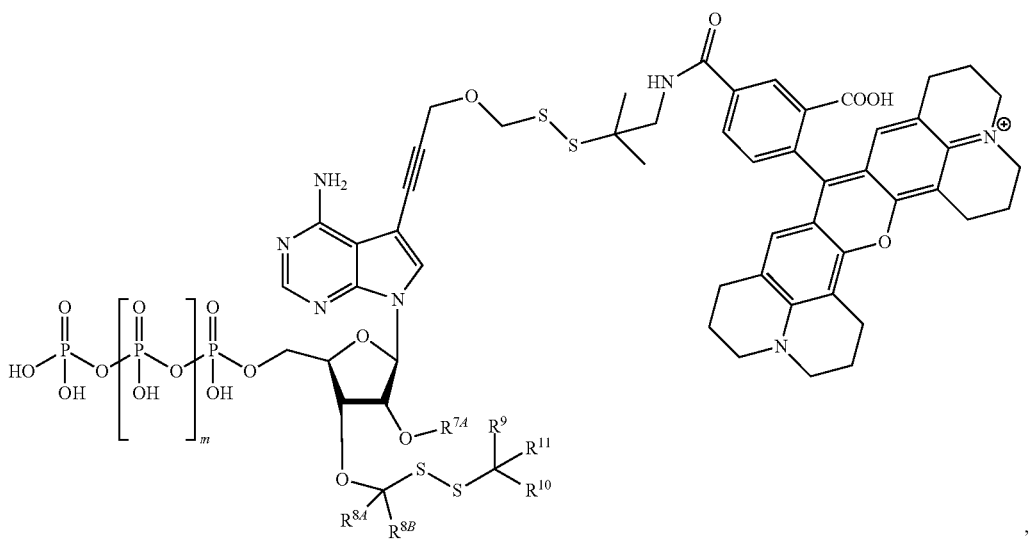
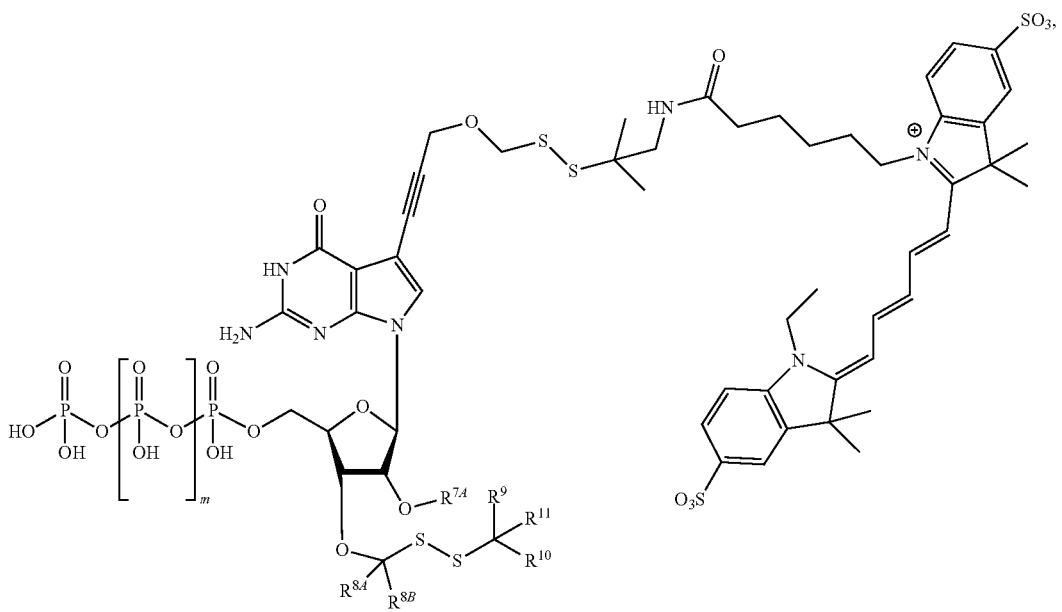

-continued

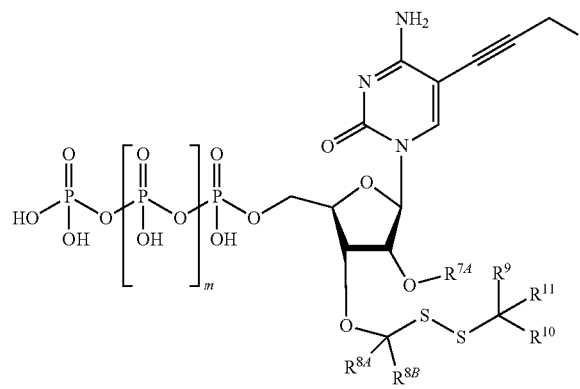
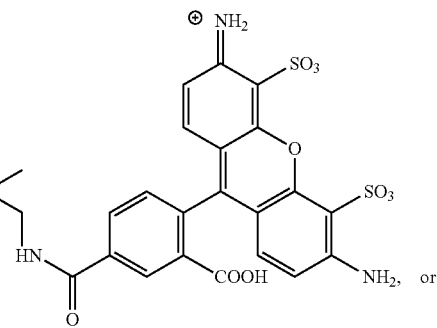

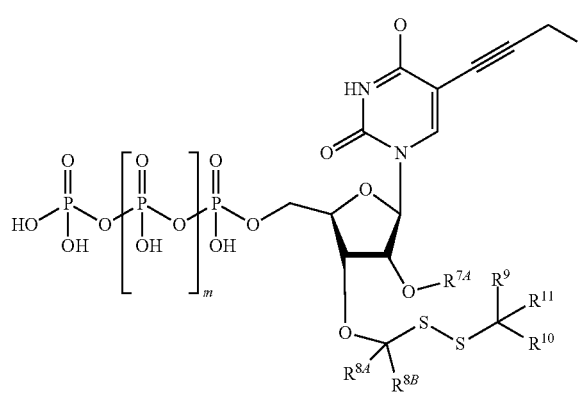
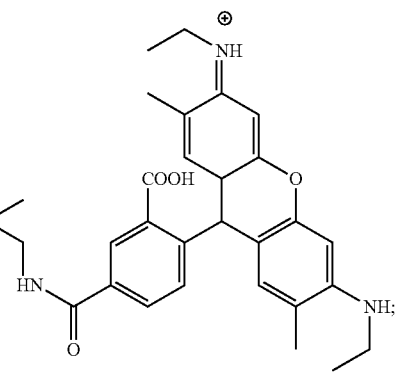

wherein $R^{7A}$, $R^{8A}$, $R^{8B}$, $R^9$, $R^{10}$, and $R^{11}$ are as described herein and m is an integer from 1 to 4. In embodiments, $R^{8A}$ is hydrogen, deuterium, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, $R^{8A}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, $R^{8B}$ is hydrogen, deuterium, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, $R^{8B}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$. —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, —CR$^9$R$^{10}$R$^{11}$ is unsubstituted methyl, unsubstituted ethyl, unsubstituted propyl, unsubstituted isopropyl, unsubstituted butyl, or unsubstituted tert-butyl. In embodiments, $R^9$ is hydrogen, —C(CH$_3$)$_3$, —CH(CH$_3$)$_2$, —CH$_2$CH$_2$CH$_3$, —CH$_2$CH$_3$, —CH$_3$, —OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, —CN, or -Ph. In embodiments, $R^{10}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —CH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, or -Ph. In embodiments, $R^H$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH₂CH₃, —OCH₃, —SC(CH₃)₃, —SCH(CH₃)₂, —SCH₂CH₂CH₃, —SCH₂CH₃, —SCH₃, —NHC(CH₃)₃, —NHCH(CH₃)₂, —NHCH₂CH₂CH₃, —NHCH₂CH₃, —NHCH₃, or -Ph. In embodiments, B is
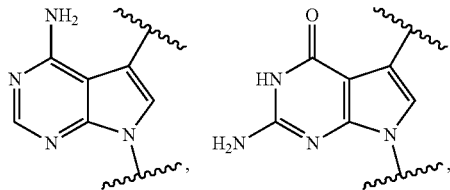
In embodiments, B is
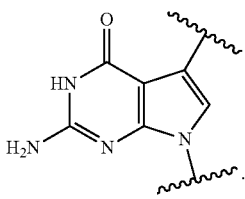 [SMILES: *c1cn(*)c2nc(N)[nH]c(=O)c12]
In embodiments, B is
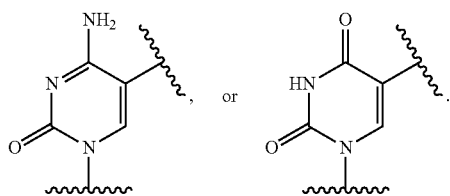
In embodiments, B is
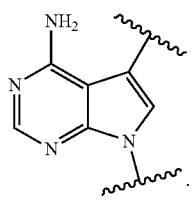 [SMILES: *c1cn(*)c2ncnc(N)c12]
In embodiments, B is
In embodiments, the compound has the formula:
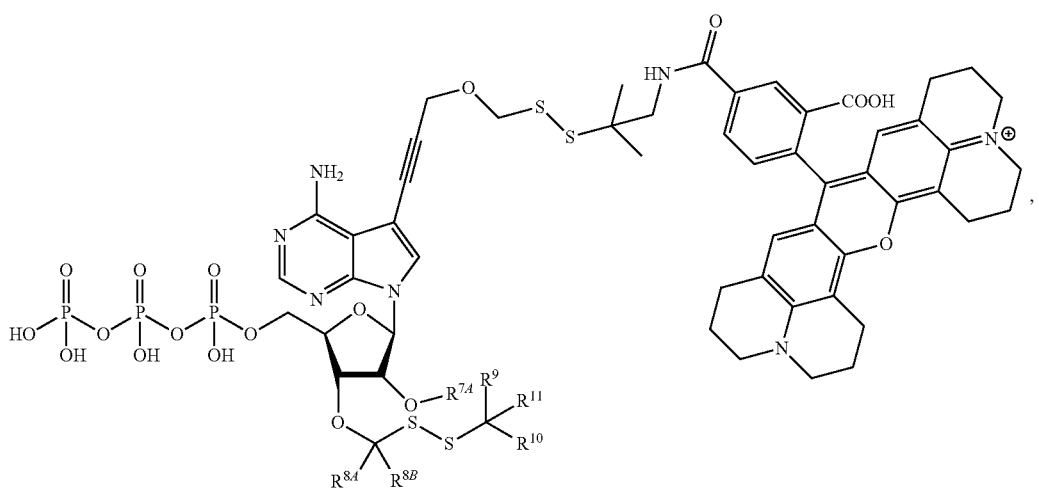

-continued
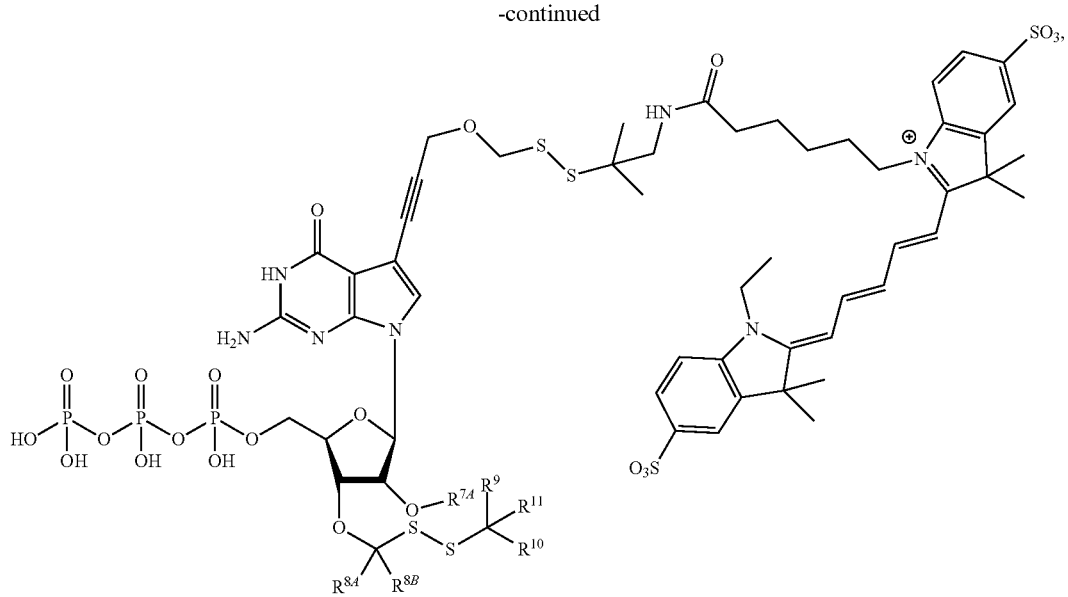
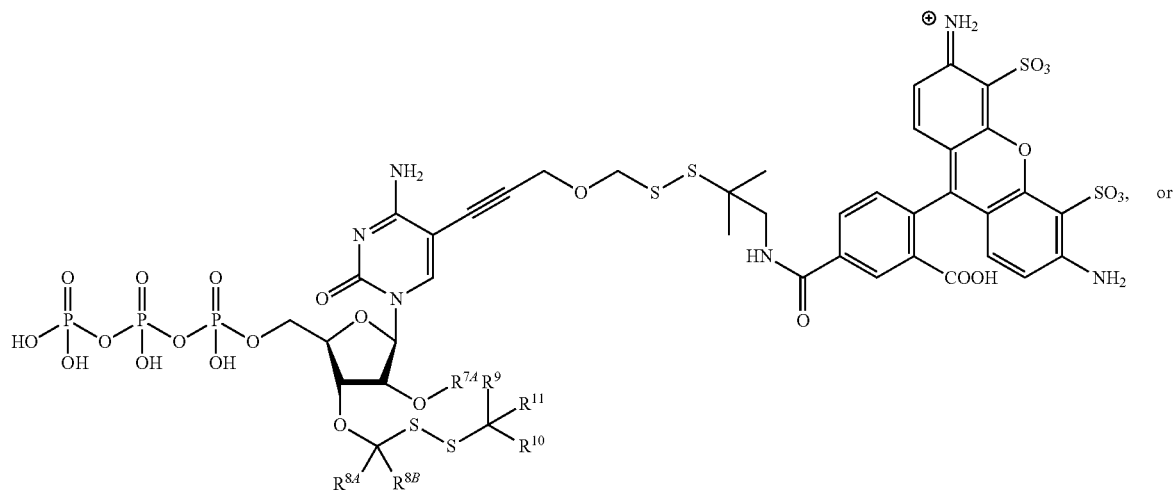
or
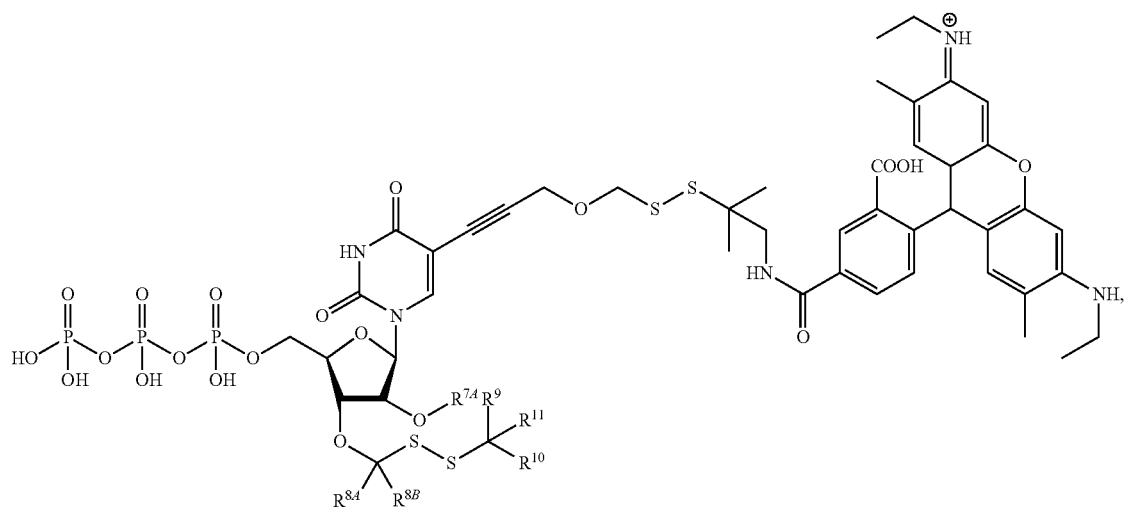

wherein $R^{7A}$, $R^{8A}$, $R^{8B}$, $R^9$, $R^{10}$, and are as described herein. In embodiments, $R^{8A}$ is hydrogen, deuterium, —C(CH₃)₃, —CH(CH₃)₂, —CH₂CH₂CH₃, —CH₂CH₃, —CH₃, OC(CH₃)₃, —OCH(CH₃)₂, —OCH₂CH₂CH₃, —OCH₂CH₃, —OCH₃, —SC(CH₃)₃, —SCH(CH₃)₂, —SCH₂CH₂CH₃, —SCH₂CH₃, —SCH₃, —NHC(CH₃)₃, —NHCH(CH₃)₂, —NHCH₂CH₂CH₃, —NHCH₂CH₃, —NHCH₃—CN, or -Ph. In embodiments, $R^{8A}$ is hydrogen, —C(CH₃)₃, —CH(CH₃)₂, —CH₂CH₂CH₃, —CH₂CH₃, —CH₃, OC(CH₃)₃, —OCH(CH₃)₂, —OCH₂CH₂CH₃, —OCH₂CH₃, —OCH₃, SC(CH₃)₃, —SCH(CH₃)₂, —SCH₂CH₂CH₃, —SCH₂CH₃, —SCH₃, NHC(CH₃)₃, —NHCH(CH₃)₂, —NHCH₂CH₂CH₃, —NHCH₂CH₃, —NHCH₃—CN, or -Ph. In embodiments, $R^{8B}$ is hydrogen, deuterium, —C(CH₃)₃, —CH(CH₃)₂, —CH₂CH₂CH₃, —CH₂CH₃, —CH₃, OC(CH₃)₃, —OCH(CH₃)₂, —OCH₂CH₂CH₃, —OCH₂CH₃, —OCH₃, SC(CH₃)₃, —SCH(CH₃)₂, —SCH₂CH₂CH₃, —SCH₂CH₃, —SCH₃, NHC(CH₃)₃, —NHCH(CH₃)₂, —NHCH₂CH₂CH₃, —NHCH₂CH₃, —NHCH₃—CN, or -Ph. In embodiments, $R^{8B}$ is hydrogen, —C(CH₃)₃, —CH(CH₃)₂, —CH₂CH₂CH₃, —CH₂CH₃, —CH₃, OC(CH₃)₃, —OCH(CH₃)₂, —OCH₂CH₂CH₃, —OCH₂CH₃, —OCH₃, —SC(CH₃)₃, —SCH(CH₃)₂, —SCH₂CH₂CH₃, —SCH₂CH₃, —SCH₃, —NHC(CH₃)₃, —NHCH(CH₃)₂, —NHCH₂CH₂CH₃, —NHCH₂CH₃, —NHCH₃—CN, or -Ph. In embodiments, —CR⁹R¹⁰R¹¹ is unsubstituted methyl, unsubstituted ethyl, unsubstituted propyl, unsubstituted isopropyl, unsubstituted butyl, or unsubstituted tert-butyl. In embodiments, $R^9$ is hydrogen, C(CH₃)₃, —CH(CH₃)₂, —CH₂CH₂CH₃, —CH₂CH₃, —CH₃, —OC(CH₃)₃, —OCH(CH₃)₂, —OCH₂CH₂CH₃, —OCH₂CH₃, —OCH₃, —SC(CH₃)₃, —SCH(CH₃)₂, —SCH₂CH₂CH₃, —SCH₂CH₃, —SCH₃, —NHC(CH₃)₃, —NHCH(CH₃)₂, —NHCH₂CH₂CH₃, —NHCH₂CH₃, —NHCH₃, or -Ph. In embodiments, $R^{10}$ is hydrogen, —C(CH₃)₃, —CH(CH₃)₂, —CH₂CH₂CH₃, —CH₂CH₃, —CH₃, OC(CH₃)₃, —OCH(CH₃)₂, —OCH₂CH₂CH₃, —OCH₂CH₃, —OCH₃, —SC(CH₃)₃, —SCH(CH₃)₂, —SCH₂CH₂CH₃, —SCH₂CH₃, —SCH₃, —NHC(CH₃)₃, —NHCH(CH₃)₂, —NHCH₂CH₂CH₃, —NHCH₂CH₃, —NHCH₃, —CN, or -Ph. In embodiments, $R^{11}$ is hydrogen, —C(CH₃)₃, —CH(CH₃)₂, —CH₂CH₂CH₃, —CH₂CH₃, —CH₃, OC(CH₃)₃, —OCH(CH₃)₂, —OCH₂CH₂CH₃, —OCH₂CH₃, —OCH₃, —SC(CH₃)₃, —SCH(CH₃)₂, —SCH₂CH₂CH₃, —SCH₂CH₃, —SCH₃, —NHC(CH₃)₃, —NHCH(CH₃)₂, —NHCH₂CH₂CH₃, —NHCH₂CH₃, —NHCH₃, —CN, or -Ph. In embodiments, B is

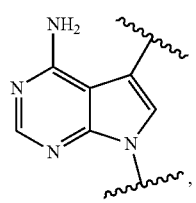 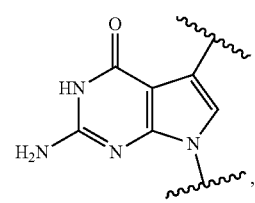

-continued

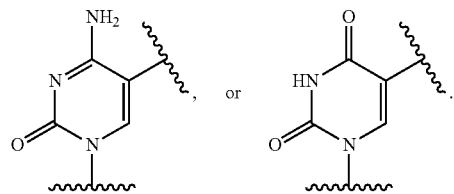

In embodiments, B is

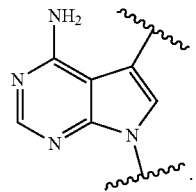 [SMILES: *c1cn(*)c2ncnc(N)c12]

In embodiments, B is

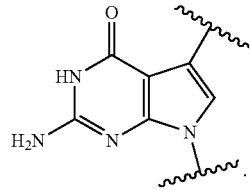 [SMILES: *c1cn(*)c2nc(N)[nH]c(=O)c12]

In embodiments, B is

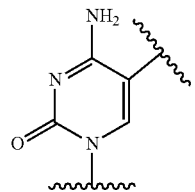

In embodiments, B is

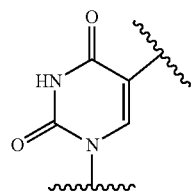

In embodiments, the compound has the formula:
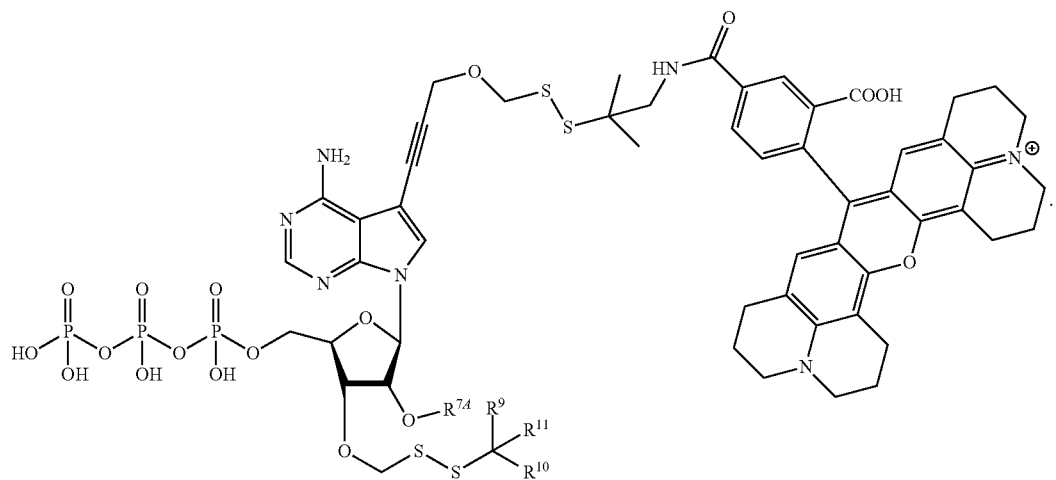
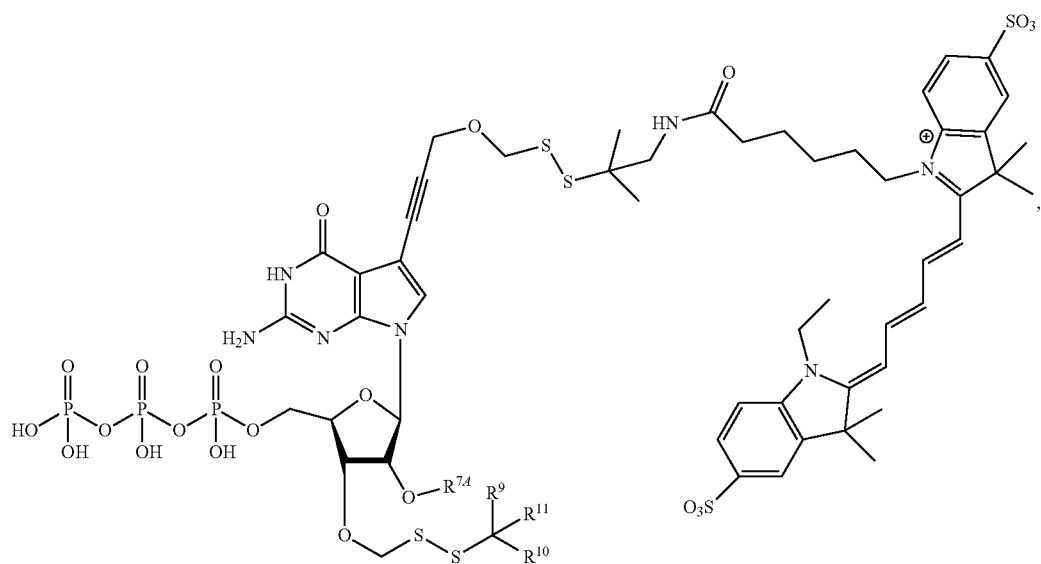
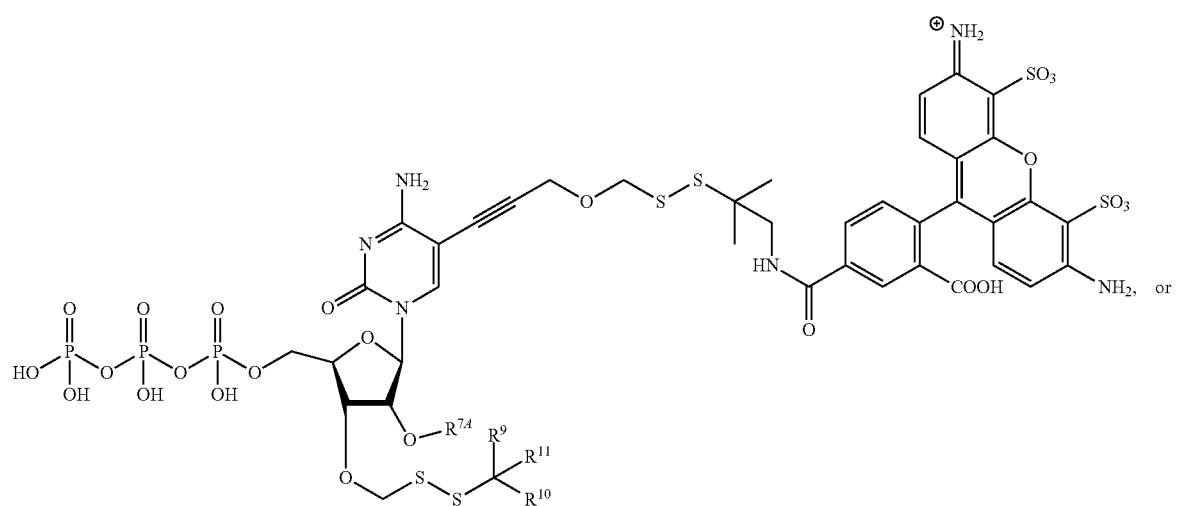

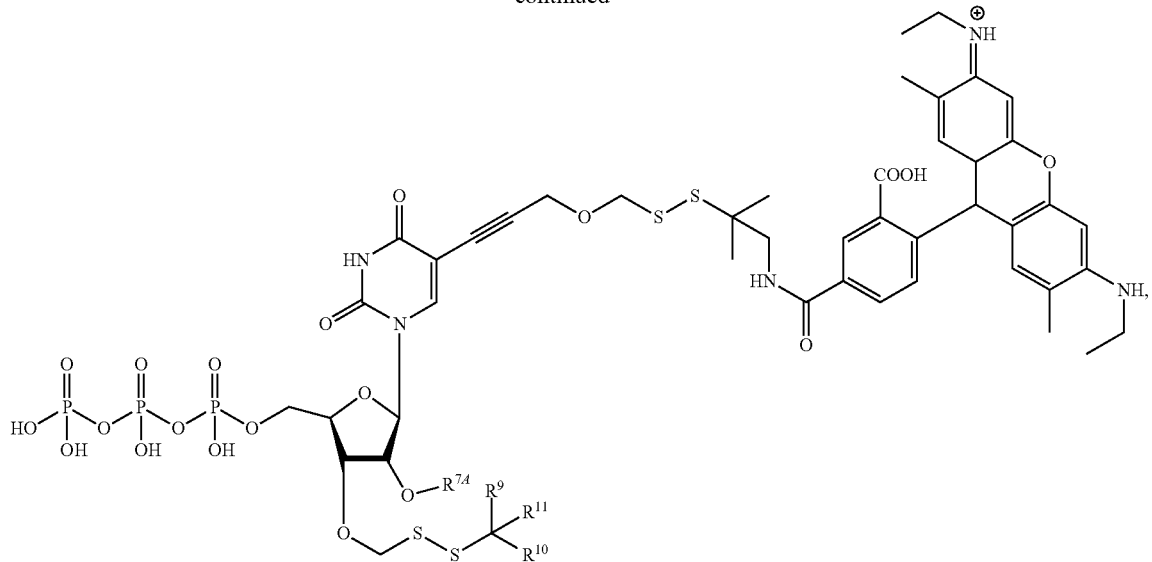
wherein $R^{7A}$, $R^9$, $R^{10}$, and $R^{11}$ are as described herein.
In embodiments, the compound has the formula:
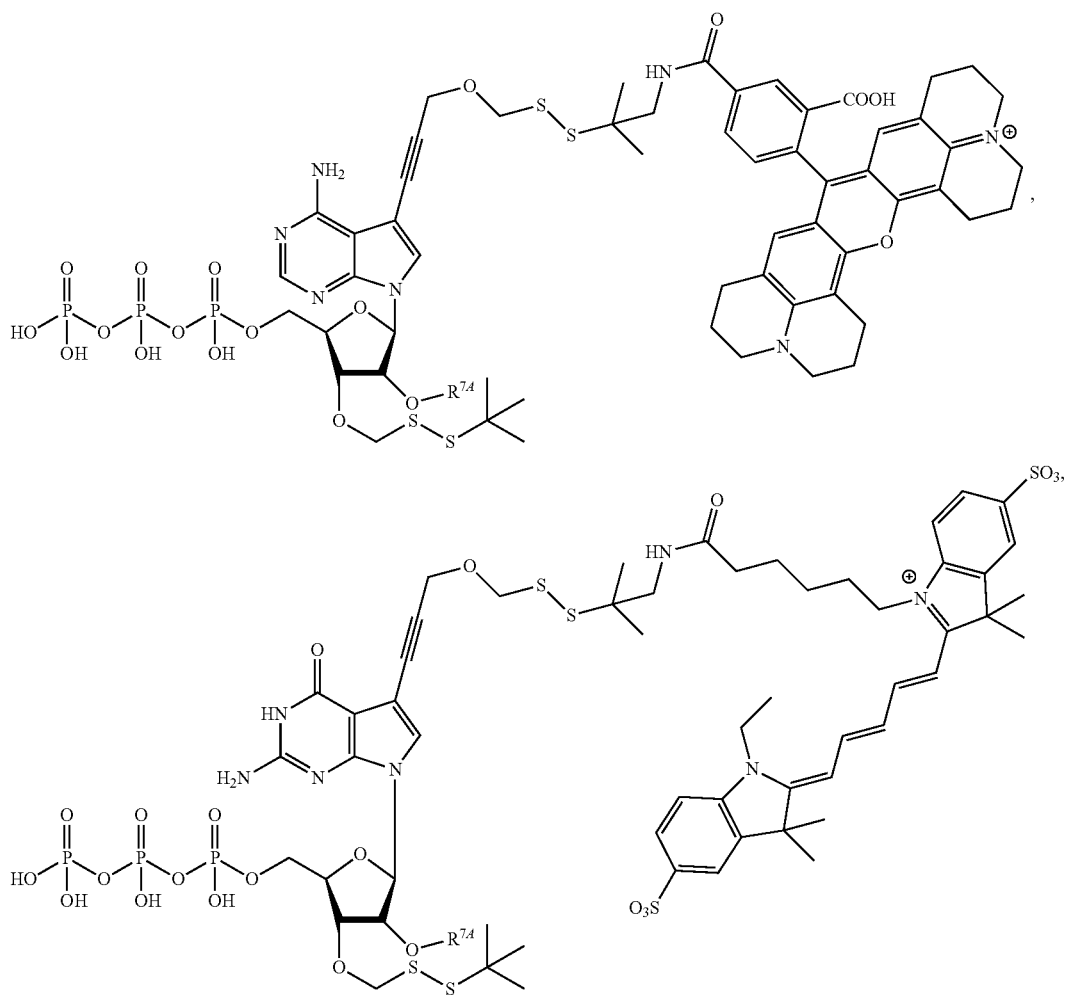

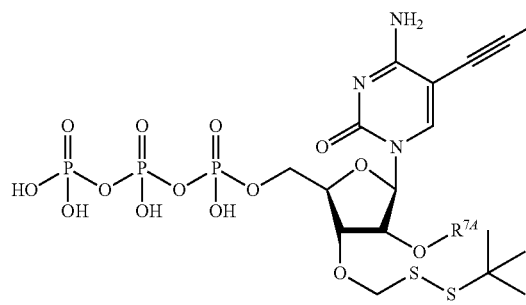
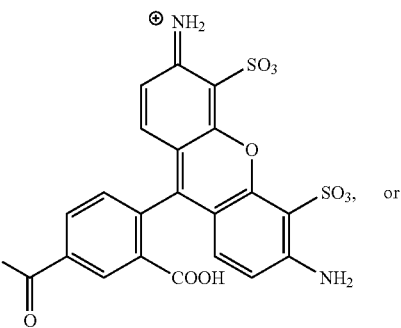
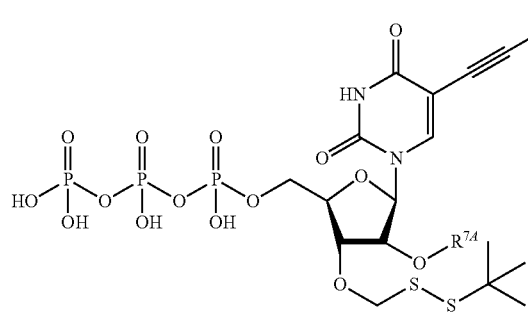
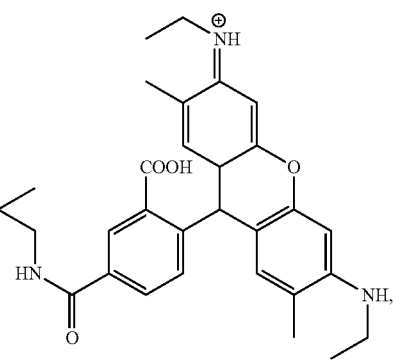
wherein $R^{7A}$ is as described herein.
In embodiments, the compound has the formula:
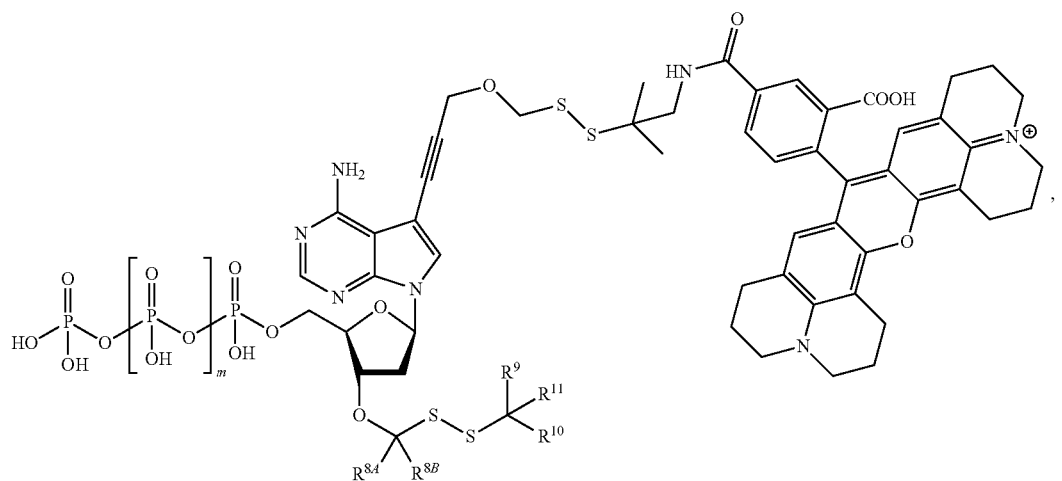

183
-continued
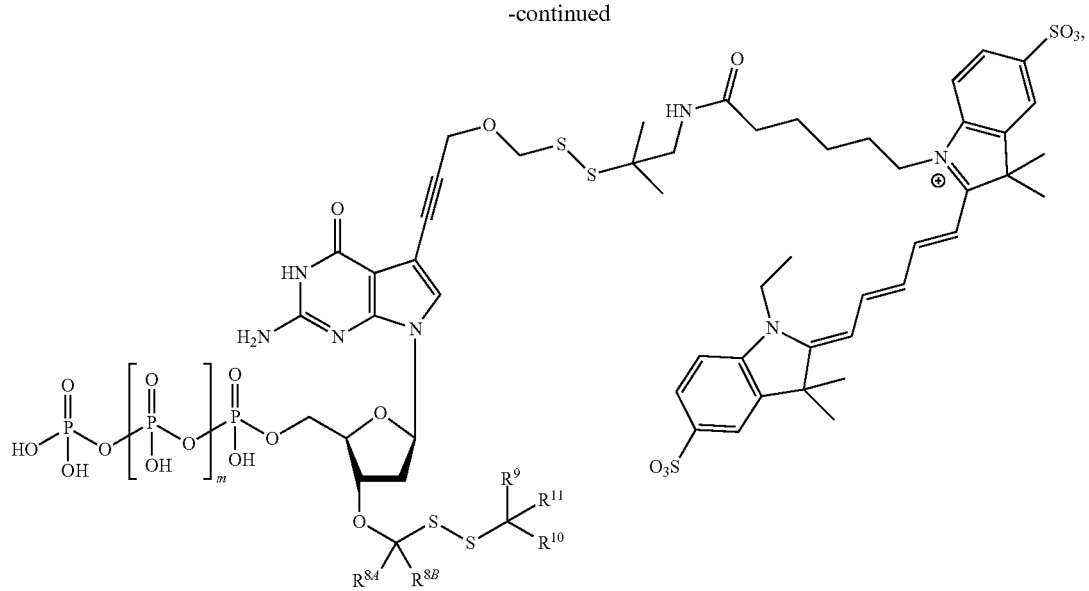
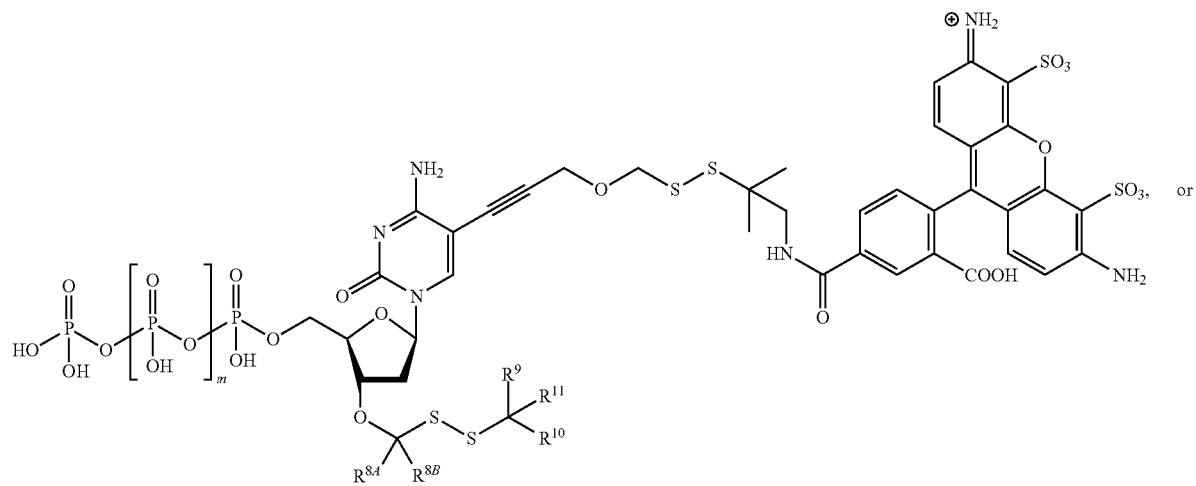
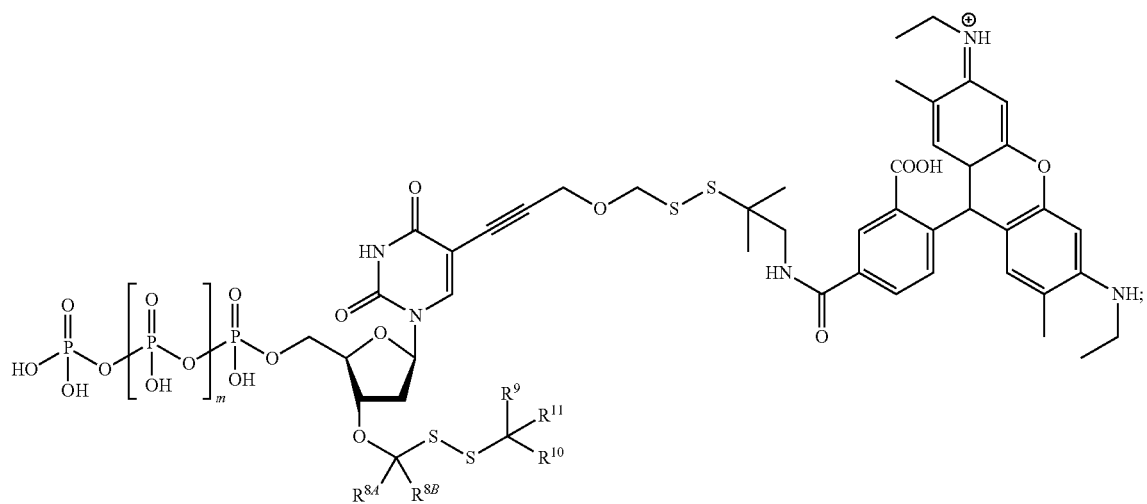

wherein $R^{8A}$, $R^{8B}$, $R^9$, $R^{10}$, and $R^{11}$ are as described herein and m is an integer from 1 to 4. In embodiments, $R^{8A}$ is hydrogen, deuterium, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, $R^{8A}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH—CN$_3$, or -Ph. In embodiments, $R^{8B}$ is hydrogen, deuterium, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, $R^{8B}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, —CR$^9$R$^{10}$R$^{11}$ is unsubstituted methyl, unsubstituted ethyl, unsubstituted propyl, unsubstituted isopropyl, unsubstituted butyl, or unsubstituted tert-butyl. In embodiments, $R^9$ is hydrogen, —C(CH$_3$)$_3$, —CH(CH$_3$)$_2$, —CH$_2$CH$_2$CH$_3$, —CH$_2$CH$_3$, —CH$_3$, —OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$. —NHCH$_3$, or -Ph. In embodiments, $R^{10}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, —CN, or -Ph. In embodiments, $R^{11}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_2$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, —CN, or -Ph. In embodiments, B is

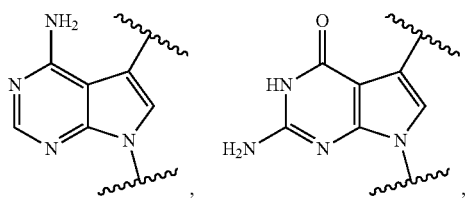

In embodiments, B is

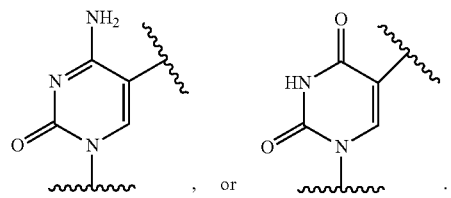, or

In embodiments, B is

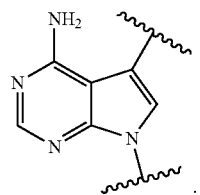 [SMILES: *c1cn(*)c2ncnc(N)c12]

In embodiments, B is

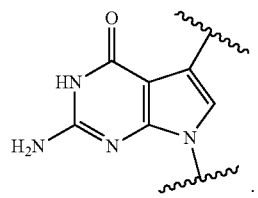

In embodiments, B is

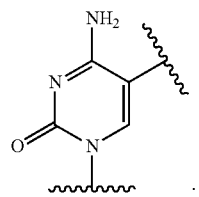 [SMILES: *c1cn(*)c(=O)nc1N]

In embodiments, B is

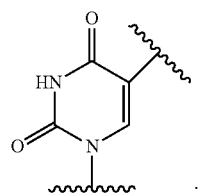 [SMILES: *c1cn(*)c(=O)[nH]c1=O]

In embodiments, the compound has the formula:
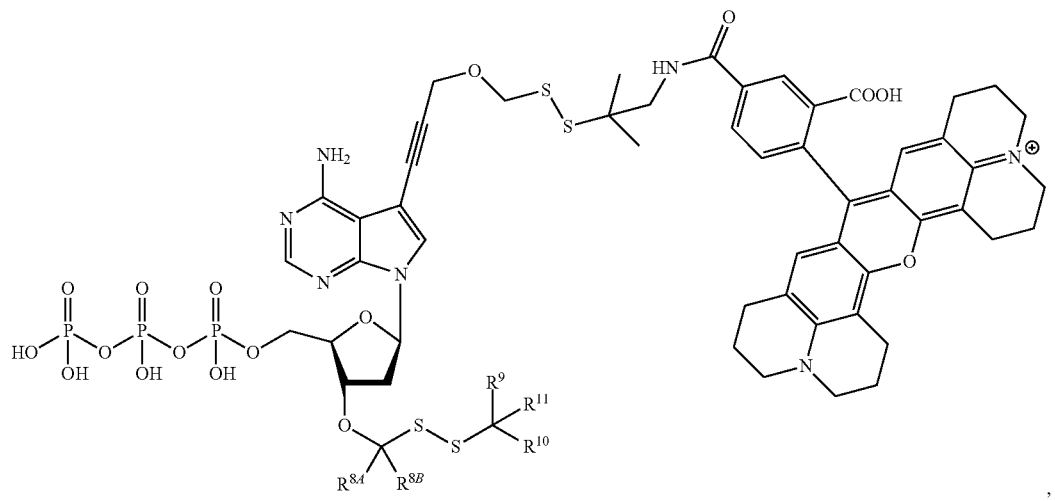
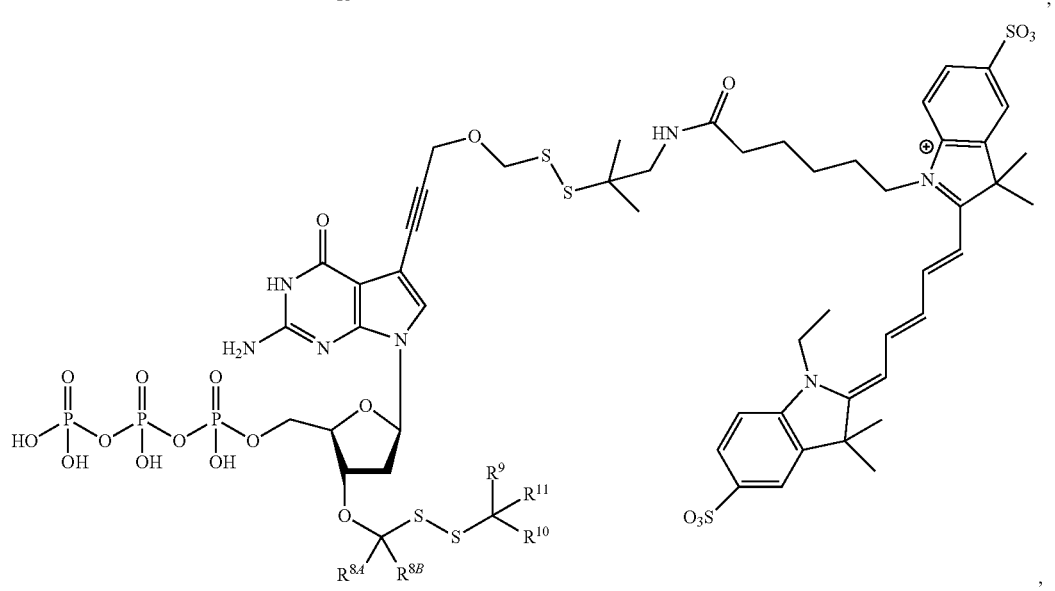
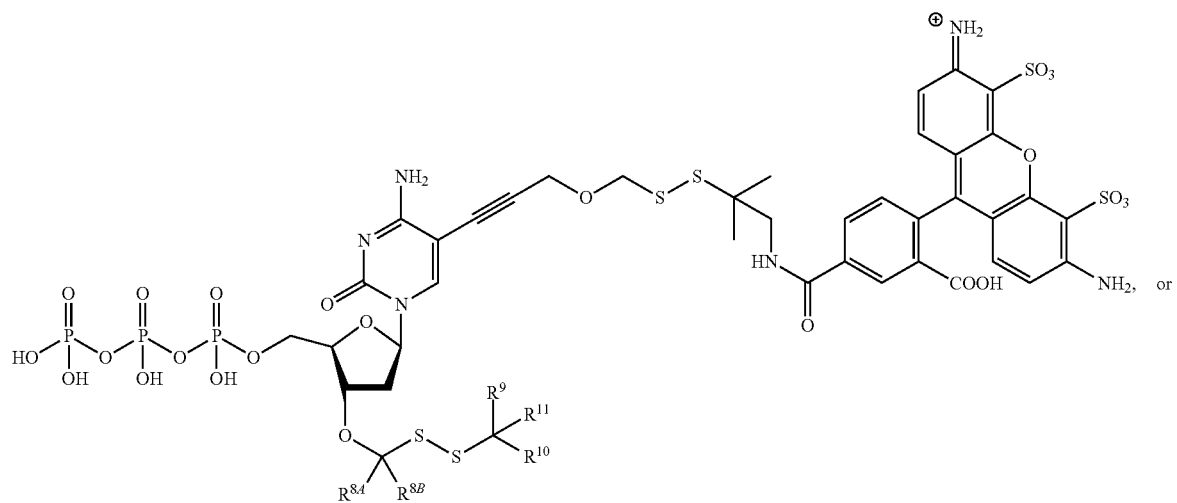

-continued

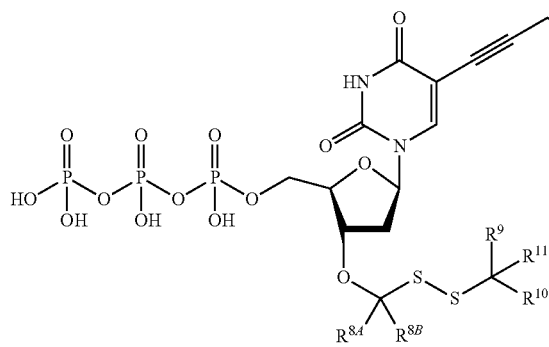
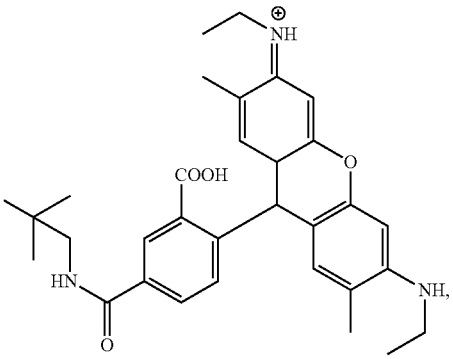

wherein $R^{8A}$, $R^{8B}$, $R^9$, $R^{10}$, and $R^{11}$ are as described herein. In embodiments, $R^{8A}$ is hydrogen, deuterium, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, $R^{8A}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, $R^{8B}$ is hydrogen, deuterium, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, $R^{8B}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, —CR$^9$R$^{10}$R$^{11}$ is unsubstituted methyl, unsubstituted ethyl, unsubstituted propyl, unsubstituted isopropyl, unsubstituted butyl, or unsubstituted tort-butyl. In embodiments, $R^9$ is hydrogen, —C(CH$_3$)$_3$, —CH(CH$_3$)$_2$, —CH$_2$CH$_2$CH$_3$, —CH$_2$CH$_3$, —CH$_3$, —OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$. —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, —CN, or -Ph. In embodiments, $R^{10}$ is hydrogen, —C(CH$_3$)$_3$, CH(CH$_3$)$_2$, —CH$_2$CH$_2$CH$_3$, —CH$_2$CH$_3$, —CH$_3$, OC(CH$_3$)$_3$CH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, —CN, or -Ph. In embodiments, $R^{11}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, —CN, or -Ph.

In embodiments, B is

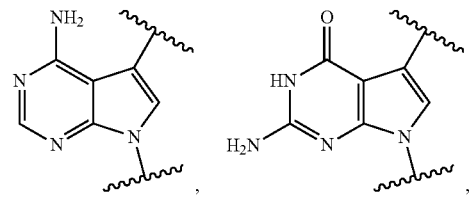

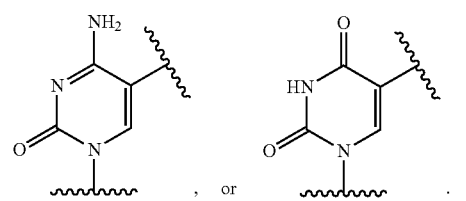, or

In embodiments, B is

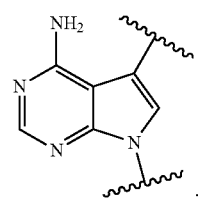.

In embodiments, B is
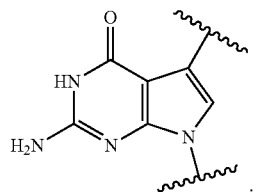 [SMILES: *c1cn(*)c2nc(N)[nH]c(=O)c12]
In embodiments, B is
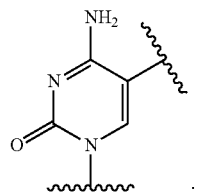 [SMILES: *c1cn(*)c(=O)nc1N]
In embodiments, B is
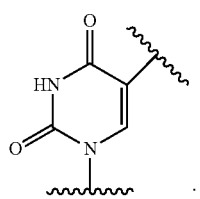 [SMILES: *c1cn(*)c(=O)[nH]c1=O]
In embodiments, the compound has the formula:
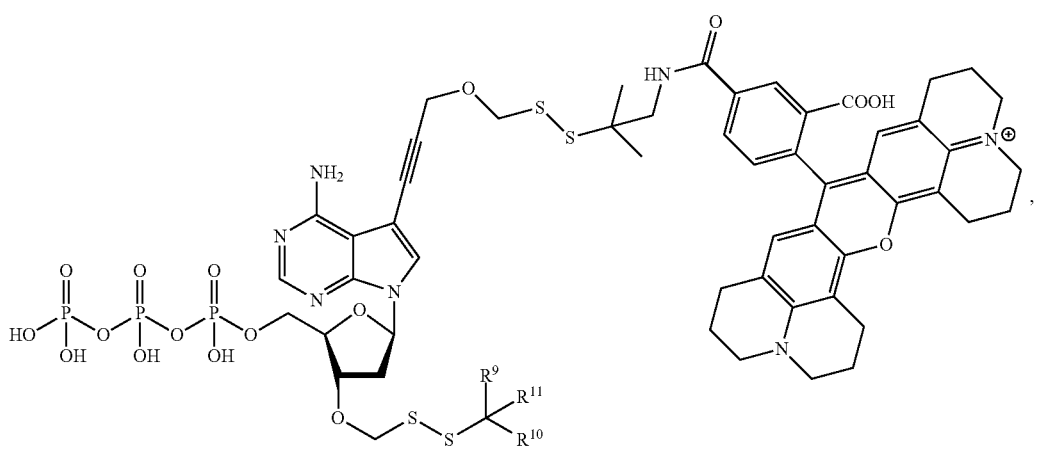
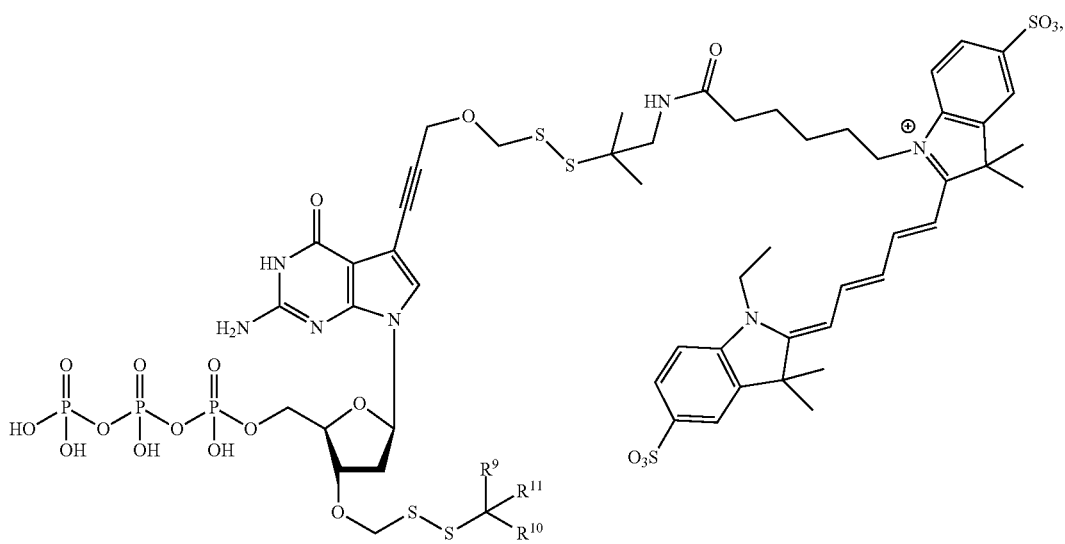

193
-continued
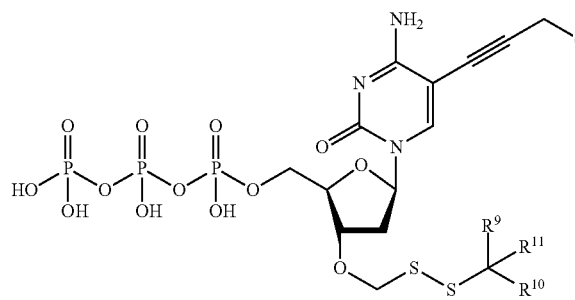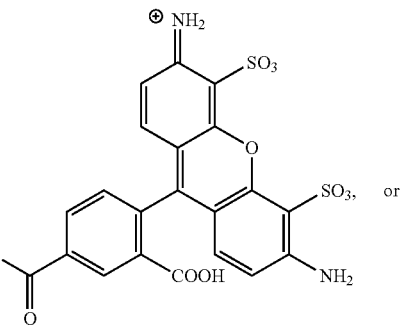
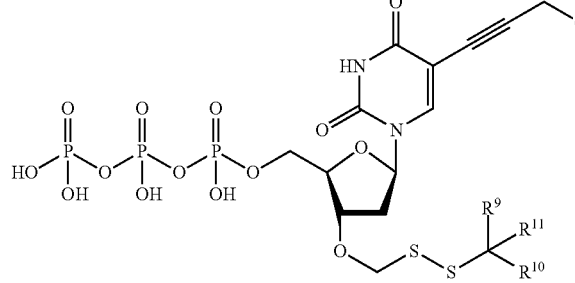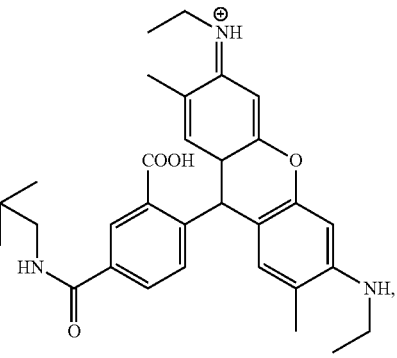
wherein R⁹, R¹⁰, and R¹¹ are as described herein.
In embodiments, the compound has the formula:
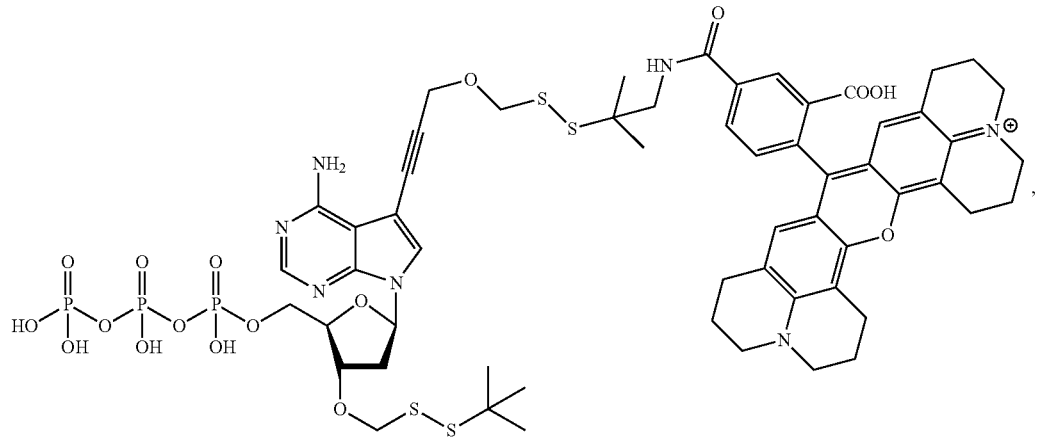

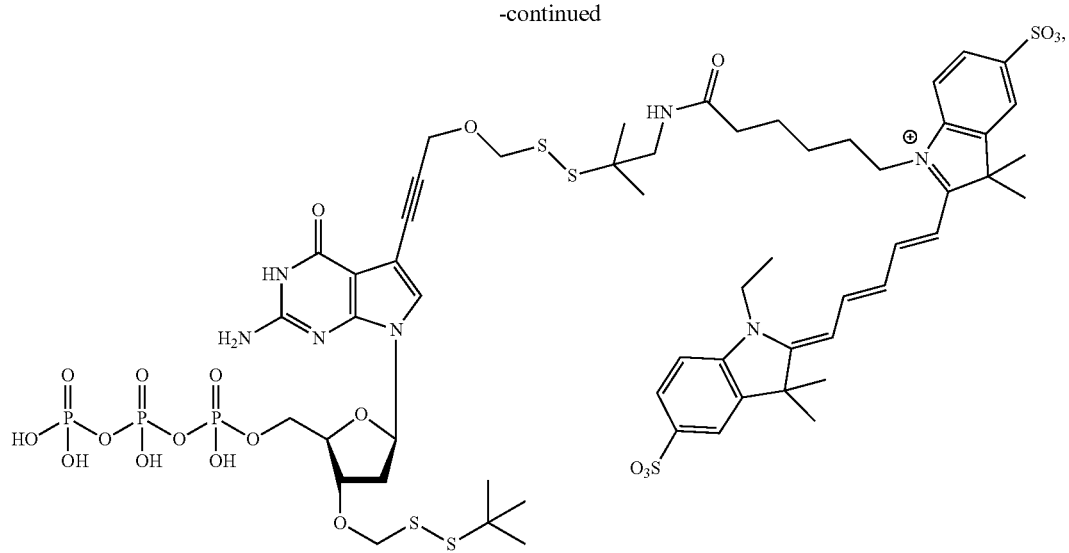
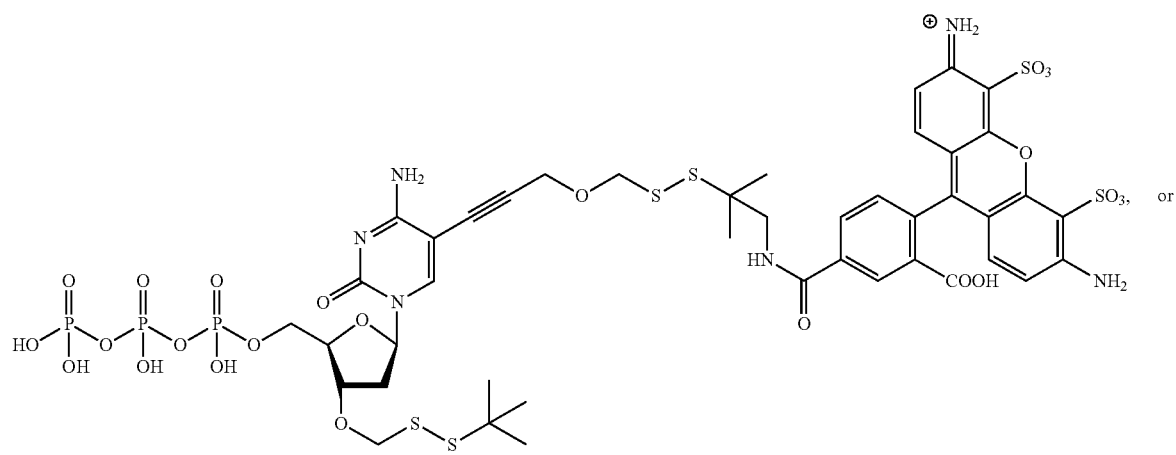
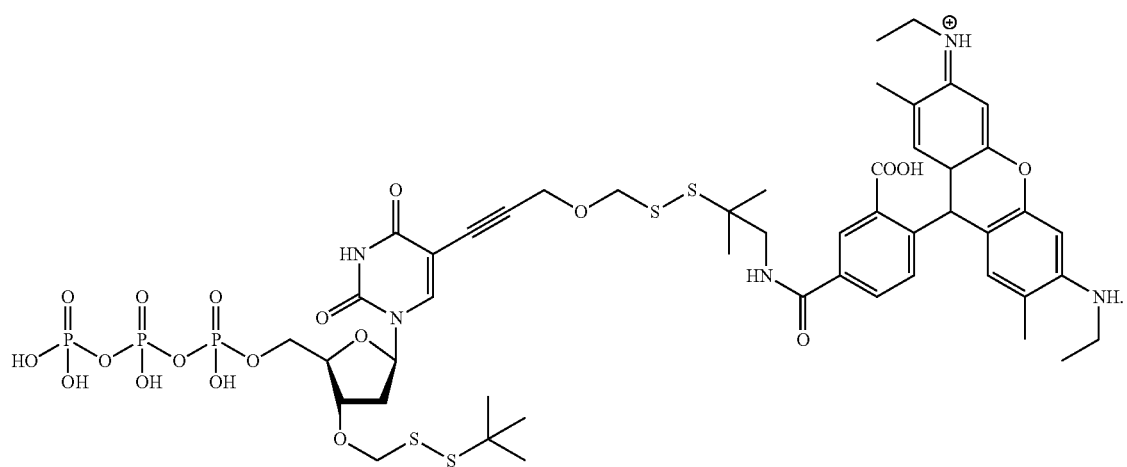

In embodiments, the compound has the formula:
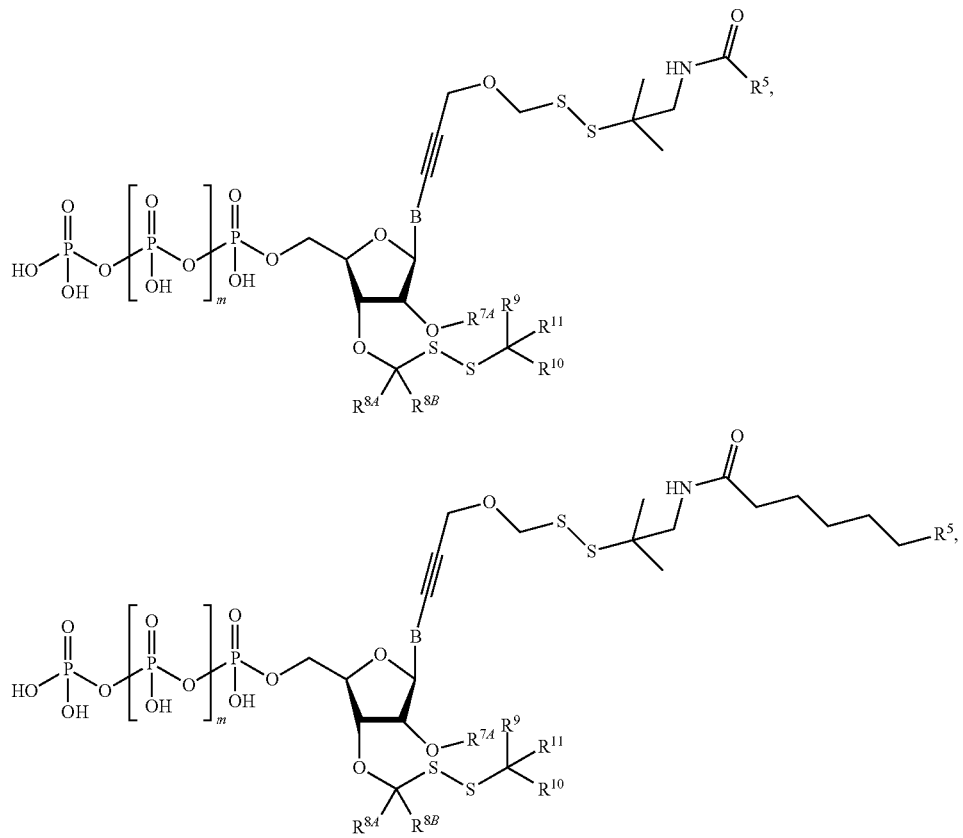
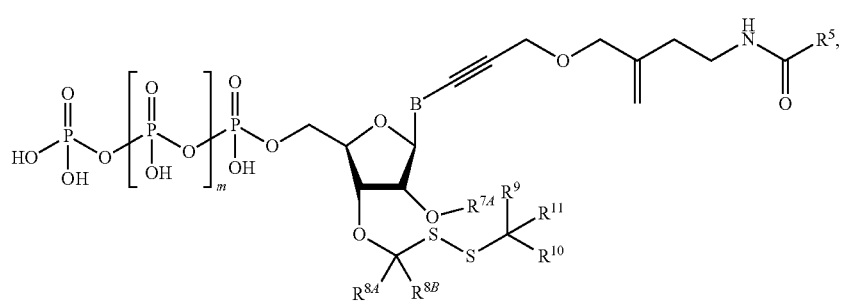
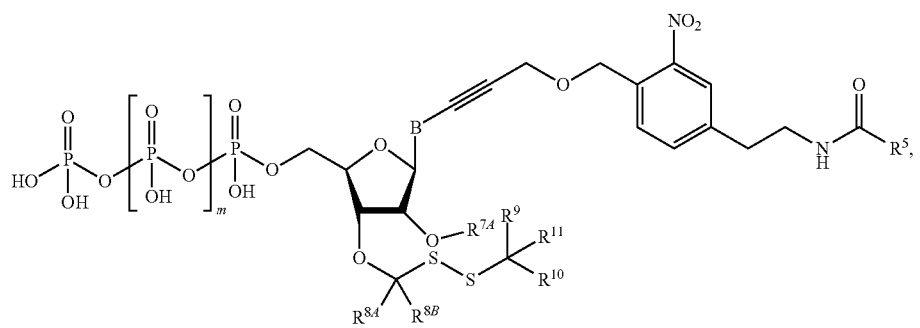

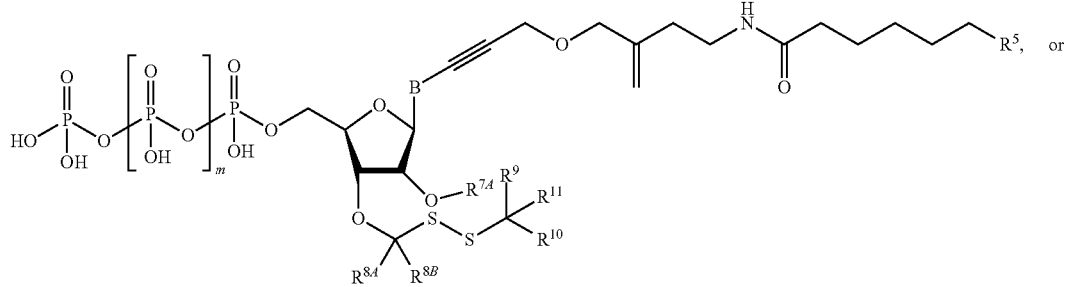
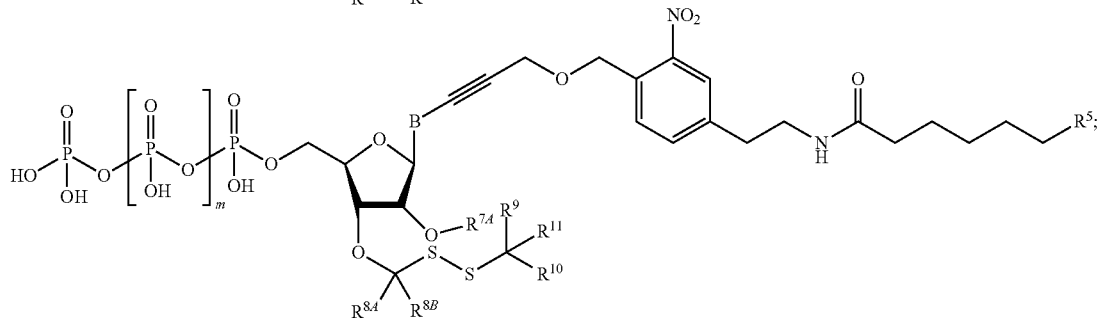
wherein B, $R^5$, $R^{7A}$, $R^{8A}$, $R^{8B}$, $R^9$, $R^{10}$, and $R^{11}$ are as described herein and m is art integer from 1 to 4.
In embodiments, the compound has the formula:
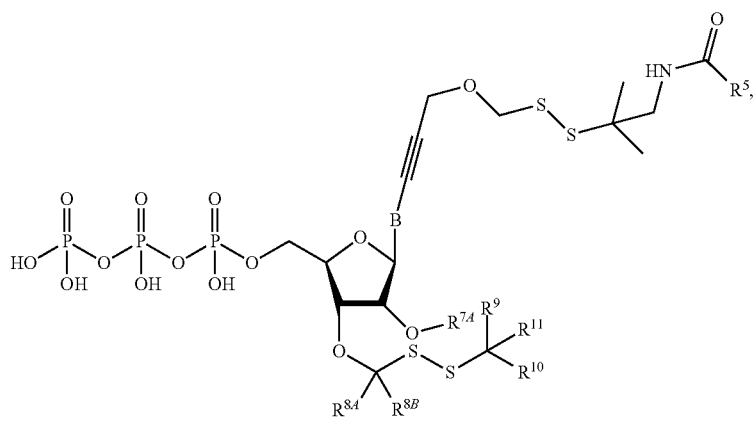
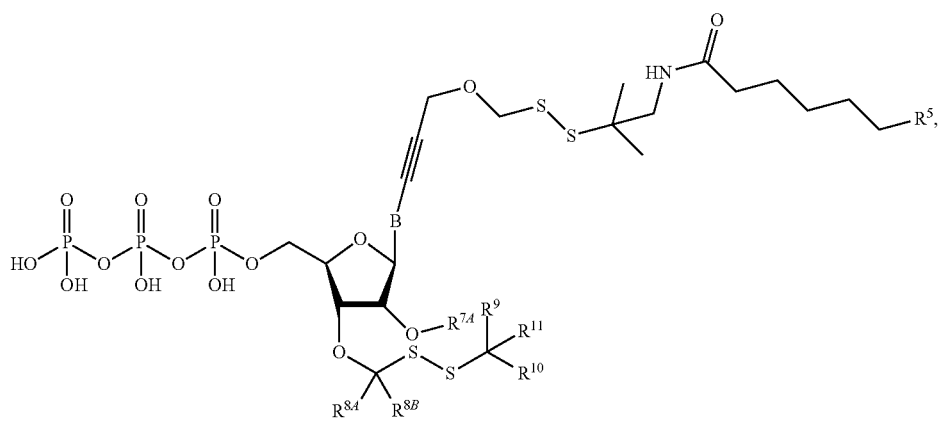

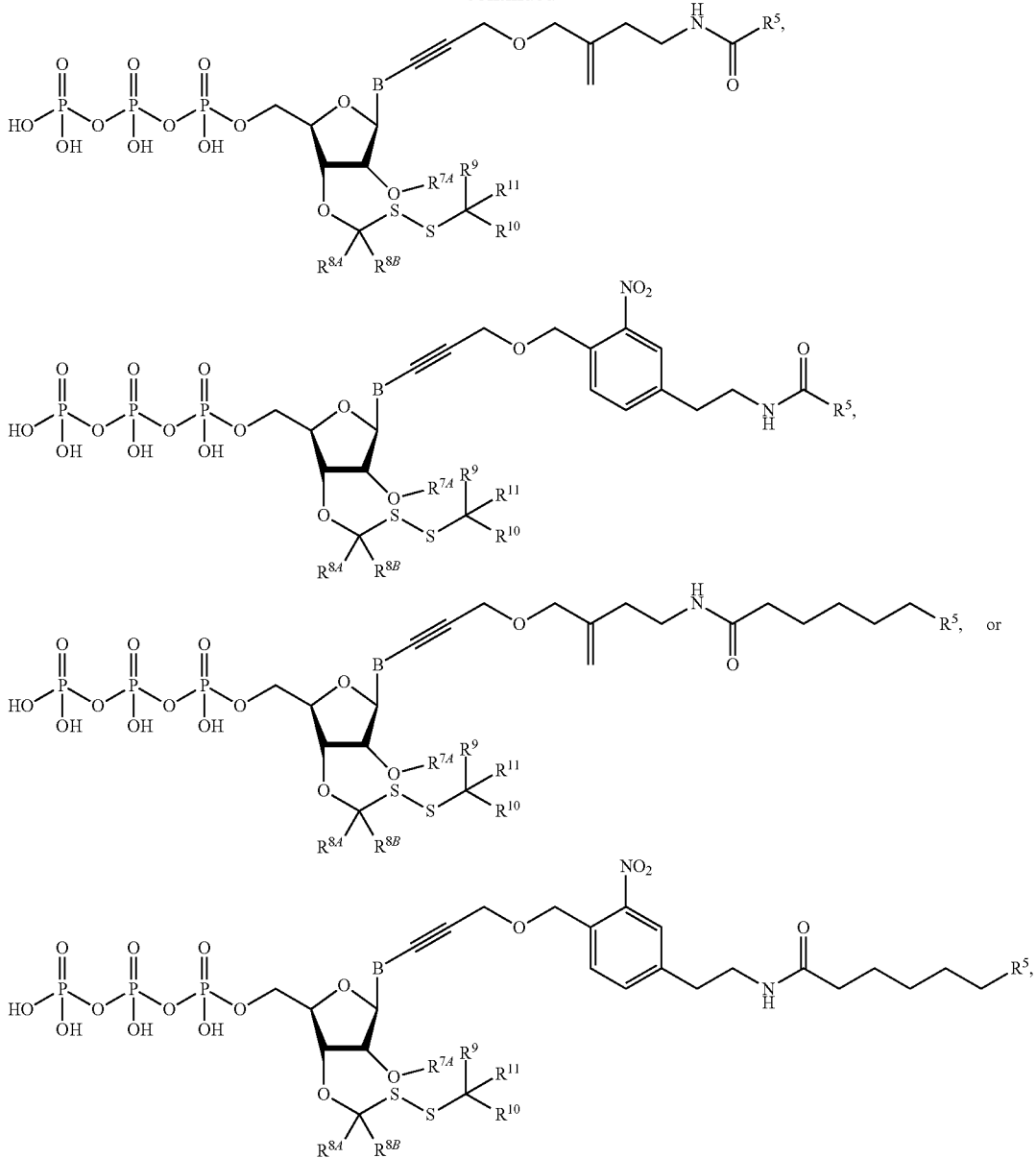

wherein B, $R^5$, $R^{7A}$, $R^{8A}$, $R^{8B}$, $R^9$, $R^{10}$, and $R^{11}$ are as described herein. In embodiments, $R^{8A}$ is hydrogen, deuterium, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, $R^{8A}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, $R^{8A}$ is hydrogen, deuterium, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, $R^{8B}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, —CR$^9$R$^{10}$R$^{11}$ is unsubstituted methyl, unsubstituted ethyl, unsubstituted propyl, unsubstituted isopropyl, unsubstituted butyl, or unsubstituted tert-butyl. In embodiments, $R^9$ is hydrogen, —C(CH$_3$)$_3$, —CH(CH$_3$)$_2$, —CH$_2$CH$_2$CH$_3$, —CH$_2$CH$_3$, —CH$_3$, —OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$. —CN, or -Ph. In embodiments, $R^{10}$ is hydrogen, —C(CH$_3$)$_3$, —CH (CH₃)₂, —CH₂CH₂CH₃, —CH₂CH₃, —CH₃, OC(CH₃)₃, —OCH(CH₃)₂, —OCH₂CH₂CH₃, —OCH₂CH₃, —OCH₃, —SC(CH₃)₃, —SCH(CH₃)₂, —SCH₂CH₂CH₃, —SCH₂CH₃, —SCH₃, —NHC(CH₃)₃, —NHCH(CH₃)₂, —NHCH₂CH₂CH₃, —NHCH₂CH₃, —NHCH₃, —CN, or -Ph. In embodiments, R¹¹ is hydrogen, —C(CH₃)₃, —CH(CH₃)₂, —CH₂CH₂CH₃, —CH₂CH₃, —CH₃, OC(CH₃)₃, —OCH(CH₃)₂, —OCH₂CH₂CH₃, —OCH₂CH₃, —OCH₃, —SC(CH₃)₃, —SCH(CH₃)₂, —SCH₂CH₂CH₃, —SCH₂CH₃, —SCH₃, —NHC(CH₃)₃, —NHCH(CH₃)₂, —NHCH₂CH₂CH₃, —NHCH₂CH₃, —NHCH₃, —CN, or -Ph. In embodiments, B is

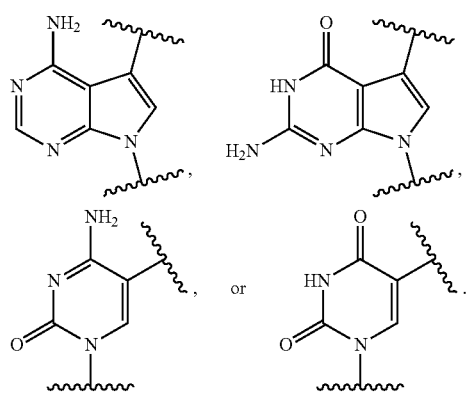

In embodiments, B is

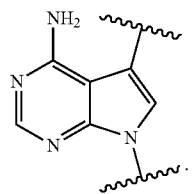

In embodiments, B is

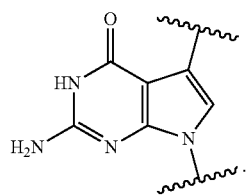

In embodiments, B is

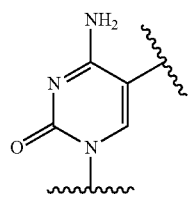

In embodiments, B is

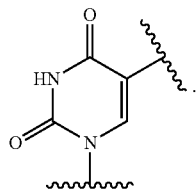 [SMILES: *c1cn(*)c(=O)[nH]c1=O]

In embodiments, R⁵ is

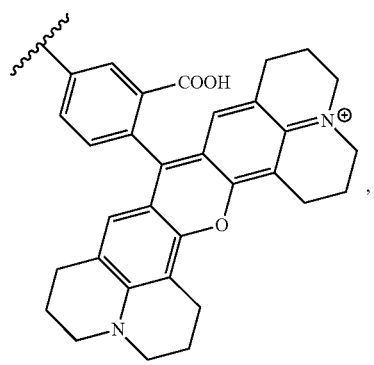

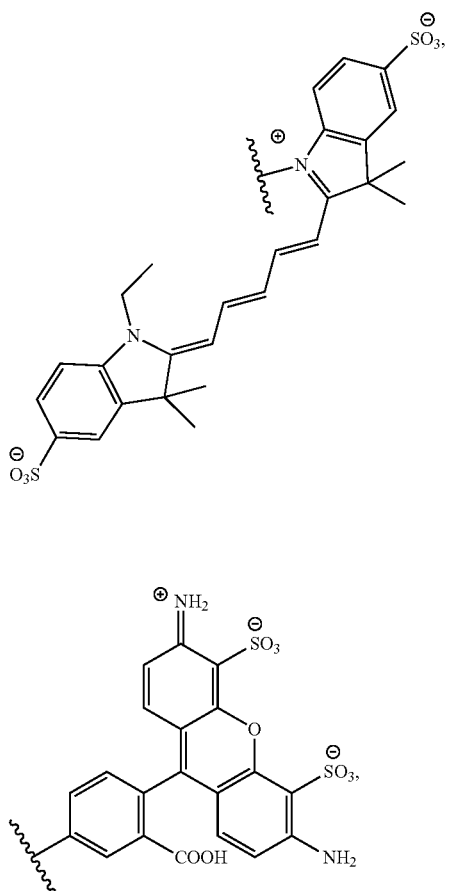

-continued
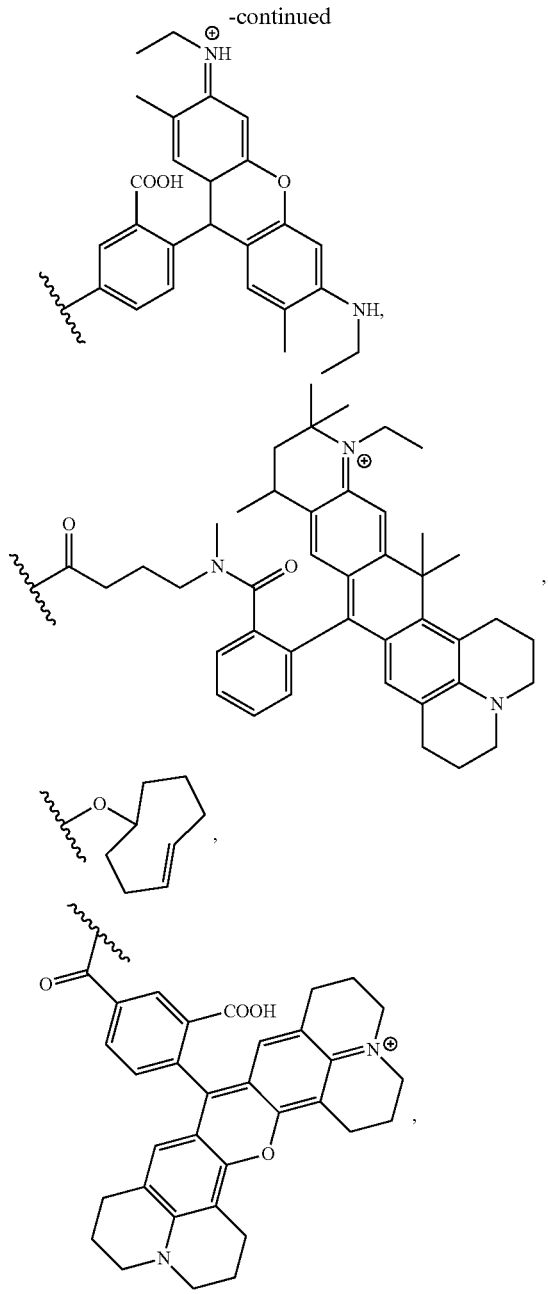
-continued
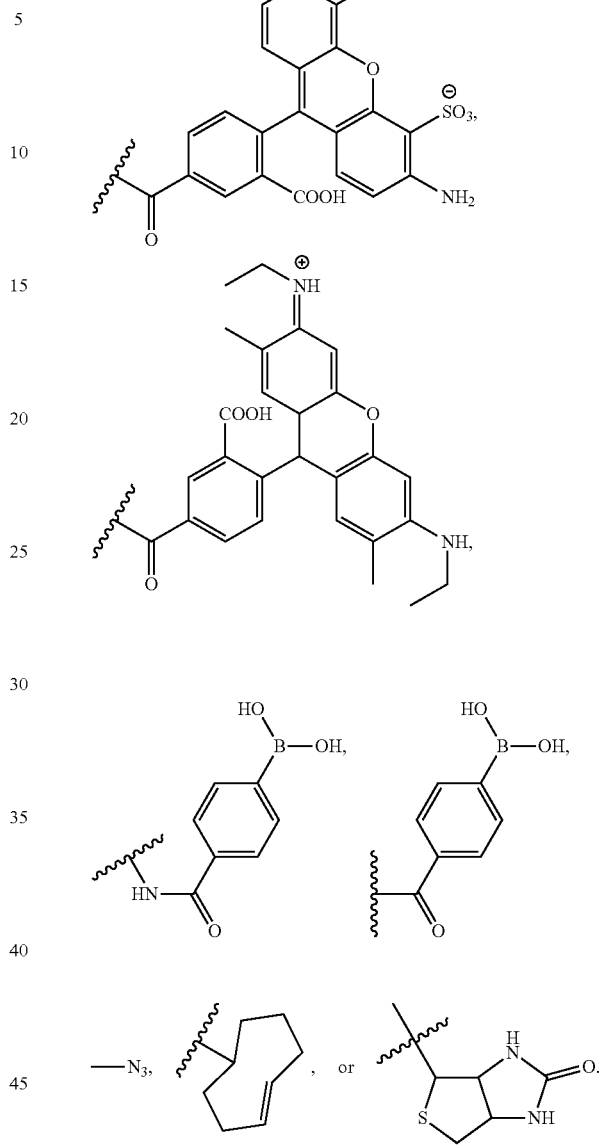
In embodiments, the compound has the formula:
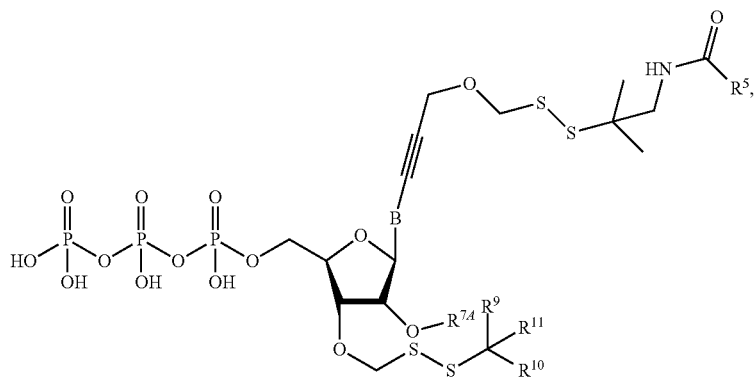

-continued
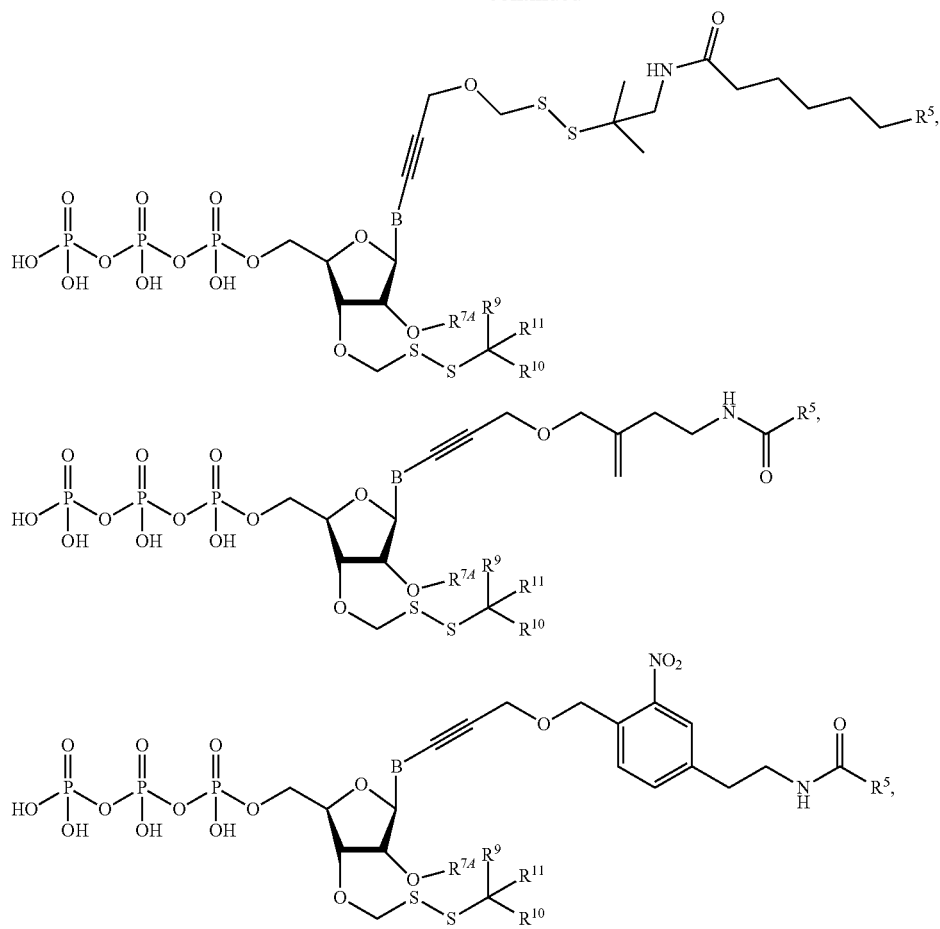
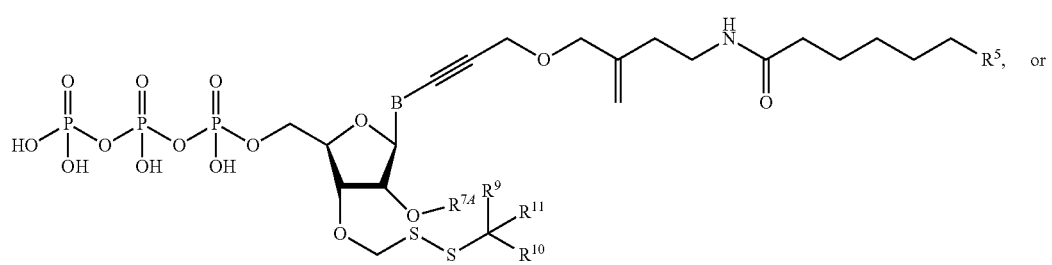
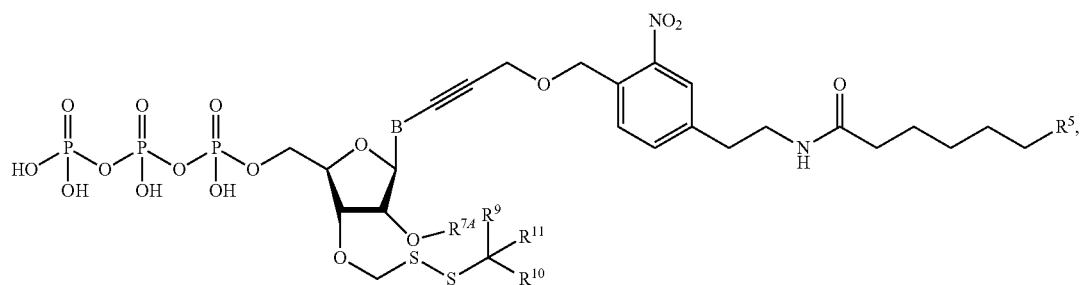

wherein B, $R^5$, $R^{7A}$, $R^9$, $R^{10}$, and $R^{11}$ are as described herein.
In embodiments, B is
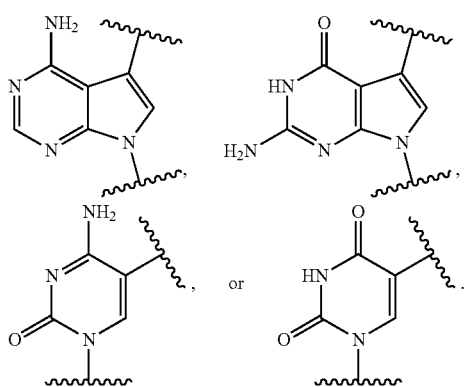
In embodiments, B is
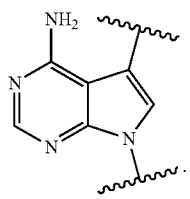
In embodiments, B is
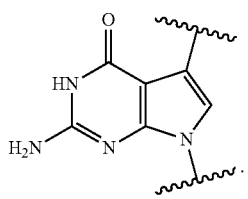 [SMILES: *c1cn(*)c2nc(N)[nH]c(=O)c12]
In embodiments, B is
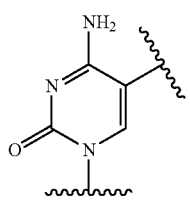
In embodiments, B is
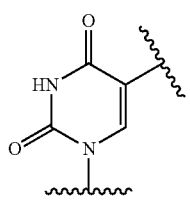
In embodiments, $R^5$ is
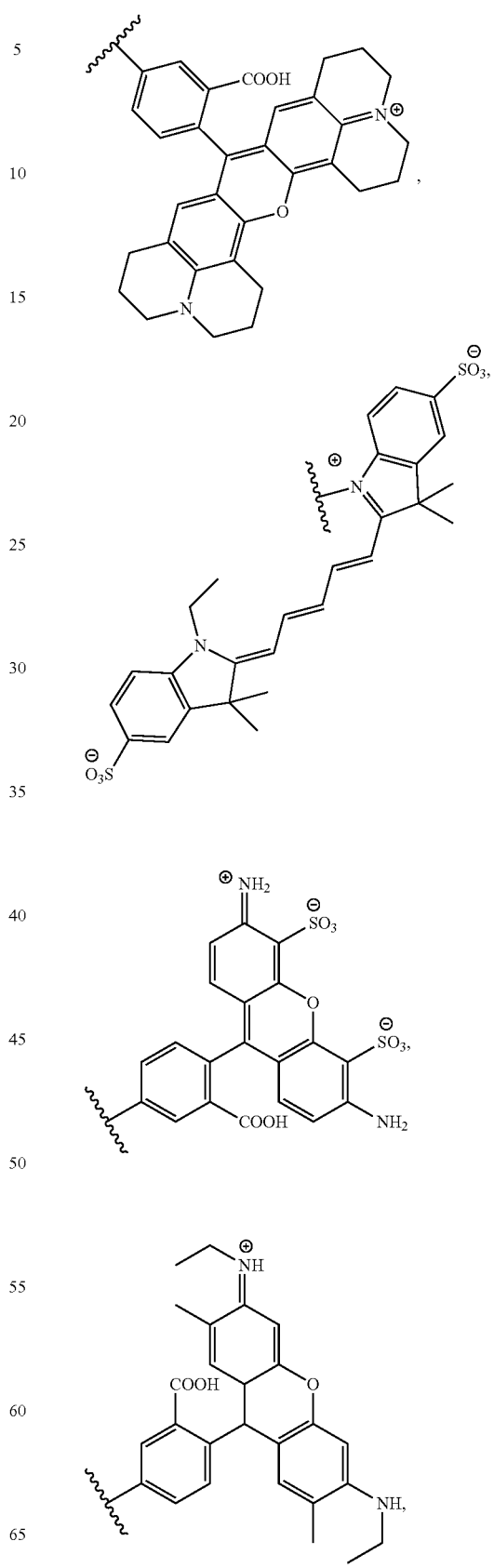

211
-continued
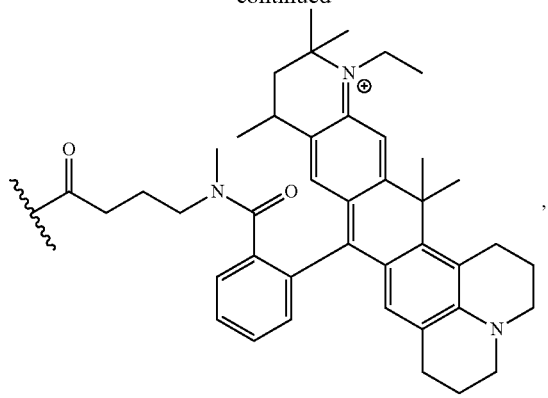
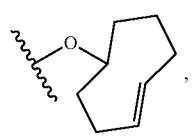
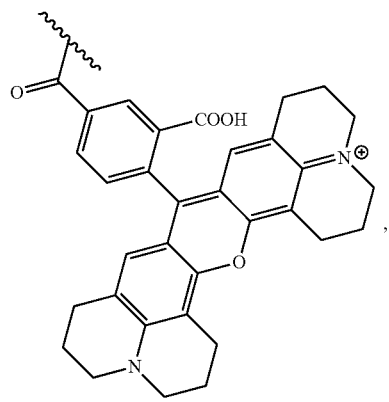
212
-continued
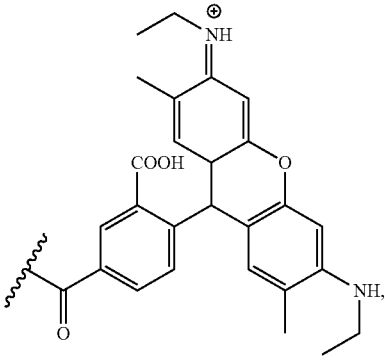
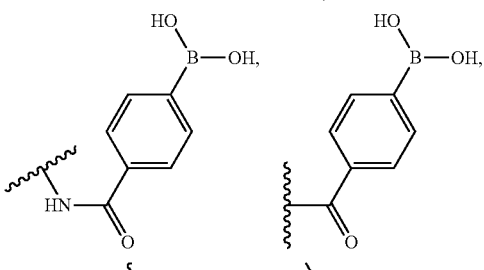
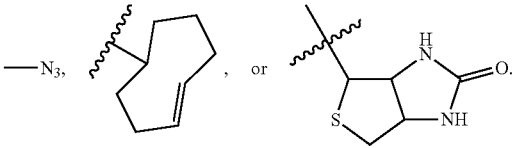
In embodiments, the compound has the formula:
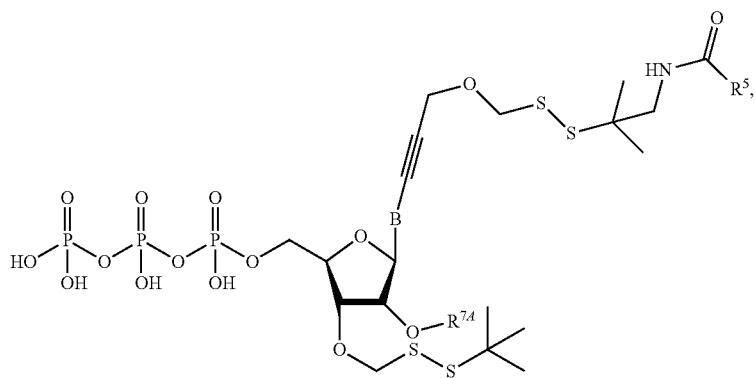

-continued
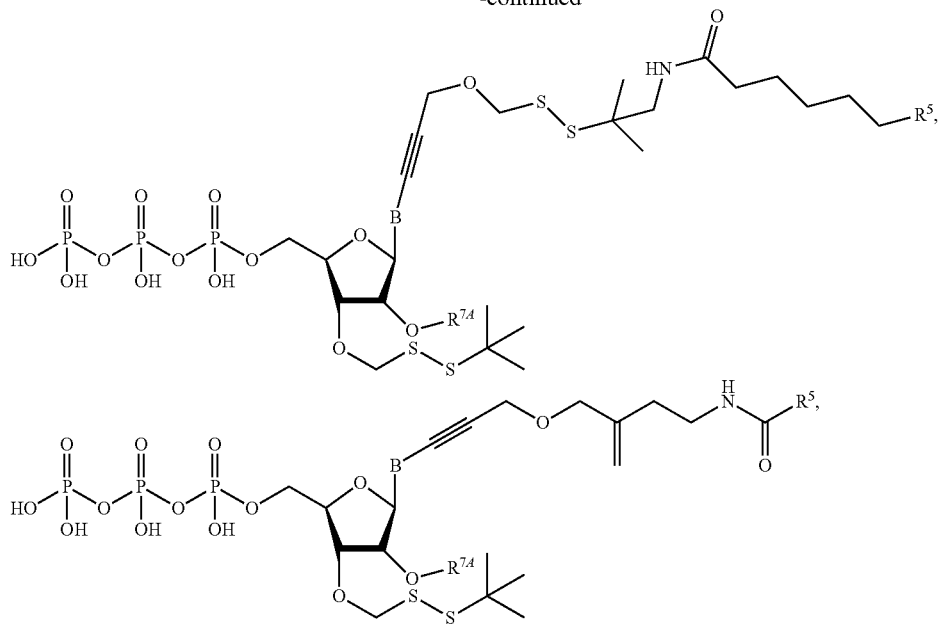
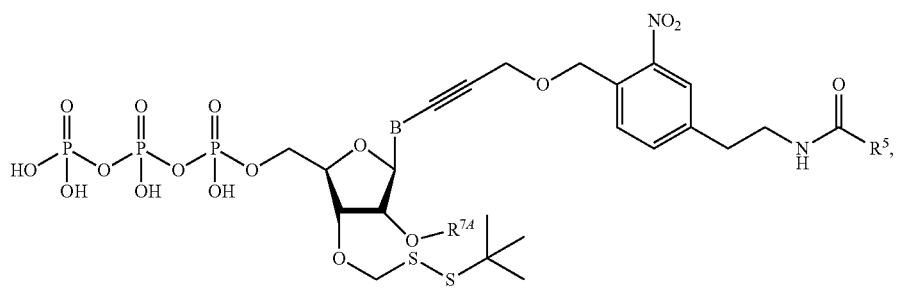
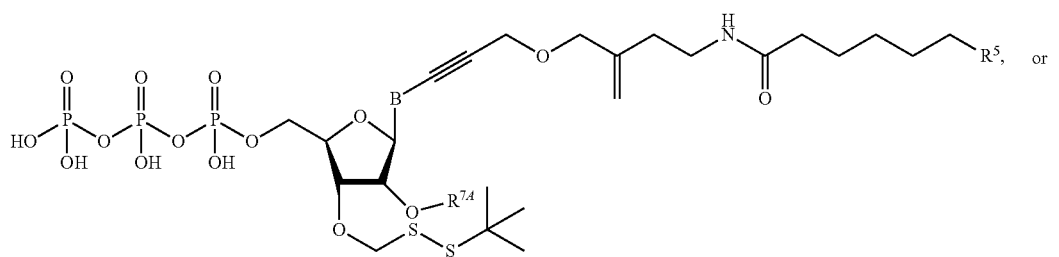
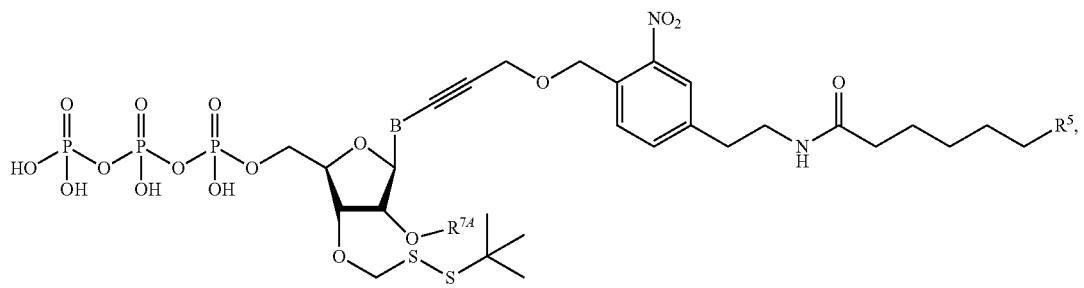

wherein B, $R^{7A}$ and $R^5$ are as described herein. In embodiments, B is
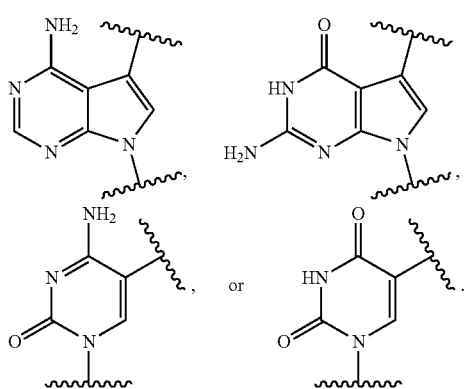
In embodiments, B is
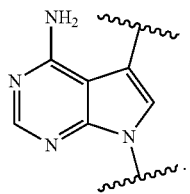
In embodiments, B is
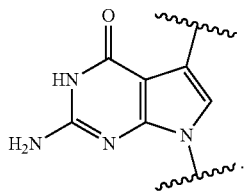 [SMILES: *c1cn(*)c2nc(N)[nH]c(=O)c12]
In embodiments, B is
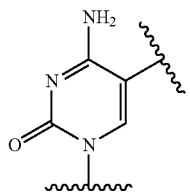
In embodiments, B is
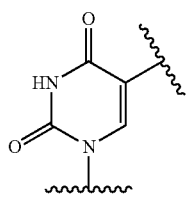
In embodiments, $R^5$ is
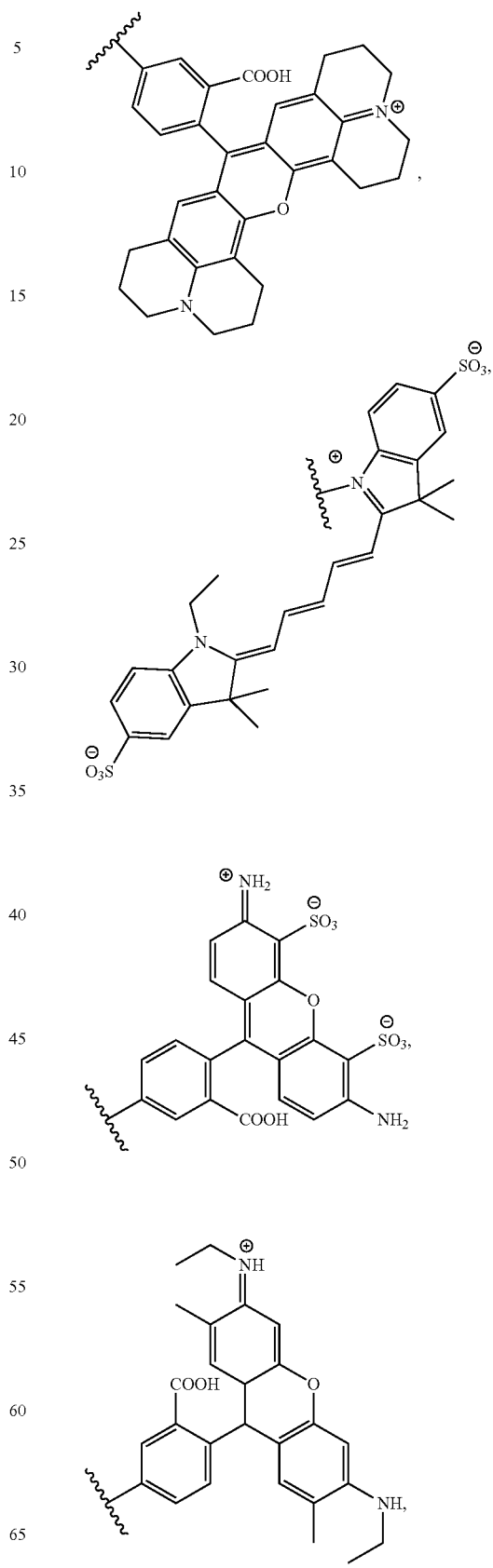

217
-continued
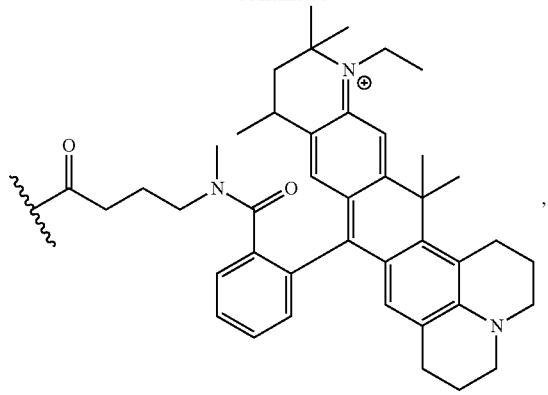
218
-continued
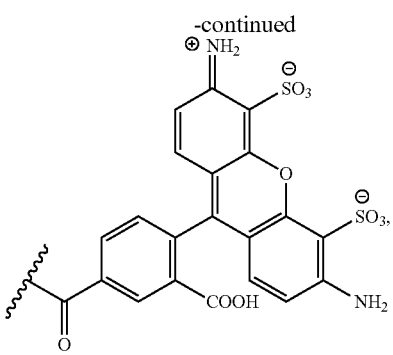
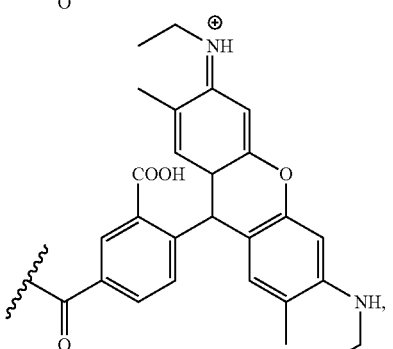
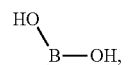 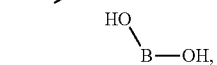
—N₃, 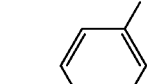, or 
In embodiments, the compound has the formula:
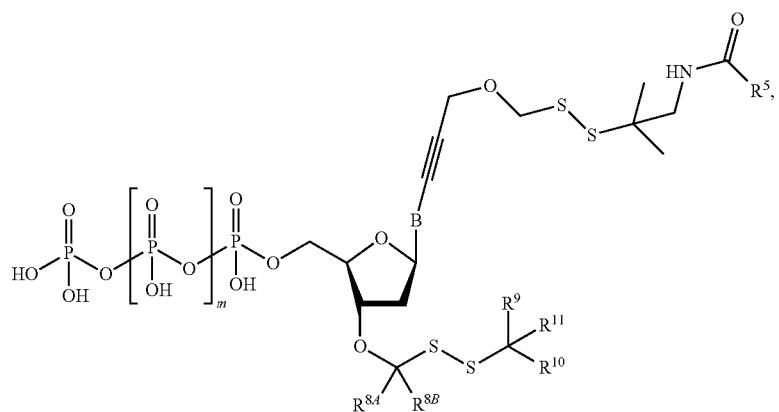

-continued
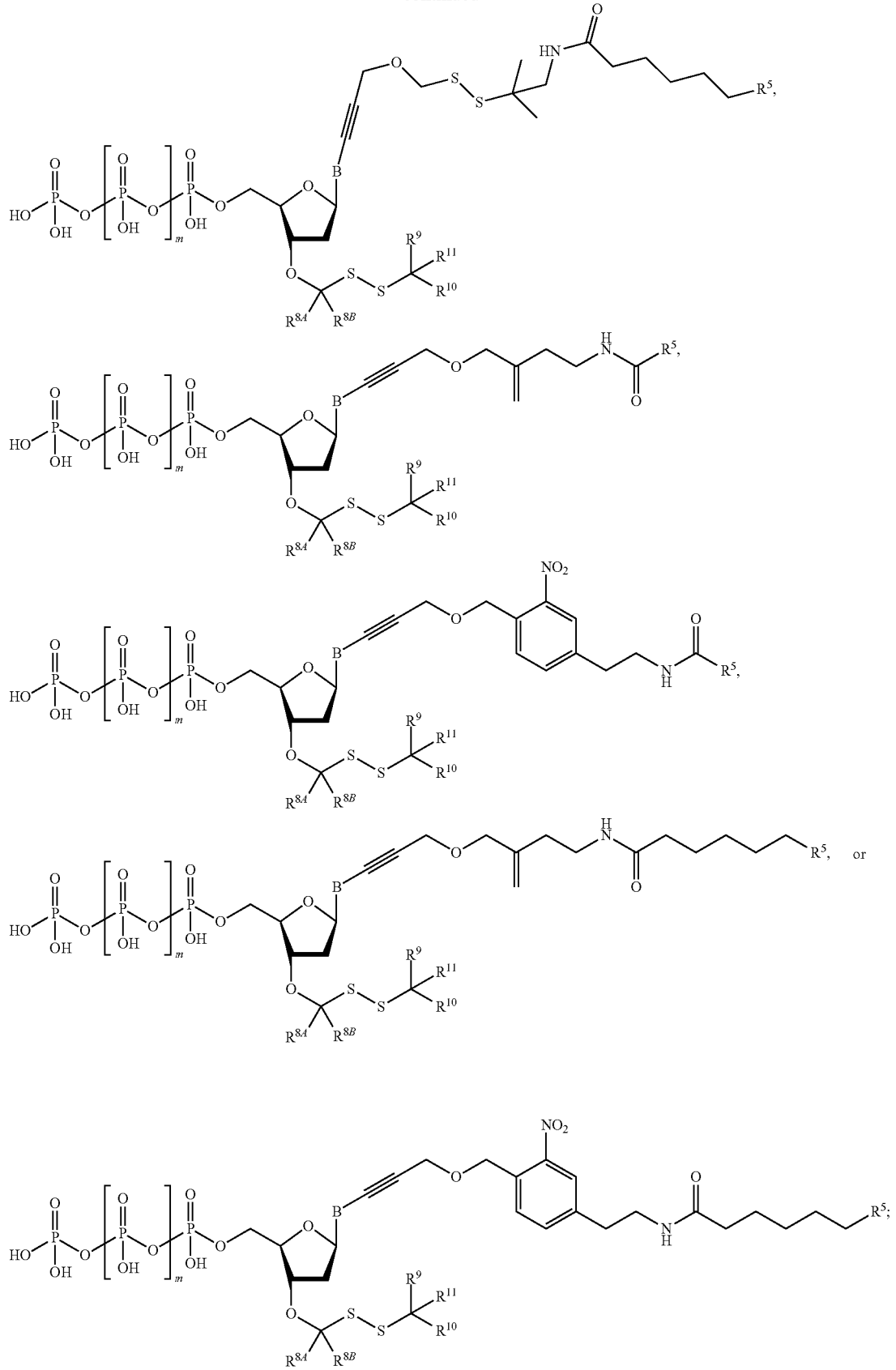

wherein B, $R^5$, $R^{8A}$, $R^{8B}$, $R^9$, $R^{10}$, and $R^{11}$ are as described herein and in is an integer from 1 to 4. In embodiments, $R^{8A}$ is hydrogen, deuterium, —C(CH₃)₃, —CH(CH₃)₂, —CH₂CH₂CH₃, —CH₂CH₃, —CH₃, OC(CH₃)₃, —OCH(CH₃)₂, —OCH₂CH₂CH₃, —OCH₂CH₃, —OCH₃, —SC(CH₃)₃, —SCH(CH₃)₂, —SCH₂CH₂CH₃, —SCH₂CH₃, —SCH₃, —NHC(CH₃)₃, —NHCH(CH₃)₂, —NHCH₂CH₂CH₃, —NHCH₂CH₃, —NHCH₃—CN, or -Ph. In embodiments, $R^{8A}$ is hydrogen, —C(CH₃)₃, —CH(CH₃)₂, —CH₂CH₂CH₃, —CH₂CH₃, —CH₃, OC(CH₃)₃, —OCH(CH₃)₂, —OCH₂CH₂CH₃, —OCH₂CH₃, —OCH₃, —SC(CH₃)₃, —SCH(CH₃)₂, —SCH₂CH₂CH₃, —SCH₂CH₃, —SCH₃, —NHC(CH₃)₃, —NHCH(CH₃)₂, —NHCH₂CH₂CH₃, —NHCH₂CH₃, —NHCH₃—CN, or -Ph. In embodiments, $R^{8B}$ is hydrogen, deuterium, —C(CH₃)₃, —CH(CH₃)₂, —CH₂CH₂CH₃, —CH₂CH₃, —CH₃, OC(CH₃)₃, —OCH(CH₃)₂, —OCH₂CH₂CH₃, —OCH₂CH₃, —OCH₃, —SC(CH₃)₃, —SCH(CH₃)₂, —SCH₂CH₂CH₃, —SCH₂CH₃, —SCH₃, IC(CH₃)₃, —NHCH(CH₃)₂, —NHCH₂CH₂CH₃, —NHCH₂CH₃, —NHCH₃—CN, or -Ph. In embodiments, $R^{8B}$ is hydrogen, —C(CH₃)₃, —CH(CH₃)₂, —CH₂CH₂CH₃, CH₂CH₃, —CH₃, OC(CH₃)₃, —OCH(CH₃)₂, OCH₂CH₂CH₃, —OCH₂CH₃, —OCH₃, —SC(CH₃)₃, —SCH(CH₃)₂, —SCH₂CH₂CH₃, —SCH₂CH₃, —SCH₃, —NHC(CH₃)₃, —NHCH(CH₃)₂, —NHCH₂CH₂CH₃, —NHCH₂CH₃, —NHCH₃—CN, or -Ph. In embodiments, —CR⁹R¹⁰R¹¹ is unsubstituted methyl, unsubstituted ethyl, unsubstituted propyl, unsubstituted isopropyl, unsubstituted butyl, or unsubstituted tert-butyl. In embodiments, $R^9$ is hydrogen, —C(CH₃)₃, —CH(CH₃)₂, —CH₂CH₂CH₃, —CH₂CH₃, —CH₃, —OC(CH₃)₃, —OCH(CH₃)₂, —OCH₂CH₂CH₃, —OCH₂CH₃, —OCH₃, —SC(CH₃)₃, —SCH(CH₃)₂, —SCH₂CH₂CH₃, —SCH₂CH₃, —SCH₃, —NHC(CH₃)₃, —NHCH(CH₃)₂, —NHCH₂CH₂CH₃, —NHCH₂CH₃, —NHCH₃, or -Ph. In embodiments, $R^{10}$ is hydrogen, —C(CH₃)₃, —CH(CH₃)₂, —CH₂CH₂CH₃, —CH₂CH₃, —CH₃, OC(CH₃)₃, —OCH(CH₃)₂, —OCH₂CH₂CH₃, —OCH₂CH₃, —OCH₃, —SC(CH₃)₃, —SCH(CH₃)₂, —SCH₂CH₂CH₃, —SCH₂CH₃, —SCH₃, —NHC(CH₃)₃, —NHCH(CH₃)₂, —NHCH₂CH₂CH₃, —NHCH₂CH₃, —NHCH₃, —CN, or -Ph. In embodiments, $R^{11}$ is hydrogen, —C(CH₃)₃, —CH(CH₃)₂, —CH₂CH₂CH₃, —CH₂CH₃, —CH₃, OC(CH₃)₃, —OCH(CH₃)₂, —OCH₂CH₂CH₃, —OCH₂CH₃, —OCH₃, —SC(CH₃)₃, —SCH(CH₃)₂, —SCH₂CH₂CH₃, —SCH₂CH₃, —SCH₃, —NHC(CH₃)₃, —NHCH(CH₃)₂, —NHCH₂CH₂CH₃, —NHCH₂CH₃, —NHCH₃, —CN, or -Ph. In embodiments, B is

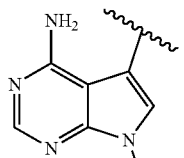 , 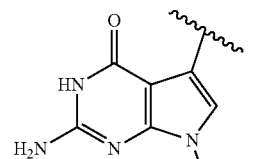 ,

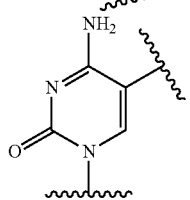 , or 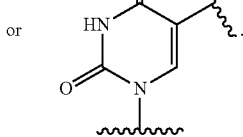 .

In embodiments, B is

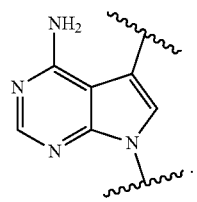 .

In embodiments, B is

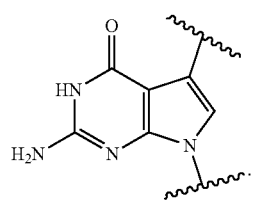 [SMILES: *c1cn(*)c2nc(N)[nH]c(=O)c12] .

In embodiments, B is

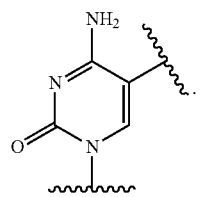 [SMILES: *c1cn(*)c(=O)nc1N] .

In embodiments, B is

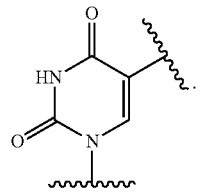 .

In embodiments, $R^5$ is

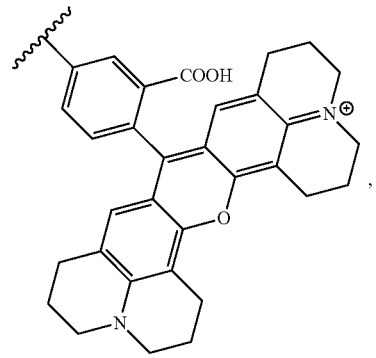 ,

223
-continued
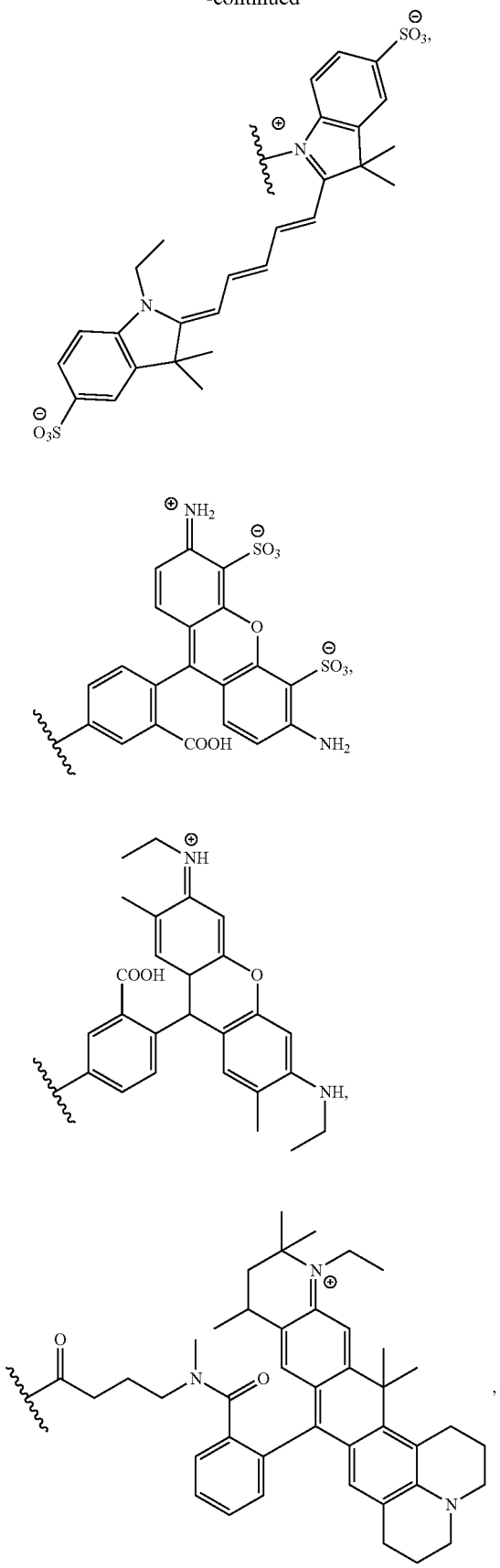
224
-continued
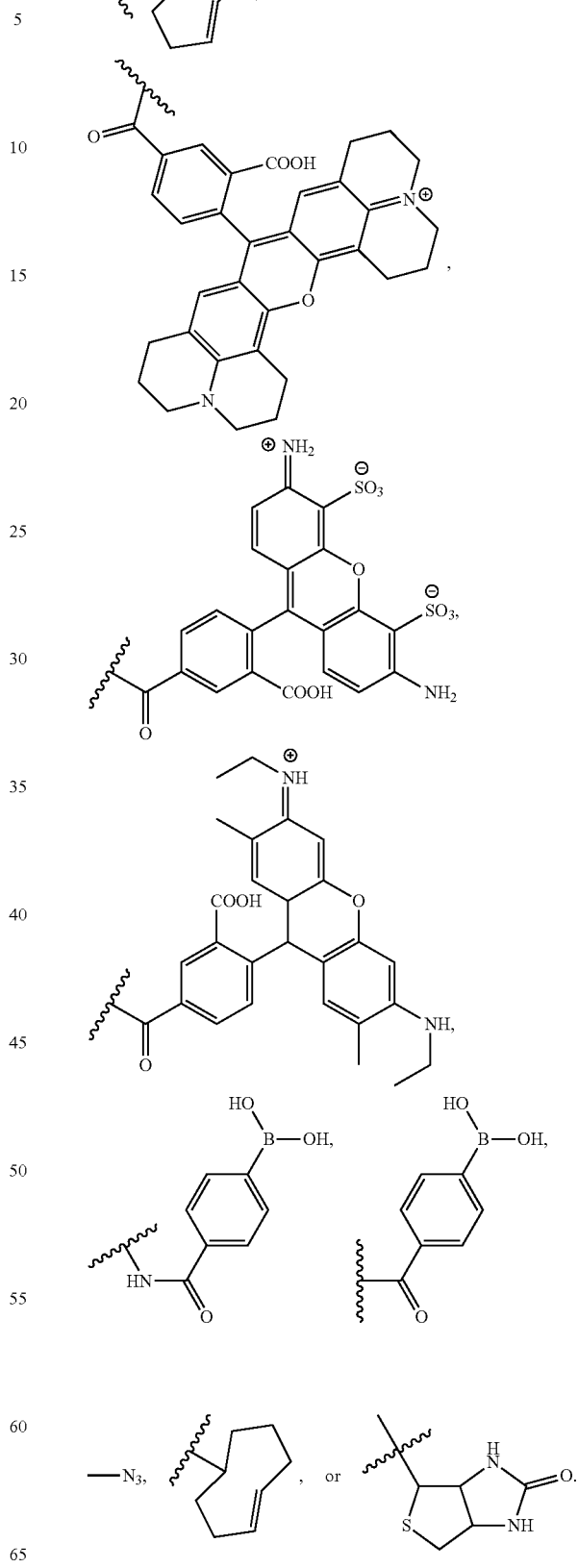

In embodiments, the compound has the formula:
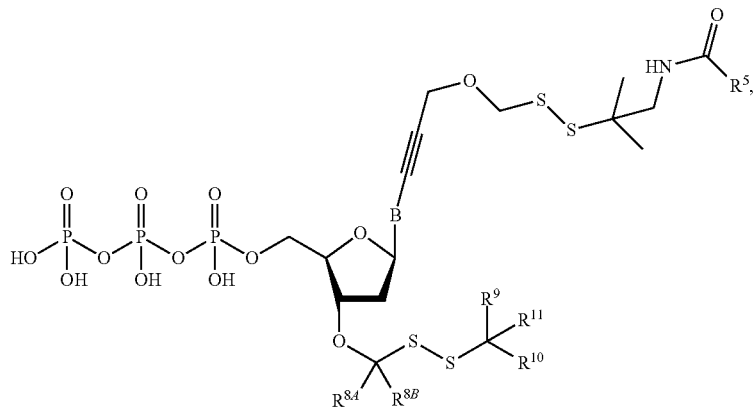
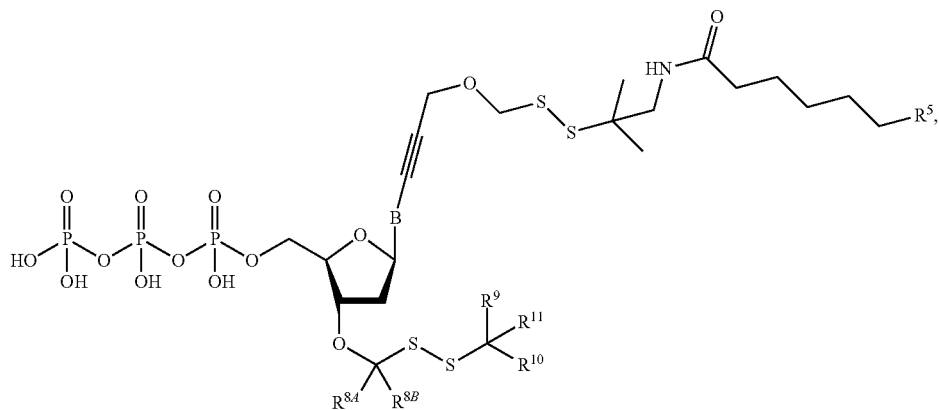
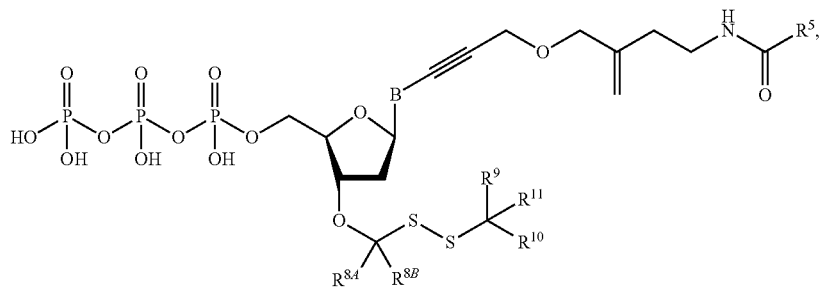
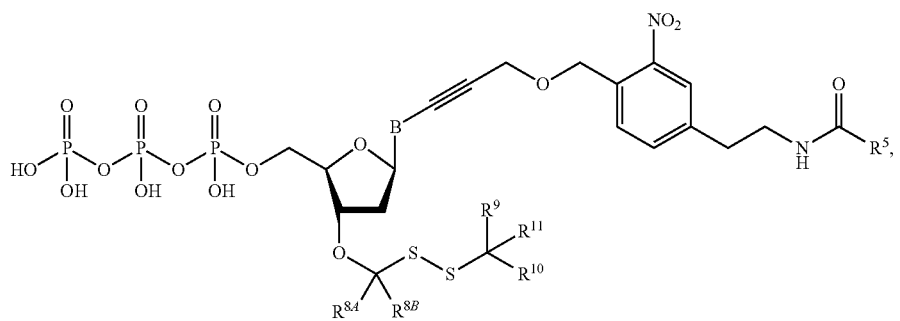

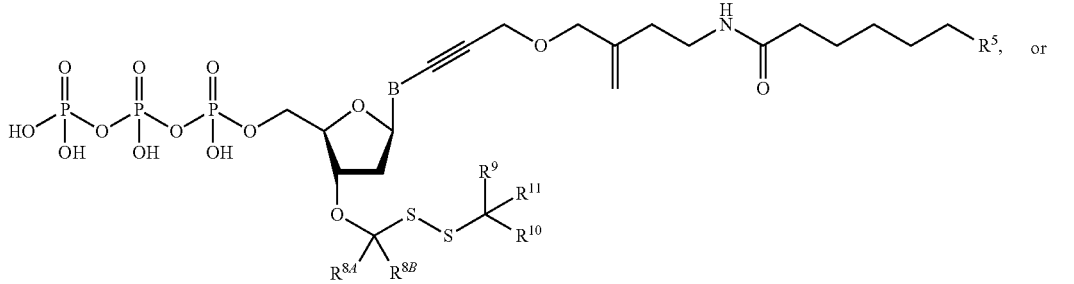

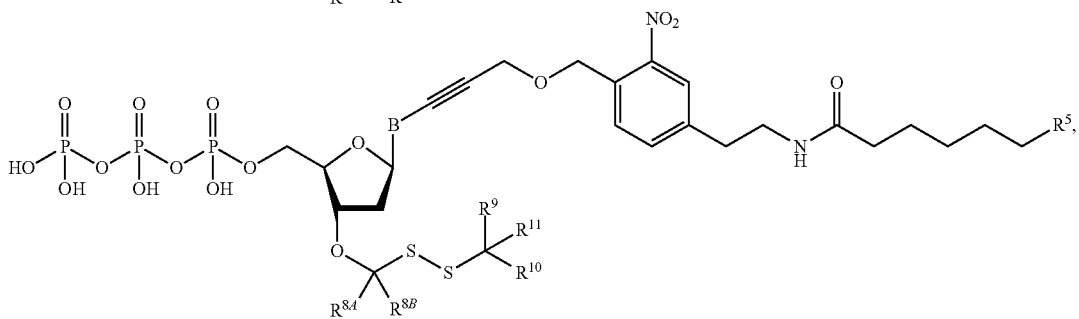

wherein B, $R^5$, $R^{8A}$, $R^{8B}$, $R^9$, $R^{10}$, and $R^{11}$ are as described herein are as described herein. In embodiments, $R^{8A}$ is hydrogen, deuterium, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, $R^{8A}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, $R^{8B}$ is hydrogen, deuterium, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, $R^{8B}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$—CN, or -Ph. In embodiments, —CR$^9$R$^{10}$R$^{11}$ is unsubstituted methyl, unsubstituted ethyl, unsubstituted propyl, unsubstituted isopropyl, unsubstituted butyl, or unsubstituted tert-butyl. In embodiments, $R^9$ is hydrogen, —C(CH$_3$)$_3$, —CH(CH$_3$)$_2$, —CH$_2$CH$_2$CH$_3$, —CH$_2$CH$_3$, —CH$_3$, —OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$. —CN, or -Ph. In embodiments, $R^{10}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, —CN, or -Ph. In embodiments, $R^H$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, —CN, or -Ph. In embodiments, B is

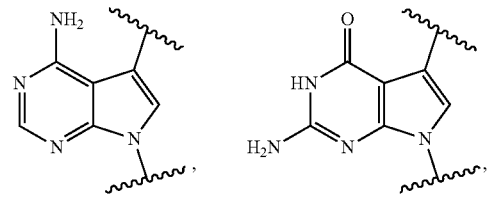

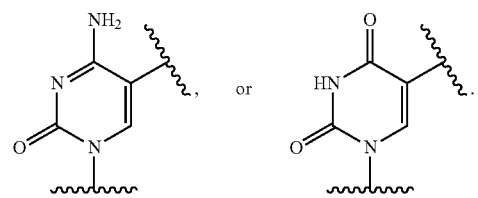

In embodiments, B is

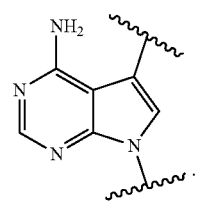 [SMILES: *c1cn(*)c2ncnc(N)c12]

In embodiments, B is
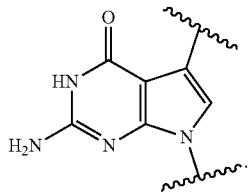 [SMILES: *c1cn(*)c2nc(N)[nH]c(=O)c12]
In embodiments, B is
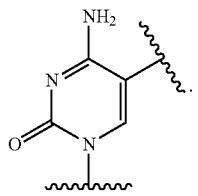 [SMILES: *c1cn(*)c(=O)nc1N]
In embodiments, B is
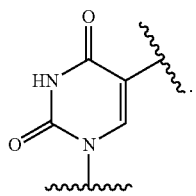 [SMILES: *c1cn(*)c(=O)[nH]c1=O]
In embodiments, R⁵ is
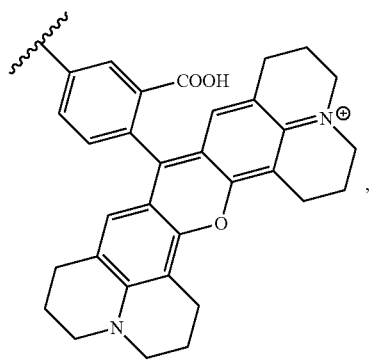
-continued
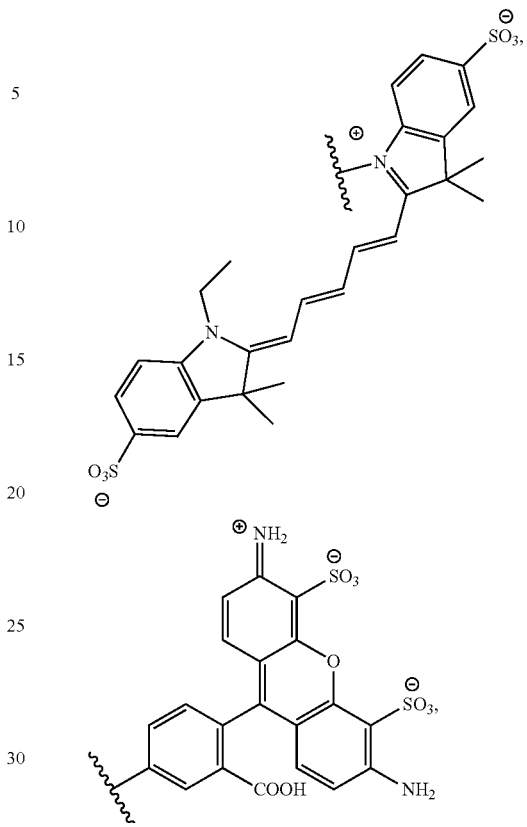
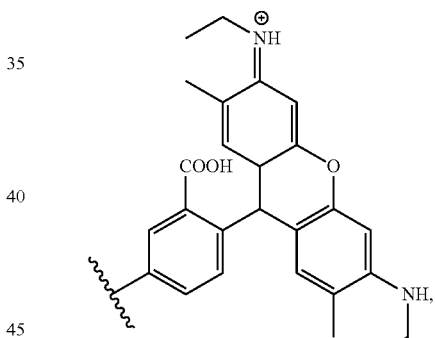
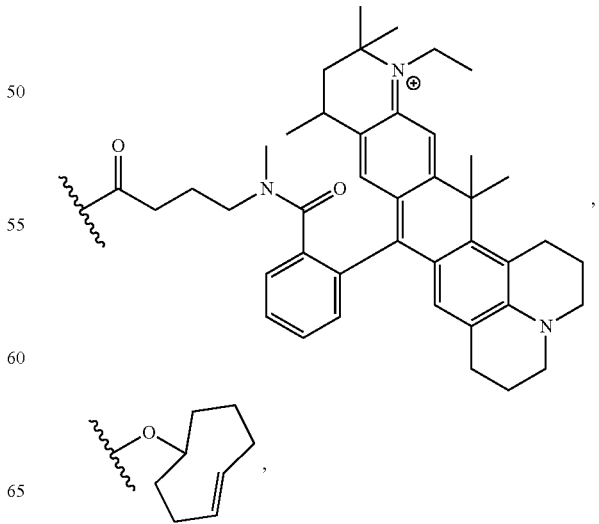

231
-continued
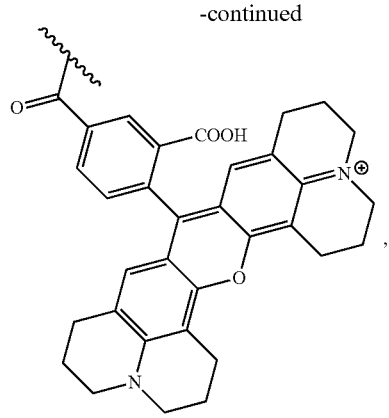
232
-continued
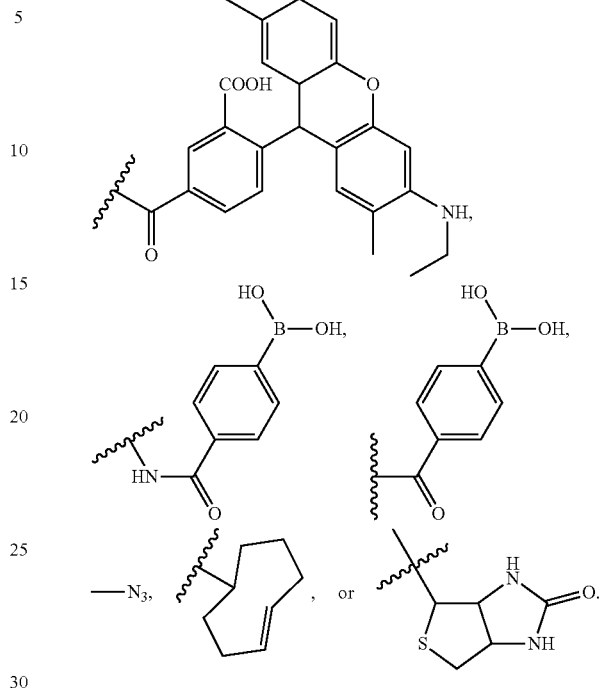
in embodiments, the compound as the formula:
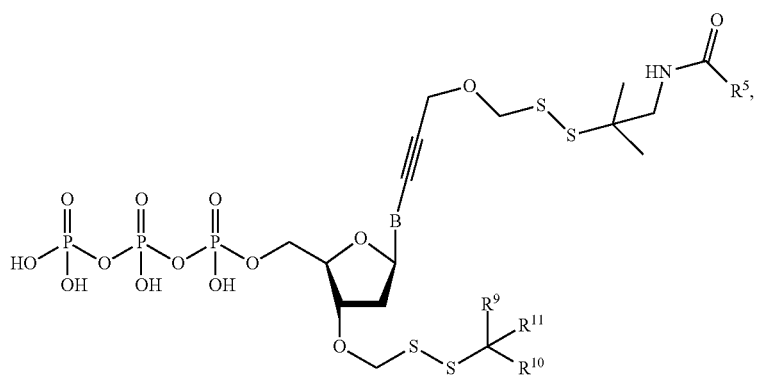
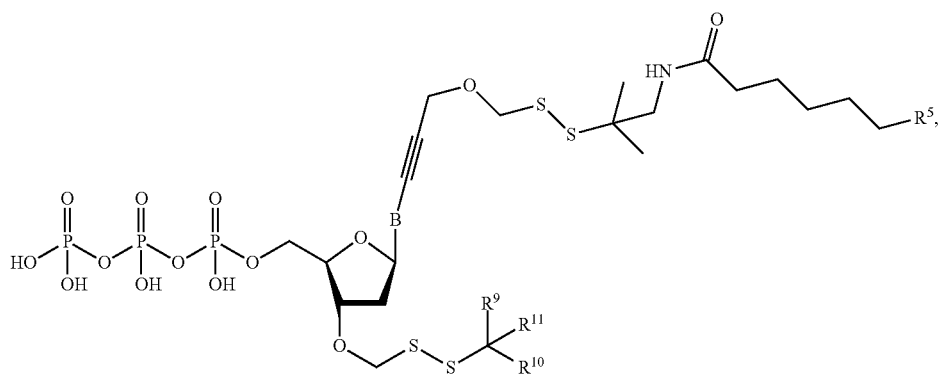

233
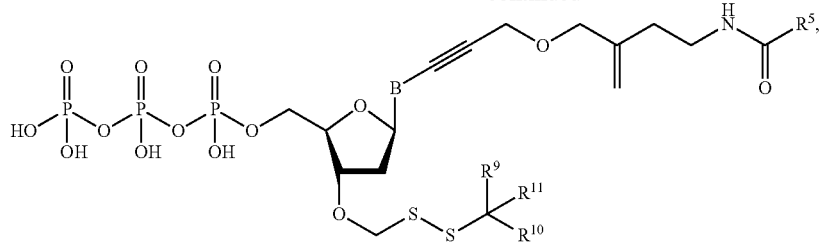
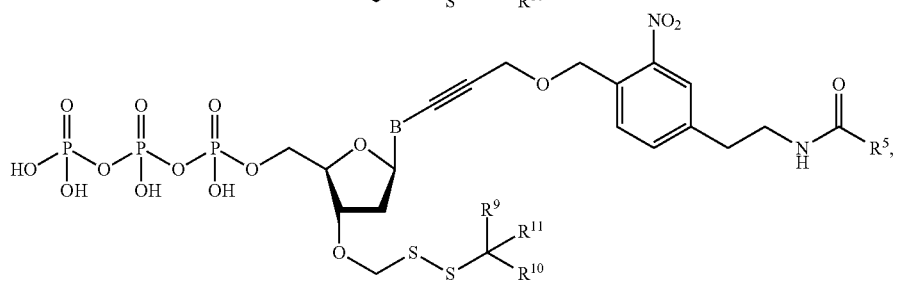
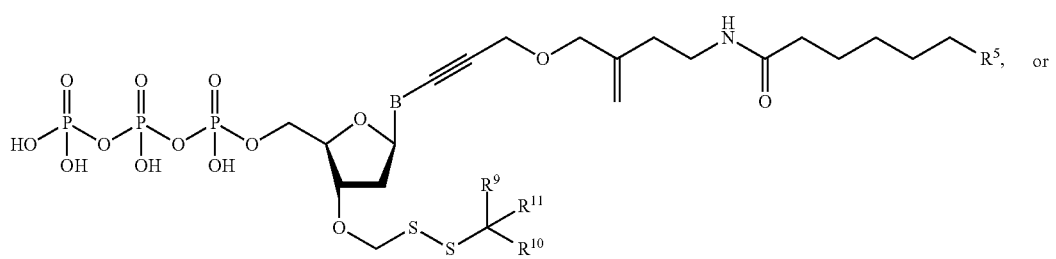
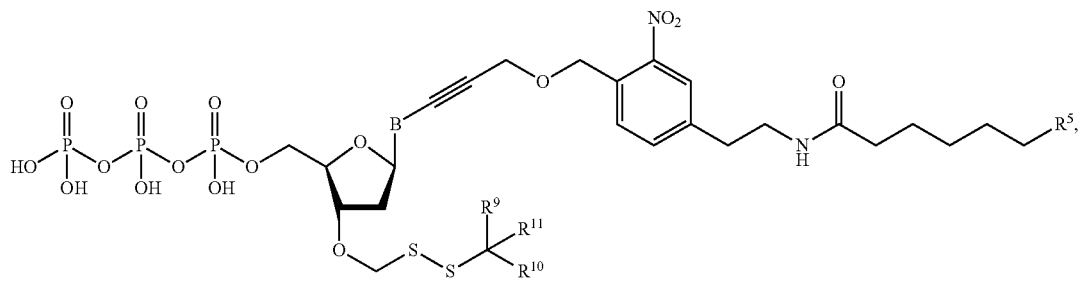
wherein B, R$^5$, R$^9$, R$^{10}$, and R$^{11}$ are as described herein, in embodiments, R$^5$ is
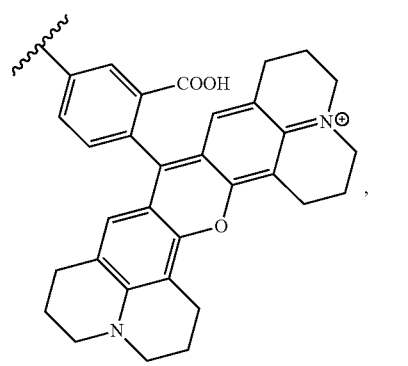
234
-continued
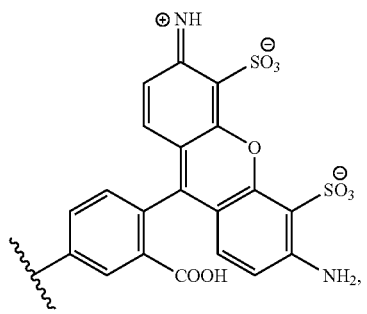

235
-continued
236
-continued
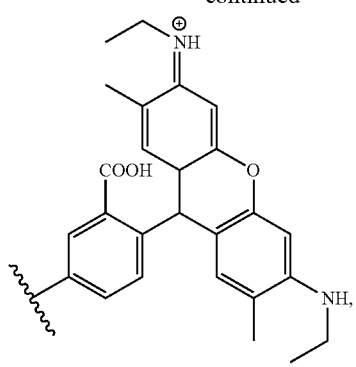
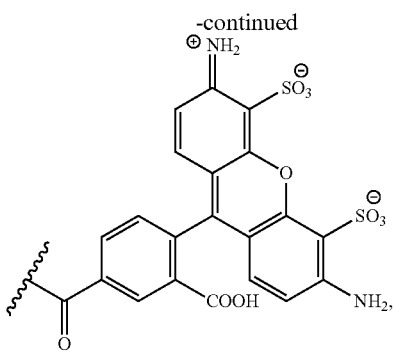
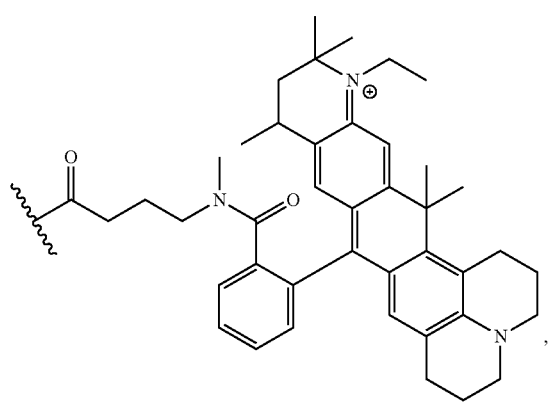
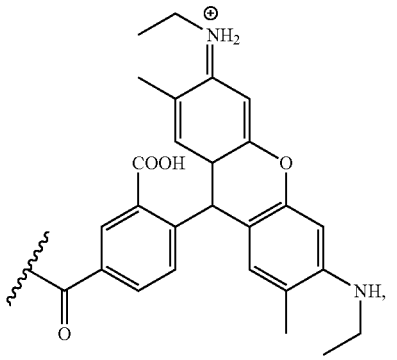
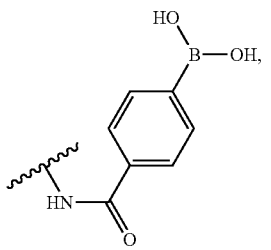
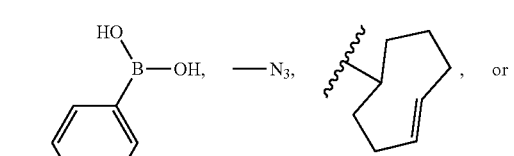
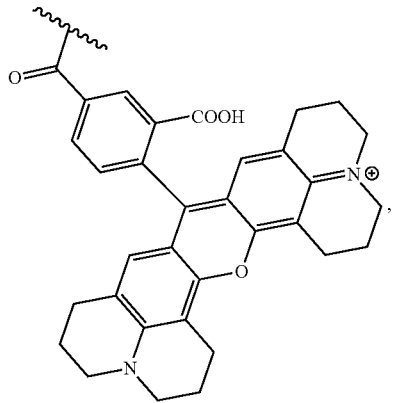
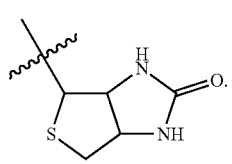

In embodiments, the compound has the formula:
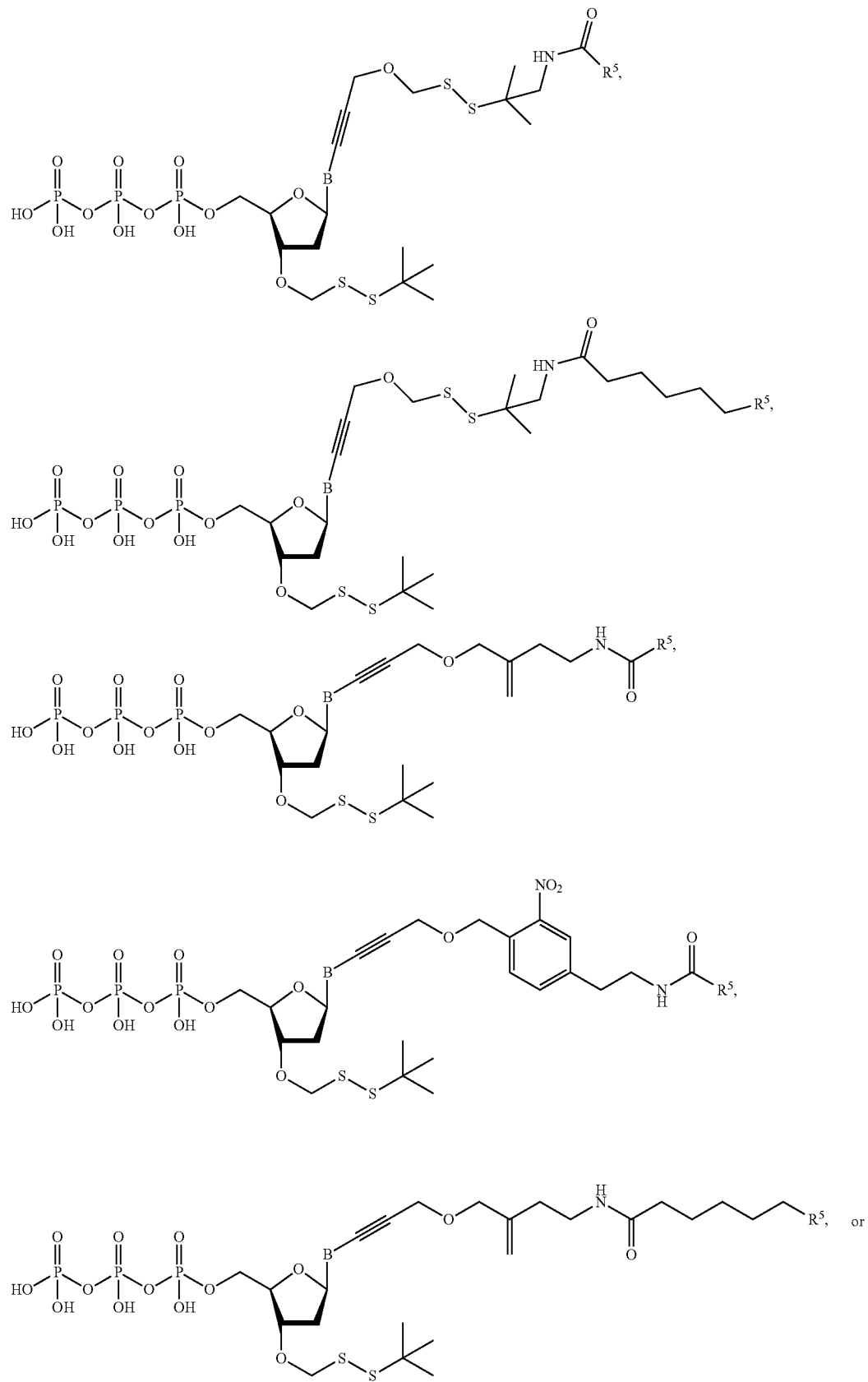

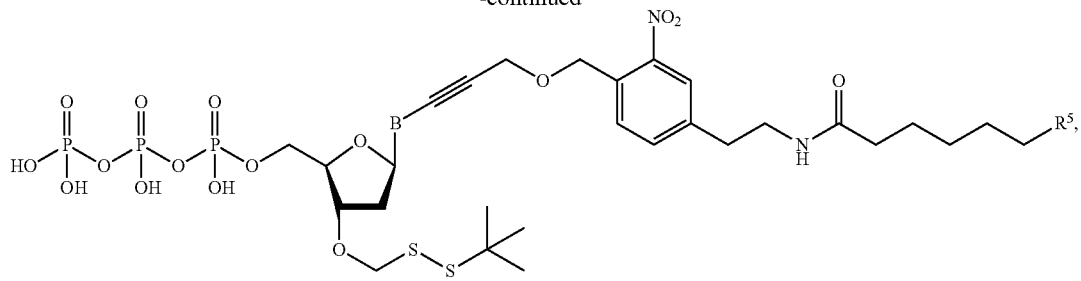
wherein B and R[5] are as described herein. In embodiments, R[5] is
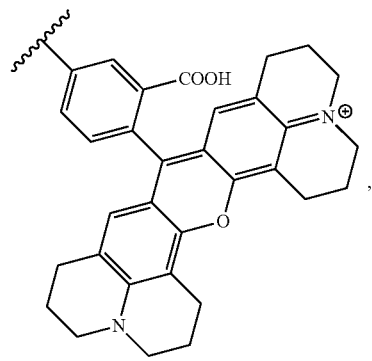
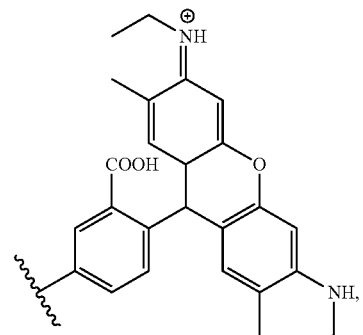
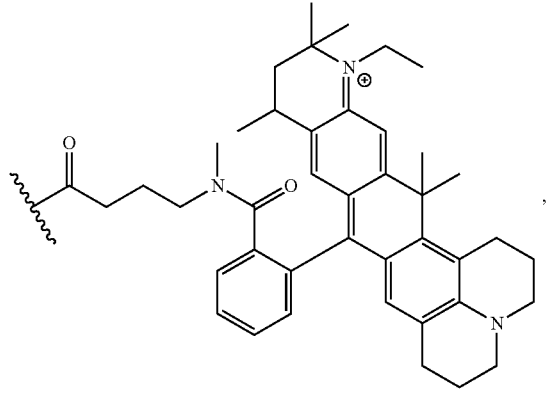
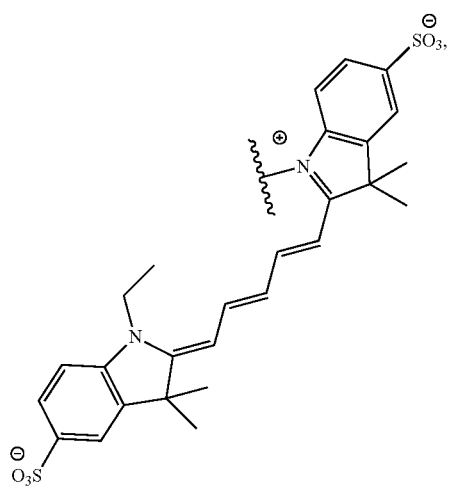
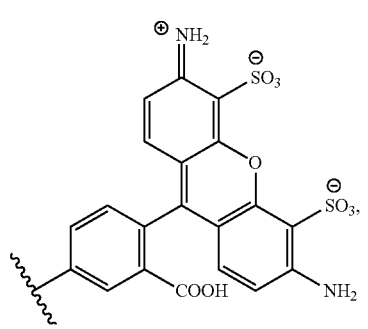
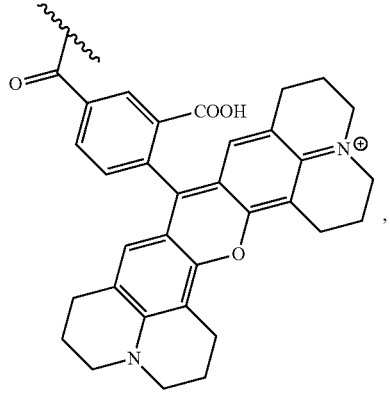

241

-continued

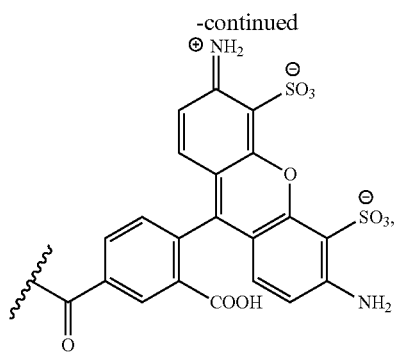

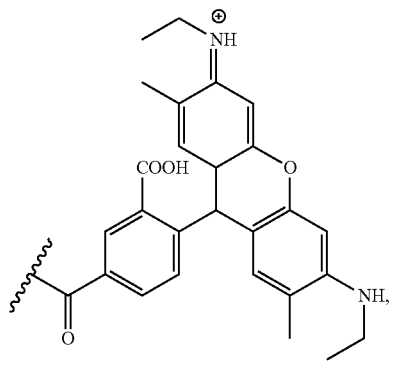

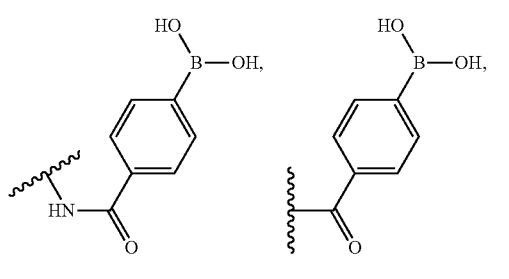

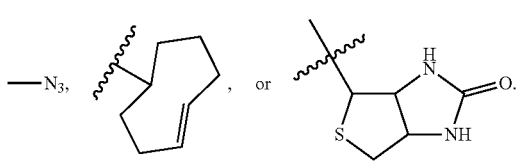

In embodiments, the compound has the formula:

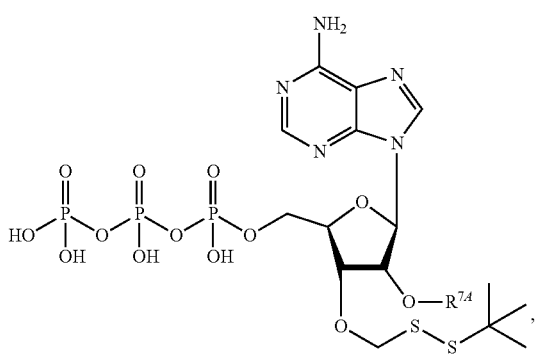

242

-continued

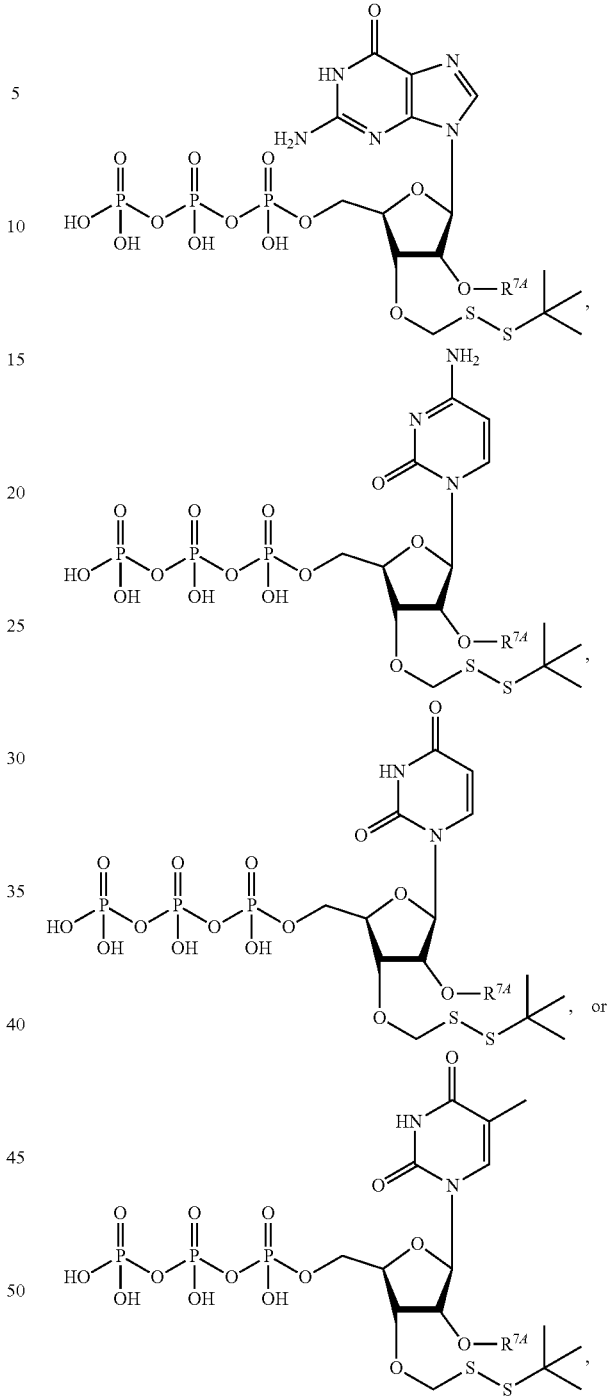

wherein $R^{7A}$ is as described herein.

In embodiments the detectable label is a Alexa Fluor® 350 moiety, Alexa Fluor® 405 moiety, Alexa Fluor® 430 moiety, Alexa Fluor® 488 moiety, Alexa Fluor® 532 moiety, Alexa Fluor® 546 moiety, Alexa Fluor® 555 moiety, Alexa Fluor® 568 moiety, Alexa Fluor® 594 moiety, Alexa Fluor® 610 moiety, Alexa Fluor® 633 moiety, Alexa Fluor® 635 moiety, Alexa Fluor® 647 moiety, Alexa Fluor® 660 moiety, Alexa Fluor® 680 moiety, Alexa Fluor® 700 moiety, Alexa Fluor® 750 moiety, or Alexa Fluor® 790 moiety. In embodiments the detectable moiety is a Alexa Fluor® 488 moiety, Rhodamine 6G (R6G) moiety, ROX Reference Dye (ROX) moiety, or Cy5 moiety.

In embodiments the detectable moiety is a FAM™ moiety, TET™ moiety, JOE™ moiety, VIC® moiety, HEX™ moiety, NED™ moiety, PET® moiety, ROX™ moiety, TAMRA™ moiety, TET™ moiety, Texas Red® moiety, Alexa Fluor® 488 moiety, Rhodamine 6G (R6G) moiety, ROX Reference Dye (ROX) moiety, Sulfo-Cy5, or Cy5 moiety.

In embodiments, the compound has the formula:

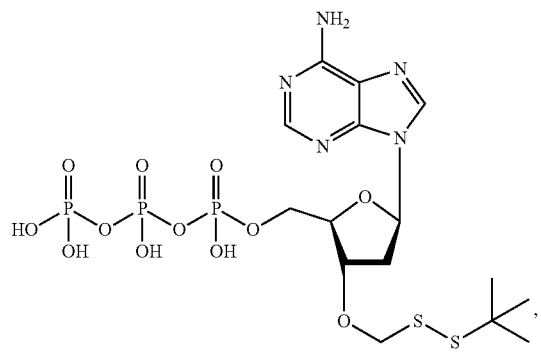

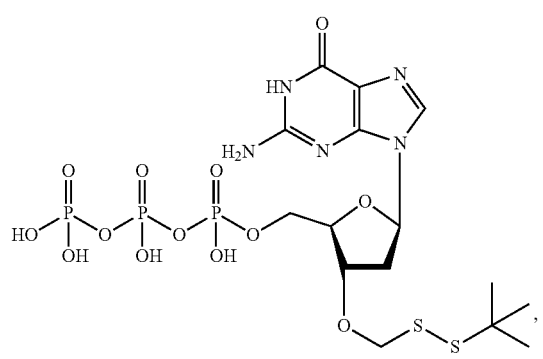

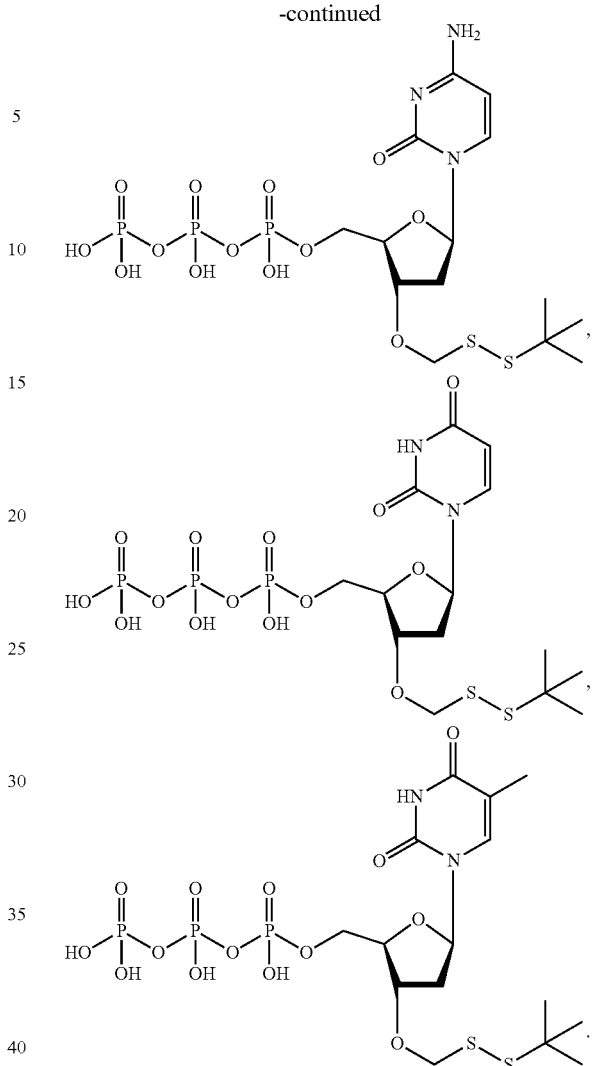

In an aspect is provided a compound having the formula: $R^{12z}$-$L^{4z}$-$R^{13}$. $L^{4z}$ is a covalent linker. $R^{12z}$ is a complementary anchor moiety reactive group. $R^{13}$ is a detectable label. In embodiments, the compound has the formula:

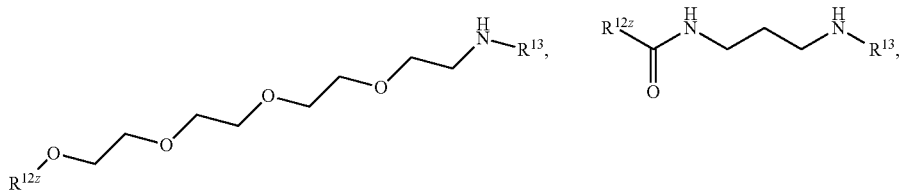

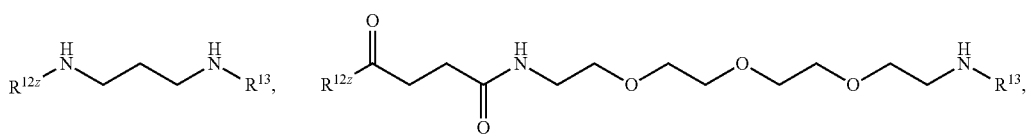

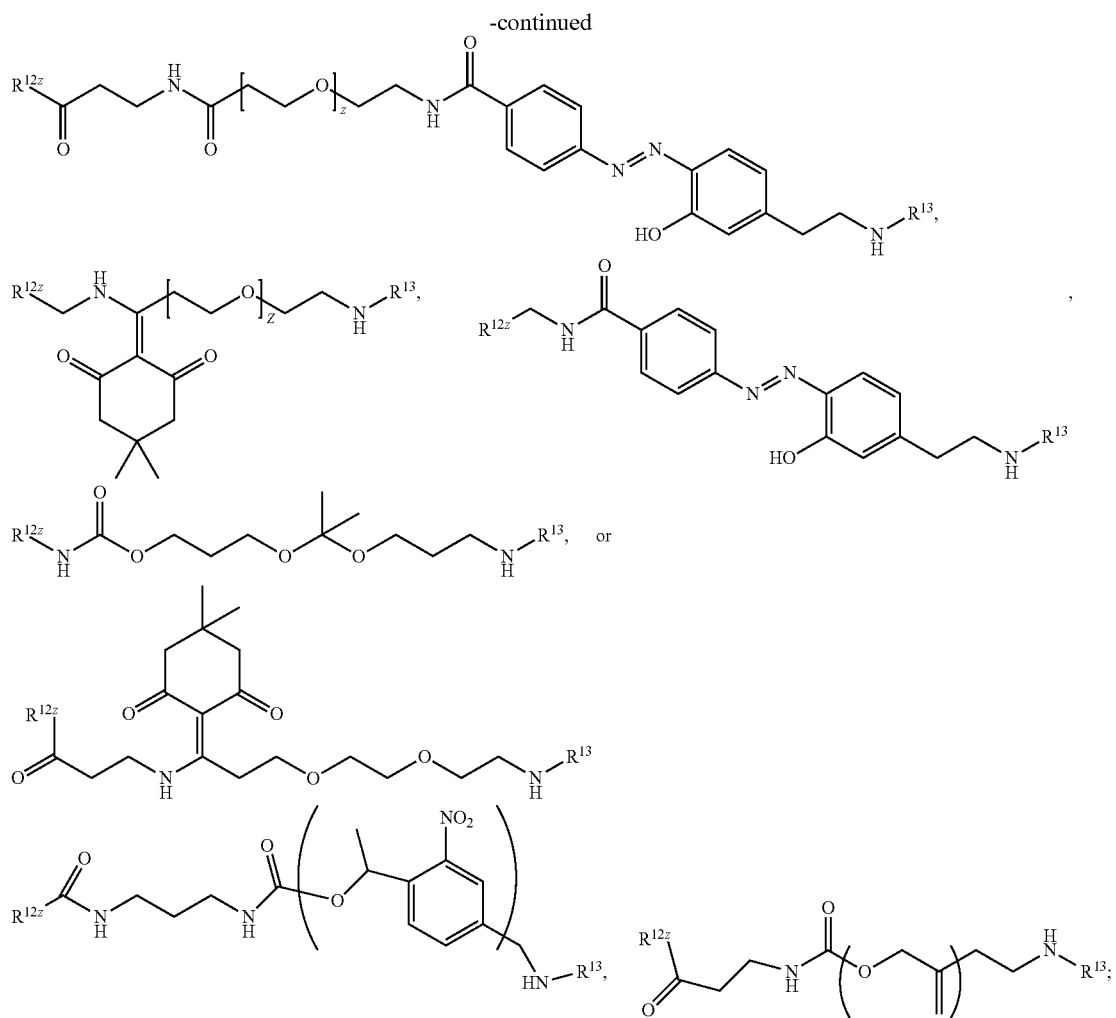
wherein $R^{12z}$ is as described herein and z is an integer from 0 to 20.
In embodiments, $R^{12z}$ is
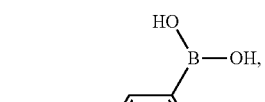
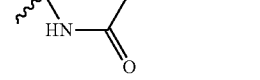
-continued
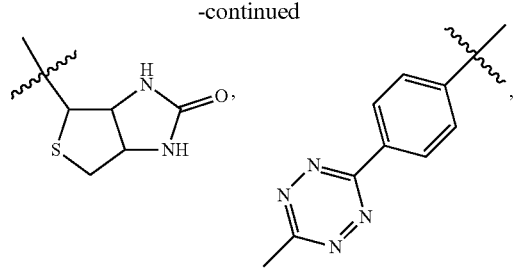
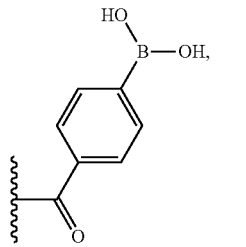
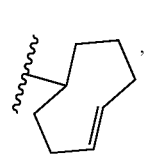
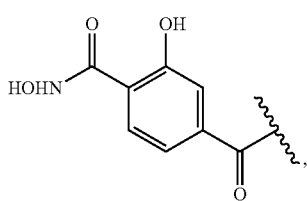

a streptavidin moiety, or

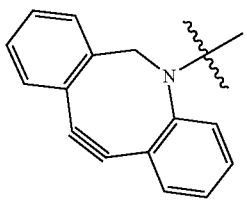

In embodiments, $R^{12z}$ is

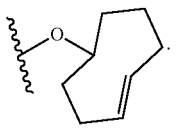 [SMILES: *OC1CC/C=C/CCC1 ; "."]

In embodiments, $R^{12z}$ is

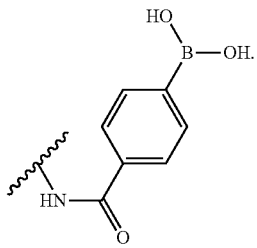 [SMILES: *NC(=O)c1ccc(B(O)O)cc1]

In embodiments, $R^{12z}$ is

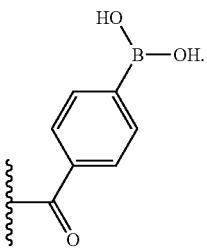 [SMILES: *C(=O)c1ccc(B(O)O)cc1]

In embodiments, $R^{12z}$ is

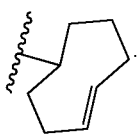 [SMILES: *C1CC/C=C/CCC1 ; "."]

In embodiments, $R^{12z}$ is

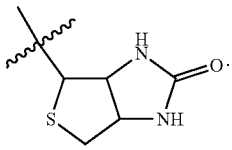 [SMILES: *C1SCC2NC(=O)NC21]

In embodiments, $R^{12z}$ is

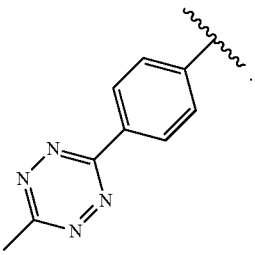 [SMILES: *c1ccc(-c2nnc(C)nn2)cc1]

In embodiments, $R^{12z}$ is

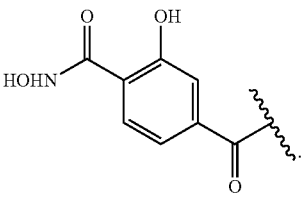

In embodiments, $R^{12z}$ is a streptavidin moiety. In embodiments, $R^{12z}$ is

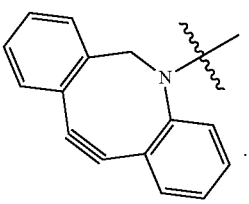 [SMILES: *N1Cc2ccccc2C#Cc2ccccc21]

In embodiments, $R^{13}$ is a fluorescent dye. In embodiments, $R^{13}$ includes a fluorescence resonance energy transfer donor fluorescent dye. In embodiments, $R^{13}$ includes a fluorescence resonance energy transfer acceptor fluorescent dye. In embodiments, $R^{13}$ includes a fluorescence resonance energy transfer donor and acceptor fluorescent dye pair connected by a linker.

In embodiments, $R^{13}$ includes a fluorescence resonance energy transfer donor and acceptor fluorescent dye pair connected by a linker and separated by 0.1 nm to 10 nm.

In embodiments, $R^{13}$ is
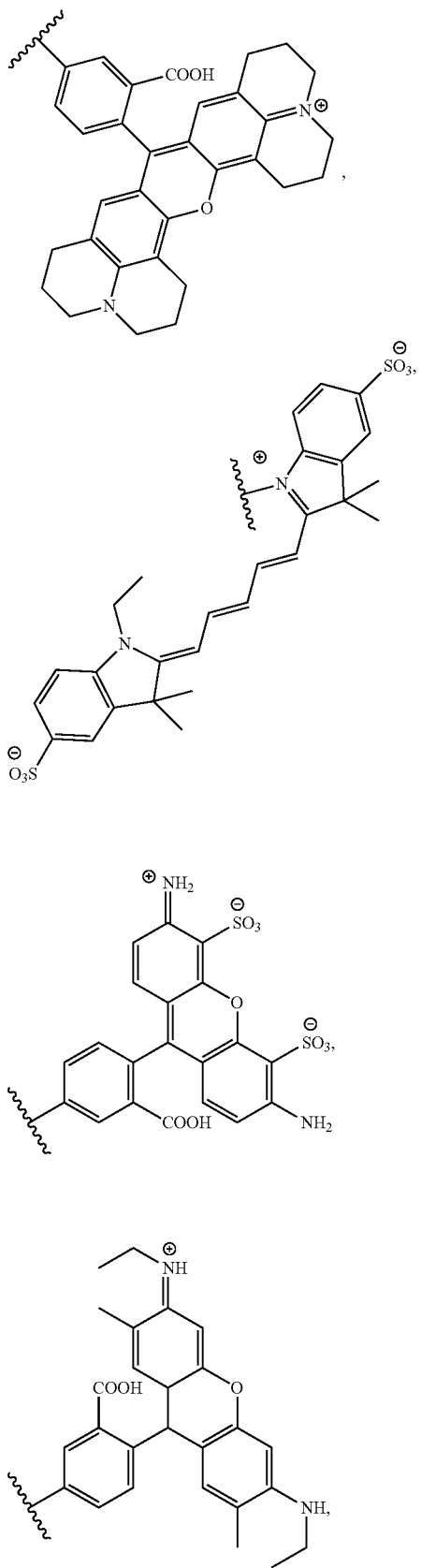
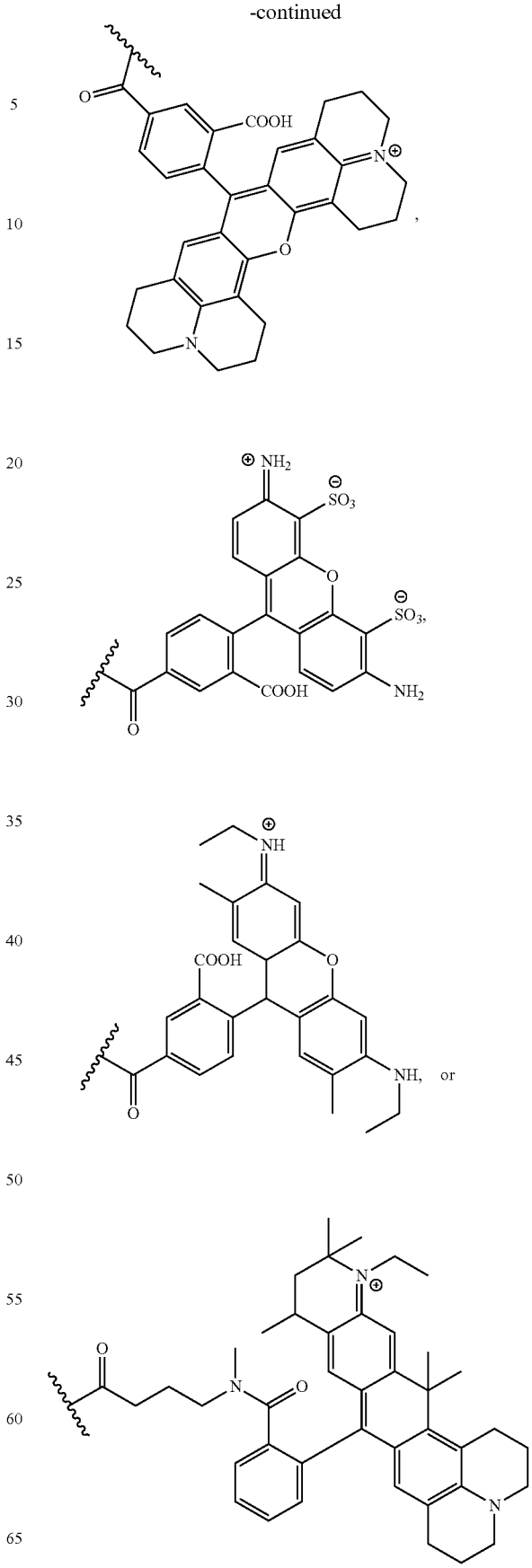
, or

In embodiments, the compound has the formula:
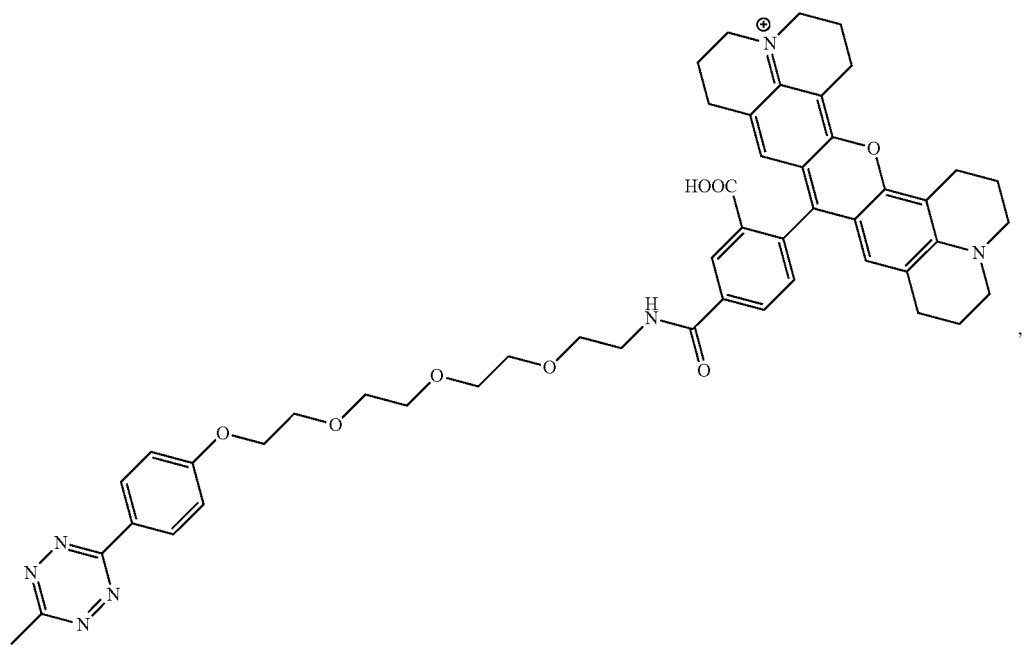 [SMILES: Cc1nnc(-c2ccc(OCCOCCOCCOCCNC(=O)c3ccc(C4=c5cc6c7c(c5Oc5c4cc4c8c5CCCN8CCC4)CCC[N+]=7CCC6)c(C(=O)O)c3)cc2)nn1]
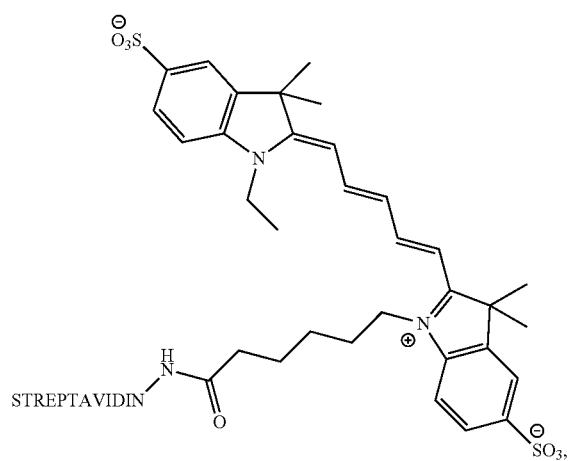
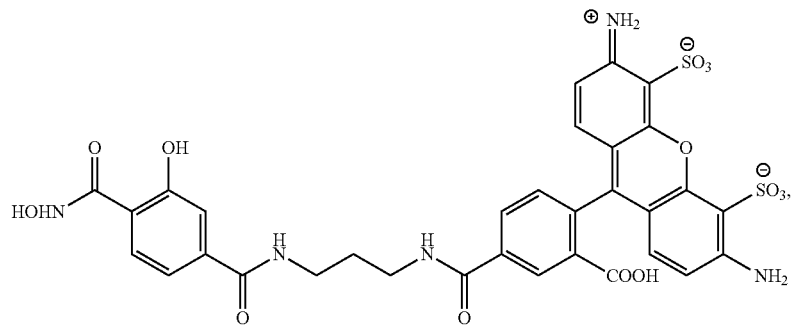

-continued
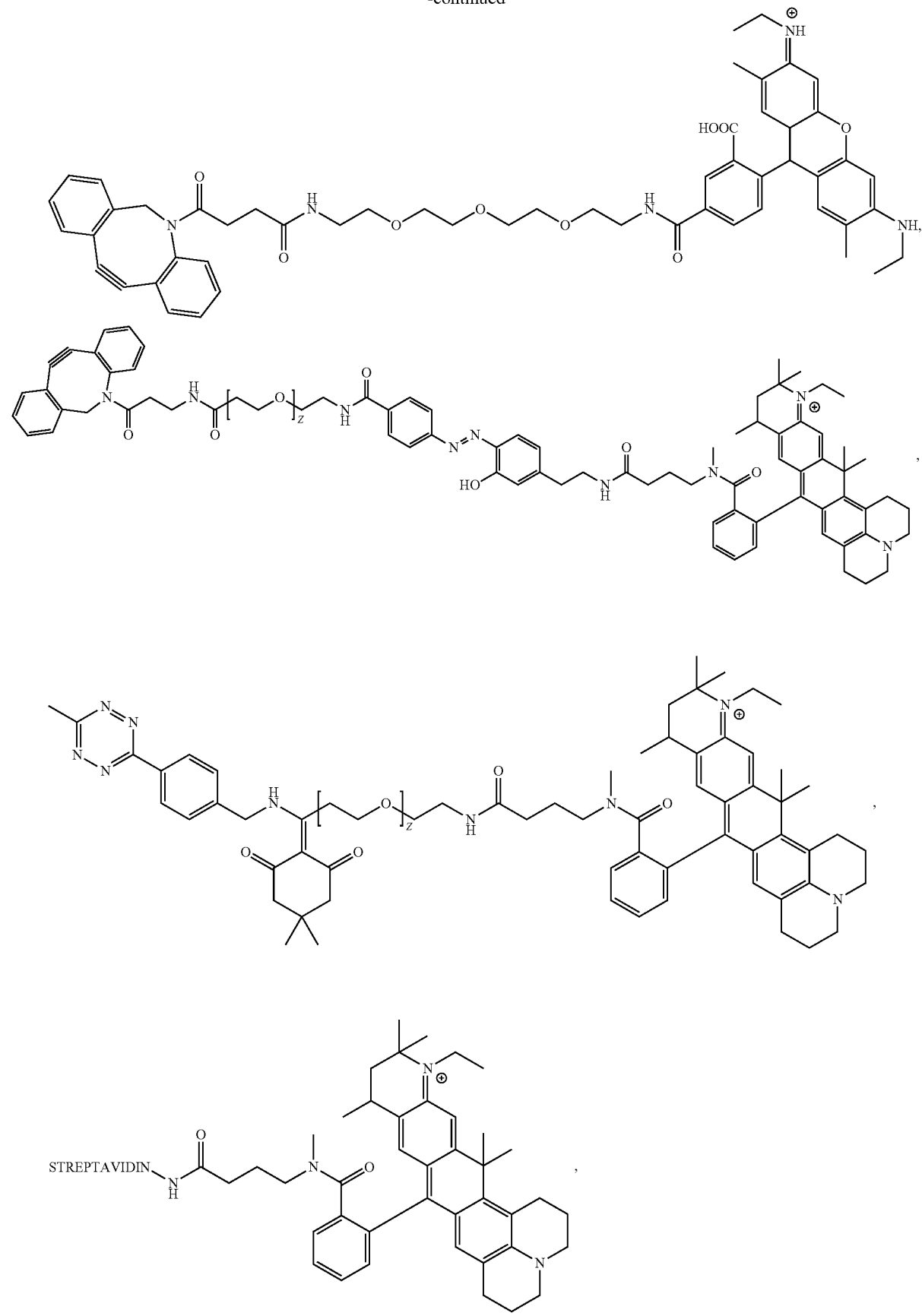

255
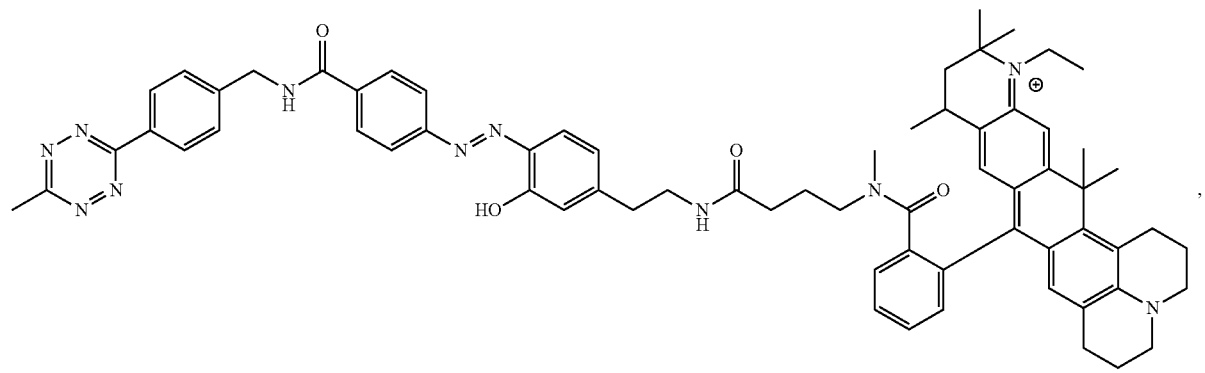
256
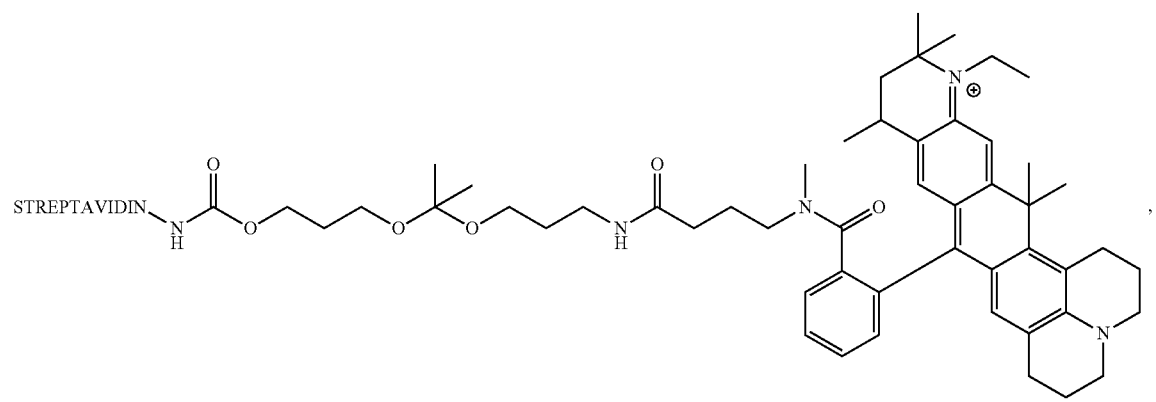
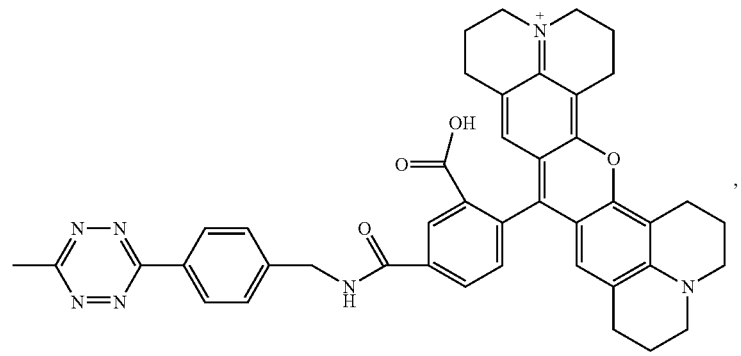

257
258
-continued
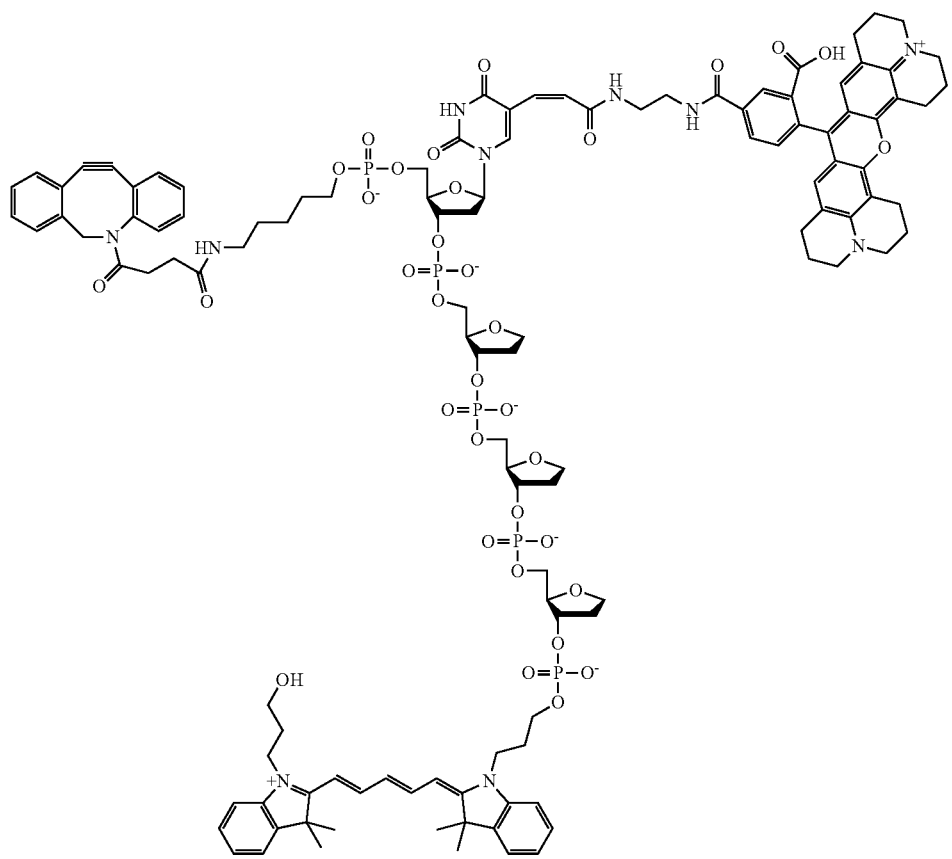
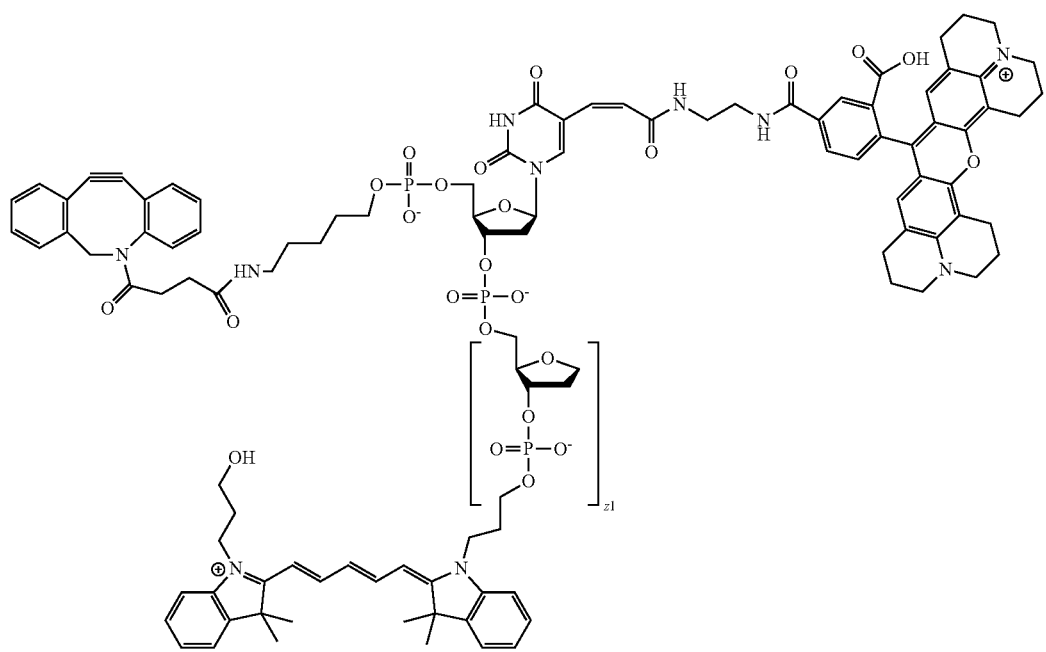

wherein z1 is an integer from 0 to 50,
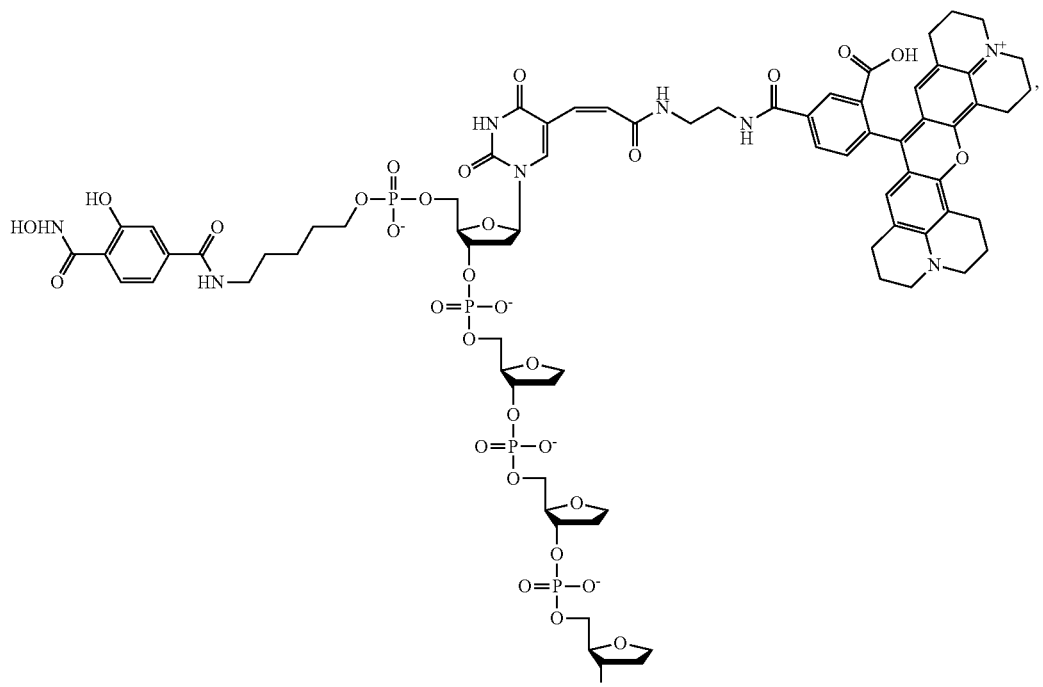
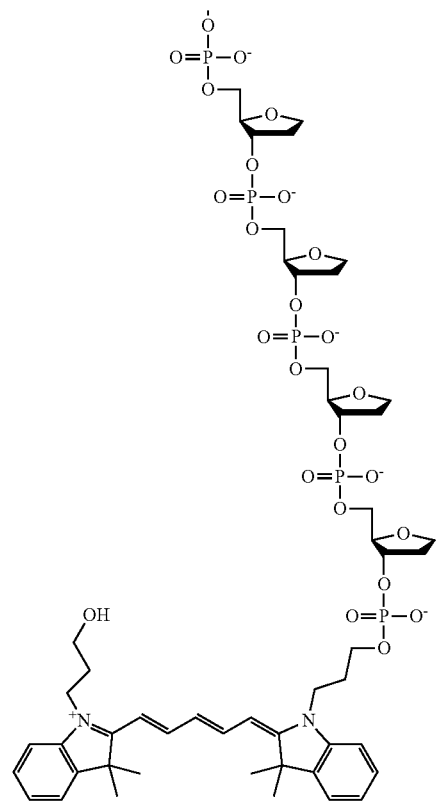

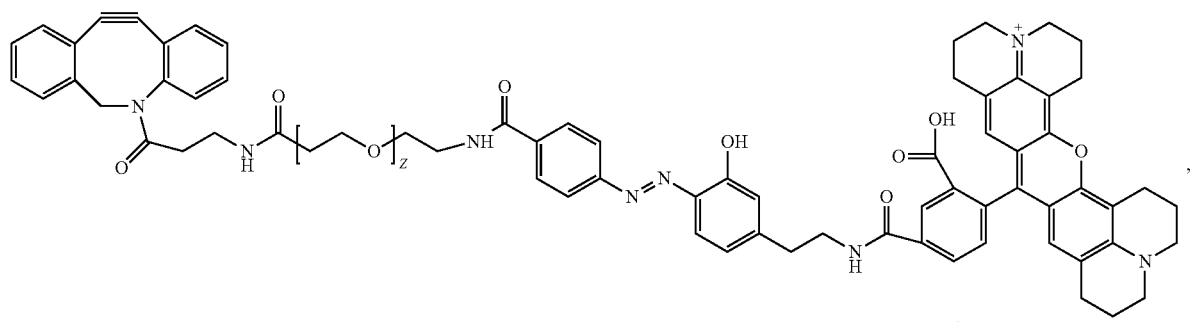

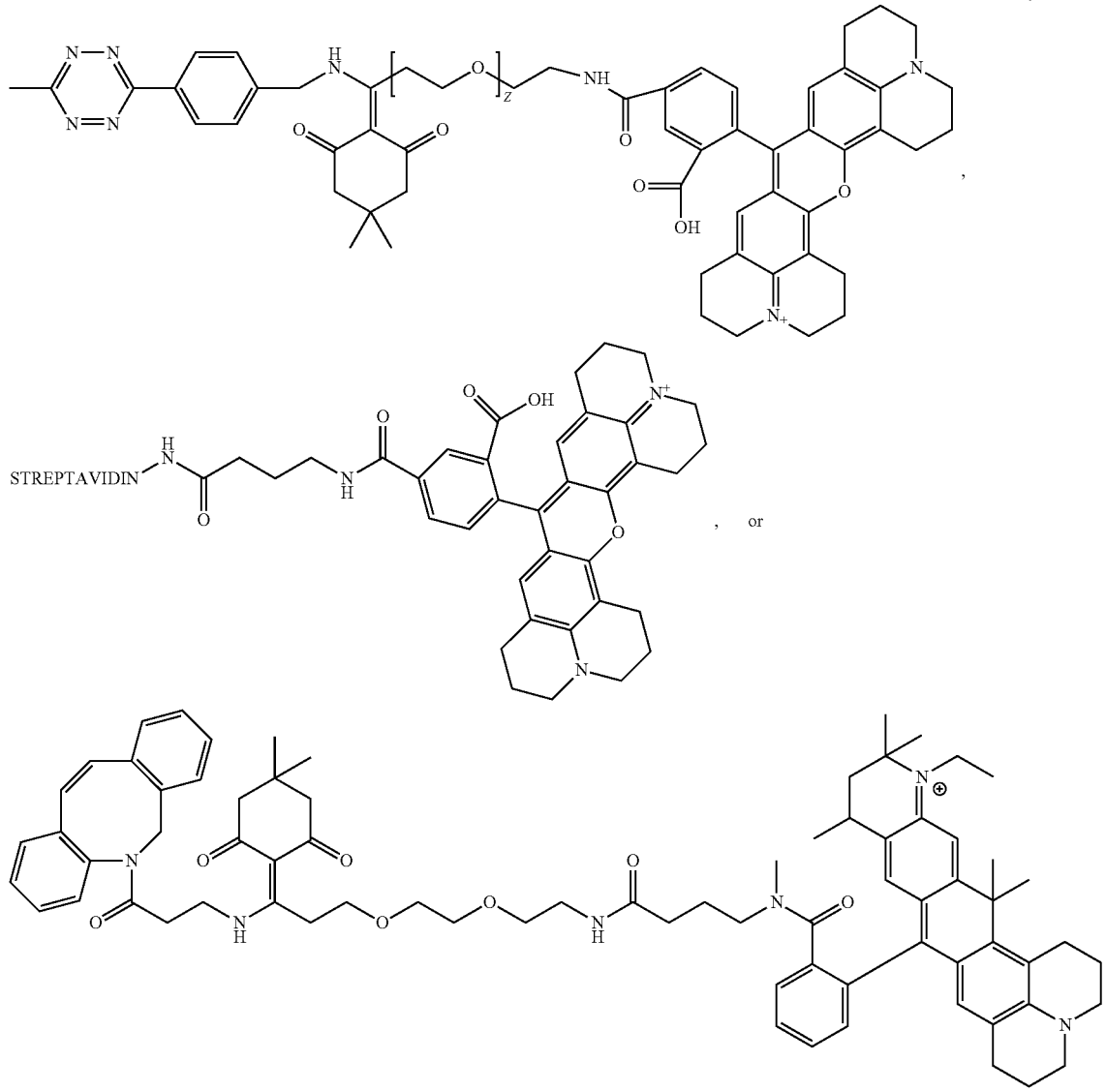

In an aspect is provided a compound of the formula: $R^{12z}$-$R^{14}$. $R^{12z}$ is a complementary anchor moiety reactive group. $R^{14}$ is $R^{15}$-substituted alkyl, $R^{15}$-substituted heteroalkyl, $R^{15}$-substituted cycloalkyl, $R^{15}$-substituted heterocycloalkyl, $R^{15}$-substituted aryl, or $R^{15}$-substituted heteroaryl. $R^{15}$ is independently $R^{16}$-substituted alkyl, $R^{16}$-substituted heteroalkyl, $R^{16}$-substituted cycloalkyl, $R^{16}$-substituted heterocycloalkyl, $R^{16}$-substituted aryl, $R^{16}$-substituted heteroaryl, or a detectable dye. $R^{16}$ is independently $R^{17}$-substituted alkyl, $R^{17}$-substituted heteroalkyl, $R^{17}$-substituted cycloalkyl, $R^{17}$-substituted heterocycloalkyl, $R^{17}$-substituted aryl, $R^{17}$-substituted heteroaryl, or a detectable dye. $R^{17}$ is independently $R^{18}$-substituted alkyl, $R^{18}$-substituted heteroalkyl, $R^{18}$-substituted cycloalkyl, substituted heterocycloalkyl, $R^{18}$-substituted aryl, $R^{18}$-substituted heteroaryl, or a detectable dye $R^{18}$ is a detectable dye. $R^{14}$ is substituted with a plurality of $R^{15}$ moieties, $R^{15}$ is substituted with a plurality of $R^{16}$ moieties, and $R^{16}$ is substituted with a plurality of $R^{17}$ moieties.

In embodiments, $R^{12z}$ is
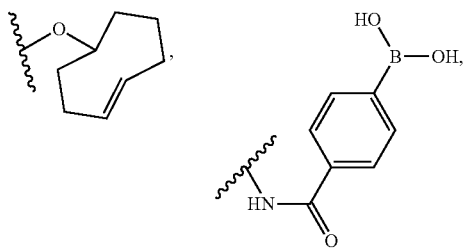 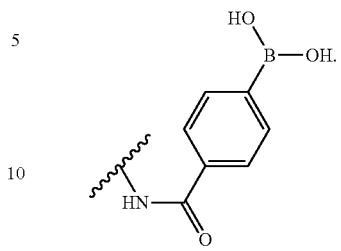
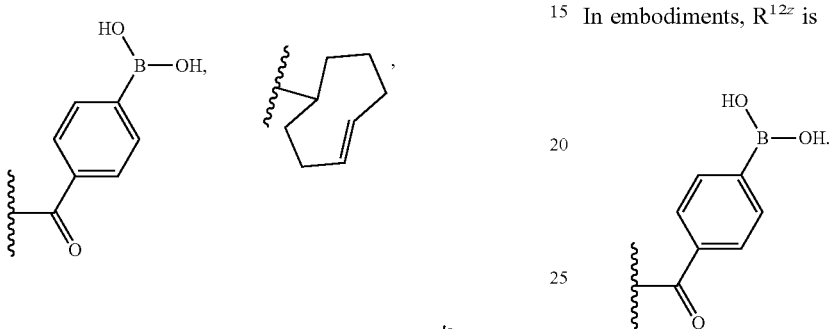
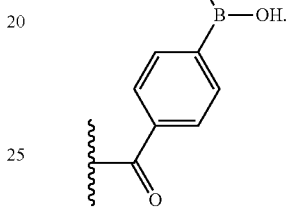
In embodiments, $R^{12z}$ is
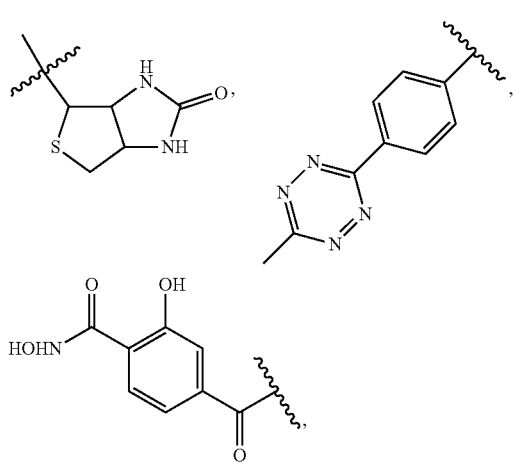
a streptavidin moiety, or
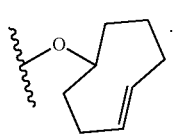.
In embodiments, $R^{12z}$ is
In embodiments, $R^{12z}$ is
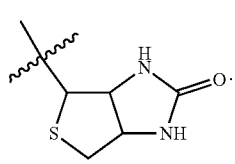
In embodiments, $R^{12z}$ is
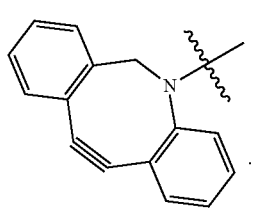 [SMILES: *N1Cc2ccccc2C#Cc2ccccc21]
In embodiments, $R^{12z}$ is
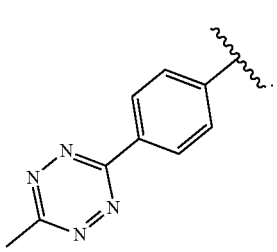 [SMILES: *c1ccc(-c2nnc(C)nn2)cc1]

In embodiments, $R^{12z}$ is

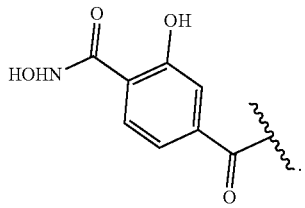

In embodiments, $R^{12z}$ is a streptavidin moiety. In embodiments, $R^{12z}$ is

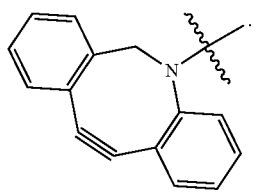 [SMILES: *N1Cc2ccccc2C#Cc2ccccc21]

In embodiments, the detectable dye is a fluorescent dye. In embodiments, the detectable dye includes a fluorescence resonance energy transfer donor fluorescent dye. In embodiments, the detectable dye includes a fluorescence resonance energy transfer acceptor fluorescent dye. In embodiments, the detectable dye includes a fluorescence resonance energy transfer donor and acceptor fluorescent dye pair connected by a linker. In embodiments, the detectable dye includes a fluorescence resonance energy transfer donor and acceptor fluorescent dye pair connected by a linker and separated by 0.1 nm to 10 nm.

In embodiments, the detectable dye is

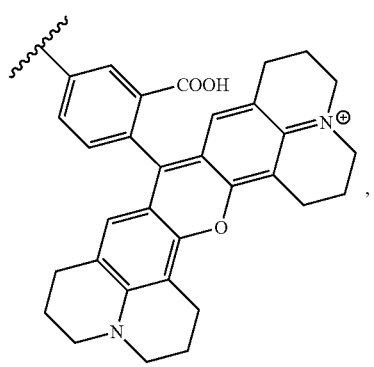

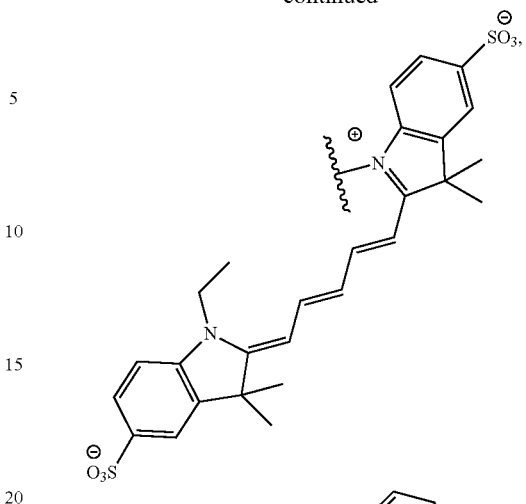

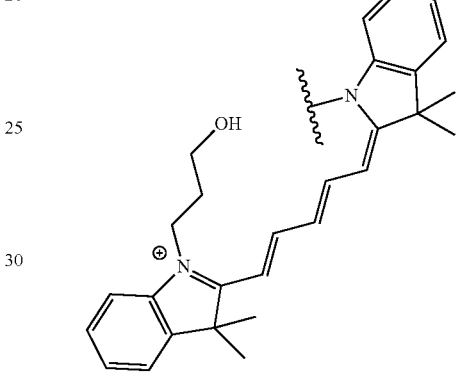

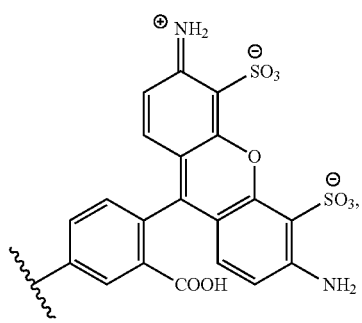

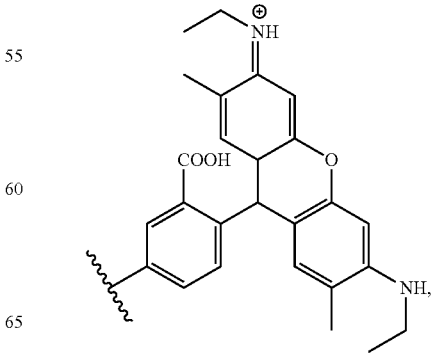

267
-continued
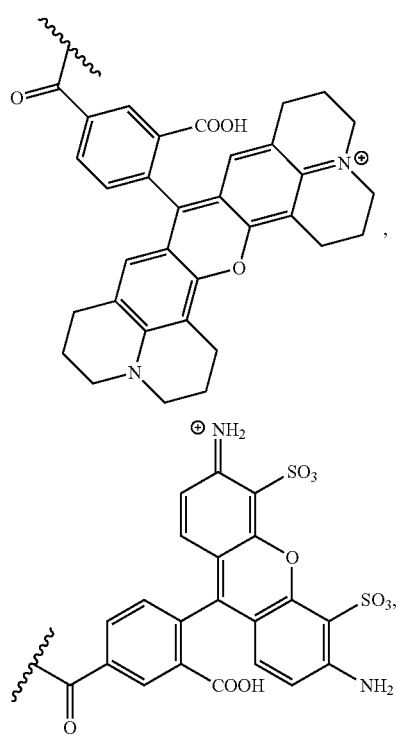
268
-continued
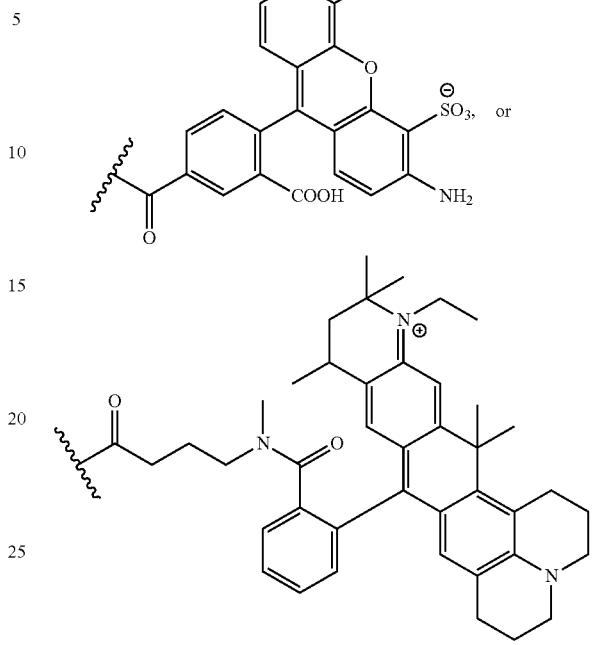
In embodiments, the compound has the formula:
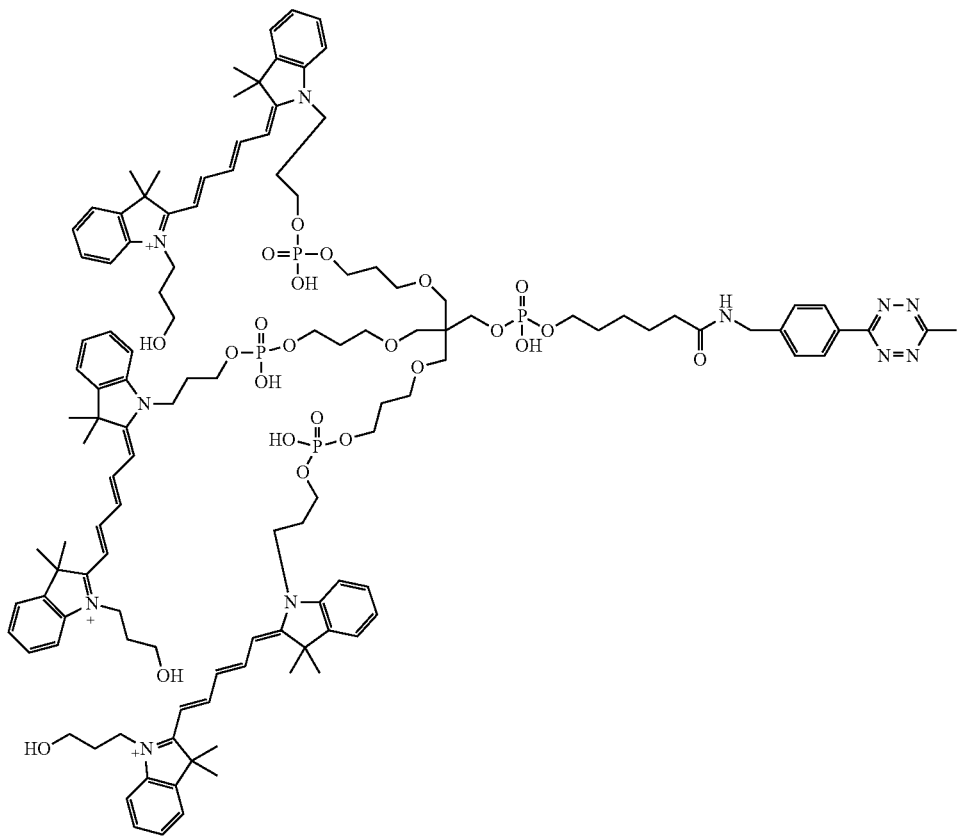

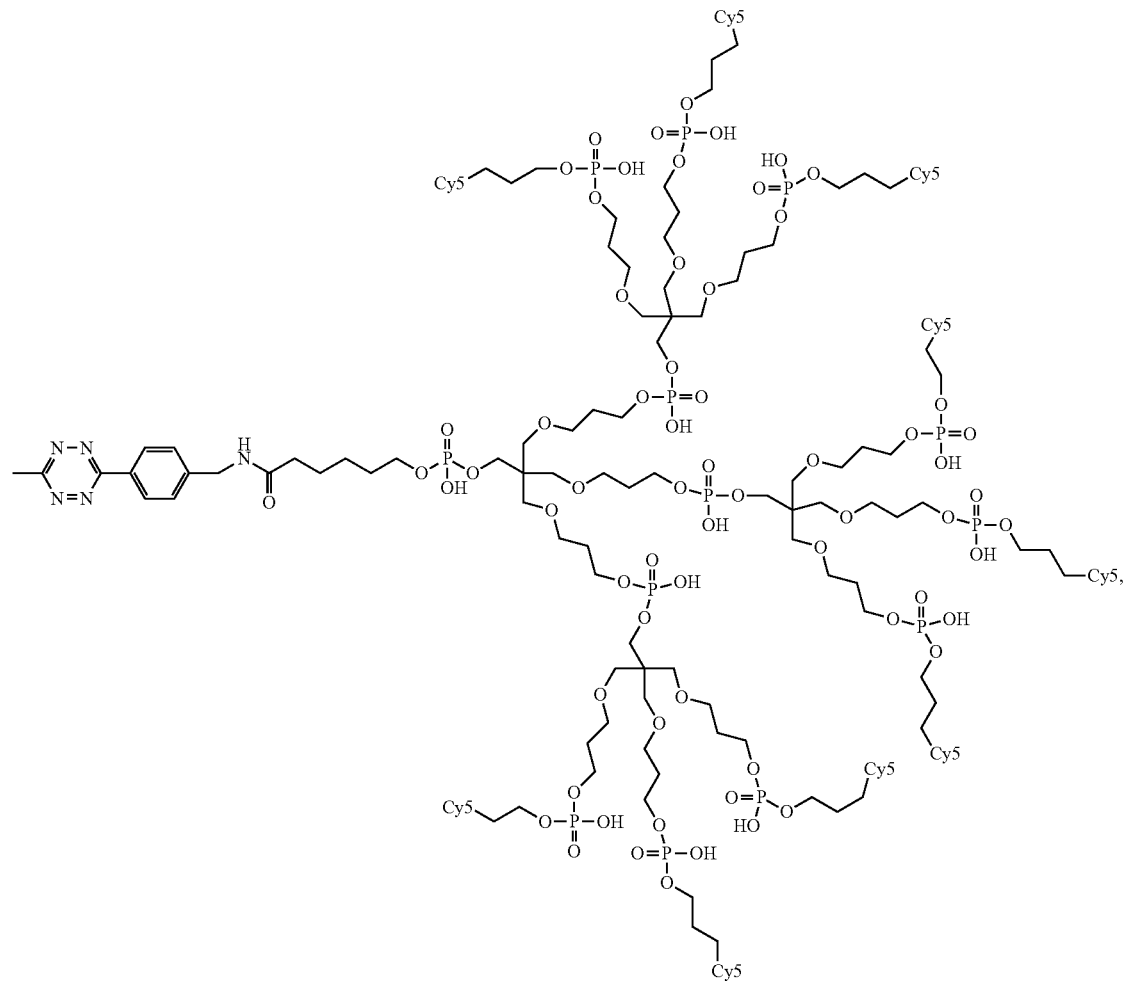
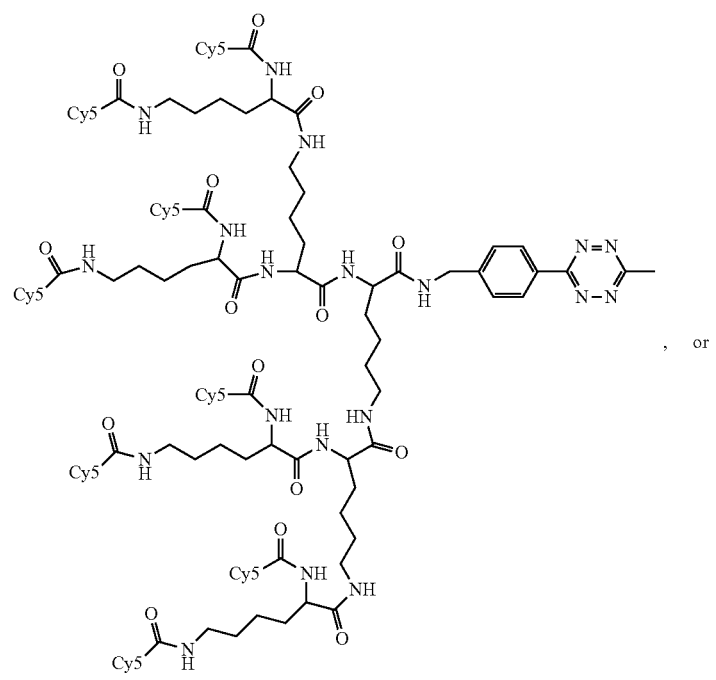

-continued
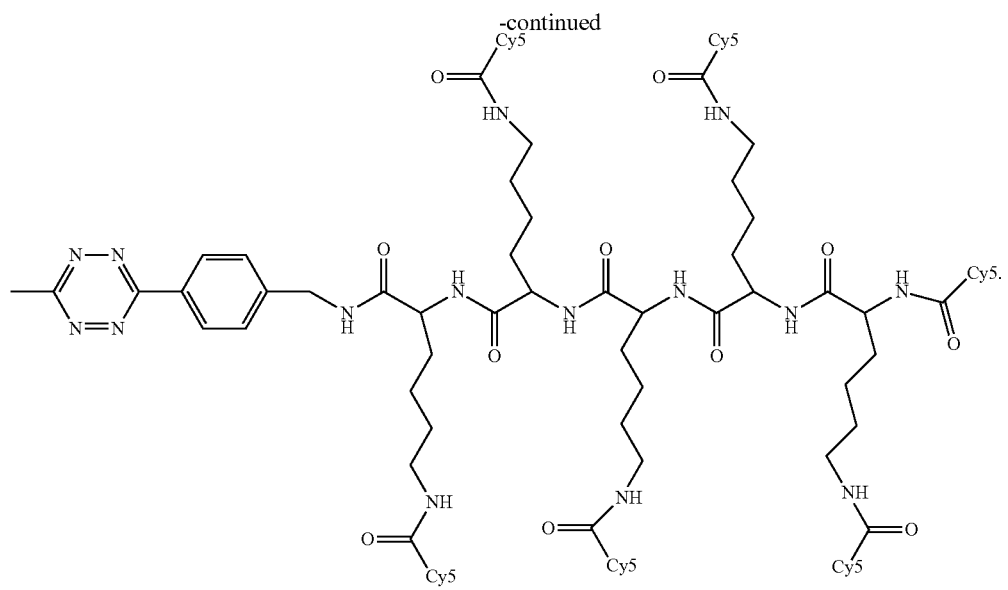
In embodiments, the compound has the formula:
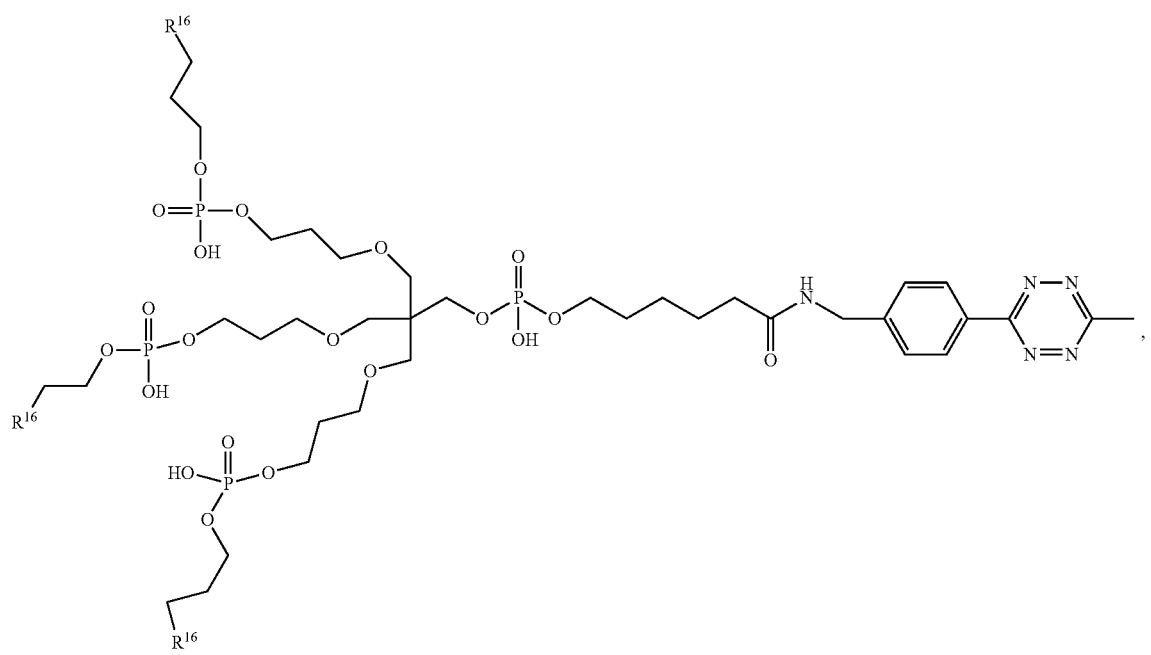

-continued
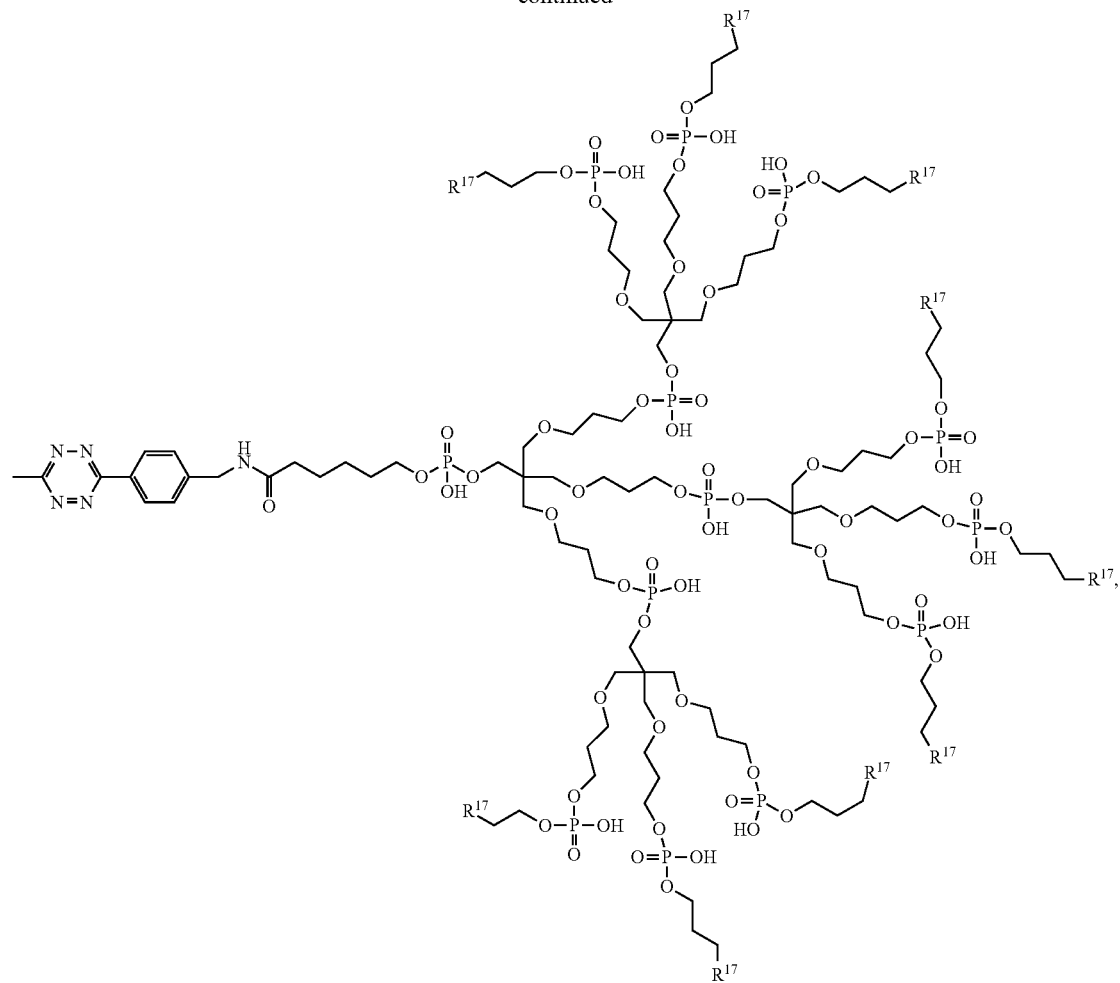
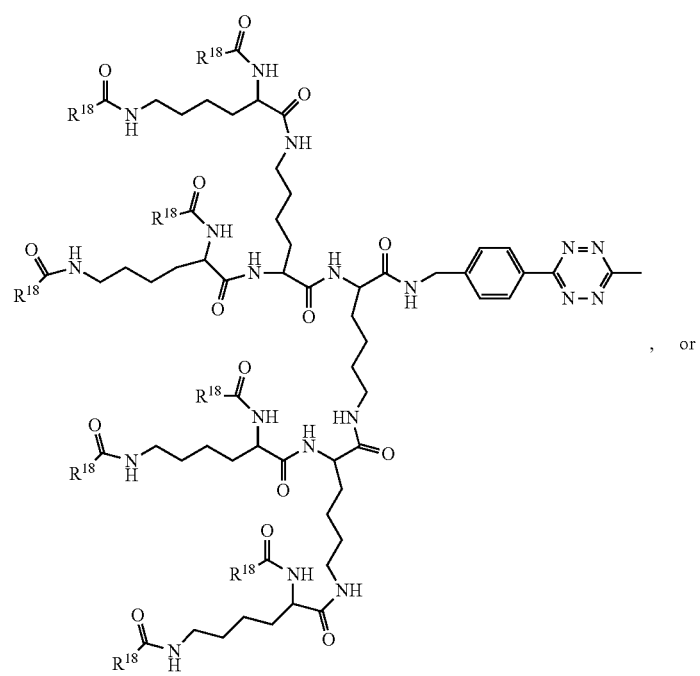
, or

-continued

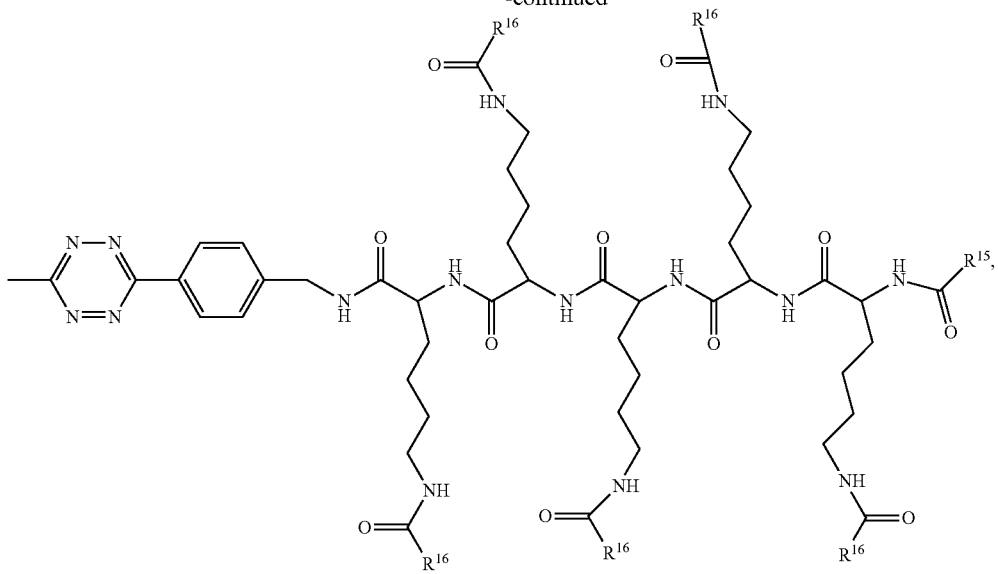

wherein $R^{12z}$ is as described herein.

III. Methods of Use

Provided in an aspect is a method for sequencing a nucleic acid, including: (i) incorporating in series with a nucleic acid polymerase, within a reaction vessel, one of four different labeled nucleotide analogues into a primer to create an extension strand, wherein the primer is hybridized to the nucleic acid and wherein each of the four different labeled nucleotide analogues include a unique detectable label; (ii) detecting the unique detectable label of each incorporated nucleotide analogue, so as to thereby identify each incorporated nucleotide analogue in the extension strand, thereby sequencing the nucleic acid. Each of the four different labeled nucleotide analogues are of the structure as described herein, including embodiments, wherein in the first of the four different labeled nucleotide analogues, B is a thymidine or uridine hybridizing base; in the second of the four different labeled nucleotide analogues, B is an adenosine hybridizing base; in the third of the four different labeled nucleotide analogues, B is an guanosine hybridizing base; and in the fourth of the four different labeled nucleotide analogues, B is an cytosine hybridizing base.

In embodiments, the method further includes further including, after each of the incorporating steps, adding to the reaction vessel four different unlabeled nucleotide analogues, wherein each of the four different unlabeled nucleotide analogues are of the structure as described herein, including embodiments, wherein in the first of the four different unlabeled nucleotide analogues, B is a thymidine or uridine hybridizing base; in the second of the four different unlabeled nucleotide analogues, B is an adenosine hybridizing base; in the third of the four different unlabeled nucleotide analogues, B is a guanosine hybridizing base; and in the fourth of the four different unlabeled nucleotide analogues, B is a cytosine hybridizing base.

In embodiments, at least one of the four different labeled nucleotide analogues is an orthogonally cleavable labeled nucleotide analogue including a cleavable moiety, the orthogonally cleavable labeled nucleotide analogue having the structure as described herein, and wherein the method further includes, after each of the incorporating steps, adding to the reaction vessel a cleaving reagent capable of cleaving the cleavable moiety. In embodiments, the cleaving reagent is an acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), or hydrazine ($N_2H_4$). In embodiments, the cleaving reagent includes an acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), or hydrazine ($N_2H_4$).

In another aspect is a method for sequencing a nucleic acid, including: (i) incorporating in series with a nucleic acid polymerase, within a reaction vessel, one of four different nucleotide analogues into a primer to create an extension strand, wherein the primer is hybridized to the nucleic acid and wherein three of the four different nucleotide analogues are different labeled nucleotide analogues each including a unique detectable label and one of the four different nucleotide analogues is a different unlabeled nucleotide analogue; (ii) detecting the presence or absence of the unique detectable label of each incorporated nucleotide analogue, so as to thereby identify each incorporated nucleotide analogue in the extension strand, thereby sequencing the nucleic acid; and wherein each of the four different labeled nucleotide analogues are of the structure as described herein, including embodiments, wherein in the first of the four different labeled nucleotide analogues, B is a thymidine or uridine hybridizing base; in the second of the four different labeled nucleotide analogues. B is an adenosine hybridizing base; in the third of the four different labeled nucleotide analogues, B is a guanosine hybridizing base; and in the fourth of the four different labeled nucleotide analogues, B is a cytosine hybridizing base.

In embodiments, the method further including, after each of the incorporating steps, adding to the reaction vessel four different unlabeled nucleotide analogues, wherein each of the four different unlabeled nucleotide analogues are of the structure as described herein, including embodiments, wherein in the first of the four different unlabeled nucleotide analogues, B is a thymidine or uridine hybridizing base; in the second of the four different unlabeled nucleotide analogues, B is an adenosine hybridizing base; in the third of the four different unlabeled nucleotide analogues, B is a guanosine hybridizing base; and in the fourth of the four different unlabeled nucleotide analogues, B is a cytosine hybridizing base.

In embodiments, at least one of the three different labeled nucleotide analogues is an orthogonally cleavable labeled nucleotide analogue including a cleavable moiety, the orthogonally cleavable labeled nucleotide analogue having the structure as described herein, including embodiments, and wherein the method further includes, after each of the incorporating steps, adding to the reaction vessel a cleaving reagent capable of cleaving the cleavable moiety. In embodiments, the cleaving reagent is an acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), or hydrazine ($N_2H_4$). In embodiments, the cleaving reagent includes an acid, base, oxidizing agent, reducing agent, Pd(0), tris-(2-carboxyethyl)phosphine, dilute nitrous acid; fluoride, tris(3-hydroxypropyl)phosphine), sodium dithionite ($Na_2S_2O_4$), or hydrazine ($N_2H_4$).

In an aspect is provided a method of incorporating a nucleotide analogue into a primer, the method including combining a polymerase, a primer hybridized to nucleic acid template and a nucleotide analogue within a reaction vessel and allowing the polymerase to incorporate the nucleotide analogue into the primer thereby forming an extended primer, wherein the nucleotide analogue is of the structure as described herein, including embodiments.

In embodiments, $L^2$ is a cleavable moiety and $R^5$ is a detectable label, the method further including, after the incorporating, cleaving the cleavable moiety with a cleaving reagent. In embodiments, the cleaving reagent is an acid; base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), or hydrazine ($N_2H_4$). In embodiments, the cleaving reagent includes an acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), or hydrazine ($N_2H_4$).

In embodiments, $R^5$ is anchor moiety, the method further including, after the incorporating, labeling the nucleotide analog with a detectable label. In embodiments, $R^5$ is an affinity anchor moiety. In embodiments, the labeling includes adding to the reaction vessel a compound having the formula $R^{12}$-$L^4$-$R^{13}$, wherein $R^{12}$ is a complementary affinity anchor moiety binder; $R^{13}$ is a detectable label; and $L^4$ is a covalent linker.

In embodiments, $R^5$ is a chemically reactive anchor moiety. In embodiments, $R^5$ is a bioconjugate reactive group.

In embodiments, the labeling includes adding to the reaction vessel a compound having the formula $R^{12z}$-$L^{4z}$-$R^{13}$, wherein $R^{12z}$ is a complementary anchor moiety reactive group; $R^{13}$ is a detectable label; and $L^{4z}$ is a covalent linker. In embodiments, $R^{12z}$-$L^{4z}$-$R^{13}$ has the structure as described herein. In embodiments, $L^{4z}$ is a cleavable linker.

In embodiments, the method further including, after the incorporating, cleaving the cleavable moiety with a cleaving reagent. In embodiments, the cleaving reagent is an acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), or hydrazine ($N_2H_4$). In embodiments, the cleaving reagent includes an acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), or hydrazine ($N_2H_4$).

In embodiments, the method further including, after the incorporating, adding to the reaction vessel an unlabeled nucleotide analogue including a 3'-polymerase-compatible cleavable moiety.

In embodiments, the method forms part of a sequencing by synthesis method.

In embodiments, the ratio of fluorescently labeled to unlabeled compounds described herein (e.g., nucleotide reversible terminators) is about 1:9 to about 9:1. (See FIG. 27A-27B)

In an embodiment, a method of sequencing nucleic acids comprising addition of the DNA polymerase and a labeled nucleotide analogue to the primed DNA template to enable the incorporation of the complementary labeled nucleotide analogue into the growing DNA strand and identifying the labeled nucleotide directly or through indirect labeling, so as to sequence the nucleic acid.

In an embodiment, a method of sequencing nucleic acid comprising: a) providing a nucleic acid template hybridized to a primer; b) extending the primer hybridized to said nucleic acid template with a labeled nucleotide or nucleotide analogue, wherein said labeled nucleotide or nucleotide analogue has the label linked to the base and a polymerase-compatible cleavable blocking group on the 3'-hydroxyl group; and c) identifying the labeled nucleotide, so as to sequence the nucleic acid.

In an embodiment, a method of simultaneously sequencing a plurality of different nucleic acids, comprising: a) growing a plurality of double-stranded DNA, each of which comprises one of said DNA strands, by incorporating a labeled nucleotide; and b) identifying each labeled nucleotide, so as to simultaneously sequence the plurality of different nucleic acids.

In another embodiment said labeled nucleotide has the label linked to the base and a polymerase-compatible cleavable blocking group on the 3'-hydroxyl group.

For any of the above three embodiments, wherein:

1. The polymerase-compatible cleavable blocking group comprises a dithiol linker.
2. The polymerase-compatible cleavable blocking group comprises an azido moiety.
3. The polymerase-compatible cleavable blocking group comprises —$CH_2SS$-R, —$CH_2N_3$, allyl, 2-nitrobenzyl, cyanoethyl, or azo.
4. The polymerase-compatible cleavable blocking group is a dithiol having the following structure:

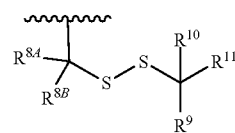

$R^{8A}$ is hydrogen, —$CH_3$, —$CX^3_3$, —$CHX^3_2$, —$CH_2X^3$, —CN, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{8B}$ is hydrogen, —$CH_3$. —$CX^4_3$, —$CHX^4_2$, —$CH_2X^4$, —CN, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, —$CX^1_3$, —$CHX^5_2$, —$CH_2X^5$, —$OCH_3$, —$SCH_3$, —$NHCH_3$, —CN, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is hydrogen, —$CX^6_3$, —$CHX^6_2$, —$CH_2X^6$, —$OCH_3$, —$SCH_3$, —$NHCH_3$, —CN, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is hydrogen, —$CX^7_3$, —$CHX^7_2$, —$CH_2X^7$, —$OCH_3$, —$SCH_3$, —$NHCH_3$, —CN, -Ph substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $X^3$, $X^4$, $X^5$, $X^6$ and $X^7$ are independently halogen.

5. The label is attached to the base via a cleavable linker.

6. The labeled nucleotide has the label attached to the 5 or 7 position of the base via a cleavable linker.

7. The nucleotide analogue comprises a deazapurine base.

8. The said cleavable linker is indicated by L3 in the following structure:

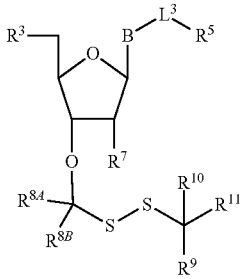

wherein

B is a base;

$L^3$ is a cleavable linker;

$R^3$ is —OH, monophosphate, triphosphate; polyphosphate or a nucleic acid;

$R^5$ is a detectable label or anchor moiety;

$R^7$ is hydrogen or —$OR^{7A}$, wherein $R^{7A}$ is hydrogen;

R8A, R8b, R9, R10 and R11 are as described in claim 6, and $X^3$, $X^4$, $X^5$, $X^6$ and $X^7$ are independently halogen.

9. The cleavable moiety in L3 comprises dithiol, allyl, azido, nitrobenzyl, cyanoethyl, dimethylketal, Dde or azo.

10. The label on the base and the blocking group on the 3'-OH are chemically cleaved with high efficiency.

11. The label on the base and the blocking group on the 3'-OH are simultaneously cleaved.

12. The label on the base and the blocking group on the 3'-OH are cleaved in separate chemical reactions.

13. Treatment of a disulfide-based linker or disulfide-based blocking group with a reducing agent cleaves the disulfide bond without leaving any sulfhydryl remnant attached to the nucleotide added to the primer.

14. The reducing agent is THP or TCEP.

15. The polymerase is a variant of 9° N DNA polymerase or other mutated Family B or Family A polymerases or mutants thereof, and the reaction buffer may contain $Mn^{2+}$ or other divalent cations which can be used to efficiently incorporate the labeled nucleotide analogue.

An embodiment of the present invention includes a 4-color method for sequencing a nucleic acid comprising:
a) providing
1) a nucleic acid
2) a nucleic acid polymerase
3) a primer capable of hybridizing to said nucleic acid, and
4) four different nucleotide analogues, each comprising (i) a base, (ii) a deoxyribose or ribose, (iii) an alkyldithiomethyl moiety or variant thereof bound to the 3'-oxygen of the deoxyribose or ribose including but not limited to those in Embodiments as described herein, hereinafter referred to as a SS-cleavable blocking group, and (iv) an anchor bound to the base via a dithiomethyl linker or variant thereof including but not limited to those in Embodiments described herein, hereinafter referred to as a SS-cleavable anchors, and wherein each nucleotide analogue comprises a unique base and a unique anchor (including but not limited to TCO, PBA, Biotin, and Azido);
b) incorporating with said nucleic acid polymerase one of said nucleotide analogues into said primer to create an extended strand;
c) incubating with a correspondingly matched dye labeled binding molecule (including but not limited to Rox-labeled Tetrazine, Alexa-488 labeled SHA, Cy5-labeled Streptavidin, and R6G-labeled Dibenzocyclooctyne (DBCO)) to label the DNA products carrying the unique anchors on the base of the incorporated nucleotide;
d) detecting said unique detectable label of each incorporated nucleotide analogue, so as to thereby identify each incorporated nucleotide analogue in said extension strand;
e) treating said extended primer with TCEP or THP to remove the SS-blocking group and cleave the SS-cleavable linker; and
f) repeating steps a) through e) up to 30, or up to 100, or up to 1000 times to determine additional nucleotide analogues added to extended primer strand, thereby sequencing the nucleic acid.

In an embodiment four different unlabeled nucleotide analogues consisting of: (i) a base, (ii) a deoxyribose or ribose, and (iii) a 3'-O—S—S cleavable blocking group, hereinafter referred to as 3'-SS-NRTs are added in step a).

In an embodiment=four 3'-SS-NRTs are added with polymerase in a chase step immediately following step a).

1-color, 4 same color labeled nucs, step by step, no chase (FIGS. 4A-4D)

Embodiment A2

A 1-color method for sequencing DNA comprising:
a) providing
1) a nucleic acid
2) a nucleic acid polymerase
3) a primer capable of hybridizing to said nucleic acid, and
4) a labeled nucleotide analogue, comprising (i) a base, (ii) a deoxyribose or ribose, (iii) a SS-cleavable blocking group, and (iv) a detectable label bound to the base via a SS-cleavable linker;
b) detecting said detectable label if the labeled nucleotide analogue has been incorporated into the DNA primer, so as to identify the incorporated labeled nucleotide analogue in said extension strand;
c) repeating steps a) and b) with an identical labeled nucleotide analogue except containing a different base than in a);
d) repeating steps a) and b) with an identical labeled nucleotide analogue, except containing a different base than in a) and b);
e) repeating steps a) and b) with an identical labeled nucleotide analogue, except containing a different base than in a), b) and c);
f) treating said extended primer with TCEP or THP to remove the SS-blocking group and cleave the SS-cleavable linker; and
g) repeating steps a) through e) up to 30, or up to 100, or up to 1000 times to determine additional nucleotide analogues added to extended primer strand,
thereby sequencing the nucleic acid.

1-color, 4 same color labeled nucs, step by step, co-chase during each addition (FIGS. 4A-4D)

In an embodiment of A2, the method of embodiment JS4 in which an 3'-SS-NRT with the same base as the labeled nucleotide analogue is added in steps a)4), b)4), c)4), and d)4).

1-color, 4 same color labeled nucs, step by step, post-chase after each addition (FIGS. 4A-4D)

In another embodiment of A2, the method of embodiment JS4 in which an 3'-SS-NRT with the same base as the labeled nucleotide analogue is added in a chase step immediately following steps a)4), b)4), c)4), and d)4).

Figure 14A:
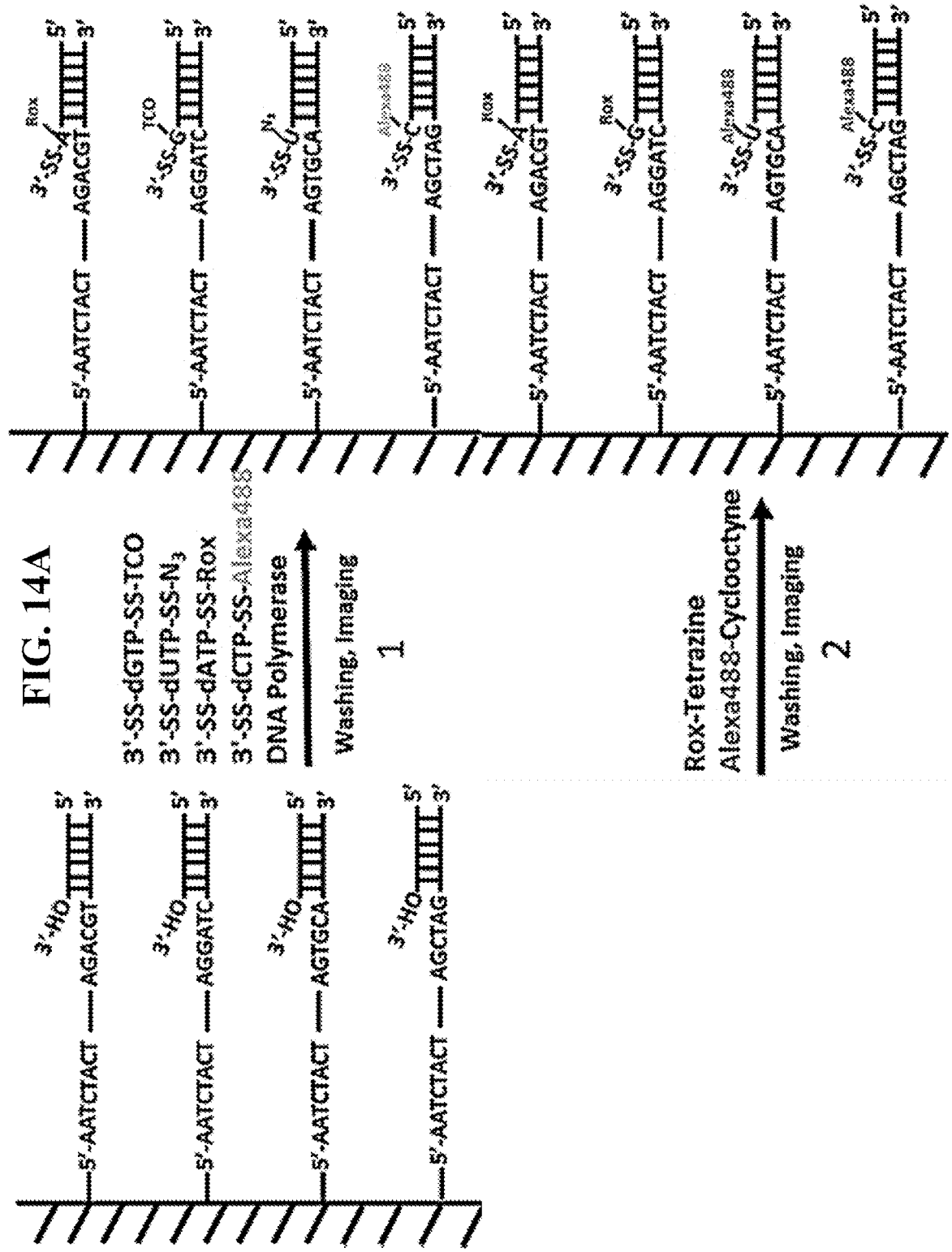
FIGS. 14A-14B. Use of 3'-O-DTM-dNTP-SS-Dyes (3'-O-DTM-dATP-7-SS-Rox, 3'-O-DTM-dCTP-5-SS-Alexa488); 3'-O-SS(DTM)-dNTP-SS-"anchors" (3'-O-DTM-dGTP-7-SS-TCO and 3'-O-DTM-dUTP-5-SS-N$_3$), with their corresponding Dye Labeled Binding Molecules (Rox Labeled Tetrazine and Alexa488 Labeled Dibenzocyclooctyne) to perform 2-color DNA SBS. Addition of DNA polymerase and the four nucleotide analogues (3'-O-DTM-dATP-7-SS-Rox, 3'-O-DTM-dCTP-5-SS-Alexa488, 3'-O-DTM-dGTP-7-SS-TCO and 3'-O-DTM-dUTP-7-SS-N$_3$) to the immobilized primed DNA template enables the incorporation of the complementary nucleotide analogue to the growing DNA strand to terminate DNA synthesis (STEP 1). After washing away the unincorporated nucleotide analogues, the fluorescent signal from Rox and BodipyFL is detected to identify the incorporated nucleotide as A (labeled with Rox) and C (labeled with BodipyFL). Next, the dye labeled binding molecules (Rox-Tetrazine and BodipyFL-Dibenzocyclooctyne) are added to the DNA extension products (STEP 2), which will specifically connect with the two unique "anchor" moieties (TCO and $N_3$) on each DNA extension product, to enable the labeling of each DNA product terminated with each of the two nucleotide analogues (G and T) with two distinct fluorescent dyes (labeled with Rox for G and labeled with BodipyFL for T). Detection of the unique, newly produced fluorescence signal from Rox and BodipyFL on the DNA extension products (in addition to the signal from STEP 1), allows for the identification of the newly incorporated nucleotides as G and T respectively. Next, treatment of the DNA products with THP cleaves the SS linker, leading to the removal of the fluorescent dye and the regeneration of a free 3'-OH group on the DNA extension product (STEP 3), which is ready for the next cycle of the DNA sequencing reaction (as shown in the subsequent steps of the figure).
Figure 14B:
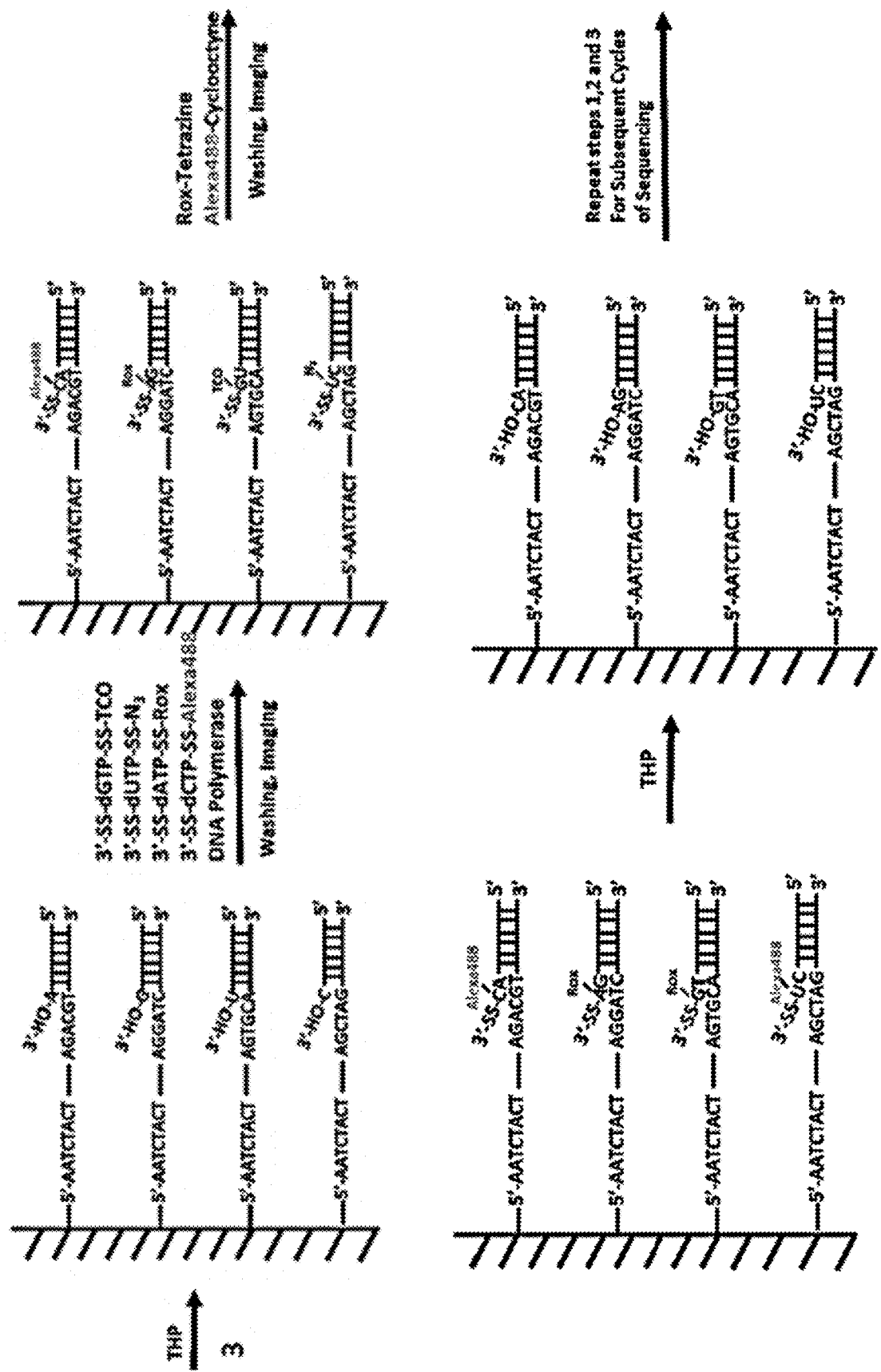

2-color, 2 labeled nucs, 2 anchor nucs, same two labels, no chase (see FIGS. 14A-14B)

Embodiment A3

A 2-color method for sequencing a nucleic acid comprising:
a) providing
  1) a nucleic acid
  2) a nucleic acid polymerase
  3) a primer capable of hybridizing to said nucleic acid,
  4) two labeled nucleotide analogues, including but not limited to those in Embodiments described herein comprising (i) a base, (ii) a deoxyribose or ribose, (iii) a SS-cleavable blocking group, and (iv) a detectable label bound to the base via a SS-cleavable linker, in which the two labeled nucleotide analogues bear a unique base and label (e.g., 3'-O-SS-dATP-SS-Rox and 3'-O-SS-dCTP-SS-Alexa-488, and
  5) two nucleotide analogues, including but not limited to those in Embodiments described herein comprising (i) a base, (ii) a deoxyribose or ribose, (iii) a SS-cleavable blocking group, and (iv) an anchor moiety bound to the base via a SS-cleavable linker, in which the two labeled nucleotides bear unique bases different from those in 4) and two different anchors (e.g., 3'-O-SS-dUTP-SS-$N_3$ and 3'-O-SS-dGTP-SS-TCO);
b) detecting said detectable label if the labeled nucleotide analogue has been incorporated into the DNA primer, so as to identify the incorporated labeled nucleotide analogue in said extension strand, e.g., A if Rox and C if Alexa-488;
c) incubating with a correspondingly matched dye labeled binding molecule including but not limited to those in Embodiments described herein (e.g., Alexa-488-labeled Dibenzocyclooctyne and Rox-labeled Tetrazine);
d) detecting said detectable label if the anchor nucleotide analogue has been incorporated into the DNA primer, so as to identify the incorporated anchor nucleotide analogue in said extension strand, e.g., U if Alexa-488 and G if Rox.
e) treating said extended primer with TCEP or THP to remove the SS-blocking group and cleave the SS-cleavable linker; and
f) repeating steps a) through e) up to 30, or up to 100, or up to 1000 times to determine additional nucleotide analogues added to extended primer strand, thereby sequencing the nucleic acid.

2-color, 2 labeled nucs, 2 anchor nucs, same two labels, co-chase (see FIGS. 14A-14B)

In an embodiment of A3, the method of embodiment JS7 in which four 3'-SS-NRTs are added in step a).

2-color, 2 labeled nucs, 2 anchor nucs, same two labels, post-chase (see FIGS. 14A-14B)

In another embodiment of A3, the method of embodiment JS4 in which four 3'-SS-NRTs are added immediately after step a).

Figure 17A:
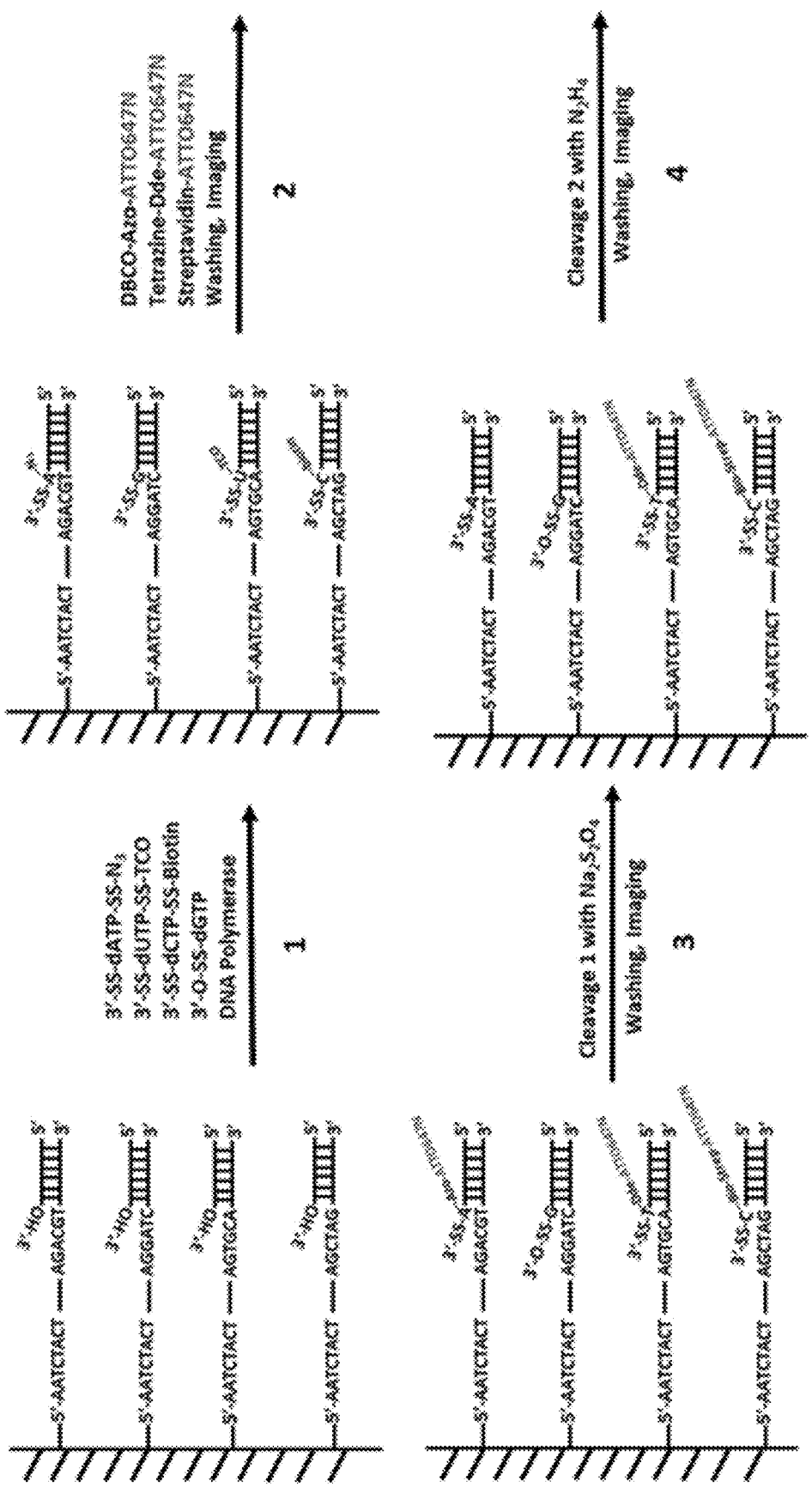
FIGS. 17A-17B. One color SBS reaction scheme approach 1: (1) In the presence of DNA polymerase, three nucleotides with anchor [3'-O-DTM-dATP-7-SS-$N_3$, 3'-O-DTM-dCTP-5-SS-Biotin, 3'-O-DTM-dUTP-5-SS-TCO] and 3'-t-Butyl-SS(DTM)-dGTP, as shown in FIG. 161 are added to the primed DNA templates to allow incorporation into the primer; (2) The fluorescent label (ATTO647N, for example) is attached by adding DBCO-Azo-(—N═N-Linker)-ATTO647N, Tetrazine-Dde(Linker)-ATTO647N and Streptavidin-ATTO647N (as shown in FIG. 16) to the DNA extension products that contain the incorporated nucleotide analogues with anchor, which leads to the labeling of all the incorporated nucleotides (except G) due to specific anchor-binding molecule interaction; (3) After washing, the first round of imaging is performed, and the DNA products terminated with A, C and T all display the same color, while the DNA products that do not emit a signal are terminated by the nucleotide G; (4) The first cleavage (I) is conducted by treatment with sodium dithionite ($Na_2S_2O_4$), which only cleaves the azo linkage to remove the fluorescent dye from the DNA products terminated with the A nucleotide. The second round of imaging is performed. If the fluorescent signal disappears after cleavage I, the DNA products are determined as having incorporated an A nucleotide; (5) The second cleavage (II) is conducted by treatment with hydrazine ($N_2H_4$), which will cleave the Dde linkage to remove the fluorescent dye from the DNA products terminated with the T nucleotide. The third round of imaging is performed. If the fluorescent signal disappears after cleavage II, the DNA products are determined as having incorporated a T nucleotide. The DNA products with unchanged fluorescent signals are identified by inference as being terminated by a C nucleotide; (6) The third cleavage (III) is conducted with THP to cleave the disulfide bond and remove the dye on C, so the change of the signal after the THP treatment verifies the DNA products as being terminated by a C nucleotide. Meanwhile, the THP treatment will also cleave the DTM (SS) bond to regenerate free 3'-OH on all the DNA extension products, which are ready for subsequent cycles of single-color DNA SBS. (7) Steps 1 to 6 are repeated to continue subsequent cycles of single-color DNA SBS.
Figure 17B:
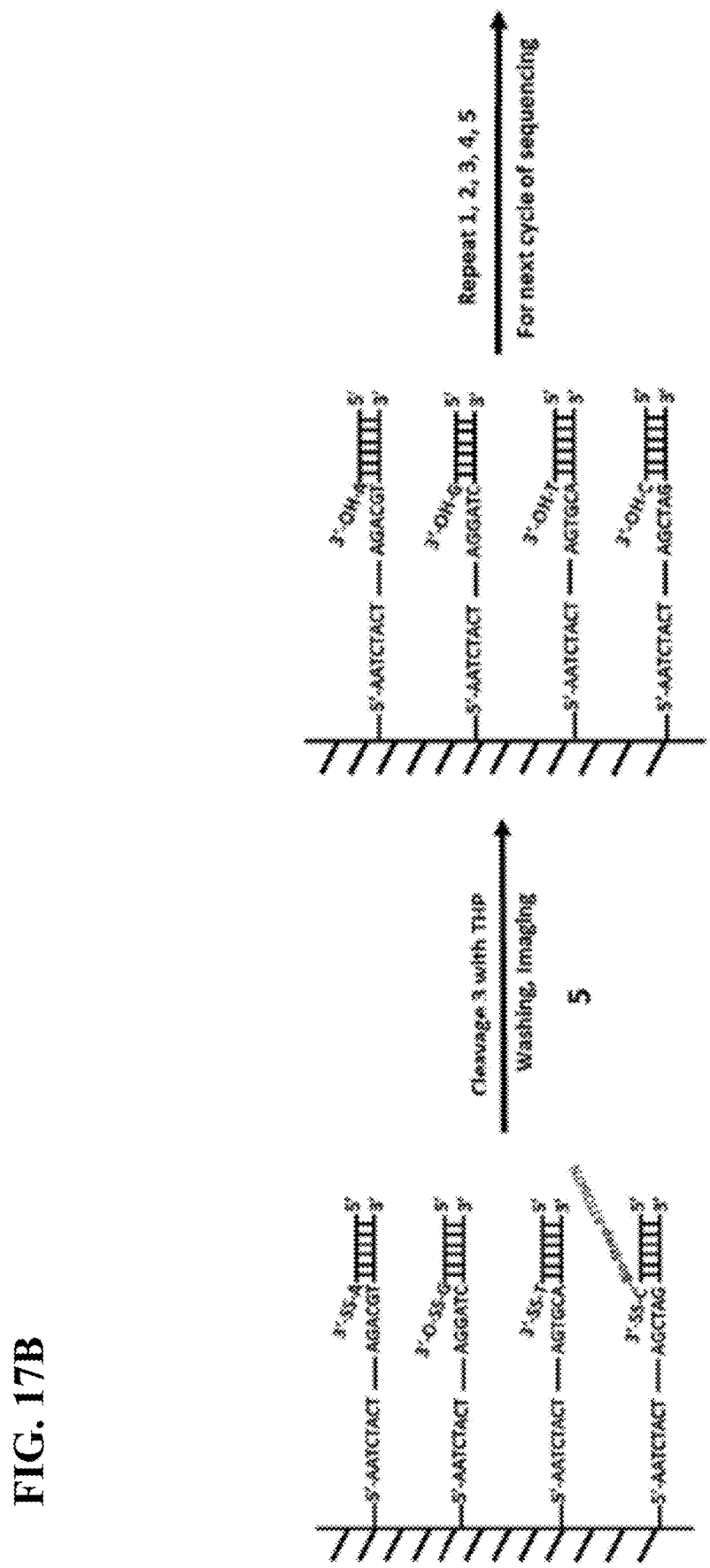

1-color, 3 anchor flues, 3 same labels (3 orthogonal cleavable linkers), 1 dark NRT (see FIGS. 17A-17B)

Embodiment A4

A 1-color method for sequencing a nucleic acid comprising:
a) providing
  1) a nucleic acid
  2) a nucleic acid polymerase
  3) a primer capable of hybridizing to said nucleic acid, and
  4) three anchor nucleotide analogues, including but not limited to those in Embodiments described herein comprising (i) a base, (ii) a deoxyribose or ribose, (iii) a SS-cleavable blocking group, and (iv) an anchor bound to the base via a SS-cleavable linker, in which the three labeled nucleotide analogues each bears a unique base and anchor (e.g., 3'-O-SS-dATP-SS-$N_3$, 3'-O—SS-dUTP-SS-TCO and 3'-O-SS-dCTP-SS-Biotin, and
  5) a 3'-SS-NRT, with a different base from those in 4) (e.g., 3'-SS-dGTP);
b) incubating with a correspondingly matched dye labeled binding molecule including but not limited to those in Embodiments described herein (e.g., DBCO-Azo Linker-ATTO647N, Tetrazine-Dde-ATTO647N and Streptavidin-ATTO647N) to label the DNA products carrying the unique anchors on the base of the incorporated nucleotide;
c) detecting said detectable label if the anchor nucleotide analogue has been incorporated into the DNA primer, so as to identify the incorporated anchor nucleotide analogue in said extension strand (e.g., A, C or T incorporated if fluorescent, G if not);
d) treating said extended primer with sodium dithionite to cleave the azo linkage if such nucleotide has been incorporated;
e) detecting said detectable label (e.g., if label lost, indicates A was incorporated);
f) treating said extended primer with hydrazine to cleave the Dde linkage if such nucleotide has been incorporated;
g) detecting said detectable label (e.g., if label now lost, indicates U was incorporated);

h) treating said extended primer with TCEP or THP to cleave the S—S bond which would remove any remaining dye and reinstall a 3'-OH at the same time;
i) detecting said detectable label (e.g., if label now lost, indicates C was incorporated);
j) optionally, chasing with three 3'-SS-dNTPs not already used;
k) repeating steps a) through j) up to 30, or up to 100, or up to 1000 times to determine additional nucleotide analogues added to extended primer strand;

thereby sequencing the nucleic acid.

Figure 19A:
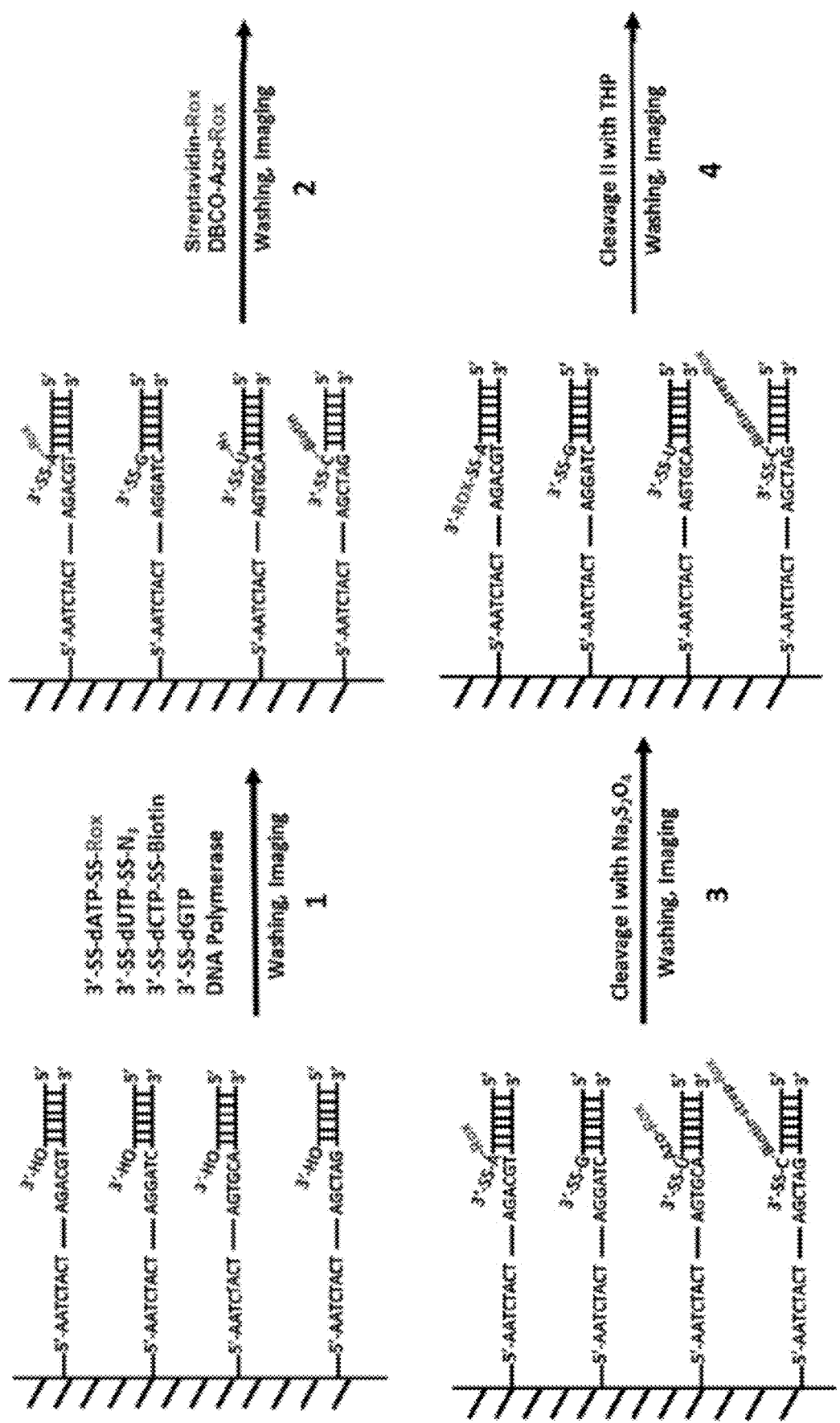
FIGS. 19A-19B. One color SBS reaction scheme approach 2: (1) In the presence of DNA polymerase, two anchor labeled nucleotides (3'-O-DTM-dUTP-5-SS-$N_3$ and 3'-O-DTM-dCTP-5-SS-Biotin), 3'-O-DTM-dATP-7-SS-Rox and 3'-O-t-Butyl-SS(DTM)-dGTP, as shown in FIG. 18, are added to the primed DNA templates to allow incorporation into the primer; (2) After washing, the first round of imaging is performed, and the DNA products terminated with an A nucleotide analogue display the Rox signal and therefore are determined as having incorporated an A nucleotide, while the other DNA products terminated at G, C, T will not display any fluorescent signals; (3) The fluorescent label (Rox, for example) is attached to DNA by adding DBCO-Azo-(—N═N-Linker)-Rox and Streptavidin-Rox (as shown in FIG. 18) to the DNA extension products that contain the incorporated anchor labeled nucleotide analogues, which leads to the labeling of all the incorporated nucleotides (except G) due to specific anchor-binding molecule interaction; (4) After washing, the second round of imaging is performed, and the DNA products terminated with A, C and T all display the same Rox signal, while the DNA products that do not emit a signal are terminated by the nucleotide G; (5) The first cleavage (T) is conducted by treatment with sodium dithionite ($Na_2S_2O_4$), which only cleaves the azo linkage to remove the fluorescent dye Rox from the DNA products terminated with the T nucleotide. The second round of imaging is performed. If the Rox fluorescent signal disappears after cleavage I, the DNA products are determined as having incorporated a T nucleotide; (6) The second cleavage (II) is conducted with THP to cleave the disulfide bond and remove the dye from the DNA extension products terminated with nucleotides A and C, so the change of the signal after the THP treatment determines the DNA products as being terminated by a C nucleotide, because DNA products terminated by an A nucleotide have already being determined in the first round of imaging described above. Meanwhile, the THP treatment will also cleave the DTM (SS) bond to regenerate free 3'-OH on all the DNA extension products, which are ready for subsequent cycles of single-color DNA SBS. Steps 1 to 6 are repeated to continue subsequent cycles of single-color DNA SBS.
Figure 19B:
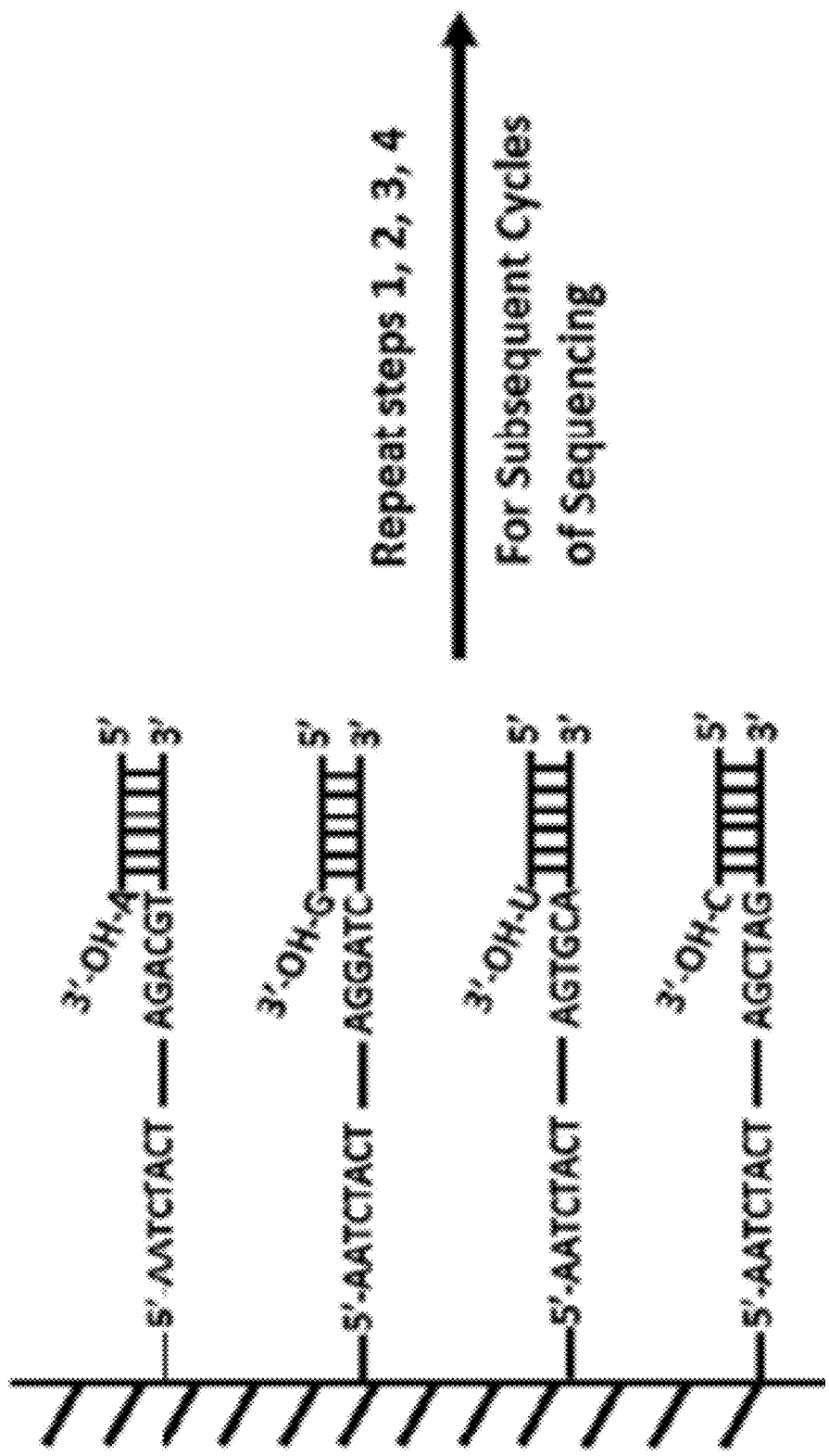

1-color, 2 anchor nucs, 2 same color labels (cleavable), 1 same color labeled nuc, 1 dark NRT (see FIGS. 19A-19B)

Embodiment A5

A 1-color method for sequencing a nucleic acid comprising:
a) providing
  1) a nucleic acid
  2) a nucleic acid polymerase
  3) a primer capable of hybridizing to said nucleic acid,
  4) two anchor nucleotide analogues, including but not limited to those in Embodiments described herein, comprising (i) a base, (ii) a deoxyribose or ribose, (iii) a SS-cleavable blocking group, and (iv) an anchor bound to the base via a SS-cleavable linker, in which the two labeled nucleotide analogues each bears a unique base and anchor (e.g., 3'-O-SS-dUTP-SS-N₃ and 3'-O-SS-dUTP-SS-Biotin, and
  5) one labeled nucleotide analogue, including but not limited to those in Embodiments described herein with a different base from those in 4) (e.g., 3'-O-SS-dATP-Rox);
  6) one 3'-SS-NRT, with a base different from those in 4) and 5);
b) detecting said detectable label if the anchor nucleotide analogue has been incorporated into the DNA primer, so as to identify the incorporated anchor nucleotide analogue in said extension strand (e.g., A if fluorescent, C, G or T if not);
c) incubating with two correspondingly matched dye labeled binding molecules including but not limited to those in Embodiments described herein (e.g., Rox-labeled DBCO-Azo Linker and Rox-labeled Streptavidin) to label the DNA products carrying the unique anchors on the base of the incorporated nucleotide;
d) detecting said detectable label if the anchor nucleotide analogue has been incorporated into the DNA primer, so as to identify the incorporated anchor nucleotide analogue in said extension strand (e.g., A, C or T if fluorescent, G if not);
d) treating said extended primer with sodium dithionite to cleave the azo linkage if such nucleotide has been incorporated;
e) detecting said detectable label (e.g., if label lost, indicates T was incorporated);
f) treating said extended primer with TCEP or THP to cleave the S—S bond which would remove any remaining dye and reinstall a 3'-OH at the same time;
g) detecting said detectable label (e.g., if label now lost, indicates C was incorporated, since if A, would have been determined in step b);
h) optionally, chasing with four 3'-SS-dNTPs used;
i) repeating steps a) through h) up to 30, or up to 100, or up to 1000 times to determine additional nucleotide analogues added to extended primer strand;

thereby sequencing the nucleic acid.

1-color, 3 anchor nucs, 3 same dye labels (orthogonally cleavable linkers), 1 labeled nuc (see FIGS. 21A-21F)

Embodiment A6

A 1-color method for sequencing a nucleic acid comprising:
a) providing
  1) a nucleic acid
  2) a nucleic acid polymerase
  3) a primer capable of hybridizing to said nucleic acid,
  4) three anchor nucleotide analogues, including but not limited to those in Embodiments described herein comprising (i) a base, (ii) a deoxyribose or ribose, (iii) a SS-cleavable blocking group, and (iv) an anchor bound to the base via a SS-cleavable linker, in which the two labeled nucleotide analogues each bears a unique base and anchor (e.g., 3'-O-SS-dGTP-SS-N₃, 3'-O-SS-dCTP-Biotin and 3'-O-SS-dATP-TCO, and
  5) one labeled nucleotide analogue, including but not limited to those in Embodiments described herein with a different base from those in 4) (e.g., 3'-O-SS-dATP-SS-Rox);
b) detecting said detectable label if the anchor nucleotide analogue has been incorporated into the DNA primer, so as to identify the incorporated anchor nucleotide analogue in said extension strand (e.g., A if fluorescent, C, G or T if not);
c) incubating with correspondingly matched dye labeled binding molecules including but not limited to those in Embodiments described herein (e.g., Rox-Azo-labeled DBCO, Rox-labeled Tetrazine-Azo-Linker and Rox-labeled Streptavidin) to label the DNA products carrying the unique anchors on the base of the incorporated nucleotide;
d) detecting said detectable label if the anchor nucleotide analogue has been incorporated into the DNA primer, so as to identify the incorporated anchor nucleotide analogue in said extension strand (e.g., C, G or T if now fluorescent);
d) treating said extended primer with sodium dithionite to cleave the azo linkage if such nucleotide has been incorporated;
e) detecting said detectable label (e.g., if label lost, indicates G was incorporated);
f) treating said extended primer with hydrazine to cleave the Dde linkage if such nucleotide has been incorporated;
g) detecting said detectable label (e.g., if label now lost, indicates U was incorporated, otherwise C);
h) treating said extended primer with TCEP or THP to cleave the S—S bond which would remove any remaining dye and reinstall a 3'-OH at the same time;
i) detecting said detectable label (e.g., if label now lost, confirms C was incorporated, since if A, would have been determined in step b));
j) optionally, chasing with four 3'-SS-dNTPs;
k) repeating steps a) through h) up to 30, or up to 100, or up to 1000 times to determine additional nucleotide analogues added to extended primer strand;

thereby sequencing the nucleic acid.

1-color, 3 labeled nucs, 2 same color labels (orthogonally cleavable linkers), 1 dark NRT (see FIGS. 23A-23D)

Embodiment A7

A 1-color method for sequencing a nucleic acid comprising:
  a) providing
    1) a nucleic acid
    2) a nucleic acid polymerase
    3) a primer capable of hybridizing to said nucleic acid,
    4) three labeled nucleotide analogues, including but not limited to those in Embodiments described herein comprising (i) a base, (ii) a deoxyribose or ribose, (iii) a SS-cleavable blocking group, and (iv) a label bound to the base via a chemically or photocleavable linker, in which the three labeled nucleotide analogues each bears a unique base, cleavable linker and label (e.g., 3' SS-dATP-SS-Rox, 3'-O-SS-dUTP-Allyl-Rox and 3'-O-SS-dCTP-Nitrobenzyl-Rox, and
    5) one 3'-SS-NRT with a different base from those in 4) (e.g., 3'-O-t-Butyl-SS-dGTP);
  b) detecting said detectable label if the labeled nucleotide analogue has been incorporated into the DNA primer, so as to identify the incorporated anchor nucleotide analogue in said extension strand (e.g., A, U or C if fluorescent, G if not);
  c) photo-irradiating at ~350 nm to cleave the nitrobenzyl-containing linkers if such nucleotide has been incorporated;
  d) detecting said detectable label if the labeled nucleotide analogue has been incorporated into the DNA primer, so as to identify the incorporated anchor nucleotide analogue in said extension strand (e.g., if label lost, C was incorporated);
  e) cleavage with Pd (0) to cleave the allyl-containing linkers if such nucleotide has been incorporated;
  f) detecting said detectable label if the labeled nucleotide analogue has been incorporated into the DNA primer, so as to identify the incorporated anchor nucleotide analogue in said extension strand (e.g., if label lost, U was incorporated);
  g) treating said extended primer with TCEP or THP to cleave the S—S bond which would remove any remaining dye and reinstall a 3'-OH at the same time;
  h) detecting said detectable label (e.g., if label now lost, confirms A was incorporated);
  j) optionally, chasing with three 3'-SS-dNTPs not already used;
  k) repeating steps a) through h) up to 30, or up to 100, or up to 1000 times to determine additional nucleotide analogues added to extended primer strand;
thereby sequencing the nucleic acid.

4-color, 4 labeled nucs, no chase (see FIGS. 26A-26F)

Embodiment A8

A 4-color method for sequencing a nucleic acid comprising:
  a) providing
    1) a nucleic acid
    2) a nucleic acid polymerase
    3) a primer capable of hybridizing to said nucleic acid, and
    4) four different nucleotide analogues, each comprising (i) a base, (ii) a deoxyribose or ribose, (iii) an alkyldithiomethyl moiety or variant thereof bound to the 3'-oxygen of the deoxyribose or ribose including but not limited to those in Embodiments as described herein hereinafter referred to as a SS-cleavable blocking group, and (iv) a label bound to the base via a dithiomethyl linker or variant thereof including but not limited to those in Embodiments described herein, hereinafter referred to as a SS-cleavable anchors, and wherein each nucleotide analogue comprises a unique base and a unique label (including but not limited to Rox, Alexa-488, Cy5 and R6G) (e.g., 3''-O-SS-dATP-SS-Rox, 3'-O-SS-dCTP-SS-Alexa-488, 3'-O-SS-dGTP-SS-Cy5, and 3'-O-SS-dUTP-R6G)
  b) incorporating with said nucleic acid polymerase one of said nucleotide analogues into said primer to create an extended strand;
  c) detecting said unique detectable label of each incorporated nucleotide analogue, so as to thereby identify each incorporated nucleotide analogue in said extension strand;
  d) treating said extended primer with TCEP or THP to remove the SS-blocking group and cleave the SS-cleavable linker; and
  e) repeating steps a) through d) up to 30, or up to 100, or up to 1000 times to determine additional nucleotide analogues added to extended primer strand, thereby sequencing the nucleic acid.

4-color, 4 labeled nucs, mix label and unlabel (see FIGS. 27A-27B)

In an embodiment of A8, the method of embodiment JS14 in which all four 3'-SS-NRTs are added in step a).

4-color, 4 labeled nucs, chase (see FIGS. 25A-25F)

In another embodiment of A8, the method of embodiment JS14 in which all four 3'-SS-NRTs are added in a chase step immediately following step a). [0372] General sequencing plus walking (see FIG. 28)

Embodiment A9

A 4-color method for sequencing and walking within a nucleic acid comprising:
  a) obtaining a sequence of up to 100 or up to 200 nucleotides using any of the methods of Claims S1 to S14 or other sequencing methods known in the art.
  b) denaturing the DNA to strip off the extended primer and reannealing the original primer;
  c) adding a mixture containing three natural nucleotides (e.g., dATP, dCTP and dTTP) and one 3'-O-SS-dNTP (e.g., 3'-O-SS-dGTP) ("walking step") to extend the primer in a single step to the next C in the template;
  d) adding TCEP or THP to restore the 3'-OH group on the last incorporated nucleotide;
  e) repeating steps c) and d) enough times to reach approximately the position where the original sequencing run ended;
  f) repeating steps a) to e) to sequence another stretch of the nucleic acid and walk to the position where the second sequencing run ended;
  g) repeating step j) as necessary to obtain long assembled read (3 or 4 times the length of any individual read), thereby obtaining a long stretch of nucleic acid synthesis.

4-color sequencing plus walking (see FIG. 28A-28B)

Embodiment A10

A 4-color method for sequencing and walking within a nucleic acid comprising:
  a) providing
    1) a nucleic acid
    2) a nucleic acid polymerase
    3) a primer capable of hybridizing to said nucleic acid, and 4) four different nucleotide analogues, each comprising (i) a base, (ii) a deoxyribose or ribose, (iii) an alkyldithiomethyl moiety or variant thereof bound to the 3'-oxygen of the deoxyribose or ribose including but not limited to those in Embodiments described herein, hereinafter referred to as a SS-cleavable blocking group, and (iv) a label bound to the base via a dithiomethyl linker or variant thereof including but not limited to those in Embodiments described herein, hereinafter referred to as a SS-cleavable anchors, and wherein each nucleotide analogue comprises a unique base and a unique label (including but not limited to Rox, Alexa-488, Cy5 and R6G) (e.g., 3'-O-SS-dATP-SS-Rox, 3'-O-SS-dCTP-SS-Alexa-488, 3'-O-SS-dGTP-SS-Cy5, and 3'-O-SS-dUTP-R6G)

b) incorporating with said nucleic acid polymerase one of said nucleotide analogues into said primer to create an extended strand;

c) detecting said unique detectable label of each incorporated nucleotide analogue, so as to thereby identify each incorporated nucleotide analogue in said extension strand;

d) treating said extended primer with TCEP or THP to remove the SS-blocking group and cleave the SS-cleavable linker; and e) repeating steps a) through d) up to 100 times to determine additional nucleotide analogues added to extended primer strand, f) denaturing the DNA to strip off the extended primer and reannealing the original primer;

g) adding a mixture containing three natural nucleotides (e.g., dATP, dCTP and dTTP) and one 3'-O-SS-dNTP (e.g., 3'-O-SS-dGTP) ("walking step") to extend the primer in a single step to the next C in the template;

h) adding TCEP or THP to restore the 3'-OH group on the last incorporated nucleotide;

i) repeating steps g) and h) enough times to reach approximately the position where the original sequencing run ended;

j) repeating steps a) to i) to sequence another stretch of the nucleic acid and walk to the position where the second sequencing run ended;

k) repeating step j) as necessary to obtain long assembled read (3 or 4 times the length of any individual read), thereby obtaining a long stretch of nucleic acid synthesis.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EMBODIMENTS

While various embodiments of the invention are shown and described herein, it will be obvious to those skilled in the art that such embodiments are provided by way of example only. Numerous variations, changes, and substitutes may occur to those skilled in the art without departing from the invention. It should be understood that various alternatives to the embodiments of the invention described herein may be employed.

As used herein, and unless stated otherwise, each of the following terms shall have the definition set forth below:
A—Adenine;
C—Cytosine;
DNA—Deoxyribonucleic acid;
G—Guanine;
RNA—Ribonucleic acid;
T—Thymine; and
U—Uracil.

The articles "a", "an" and "the" are non-limiting. For example, "the method" includes the broadest definition of the meaning of the phrase, which can be more than one method.

"Nucleic acid" shall mean any nucleic acid molecule and its derivatives, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, New Jersey, USA).

As used herein, "nucleotide analogue" shall mean an analogue of A, G, C, T or U (that is, an analogue of a nucleotide comprising the base A, G. C, T or U), comprising a phosphate group, which is recognized by DNA or RNA polymerase (whichever is applicable) and incorporated into a strand of DNA or RNA (whichever is appropriate). Examples of nucleotide analogues include, without limitation, 7-deaza-adenine, 7-deaza-guanine, the analogues of deoxynucleotides shown in herein analogues in which a label is attached through a cleavable linker to the 5-position of cytosine or thymine or to the 7-position of deaza-adenine or deaza-guanine, and analogues in which a small chemical moiety is used to cap the —OH group at the 3'-position of deoxyribose. Nucleotide analogues and DNA polymerase-based DNA sequencing are also described in U.S. Pat. No. 6,664,079.

All embodiments of U.S. Pat. No. 6,664,079 (the contents of which are hereby incorporated by reference) with regard to sequencing a nucleic acid are specifically envisioned here.

"Alkyldithiomethyl" refers to a compound, or portion thereof, comprising a dithio group, where one of the sulfurs is directly connected to a methyl group and the other sulfur is directly connected to an alkyl group. An example is the structure

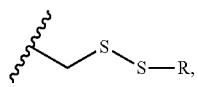

wherein R is an alkyl group and the wavy line represents a point of connection to another portion of the compound. In some cases, the alkyldithiomethyl is methyldithiomethyl, ethyldithiomethyl, propyldithiomethyl, isopropyldithiomethyl, butyldithiomethyl, t-butyldithiomethyl or phenyldithiomethyl.

Embodiment P1

A nucleotide analogue comprising (i) a base, (ii) a deoxyribose or ribose, (iii) an alkyldithiomethyl moiety bound to the 3'-oxygen of the deoxyribose or ribose, and (iv) a detectable label bound to the base via a dithiomethyl linker.

Embodiment P2

The nucleotide analogue of embodiment P1, wherein the nucleotide analogue comprises a deoxyribose.

Embodiment P3

The nucleotide analogue of embodiments P1, wherein the nucleotide analogue comprises a ribose.

Embodiment P4

The nucleotide analogue of any of embodiments P1-3, wherein the nucleotide analogue is a nucleoside triphosphate, a nucleoside tetraphosphate, a nucleoside pentaphosphate, or a nucleoside hexaphosphate.

Embodiment P5

The nucleotide analogue of any of embodiments P1-4, wherein the base is selected from the group consisting of adenine or an analogue of adenine, guanine or an analogue of guanine, cytosine or an analogue of cytosine, thymine or an analogue of thymine and uracil or an analogue of uracil.

Embodiment P6

The nucleotide analogue of any of embodiments P1-5, wherein the alkyldithiomethyl moiety bound to the 3'-oxygen is selected from the group consisting of methyldithiomethyl, ethyldithiomethyl, propyldithiomethyl, isopropyldithiomethyl, butyldithiomethyl, t-butyldithiomethyl, and phenyldithiomethyl.

Embodiment P7

The nucleotide analogue of any of embodiments P1-6, wherein the alkyldithiomethyl moiety has the structure

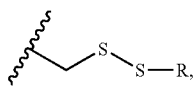

wherein R is the alkyl portion of the alkyldithiomethyl moiety and the wavy line represents the point of connection to the 3'-oxygen.

Embodiment P8

The nucleotide analogue of any of embodiments P1-7, wherein the detectable label bound to the base via a dithiomethyl linker is bound to the 5-position of the base if the base is T, U, or C or an analogue of T, U, or C, and to the 7-position of the base if the base is A or G or an analogue of A or G.

Embodiment P9

The nucleotide analogue of any of embodiments P1-8, wherein the base is a deaza analogue.

Embodiment P10

The nucleotide analogue of embodiment P9, wherein the deaza analogue is a 7-deazapurine.

Embodiment P11

The nucleotide analogue of any of embodiments P1-10, wherein the alkyldithiomethyl moiety and the dithiomethyl linker are both cleavable with tris-(2-carboxyethyl)phosphine (TCEP) or tris(hydroxypropyl)phosphine (THP).

Embodiment P12

The nucleotide analogue of any of embodiments P1-11, wherein the dithiomethyl linker has a structure as follows:

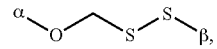

wherein α represents one or more atoms through which a covalent connection is established to the base, and β represents one or more atoms through which a covalent connection is established to the detectable label.

Embodiment P13

The nucleotide analogue of embodiment P12, wherein the dithiomethyl linker has a structure as follows:

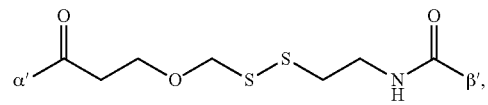

wherein α' represents one or more atoms through which a covalent connection is established to the base, and β' represents one or more atoms through which a covalent connection is established to the detectable label.

Embodiment P14

The nucleotide analogue of embodiments P13, wherein the dithiomethyl linker is included within a a structure as follows:

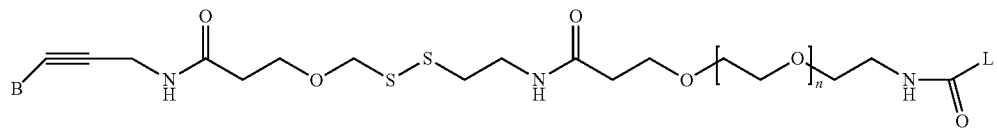

wherein B represents the point of connection to the base; wherein L represents the point of connection to the detectable label; and wherein n is 1-11.

Embodiment P15

The nucleotide analogue of any of embodiments P1-14, wherein the detectable label is selected from the group consisting of a dye, a fluorophore, a combinatorial fluorescence energy transfer tag, a chemiluminescent compound, a chromophore, a mass tag, and an electrophore.

Embodiment P16

The nucleotide analogue of embodiments P15, wherein the detectable label is a fluorophore.

Embodiment P17

The nucleotide analogue of embodiments P16, wherein the fluorophore is selected from the group including but not limited to BodipyFL, R6G, ROX, and Cy5.

Embodiment P18

The nucleotide analogue of embodiments P1, wherein the nucleotide analogue is selected from the group consisting of 3'-O-t-butyl-dithiomethyl-dCTP-S—S-BodipyFL, 3'-O-t-butyl-dithiomethyl-dUTP-S—S-R6G, 3'-O-t-butyl-dithiomethyl-dATP-S—S—ROX, and 3'-O-t-butyl-dithiomethyl-dGTP-S—S-Cy5, where S—S represents the dithio linker.

Embodiment P19

The nucleotide analogue of embodiments P1, wherein the structure of the nucleotide analogue is selected from

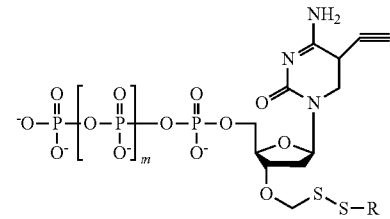
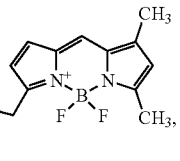

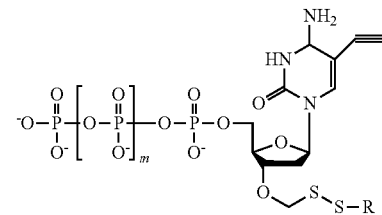
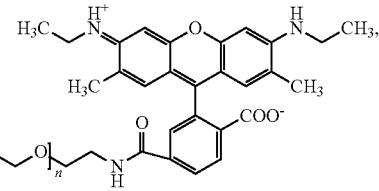

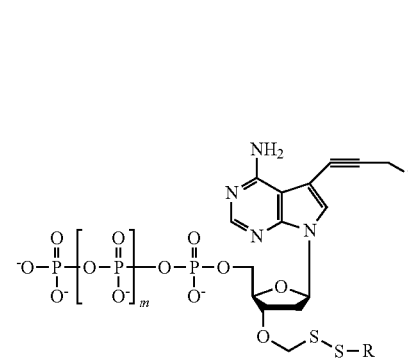
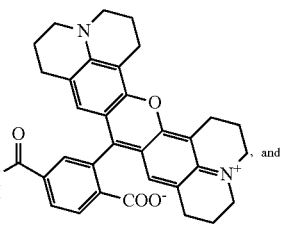

-continued

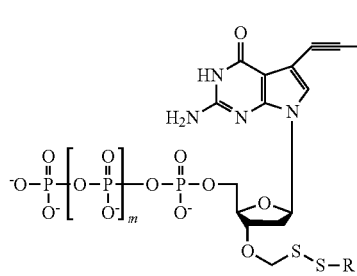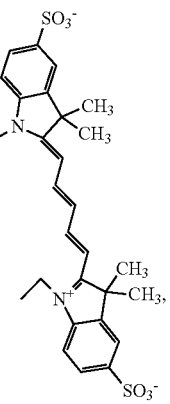

wherein R is methyl, ethyl, propyl, isopropyl, butyl, t-butyl, or phenyl; n is 2-11, and m is 1-4.

Embodiment P20

A composition comprising at least two different types of a nucleotide analogue of any of embodiments P1-18, wherein each type of nucleotide analogue comprises a different base and a different detectable label from each of the other types of nucleotide analogue.

Embodiment P21

A composition comprising a first type of nucleotide analogue of any of claims 1-18 and a second type of nucleotide analogue of any of embodiments P1-18, wherein the second type of nucleotide analogue comprises a different base and a different detectable label from the first type of nucleotide analogue.

Embodiment P22

The composition of embodiments P21, further comprising a third type of nucleotide analogue of any of claims 1-18, wherein the third type of nucleotide analogue comprises a different base and a different detectable label from each of the other two types of nucleotide analogue.

Embodiment P23

The composition of embodiments P22, further comprising a fourth type of nucleotide analogue of any of claims 1-18, wherein the fourth type of nucleotide analogue comprises a different base and a different detectable label from each of the other three types of nucleotide analogue.

Embodiment P24

The composition of embodiments P23, further comprising a fifth type of nucleotide analogue of any of claims 1-18, wherein the fifth type of nucleotide analogue comprises a different base and a different detectable label from each of the other four types of nucleotide analogue.

Embodiment P25

A nucleotide analogue comprising (i) a base selected from the group consisting of adenine or an analogue of adenine, guanine or an analogue of guanine, cytosine or an analogue of cytosine, thymine or an analogue of thymine and uracil or an analogue of uracil, (ii) a deoxyribose or ribose, (iii) an alkyldithiomethyl moiety bound to the 3'-oxygen of the deoxyribose or ribose, and (iv) a 3-aminopropynyl group bound to the 5-position of the base if the base is T, U, or C or an analogue of T, U, or C, and bound to the 7-position of the base if the base is A or G or an analogue of A or G.

Embodiment P26

A method for sequencing a nucleic acid, comprising:
a) providing
  1. a nucleic acid,
  2. a nucleic acid polymerase,
  3. a primer capable of hybridizing to said nucleic acid, and
  4. four different labeled nucleotide analogues, each comprising (i) a base, (ii) a deoxyribose or ribose, (iii) an alkyldithiomethyl moiety bound to the 3'-oxygen of the deoxyribose or ribose, and (iv) a detectable label bound to the base via a dithiomethyl linker, and wherein each nucleotide analogue comprises a unique base and a unique detectable label;
b) incorporating with said nucleic acid polymerase one or more of said nucleotide analogues into said primer to create an extension strand;
c) detecting said unique detectable label of each incorporated nucleotide analogue, so as to thereby identify each incorporated nucleotide analogue in said extension strand, thereby sequencing the nucleic acid.

Embodiment P27

A method for sequencing a nucleic acid, comprising:
a) providing
  a) a nucleic acid,
  b) a nucleic acid polymerase,
  c) a primer capable of hybridizing to said nucleic acid,
  d) three different types of labeled nucleotide analogues, each comprising (i) a base, (ii) a deoxyribose or ribose, (iii) an alkyldithiomethyl moiety bound to the 3'-oxygen of the deoxyribose or ribose, and (iv) a detectable label bound to the base via a dithiomethyl linker, and wherein each nucleotide analogue comprises a unique base and a unique detectable label; and
  e) an unlabeled nucleotide analogue, comprising (i) a base, (ii) a deoxyribose or ribose, and (iii) an alkyldithiomethyl moiety bound to the 3'-oxygen of the deoxyribose or ribose, and wherein the base is different from each base of the labeled nucleotide analogues;
b) incorporating with said nucleic acid polymerase one or more of said nucleotide analogues into said primer to create an extension strand;
c) detecting a unique detectable label, if present, of each incorporated nucleotide analogue, so as to thereby identify each incorporated nucleotide analogue in said extension strand,
thereby sequencing the nucleic acid.

Embodiment P28

The method of any of embodiments P26-27, further comprising removing the alkyldithiomethyl moiety bound to the 3'-oxygen of the deoxyribose or ribose by cleaving the S—S bond, so as to permit incorporation of another analogue into each of said extension strands.

Embodiment P29

The method of any of embodiments P26-28, further comprising removing a unique detectable label, if present, from each incorporated nucleotide analogue by cleaving the dithio bond.

Embodiment P30

The method of any of embodiments P28-29, wherein the dithio bond in at least one of the alkyldithiomethyl moiety and the dithiomethyl linker, if present, is cleaved by tris-(2-carboxyethyl)phosphine (TCEP) or tris(hydroxypropyl)phosphine (THP).

Embodiment P31

The method of any of embodiments P26-30, wherein each nucleoside analogue is a nucleoside triphosphate, a nucleoside tetraphosphate, a nucleoside pentaphosphate, or a nucleoside hexaphosphate.

Embodiment P32

The method of any of embodiments P26-31, wherein each base is selected from the group consisting of adenine or an analogue of adenine, guanine or an analogue of guanine, cytosine or an analogue of cytosine, thymine or an analogue of thymine and uracil or an analogue of uracil.

Embodiment P33

The method of any of embodiments P26-32, wherein the nucleotide analogue comprises a deoxyribose.

Embodiment P34

The method of embodiments P33, wherein the polymerase is a DNA polymerase and the nucleic acid is DNA.

Embodiment P35

The method of embodiments P33, wherein the polymerase is a reverse transcriptase and the nucleic acid is RNA.

Embodiment P36

The method of any of embodiments P26-32, wherein the nucleotide analogue comprises a ribose.

Embodiment P37

The method of embodiments P36, wherein the polymerase is a DNA-based RNA polymerase and the nucleic acid is DNA.

Embodiment P38

The method of embodiments P36, wherein the polymerase is an RNA-based RNA polymerase and the nucleic acid is RNA.

Embodiment P39

The method of any of embodiments P26-38, wherein each alkyldithiomethyl moiety bound to the 3'-oxygen is independently selected from the group consisting of methyldithiomethyl, ethyldithiomethyl, propyldithiomethyl, isopropyldithiomethyl, butyldithiomethyl, t-butyldithiomethyl, and phenyldithiomethyl.

Embodiment P40

The method of any of embodiments P25-39, wherein each alkyldithiomethyl moiety has the structure

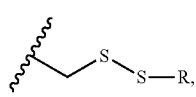

wherein R is the alkyl portion of the alkyldithiomethyl moiety and the wavy line represents the point of connection to the 3'-oxygen.

Embodiment P41

The method of any of embodiments P26-40, wherein each detectable label bound to the base via a dithiomethyl linker is bound to the 5-position of the base if the base is T, U, or C or an analogue of T, U, or C, and to the 7-position of the base if the base is A or G or an analogue of A or G.

Embodiment P42

The method of any of embodiments P26-41, wherein the base of at least one of the nucleotide analogues is a deaza analogue.

Embodiment P43

The method of embodiments P42, wherein the deaza analogue is a 7-deazapurine.

Embodiment P44

The method of any of embodiments P25-43, wherein each dithiomethyl linker has a structure as follows:

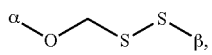

wherein α represents one or more atoms through which a covalent connection is established to the base, and β represents one or more atoms through which a covalent connection is established to the detectable label.

Embodiment P45

The method of embodiment P44, wherein each dithiomethyl linker has a structure as follows:

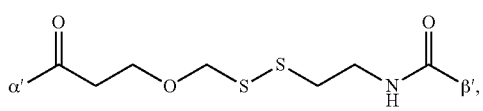

wherein α' represents one or more atoms through which a covalent connection is established to the base, and β' represents one or more atoms through which a covalent connection is established to the detectable label.

Embodiment P46

The method of embodiment P45, wherein each dithiomethyl linker is included within a structure as follows:

wherein B represents the point of connection to the base; wherein L represents the point of connection to the detectable label; and wherein n is 1-11.

Embodiment P47

The method of any of embodiments P26-46, wherein each detectable label is selected from the group consisting of a dye, a fluorophore, a combinatorial fluorescence energy transfer tag, a chemiluminescent compound, a chromophore, a mass tag, and an electrophore.

Embodiment P48

The method of embodiments P47, wherein each detectable label is a fluorophore.

Embodiment P49

The method of embodiment P48, wherein the fluorophore is selected from the group consisting of BodipyFL, R6G, ROX, and Cy5.

Embodiment P50

The method of any of embodiments P26-27, wherein each labeled nucleotide analogue is selected from the group consisting of 3'-O-t-butyl-dithiomethyl-dCTP-S—S-BodipyFL, 3'-O-t-butyl-dithiomethyl-dUTP-S—S-R6G, 3'-O-t-butyl-dithiomethyl-dATP-S—S—ROX, and 3'-O-t-butyl-dithiomethyl-dGTP-S—S-Cy5, where S—S represents a dithio linker.

Embodiment P51

The method of any of embodiments P26-27, wherein the structure of each labeled nucleotide analogue is selected from

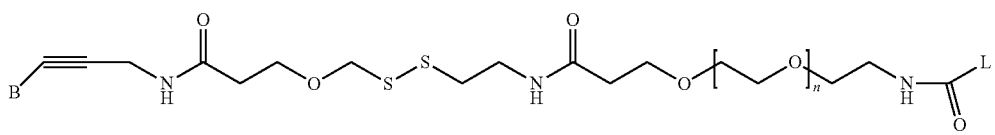

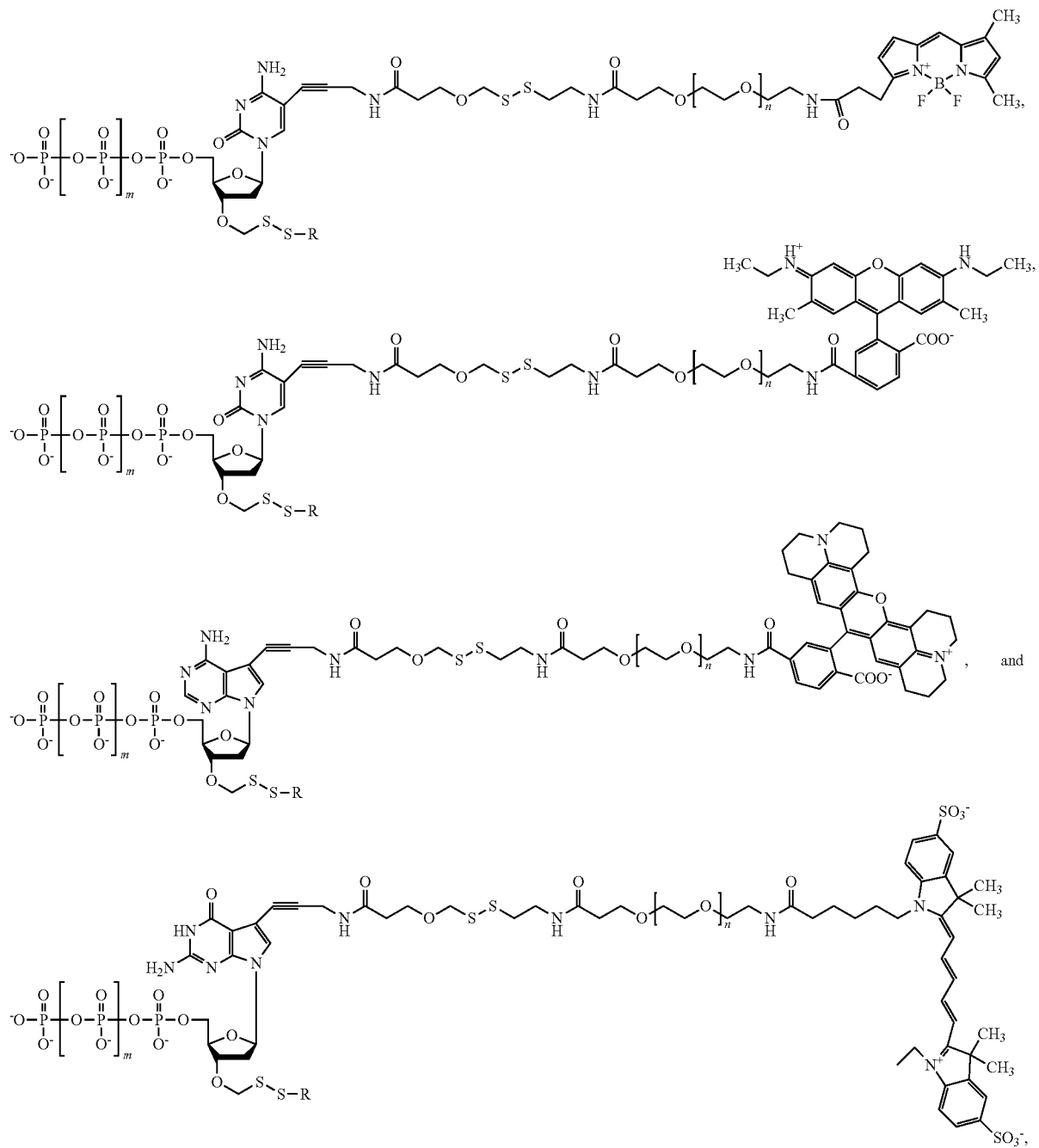

wherein R is methyl, ethyl, propyl, isopropyl, butyl, t-butyl, or phenyl; n is 1-11, and m is 1-4.

Embodiment P52

The method of any of embodiments P26-51, wherein the nucleic acid is immobilized on a solid substrate.

Embodiment P53

The method of embodiment P52, wherein the nucleic acid is immobilized on the solid substrate via a 1,3-dipolar cycloaddition reaction between an azido and alkyne functional group, or a biotin-streptavidin interaction.

Embodiment P54

The method of any of embodiments P52-53, wherein the solid substrate is in the form of a chip, a bead, a well, a capillary tube, or a slide.

Embodiment P55

The method of any of embodiments P52-54, wherein the solid substrate is gold, quartz, silica, or plastic.

Embodiment P56

The method of any of embodiments P52-55, wherein the solid substrate is porous.

Embodiment P57

The method of any of embodiments P26-56, simultaneously applied to a plurality of different nucleic acids.

Embodiment P58

A process for producing a 3'-O-ethyldithiomethyl nucleoside, comprising:
a) providing,
  a) a nucleoside,
  b) acetic acid,
  c) acetic anhydride, and
  d) DMSO
under conditions permitting the production of a 3'-O-methylthiomethyl nucleoside;
b) contacting the 3'-O-methylthiomethyl nucleoside produced in part a) with trimethylamine, molecular sieve, and sulfuryl chloride under conditions permitting the production of a 3'-O-chloromethyl nucleoside;
c) contacting the 3'-O-chloromethyl nucleoside produced in part b) with potassium p-toluenethiosulfonate and ethanethiol under conditions permitting the production of a 3' ethyldithiomethyl nucleoside.

Embodiment P59

A process for producing a n-(3-aminopropynyl)-3'-O-t-butyldithiomethyl-dNTP, wherein n is 5 if the base is C, T, or U, and n is 7 if the base is A or G, using the example here for the synthesis of 5-(3-aminopropynyl)-3'-O-t-butyldithomethyl-dCTP, comprising:
a) providing
  a) a 5-iodo-2'-deoxy nucleoside (C), and
  b) N,N-dimethylformamide dimethyl acetal under conditions permitting the formation of a $N^4$-DMF-5-iodo-2'-deoxy nucleoside (C); contacting the $N^4$-DMF-5-iodo-2'-deoxy nucleoside produced in step a) with trityl-Cl under conditions permitting the formation of a $N^4$-DMF-5-iodo-5'-O-trityl-2'-deoxy nucleoside (C);
c) contacting the $N^4$-DMF-5-iodo-5'-O-trityl-2'-deoxy nucleoside (C) produced in step b) with triethylamine and N-propargyl trifluoroacetamide under conditions permitting the formation of a $N^4$-DMF-5-[3-(trifluoroacetamido)propynyl]-5'-O-trityl-2, -deoxy nucleoside (C);
d) contacting the $N^4$-DMF-5-[3-(trifluoroacetamido)propynyl]-5'-O-trityl-2'-deoxy nucleoside (C) produced in step c) with DMSO, acetic acid and acetic anhydride under conditions permitting the formation of a $N^4$-DMF-5-[3-(trifluoroacetamido)propynyl]-5'-O-trityl-3'-O-methylthiomethyl-2'-deoxy nucleoside (C);
e) contacting the $N^4$-DMF-5-[3-(trifluoroacetamido)propynyl]-5'-O-trityl-3'-O-methylthiomethyl-T-deoxy nucleoside (C) produced in step d) with triethylamine, molecular sieves, sulfuryl chloride, potassium p-toluenethiosulfonate, and t-butyl mercaptan, under conditions permitting the formation of a $N^4$-DMF-5-[3-(trifluoroacetamido)propynyl]-5'-O-trityl-3'-O-(t-butyldithiomethyl)-2'-deoxy nucleoside (C);
f) contacting the $N^4$-DMF-5-[3-(trifluoroacetamido)propynyl]-5'-O-trityl-3'-O-(t-butyldithiomethyl)-2'-deoxy nucleoside (C) produced in step e) with trichloroacetic acid under conditions permitting the formation of a $N^4$-DMF-5-[3-(trifluoroacetamido)propynyl]-3'-O-(t-butyldithiomethyl)-2'-deoxy nucleoside (C);
g) contacting the $N^4$-DMF-5-[3-(trifluoroacetamido)propynyl]-3'-O-(t-butyldithiomethyl)-2'-deoxy nucleoside (C) produced in step f) with tetrabutylammonium pyrophosphate, tributylamine, $I_2$, pyridine, and $NH_4OH$ under conditions permitting the formation of a 5-[3aminopropynyl]-3'-O-(t-butyldithiomethyl)-dCTP.

Embodiment P60

A process for producing a 3'-O-alkyldithiomethyl-dNTP-SS-dye, where SS is an alkyldithio linker, comprising:
354. providing
  a) a compound comprising the structure $$\alpha\diagdown_O\diagup\diagdown_S\diagup^S\diagdown_\beta,$$

wherein α represents one or more atoms through which a covalent connection is established to a carboxylic acid group, and β represents one or more atoms through which a covalent connection is established to a dye, and
b) a 3'-O-alkyldithiomethyl-dNTP-n-(3-aminopropynyl), wherein n is 5 if the base is C, T, or U, and n is 7 if the base is A or G,
under conditions permitting the formation of a 3'-O-alkyldithiomethyl-dNTP-SS-dye.

Embodiment P61

A plurality of different nucleic acids immobilized on a solid substrate and hybridized to primers, a portion of said primers comprising incorporated nucleotide analogues, said nucleotide analogues comprising (i) a base, (ii) a deoxyribose or a ribose, (iii) an alkyldithiomethyl moiety bound to the 3'-oxygen of the deoxyribose or ribose, and (iv) a detectable label bound to the base via a dithiomethyl linker.

Embodiment P62

The plurality of different nucleic acids of embodiments P61, wherein each base is selected from the group consisting of adenine or an analogue of adenine, guanine or an analogue of guanine, cytosine or an analogue of cytosine, thymine or an analogue of thymine and uracil or an analogue of uracil.

Embodiment P63

The plurality of different nucleic acids of any of embodiments P61-62, wherein said alkyldithiomethyl moieties bound to the 3'-oxygen are selected from the group consisting of methyldithiomethyl, ethyldithiomethyl, propyldithiomethyl, isopropyldithiomethyl, butyldithiomethyl, t-butyldithiomethyl, and phenyldithiomethyl.

Embodiment P64

The plurality of different nucleic acids of any of embodiments P61-63, wherein each alkyldithiomethyl moiety has the structure

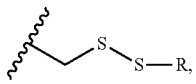

wherein R is the alkyl portion of the alkyldithiomethyl moiety and the wavy line represents the point of connection to the 3'-oxygen.

Embodiment P65

The plurality of different nucleic acids of any of embodiments P61-64, wherein at least one of said nucleotide analogues is a deaza analogue.

Embodiment P66

The plurality of different nucleic acids of embodiments P65, wherein the deaza analogue is a 7-deazapurine.

Embodiment P67

The plurality of different nucleic acids of any of embodiments P61-66, wherein each linker has a structure as follows:

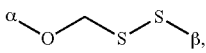

wherein α represents one or more atoms through which a covalent connection is established to the base, and β represents one or more atoms through which a covalent connection is established to the detectable label.

Embodiment P68

The plurality of different nucleic acids of embodiments P67, wherein each dithiomethyl linker has a structure as follows:

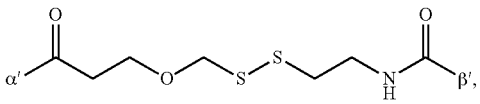

wherein α' represents one or more atoms through which a covalent connection is established to the base, and β' represents one or more atoms through which a covalent connection is established to the detectable label.

Embodiment P69

The plurality of different nucleic acids of embodiments P68, wherein each linker is included within a structure as follows:

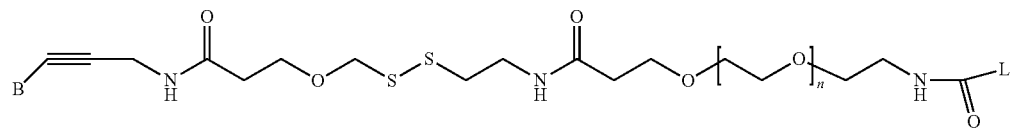

wherein B represents the point of connection to the base; wherein L represents the point of connection to the detectable label; and wherein n is 1-11.

Embodiment P70

The plurality of different nucleic acids of any of embodiments P61-69, wherein said detectable labels are selected from the group consisting of a dye, a fluorophore, a combinatorial fluorescence energy transfer tag, a chemiluminescent compound, a chromophore, a mass tag, and an electrophore.

Embodiment P71

The plurality of different nucleic acids of embodiments P70, wherein said detectable labels are fluorophores.

Embodiment P72

A kit for nucleic acid sequencing, comprising, in separate compartments:
  a) a plurality of nucleotide analogues, each comprising (i) a base, (ii) a deoxyribose or ribose, (iii) an alkyldithiomethyl moiety bound to the 3'-oxygen of the deoxyribose or ribose, and (iv) a detectable label bound to the base via a dithiomethyl linker;
  b) reagents suitable for use in nucleic acid polymerization; and
  c) instructions for use.

Embodiment P73

The kit of embodiments P72, further comprising
  a) a nucleotide analogue, comprising (i) a base, (ii) a deoxyribose or ribose, and (iii) an alkyldithiomethyl moiety bound to the 3'-oxygen of the deoxyribose or ribose.

305

Additional Embodiments

Embodiment 1

A compound of the formula:

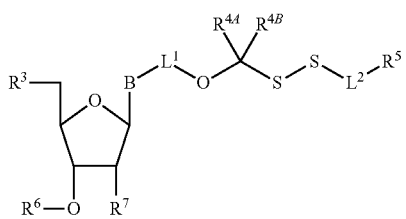

wherein
- B is a base; $L^1$ is covalent linker; $L^2$ is covalent linker;
- $R^3$ is —OH, monophosphate, polyphosphate or a nucleic acid;
- $R^{4A}$ is hydrogen, —CH$_3$, —CX$^1_3$, —CHX$^1_2$, —CH$_2$X$^1$, —OCX$^1_3$, —OCH$_2$X$^1$, —OCHX$^1_2$, —CN, —OH, —SH, —NH$_2$, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $R^{4B}$ is hydrogen, —CH$_3$, —CX$^2_3$, —CHX$^2_2$, —CH$_2$X$^2$, —OCX$^2_3$, —OCH$_2$X$^2$, —OCHX$^2_2$, —CN, —OH, —SH, —NH$_2$, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $R^5$ is a detectable label or anchor moiety;
- $R^6$ is hydrogen or a polymerase-compatible cleavable moiety;
- $R^7$ is hydrogen or —OR$^{7A}$, wherein $R^{7A}$ is hydrogen or a polymerase-compatible cleavable; and $X^1$ and $X^2$ are independently halogen.

Embodiment 2

The compound of embodiment 1, wherein B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, deaza-adenine or a derivative thereof, deaza-guanine or a derivative thereof, deaza-hypoxanthine or a derivative thereof divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof.

306

Embodiment 3

The compound of embodiment 1, wherein B is

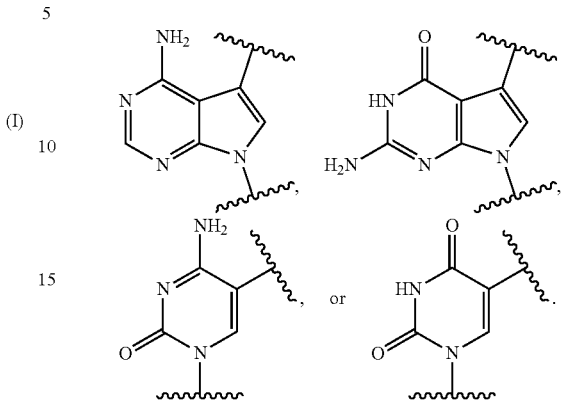

Embodiment 4

The compound of one of embodiments 1 to 3, wherein $L^1$ is $L^{1A}$-$L^{1B}$-$L^{1C}$-$L^{1D}$-$L^{1E}$; and
$L^{1A}$, $L^{1B}$, $L^{1C}$, $L^{1D}$ and $L^{1E}$ are independently a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; wherein at least one of $L^{1A}$, $L^{1B}$, $L^{1C}$, $L^{1D}$ and $L^{1E}$ is not a bond.

Embodiment 5

The compound of one of embodiments 1 to 3, wherein $L^1$ is $L^{1A}$-$L^{1B}$-$L^{1C}$-$L^{1D}$-$L^{1E}$; and $L^{1A}$, $L^{1B}$, $L^{1C}$, $L^{1D}$ and $L^{1E}$ are independently a bond, substituted or unsubstituted $C_1$-$C_8$ alkylene, substituted or unsubstituted 2 to 8 membered heteroalkylene, substituted or unsubstituted $C_3$-$C_6$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene; wherein at least one of $L^{1A}$, $L^{1B}$, $L^{1C}$, $L^{1D}$ and $L^{1E}$ is not a bond.

Embodiment 6

The compound of one of embodiments 1 to 3, wherein $L^1$ is $L^{1A}$-$L^{1B}$-$L^{1C}$-$L^{1D}$-$L^{1E}$; and $L^{1A}$, $L^{1B}$, $L^{1C}$, $L^{1D}$ and $L^{1E}$ are independently a bond, substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted phenyl, or substituted or unsubstituted 5 to 6 membered heteroarylene; wherein at least one of $L^{1A}$, $L^{1B}$, $L^{1C}$, $L^{1D}$ and $L^{1E}$ is not a bond.

Embodiment 7

The compound of one of embodiments 1 to 3, wherein $L^1$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 8

The compound of one of claims 1 to 3, wherein $L^1$ is a bond, substituted or unsubstituted $C_1$-$C_8$ alkylene, substituted or unsubstituted 2 to 8 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene.

Embodiment 9

The compound of one of embodiments 1 to 3, wherein $L^1$ is a bond, substituted or unsubstituted $C_1$-$C_8$ alkylene, substituted or unsubstituted 2 to 8 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene.

Embodiment 10

The compound of one of embodiments 1 to 3, wherein $L^1$ is a bond, substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted phenyl, or substituted or unsubstituted 5 to 6 membered heteroarylene.

Embodiment 11

The compound of one of embodiments 1 to 3, wherein $L^1$ is a substituted or unsubstituted $C_1$-$C_6$ alkylene or substituted or unsubstituted 2 to 6 membered heteroalkylene.

Embodiment 12

The compound of one of embodiments 1 to 3, wherein $L^1$ is an unsubstituted $C_1$-$C_4$ alkylene.

Embodiment 13

The compound of one of 1 to 3, wherein $L^1$ is —CEC-CH$_2$—.

Embodiment 14

The compound of one of embodiments 1 to 12, wherein $L^2$ is a cleavable linker. [0468] Embodiment 15. The compound of one of embodiments 1 to 12, wherein $L^2$ is a chemically cleavable linker.

Embodiment 16

The compound of one of embodiments 1 to 12, wherein $L^2$ is a photocleavable linker, an acid-cleavable linker, a base-cleavable linker, an oxidant-cleavable linker, a reductant-cleavable linker, or a fluoride-cleavable linker.

Embodiment 17

The compound of one of embodiments 1 to 12, wherein $L^2$ is a cleavable linker comprising a dialkylketal linker, an azo linker, an allyl linker, a cyanoethyl linker, a 1-(4,4-dimethyl-2,6-dioxocyclohex-1-ylidene)ethyl linker, or a nitrobenzyl linker.

Embodiment 18

The compound of one of embodiments 1 to 12, wherein $L^2$ is $L^{2A}$-$L^{2B}$-$L^{2C}$-$L^{2D}$-$L^{2E}$; and $L^{2A}$, $L^{2B}$, $L^{2C}$, $L^{2D}$ and $L^{2E}$ are independently a bond, —NN—, —NHC(O)—, —C(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; wherein at least one of $L^{2A}$, $L^{2B}$, $L^{2C}$, $L^{2D}$ and $L^{2E}$ is not a bond.

Embodiment 19

The compound of one of embodiments 1 to 12, wherein $L^2$ is $L^{2A}$-$L^{2B}$-$L^{2C}$-$L^{2D}$-$L^{2E}$; and $L^{2A}$, $L^{2B}$, $L^{2C}$, $L^{2D}$ and $L^{2E}$ are independently a bond, —NN—, —NHC(O)—, —C(O)NH—, substituted or unsubstituted $C_1$-$C_{20}$ alkylene, substituted or unsubstituted 2 to 20 membered heteroalkylene, substituted or unsubstituted $C_3$-$C_{20}$ cycloalkylene, substituted or unsubstituted 3 to 20 membered heterocycloalkylene, substituted or unsubstituted $C_6$-$C_{20}$ arylene, or substituted or unsubstituted 5 to 20 membered heteroarylene; wherein at least one of $L^{2A}$, $L^{2B}$, $L^{2C}$, $L^{2D}$ and $L^{2E}$ is not a bond.

Embodiment 20

The compound of one of embodiments 1 to 12, wherein $L^2$ is $L^{2A}$-$L^{2B}$-$L^{2C}$-$L^{2D}$-$L^{2E}$; and $L^{2A}$, $L^{2B}$, $L^{2C}$, $L^{2D}$ and $L^{2E}$ are independently a bond, —NN—, —NHC(O)—, —C(O)NH—, substituted or unsubstituted $C_1$-$C_{10}$ alkylene, substituted or unsubstituted 2 to 10 membered heteroalkylene, substituted or unsubstituted $C_3$-$C_6$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene; wherein at least one of $L^{2A}$, $L^{2B}$, $L^{2C}$, $L^{2D}$ and $L^{2E}$ is not a bond.

Embodiment 21

The compound of one of embodiments 1 to 12, wherein $L^2$ is $L^{2A}$-$L^{2B}$-$L^{2C}$-$L^{2D}$-$L^{2E}$; and $L^{2A}$, $L^{2B}$, $L^{2C}$, $L^{2D}$ and $L^{2E}$ are independently a bond, —NN—, —NHC(O)—, —C(O)NH—, substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted phenyl, or substituted or unsubstituted 5 to 6 membered heteroarylene; wherein at least one of $L^{2A}$, $L^{2B}$, $L^{2C}$, $L^{2D}$ and $L^{2E}$ is not a bond.

Embodiment 22

The compound of one of embodiments 1 to 12, wherein $L^2$ is $L^{2A}$-$L^{2B}$-$L^{2C}$-$L^{2D}$-$L^{2E}$; and $L^{2A}$ is a bond, substituted or unsubstituted alkylene, substituted or unsubstituted heteroalkylene; $L^{2B}$ is a bond, substituted or unsubstituted cycloalkylene, substituted or unsubstituted heterocycloalkylene, substituted or unsubstituted arylene, substituted or unsubstituted heteroarylene; $L^{2C}$ is a bond, substituted or unsubstituted cycloalkylene, substituted or unsubstituted heterocycloalkylene, substituted or unsubstituted arylene, substituted or unsubstituted heteroarylene; $L^{2D}$ is a bond, substituted or unsubstituted alkylene, substituted or unsubstituted heteroalkylene; and $L^{2E}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; wherein at least one of $L^{2A}$, $L^{2B}$, $L^{2C}$, $L^{2D}$ and $L^{2E}$ is not a bond.

Embodiment 23

The compound of one of embodiments 1 to 12, wherein $L^2$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 24

The compound of one of embodiments 1 to 12, wherein $L^2$ is a bond, substituted or unsubstituted $C_1$-$C_{20}$ alkylene, substituted or unsubstituted 2 to 20 membered heteroalkylene, substituted or unsubstituted $C_3$-$C_{20}$ cycloalkylene, substituted or unsubstituted 3 to 20 membered heterocycloalkylene, substituted or unsubstituted $C_6$-$C_{20}$ arylene, or substituted or unsubstituted 5 to 20 membered heteroarylene.

Embodiment 25

The compound of one of embodiments 1 to 12, wherein $L^2$ is a bond, substituted or unsubstituted $C_1$-$C_8$ alkylene, substituted or unsubstituted 2 to 8 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene.

Embodiment 26

The compound of one of embodiments 1 to 12, wherein $L^2$ is a bond, substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted phenyl, or substituted or unsubstituted 5 to 6 membered heteroarylene.

Embodiment 27

The compound of one of embodiments 1 to 12, wherein $L^2$ is a substituted or unsubstituted 4 to 10 membered heteroalkylene.

Embodiment 28

The compound of one of embodiments 1 to 12, wherein $L^2$ is a substituted or unsubstituted 4 to 8 membered heteroalkylene.

Embodiment 29

The compound of one of embodiments 1 to 12, wherein $L^2$-C(CH$_3$)$_2$CH$_2$NHC(O)—.

Embodiment 30

The compound of one of embodiments 1 to 28, wherein $R^3$ is —OH.

Embodiment 31

The compound of one of embodiments 1 to 28, wherein $R^3$ is monophosphate.

Embodiment 32

The compound of one of embodiments 1 to 28, wherein $R^3$ is polyphosphate.

Embodiment 33

The compound of one of embodiments 1 to 28, wherein $R^3$ is triphosphate.

Embodiment 34

The compound of one of embodiments 1 to 28, wherein $R^3$ is tetraphosphate, pentaphosphate, or hexaphosphate.

Embodiment 35

The compound of one of embodiments 1 to 28, wherein $R^3$ is a residue of a nucleic acid.

Embodiment 36

The compound of one of embodiments 1 to 28, wherein $R^3$ is a 10 to 25 base residue of a nucleic acid.

Embodiment 37

The compound of one of embodiments 1 to 28, wherein $R^3$ is a 10 to 10,000 base residue of a nucleic acid.

Embodiment 38

The compound of one of embodiments 1 to 36, wherein $R^{4A}$ is hydrogen, —CH$_3$, —CX$^1_3$, —CHX$^1_2$, —CN, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 39

The compound of one of embodiments 1 to 36, wherein $R^{4A}$ is hydrogen, —CH$_3$, —CX$^1_3$, —CHX$^1_2$, —CN, -Ph, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 40

The compound of one of embodiments 1 to 36, wherein $R^{4A}$ is hydrogen.

Embodiment 41

The compound of one of embodiments 1 to 39, wherein $R^{4H}$ is hydrogen, —CH$_3$, —CX$^2_3$, —CHX$^2_2$, —CH$_2$X$^2$, —CN, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 42

The compound of one of embodiments 1 to 39, wherein $R^{4B}$ is hydrogen, —$CH_3$, —$CX^2{}_3$, —$CHX^2{}_2$, —$CH_2X^2$, —CN, -Ph, $H_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 43

The compound of one of embodiments 1 to 39, wherein $R^{4B}$ is hydrogen.

Embodiment 44

The compound of one of embodiments 1 to 42, wherein $R^5$ is a detectable label

Embodiment 45

The compound of one of embodiments 1 to 42, wherein $R^5$ is a fluorescent dye.

Embodiment 46

The compound of one of embodiments 1 to 42, wherein $R^5$ is an anchor moiety.

Embodiment 47

The compound of one of embodiments 1 to 42, wherein $R^5$ is a click chemistry reactant moiety.

Embodiment 48

The compound of one of embodiments 1 to 42, wherein $R^5$ is a trans-cyclooctene moiety or azide moiety.

Embodiment 49

The compound of one of embodiments 1 to 42, wherein $R^5$ is an affinity anchor moiety.

Embodiment 50

The compound of one of embodiments 1 to 42, wherein $R^5$ is a biotin moiety.

Embodiment 51

The compound of one of embodiments 1 to 49, wherein $R^6$ is hydrogen.

Embodiment 52

The compound of one of embodiments 1 to 49, wherein $R^6$ is a polymerase-compatible cleavable moiety.

Embodiment 53

The compound of one of embodiments 1 to 49, wherein $R^6$ is a polymerase-compatible cleavable moiety comprising an azido moiety.

Embodiment 54

The compound of one of embodiments 1 to 49, wherein $R^6$ is a polymerase-compatible cleavable moiety comprising a dithiol linker.

Embodiment 55

The compound of one of embodiments 1 to 49, wherein $R^6$ is a polymerase-compatible cleavable moiety; and the polymerase-compatible cleavable moiety is —$CH_2N_3$.

Embodiment 56

The compound of one of embodiments 1 to 49, wherein $R^6$ is a polymerase-compatible cleavable moiety; and the polymerase-compatible cleavable moiety is:

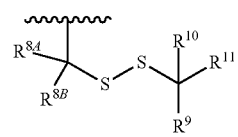

$R^{8A}$ is independently hydrogen, —$CH_3$, —$CX^3{}_3$, —$CHX^3{}_2$, —$CH_2X^3$, —CN, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{8B}$ is independently hydrogen, —$CH_3$, —$CX^4{}_3$, —$CHX^4{}_2$, —$CH_2X^4$, —CN, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or un substituted heteroaryl;

$R^9$ is independently hydrogen, —$CX^5{}_3$, —$CHX^5{}_2$, —$CH_2X^5$, —$OCH_3$, —$SCH_3$, —$NHCH_3$, —CN, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is independently hydrogen, —$CX^6{}_3$, —$CHX^6{}_2$, —$CH_2X^6$, —$OCH_3$, —$SCH_3$, —$NHCH_3$, —CN, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is independently hydrogen, —$CX^7{}_3$, —$CHX^7{}_2$, —$CH_2X^7$, —$OCH_3$, —$SCH_3$, —$NHCH_3$, —CN, -Ph substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $X^3$, $X^4$, $X^5$, $X^6$ and $X^1$ are independently halogen.

Embodiment 57

The compound of one of embodiments 1 to 49, wherein $R^6$ is a polymerase-compatible cleavable moiety; and the polymerase-compatible cleavable moiety is:

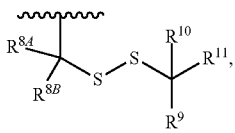

$R^{8A}$ is hydrogen, —$CH_3$, —$CX^3_3$, —$CHX^3_2$, —$CH_2X^3$, —CN, -Ph, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; $R^{8B}$ is hydrogen, —$CH_3$, —$CX^4_3$, —$CHX^4_2$, —$CH_2X^4$, —CN, -Ph, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl;
$R^9$ is hydrogen, —$CX^5_3$, —$CHX^3_2$, —$CH_2X^3$, —$OCH_3$, —$SCH_3$, —$NHCH_3$, —CN, -Ph, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl;
$R^{10}$ is hydrogen, —$CX^6_3$, —$CHX^6_2$, —$CH_2X^6$, —$OCH_3$, —$SCH_3$, —$NHCH_3$, —CN, -Ph, —OH, —SH, —$NH_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl;
$R^{11}$ is hydrogen, —$CX^7_3$, —$CHX^7_2$, —$CH_2X^7$, —$OCH_3$, —$SCH_3$, —$NHCH_3$, —CN, -Ph, —OH, —SH, —$NH_2$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; and $X^8$, $X^4$, $X^8$, $X^6$ and $X^7$ are independently halogen.

Embodiment 58

The compound of one of embodiments 1 to 49, wherein $R^6$ is a polymerase-compatible cleavable moiety; and the polymerase-compatible cleavable moiety is:

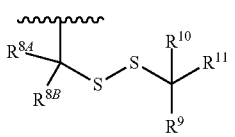

$R^{8A}$ and $R^{8B}$ are independently hydrogen or unsubstituted alkyl; and $R^9$, $R^{10}$, and $R^{11}$ are independently unsubstituted alkyl or unsubstituted heteroalkyl.

Embodiment 59

The compound of one of embodiments 1 to 49, wherein $R^6$ is a polymerase-compatible cleavable moiety; and the polymerase-compatible cleavable moiety is:

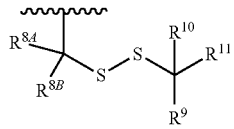

$R^{8A}$ and $R^{8B}$ are independently hydrogen or unsubstituted $C_1$-$C_4$ alkyl; and
$R^9$, $R^{10}$, and $R^{11}$ are independently unsubstituted $C_1$-$C_6$ alkyl or unsubstituted 2 to 4 membered heteroalkyl.

Embodiment 60

The compound of one of embodiments 1 to 49, wherein $R^6$ is a polymerase-compatible cleavable moiety; and the polymerase-compatible cleavable moiety is:

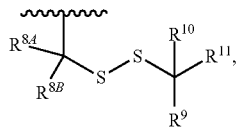

$R^{8A}$ and $R^{8B}$ are independently hydrogen; and $R^9$, $R^{10}$, and $R^{11}$ are independently unsubstituted $C_1$-$C_6$ alkyl or unsubstituted 2 to 4 membered heteroalkyl.

Embodiment 61

The compound of one of embodiments 1 to 49, wherein $R^6$ is a polymerase-compatible cleavable moiety; and the polymerase-compatible cleavable moiety is:

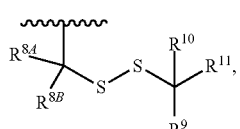

$R^{8A}$ and $R^{8B}$ are independently hydrogen; and $R^9$, $R^{10}$, and $R^{11}$ are independently un substituted methyl or unsubstituted methoxy.

Embodiment 62

The compound of one of embodiments 1 to 49, wherein $R^6$ is a polymerase-compatible cleavable moiety; and the polymerase-compatible cleavable moiety is:

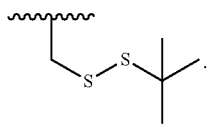 [SMILES: *CSSC(C)(C)C]

Embodiment 63

The compound of one of embodiments 1 to 49, wherein $R^7$ is hydrogen.

Embodiment 64

The compound of one of embodiments 1 to 70, wherein $R^7$ is $-OR^{7A}$; and $R^{7A}$ is hydrogen.

Embodiment 65

The compound of one of embodiments 1 to 49, wherein $R^7$ is $-OR^{7A}$; and $R^{7A}$ is a polymerase-compatible cleavable moiety.

Embodiment 66

The compound of one of embodiments 1 to 49, wherein $R^7$ is $-OR^{7A}$; and $R^{7A}$ is a polymerase-compatible cleavable moiety comprising an azido moiety.

Embodiment 67

The compound of one of embodiments 1 to 49 wherein $R^7$ is $-OR^{7A}$; and $R^{7A}$ is a polymerase-compatible cleavable moiety comprising a dithiol linker, an allyl group, or a 2-nitrobenzyl group.

Embodiment 68

The compound of one of embodiments 1 to 49, wherein $R^7$ is $-OR^{7A}$; $R^{7A}$ is a polymerase-compatible cleavable moiety; and the polymerase-compatible cleavable moiety is $-CH_2N_3$.

Embodiment 69

The compound of one of embodiments 1 to 49, wherein $R^7$ is $-OR^{7A}$; $R^{7A}$ is a polymerase-compatible cleavable moiety; and the polymerase-compatible cleavable moiety is:

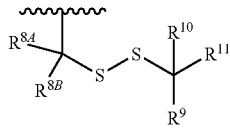

$R^{8A}$ is hydrogen, $-CH_3$, $-CX^3_3$, $-CHX^3_2$, $-CH_2X^3$, $-CN$, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{8B}$ is hydrogen, $-CH_3$, $-CX^4_3$, $-CHX^4_2$, $-CH_2X^4$, $-CN$, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, $-CX^5_3$, $-CHX^5_2$, $-CH_2X^5$, $-OCH_3$, $-SCH_3$, $-NHCH_3$, $-CN$, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is hydrogen, $-CX^6_3$, $-CHX^6_2$, $-CH_2X^6$, $-OCH_3$, $-SCH_3$, $-NHCH_3$, $-CN$, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is hydrogen, $-CX^7_3$, $-CHX^7_2$, $-CH_2X^7$, $-OCH_3$, $-SCH_3$, $-NHCH_3$, $-CN$, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $X^3$, $X^4$, $X^5$, $X^6$ and $X^7$ are independently halogen.

Embodiment 70

The compound of one of embodiments 1 to 49, wherein $R^7$ is $-OR^{7A}$; $R^{7A}$ is a polymerase-compatible cleavable moiety; and the polymerase-compatible cleavable moiety is:

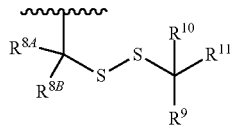

$R^{8A}$ is hydrogen, $-CH_3$, $-CX^3_3$, $-CHX^3_2$, $-CH_2X^3$, $-CN$, -Ph, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl;

$R^{8B}$ is hydrogen, $-CH_3$, $-CX^4_3$, $-CHX^4_2$, $-CH_2X^4$, $-CN$, -Ph, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl;

$R^9$ is hydrogen, $-CX^5_3$, $-CHX^5_2$, $-CH_2X^5$, $-OCH_3$, $-SCH_3$, $-NHCH_3$, $-CN$, -Ph, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl;

$R^{10}$ is hydrogen, —$CX^6_3$, —$CHX^6_2$, —$CH_2X^6$, —$OCH_3$, —$SCH_3$, —$NHCH_3$, —CN, -Ph, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl;

$R^{11}$ is hydrogen, —$CX^7_3$, —$CHX^7_2$, —$CH_2X^7$, —$OCH_3$, —$SCH_3$, —$NHCH_3$, —CN, -Ph, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; and $X^3$, $X^4$, $X^5$, $X^6$ and $X^7$ are independently halogen.

Embodiment 71

The compound of one of embodiments 1 to 70, wherein $R^7$ is -$OR^{7A}$; $R^{7A}$ is a polymerase-compatible cleavable moiety; and the polymerase-compatible cleavable moiety is:

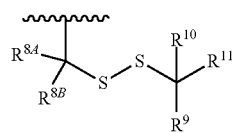

$R^{8A}$, $R^{8B}$, $R^{10}$, and $R^{11}$ are independently hydrogen or unsubstituted methyl.

Embodiment 72

The compound of one of embodiments 1 to 70, wherein $R^7$ is —$OR^{7A}$; $R^{7A}$ is a polymerase-compatible cleavable, moiety; and the polymerase-compatible cleavable moiety is:

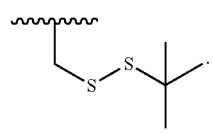 [SMILES: *CSSC(C)(C)C]

Embodiment 73

The compound of embodiment 1, having the formula:

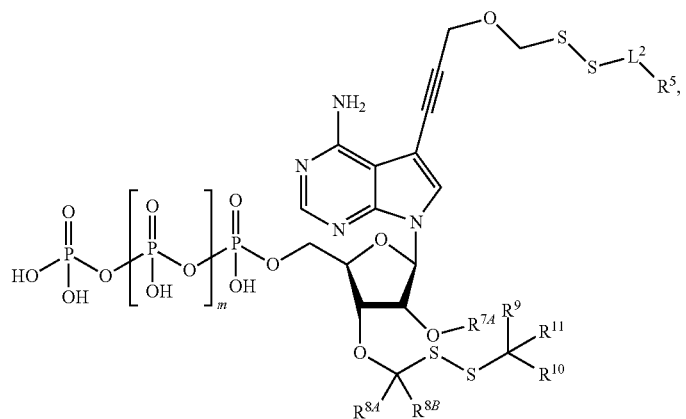

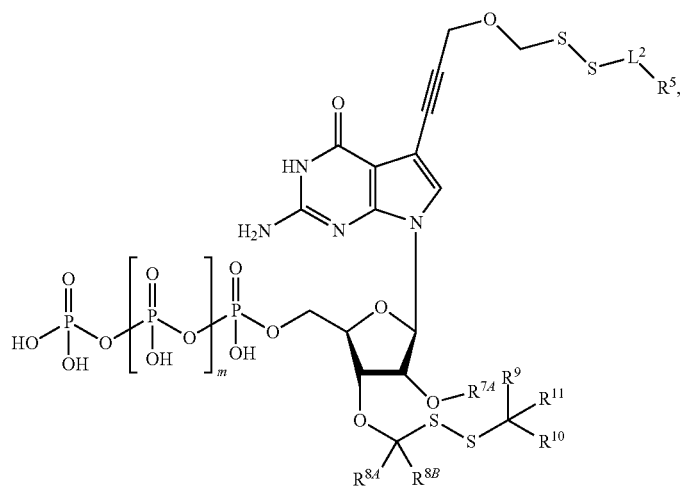

-continued
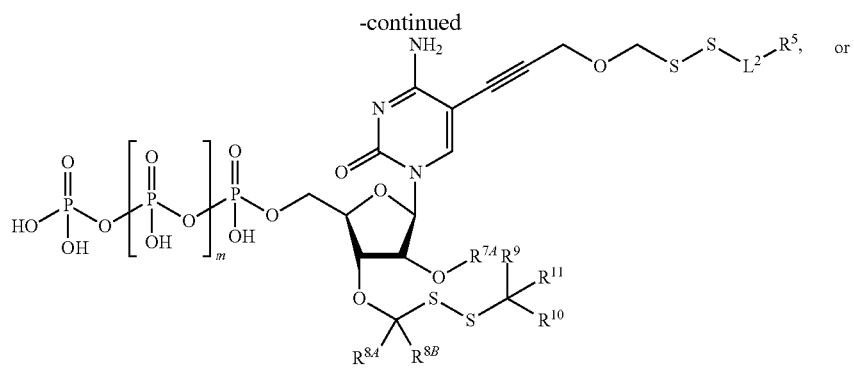
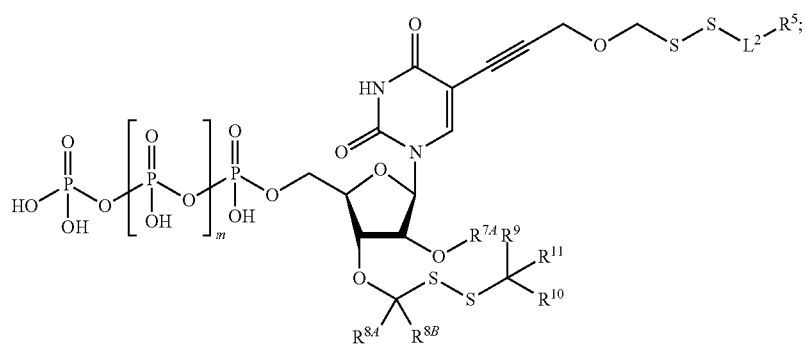
wherein m is an integer from 1 to 4.
Embodiment 74
The compound of embodiment 1, having the formula:
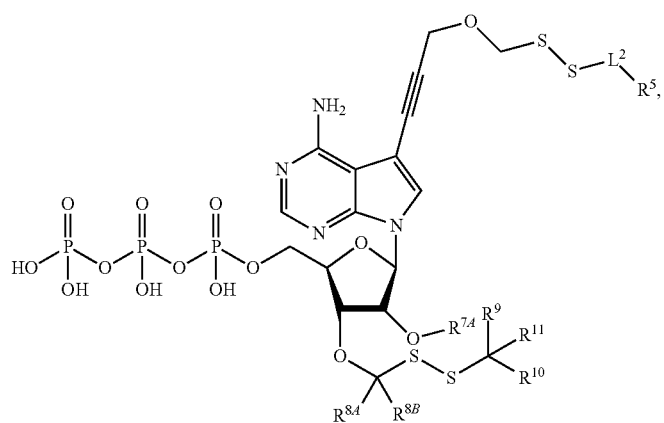

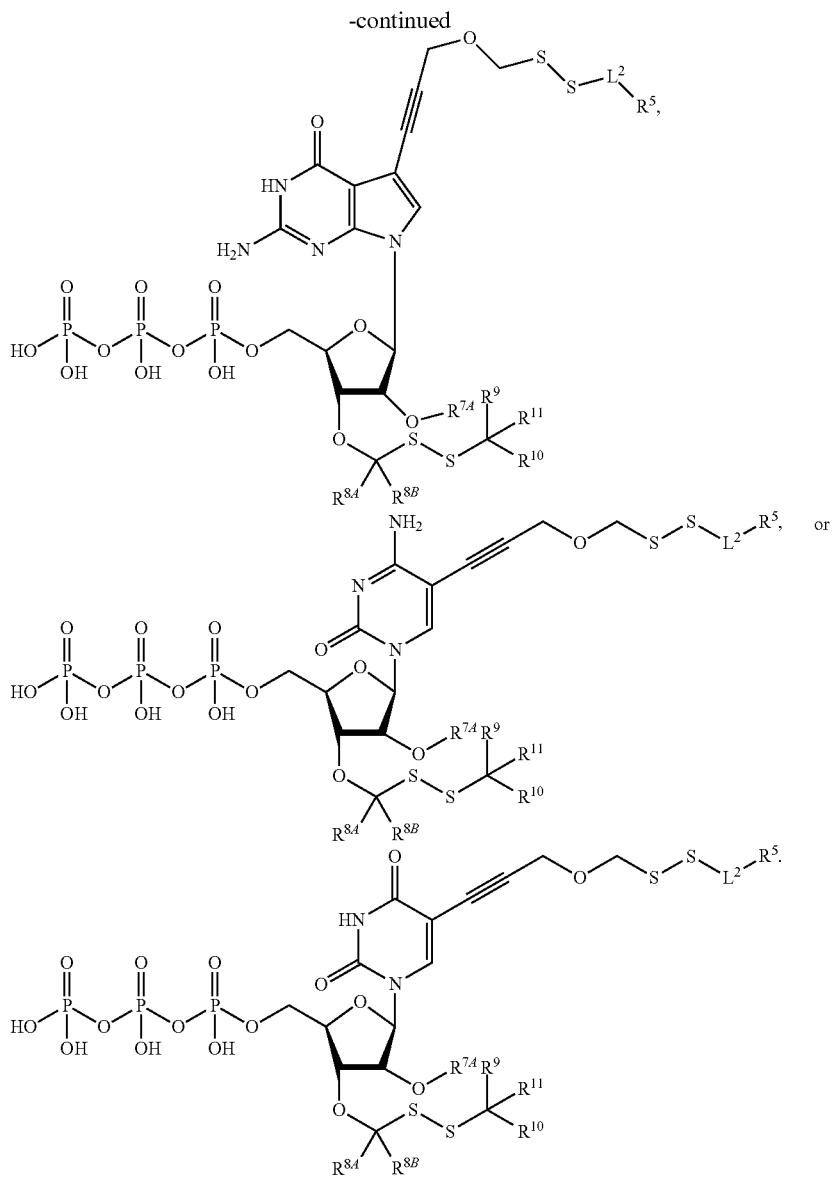

Embodiment 75

The compound of one of embodiments 73 to 74, wherein —$CR^9R^{10}R^{11}$ is unsubstituted methyl, unsubstituted ethyl, unsubstituted propyl, unsubstituted isopropyl, unsubstituted butyl, or unsubstituted tert-butyl.

Embodiment 76

The compound of one of embodiments 73 to 74, wherein $R^9$ is hydrogen, —$C(CH_3)_3$, —$CH(CH_3)_2$, —$CH_2CH_2CH_3$, —$CH_2CH_3$, —$CH_3$, —$OC(CH_3)_3$, —$OCH(CH_3)_2$, —$OCH_2CH_2CH_3$, —$OCH_2CH_3$, —$OCH_3$, —$SC(CH_3)_3$, —$SCH(CH_3)_2$, —$SCH_2CH_2CH_3$, —$SCH_2CH_3$, —$SCH_3$, —$NHC(CH_3)_3$, —$NHCH(CH_3)_2$, —$NHCH_2CH_2CH_3$, —$NHCH_2CH_3$, —$NHCH_3$, or -Ph.

Embodiment 77

The compound of one of embodiments 73 to 74, wherein $R^{10}$ is hydrogen, —$C(CH_3)_3$, —$CH(CH_3)_2$, —$CH_2CH_2CH_3$, —$CH_2CH_3$, —$CH_3$, —$OC(CH_3)_3$, —$OCH(CH_3)_2$, —$OCH_2CH_2CH_3$, —$OCH_2CH_3$, —$OCH_3$, —$SC(CH_3)_3$, —$SCH(CH_3)_2$, —$SCH_2CH_2CH_3$, —$SCH_2CH_3$, —$SCH_3$, —$NHC(CH_3)_3$, —$NHCH(CH_3)_2$, —$NHCH_2CH_2CH_3$, —$NHCH_2CH_3$, —$NHCH_3$, or -Ph.

Embodiment 78

The compound of one of embodiments 73 to 74, wherein $R^{11}$ is hydrogen, —$C(CH_3)_3$, —$CH(CH_3)_2$, —$CH_2CH_2CH_3$, —$CH_2CH_3$, —$CH_3$, —$OC(CH_3)_3$, —$OCH(CH_3)_2$, —$OCH_2CH_2CH_3$, —$OCH_2CH_3$, —$OCH_3$, —$SC(CH_3)_3$, —$SCH(CH_3)_2$, —$SCH_2CH_2CH_3$, —$SCH_2CH_3$, —$SCH_3$, —$NHC(CH_3)_3$, —$NHCH(CH_3)_2$, —$NHCH_2CH_2CH_3$, —$NHCH_2CH_3$, —$NHCH_3$, or -Ph.

Embodiment 79

The compound of one of embodiments 73 to 74, wherein $R^{8A}$ is independently hydrogen, deuterium, —$C(CH_3)_3$, —CH(CH₃)₂, —CH₂CH₂CH₃, —CH₂CH₃, —CH₃, —CX³₃, —CHX³₂, —CH₂X³, —CN, or -Ph.

Embodiment 80

The compound of one of embodiments 73 to 74, wherein R⁸ᴮ independently is independently hydrogen, deuterium, —C(CH₃)₃, —CH(CH₃)₂, —CH₂CH₂CH₃, —CH₂CH₃, —CH₃, —CX⁴₃, —CHX⁴₂, —CH₂X⁴, —CN, or -Ph.

Embodiment 81

The compound of one of embodiments 73 to 80, wherein —R⁷ᴬ is hydrogen.

Embodiment 82

The compound of one of embodiments 73 to 80, wherein —R⁷ᴬ is

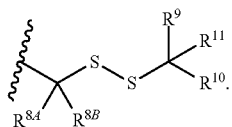

Embodiment 83

The compound of one of embodiments 73 to 80, wherein —R⁷ᴬ is

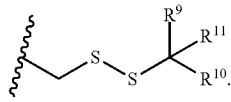

Embodiment 84

The compound of one of embodiments 73 to 80, wherein —R⁷ᴬ is

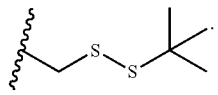

Embodiment 85

The compound of one of embodiments 73 to 85 having the formula:

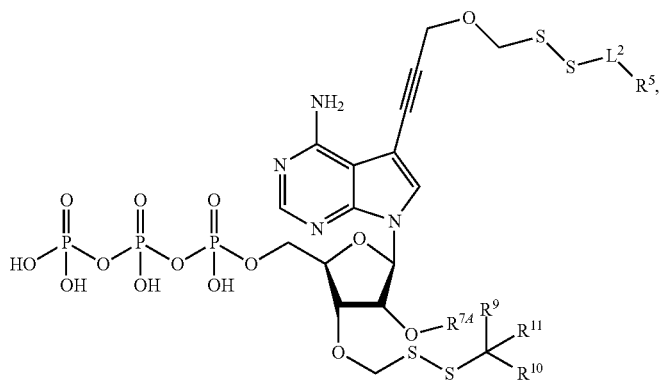

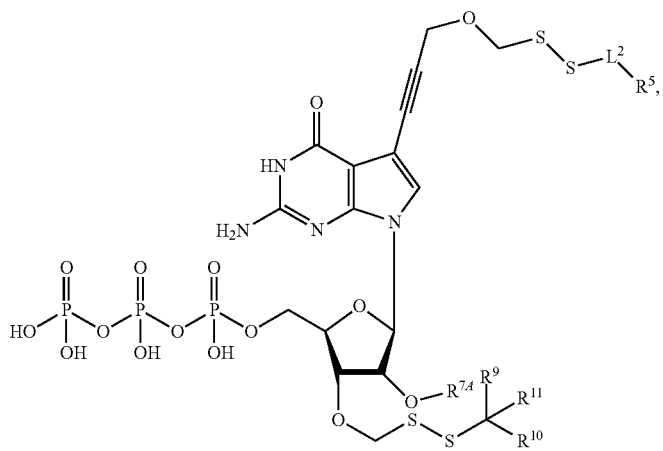

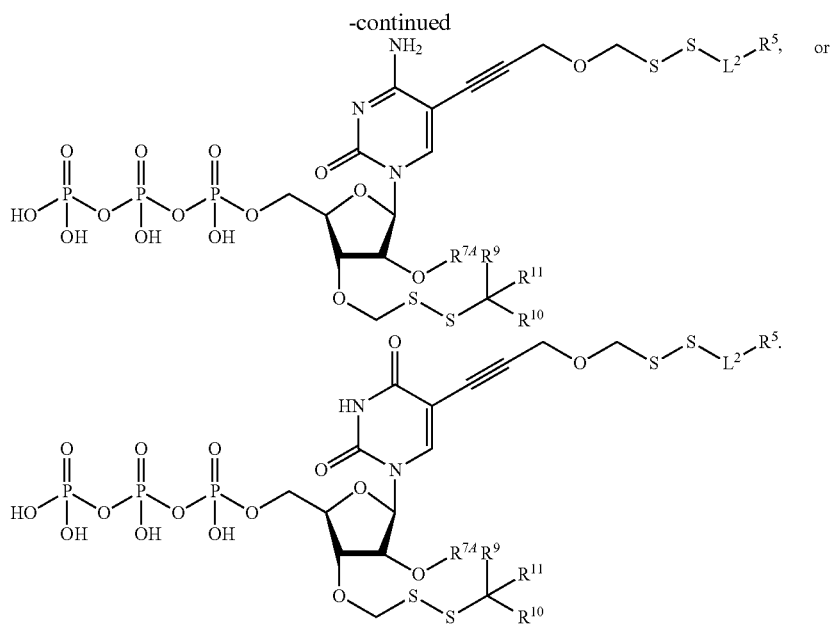
Embodiment 86
The compound of one of embodiments 73 to 85 having the formula:
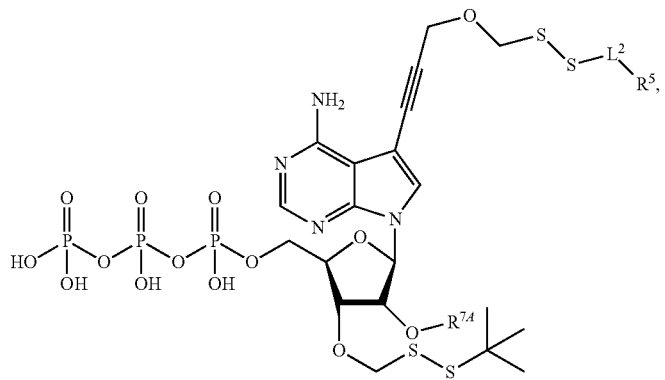
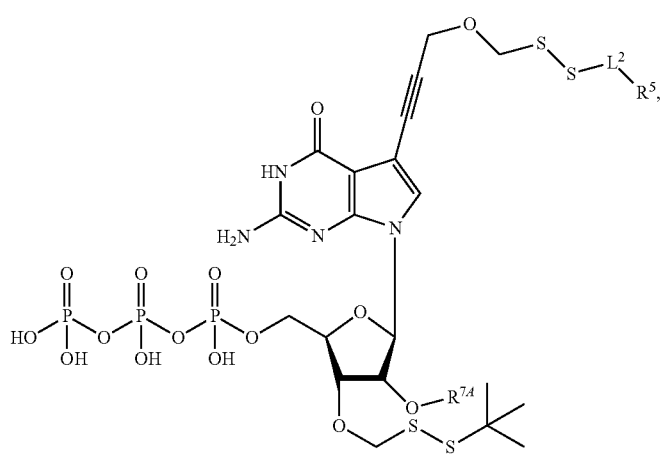

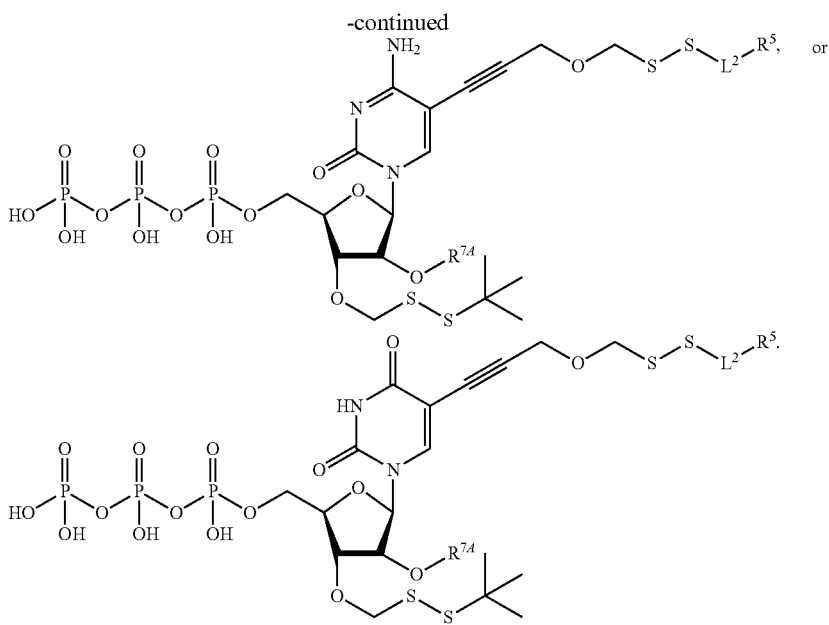
Embodiment 87
The compound of embodiment 1, having the formula:
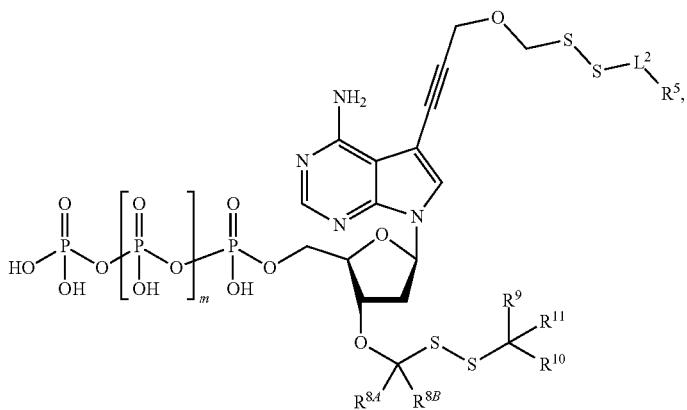
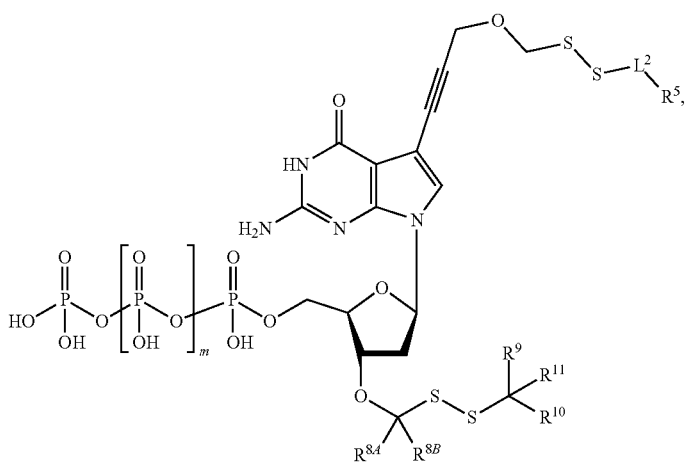

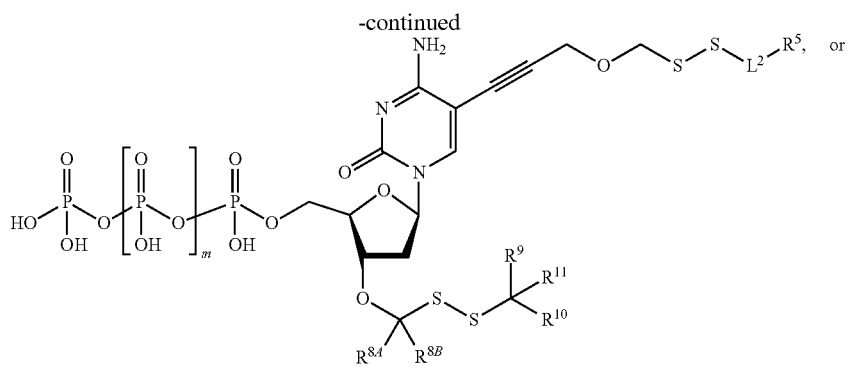
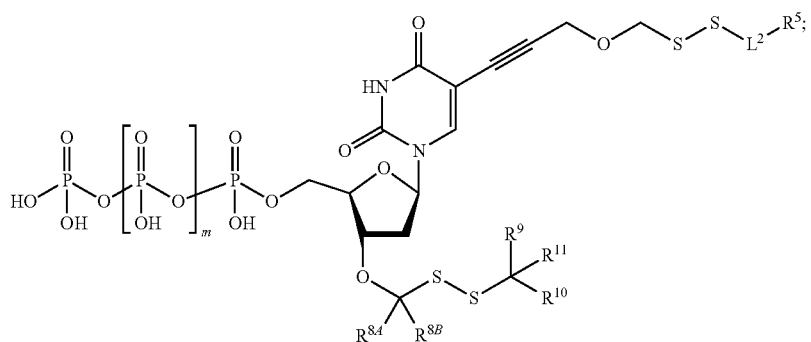
wherein m is an integer from 1 to 4.
Embodiment 88
The compound of embodiment 1, having the formula:
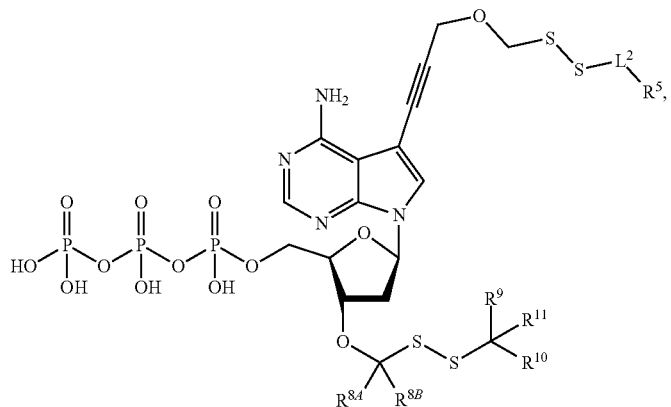

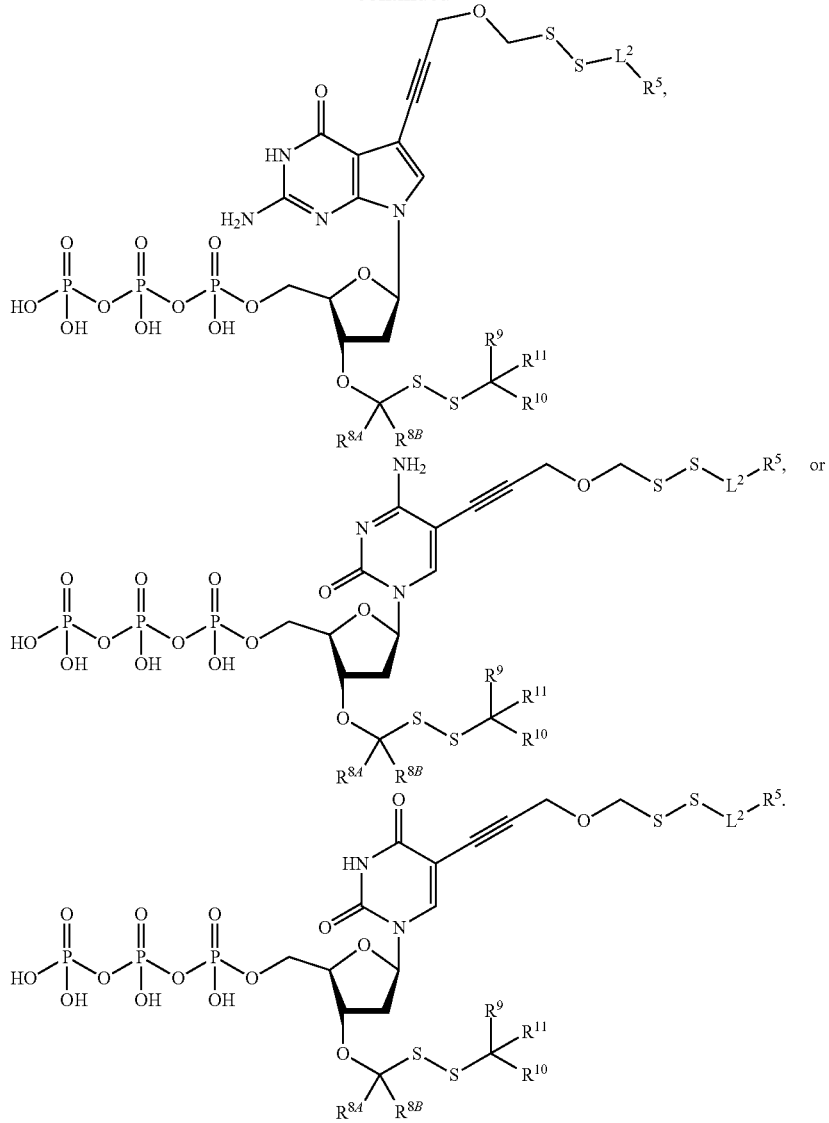

Embodiment 89

The compound of one of embodiments 87 to 88, wherein —CR$^9$R$^{10}$R$^{11}$ is unsubstituted methyl, unsubstituted ethyl, unsubstituted propyl, unsubstituted isopropyl, unsubstituted butyl, or unsubstituted tert-butyl.

Embodiment 90

The compound of one of embodiments 87 to 88, wherein R$^9$ is independently hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, or -Ph.

Embodiment 91

The compound of one of embodiments 87 to 88, wherein R$^{10}$ is independently hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, or -Ph.

Embodiment 92

The compound of one of embodiments 87 to 88, wherein R$^{10}$ is independently hydrogen, —C(CH$_3$)$_3$, —CH(CH$_3$)$_2$, —CH$_2$CH$_2$CH$_3$, —CH$_2$CH$_3$, —CH$_3$, —OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$; —SCH$_3$, —NHC(CH$_3$)$_3$, —NHCH(CH$_3$)$_2$, —NHCH$_2$CH$_2$Cl$^{-1}$$_3$, —NHCH$_2$CH$_3$, —NHCH$_3$, or -Ph.

Embodiment 93

The compound of one of embodiments 87 to 88, wherein R$^{8B}$ is independently hydrogen, deuterium, —C(CH$_3$)$_3$,

333
—CH(CH$_3$)$_2$, —CH$_2$CH$_2$CH$_3$, —CH$_2$CH$_3$, —CH$_3$, —CX$^3$$_3$, —CHX$^3$$_2$, —CH$_2$X$^3$, —CN or -Ph.
Embodiment 94
The compound of one of embodiments 87 to 88, wherein wherein R$^{8B}$ is independently hydrogen, deuterium,
334
—C(CH$_3$)$_3$, —CH$_2$CH$_2$CH$_3$, —CH$_2$CH$_3$, —CH$_3$, —CX$^4$$_3$, —CHX$^4$$_2$, —CH$_2$X$^4$, —CN, or -Ph.
Embodiment 95
The compound of one of embodiments 87 to 94 having the formula:
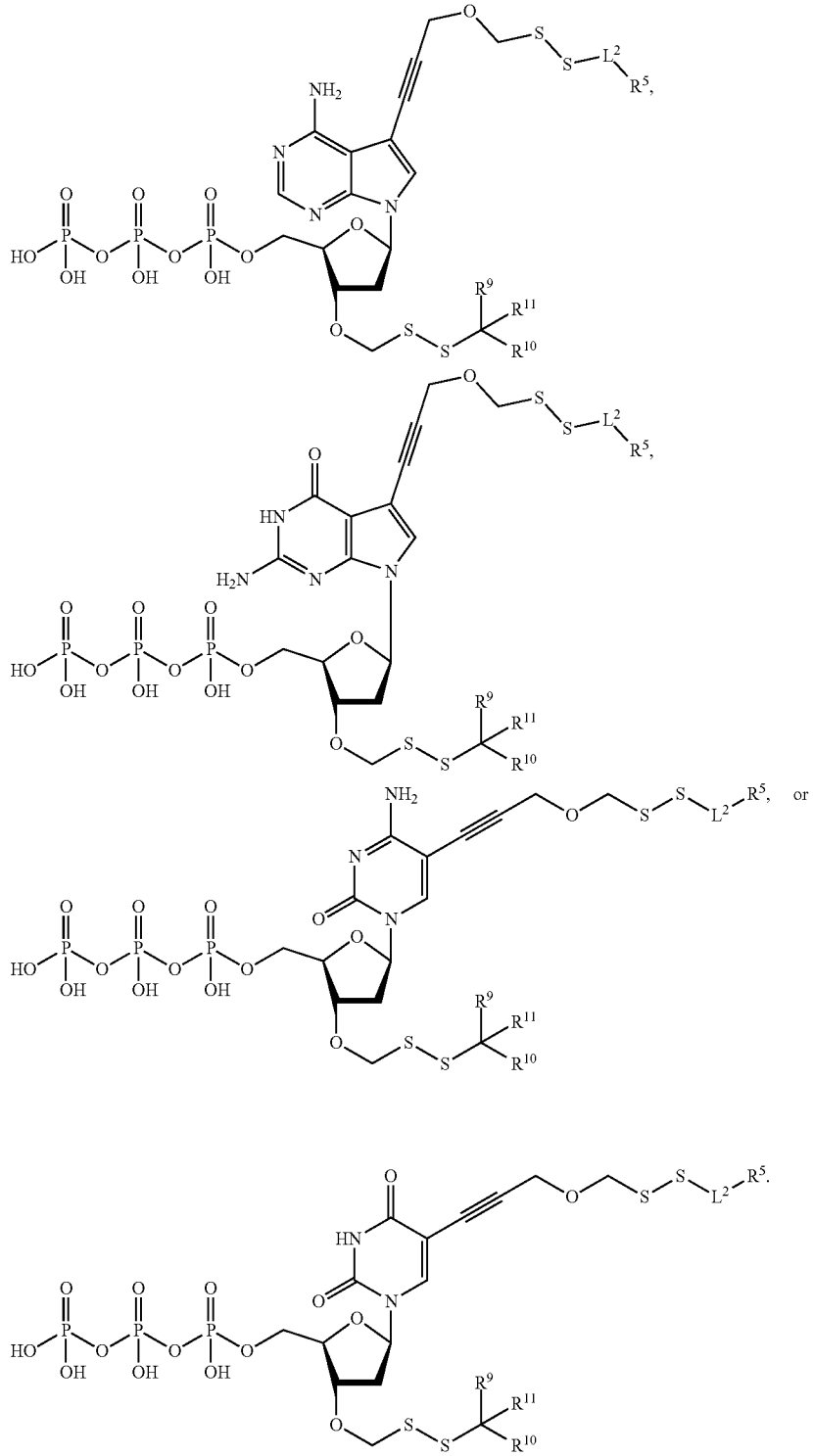

Embodiment 96
The compound of one of embodiments 87 to 95 having the formula:
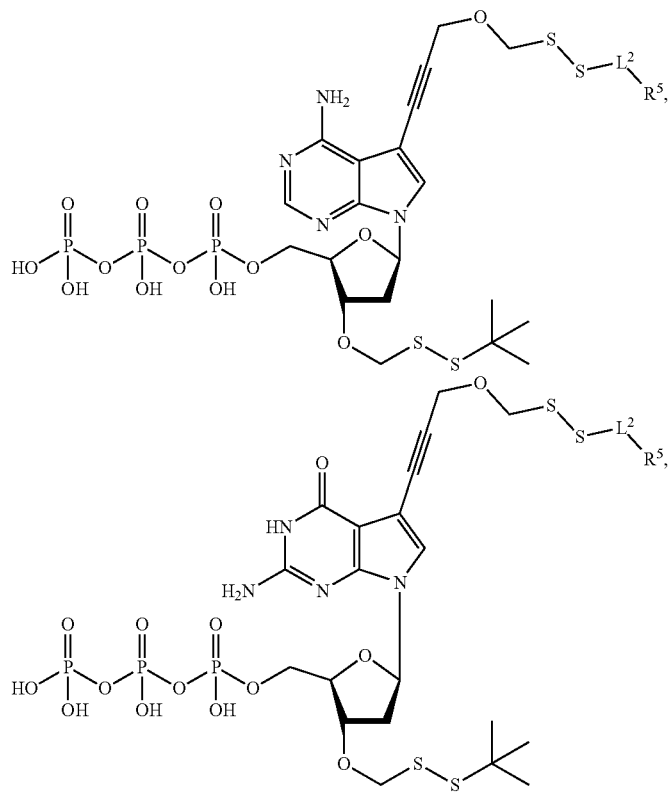
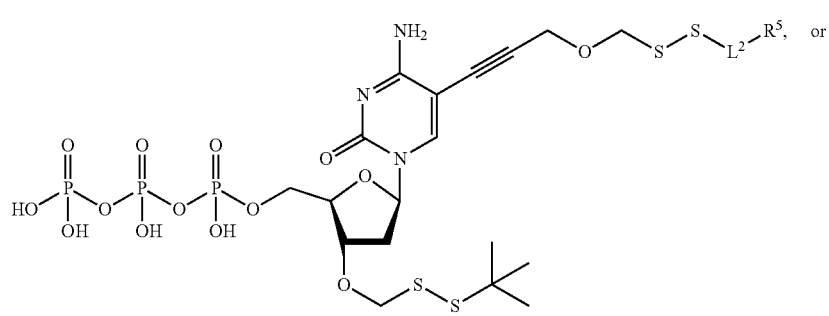
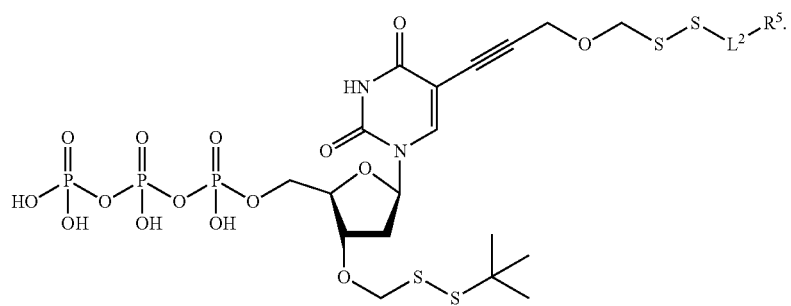

Embodiment 97
The compound of one of embodiments 77 to 96, wherein
-L²-R⁵ is
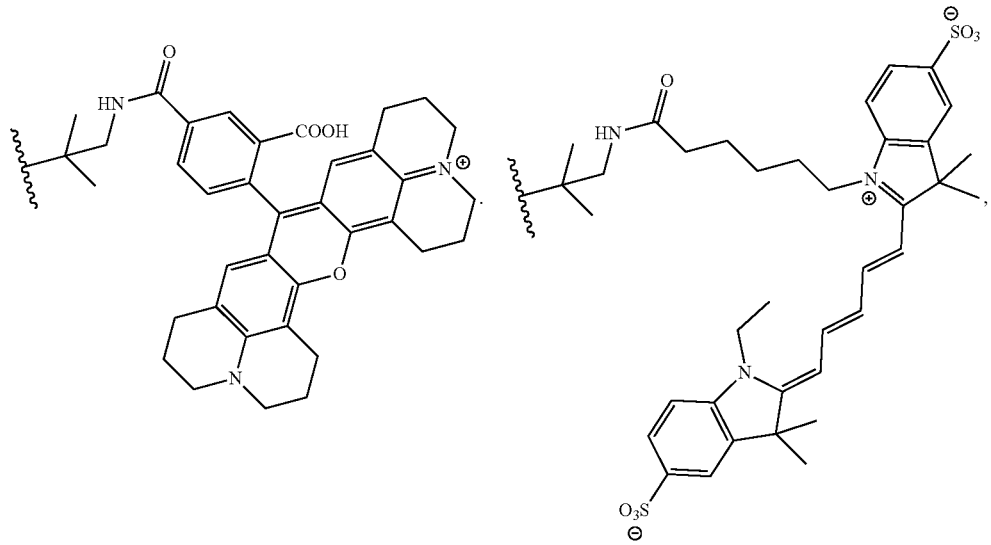
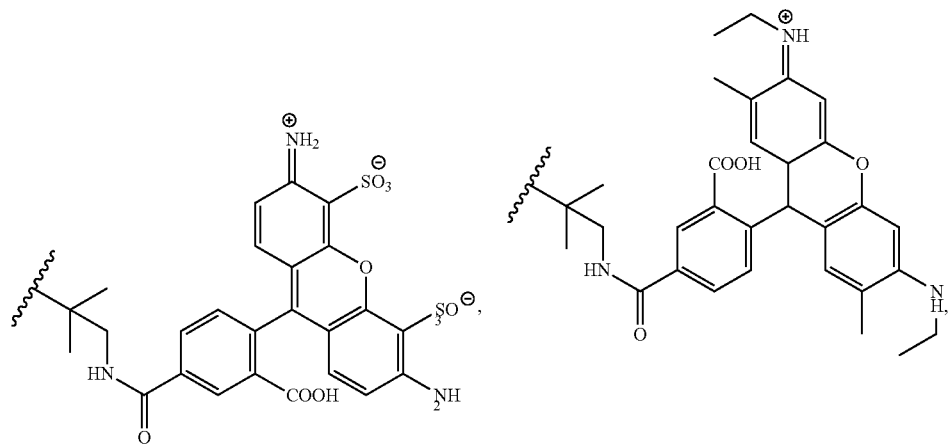
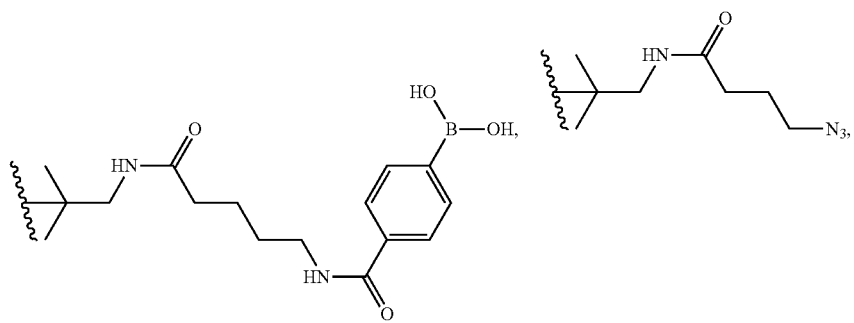

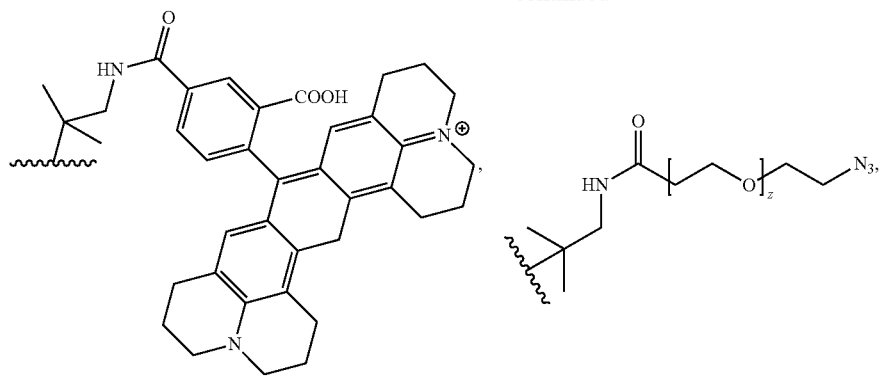
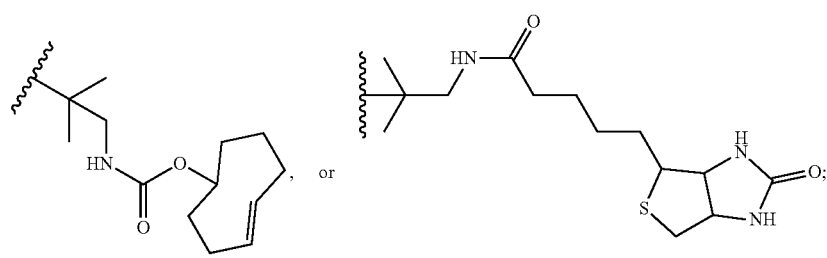
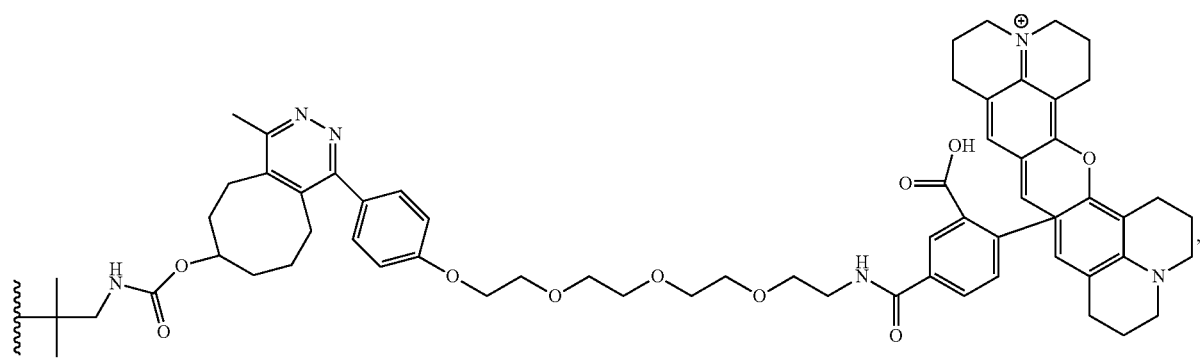
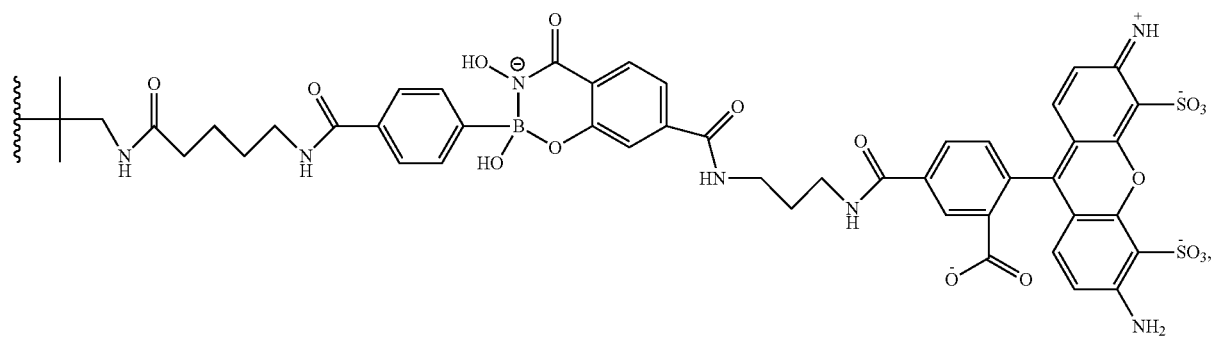

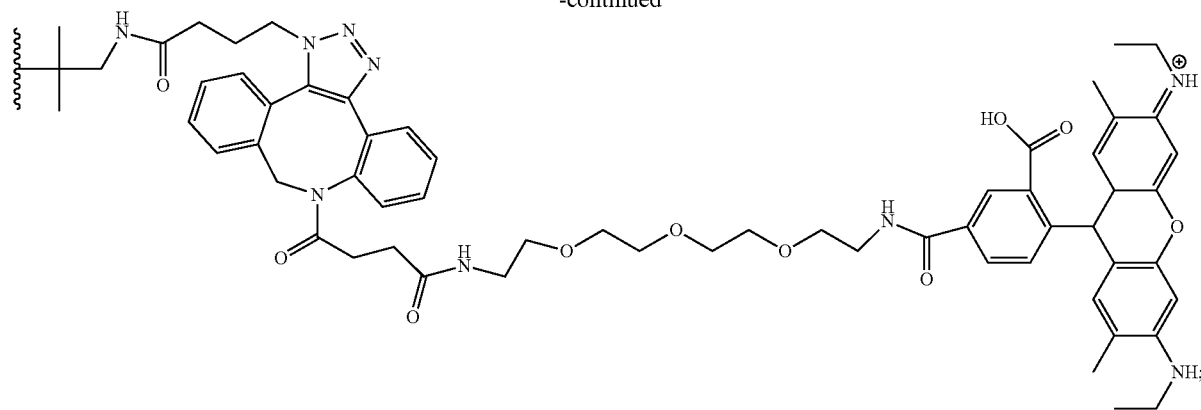
and z is an integer from 0 to 10.
Embodiment 98
The compound of embodiment 1, having the formula:
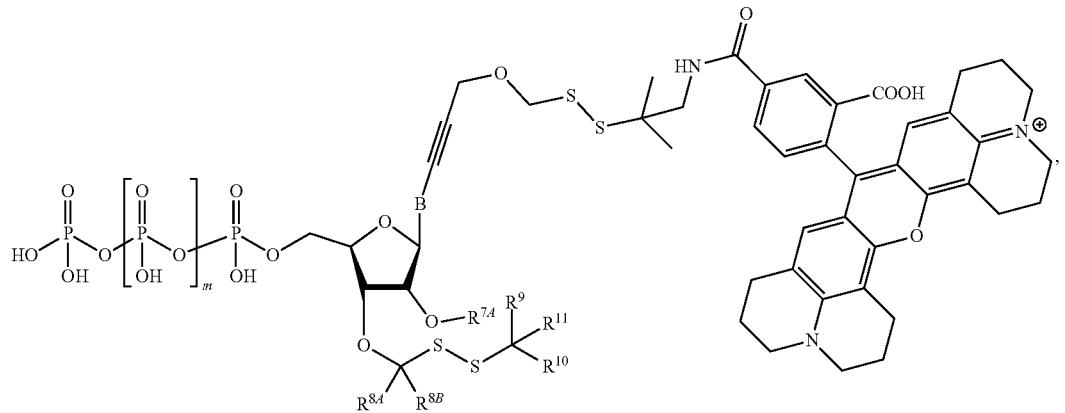
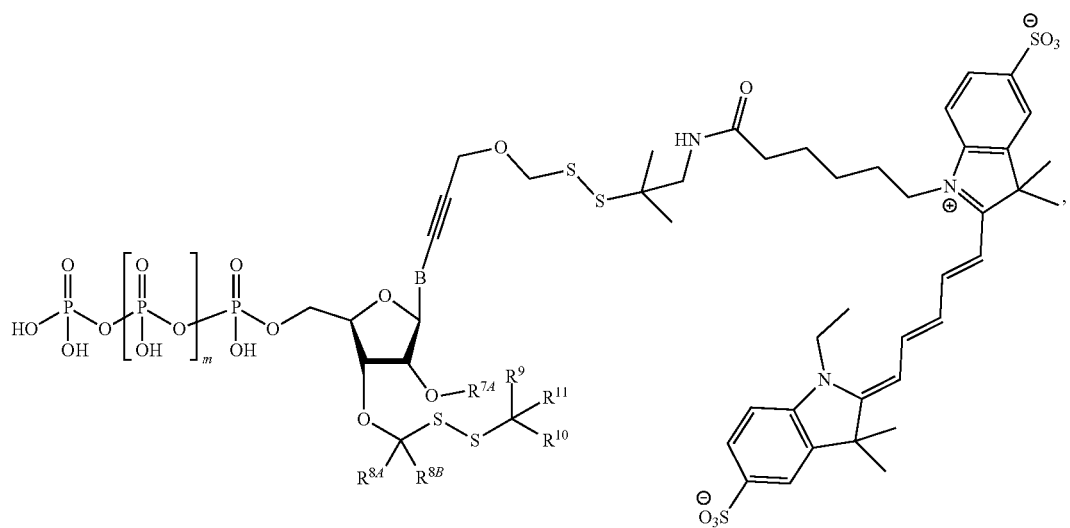

343
344
-continued
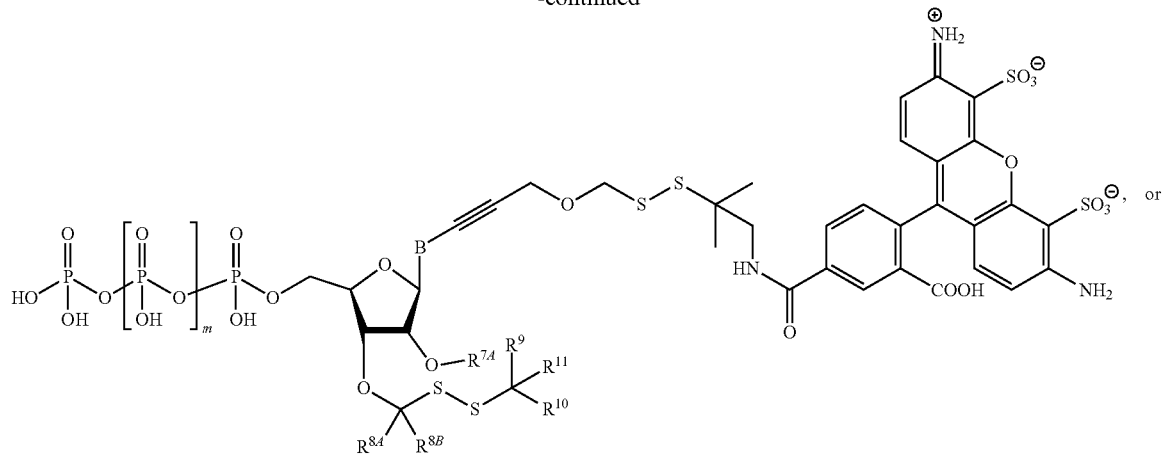
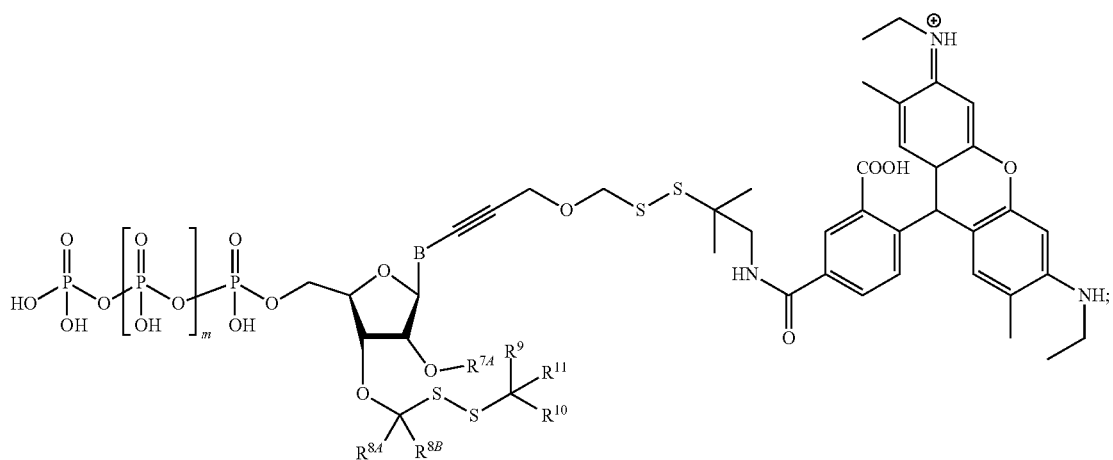
wherein m is an integer from 1 to 4.
Embodiment 99
The compound of embodiment 1, having the formula:
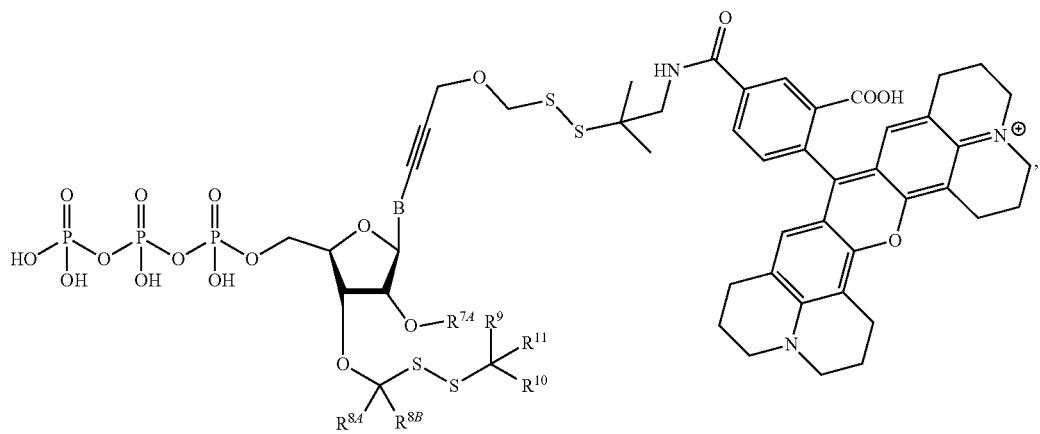

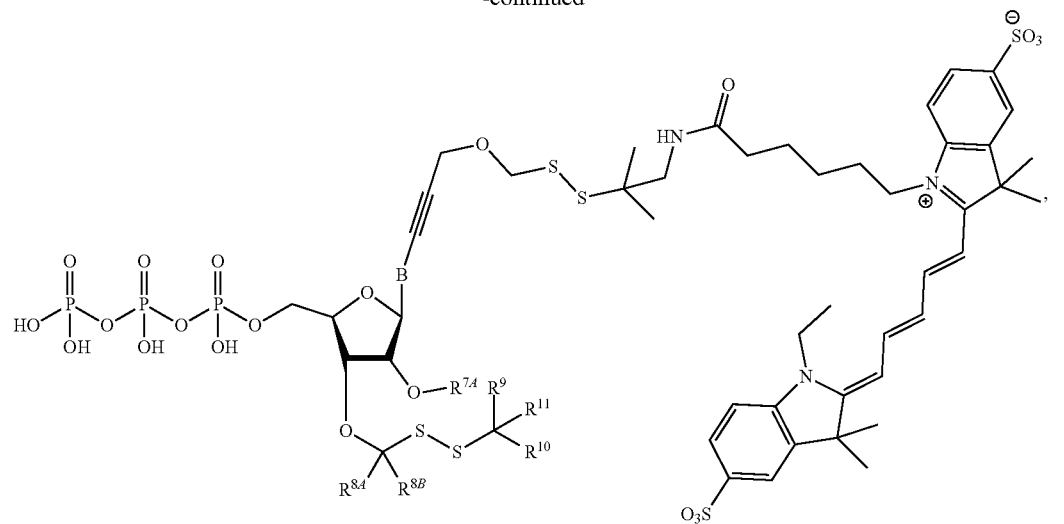
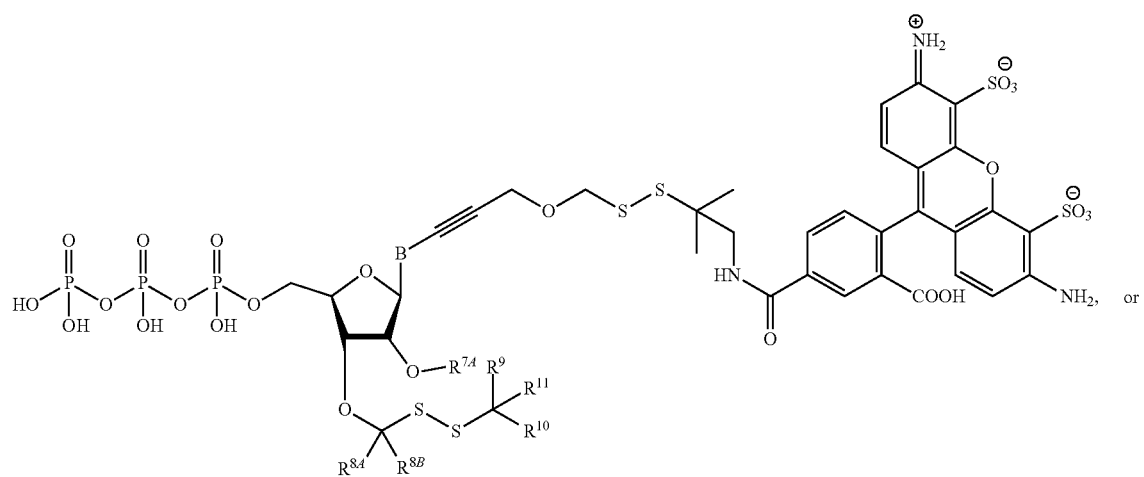
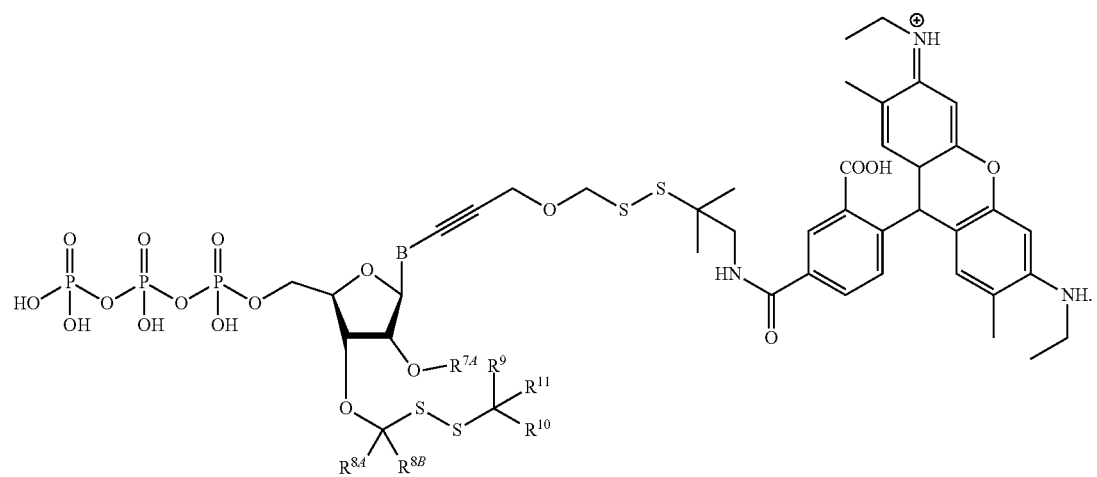

Embodiment 100

The compound of one of embodiments 98 to 99, wherein —CR$^9$R$^{10}$R$^{11}$ is unsubstituted methyl, unsubstituted ethyl, unsubstituted propyl, unsubstituted isopropyl, unsubstituted butyl, or unsubstituted tert-butyl.

Embodiment 101

The compound of one of embodiments 98 to 99, wherein R$^9$ is hydrogen, —C(CH$_3$)$_3$, —CH(CH$_3$)$_2$, —CH$_2$CH$_2$CH$_3$, —CH$_2$CH$_3$, —CH$_3$, —OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, or -Ph.

Embodiment 102

The compound of one of embodiments 98 to 99, wherein R$^{11}$ is hydrogen, —C(CH$_3$)$_3$, —CH(CH$_3$)$_2$, —CH$_2$CH$_2$CH$_3$, —CH$_2$CH$_3$, —CH$_3$, —OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, or -Ph.

Embodiment 103

The compound of one of embodiments 98 to 99, wherein R$^{11}$ is hydrogen, —C(CH$_3$)$_3$, —CH(CH$_3$)$_2$, —CH$_2$CH$_2$CH$_3$, —CH$_2$CH$_3$, —CH$_3$, —OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, or -Ph.

Embodiment 104

The compound of one of embodiments 98 to 99, wherein R$^{8A}$ is independently hydrogen, deuterium, —C(CH$_3$)$_3$, —CH(CH$_3$)$_2$, —CH$_2$CH$_2$CH$_3$, —CH$_2$CH$_3$, —CH$_3$, —CX$^3{}_3$, —CHX$^3{}_2$, —CH$_2$X$^3$, —CN, or -Ph.

Embodiment 105

The compound of one of embodiments 98 to 99, wherein R$^{8B}$ is independently hydrogen, deuterium, —C(CH$_3$)$_3$, —CH(CH$_3$)$_2$, —CH$_2$CH$_2$CH$_3$, —CH$_2$CH$_3$, —CH$_3$, —CX$^4{}_3$, —CHX$^4{}_2$, —CH$_2$X$^4$, —CN, or -Ph.

Embodiment 106

The compound of one of embodiments 98 to 105, wherein —R$^{7A}$ is hydrogen.

Embodiment 107

The compound of one of embodiments 98 to 105, wherein —R$^{7A}$ is

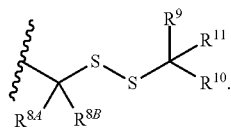

Embodiment 108

The compound of one of embodiments 98 to 105, wherein R$^{7A}$ is

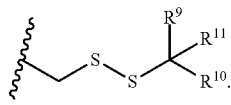

Embodiment 109

The compound of one of embodiments 98 to 105, wherein R$^{7A}$ is

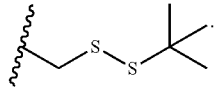 [SMILES: *CSSC(C)(C)C]

Embodiment 110

The compound of one of embodiments 98 to 105 having the formula:

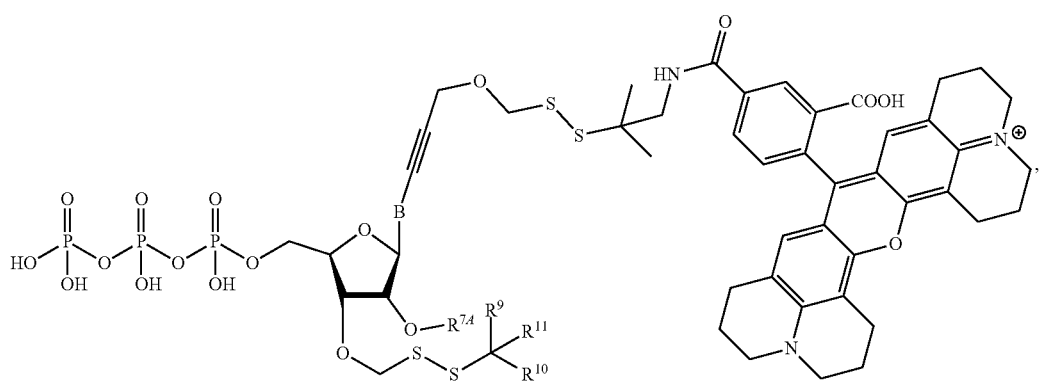

-continued
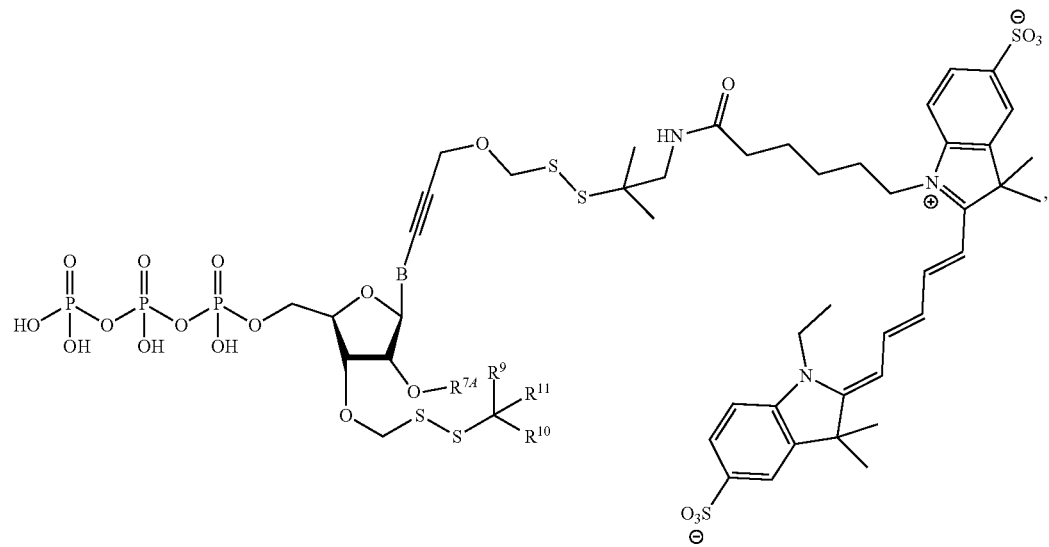
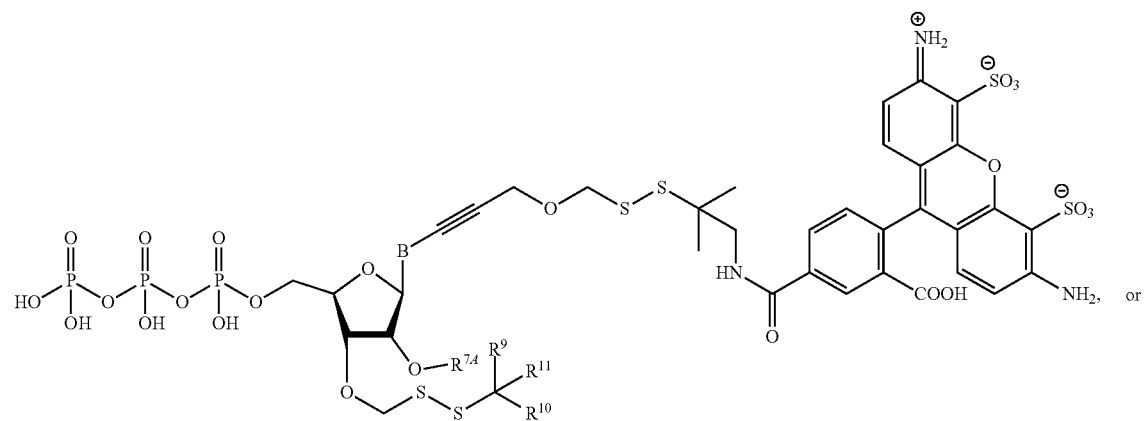
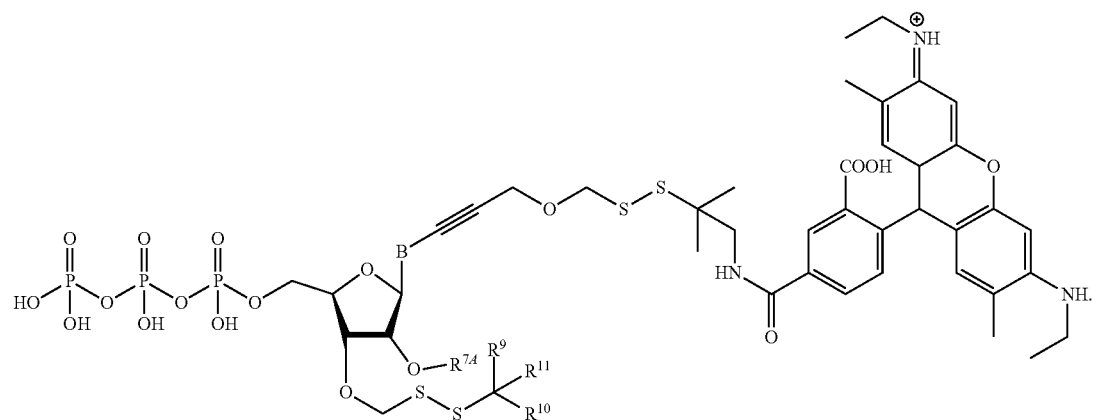

Embodiment 111
The compound of one of embodiments 115 to 126 having the formula:
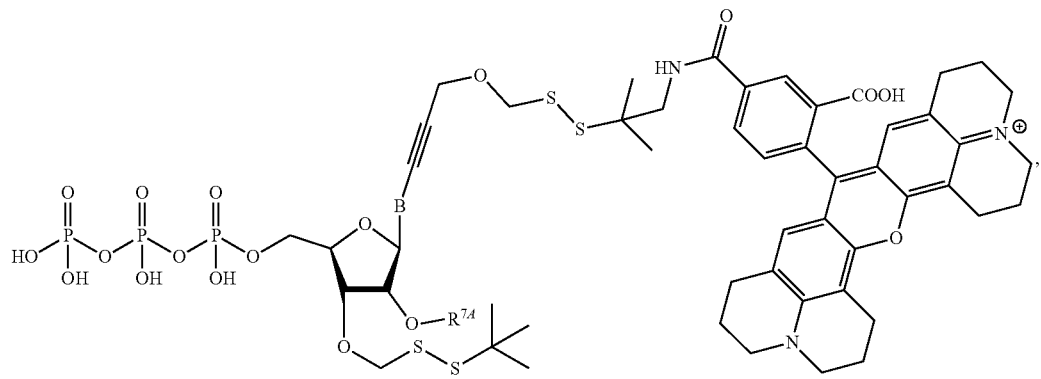
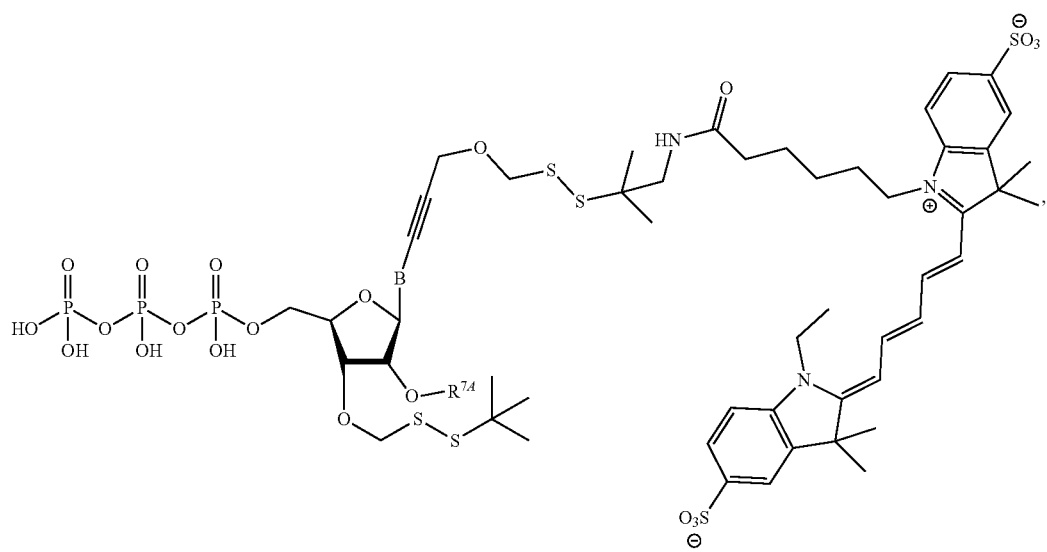
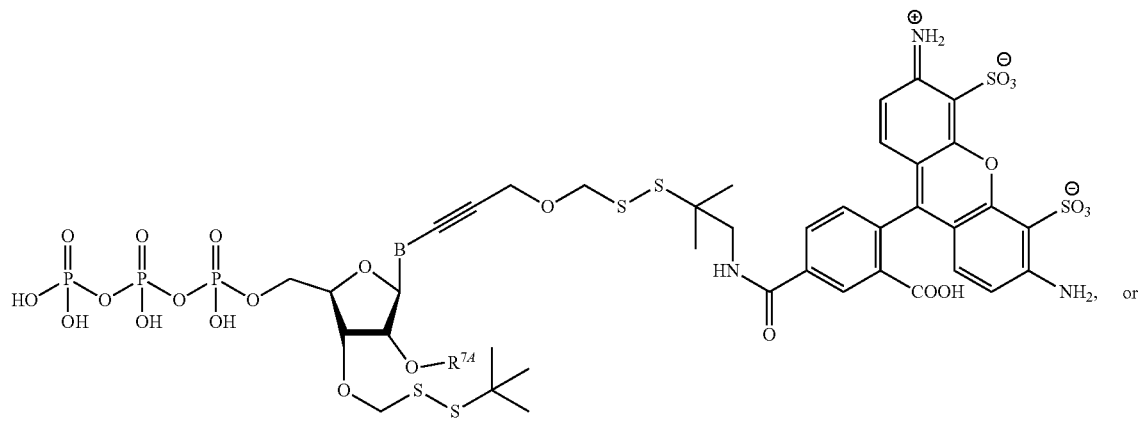

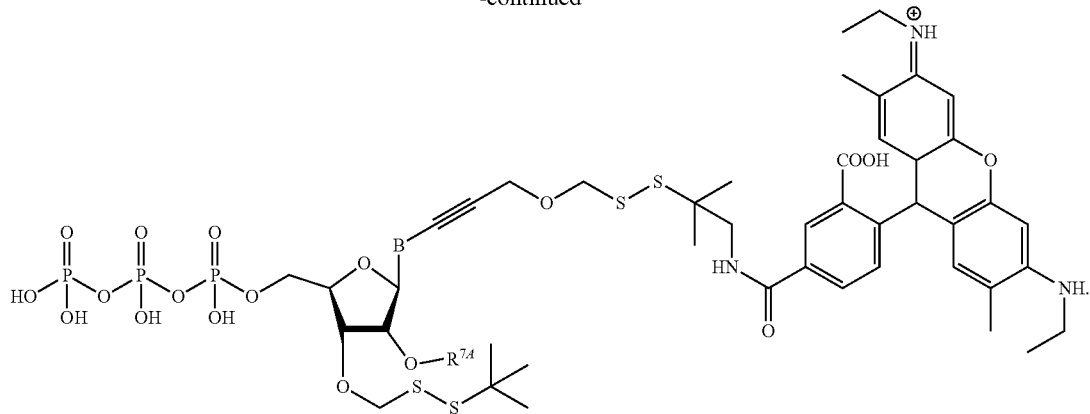
Embodiment 112
The compound of embodiment 1, having the formula:
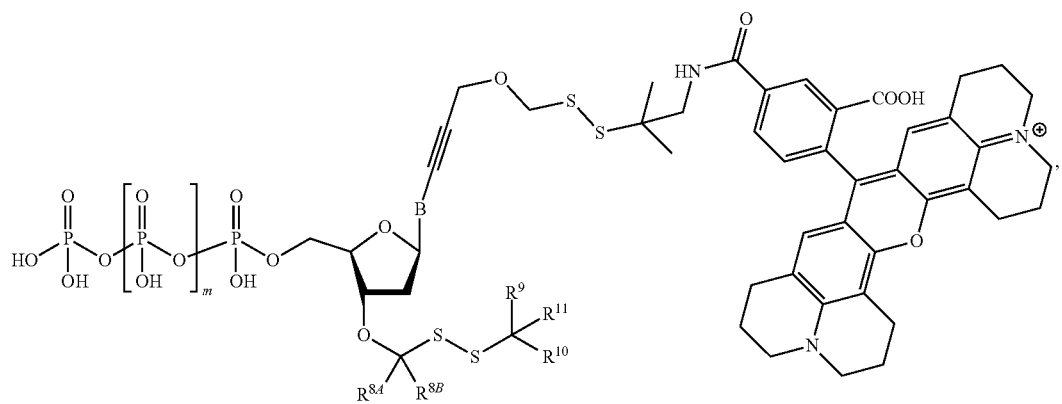
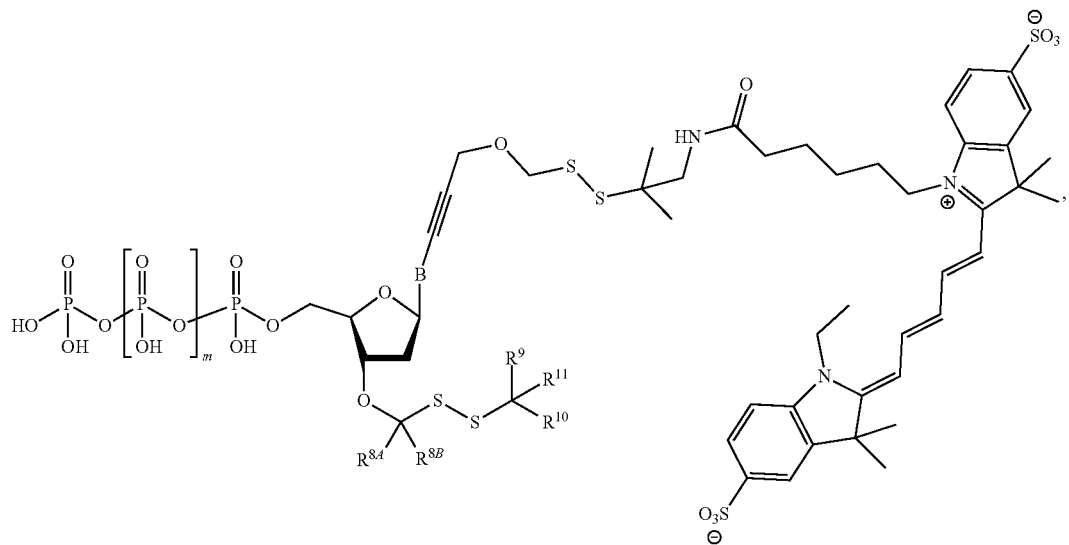

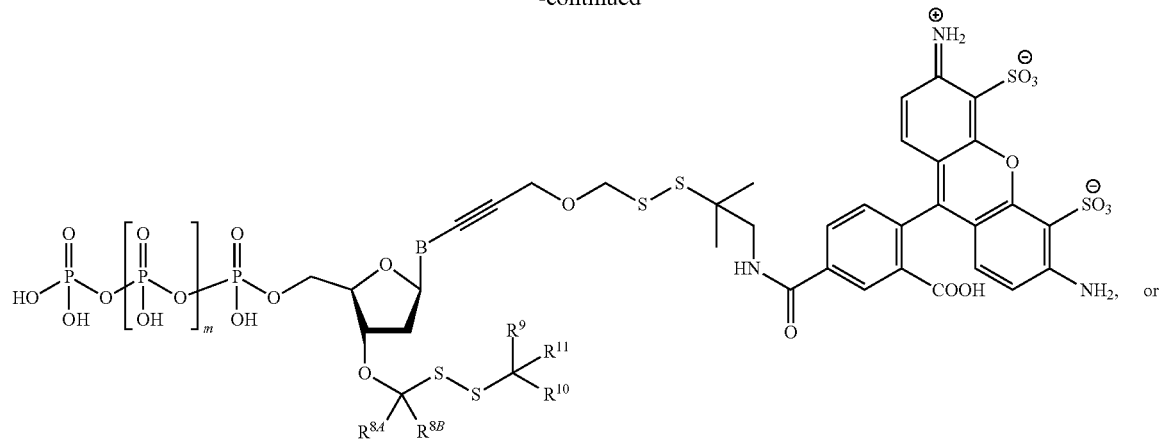
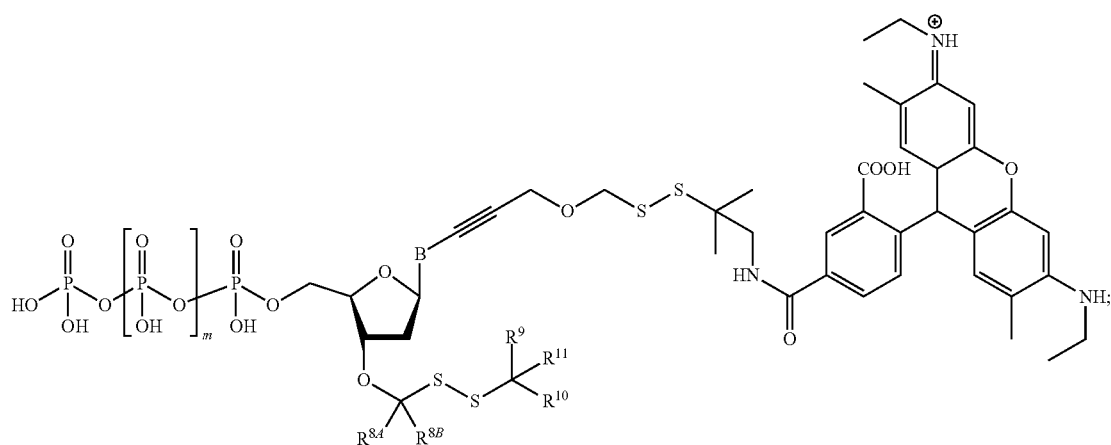
wherein m is an integer from 1 to 4.
Embodiment 113
The compound of embodiment 1, having the formula:
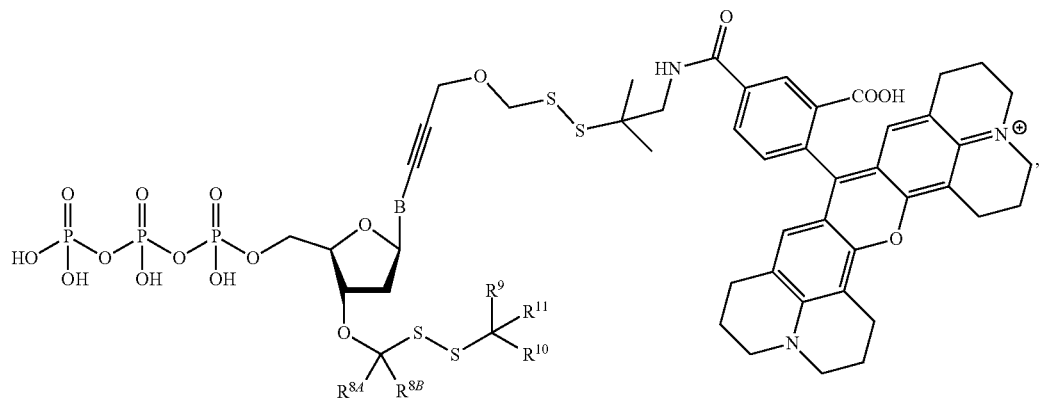

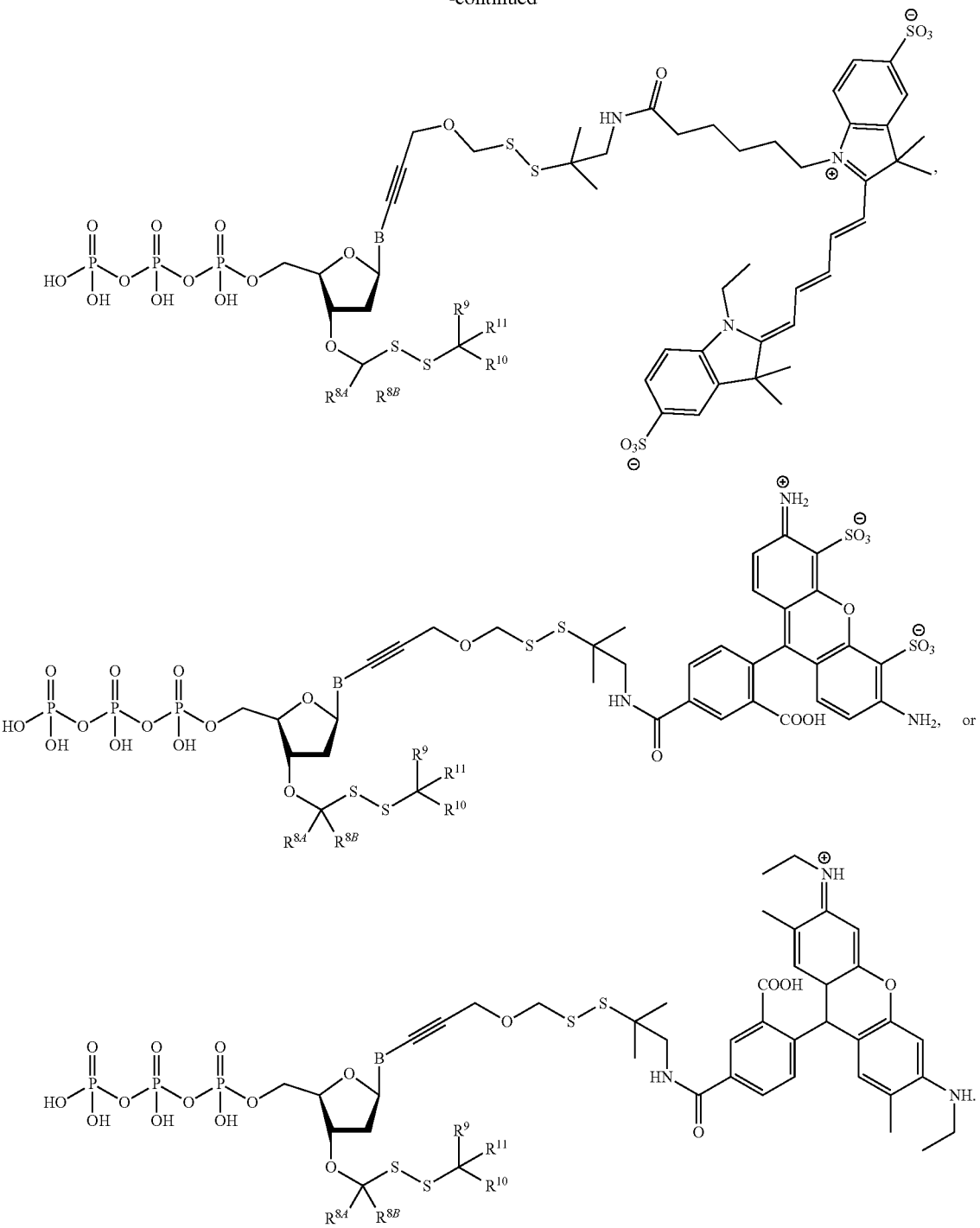

Embodiment 114

The compound of one of embodiments 129 to 130, wherein —CR$^9$R$^{10}$R$^{11}$ is unsubstituted methyl, unsubstituted ethyl, unsubstituted propyl, unsubstituted isopropyl, unsubstituted butyl, or unsubstituted ten-butyl.

Embodiment 115

The compound of one of embodiments 129 to 130, wherein R$^9$ is hydrogen, —C(CH$_3$)$_3$, —CH(CH$_3$)$_2$, —CH$_2$CH$_2$CH$_3$, —CH$_2$CH$_3$, —CH$_3$, —OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, or -Ph.

Embodiment 116

The compound of one of embodiments 129 to 130, wherein —R$^{10}$ is hydrogen, —C(CH$_3$)$_2$, —CH(CH$_3$)$_2$,

359

—CH₂CH₂CH₃, —CH₂CH₃, —CH₃, OC(CH₃)₃, —OCH(CH₃)₂, —OCH₂CH₂CH₃, —OCH₂CH₃, —OCH, —SC(CH₃)₃, —SCH(CH₃)₂, —SCH₂CH₂CH₃, —SCH₂CH₃, —SCH₃, —NHC(CH₃)₃, —NHCH(CH₃)₂, —NHCH₂CH₂CH₃, —NHCH₂CH₃, —NHCH₃, or -Ph.

Embodiment 117

The compound of one of embodiments 129 to 130, wherein —R¹¹ is hydrogen, —C(CH₃)₃, —CH(CH₃)₂, —CH₂CH₂CH₃, —CH₂CH₃, —CH₃, OC(CH₃)₃, —OCH(CH₃)₂, —OCH₂CH₂CH₃, —OCH₂CH₃, —OCH₃, —SC(CH₃)₃, —SCH(CH₃)₂, —SCH₂CH₂CH₃, —SCH₂CH₃. —SCH₃, —NHC(CH₃)₃, —NHCH(CH₃)₂, —NHCH₂CH₂CH₃, —NHCH₂CH₃, —NHCH₃, or -Ph.

360

Embodiment 118

The compound of one of embodiments 129 to 130, wherein R⁸ᴬ is hydrogen, deuterium, C(CH₃)₃, —CH(CH₃)₂, —CH₂CH₂CH₃, —CH₂CH₃, —CH₃, —CX³₃, —CHX³₂, —CH₂X³, —CN, or -Ph.

Embodiment 119

The compound of one of embodiments 129 to 130, wherein R⁸ᴮ is hydrogen, deuterium, —C(CH₃)₃, —CH(CH₃)₂, —CH₂CH₂CH₃, —CH₂CH₃, —CH₃, —CX⁴₃, —CHX⁴₂, —CH₂X⁴. —CN, or -Ph.

Embodiment 120

The compound of one of embodiments 129 to 136 having the formula:

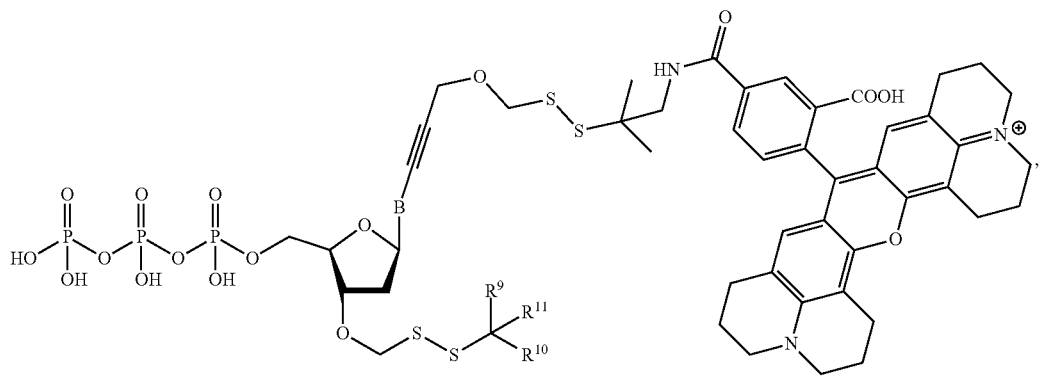

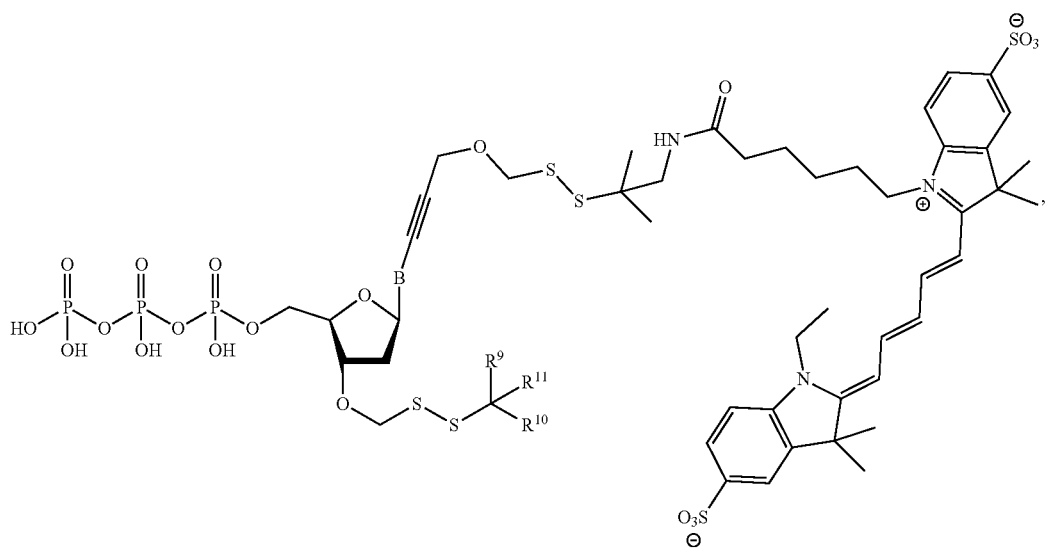

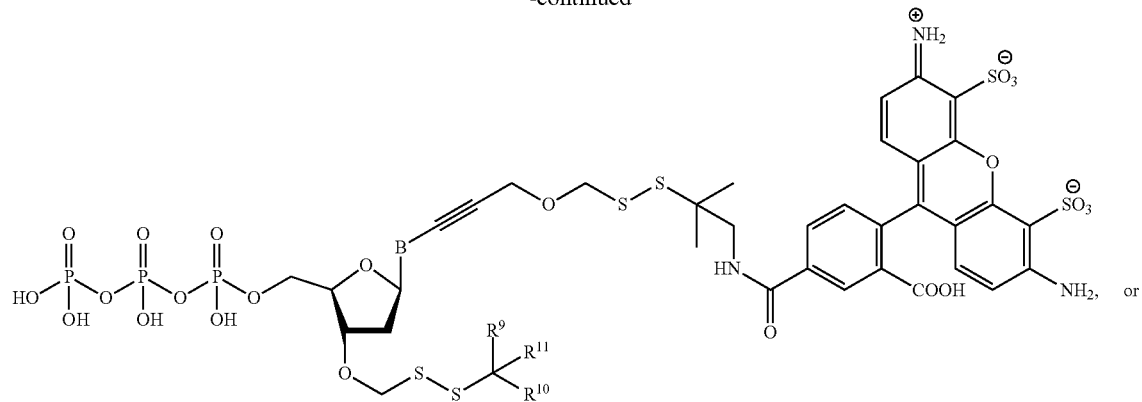
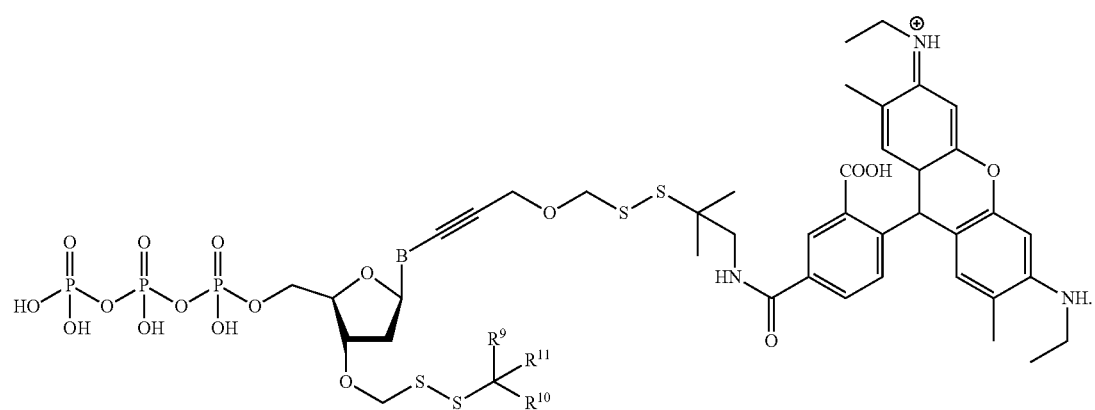
Embodiment 121
The compound of one of embodiments 115 to 122 having the formula:
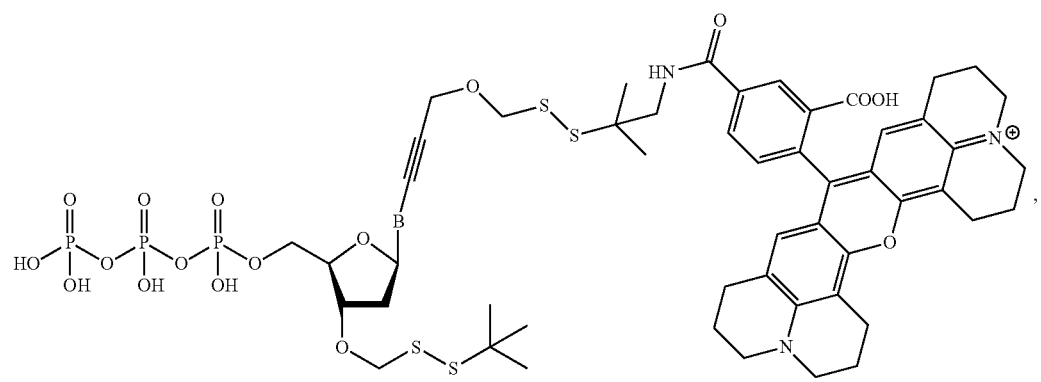

-continued
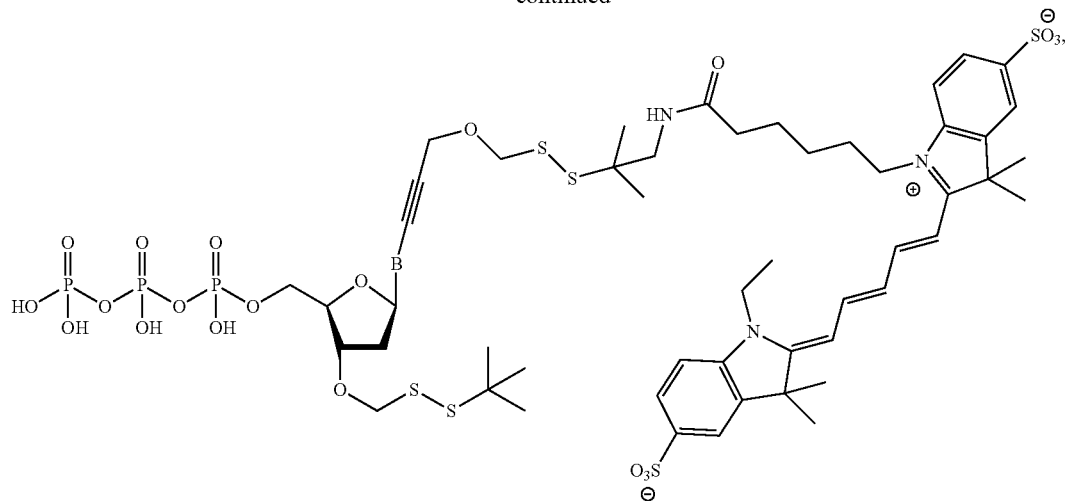
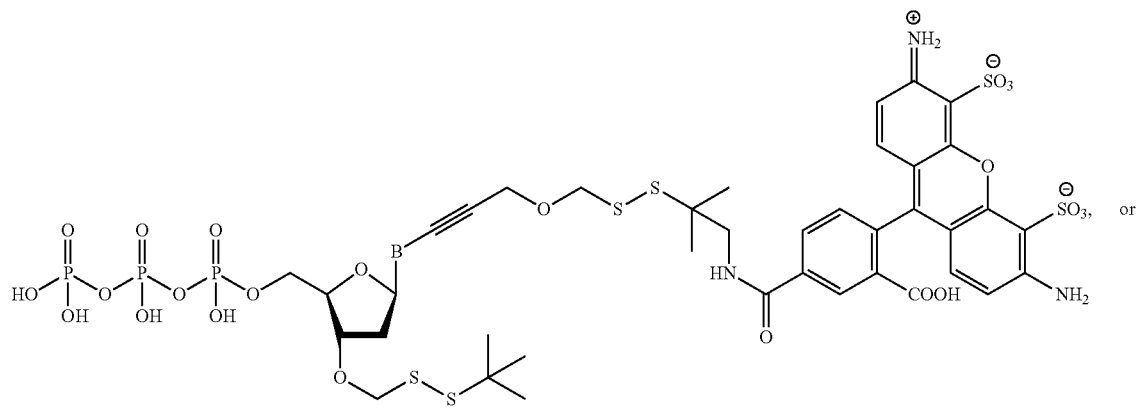
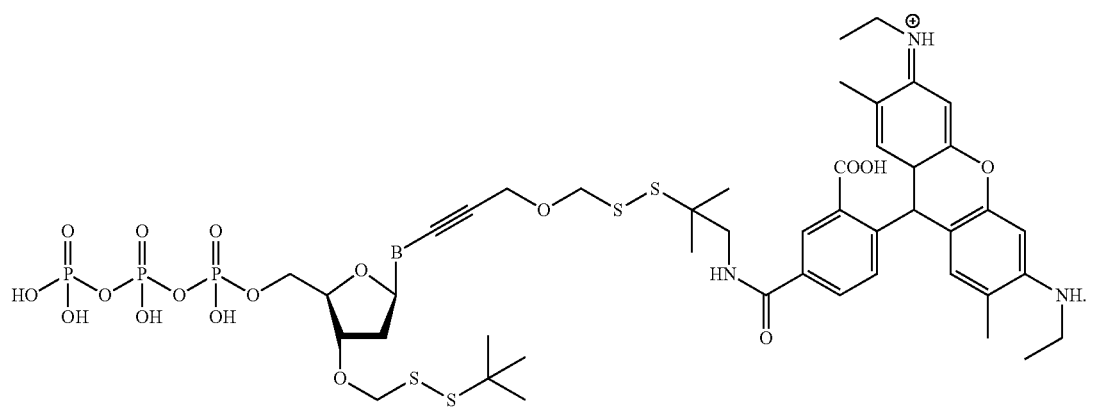

365
Embodiment 122
The compound of one of embodiments 115 to 138, wherein B is
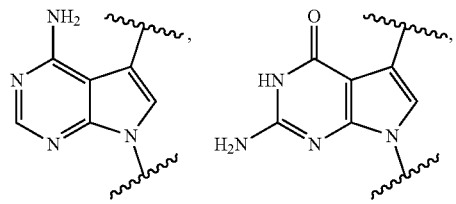
366
-continued
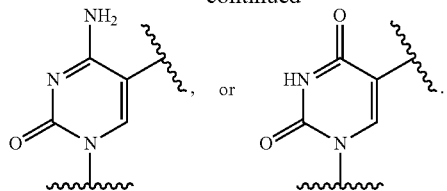
Embodiment 123
The compound of embodiment 1, having the formula:
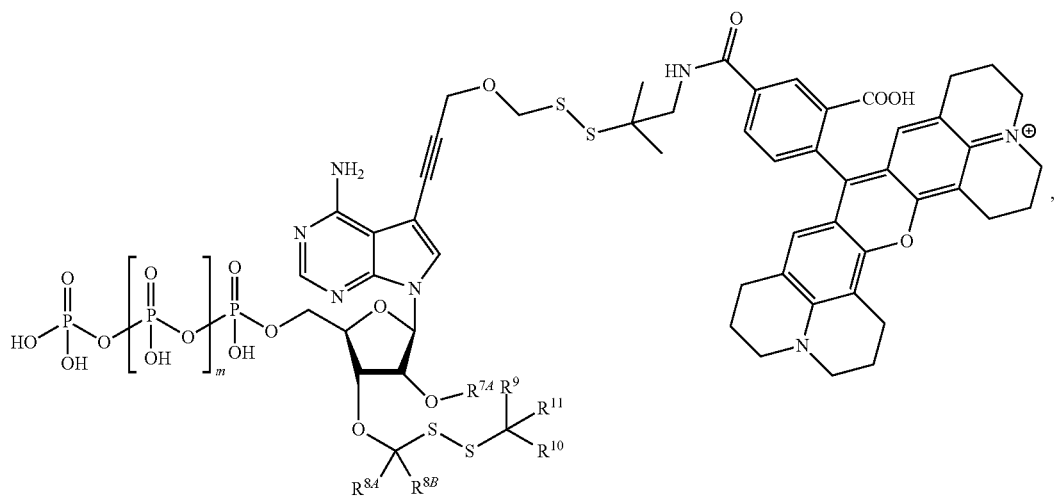
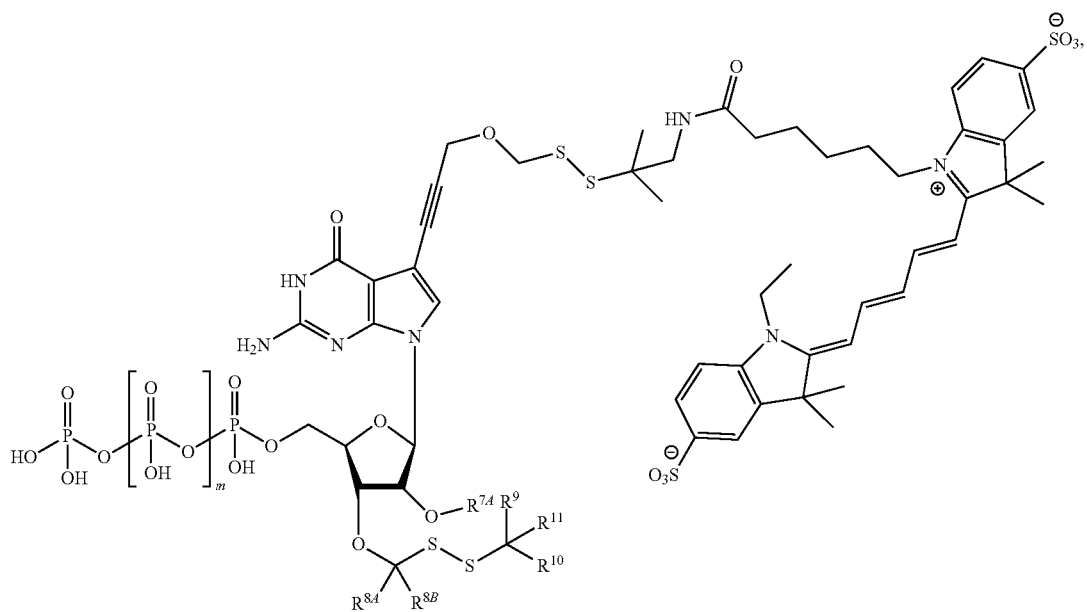

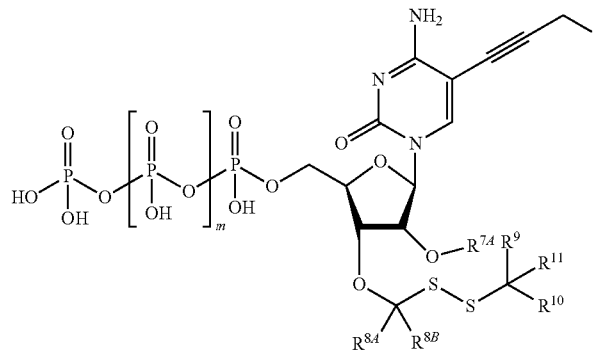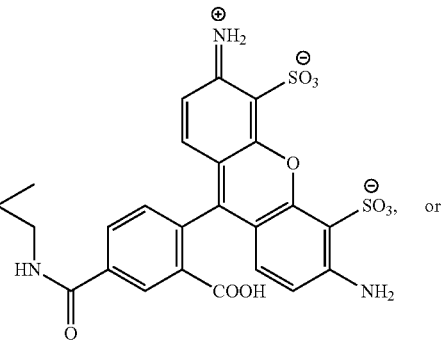
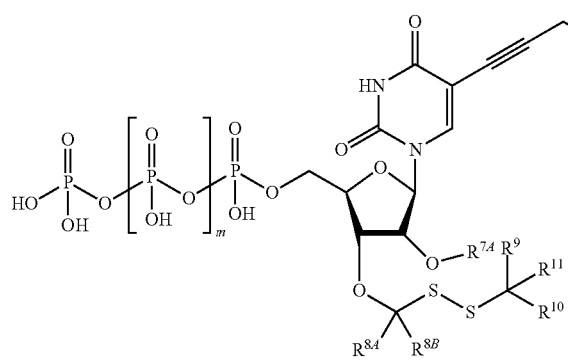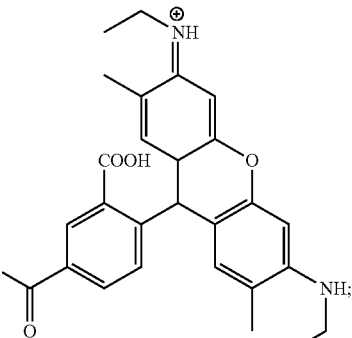
wherein m is an integer from 1 to 4.
Embodiment 124
The compound of embodiment 1, having the formula:
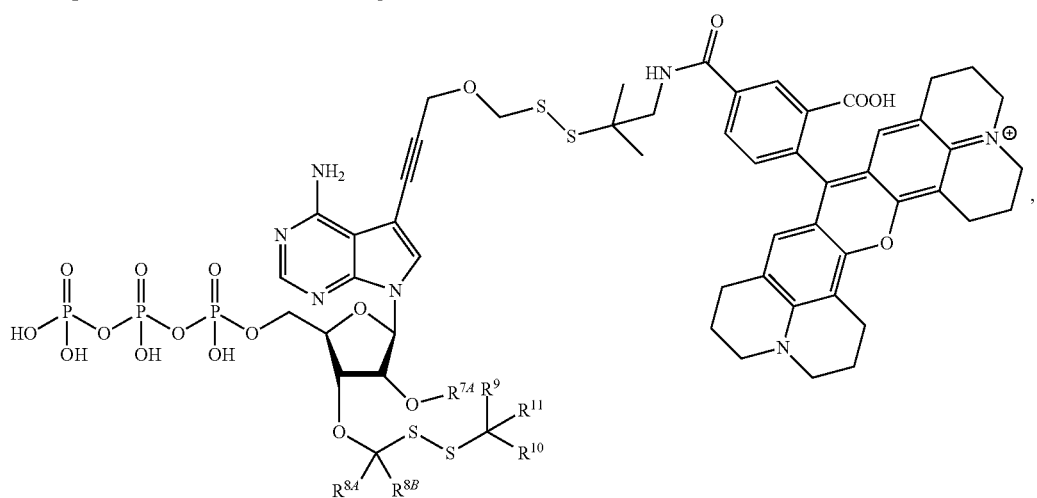

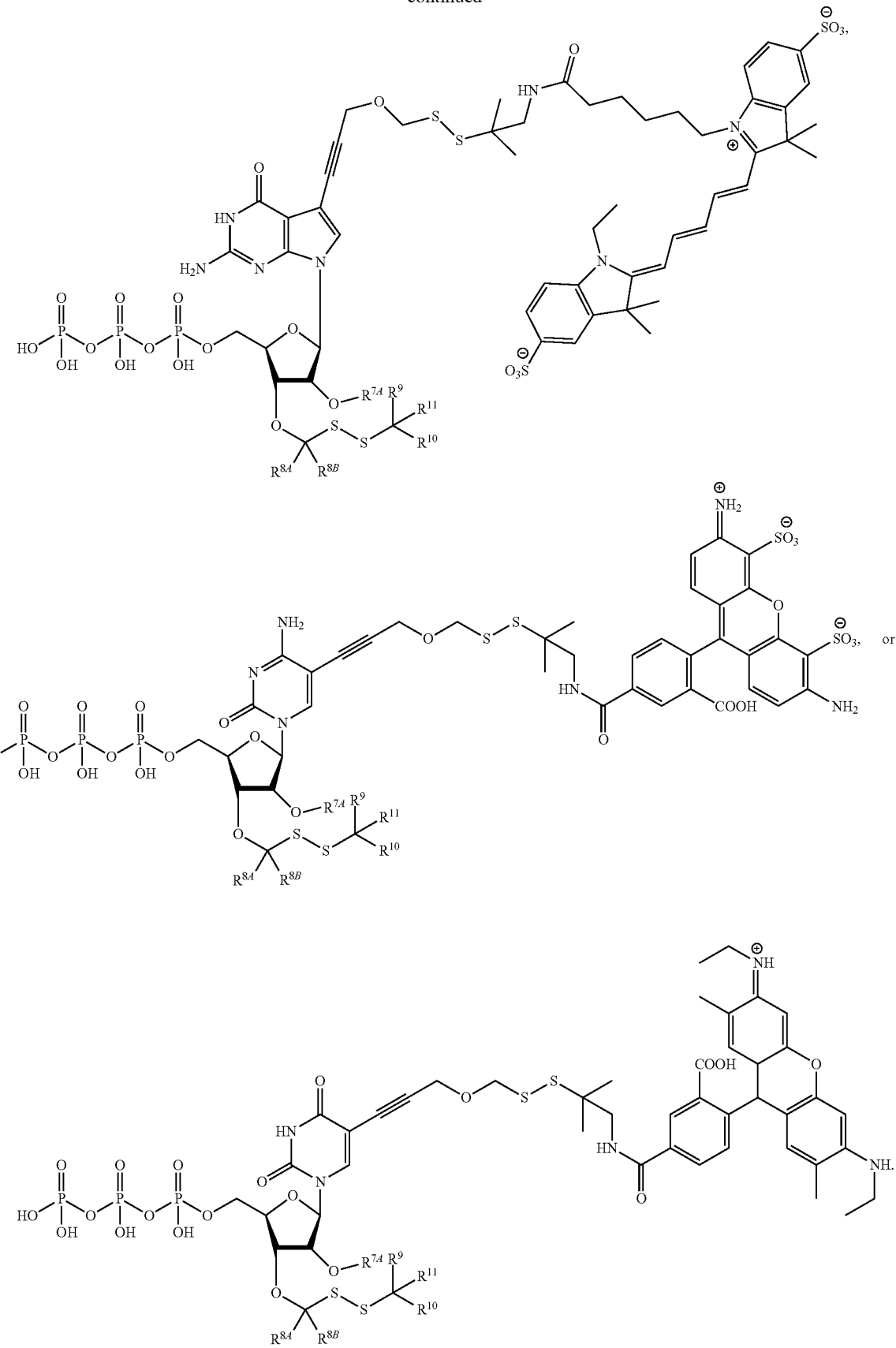

Embodiment 125

The compound of one of embodiments 140 to 141, wherein —CR$^9$R$^{10}$R$^{11}$ is unsubstituted methyl, unsubstituted ethyl, unsubstituted propyl, unsubstituted isopropyl, unsubstituted butyl, or unsubstituted tert-butyl.

Embodiment 126

The compound of one of embodiments 140 to 141, wherein R$^9$ is hydrogen, —C(H$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, or -Ph.

Embodiment 127

The compound of one of embodiments 140 to 141, wherein —R$^{10}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, or -Ph.

Embodiment 128

The compound of one of embodiments 140 to 141, wherein —R$^{11}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, SC(CH$_3$)$_3$, —SCH(CH$_3$)$_2$, —SCH$_2$CH$_2$CH$_3$, —SCH$_2$CH$_3$, —SCH$_3$, NHC(CH$_3$)$_3$, —NHCH(CH$_3$)$_2$, —NHCH$_2$CH$_2$CH$_3$, —NHCH$_2$CH$_3$, —NHCH$_3$, or -Ph.

Embodiment 129

The compound of one of embodiments 140 to 141, wherein R$^{8A}$ is independently hydrogen, deuterium, —C(CH$_3$)$_3$, —CH(CH$_3$)$_2$, —CH$_2$CH$_2$CH$_3$, —CH$_2$CH$_3$, —CH$_3$, —CX$^3$$_3$, —CHX$^3$$_2$, —CH$_2$X$^3$, —CN, or -Ph.

Embodiment 130

The compound of one of embodiments 140 to 141, wherein R$^{8B}$ is independently hydrogen, deuterium, —C(CH$_3$)$_3$, —CH(CH$_3$)$_2$, —CH$_2$CH$_2$CH$_3$, —CH$_2$CH$_3$, —CH$_3$, —CX$^4$$_3$, —CHX$^4$$_2$, —CH$_2$X$^4$, —CN, or -Ph.

Embodiment 131

The compound of one of embodiments 140 to 147, wherein —R$^{7A}$ is hydrogen.

Embodiment 132

The compound of one of embodiments 140 to 147, wherein —R$^{7A}$ is

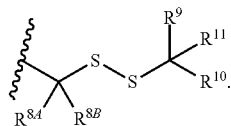

Embodiment 133

The compound of one of embodiments 140 to 147, wherein —R$^{7A}$ is

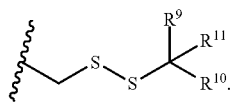

Embodiment 134

The compound of one of embodiments 140 to 147, wherein —R$^{7A}$ is

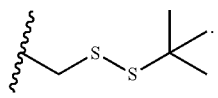 [SMILES: *CSSC(C)(C)C]

Embodiment 135

The compound of one of embodiments 140 to 147 having the formula:

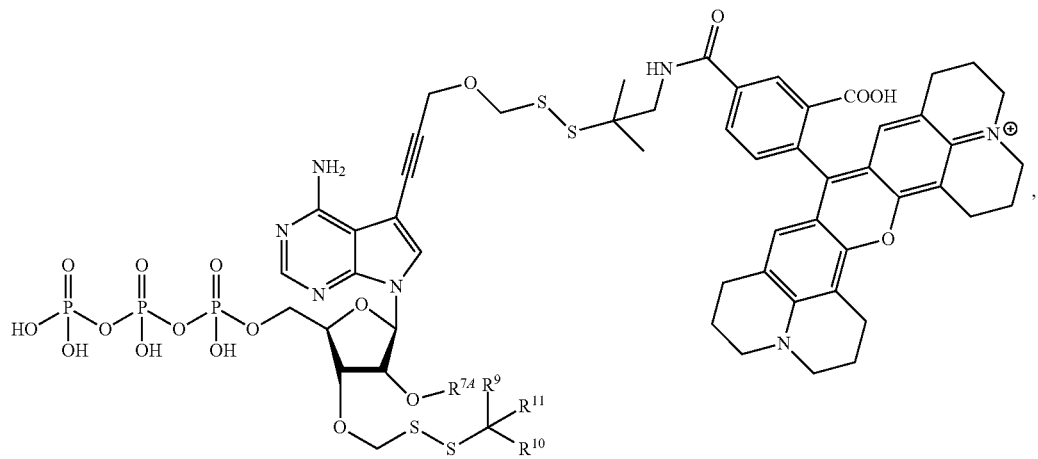

,

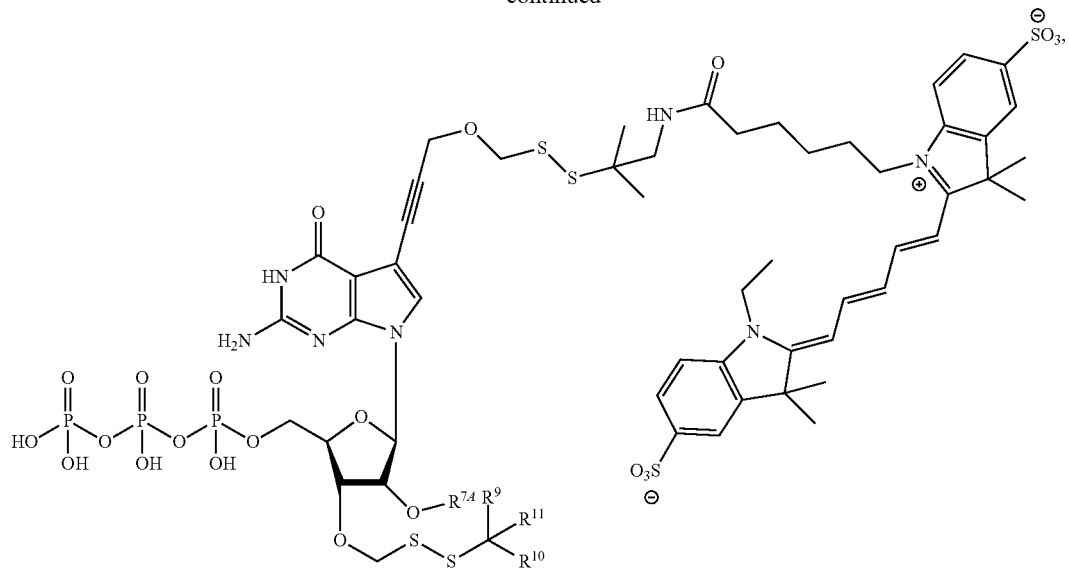
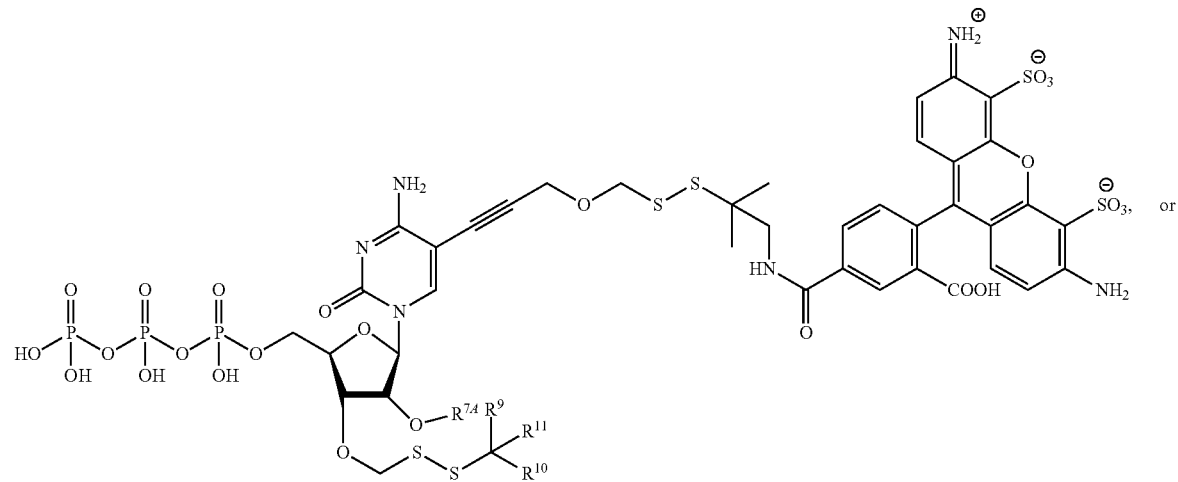
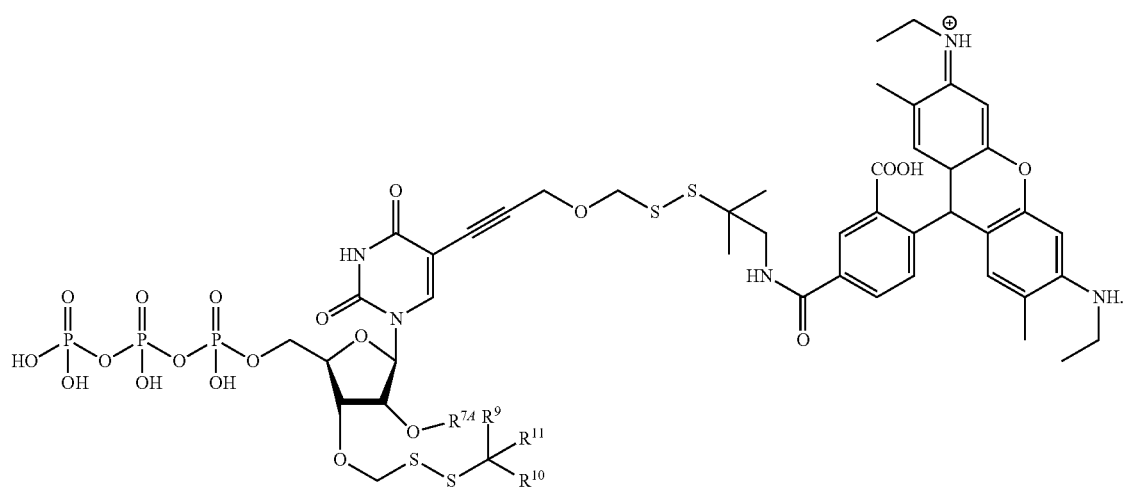

Embodiment 136
The compound of one of embodiments 140 to 147 having the formula:
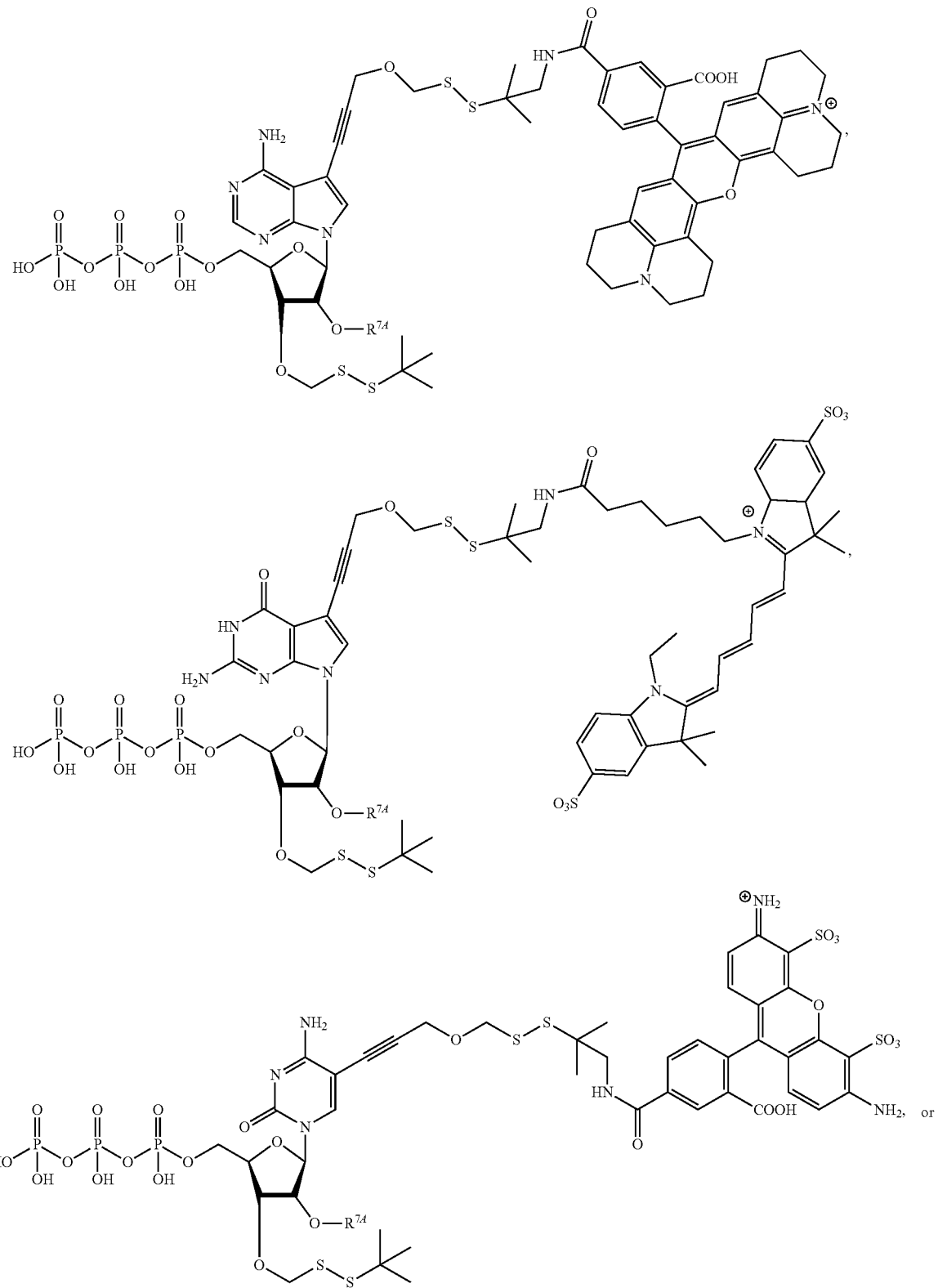

-continued
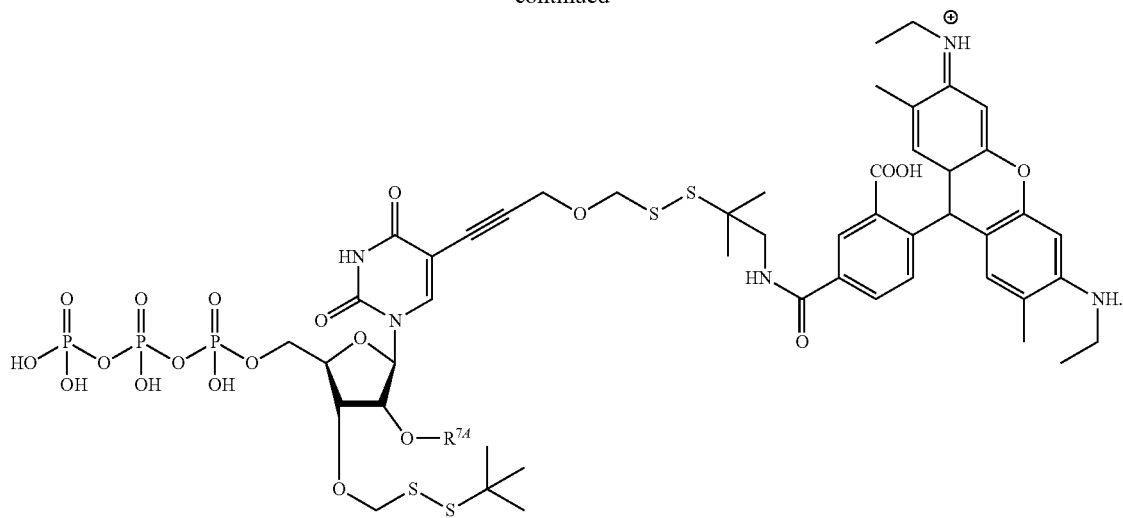
Embodiment 137
The compound of embodiment 1, having the formula:
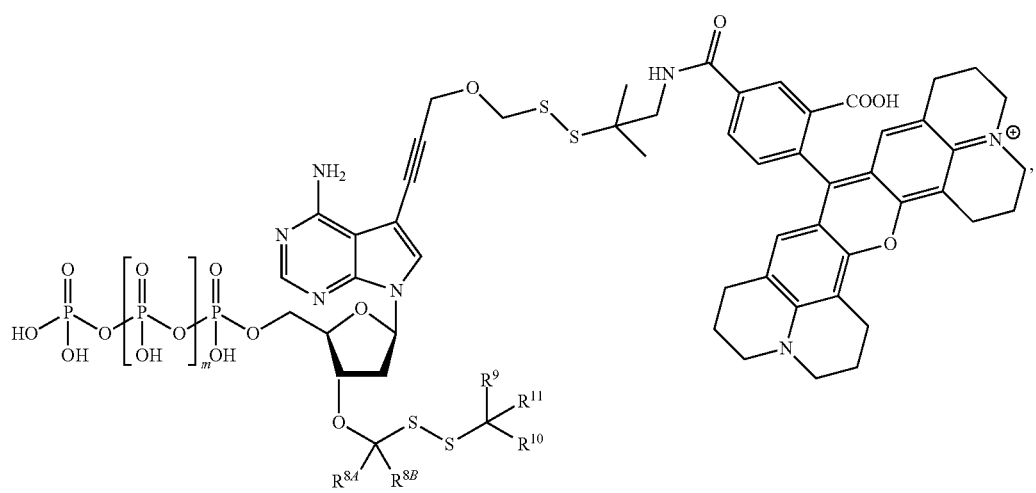

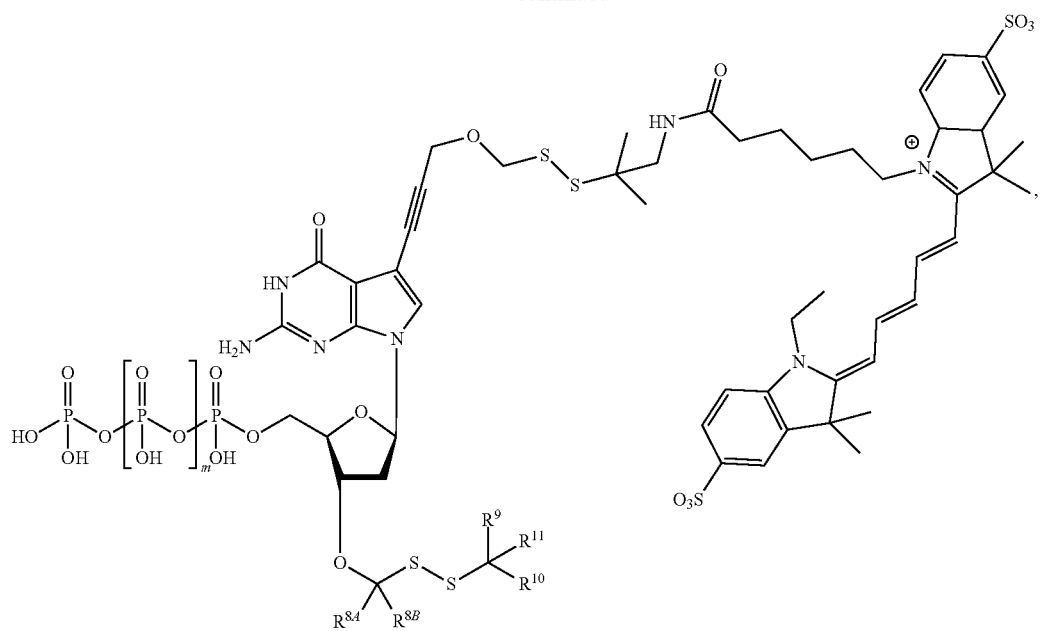
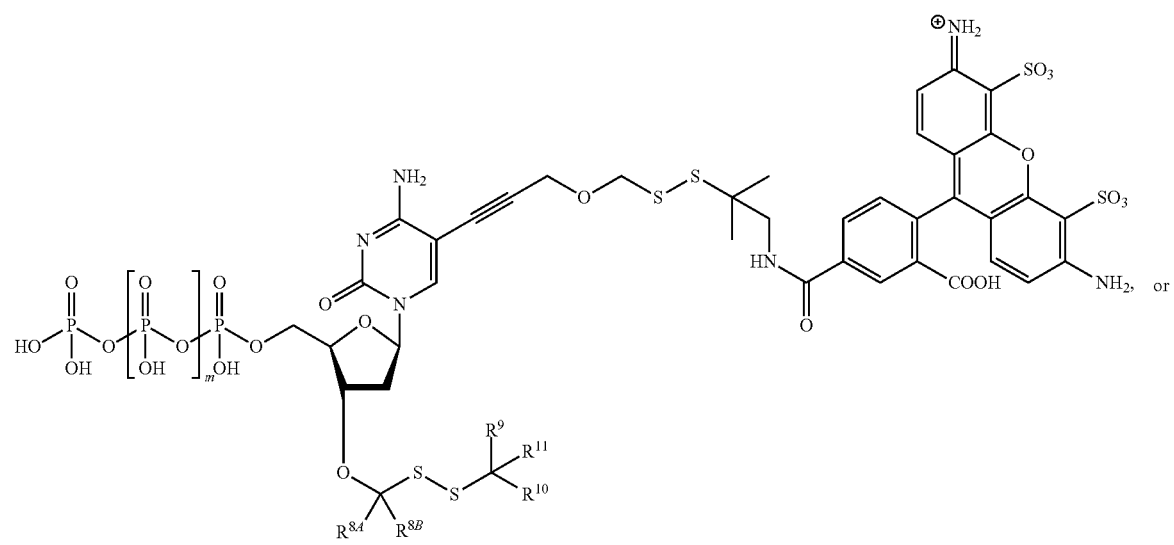

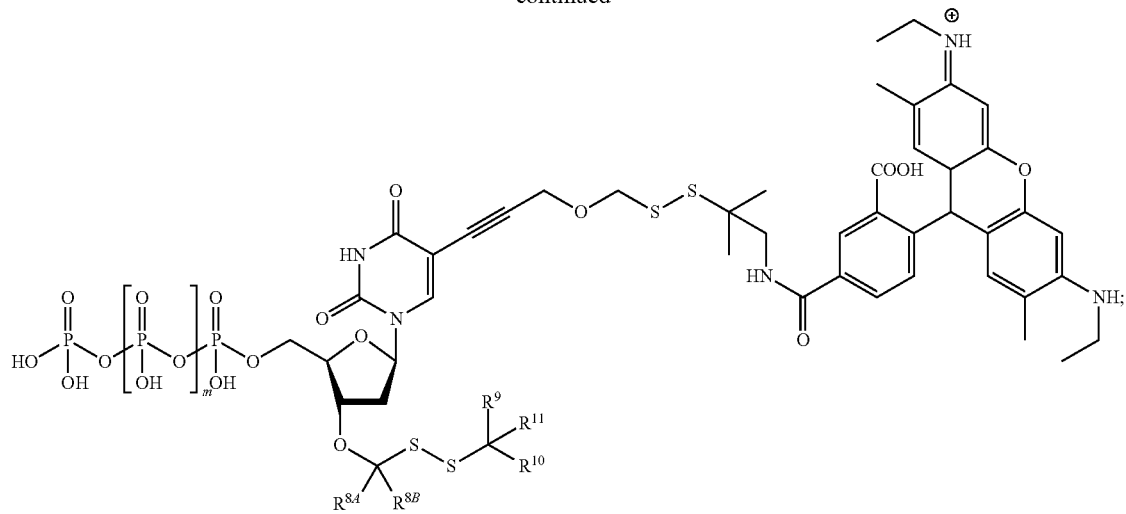
wherein m is an integer from 1 to 4.
Embodiment 138
The compound of embodiment 1, having the formula:
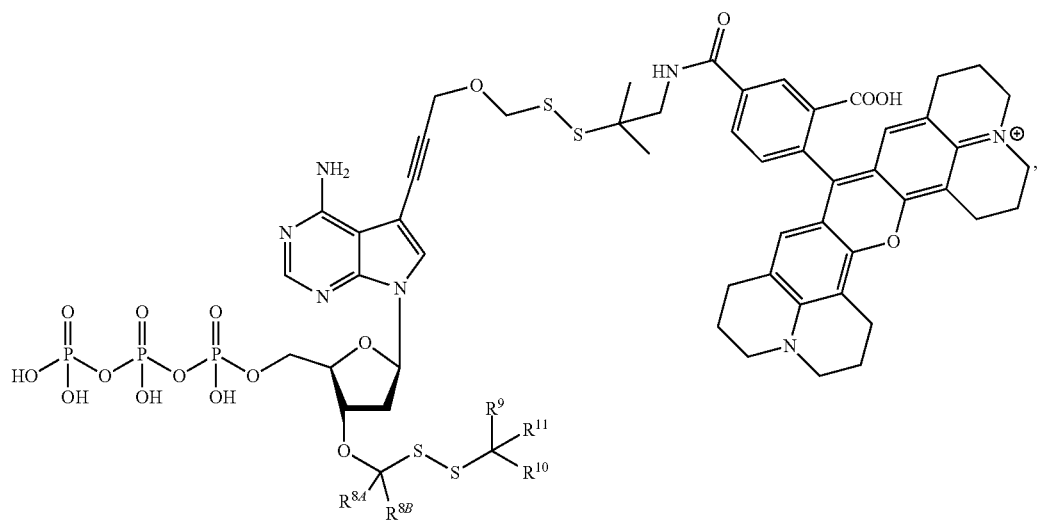

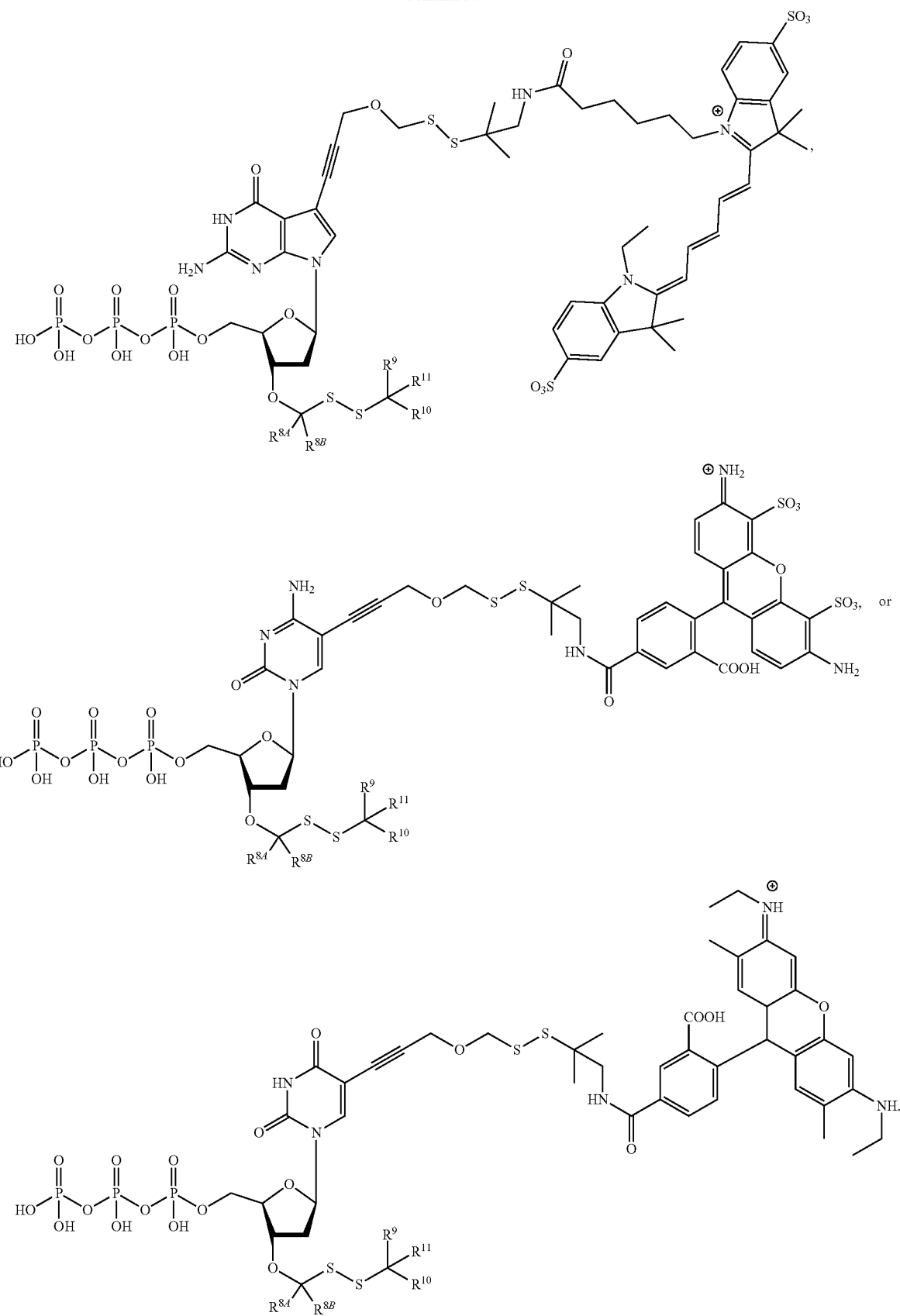

Embodiment 139

The compound of one of embodiments 154 to 155, wherein —CR$^9$R$^{10}$R$^{11}$ is unsubstituted methyl, unsubstituted ethyl, unsubstituted propyl, unsubstituted isopropyl, unsubstituted butyl, or unsubstituted tert-butyl.

Embodiment 140

The compound of one of embodiments 154 to 155, wherein R$^9$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$. —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, or -Ph.

Embodiment 141

The compound of one of embodiments 154 to 155, wherein —R$^{10}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$. —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, or -Ph.

Embodiment 142

The compound of one of embodiments 154 to 155, wherein —R$^{11}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, or -Ph.

Embodiment 143

The compound of one of embodiments 154 to 155, wherein R$^{8A}$ is hydrogen, deuterium, —C(CH$_3$)$_3$, —CH(CH$_3$)$_2$, —CH$_2$CH$_2$CH$_3$, —CH$_2$CH$_3$, —CH$_3$, —CX$^3{}_3$, —CHX$^3{}_2$, —CH$_2$X$^3$, —CN, or -Ph.

Embodiment 144

The compound of one of embodiments 154 to 155, wherein R$^{8B}$ is hydrogen, deuterium, —C(CH$_3$)$_3$, —CH(CH$_3$)$_2$, —CH$_2$CH$_2$CH$_3$, —CH$_2$CH$_3$, —CH$_3$, —CX$^4{}_3$, —CHX$^4{}_2$, —CH$_2$X$^4$, —CN, or -Ph.

Embodiment 145

The compound of one of embodiments 154 to 161 having the formula:

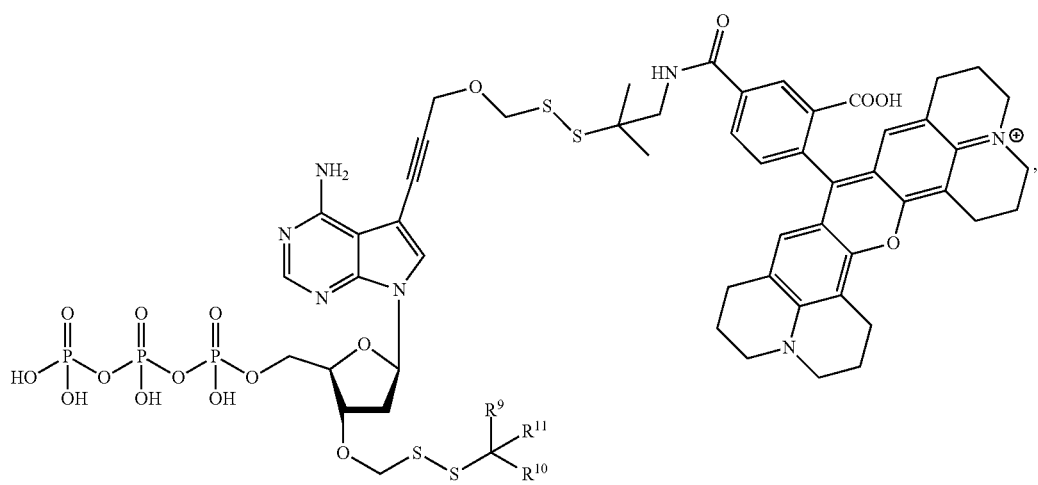

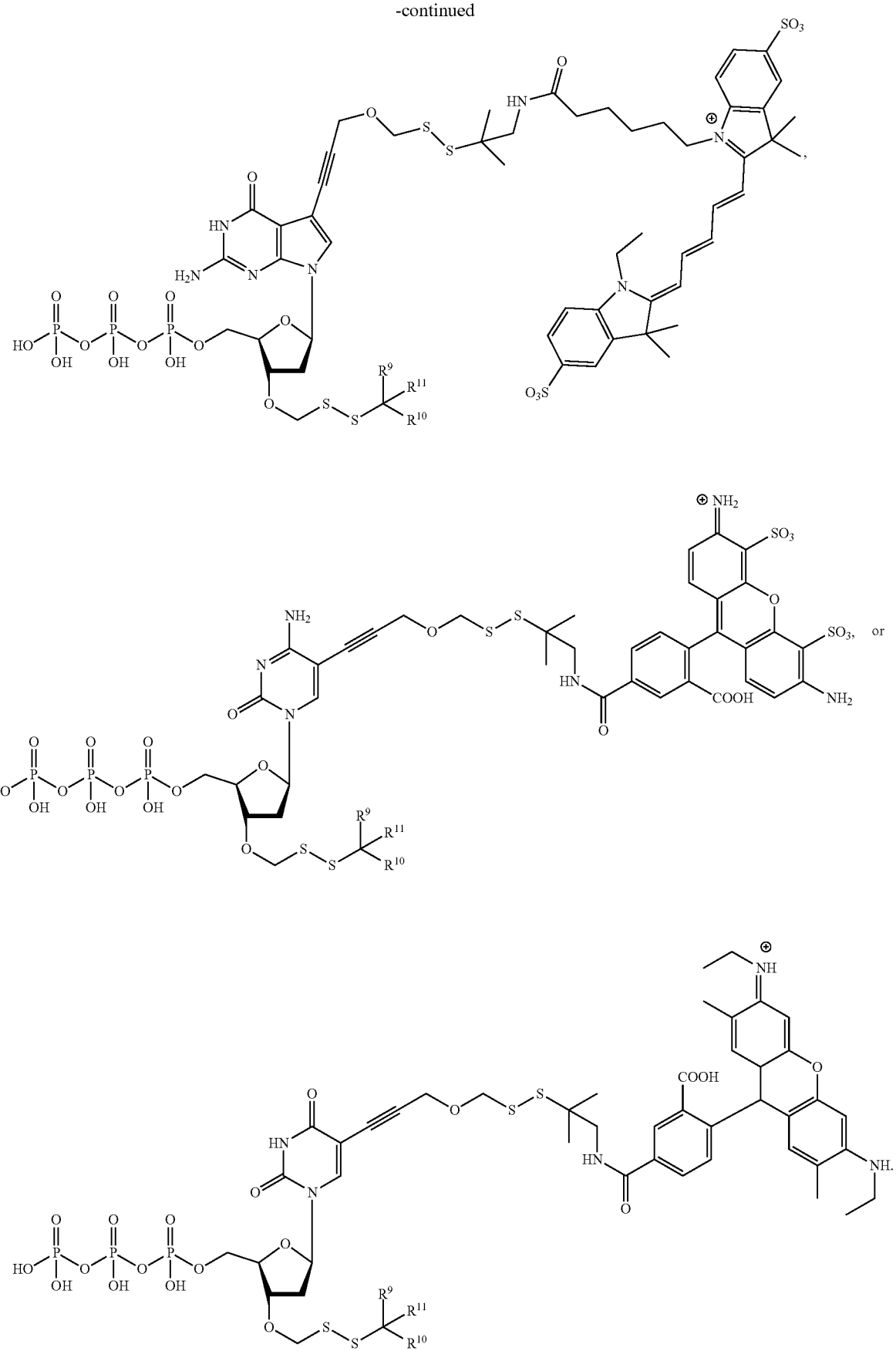

Embodiment 146
The compound of one of embodiments 154 to 161 having the formula:
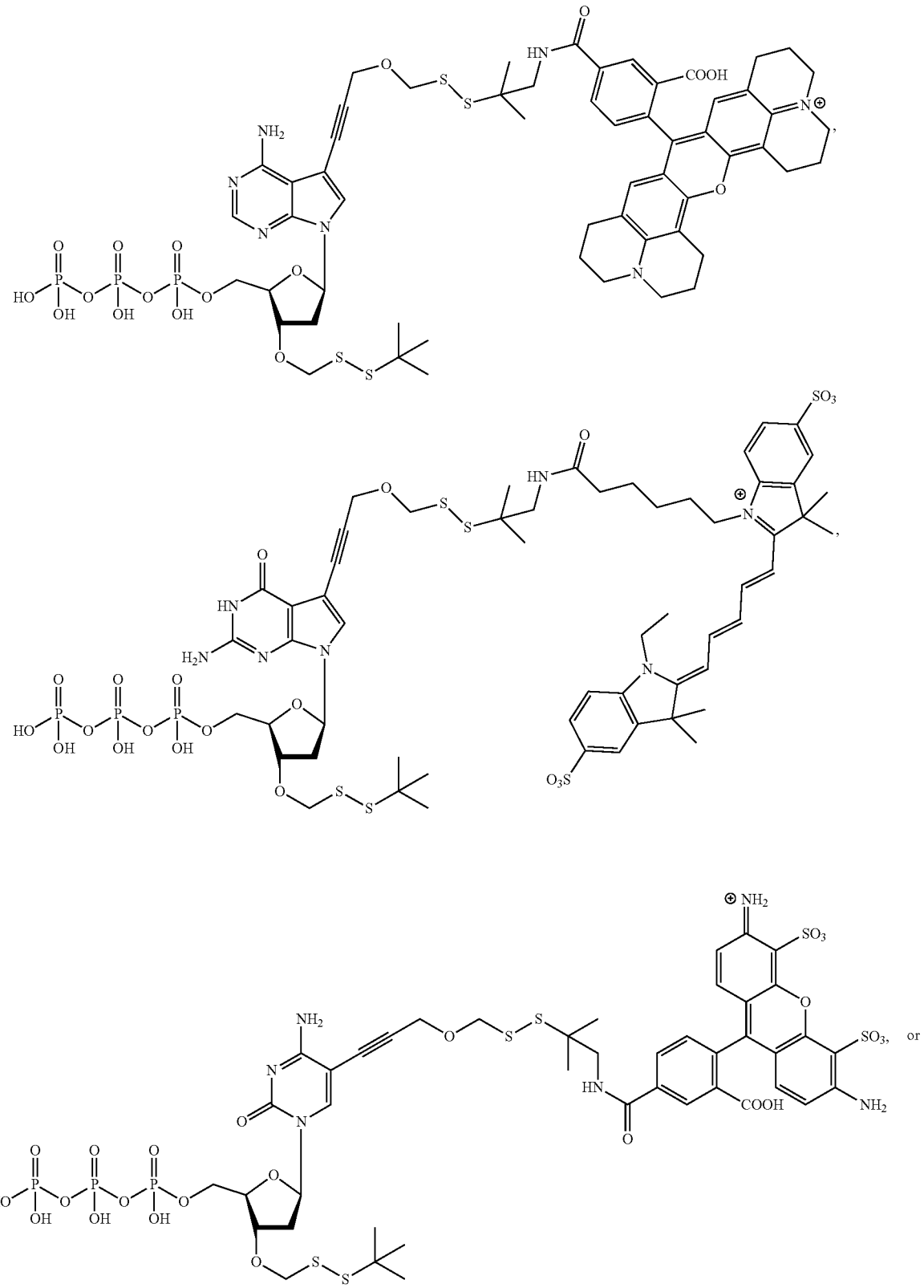

-continued

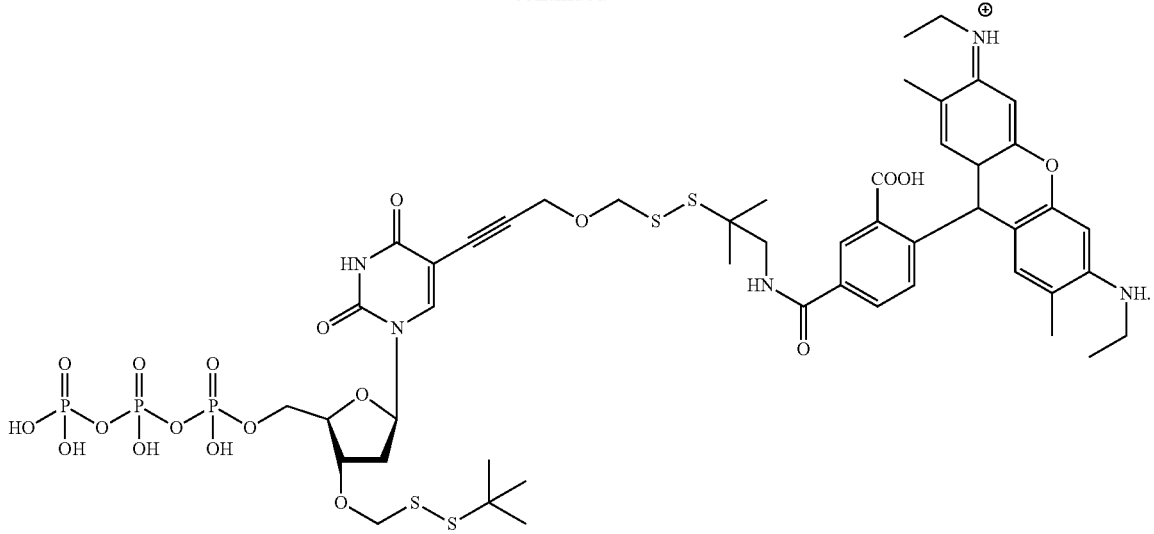

Embodiment 147

A composition of the formula:

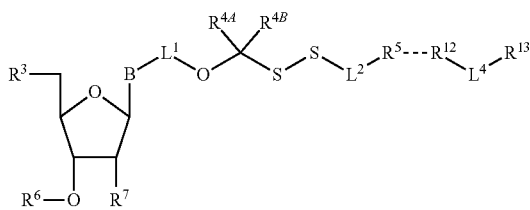

(IV)

wherein --- is a non-covalent bond; B is a base;
L$^1$ is covalent linker;
L$^2$ is covalent linker;
L$^4$ is a covalent linker;
R$^3$ is —OH, monophosphate, polyphosphate or a nucleic acid;
R$^{4A}$ is hydrogen, —CH$_3$, —CX$^1{}_3$, —CHX$^1{}_2$, —CH$_2$X$^1$, —CN, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^{4B}$ is hydrogen, —CH$_3$, —CX$^2{}_3$, —CHX$^2{}_2$, —CH$_2$X$^2$, —CN, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^5$ is an affinity anchor moiety;
R$^6$ is hydrogen or a polymerase-compatible cleavable moiety;
R$^7$ is hydrogen or —OR$^4$, wherein R$^{7A}$ is hydrogen or a polymerase-compatible cleavable moiety;
R$^{12}$ is a complementary affinity anchor moiety binder;
R$^{13}$ is a detectable label; and X$^1$ and X$^2$ are independently halogen.

Embodiment 148

The composition of embodiment 147, wherein R$^5$ is a biotin moiety and R$^{12}$ is a streptavidin moiety.

Embodiment 149

The composition of one of embodiments 147 to 148, wherein L$^4$ is an orthogonally cleavable linker.

Embodiment 150

The composition of one of embodiments 147 to 148, wherein L$^4$ is a cleavable linker.

Embodiment 151

The composition of one of embodiments 147 to 148, wherein L$^4$ is a chemically cleavable linker.

Embodiment 152

The composition of one of embodiments 147 to 148, wherein L$^4$ is a photocleavable linker, an acid-cleavable linker, a base-cleavable linker, an oxidant-cleavable linker, a reductant-cleavable linker, or a fluoride-cleavable linker.

Embodiment 153

The composition of one of embodiments 147 to 148, wherein L$^4$ is a cleavable linker comprising a dialkylketal linker, an azo linker, an allyl linker, a cyanoethyl linker, a 1-(4,4-dimethyl-2,6-dioxocyclohex-1-ylidene)ethyl linker, or a nitrobenzyl linker.

Embodiment 154

The composition of one of embodiments 147 to 148, wherein
L$^4$ is L$^{4A}$-L$^{4B}$-L$^{4C}$-L$^{4D}$-L$^{4E}$; and
L$^{4A}$, L$^{4B}$, L$^{4C}$, L$^{4D}$ and L$^{4E}$ are independently a bond, —NN—, —NHC(O)—, —C(O)NH— substituted or unsubstituted alkylene, substituted or unsubstituted heteroalkylene, substituted or unsubstituted cycloal-

Embodiment 155

The composition of one of embodiments 147 to 148, wherein $L^4$ is $L^{4A}$-$L^{4B}$-$L^{4C}$-$L^{4D}$-$L^{4E}$; and $L^{4A}$, $L^{4B}$, $L^{4C}$, $L^{4D}$ and $L^{4E}$ are independently a bond, —NN—, —NHC(O)—, —C(O)NH—, substituted or unsubstituted $C_1$-$C_{20}$ alkylene, substituted or unsubstituted 2 to 20 membered heteroalkylene, substituted or unsubstituted $C_3$-$C_{20}$ cycloalkylene, substituted or unsubstituted 3 to 20 membered heterocycloalkylene, substituted or unsubstituted $C_6$-$C_{20}$ arylene, or substituted or unsubstituted 5 to 20 membered heteroarylene; wherein at least one of $L^{4A}$, $L^{4B}$, $L^{4C}$, $L^{4D}$ and $L^{4E}$ is not a bond.

Embodiment 156

The composition of one of embodiments 147 to 148, wherein
$L^{4A}$-$L^{4B}$-$L^{4C}$-$L^{4D}$-$L^{4E}$; and
$L^{4A}$, $L^{4B}$, $L^{4C}$, $L^{4D}$ and $L^{4E}$ are independently a bond, —NN—, —NHC(O)—, —C(O)NH—, substituted or unsubstituted $C_1$-$C_{10}$ alkylene, substituted or unsubstituted 2 to 10 membered heteroalkylene, substituted or unsubstituted $C_3$-$C_6$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene; wherein at least one of $L^{4A}$, $L^{4B}$, $L^{4C}$, $L^{4D}$ and $L^{4E}$ is not a bond.

Embodiment 157

The composition of one of embodiments 147 to 148, wherein
$L^{4A}$-$L^{4B}$-$L^{4C}$-$L^{4D}$-$L^{4E}$; and
$L^{4A}$, $L^{4B}$, $L^{4C}$, $L^{4D}$ and $L^{4E}$ are independently a bond, —NN—, —NHC(O)—, —C(O)NH—, substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted phenyl, or substituted or unsubstituted 5 to 6 membered heteroarylene; wherein at least one of $L^{4A}$, $L^{4B}$, $L^{4C}$, $L^{4D}$ and $L^{4E}$ is not a bond.

Embodiment 158

The composition of one of embodiments 147 to 148, wherein
$L^{4A}$-$L^{4B}$-$L^{4C}$-$L^{4D}$-$L^{4E}$;
$L^{4A}$ is a bond, —NN—, —NHC(O)—, —C(O)NH—, substituted or unsubstituted alkylene, substituted or unsubstituted heteroalkylene;
$L^{4B}$ is a bond, —NN—, —NHC(O)—, —C(O)NH—, substituted or unsubstituted cycloalkylene, substituted or unsubstituted heterocycloalkylene, substituted or unsubstituted arylene, substituted or unsubstituted heteroarylene;
$L^{4C}$ is a bond, —NN—, —NHC(O)—, —C(O)NH—, substituted or unsubstituted cycloalkylene, substituted or unsubstituted heterocycloalkylene, substituted or unsubstituted arylene, substituted or unsubstituted heteroarylene;
$L^{4D}$ is a bond, —NN—, —NHC(O)—, —C(O)NH—, substituted or unsubstituted alkylene, substituted or unsubstituted heteroalkylene; and
$L^{4E}$ is a bond, —NN—, —NHC(O)—, —C(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; wherein at least one of $L^{4A}$, $L^{4B}$, $L^{4C}$, $L^{4D}$ and $L^{4E}$ is not a bond.

Embodiment 159

The composition of one of embodiments 147 to 148, wherein $L^4$ is a bond, substituted or unsubstituted alkylene, substituted or unsubstituted heteroalkylene, substituted or unsubstituted cycloalkylene, substituted or unsubstituted heterocycloalkylene, substituted or un substituted arylene, or substituted or unsubstituted heteroarylene.

Embodiment 160

The composition of one of embodiments 147 to 148, wherein $L^4$ is a bond, substituted or unsubstituted $C_1$-$C_{20}$ alkylene, substituted or unsubstituted 2 to 20 membered heteroalkylene, substituted or unsubstituted $C_3$-$C_{20}$ cycloalkylene, substituted or unsubstituted 3 to 20 membered heterocycloalkylene, substituted or unsubstituted $C_6$-$C_{20}$ arylene, or substituted or unsubstituted 5 to 20 membered heteroarylene.

Embodiment 161

The composition of one of embodiments 147 to 148, wherein $L^4$ is a bond, substituted or unsubstituted $C_1$-$C_8$ alkylene, substituted or unsubstituted 2 to 8 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene.

Embodiment 162

The composition of one of embodiments 147 to 148, wherein $L^4$ is a bond, substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted phenyl, or substituted or unsubstituted 5 to 6 membered heteroarylene.

Embodiment 163

The composition of one of embodiments 147 to 148, wherein $L^4$ is a substituted or unsubstituted 3 to 10 membered heteroalkylene.

Embodiment 164

The composition of one of embodiments 147 to 148, wherein $L^4$ is a substituted or unsubstituted 3 to 8 membered heteroalkylene.

Embodiment 165

The compound of one of embodiments 147 to 164, wherein $R^n$ is a fluorescent dye.

Embodiment 166

A compound of the formula:

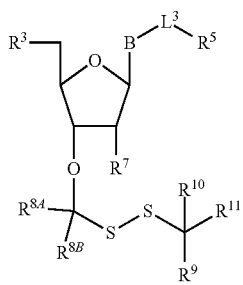

(III)

wherein
- B is a base;
- $L^3$ is a cleavable linker;
- $R^3$ is —OH, monophosphate, polyphosphate or a nucleic acid;
- $R^5$ is a detectable label or anchor moiety;
- $R^7$ is hydrogen or —$OR^{7A}$, wherein $R^{7A}$ is hydrogen or

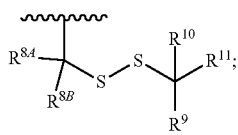

- $R^{8A}$ is hydrogen, —$CH_3$, —$CX^3_3$, —$CHX^3_2$, —$CH_2X^3$, —CN, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $R^{8B}$ is hydrogen, —$CH_3$, —$CX^4_3$, —$CHX^4_2$, —$CH_2X^4$, —CN, -Ph substituted or unsubstituted alkyl, substituted or unsubstituted heteroalkyl, substituted or unsubstituted cycloalkyl, substituted or unsubstituted heterocycloalkyl, substituted or unsubstituted aryl; or substituted or unsubstituted heteroaryl;
- $R^9$ is hydrogen, —$CX^5_3$, —$CHX^5_2$, —$CH_2X^5$, —$OCH_3$, —$SCH_3$, —$NHCH_3$, —CN, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $R^{10}$ is hydrogen, —$CX^6_3$, —$CHX^6_2$, —$CH_2X^6$, —$OCH_3$, —$SCH_3$, —$NHCH_3$, —CN, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $R^{11}$ is hydrogen, —$CX^7_3$, —$CHX^7_2$, —$CH_2X^7$, —$OCH_3$, —$SCH_3$, —$NHCH_3$, —CN, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $X^3$, $X^4$, $X^5$, $X^6$ and $X^7$ are independently halogen.

Embodiment 167

The compound of embodiment 183, wherein B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof.

Embodiment 168

The compound of embodiment 166, wherein B is

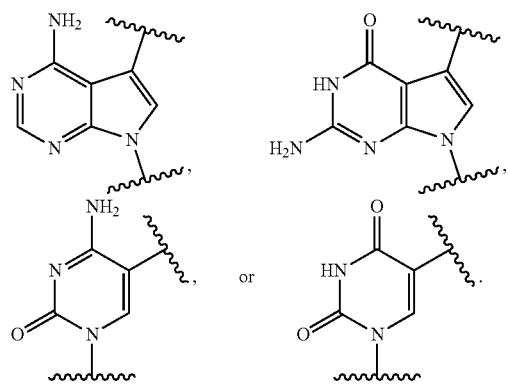

Embodiment 169

The compound of one of embodiments 166 to 168, wherein $L^3$ is

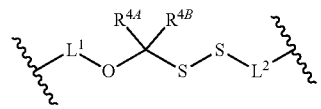

wherein
- $L^1$ is a bond, substituted or unsubstituted a substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
- $L^2$ is a bond, substituted or unsubstituted a substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, an orthogonally cleavable linker, non-covalent linker or -L$^{2A}$-L$^{2B}$-L$^{2C}$-L$^{2D}$-, wherein L$^{2A}$ is a bond, substituted or unsubstituted a substituted or unsubstituted alkylene, substituted or unsubstituted heteroalkylene;

L$^{2B}$ is a bond substituted or unsubstituted cycloalkylene, substituted or unsubstituted heterocycloalkylene, substituted or unsubstituted arylene, substituted or unsubstituted heteroarylene;

L$^{2C}$ is a bond substituted or unsubstituted cycloalkylene, substituted or unsubstituted heterocycloalkylene, substituted or unsubstituted arylene, substituted or unsubstituted heteroarylene; and L$^{2D}$ is a bond, substituted or unsubstituted a substituted or unsubstituted alkylene, substituted or unsubstituted heteroalkylene, wherein at least one of L$^{2A}$, L$^{2B}$, L$^{2C}$, L$^{2D}$ is not a bond;

R$^{4A}$ is hydrogen, —CH$_3$, —CX$^1_3$, —CHX$^1_2$, —CH$_2$X$^1$, —CN, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{4B}$ is hydrogen, —CH$_3$, —CX$^2_3$, —CHX$^2_2$, —CH$_2$X$^2$, —CN, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and X$^1$ and X$^2$ are independently halogen.

Embodiment 170

The compound of one of embodiments 166 to 169, wherein L$^3$ is

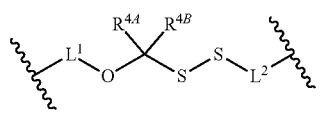

L$^1$ is covalent linker;
L$^2$ is covalent linker;
R$^{4A}$ is hydrogen, —CH$_3$, —CX$^1_3$, —CHX$^1_2$, —CH$_2$X$^1$, —CN, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^{4B}$ is hydrogen, —CH$_3$, —CX$^2_3$, —CHX$^2_2$, —CH$_2$X$^2$, —CN, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and
X$^1$ and X$^2$ are independently halogen.

Embodiment 171

The compound of embodiment 170, wherein L$^1$ is L$^{1A}$-L$^{1B}$-L$^{1C}$-L$^{1D}$-L$^{1E}$; and L$^{1A}$, L$^{1B}$, L$^{1C}$, L$^{1D}$, and L$^{1E}$ are independently a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; wherein at least one of L$^{1A}$, L$^{1B}$, L$^{1C}$, L$^{1D}$, and L$^{1E}$ is not a bond.

Embodiment 172

The compound of embodiment 170, wherein is L$^{1A}$-L$^{1B}$-L$^{1C}$-L$^{1D}$-L$^{1E}$; and L$^{1A}$, L$^{1B}$, L$^{1C}$, L$^{1D}$, and L$^{1E}$ are independently a bond, substituted or unsubstituted C$_1$-C$_8$ alkylene, substituted or unsubstituted 2 to 8 membered heteroalkylene, substituted or unsubstituted C$_3$-C$_8$ cycloalkylene, substituted or unsubstituted 3 to 8 membered heterocycloalkylene, substituted or unsubstituted C$_6$-C$_{10}$ arylene, or substituted or unsubstituted 5 to 10 membered heteroarylene; wherein at least one of L$^{1A}$, L$^{1B}$, L$^{1C}$, L$^{1D}$, and L$^{1E}$ is not a bond Embodiment 173

The compound of embodiment 170, wherein L$^1$ is L$^{1A}$-L$^{1B}$-L$^{1C}$-L$^{1D}$-L$^{1E}$; and L$^{1A}$, L$^{1B}$, L$^{1C}$, L$^{1D}$, and L$^{1E}$ are independently a bond, substituted or unsubstituted C$_1$-C$_6$ alkylene, substituted or unsubstituted 2 to 6 membered heteroalkylene, substituted or unsubstituted C$_3$-C$_6$ cycloalkylene, substituted or unsubstituted 3 to 6 membered heterocycloalkylene, substituted or unsubstituted phenyl, or substituted or unsubstituted 5 to 6 membered heteroarylene; wherein at least one of L$^{1A}$, L$^{1B}$, L$^{1C}$, L$^{1D}$, and L$^{1E}$ is not a bond.

Embodiment 174

The compound of embodiment 170, wherein L$^1$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 175

The compound of embodiment 170, wherein L$^1$ is a bond, substituted or unsubstituted C$_1$-C$_8$ alkylene, substituted or unsubstituted 2 to 8 membered heteroalkylene, substituted or unsubstituted C$_3$-C$_8$ cycloalkylene, substituted or unsubstituted 3 to 8 membered heterocycloalkylene, substituted or unsubstituted C$_6$-C$_{10}$ arylene, or substituted or unsubstituted 5 to 10 membered heteroarylene.

Embodiment 176

The compound of embodiment 170, wherein L$^1$ is a bond, substituted or unsubstituted C$_1$-C$_6$ alkylene, substituted or unsubstituted 2 to 6 membered heteroalkylene, substituted or unsubstituted C$_3$-C$_6$ cycloalkylene, substituted or unsubstituted 3 to 6 membered heterocycloalkylene, substituted or unsubstituted phenyl, or substituted or unsubstituted 5 to 6 membered heteroarylene.

Embodiment 177

The compound of embodiment 170, wherein L$^1$ is a substituted or unsubstituted C$_1$-C$_6$ alkylene or substituted or unsubstituted 2 to 6 membered heteroalkylene.

Embodiment 178

The compound of embodiment 170, wherein $L^1$ is an unsubstituted $C_1$-$C_4$ alkylene.

Embodiment 179

The compound of embodiment 170, wherein $L^1$ is —C≡C—CH$_2$—.

Embodiment 180

The compound of one of embodiments 170 to 179, wherein $L^2$ is an orthogonally cleavable linker or a non-covalent linker.

Embodiment 181

The compound of one of embodiments 170 to 179, wherein $L^2$ is a cleavable linker.

Embodiment 182

The compound of one of embodiments 170 to 179, wherein $L^2$ is a chemically cleavable linker.

Embodiment 183

The compound of one of embodiments 170 to 179, wherein $L^2$ is a photocleavable linker, an acid-cleavable linker, a base-cleavable linker, an oxidant-cleavable linker, a reductant-cleavable linker, or a fluoride-cleavable linker.

Embodiment 184

The compound of one of embodiments 170 to 179, wherein $L^2$ is a cleavable linker comprising a dialkylketal linker, an azo linker, an allyl linker, a cyanoethyl linker, a 1-(4,4-dimethyl-2,6-dioxocyclohex-1-ylidene)ethyl linker, or a nitrobenzyl linker.

Embodiment 185

The compound of one of embodiments 170 to 179, wherein
$L^2$ is $L^{2A}$-$L^{2B}$-$L^{2C}$-$L^{2D}$-$L^{2E}$; and
$L^{2A}$, $L^{2B}$, $L^{2C}$, $L^{2D}$, and $L^{2E}$ are independently a —NN—, —NHC(O)—, —C(O)NH—, bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
wherein at least one of $L^{2A}$, $L^{2B}$, $L^{2C}$, $L^{2D}$, and $L^{2E}$ is not a bond.

Embodiment 186

The compound of one of embodiments 170 to 179, wherein
$L^2$ is $L^{2A}$-$L^{2B}$-$L^{2C}$-$L^{2D}$-$L^{2E}$; and
$L^{2A}$, $L^{2B}$, $L^{2C}$, $L^{2D}$, and $L^{2E}$ are independently a bond, —NN—, —NHC(O)—, —C(O)NH—, substituted or unsubstituted $C_1$-$C_{20}$ alkylene, substituted or unsubstituted 2 to 20 membered heteroalkylene, substituted or unsubstituted $C_3$-$C_{20}$ cycloalkylene, substituted or unsubstituted 3 to 20 membered heterocycloalkylene, substituted or unsubstituted $C_6$-$C_{20}$ arylene, or substituted or unsubstituted 5 to 20 membered heteroarylene; wherein at least one of $L^{2A}$, $L^{2B}$, $L^{2C}$, $L^{2D}$, and $L^{2E}$ is not a bond

Embodiment 187

The compound of one of embodiments 170 to 179, wherein
$L^{2A}$-$L^{2B}$-$L^{2C}$-$L^{2D}$-$L^{2E}$; and
$L^{2A}$, $L^{2B}$, $L^{2C}$, $L^{2D}$, and $L^{2E}$ are independently a bond, —NN—, —NHC(O)—, —C(O)NH—, substituted or unsubstituted $C_1$-$C_{10}$ alkylene, substituted or unsubstituted 2 to 10 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene; wherein at least one of $L^{2A}$, $L^{2B}$, $L^{2C}$, $L^{2D}$, and $L^{2E}$ is not a bond.

Embodiment 188

The compound of one of embodiments 170 to 179, wherein
$L^{2A}$-$L^{2B}$-$L^{2C}$-$L^{2D}$-$L^{2E}$; and
$L^{2A}$, $L^{2B}$, $L^{2C}$, $L^{2D}$, and $L^{2E}$ are independently a bond, —NN—, —NHC(O)—, —C(O)NH—, substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted phenyl, or substituted or unsubstituted 5 to 6 membered heteroarylene; wherein at least one of $L^{2A}$, $L^{2B}$, $L^{2C}$, $L^{2D}$, and $L^{2E}$ is not a bond.

Embodiment 189

The compound of one of embodiments 170 to 179, wherein
$L^2$ is $L^{2A}$-$L^{2B}$-$L^{2C}$-$L^{2D}$-$L^{2E}$
$L^{2A}$ is a bond, substituted or unsubstituted alkylene, substituted or unsubstituted heteroalkylene;
$L^{2B}$ is a bond, substituted or unsubstituted cycloalkylene, substituted or unsubstituted heterocycloalkylene, substituted or unsubstituted arylene, substituted or unsubstituted heteroarylene;
$L^{2C}$ is a bond, substituted or unsubstituted cycloalkylene, substituted or unsubstituted heterocycloalkylene, substituted or unsubstituted arylene, substituted or unsubstituted heteroarylene;
$L^{2D}$ is a bond, substituted or unsubstituted alkylene, substituted or unsubstituted heteroalkylene; and
$L^{2E}$ is a bond; substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; wherein at least one of $L^{2A}$, $L^{2B}$, $L^{2C}$, $L^{2D}$, and $L^{2E}$ is not a bond.

Embodiment 190

The compound of one of embodiments 170 to 179, wherein $L^2$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 191

The compound of one of embodiments 170 to 179, wherein $L^2$ is a bond, substituted or unsubstituted $C_1$-$C_{20}$ alkylene, substituted or unsubstituted 2 to 20 membered heteroalkylene, substituted or unsubstituted $C_3$-$C_{20}$ cycloalkylene, substituted or unsubstituted 3 to 20 membered heterocycloalkylene, substituted or unsubstituted $C_6$-$C_{20}$ arylene, or substituted or unsubstituted 5 to 20 membered heteroarylene.

Embodiment 192

The compound of one of embodiments 170 to 179, wherein $L^2$ is a bond, substituted or unsubstituted $C_1$-$C_8$ alkylene, substituted or unsubstituted 2 to 8 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene.

Embodiment 193

The compound of one of embodiments 170 to 179, wherein $L^2$ is a bond, substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted phenyl, or substituted or unsubstituted 5 to 6 membered heteroarylene.

Embodiment 194

The compound of one of embodiments 170 to 179, wherein $L^2$ is a substituted or unsubstituted 4 to 10 membered heteroalkylene.

Embodiment 195

The compound of one of embodiments 170 to 179, wherein $L^2$ is a substituted or unsubstituted 4 to 8 membered heteroalkylene.

Embodiment 196

The compound of one of embodiments 170 to 179, wherein $L^2$ is —C(CH$_3$)$_2$CH$_2$NHC(O)—.

Embodiment 197

The compound of one of embodiments 166 to 196, wherein $R^3$ is —OH.

Embodiment 198

The compound of one of embodiments 166 to 196, wherein $R^3$ is monophosphate.

Embodiment 199

The compound of one of embodiments 166 to 196, wherein $R^3$ is polyphosphate.

Embodiment 200

The compound of one of embodiments 166 to 196, wherein $R^3$ is triphosphate.

Embodiment 201

The compound of one of embodiments 166 to 196, wherein $R^3$ is tetraphosphate, pentaphosphate, or hexaphosphate.

Embodiment 202

The compound of one of embodiments 166 to 196, wherein $R^3$ is a residue of a nucleic acid.

Embodiment 203

The compound of one of embodiments 166 to 196, wherein $R^3$ is a residue of a 10 to 25 base nucleic acid.

Embodiment 204

The compound of one of embodiments 166 to 196, wherein $R^3$ is a residue of a 10 to 10,000 base nucleic acid.

Embodiment 205

The compound of one of embodiments 170 to 204, wherein $R^{4A}$ is independently hydrogen, —CH$_3$, —CX$^1{}_3$, —CHX$^1{}_2$, —CH$_2$X$^1$, —CN, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 206

The compound of one of embodiments 170 to 204, wherein $R^{4A}$ is independently hydrogen, —CH$_3$, —CX$^1{}_3$, —CHX$^1{}_2$, —CH$_2$X$^1$, —CN, -Ph, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

Embodiment 207

The compound of one of embodiments 170 to 204, wherein $R^{4A}$ is hydrogen.

Embodiment 208

The compound of one of embodiments 170 to 204, wherein $R^{4B}$ is independently hydrogen, —CH$_3$, —CX$^2{}_3$, —CHX$^2{}_2$, —CH$_2$X$^2$, —CN, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 209

The compound of one of embodiments 170 to 204, wherein $R^{4B}$ is independently hydrogen, —CH$_3$, —CX$^2{}_3$, —CHX$^2{}_2$, —CH$_2$X$^2$, —CN, -Ph, substituted or unsubsti-

Embodiment 210

The compound of one of embodiments 170 to 204, wherein $R^{4B}$ is hydrogen.

Embodiment 211

The compound of one of embodiments 166 to 210, wherein $R^5$ is a detectable label

Embodiment 212

The compound of one of embodiments 166 to 210, wherein $R^5$ is a fluorescent dye.

Embodiment 213

The compound of one of embodiments 166 to 210, wherein $R^5$ is an anchor moiety.

Embodiment 214

The compound of one of embodiments 166 to 210, wherein $R^5$ is a click chemistry reactant moiety.

Embodiment 215

The compound of one of embodiments 166 to 210, wherein $R^5$ is a trans-cyclooctene moiety or azide moiety.

Embodiment 216

The compound of one of embodiments 166 to 210, wherein $R^5$ is an affinity anchor moiety.

Embodiment 217

The compound of one of embodiments 166 to 210, wherein $R^5$ is a biotin moiety.

Embodiment 218

The compound of one of embodiments 166 to 217, wherein
- $R^{8A}$ is hydrogen, —$CH_3$, —$CX^3_3$, —$CHX^3_2$, —$CH_2X^3$, —CN, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $R^{8B}$ is hydrogen, —$CH_3$, —$CX^4_3$, —$CHX^4_2$, —$CH_2X^4$, —CN, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $R^9$ is hydrogen, —$CX^5_3$, —$CHX^5_2$, —$CH_2X^5$, —$OCH_3$, —$SCH_3$, —$NHCH_3$, —CN, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $R^{10}$ is hydrogen, —$CX^6_3$, —$CHX^6_2$, —$CH_2X^6$, —$OCH_3$, —$SCH_3$, —$NHCH_3$, —CN, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $R^{11}$ is hydrogen, —$CX^7_3$, —$CHX^7_2$, —$CH_2X^7$, —$OCH_3$, —$SCH_3$, —$NHCH_3$, —CN, -Ph, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and
- $X^3$, $X^4$, $X^5$, $X^6$ and $X^7$ are independently halogen.

Embodiment 219

The compound of one of embodiments 166 to 217, wherein
- $R^{8A}$ and $R^{8B}$ are independently hydrogen or unsubstituted alkyl; and
- $R^9$, $R^{10}$, and $R^{11}$ are independently unsubstituted alkyl or unsubstituted heteroalkyl.

Embodiment 220

The compound of one of embodiments 166 to 217, wherein
- $R^{8A}$ and $R^{8B}$ are independently hydrogen or unsubstituted $C_1$-$C_4$ alkyl; and
- $R^9$, $R^{10}$ and $R^{11}$ are independently unsubstituted $C_1$-$C_6$ alkyl or unsubstituted 2 to 4 membered heteroalkyl.

Embodiment 221

The compound of one of embodiments 166 to 217, wherein
- $R^{8A}$ and $R^{8B}$ are independently hydrogen; and
- R9, $R^{10}$, and $R^{11}$ are independently unsubstituted $C_1$-$C_6$ alkyl or unsubstituted 2 to 4 membered heteroalkyl.

Embodiment 222

The compound of one of embodiments 166 to 217, wherein
- $R^{8A}$ and $R^{8B}$ are independently hydrogen; and
- $R^9$, $R^{10}$, and $R^{11}$ are independently unsubstituted methyl or unsubstituted methoxy.

Embodiment 223

The compound of one of embodiments 166 to 217, wherein $R^{8A}$, $R^{8B}$, $R^9$, $R^{10}$, and $R^{11}$ are independently hydrogen or unsubstituted methyl.

Embodiment 224

The compound of one of embodiments 166 to 217, wherein $R^{8A}$ and $R^{85}$ are hydrogen and $R^9$, $R^{10}$, and $R^{11}$ are unsubstituted methyl.

Embodiment 225

The compound of one of embodiments 166 to 217, wherein $R^7$ is hydrogen.

Embodiment 226

The compound of one of embodiments 166 to 217, wherein 127 is —$OR^{7A}$; and $R^{7A}$ is hydrogen.

Embodiment 227

The compound of one of embodiments 166 to 217, wherein $R^7$ is —$OR^{7A}$ and $R^{7A}$ is:

Embodiment 228

The compound of one of embodiments 166 to 227, wherein 127 is —$OR^{7A}$ and $R^{7A}$ is:

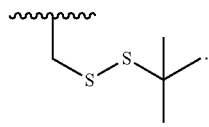 [SMILES: *CSSC(C)(C)C]

Embodiment 229

The compound of embodiment 166, having the formula:

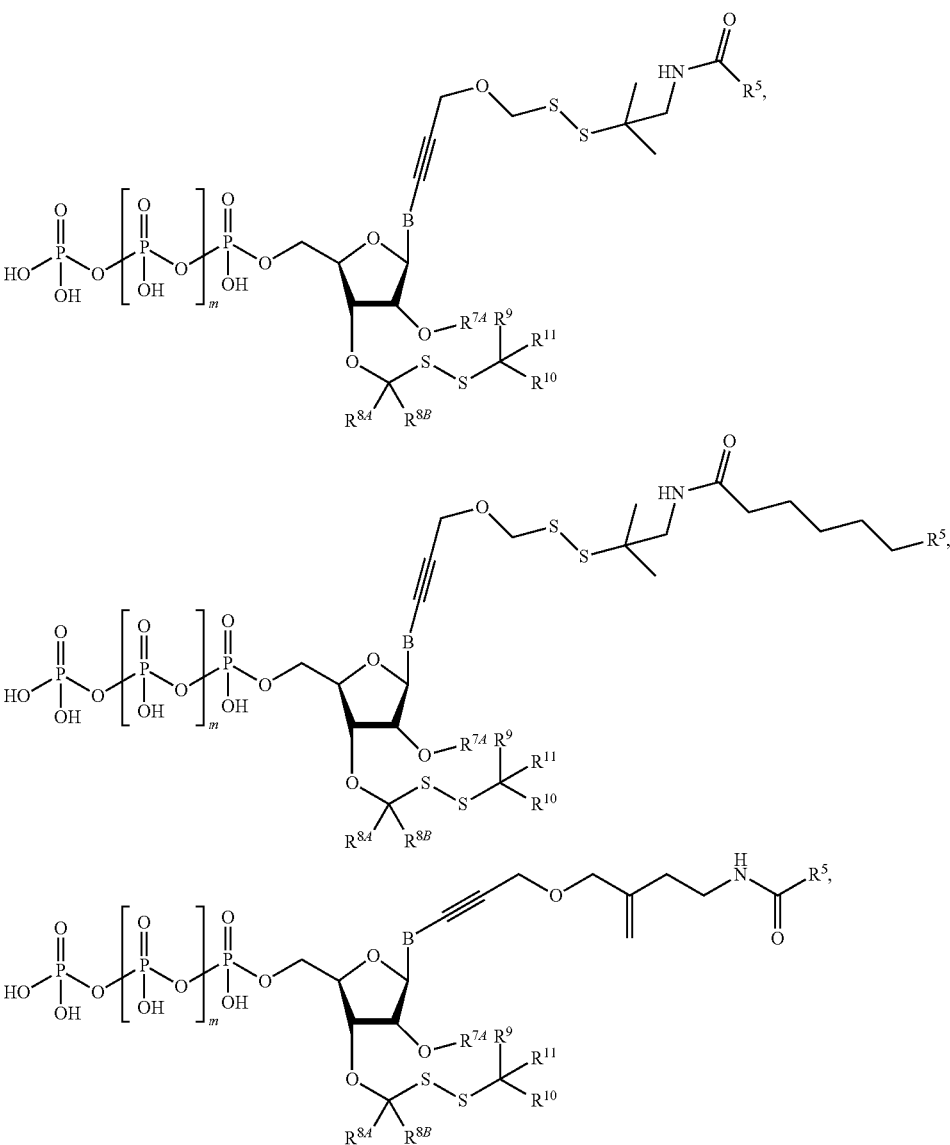

-continued
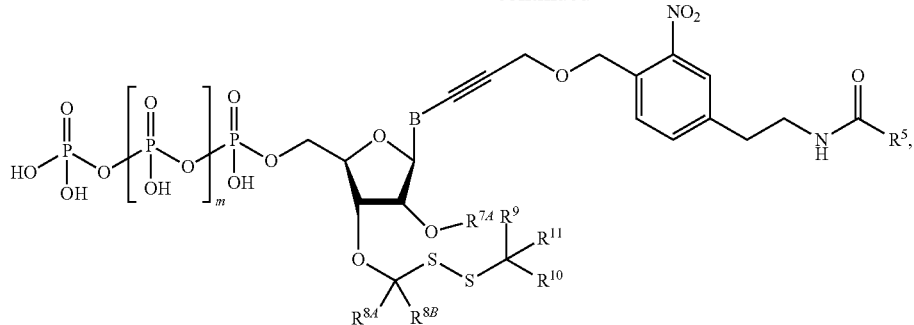
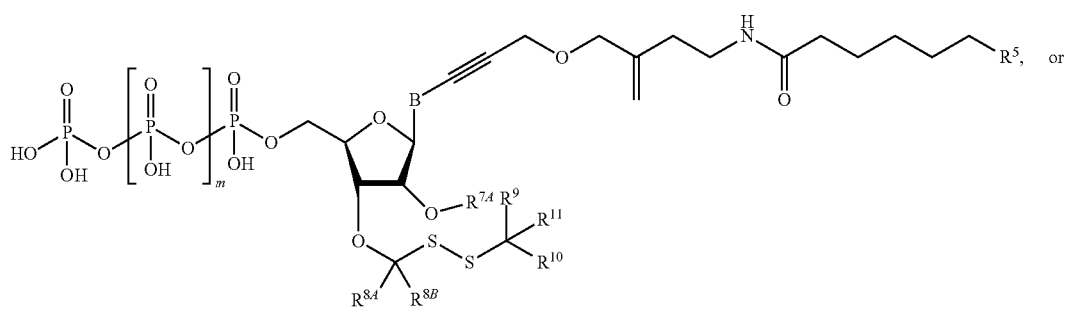
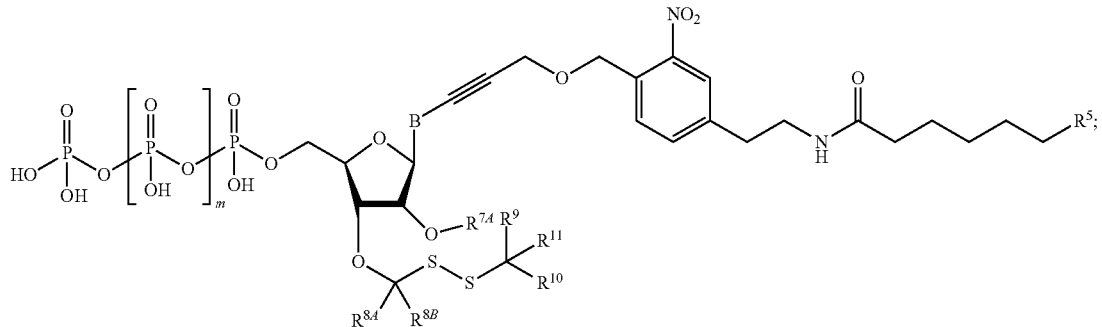
wherein m is an integer from 1 to 4.
Embodiment 230
The compound of embodiment 166, having the formula:
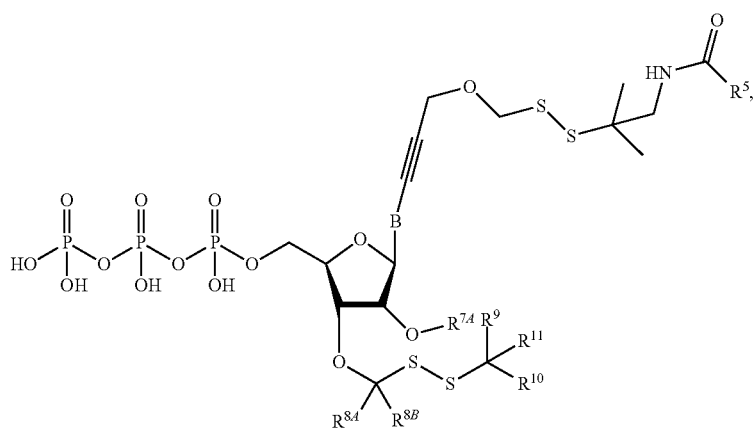

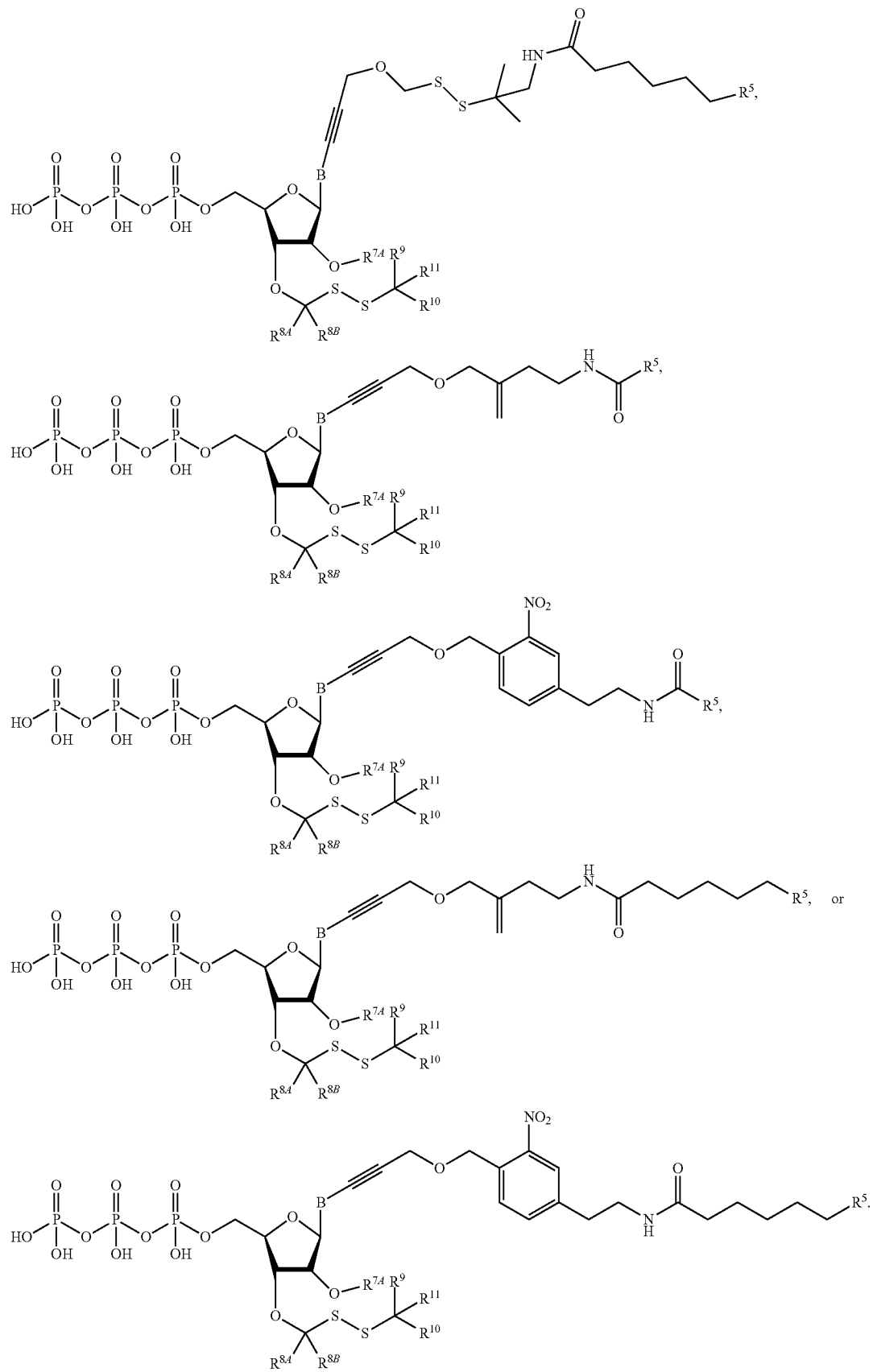

Embodiment 231

The compound of one of embodiments 229 to 230, wherein —CR$^9$R$^{10}$R$^{11}$ is unsubstituted methyl, unsubstituted ethyl, unsubstituted propyl, unsubstituted isopropyl, unsubstituted butyl, or unsubstituted tert-butyl.

Embodiment 232

The compound of one of embodiments 229 to 230, wherein R$^9$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, or -Ph.

Embodiment 233

The compound of one of embodiments 229 to 230, wherein R$^{10}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$. —NHCH(CH$_3$)$_2$, —NHCH$_2$CH$_2$CH$_3$, —NHCH$_2$CH$_3$, —NHCH$_3$, or -Ph.

Embodiment 234

The compound of one of embodiments 229 to 230, wherein R$^{11}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, or -Ph.

Embodiment 235

The compound of one of embodiments 229 to 230, wherein R$^{8A}$ is hydrogen, deuterium, —C(CH$_3$)$_3$, —CH(CH$_3$)$_2$, —CH$_2$CH$_2$CH$_3$, —CH$_2$CH$_3$, —CH$_3$, —CX$^3_3$, —CHX$^3_2$, —CH$_2$X$^3$, —CN, -Ph.

Embodiment 236

The compound of one of embodiments 229 to 230, wherein R$^{8B}$ is hydrogen, deuterium, —C(CH$_3$)$_3$, —CH(CH$_3$)$_2$, —CH$_2$CH$_2$CH$_3$, —CH$_2$CH$_3$, —CH$_3$, —CX$^4_3$, —CHX$^4_2$, —CH$_2$X$^4$, —CN, -Ph.

Embodiment 237

The compound of one of embodiments 229 to 236, wherein —R$^{7A}$ is hydrogen.

Embodiment 238

The compound of one of embodiments 229 to 236, wherein —R$^{7A}$ is

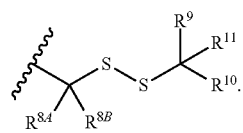

Embodiment 239

The compound of one of embodiments 229 to 236, wherein —R$^{7A}$ is

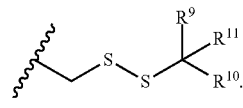

Embodiment 240

The compound of one of embodiments 229 to 236, wherein —R$^{7A}$ is

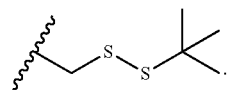 [SMILES: *CSSC(C)(C)C]

Embodiment 241

The compound of one of embodiments 229 to 236 having the formula:

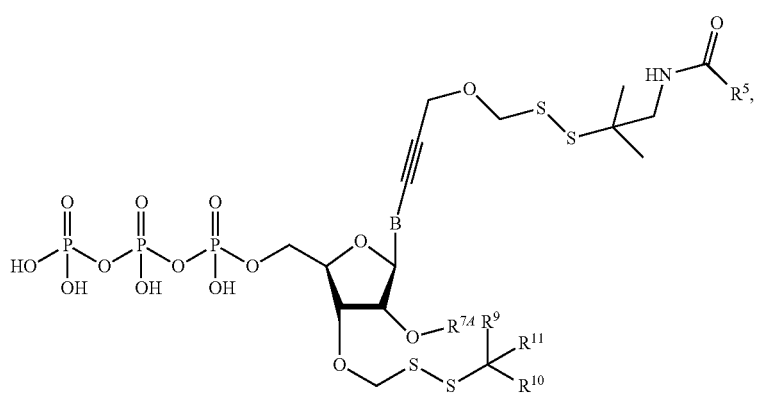

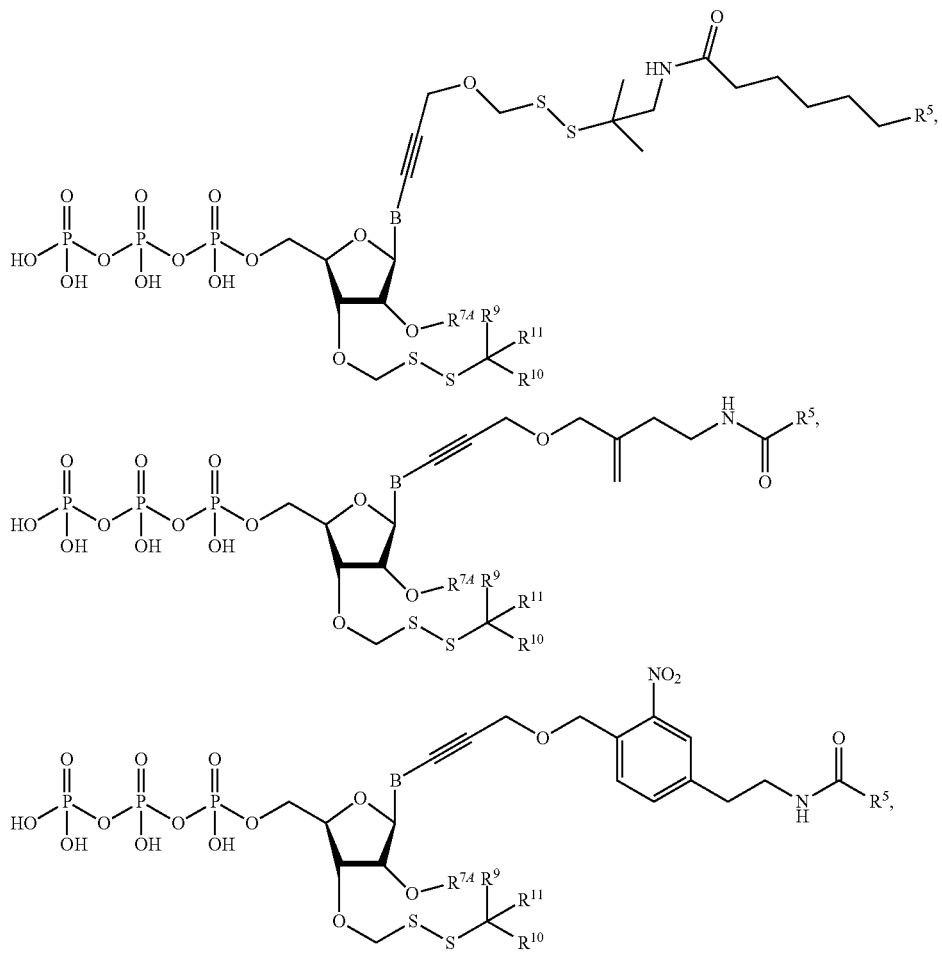
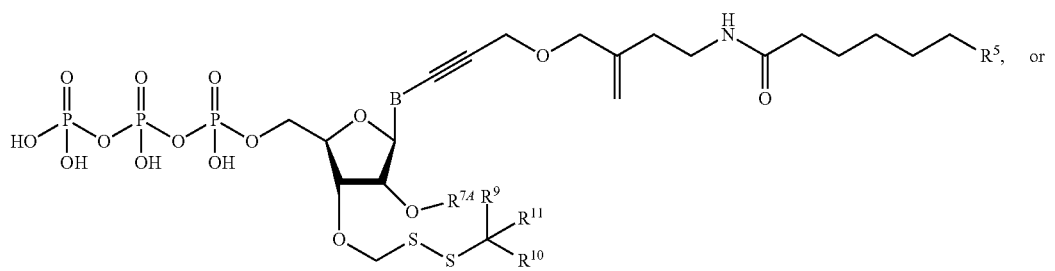
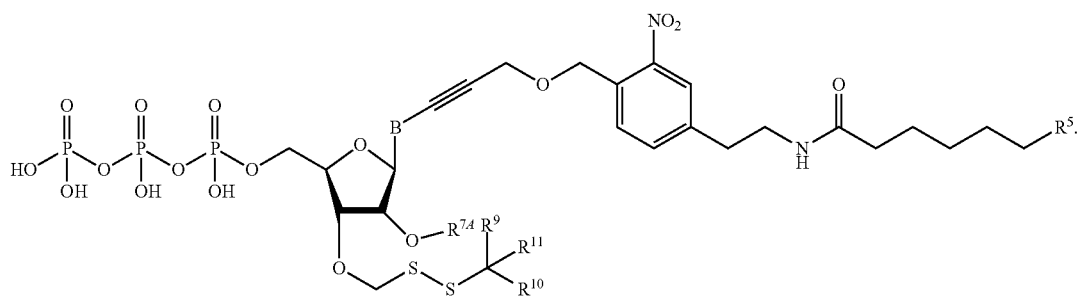

Embodiment 242
The compound of one of embodiments 229 to 236 having the formula:
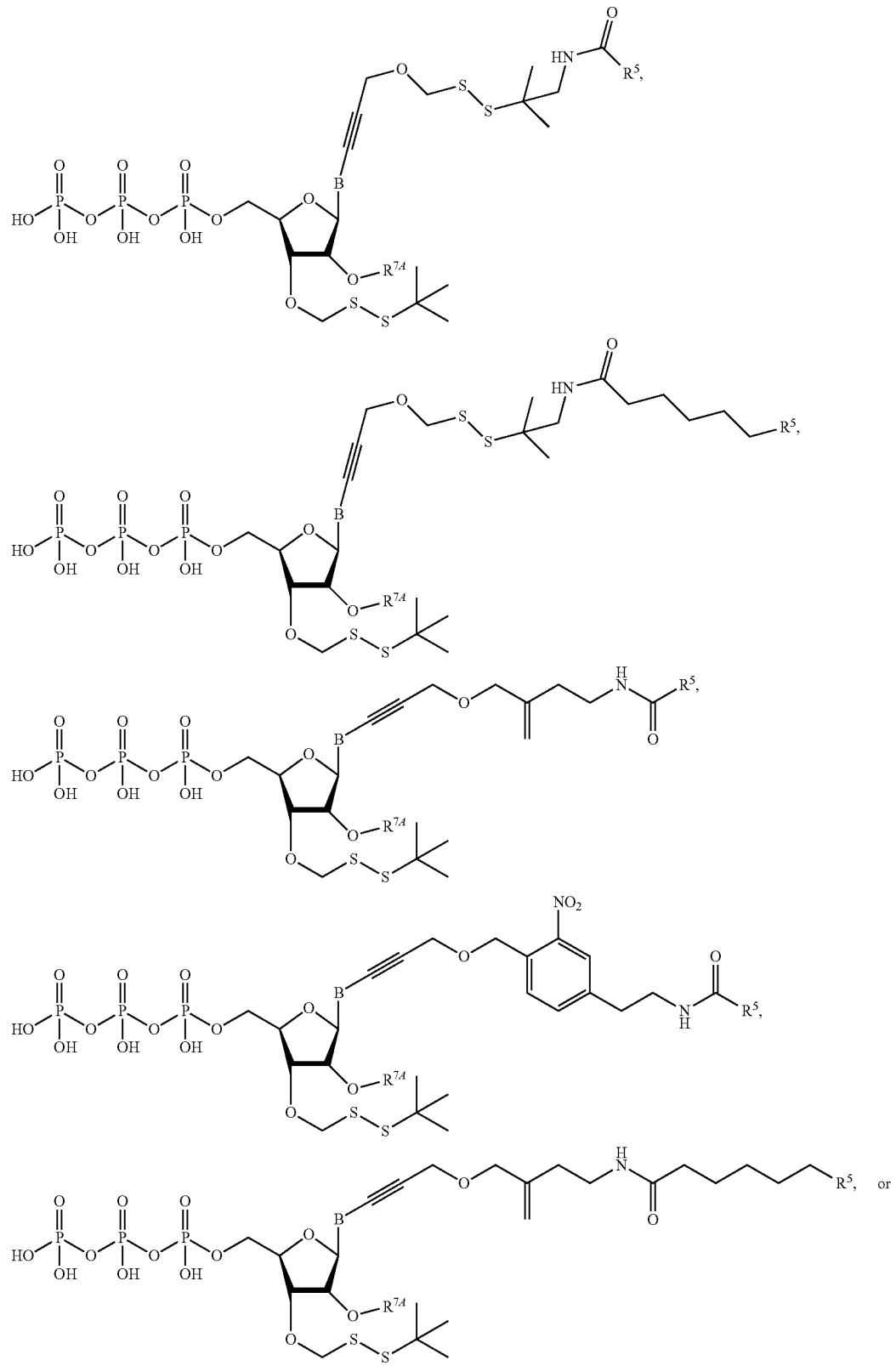

417
-continued
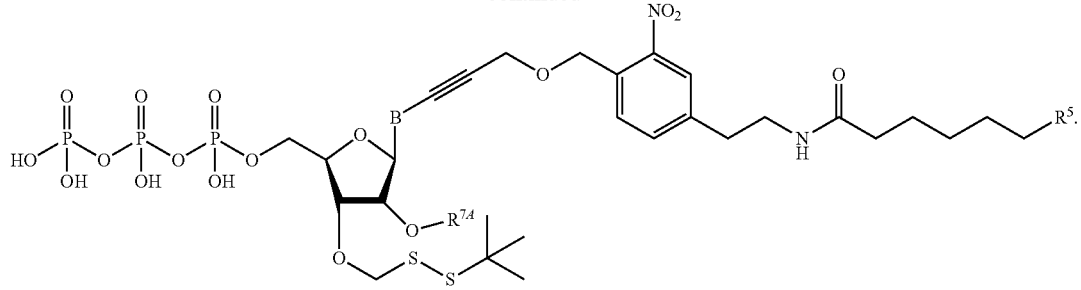
Embodiment 243
The compound of one of embodiments 229 to 242, wherein B is
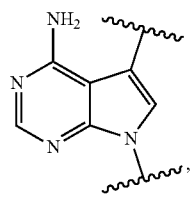 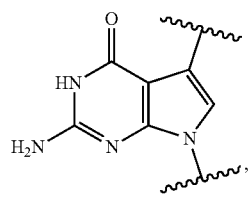
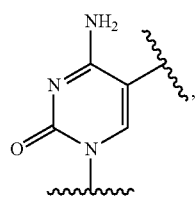 or 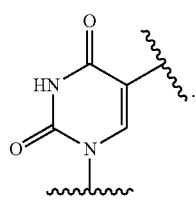
Embodiment 244
The compound of one of embodiments 229 to 243, wherein $R^5$ is
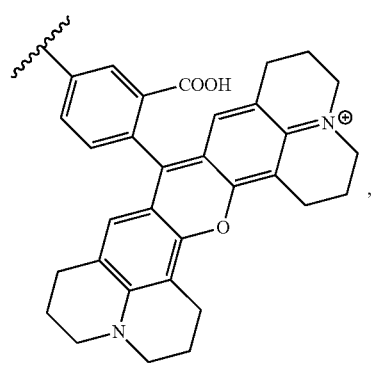
418
-continued
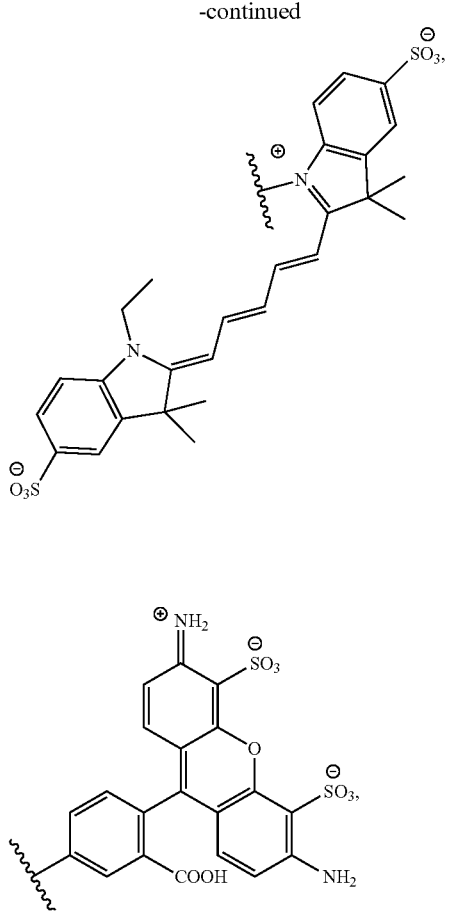
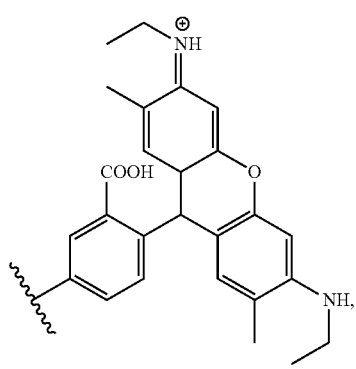

419
-continued
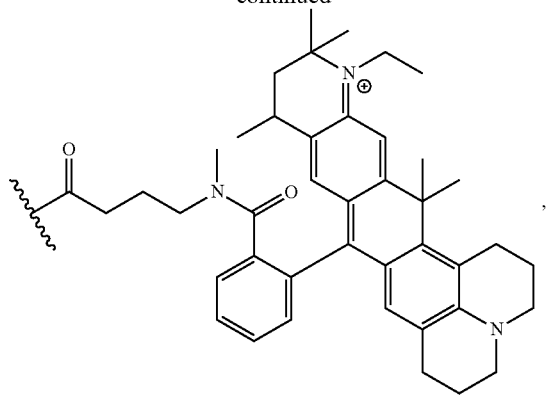
,
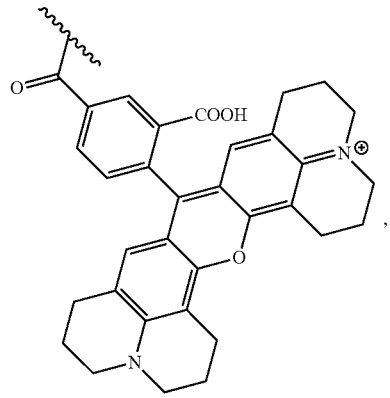,
420
-continued
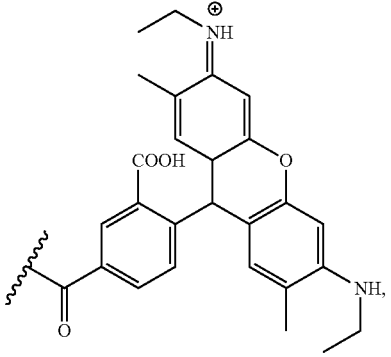
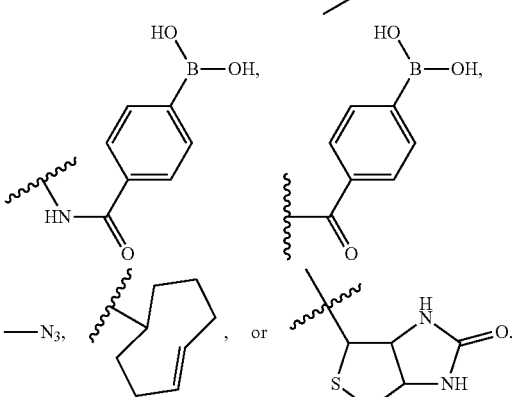
Embodiment 245
The compound of embodiment 166, having the formula:
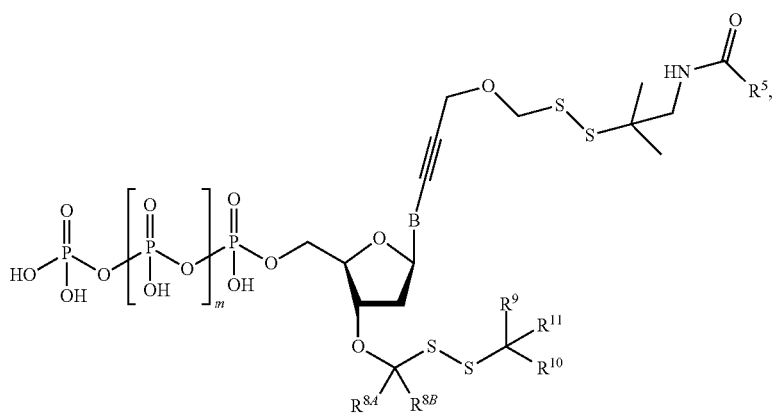

-continued
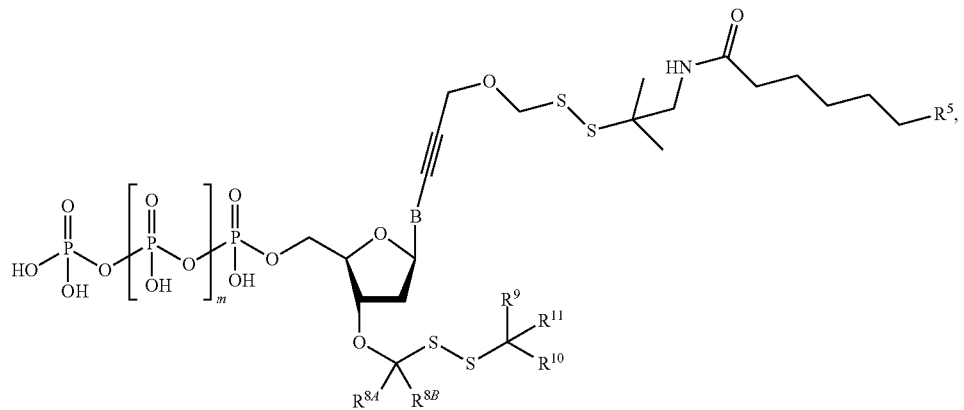
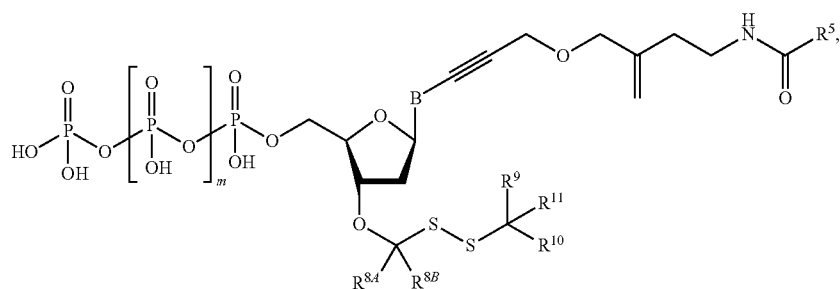
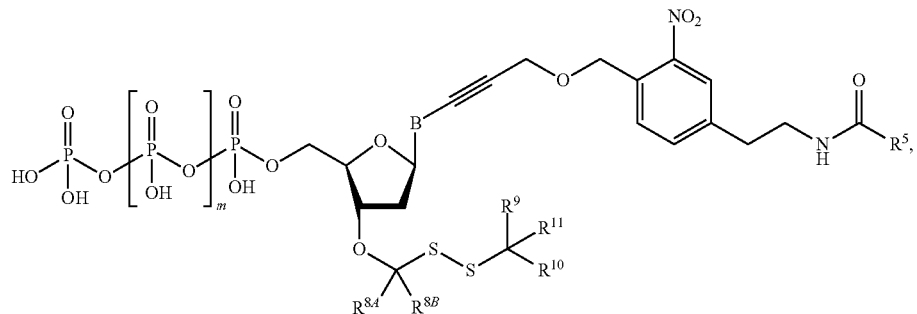
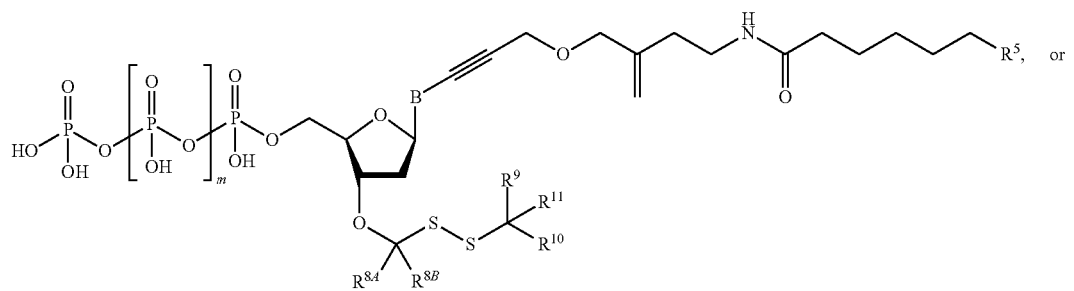

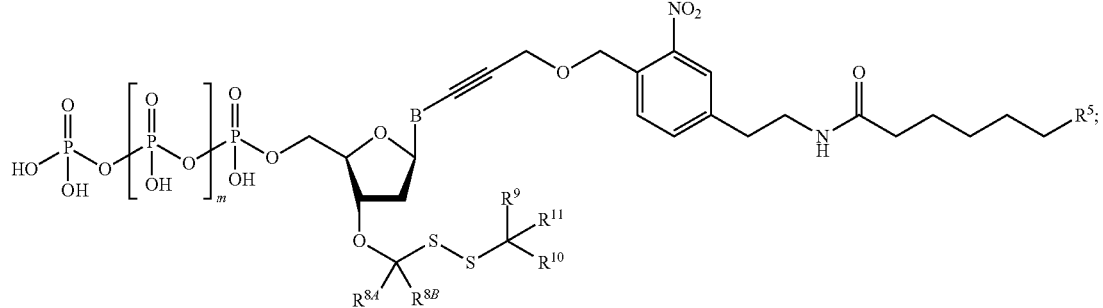
wherein m is an integer from 1 to 4.
Embodiment 246
The compound of embodiment 166, having the formula:
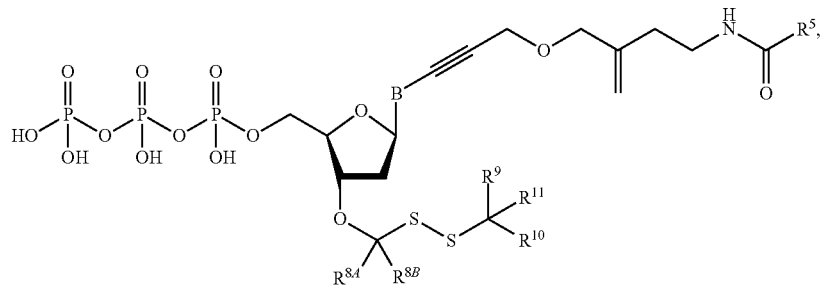
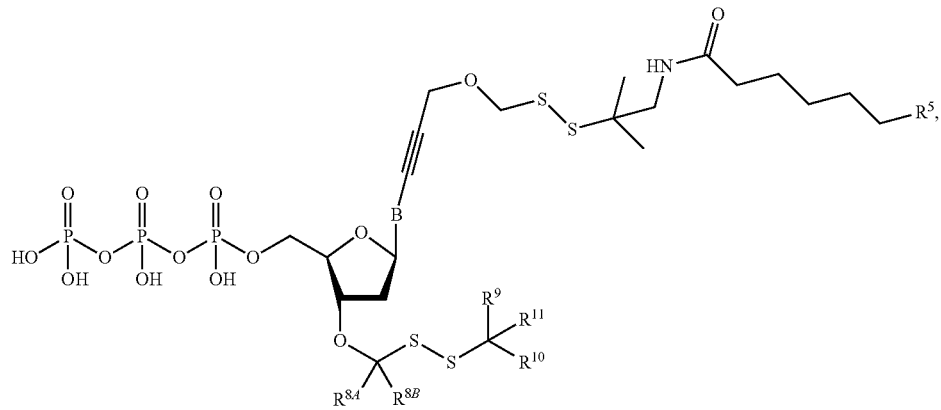
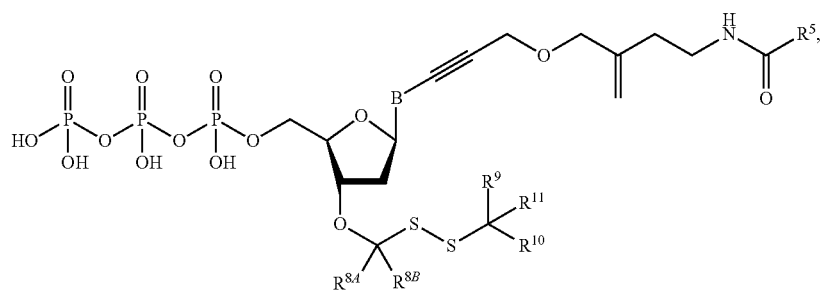

-continued

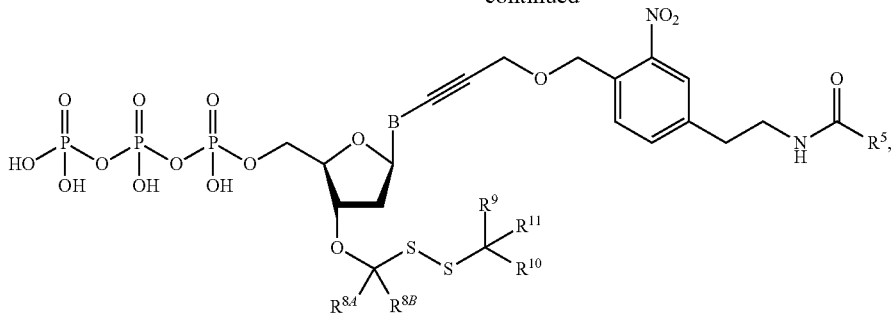

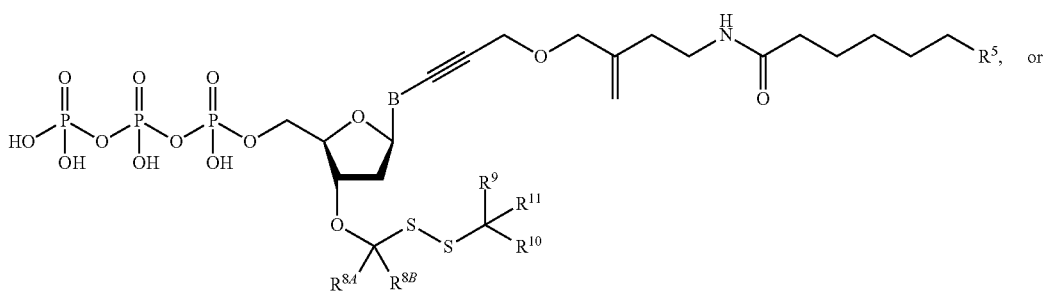

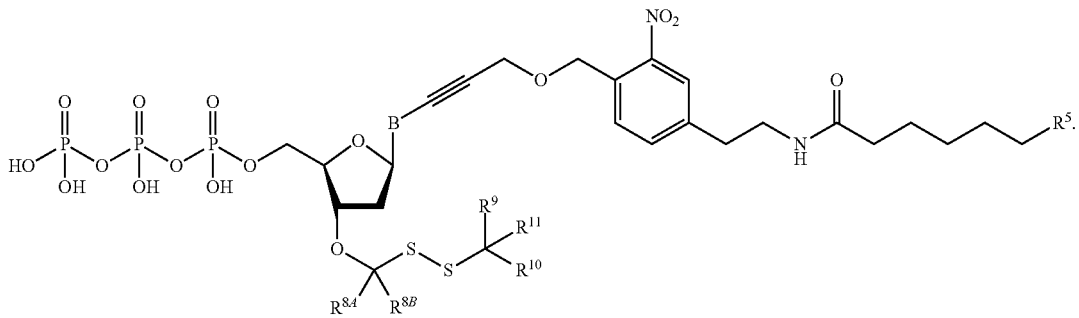

Embodiment 247

The compound of one of embodiments 245 to 246, wherein —$CR^9R^{10}R^{11}$ is unsubstituted methyl, unsubstituted ethyl, unsubstituted propyl, unsubstituted isopropyl, unsubstituted butyl, or unsubstituted tert-butyl.

Embodiment 248

The compound of one of embodiments 245 to 246, wherein $R^9$ is hydrogen, —$C(CH_3)_3$, —$CH(CH_3)_2$, —$CH_2CH_2CH_3$, —$CH_2CH_3$, —$CH_3$, $OC(CH_3)_3$, —$OCH(CH_3)_2$, —$OCH_2CH_2CH_3$, —$OCH_2CH_3$, —$OCH_3$, —$SC(CH_3)_3$, —$SCH(CH_3)_2$, —$SCH_2CH_2CH_3$, —$SCH_2CH_3$, —$SCH_3$, —$NHC(CH_3)_3$, —$NHCH(CH_3)_2$, —$NHCH_2CH_2CH_3$, —$NHCH_2CH_3$, —$NHCH_3$, or -Ph.

Embodiment 249

The compound of one of embodiments 245 to 246, wherein $R^{10}$ is hydrogen, —$C(CH_3)_3$, —$CH(CH_3)_2$, —$CH_2CH_2CH_3$, —$CH_2CH_3$, —$CH_3$, $OC(CH_3)_3$, —$OCH(CH_3)_2$, —$OCH_2CH_2CH_3$, —$OCH_2CH_3$, —$OCH_3$, —$SC(CH_3)_3$, —$SCH(CH_3)_2$, —$SCH_2CH_2CH_3$, —$SCH_2CH_3$, —$SCH_3$, —$NHC(CH_3)_3$, —$NHCH(CH_3)_2$, —$NHCH_2CH_2CH_3$, —$NHCH_2CH_3$, —$NHCH_3$, or -Ph.

Embodiment 250

The compound of one of embodiments 245 to 246, wherein $R^{11}$ is hydrogen, —$C(CH_3)_3$, —$CH(CH_3)_2$, —$CH_2CH_2CH_3$, —$CH_2CH_3$, —$CH_3$, $OC(CH_3)_3$, —$OCH(CH_3)_2$, —$OCH_2CH_2CH_3$, —$OCH_2CH_3$, —$OCH_3$, —$SC(CH_3)_3$, —$SCH(CH_3)_2$, —$SCH_2CH_2CH_3$, —$SCH_2CH_3$, —$SCH_3$, —$NHC(CH_3)_3$, —$NHCH(CH_3)_2$, —$NHCH_2CH_2CH_3$, —$NHCH_2CH_3$, —$NHCH_3$, or -Ph.

Embodiment 251

The compound of one of embodiments 245 to 246, wherein $R^{8A}$ is hydrogen, deuterium, —$C(CH_3)_3$, —$CH(CH_3)_2$, —$CH_2CH_2CH_3$, —$CH_2CH_3$, —$CH_3$, —$CX^3{}_3$, —$CHX^3{}_2$, —$CH_2X^3$, —CN, -Ph.

Embodiment 252

The compound of one of embodiments 245 to 246, wherein $R^{8B}$ is hydrogen, deuterium, —$C(CH_3)_3$, —$CH(CH_3)_2$, —$CH_2CH_2CH_3$, —$CH_2CH_3$, —$CH_3$, —$CX^4{}_3$, —$CHX^4{}_2$, —$CH_2X^4$, —CN, -Ph.

Embodiment 253
The compound of one of embodiments 245 to 246 having the formula:
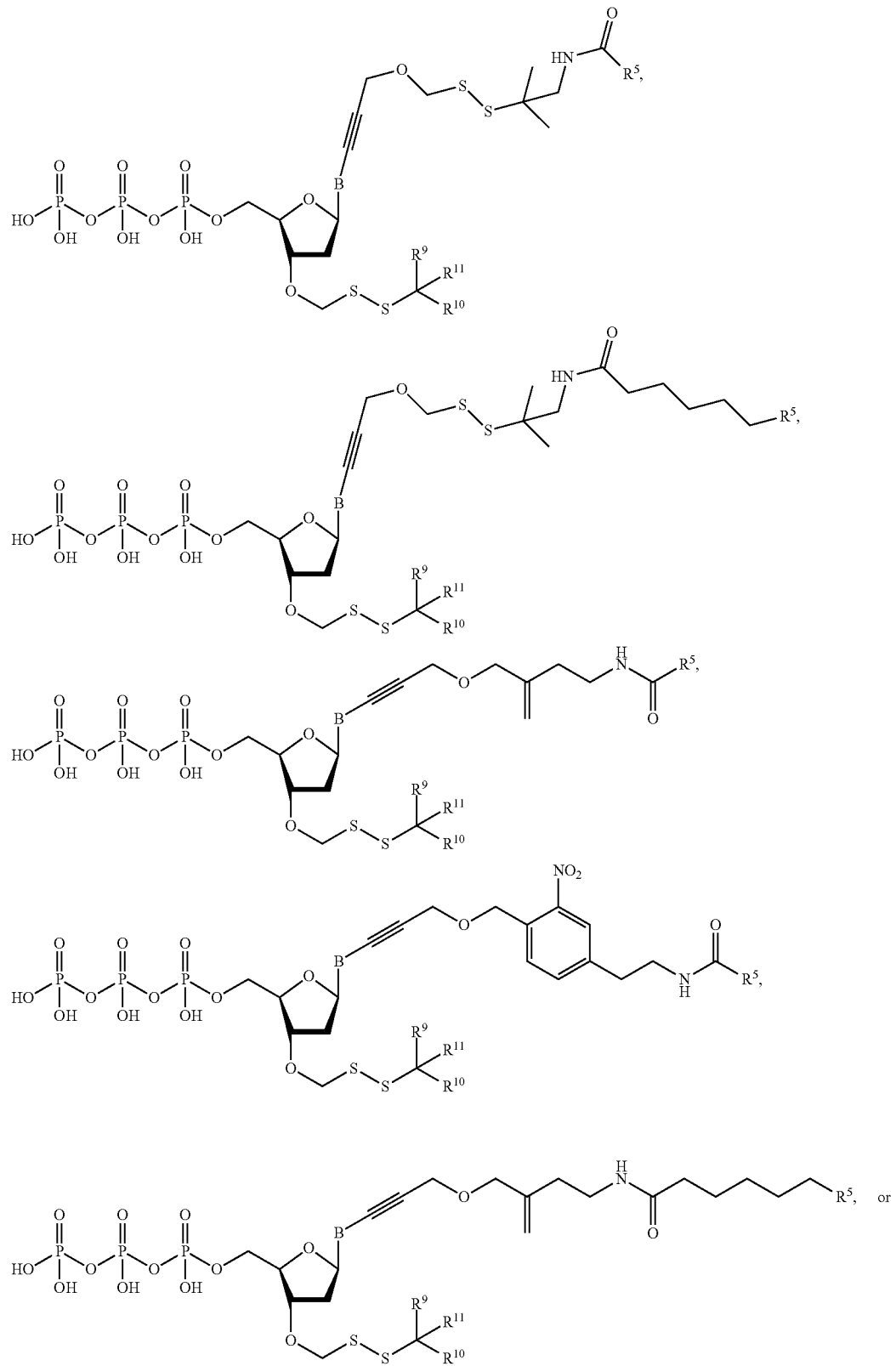

-continued
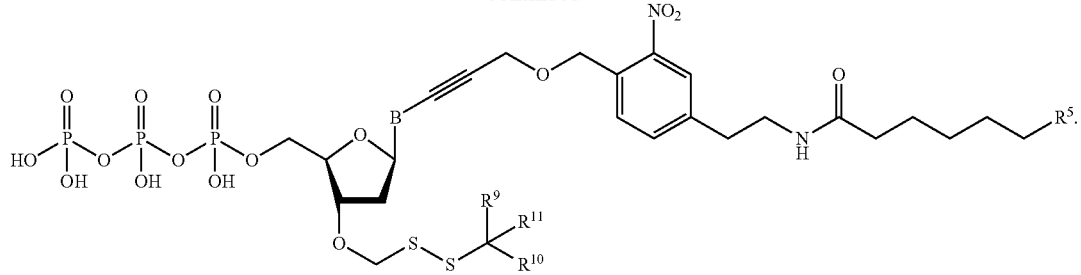
Embodiment 254
The compound of one of embodiments 242 to 246 having the formula:
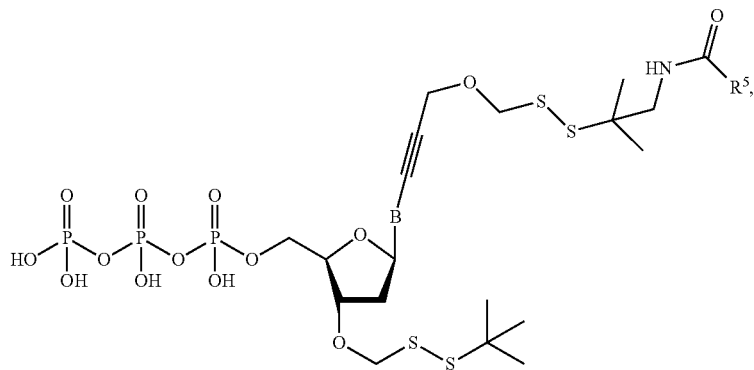
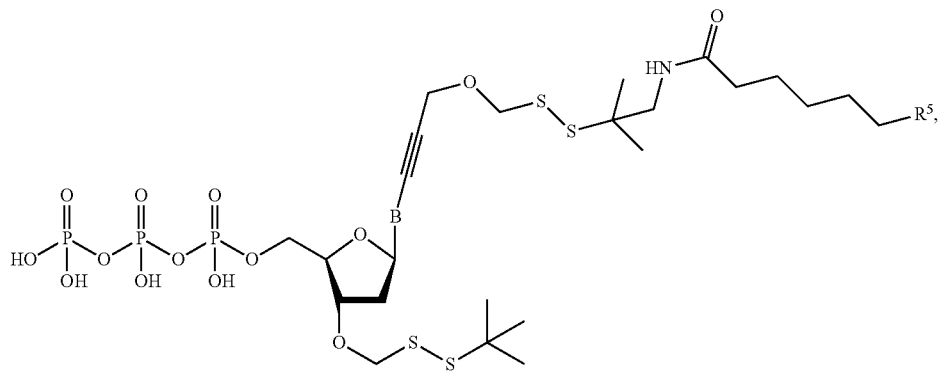
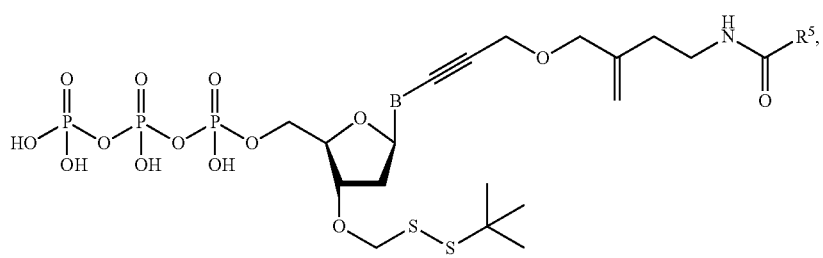

-continued
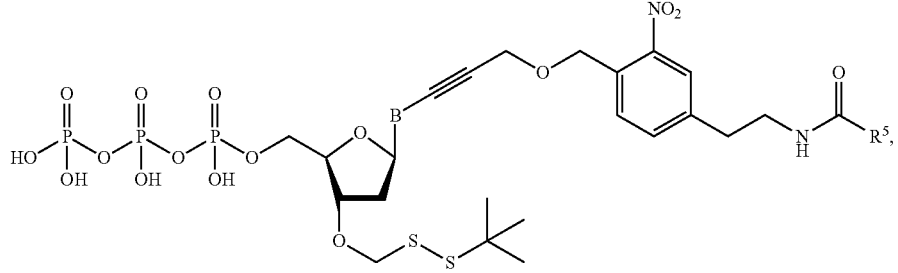
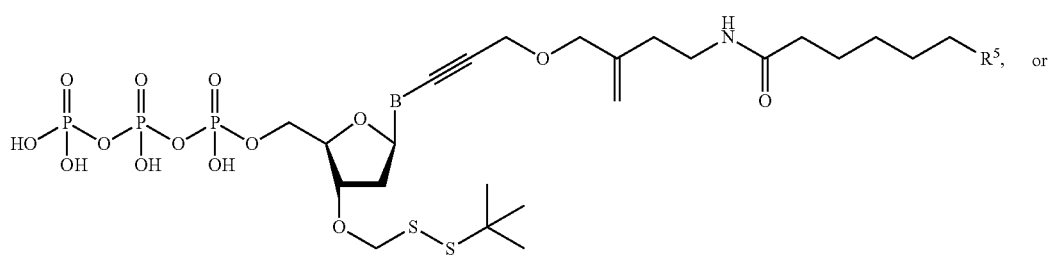
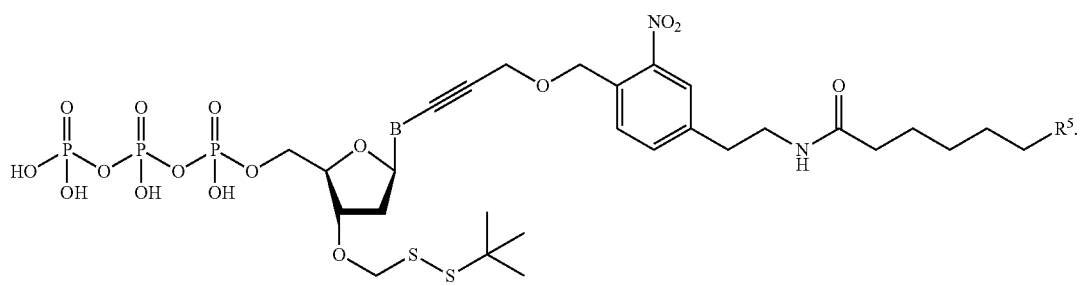
Embodiment 255
The compound of one of embodiments 229 to 254, wherein B is
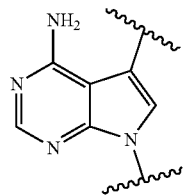 , 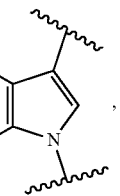 ,
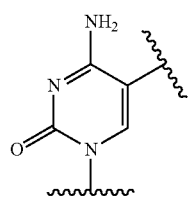 , or 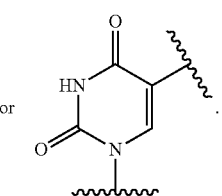 .
Embodiment 256
The compound of one of embodiments 229 to 255, wherein $R^5$ is
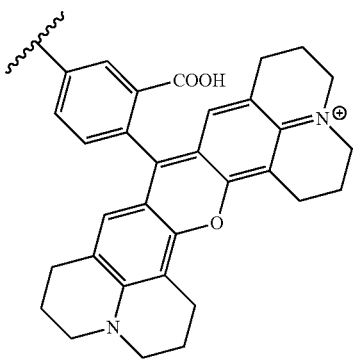 , 433
-continued
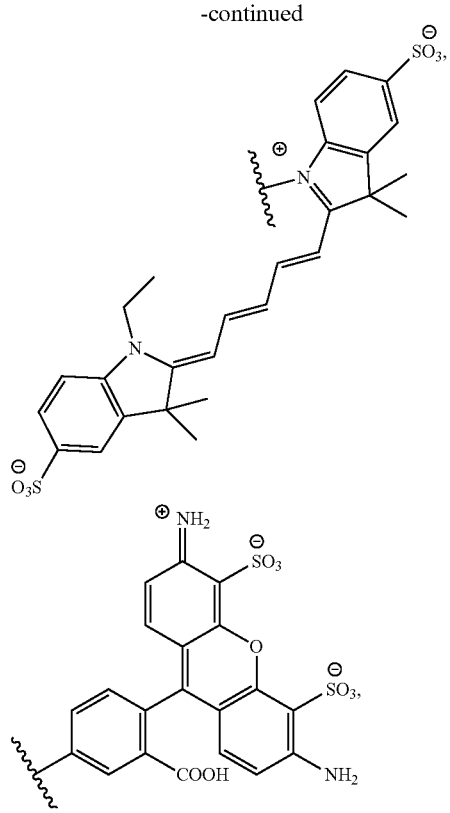
434
-continued
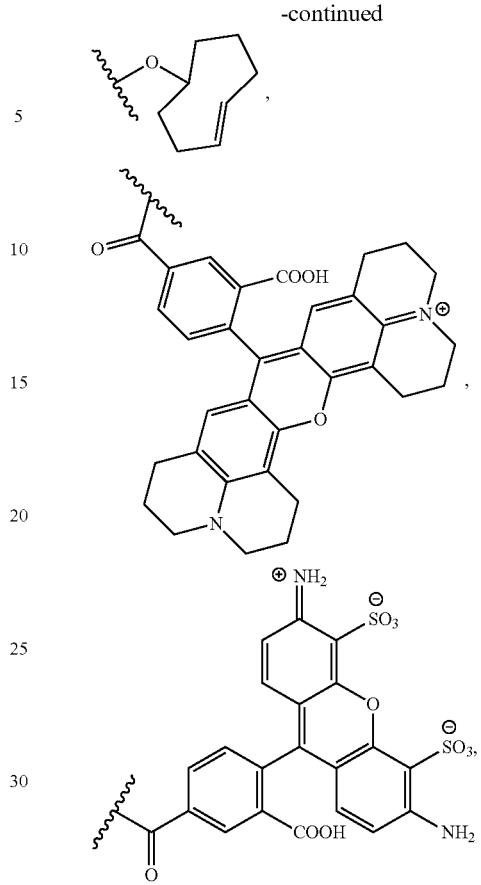
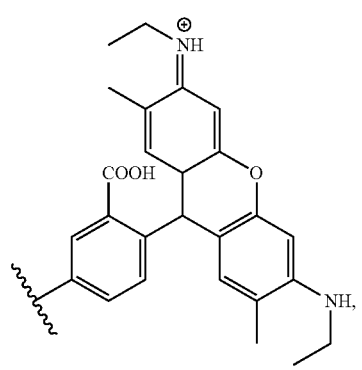
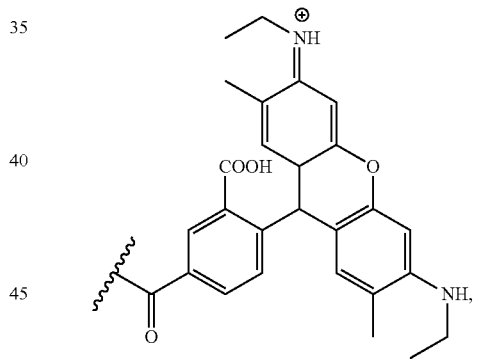
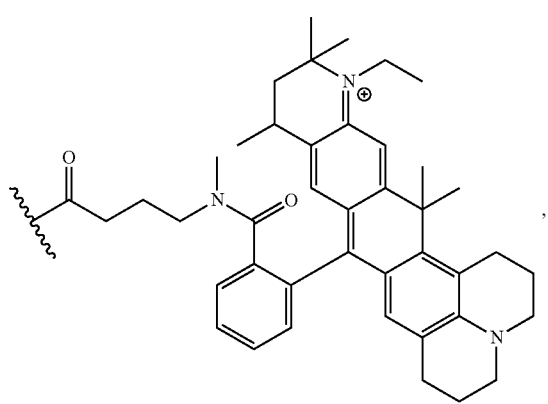
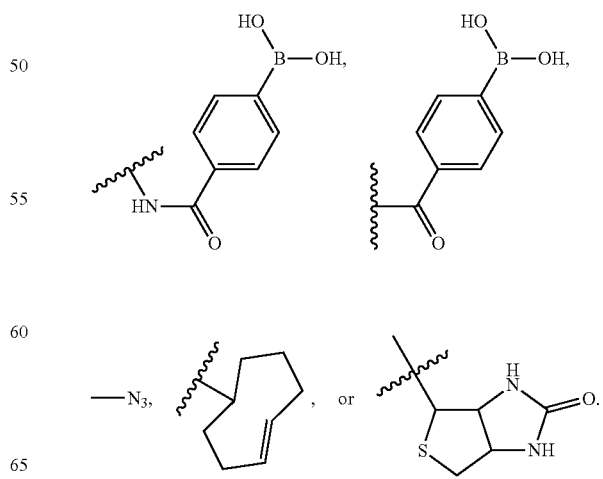

Embodiment 257

A compound of the formula:

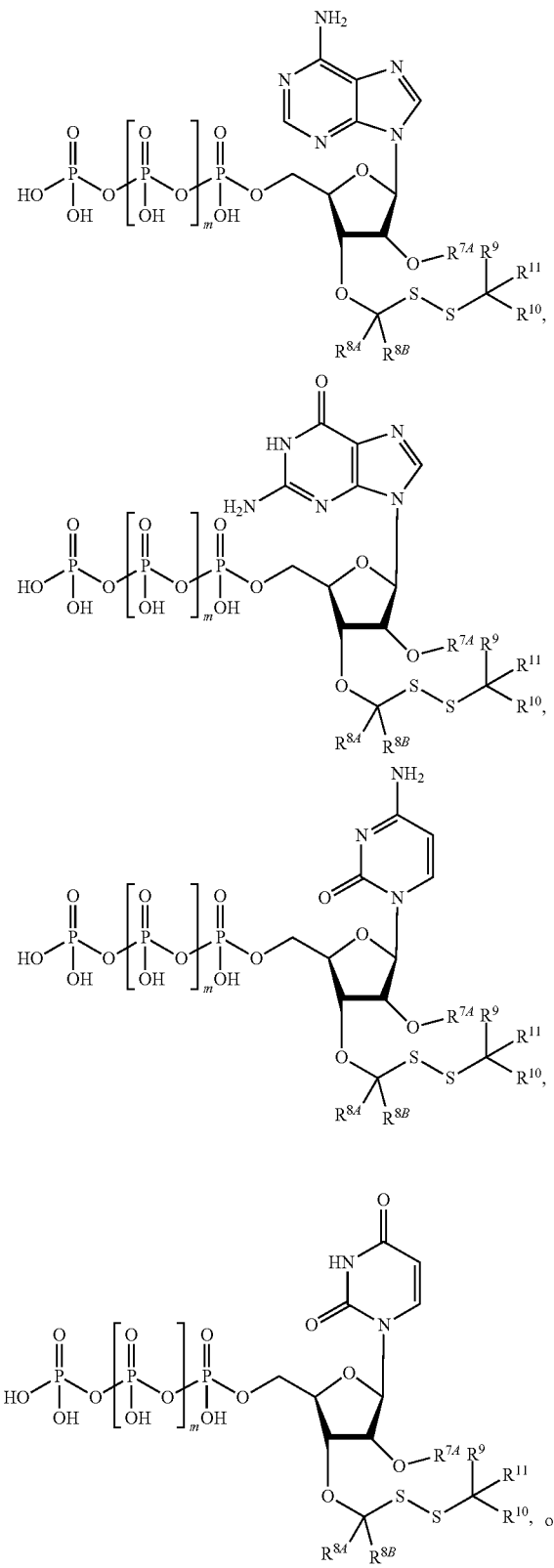

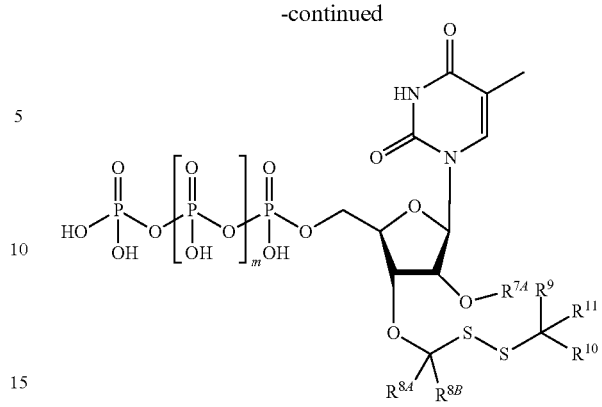

wherein

R$^{7A}$ is hydrogen or a polymerase-compatible cleavable moiety;

R$^{8A}$ is hydrogen, —CX$^3_3$, —CHX$^3_2$, —CH$_2$X$^3$, —OCX$^3_3$, —OCH$_2$X$^3$, —OCHX$^3_2$, —CN, —OH, —SH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{8B}$ is hydrogen, —CX$^4_3$, —CHX$^4_2$, —CH$_2$X$^4$. —OCX$^4_3$, —OCH$_2$X$^4$, —OCHX$^4_2$, —CN, —OH, —SH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$ is hydrogen, —CX$^5_3$, —CHX$^5_2$, —CH$_2$X$^5$, —OCX$^5_3$, —OCH$_2$X$^5$, —OCHX$^5_2$, —CN, —OH, —SH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{10}$ is hydrogen, —CX$^6_3$, —CHX$^6_2$, —CH$_2$X$^6$, —OCX$^6_3$, —OCH$_2$X$^6$, —OCHX$^6_2$, —CN, —OH, —SH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{11}$ is hydrogen, —CX$^7_3$, —CHX$^7_2$, —CH$_2$X$^7$, —OCX$^7_3$, —OCH$_2$V, —OCHX$^7_2$, —CN, —OH, —SH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and X$^3$, X$^4$, X$^5$, X$^6$ and X$^7$ are independently halogen; and m is an integer from 1 to 4.

Embodiment 258

A compound of the formula:

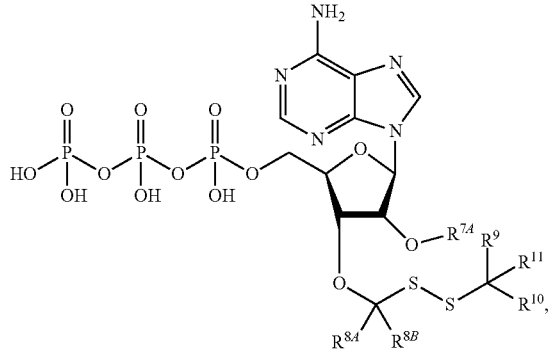

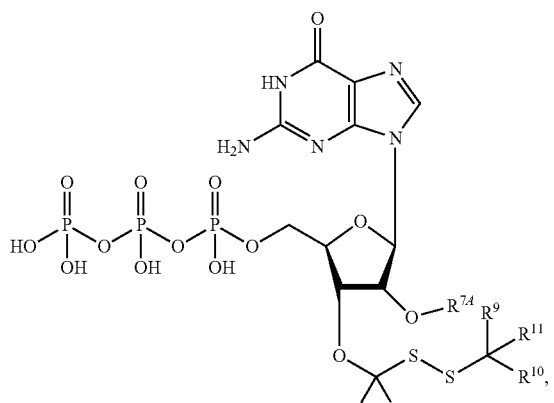

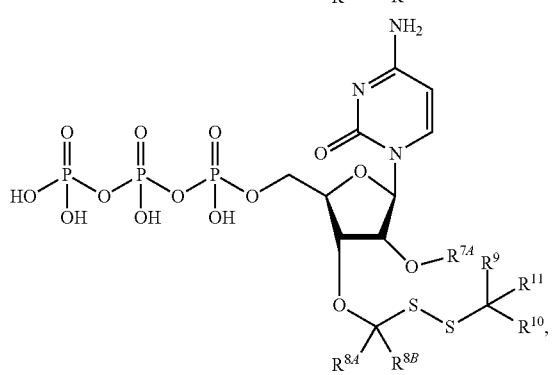

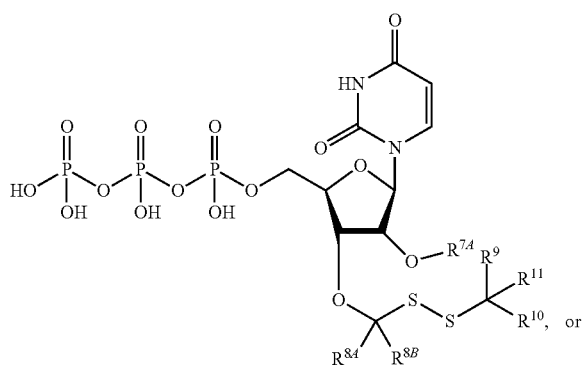

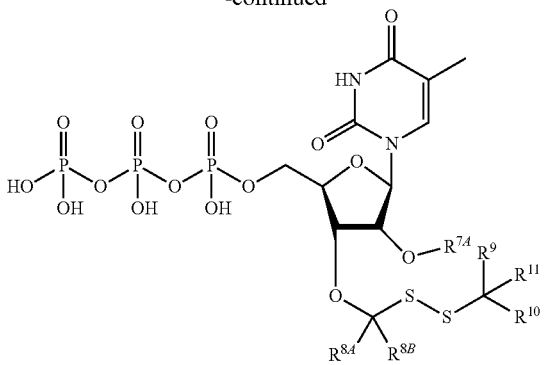

wherein
$R^{7A}$ is hydrogen or a polymerase-compatible cleavable moiety;

$R^{8A}$ is independently hydrogen, $-CX^3_3$, $-CHX^3_2$, $-CH_2X^3$, $-OCH_2X^3$, $-OCHX^3_2$, $-CN$, $-OH$, $-SH$, $-NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{8B}$ is independently hydrogen, $-CX^4_3$, $-CHX^4_2$, $-CH_2X^4$, $-OCX^4_3$, $-OCH_2X^4$, $-OCHX^4_2$, $-CN$, $-OH$, $-SH$, $-NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is independently hydrogen, $-CX^5_3$, $-CHX^5_2$, $-CH_2X^5$, $-OCX^5_3$, $-OCH_2X^5$, $-OCHX^5_2$, $-CN$, $-OH$, $-SH$, $-NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is independently hydrogen, $-CX^6_3$, $-CHX^6_2$, $-CH_2X^6$, $-OCX^6_3$, $-OCH_2X^6$, $-OCHX^6_2$, $-CN$, $-OH$, $-SH$, $-NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is independently hydrogen, $-CX^7_3$, $-CHX^7_2$, $-CH_2X^7$, $-OCX^7_3$, $-OCH_2X^7$, $-OCHX^7_2$, $-CN$, $-OH$, $-SH$, $-NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $X^3$, $X^4$, $X^5$, $X^6$ and $X^1$ are independently halogen.

Embodiment 259

The compound of one of embodiments 257 to 258, wherein $-CR^9R^{10}R^{11}$ is unsubstituted methyl, unsubstituted ethyl, unsubstituted propyl, unsubstituted isopropyl, unsubstituted butyl, or unsubstituted tert-butyl.

Embodiment 260

The compound of one of embodiments 257 to 258, wherein $R^9$ is hydrogen, $-C(CH_3)_3$, $-CH(CH_3)_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, or -Ph.

Embodiment 261

The compound of one of embodiments 257 to 258, wherein R$^{10}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, or -Ph.

Embodiment 262

The compound of one of embodiments 257 to 258, wherein R$^{11}$ is hydrogen, —C(CH$_3$)$_3$, —CH(CH$_3$)$_2$, —CH$_2$CH$_2$CH$_3$, —CH$_2$CH$_3$, —CH$_3$, OC(CH$_3$)$_3$, —OCH(CH$_3$)$_2$, —OCH$_2$CH$_2$CH$_3$, —OCH$_2$CH$_3$, —OCH$_3$, —SC(CH$_3$)$_3$, —SCH(CH$_3$)$_2$, —SCH$_2$CH$_2$CH$_3$, —SCH$_2$CH$_3$, —SCH$_3$, —NHC(CH$_3$)$_3$, —NHCH(CH$_3$)$_2$, —NHCH$_2$CH$_2$CH$_3$, —NHCH$_2$CH$_3$, —NHCH$_3$, or -Ph.

Embodiment 263

The compound of one of embodiments 257 to 258, wherein R$^{8A}$ is hydrogen, deuterium, —C(CH$_3$)$_3$, —CH(CH$_3$)$_2$, —CH$_2$CH$_2$CH$_3$, —CH$_2$CH$_3$, —CH$_3$, —CX$^3{}_3$, —CHX$^3{}_2$, —CH$_2$X$^3$, —CN, -Ph.

Embodiment 264

The compound of one of embodiments 257 to 258, wherein R$^{8B}$ is hydrogen, deuterium, —C(CH$_3$)$_3$, —CH(CH$_3$)$_2$, —CH$_2$CH$_2$CH$_3$, —CH$_2$CH$_3$, —CH$_3$, —CX$^4{}_3$, —CHX$^4{}_2$, —CH$_2$X$^4$, —CN, -Ph.

Embodiment 265

The compound of one of embodiments 257 to 258, wherein —R$^{7A}$ is hydrogen.

Embodiment 266

The compound of one of embodiments 257 to 258, wherein —R$^{7A}$ is

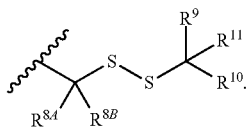

Embodiment 267

The compound of one of embodiments 257 to 258, wherein —R$^{7A}$ is

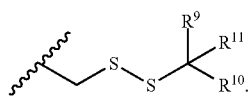

Embodiment 268

The compound of one of embodiments 257 to 258, wherein —R$^{7A}$ is

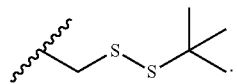 [SMILES: *CSSC(C)(C)C]

Embodiment 269

The compound of one of embodiments 257 to 258 having the formula:

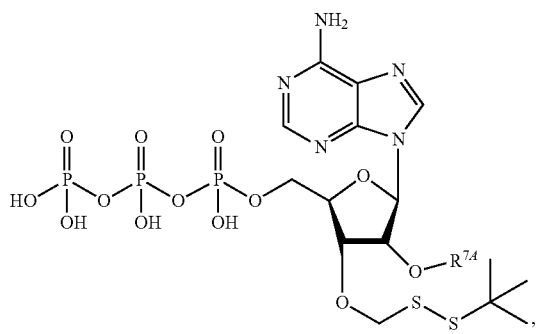

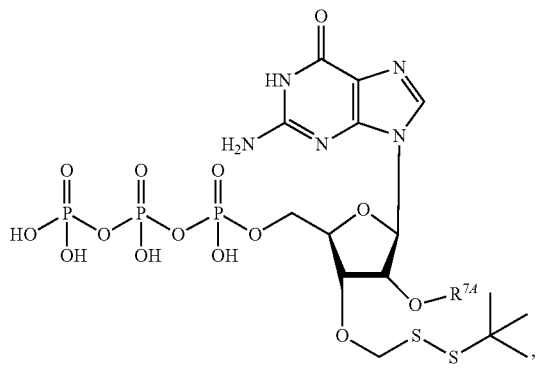

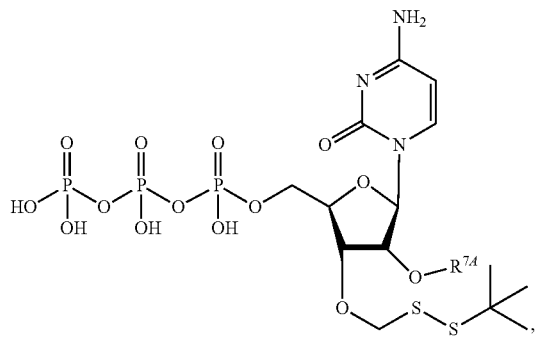

441

-continued

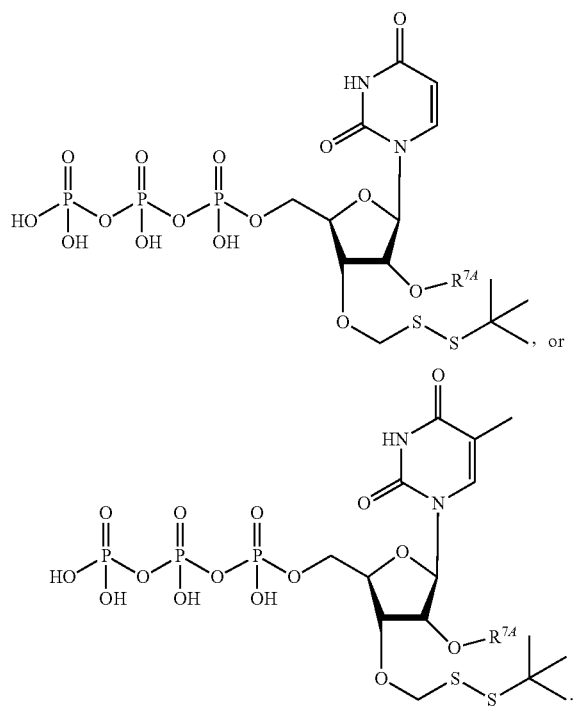

, or

Embodiment 270

A compound of the formula:

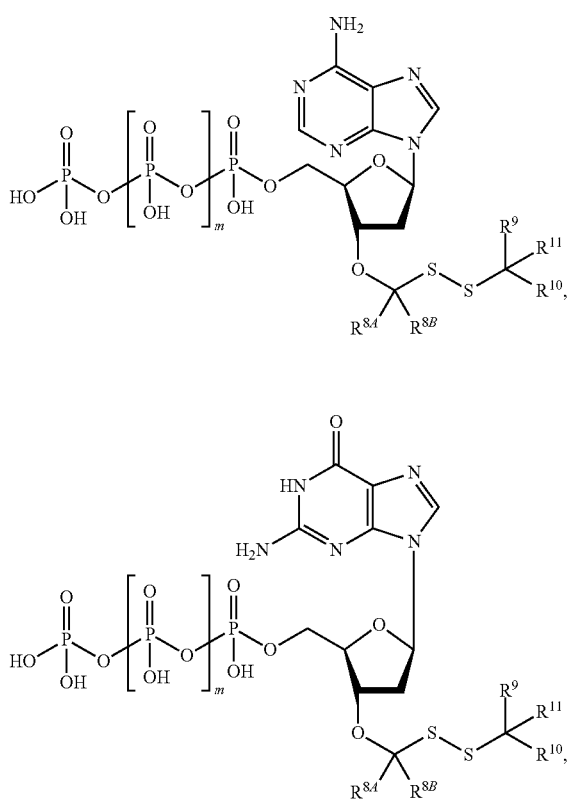

442

-continued

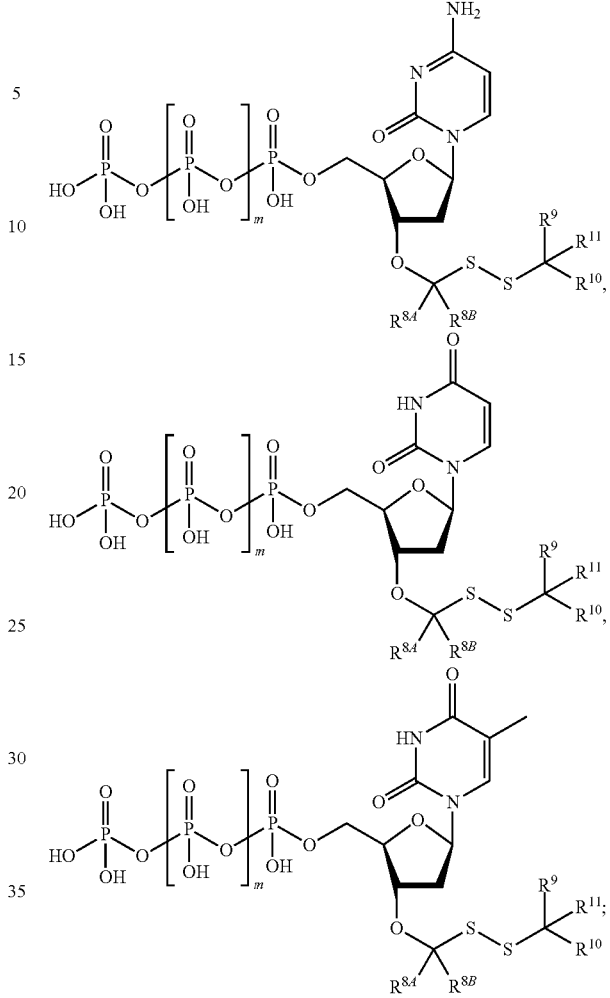

wherein $R^{8A}$ is independently hydrogen, $CH_3$, $-CX^3{}_3$, $-CHX^3{}_2$, $-CH_2X^3$, $-OCX^3{}_3$, $-OCH_2X^3$, $-OCHX^3{}_2$, $-CN$, -Ph $-OH$, $-SH$, $-NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{8B}$ is independently hydrogen, $CH_3$, $-CX^4{}_3$, $-CHX^4{}_2$, $-CH_2X^4$, $-OCX^4{}_3$, $-OCH_2X^4$, $-OCHX^4{}_2$, $-CN$, -Ph $-OH$, $-SH$, $-NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is independently hydrogen, $-CX^5{}_3$, $-CHX^5{}_2$, $-CH_2X^5$, $-OCX^5{}_3$, $-OCH_2X^5$, $-OCHX^5{}_2$, $-CN$, $-OH$, $-SH$, $-NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is independently hydrogen, $-CX^6{}_3$, $-CHX^6{}_2$, $-CH_2X^6$, $-OCX^6{}_3$, $-OCH_2X^6$, $-OCHX^6{}_2$, $-CN$, $-OH$, $-SH$, $-NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is independently hydrogen, $-CX^7_3$, $-CHX^7_2$, $-CH_2X^7$, $-OCX^7_3$, $-OCH_2X^7$, $-OCHX^7_2$, $-CN$, $-OH$, $-SH$, $-NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $X^3$, $X^4$, $X^5$, $X^6$ and $X^7$ are independently halogen; and m is an integer from 1 to 4.

Embodiment 271

A compound of the formula:

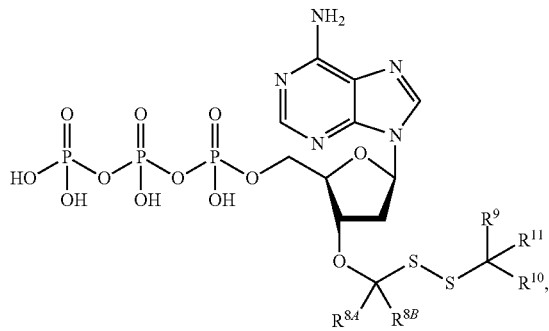

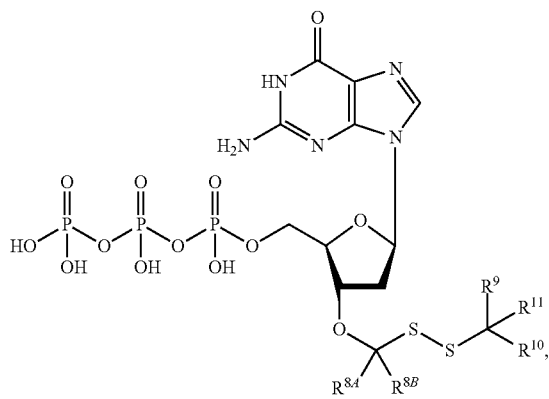

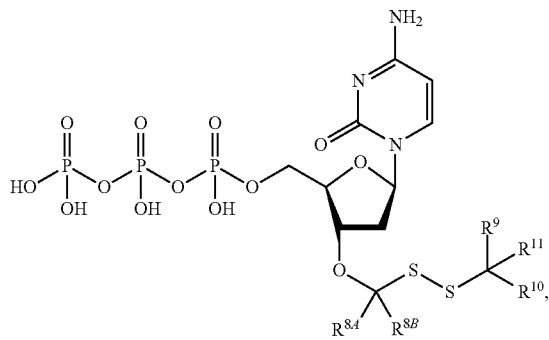

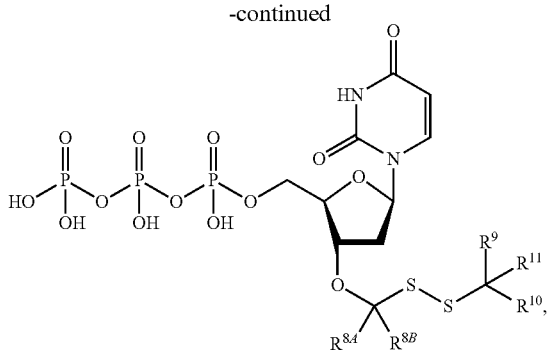

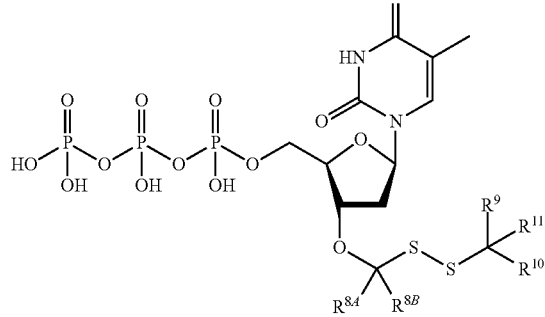

wherein $R^{8A}$ is independently hydrogen, $CH_3$, $-CX^3_3$, $-CHX^3_2$, $-CH_2X^3$, $-OCX^3_3$, $-OCH_2X^3$, $-OCHX^3_2$, $-CN$, -Ph, $-OH$, $-SH$, $-NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{8B}$ is independently hydrogen, $CH_3$, $-CX^4_3$, $-CHX^4_2$, $-CH_2X^4$, $-OCX^4_3$, $-OCH_2X^4$, $-OCHX^4_2$, $-CN$, -Ph, $-OH$, $-SH$, $-NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is independently hydrogen, $-CX^5_3$, $-CHX^5_2$, $-CH_2X^5$, $-OCX^5_3$, $-OCH_2X^5$, $-OCHX^5_2$, $-CN$, $-OH$, $-SH$, $-NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is independently hydrogen, $-CX^6_3$, $-CHX^6_2$, $-CH_2X^6$, $-OCX^6_3$, $-OCH_2X^6$, $-OCHX^6_2$, $-CN$, $-OH$, $-SH$, $-NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is independently hydrogen, $-CX^7_3$, $-CHX^7_2$, $-CH_2X^7$, $-OCX^7_3$, $-OCH_2X^7$, $-OCHX^7_2$, $-CN$, $-OH$, $-SH$, $-NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $X^3$, $X^4$, $X^5$, $X^6$ and $X^7$ are independently halogen.

Embodiment 272

The compound of one of embodiments 270 to 271, wherein $-CR^9R^{10}R^{11}$ is unsubstituted methyl, unsubsti-

Embodiment 273

The compound of one of embodiments 270 to 271, wherein R⁹ is hydrogen, —C(CH₃)₃, —CH(CH₃)₂, —CH₂CH₂CH₃, —CH₂CH₃, —CH₃, OC(CH₃)₃, —OCH(CH₃)₂, —OCH₂CH₂CH₃, —OCH₂CH₃, —OCH₃, —SC(CH₃)₃, —SCH(CH₃)₂, —SCH₂CH₂CH₃, —SCH₂CH₃, —SCH₃, —NHC(CH₃)₃, —NHCH(CH₃)₂, —NHCH₂CH₂CH₃, —NHCH₂CH₃, —NHCH₃, or -Ph.

Embodiment 274

The compound of one of embodiments 270 to 271, wherein —R¹⁰ is hydrogen, —C(CH₃)₃, —CH(CH₃)₂, —CH₂CH₂CH₃, —CH₂CH₃, —CH₃, OC(CH₃)₃, —OCH(CH₃)₂, —OCH₂CH₂CH₃, —OCH₂CH₃, —OCH₃, —SC(CH)₃, —SCH(CH₃)₂, —SCH₂CH₂CH₃, —SCH₂CH₃, —SCH₃, —NHC(CH₃)₃, —NHCH(CH₃)₂, —NHCH₂CH₂CH₃, —NHCH₂CH₃, —NHCH₃, or -Ph.

Embodiment 275

The compound of one of embodiments 270 to 271, wherein —R¹¹ is hydrogen, —C(CH₃)₃, —CH(CH₃)₂, —CH₂CH₂CH₃, —CH₂CH₃, —CH₃, OC(CH₃)₃, —OCH(CH₃)₂, —OCH₂CH₂CH₃, —OCH₂CH₃, —OCH₃, —SC(CH₃)₃, —SCH(CH₃)₂, —SCH₂CH₂CH₃, —SCH₂CH₃, —SCH₃, —NHC(CH₃)₃, —NHCH(CH₃)₂, —NHCH₂CH₂CH₃, —NHCH₂CH₃, —NHCH₃, or -Ph.

Embodiment 276

The compound of one of embodiments 270 to 271, wherein $R^{8A}$ is independently hydrogen, deuterium, —C(CH₃)₃, —CH(CH₃)₂, —CH₂CH₂CH₃, —CH₂CH₃, —CH₃, OC(CH₃)₃, —OCH(CH₃)₂, —OCH₂CH₂CH₃, —OCH₂CH₃, —OCH₃, —SC(CH₃)₃, —SCH(CH₃)₂, —SCH₂CH₂CH₃, —SCH₂CH₃, —SCH₃, —NHC(CH₃)₃, —NHCH(CH₃)₂, —NHCH₂CH₂CH₃, —NHCH₂CH₃, —NHCH₃, or -Ph.

Embodiment 277

The compound of one of embodiments 270 to 271, wherein $R^{8B}$ is independently hydrogen, deuterium, —C(CH₃)₃, —CH(CH₃)₂, —CH₂CH₂CH₃, —CH₂CH₃, —CH₃, OC(CH₃)₃, —OCH(CH₃)₂, —OCH₂CH₂CH₃, —OCH₂CH₃, —OCH₃, —SC(CH₃)₃, —SCH(CH₃)₂, —SCH₂CH₂CH₃, —SCH₂CH₃, —SCH₃, —NHC(CH₃)₃, —NHCH(CH₃)₂, —NHCH₂CH₂CH₃, —NHCH₂CH₃, —NHCH₃, or -Ph.

Embodiment 278

The compound of one of embodiments 271 to 277 having the formula:

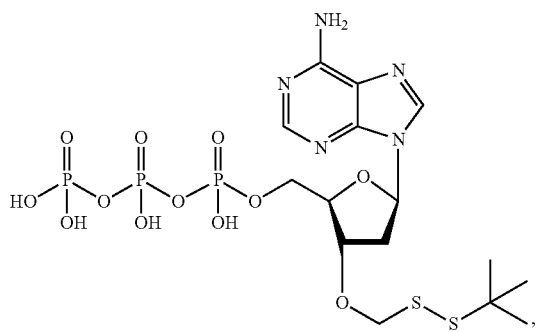

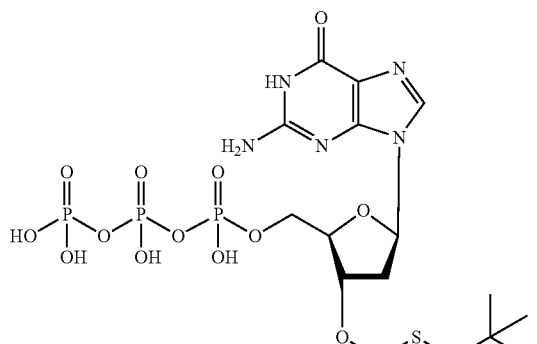

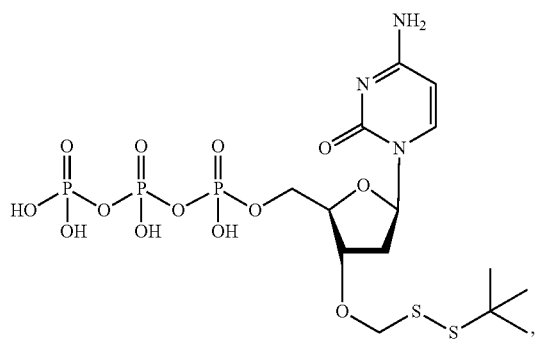

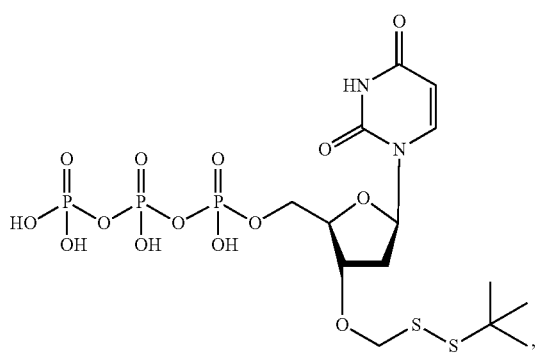

-continued

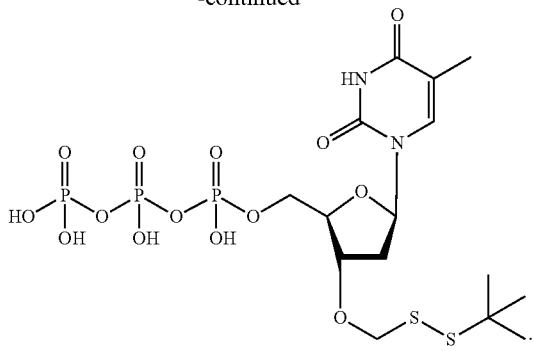

Embodiment 279

A compound of the formula:
$R^{12z}$-$L^{4z}$-$R^{13}$;
wherein
$L^{4z}$ is a covalent linker;
$R^{12z}$ is a complementary anchor moiety reactive group; and
$R^{13}$ is a detectable label.

Embodiment 280

The compound of embodiment 279, wherein $L^{4z}$ is an orthogonally cleavable linker.

Embodiment 281

The compound of embodiment 279, wherein $L^{4z}$ is a cleavable linker.

Embodiment 282

The compound of embodiment 279, wherein $L^{4z}$ is a chemically cleavable linker.

Embodiment 283

The compound of embodiment 279, wherein $L^{4z}$ is a photocleavable linker, an acid-cleavable linker, a base-cleavable linker, an oxidant-cleavable linker, a reductant-cleavable linker, or a fluoride-cleavable linker.

Embodiment 284

The compound of embodiment 279, wherein $L^{4z}$ is a cleavable linker comprising a dialkylketal linker, an azo linker, an allyl linker, a cyanoethyl linker, a 1-(4,4-dimethyl-2,6-dioxocyclohex-1-ylidene)ethyl linker, or a nitrobenzyl linker.

Embodiment 285

The compound of embodiment 279, wherein
$L^{4z}$ is $L^{4zA}$-$L^{4zB}$-$L^{4zC}$-$L^{4zD}$-$L^{4zE}$; and
$L^{4zA}$, $L^{4zB}$, $L^{4zC}$, $L^{4zD}$, and $L^{4zE}$ are independently a bond, —NN—, —NHC(O)—, —C(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
wherein at least one of $L^{4zA}$, $L^{4zB}$, $L^{4zC}$, $L^{4zD}$, and $L^{4zE}$ is not a bond.

Embodiment 286

The compound of embodiment 279, wherein
$L^{4z}$ is $L^{4zA}$-$L^{4zB}$-$L^{4zC}$-$L^{4zD}$-$L^{4zE}$; and
$L^{4zA}$, $L^{4zB}$, $L^{4zC}$, $L^{4zD}$, and $L^{4zE}$ are independently a bond, —NN—, —NHC(O)—, —C(O)NH—, substituted or unsubstituted $C_1$-$C_{20}$ alkylene, substituted or unsubstituted 2 to 20 membered heteroalkylene, substituted or unsubstituted $C_3$-$C_{20}$ cycloalkylene, substituted or unsubstituted 3 to 20 membered heterocycloalkylene, substituted or unsubstituted $C_6$-$C_{20}$ arylene, or substituted or unsubstituted 5 to 20 membered heteroarylene;
wherein at least one of $L^{4zA}$, $L^{4zB}$, $L^{4zC}$, $L^{4zD}$, and $L^{4zE}$ is not a bond.

Embodiment 287

The compound of embodiment 279, wherein
$L^{4z}$ is $L^{4zA}$-$L^{4zB}$-$L^{4zC}$-$L^{4zD}$-$L^{4zE}$; and
$L^{4zA}$, $L^{4zB}$, $L^{4zC}$, $L^{4zD}$, and $L^{4zE}$ are independently a bond, —NN—, —NHC(O)—, —C(O)NH—, substituted or unsubstituted $C_1$-$C_{10}$ alkylene, substituted or unsubstituted 2 to 10 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene;
wherein at least one of $L^{4zA}$, $L^{4zB}$, $L^{4zC}$, $L^{4zD}$, and $L^{4zE}$ is not a bond.

Embodiment 288

The compound of embodiment 279, wherein
$L^{4z}$ is $L^{4zA}$-$L^{4zB}$-$L^{4zC}$-$L^{4zD}$-$L^{4zE}$; and
$L^{4zA}$, $L^{4zB}$, $L^{4zC}$, $L^{4zD}$, and $L^{4zE}$ are independently a bond, —NN—, —NHC(O)—, —C(O)NH—, substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted phenyl, or substituted or unsubstituted 5 to 6 membered heteroarylene;
wherein at least one of $L^{4zA}$, $L^{4zB}$, $L^{4zC}$, $L^{4zD}$, and $L^{4zE}$ is not a bond.

Embodiment 289

The compound of embodiment 279, wherein
$L^{4z}$ is $L^{4zA}$-$L^{4zB}$-$L^{4zC}$-$L^{4zD}$-$L^{4zE}$;
$L^{4zA}$ is a bond, —NN—, —NHC(O)—, —C(O)NH—, substituted or unsubstituted alkylene, substituted or unsubstituted heteroalkylene;
$L^{4zB}$ is a bond, —NN—, —NHC(O)—, —C(O)NH—, substituted or unsubstituted cycloalkylene, substituted or unsubstituted heterocycloalkylene, substituted or unsubstituted arylene, substituted or unsubstituted heteroarylene;
$L^{4zC}$ is a bond, —NN—, —NHC(O)—, —C(O)NH—, substituted or unsubstituted cycloalkylene, substituted or unsubstituted heterocycloalkylene, substituted or unsubstituted arylene, substituted or unsubstituted heteroarylene;

$L^{4zD}$ is a bond, —NN—, —NHC(O)—, —C(O)NH—, substituted or unsubstituted alkylene, substituted or unsubstituted heteroalkylene; and $L^{4zE}$ is a bond, —NN—, —NHC(O)—, —C(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

wherein at least one of $L^{4zA}$, $L^{4zB}$, $L^{4zC}$, $L^{4zD}$, and $L^{4zE}$ is not a bond.

Embodiment 290

The compound of embodiment 279, wherein $L^{4z}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 291

The compound of embodiment 279, wherein $L^{4z}$ is a bond, substituted or unsubstituted $C_1$-$C_{20}$ alkylene, substituted or unsubstituted 2 to 20 membered heteroalkylene, substituted or unsubstituted $C_3$-$C_{20}$ cycloalkylene, substituted or unsubstituted 3 to 20 membered heterocycloalkylene, substituted or unsubstituted $C_6$-$C_{20}$ arylene, or substituted or unsubstituted 5 to 20 membered heteroarylene.

Embodiment 292

The compound of embodiment 279, wherein $L^{4z}$ is a bond, substituted or unsubstituted $C_1$-$C_8$ alkylene, substituted or unsubstituted 2 to 8 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene.

Embodiment 293

The compound of embodiment 279, wherein $L^{4z}$ is a bond, substituted or unsubstituted $C_1$-$C_6$ alkylene, substituted or unsubstituted 2 to 6 membered heteroalkylene, substituted or unsubstituted $C_3$-$C_6$ cycloalkylene, substituted or unsubstituted 3 to 6 membered heterocycloalkylene, substituted or unsubstituted phenyl, or substituted or unsubstituted 5 to 6 membered heteroarylene.

Embodiment 294

The compound of embodiment 279, wherein $L^{4z}$ is a substituted or unsubstituted 3 to 10 membered heteroalkylene.

Embodiment 295

The compound of embodiment 279, wherein $L^{4z}$ is a substituted or unsubstituted 3 to 8 membered heteroalkylene.

Embodiment 296

The compound of embodiment 279 having the formula:

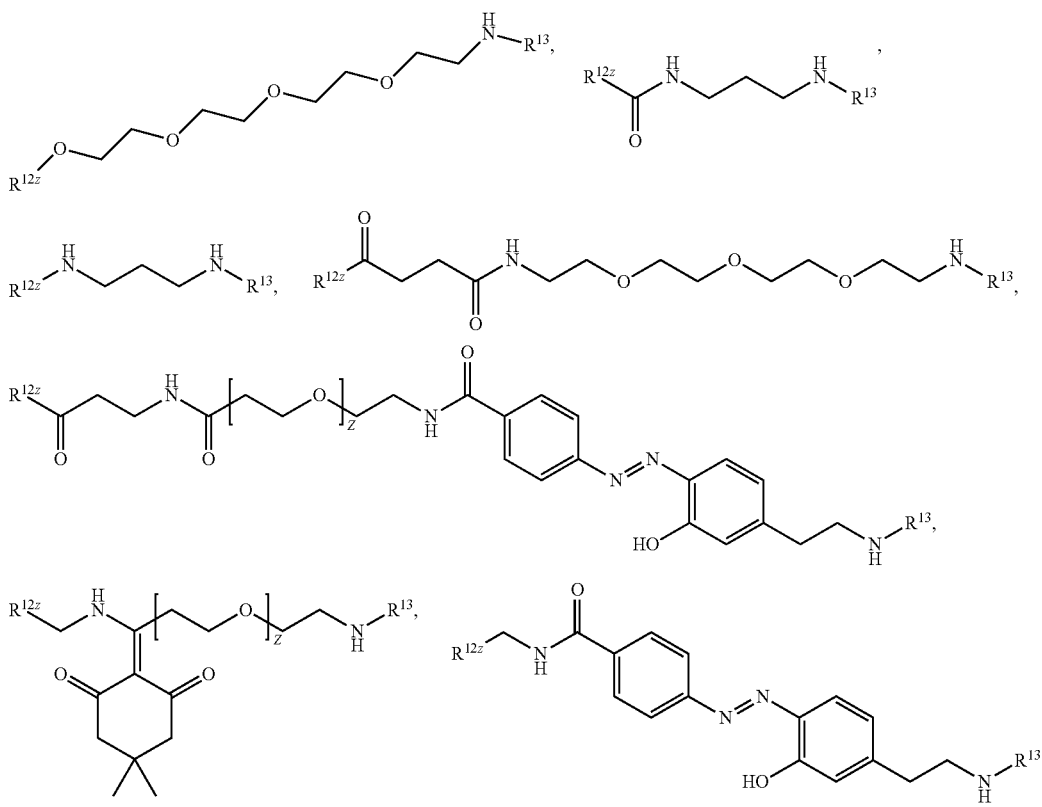

451

-continued

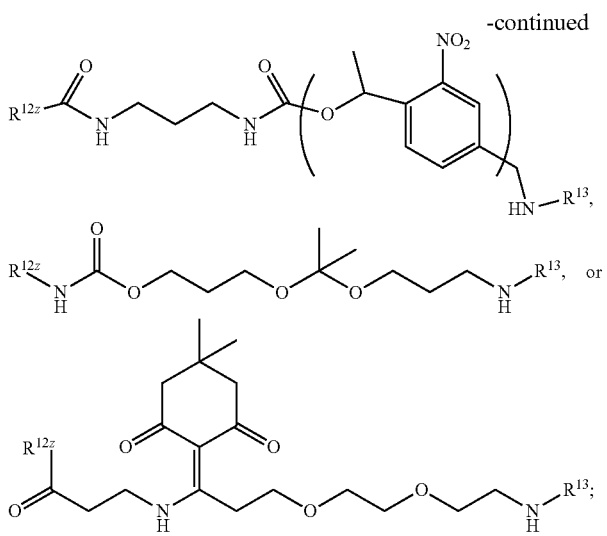

wherein
z is an integer from 0 to 20.

Embodiment 297

The compound of one of embodiments 279 to 296, wherein $R^{12z}$ is

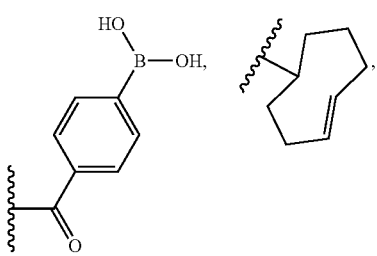

452

-continued

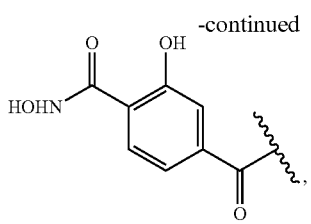

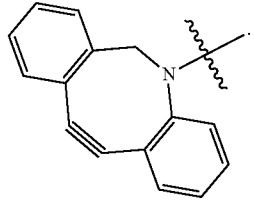 [SMILES: *N1Cc2ccccc2C#Cc2ccccc21]

a streptavidin moiety, or

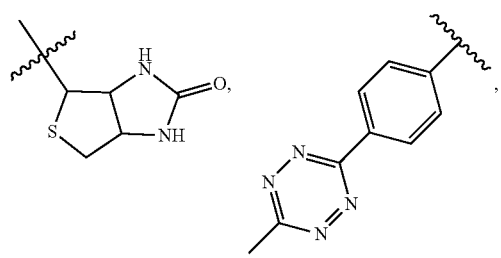

Embodiment 298

The compound of one of embodiments 279 to 296, wherein $R^{13}$ is a fluorescent dye.

Embodiment 299

The compound of one of embodiments 279 to 296, wherein $R^{13}$ comprises a fluorescence resonance energy transfer donor fluorescent dye.

Embodiment 300

The compound of one of embodiments 279 to 296, wherein $R^{13}$ comprises a fluorescence resonance energy transfer acceptor fluorescent dye.

Embodiment 301

The compound of one of embodiments 279 to 296, wherein $R^{13}$ comprises a fluorescence resonance energy transfer donor and acceptor fluorescent dye pair connected by a linker.

Embodiment 302
The compound of one of embodiments 279 to 296, wherein R$^{13}$ comprises a fluorescence resonance energy transfer donor and acceptor fluorescent dye pair connected by a linker and separated by from 0.1 nm to 10 nm.
Embodiment 303
The compound of one of embodiments 279 to 296, wherein R$^{13}$ is
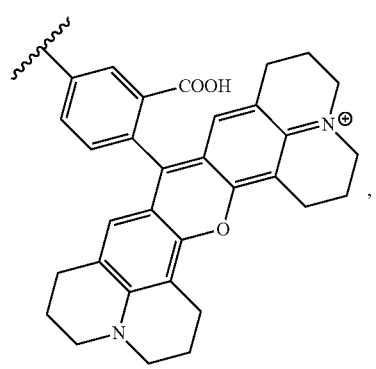
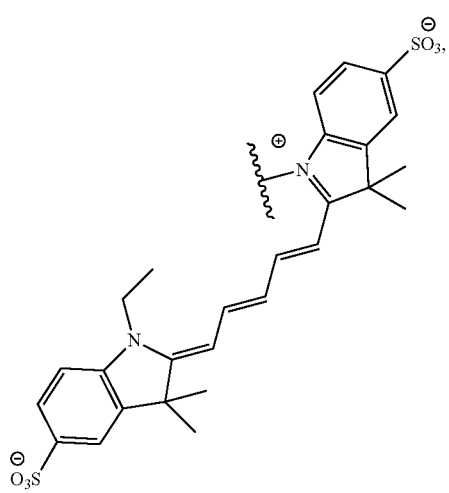
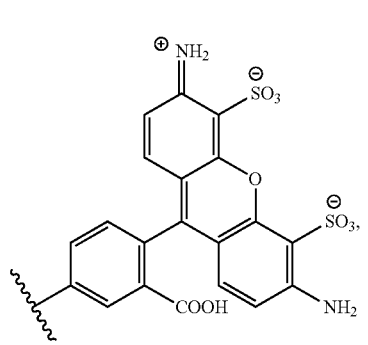
-continued
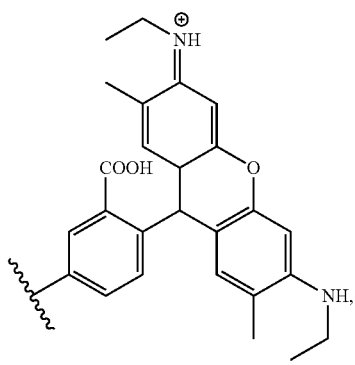
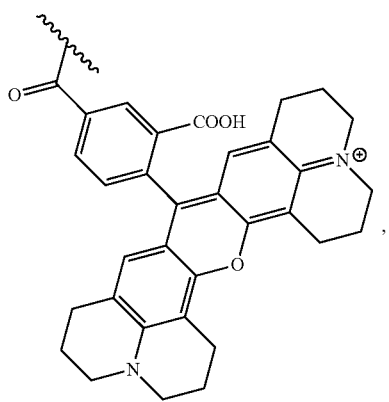
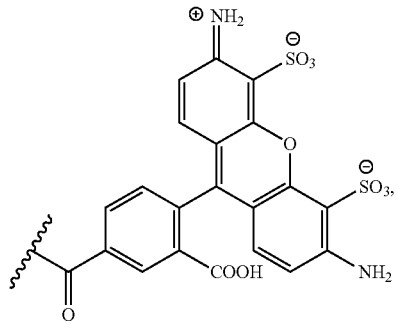

455
-continued
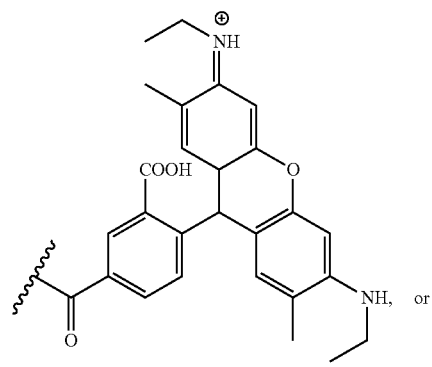
456
-continued
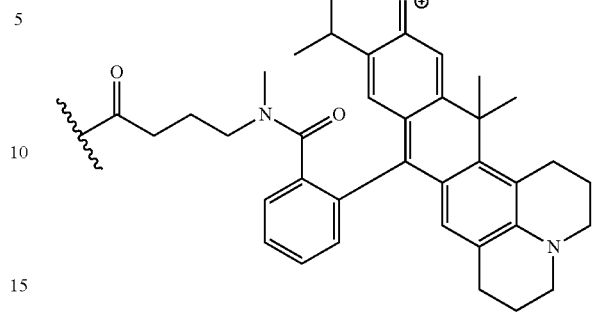
Embodiment 304
The compound of embodiment 296 having the formula:
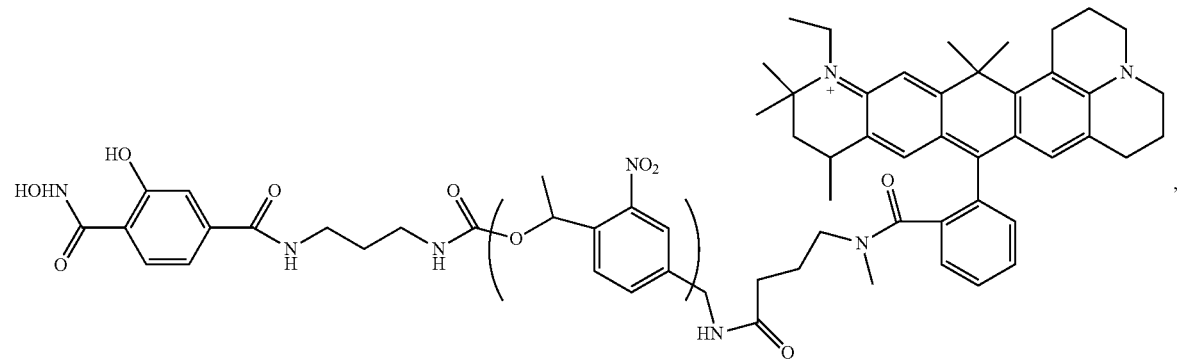
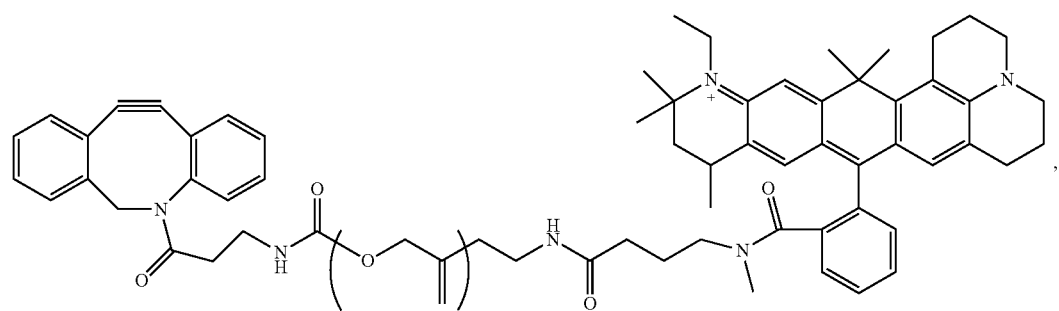

457
458
-continued
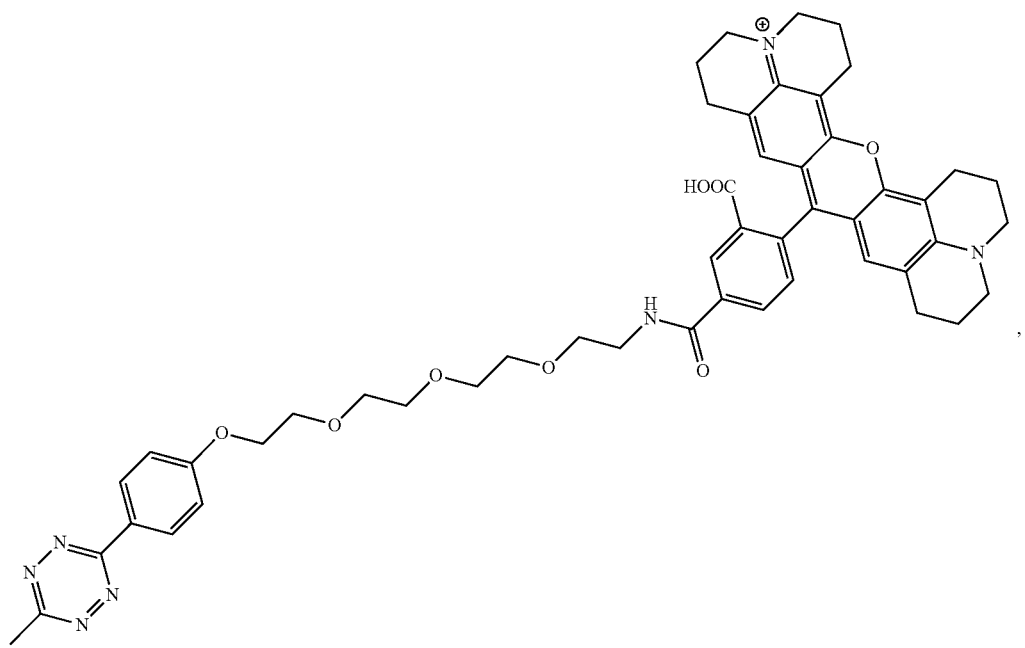
,
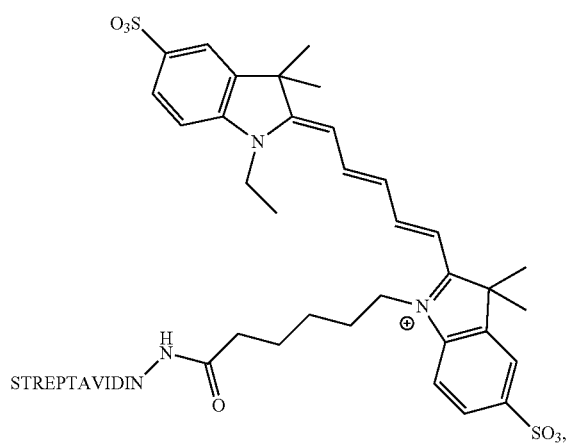
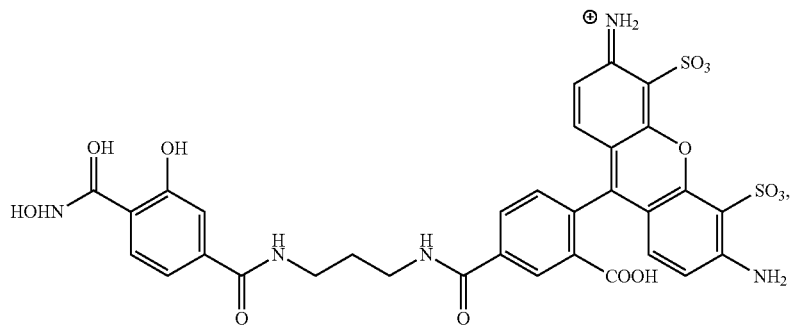

-continued
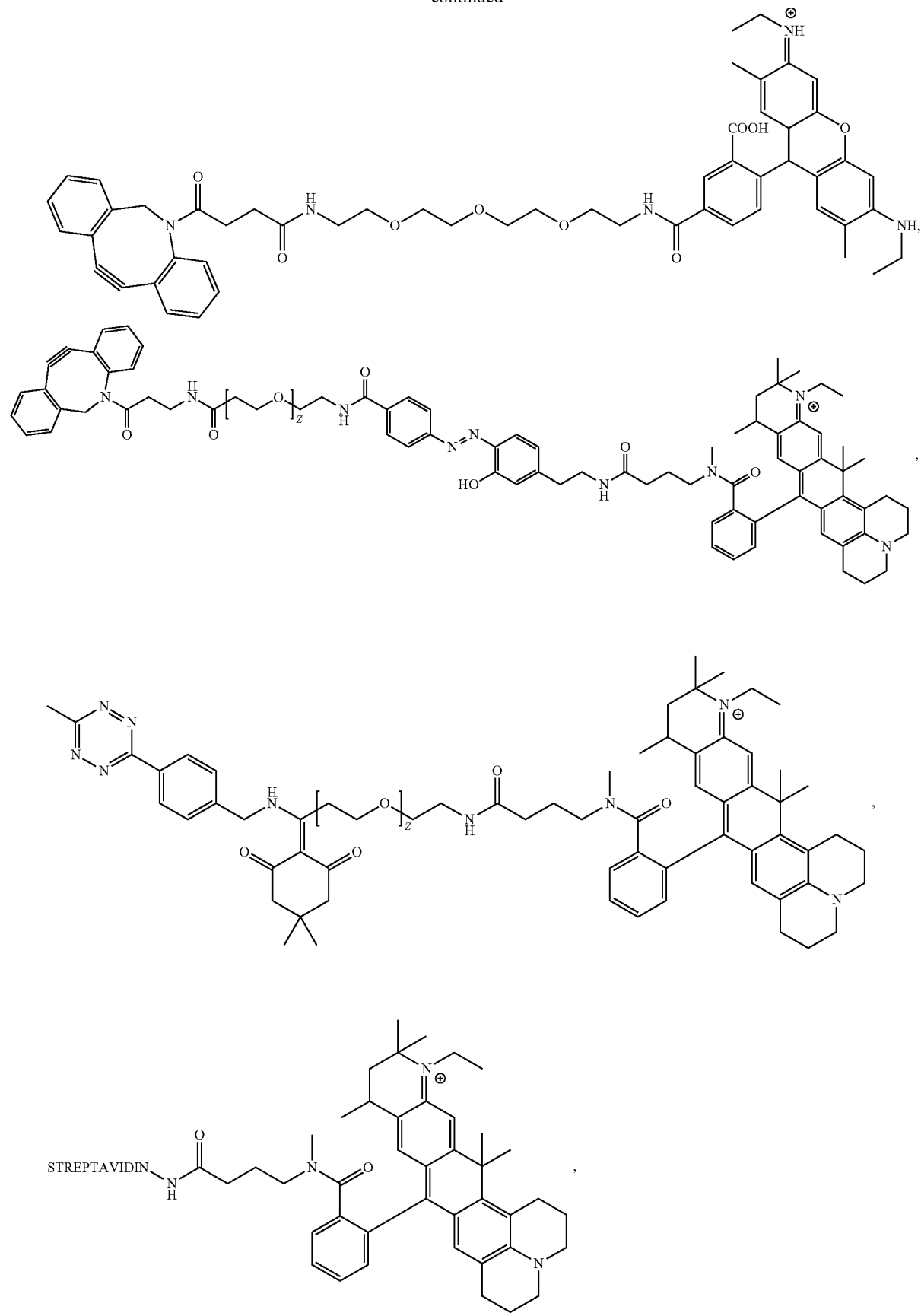

461
462
-continued
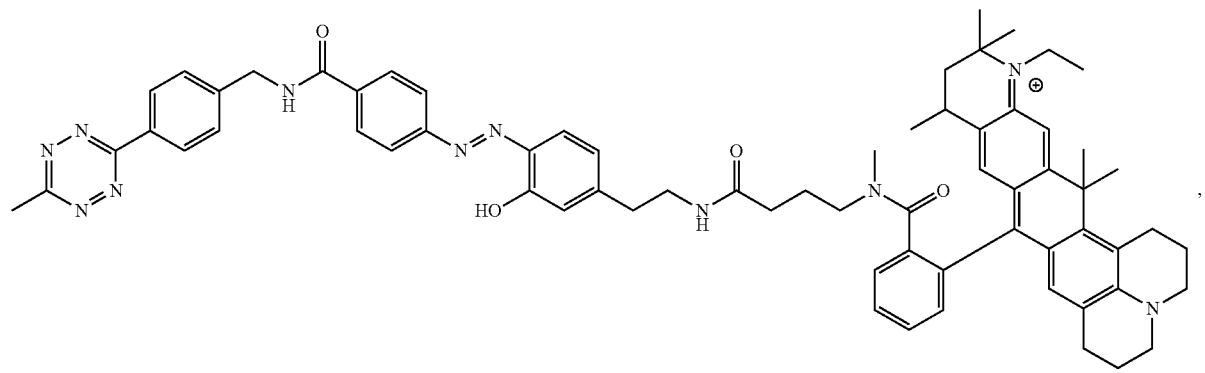
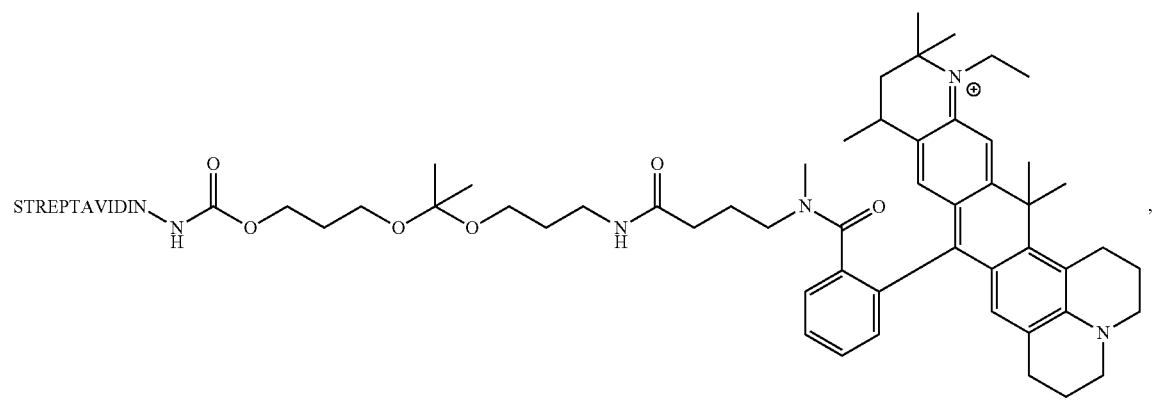
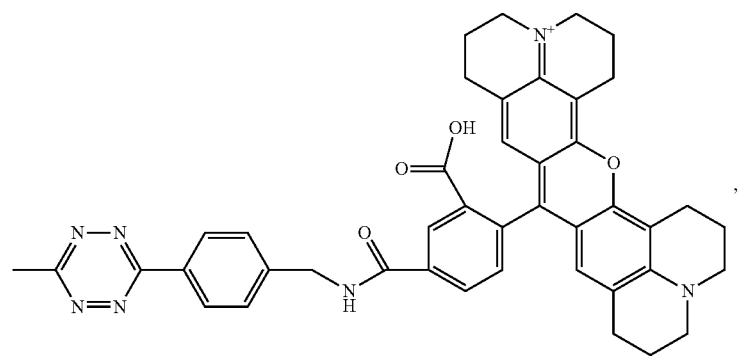

-continued
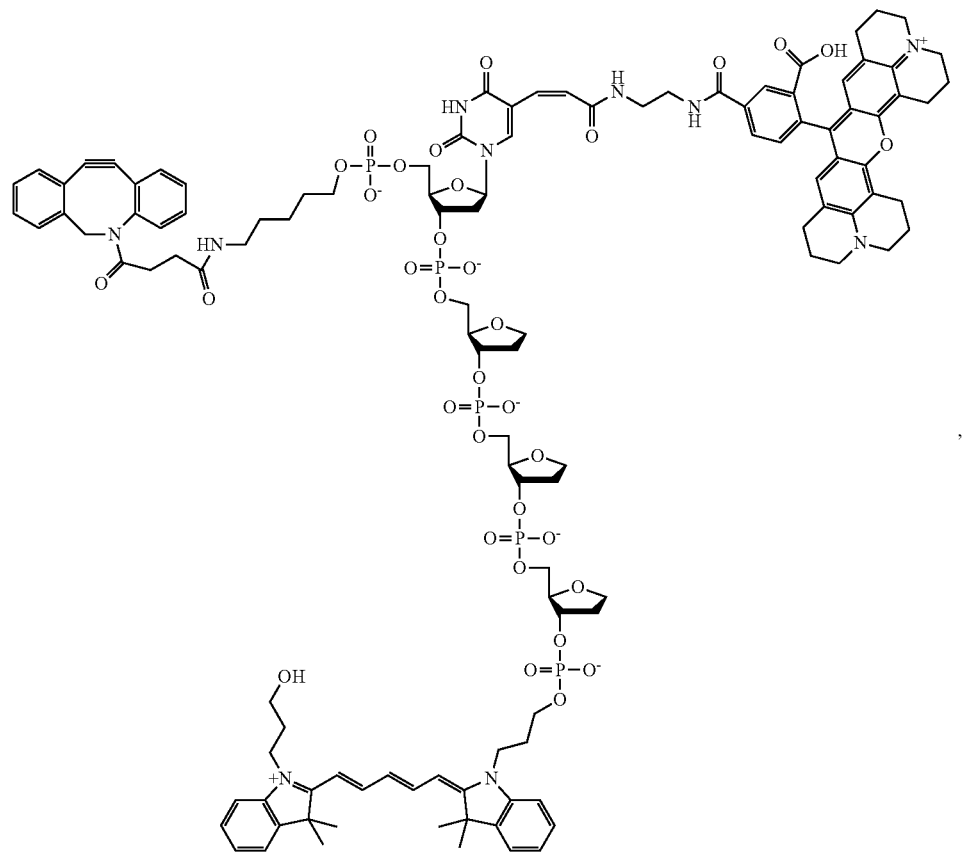

465 466
-continued
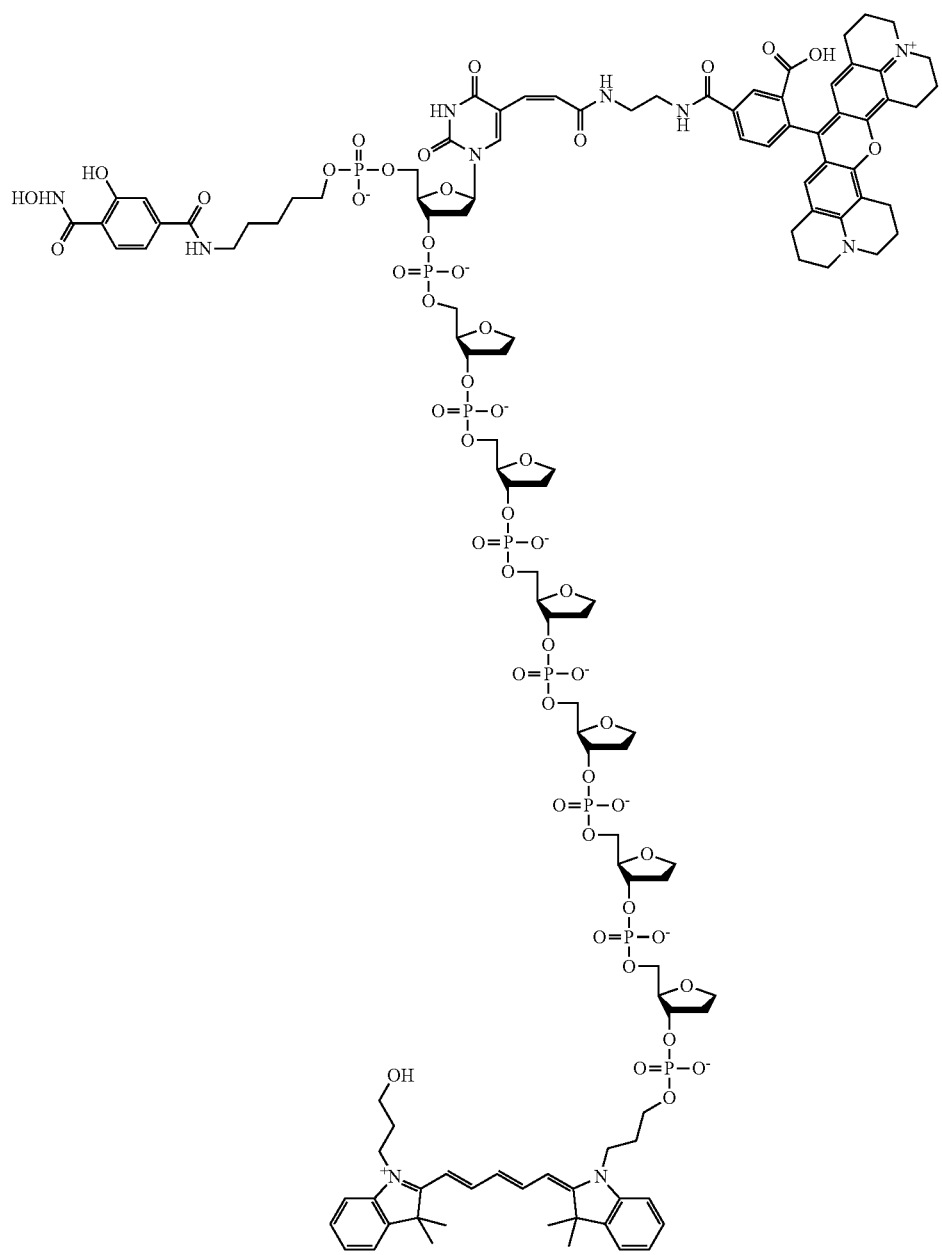
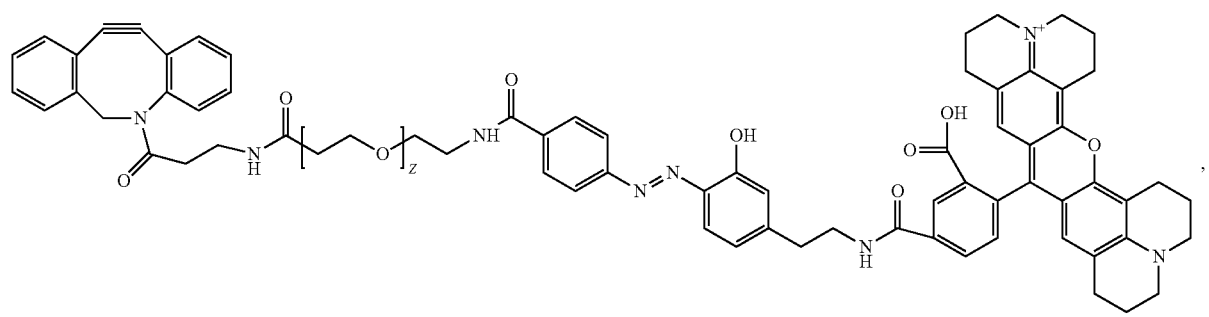

-continued

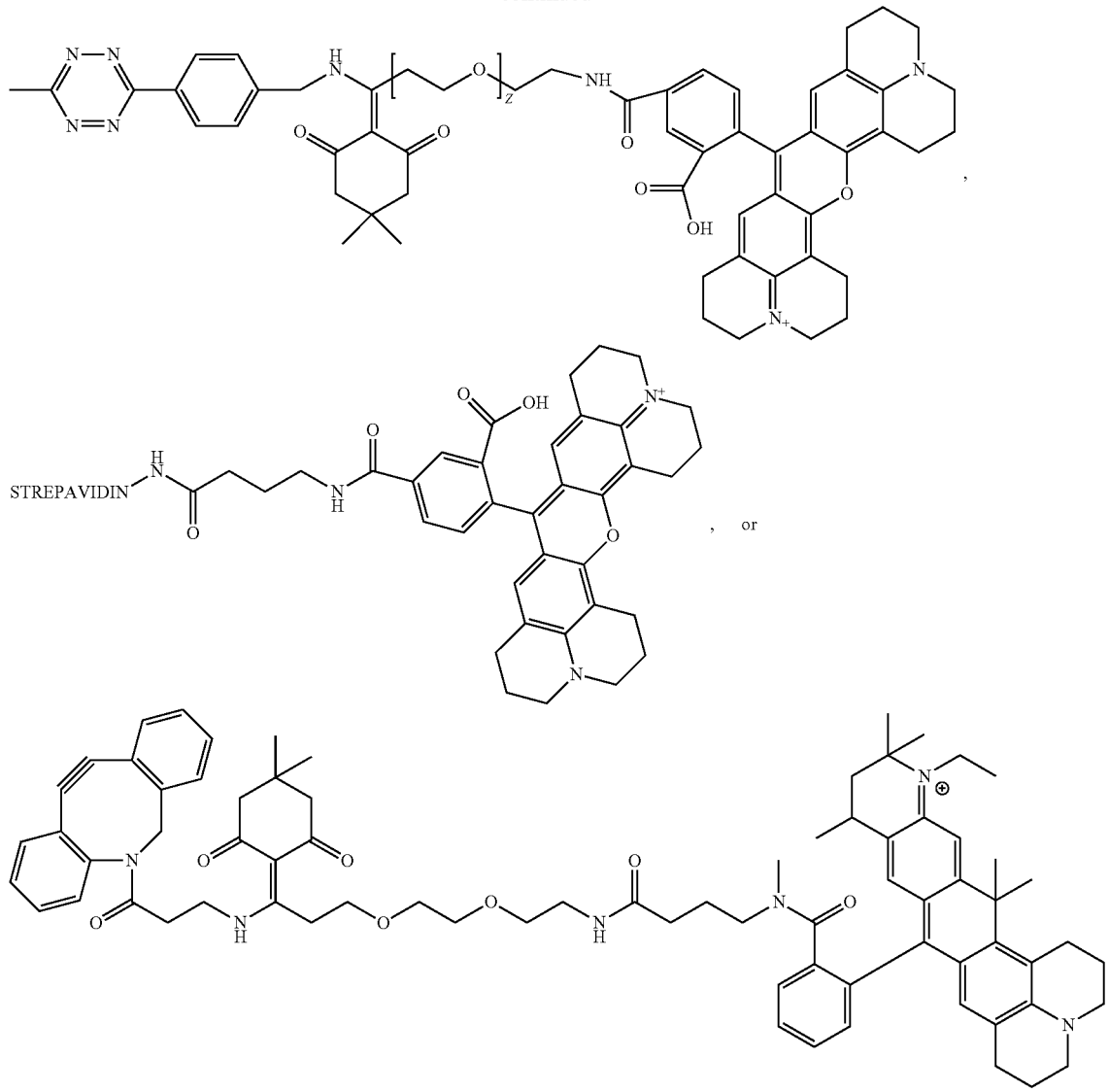

Embodiment 305

A compound of the formula:
$R^{12z}\text{-}R^{14}$;
wherein
$R^{12z}$ is a complementary anchor moiety reactive group; and
$R^{14}$ is $R^{15}$-substituted alkyl, $R^{15}$-substituted heteroalkyl, le-substituted cycloalkyl, $R^{15}$-substituted heterocycloalkyl, $R^{15}$-substituted aryl, or $R^{15}$-substituted heteroaryl;
$R^{15}$ is independently $R^{16}$-substituted alkyl, $R^{16}$-substituted heteroalkyl, le-substituted cycloalkyl, $R^{16}$-substituted heterocycloalkyl, $R^{16}$-substituted aryl, $R^{16}$-substituted heteroaryl, or a detectable dye;
$R^{16}$ is independently $R^{17}$-substituted alkyl, $R^{17}$-substituted heteroalkyl, $R^{17}$-substituted cycloalkyl, $R^{17}$-substituted heterocycloalkyl, $R^{17}$-substituted aryl, $R^{17}$-substituted heteroaryl, or a detectable dye;
$R^{17}$ is independently $R^{18}$-substituted alkyl, $R^{18}$-substituted heteroalkyl, $R^{18}$-substituted cycloalkyl, $R^{18}$-substituted heterocycloalkyl, $R^{18}$-substituted aryl, $R^{18}$-substituted heteroaryl, or a detectable dye;
$R^{18}$ is a detectable dye;
wherein $R^{14}$ is substituted with a plurality of $R^{15}$ moieties, $R^{15}$ is substituted with a plurality of $R^{16}$ moieties, and $R^{16}$ is substituted with a plurality of $R^{17}$ moieties.

Embodiment 305

The compound of embodiment 304, wherein $R^{12z}$ is

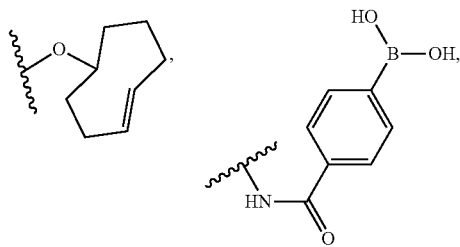

-continued

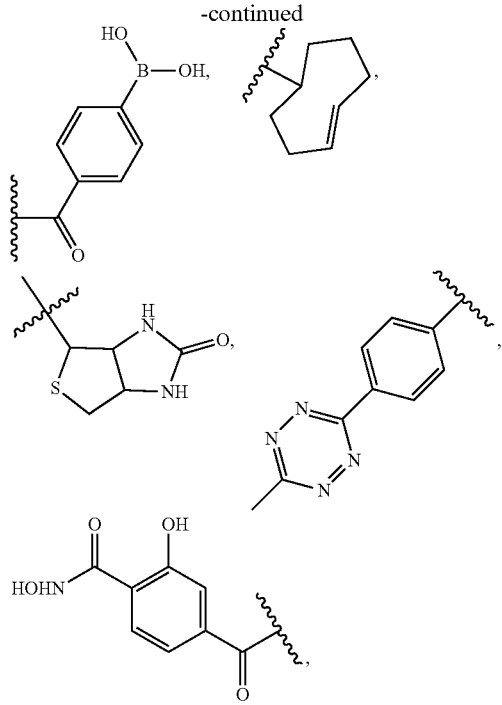

a streptavidin moiety, or

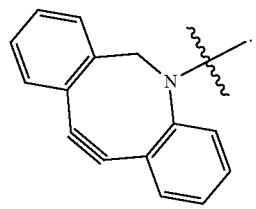 [SMILES: *N1Cc2ccccc2C#Cc2ccccc21]

Embodiment 306

The compound of one of embodiments 304 to 305, wherein the detectable dye is a fluorescent dye.

Embodiment 307

The compound of one of embodiments 304 to 305, wherein the detectable dye comprises a fluorescence resonance energy transfer donor fluorescent dye.

Embodiment 308

The compound of one of embodiments 304 to 305, wherein the detectable dye comprises a fluorescence resonance energy transfer acceptor fluorescent dye.

Embodiment 309

The compound of one of embodiments 304 to 305, wherein the detectable dye comprises a fluorescence resonance energy transfer donor and acceptor fluorescent dye pair connected by a linker.

Embodiment 310

The compound of one of embodiments 304 to 305, wherein the detectable dye comprises a fluorescence resonance energy transfer donor and acceptor fluorescent dye pair connected by a linker and separated by from 0.1 nm to 10 nm.

Embodiment 311

The compound of one of embodiments 304 to 305, wherein the detectable dye is

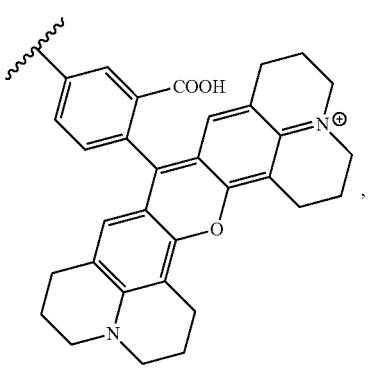

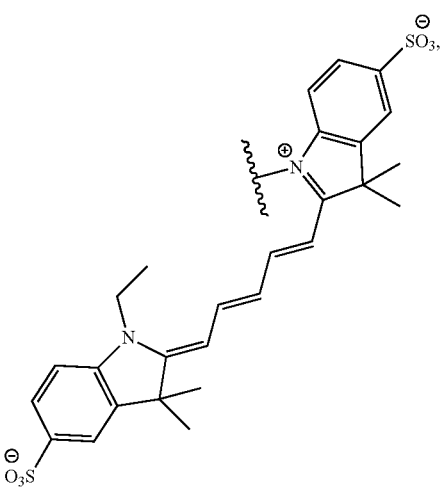

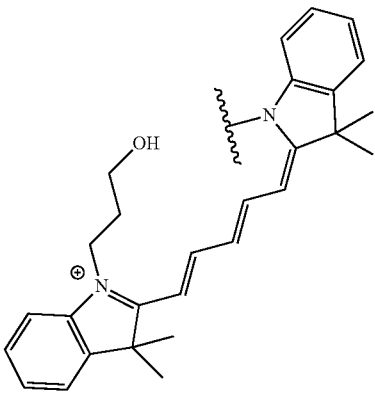

471
-continued
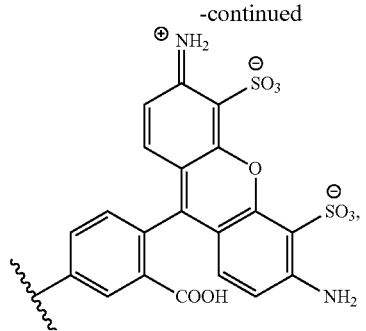
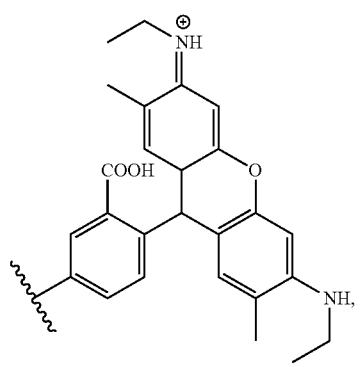
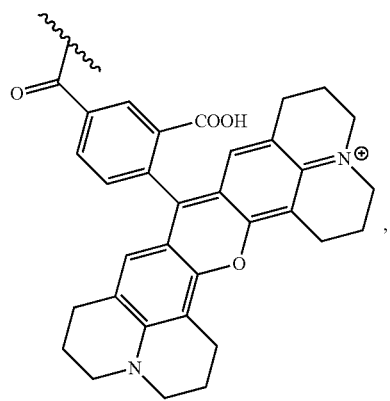
472
-continued
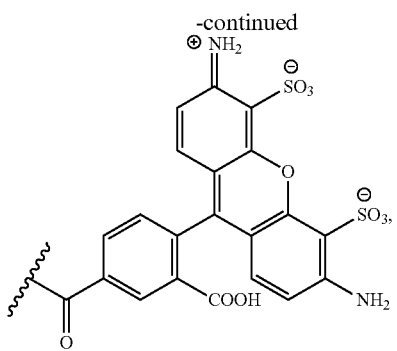
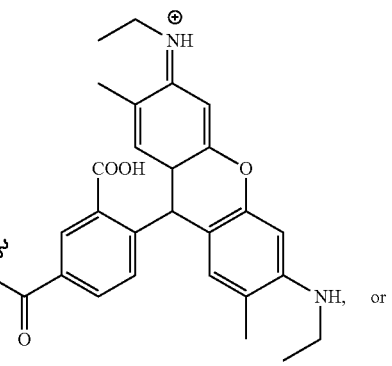, or
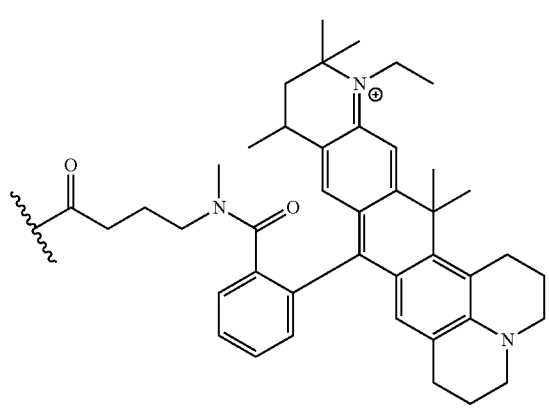

Embodiment 312
The compound of one of embodiments 304 to 311 having the formula:
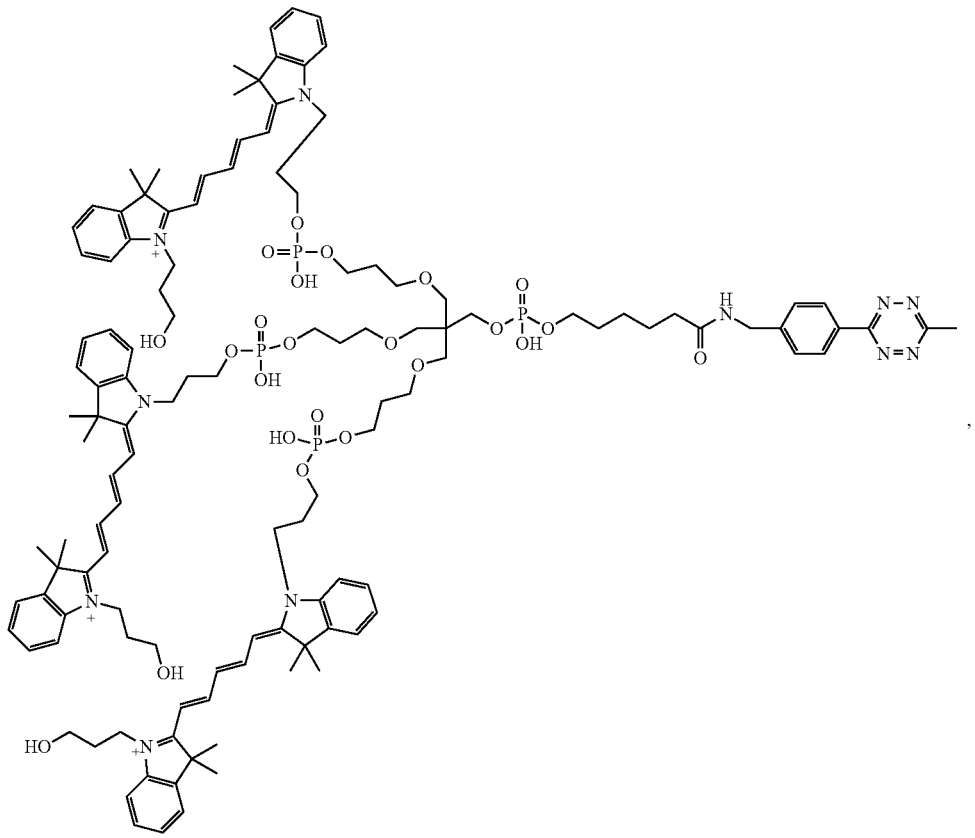
, -continued
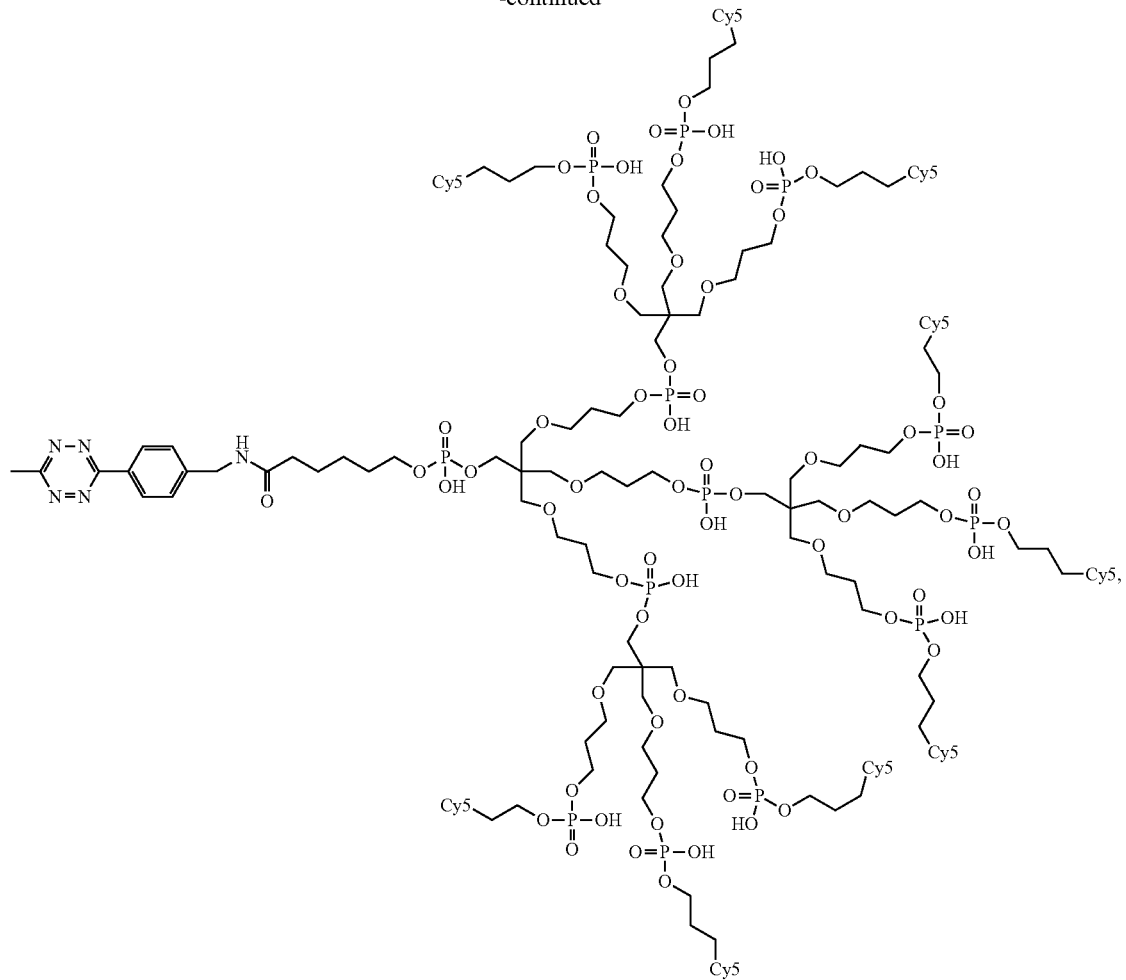
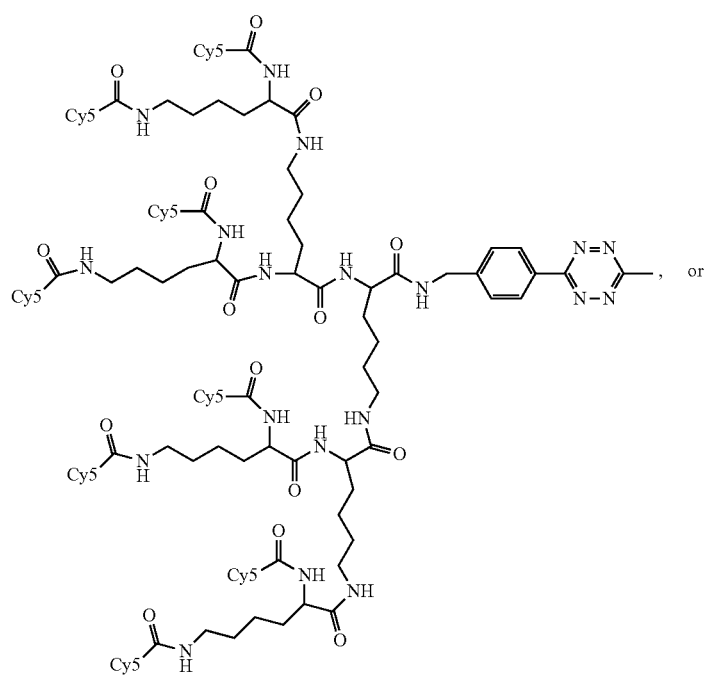

-continued

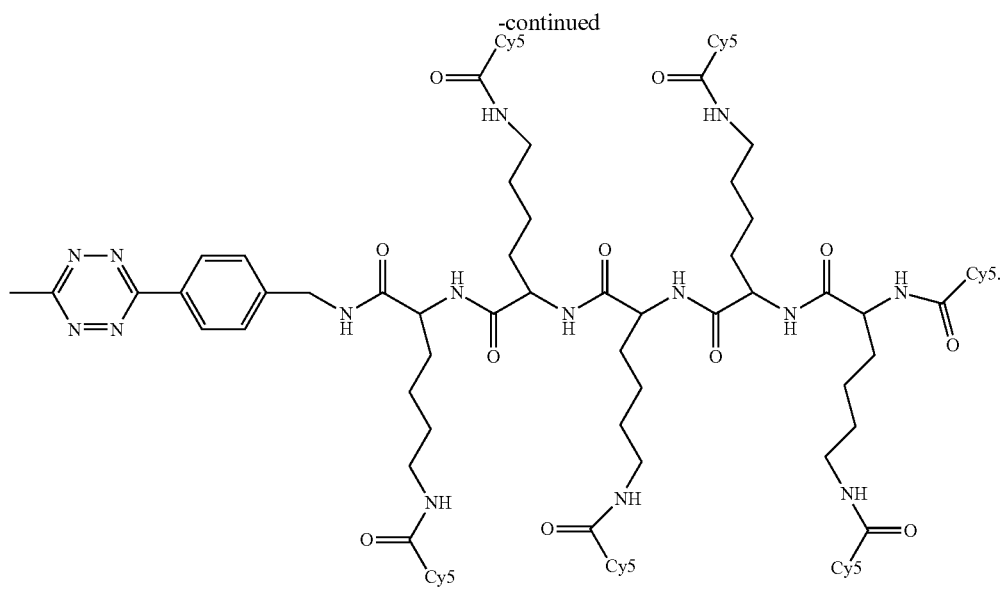

313

A method for sequencing a nucleic acid, comprising:
incorporating in series with a nucleic acid polymerase, within a reaction vessel, one of four different labeled nucleotide analogues into a primer to create an extension strand, wherein said primer is hybridized to said nucleic acid and wherein each of the four different labeled nucleotide analogues comprise a unique detectable label;
(ii) detecting said unique detectable label of each incorporated nucleotide analogue, so as to thereby identify each incorporated nucleotide analogue in said extension strand, thereby sequencing the nucleic acid; and
wherein each of said four different labeled nucleotide analogues are of the structure of one of embodiments 1 to 28, 31 to 33, 37 to 44, 50 to 163, 183 to 213, 216 to 218, and 222 to 273, wherein
in the first of said four different labeled nucleotide analogues, B is a thymidine or uridine hybridizing base;
in the second of said four different labeled nucleotide analogues, B is an adenosine hybridizing base;
in the third of said four different labeled nucleotide analogues, B is an guanosine hybridizing base; and
in the fourth of said four different labeled nucleotide analogues, B is an cytosine hybridizing base.

Embodiment 314

The method of embodiment 313, further comprising, after each of said incorporating steps, adding to said reaction vessel four different unlabeled nucleotide analogues, wherein each of said four different unlabeled nucleotide analogues are of the structure of one of embodiments 257 to 279, wherein
in the first of said four different unlabeled nucleotide analogues; B is a thymidine or uridine hybridizing base;
in the second of said four different unlabeled nucleotide analogues, B is an adenosine hybridizing base;
in the third of said four different unlabeled nucleotide analogues, B is a guanosine hybridizing base; and
in the fourth of said four different unlabeled nucleotide analogues, B is a cytosine hybridizing base.

Embodiment 315

The method of one of embodiments 313 or 314, wherein at least one of said four different labeled nucleotide analogues is an orthogonally cleavable labeled nucleotide analogue comprising a cleavable moiety, said orthogonally cleavable labeled nucleotide analogue having the structure of one of embodiments 1 to 27, 31 to 33, 37 to 44, 50 to 114, 183 to 212, 216 to 218, and 222 to 246, and wherein the method further comprises, after each of said incorporating steps, adding to said reaction vessel a cleaving reagent capable of cleaving the cleavable moiety.

Embodiment 316

A method for sequencing a nucleic acid, comprising:
incorporating in series with a nucleic acid polymerase, within a reaction vessel, one of four different nucleotide analogues into a primer to create an extension strand, wherein said primer is hybridized to said nucleic acid and wherein three of the four different nucleotide analogues are different labeled nucleotide analogues each comprising a unique detectable label and one of the four different nucleotide analogues is a different unlabeled nucleotide analogue;
detecting the presence or absence of said unique detectable label of each incorporated nucleotide analogue, so as to thereby identify each incorporated nucleotide analogue in said extension strand, thereby sequencing the nucleic acid; and
wherein each of said four different labeled nucleotide analogues are of the structure of one of embodiments 1 to 28, 31 to 33, 37 to 44, 50 to 163, 183 to 213, 216 to 218, and 222 to 273, wherein
in the first of said four different labeled nucleotide analogues, B is a thymidine or uridine hybridizing base;
in the second of said four different labeled nucleotide analogues, B is an adenosine hybridizing base;

in the third of said four different labeled nucleotide analogues, B is a guanosine hybridizing base; and in the fourth of said four different labeled nucleotide analogues, B is a cytosine hybridizing base.

Embodiment 317

The method of embodiment 316, further comprising, after each of said incorporating steps, adding to said reaction vessel four different unlabeled nucleotide analogues, wherein each of said four different unlabeled nucleotide analogues are of the structure of one of embodiments 274 to 295, wherein
- in the first of said four different unlabeled nucleotide analogues, B is a thymidine or uridine hybridizing base;
- in the second of said four different unlabeled nucleotide analogues, B is an adenosine hybridizing base;
- in the third of said four different unlabeled nucleotide analogues, B is a guanosine hybridizing base; and
- in the fourth of said four different unlabeled nucleotide analogues, B is a cytosine hybridizing base.

Embodiment 318

The method of one of embodiments 316 or 317, wherein at least one of said three different labeled nucleotide analogues is an orthogonally cleavable labeled nucleotide analogue comprising a cleavable moiety, said orthogonally cleavable labeled nucleotide analogue having the structure of one of embodiments 1 to 27, 31 to 33, 37 to 44, 50 to 114, 183 to 212, 216 to 218, and 222 to 246, and wherein the method further comprises, after each of said incorporating steps, adding to said reaction vessel a cleaving reagent capable of cleaving the cleavable moiety.

Embodiment 319

A method of incorporating a nucleotide analogue into a primer, the method comprising combining a polymerase, a primer hybridized to nucleic acid template and a nucleotide analogue within a reaction vessel and allowing said polymerase to incorporate said nucleotide analogue into said primer thereby forming an extended primer, wherein said nucleotide analogue is of the structure of one of embodiments 1 to 163 and 183 to 273.

Embodiment 320

The method of embodiment 319, wherein $L^2$ is a cleavable moiety and $R^5$ is a detectable label, said method further comprising, after said incorporating, cleaving said cleavable moiety with a cleaving reagent.

Embodiment 321

The method of embodiment 319, wherein $R^5$ is anchor moiety, said method further comprising, after said incorporating, labeling said nucleotide analog with a detectable label.

Embodiment 322

The method of embodiment 321, wherein $R^5$ is an affinity anchor moiety.

Embodiment 323

The method of embodiment 322, wherein said labeling comprises adding to the reaction vessel a compound having the formula $R^{12}$-$L^4$-$R^{13}$, wherein
$R^{12}$ is a complementary affinity anchor moiety binder;
$R^{13}$ is a detectable label; and
$L^4$ is a covalent linker.

Embodiment 324

The method of embodiment 321, wherein $R^5$ is a chemically reactive anchor moiety.

Embodiment 325

The method of embodiment 324, wherein said labeling comprises adding to the reaction vessel a compound having the formula $R^{12z}$-$L^{4z}$-$R^{13}$, wherein
$R^{12z}$ is a complementary anchor moiety reactive group;
$R^{12}$ is a detectable label; and
$L^{4z}$ is a covalent linker.

Embodiment 326

The method of embodiment 325, wherein $R^{12z}$-$L^{4z}$-$R^{13}$ has the structure of one of embodiments 296 to 321.

Embodiment 327

The method of embodiment 325, wherein $L^{4z}$ is a cleavable linker.

Embodiment 328

The method of embodiment 327, further comprising, after said incorporating, cleaving said cleavable moiety with a cleaving reagent.

Embodiment 329

The method of one of embodiments 319-328, further comprising, after said incorporating, adding to said reaction vessel an unlabeled nucleotide analogue comprising a 3'-polymerase-compatible cleavable moiety.

Embodiment 330

The method of one of embodiments 319-329, wherein said method forms part of a sequencing by synthesis method.

Embodiment 331

A method for sequencing a nucleic acid comprising:
contacting a nucleic acid having a primer hybridized to a portion thereof, with a polymerase and a first type of nucleotide analogue under conditions permitting the nucleotide polymerase to catalyze incorporation of the nucleotide analogue into the primer if the nucleotide analogue is complementary to a nucleotide residue of the nucleic acid that is immediately 5' to a nucleotide residue of the nucleic acid hybridized to the 3' terminal nucleotide residue of the primer, so as to form a nucleic acid extension product, wherein the nucleotide analogue has the structure:

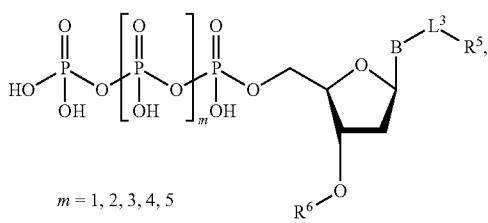

$m = 1, 2, 3, 4, 5$ wherein,
B is a nucleobase; $L^3$ is a cleavable linker having the structure:

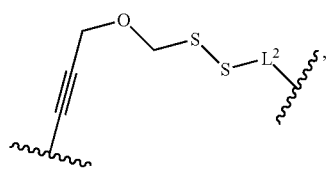

wherein $L^2$ is a linker;
$R^6$ is a polymerase-compatible cleavable dithio moiety that when bound to the 3'-O of the nucleotide analogues prevents a polymerase from catalyzing a polymerase reaction with the 3'-O of the nucleotide analogue, wherein R6 has the structure:

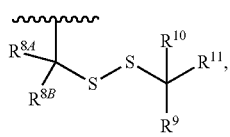

Wherein $R^{8A}$ and $R^{8B}$ are independently hydrogen, —CH$_3$, —CX$_3$, —CHX$_2$, —CH$_2$X, —CN, -Ph, substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl, wherein X is a halogen;
wherein $R^9$, $R^{10}$, and $R^{11}$ are each independently hydrogen, —CX$_3$, —CHX$_2$, —CH$_2$X, —OCH$_3$, —SCH$_3$, —NHCH$_3$, —CN, -Ph, substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroary, wherein X is a halogen;
$R^3$ is an anchor moiety, wherein the identity of the anchor moiety is predetermined and correlated to the identity of the nucleobase;
removing any nucleotide analogue not incorporated into the primer in step a); contacting the nucleic acid in step a) with at least one compound having the formula $R^{12}$-$L^4$-$R^{13}$, wherein $R^{12}$ is a complementary anchor moiety binder that rapidly reacts with the anchor moiety, thereby forming a conjugate with the anchor moiety, $L^4$ is a covalent or a non-covalent linker, and $R^{13}$ is a detectable label;

detecting the presence of the detectable label so as to thereby determine whether the nucleotide analogue of step a) was incorporated so as to thereby determine the identity of the complementary nucleotide residue in the template DNA, and
wherein if the base of the nucleotide analogue a) is not complementary to the nucleotide residue of the nucleic acid which is immediately 5' to the nucleotide residue of the single-stranded DNA hybridized to the 3' terminal nucleotide residue of the primer, then iteratively repeating steps a) through c) with a second, third, and then fourth type of nucleotide analogue, wherein each different type of nucleotide analogue has a different base from each other type of nucleotide analogue, until the nucleotide analogue has a base that is complementary.
contacting the nucleic acid with a cleaving agent, so as to (i) cleave the cleavable linker attached to the nucleobase, and (ii) cleave the cleavable dithio moiety, thereby resulting in a 3'-OH on the growing DNA strand; and
iteratively performing steps a) through e) for each nucleotide residue of the nucleic acid to be sequenced so as to thereby determine the sequence of the nucleic acid.

Embodiment 332

The embodiment of 331 wherein the first, second, third, and fourth type of nucleotide analogue have different anchor moieties, and wherein each different anchor moiety is complementary to a different anchor moiety binder containing a detectable label.

Embodiment 333

The method of any one of embodiments 331-332, wherein the different binding molecules each have a different detectable label.

Embodiment 334

The method of any one of claims 332-333, wherein during or subsequent to step a) the nucleic acid is contacted with a nucleotide analogue having the structure:

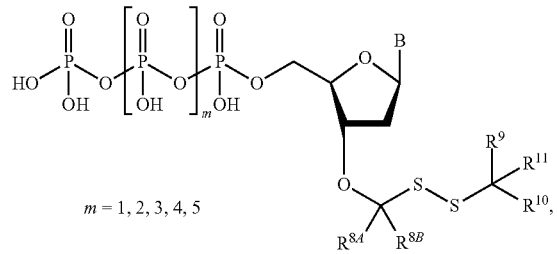

$m = 1, 2, 3, 4, 5$

B is a nucleobase, which is complementary to the same nucleobase as is the nucleotide analogue of step a);
$R^{8A}$ and $R^{8B}$ are independently hydrogen, —CH$_3$, —CX$_3$; —CHX$_2$, —CH$_2$X, —CN, -Ph, substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl, wherein X is a halogen;

$R^9$, $R^{10}$, and $R^{11}$ are each independently hydrogen, —$CX_3$, —$CHX_2$, —$CH_2X$, —$OCH_3$, —$SCH_3$, —$NHCH_3$, —CN, -Ph, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl, wherein X is a halogen.

Embodiment 335

A method for sequencing a nucleic acid comprising:

a) contacting a nucleic acid having a primer hybridized to a portion thereof, with a polymerase and a first, second, third, and fourth type of nucleotide analogue under conditions permitting the polymerase to catalyze incorporation of the nucleotide analogue into the primer if the nucleotide analogue is complementary to a nucleotide residue of the nucleic acid that is immediately 5' to a nucleotide residue of the nucleic acid hybridized to the 3' terminal nucleotide residue of the primer, so as to form a DNA extension product, wherein each type of nucleotide analogue has the structure:

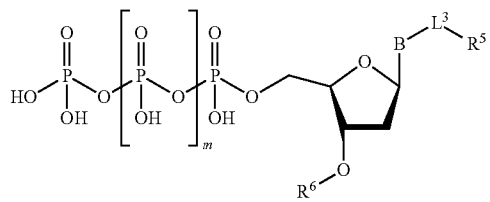

m = 1, 2, 3, 4, 5 wherein, $L^3$ is a cleavable linker having the structure:

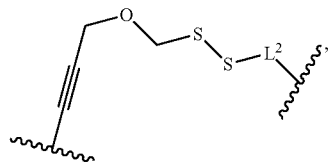

wherein $L^2$ is a linker;

wherein B is a nucleobase, wherein the base of each type of nucleotide analogue is independently different from the base of the remaining three types of nucleotide analogue, wherein one base is a thymidine or uridine hybridizing base, one base is an adenosine hybridizing base, one base is a guanosine hybridizing base, and one base is a cytosine hybridizing base;

$R^6$ is a polymerase-compatible cleavable dithio moiety that when bound to the 3'-O prevents a nucleotide polymerase from catalyzing a polymerase reaction with the 3'-O of the nucleotide analogue, wherein $R^6$ has the structure:

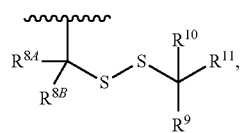

wherein $R^{8A}$ and $R^{8B}$ are independently hydrogen, —$CH_3$, —$CX_3$, —$CHX_2$, —$CH_2X$, —CN, -Ph, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl, wherein X is a halogen;

wherein $R^9$, $R^{10}$, and $R^{11}$ are each independently hydrogen, —$CX_3$, —$CHX_2$, —$CH_2X$, —$OCH_3$, —$SCH_3$, —$NHCH_3$, —CN, -Ph, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted;

$R^5$ is an anchor moiety, wherein the identity of the anchor moiety is predetermined and correlated to the identity of the nucleobase, and wherein the anchor moiety of each type of nucleotide analogue is complementary to a different anchor binding moiety from each of the remaining nucleotide analogues;

b) contacting the nucleic acid in step a) with at least a first, second, third, and fourth type of compound having the formula $R^{12}$-$L^4$-$R^{13}$, wherein $R^{12}$ is a complementary anchor moiety binder that rapidly reacts with an anchor moiety, thereby forming a conjugate with the anchor moiety, wherein the anchor moiety binder of each type of compound is complementary to the anchor moiety of one type of nucleotide analogue from step a), wherein $L^4$ is a covalent linker, and $R^{13}$ is a detectable label, wherein each type of compound has a different detectable label, that is correlated to the identity of the anchor moiety binder;

c) determining the identity of the detectable label bound to the nucleotide analogue incorporated in step a) so as to thereby determine the identity of the incorporated nucleotide analogue, d) contacting the nucleic acid with a cleaving agent, so as to (i) cleave the cleavable linker attached to the nucleobase, and (ii) cleave the cleavable dithio moiety, thereby resulting in a 3'-OH in the growing DNA strand; and e) iteratively performing steps a) through d) for each nucleotide residue of the nucleic acid to be sequenced so as to thereby determine the sequence of the nucleic acid.

Embodiment 336

A method for sequencing a nucleic acid comprising:

a) contacting a nucleic acid having a primer hybridized to a portion thereof, with a nucleotide polymerase and a first, second, third, and fourth type of nucleotide analogue under conditions permitting the nucleotide polymerase to catalyze incorporation of the nucleotide analogue into the primer if the nucleotide analogue is complementary to a nucleotide residue of the nucleic acid that is immediately 5' to a nucleotide residue of the nucleic acid hybridized to the 3' terminal nucleotide residue of the primer, so as to form a nucleotide extension product, wherein each type of nucleotide analogue has the structure:

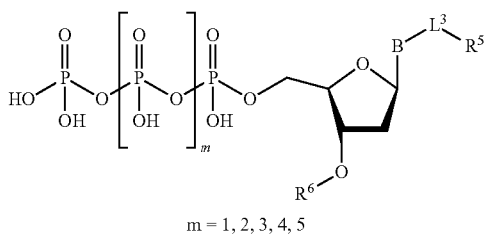

m = 1, 2, 3, 4, 5 wherein, $L^3$ is a cleavable linker having the structure:

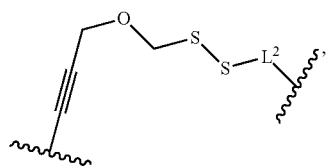

wherein $L^2$ is a linker;

wherein B is a nucleobase, wherein the base of each type of nucleotide analogue is independently different from the base of the remaining three types of nucleotide analogue, wherein one base is a thymidine or uridine hybridizing base, one base is an adenosine hybridizing base, one base is a guanosine hybridizing base; and one base is a cytosine hybridizing base;

$R^6$ is a polymerase-compatible cleavable dithio moiety that when bound to the 3'-O prevents a nucleotide polymerase from catalyzing a polymerase reaction with the 3'-O of the nucleotide analogue, wherein $R^6$ has the structure:

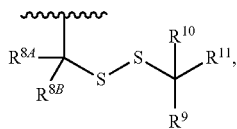

wherein $R^{8A}$ and $R^{8B}$ are independently hydrogen, —$CH_3$, —$CX_3$, —$CHX_2$, —CN, -Ph, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl, wherein X is a halogen;

wherein $R^9$, $R^{10}$, and $R^{11}$ are each independently hydrogen, —$CX_3$, —$OCH_3$, —$SCH_3$, —$NHCH_3$, —CN, -Ph, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted;

wherein for the first and second type of nucleotide analogue $R^5$ is an anchor moiety, wherein the identity of the anchor moiety is predetermined and correlated to the identity of the nucleobase, and wherein the anchor moiety of each type of nucleotide analogue is complementary to a different anchor binding moiety from the remaining nucleotide analogue;

wherein for the third and fourth type of nucleotide analogue R5 is a detectable label, wherein the detectable label for the third type of nucleotide analogue is different from the fourth type;

b) removing any non-incorporated nucleotide analogue;

c) detecting the presence of either of the detectable label of the third or fourth type of nucleotide analogue incorporated in step a) so as to thereby determine the identity of the incorporated nucleotide and the identity of the complementary residue in the nucleic acid;

wherein if the base of the third and fourth type of nucleotide analogue is not complementary, contacting the nucleic acid in step a) with at least a first, and second type of compound having the formula $R^{12}$-$L^4$-$R^{13}$, wherein $R^{12}$ is a complementary anchor moiety binder that rapidly reacts with an anchor moiety, thereby forming a conjugate with the anchor moiety, wherein the anchor moiety binder of first type of compound is complementary to the anchor moiety of first type of nucleotide analogue and the anchor moiety binder of second type of compound is complementary to the anchor moiety of second type of nucleotide analogue, wherein $L^4$ is a covalent linker, and $R^{13}$ is a detectable label, wherein the label on the first type of compound and second type of compound are different;

d) determining the identity of the detectable label bound to the nucleotide analogue incorporated in step a) so as to thereby determine the identity of the incorporated nucleotide analogue, e) contacting the nucleic acid with a cleaving agent, so as to (i) cleave the cleavable linker attached to the nucleobase, and (ii) cleave the cleavable dithio moiety, thereby resulting in a 3'-OH; and f) iteratively performing steps a) through e) for each nucleotide residue of the nucleic acid to be sequenced so as to thereby determine the sequence of the nucleic acid.

Embodiment 337

A method for sequencing a nucleic acid comprising:

a) contacting a nucleic acid having a primer hybridized to a portion thereof, with a nucleotide polymerase and a first, second, third, and fourth type of nucleotide analogue under conditions permitting the nucleotide polymerase to catalyze incorporation of the nucleotide analogue into the primer if the nucleotide analogue is complementary to a nucleotide residue of the nucleic acid that is immediately 5' to a nucleotide residue of the nucleic acid hybridized to the 3' terminal nucleotide residue of the primer, so as to form a nucleotide extension product, wherein the first, second, and third type of nucleotide analogue each have the structure:

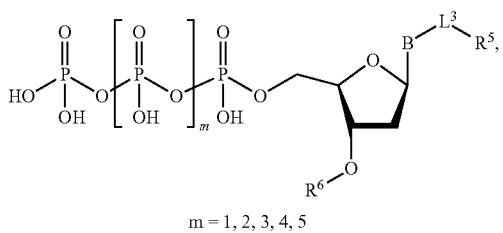

m = 1, 2, 3, 4, 5 wherein, B is a nucleobase, wherein $L^3$ is a cleavable linker having the structure:

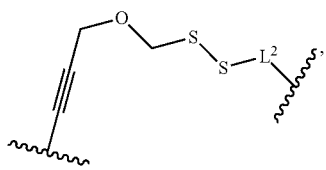

wherein $L^2$ is a linker;
wherein $R^5$ is an anchor moiety, wherein the identity of the anchor moiety is predetermined and correlated to the identity of the nucleobase, and wherein the anchor moiety of each type of nucleotide analogue is complementary to a different anchor binding moiety from the remaining nucleotide analogues;
wherein the fourth type of nucleotide analogue has the structure:

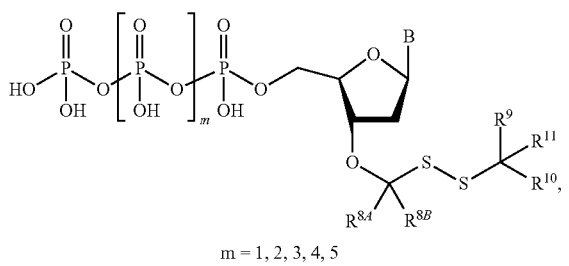

m = 1, 2, 3, 4, 5 wherein B is a nucleobase;
wherein the base of each type of nucleotide analogue is independently different from the base of the remaining three types of nucleotide analogue, wherein one base is a thymidine or uridine hybridizing base, one base is an adenosine hybridizing base, one base is a guanosine hybridizing base, and one base is a cytosine hybridizing base;
wherein $R^6$ for each of the first, second, third, and fourth types of nucleotide analogue is a polymerase-compatible cleavable dithio moiety that when bound to the 3'-O prevents a nucleotide polymerase from catalyzing a polymerase reaction with the 3'-O of the nucleotide analogue, wherein $R^6$ has the structure:

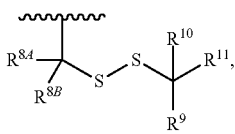

wherein $R^{8A}$ and $R^{8B}$ are independently hydrogen, —CH$_3$, —CX$_3$, —CHX$_2$, —CH$_2$X, —CN, -Ph, substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl, wherein X is a halogen;
wherein $R^9$, $R^{10}$, and $R^{11}$ are each independently hydrogen, —CX$_3$, —CHX$_2$, —CH$_2$X, —OCH$_3$, —SCH$_3$, —NHCH$_3$, —CN, -Ph, substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted;

b) removing any non-incorporated nucleotide analogue;
c) contacting the nucleic acid with a first, second, and third type of compound having the formula $R^{12}$-$L^4$-$R^{13}$, wherein $R^{12}$ is a complementary anchor moiety binder that rapidly reacts with an anchor moiety, thereby forming a conjugate with the anchor moiety,
wherein the anchor moiety binder of the first type of compound is complementary to the anchor moiety of first type of nucleotide analogue, the anchor moiety binder of second type of compound is complementary to the anchor moiety of second type of nucleotide analogue, and the anchor moiety binder of the third type of compound is complementary to the anchor moiety of the third type of nucleotide analogue, wherein $L^4$ is a cleavable linker,
wherein $L^4$ of each type of compound is different;
d) removing any unincorporated nucleotides or unconjugated anchor moiety binders and detecting whether there is an absence of detectable label bound to the incorporated nucleotide analogue of step a), thereby determining whether the incorporated nucleotide was of the fourth type of nucleotide analogue;
e) if a detectable label is detected in step d), contacting the nucleic acid with a means of cleaving $L^4$ of the first type of compound, wherein the means does not cleave $L^3$ or $R^6$ of any type of nucleotide analogue, and the means does not cleave $L^4$ of the second and third type of compound;
f) removing any unconjugated anchor moiety binders and detecting whether there is an absence of detectable label bound to the incorporated nucleotide of step a), thereby determining that identity of the incorporated nucleotide is of the first type of nucleotide analogue;
g) if a detectable label is detected in step f), contacting the nucleic acid with a means of cleaving $L^4$ of the second type of compound, wherein the means does not cleave $L^3$ or $R^6$ of any type of nucleotide analogue, and the means does not cleave $L^4$ of the third type of compound;
h) removing any unconjugated anchor moiety binders and detecting whether there is an absence of detectable label bound to the incorporated nucleotide of step a), thereby determining that identity of the incorporated nucleotide is of the second type of nucleotide analogue;
i) contacting the nucleic acid with a cleaving agent, so as to (i) cleave the cleavable linker attached to the nucleobase, and (ii) cleave the cleavable dithio moiety, thereby resulting in a 3'-OH; and j) iteratively performing steps a) through i) for each nucleotide residue of the nucleic acid to be sequenced so as to thereby determine the sequence of the nucleic acid.

Embodiment 338

The method of any one of embodiments 333-337, wherein during or subsequent to step a) the nucleic acid is contacted with four different types of nucleotide analogue, each having the structure:

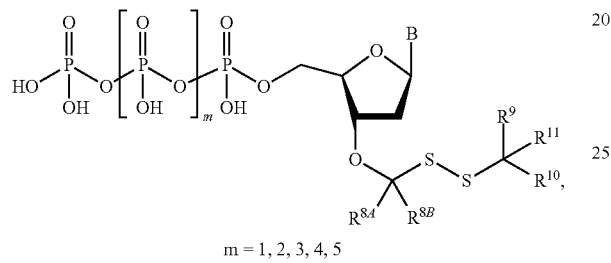

m = 1, 2, 3, 4, 5 wherein B is a nucleobase, wherein the base of each type of nucleotide analogue is independently different from the base of the remaining three types of nucleotide analogue, and wherein one base is a thymidine or uridine hybridizing base, one base is an adenosine hybridizing base, one base is a guanosine hybridizing base, and one base is a cytosine hybridizing base;

wherein $R^{8A}$ and $R^{8B}$ are independently hydrogen, —$CH_3$, —$CX_3$, —$CHX_2$, —$CH_2X$, —CN, -Ph, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl, wherein X is a halogen; and wherein $R^9$, $R^{10}$, and $R^{11}$ are each independently hydrogen, —$CX_3$, —$CHX_2$, —$CH_2X$, —$OCH_3$, —$SCH_3$, —$NHCH_3$, —CN, -Ph, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroary, wherein X is a halogen.

Embodiment 339

The method of any one of embodiments 332-338, wherein the anchor moieties and labeling moieties are selected from the group comprising:

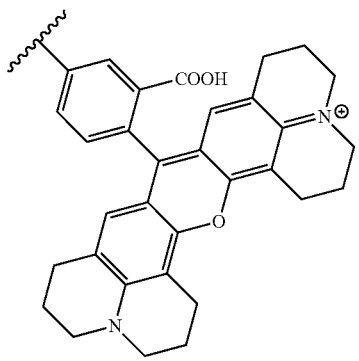

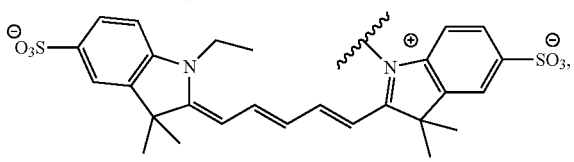

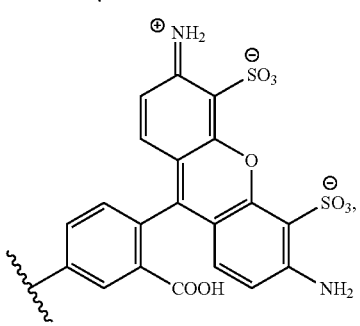

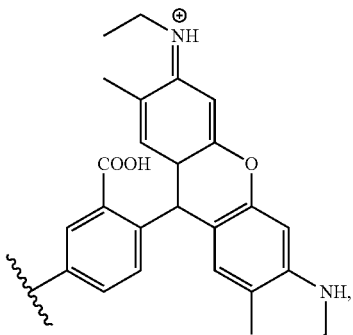

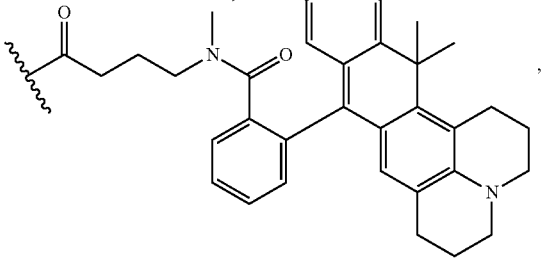

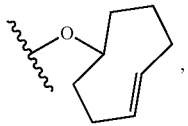

491
-continued
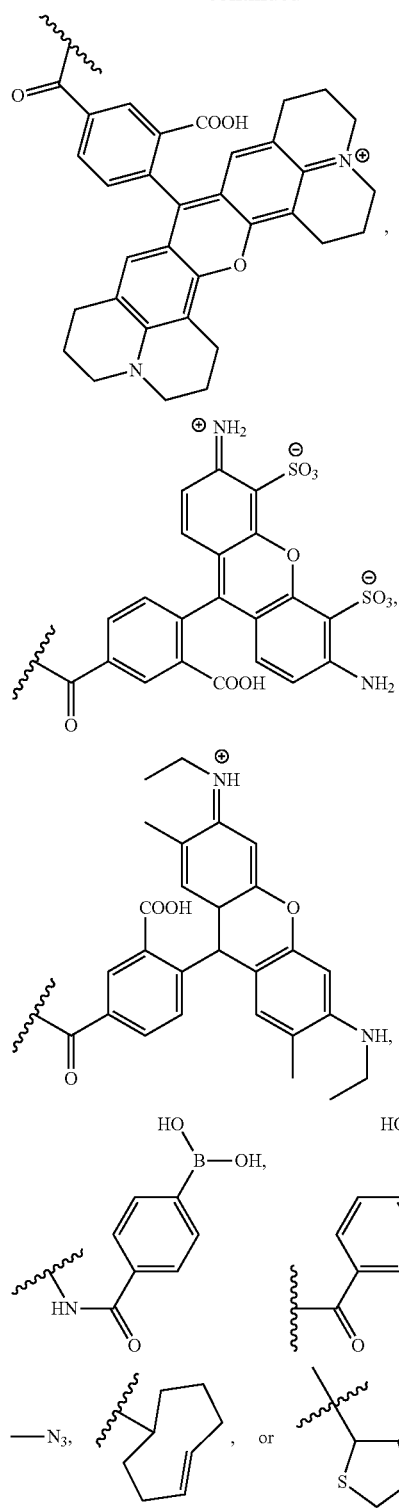
492
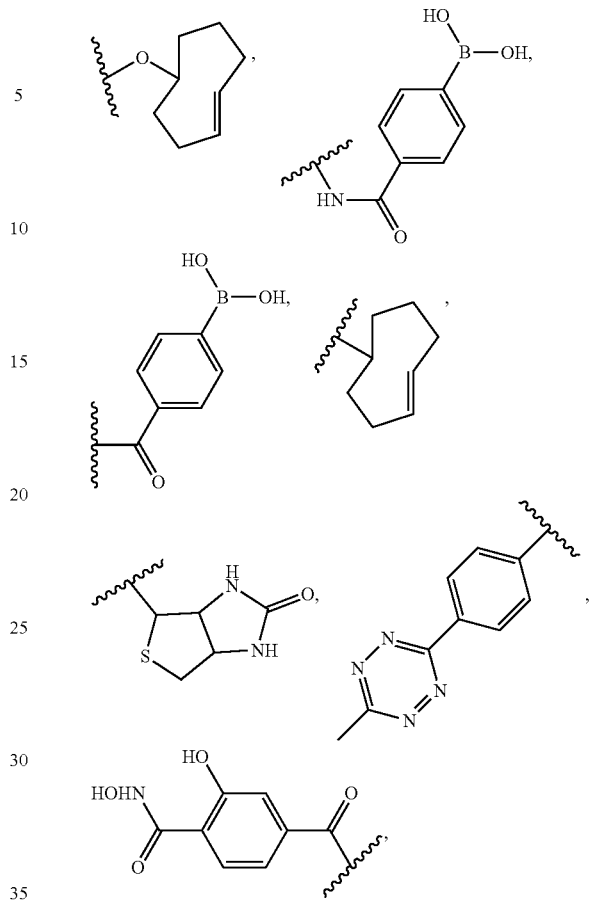
a streptavidin moiety, or
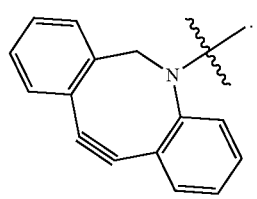 [SMILES: *N1Cc2ccccc2C#Cc2ccccc21]
Embodiment 341
The method of any one of embodiments 332-340, wherein $L^3$ has the structure:
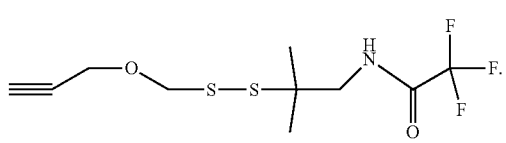
Embodiment 340
The method of any one of embodiments 332-339, wherein the complementary anchor binding moiety is selected from the group consisting of:

Embodiment 342

A method of synthesizing a base-attached cleavable linker having the structure:

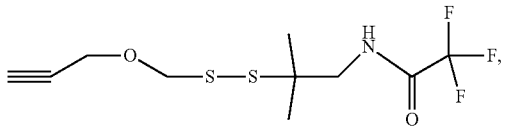 [SMILES: C#CCOCSSC(C)(C)CNC(=O)C(F)(F)F]

comprising:
a) reacting 3-trimethylsilanyl-prop-2-yn-1-ol with DMSO, acetic acid and acetic anhydride to provide Trimethyl(3-((methylthio)methoxy)prop-1-yn-1-yl)silane;
b) contacting Trimethyl(3-((methylthio)methoxy)prop-1-yn-1-yl)silane with Sulfuryl chloride/cyclohexene followed by reaction with potassium thiotosylate to produce S-(((3-(trimethylsilyl)prop-2-yn-1-yl)oxy)methyl) 4-methylbenzenesulfonothioate;
c) contacting S-(((3-(trimethylsilyl)prop-2-yn-1-yl)oxy)methyl) 4-methylbenzenesulfonothioate with 2,2,2-trifluoro-N-(2-mercapto-2-methylpropyl) acetamide in the presence of triethylamine, followed by;
d) contacting with tetrabutylammonium fluoride to form 2,2,2-trifluoro-N-(2-methyl-2-(((prop-2-yn-1-yloxy)methyl)disulfanyl)propyl)acetamide.
e) reacting 5'-O-tBDMS-3'-O-polymerase compatible cleavable blocking group-5(7)-Iodo-nucleoside with 2,2,2-trifluoro-N-(2-methyl-2-(((prop-2-yn-1-yloxy)methyl)disulfanyl)propyl)acetamide in the presence of Pd(0), CuI, triethylamine which results in the formation of 5'-O-tBDMS-3'-O-polymerase compatible cleavable blocking group-2'-deoxynucleoside-5(7)-2,2,2-trifluoro-5-yl)ethynyl)oxy)methyl)disulfanyl)-2-methylpropyl)acetamide.
f) reacting the above product from step e) with tetrabutylammonium fluoride to remove 5'-O-tBDMS group permitting the formation of 3'-O-polymerase compatible cleavable blocking group-2'-deoxynucleoside-5(7)-2,2,2-trifluoro-5-yl)ethynyl)oxy)methyl)disulfanyl)-2-methylpropyl)acetamide;
g) contacting the 3'-O-polymerase compatible cleavable blocking group-2'-deoxynucleoside-5(7)-2,2,2-trifluoro-5-yl)ethynyl)oxy)methyl)disulfanyl)-2-methylpropyl)acetamide produced in step f) with 2-chloro-4-H-1,3,2-benzodioxaphosphorin-4-one, tetrabutylammonium pyrophosphate, tributylamine, 12, pyridine, and $NH_4OH$ under condition permitting the formation of 3'-O-polymerase compatible cleavable blocking group-5(7)-(3-(((1-amino methylpropan-2-yl)disulfanyl)methoxy)prop-1-yn-1-yl)-2'-deoxynucleoside-5'-triphosphate

EXAMPLES

Figure 30D:
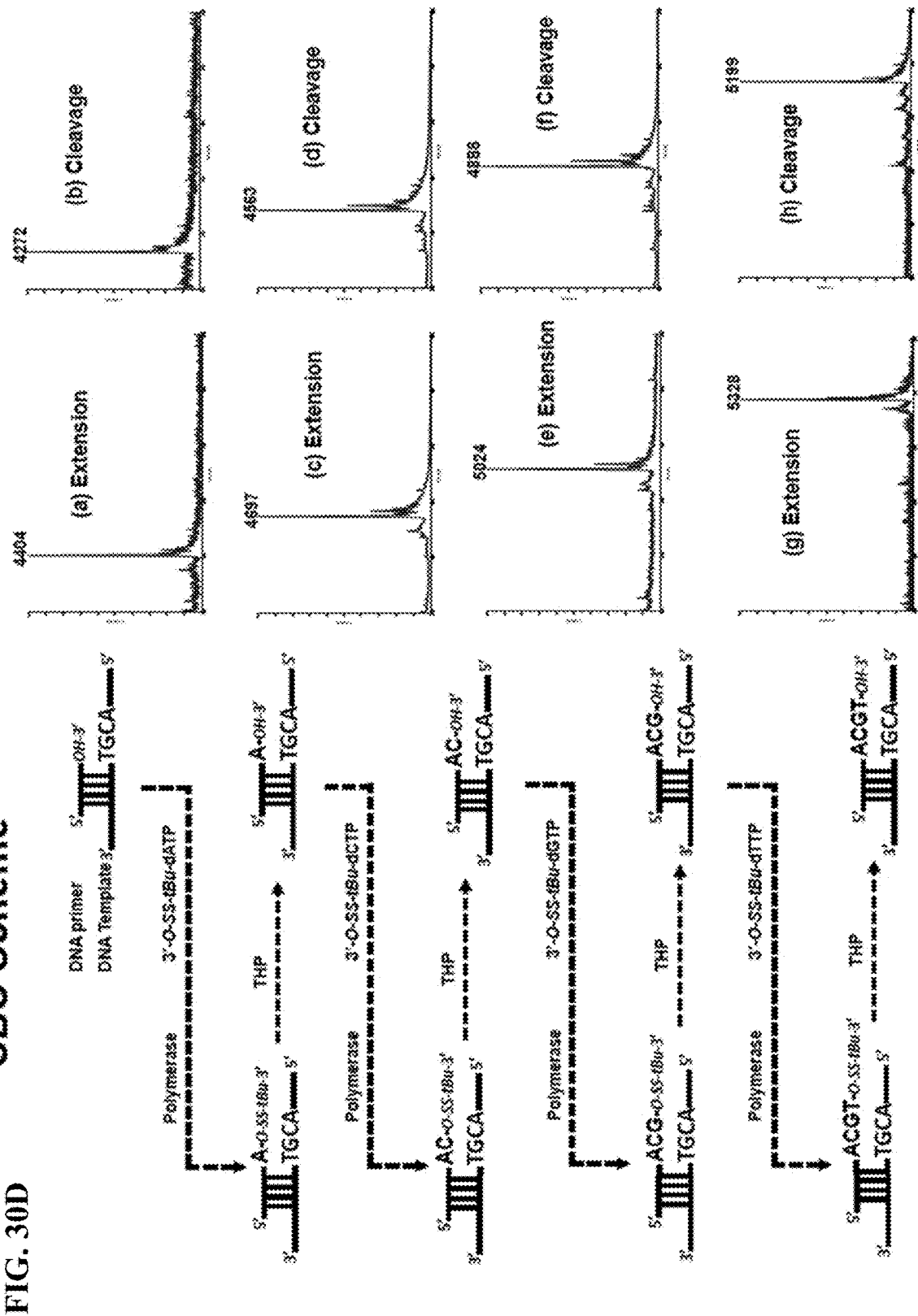

Example 1. Design and Synthesis of Novel Disulfide Linker Based Nucleotides as Reversible Terminators for DNA Sequencing by Synthesis We first demonstrated that the four 3'-O-alkyldithiomethyl-dNTPs (3'-O-DTM NRTs) (FIGS. 30A-30D) can extend a primer in a single base extension reaction and terminates its further extension. Using these 4 nucleotide analogues as substrates, we then performed a complete 4-step SBS reaction. We used MALDI-TOF MS analysis to evaluate the results of polymerase extension by a single 3'-O-DTM-dNTP into the growing DNA strand (FIGS. 30B and 30D). Due to the small size of the DTM label, the 3'-O-DTM-dNTPs are efficient substrates for the DNA polymerase. In the SBS cycles, the natural nucleotides are restored after each incorporation and cleavage, producing a growing DNA strand that bears no modifications and will not impede further polymerase reactions.

We have also carried out similar single base extension and termination reactions using the chemically cleavable fluorescent nucleotide reversible terminator 3'-O-DTM-dCTP-SS-BodipyFL. After single base extension and cleavage of the DTM moiety from the 3'-O and between the base and fluorophore, the resulted extended primer can be further extended with the same nucleotide, 3'-O-DTM-dCTP-SS-Bodip/FL (FIG. 46). These results clearly indicate that multiple NRTs, 3'-O-DTM-dNTP-SS-Dye, can be incorporated and cleaved simultaneously resulting in long read sequencing.

Continuous Polymerase Extension Using 3'-O-Et-SS-dNTPs (3'-O-DTM-dNTPs) and Characterization by MALDI-TOF Mass Spectrometry. To verify that the 3'-O-DTM-dNTPs are incorporated accurately in a base-specific manner in the polymerase reaction, four consecutive DNA extension and cleavage reactions were carried out in solution with 3'-O-DTM-dNTPs as substrates. This allowed the isolation of the DNA product at each step for detailed molecular structure characterization as shown in FIG. 30B.

We performed a complete consecutive 4-step SBS reaction that involved incorporation of each complementary 3'-O-DTM-dNTPs, followed by MALDI-TOF MS analysis for sequence determination, and cleavage of the 3'-O-DTM blocking group from the DNA extension product to yield a free 3'-OH group for incorporating the next nucleotide analogue. A template-primer combination was designed in which the next four nucleotides to be added were A, C, G and T. As shown in FIG. 30B, the SBS reaction was initiated with the 13-mer primer annealed to a DNA template. When the first complementary nucleotide, 3'-O-Et-SS-dATP (3'-O-DTM-dATP), was used in the polymerase reaction, it was incorporated into the primer to form a DNA extension product with a molecular weight of 4387 Dalton as confirmed by MALDI-TOF MS with the appearance of a single peak (FIG. 30B (a)Top left). These results indicated that the 3'-O-DTMdATP was quantitatively incorporated into the 13-mer DNA primer. After THP treatment to remove the DTM group from the DNA product and HPLC purification, the cleavage was confirmed by the presence of a single MS peak at 4268 Da, corresponding to the DNA product with the 3'-O-DTM group removed (FIG. 30B (b)Top right). The newly formed DNA extension product with a free 3'-OH group was then used in a second polymerase reaction to incorporate a 3'-O-Et-SS-dCTP (3'-O-DTM-dCTP) which gave a single MS peak at 4675 Da (FIG. 30B (c), indicating incorporation of a 3'-O-DTM-dCTP into the growing DNA strand in this cycle. After THP treatment, a single MS peak of the cleavage DNA product appeared at 4551 Da (FIG. 30B (d), which demonstrated the complete removal of the DTM group from the DNA extension product. FIG. 30B (left) shows the third incorporation of 3'-O-Et-SS-dGTP (3'-O-DTM-dGTP) into this growing DNA strand. The accurate masses of the corresponding DNA products were obtained by MALDI-TOF MS for the third nucleotide incorporation (5002 Da, FIG. 30B (e), and cleavage reaction (4887 Da, FIG. 30B, f). Finally, 3'-O-Et-SS-dTTP (3'-O-

DTM-dTTP) incorporation in the fourth cycle and a final removal of the DTM group by THP was verified, as appropriate masses for the corresponding DNA products were obtained by MALDI-TOF MS for the fourth nucleotide incorporation (5301 Da, FIG. 30B, (g) and cleavage reaction (5194 Da, FIG. 30B (h). These results demonstrate that all four 3'-O-DTM-dNTPs are efficiently incorporated base-specifically as reversible terminators into the growing DNA strand in a continuous polymerase reaction, and that the 3'-OH capping group on the DNA extension products is quantitatively cleaved by THP.

Polymerase Extension reaction Using 3'-O-tBu-SS-dCTP-SS-BodipyFL (3'-O-DTM-dCTPSS-BodipyFL) and Characterization by MALDI-TOF Mass Spectrometry (FIG. 46). Polymerase extension reactions consisted of 20 pmol of a synthetic DNA template, 60 pmol of primer (5'-TCTCTGGCCGCGTGTCT-3') (SEQ ID NO:3), 100 pmol of a single nucleotide reversible terminator (3'-O-tBu-SS-dCTP-SS-Bodipy), 1×ThermoPol II reaction buffer (New England Biolabs, MA), 2 units Therminator II DNA polymerase, 2 nmol $MnCl_2$, and deionized $H_2O$ in a total volume of 20 µL. Reactions were conducted in an ABI GeneAmp PCR System 9700 with initial incubation at 94° C. for 20 sec, followed by 38 cycles of 80° C. for 20 sec, 45° C. for 30 sec, and 65° C. for 90 sec. After the extension reaction, the extension product was precipitated by ethanol and pellet dissolved in 10 µL deionized water. A fraction of extension reaction was desalted using a C18 ZipTip column (Millipore, MA) and analyzed by MALDI-TOF MS (ABI Voyager, DE). The remaining large fraction treated with THP (tris-(hydroxypropyl)phosphine) at a final concentration of 5 mM and incubated at 65° C. for 3 minutes to regenerate the 3'-OH group in preparation for the next extension reaction. A small fraction was desalted as before and analyzed by MALDI-TOF MS. Remaining fraction of extended primer was used for second round of extension reaction (FIG. 46).

Sequencing by Synthesis Reactions using 3'-O-DTM-dNTPs. Polymerase extension reactions consisted of 20 pmol of a synthetic 51-mer DNA template (5'GAGGC-CAAGTACGGCGGGTACGTCCTTGACAATGTGTA-CATCAACATCACC-3') (SEQ ID NO:9), 60 pmol of primer (5'-CACATTGTCAAGG-3') (SEQ ID NO:2) or a previously extended and THP cleaved DNA product, 100 pmol of a single 3'-O-DTM nucleotide reversible terminator (3'-ODTM-dATP, 3'-O-DTM-dCTP, 3'-O-DTM-dGTP, or 3'-O-DTM-dTTP), 1× ThermoPol reaction buffer (New England Biolabs, MA), 2 unit Therminator™ III DNA polymerase and deionized $H_2O$ in a total volume of 20 µL. Reactions were conducted in a thermal cycler (MJ Research, MA). After initial incubation at 94° C. for 20 sec, the reaction was performed for 36 cycles at 80° C. for 20 sec, 45° C. for 40 sec and 65° C. for 90 sec.

After the extension reaction, a small aliquot of the reaction product was desalted using a C18 ZipTip column (Millipore, MA) and analyzed by MALDI-TOF MS (ABT Voyager, DE). The remaining product was concentrated under vacuum and purified by reverse phase HPLC on an XTerra MS C18, 2.5 µm 4.6 mm×50 mm column (Waters, MA) to obtain the pure extension product. Mobile phase: A, 8.6 mM triethylamine/100 mM 1,1,1,3,3,3-hexafluoro-2-propanol in water (pH 8.1); B, methanol. Elution was performed at 40° C. with a 0.5 mL/min flow rate, and from 88% A/12% B to 65.5% A/34.5% B linear gradient for 90 min. The purified product was used in the subsequent polymerase extension reaction.

Cleavage reactions to remove the 3'-O-DTM group from the DNA extension products with THP to regenerate the 3'-OH group were carried out by dissolving 100 pmol extension products in 10 µL of 5 mM Tris(2-hydroxypropyl)phosphine (THP) solution (pH 9.0), and incubating at 65° C. for 3 min. Following dilution in 1 mL deionized $H_2O$ and desalting in an Amicon Ultra-0.5 centrifugal filter unit with Ultracel-3 membrane (Millipore), 2 µL of the resulting solution was used to obtain the MALDI-TOF mass spectrum. After further reverse phase HPLC as above, each cleavage product was used as primer in the subsequent polymerase extension reaction. Four consecutive nucleotide additions are shown in FIGS. 30A-30D.

Synthesis of 3'-O-ethyldithiomethyl-2'-deoxynucleoside-5'-triphosphates (3'-O-DTMdNTPs): Synthesis of 3'-O-ethyldithiomethyl-dTTP (7a) FIG. 47)

3'-O-methylthiomethyl-5'-O-tert-butyldimethylsilyl thymidine (2a): To a stirring solution of the 5'-O-tert-butyldimethylsilyl thymidine (1a, 1.07 g, 3 mmol) in DMSO (10 mL) was added acetic acid (2.6 mL, 45 mmol) and acetic anhydride (8.6 mL, 90 mmol). The reaction mixture was stirred at room temperature until the reaction was complete (48 h), which was monitored by TLC. Then the mixture was added slowly to a saturated solution of sodium bicarbonate under vigorous stirring and extracted with ethyl acetate (3×30 mL). The combined organic layers were dried over $Na_2SO_4$ and filtered. The filtrate was concentrated to dryness under reduced pressure and the compound was purified by silica gel column chromatography (ethyl acetate/hexane: 1:2) to give pure product 2a (0.97 g, 74%). $^1$H NMR (400 MHz, $CDCl_3$) (S: 8.16 (s, 1H), 7.48 (s, 1H), 6.28 (m, 1H), 4.62 (m, 2H), 4.46 (m, 1H), 4.10 (m, 1H), 3.78-3.90 (m, 2H), 2.39 (m, 1H), 2.14 (s, 3H), 1.97 (m, 1H), 1.92 (s, 3H), 0.93 (s, 9H). 0.13 (s, 3H); HRMS ($FAB^+$) calc'd for $C_{18}H_{33}N_2O_5SSi$ [(M+H)+]: 417.1879, found: 417.1890.

3'-O-ethyldithiomethyl-5'-O-tert-butyldimethylsilyl thymidine (5a) 3'-O-methylthiomethyl5'-O-tert-butyldimethylsilyl thymidine (2a, 453 mg, 1.09 mmol) was dissolved in anhydrous dichloromethane (20 mL), followed by addition of triethylamine (0.18 mL, 1.31 mmol, 1.2 eq.) and molecular sieve (3 Å, 2 g). The mixture was cooled in an ice-bath after stirring at room temperature for 30 min and then a solution of sulfuryl chloride (redistilled, 0.1 mL, 1.31 mmol, 1.2 eq.) in anhydrous dichloromethane (3 mL) was added dropwise over 2 minutes. The ice-bath was removed and the reaction mixture was stirred further for 30 min. Then potassium ptoluenethiosulfonate (375 mg, 1.65 mmol, 1.5 eq.) in anhydrous DMF (2 mL) was added to the mixture. Stirring was continued at room temperature for additional hour followed by addition of ethanethiol (0.17 mL, 2.2 mmol, 2 eq.). The reaction mixture was stirred at room temperature for 30 min and quickly filtered through celite. The filter was washed with dichloromethane and the organic fraction was concentrated. The residue was purified by Flash column chromatography (ethyl acetate/hexane: 2:1) to give pure product 5a (261 mg, 52%). $^1$H NMR (400 MHz, $CDCl_3$) δ: 8.66 (br. s, 1H), 7.49 (s, 1H), 6.30 (dd, J=7.2, 11.2 Hz, 1H), 4.83 (dd, J=15.2, 37.2 Hz, 2H), 4.49 (d, J=8.0 Hz, 1H), 4.14 (d, J=3.2 Hz, 1H), 3.80 (m, 2H), 2.77 (dd, J=10.0, 19.6 Hz, 2H), 2.47 (m, 1H), 2.03 (m, 1H), 1.93 (s, 3H), 1.35 (t, J=8.8 Hz, 2H), 0.95 (s, 9H), 0.14 (s, 6H). $^{13}$C NMR (75 MHz, $CDCl_3$): δ 164.00, 150.59, 135.61, 111.35, 85.33, 79.76, 77.98, 77.81, 63.89, 38.10, 33.64, 26.33, 18.74, 14.84, 12.89, −4.85, −5.03.

3'-O-ethyldithiomethyl thymidine (3'-O-DTM-T, 6a): 3'-O-ethyldithiomethyl-5'-O-tert-butyldimethylsilyl thymidine (5a, 240 mg, 0.52 mmol) was dissolved in anhydrous THF (10 mL) and a THF solution of tetrabutylammonium fluoride (1.0M, 1.04 mL, 1.04 mmol, 1.5 eq.) was added. The reaction mixture was stirred at room temperature for 4 hours. The reaction mixture was concentrated in vacuo, saturated NaHCO3 solution (50 mL) was added and the mixture was extracted with dichloromethane (3×20 mL). The organic layer was dried over anhydrous Na2SO4, filtered, concentrated and the obtained crude mixture was purified by flash column chromatography (dichloromethane/methanol: 20/1) to give 3'-O-ethyldithiomethyl thymidine 6a (119 mg, 66%). 1H NMR (300 MHz, CDCl$_3$) δ: 7.44 (s, 1H), 6.15 (t, J=8.8 Hz, 1H), 4.83 (dd, J=11.4, 23.4 Hz, 2H), 4.46 (m, 1H), 4.12 (m, 2H), 3.80 (m, 2H), 2.77 (dd, J=7.5, 14.7 Hz, 2H), 2.34 (m, 2H), 2.04 (s, 1H), 1.90 (s, 3H), 1.34 (t, J=7.5 Hz, 3H). 13C NMR (75 MHz, CDCl3): δ 164.37, 150.88, 137.26, 111.53, 87.20, 85.29, 78.52, 62.82, 37.49, 33.59, 14.85, 12.89. HRMS (ESI+) calc'd for C13H20N2O5S2Na [(M+Na)+]: 371.0711, found: 371.0716.

3'-O-ethyldithiomethyl-dTTP (3'-O-DTM-TTP 7a): 3'-O-ethyldithiomethyl thymidine (6a, 50 mg, 0.14 mmol), tetrabutylammonium pyrophosphate (197 mg, 0.36 mmol, 2.5 eq.) and 2-chloro-4-H-1,3,2-benzodioxaphosphorin-4-one (44 mg, 0.22 mmol, 1.5 eq) were dried separately overnight under high vacuum at ambient temperature. The tetrabutylammonium pyrophosphate was dissolved in dimethylformamide (DMF, 1 mL) under argon followed by addition of tributylamine (1 mL). This mixture was injected into the solution of 2-chloro-4-H-1,3,2-benzodioxaphosphorin-4-one in (DMF, 2 mL) under argon. After stirring for 1 h, the reaction mixture was added to the solution of 3'-O-ethyldithiomethyl thymidine and stirred further for 1 hour at room temperature. Iodine solution (0.02 M iodine/pyridine/water) was then injected into the reaction mixture until a permanent brown color was observed. After 10 min, water (30 mL) was added and the reaction mixture was stirred at room temperature for additional 2 hours. The resulting solution was extracted with ethyl acetate (2×30 mL). The aqueous layer was concentrated in vacuo to approximately 20 mL, and transferred to two centrifuge tubes (50 mL), brine (1.5 mL) and absolute ethanol (35 mL) were added to each tube, followed by vigorous shaking After being placed at −80° C. for 2 h, the tube was centrifuged (10 min at 4200 rpm) to afford the crude product as a white precipitate. The supernatant was poured out, the white precipitate was diluted with 5 ml of water and purified by ion exchange chromatography on DEAE-Sephadex A-25 at 4° C. using a gradient of TEAB (pH 8.0; 0.1-1.0 M). The crude product was further purified by reverse-phase HPLC to afford 7a. HRMS (ESI⁻) calc'd for $C_{13}H_{22}N_2O_{14}S_2P_3$ [(M–H)⁻]: 586.9725, found: 586.9727. ³¹P-NMR (121.4 MHz, D$_2$O): δ−10.83 (s, 1P), −10.98 (s, 1P), −20.53 (t, J=21 Hz, 1P).

Scheme 2. Synthesis of 3'-O-ethyldithiomethyl-dGTP (9b):

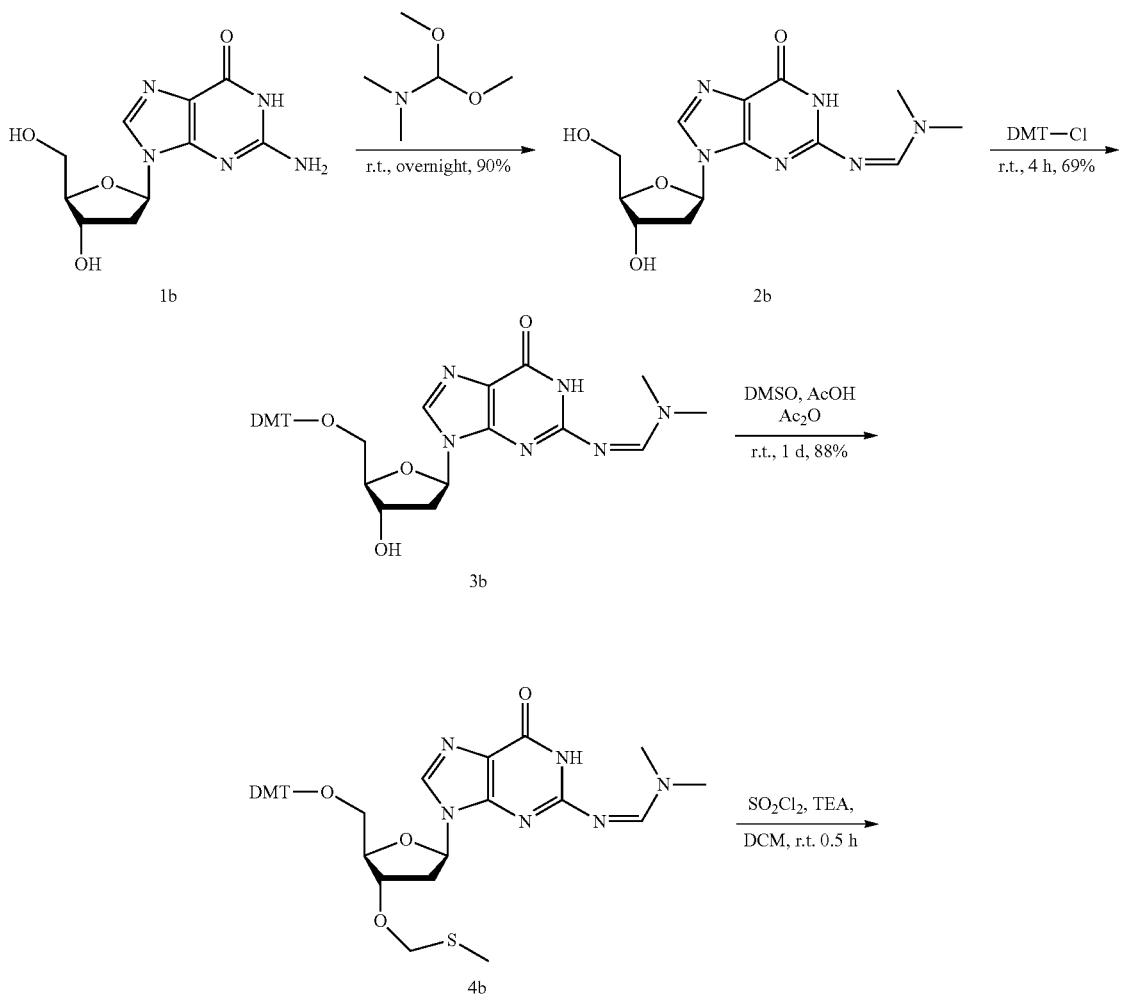

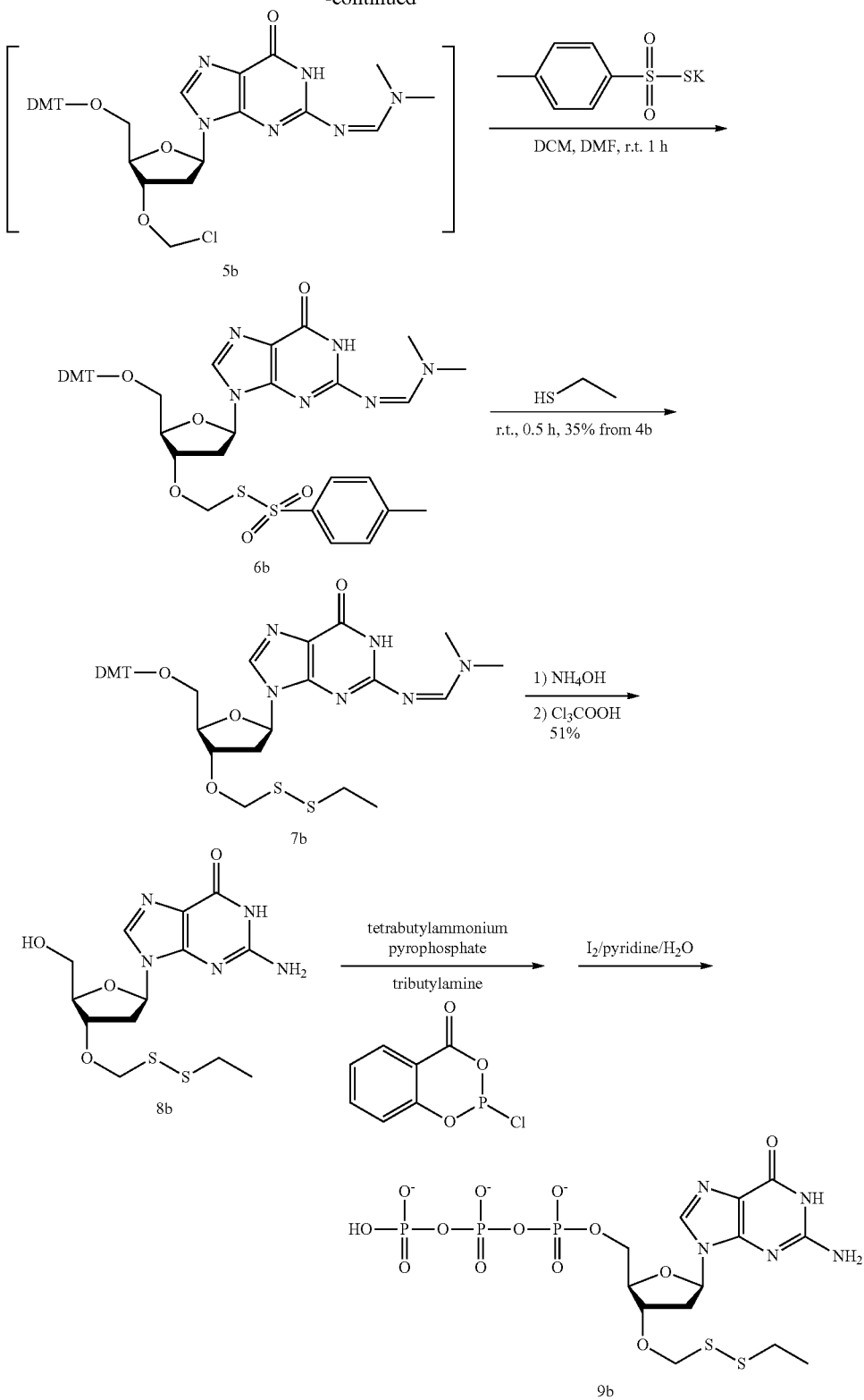

N²-Dimethylformamidino-2'-deoxyguanosine (2b): To a suspension of 2'-deoxyguanosine (1b, 1.33 g, 5 mmol) in dry DMF (20 mL) was added N, N-dimethylformamide dimethyl acetal (1.5 mL, 11 mmol) and the reaction mixture was stirred at room temperature overnight. The solvent was removed and the residue triturated with methanol and filtered. The solid was washed with methanol to give a white solid 2b (90%, 1.44 g). $^1$H NMR (400 MHz, DMSO-$d_6$) δ 11.28 (s, 1H), 8.57 (s, 1H), 8.04 (s, 1H), 6.26 (dd, J=7.9, 6.1 Hz, 1H), 5.30 (d, J=3.8 Hz, 1H), 4.93 (t, J=5.5 Hz, 1H), 4.40

(dt, J=5.8, 2.8 Hz, 1H), 3.85 (td, J=4.5, 2.5 Hz, 1H), 3.56 (m, 2H), 3.17 (s, 3H), 3.04 (s, 3H), 2.60 (m, 1H), 2.25 (m, 1H).

Dimethylformamidino-5'-O-DMT-2'-deoxyguanosine (3b): $N^2$-DMF-2'-deoxyguanosine (2b, 1.38 g, 4.3 mmol, 1 eq.) was dissolved in anhydrous pyridine (30 mL), and 4,4'-dimethoxytrityl chloride (1.74 g, 5.2 mmol, 1.2 eq.) was added. After stirring at room temperature for 4 hours, the reaction mixture was poured into saturated sodium bicarbonate solution (200 mL) and the precipitate was collected by suction filtration, washed with water and hexane. The obtained crude produce was purified by silica gel column chromatography (dichloromethane/methanol: 30/1) to give $N^2$-DMF-5'-O-DMT-2'deoxyguanosine 3b (1.84 g, 69%) as a white solid. $^1$H NMR (400 MHz, CDCl$_3$) δ 9.13 (s, 1H), 8.57 (s, 1H), 7.71 (s, 1H), 7.3 (m, 2H), 7.34-7.20 (m, 6H), 7.18 (t, J=2.8 Hz, 1H), 6.90-6.72 (m, 4H), 6.40 (t, J=6.6 Hz, 1H), 4.64 (m, 1H), 4.15 (m, 1H). 3.81 (m, 1H), 3.78 (m, 6H), 3.43 (dd, J=10.1, 4.8 Hz, 1H), 3.32 (dd, J=10.1, 5.0 Hz, 1H), 3.11 (s, 3H), 3.06 (s, 3H), 2.65-2.48 (m, 2H).

$N^2$-Dimethylformamidino-3'-O-methylthiomethyl-5'-O-DMT-2'-deoxyguanosine (4b): To a stirred solution of the $N^2$-DMF-5'-O-DMT-2'-deoxyguanosine (1.33 g, 2.1 mmol) in DMSO (10 mL) was added acetic acid (2.1 mL, 36 mmol) and acetic anhydride (5.4 mL, 56 mmol). The reaction mixture was stirred at room temperature until the reaction was complete (24 h), which was monitored by TLC. Then the mixture was added slowly to a solution of sodium bicarbonate under vigorous stirring and extracted with ethyl acetate (3×30 mL). The combined organic layers were dried over Na$_2$SO$_4$ and filtered. The filtrate was concentrated to dryness under reduced pressure and the desired compound was purified by silica gel column chromatography (ethyl acetate/hexane: 1/2) to give pure product 4b (1.27 g, 88%) as a white solid. $^1$H NMR (400 MHz, CDCl$_3$) δ 9.73 (s, 1H), 8.58 (s, 1H), 7.73 (s, 1H), 7.47-7.38 (m, 2H), 7.37-7.17 (m, 7H), 6.87-6.77 (m, 4H), 6.33 (dd, J=7.7, 6.1 Hz, 1H), 4.72-4.63 (m, 3H), 4.25-4.18 (m, 1H), 3.80 (s, 6H), 3.34 (m, 2H), 3.14 (s, 3H), 3.09 (s, 3H), 2.64-2.48 (m, 2H), 2.13 (s, 3H): $^{13}$C NMR (75 MHz, CDCl$_3$): δ 158.96, 158.69, 158.50, 150.61, 144.88, 136.19, 136.02, 130.41, 128.49, 128.33, 127.35, 120.85, 113.61, 86.96, 84.19, 83.64, 74.01, 64.05, 55.65, 41.74, 38.31, 35.61, 14.26.

$N^2$-Dimethylformamidino-3'-O-ethyldithiomethyl-5'-O-DMT-2'-deoxyguanosine (7b): $N^2$-DMF-3'-O-methylthiomethyl-5'-O-DMT-2'-deoxyguanosine (684 mg, 1.0 mmol) was dissolved in anhydrous dichloromethane (20 mL), followed by addition of triethylamine (0.17 mL, 1.2 mmol, 1.2 eq.) and molecular sieve (3 Å, 2 g). The mixture was cooled in an ice-bath after stirring at room temperature for 30 min and then a solution of sulfuryl chloride (0.095 mL, 1.2 mmol, 1.2 eq.) in anhydrous dichloromethane (3 mL) was added dropwise over 2 minutes. The ice-bath was removed and the reaction mixture was stirred further for 30 min. Then potassium 4-toluenethiosulfonate (341 mg, 1.5 mmol, 1.5 eq.) in anhydrous DMF (2 mL) was added to the mixture. Stirring was continued at room temperature for an additional hour followed by addition of ethanethiol (0.16 mL, 2.0 mmol, 2 eq.). The reaction mixture was stirred at room temperature for 30 min and quickly filtered through celite. The filter was washed with dichloromethane and the organic fraction was concentrated. The residue was purified by silica gel column chromatography (ethyl acetate/hexane: 2/1) to give pure product 7b (255 mg. 35%). $^1$H NMR (400 MHz, CDCl$_3$) δ 9.55 (s, 1H), 8.58 (s, 1H), 7.73 (s, 1H), 7.47-7.38 (m, 2H), 7.37-7.27 (m, 6H), 7.27-7.18 (m, 1H), 6.88-6.79 (m, 4H), 6.34 (t, J=7.0 Hz, 1H), 4.86 (s, 2H), 4.65 (m, 1H), 4.25 (m, 1H), 3.80 (d, J=0.9 Hz, 6H), 3.44-3.28 (m, 2H), 3.16-3.07 (s, 3H), 3.10 (s, 3H), 2.75 (qd, J=7.4, 0.7 Hz, 2H), 2.62-2.54 (m, 2H), 1.29 (t, J=13.5, 4H). $^{13}$C NMR (75 MHz, CDCl$_3$): δ 158.99, 158.50, 157.30, 150.57, 144.84, 136.06, 135.95, 130.41, 128.47, 128.36, 127.38, 120.88, 113.65, 87.04, 84.12, 83.61, 79.68, 78.48, 64.02, 55.65, 41.74, 38.34, 35.60, 33.60, 14.87, 14.59.

3'-O-ethyldithiomethyl-2'-deoxyguanosine (8b): The mixture of $N^2$-DMF-3'-ethyldithiomethyl-5'-O-DMT-2'-deoxyguanosine (280 mg, 0.38 mmol), ammonium hydroxide (10 mL) and methanol (10 mL) was stirred at room temperature until the reaction was complete (4 h), which was monitored by TLC. After evaporation of the solvent under reduced pressure, the crude solid was treated with 3% trichloroacetic acid solution in dichloromethane for 10 min. Then the mixture was added slowly to the solution of sodium bicarbonate under vigorous stirring and extracted with ethyl acetate (3×30 mL). The combined organic layers were dried over Na$_2$SO$_4$ and filtered. The filtrate was concentrated to dryness under reduced pressure and the desired compound was purified by silica gel column chromatography (dichloromethane/methanol: 20/1) to give 3'-ethyldithiomethyl-2'deoxyguanosine 8b (72 mg, 51%). $^1$H NMR (300 MHz, DMSO-d$_6$) δ 10.61 (s, 1H), 7.93 (s, 1H), 6.45 (bs, 2H), 6.07 (dd, J=8.5, 5.7 Hz, 1H), 5.06 (bs, 1H), 4.95 (s, 2H), 4.51 (d, J=5.3 Hz, 1H), 3.99 (m, 1H), 3.55 (d, J=4.3 Hz, 2H), 2.80 (q, J=7.3 Hz, 2H), 2.72-2.56 (m, 1H), 2.43-2.39 (m, 1H), 1.28 (t, J=7.3 Hz, 3H). HRMS (ESI$^+$) calc'd for C$_{13}$H$^{19}$N$_5$O$_4$S$_2$Na [(M+Na)$^+$]: 396.0776, found: 396.0770.

3'-O-ethyldithiomethyl-dGTP (9b): The preparation procedure was similar to the synthesis of 7a. 3'-ethyldithiomethyl-2'deoxyguanosine (8b, 64 mg, 0.17 mmol), tetrabutylammonium pyrophosphate (238 mg, 0.44 mmol, 2.5 eq.) and 2-chloro-4-H-1,3,2-benzodioxaphosphorin-4-one (53 mg, 0.27 mmol, 1.5 eq) were dried separately over night under high vacuum at ambient temperature in three round bottom flasks. The tetrabutylammonium pyrophosphate was dissolved in dimethylformamide (DMF, 1 mL) under argon followed by addition of tributylamine (1 mL). The mixture was injected into the solution of 2-chloro-4-H-1,3,2-benzodioxaphosphorin-4-one in (DMF, 2 mL) under argon. After stirring for 1 h, the reaction mixture was added to the solution of 3'-O-ethyldithiomethyl thymidine and stirred further for 1 hour at room temperature. Iodine solution (0.02 M iodine/pyridine/water) was then injected into the reaction mixture until a permanent brown color was observed. After 10 min, water (30 mL) was added and the reaction mixture was stirred at room temperature for an additional 2 hours. The resulting solution was extracted with ethyl acetate (2×30 mL). The aqueous layer was concentrated in vacuo to approximately 20 mL, and transferred to two centrifuge tubes (50 mL). Brine (1.5 mL) and absolute ethanol (35 mL) were added to each tube, followed by vigorous shaking. After being placed at −80° C. for 2 h, the tube was centrifuged (10 min at 4200 rpm) to offer the crude product as a white precipitate. The supernatant was poured out, the white precipitate was diluted with 5 ml of water and purified with anion exchange chromatography on DEAE-Sephadex A-25 at 4° C. using a gradient of TEAB (pH 8.0; 0.1-1.0 M). The crude product was further purified by reverse-phase HPLC to afford 9b.

3) Synthesis of 3'-O-ethyldithiomethyl-dATP (8c) (FIG. 48). N6-Benzoyl-5'-O-trityl-2'-deoxyadenosine (2c): $N^6$—Benzoyl-2'-deoxyadenosine (1c, 1.07 g, 3.0 mmol, 1 eq.) was dissolved in anhydrous pyridine (30 mL), and trityl chloride (1.00 g, 3.6 mmol, 1.2 eq.) was added. After stirring at room temperature for 1 day, the reaction mixture was poured into saturated sodium bicarbonate solution (200 mL)

and the precipitate was collected by suction filtration, washed with water and hexane. The obtained crude product was purified by silica gel column chromatography (dichloromethane/methanol: 30/1) to give N$^6$-Benzoyl-5'-O-trityl-2'-deoxygadenosine 2c (1.45 g, 81%) as a white solid. $^1$H NMR (400 MHz, CDCl$_3$) δ 9.12 (s, 1H), 8.74 (s, 1H), 8.15 (s, 1H), 8.08-8.00 (m, 2H), 7.62 (m, 1H), 7.52 (m, 2H), 7.46-7.38 (m, 6H), 7.34-7.20 (m, 9H), 6.50 (t, J=6.5 Hz, 1H), 4.74 (d, J=4.7 Hz, 1H), 4.19 (td, J=4.8, 3.5 Hz, 1H), 3.49-3.42 (m, 2H), 2.90 (m, 1H), 2.58 (m, 1H).

N$^6$-Benzoyl-3'-O-methylthiomethyl-5'-O-trityl-2'-deoxyadenosine (3c): To a stirred solution of the N$^6$-Benzoyl-5'-O-trityl-2'-deoxyadenosine (1.72 g, 2.93 mmol) in DMSO (10 mL) was added acetic acid (2.8 mL, 48 mmol) and acetic anhydride (72 mL, 75 mmol). The reaction mixture was stirred at room temperature until the reaction was complete (24 h), which was monitored by TLC. Then the mixture was added slowly to a solution of sodium bicarbonate under vigorous stirring and extracted with ethyl acetate (3×30 mL). The combined organic layers were dried over Na$_2$SO$_4$ and filtered. The filtrate was concentrated to dryness under reduced pressure and the desired compound was purified by silica gel column chromatography (ethyl acetate/hexane: 1/2) to give pure product 3c (1.35 g, 71%) as a white solid. $^1$H NMR (400 MHz, CDCl$_3$) δ 9.07 (s, 1H), 8.74 (s, 1H), 8.19 (s, 1H), 8.05 (dt, J=7.2, 1.4 Hz, 2H), 7.67-7.49 (m, 3H), 7.49-7.39 (m, 6H), 7.36-7.22 (m, 9H), 6.48 (dd, =7.6, 6.0 Hz, 1H), 4.79 (m, 1H), 4.66 (m, 2H), 4.31 (td, 0.1=4.8, 2.7 Hz, 1H), 3.51-3.38 (m, 2H), 2.89 (m, 1H), 2.64 (m, 1H), 2.15 (s, 3H). $^{13}$C NMR (75 MHz, CDCl$_3$): δ 165.03, 153.03, 151.82, 149.88, 143.87, 141.78, 134.05, 133.19, 129.27, 129.02, 128.35, 128.28, 127.67, 123.83, 87.52, 85.43, 85.59, 76.85, 74.05, 63.98, 37.94, 30.13, 14.27.

N$^6$-Benzoyl-3'-O-ethyldithiomethyl-5'-O-trityl-2'-deoxyadenosine (6c): 3'-O-methylthiomethyl-5'-O-Trityl-2'-deoxyadenosine (3c, 861 mg, 1.31 mmol) was dissolved in anhydrous dichloromethane (20 mL), followed by addition of triethylamine (0.19 mL, 1.5 mmol, 1.2 eq.) and molecular sieve (3 Å, 2 g). The mixture was cooled in an ice-bath after stirring at room temperature for 0.5 hour and then a solution of sulfuryl chloride (0.11 mL, 1.5 mmol, 1.2 eq.) in anhydrous dichloromethane (3 mL) was added dropwise during 2 minutes. The ice-bath was removed and the reaction mixture was stirred further for 30 min. Then potassium ptoluenethiosulfonate (595 mg, 2.62 mmol, 1.5 eq.) in anhydrous DMF (3 mL) was added to the mixture. Stirring was continued at room temperature for an additional hour followed by addition of ethanethiol (0.47 mL, 6.55 mmol, 2 eq.). The reaction mixture was stirred at room temperature for 30 min and quickly filtered through celite. The filter was washed with dichloromethane and the organic fraction was concentrated. The residue was purified by silica gel column chromatography (ethyl acetate/hexane: 2/1) to give pure product 6c (615 mg, 67%). $^{1H}$ NMR (400 MHz, CDCl$_3$) δ 9.04 (s, 1H), 8.74 (s, 1H), 8.18 (s, 1H), 8.05 (d, J=7.2 Hz, 2H), 7.67-7.59 (m, 1H), 7.59-7.50 (m, 2H), 7.50-7.38 (m, 6H), 7.36-7.21 (m, 9H), 6.47 (dd, J=7.8, 5.9 Hz, 1H), 4.90 (s, 2H), 4.75 (dt, J=5.4, 2.5 Hz, 1H), 4.35 (td, J=4.9, 2.5 Hz, 1H), 3.45 (m, 2H), 3.00-2.86 (m, 1H), 2.85-2.71 (m, 2H), 2.68 (m, 1H), 1.33 (t, J=7.4, 3H).

N$^6$-Benzoyl-3'-O-ethyldithiomethyl-2'-deoxyadenosine (7c): N$^6$—Benzoyl-3'-ethyldithiomethyl-5'-O-trityl-2'-deoxyadenosine (6c, 381 mg, 0.54 mmol) was treated with 3% trichloroacetic acid solution in dichloromethane at room temperature for 10 min. Then the mixture was added slowly to a solution of sodium bicarbonate under vigorous stirring and extracted with ethyl acetate (3×30 mL). The combined organic layers were dried over Na$_2$SO$_4$ and filtered. The filtrate was concentrated to dryness under reduced pressure and the residue of the desired compound was purified by silica gel column chromatography (dichloromethane/methanol: 20/1) to give 7c (169 mg, 68%). NMR (400 MHz, DMSO-d$_6$) δ 11.18 (s, 1H), 8.77 (s, 1H), 8.71 (s, 1H), 8.10-8.02 (m, 2H), 7.66 (t, J=7.6 Hz, 1H), 7.56 (t, J=7.6 Hz 2H), 6.47 (dd, J=8.0, 6.0 Hz, 1H), 5.15 (t, J=5.5 Hz, 1H), 5.00 (s, 2H), 4.65 (dt, J=5.4, 2.4 Hz, 1H), 4.12 (td, J=4.7, 2.2 Hz, 1H), 3.72-3.55 (m, 2H), 3.02-2.88 (m, 1H), 2.84 (q, J=7.3 Hz, 2H), 2.61 (m, 1H), 1.40-1.15 (m, 3H). $^{13}$C NMR (75 MHz, DMSO-d$_6$): δ 166.47, 152.83, 152.47, 151.27, 143.87, 134.22, 133.30, 129.33, 126.78, 86.18, 84.79, 79.35, 78.80, 62.37, 36.93, 33.04, 15.21.

3'-O-ethyldithiomethyl-dATP (8c): Compound 7c (100 mg, 0.22 mmol) and proton sponge (60 mg, 0.28 mmol) were dried in a vacuum desiccator over P$_2$O$_5$ overnight and dissolved in trimethyl phosphate (2 ml). Freshly distilled POCl$_3$ (30 µL, 0.32 mmol) was added dropwise and the mixture was stirred for 2 h at 0° C. Tributylammonium pyrophosphate (452 mg, 0.82 mmol) and tributylamine (450 uL, 1.90 mmol) in anhydrous DMF (1.9 mL) was added in one portion at room temperature and the solution stirred for additional 30 min. Triethylammonium bicarbonate solution (TEAB, 0.1 M; pH 8.0; 10 mL) was added and the mixture was stirred for 1 h at room temperature. Then concentrated NH$_4$OH (10 mL) was added and stirring continued for 3 h at room temperature. The mixture was concentrated under vacuum and the crude product was purified by anion exchange chromatography on DEAE-Sephadex A-25 at 4° C. using a gradient of TEAB (pH 8.0; 0.1-1.0 M), followed by a further purification by reverse-phase HPLC to afford 8c.

Synthesis of 3'-O-ethyldithiomethyl-dCTP (3'-O-DTM-dCTP, 7d) (FIG. 49). N$^4$-Benzoyl-3'-O-methylthiomethyl-5'-O-tert-butyldimethylsilyl-2'-deoxycytidine(2d): To a stirred solution of N$^4$-Benzoyl-5'-O-tert-butyldimethylsilyl-2'-deoxycytidine (1.5 g, 3.37 mmol) in anhy DMSO (6.5 ml) was added acetic acid (2.9 ml) and acetic anhydride (9.3 ml). The mixture was stirred at room temperature for 2 days, and then quenched by adding saturated NaHCO$_3$ solution (50 ml). The reaction mixture was extracted with ethyl acetate (50 mL×3) and the combined organic layers dried over anhydrous Na$_2$SO$_4$. The crude product after concentration was purified by flash column chromatography (ethyl acetate: Hexane 8:2) to give a white powder (1.26 g, 74%). $^1$H NMR (400 MHz, Methanol-d$_4$) δ 8.50 (d, J=7.5 Hz, 1H), 8.05-7.97 (m, 2H), 7.72-7.61 (m, 2H), 7.61-7.52 (m, 2H), 6.23 (t, J=6.3 Hz, 1H), 4.81-4.71 (m, 2H), 4.58 (dt, J=6.4, 3.3 Hz, 1H), 4.24 (q, J=3.1 Hz, 1H), 4.02 (dd, J=11.5, 3.3 Hz, 1H), 3.91 (dd, J=11.5, 2.8 Hz, 1H), 2.75-2.59 (m, 1H), 2.24 (dt, J=13.9, 6.3 Hz, 1H), 2.18 (s, 3H), 0.98 (s, 9H), 0.19 (d, J=3.3 Hz, 6H). HRMS (APCI$^+$) calc'd for C$_{24}$H$_{35}$N$_3$O$_5$SSi 506.2145, found: 506.2124.

N$^4$-Benzoyl-3'-O-ethyldithiomethyl-5'-O-tert-butyldimethylsilyl-2'-deoxycytidine(5d): To a stirred solution of 2d (612 mg, 1.21 mmol) in anhydrous dichloromethane (10 ml), triethylamine (168 µL, 1.21 mmol) and 4A molecular sieve (1 g) were added. The reaction mixture was stirred at room temperature for 30 minutes and then cooled in an ice-bath. SO$_2$Cl$_2$ (98 µL, 1.21 mmol) dissolved in anhydrous dichloromethane (5 ml) was added dropwise to the mixture. Then the ice bath was removed, and the reaction mixture was stirred for at room temperature for 30 minutes. Potassium p-toluenethiosulfonate (425 mg, 1.9 mmol) dissolved in anhydrous DMF (6254) was added into the reaction mixture, and after being stirred for additional 30 minutes, ethanethiol (174 µL, 2.4 mmol) was added and stirring continued at room temperature for an additional 30 minutes. The reaction mixture was filtered, concentrated, and then extracted with saturated sodium bicarbonate and dichloromethane (3×50 mL). The organic phase was dried over $Na_2SO_4$, concentrated, and purified by flash column chromatography using a gradient of ethyl acetate-hexane from 5:5 (v/v) to 8:2 (v/v), yielding 563.2 mg (84%) white foam. $^1H$ NMR (400 MHz, Methanol-$d_4$) δ 8.55-8.42 (m, 1H), 8.00 (dt, J=8.4, 1.1 Hz, 2H), 7.70-7.45 (m, 4H), 6.23 (q, J=6.9, 6.4 Hz, 1H), 5.01-4.88 (m, 2H), 4.56 (tt, J=6.5, 3.1 Hz, 1H), 4.30-4.19 (m, 1H), 4.00 (m, J=11.4, 3.2, 0.8 Hz, 1H), 3.94-3.76 (m, 1H), 2.81 (qd, J=7.3, 0.9 Hz, 2H), 2.76-2.68 (m, 1H), 2.31-2.17 (m, 1H), 1.40-1.25 (m, 3H), 1.00-0.85 (m, 9H), 0.21-0.03 (m, 6H). HRMS (APCI$^+$) calc'd for $C_{25}H_{37}N_3O_5S_2Si$ [(M+Na)$^+$]: 574.1841, found: 574.1826.

$N^4$-Benzoyl-3'-O-ethyldithiomethyl-2'-deoxycytidine (6d): To a stirred solution of 5d (526 mg, 0.95 mmol) in a mixture of tetrahydrofuran (3 ml) and methanol (9 ml), $NH_4F$ (1.8 g) powder was added in small portions and stirred at room temperature for 3 days. The crude product was concentrated and purified by flash column chromatography using a gradient of ethyl acetate-Hexane from 2:8 (v/v) to 7:3 (v/v), affording a white solid powder (233 mg, 56%). $^1H$ NMR (400 MHz, Methanol-$d_4$) 1H NMR (400 MHz, Methanol-d4) δ 8.54 (d, J=7.5 Hz, 1H), 8.04-7.97 (m, 2H), 7.71-7.43 (m, 4H), 6.25 (t, 1H), 5.01-4.89 (m, 2H), 4.56 (dt, J=6.0, 3.0 Hz, 1H), 4.23 (q, J=3.4 Hz, 1H), 3.92-3.76 (m, 2H), 2.84 (q, J=7.3 Hz, 2H), 2.71 (m, J=13.9, 5.9, 2.9 Hz, 1H), 2.31-2.19 (m, 1H), 1.36 (t, J=7.3 Hz, 3H). HRMS (APCI$^+$) calc'd for $C_{19}H_{23}N_3O_5S_2$ [(M+H)$^+$]: 438.1157, found: 438.1136.

3'-O-ethyldithiomethyl)-dCTP (7d): Compound 6d (60 mg, 0.14 mmol) and proton sponge (40 mg, 0.19 mmol) were dried in a vacuum desiccator over $P_2O_5$ overnight, dissolved in trimethyl phosphate (1 ml) and cooled in an icebath. Freshly distillated $POCl_3$ (19 μL, 0.2 mmol) was added dropwise and stirred for 2 h at 0° C. Tributylammonium pyrophosphate (255 mg, 0.47 mmol) and tributylamine (27.6 uL, 0.12 mmol) in anhydrous DMF (1.5 mL) was added in one portion at room temperature followed by an additional stirring for 30 min. Triethylammonium bicarbonate solution (TEAB) (0.1 M; pH 8.0; 7.5 mL) was added and the mixture was stirred for 1 h at room temperature. Then concentrated $NH_4OH$ (7.5 mL) was added and stirring continued overnight at room temperature. The mixture was concentrated under vacuum and the crude product was purified by anion exchange chromatography on DEAE-Sephadex A-25 at 4° C. using a gradient of TEAB (pH 8.0; 0.1-1.0 M), followed by a further purification by reverse-phase HPLC to afford 7d.

Synthesis of Aminopropynyl-3'-O-t-butyldithiomethyl-2'-Deoxynucleoside-5'Triphosphates (PA-3'-O-DTM-dNTPs, FIG. 50). 5-(3-aminopropynyl)-3'-O-t-butyldithiomethyl-dCTP (5-PA-3'-O-DTM-dCTP).

$N^4$-DMF-5-Iodo-2'-deoxycytidine (2): A mixture of 5-iodo-2'-deoxycytidine (1, 1.25 g, 3.5 mmol) and N,N-dimethylformamide dimethyl acetal (1.25 mL, 9.1 mmol) in dry DMF (20 mL) was stirred at room temperature overnight. After this period, the solvent was removed and the residue triturated with methanol and filtered. The solid was washed with methanol to give a white solid 2 (88%, 1.25 g). $^1H$ NMR (400 MHz, DMSO-$d_6$) δ 8.57 (s, 1H), 8.46 (s, 1H), 6.10 (t, J=6.4 Hz, 1H), 5.21 (d, J=4.3 Hz, 1H), 5.11 (t, J=5.0 Hz, 1H), 4.24 (p, J=4.8, 4.1 Hz, 1H), 3.83 (q, J=3.4 Hz, 1H), 3.71-3.53 (m, 2H), 3.21 (s, 3H), 3.13 (s, 3H), 2.21 (dt, J=13.7, 5.0 Hz, 1H), 2.04 (dt, J=12.9, 6.3 Hz, 1H).

$N^4$-DMF-5-Iodo-5'-O-Trityl-2'-deoxycytidine (3): $N^4$-DMF-5-iodo-2'-deoxycytidine (2, 0.93 g, 2.3 mmol, 1 eq.) was dissolved in anhydrous pyridine (30 mL), and trityl chloride (0.78 g, 2.8 mmol, 1.2 eq.) was added. After stirring at room temperature for 1 day, the reaction mixture was poured into saturated sodium bicarbonate solution (200 mL) and the precipitate was collected by filtration, washed with water and hexane. The obtained crude product was purified by column chromatography (dichloromethane/methanol: 30/1) to give $N^4$-DMF-5-iodo-5'-O-Trityl-2'-deoxycytidine 3 (1.12 g, 75%) as a white solid. $^1H$ NMR (400 MHz, DMSO-$d_6$) δ 8.59 (s, 1H), 8.13 (s, 1H), 7.45 (m, 6H), 7.30 (m, 6H), 7.26 (m, 3H), 6.13 (t, J=6.0 Hz, 1H), 5.29 (d, J=4.5 Hz, 1H), 4.23 (td, J=6.8, 5.5, 3.2 Hz, 1H), 3.94 (m, 1H), 3.28-3.18 (m, 5H), 3.14 (d, J=0.8 Hz, 3H), 2.28 (ddd, J=13.3, 6.0, 3.3 Hz, 1H), 2.18-2.06 (m, 1H).

$N^4$-DMF-5-[3-(trifluoroacetamido)propynyl]-5'-O-trityl-2'-deoxycytidine (4): Under nitrogen, a mixture of $N^4$-DMF-5-iodo-5'-O-Trityl-2'-deoxycytidine (244 mg, 0.375 mmol, 1.2 eq.), CuI (20 mg, 0.11 mmol) and Triethylamine (0.15 mL) in dry DMF (5 mL) was stirred at room temperature for 5 min followed by the addition of N-propargyl trifluoroacetamide (0.2 g, 1.36 mmol), and Pd(PPh$_3$)$_4$ (50 mg, 0.04 mmol). After stirring at room temperature in the dark overnight, the reaction mixture was added dropwise into brine (200 mL) under vigorous stirring and the precipitate was collected by suction filtration, and washed with water and hexane. The obtained crude produce was purified by column chromatography (100% ethyl acetate followed by dichloromethane/methanol: 30/1) to give $N^4$-DMF-5-[3-(trifluoroacetamido)propynyl]-5'-O-trityl-2'-deoxycytidine 4 (199 mg, 79%) as alight yellowbrown solid. NMR (400 MHz, DMSO-$d_6$) δ 9.97 (t, J=5.5 Hz, 1H), 8.62 (s, 1H), 8.03 (s, 1H), 0.45 (m, 6H), 7.30 (m, 6H), 7.26 (m, 3H), 6.14 (t, J=6.6 Hz, 1H), 5.32 (d, J=4.5 Hz, 1H), 4.26 (dq, J=7.8, 3.8 Hz, 1H), 4.06 (d, J=5.5 Hz, 2H), 4.04-3.94 (m, 1H), 3.29 (m, 1H), 3.20 (s, 3H), 3.16 (m, 1H), 3.09 (s, 3H), 2.29 (m, 1H), 2.14 (m, 1H).

$N^4$-DMF-5-[3-(trifluoroacetamido)propynyl]-5'-O-trityl-3'-O-methylthiomethyl-2'deoxycytidine (5): To a solution of the $N^4$-DMF-5-[3-(trifluoroacetamido)propynyl]-5'-O-Trityl-2'-deoxycytidine (4, 1.47 g, 2.19 mmol) in DMSO (10 mL) with stirring was added acetic acid (2.3 mL, 39 mmol) and acetic anhydride (6.1 mL, 64 mmol). The reaction mixture was stirred at room temperature until the reaction was complete (24 h), which was monitored by TLC. Then the reaction mixture was added to a solution of sodium bicarbonate under vigorous stirring, the precipitate was collected by suction filtration, and washed with water and hexane. The obtained crude product was purified by column chromatography dichloromethane/methanol: 30/1) to give pure product 5 (1.22 g, 77%) as a white solid. $^1H$ NMR (400 MHz, CDCl$_3$) δ 8.81 (s, 1H), 8.47 (s, 1H), 7.48 (m, 6H), 7.34 (m, 6H), 7.25 (m, 3H), 6.31 (t, J=6.3 Hz, 1H), 6.24 (s, 1H), 4.66 (m, 1H), 4.61 (m, 2H), 4.16 (m, 1H), 3.90 (m, 2H), 3.54 (dd, J=10.8, 2.9 Hz, 1H), 3.29 (dd, J=10.8, 3.4 Hz, 1H), 3.18 (d, J=4.5 Hz, 6H), 2.70 (m, J=13.9, 6.2, 3.9 Hz, 1H), 2.25 (dt, J=13.8, 6.4 Hz, 1H), 2.05 (s, 3H).

$N^4$-DMF-5-[3-(trifluoroacetamido)propynyl]-5'-O-trityl-3'-O-(tert-butyldithiomethyl)-2'deoxycytidine (7): $N^4$-DMF-5-[3-(trifluoroacetamido)propynyl]-5'-O-trityl-3'-O-methylthiomethyl-2'deoxycytidine (5, 1.05 g, 1.74 mmol) was dissolved in anhydrous dichloromethane (20 mL), followed by addition of triethylamine (0.3 mL) and molecular sieve (3 Å, 2 g). The mixture was cooled in an ice-bath after stirring at room temperature for 0.5 hour and then a solution of sulfuryl chloride (0.16 mL) in anhydrous dichloromethane (3 mL) was added dropwise during 2 minutes. The ice-bath was removed and the reaction mixture was stirred further for 30 min. Then potassium p-toluenethiosulfonate (620 mg) in anhydrous DMF (3 mL) was added to the mixture. Stirring was continued at room temperature for additional 1 hour followed by addition of tertbutyl mercaptan (0.38 mL). The reaction mixture was stirred at room temperature for 0.5 hour and quickly filtered through celite. The filter was washed with dichloromethane and the organic fraction was concentrated. The residue was purified by silica gel column chromatography (dichloromethane/methanol: 30/1) to give crude 7.

5-[3-(trifluoroacetamido)propynyl]-3'-O-(tert-butyldithiomethyl)-2'-deoxycytidine (8): Crude $N^4$-DMF-5-[3-(trifluoroacetamido)propynyl]-5'-O-Trity-3'-O-(tert-butyldithiomethyl)-2'deoxycytidine 7 was dissolved in dichloromethane and treated with 3% trichloroacetic acid solution at room temperature for 10 min. The mixture was added slowly to a saturated solution of sodium bicarbonate under stirring and extracted with ethyl acetate (3×30 mL). The combined organic layers were dried over $Na_2SO_4$ and filtered. The filtrate was concentrated to dryness under reduced pressure and the residue of the desired compound was purified by column chromatography (dichloromethane/methanol: 30/1) to give 8 (206 mg, 23% from 5). $^1$H NMR (400 MHz, CDCl$_3$) δ 8.88 (bs, 1H), 8.77 (s, 1H), 8.17 (bs, 1H), 8.03 (s, 1H), 6.20 (bs, 1H), 6.12 (t, J=6.4 Hz, 1H), 4.80 (m, 2H), 4.52 (m, 1H), 4.32 (m, 2H), 4.17 (d, J=2.4 Hz, 1H), 3.97-3.83 (m, 2H), 2.52 (m, 1H), 2.25 (m, 1H), 1.30 (s, 9H). HRMS (Fab$^+$) calc'd for $C_{19}H_{26}F_3N_4O_5S_2$ (M+H)$^+$1: 511.1297, found: 511.1288.

5-(3-trifluoroacetamidopropynyl)-3'-O-tert-butyldithiomethyl-dCTP (9): 5-[3-(trifluoroacetamido)propynyl]-3'-O-(tert-butyldithiomethyl)-2'-deoxycytidine (8, 70 mg, 0.14 mmol), 2-chloro-4-H-1,3,2-benzodioxaphosphorin-4-one (44 mg, 0.22 mmol) and tetrabutylammonium pyrophosphate (197 mg, 0.36 mmol) were dried separately overnight under high vacuum. Under argon, the tetrabutylammonium pyrophosphate was dissolved in DMF (1 mL) followed by addition of tributylamine (1 mL). The mixture was injected into the solution of 2-chloro-4-H-1,3,2-benzodioxaphosphorin-4-one in DMF (2 mL). After stirring for 1 h, the reaction mixture was added to the solution of 3'-O-tert-butyldithiomethyl thymidine and stirred further for 1 hour at room temperature. Iodine solution (0.02 M iodine/pyridine/water) was then added to the reaction mixture until a permanent brown color was observed. After 10 min, water (30 mL) was added and the reaction mixture was stirred at room temperature for an additional 2 hours. The resulting solution was extracted with ethyl acetate (2×30 mL). The aqueous layer was concentrated in vacuo to approximately 20 mL, and transferred to two centrifuge tubes (50 mL). Brine (1.5 mL) and absolute ethanol (35 mL) were added to each tube, followed by vigorous shaking. After being placed at −80° C. for 2 h, the tube was centrifuged (10 min at 4200 rpm) to afford the crude product as a white precipitate, which was diluted with 5 mL of water and 5 mL ammonium hydroxide. The reaction mixture was stirred at room temperature overnight. After evaporation of the solvent under reduced pressure, the mixture was purified by anion exchange chromatography on DEAE-Sephadex A-25 at 4° C. using a gradient of TEAB (pH 8.0; 0.1-1.0 M). The crude product was further purified by reverse-phase HPLC to afford 9.

The synthesis of other three nucleotides 5-(3-aminopropynyl)-3'-O-tert-butyldithiomethyl-dTTP, 7-(3-aminopropynyl)-3'-O-tert-butyldithiomethyl-7-deaza-2'-dATP, and 7-(3-aminopropynyl)$_3$'-O-tert-butyldithiomethyl-7-deaza-2'-dGTP follows the same procedure as reported above.

Synthesis of Linker, attachment of Dye to the linker and coupling reaction with PA-3'-ODTM-dNTPs to make 3'-O and base protected 3'-O-DTM-dNTPs-SS-Dye terminators (FIG. 43 and FIG. 45).

3-(methylthio)methoxy)propanenitrile (2). To a stirred solution of 3-hydroxypropanenitrile (1, 3 g, 42.3 mmol) in dry DMSO (78 ml), acetic acid (36 ml) and acetic anhydride (120 ml) were added. The mixture was stirred at room temperature for 2 days, and then quenched by adding to a saturated NaHCO$_3$ solution (150 ml). The aqueous solution was extracted with ethyl acetate (150 mL×3) and the combined organic phase was dried over anhydrous $Na_2SO_4$. The crude product 2 was concentrated and purified by flash column chromatography (ethyl acetate:hexane 8:2). Light yellow oil (2.41 g, 44%) was afforded. $^1$H NMR (400 MHz, Chloroform-d) δ 4.69 (s, 2H), 3.77 (t, J=6.2 Hz, 2H), 2.65 (t, J=6.3 Hz, 2H), 2.19 (s, 3H).

Fmoc-NH-PEG$_4$-SH (5). Fmoc-NH-PEG$_4$-NHS ester (200 mg, 0.34 mmole) was dissolved in 4 ml DCM, then 2-aminoethanethio-HCl (38.8 mg, 0.37 mmole) and DIPEA (0.24 ml, 1.36 mmole) were added. The reaction mixture was stirred at r.t. for 4 h. Then the solvent was evaporated under reduced pressure. The product was purified using a silica gel column (DCM/Methanol, 10/1). Removal of solvent afforded compound 5 as a colorless syrup. MALDI-TOF MS found: 548; Cal: 546.6.

S-(2-cyanoethoxy)methyl) 4-methylbenzenesulphonothioate (3) and Compound 6. To a stirred solution of 2 (50 mg, 0.38 mmol) in anhydrous dichloromethane (3.75 ml), cyclohexene (195 μL, 1.92 mmol) was added. The reaction mixture was cooled in an ice-bath. SO$_2$Cl$_2$ (34.5 uL, 0.42 mmol) were added dropwise to the mixture. Then the ice bath was removed, and the reaction mixture was stirred at room temperature for 30 min. Potassium p-toluenethiosulfonate (87 mg, 0.38 mmol) dissolved in anhydrous DMF (3 mL) was added into the reaction mixture to afford 3, and after stirring for an additional hour, Fmoc-NH-PEG$_4$-SH (5, 197 mg, 2.4 mmol) in anhydrous dichloromethane (0.5 ml) was added, followed by additional stirring at room temperature for 1 h. The reaction mixture was concentrated; and to the residue DCM (2 ml) was added to dissolve the syrup, and 15 times (volume) of diethyl ether was added at 0° C. allowing formation of precipitate. Centrifugation was used to collect the precipitate giving the crude product 6. HPLC (C18 column, elution gradient:B from 10% in A to 80% in 40 min, A: 0.1% TFA in water, B: Acetonitrile) was used to purify the product, removal of solvent offered pure product 6 as a colorless syrup. MALDI-TOF MS found: 663; Cal: 661.6.

Hydrolysis of 6 to compound 7. Compound 6 (20 mg) was dissolved in 600 ul acetonitrile, 200 ul of TEA was added and the reaction mixture was shaken at r.t. for 16 h. Then the solvent and TEA were evaporated to dryness and 100 ul dichloromethane (DCM) was added to dissolve the residue. Diethyl ether (1.2 ml) was added to the DCM solution allowing formation of precipitate. Centrifugation was used to spin down the precipitate and the supernatant was discarded. This DCM-dissolving ethyl ether precipitation process was repeated 3 times. Thorough removal of the solvent gave product 7 as a white solid. MALDI-TOF MS found: 442, Cal: 439

Bodipy addition (8). Compound 7 (8 mg) was dissolved in DMF (0.2 ml) and Bodipy NHS ester (5 mg, dissolved in 300 ul Methanol) was added. After addition of 1 ul TEA, the reaction mixture was shaken for 4 h. The solvent was removed by evaporation and the product was purified by HPLC (C-18 reverse phase column, elution gradient: B 10% in A to 80% in 40 min, A: 0.1% TFA in water, B: Acetonitrile). The fraction containing product was collected, combined and dried; yielding product 8, MALDI-TOF MS found: 714, Cal: 714.2

Hydrolysis of CN to COOH (9). Compound 8 (4 mg) was dissolved in a mixed solution of PBS buffer (100 mM, pH 7.5) and methanol (400 ul/100 ul), then 0.5 mg of nitrilase (dissolved in 10 ul PBS) was added. The reaction mixture was shaken in a 37° C. incubator for 24 h, and another 0.5 mg nitrilase was added. The reaction mixture was kept in the incubator for 3 days. HPLC was used to purify the final product 9 (C-18 reverse phase column, elution gradient: B 0% in A to 50% in 40 min, A: HFIP-TEA buffer, B: Methanol). TOF-MALDI MS found (M+1): 735; Cal: 733.2.

3'-O-t-butyl-dithiomethyl-dCTP-SS-BodipyFL (3'-O-DTM-dCTP-SS-BodipyFL) (10). Compound 9 (1 mg) was dissolved in DMF (200 ul), and DSC (0.4 mg) and DIPEA (0.6 ul) were added. After shaking the reaction mixture for an hour, it was added into a 300 ul solution of 3'-O-SS-dCTP-PA-$NH_2$ (compound 9 in prior scheme) in 0.1 M $Na_2CO_3$/$NaHCO_3$ buffer (pH 8.8). The mixture was shaken for 6 h, and 0.4 ml 0.1 M TEAC buffer (pH.8) was added. The resulting solution was subjected to DEAE ion exchange purification. The column was eluted using TEAC buffer (pH.8) gradient from 0.1M to 0.8M. The product containing fraction was collected and concentrated. HPLC was used to purify the final product (C-18 reverse phase column; elution gradient: B from 0% in A to 50% in 40 min, A: HFIP-TEA buffer, B: Methanol). TOF-MALDI MS found (M+1): 1370; Cal: 1365.

The synthesis of other three reversible terminators 3'-O-SS-tert-butyl-dUTP-S—S-R6G (3'-O-DTM-dUTP-SS-R6G, 3'-O-SS-tert-butyl-dATP-S—S—ROX (3'-O-DTM-dATP-SS-ROX), and 3'-O-SS-tert-butyl-dGTP-S—S-Cy5 (3'-O-DTM-dGTP-SS-Cy5) follows essentially the same method as reported for 3'-O-SS-tert-butyl-dCTP-S—S-BodipyFL (3'-O-DTM-dCTP-SS-BodipyFL).

Figure 1A:
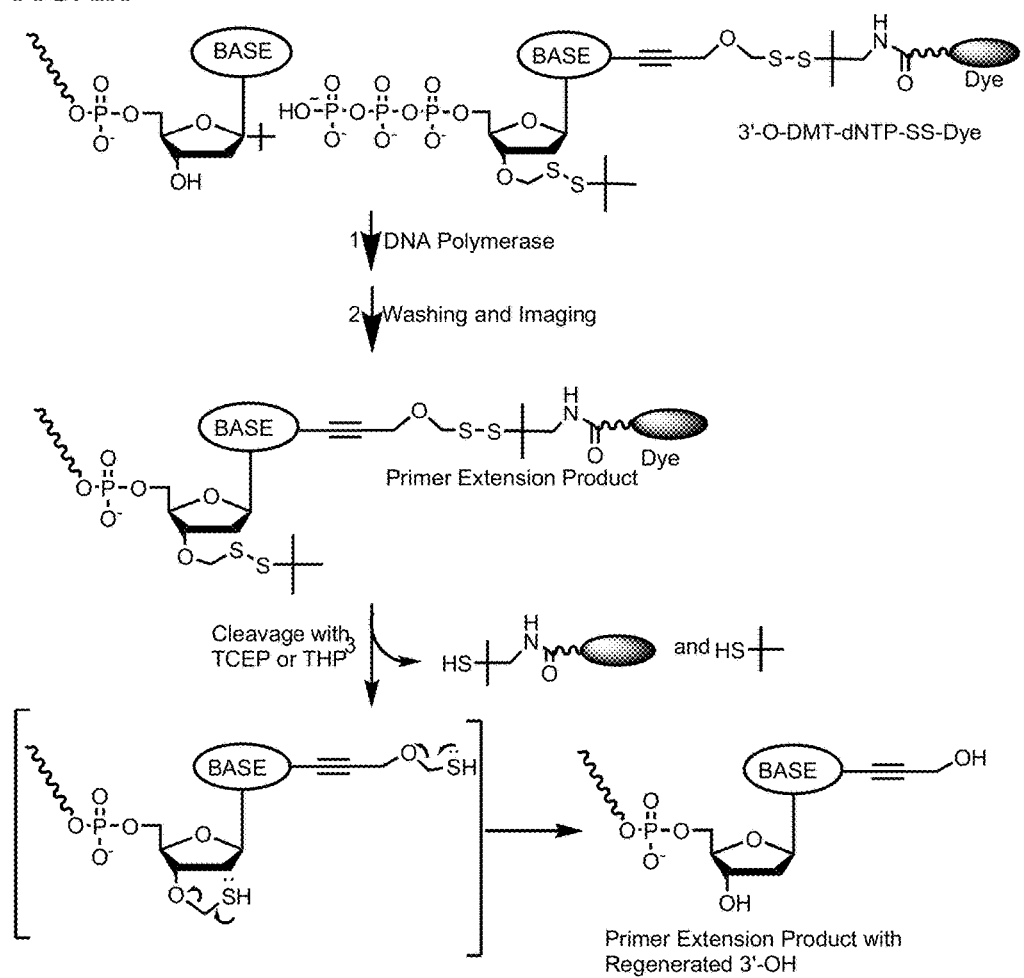
FIGS. 1A-1B. SBS using 3'-O-SS(DTM)-dNTP-SS-Dye (where "DTM" refers to the Dithiomethyl group). (STEP 1) Addition of a DNA polymerase to the primed template moiety (only the primer strand is shown above) leads to the incorporation of a complementary 3'-O-SS(DTM)-dNTP-SS-Dye to the 3' end of a primer with high efficiency and specificity. (STEP 2) After washing away the unincorporated labeled molecules, the detection of the unique label attached to the primer extension product determines the identity of the incorporated nucleotide. (STEP 3) Addition of TCEP or THP results in the cleavage of the disulfide bond, and therefore to the removal of the label on the primer extension product and the regeneration of the 3'-OH on the primer extension product. The repetition of STEP 1 through STEP 3 allows for continuous DNA sequence determination.
Figure 1B:
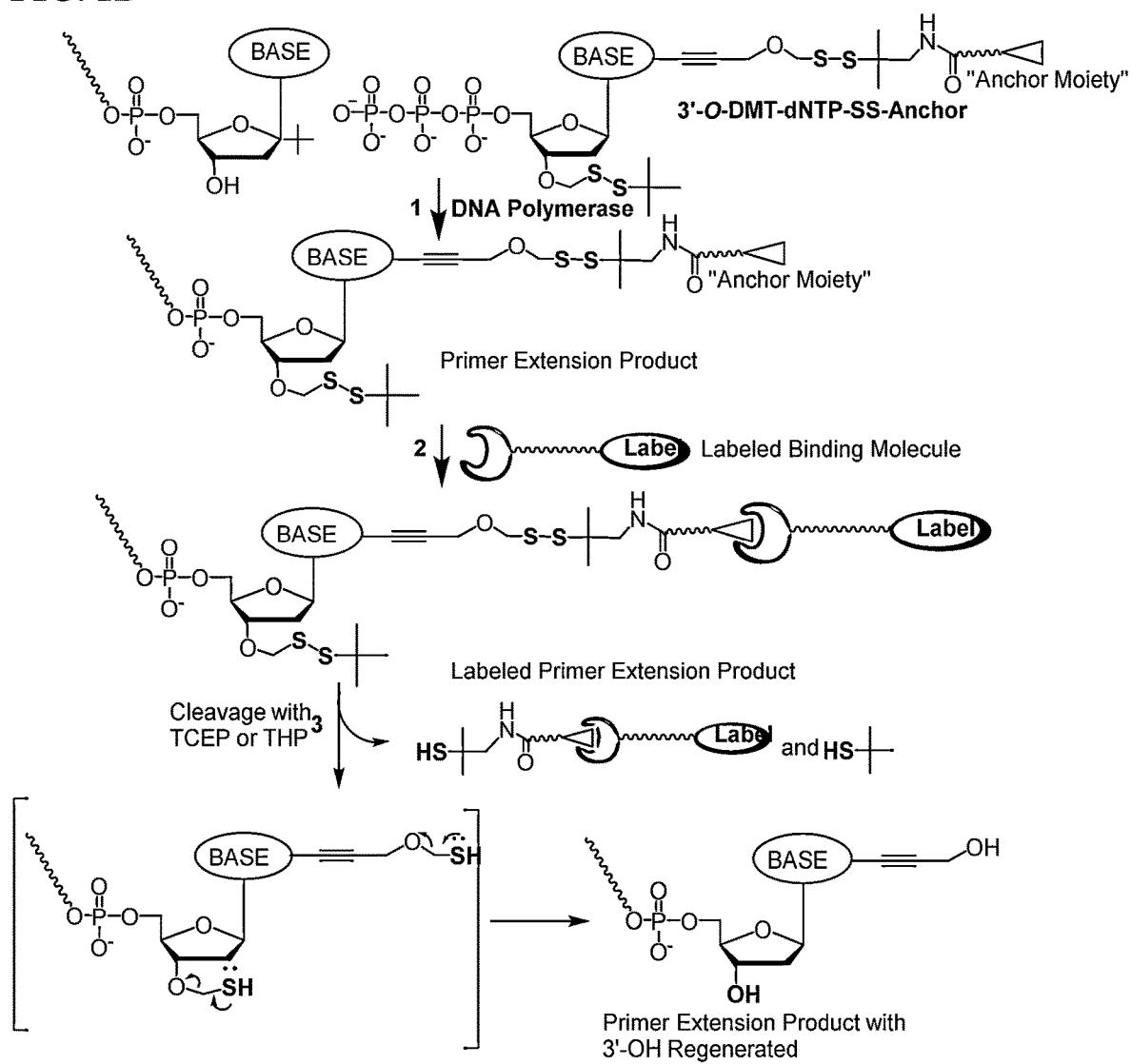
Figure 2:
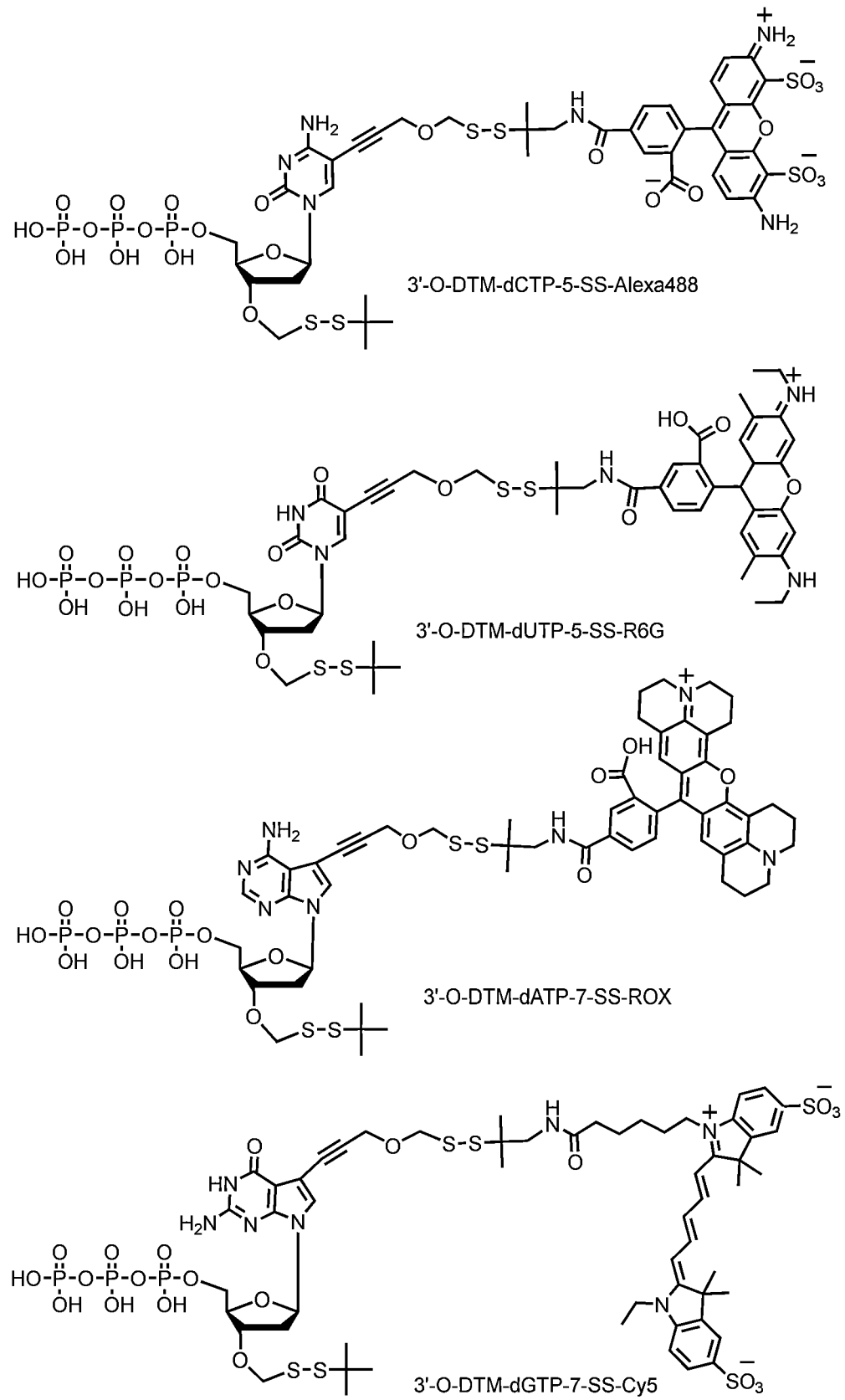
FIG. 2. Structures of 3'-O-DTM-dNTPs-SS-Dye (3'-O-t-Butyldithiomethyl-dCTP-5-SS-Alexa488, 3'-O-t-Butyldithiomethyl-dUTP-5-SS-R6G, 3'-O-t-Butyldithiomethyl-dATP-7-SS-Rox) and 3'-O-t-Butyldithiomethyl-dGTP-7-SS-Cy5 (wherein "DTM" refers to the Dithiomethyl group).
Figure 3A:
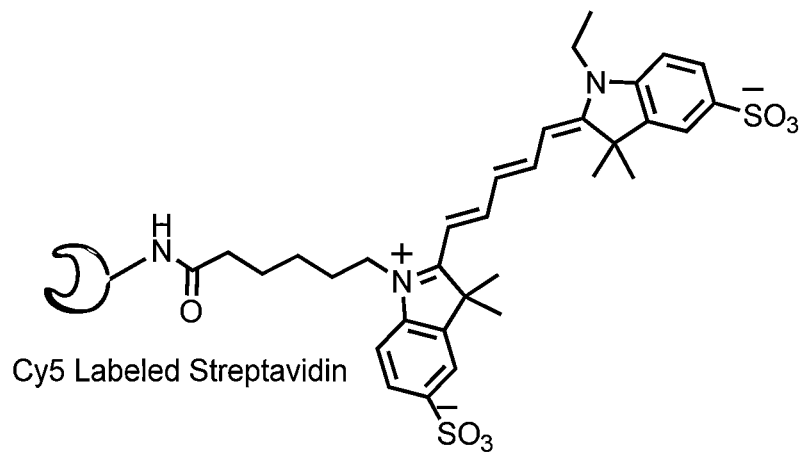
FIGS. 3A-3E. Structures of 3'-O-DTM-dNTPs-SS-Biotin (3'-O-t-Butyldithiomethyl-dATP-7-SS-Biotin, 3'-O-t-Butyldithiomethyl-dGTP-7-SS-Biotin, 3'-O-t-Butyldithiomethyl-dUTP-5-SS-Biotin, 3'-O-t-Butyldithiomethyl-dCTP-5-SS-Biotin) and Cy5 dye labeled streptavidin as an example tagging moiety (multiple Cy5 dyes can be attached to a single streptavidin molecule to increase detection sensitivity).
Figure 3B:
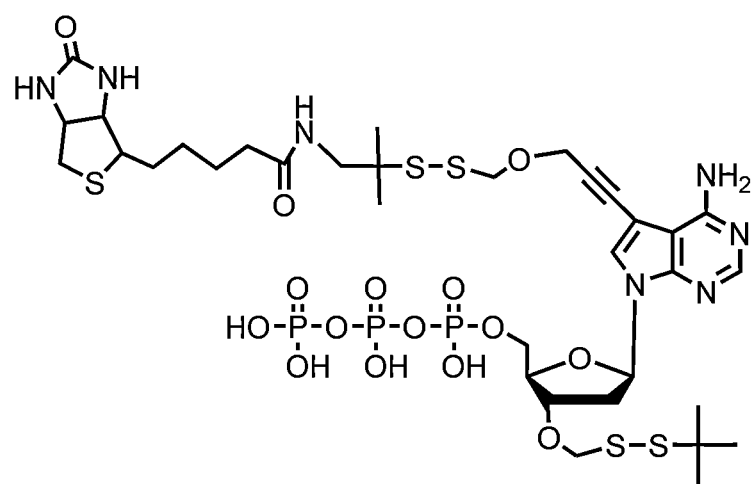
Figure 3C:
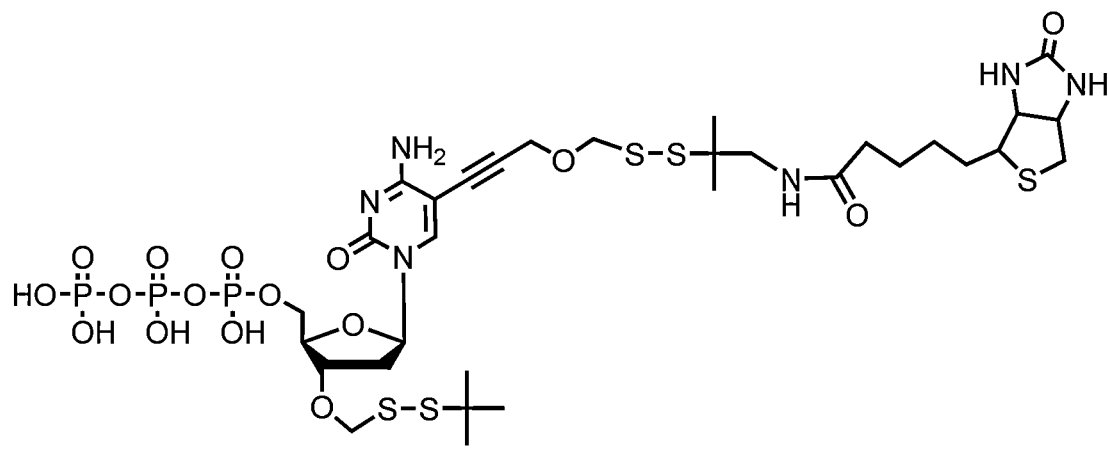
Figure 3D:
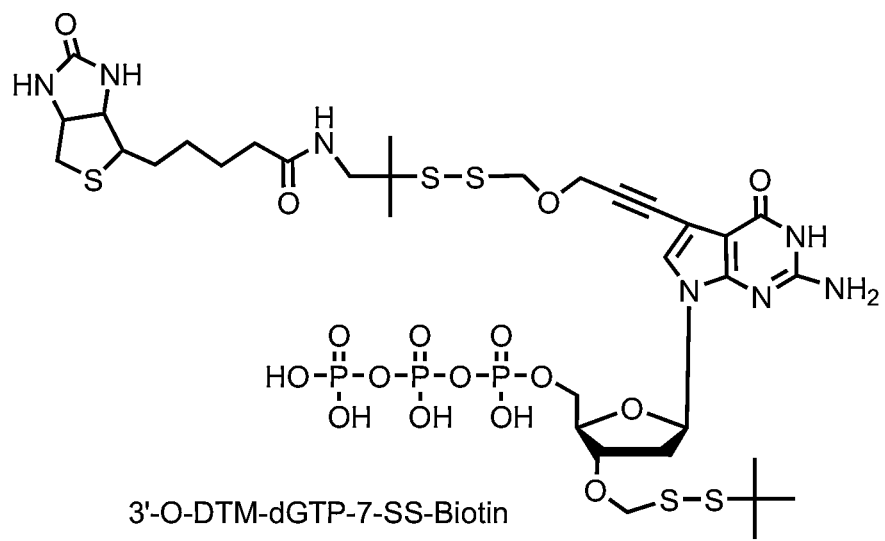
Figure 3E:
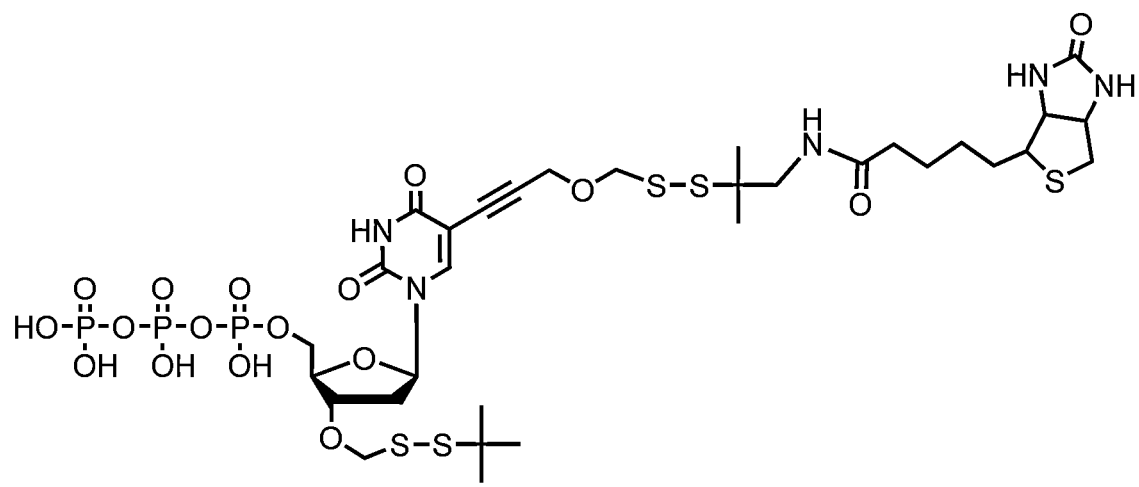

Example 2. Cleavable Group Modified Nucleotide Analogues as Reversible Terminators for DNA Sequencing by Synthesis We designed and synthesized new dye labeled 3'-O-DTM dNTPs in which the Dye-DTM moiety is more closely attached to the base through a shorter linker (FIGS. 1A-1B, FIG. 2), so that after incorporation and cleavage a much smaller tail is left on the base, greatly facilitating upcoming enzymatic reactions. In addition, we have described the design and synthesis of nucleotide analogues that are attached with small "anchor" moieties to the nucleobase via the DTM linker (FIG. 3B). Since attaching smaller groups to the nucleobase will substantially decrease interference with recognition of these molecules as substrates by polymerase, these NRTs are more efficiently incorporated into the growing DNA strand in SBS. After nucleotide incorporation, a corresponding labeled binding molecule tethered to a fluorescent dye will orthogonally react with the anchor on the DNA extension product. Imaging of the fluorescent dye on this DNA extension product will identify the incorporated nucleotide for sequence determination. A general scheme to use these molecules for SBS is shown in FIG. 1B and FIGS. 4A-4D.

Figure 5:
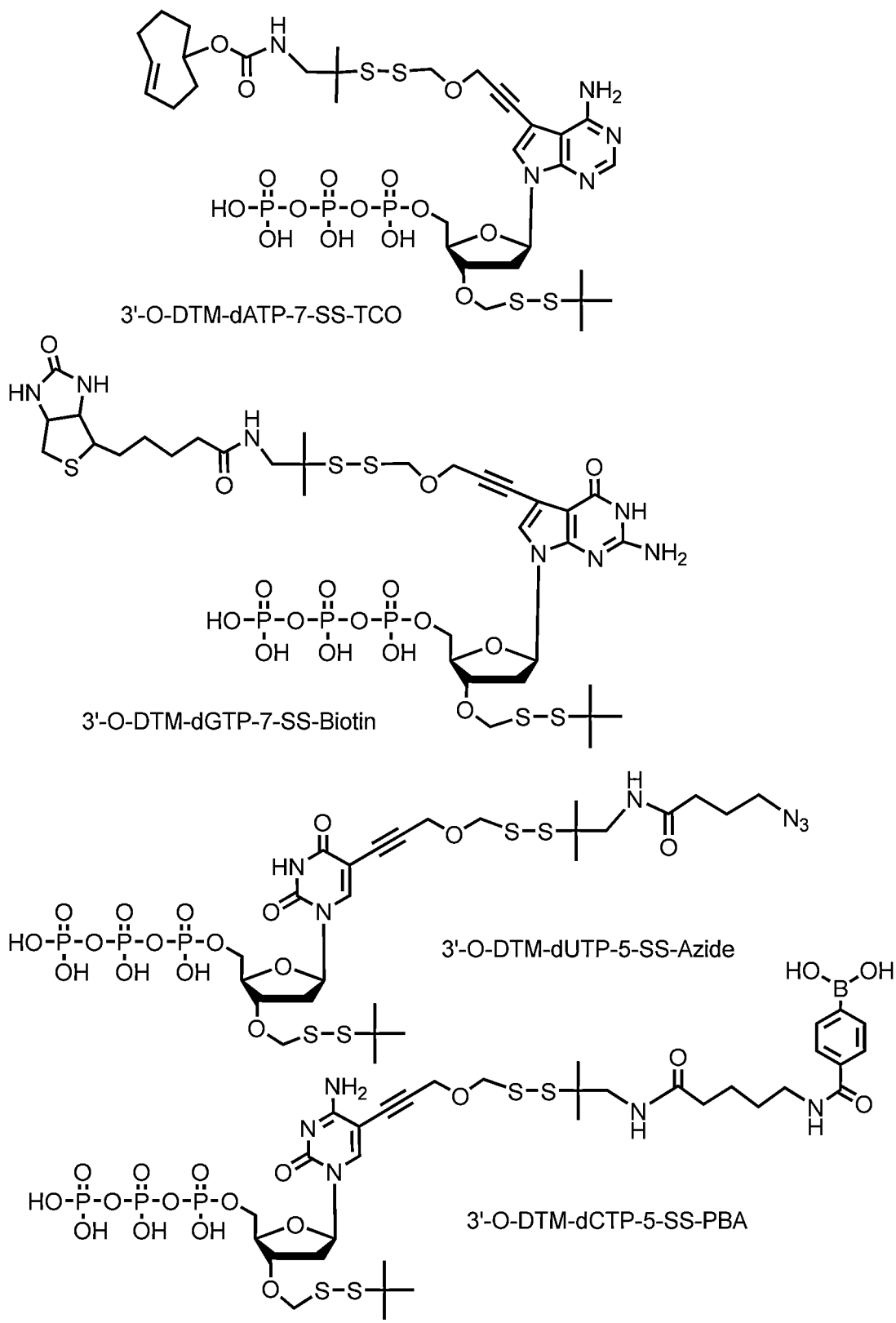
FIG. 5. Structures of 3'-O-DTM-dNTP-SS-"Anchors" (3'-O-t-Butyldithiomethyl-dATP-7-SS-TCO, 3'-O-t-Butyldithiomethyl-dCTP-5-SS-PBA, 3'-O-t-Butyldithiomethyl-dGTP-7-SS-Biotin, Butyldithiomethyl-dUTP-5-SS-N$_3$). In this set of nucleotide analogues, four different "anchor" moieties, TCO, PBA, Biotin and Azido groups, are attached to the base of dATP, dCTP, dGTP and dTTP, respectively, through the DTM linkage, as shown in this figure.
Figure 7:
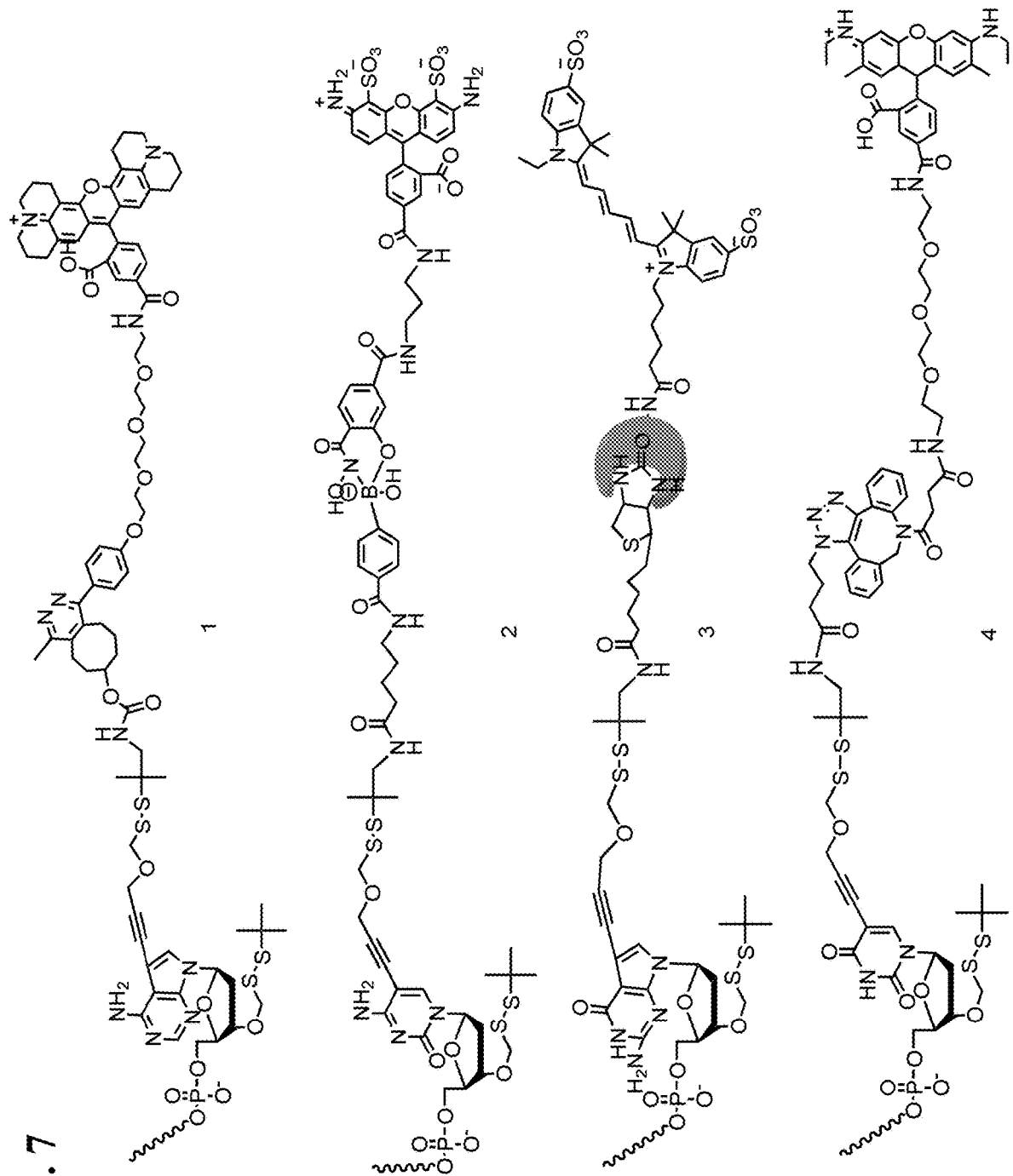
FIG. 7. Conjugates or complexes between DNA products produced by incorporating anchor labeled 3'-O-DTM nucleotides (3'-O-t-Butyldithiomethyl-dATP-7-SS-TCO, 3'-O-t-Butyldithiomethyl-dCTP-5-SS-PBA, 3'-O-t-Butyldithiomethyl-dGTP-7-SS-Biotin, 3'-O-t-Butyldithiomethyl-dUTP-5-SS-Azo) with four correspondingly-matched labeled binding molecules (Rox-Labeled Tetrazine, Alexa488-Labeled SHA, Cy5-Labeled Streptavidin, and R6G-Labeled Dibenzocyclooctyne). The reaction of the DNA extension product containing four "anchor" moieties on the base (FIG. 5) with four correspondingly-matched labeled binding molecules (FIG. 6) leads to each incorporated nucleotide in the DNA extension product being labeled with a unique dye. Thus, Rox will be tethered to the DNA extension product through a specific Tetrazine TCO ligation to form PRODUCT 1; Alexa488 will be tethered to the DNA extension product through a stable PBA-SHA complex to form PRODUCT 2; Cy5 will be tethered to the DNA extension product through a Biotin Streptavidin complex to form PRODUCT 3; and R6G will be tethered to the DNA extension product through triazole formation via a click reaction between Dibenzocyclooctyne and an azido group to form PRODUCT 4.

The anchor moieties include a variety of orthogonally reactive or affinitive functionalities, such as biotin, azide, trans-cyclooctene (TCO) and phenyl boric acid (PBA) (FIG. 5), which will specifically and efficiently bind or react with streptavidin, dibenzocyclooctyne (DBCO),[29,30] tetrazine (TZ)[31,32] and salicylhydroxamic acid (SHA)[33] respectively (FIG. 6, FIG. 7). The DNA polymerase will readily incorporate these 3'-O-anchor-modified nucleotides to the growing DNA strand to terminate DNA synthesis. Addition of the labeled binding molecules (such as different fluorophore-labeled streptavidin, DBCO, TZ and SHA) to the corresponding primer extension product leads to orthogonal binding of the labeled binding molecules with the corresponding "anchor" moiety on the primer extension product; after washing away the unbound labeled molecule, the detection of the unique label attached to the 3' end of the primer extension product determines the identity of the incorporated nucleotide. Labeling moieties can contain multiple fluorophors enabling high sensitivity detection in SBS, potentially for single molecule SBS.

In addition to performing four-color SBS using the aforementioned nucleotide analogues, these molecules also allow a wide spectrum of new DNA sequencing methods including one-color or two-color SBS at the single-molecule level or at an ensemble level. Instead of attaching a single dye to the labeled binding molecules, multiple dyes can also be attached to the incorporated nucleotide through conjugation with labeled binding molecules that carry multiple dyes (or dendrimers labeled with multiple dyes) (FIGS. 9A-9C, FIG. 10), so that amplification of fluorescent signals can be achieved to facilitate single-molecule detection of the DNA extension product via SBS. The anchor labeled NRTs are especially advantageous in this regard. Small anchor tethered NRTs tend to be incorporated by polymerases more efficiently, and the subsequent labeling reactions using large substituents (such as dye labeled dendrimers and FRET cassettes) (FIGS. 11A-11D, FIG. 12) will enable high sensitivity or even single molecule detection. Two-color SBS can be achieved by connecting a binding molecule to a Fluorescence Resonance Energy Transfer (FRET) cassette formed by two different fluorescent dyes, with distinct emissions, which generate four different FRET signal signatures to identify the four DNA bases (A, C, G, T).[34,35] If each labeled binding molecule is constructed by conjugation with a dye reporter using a uniquely cleavable linker for labeling the DNA extension product, different cleavage methods can be used for the selective removal of the dye from the DNA extension product; the detected signal changes will therefore determine the incorporated nucleotide at the single-molecule level, or at the ensemble level, to perform SBS. A well-established cleavable linker toolbox [azo,[36-38] dimethylketa[39,40] Dde ((4,4-dimethyl-2,6-dioxo-cyclohexylidene)ethyl)[41,42] ally and nitrobenzyl[3,4,8,9]] is available to develop the linkage between the labeled binding molecules and the reporting dye. These linkers can be readily cleaved under specific conditions by mild treatment with sodium dithionite ($Na_2S_2O_4$), weak acid, hydrazine ($N_2H_4$), Pd(0) and light-irradiation, respectively.

In order to perfect the sequencing technology using the above mentioned dye or anchor labeled NRTs, we designed and synthesized 3'-O-DTM-dNTPs and their derivatives (cf., FIG. 33, FIG. 34). These 3'-O-DTM-dNTPs are used in combination with the dye or anchor labeled 3'-O-DTM-dNTPs to achieve synchronization of DNA sequencing reactions[8,10] and walking strategies[43] therefore greatly increase sequencing read length and accuracy.

MALDI-TOF MS was used to analyze the DNA extension products resulting from the use of the abovementioned nucleotide analogues in polymerase reactions (FIGS. 29A-29H, FIG. 30B, and FIG. 31). We established that these 3'-O-DTM nucleotide analogues and their derivatives are efficient substrates for DNA polymerase to terminate the DNA synthesis. These results also established that both the fluorophore (or anchor moiety) and the 3'-O-DTM group are removable with high efficiency in a single step in aqueous solution. Furthermore, accurate 4-color sequencing data were obtained using 3'-O-SS-dNTP-(SS)CleavableLinker-Dyes and 3'-O-SS-dNTPs (FIGS. 24A-24B) on surface-immobilized DNA (FIG. 32).

A variety of new DNA sequencing methods based on the combinatorial use of 3'-O-DTM-dNTPs, 3'-O-dNTP-SS-Dye, 3'-O-dNTP-SS-Anchor and their orthogonal reporter dye labeled binding molecule counterparts or cleavable reporter dye labeled binding counterparts are described herein.

Descriptions of Methods for DNA SBS using 3'-O-DTM-dNTPs-SS-Label(Anchor). Combinatorial use of 3'-O-SS(DTM)-dNTPs-SS-Dye, 3'-O-SS(DTM)-dNTPs-SS-anchor and 3'-O-SS(DTM)-dNTPs along with orthogonal binding molecules conjugated with fluorescent dyes (or conjugated with fluorescent dyes using different cleavable linkages) allows the construction of a wide spectrum of new methods for four-color, two-color and one-color DNA SBS at the single molecule level or the ensemble level.

One-Color DNA SBS (FIGS. 4A-4D). A one-color SBS scheme using 3'-O-SS(DTM)-dNTPs-SS-Biotin and Cy5 labeled streptavidin is shown in FIGS. 4A-4D. The DNA polymerase incorporation reaction is conducted by using one of the four 3'-O-SS-dNTPs-SS-Biotin (FIG. 3), followed by the addition of the Cy5 labeled streptavidin and imaging to determine DNA sequences as described in STEP 1 through STEP 4 (as shown in FIG. 4.1 and repeated in FIGS. 4.2, 4.3 and 4.4 (see FIGS. 4A-4D)). Each step uses a different added nucleotide analogue and consists of three parts: (PART a) Add polymerase and one of the four 3'-O-SS-dNTPs-SS-Biotin followed by washing; if the added nucleotide is complementary to the nucleotide on the template immediately next to the 3' end of the primer, then the added nucleotide will be incorporated into the primer to produce a DNA extension product that has a Biotin at the 3' end. (PART b) Add Cy5 labeled streptavidin, which will bind to the biotin at the 3' end of the DNA extension product. (PART c) After washing away the unbound Cy5 labeled streptavidin, perform imaging to detect the Cy5 signal for the identification of the incorporated nucleotide. Note that in this single dye SBS approach, nucleotides are added one at a time. Only one of the four 3'-O-SS-dNTP-SS-Biotins will be incorporated and subsequently labeled by Cy5-Streptavidin. Following STEP 4, addition of THP to the DNA extension products will cleave the disulfide bond and regenerate a free 3'-OH group on the 3' end of the DNA extension products. Simultaneously, the dye or anchor attached on the base of the nucleotide will be removed. Sequentially repeat the process, consisting of STEP 1 through STEP 4, followed by THP cleavage, for continuing sequence determination. Multiple Cy5 dyes can be attached to streptavidin, enabling high sensitivity detection, such as single molecule SBS.

Figure 8:
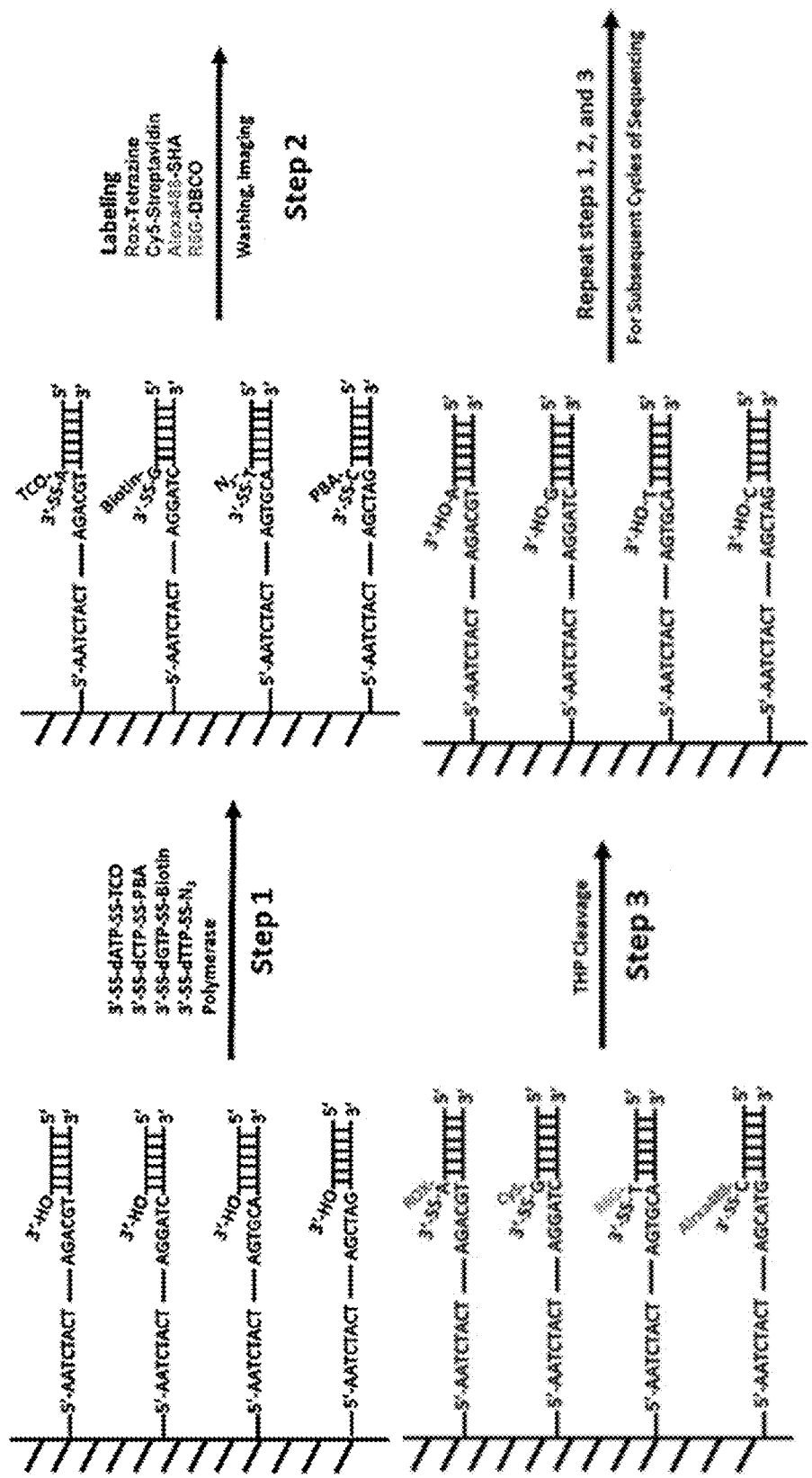
FIG. 8. SBS using 3'-O-SS(DTM)-dNTP-SS-"anchors" (3'-O-t-Butyldithiomethyl-dATP-7-SS-TCO, 3'-O-t-Butyldithiomethyl-dCTP-5-SS-PBA, 3'-O-t-Butyldithiomethyl-dGTP-7-SS-Biotin, 3'-O-t-Butyldithiomethyl-dUTP-5-SS-N$_3$) and four correspondingly matched dye labeled binding molecules (Rox-Labeled Tetrazine, Alexa488-Labeled SHA, Cy5-Labeled Streptavidin, and R6G-Labeled Dibenzocyclooctyne). Addition of the DNA polymerase and the four 3'-O-SS(DTM)-dNTP-SS-anchors (3'-O-DTM-dATP-7-SS-TCO, 3'-O-DTM-dCTP-5-SS-PBA, 3'-O-DTM-dGTP-7-SS-Biotin and 3'-O-DTM-dUTP-5-SS-N$_3$) (FIG. 5) to the immobilized primed DNA template enables the incorporation of the complementary nucleotide analogue to the growing DNA strand to terminate DNA synthesis. After washing away the unincorporated nucleotide analogues, the dye labeled binding molecules (FIG. 6) are added; these will specifically connect with each of the four unique "anchor" moieties on the DNA extension product to enable the labeling of each DNA product terminated with each of the four nucleotide analogues (A, C, G, T) with the four distinct fluorescent dyes (FIG. 7). Detection of the unique fluorescence signal from each of the fluorescent dyes on the DNA products allows for the identification of the incorporated nucleotide. Next, treatment of the DNA products with THP cleaves the SS linker, leading to the removal of the fluorescent dye and the regeneration of a free 3'-OH group on the DNA extension product, which is ready for the next cycle of the DNA sequencing reaction (as shown in the subsequent steps of the figure).
Figure 9A:
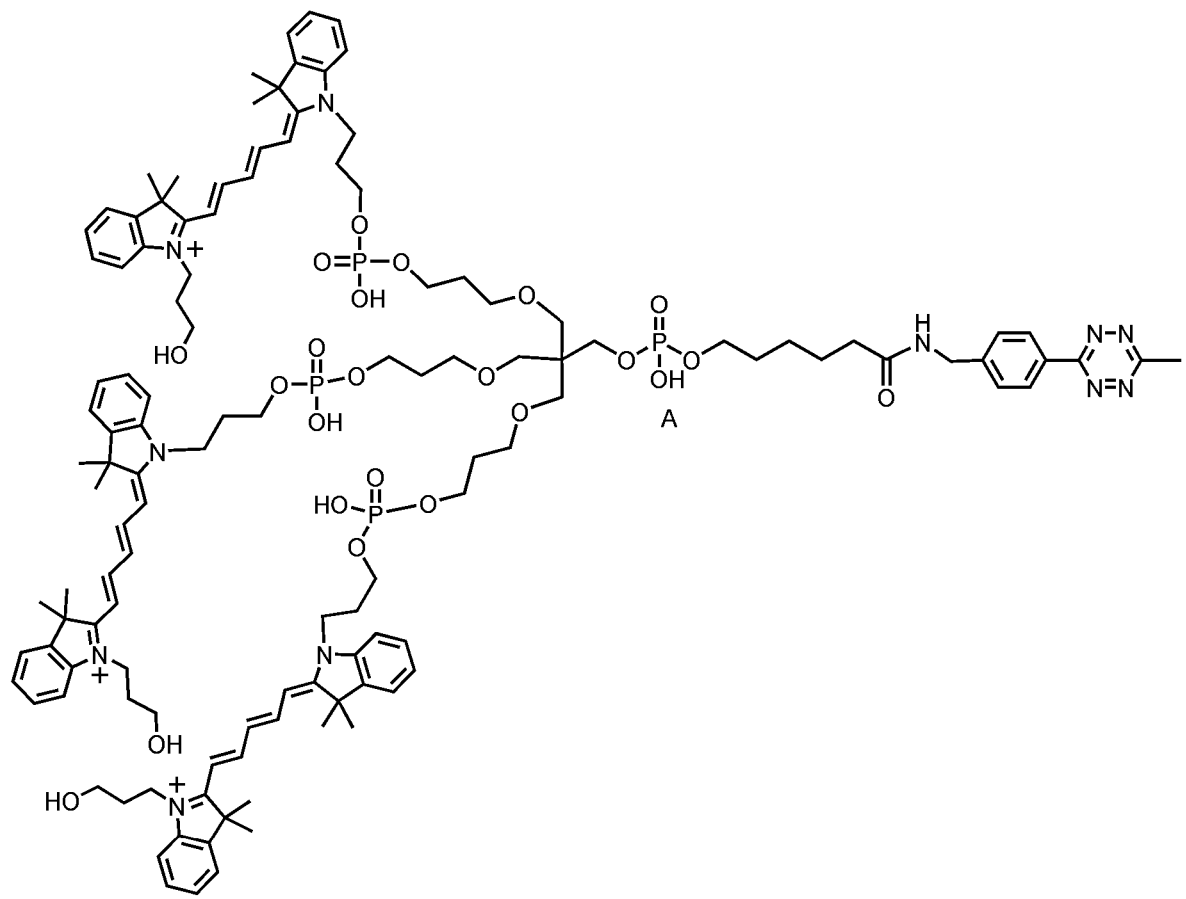
FIGS. 9A-9C. Structures of Fluorescent (Cy5) Dendrimer Conjugated Tetrazine (FIG. 9A and FIG. 9C) and 3'-O-SS (DTM)-dNTPs-SS-TCO (FIG. 9B). Incorporation of each of the four 3'-O-DTM-dNTP-SS-TCO into the growing DNA strand in the polymerase reaction terminates the DNA synthesis, leading to DNA products that have a TCO group. Coupling of the DNA products that have a TCO group with either Molecule A (FIG. 9A) or Molecule B (FIG. 9C) that has the Tetrazine moiety through TCO-Tetrazine ligation allows the DNA product to be labeled with multiple fluorescent dyes, thereby facilitating signal amplification for detection to perform either SBS at the single-molecule level or at an ensemble level (following a scheme similar to the one shown in FIGS. 4A-4D)
Figure 9B:
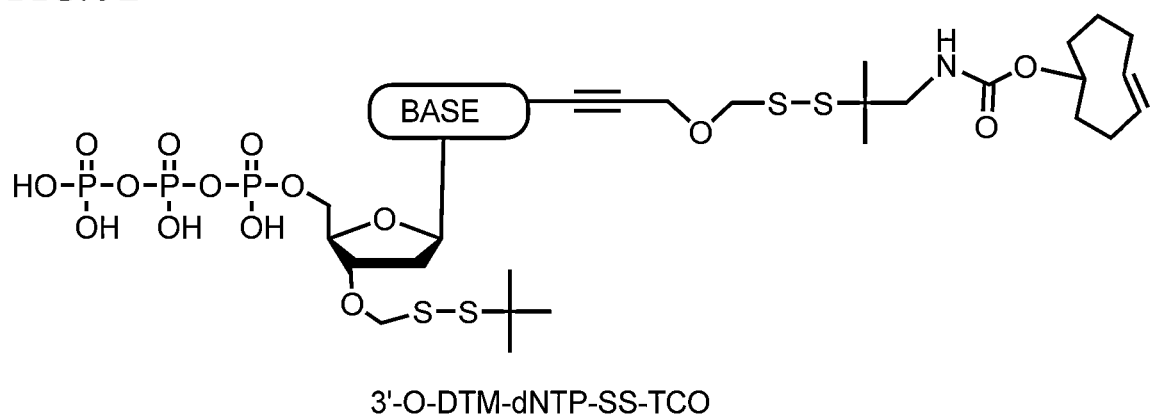
Figure 9C:
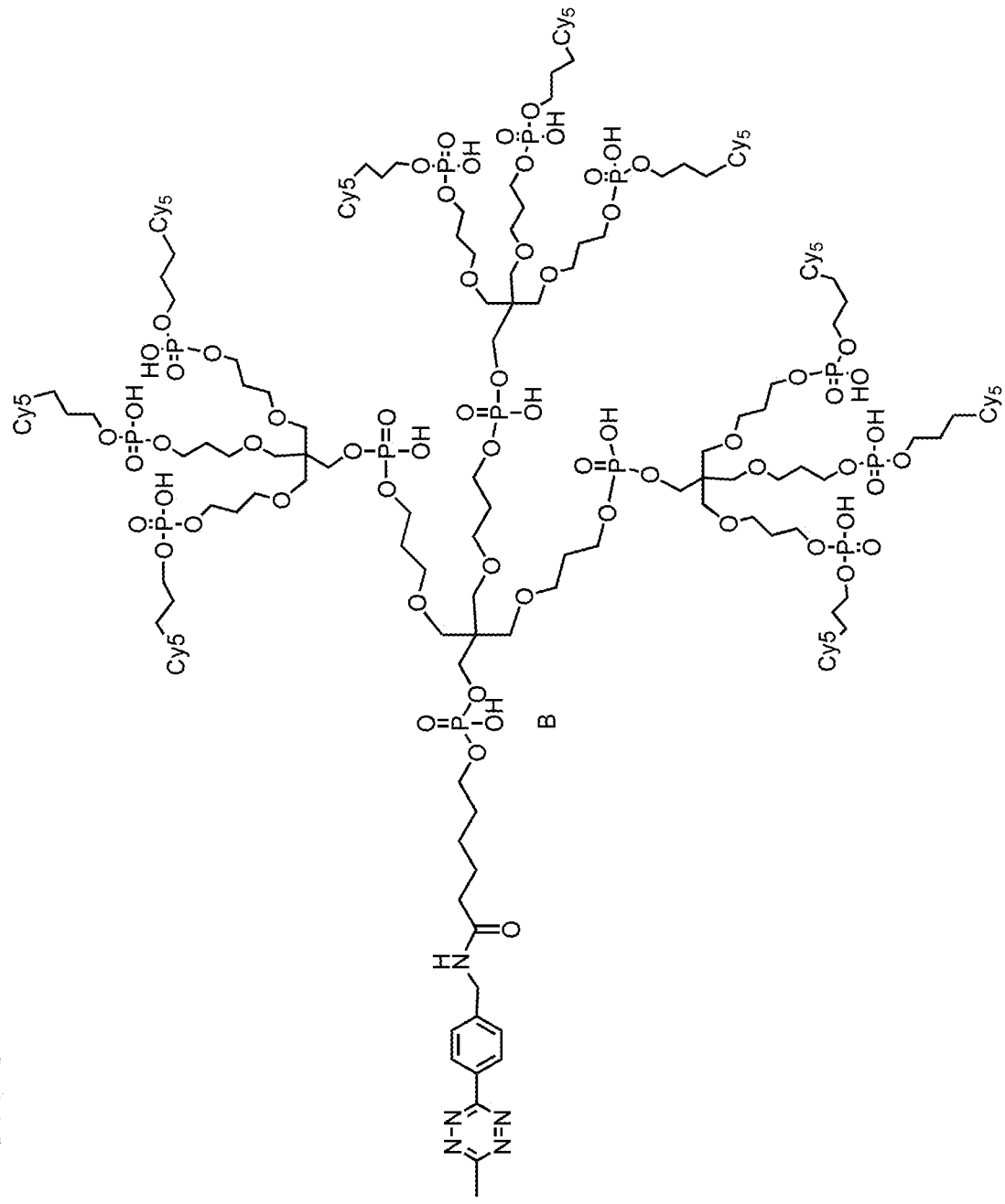
Figure 10:
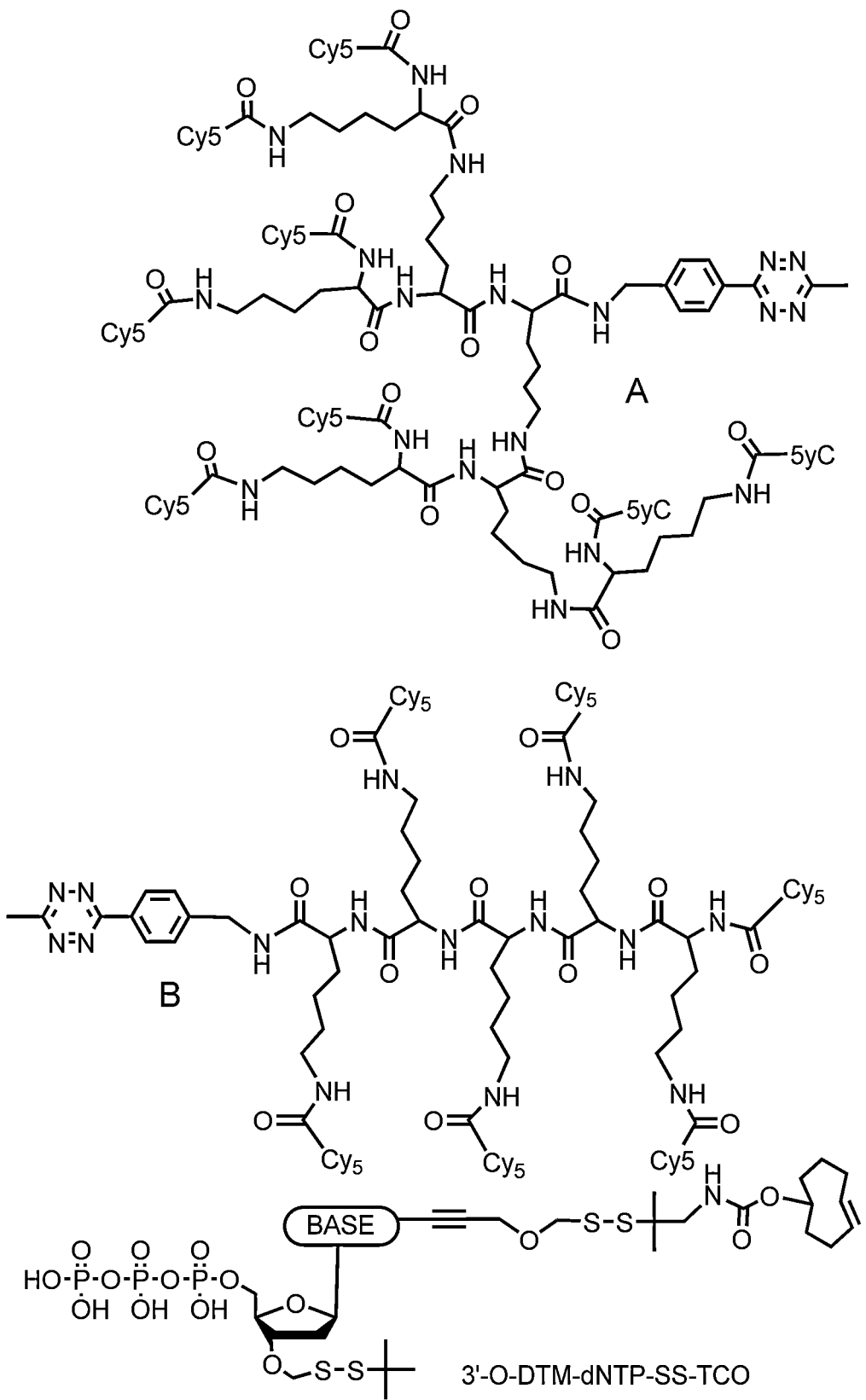
FIG. 10. Example of a Peptide-Based Fluorescent (Cy5) Dendrimer Conjugated Tetrazine (Molecule A) and Polymer Conjugated Tetrazine (Molecule B). Incorporation of each of the four 3'-O-DTM-dNTP-SS-TCO into the growing DNA strand in the polymerase reaction terminates the DNA synthesis, leading to DNA products that have a TCO group. Coupling of the DNA products that have a TCO group with either Molecule A or Molecule B (shown above) that has a Tetrazine moiety through TCO-Tetrazine ligation allows the DNA product to be labeled with multiple fluorescent dyes, thereby facilitating signal amplification for detection to perform either SBS at the single-molecule level or at an ensemble level (following a scheme similar to the one shown in FIG. 4).

Four-Color DNA SBS (FIG. 8). SBS is performed using 3'-O-SS(DTM)-dNTPs-SS-"anchor" (3'-O-t-Butyldithiomethyl (SS)-dATP-SS-TCO, 3'-O-t-Butyldithiomethyl (SS)-dCTP-SS-PBA, 3'-O-t-Butyldithiomethyl(SS)-dGTP-SS-Biotin, 3'-O-t-Butyldithiomethyl(SS)-dUTP-SS-N₃) (FIG. 5) and four correspondingly matched dye labeled binding molecules (Rox-Labeled Tetrazine, Alexa488-Labeled SHA, Cy5-Labeled Streptavidin, and R6G-Labeled Dibenzocyclooctyne) (FIG. 6). Addition of the DNA polymerase and the four 3'-O-SS(DTM)-dNTPs-SS-"anchor" (3'-O-SS-dATP-SS-TCO, 3'-O-SS-dCTP-SS-PBA, 3'-O-SS-dGTP-SS-Biotin and 3'-O-SS-dUTP-SS-N₃) to the immobilized primed DNA template enables the incorporation of the complementary nucleotide analogue to the growing DNA strand to terminate DNA synthesis. After washing away the unincorporated nucleotide analogues, add the dye labeled binding molecules are added; these will specifically connect with each of the four unique "anchor" moieties at the 3'-end of each DNA extension product to enable the labeling of each DNA product terminated with each of the four nucleotide analogues (A, C, G, T) with the four distinct fluorescent dyes. Detection of the unique fluorescence signal from each of the fluorescent dyes on the DNA products allows for the identification of the incorporated nucleotide. Next, treatment of the DNA products with THP cleaves the SS linker, leading to the removal of the fluorescent dye and the regeneration of a free 3'-OH group on the DNA extension product, which is ready for the next cycle of the DNA sequencing reaction (as shown in the subsequent steps of FIG. 8).

FIG. 7 shows the formation of the conjugates or complexes between DNA products produced by incorporating the "anchor" labeled nucleotides (3'-O-t-Butyldithiomethyl-dATP-SS-TCO, 3'-O-t-Butyldithiomethyl-dCTP-SS-PBA, 3'-O-t-Butyldithiomethyl-dGTP-SS-Biotin, 3'-O-t-Butyldithiomethyl-dUTP-SS-N₃) with four correspondingly matched labeled binding molecules (Rox-Labeled Tetrazine, Alexa488-Labeled SHA, Cy5-Labeled Streptavidin, and R6G-Labeled Dibenzocyclooctyne).

Labeling molecules consisting of multiple dyes such as fluorescent dendrimers (FIGS. 9A-9C and FIG. 10), and fluorescent energy transfer cassettes (FIGS. 11A-11D and 12) can be used to greatly increase the sensitivity of these SBS approaches as well as simplify the optical set-up.

Two-Color DNA SBS (FIGS. 14A-14B). A scheme using 3'-O-SS(DTM)-dNTPs-SS-Dye (3'-O-SS-dATP-SS-Rox and 3'-O-SS-dCTP-SS-Alexa488), 3'-O-SS(DTM)-dNTPs-SS-Anchor (3'-0-SS-dUTP-SS-N₃ and 3'-O-SS-dGTP-SS-TCO) and their corresponding dye labeled binding molecules (Rox-Tetrazine & BodipyFL-Dibenzocyclooctyne) (FIG. 13) to perform 2-color DNA SBS is shown in FIG. 14. Addition of the DNA polymerase and the four nucleotide analogues (3'-O-SS-dATP-SS-Rox, 3'-O-SS-dCTP-SS-Alexa488, 3'-O-SS-dUTP-SS-N₃ and 3'-O-SS-dGTP-SS-TCO) to the immobilized primed DNA template enables the incorporation of the complementary nucleotide analogue to the growing DNA strand to terminate DNA synthesis (STEP 1). After washing away the unincorporated nucleotide analogues, the fluorescent signal from Rox and Alexa488 is detected to identify the incorporated nucleotide as A (labeled with Rox) or C (labeled with Alexa488). The dye labeled binding molecules (Rox-Tetrazinc & Alexa488-Dibenzocyclooctyne) are then added to the DNA extension products (STEP 2), which will specifically connect with the two unique "anchor" moieties (TCO and N₃) on the base at the 3'-end of each DNA extension product, to enable the labeling of each DNA product terminated with each of the two nucleotide analogues (G and T) with two distinct fluorescent dyes (labeled with Rox for G and labeled with Alexa488 for T). Detection of the unique, newly produced fluorescence signal from Rox or Alexa488 on the DNA extension products (in addition to the absence of signal from STEP 1), allows for the identification of the newly-incorporated nucleotides as G or T respectively. Next, treatment of the DNA products with THP cleaves the SS linker, leading to the removal of the fluorescent dye and the regeneration of a free 3'-OH group on the DNA extension product (STEP 3), which is ready for the next cycle of the DNA sequencing reaction (as shown in the subsequent steps of FIGS. 14A-14B).

Figure 15A:
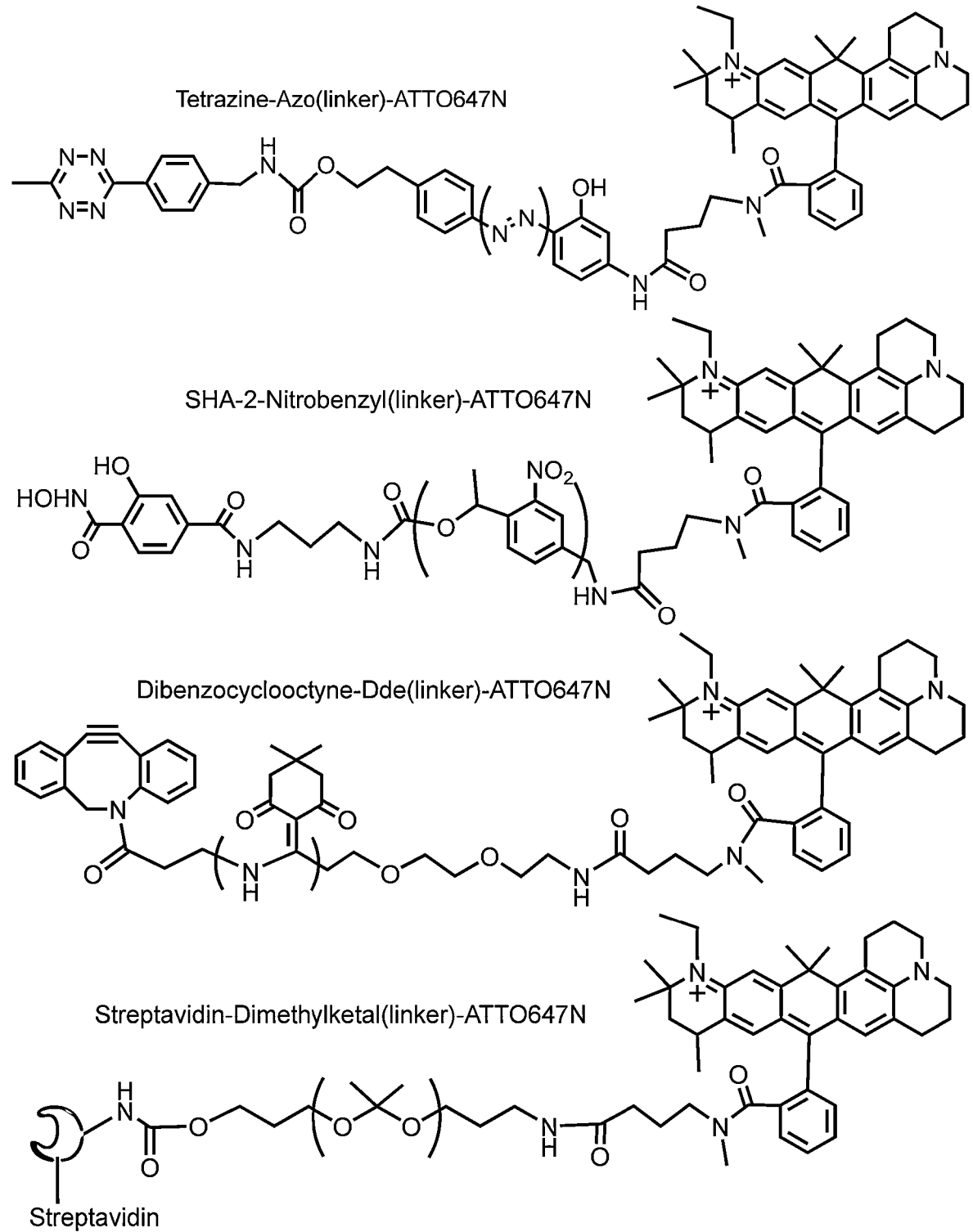
FIGS. 15A-15B. Structures of Labeled Binding Molecules conjugated with fluorescent dyes via different cleavable linkers (which are highlighted in parentheses in this Figure). Tetrazine is tethered to ATTO647N via an azo linkage (Tetrazine-Azo(linker)-ATTO647N), which can be cleaved by sodium dithionite ($Na_2S_2O_4$); Streptavidin is tethered to ATTO647N via a dimethylketal linkage (Streptavidin-Dimethylketal(linker)-ATTO647N)), which can be cleaved under weak acidic conditions such as a citric acid buffer (pH 4); SHA is tethered to ATTO647N via a photocleavable nitrobenzyl linkage (SHA-2-Nitrobenzyl(linker)-ATTO647N), which can be cleaved by photoirradiation; DBCO is tethered to ATTO647N via an allyl linkage (Dibenzocyclooctyne-Allyl(linker)-ATTO647N), which can be cleaved by Pd(0); DBCO can also be tethered to ATTO647N via Dde linkage (Dibenzocyclooctyne-Dde(linker)-ATTO647N), which can be cleaved by hydrazine. ATTO647N labeled Streptavidin (Streptavidin-ATTO647N) can also be used in combination with three other binding molecules conjugated with fluorescent dyes via different cleavable linkers.
Figure 15B:
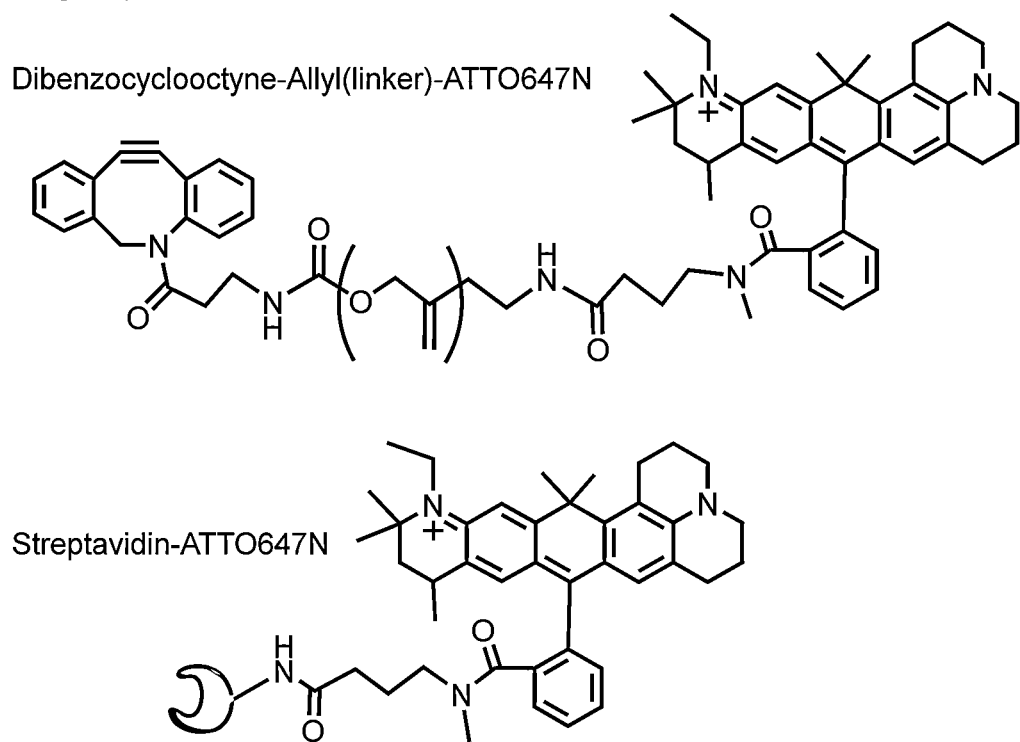

Use of 3'-O-CleavableGroup-dNTPs-CleavableLinker-Label, 3'-O-CleavableGroup-dNTPs-CleavableLinker-Anchor and 3'-O-CleavableGroup-dNTPs (FIGS. 16A-16B) combined with labeled binding molecules (FIGS. 15A-15B) that are conjugated with fluorescent dyes via different cleavable linkers allows the construction of one-color SBS at the single molecule or the ensemble molecule levels. After incorporating the 3'-O-DTM-dNTPs-SS-"anchor" and the 3'-O-DTM-dNTP, treatment with orthogonal labeled binding molecules conjugated with fluorescent dyes (ATTO647N, Cy5, Rox, etc.) via different cleavable linkages (Azo, Dde, Nitrobenzyl, Dimethylketal, etc.) (FIGS. 15A-15B) results in the labeling of all incorporated nucleotides with an anchor on the base at the 3'-end of the DNA extension products due to the specific anchor-binding molecule reaction. Sequential and specific cleavage, followed by imaging, are carried out to remove the dye from the 3'-end of the DNA extension products, allowing signal changes to be accurately detected. Each cleavage method only cleaves one type of linker which is uniquely attached to one of the labeled binding molecules, therefore each cleavage method can be used to encode one of the DNA bases on their corresponding anchor moiety for that particular nucleotide analogue. In general, only three of the four DNA bases (A, C, G, T) are required to have a label for selective detection. Once the first three of these bases are labeled, the fourth one does not require a label to be differentiated from the other three for sequence determination, as exemplified in the following schemes.

Synthetic Method for Base-Linked Dithiomethyl Linker:

The structure of the cleavable dithiomethyl linker attached to the base moiety is as follows:

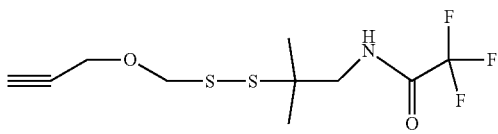 [SMILES: C#CCOCSSC(C)(C)CNC(=O)C(F)(F)F]

The synthesis comprises:

reacting 3-trimethylsilanyl-prop-2-yn-1-ol with DMSO, acetic acid and acetic anhydride to provide Ttrimethyl (3-((methylthio)methoxy)prop-1-yn-1-yl)silane;

contacting trimethyl(3-((methylthio)methoxy)prop-1-yn-1-yl)silane with sulfuryl chloride/cyclohexene followed by reaction with potassium thiotosylate to produce S-(((3-(trimethylsilyl)prop-2-yn-1-yl)oxy)methyl) 4-methylbenzenesulfonothioate;

contacting S-4(3-(trimethylsilyl)prop-2-yn-1-yl)oxy)methyl) 4-methylbenzenesulfonothioate with 2,2,2-trifluoro-N-(2-mercapto-2-methylpropyl) acetamide in the presence of triethylamine, followed by;

contacting with tetrabutylammonium fluoride to form 2,2,2-trifluoro-N-(2-methyl-2-(((prop-2-yn-1-yloxy) methyl)disulfanyl)propyl)acetamide.

The method also provides:

reacting 5'-O-tBDMS-3'-O-polymerase compatible cleavable blocking group-5(7)-Iodo-nucleoside with 2,2,2-trifluoro-N-(2-methyl-2-(((prop-2-yn-1-yloxy)methyl) disulfanyl)propyl)acetamide in the presence of Pd(0), CuI, triethylamine which results in the formation of 5'-O-tBDMS-3'-O-polymerase compatible cleavable blocking group-2'-deoxynucleoside-5(7)-2,2,2-trifluoro-5-yl)ethynyl)oxy)methyl)disulfanyl)-2-methylpropyl)acetamide;

reacting the above product from step e) with tetrabutylammonium fluoride to remove 5. BDMS group permitting the formation of 3'-O-polymerase compatible cleavable blocking group-2'-deoxynucleoside-5(7)-2,2,2-trifluoro-5-yl)ethynyl)oxy)methyl)disulfanyl)methylpropyl)acetamide;

contacting the 3'-O-polymerase compatible cleavable blocking group-2'-deoxynucleoside-5(7)-2,2,2-trifluoro-5-yl)ethynyl)oxy)methyl)disulfanyl)-2-methylpropyl)acetamide produced in step f) with 2-chloro-4-H-1,3,2-benzodioxaphosphorin-4-one, tetrabutylammonium pyrophosphate, tributylamine, 12, pyridine, and $NH_4OH$ under condition permitting the formation of 3'-O-polymerase compatible cleavable blocking group-5(7)-(34(1-amino methylpropan-2-yl) disulfanyl)methoxy)prop-1-yn-1-yl)-2'-deoxynucleoside-5'-triphosphate.

Figure 16A:
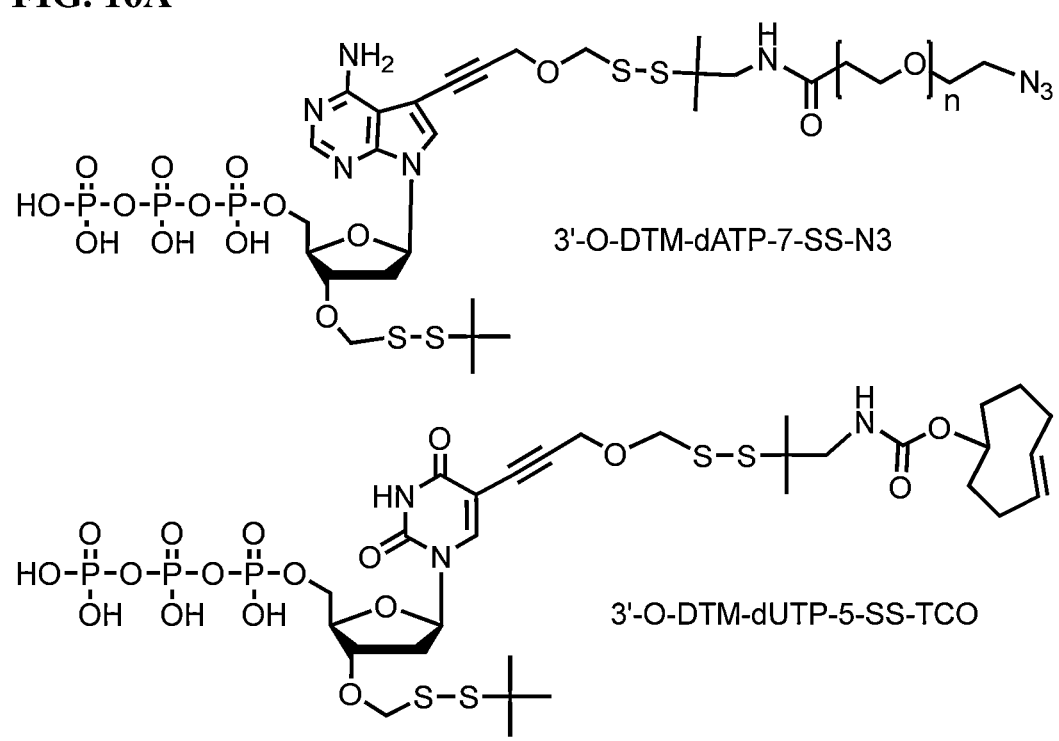
FIGS. 16A-16B. Sample Structures of 3'-O-SS(DTM)-dNTP-SS-"anchors" (3'-O-DTM-dATP-7-SS-$N_3$, 3'-O-DTM-dCTP-5-SS-Biotin, 3'-O-DTM-dUTP-5-SS-TCO] along with their corresponding Labeled Binding Molecules [DBCO-Azo(—N═N-Linker)-ATTO647N, Tetrazine-Dde(Linker)-ATTO647N, and Streptavidin-ATTO647N] conjugated with one fluorescent dye via different cleavable linkers in combination with 3'-O-t-Butyl-SS(DTM)-dGTP (3'-O-SS-dGTP) for performing one-color SBS at the single-molecule level or at the ensemble level.
Figure 16B:
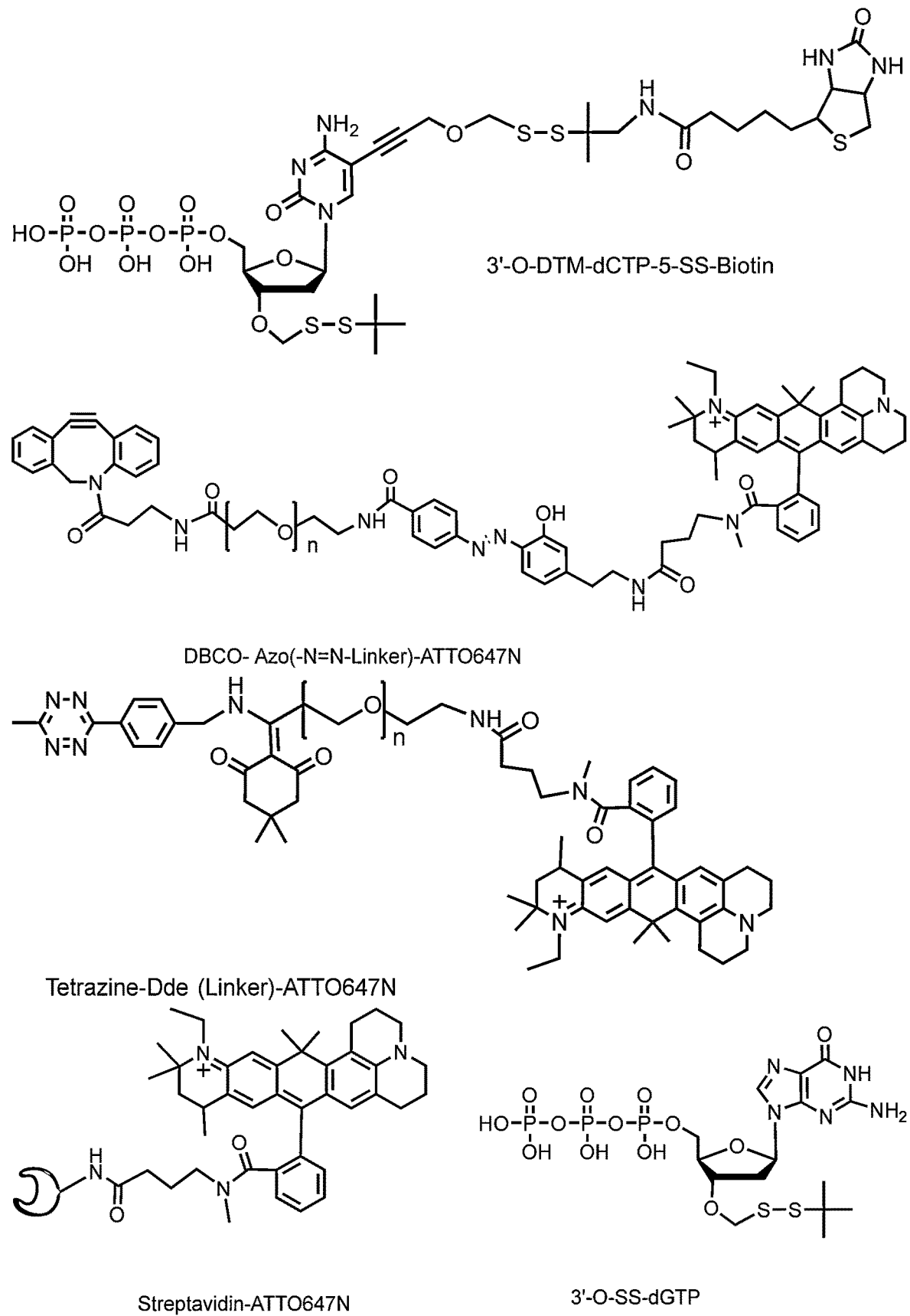

One-Color DNA SBS Using Selective Linker Cleavage to Remove the Dye (FIGS. 17A-17B). 1. In the presence of DNA polymerase, three anchor modified nucleotides [3'-SS(DTM)-dATP-SS-$N_3$, 3'-SS(DTM)-dUTP-SS-TCO, 3'-SS(DTM)-dCTP-SS-Biotin] and 3'-t-Butyl-SS(DTM)-dGTP, as shown in FIG. 16] are added to the primed DNA templates to allow incorporation into the primer. 2. The fluorescent label (ATTO647N, for example) is attached by adding DBCO-Azo-(—N═N-Linker)-ATTO647N, Tetrazine-Dde (Linker)-ATTO647N, and Streptavidin-ATTO647N (shown in FIGS. 16A-16B) to the DNA extension products that contain the incorporated anchor modified nucleotide analogues, which leads to the labeling of all the incorporated nucleotides (except G) at their base due to specific anchor-binding molecule interaction. 3. After washing, the first round of imaging is performed, and the DNA products terminated with A, C and T all display the same color, while the DNA products that do not emit a signal are terminated by a G. 4. The first cleavage (I) is conducted by treatment with sodium dithionite ($Na_2S_2O_4$), which only cleaves the azo linkage to remove the fluorescent dye from the DNA products terminated with the A nucleotide. The second round of imaging is performed. If the fluorescent signal disappears after cleavage I, the DNA products are determined as having incorporated an A nucleotide. 5. The second cleavage (II) is conducted by treatment with hydrazine ($N_2H_4$), which will cleave the Dde linkage to remove the fluorescent dye from the DNA products terminated with the T nucleotide. The third round of imaging is performed. If the fluorescent signal disappears after cleavage II, the DNA products are determined as having incorporated a T nucleotide. The DNA products with unchanged fluorescent signals are identified by inference as being terminated by a C nucleotide. 6. The third cleavage (III) is conducted with THP to cleave the disulfide bond and remove the dye on C, so the change of the signal after the THP treatment confirms the DNA products as being terminated by a C nucleotide. Meanwhile, the THP treatment will also cleave the DTM (SS) bond to regenerate free 3'-OH on all the DNA extension products, which are ready for subsequent cycles of single-color DNA SBS. 7. Steps 1 to 6 are repeated to continue subsequent cycles of single-color DNA SBS.

One-Color DNA SBS Using a Reduced Number of Selective Cleavage Reactions to Remove the Dye (FIG. 19)

Figure 18A:
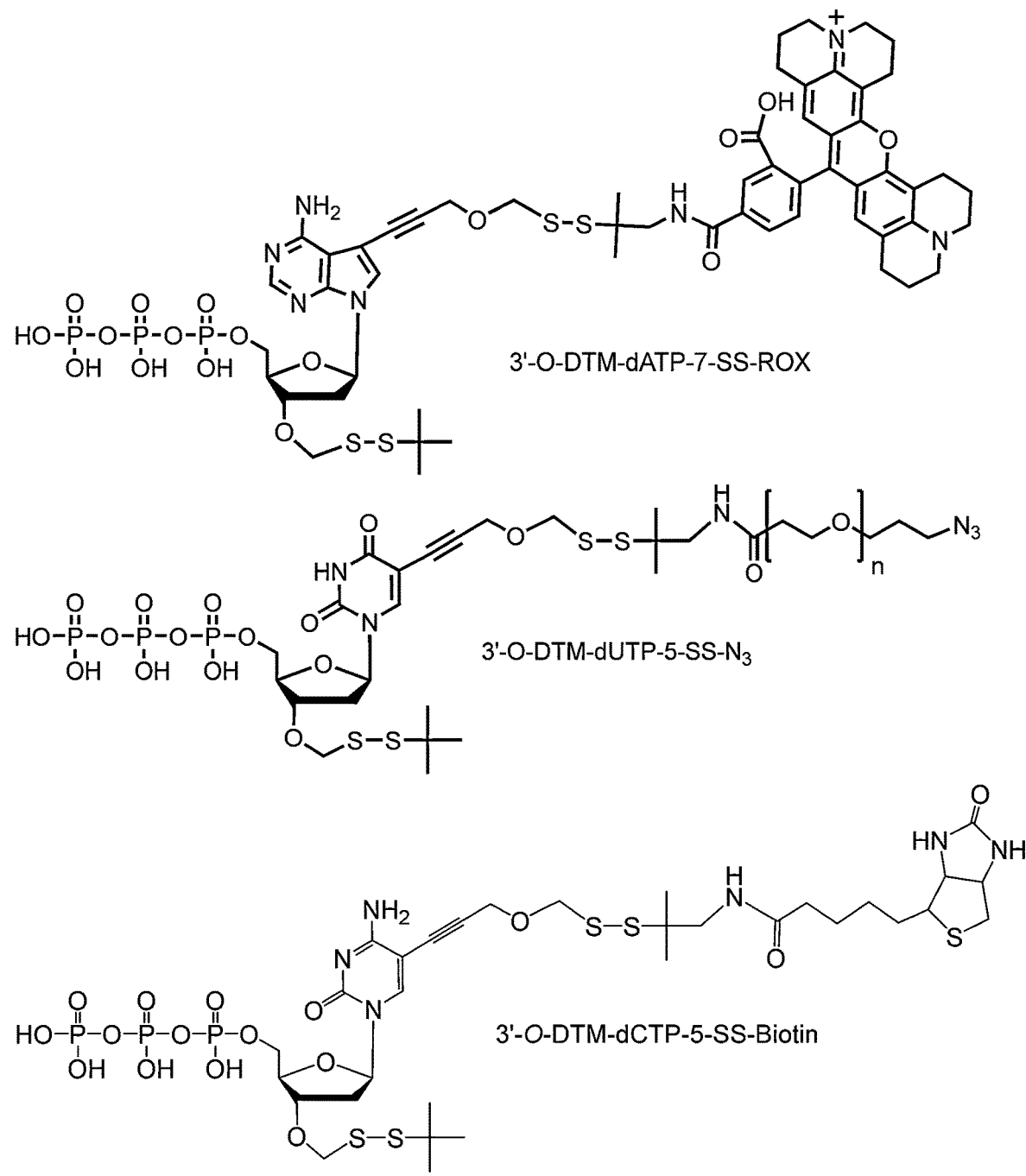
FIGS. 18A-18B. Sample structures of 3'-O-DTM-dNTP-SS-Dyes (3'-O-DTM-dATP-7-SS-Rox), 3'-O-SS (DTM)-dNTP-SS-"anchors" (3'-O-DTM-dUTP-5-SS-$N_3$ and 3'-O-DTM-dCTP-5-SS-Biotin) along with their corresponding Labeled Binding Molecules [DBCO-Azo(—N═N-Linker)-Rox and Streptavidin-Rox] conjugated with one fluorescent dye via different cleavable linkers in combination with 3'-O-t-Butyl-SS(DTM)-dGTP (3'-O-SS-dGTP) for performing one-color SBS at the single-molecule level or at the ensemble level.
Figure 18B:
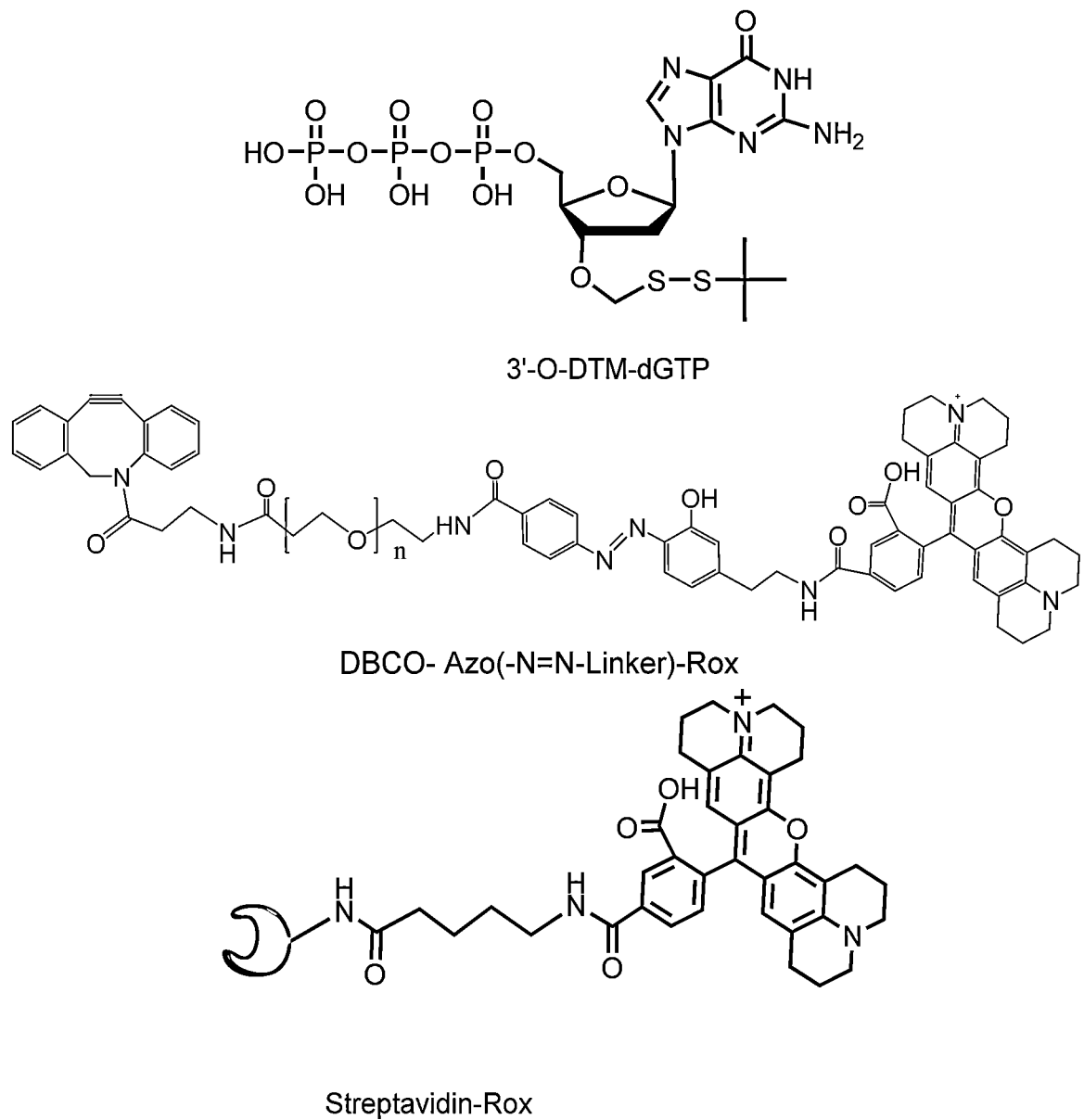

In the presence of DNA polymerase, two nucleotides with an anchor on the base [(3'-O-SS(DTM)-dUTP-SS-$N_3$, 3'-O-SS(DTM)-dCTP-SS-Biotin)], 3'-O-SS(DTM)-dATP-SS-Rox and 3'-O-t-Butyl-SS(DTM)-dGTP, shown in FIG. 18] are added to the primed DNA templates to allow incorporation into the primer.

After washing, the first round of imaging is performed, and the DNA products terminated with an A nucleotide analogue display the Rox signal and therefore are determined as having incorporated an A nucleotide, while the other DNA products terminated at G, C, T will not display any fluorescent signals.

The fluorescent label (Rox, for example) is attached to the DNA by adding DBCO-Azo-(—N═N-Linker)-Rox and Streptavidin-Rox (as shown in FIG. 18) to the DNA extension products that contain the incorporated anchor modified nucleotide analogues, which leads to the labeling of all the incorporated nucleotides (except G) on the base at their 3'-end due to specific anchor-binding molecule interaction.

After washing, the second round of imaging is performed, and the DNA products are terminated with A, C and T all display the same Rox signal, while the DNA products that do not emit a signal are terminated by a G nucleotide.

The first cleavage (I) is conducted by treatment with sodium dithionite ($Na_2S_2O_4$), which only cleaves the azo linkage to remove the fluorescent dye Rox from the DNA products terminated with the T nucleotide. The second round of imaging is performed. If the Rox fluorescent signal disappears after cleavage I, the DNA products are determined as having incorporated a T nucleotide.

The second cleavage (11) is conducted with THP to cleave the disulfide bond and remove the dye from the DNA extension products terminated with nucleotides A and C, so the change of the signal after the THP treatment determines the DNA products as being terminated by a C nucleotide, because DNA products terminated by an A have already being determined in the first round of imaging described above. Meanwhile, the THP treatment will also cleave the DTM (SS) bond to regenerate free 3'-OH on all the DNA extension products, which are ready for subsequent cycles of single-color DNA SBS. Steps 1 to 6 are repeated to continue subsequent cycles of single-color DNA SBS.

Figure 20A:
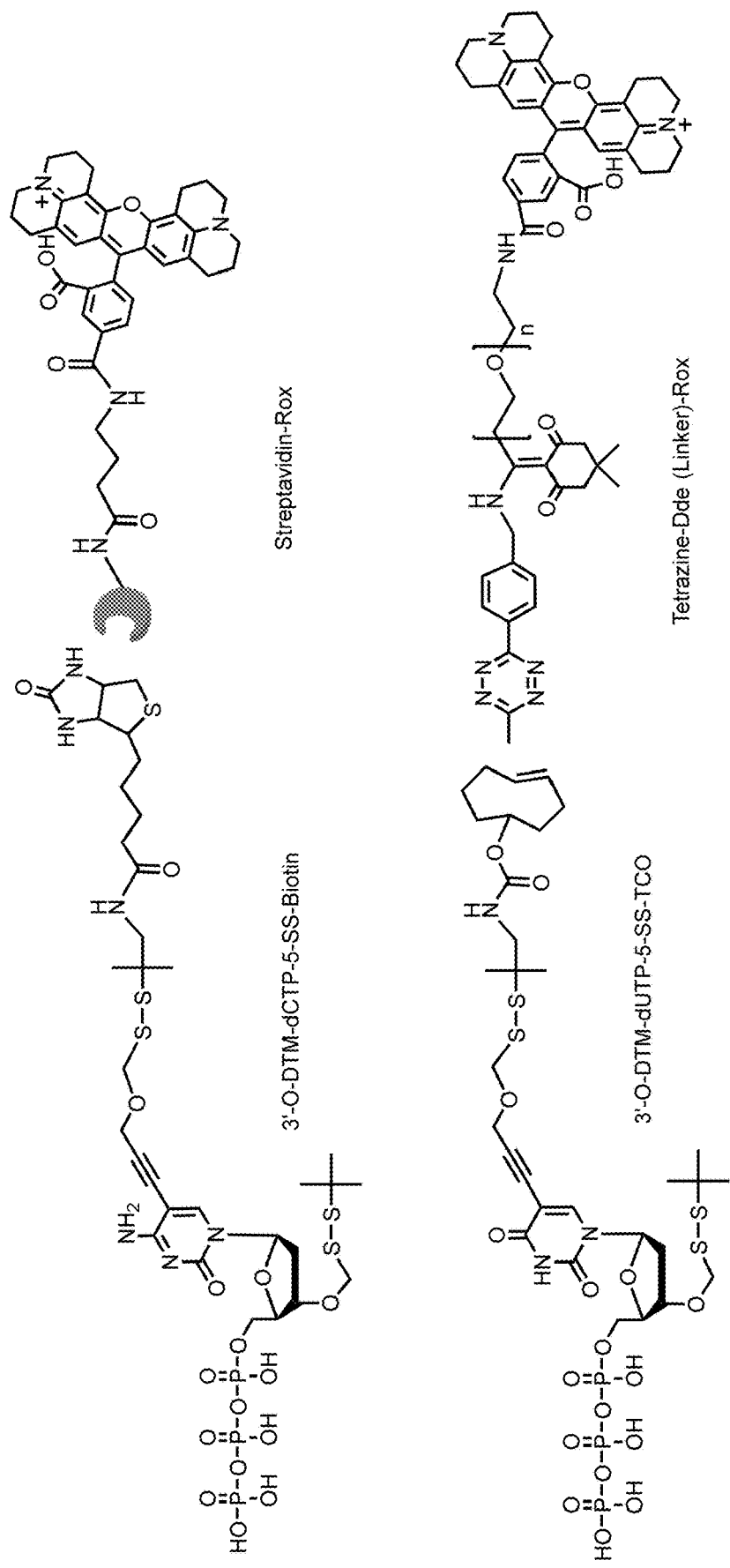
FIGS. 20A-20B. Sample structures of 3'-O-DTM-dNTP-SS-Dye (3'-O-DTM-dATP-7-SS-Rox), 3'-O-SS(DTM)-dNTP-SS-"anchors" (3'-O-DTM-dUTP-5-SS-TCO, 3'-O-DTM-dCTP-5-SS-Biotin and 3'-O-DTM-dGTP-7-SS-$N_3$) along with their corresponding Labeled Binding Molecules [Tetrazine-Dde(Linker)-Rox, Streptavidin-Rox and DBCO-Azo(—N=N-Linker)-Rox] conjugated with one fluorescent dye via different cleavable linkers for performing one-color SBS at the single-molecule level or at the ensemble level.
Figure 20B:
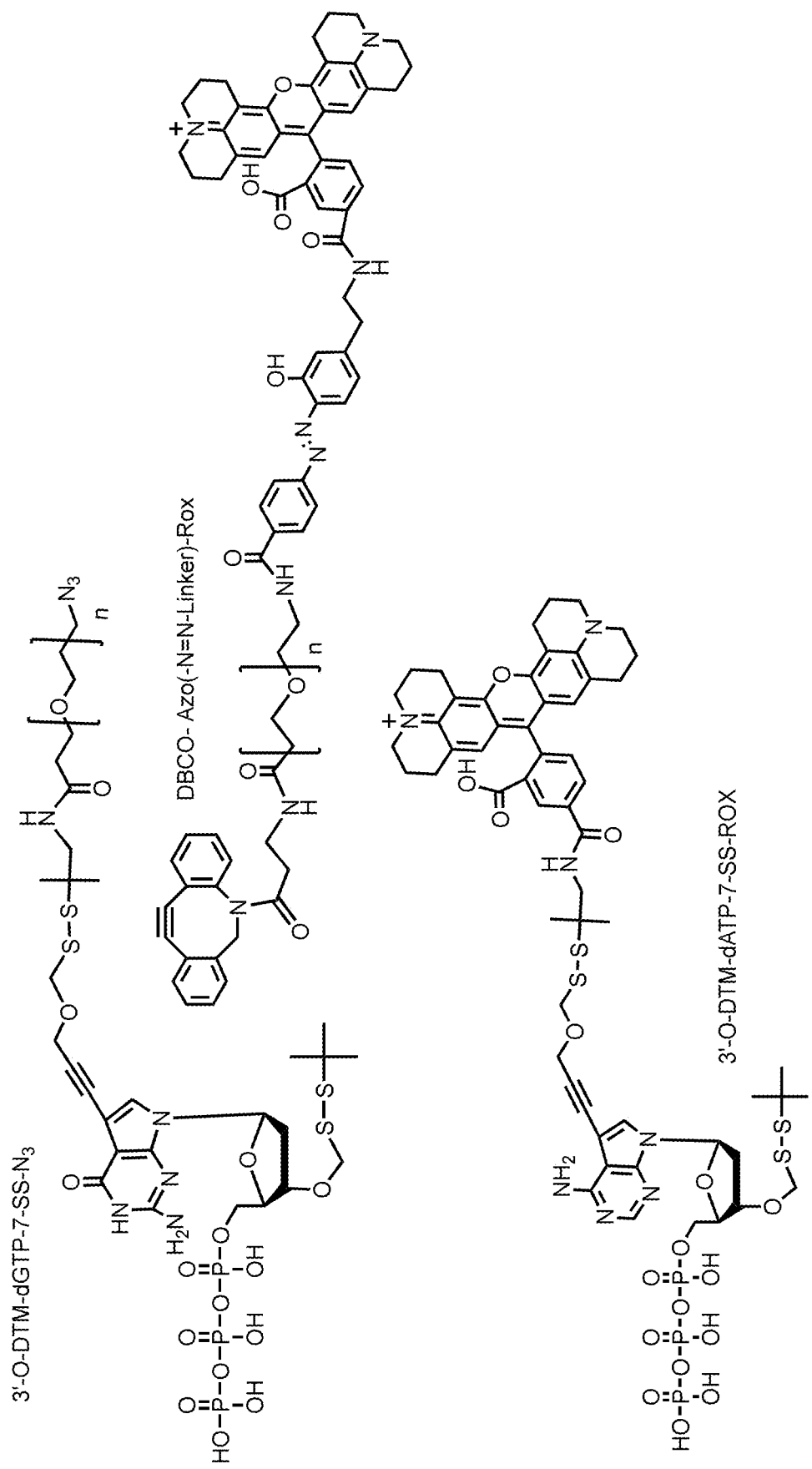
Figure 21A:
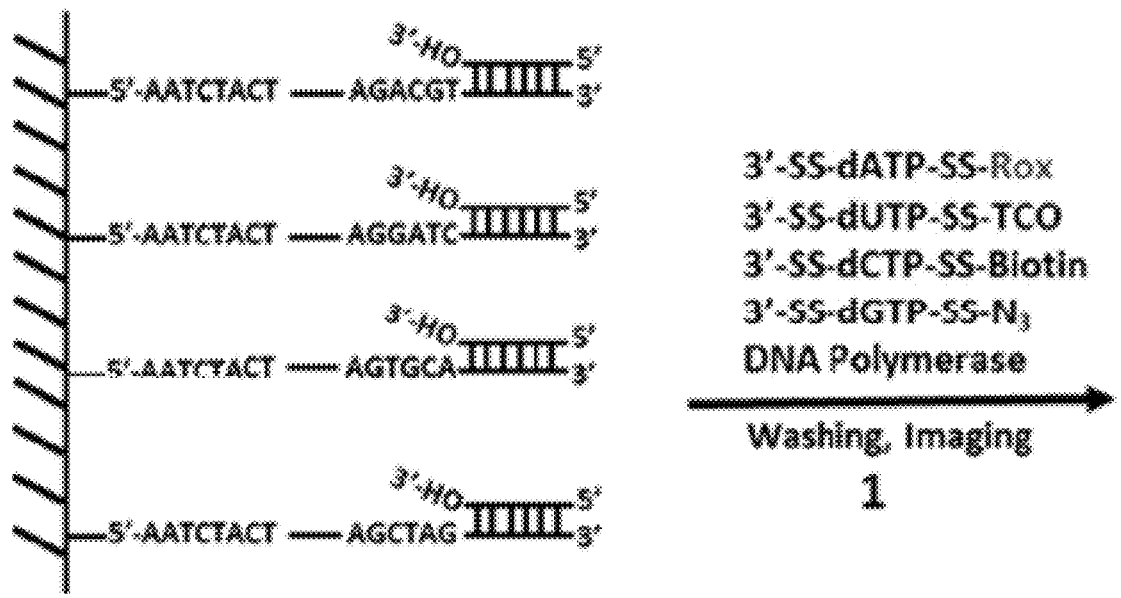
FIGS. 21A-21F. One color SBS reaction scheme approach 3: (1) In the presence of DNA polymerase, three anchor labeled nucleotides (3'-O-DTM-dUTP-5-SS-TCO, 3'-O-DTM-dCTP-5-SS-Biotin and 3'-O-DTM-dGTP-7-SS-$N_3$) and 3'-O-DTM-dATP-7-SS-Rox, as shown in FIG. 20] are added to the primed DNA templates to allow incorporation into the primer; (2) After washing, the first round of imaging is performed, and the DNA products terminated with an A nucleotide analogue display the Rox signal and therefore are determined as having incorporated an A nucleotide, while the other DNA products terminated at G, C, T will not display any fluorescent signals; (3) The fluorescent label (Rox, for example) is attached to DNA by adding DBCO-Azo-(—N=N-Linker)-Rox, Tetrazine-Dde-Rox and Streptavidin-Rox (as shown in FIG. 20) to the DNA extension products that contain the incorporated anchor labeled nucleotide analogues, which leads to the labeling of all the incorporated nucleotides due to specific anchor-binding molecule interaction; (4) After washing, the second round of imaging is performed, and the DNA products terminated with A, G, T, C all display the same Rox signal. Subtraction of the Rox signals from the DNA products determined in the first round of imaging as being terminated at an A nucleotide reveals the DNA products terminated at G, T, C; (5) The first cleavage (I) is conducted by treatment with sodium dithionite ($Na_2S_2O_4$), which only cleaves the azo linkage to remove the fluorescent dye Rox from the DNA products terminated with the G nucleotide. The second round of imaging is performed. If the Rox fluorescent signal disappears after cleavage I, the DNA products are determined as having incorporated a G nucleotide; (6) The second cleavage (II) is conducted with hydrazine ($N_2H_4$), which will cleave the Dde linkage to remove the fluorescent dye Rox from the DNA products terminated with the T nucleotide. The third round of imaging is performed. If the Rox fluorescent signal disappears after cleavage II, the DNA products are determined as having incorporated a T nucleotide. If the Rox fluorescent signal stays after cleavage II, the DNA products are determined as having incorporated a C nucleotide; (7) The third cleavage (III) is conducted with THP to cleave the disulfide bond and remove the Rox dye from the DNA extension products terminated with nucleotides A and C, so the change of the signal after the THP treatment confirms the DNA products as being terminated by a C nucleotide, because DNA products terminated by an A nucleotide have already being determined in the first round of imaging described above. Meanwhile, the THP treatment will also cleave the DTM (SS) bond to regenerate free 3'-OH on all the DNA extension products, which are ready for subsequent cycles of single-color DNA SBS. Steps 1 to 7 are repeated to continue subsequent cycles of single-color DNA SBS.
Figure 21B:
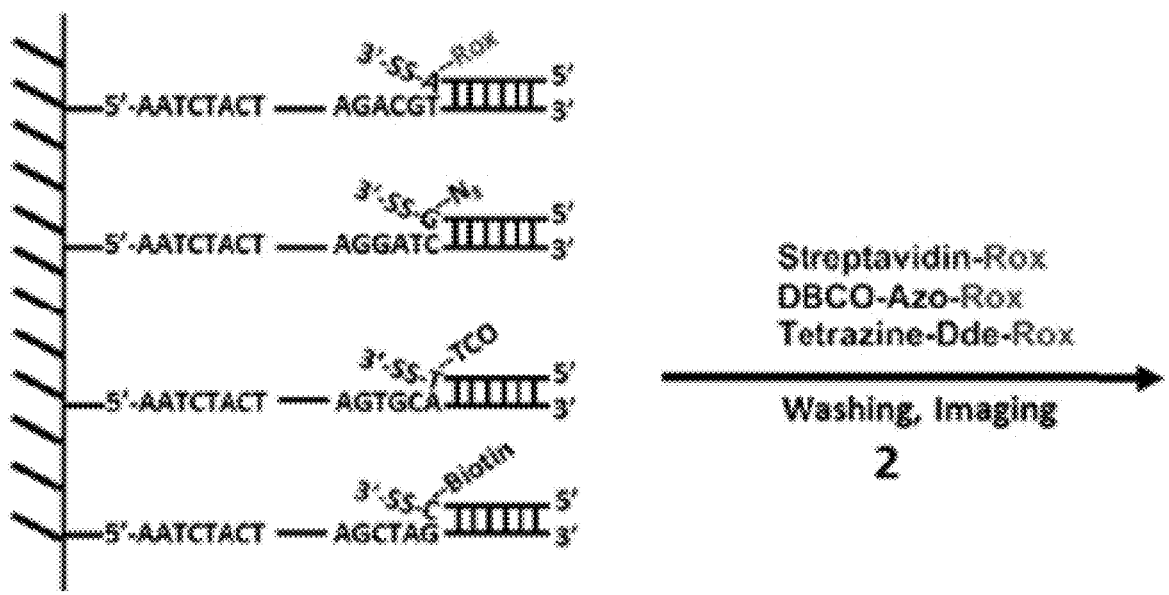
Figure 21C:
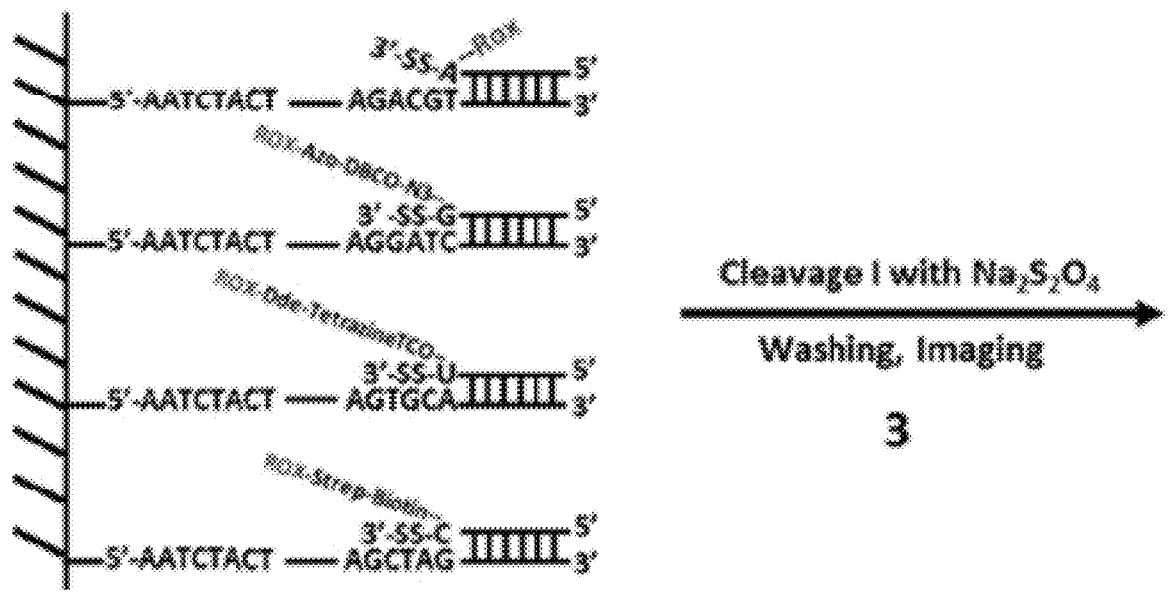
Figure 21D:
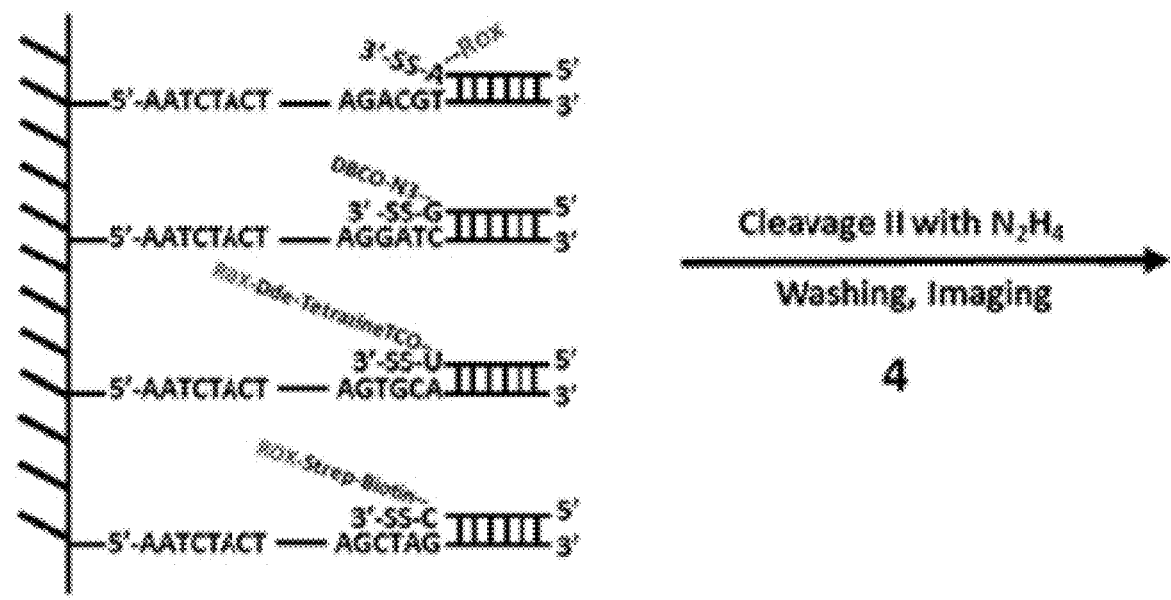
Figure 21E:
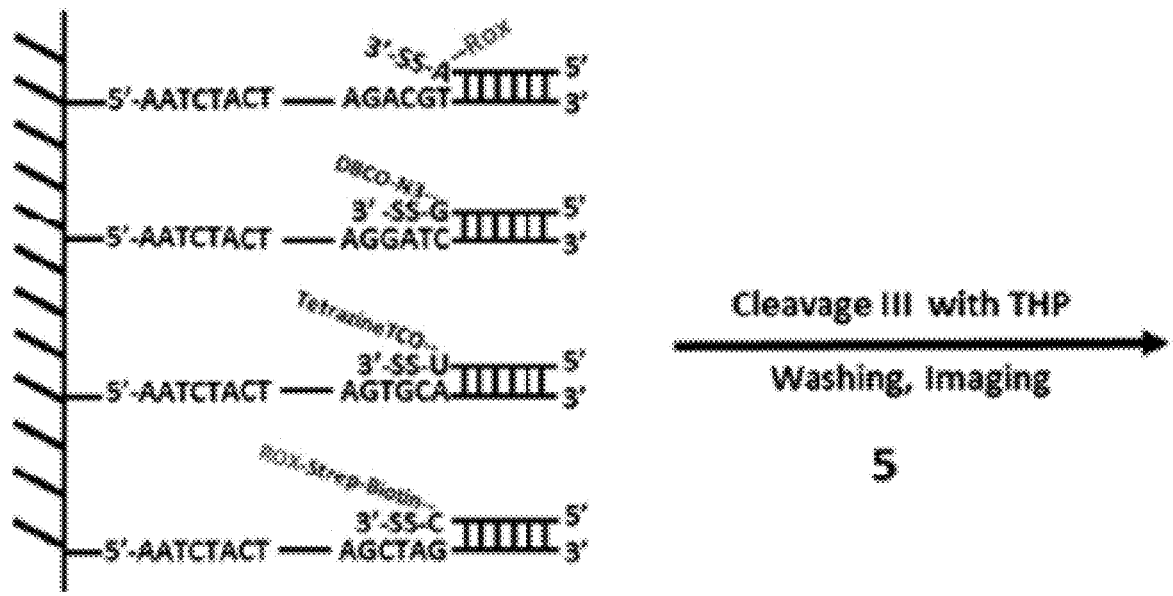
Figure 21F:
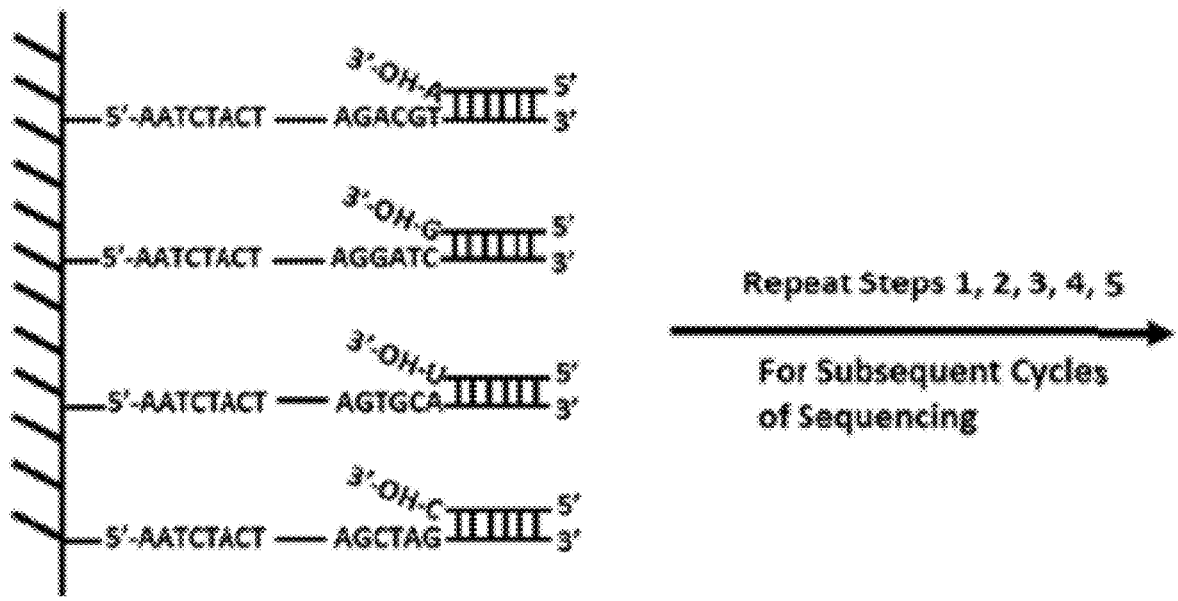

One-Color DNA SBS with All Labeled Nucleotides Using Selective Linker Cleavage to Remove the Dye (FIGS. 21A-21F). 1. In the presence of DNA polymerase, three anchor modified nucleotides [3'-O-SS(DTM)-dGTP-SS-$N_3$, 3'-O-SS(DTM)-dCTP-SS-Biotin, 3'-O-SS(DTM)-dUTP-SS-TCO)] and 3'-O-SS(DTM)-dATP-SS-Rox, as shown in FIGS. 20A-20B] are added to the primed DNA templates to allow incorporation into the primer. 2. After washing, the first round of imaging is performed, and the DNA products terminated with an A nucleotide analogue display the Rox signal and therefore are determined as having incorporated an A, while the other DNA products terminated at G, C, T will not display any fluorescent signals. 3. The fluorescent label (Rox, for example) is attached to the DNA by adding DBCO-Azo-(—N═N-Linker)-Rox, Tetrazine-Dde-Rox and Streptavidin-Rox (shown in FIGS. 20A-20B) to the DNA extension products that contain the incorporated anchor nucleotide analogues, which leads to the labeling of all the incorporated nucleotides at their base due to specific anchor-binding molecule interaction. 4. After washing, the second round of imaging is performed, and the DNA products terminated with A, G, T, C all display the same Rox signal. Subtraction of the Rox signals from the DNA products determined in the first round of imaging as terminated at an A nucleotide reveals the DNA products terminated at G, T, C. 5. The first cleavage (I) is conducted by treatment with sodium dithionite ($Na_2S_2O_4$), which only cleaves the azo linkage to remove the fluorescent dye Rox from the DNA products terminated with the G nucleotide. The second round of imaging is performed. If the Rox fluorescent signal disappears after cleavage I, the DNA products are determined as having incorporated a G nucleotide. 6. The second cleavage (II) is conducted with hydrazine ($N_2H_4$), which will cleave the Dde linkage to remove the fluorescent dye Rox from the DNA products terminated with the T nucleotide. The third round of imaging is performed. If the Rox fluorescent signal disappears after cleavage II, the DNA products are determined as having incorporated a T nucleotide. If the Rox fluorescent signal stays after cleavage II, the DNA products are determined as having incorporated a C nucleotide. 7. The third cleavage (III) is conducted with THP to cleave the disulfide bond and remove the Rox dye from the DNA extension products terminated with nucleotides A and C, so the change of the signal after the THP treatment verifies the DNA products as been terminated by a C nucleotide, because DNA products terminated by an A nucleotide have already being determined in the first round of imaging described above. Meanwhile, the THP treatment will also cleave the DTM (SS) bond to regenerate free 3'-OH on all the DNA extension products, which are ready for subsequent cycles of single-color DNA SBS. Steps 1 to 7 are repeated to continue subsequent cycles of single-color DNA SBS.

Figure 22:
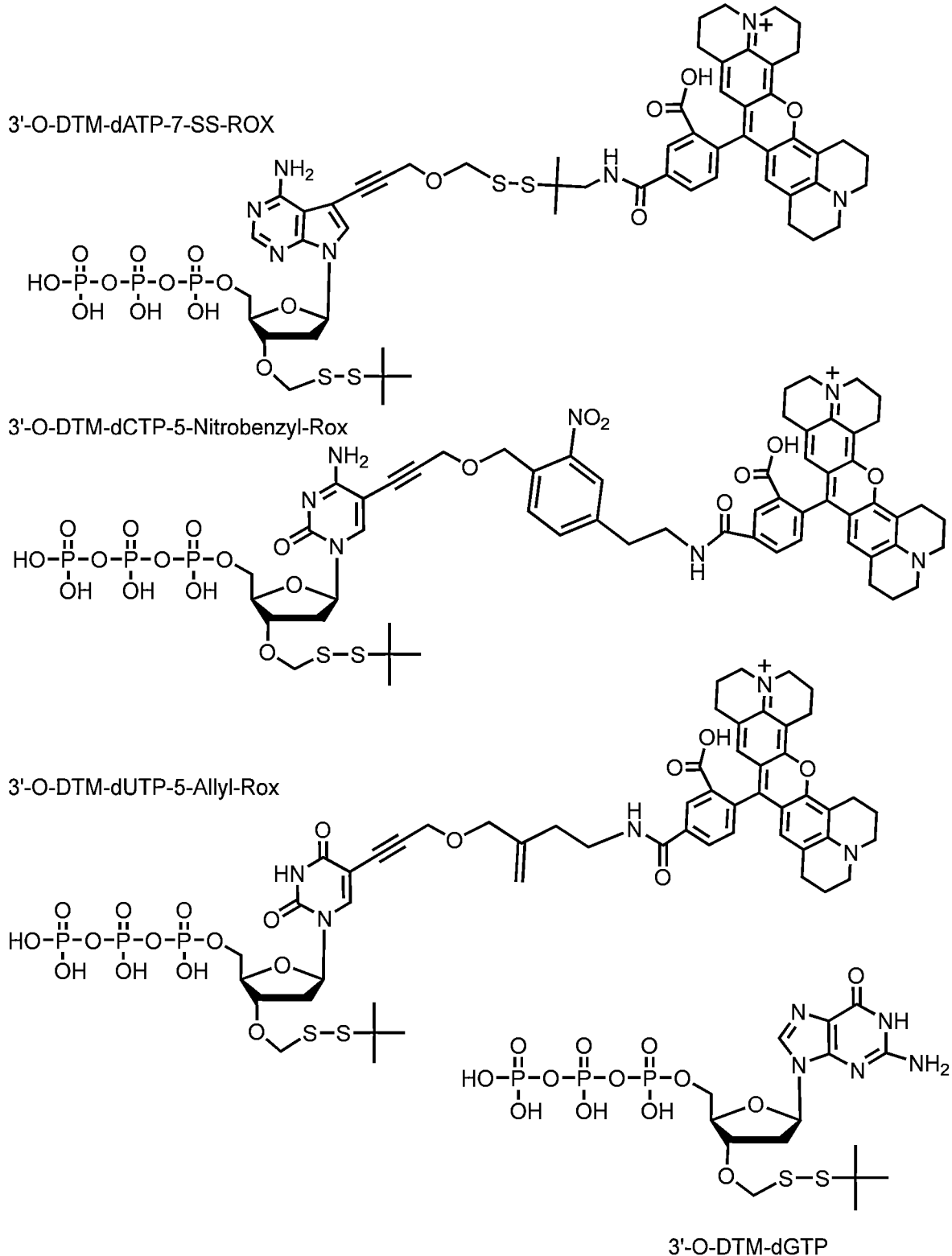
FIG. 22. Structures of 3'-O-SS-dNTP-CleavableLinker-Dye (3'-O-DTM-dATP-7-SS-Rox, 3'-O-DTM-dCTP-5-Nitrobenzyl-Rox and 3'-O-DTM-dUTP-5-Allyl-Rox) and 3'-O-SS(DTM)-dGTP.
Figure 23A:
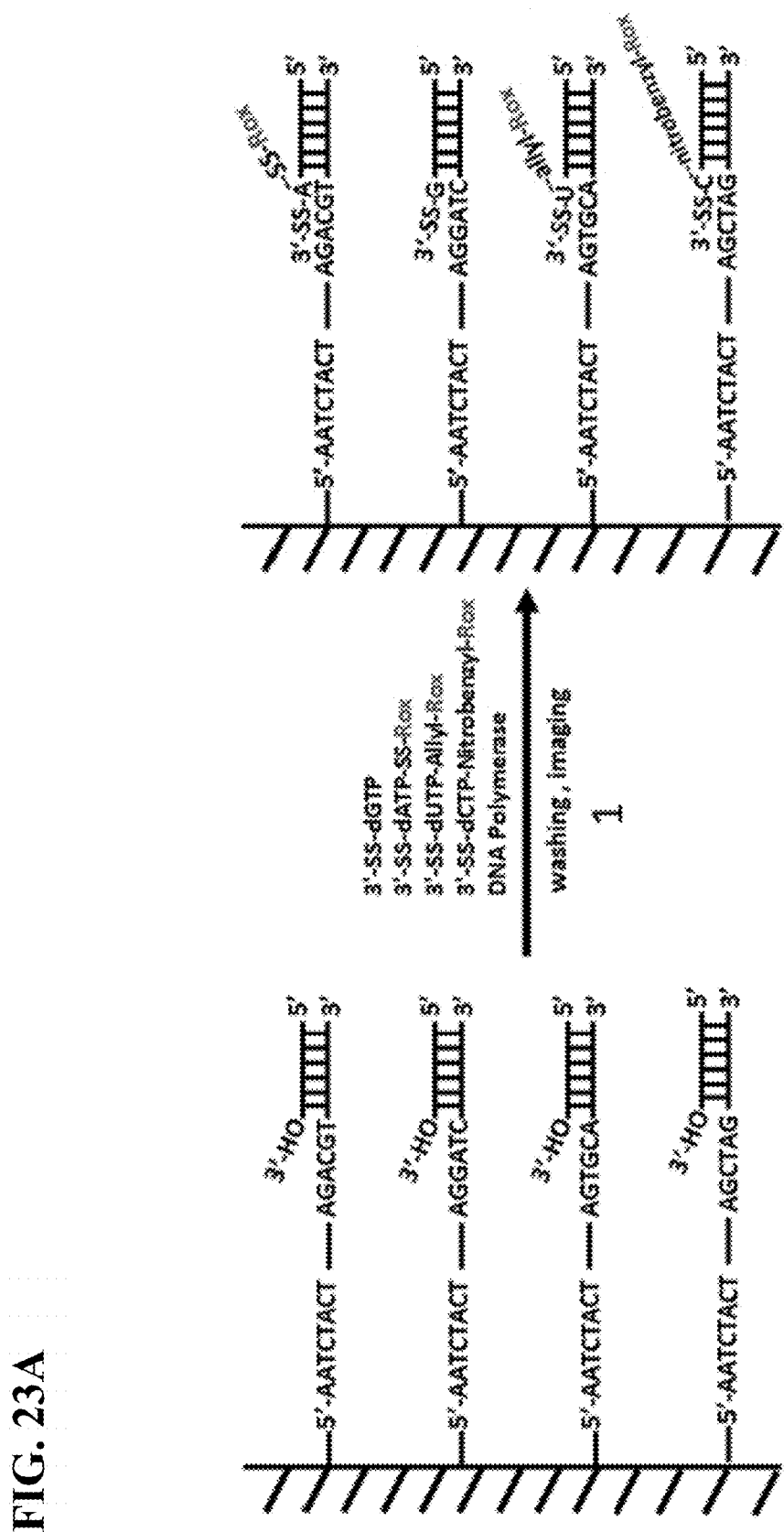
FIGS. 23A-23D. One color SBS reaction scheme approach 4: (1) In the presence of DNA polymerase, the three 3'-O-DTM-dNTP-CleavableLinker-Dyes (3'-O-DTM-dATP-7-SS-Rox, 3'-O-DTM-dCTP-5-Nitrobenzyl-Rox and 3'-O-DTM-dUTP-5-Allyl-Rox) and 3'-O-tButyl-SS-dGTP, as shown in FIG. 22] are added to the primed DNA templates to allow incorporation into the primer; (2) After washing, the first round of imaging is performed, and the DNA products terminated with C, T and A all display the same Rox signal, while the DNA products that do not emit a signal are terminated by the nucleotide G; (3) The first cleavage (I) is conducted by photo-irradiation at ~350 nm to remove the fluorescent dye Rox from the DNA products terminated with the C nucleotide. The second round of imaging is performed. If the Rox fluorescent signal disappears after cleavage I, the DNA products are determined as having incorporated a C nucleotide; (4) The second cleavage (II) is conducted with Pd (0), which will cleave the allyl linkage to remove the fluorescent dye Rox from the DNA products terminated with the T nucleotide. The third round of imaging is performed. If the Rox fluorescent signal disappears after cleavage II, the DNA products are determined as having incorporated a T nucleotide. If the Rox fluorescent signal remains after cleavage II, the DNA products are determined as having incorporated an A nucleotide; (5) The third cleavage (III) is conducted with THP to cleave the disulfide bond and remove the Rox dye from the DNA extension products terminated with nucleotide A, so the change of the signal after the THP treatment confirms the DNA products as being terminated by an A nucleotide. Meanwhile, the THP treatment will also cleave the DTM (SS) bond to regenerate free 3'-OH on all the DNA extension products, which are ready for subsequent cycles of single-color DNA SBS. Steps 1 to 4 are repeated to continue subsequent cycles of single-color DNA SBS FIGS. 24A-24B. Structures of Four 3'-O-SS-dNTP-(SS) CleavableLinker-Dyes and 3'-O-SS-dNTP Used for Four Color Sequencing. (Sequencing data using these nucleotides are shown in FIG. 32.)
Figure 23B:
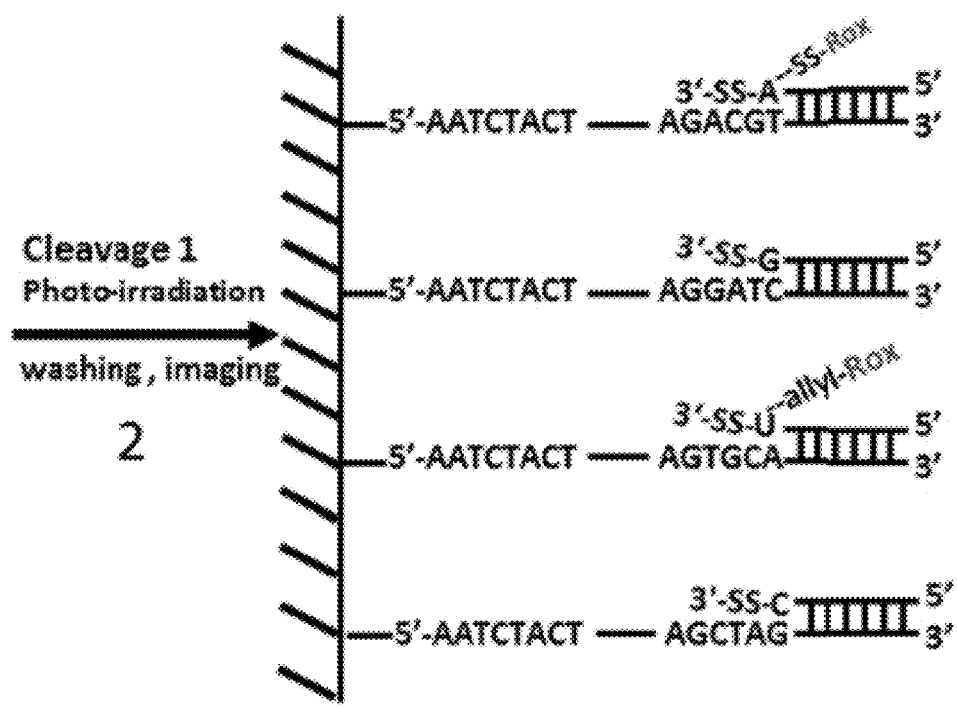
Figure 23C:
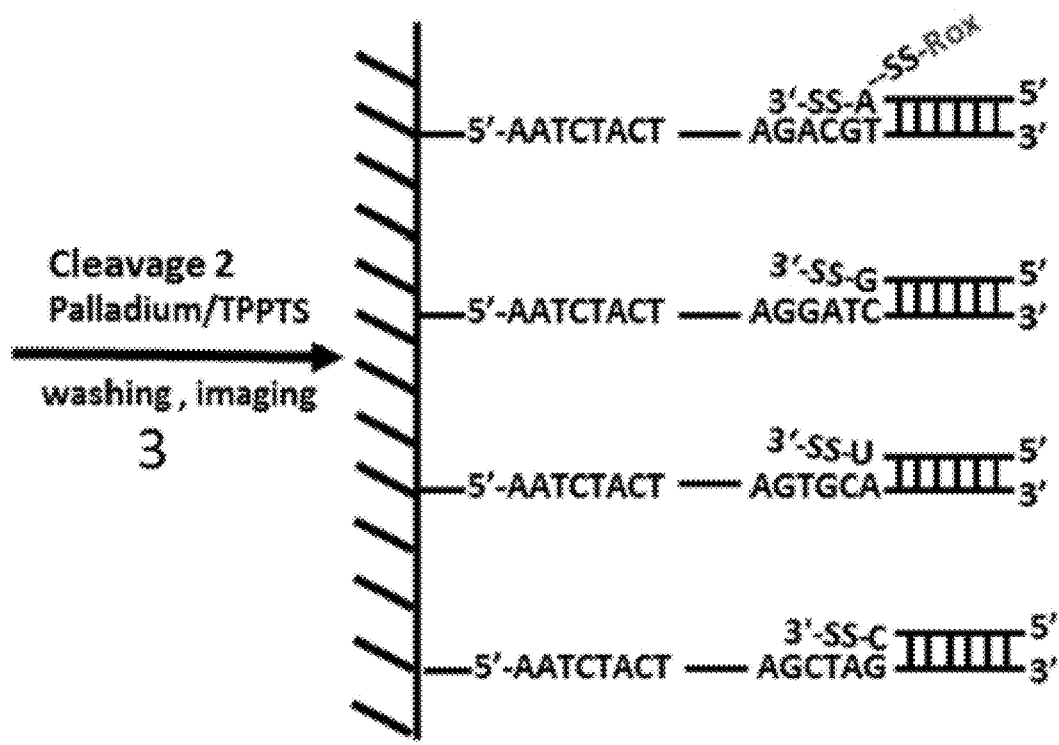
Figure 23D:
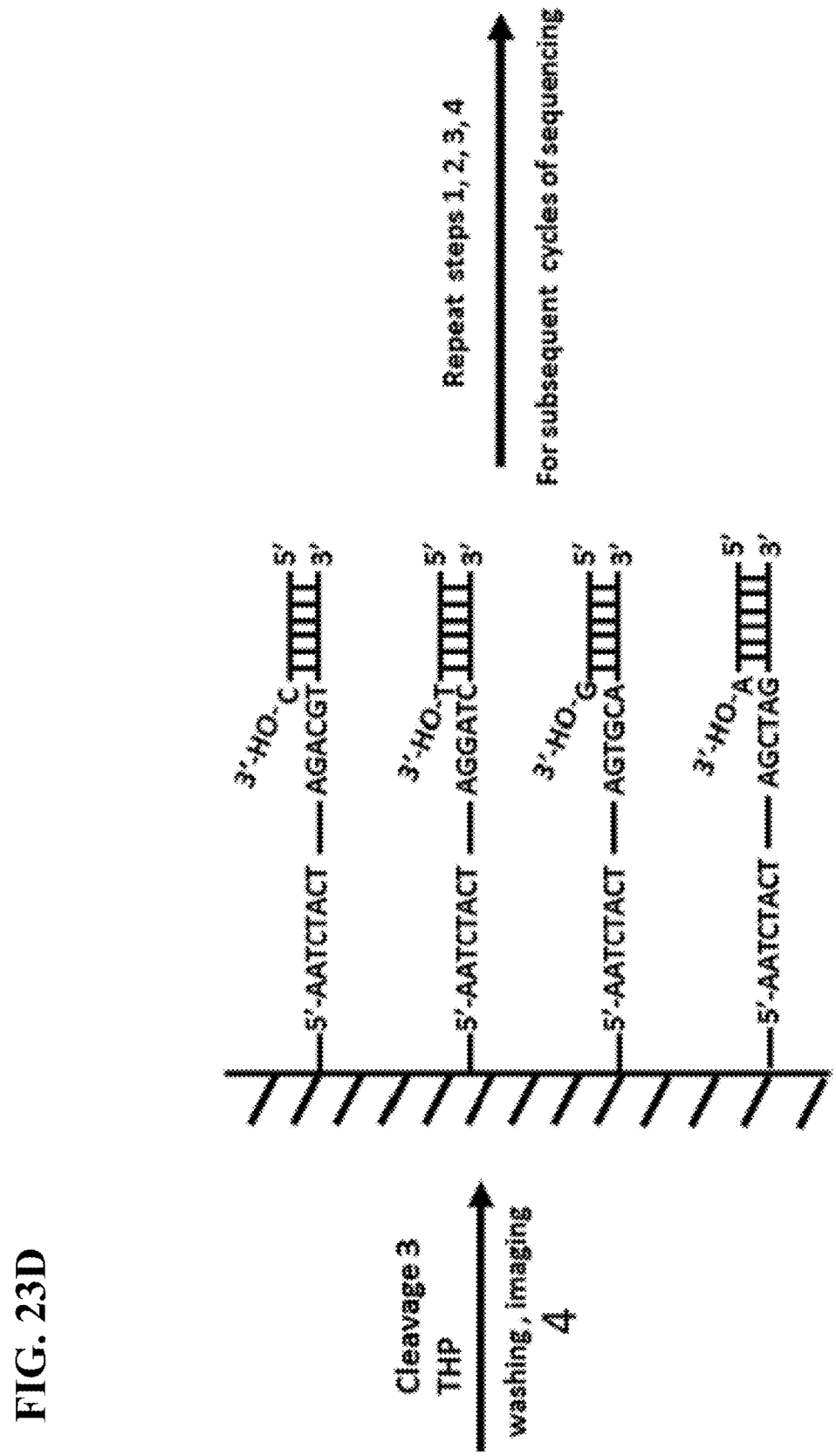

One-Color DNA SBS Using Uniquely Cleavable Dye Labeled dNTPs (FIGS. 23A-23D). 1. In the presence of DNA polymerase, the three 3'-O-CleavableGroup-dNTPs-CleavableLinker-Label [3'-O-SS(DTM)-dATP-SS-Rox, 3'-O-SS(DTM)-dUTP-Allyl-Rox, 3'-O-SS(DTM)-dCTP-Nitrobenzyl-Rox] and 3'-O-tButyl-SS-dGTP, as shown in FIG. 22] are added to the primed DNA templates to allow incorporation into the primer. 2. After washing, the first round of imaging is performed, and the DNA products terminated with C, T and A all display the same Rox signal, while the DNA products that do not emit a signal are terminated by a G. 3. The first cleavage (I) is conducted by photo-irradiation at ~350 nm to remove the fluorescent dye Rox from the DNA products terminated with the C nucleotide. The second round of imaging is performed. If the Rox fluorescent signal disappears after cleavage the DNA products are determined as having incorporated a C nucleotide. 4. The second cleavage (II) is conducted with Pd (0), which will cleave the allyl linkage to remove the fluorescent dye Rox from the DNA products terminated with the T nucleotide. The third round of imaging is performed. If the Rox fluorescent signal disappears after cleavage II, the DNA products are determined as having incorporated a T nucleotide. If the Rox fluorescent signal stays after cleavage II, the DNA products are determined as having incorporated an A nucleotide. 5. The third cleavage (III) is conducted with THP to cleave the disulfide bond and remove the Rox dye from the DNA extension products terminated with nucleotide A, so the change of the signal after the THP treatment verifies the DNA products as being terminated by an A. Meanwhile, the THP treatment will also cleave the DTM (SS) bond to regenerate free 3'-OH on all the DNA extension products, which are ready for subsequent cycles of single-color DNA SBS. Steps 1 to 4 are repeated to continue subsequent cycles of single-color DNA SBS.

All of the above example sequencing methods can be modified by including a chasing step[8,10] with unlabeled nucleotide reversible terminators, for instance by using the 3'-O-t-Butyl-SS-dNTPs described herein. In this procedure, 3'-O-t-Butyl-SS-dNTPs will be used to run polymerase extension after each step of the polymerase extension reaction using 3'-O-CleavableGroup-dNTPs-CleavableLinker-Label and 3'-O-CleavableGroup-dNTPs-CleavableLinker-Anchor to ensure complete primer extension at the 3'-end for ensemble SBS.

Four-Color DNA SBS with Chasing (FIGS. 25A-25F). A scheme using 3'-O-SS(DTM)-dNTP-SS-Dye (3'-O-t-Butyldithiomethyl(SS)-dATP-SS-Rox, 3'-O-t-Butyldithiomethyl(SS)-dCTP-SS-Alexa488, 3'-O-t-Butyldithiomethyl(SS)-dGTP-SS-Cy5, 3'-O-t-Butyldithiomethyl(SS)-dUTP-SS-R6G) and four 3'-O-t-Butyldithiomethyl(SS)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) (FIGS. 24A-24B) is shown in FIGS. 25A-25F. Step 1, addition of DNA polymerase and the four 3'-O-SS(DTM)-dNTP-SS-Dye (3'-O-t-Butyldithiomethyl(SS)-dATP-SS-Rox, 3'-O-t-Butyldithiomethyl(SS)-dCTP-SS-Alexa488, 3'-O-t-Butyldithiomethyl(SS)-dGTP-SS-Cy5 and 3 Butyldithiomethyl(SS)-dUTP-SS-R6G) to the immobilized primed DNA template enables the incorporation of the complementary dye labeled nucleotide analogue to the growing DNA strand. The growing DNA strand is terminated with each of the four nucleotide analogues (A, C, G, T) with the four distinct fluorescent dyes. Step 2, addition of DNA polymerase and four 3'-O-t-Butyldithiomethyl(SS)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary 3'-O-SS-nucleotide analogue to the growing DNA strand which is not extended with one of the dye labeled 3'-O-t-Butyldithiomethyl(SS)-dNTP in step 1, a process defined as chasing. The growing DNA strands are terminated with one of the four nucleotide analogues (A, C, G, T) with the four distinct fluorescent dyes or the one of the four chase nucleotide analogues (A, C, G, T) without dye. After washing away the unincorporated nucleotide analogues (Step 3), detection of the unique fluorescence signal from each of the fluorescent dyes on the DNA products allows for the identification of the incorporated nucleotide for sequence determination (Step 4). Next, in Step 5, treatment of the DNA products with THP cleaves the SS linker, leading to the removal of the fluorescent dye and the regeneration of a free 3'-OH group on the DNA extension products, which are ready for the next cycle of the DNA sequencing reaction. The chasing NRTs without base modifications are more efficiently incorporated into DNA than the base-labeled NRTs, and after the removal of the 3'-blocking group, there are no scars on the DNA extension products, both of which lead to higher accuracy and long reads.

Four-Color DNA SBS without Chasing (FIGS. 26A-26F). A scheme using 3'-O-SS(DTM)-dNTP-SS-Dye (3'-O-t-Butyldithiomethyl(SS)-dATP-SS-Rox, 3'-O-t-Butyldithiomethyl(SS)-dCTP-SS-Alexa488, 3'-O-t-Butyldithiomethyl(SS)-dGTP-SS-Cy5, 3'-O-t-Butyldithiomethyl(SS)-dUTP-SS-R6G) (FIGS. 24A-24B) without chasing is shown in FIGS. 26A-26F. Step 1, addition of the DNA polymerase and the four 3'-O-SS(DTM)-dNTP-SS-Dye (3'-O-t-Butyldithiomethyl(SS)-dATP-SS-Rox, 3'-O-t-Butyldithiomethyl(SS)-dCTP-SS-Alexa488, 3'-O-t-Butyldithiomethyl(SS)-dGTP-SS-Cy5, 3'-O-t-Butyldithiomethyl(SS)-dUTP-SS-R6G) to the immobilized primed DNA template enables the incorporation of the complementary nucleotide analogue to the growing DNA strand. The growing DNA strand is terminated with each of the four nucleotide analogues (A, C, G, T) labeled with the four distinct fluorescent dyes. After washing (Step 2) to remove unincorporated dye labeled nucleotide analogues, detection of the unique fluorescent signal (Step 3) from each of the fluorescent dyes on the DNA products allows for the identification of the incorporated nucleotide for sequence determination. Next, in Step 4, treatment of the DNA products with THP cleaves the SS linker, leading to the removal of the fluorescent dye and the regeneration of a free 3'-OH group on the DNA extension product, which is ready for the next cycle of the DNA sequencing reaction.

Figure 24A:
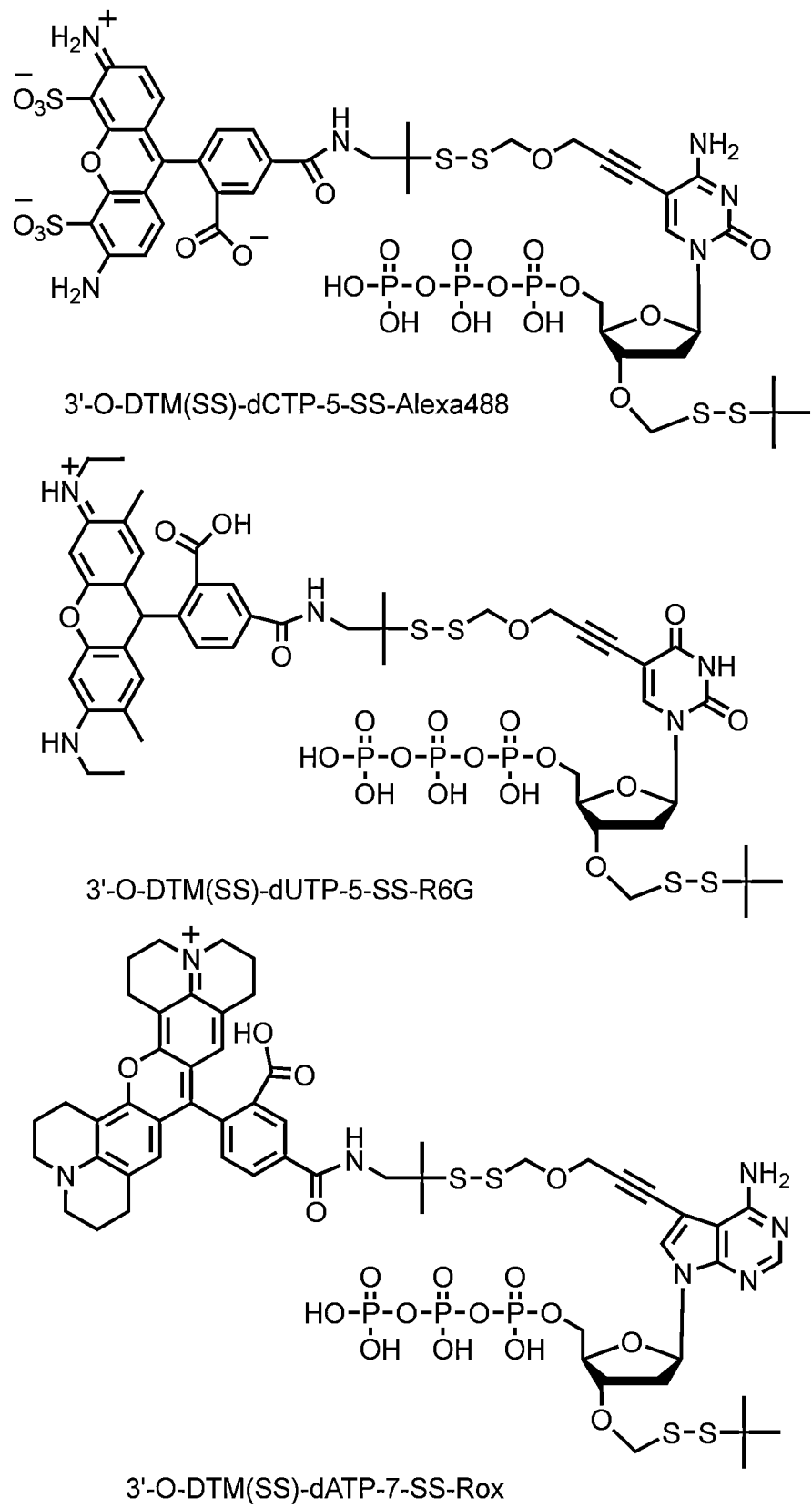
Figure 25A:
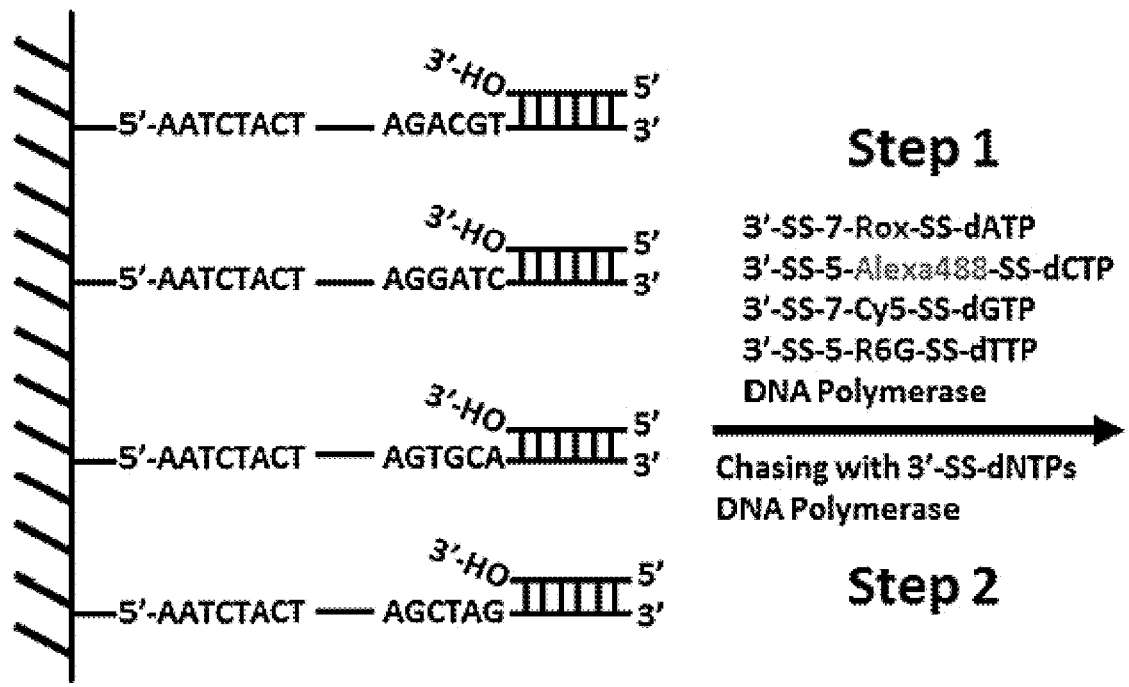
FIGS. 25A-25F. Four color SBS with chasing. SBS using 3'-O-SS(DTM)-dNTP-SS-Dye (3'-O-t-Butyldithiomethyl (SS)-dATP-SS-Rox, 3'-O-t-Butyldithiomethyl(SS)-dCTP-SS-Alexa488, Butyldithiomethyl(SS)-dGTP-SS-Cy5, 3'-O-t-Butyldithiomethyl(SS)-dUTP-SS-R6G) (FIG. 24) and four 3'-O-t-Butyldithiomethyl(SS)-dN'TPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) (FIG. 24). Step 1, Labeling: addition of the DNA polymerase and the four 3'-O-SS(DTM)-dNTP-SS-Dye (3'-O-t-Butyldithiomethyl(SS)-dATP-SS-Rox, 3'-O-t-Butyldithiomethyl(SS)-dCTP-SS-Alexa488, 3'-O-t-Butyldithiomethyl(SS)-dGTP-SS-Cy5 and 3'-O-t-Butyldithiomethyl(SS)-dUTP-SS-R6G) to the immobilized primed DNA template enables the incorporation of the complementary dye labeled nucleotide analogue to the growing DNA strand, the growing DNA strand is terminated with each of the four nucleotide analogues (A, C, G, T) with the four distinct fluorescent dyes. Step 2, Chase: addition of the DNA polymerase and four 3'-O-t-Butyldithiomethyl (SS)-dNTPs (3'-O-t-Butyldithiomethyl(SS)-dATP, 3'-O-t-
Figure 25B:
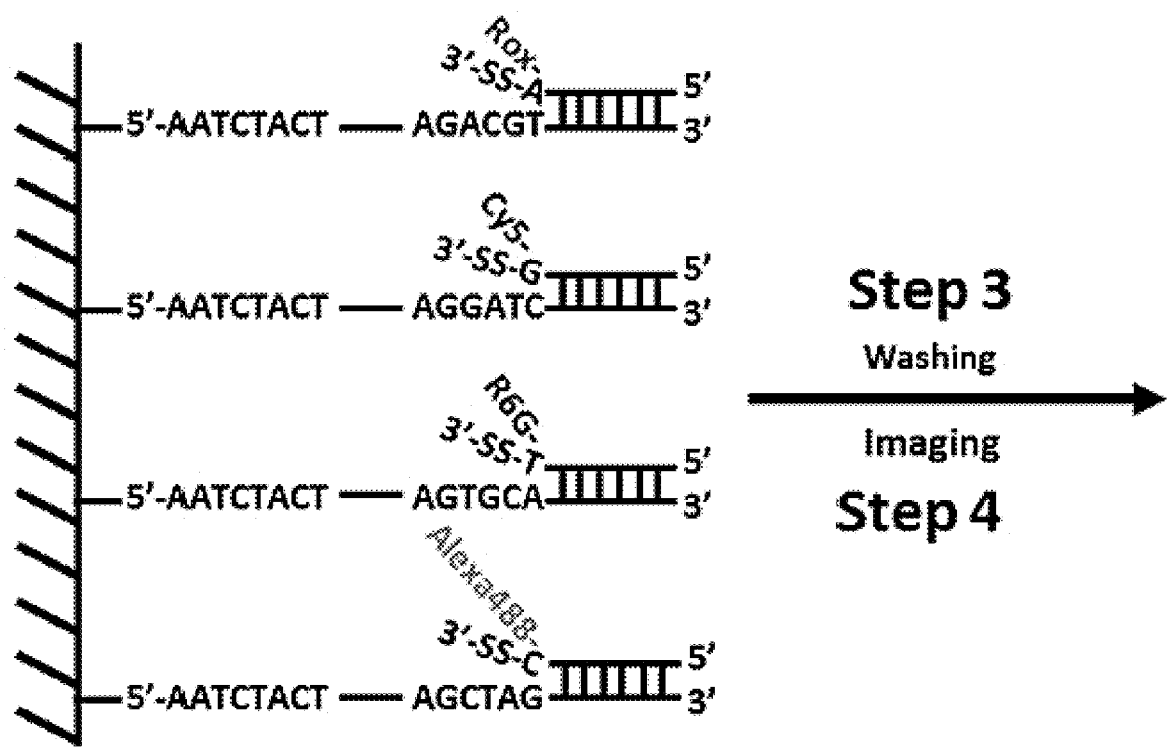
Figure 25C:
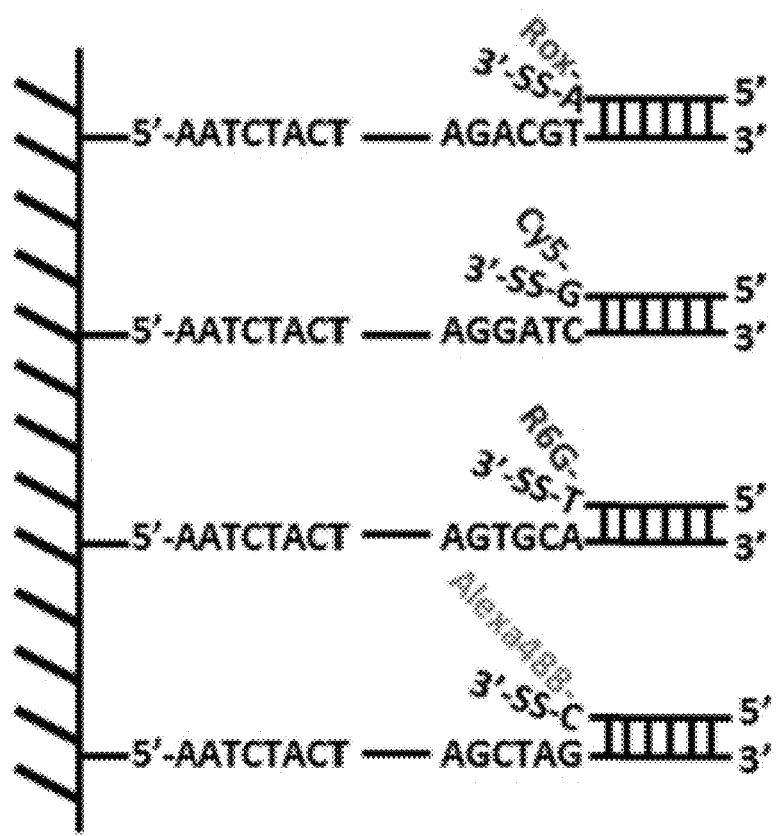
Figure 25D:
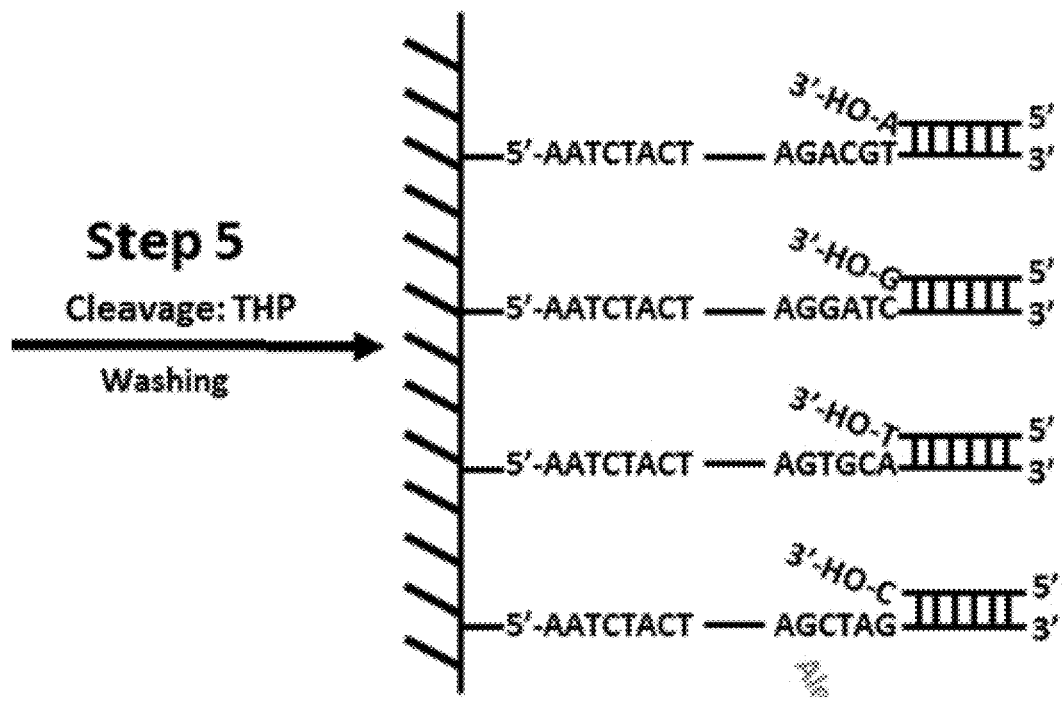
Figure 25E:
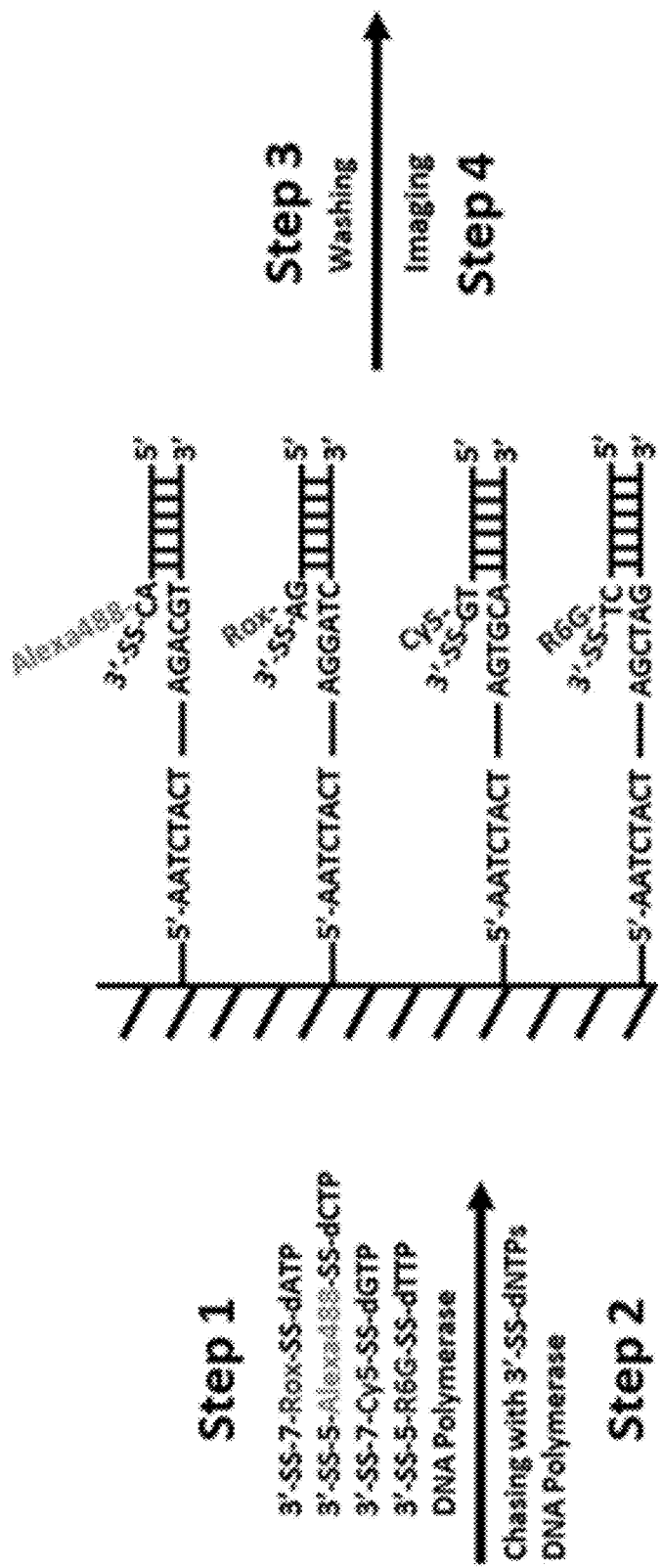
Figure 25F:
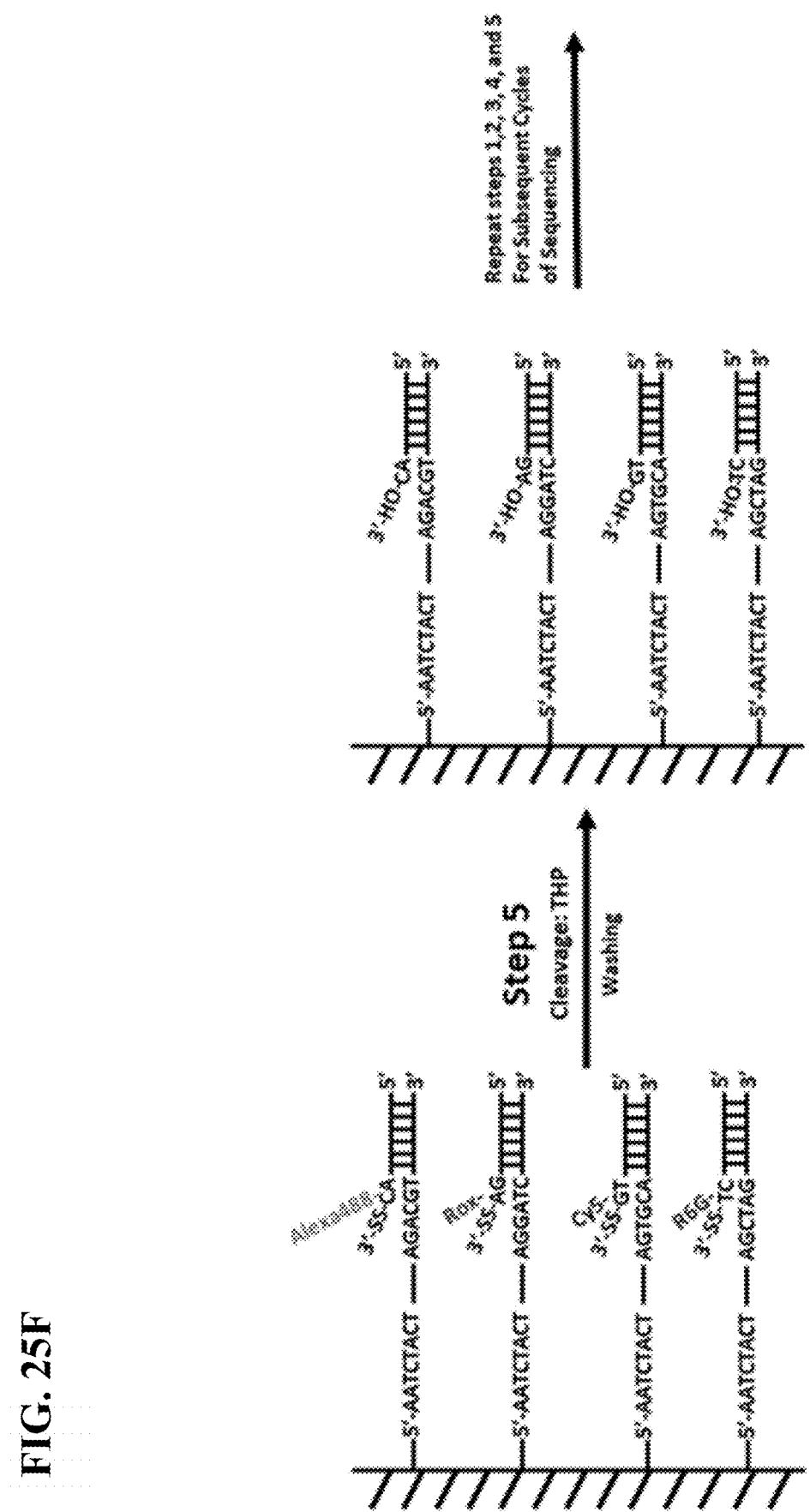
Figure 26A:
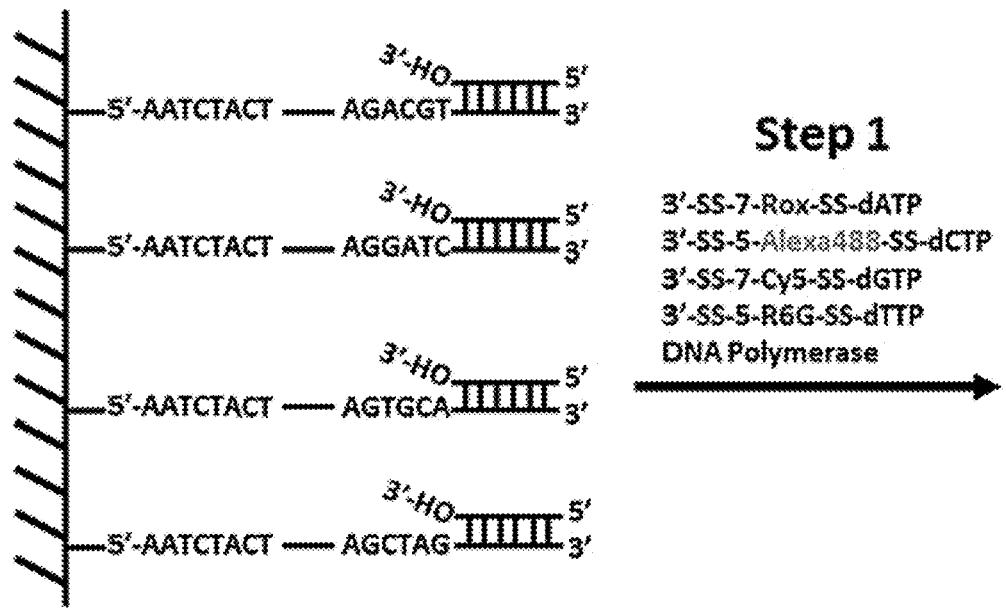
Figure 26B:
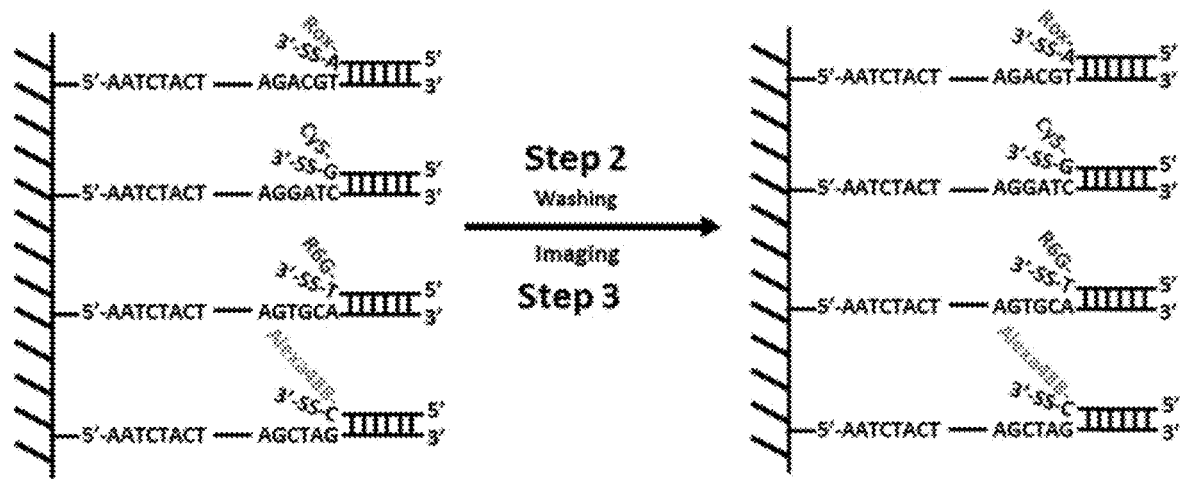
Figure 26C:
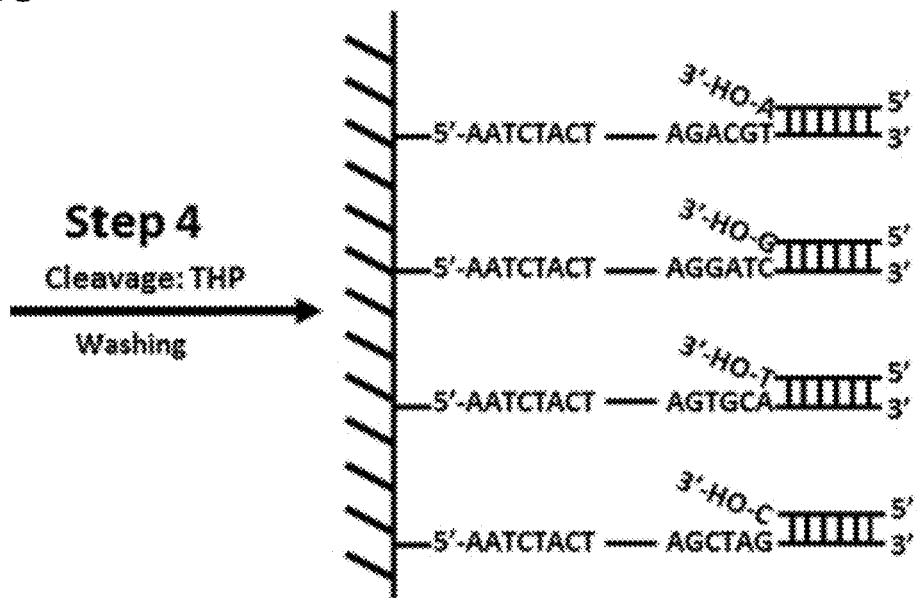
Figure 26D:
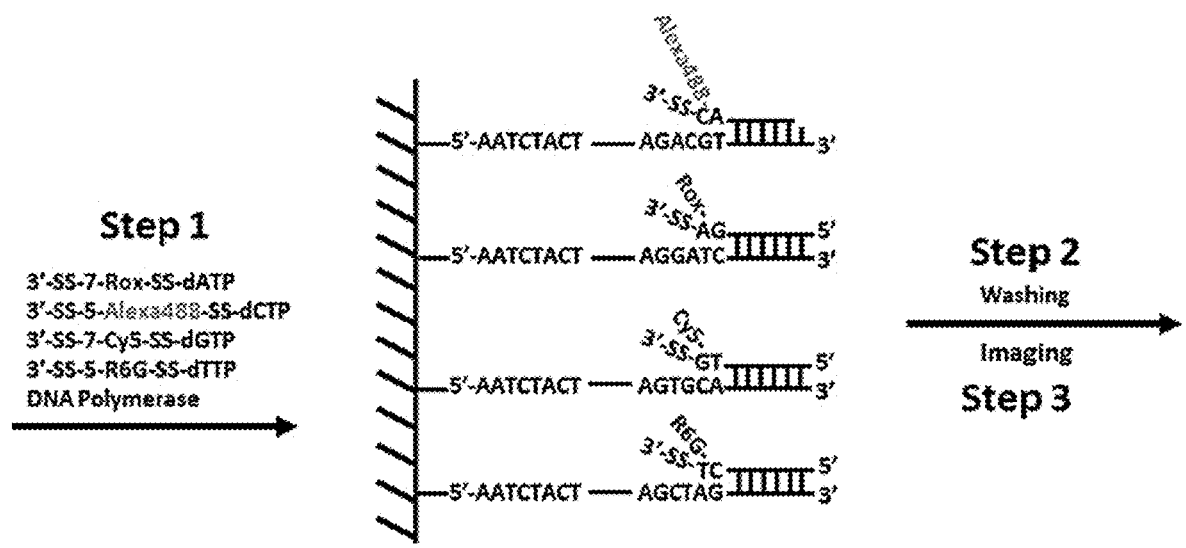
Figure 26E:
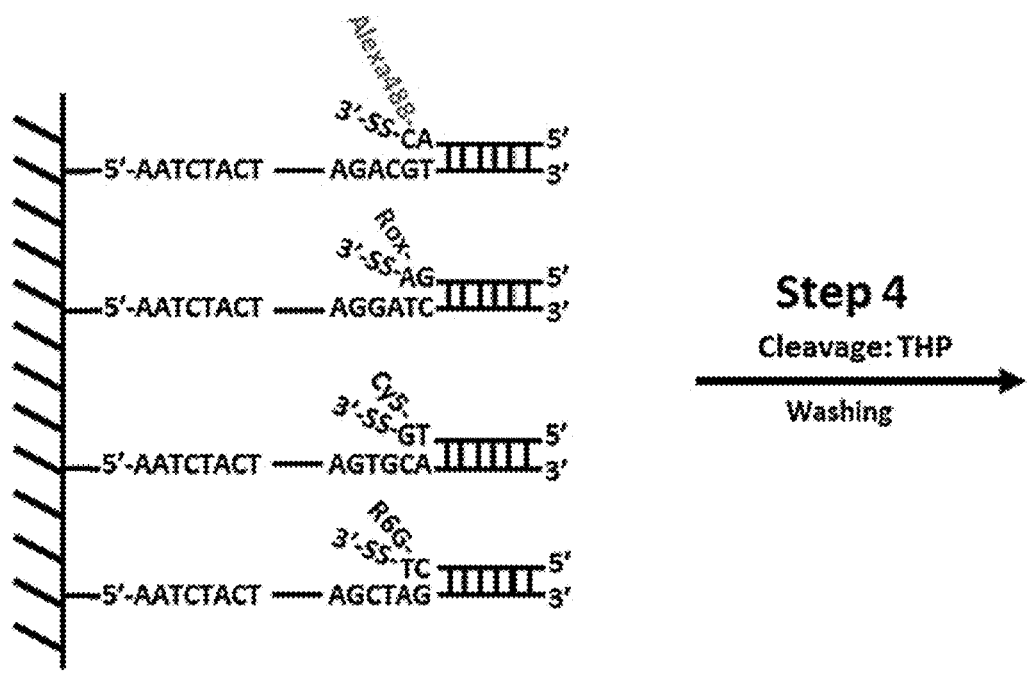
Figure 26F:
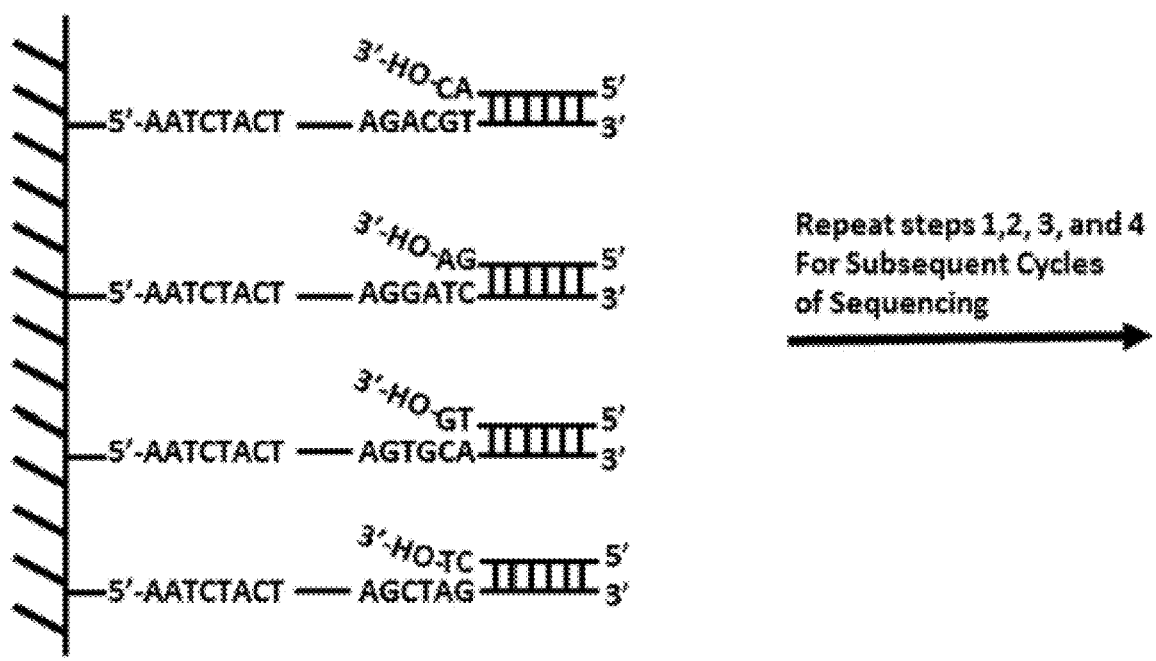

Four-Color DNA SBS with mixed labeled and unlabeled reversible terminators (FIG. 27A-27B). SBS using 3'-O-SS(DTM)-dNTP-SS-Dye (3'-O-t-Butyldithiomethyl(SS)-dATP-SS-Rox, 3'-O-t-Butyldithiomethyl(SS)-dCTP-SS-Alexa488, 3'-O-t-Butyldithiomethyl(SS)-dGTP-SS-Cy5, 3'-O-t-Butyldithiomethyl(SS)-dUTP-SS-R6G) and four 3'-O-t-Butyldithiomethyl(SS)-dNTPs (3'-O-t-Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) (FIGS. 24A-24B). Step 1, addition of the DNA polymerase, the four 3'-O-SS(DTM)-dNTP-SS-Dye ((3'-O-t-Butyldithiomethyl(SS)-dATP-SS-Rox, 3'-O-t-Butyldithiomethyl(SS)-dCTP-SS-Alexa488, 3'-O-t-Butyldithiomethyl(SS)-dGTP-SS-Cy5, 3'-O-t-Butyldithiomethyl(SS)-dUTP-SS-R6G) and four 3'-O-t-Butyldithiomethyl(SS)-dNTPs (3 Butyldithiomethyl(SS)-dATP, 3'-O-t-Butyldithiomethyl(SS)-dCTP, 3'-O-t-Butyldithiomethyl(SS)-dTTP and 3'-O-t-Butyldithiomethyl(SS)-dGTP) to the immobilized primed DNA template enables the incorporation of the complementary nucleotide analogue to the growing DNA strand. The ratio of the labeled and unlabeled NRTs can range from below 1:9 to above 9:1. The growing DNA strand is terminated with each of the four nucleotide analogues (A, C, G, T) with the four distinct fluorescent dyes or without dye labeling. After washing away (Step 2) the unincorporated nucleotide analogues, detection of the unique fluorescent signal (Step 4) from each of the fluorescent dyes on the DNA products allows for the identification of the incorporated nucleotide. Next, in Step 4, treatment of the DNA products with THP cleaves the SS linker, leading to the removal of the fluorescent dye and the regeneration of a free 3'-OH group on the DNA extension product, which is ready for the next cycle of the DNA sequencing reaction.

A combined walking and sequencing approach to obtain longer total read length using a combination of labeled and unlabeled NRTs (FIGS. 28A-28B). A walking approach is designed to obtain longer runs of sequence than would be achievable with SBS alone. Among the issues that might prevent long reads are the presence of chemical "scars" on the bases of the incorporated nucleotides, which will eventually prevent further extension, and the inevitable loss of synchronization in ensemble SBS, even with chase-style "fill-in" reactions. Briefly, as schematized in FIGS. 28A-28B, sequencing by synthesis reactions are carried out to the desired length (30-100 or more nucleotides), for instance by using any of the above described strategies (1-color, 2-color or 4-color) and nucleotide analogues, or any other SBS sequencing approaches. Subsequently, the extended primer is stripped from the template strand and the original primer is re-annealed to it. Next, three natural nucleotides and one reversible terminator (dATP, dCTP, dTTP and 3'-O-t-butyl-SS-dGTP as an example), all without any fluorescent labels, are used to extend the primer to the position of the next base in the template that is complementary to the reversible terminator (a C in this example). After cleavage of the blocking group (with THP in this example) to regenerate the 3' OH group, an identical extension reaction is performed to reach the subsequent C in the template, and the resulting 3' blocking group is again removed. Repeated rounds of walking and cleavage will be used to approach the position where the first sequencing round ended (this is estimated based on the percent G's in the genome being sequenced). A second round of SBS with fluorescent NRTs is then carried out to obtain a further sequence stretch. If desired, the denaturation step is then repeated to strip off the extended primer and replace it again with the original primer. A new round of walking is carried out to reach the end of the second sequence stretch. This process can be repeated several times, resulting in a sequence twice, three times or higher-fold than that obtained in one round of sequencing. The blocking nucleotide for the walking steps can be replaced with an alternative one (e.g., 3'-O-t-butyl-SS-dATP along with dCTP, dGTP and dTTP, etc.). Alternative variants could include the use of two, three or four 3'-blocked nucleotide with two, one or zero natural nucleotides. Importantly, the walking steps will result in extension of the primer with only natural nucleotides, so very long walks to reach the appropriate vicinity for the third or fourth round of sequencing should not be problematic. An actual series of walking steps with one 3'-O-DTM blocked nucleotide and three natural nucleotides is shown in FIG. 31.

Polymerase extension using reversible terminators 3'-SS-dATP-SS-Rox, 3'-SS-dCTP-SS-Alexa488, 3'-SS-dGTP-SS-Cy5, and 3'-SS-dUTP-SS-R6G and characterization by MALDI-TOF mass spectrometry (FIGS. 29A-29H). Extension reactions were carried out using 200 pmol of reversible terminator, 2 units of Therminator IX DNA Polymerase (NEB), 20 pmol of DNA primer (MM. 6084), 100 pmol of DNA template in 20 µl buffer containing 20 mM Tris-HCl, 10 mM (NH$_4$)$_2$SO$_4$, 10 mM KCl, 2 mM MgSO$_4$, 0.1% Triton X-100, pH 8.8 @25° C., and 2 mM MnCl$_2$. The reactions were conducted in an ABI GeneAmp PCR System 9700 with initial incubation at 65° C. for 30 second, followed by 38 cycles of 65° C./30 sec, 45° C./30 sec, 65° C./30 sec. The reaction mixtures were desalted using Oligo Clean & Concentrator™ (ZYMO Research) and analyzed by MALDI-TOF MS (ABI Voyager DE). The cleavage reactions were carried out using THP at a final concentration of 5 mM, incubating at 65° C. for 10 minutes, then the reaction mixtures were desalted using Oligo Clean & Concentrator™ (ZYMO Research) and analyzed by MALDI-TOF MS. The results of each individual extension and cleavage are shown in FIGS. 29A-29H, indicating that all these nucleotide analogues are efficient substrates for the polymerase, with complete extension and cleavage.

Each of the four different primers indicated below were designed to allow extension by a different nucleotide (A, C, T or G from top to bottom). Exon8_template (SEQ ID NO:4) was used for A, C and T extensions; Exon7_template (SEQ ID NO:5) was used for G extension. The presence of two identical complementary bases in a row at the extension site on the template was a built-in control to account for any incomplete termination.

```
Exon8_template:
                                       (SEQ ID NO: 4)
5'-AAGGAGACACGCGGCCAGAGAGGGTCCTGTCCGTGTTTGTGCGTGGA

GTTCGACAAGGCAGGGTCATCTAATGGTGATGAGTCCTATCCTTTTCTCT

TCGTTCTCCGT- 3'.

Exon7_template:
                                       (SEQ ID NO: 5)
5'-TACCCGGAGGCCAAGTACGGCGGGTACGTCCTTGACAATGTGTACAT

CAACATCACCTACCACCATGTCAGTCTCGGTTGGATCCTCTATTGTGTCC

GGG-3'.
```

The following 3 primers are used for extension with Exon_8 template: i) 5'-TAGATGACCCTGCCTTGTCG-3' (SEQ ID NO:6); ii) 5'-TCTCTGGCCGCGTGTCT-3'(SEQ ID NO:3); iii) 5'-GATAGGACTCATCACCA-3'(SEQ ID NO:7). The following primer is used for extension with Exon 7 template: 5'-GTTGATGTACACATTGTCAA-3' (SEQ ID NO:8).

Continuous Polymerase Extension Using 3'-O-t-Butyl-SS-dNTPs (3'-O-DTM-dNTPs) and Characterization by MALDI-TOF Mass Spectrometry (FIGS. 30A-30B). To verify that the 3'-O-DTM-dNTPs are incorporated accurately in a base-specific manner in the polymerase reaction, four consecutive DNA extension and cleavage reactions were carried out in solution with 3'-O-DTM-dNTPs as substrates. This allowed the isolation of the DNA product at each step for detailed molecular structure characterization.

We performed a complete consecutive 4-step SBS reaction that involved incorporation of each complementary 3'-O-DTM-dNTP, followed by MALDI-TOF MS analysis for sequence determination, and cleavage of the 3'-O-DTM blocking group from the DNA extension product to yield a free 3'-OH group for incorporating the next nucleotide analogue. A template-primer combination was designed in which the next four nucleotides to be added were A, C, G and T. As shown in FIG. 30, the SBS reaction was initiated with the 13-mer primer annealed to a DNA template. When the first complementary nucleotide, 3'-O-tButyl-SS-dATP (3'-O-DTM-dATP), was used in the polymerase reaction, it was incorporated into the primer to form a DNA extension product with a molecular weight of 4404 Daltons (Da) as confirmed by MALDI-TOF MS with the appearance of a single peak (FIG. 30B (a) Top left). These results indicated that the 3'-O-DTM-dATP was quantitatively incorporated into the 13-mer DNA primer. After THP treatment to remove the DTM group from the DNA product and HPLC purification, the cleavage was confirmed by the presence of a single MS peak at 4272 Da, corresponding to the DNA product with the 3'-O-DTM group removed (FIG. 30B (b)Top right). The newly formed DNA extension product with a free 3'-OH group was then used in a second polymerase reaction to incorporate a 3'-O-t-Butyl-SS-dCTP (3'-O-DTM-dCTP) which gave a single MS peak at 4697 Da (FIG. 30B (c)), indicating incorporation of a 3'-O-DTM-dCTP into the growing DNA strand in this cycle. After THP treatment, a single MS peak of the cleaved DNA product appeared at 4563 Da (FIG. 30B (d)), which demonstrated the complete removal of the DTM group from the DNA extension product.

The third incorporation was with 3'-O-Butyl-SS-dGTP (3'-O-DTM-dGTP); accurate masses of the corresponding DNA products were obtained by MALDI-TOF MS for the third nucleotide incorporation (5024 Da, FIG. 30B (e), and cleavage reaction (4888 Da, FIG. 30B (f)). Finally, 3'-O-tButyl-SS-dTTP (3'-O-DTM-dTTP) incorporation in the fourth cycle and a final removal of the DTM group by THP was verified, as appropriate masses for the corresponding DNA products were obtained by MALDI-TOF MS for the fourth nucleotide incorporation (5328 Da, FIG. 30B (g)) and cleavage reaction (5199 Da, FIG. 30B (h)). These results demonstrate that all four 3'-O-DTM-dNTPs are efficiently incorporated base-specifically as reversible terminators into the growing DNA strand in a continuous polymerase reaction, and that the 3'-OH capping, group on the DNA extension products is quantitatively cleaved by THP.

Experiment demonstrating walking in solution using three natural dNTPs (dATP, dCTP and dTTP) and one 3'-O-t-Butyl-SS-dNTP (3'-O-DTM-dGTP) (FIG. 31). We carried out a series of 3 walking steps using dATP, dCTP, dTTP and 3'-O-t-butyl-SS-dGTP. The results are presented in FIG. 31.

WT49G (5'-CAGCTTAAGCAATGGTA-CATGCCTTGACAATGTGTACATCAACATCACC-3') (SEQ ID NO:10) was designed as template for a $1^{st}$ walk extension of 4 bases on the primer (13mer, 5'-CACATTGT-CAAGG-3') (SEQ ID NO:2), 8 base extension in the $2^{nd}$ walk and 6 base extension in the $3^{rd}$ walk; in each case, the reaction will stop at the first corresponding C on the template (shown in red from right to left in the template). The WT49G template and 13mer primer were designed for efficient characterization of walking by MALDI-TOF mass spectrometry.

The reaction (50 µl) was carried out using 1 µmol of reversible terminator, 1 µmol of dATP, dCTP and dTTP, 500 pmol of primer (MM. 3939), 5 units of Therminator IX DNA Polymerase (NEB), 300 pmol of WT49G in a 5 µl buffer containing 20 mM Tris-HCl, 10 mM $(NH_4)_2SO_4$, 10 mM KCl, 2 mM $MgSO_4$, 0.1% Triton X-100, pH 8.8 @ 25° C., and 100 pmol $MnCl_2$. The reactions were conducted in an ABI GeneAmp PCR System 9700 with initial incubation at 65° C. for 30 seconds, followed by 38 cycles of 65° C./30 sec, 45° C./30 sec, 65° C./30 sec. the reaction mixtures were desalted using Oligo Clean & Concentrator™ (ZYMO Research) and analyzed by MALDI-TOF MS (ABT Voyager DE). The cleavage reaction was carried out using THP at a final concentration of 5 mM incubated at 65° C. for 5 minutes, then the reaction mixtures were desalted using oligo Clean & Concentrator™ (ZYMO Research) and analyzed by MALDI-TOF MS. The results of each individual extension and cleavage are shown in FIG. 31.

After the first walk, the primer was extended to the point of the next C in the template (rightmost C highlighted in red in the template strand). The size of the extension product was 5330 Daltons (5328 Da expected) as shown in the top left MALDI-TOF MS trace. After cleavage with THP, the 5198 Da product shown at the top right was observed (5194 Da expected). A second walk was performed using this extended and cleaved primer, again using Therminator IX DNA polymerase, dATP, dCTP, dTTP and 3'-O-t-butyl-dGTP, to obtain the product shown in the middle left trace (7771 Da observed, 7775 Da expected to reach the middle C). After cleavage, a product of 7643 Da was obtained (expected 7641 Da). Finally a third walk and cleavage using the previously extended and cleaved primer were performed, giving products of 9625 Da (9628 Da expected to extend to the leftmost red highlighted C) and 9513 Da (9493 Da expected), respectively. The amount of nucleotides was adjusted in each walk according to extension length (2 µmol in $2^{nd}$ walk, 1.5 µmol in $3^{rd}$ walk). This demonstrates the ability to use a 3'4)-t-butyl nucleotide as a terminator for walking reactions. These can be incorporated into a combined sequencing and walking scheme such as the one depicted in FIGS. 28A-28B.

Experiment demonstrating four-color SBS on surface-immobilized DNA (FIG. 32). The 5'-amino modified self-priming template DNA (5'-CACTCACATATGTTTTT-TAGCTTTTTTAATTTCTTAATGATGTTGTTGC ATGCTGACCTCAG CTGCACGTAAGTGCAGCT-GAGGTCAG-3') (SEQ ID NO:1) was dissolved in 50 mM sodium phosphate buffer, pH 9.0, at a concentration of 30 µM and spotted on NHS ester-activated CodeLink slides (Surmodics Inc., MN) using a SpotArray 72 microarray-printing robot (PerkinElmer, MA). After spotting, the slides were incubated overnight at 37° C. in a humid chamber containing a solution of saturated sodium chloride to immobilize the DNA. Upon immobilization, unreacted NHS ester groups were quenched by incubating the slides in a solution of 50 mM 3-amino-1-propanol in 100 mM tris-HCl buffer, pH9.0 for 2 hours at ambient temperature. Finally, the slides were briefly rinsed in water, air-dried under compressed air and stored desiccated in a dark container until further use.

The slide was then covered with a silicone isolator and 8 µl of extension mixture containing four reversible terminators (3'-SS-dARP-SS-Rox, 3'-SS-dCTP-SS-Alexa488, 3'-SS-dGTP-SS-Cy5, and 3'-SS-dUTP-SS-R6G) (FIGS. 24A-24B), 5 units of Therminator IX DNA Polymerase (NEB), 1× Thermo Pol Reaction Buffer (NEB). 2 mM $MnCl_2$ was added to the area coated with self-priming DNA template. The slide was incubated at 65° C. for 15 minutes then washed with 1× Thermo Pol Reaction Buffer (NEB), 2 mM $MnCl_2$ twice at room temperature. Eight microliters of a chase mixture containing 1 µM each of 3'-SS-dNTPs (FIGS. 24A-24B), 5 units of Therminator TX DNA Polymerase (NEB), 1× Thermo Pol Reaction Buffer (NEB), 2 mM $MnCl_2$ was then added and incubation carried out at 65° C. for 15 minutes. The silicone isolator was then removed and the slide was washed with SPSS buffer containing 2% Tween 20 at 37° C. for 30 minutes then rinsed with distilled water. Imaging was carried out using a ScanArray Express Microarray Scanner (Perkin Elmer). Four channel scanning using excitation at 488 nm, 543 nm, 594 nm, and 633 nm was performed, and the fluorescence intensity was recorded.

The slide was again covered with a silicone isolator and 8 µl of THP at 5 mM in 1×PBS was added and incubated at 65° C. for 15 minutes to remove the fluorescent dye and reestablish the hydroxyl group at the 3' end. The silicone isolator was removed again and the slide was washed with SPSS buffer containing 2% Tween 20 and re-scanned to confirm successful removal of the dye on the base along with the 3' blocking group. The above procedure was repeated for each of the subsequent sequencing cycles.

Four-color sequencing data on a surface are shown in FIG. 32. The intensity of the emitted light at the following four wavelengths (488 nm, 543 nm, 594 nm, and 633 nm) is indicated by the height of the bars (first: Alexa 488=C; second: R6G=T; third: Rox=A; fourth: Cy5=G, respectively). From left to right, the sets of 4 bars are for the $1^{st}$ extension reaction, the $1^{st}$ cleavage reaction, the $2^{nd}$ extension reaction, the $2^{nd}$ cleavage reaction, the $3^{rd}$ extension reaction, the $3^{rd}$ cleavage reaction, the $4^{th}$ extension reaction, and the $4^{th}$ cleavage reaction. The expected fluorescence emission wavelength was obtained for each cycle of nucleotide addition based on the nucleotide at that position in the template, demonstrating excellent fidelity with this combination of labeled, blocked nucleotides (3'-SS-dARP-SS-Rox, 3'-SS-dCTP-SS-Alexa488, 3'-SS-dGTP-SS-Cy5, and 3'-SS-dUTP-SS-R6G) and Therminator IX polymerase. Furthermore, the emission was reduced to background after treatment with THP, indicating complete cleavage of the dye from the base.

Scheme 3. Synthesis of 3'-O-tert-butyldithiomethyl-dTTP.

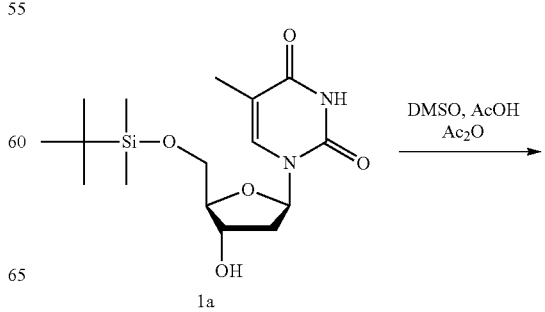

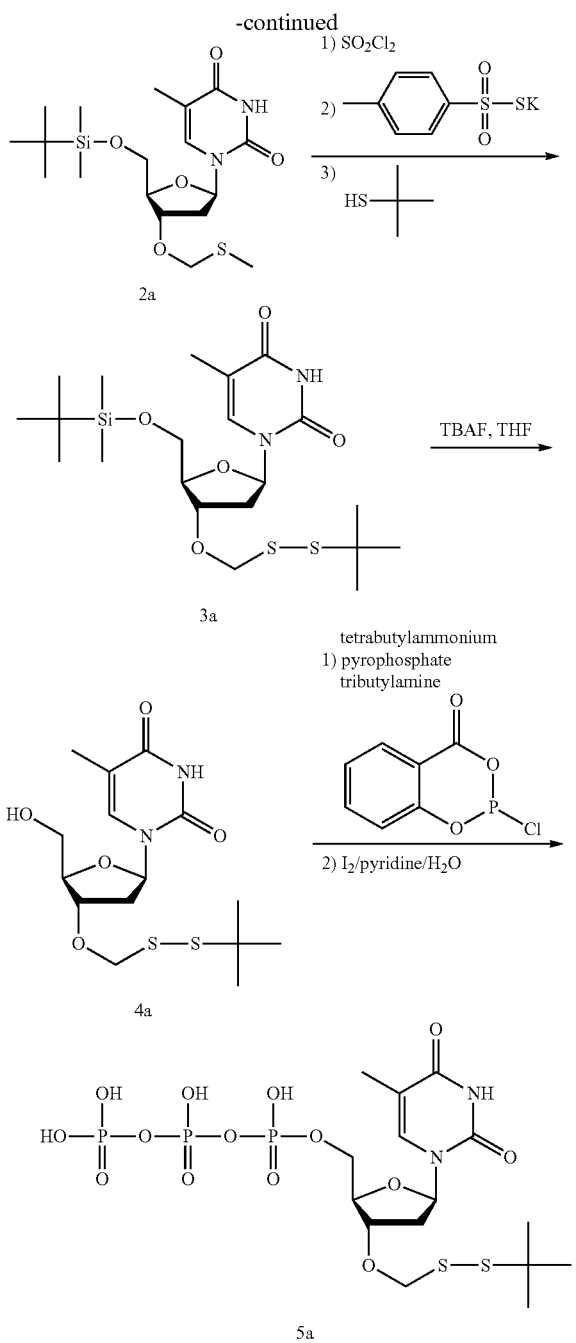

2.39 (m, 1H), 2.14 (s, 3H), 1.97 (m, 1H), 1.92 (s, 3H), 0.93 (s, 9H), 0.13 (s, 3H); HRMS (FAB+) calc'd for $C_{18}H_{33}N_2O_5SSi$ [(M+H)+]: 417.1879, found: 417.1890.

3'-O-tert-butyldithiomethyl-5'-O-tert-butyldimethylsilyl thymidine (3a): 3'-O-methylthiomethyl-5'-O-tert-butyldimethylsilyl thymidine (2a, 420 mg, 1 mmol) was dissolved in anhydrous dichloromethane (20 mL), followed by addition of triethylamine (0.18 mL, 1.31 mmol, 1.2 eq.) and molecular sieves (3 Å, 2 g). The mixture was cooled in an ice bath after stirring at room temperature for 30 min and then a solution of sulfuryl chloride (redistilled, 0.1 mL, 1.31 mmol, 1.2 eq.) in anhydrous dichloromethane (3 mL) was added dropwise over 2 minutes. The ice bath was removed and the reaction mixture was stirred further for 30 min. Then potassium p-toluenethiosulfonate (375 mg, 1.65 mmol) in anhydrous DMF (2 mL) was added to the mixture. Stirring was continued at room temperature for an additional hour followed by addition of tert-butyl mercaptan (1 mL). The reaction mixture was stirred at room temperature for 30 min and quickly filtered through celite. The filter was washed with dichloromethane and the organic fraction was concentrated to give crude product 3a.

3'-O-tert-butyldithiomethyl-thymidine (4a): Without isolation, the crude compound 3a was dissolved in THF (10 mL) and a THF solution of tetrabutylammonium fluoride (1.0M, 1.04 mL 1.04 mmol) was added. The reaction mixture was stirred at room temperature for 4 hours. The reaction mixture was concentrated in vacuo, saturated $NaHCO_3$ solution (50 mL) was added and the mixture was extracted with dichloromethane (3×20 mL). The organic layer was dried over anhydrous $Na_2SO_4$, filtered, concentrated and the obtained crude mixture was purified by flash column chromatography (dichloromethane/methanol: 20:1) to give 3'-O-Cert-butyldithiomethyl-thymidine 4a (132 mg, 35% from compound 2a). $^1$H NMR (300 MHz, $CDCl_3$) δ: 7.41 (q, J=1.2 Hz, 1H), 6.15 (dd, J=7.4, 6.5 Hz, 1H), 4.89-4.82 (m, 2H), 4.62-4.54 (m, 1H), 4.15 (q, J=3.0 Hz, 1H), 3.97-3.86 (m, 2H), 2.42 (ddd, J=7.5, 4.8, 2.5 Hz, 2H), 1.95 (d, J=1.2 Hz, 3H), 1.36 (s, 8H).

3'-O-tert-butyldithiomethyl-dTTP (5a): 3'-O-tert-butyldithiomethyl-thymidine (4a, 50 mg, 0.13 mmol), tetrabutylammonium pyrophosphate (197 mg, 0.36 mmol) and 2-chloro-4-H-1,3,2-benzodioxaphosphorin-4-one (44 mg, 0.22 mmol) were dried separately overnight under high vacuum at ambient temperature. The tetrabutylammonium pyrophosphate was dissolved in dimethylformamide (DMF, 1 mL) under argon followed by addition of tributylamine (1 mL). This mixture was injected into the solution of 2-chloro-4-H-1,3,2-benzodioxaphosphorin-4-one in (DMF, 2 mL) under argon. After stirring for 1 h, the reaction mixture was added to the solution of 3'-O-tert-butyldithiomethyl-thymidine and stirred further for 1 hour at room temperature. Iodine solution (0.02 M iodine/pyridine/water) was then injected into the reaction mixture until a permanent brown color was observed. After 10 min, water (30 mL) was added and the reaction mixture was stirred at room temperature for an additional 2 hours. The resulting solution was extracted with ethyl acetate (2×30 mL). The aqueous layer was concentrated under vacuum and the residue was diluted with 5 ml of water. The crude mixture was then purified with anion exchange chromatography on DEAE-Sephadex A-25 at 4° C. using a gradient of TEAB (pH 8.0; 0.1-1.0 M). The crude product was further purified by reverse-phase HPLC to afford 5a, which was characterized by MALDI-TOF MS: calc'd for $C_{15}H_{27}N_2O_{14}P_3S_2$: 616.4, found: 615.4.

Scheme 4. Synthesis of 3'-O-tert-butyldithiomethyl-dGTP.

3'-O-methylthiomethyl-5'-O-tert-butyldimethylsilyl thymidine (2a): To a stirring solution of the 5'-O-tert-butyldimethylsilyl thymidine (1a, 1.07 g, 3 mmol) in DMSO (10 mL) was added acetic acid (2.6 mL, 45 mmol) and acetic anhydride (8.6 mL, 90 mmol). The reaction mixture was stirred overnight at room temperature. Then the mixture was added slowly to a saturated solution of sodium bicarbonate under vigorous stirring and extracted with ethyl acetate (3×30 mL). The combined organic layers were dried over $Na_2SO_4$ and filtered. The filtrate was concentrated to dryness under reduced pressure and the compound was purified by silica gel column chromatography (ethyl acetate/hexane: 1:2) to give pure product 2a (0.97 g, 74%). $^1$H NMR (400 MHz, $CDCl_3$) δ: 8.16 (s, 1H), 7.48 (s, 1H), 6.28 (m, 1H), 4.62 (m, 2H), 4.46 (m, 1H), 4.10 (m, 1H), 3.78-3.90 (m, 2H),

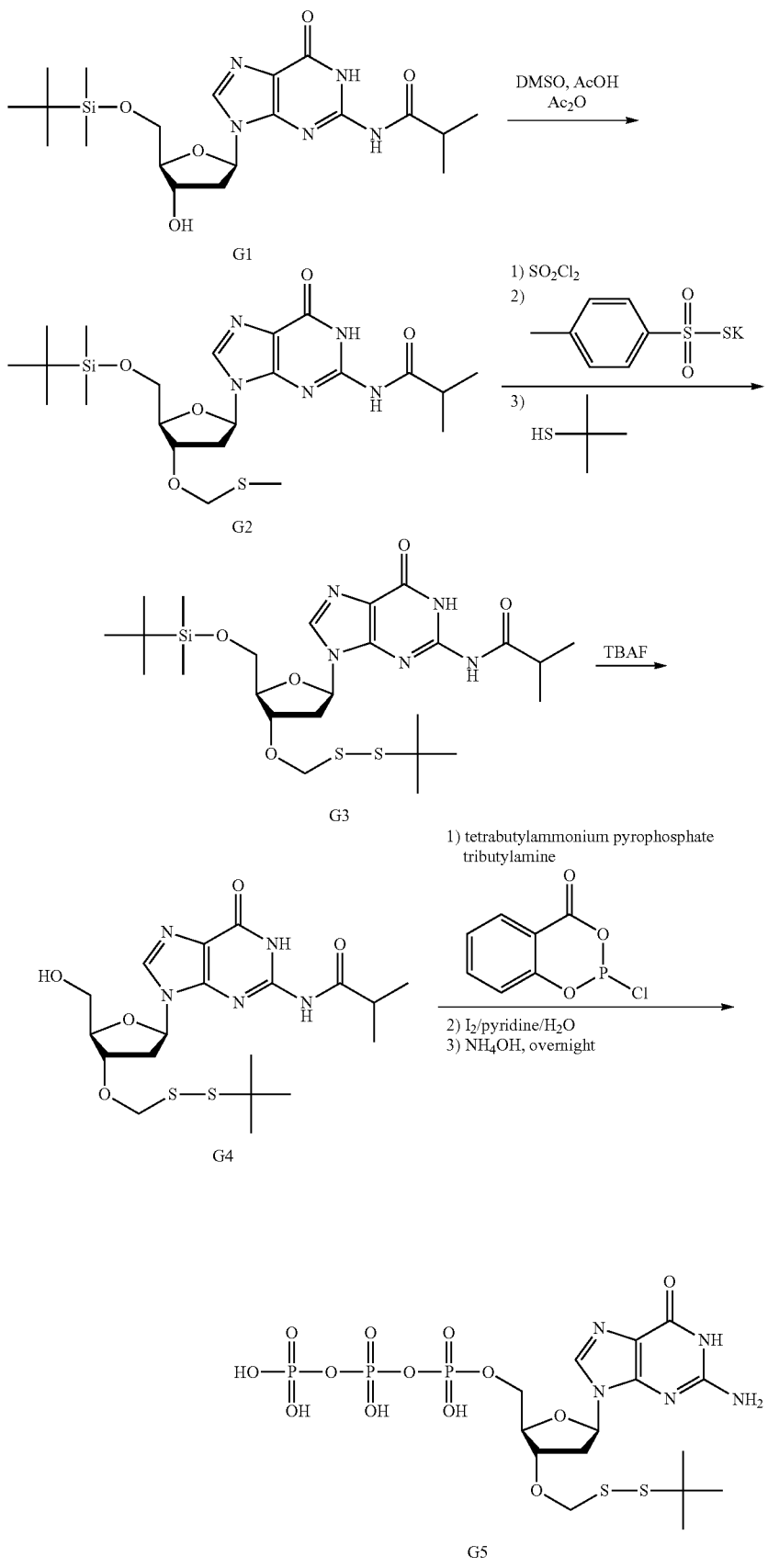

N²-isobutyryl-3'-O-methylthiomethyl-5'-O-tert-butyldimethylsilyl-T-deoxyguanosine (G2): To a stirring solution of N²-isobutyryl-5'-O-Cert-butyldimethylsilyl-2'-deoxyguanosine (G1, 1.31 g, 3 mmol) in DMSO (10 mL) was added acetic acid (2.6 mL, 45 mmol) and acetic anhydride (8.6 mL, 90 mmol). The reaction mixture was stirred at room temperature until the reaction was complete, which was monitored by TLC. Then the mixture was added slowly to a saturated solution of sodium bicarbonate under vigorous stirring and extracted with ethyl acetate (3×30 mL). The combined organic layers were dried over Na$_2$SO$_4$ and filtered. The filtrate was concentrated to dryness under reduced pressure and the compound was purified by silica gel column chromatography (DCM/methanol: 20:1) to give pure product G2 (75%, 1.15 g). $^1$H NMR (400 MHz, CDCl$_3$) δ 12.10 (d, J=2.9 Hz, 1H), 9.17 (d, J=3.0 Hz, 1H), 8.03 (m, 1H), 6.18 (td, J=6.9, 2.9 Hz, 1H), 4.74-4.60 (m, 3H), 4.13 (dq, J=6.8, 3.3 Hz, 1H), 3.84-3.75 (m, 2H), 2.78 (m, 1H), 2.54 (m, 2H), 2.16 (s, 3H), 1.33-1.22 (m, 6H), 0.96-0.87 (m, 9H), 0.09 (dd, J=6.7, 3.8 Hz, 6H).

N²-isobutyryl-3'-O-tert-butyldithiomethyl-5'-O-tert-butyldimethylsilyl-2'-deoxyguanosine (G3): N²-isobutyryl-3'-O-methylthiomethyl-5'-O-tert-butyldimethylsilyl-2'-deoxyguanosine (G2, 511 mg, 1.0 mmol) was dissolved in anhydrous dichloromethane (20 mL), followed by addition of triethylamine (0.17 mL, 1.2 mmol) and molecular sieves (3 Å, 2 g). The mixture was cooled in an ice bath after stirring at room temperature for 30 min and then a solution of sulfuryl chloride (0.095 mL, 1.2 mmol) in anhydrous dichloromethane (3 mL) was added dropwise over 2 minutes. The ice bath was removed and the reaction mixture was stirred further for 30 min. Then potassium 4-toluenethiosulfonate (341 mg, 1.5 mmol) in anhydrous DMF (2 mL) was added to the mixture. Stirring was continued at room temperature for an additional hour followed by addition of tert-butyl mercaptan (1 mL). The reaction mixture was stirred at room temperature for 30 min and quickly filtered through celite. The filter was washed with dichloromethane and the organic fraction was concentrated to give crude product G3.

N²-isobutyryl-3'-O-tert-butyldithiomethyl-2'-deoxyguanosine (G4). Without isolation, the crude compound G3 was dissolved in THF (10 mL) and a THF solution of tetrabutylammonium fluoride (1.0M, 1.04 mL, 1.04 mmol) was added. The reaction mixture was stirred at room temperature for 4 hours. The reaction mixture was concentrated in vacuo, saturated NaHCO$_3$ solution (50 mL) was added and the mixture was extracted with dichloromethane (3×20 mL). The organic layer was dried over anhydrous Na$_2$SO$_4$, filtered, concentrated and the obtained crude mixture was purified by flash column chromatography (dichloromethane/methanol: 20:1) to give N²-isobutyryl-3'-O-tert-butyldithiomethyl-2'-deoxyguanosine G4 (155 mg, 33% from compound G2). $^1$H NMR (400 MHz, CDCl$_3$) δ 12.19 (s, 1H), 9.44 (s, 1H), 7.97 (s, 1H), 6.17 (dd, J=8.4, 5.9 Hz, 1H), 5.04 (s, 1H), 4.92-4.80 (m, 2H), 4.76-4.64 (m, 1H), 4.26 (q, J=2.6 Hz, 1H), 3.98 (dd, J=12.2, 2.8 Hz, 1H), 3.80 (d, J=12.3 Hz, 1H), 2.91-2.73 (m, 2H), 2.49 (m, 1H), 1.35 (s, 9H), 1.36-1.22 (in, 6H). $^{13}$C NMR (75 MHz, CDCl$_3$) δ 179.60, 155.80, 148.10, 147.96, 139.11, 122.30, 86.29, 81.22, 78.96, 63.21, 48.07, 38.18, 36.64, 30.29, 19.39, 19.34.

3'-O-tert-butyldithiomethyl-dGTP (G5). N²-isobutyryl-3'-O-tert-butyldithiomethyl-2'-deoxyguanosine (G4, 50 mg, 0.11 mmol), tetrabutylammonium pyrophosphate (180 mg, 0.33 mmol) and 2-chloro-4-H-1,3,2-benzodioxaphosphorin-4-one (44 mg, 0.22 mmol) were dried separately overnight under high vacuum at ambient temperature. The tetrabutylammonium pyrophosphate was dissolved in dimethylformamide (DMF, 1 mL) under argon followed by addition of tributylamine (1 mL). This mixture was injected into the solution of 2-chloro-4-H-1,3,2-benzodioxaphosphorin-4-one in (DMF, 2 mL) under argon. After stirring for 1 h, the reaction mixture was added to the solution of N²-isobutyryl-3'-O-tort-butyldithiomethyl-2'-deoxyguanosine and stirred further for 1 hour at room temperature. Iodine solution (0.02 M iodine/pyridine/water) was then injected into the reaction mixture until a permanent brown color was observed. After 10 min, water (30 mL) was added and the reaction mixture was stirred at room temperature for an additional 2 hours. The resulting solution was extracted with ethyl acetate. The aqueous layer was concentrated in vacuo to approximately 20 mL, then concentrated NH$_4$OH (20 ml) was added and the mixture stirred overnight at room temperature. The resulting mixture was concentrated under vacuum and the residue was diluted with 5 ml of water. The crude mixture was then purified with anion exchange chromatography on DEAE-Sephadex A-25 at 4° C. using a gradient of TEAB (pH 8.0; 0.1-1.0 M). The crude product was further purified by reverse-phase HPLC to afford G5. HRMS (ESI) calc'd for C$_{15}$H$_{25}$H$_5$O$_{13}$P$_3$S$_2$ [(M–H)$^-$]: 640.0103, found: 640.0148.

Scheme 5. Synthesis of 3'-O-tert-butyldithiomethyl-dATP.

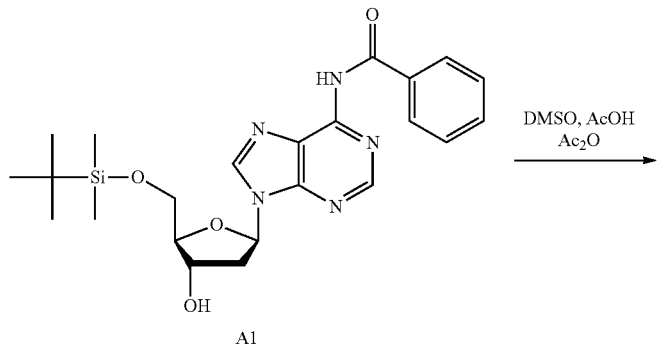

A1

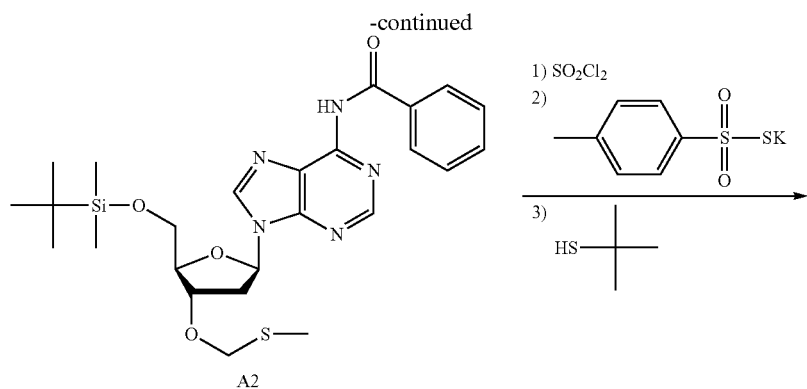

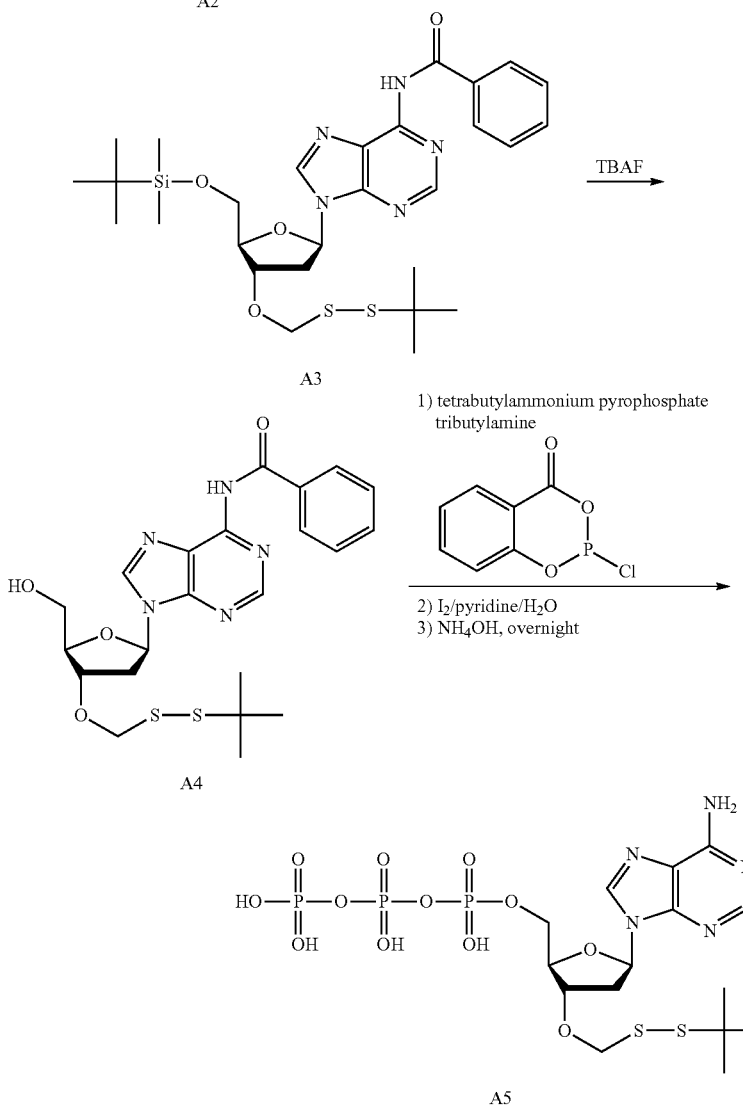

$N^6$-Benzoyl-5'-O-tert-butyldimethylsilyl-3'-O-methylthiomethyl-2'-deoxyadenosine (A2): To a stirring solution of the $N^6$-Benzoyl-5'-O-tert-butyldimethylsilyl-2'-deoxyadenosine (A1, 1.41 g, 3 mmol) in DMSO (10 mL) was added acetic acid (3 mL) and acetic anhydride (9 mL). The reaction mixture was stirred at room temperature until the reaction was complete, which was monitored by TLC. Then the mixture was added slowly to a solution of sodium bicarbonate under vigorous stirring and extracted with ethyl acetate (3×30 mL). The combined organic layers were dried over $Na_2SO_4$ and filtered. The filtrate was concentrated to dryness under reduced pressure and the residue of the desired compound was purified by silica gel column chromatography (dichloromethane/methanol: 30:1) to give pure product A2 (1.39 g, 88%). NMR (400 MHz, $CDCl_3$) δ 9.12 (s, 1H), 8.81 (s, 1H), 8.35 (s, 1H), 8.10-8.01 (m, 2H), 7.68 (m, 1H), 7.49 (m, 2H), 6.53 (dd, J=7.5, 6.0 Hz, 1H), 4.78-4.65 (m, 3H), 4.24 (dt, J=4.3, 3.1 Hz, 1H), 3.98-3.81

(m, 2H), 2.80-2.60 (m, 2H), 2.21 (s, 3H), 0.94 (s, 10H), 0.13 (s, 6H): MS (APCI⁺) calc'd for $C_{26}H_{36}N_4O_4SSi$: 528.74, found: 529.4 [M+H]⁺.

N⁶-Benzoyl-5'-O-tert-butyldimethylsilyl-3'-O-tert-butyl-dithiomethyl-2'-deoxyadenosine (A3): N⁶—Benzoyl-5'-O-tert-butyldimethylsilyl-3'-O-methylthiomethyl-2'-deoxyadenosine (A2, 529 mg, 1.0 mmol) was dissolved in anhydrous dichloromethane (20 mL), followed by addition of triethylamine (0.17 mL, 1.2 mmol) and molecular sieves (3 Å, 2 g). The mixture was cooled in an ice bath after stirring at room temperature for 30 min and then a solution of sulfuryl chloride (0.095 mL, 1.2 mmol) in anhydrous dichloromethane (3 mL) was added dropwise over 2 minutes. The ice bath was removed and the reaction mixture was stirred further for 30 min. Then potassium 4-toluenethiosulfonate (341 mg, 1.5 mmol) in anhydrous DMF (2 mL) was added to the mixture. Stirring was continued at room temperature for an additional hour followed by addition of tert-butyl mercaptan (1 mL). The reaction mixture was stirred at room temperature for 30 min and quickly filtered through celite. The filter was washed with dichloromethane and the organic fraction was concentrated to give crude product A3.

N⁶-Benzoyl-3'-O-tert-butyldithiomethyl-2'-deoxyadenosine (A4): Without isolation, the crude compound A3 was dissolved in THF (10 mL) and a THF solution of tetrabutylammonium fluoride (1.0M, 1.04 mL, 1.04 mmol) was added. The reaction mixture was stirred at room temperature for 4 hours. The reaction mixture was concentrated in vacuo, saturated NaHCO₃ solution (50 mL) was added and the mixture was extracted with dichloromethane (3×20 mL). The organic layer was dried over anhydrous Na₂SO₄, filtered, concentrated and the obtained crude mixture was purified by flash column chromatography (dichloromethane/methanol: 20:1) to give N⁶-Benzoyl-3'-0-tert-butyldithiomethyl-2'-deoxyadenosine A4 (128 mg, 26% from compound A2). ¹H NMR (400 MHz, DMSO-d₆) δ 11.18 (s, 1H), 8.77 (s, 1H), 8.71 (s, 1H), 8.10-8.02 (m, 2H), 7.66 (t, J=7.6 Hz, 1H), 7.56 (t, J=7.6 Hz 2H), 6.47 (dd, J=8.0, 6.0 Hz, 1H), 5.15 (t, J=5.5 Hz, 1H), 5.00 (s, 2H), 4.65 (dt, J=5.4, 2.4 Hz, 1H), 4.12 (td, J=4.7, 2.2 Hz, 1H), 3.02-2.88 (m, 1H), 2.84 (q, J=7.3 Hz, 2H), 2.61 (m, 1H), 1.35 (s, 9H).

3'-O-tert-butyldithiomethyl-dATP (A5): N⁶-Benzoyl-3'-O-tert-butyldithiomethyl-2'-deoxyadenosine (A4, 50 mg, 0.10 mmol), tetrabutylammonium pyrophosphate (180 mg, 0.33 mmol) and 2-chloro-4-H-1,3,2-benzodioxaphosphorin-4-one (44 mg, 0.22 mmol) were dried separately overnight under high vacuum at ambient temperature. The tetrabutylammonium pyrophosphate was dissolved in dimethylformamide (DMF, 1 mL) under argon followed by addition of tributylamine (1 mL). This mixture was injected into the solution of 2-chloro-4-H-1,3,2-benzodioxaphosphorin-4-one in (DMF, 2 mL) under argon. After stirring for 1 h, the reaction mixture was added to the solution of N⁶-Benzoyl-3'-O-tert-butyldithiomethyl-2'-deoxyadenosine and stirred further for 1 hour at room temperature. Iodine solution (0.02 M iodine/pyridine/water) was then injected into the reaction mixture until a permanent brown color was observed. After 10 min, water (30 mL) was added and the reaction mixture was stirred at room temperature for an additional 2 hours. The resulting solution was extracted with ethyl acetate. The aqueous layer was concentrated in vacuo to approximately 20 mL, then concentrated NH₄OH (20 ml) was added and stirring continued overnight at room temperature. The resulting mixture was concentrated under vacuum and the residue was diluted with 5 ml of water. The crude mixture was then purified by anion exchange chromatography on DEAE-Sephadex A-25 at 4° C. using a gradient of TEAB (pH 8.0; 0.1-1.0 M). The crude product was further purified by reverse-phase HPLC to afford A5, which was characterized by MALDI-TOF MS calc'd for $C_{15}H_{26}N_5O_{12}P_3S_2$: 625.4, found: 625.0.

Scheme 6. Synthesis of 3'-O-tert-butyldithiomethyl-dCTP.

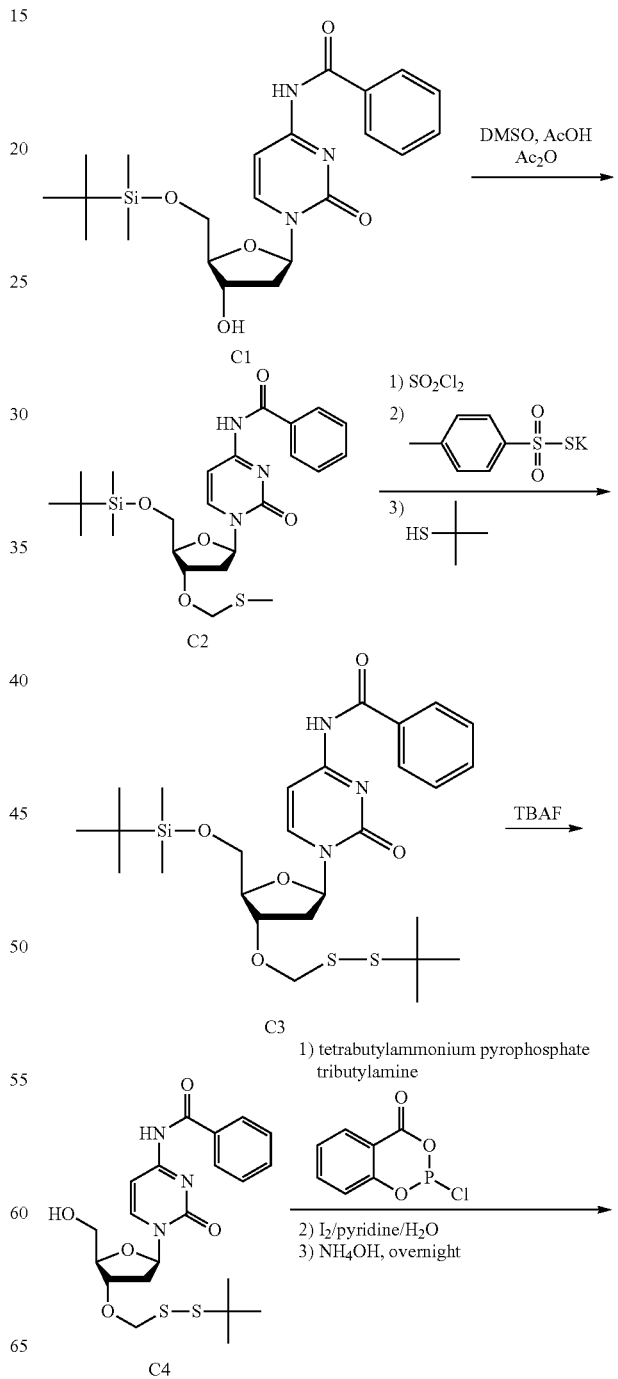

-continued

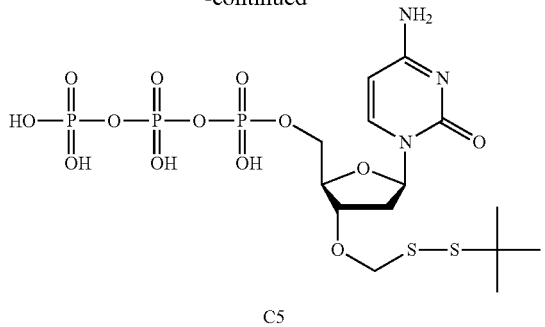

C5

N⁴-Benzoyl-3'-O-methylthiomethyl-5'-O-tert-butyldimethylsilyl-2'-deoxycytidine (C2): To a stirring solution of N⁴-Benzoyl-5'-O-tert-butyldimethylsilyl-2'-deoxycytidine (C1, 1.5 g, 3.4 mmol) in DMSO (6.5 mL) was added acetic acid (2.91 mL) and acetic anhydride (9.29 mL). The reaction mixture was stirred at room temperature for 2 days. Then the reaction mixture was added dropwise to solution of sodium bicarbonate and extracted by ethyl acetate (50 ml×3). The obtained crude product was purified by column chromatography (ethyl acetate/hexane: 8:2) to give pure product C2 (1.26 g, 74%) as a white solid. 1H NMR (400 MHz, CDCl₃) δ 8.43 (d, J=7.4 Hz, 1H), 7.92 (d, J=7.6 Hz, 2H), 7.69-7.50 (m, 4H), 6.31 (t, J=6.1 Hz, 1H), 4.75-4.59 (m, 2H), 4.51 (dt, J=6.2, 3.9 Hz, 1H), 4.20 (dt, J=3.7, 2.6 Hz, 1H), 4.01 (dd, J=11.4, 2.9 Hz, 1H), 3.86 (dd, J=11.4, 2.4 Hz, 1H), 2.72 (ddd, J=13.8, 6.2, 4.1 Hz, 1H), 2.18 (s, 4H), 0.97 (s, 9H), 0.17 (d, J=3.9 Hz, 6H). HRMS (ESI⁺) calc'd for $C_{24}H_{35}N_3O_5SSi$ [(M-hH)⁺]: 506.2145, found: 506.2146.

N⁴-Benzoyl-3'-O-tert-butyldithiomethyl-5'-O-tert-butyldimethylsilyl-2'-deoxycytidine (C3): N⁴—Benzoyl-3'-O-methylthiomethyl-5'-O-tert-butyldimethylsilyl-2'-deoxycytidine (C2, 1.01 g, 2 mmol) was dissolved in anhydrous dichloromethane (8 mL), followed by addition of triethylamine (278 μL, 2 mmol) and molecular sieves (3 Å, 1 g). The mixture was cooled in an ice bath after stirring at room temperature for 0.5 hour and then a solution of sulfuryl chloride (161 μL, 2.2 mmol) in anhydrous dichloromethane (8 mL) was added dropwise. The ice bath was removed and the reaction mixture was stirred further for 0.5 hour. Then potassium p-toluenethiosulfonate (678 mg, 3 mmol) in anhydrous DMF (1 mL) was added to the mixture. Stirring was continued at room temperature for an additional 1 hour followed by addition of tert-butyl mercaptan (1 mL). The reaction mixture was stirred at room temperature for 0.5 hour and quickly filtered. The solvent was removed under reduced pressure and the residue was dissolved in ethyl acetate and washed in brine (3×50 mL). The combined organic layers were dried over $Na_2SO_4$ and filtered. The filtrate was concentrated to dryness under reduced pressure and the residue of the desired compound was purified by silica gel column chromatography using a gradient of ethyl acetate-hexane from 3:7 (v/v) to 5:5 (v/v), yielding 959 mg (83%) C3 as a white foam. ¹H NMR (400 MHz, CDCl₃) δ 8.43 (d, J=7.4 Hz, 1H); 7.92 (d, J=7.6 Hz, 2H), 7.69-7.50 (m, 4H), 6.31 (t, J=6.1 Hz, 1H), 4.75-4.59 (m, 2H), 4.51 (dt, J=6.2, 3.9 Hz, 1H), 4.20 (dt, J=3.7, 2.6 Hz, 1H), 4.01 (dd, J=11.4, 2.9 Hz, 1H), 3.86 (dd, J=11.4, 2.4 Hz, 1H), 2.72 (ddd, J=13.8, 6.2, 4.1 Hz, 1H), 2.18 (s, 4H), 0.97 (s, 9H), 0.17 (d, J=3.9 Hz, 6H), 0.10 (s, 2H). HRMS (ESI⁺) calc'd for: $C_{27}H_{41}N_3O_5S_2Si$ [(M+Na)⁺]: 602.2155, found: 602.2147.

N⁴-Benzoyl-3'-O-tert-butyldithiomethyl-2'-deoxycytidine (C4) To a stirring solution of N⁴-Benzoyl-3'-O-tert-butyldithiomethyl-5'-O-tert-butyldimethylsilyl-2'-deoxycytidine (C3, 958 mg, 1.66 mmol) in a mixture of tetrahydrofuran (24 ml), tetrabutylammonium fluoride (1.0M, 2.48 mL) was added in small portions, and stirred at room temperature for 3 hours. The reaction mixture was poured into a saturated sodium bicarbonate solution (50 mL) and extracted with ethyl acetate (3×50 mL). The combined organic layers were dried over $Na_2SO_4$ and filtered. The filtrate was concentrated to dryness under reduced pressure and the residue of the desired compound was purified by silica gel column chromatography using a gradient of ethyl acetate-hexane from 5:5 (v/v), affording 435 mg (56%) C4 as a solid white powder. ¹H NMR (400 MHz, Methanol-d₄) δ 8.52 (d, J=7.5 Hz, 1H), 8.04-7.96 (m, 2H), 7.71-7.60 (m, 2H), 7.61-7.51 (m, 2H), 6.28-6.19 (m, 1H), 4.95-4.86 (m, 2H), 4.54 (dt, J=6.0, 3.0 Hz, 1H), 4.23 (q, J=3.4 Hz, 1H); 3.92-3.76 (m, 2H), 2.70 (ddd, J=13.9, 6.0, 2.9 Hz, 1H), 2.25 (ddd, J=13.6, 7.2, 6.2 Hz, 1H), 1.37 (s, 9H). HRMS (ESI⁺) calc'd for $C_2H_{27}N_3O_5S_2$[(M+Na)⁺]: 488.1290, found: 488.1297.

3'-O-tert-butyldithiomethyl-dCTP (C5): N⁴—Benzoyl-3'-O-tert-butyldithiomethyl-2'-deoxycytidine (C4, 50 mg, 0.11 mmol), tetrabutylammonium pyrophosphate (180 mg, 0.33 mmol) and 2-chloro-4-H-1,3,2-benzodioxaphosphorin-4-one (44 mg, 0.22 mmol) were dried separately overnight under high vacuum at ambient temperature. The tetrabutylammonium pyrophosphate was dissolved in dimethylformamide (DMF, 1 mL) under argon followed by addition of tributylamine (1 mL). This mixture was injected into the solution of 2-chloro-4-H-1,3,2-benzodioxaphosphorin-4-one in (DMF, 2 mL) under argon. After stirring for 1 h; the reaction mixture was added to the solution of N⁴-benzoyl-3'-O-tert-butyldithiomethyl-2'-deoxycytidine and stirred further for 1 hour at room temperature. Iodine solution (0.02 M iodine/pyridine/water) was then injected into the reaction mixture until a permanent brown color was observed. After 10 min, water (30 mL) was added and the reaction mixture was stirred at room temperature for an additional 2 hours. The resulting solution was extracted with ethyl acetate. The aqueous layer was concentrated in vacuo to approximately 20 mL, then concentrated $NH_4OH$ (20 ml) was added and the mixture stirred overnight at room temperature. The resulting mixture was concentrated under vacuum and the residue was diluted with 5 ml of water. The crude mixture was then purified by anion exchange chromatography on DEAE-Sephadex A-25 at 4° C. using a gradient of TEAB (pH 8.0; 0.1-1.0 M). The crude product was further purified by reverse-phase HPLC to afford C5. HRMS (ESI−) calc'd for $C_{14}H_{25}N_3O_{13}P_3S_2$[(M−H)⁻]: 600.0042, found: 600.0033.

Scheme 7. Synthesis of the DTM Linker.

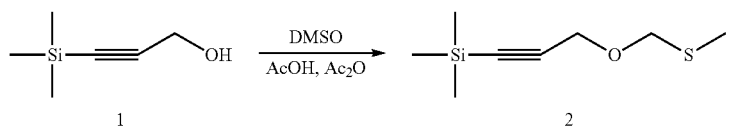

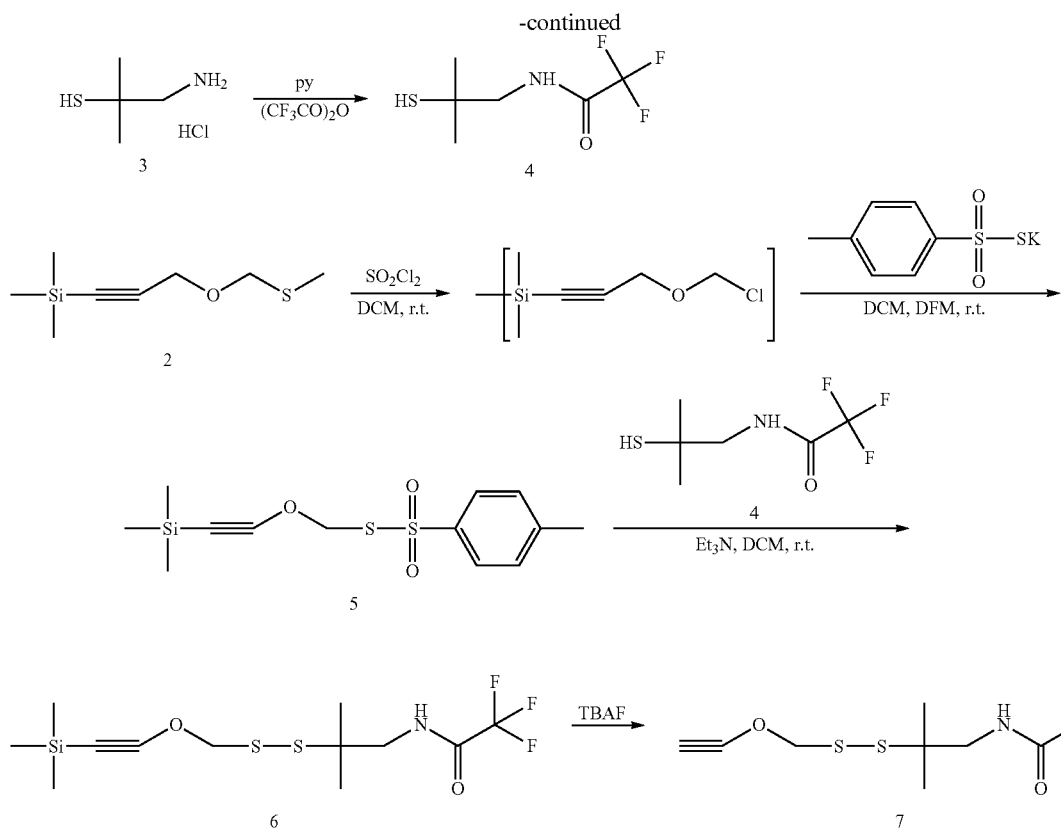

Trimethyl(3-((methylthio)methoxy)prop-1-yn-1-yl)silane (2): To a solution of 3-trimethylsilanyl-prop-2-yn-1-ol (1, 1.28 g, 10 mmol) in DMSO (10 mL) acetic acid (2.6 mL, 45 mmol) and acetic anhydride (8.6 mL, 90 mmol) were added with stirring. The reaction mixture was stirred at room temperature until the reaction was complete (24 h), which was monitored by TLC. Then the mixture was added slowly to a solution of sodium bicarbonate under vigorous stirring and extracted with ethyl acetate (3×30 mL). The combined organic layers were dried over $Na_2SO_4$ and filtered. The filtrate was concentrated to dryness under reduced pressure and the desired compound was purified by silica gel column chromatography (ethyl acetate/hexane: 1:10) to give pure product 2 (0.97 g, 67%): $^1H$ NMR (300 MHz, $CDCl_3$) δ: 4.75 (s, 2H), 4.28 (s, 2H), 2.16 (s, 3H), 0.20 (s, 9H); $^{13}C$ NMR (75 MHz, $CDCl_3$) δ:101.12, 92.07, 74.04, 55.48, 14.42, 0.18.

2,2,2-trifluoro-N-(2-mercapto-2-methylpropyl)acetamide (4): 1-amino-2-methylpropane-2-thiol hydrochloride (3) (1.0 g, 7 mmol) was mixed with pyridine (2 mL) in dried benzene (15 mL). At 0° C., trifluoroacetic anhydride (1.30 mL, 9.2 mmol) was slowly added to the stirred mixture, and stirring was continued overnight at ambient temperature. Careful addition of 0.5 M $Na_2CO_3/H_2O$ was followed by extraction (EtOAc) of the aqueous layer and removal of volatiles from the combined organic layers under vacuum. Flash chromatography of the residue (30% ethyl acetate/hexane) gave 4 (4.0 g, 88%): $^1H$ NMR (400 MHz, $CDCl_3$) 6.85 (br, 1H), 3.45 (m, 2H), 1.69 (s, 1H), 1.41 (s, 6H).

S-(((3-(trimethylsilyl)prop-2-yn-1-yl)oxy)methyl) 4-methylbenzenesulfonothioate (5): Trimethyl(3-((methylthio)methoxy)prop-1-yn-1-yl)silane (2, 1.0 g, 5.32 mmol) was dissolved in anhydrous dichloromethane (10 mL), followed by addition of cyclohexene (3.4 mL). The mixture was cooled in an ice bath and then a solution of sulfuryl chloride (0.47 mL, 5.85 mmol) in anhydrous dichloromethane (3 mL) was added dropwise during 2 minutes. The ice bath was removed and the reaction mixture was stirred further for 1 hour. Then potassium thiotosylate (1.44 g, 6.38 mmol) in anhydrous DMF (5 mL) was added to the mixture. Stirring was continued at room temperature for an additional 1 hour. After concentrating the solution, the residue was purified by silica gel column chromatography (ethyl acetate/hexane: 10:1) to give pure product 5 (1.29 g, 74%): NMR (300 MHz, $CDCl_3$) 7.86 (d, J=8.4 Hz, 2H), 7.32 (d, J=8.4 Hz, 2H), 5.40 (s, 2H), 4.03 (s, 2H), 2.46 (s, 3H), 0.19 (s, 9H).

2,2,2-trifluoro-N-(2-methyl-2-(((prop-2-yn-1-yloxy) methyl)disulfanyl)propyl)acetamide (7): $Et_3N$ (0.3 mL) was added to a stirred mixture of 2,2,2-trifluoro-N-(2-mercapto-2-methylpropyl)acetamide (4, 0.87 g, 4.32 mmol) and S-4 (3-(trimethylsilyl)prop-2-yn-1-yl)oxy)methyl) 4-methylbenzenesulfonothioate (5, 1.29 g, 3.93 mmol) in anhydrous dichloromethane (20 mL) at ambient temperature and stirring was continued for 0.5 hour. Then, tetrabutylammonium fluoride THF solution (1.0M, 5.89 mL, 5.89 mmol) was added. The reaction mixture was stirred at room temperature for ~10 minutes, and volatiles were evaporated under vacuum. Flash chromatography of the residue gave 2,2,2-trifluoro-N-(2-methyl-2-(((prop-2-yn-1-yloxy)methyl)disulfanyl)propyl)acetamide (7, 0.83 g, 70%): $^1H$ NMR (300 MHz, $CDCl_3$) δ: 7.22 (br, 1H), 4.87 (s, 2H), 4.30 (d, J=2.4 Hz, 2H), 3.45 (d, J=6.4 Hz, 2H), 2.50 (s, J=2.4 Hz, 1H), 1.27 (s, 6H); $^{13}C$ NMR (75 MHz, $CDCl_3$) δ:158.16, 118.26, 79.81, 77.93, 76.27, 56.50, 50.93, 47.32, 25.30.

Scheme 8. Synthesis of 3'-O-DTM-5-SS-R6G-dUTP.
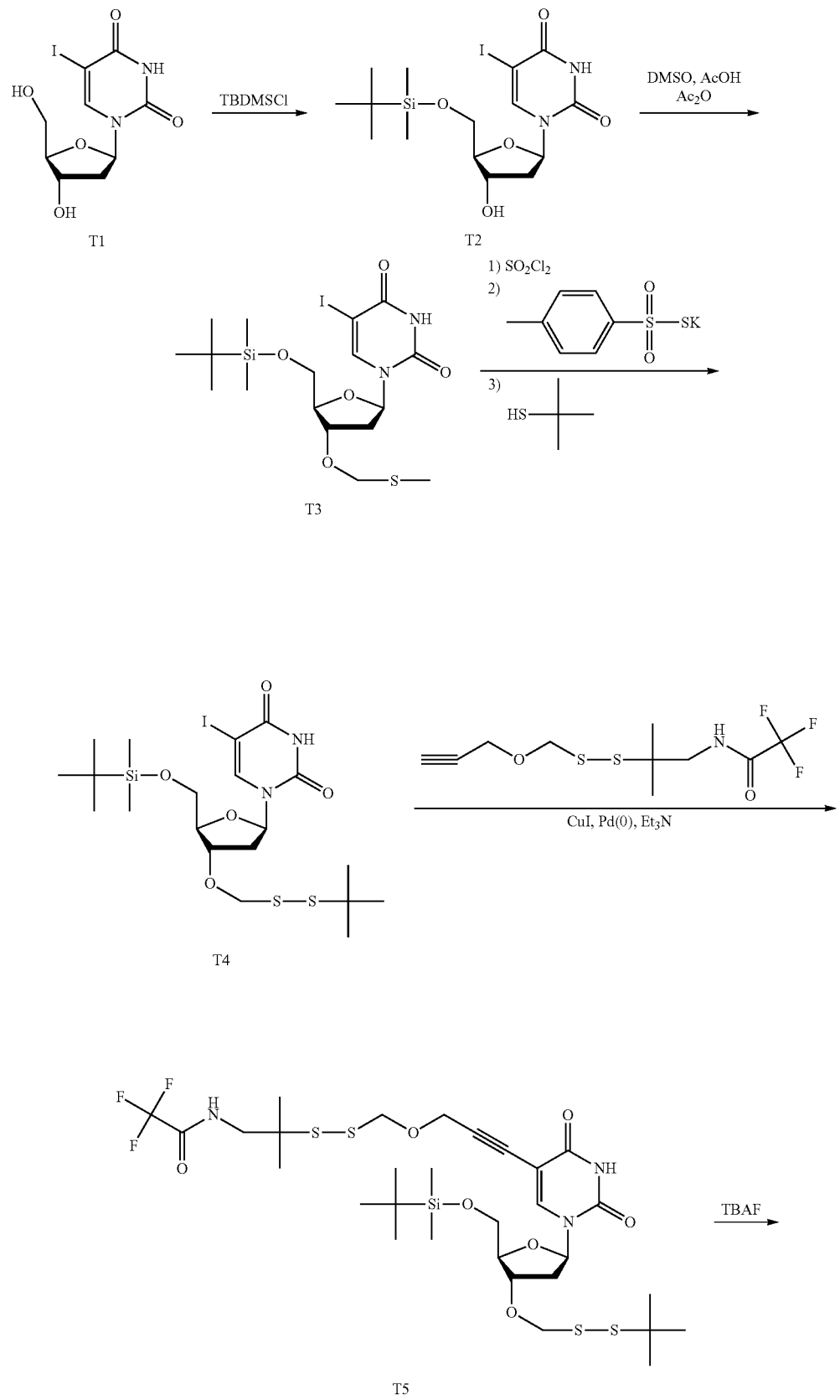

539                                                                       540
-continued
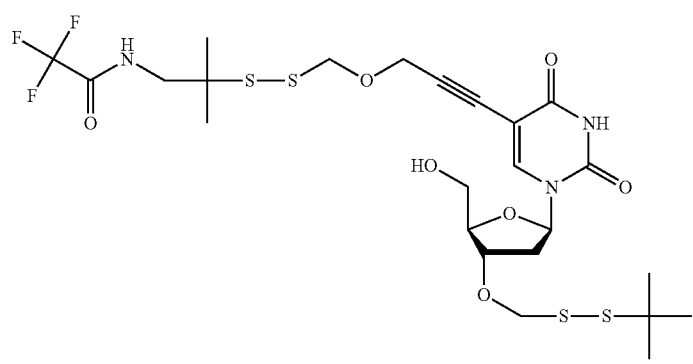 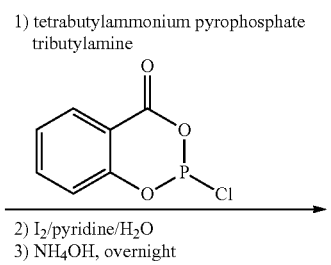
T6
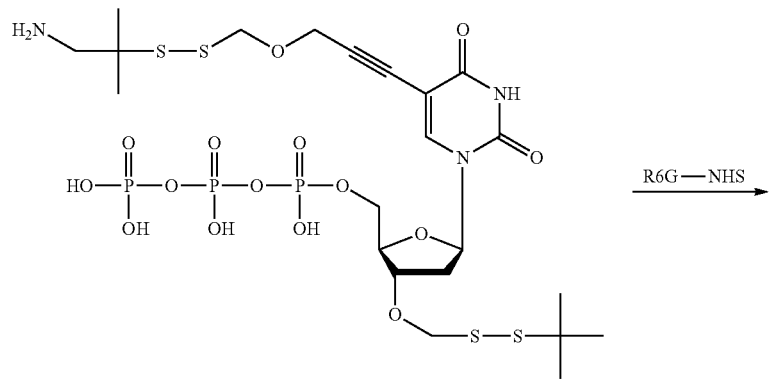
T7
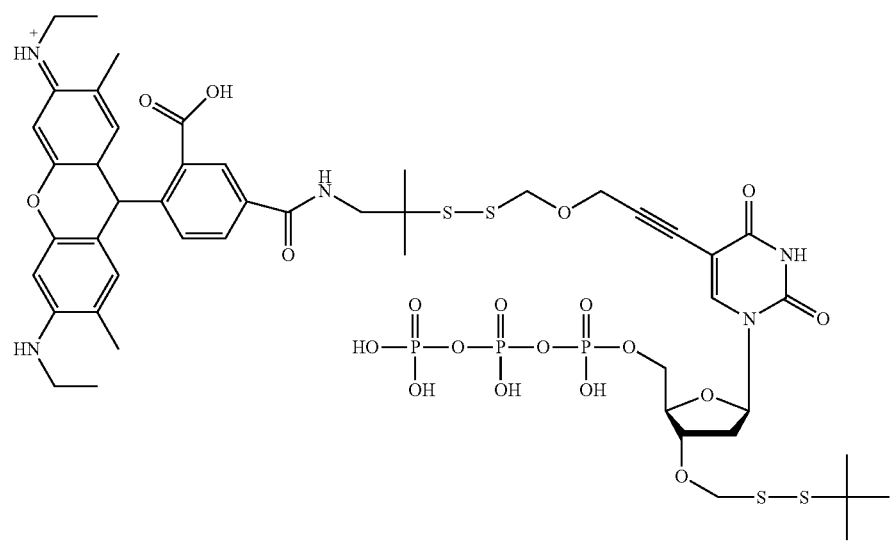
T8

5-Iodo-5'-O-tert-butyldimethylsilyl-thymidine (T2): A mixture of 5-iodo-2'-deoxythymidine (T1, 1 g, 2.8 mmol), tert-butyldimethylsilyl chloride (453 mg, 3.0 mmol) and imidazole (199 mg, 3.0 mmol) was dissolved in dry DMF (15 mL) and stirred at room temperature overnight. The reaction mixture was poured into ice water (200 mL) under stirring and the precipitate was collected by suction filtration, then washed with water and hexane. The obtained crude product was purified by column chromatography (dichloromethane/methanol: 20:1) to give 5-iodo-5'-O-tert-butyldimethylsilyl-thymidine (T2, 1.152 g, 88%), $^1$H NMR (400 MHz, CDCl$_3$) δ 8.19 (s, 1H), 8.12 (s, 1H), 6.36-6.27 (m, 1H), 4.51 (dd, J=5.7, 2.9 Hz, 1H), 4.11 (q, J=2.5 Hz, 1H), 4.04-3.83 (m, 2H), 2.45 (ddd, J=13.5, 5.7, 2.3 Hz, 1H), 2.14 (ddd, J=13.6, 8.0, 5.8 Hz, 1H), 1.86 (d, J=3.5 Hz, 1H), 0.97 (s, 9H), 0.19 (d, J=6.7 Hz, 6H).

5-Iodo-5'-O-tert-butyldimethylsilyl-3'-O-methylthiomethyl-thymidine (T3): To a stirring solution of the 5-iodo-5'-O-tert-butyldimethylsilyl-thymidine (T2, 1009 mg, 2.35 mmol) in DMSO (10 mL) was added acetic acid (3.0 mL) and acetic anhydride (8 mL). The reaction mixture was stirred overnight at room temperature, then added dropwise to a saturated solution of sodium bicarbonate under vigorous stirring and extracted with ethyl acetate. The combined organic layers were dried over Na$_2$SO$_4$ and filtered. The filtrate was concentrated to dryness under reduced pressure to give the crude compound which was purified by column chromatography (dichloromethane/methanol: 30:1) to give pure product 5-iodo-51-O-tert-butyldimethylsilyl-3'-O-methylthiomethyl-thymidine (T3, 789 mg, 64%) as a white solid. $^1$H NMR (400 MHz, CDCl$_3$) δ 8.53 (s, 1H), 8.13 (s, 1H), 6.26 (dd, J=8.5, 5.5 Hz, 1H), 4.75-4.60 (m, 2H), 4.50 (dt, J=5.9, 1.8 Hz, 1H), 4.18 (q, =2.3 Hz, 1H), 3.89 (ddd, J=43.8, 11.4, 2.5 Hz, 2H), 2.51 (ddd, J=13.5, 5.5, 1.7 Hz, 1H), 2.18 (s, 3H), 2.08-1.97 (m, 1H), 0.98 (s, 9H), 0.20 (d, J=5.3 Hz, 6H).

5-Iodo-5'-O-tert-butyldimethylsilyl-3'-O-(tert-butyldithiomethyl)-2'-thymidine (T4): 5-Iodo-5'-O-tert-butyldimethylsilyl-3'-O-methylthiomethyl-thymidine (T3, 754 mg, 1.42 mmol) was dissolved in anhydrous dichloromethane (20 mL), followed by addition of triethylamine (0.3 mL) and molecular sieves (3 Å, 2 g). The mixture was cooled in an ice bath after stirring at room temperature for 0.5 hour and then a solution of sulfuryl chloride (0.12 mL, 1.50 mmol) in anhydrous dichloromethane (3 mL) was added dropwise over 2 minutes. The ice bath was removed and the reaction mixture was stirred for a further 0.5 hour. Then potassium p-toluenethiosulfonate (0.61 g, 2.25 mmol) in anhydrous DMF (3 mL) was added to the mixture. Stirring was continued at room temperature for an additional 1 hour followed by addition of tert-butyl mercaptan (1 mL). The reaction mixture was stirred at room temperature for 0.5 hour and quickly filtered through celite. The filter was washed with dichloromethane and the organic fraction was concentrated. The residue was purified by silica gel column chromatography (dichloromethane/methanol 30:1) to give compound T4. (561 mg, 66%). $^1$H NMR (400 MHz, CDCl$_3$) δ 9.11 (s, 1H), 8.12 (s, 1H), 6.25 (dd, J=8.5, 5.4 Hz, 1H), 4.91 (d, J=11.2 Hz, 1H), 4.80 (d, J=11.2 Hz, 1H), 4.53 (dt, J=6.0, 1.7 Hz, 1H), 4.22 (q, J=2.2 Hz, 1H), 4.00-3.80 (m, 2H), 2.59-2.45 (m, 1H), 2.02 (ddd, J=13.6, 8.5, 5.9 Hz, 1H), 1.36 (s, 9H), 0.98 (s, 9H), 0.19 (d, J=4.9 Hz, 6H).

Compound T5: Under nitrogen, a mixture of T4 (501 mg, 0.83 mmol), CuI (20 mg, 0.11 mmol) and triethylamine (0.30 mL) in thy DMF (5 mL) was stirred at room temperature for 5 min followed by the addition of DTM linker 7 (277 mg, 0.91 mmol), and Pd(0) (150 mg, 0.13 mmol). After stirring at room temperature in the dark overnight, the reaction mixture was added dropwise into brine (200 mL) under vigorous stirring and extracted with ethyl acetate. The combined organic layers were dried over Na$_2$SO$_4$ and filtered. The filtrate was concentrated to dryness under reduced pressure to give the crude compound T5. MS (APCI$^-$) calc'd for C$_{30}$H$_{48}$F$_3$N$_3$O$_7$S$_4$Si: 776.0, found: 774.5.

Compound T6: Without isolation, the crude compound T5 was dissolved in THF (10 mL) followed by the addition of TBAF THF solution (1.0M, 1.0 mL, 1.0 mmol). The mixture was stirred overnight at room temperature. Then, the mixture was concentrated in vacuo, saturated NaHCO$_3$ solution (50 mL) was added and the mixture was extracted with dichloromethane. The organic layer was dried over anhydrous Na$_2$SO$_4$, filtered, concentrated and the obtained crude mixture was purified by flash column chromatography (dichloromethane/methanol: 20:1) to give compound T6 (161 mg, 29% from compound T4). $^1$H NMR (400 MHz, CDCl$_3$) δ 8.50 (s, 1H), 8.11 (s, 1H), 7.45 (s, 1H), 6.22 (dd, J=7.6, 5.9 Hz, 1H), 4.93-4.85 (m, 3H), 4.81 (d, J=11.2 Hz, 1H), 4.58 (dt, J=6.0, 2.9 Hz, 1H), 4.52 (s, 2H), 4.20 (q, J=2.7 Hz, 1H), 4.02 (ddd, J=11.9, 4.4, 2.6 Hz, 1H), 3.89 (ddd, J=11.8, 5.0, 2.7 Hz, 1H), 3.54-3.47 (m, 2H), 2.76 (t, J=4.7 Hz, 1H), 2.54 (ddd, J=13.8, 6.0, 2.8 Hz, 1H), 2.25 (ddd, J=13.8, 7.6, 6.4 Hz, 1H), 1.37 (s, 9H), 1.34 (s, 6H). $^{13}$C NMR (75 MHz, CDCl$_3$) δ 162.00, 158.47, 157.99, 149.59, 144.64, 118.29, 114.47, 99.27, 87.93, 86.84, 85.66, 81.24, 80.62, 78.95, 77.86, 77.70, 77.43, 77.01, 62.54, 57.67, 53.82, 50.82, 48.03, 47.41, 38.52, 35.04, 31.95, 30.28, 29.43, 25.97, 25.66, 23.01, 21.08, 14.48, 11.79. MS (APCI$^+$) calc'd for C$_{24}$H$_{34}$F$_3$N$_3$O$_7$S$_4$: 661.8, found: 661.4.

3'-O-DTM-dUTP-5-SS-NH$_2$ (Compound T7): Compound T6 (50 mg, 76 μmol), tetrabutylammonium pyrophosphate (100 mg, 0.18 mmol) and 2-chloro-4-H-1,3,2-benzodioxaphosphorin-4-one (22 mg, 0.11 mmol) were dried separately overnight under high vacuum at ambient temperature. The tetrabutylammonium pyrophosphate was dissolved in dimethylformamide (DMF, 1 mL) under argon followed by addition of tributylamine (1 mL). The mixture was injected into the solution of 2-chloro-4-H-1,3,2-benzodioxaphosphorin-4-one in (DMF, 2 mL) under argon. After stirring for 1 h, the reaction mixture was added to the solution of T6 in DMF and stirred further for 1 hour at room temperature. Iodine solution (0.02 M iodine/pyridine/water) was then injected into the reaction mixture until a permanent brown color was observed. After 10 min, water (30 mL) was added and the reaction mixture was stirred at room temperature for an additional 2 hours. The resulting solution was extracted with ethyl acetate. The aqueous layer was concentrated in vacuo to approximately 20 mL, then concentrated NH$_4$OH (20 ml) was added and stirring continued overnight at room temperature. The resulting mixture was concentrated under vacuum and the residue was diluted with 5 ml of water. The crude mixture was then purified by anion exchange chromatography with DEAE-Sephadex A-25 at 4° C. using a gradient of TEAB (pH 8.0; 0.1-1.0 M). The crude product was further purified by reverse-phase HPLC to afford T7, which was characterized by MALDI-TOF MS: calc'd for $C_{22}H_{38}N_3O_{15}P_3S_4$: 805.0, found: 809.1.

3'-O-DTM-dUTP-5-SS-R6G (Compound T8): To a stirred solution of Rhodamine 6G-NHS ester (2 mg, 3.6 μmol) in DMF (0.2 ml), 3'-O-DTM-dUTP-5-SS-NH$_2$ (compound T7, 1.5 μmol) in NaHCO$_3$/Na$_2$CO$_3$ buffer (pH 8.9, 0.1 M, 0.3 ml) was added. The reaction mixture was stirred at room temperature for 3 h with exclusion of light. The reaction mixture was purified by anion exchange chromatography on DEAE-Sephadex A-25 at 4° C. using a gradient of TEAB (pH 8.0; 0.1-1.0 M). The crude product was further purified on reverse-phase HPLC to afford compound T8, which was characterized by MALDI-TOF MS: calc'd for $C_{49}H_{65}N_5O_{19}P_3S_4^+$: 1249.2, found: 1248.9.

Scheme 9. Synthesis of 3'-O-DTM-dCTP-5-SS-Alexa488.

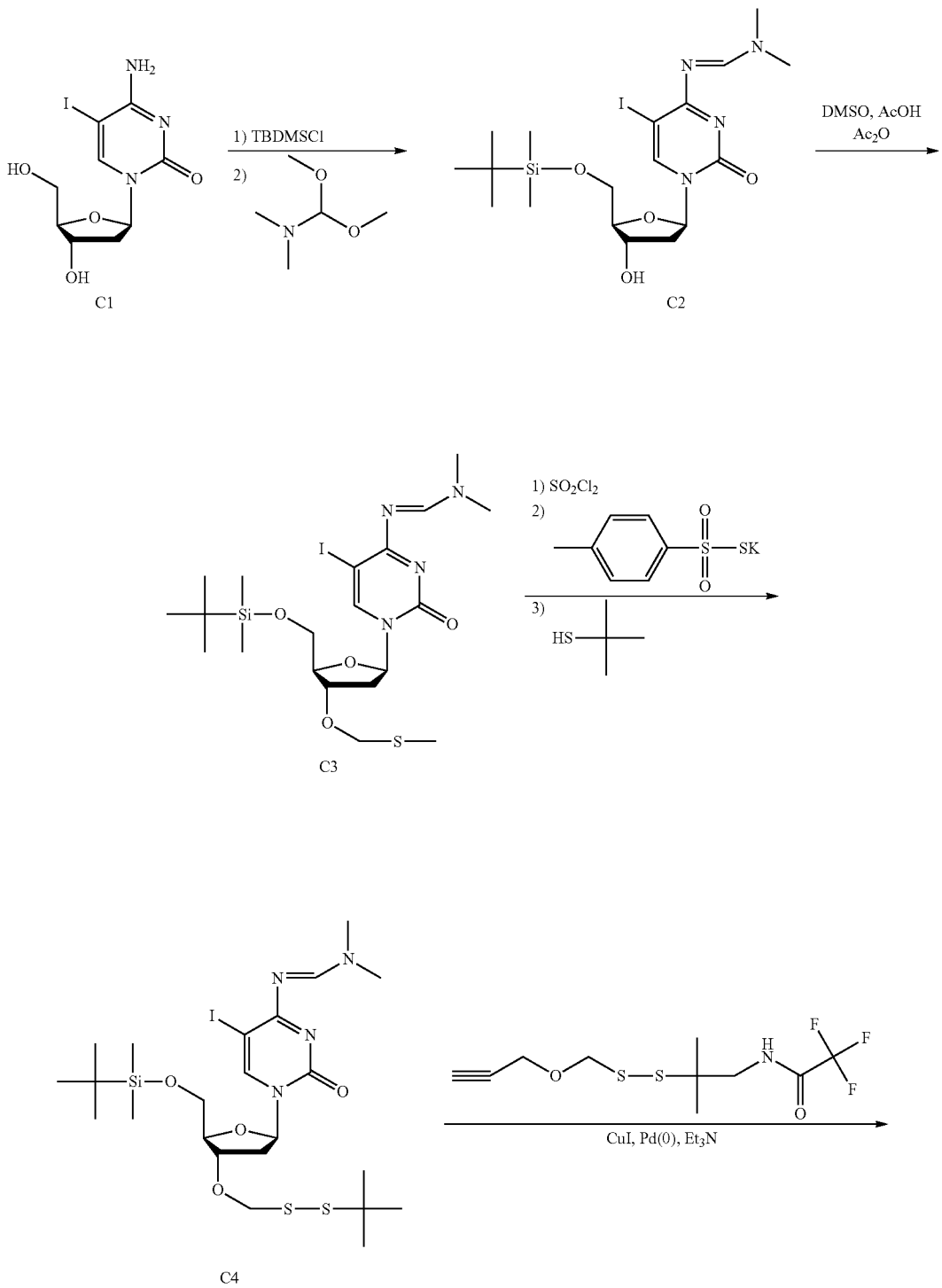

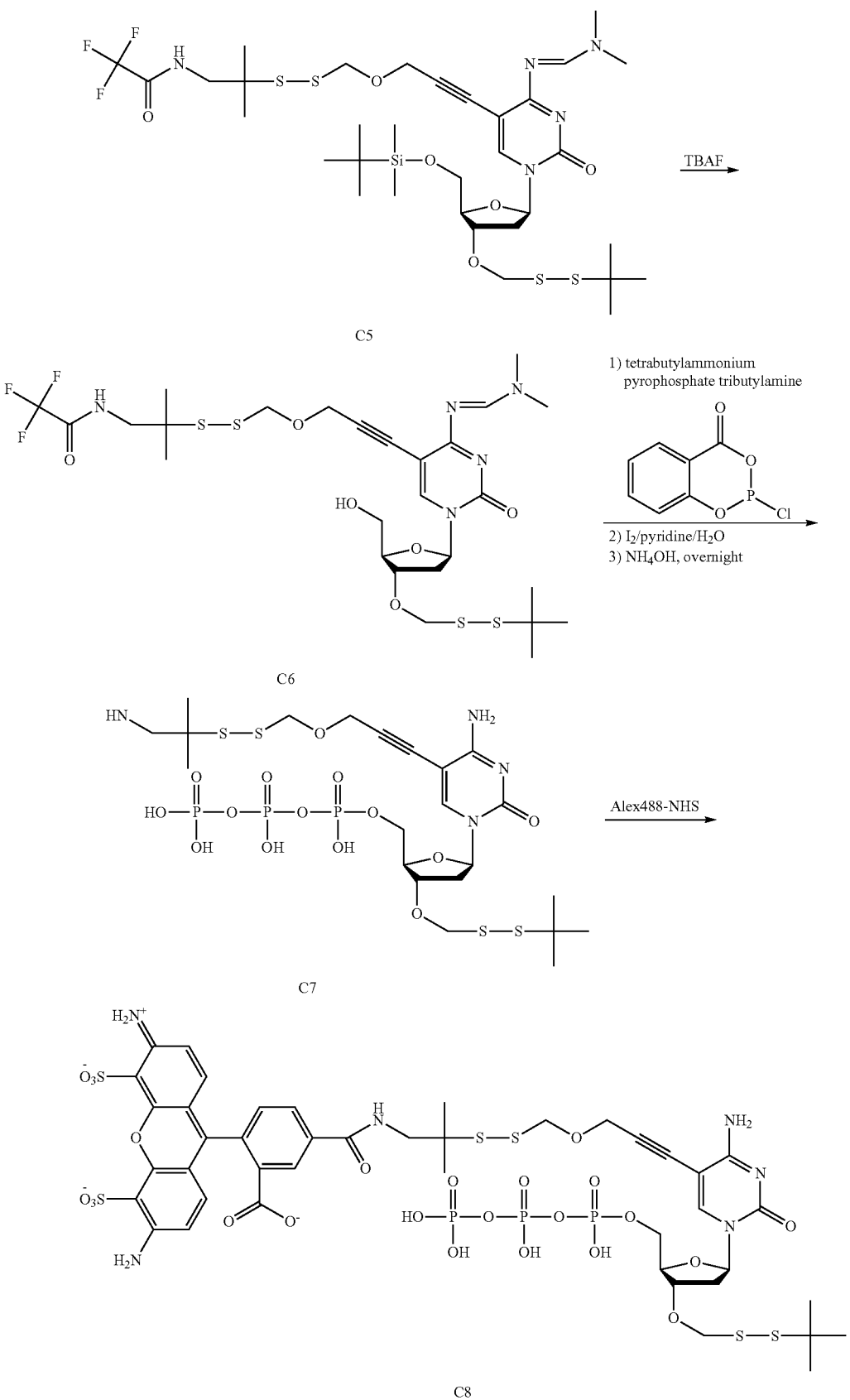

N⁴-DMF-5-iodo-5'-O-tert-butyldimethylsilyl-2'-deoxycytidine (C2): A mixture of 5-iodo-2'-deoxycytidine (C1, 1 g, 2.8 mmol), tert-butyldimethylsilyl chloride (450 mg, 3.0 mmol) and imidazole (200 mg, 3.0 mmol) was dissolved in dry DMF (15 mL) and stirred overnight at room temperature. After this period, the solvent was removed and the residue was added to N,N-dimethylformamide dimethyl acetal (1.5 mL) in dry DMF (10 mL). Stirring was continued at room temperature for an additional 10 hours, then the reaction mixture was poured into ice water (200 mL) under stirring, The precipitate was collected by filtration, and washed with water and hexane. The obtained crude product was purified by column chromatography (dichloromethane/methanol: 20:1) to give N⁴-DMF-5-iodo-5'-O-tert-butyldimethylsilyl-2'-deoxycytidine (C2, 1.02 g, 70%). ¹H NMR (400 MHz, CDCl₃) δ 8.74-8.69 (m, 1H), 8.27 (s, 1H), 6.37 (dd, =7.8, 5.6 Hz, 1H), 4.46 (dt, 0.1=5.9, 2.3 Hz, 1H), 4.16 (q, J=2.6 Hz, 1H), 3.94 (dd, J=11.3, 2.8 Hz, 1H), 3.84 (dd, J=11.3, 2.7 Hz, 1H), 3.22 (d, 0.1=0.8 Hz, 3H), 3.19 (d, =0.5 Hz, 3H), 2.69 (ddd, =13.5, 5.7, 2.4 Hz, 1H), 2.05 (ddd, =13.5, 7.8, 5.7 Hz, 1H), 0.93 (s, 9H), 0.15 (d, J=8.9 Hz, 6H). MS (APCI⁺) calc'd for $C_{18}H_{31}IN_4O_4Si$: 522.5, found: 522.5.

N⁴-DMF-5-iodo-5'-O-tert-butyldimethylsilyl-3'-O-methylthiomethyl-2'-deoxycytidine (C3): To a stirring solution of the N⁴-DMF-5-iodo-5'-O-tort-butyldimethylsilyl-2'-deoxycytidine (C2, 1.02 g, 2.29 mmol) in DMSO (10 mL) was added acetic acid (2.3 mL) and acetic anhydride (6.1 mL). The reaction mixture was stirred at room temperature overnight. Then the reaction mixture was added dropwise to a saturated solution of sodium bicarbonate under vigorous stirring and the precipitate was collected by suction filtration, washed with water and hexane. The obtained crude product was purified by column chromatography (dichloromethane/methanol: 30:1) to give pure product N⁴-DMF-5-iodo-5'-O-tert-butyldimethylsilyl-3'-O-methylthiomethyl-2'-deoxycytidine as a white solid (C3, 1.05 mg, 79%). ¹H NMR (400 MHz, CDCl₃) δ 8.4 (s, 1H), 8.22 (s, 1H), 6.28 (dd, J=7.9, 5.6 Hz, 1H), 4.70 (d, J=11.6 Hz, 1H), 4.61 (d, J=11.6 Hz, 1H), 4.48 (dt, J=6.1, 2.3 Hz, 1H), 4.17 (q, J=2.7 Hz, 1H), 3.97-3.88 (m, 1H), 3.82 (dd, J=11.2, 2.8 Hz, 1H), 3.21 (ddd, J=17.7, 2.0, 0.6 Hz, 7H), 2.68 (ddd, J=13.6, 5.7, 2.1 Hz, 1H), 2.16 (s, 3H), 1.97 (ddd, J=13.8, 7.9, 6.1 Hz, 1H), 0.96 (s, 9H), 0.17 (d, J=6.1 Hz, 6H). MS (APCI⁺) calc'd for $C_{20}H_{35}IN_4O_4SSi$: 582.5, found: 582.4.

N⁴-DMF-5-iodo-5'-O-tert-butyldimethylsilyl-3'-O-(tert-butyldithiomethyl)-2'-deoxycytidine (C4): N⁴-DMF-5-iodo-5'-O-tert-butyldimethylsilyl-3'-O-methylthiomethyl-2'-deoxycytidine (C3, 1.05 g, 1.81 mmol) was dissolved in anhydrous dichloromethane (20 mL), followed by addition of triethylamine (0.3 mL) and molecular sieves (3 Å, 2 g). The mixture was cooled in an ice bath, stirred at room temperature for 0.5 hour and then a solution of sulfuryl chloride (0.16 mL, 1.99 mmol) in anhydrous dichloromethane (3 mL) was added dropwise over 2 minutes. The ice bath was removed and the reaction mixture was stirred for a further 0.5 hour. Then potassium p-toluenethiosulfonate (614 mg, 2.71 mmol) in anhydrous DMF (3 mL) was added to the mixture. Stirring was continued at room temperature for an additional 1 hour followed by addition of tert-butyl mercaptan (1 mL). The reaction mixture was stirred at room temperature for 0.5 hour and quickly filtered through celite. The filter was washed with dichloromethane and the organic fraction was concentrated. The residue was purified by silica gel column chromatography (dichloromethane/methanol: 30:1) to give compound C4 (648 mg, 53%). ¹H NMR (400 MHz, CDCl₃) δ 8.77-8.71 (m, 1H), 8.23 (s, 1H), 6.28 (dd, J=8.0, 5.6 Hz, 1H), 4.92 (d, J=11.2 Hz, 1H), 4.77 (d. J=11.2 Hz, 1H), 4.52 (dt, J=5.9, 1.9 Hz, 1H), 4.21 (q, J=2.5 Hz, 1H), 3.95 (dd, J=11.3, 2.7 Hz, 1H), 3.84 (dd, J=11.3, 2.6 Hz, 1H), 3.23 (d, J=0.7 Hz, 3H), 3.19 (d, J=0.5 Hz, 3H), 2.72 (ddd, J=13.7, 5.6, 1.9 Hz, 1H), 1.96 (ddd, J=13.9, 8.1, 6.0 Hz, 1H), 1.35 (s, 9H), 0.96 (s, 9H), 0.18 (d, J=5.9 Hz, 6H); MS (APO): calc'd for $C_{23}H_{41}IN_4O_4S_2Si$: 656.7, found: 656.5.

Compound C5: Under nitrogen, a mixture of N⁴-DMF-5-iodo-5'-O-tert-butyldimethylsilyl-3'-O-(tert-butyldithiomethyl)-2'-deoxycytidine (C4, 420 mg, 0.64 mmol 0.375 mmol), CuI (20 mg, 0.11 mmol) and triethylamine (0.30 mL) in dry DMF (5 mL) was stirred at room temperature for 5 min followed by the addition of DTM linker 7 (213 mg, 0.70 mmol), and Pd(0) (150 mg, 0.13 mmol). After stirring at room temperature in the dark overnight, the reaction mixture was added dropwise into brine (200 mL) under vigorous stirring and extracted with ethyl acetate. The combined organic layers were dried over Na₂SO₄ and filtered. The filtrate was concentrated to dryness under reduced pressure to give the crude compound C5. MS (APCI⁺) calc'd for $C_{33}H_{54}F_3N_5O_6S_4Si$: 830.1, found: 829.2.

Compound C6: Without isolation, the crude compound C5 was dissolved in THF (10 mL) followed by the addition of TBAF fluoride THF solution (1.0M, 1.0 mL, 1.0 mmol). The mixture was stirred for 2 h at room temperature. Then, the mixture was concentrated in vacuo, saturated NaHCO₃ solution (50 mL) was added and the mixture was extracted with dichloromethane. The organic layer was dried over anhydrous Na₂SO₄, filtered, concentrated and the obtained crude mixture was purified by flash column chromatography (dichloromethane/methanol: 20:1) to give compound C6 (146 mg, 32% from compound C4). ¹H NMR (400 MHz, CDCl₃) δ 8.77 (s, 1H), 8.09 (s, 1H), 7.44 (d, J=7.3 Hz, 1H), 6.11 (t, J=6.6 Hz, 1H), 4.95 (s, 2H), 4.87 (d, J=11.1 Hz, 1H), 4.76 (d, J=11.1 Hz, 1H), 4.60-4.48 (m. 3H), 4.18 (q, J=3.0 Hz, 1H), 3.98 (dd, J=12.1, 2.7 Hz, 1H), 3.84 (dd, J=12.0, 3.2 Hz, 1H), 3.47 (d, J=6.4 Hz, 2H), 3.20-3.15 (m, 6H), 2.96 (s, 1H), 2.88 (d, J=0.6 Hz, 1H), 2.59 (ddd, J=13.8, 6.1, 3.2 Hz, 1H), 2.35 (dt, J=13.7, 6.8 Hz, 1H), 1.33 (s, 9H), 1.31 (s, 6H). ¹³C NMR (75 MHz, CDCl₃) δ 170.96, 162.94, 159.08, 154.94, 148.67, 146.84, 98.35, 89.16, 86.47, 85.90, 82.09, 81.22, 79.85, 77.65, 62.66, 57.65, 50.94, 47.92, 47.31, 41.87, 41.81, 38.42, 38.03, 36.86, 35.76, 31.82, 30.29, 26.01. MS (APCI⁺): calc'd for $C_{27}H_{40}F_3N_5O_6S_4$: 715.9, found: 715.9.

3'-O-DTM-dCTP-5-SS-NH₂ (Compound C7). Compound C6 (50 mg, 0.07 mmol), tetrabutylammonium pyrophosphate (99 mg, 0.18 mmol) and 2-chloro-4-H-1,3,2-benzodioxaphosphorin-4-one (22 mg, 0.11 mmol) were dried separately overnight under high vacuum at ambient temperature. The tetrabutylammonium pyrophosphate was dissolved in dimethylformamide (DMF, 1 mL) under argon followed by addition of tributylamine (1 mL). The mixture was injected into the solution of 2-chloro-4-H-1,3,2-benzodioxaphosphorin-4-one in (DMF, 2 mL) under argon. After stirring for 1 h, the reaction mixture was added to the solution of C6 in DMF and stirred further for 1 hour at room temperature. Iodine solution (0.02 M iodine/pyridine/water) was then injected into the reaction mixture until a permanent brown color was observed. After 10 min, water (30 mL) was added and the reaction mixture was stirred at room temperature for an additional 2 hours. The resulting solution was extracted with ethyl acetate. The aqueous layer was concentrated in vacuo to approximately 20 mL, then concentrated NH₄OH (20 ml) was added and the mixture stirred overnight at room temperature. The resulting mixture was concentrated under vacuum and the residue was diluted with 5 ml of water. The crude mixture was then purified by anion exchange chromatography on DEAE-Sephadex A-25 at 4° C. using a gradient of TEAB (pH 8.0; 0.1-1.0 M). The crude product was further purified by reverse-phase HPLC to afford C7, which was characterized by MALDI-TOF MS: calc'd for $C_{22}H_{39}N_4O_{14}P_3S_4$: 804.0, found: 807.5.

3'-O-DTM-S—SS-Alexa488-dCTP (Compound C8). To a stirred solution of Alexa488-NHS ester (2 mg, 3.1 μmol) in DMF (0.2 ml), 3'-O-DTM-dCTP-5-SS-NH$_2$ (compound C7, 3.0 μmop in NaHCO$_3$/Na$_2$CO$_3$ buffer (pH 8.9, 0.1 M, 0.3 ml) was added. The reaction mixture was stirred at room temperature for 3 h with exclusion of light. The reaction mixture was purified by anion exchange chromatography on DEAE-Sephadex A-25 at 4° C. using a gradient of TEAB (pH 8.0; 0.1-1.0 M). The crude product was further purified on reverse-phase HPLC to afford Compound C8, which was characterized by MALDI-TOF MS: calc'd for $C_{43}H_{49}N_6O_{24}P_3S_6^{2-}$: 1319.2, found: 1325.1.

Scheme 12. Synthesis of 3'-O-DTM-dATP-7-SS-ROX.

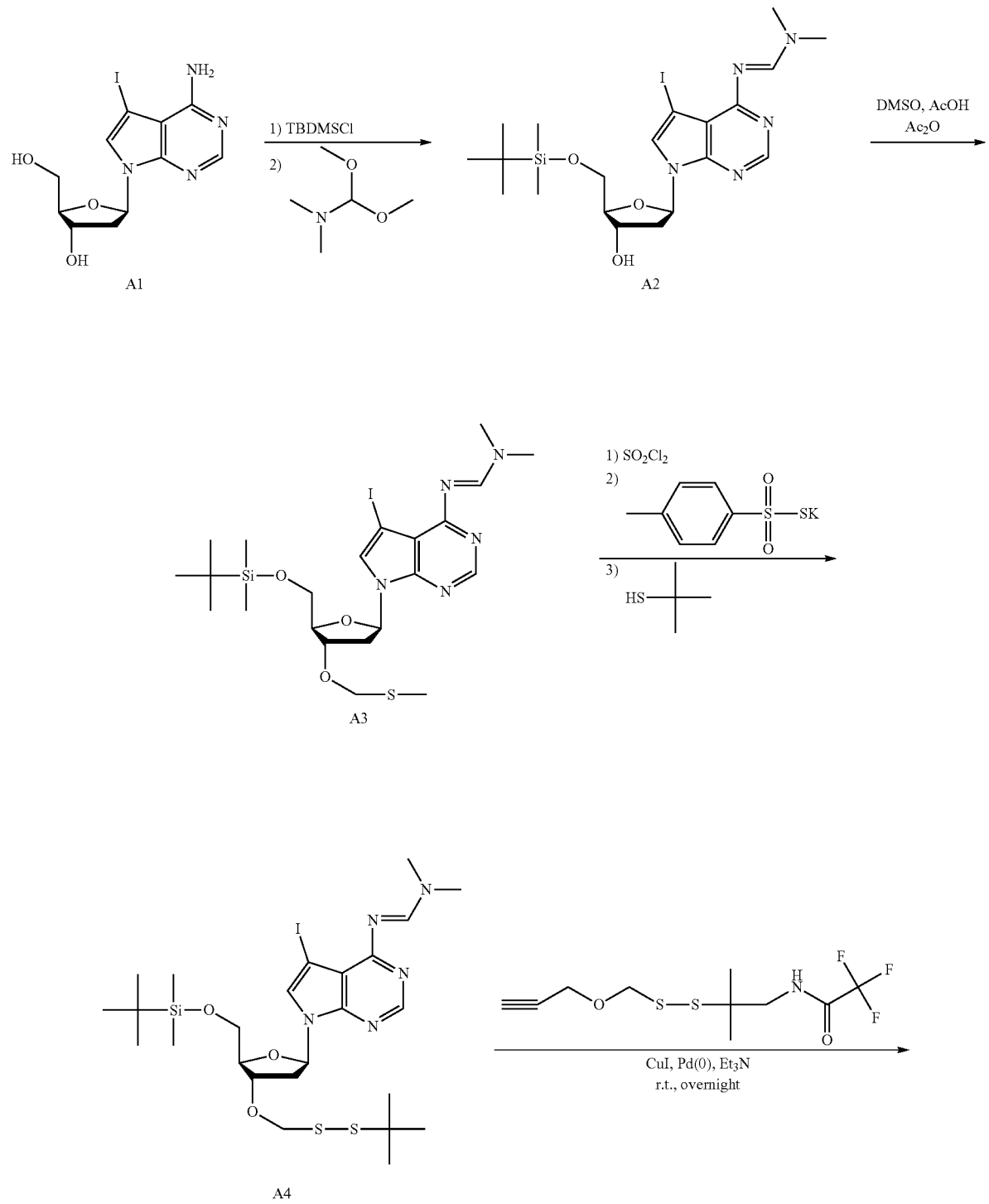

-continued
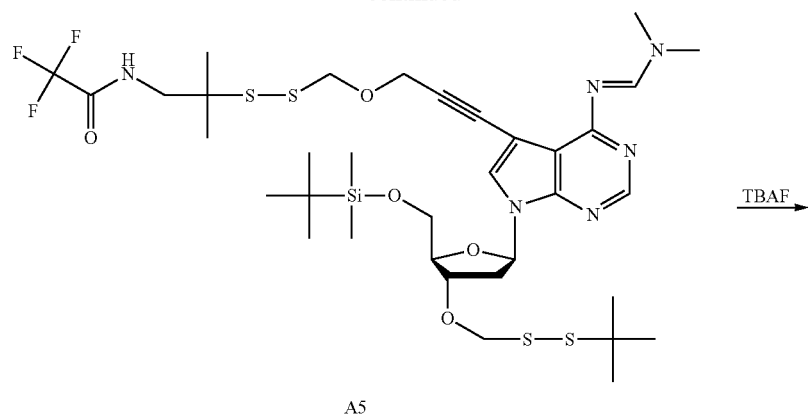
A5
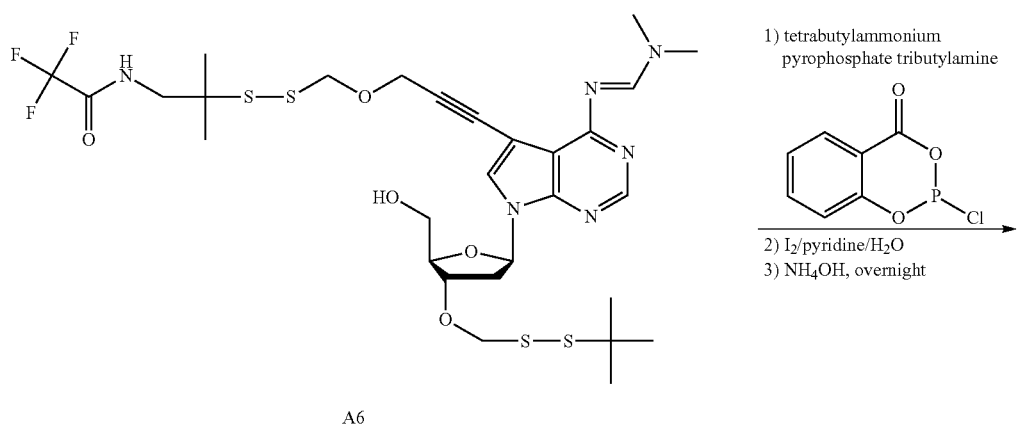
A6
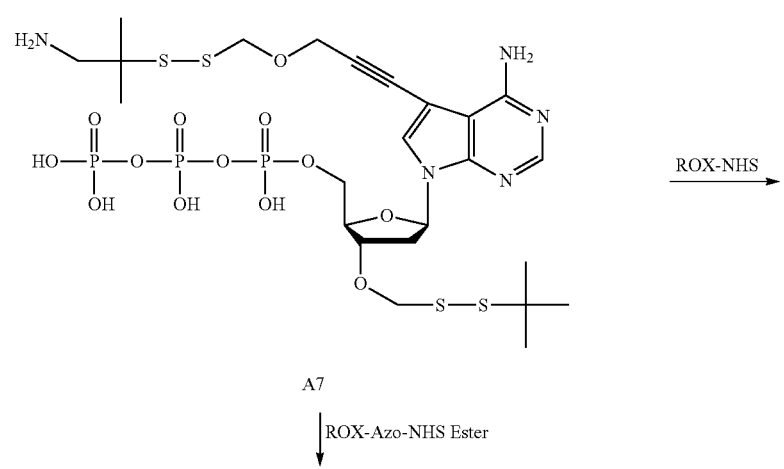
A7
↓ ROX-Azo-NHS Ester

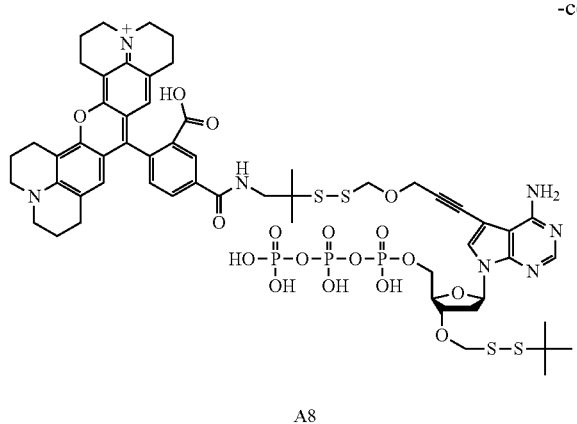

A8

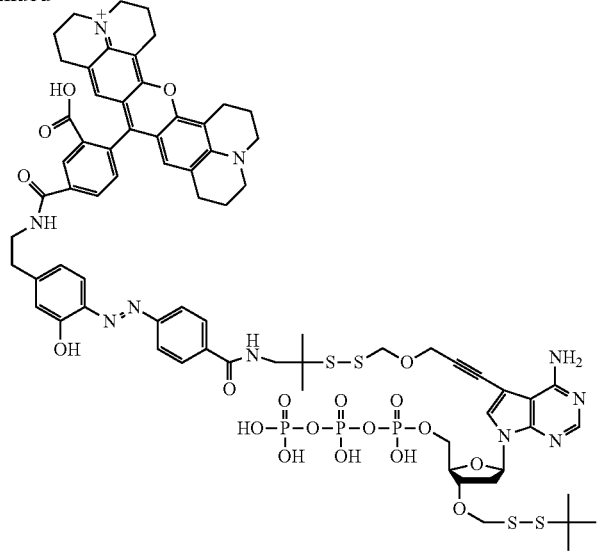

3'-O-DTM-dATP-SS-Azo-Rox

N[4]-DMF-7-deaza-7-iodo-5'-O-tert-butyldimethylsilyl-2'-deoxyadenosine (A2): A mixture of 7-deaza-7-iodo-2'-deoxyadenosine (A1, 1 g, 2.66 mmol), tert-butyldimethylsilyl chloride (440 mg, 2.9 mmol) and imidazole (200 mg, 3.0 mmol) was dissolved in dry DMF (15 mL) and stirred overnight at room temperature. After this period, the solvent was removed and the residue was added to N,N-dimethylformamide dimethyl acetal (1.5 mL) in dry DMF (10 mL). Stirring was continued at room temperature for an additional 10 hours, then the reaction mixture was poured into ice water (200 mL) under stirring. The precipitate was collected by suction filtration, then washed with water and hexane. The obtained crude product was purified by column chromatography (dichloromethane/methanol: 20:1) to give $1\backslash^{74}$-DMF-7-deaza-7-iodo-5'-O-tert-butyldimethylsilyl-2'-deoxyadenosine (A2, 1145 mg, 79%). MS (APCI$^+$) calc'd for $C_{20}H_{32}IN_5O_3Si$: 545.5, found: 545.7.

N[4]-DMF-7-deaza-7-iodo-5'-O-tert-butyldimethylsilyl-3'-O-methylthiomethyl-2'-deoxyadenosine (A3): To a stirring solution of the N[4]-DMF-7-deaza-7-iodo-5'-O-tert-butyldimethylsilyl-2'-deoxyadenosine (A2, 1324 mg, 2.43 mmol) in DMSO (10 mL) was added acetic acid (3 mL) and acetic anhydride (8 mL). The reaction mixture was stirred at room temperature overnight. Then the reaction mixture was added dropwise to a saturated solution of sodium bicarbonate under vigorous stirring and the precipitate was collected by suction filtration, and washed with water and hexane. The obtained crude product was purified by column chromatography (dichloromethane/methanol: 30:1) to give pure product N[4]-DMF-7-deaza-7-iodo-5'-O-tert-butyldimethylsilyl-3'-O-methylthiomethyl-2'-deoxyadenosine as a white solid (A3, 956 mg, 65%). $^1$H NMR (400 MHz, CDCl$_3$) δ 8.82-8.77 (m, 1H), 8.45 (s, 1H), 7.48 (s, 1H), 6.70 (dd, J=7.7, 6.2 Hz, 1H), 4.76-4.64 (m, 2H), 4.64-4.55 (m, 1H), 4.14 (td, J=3.7, 2.4 Hz, 1H), 3.86-3.80 (m, 2H), 3.32 (d, J=0.6 Hz, 3H), 3.22-3.17 (m, 3H), 2.54-2.42 (m, 2H), 2.19 (s, 3H), 0.97 (s, 9H), 0.15 (d, J=6.3 Hz, 6H). MS (APCI$^+$) calc'd for $C_{22}H_{36}IN_5O_3SSi$: 605.6, found: 605.1.

N[4]-DMF-7-deaza-7-iodo-5'-O-tert-butyldimethylsilyl-3'-O-(tert-butyldithiomethyl)-2'-deoxyadenosine (A4): N[4]-DMF-7-deaza-7-iodo-5'-O-tert-butyldimethylsilyl-3'-O-methylthiomethyl-T-deoxyadenosine (A3, 900 mg, 1.48 mmol) was dissolved in anhydrous dichloromethane (20 mL), followed by addition of triethylamine (0.3 mL) and molecular sieves (3 Å, 2 g). The mixture was cooled in an ice bath, stirred at room temperature for 0.5 hour and then a solution of sulfuryl chloride (0.13 mL, 1.63 mmol) in anhydrous dichloromethane (3 mL) was added dropwise over 2 minutes. The ice bath was removed and the reaction mixture was stirred for a further 0.5 hour. Then potassium p-toluenethiosulfonate (509 mg, 2.22 mmol) in anhydrous DMF (3 mL) was added to the mixture. Stirring was continued at room temperature for an additional 1 hour followed by addition of tert-butyl mercaptan (1 mL). The reaction mixture was stirred at room temperature for 0.5 hour and quickly filtered through celite. The filter was washed with dichloromethane and the organic fraction was concentrated. The residue was purified by silica gel column chromatography (dichloromethane/methanol: 30:1) to give N[4]-DMF-7-deaza-7-iodo-5'-O-tert-butyldimethylsilyl-3'-O-(tert-butyldithiomethyl)-2'-deoxyadenosine (A4, 733 mg, 73%). NMR (400 MHz, CDCl$_3$) δ 8.82-8.77 (m, 1H), 8.45 (s, 1H), 7.50 (s, 1H), 6.69 (dd, J=8.0, 6.0 Hz, 1H), 4.95-4.80 (m, 2H), 4.63 (dt, J=5.3, 2.5 Hz, 1H), 4.17 (td, J=3.5, 2.3 Hz, 1H), 3.85 (dd, J=3.5, 1.2 Hz, 2H), 3.32 (d, J=0.6 Hz, 3H), 3.19 (s, 3H), 2.58-2.41 (m, 2H), 1.36 (s, 9H), 0.98 (s, 9H), 0.16 (d, J=6.0 Hz, 6H). MS (APCI$^+$) calc'd for $C_{25}H_{42}IN_5O_3S_2Si$: 679.7, found: 679.4

Compound A5: Under nitrogen, a mixture of N[4]-DMF-7-deaza-7-iodo-5'-O-tert-butyldimethylsilyl-3'-O-(tert-butyldithiomethyl)-2'-deoxyadenosine (A4, 444 mg, 0.65 mmol), CuI (20 mg, 0.11 mmol) and triethylamine (0.30 mL) in dry DMF (5 mL) was stirred at room temperature for 5 min followed by the addition of DTM linker 7 (310 mg, 1.02 mmol), and Pd(0) (150 mg, 0.13 mmol). After stirring at room temperature in the dark overnight, the reaction mixture was added dropwise into brine (200 mL) under vigorous stirring and extracted with ethyl acetate. The combined organic layers were dried over Na$_2$SO$_4$ and filtered. The filtrate was concentrated to dryness under reduced pressure to give the crude compound A5. MS (APCI$^+$) calc'd for $C_{35}H_{55}F_3N_6O_5S_4Si$: 853.2, found: 853.1

Compound A6: Without isolation, the crude compound A5 was dissolved in THF (10 mL) followed by the addition of TBAF fluoride THF solution (1.0M, 1.0 mL, 1.0 mmol). The mixture was stirred at room temperature for 2 h. Then the mixture was concentrated in vacuo, saturated NaHCO$_3$ solution (50 mL) was added and the mixture was extracted with dichloromethane. The organic layer was dried over anhydrous Na$_2$SO$_4$, filtered, concentrated and the obtained crude mixture was purified by flash column chromatography (dichloromethane/methanol: 20:1) to give compound A6 (105 mg, 22% from compound A4). $^1$H NMR (400 MHz, CDCl$_3$) δ 8.81 (d, J=6.7 Hz, 1H), 8.41 (d, J=9.7 Hz, 1H), 7.28 (s, 1H), 6.12 (dt, J=12.8, 6.5 Hz, 1H), 4.98 (s, 2H), 4.88 (d, J=3.3 Hz, 2H), 4.73 (d, J=5.4 Hz, 1H), 4.58 (s, 2H), 4.33 (d, J=4.9 Hz, 1H), 4.01 (dt, J=12.9, 3.1 Hz, 1H), 3.83 (d, J=8.2 Hz, 1H), 3.48 (d, J=6.4 Hz, 2H), 3.23 (d, J=17.2 Hz, 6H), 3.13-3.00 (m, 1H), 2.40 (dt, J=13.3, 6.6 Hz, 1H), 1.36 (s, 9H), 1.34 (s, 6H). $^{13}$C NMR (75 MHz, CDCl$_3$) δ 162.23, 158.17, 157.08, 152.13, 151.48, 150.16, 131.12, 113.22, 96.29, 90.20, 86.94, 84.09, 82.11, 81.09, 80.16, 79.55, 64.07, 57.57, 51.02, 47.91, 47.28, 41.36, 37.94, 35.91, 35.34, 30.33, 26.01. MS (APCI$^-$): calc'd for C$_{29}$H$_{41}$F$_3$N$_6$O$_5$S$_4$: 738.9, found: 737.2.

3'-O-DTM-7-deaza-dATP-7-SS-NH$_2$ (Compound A7): Compound A6 (40 mg, 54 µmol), tetrabutylammonium pyrophosphate (60 mg, 108 µmol) and 2-chloro-4-H-1,3,2-benzodioxaphosphorin-4-one (22 mg, 110 µmop were dried separately over night under high vacuum at ambient temperature. The tetrabutylammonium pyrophosphate was dissolved in dimethylformamide (DMF, 1 mL) under argon followed by the addition of tributylamine (1 mL). The mixture was injected into the solution of 2-chloro-4-H-1,3, 2-benzodioxaphosphorin-4-one in (DMF, 2 mL) under argon. After stirring for 1 h, the reaction mixture was added to a solution of A6 in DMF and stirred for a further 1 hour at room temperature. Iodine solution (0.02 M iodine/pyridine/water) was then injected into the reaction mixture until a permanent brown color was observed. After 10 min, water (30 mL) was added and the reaction mixture was stirred at room temperature for an additional 2 hours. The resulting solution was extracted with ethyl acetate. The aqueous layer was concentrated in vacuo to approximately 20 mL, then concentrated NH$_4$OH (20 ml) was added and stirring continued overnight at room temperature. The resulting mixture was concentrated under vacuum and the residue was diluted with 5 ml of water. The crude mixture was then purified by anion exchange chromatography on DEAE-Sephadex A-25 at 4° C. using a gradient of TEAB (pH 8.0; 0.1-1.0 M). The crude product was further purified by reverse-phase HPLC to afford A7, which was characterized by MALDI-TOF MS: calc'd for C$_{24}$H$_{40}$N$_5$O$_{13}$P$_3$S$_4$: 827.0, found: 830.1.

3'-O-DTM-7-deaza-dATP-7-SS-ROX (Compound A8): To a stirred solution of ROX—NHS ester (2 mg, 3.2 µmop in DMF (0.2 ml), 3'-O-DTM-7-deaza-dATP-7-SS-NH$_2$ (compound A7, 3.0 mol) in NaHCO$_3$/Na$_2$CO$_3$ buffer (pH 8.9, 0.1 M, 0.3 ml) was added. The reaction mixture was stirred at room temperature for 3 h with exclusion of light. The reaction mixture was purified by anion exchange chromatography on DEAE-Sephadex A-25 at 4° C. using a gradient of TEAB (pH 8.0; 0.1-1.0 M). The crude product was further purified by reverse-phase HPLC to afford Compound A8, which was characterized by MALDI-TOF MS: calc'd for C$_{57}$H$_{69}$N$_7$O$_{17}$P$_3$S$_4^+$: 1344.3, found: 1345.5.

Scheme 11. Synthesis of 3'-O-DTM-dGTP-7-SS-Cy5.

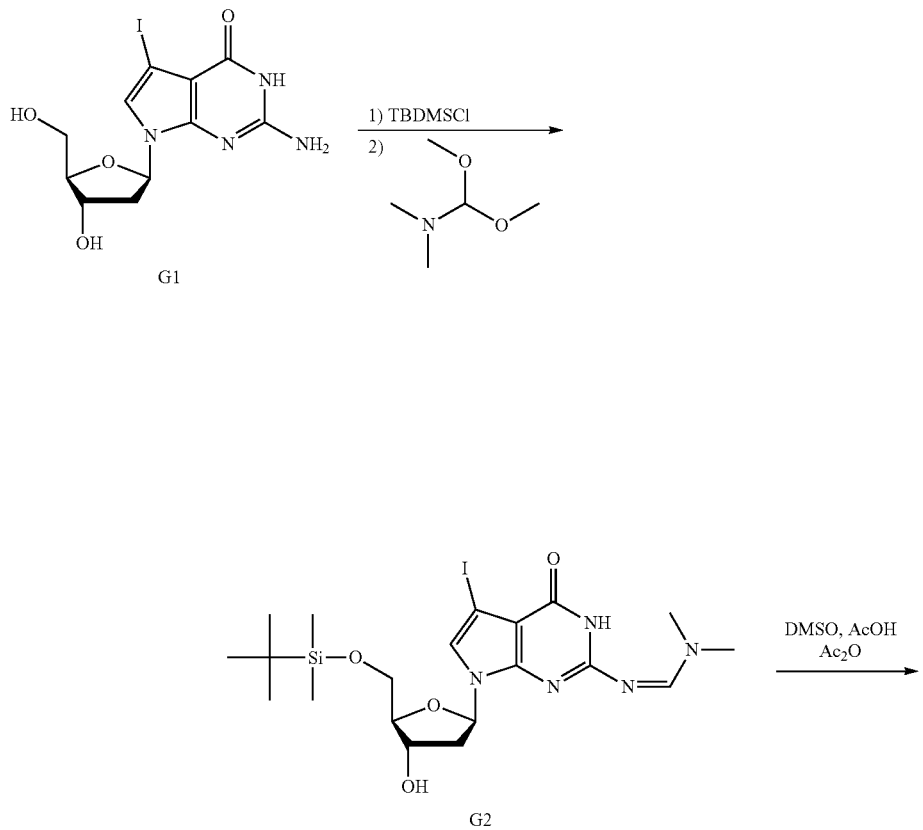

-continued
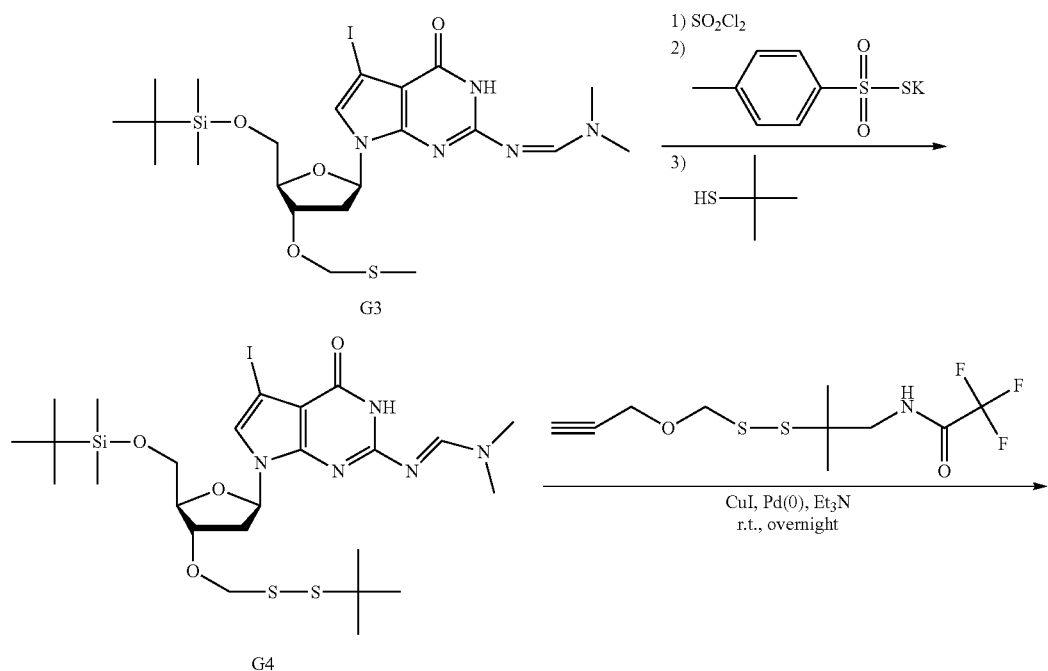
G3
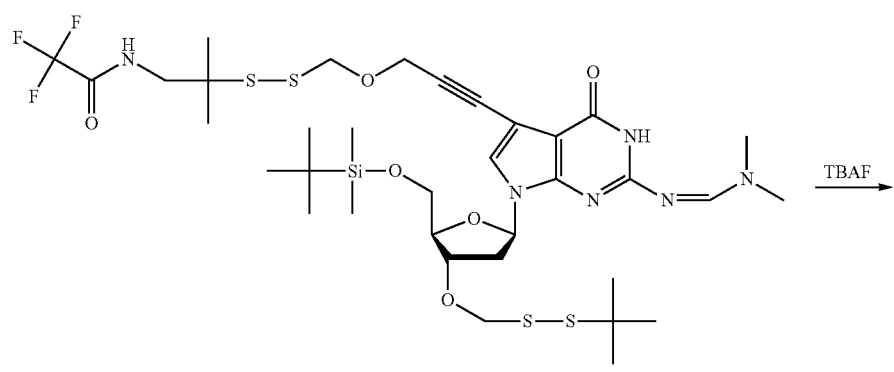
G5
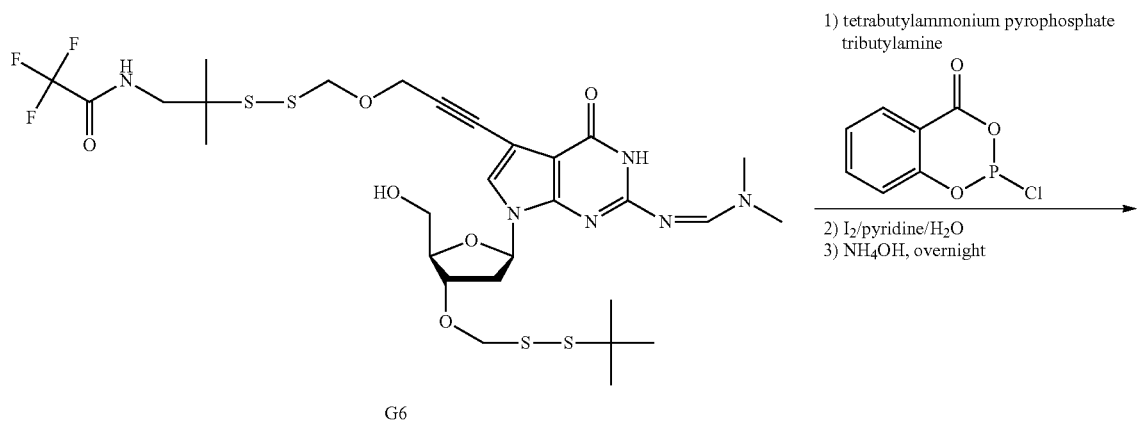
G6

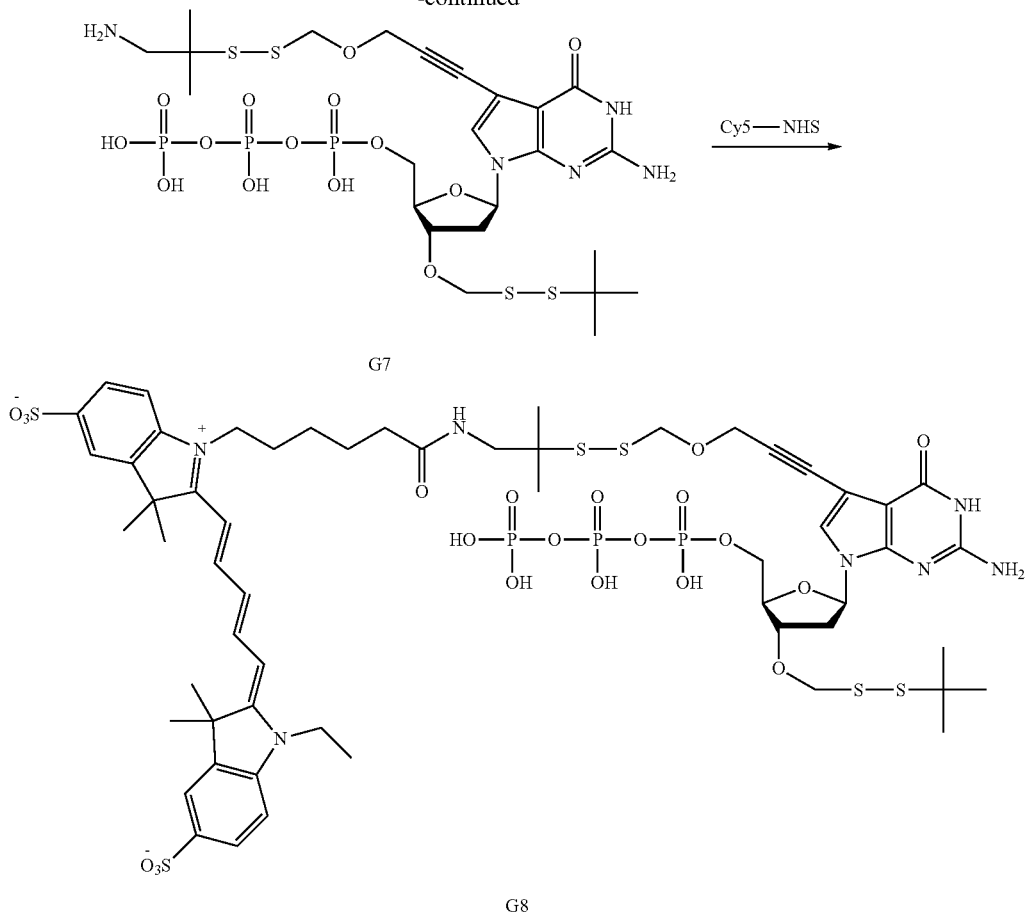

G7

G8

N[4]-DMF-7-deaza-7-iodo-5'-O-tert-butyldimethylsilyl-2'-deoxyguanosine (G2): A mixture of 7-deaza-7-iodo-2'-deoxyguanosine (G1, 1 g, 2.55 mmol), tert-butyldimethylsilyl chloride (420 mg, 2.8 mmol) and imidazole (202 mg, 3.0 mmol) was dissolved in dry DMF (15 mL) and stirred overnight at room temperature. After this period, the solvent was removed and the residue was added to N,N-dimethylformamide dimethyl acetal (1.5 mL) in dry DMF (10 mL). Stirring was continued at room temperature for an additional 10 hours, then the reaction mixture was poured into ice water (200 mL) under stirring and the precipitate was collected by suction filtration, and washed with water and hexane. The obtained crude product was purified by column chromatography (dichloromethane/methanol: 20:1) to give N[4]-DMF-7-deaza-7-iodo-5'-O-tert-butyldimethylsilyl-2'-deoxyguanosine (G2, 1.07 g, 77%). $^1$H NMR (400 MHz, CDCl$_3$) δ 8.63 (s, 1H), 8.60 (s, 1H), 7.11 (s, 1H), 6.63 (dd, J=7.5, 6.2 Hz, 1H), 4.62 (s, 1H), 4.03 (dt, J=4.7, 3.1 Hz, 1H), 3.88 (dd, J=10.8, 3.2 Hz, 1H), 3.79 (dd, J=10.8, 4.7 Hz, 1H), 3.52 (s, 1H), 3.19 (s, 3H), 3.09 (d, J=0.6 Hz, 3H), 2.53-2.34 (m, 2H), 0.97 (s, 9H), 0.21-0.10 (m, 6H).

N[4]-DMF-7-deaza-7-iodo-5'-O-tert-butyldimethylsilyl-3'-O-methylthiomethyl-2'-deoxyguanosine (G3): To a stirring solution of the N[4]-DMF-7-deaza-7-iodo-5'-O-tert-butyldimethylsilyl-2'-deoxyguanosine (G2, 950 mg, 1.74 mmol) in DMSO (10 mL) was added acetic acid (3 mL) and acetic anhydride (8 mL). The reaction mixture was stirred at room temperature overnight. The reaction mixture was added dropwise to a saturated solution of sodium bicarbonate under vigorous stirring and the precipitate was collected by suction filtration, and washed with water and hexane. The obtained crude product was purified by column chromatography (dichloromethane/methanol: 30:1) to give pure product N[4]-DMF-7-deaza-7-iodo-5'-O-tert-butyldimethylsilyl-3'-O-methylthiomethyl-2'-deoxyguanosine as a white solid (G3, 756 mg, 70%). $^1$H NMR (400 MHz, CDCl$_3$) δ 9.66 (s, 1H), 8.62 (d, J=0.9 Hz, 1H), 7.11 (s, 1H), 6.56 (dd, J=8.1, 6.2 Hz, 1H), 4.76-4.64 (m, 2H), 4.59 (dt, J=5.2, 2.7 Hz, 1H), 4.11 (ddd, J=4.4, 3.1, 2.2 Hz, 1H), 3.88-3.70 (m, 2H), 3.18 (s, 3H), 3.16-3.08 (m, 3H), 2.48-2.32 (m, 2H), 2.19 (s, 3H), 0.97 (s, 9H), 0.15 (d, J=5.9 Hz, 6H).

N[4]-DMF-7-deaza-7-iodo-5'-O-tert-butyldimethylsilyl-3'-O-(tert-butyldithiomethyl)-2'-deoxyguanosine (G4): N[4]-DMF-7-deaza-7-iodo-5'-O-tert-butyldimethylsilyl-3'-O-methylthiomethyl-2'-deoxyguanosine (G3, 731 mg, 1.18 mmol) was dissolved in anhydrous dichloromethane (20 mL), followed by addition of triethylamine (0.2 mL) and molecular sieves (3 Å, 2 g). After stirring at room temperature for 0.5 hour and cooling in an ice bath, a solution of sulfuryl chloride (0.11 mL, 1.33 mmol) in anhydrous dichloromethane (3 mL) was added dropwise over 2 minutes. The ice bath was removed and the reaction mixture was stirred for a further 0.5 hour. Then potassium p-toluenethiosulfonate (417 mg, 1.82 mmol) in anhydrous DMF (2 mL) was added to the mixture. Stirring was continued at room temperature for an additional 1 hour followed by the addition of tert-butyl mercaptan (1 mL). The reaction mixture was stirred at room temperature for 0.5 hour and quickly filtered through celite. The filter was washed with dichloromethane and the organic fraction was concentrated. The residue was purified by silica gel column chromatography (dichloromethane/methanol: 30:1) to give $N^4$-DMF-7-deaza-7-iodo-5'-O-tert-butyldimethylsilyl-3'-O-(tert-butyl-dithiomethyl)-2'-deoxyguanosine (G4, 508 mg, 62%). $^1$H NMR (400 MHz, CDCl$_3$) δ 9.11 (s, 1H), 8.64 (t, J 0.6 Hz, 1H), 7.12 (s, 1H), 6.56 (dd, J=8.4, 5.9 Hz, 1H), 4.94-4.83 (m, 2H), 4.59 (dt, J=5.8, 2.2 Hz, 1H), 4.19-4.12 (m, 1H), 3.88-3.75 (m, 2H), 3.20 (s, 3H), 3.11 (d, J=0.7 Hz, 3H), 2.52-2.34 (m, 2H), 1.42-1.30 (m, 9H), 0.98 (s, 9H), 0.16 (d, J=6.0 Hz, 6H).

Compound G5: Under nitrogen, a mixture of $N^4$-DMF-7-deaza-7-iodo-5'-O-tert-butyldimethylsilyl-3'-O-(tert-butyldithiomethyl)-2'-deoxyguanosine (G4, 471 mg, 0.68 mmol), CuI (20 mg, 0.11 mmol) and triethylamine (0.30 mL) in dry DMF (5 mL) was stirred at room temperature for 5 min followed by the addition of DTM linker 7 (300 mg, 0.99 mmol), and Pd(0) (150 mg, 0.13 mmol). After stirring at room temperature in the dark overnight, the reaction mixture was added dropwise into brine (200 mL) under vigorous stirring and extracted with ethyl acetate. The combined organic layers were dried over Na$_2$SO$_4$ and filtered. The filtrate was concentrated to dryness under reduced pressure to give crude compound G5.

Compound G6: Without isolation, the crude compound G5 was dissolved in THF (10 mL) followed by the addition of TBAF fluoride THF solution (1.0M, 1.0 mL, 1.0 mmol). The mixture was stirred at room temperature for 2 h. Then, the mixture was concentrated in vacuo, saturated NaHCO$_3$ solution (50 mL) was added and the mixture was extracted with dichloromethane. The organic layer was dried over anhydrous Na$_2$SO$_4$, filtered, concentrated and the obtained crude mixture was purified by flash column chromatography (dichloromethane/methanol: 20:1) to give compound G6 (121 mg, 24% from compound G4). $^1$H NMR (400 MHz, CDCl$_3$) δ 8.92 (s, 1H), 8.52 (s, 1H), 7.66 (s, 1H), 7.01 (s, 1H), 6.19 (t, J=7.2 Hz, 1H), 4.99 (s, 2H), 4.87 (q, J=11.1 Hz, 3H), 4.67 (s, 1H), 4.56 (s, 2H), 4.22 (s, 1H), 4.06-3.99 (m, 1H), 3.91 (d, J=12.1 Hz, 1H), 3.76 (t, J=10.2 Hz, 1H), 3.51 (d, J=6.3 Hz, 2H), 3.20 (s, 3H), 3.07 (s, 3H), 2.85 (dq, J=15.3, 7.1 Hz, 1H), 2.41 (dd, J=13.9, 6.3 Hz, 1H), 1.34 (d, J=16.5 Hz, 15H). $^{13}$C NMR (75 MHz, CDCl$_3$) δ 159.36, 158.34, 157.89, 156.59, 149.39, 125.80, 105.45, 98.98, 87.28, 85.52, 84.62, 81.21, 80.16, 78.97, 77.63, 63.33, 57.83, 50.97, 48.01, 47.51, 41.63, 37.96, 35.37, 31.95, 30.30, 26.07, 25.99, 25.66, 23.02, 14.48.

3'-O-DTM-7-deaza-dGTP-7-SS-NH$_2$ (Compound G7): Compound G6 (40 mg, 53 μmol), tetrabutylammonium pyrophosphate (89 mg, 160 μmop and 2-chloro-4-H-1,3,2-benzodioxaphosphorin-4-one (22 mg, 110 μmol) were dried separately over night under high vacuum at ambient temperature. The tetrabutylammonium pyrophosphate was dissolved in dimethylformamide (DMF, 1 mL) under argon followed by addition of tributylamine (1 mL). The mixture was injected into the solution of 2-chloro-4-H-1,3,2-benzodioxaphosphorin-4-one in (DMF, 2 mL) under argon. After stirring for 1 h, the reaction mixture was added to the solution of G6 in DMF and stirred further for 1 hour at room temperature. Iodine solution (0.02 M iodine/pyridine/water) was then injected into the reaction mixture until a permanent brown color was observed. After 10 min, water (30 mL) was added and the reaction mixture was stirred at room temperature for an additional 2 hours. The resulting solution was extracted with ethyl acetate. The aqueous layer was concentrated in vacuo to approximately 20 mL, and concentrated NH$_4$OH (20 ml) was added and stirring continued overnight at room temperature. The resulting mixture was concentrated under vacuum and the residue was diluted with 5 ml of water. The crude mixture was then purified by anion exchange chromatography on DEAE-Sephadex A-25 at 4° C. using a gradient of TEAB (pH 8.0; 0.1-1.0 M). The crude product was further purified by reverse-phase HPLC to afford G7, which was characterized by MALDI-TOF MS: calc'd for $C_{24}H_{40}N_5O_{14}P_3S_4$: 843.7, found: 848.0.

3'-O-DTM-7-deaza-dGTP-7-SS-Cy5 (Compound G8): To a stirred solution of Cy5-NHS ester (2 mg, 3.2 μmol) in DMF (0.2 ml), 7-deaza-3'-O-DTM-dGTP-7-SS-NH$_2$ (compound G7, 3.0 μmol) in NaHCO$_3$/Na$_2$CO$_3$ buffer (pH 8.9, 0.1 M, 0.3 ml) was added. The reaction mixture was stirred at room temperature for 3 h with exclusion of light. The reaction mixture was purified by anion exchange chromatography on DEAE-Sephadex A-25 at 4° C. using a gradient of TEAB (pH 8.0; 0.1-1.0 M). The crude product was further purified by reverse-phase HPLC to afford Compound G8, which was characterized by MALDI-TOF MS: calc'd for $C_{57}H_{77}N_7O_{21}P_3S_6^-$: 1481.6, found: 1485.2.

Synthesis of 3'-O-DTM(SS)-dNTP-SS-"Anchor" Molecules. Example syntheses of 3'-O-DTM(SS)-dNTP-SS-"Anchor" are shown in FIGS. 42-45 following procedures similar to those for syntheses of 3'-O-DTM(SS)-dNTP-SS-Dye. Instead of using a variety of dye-NHS esters, a variety of "Anchor" NHS esters are used to couple with 3'-O-DTM(SS)-dNTP-SS-NH$_2$ precursors yielding 3'-O-DTM(SS)-dNTP-SS-N$_3$ (FIG. 42), 3'-O-DTM(SS)-dNTP-SS-PBA (FIG. 43), 3'-O-DTM(SS)-dNTP-SS-Biotin (FIG. 44) and 3'-O-DTM(SS)-dNTP-SS-TCO (FIG. 45).

Synthesis of 3'-O-DTM(SS)-dNTP-SS-"Anchor" Molecules. Example syntheses of 3'-O-DTM(SS)-dNTP-SS-"Anchor" are shown in FIGS. 42-45 following procedures similar to those for syntheses of 3'-O-DTM(SS)-dNTP-SS-Dye. Instead of using a variety of dye-NHS esters, a variety of "Anchor" NHS esters are used to couple with 3'-O-DTM(SS)-dNTP-SS-NH$_2$ precursors yielding the 3'-O-DTM(SS)-dNTP-SS-"Anchor" Molecules depicted in schemes below.

Scheme 12. Synthesis of 3'-O-DTM(SS)-dNTP-SS-N$_3$.

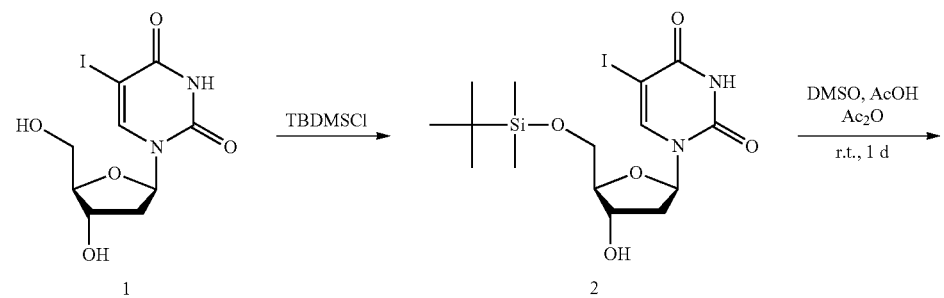

-continued
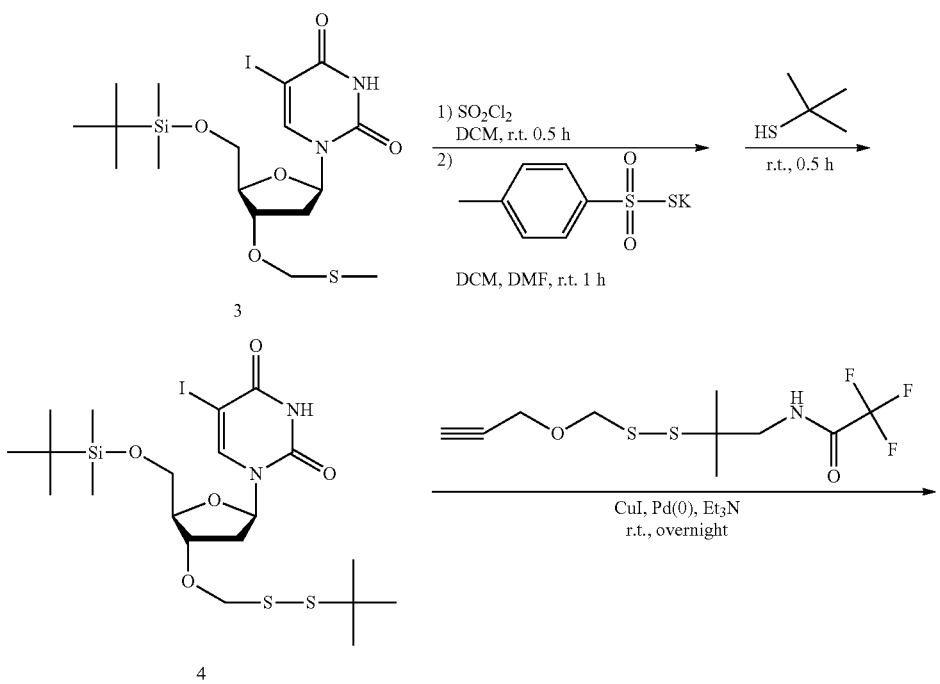
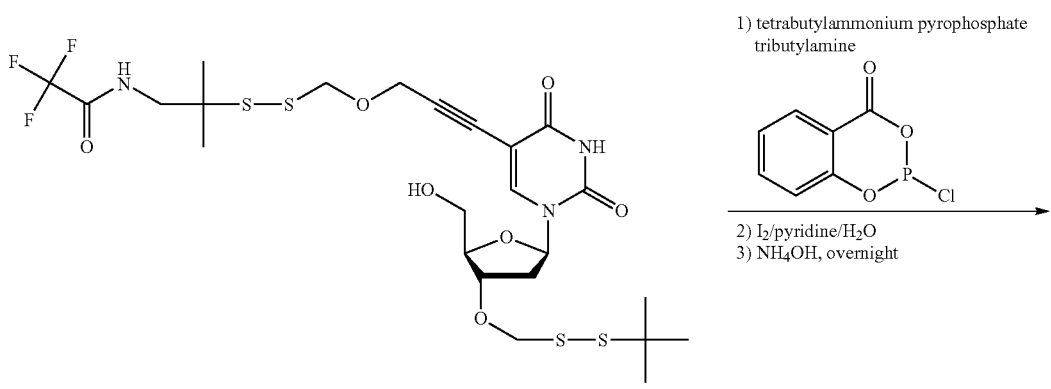

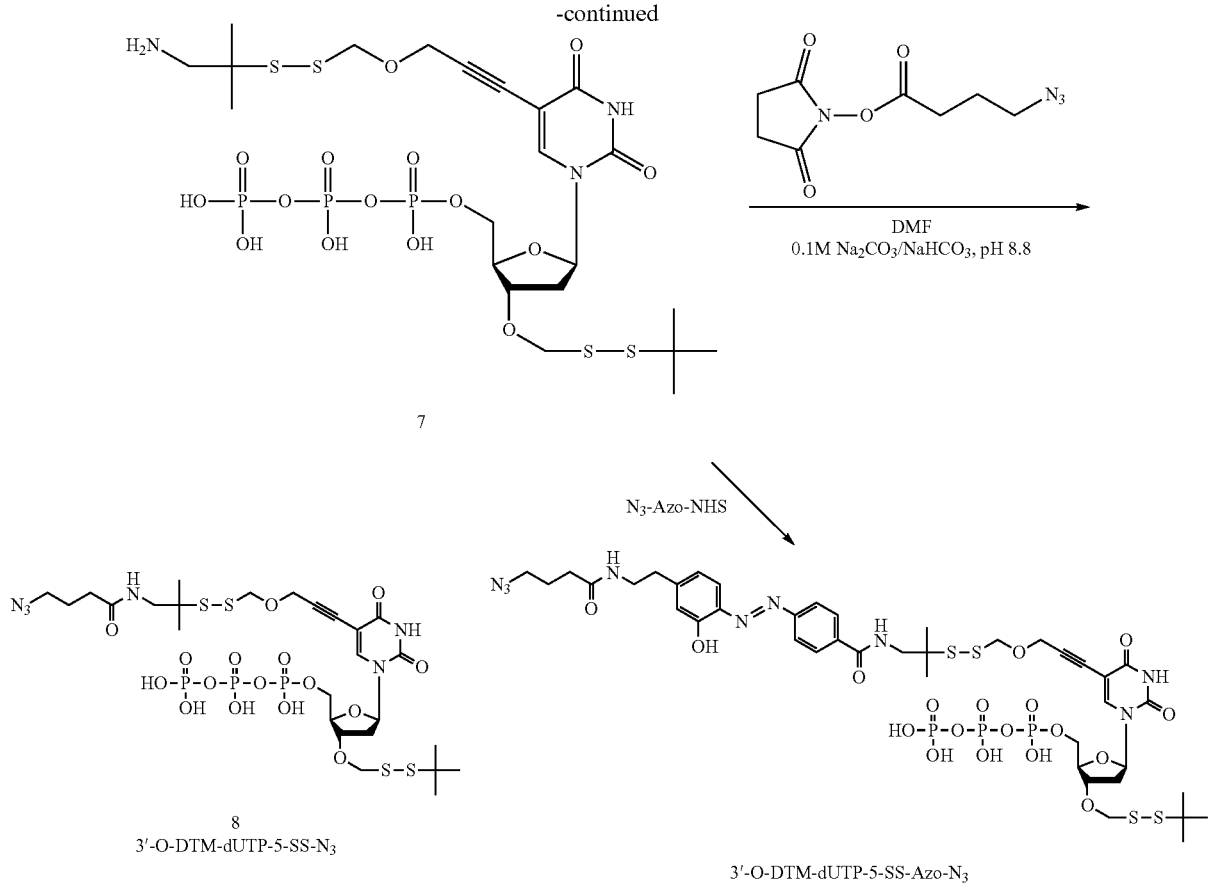
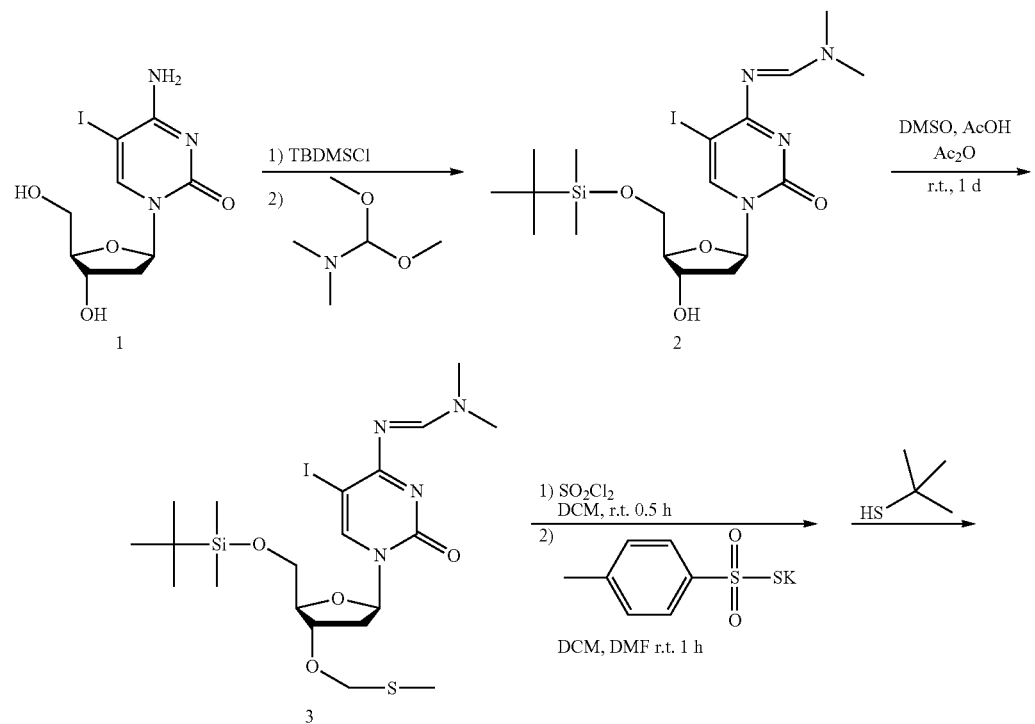
Scheme 13. Synthesis of 3′-O-DTM(SS)-dNTP-SS-PBA.

-continued
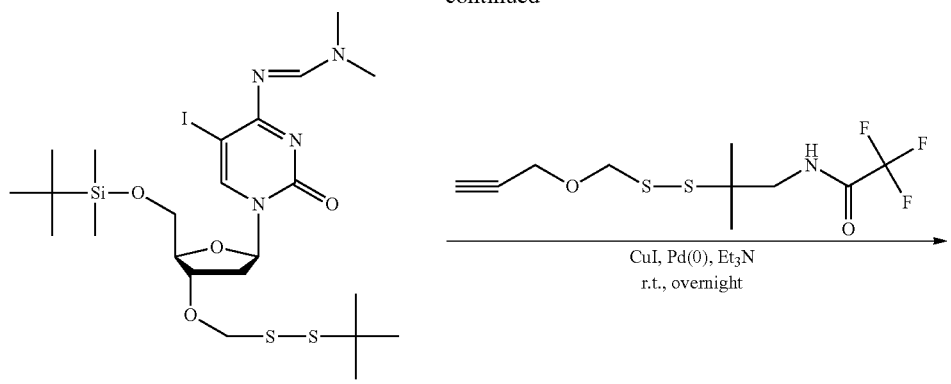
4
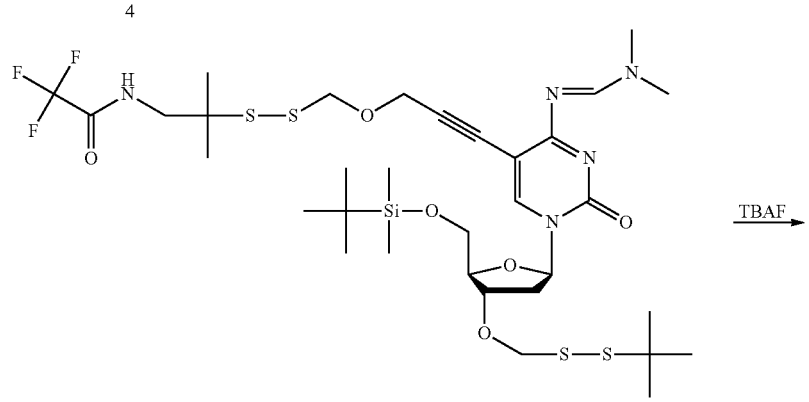
5
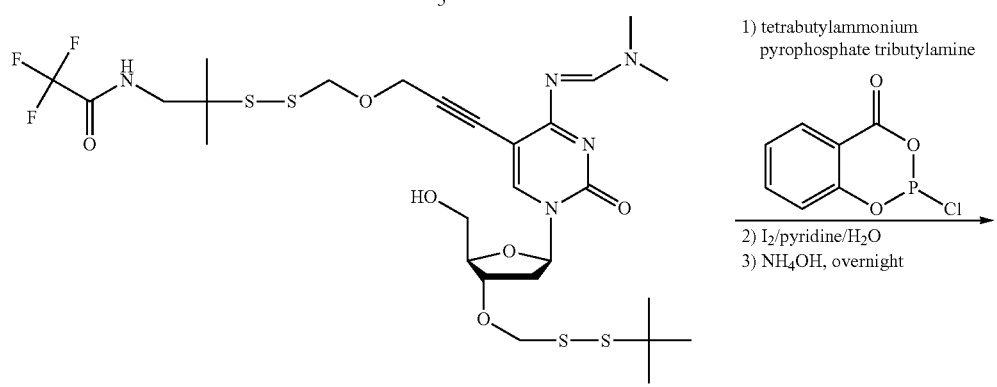
6
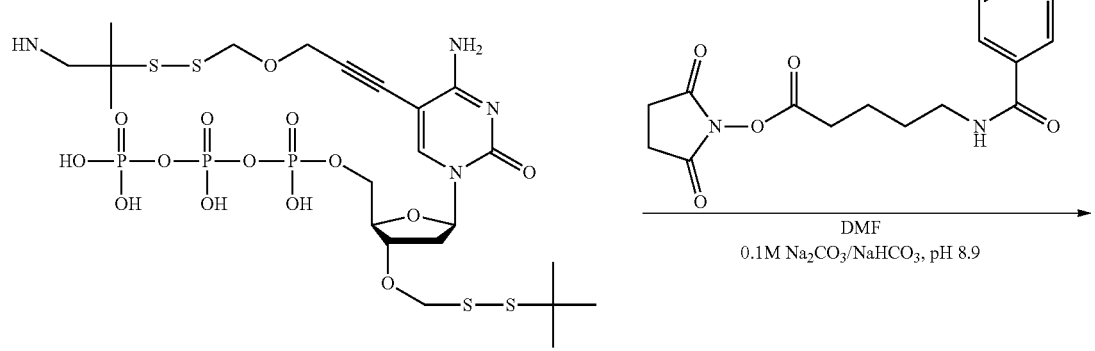
7

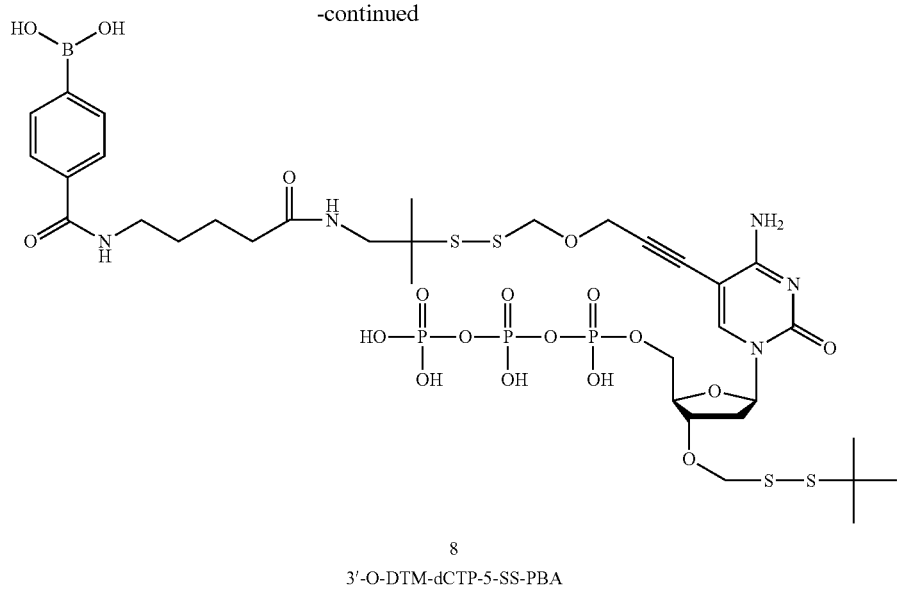
8
3'-O-DTM-dCTP-5-SS-PBA
Scheme 14. Synthesis of 3'-O-DTM(SS)-dNTP-SS-Biotin.
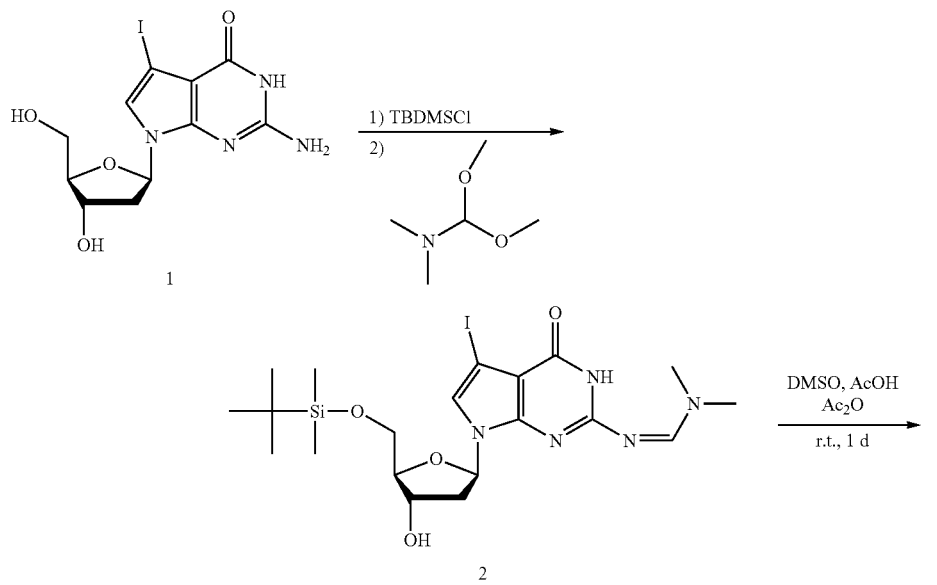
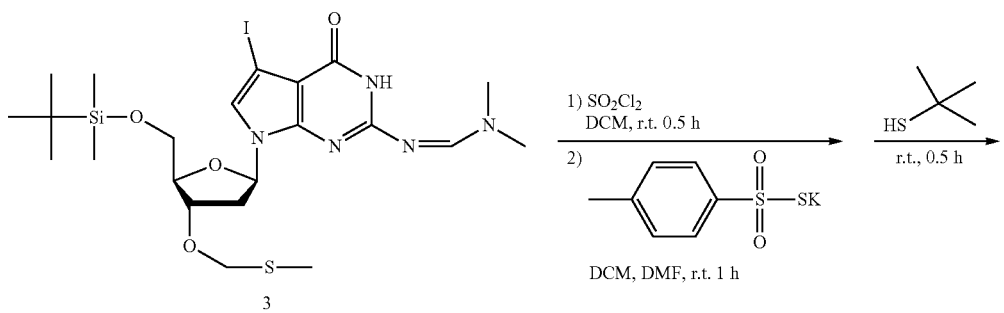

-continued
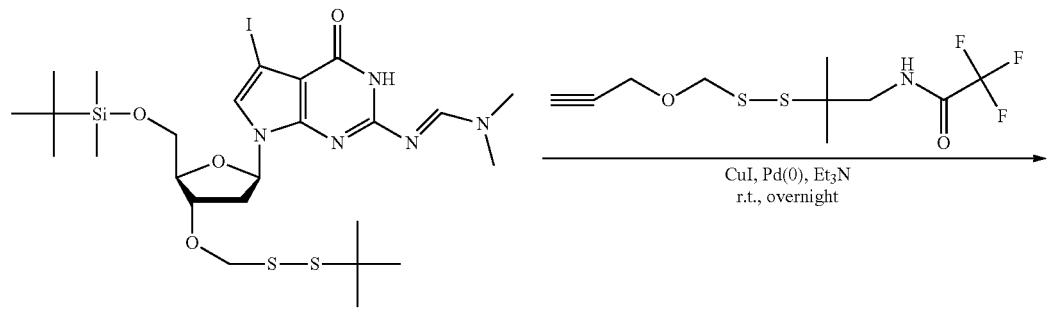
4
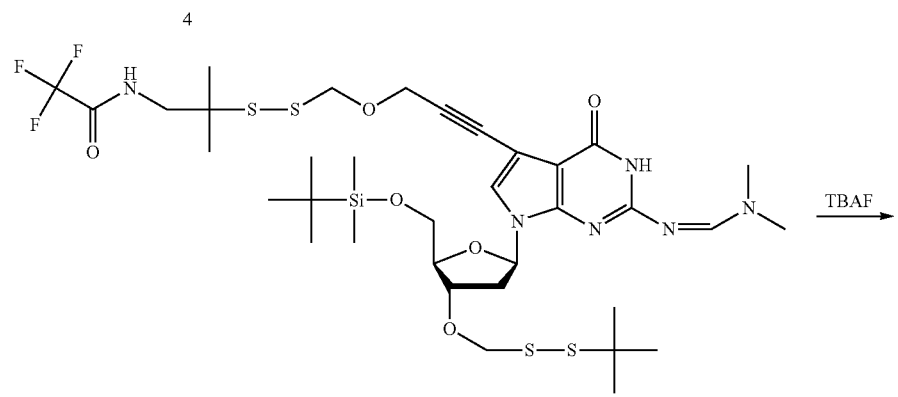
5
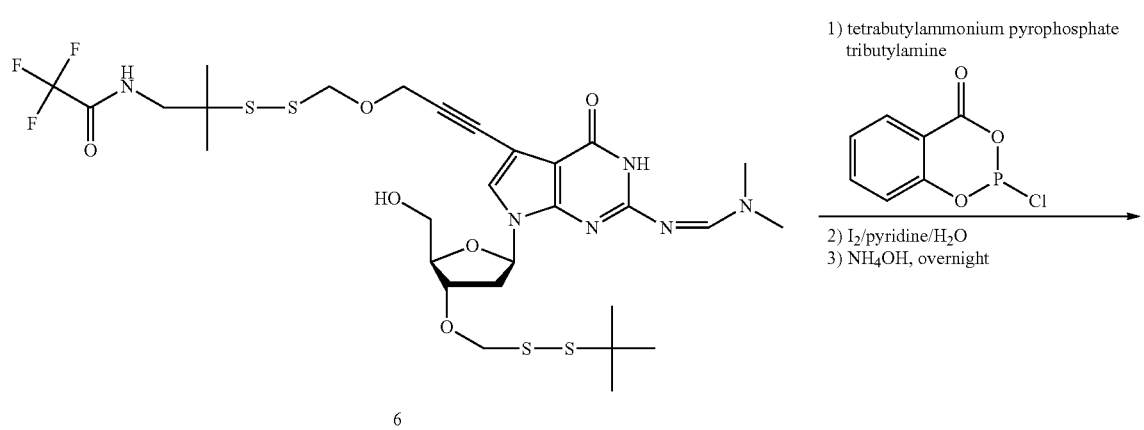
6
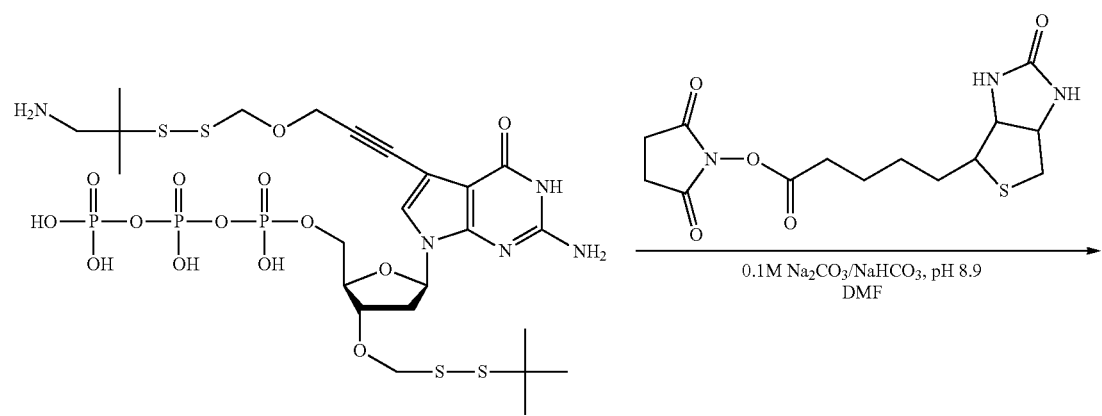
7

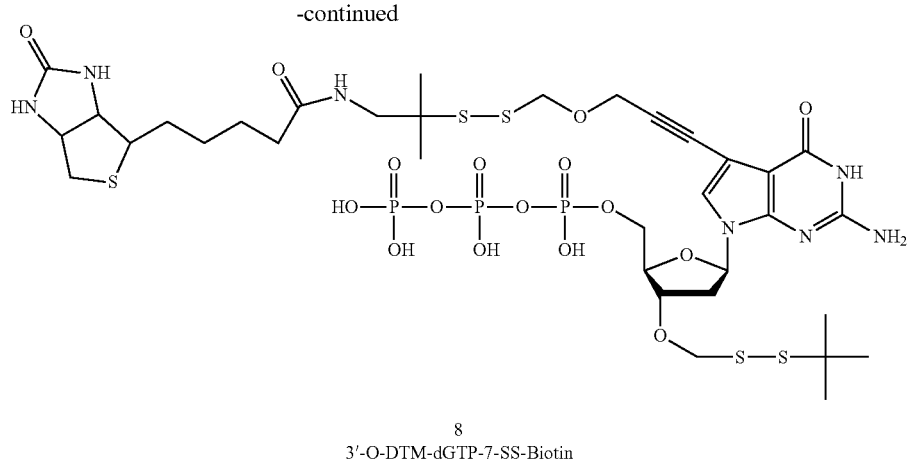
8
3'-O-DTM-dGTP-7-SS-Biotin
Scheme 15. Synthesis of 3'-O-DTM(SS)-dNTP-SS-TCO.
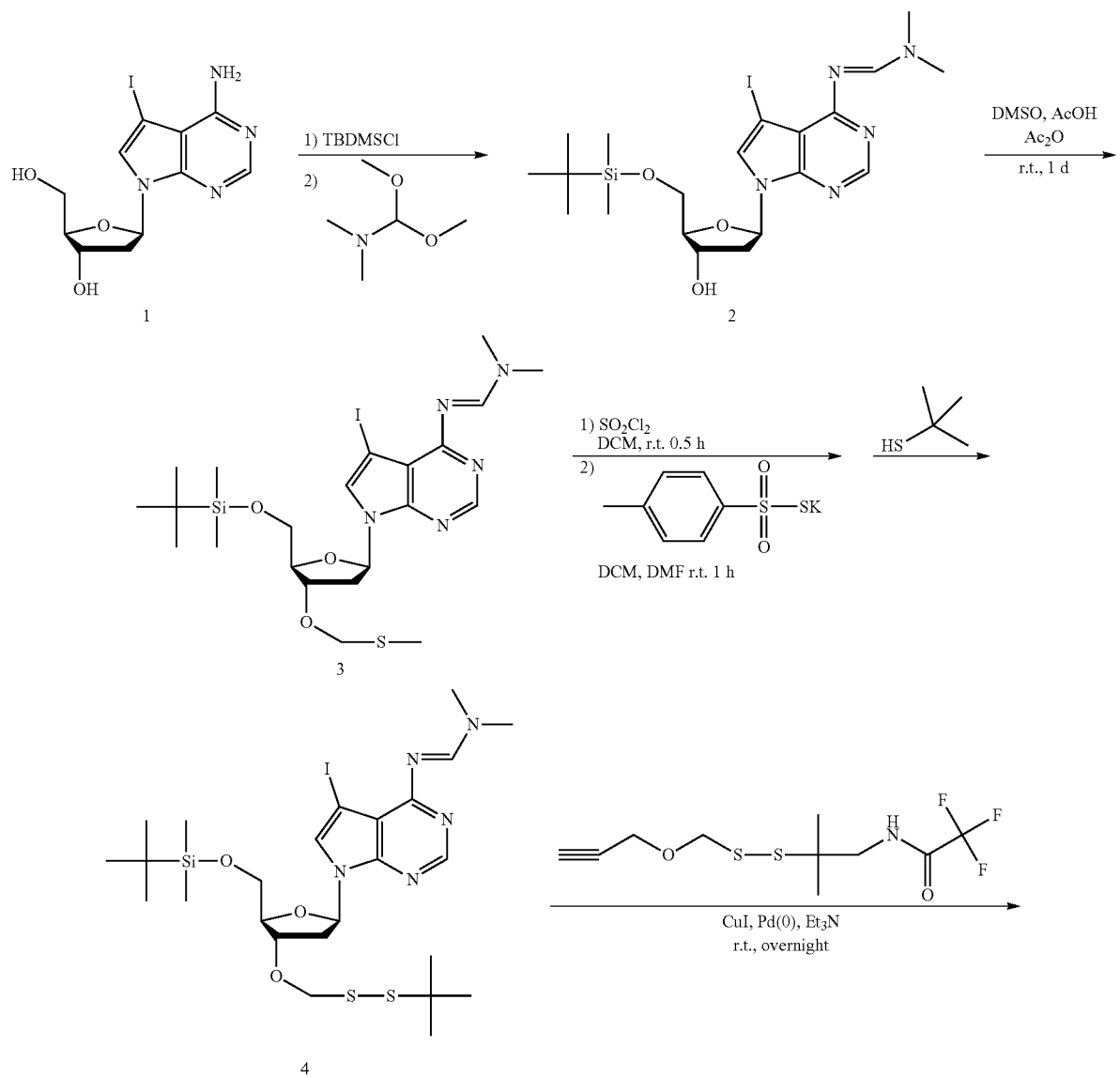

-continued
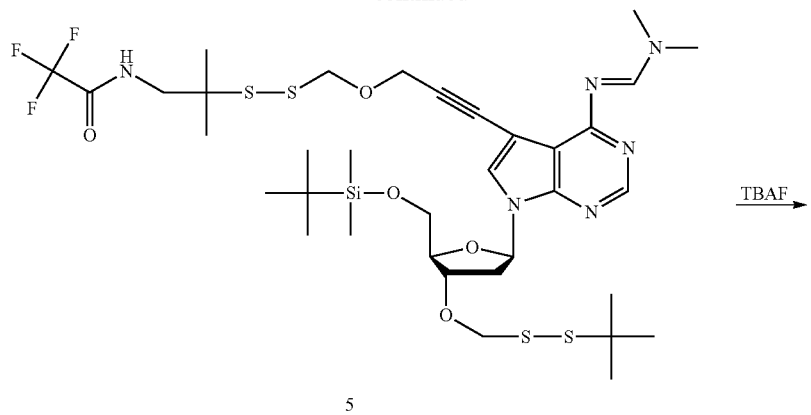
5
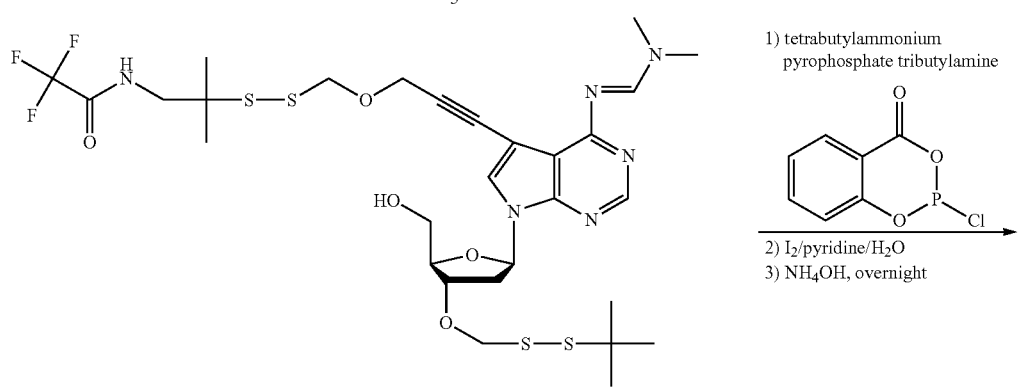
6
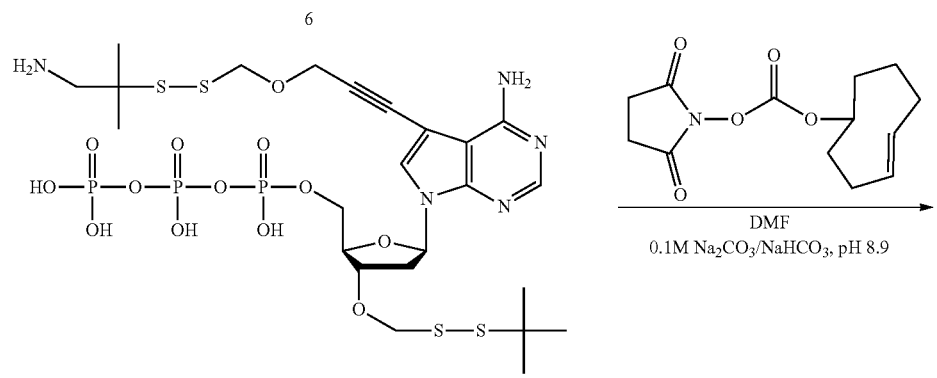
7
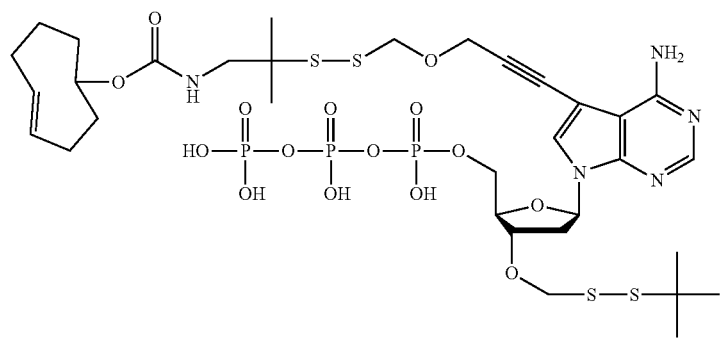
3'-O-DTM-dATP-7-SS-TCO Synthesis of 3'-DTM-Blocked Group dNTP Analogues: General structures of these derivatives are shown in FIG. 36.

Scheme 16 shows the synthesis of 3'-DTM-blocked group dNTP analogues starting from 5'-O-(tert-butyldiphenylsilyl) nucleoside.

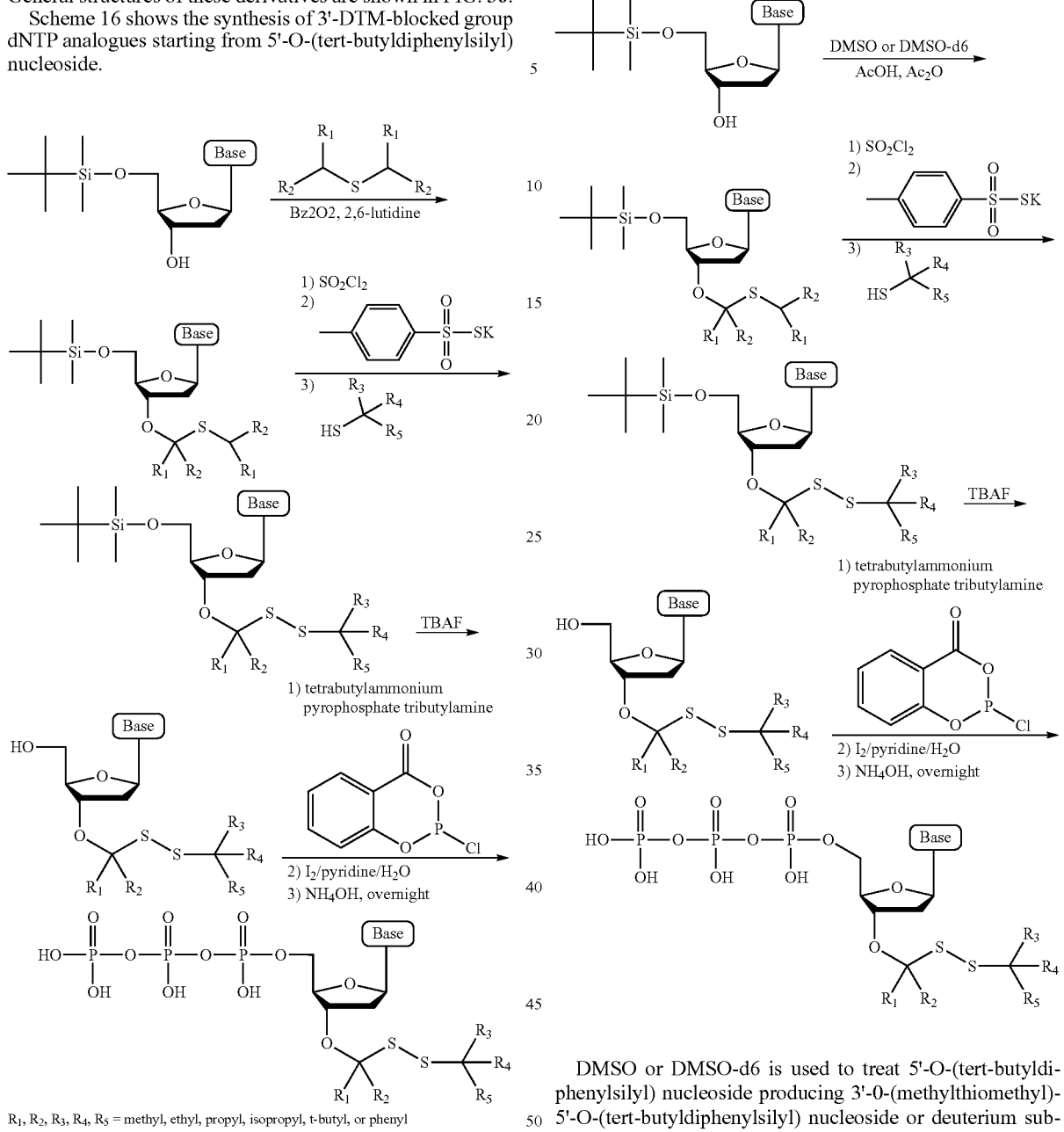

$R_1, R_2, R_3, R_4, R_5$ = methyl, ethyl, propyl, isopropyl, t-butyl, or phenyl 1,1'-thiodialkyl($R_1$—CH—$R_2$) is used to produce $R_1,R_2$ substituted 3'-O-alkyl(bearing $R_1R_2$)thiomethyl-5'-O-(tert-butyldiphenylsilyl) nucleoside in the presence of $Bz_2O_2$ and 2,6-lutidine. The resulting compounds are treated with sulfuryl chloride, potassium p-toluenethiosulfonate and corresponding thiol compounds bearing $R_3$, $R_4$ and $R_5$ groups yielding $R_1,R_2$ substituted 3'-O-alkyl(bearing $R_3$, $R_4$ and $R_5$)dithiomethyl-5'-O-(tert-butyldiphenylsilyl) nucleoside. After removal of the 5'-O-tert-butyldiphenylsilyl protecting group with 1.0M of TBAF in THF, the resulting compound with free 5'-OH can be converted to triphosphate by using established triphosphorylation methods affording $R_1,R_2$ substituted 3'-O-alkyl(with $R_3$, $R_4$ and $R_5$)dithiomethyl-dNTPs.

Scheme 17 shows the synthesis of 3'-DTM-blocked group dNTP analogues with or without deuterium substitution.

DMSO or DMSO-d6 is used to treat 5'-O-(tert-butyldiphenylsilyl) nucleoside producing 3'-O-(methylthiomethyl)-5'-O-(tert-butyldiphenylsilyl) nucleoside or deuterium substituted 3'-O-methylthiomethyl-5'-O-(tert-butyldiphenylsilyl) nucleoside. Treatment of the resulting compounds with sulfuryl chloride, potassium p-toluenethiosulfonate, and corresponding alkylthiol (bearing $R_3$, $R_4$ and $R_5$ groups) will produce 3'-O—($R_3,R_4,R_5$-alkyldithiomethyl)-5'-O-(tert-butyldiphenylsilyl) nucleoside or deuterium substituted 3'-O—($R_3,R_4,R_5$-alkyldithiomethyl(D2)-5'-O-(tert-butyldiphenylsilyl) nucleoside. Removal of the 5'-O protecting group followed by triphosphorylation and deprotection on the base (if applicable) will afford the final product 3'-O-(alkyl(with $R_3$, $R_4$, and $R_5$ groups)dithiomethyl)-dNTP or deuterium substituted 3'-O-(alkyl(with $R_3$, $R_4$, and $R_5$ groups)thiomethyl(d2))-dNTP.

Scheme 18 shows the synthesis of 3'-DTM-dNTP analogues starting from 5'-O-(tert-butyldiphenylsilyl) nucleoside.

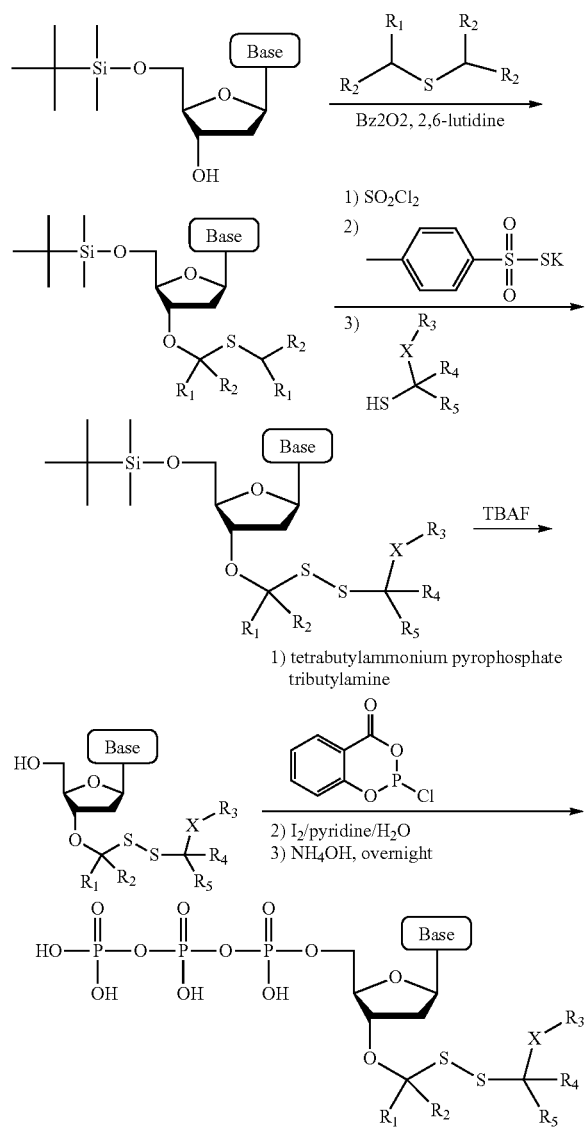

X = O, S, N
$R_1, R_2, R_3, R_4, R_5$ = methyl, ethyl, propyl, isopropyl, t-butyl, or phenyl

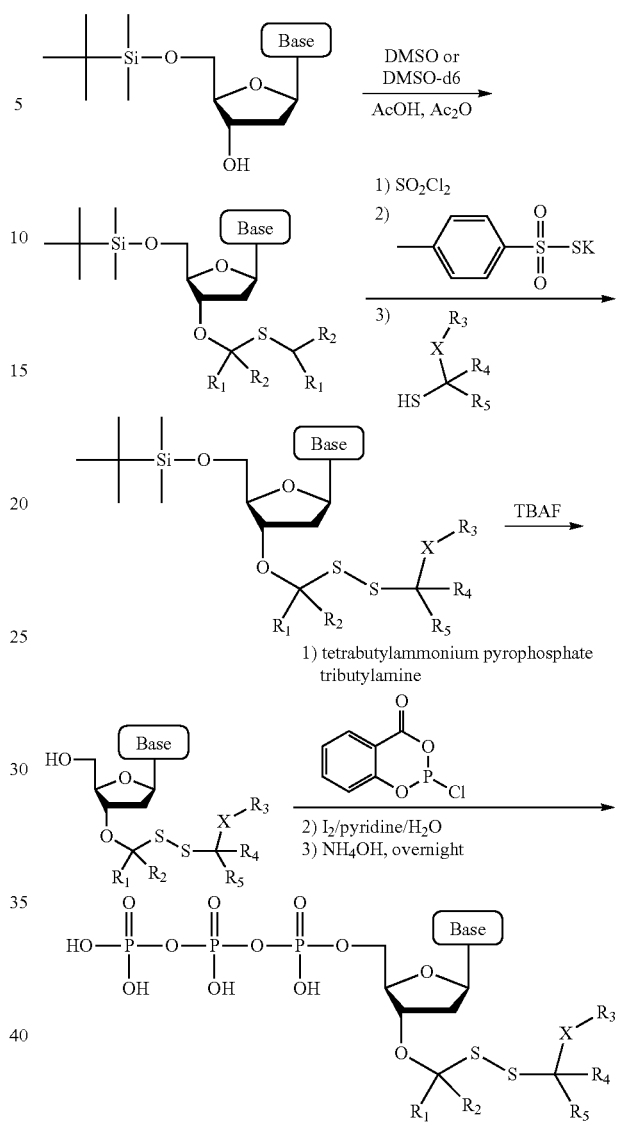

X = O, S, NH
$R_1 = R_2$ = H, D
$R_3, R_4, R_5$ = methyl, ethyl, propyl, isopropyl, t-butyl, or phenyl 1,1'-thiodialkyl($R_1$—CH—$R_2$) is used to produce $R_1,R_2$ substituted 3'-O-(alkyl(bearing $R_1,R_2$) thiomethyl)-5'-O-(tert-butyldiphenylsilyl) nucleoside in the presence of $Bz_2O_2$ and 2,6-lutidine. The resulting compounds are treated with sulfuryl chloride, potassium p-toluenethiosulfonate and corresponding thiol compounds bearing X—$R_3$, $R_4$, and $R_5$ (X=O, S or NH) groups yielding analogs of $R_1,R_2$ substituted 3'-O-(alkyl(with X—$R_3$, $R_4$, and $R_5$)dithiomethyl)-5'-O-(tert-butyldiphenylsilyl) nucleoside. After removal of the 5'-O-tert-butyldiphenylsilyl protecting group with 1.0M of TBAF in THF, the resulting compounds with free 5'-OH can be converted to triphosphate by using established triphosphorylation methods affording $R_1$ $R_2$ substituted 3'-O-(alkyl (with X—$R_3$, $R_4$, and $R_5$) dithiomethyl)-dNTP analogs.

Scheme 19 shows 5'-O-(tert-butyldiphenylsilyl) nucleoside is converted to 3'-O-(methylthiomethyl)-5'-O-(tert-butyldiphenylsilyl) nucleoside or deuterium substituted 3'-O-(methylthiomethyl)-5'-O-(tert-butyldiphenylsilyl) nucleoside by treatment with DMSO or DMSO-d6.

The resulting compounds are then treated with sulfuryl chloride, potassium p-toluenethiosulfonate and one of the corresponding thiol compounds containing X—$R_3$,$R_4$, and $R_5$ groups (X=O, S, or NH) yielding 3'-O-(alkyl(bearing X—$R_3$,$R_4$, and $R_5$ groups)dithiomethyl)-5'-O-(tert-butyldiphenylsilyl) nucleoside or deuterium substituted 3'-O-(alkyl (bearing X—$R_3$,$R_4$, and $R_5$ groups)dithiomethyl)-5'-O-(tert-butyldiphenylsilyl) nucleoside. After removal of the 5'-O protecting group with 1.0M of TBAF in THF, the 5' hydroxyl group is converted to triphosphate and the resulting compounds are treated with ammonium hydroxide to remove the protecting group on the base (if applicable) yielding the final products 3'-O-(alkyl(bearing X—$R_3$,$R_4$, and R5 groups) dithiomethyl)-dNTPs or deuterium substituted 3'-O-(alkyl (bearing X—$R_3$, $R_4$, and $R_5$ groups)dithiomethyl)-dNTPs.

Scheme 20 shows methyl substituted 3'-O-methylthiomethyl-5'-O-(tert-butyldiphenylsilyl) thymidine is produced by using 1,1'-thiodiethane treatment in the presence of $Bz_2O_2$ and 2,6-lutidine.

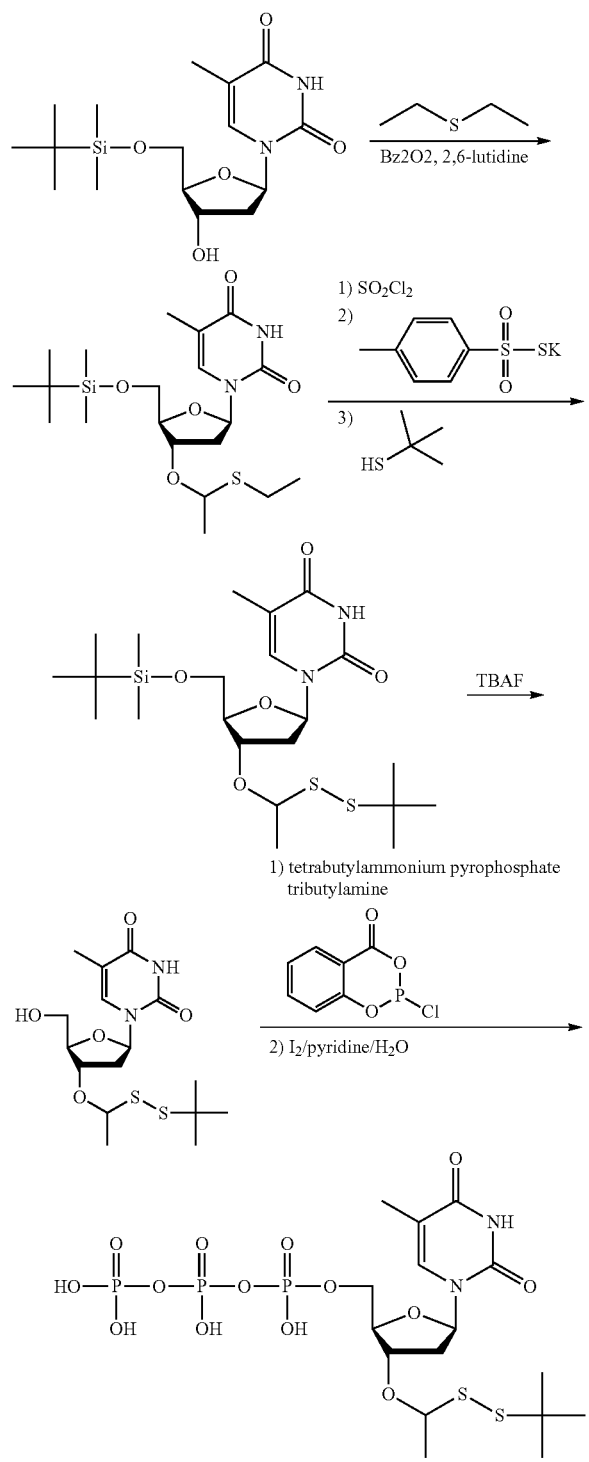

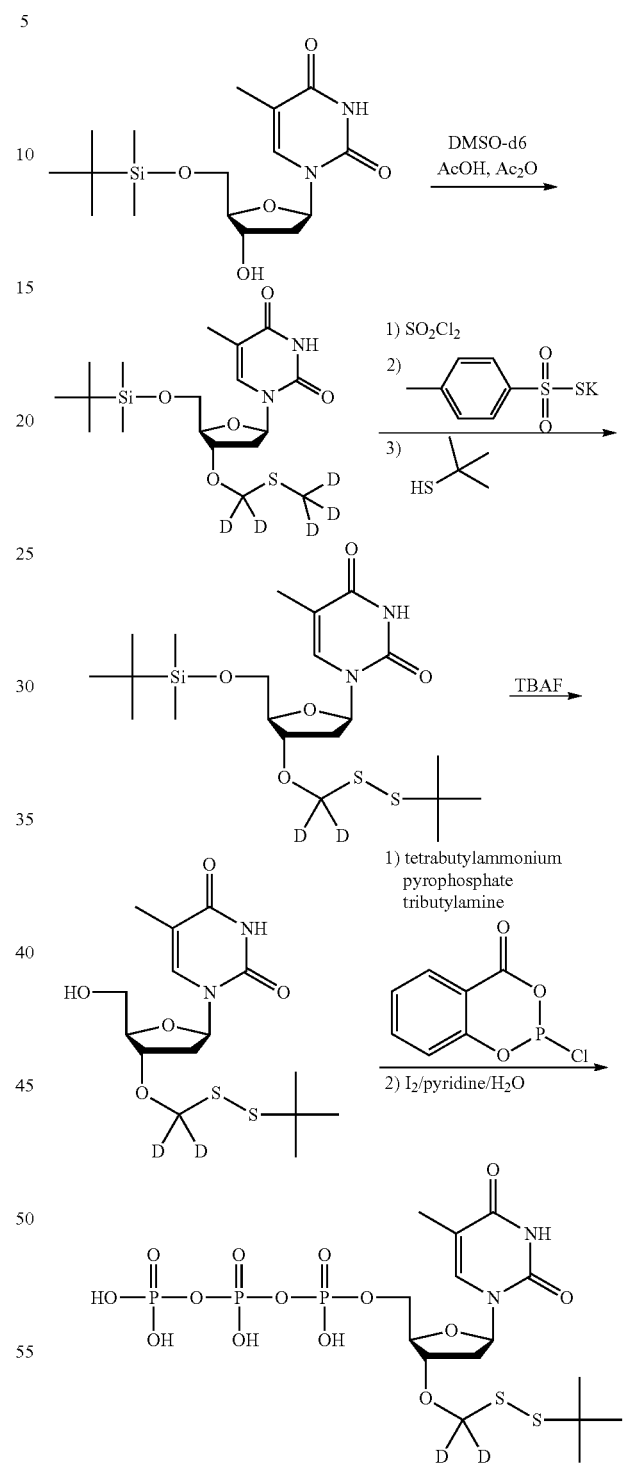

Scheme 21 shows deuterium substituted 3'-O-methyl thiomethyl-5'-O-(tert-butyldiphenylsilyl) thymidine is produced by using DMSO-d6 treatment.

The resulting compound is treated with sulfuryl chloride, potassium p-toluenethiosulfonate and 1,1-dimethylethyl-thiol producing methyl substituted 3'-O-tert-butyldithiomethyl-5'-O-(tert-butyldiphenylsilyl) thymidine. Then the tert-butyldiphenylsilyl protecting group is removed with 1.0M of TBAF in THF and the resulting compound is further converted to methyl substituted 3'-O-tert-butyldithiomethyl)-dTTP by using established triphosphorylation methods.

The resulting compound is treated with sulfuryl chloride, potassium p-toluenethiosulfonate and 1,1-dimethylethyl-thiol producing deuterium substituted 3'-O-tert-butyldithiomethyl-5'-O-(tert-butyldiphenylsilyl) thymidine. After removal of the tert-butyldiphenylsilyl protecting group with 1.0M of TBAF in THF, the resulting compound is converted to deuterium substituted 3'-O-tert-butyldithiomethyl)-dTTP by using established triphosphorylation methods.

Scheme 22 shows 3'-O-methylthiomethyl-5'-O-(tert-butyldiphenylsilyl) thymidine is produced by using DMSO treatment.

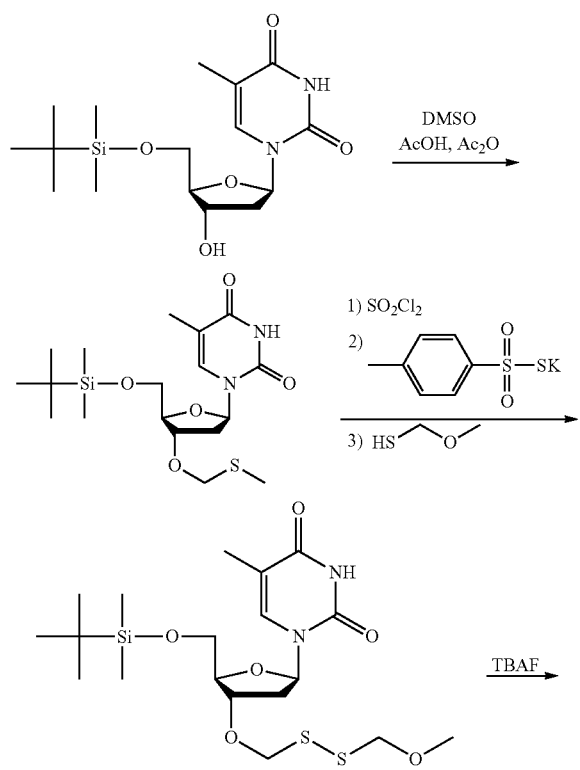

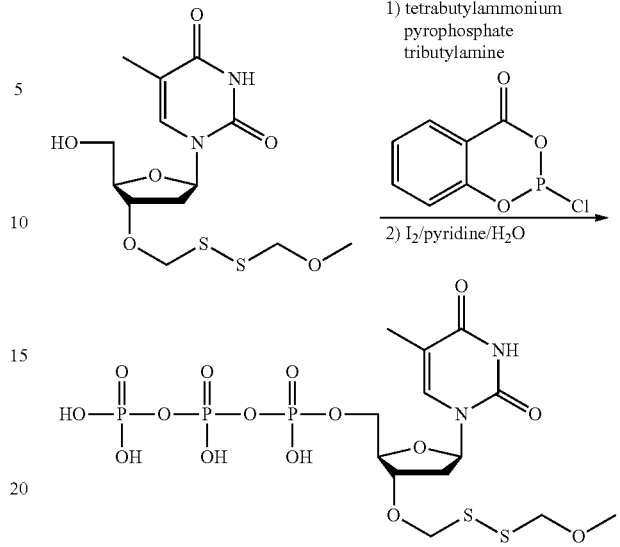

The resulting compound is then treated with sulfuryl chloride, potassium p-toluenethiosulfonate and methoxymethylthiol producing 3'-O-methoxymethyldithiomethyl-5'-O-(tert-butyldiphenylsilyl) thymidine. After removal of the tert-butyldiphenylsilyl protecting group with LOM of TBAF in THF, the resulting compound is converted to 3'-O-methoxymethyldithiomethyl-dTTP by using established triphosphorylation methods.

Synthesis of Dye Labeled Binding Molecules. Synthesis of labeled binding molecules conjugated with fluorescent dyes is conducted by coupling commercially available binding molecule starting materials with various activated dyes. Example synthesis of Rox Labeled Tetrazine, Alexa488 Labeled SHA and R6G Labeled Dibenzocyclooctyne (DBCO) is shown in the below scheme.

Scheme 23.

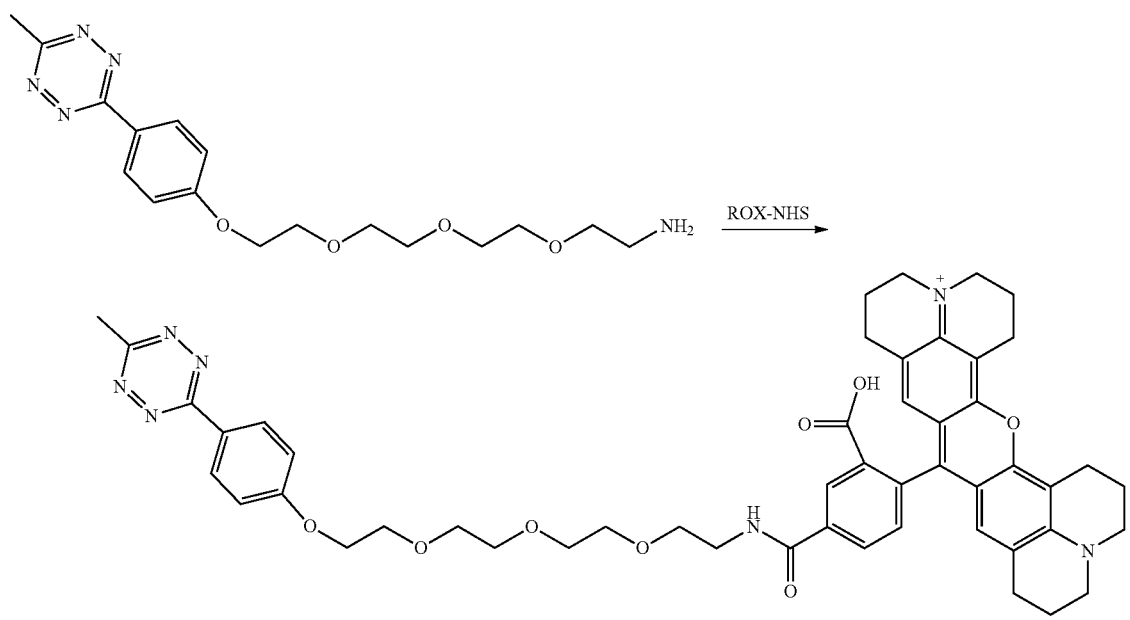

Rox Labeled Tetrazine

-continued

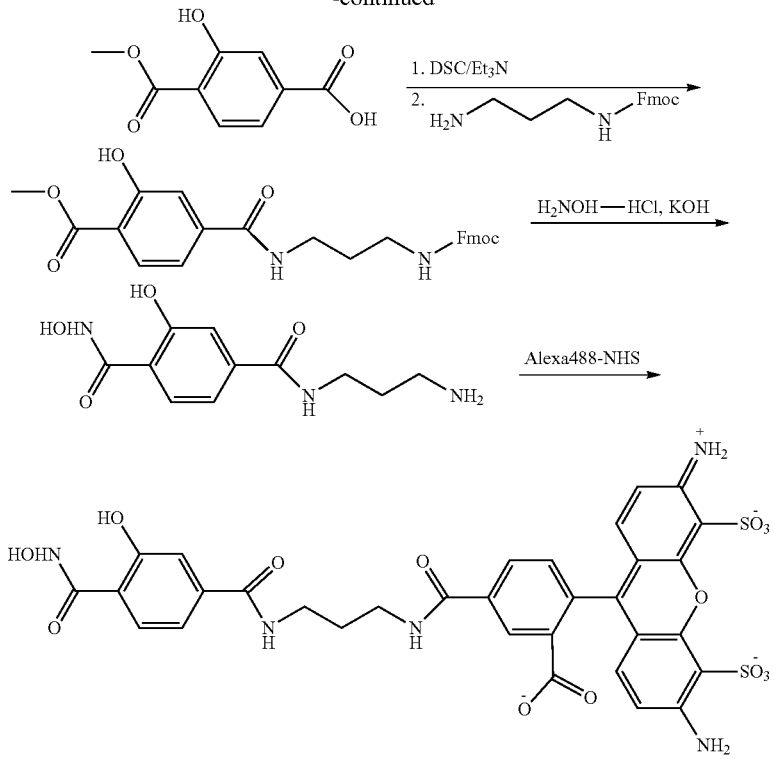

Alexa 488 Labeled SHA

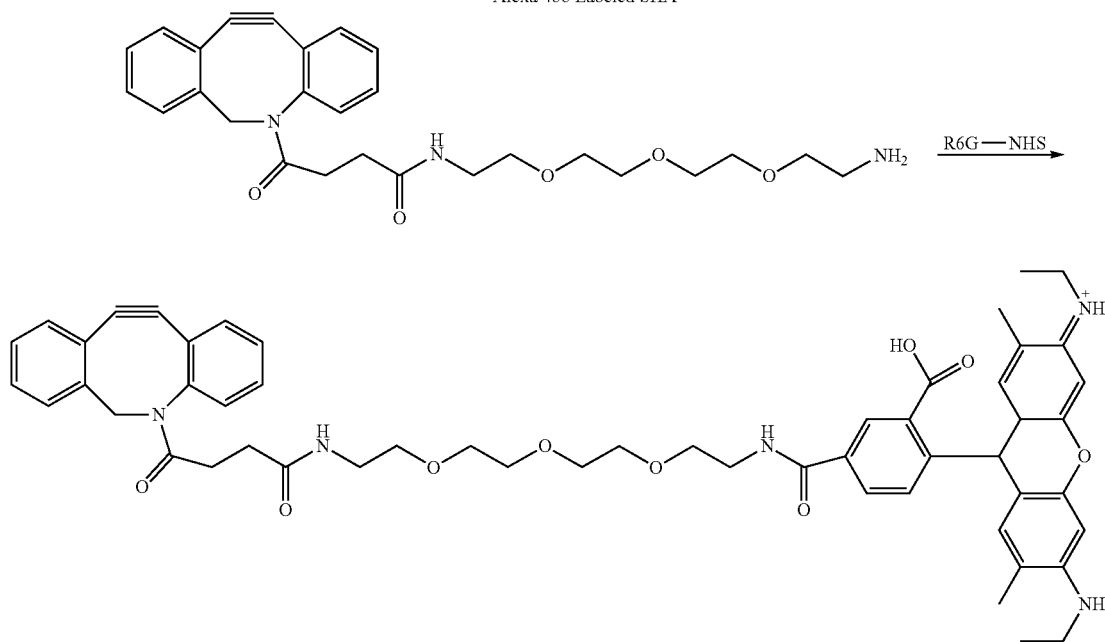

R6G Labeled Dibenzocyclooctyne(DBCO)

Synthesis of multiple-dye conjugated binding molecules (Cy5-tetrazine as an example) is shown in the schemes below.

Scheme 24. Scheme 24. Synthesis of Fluorescent (Cy5) Dendrimer Conjugated Tetrazine (A in FIG. 9A) from commercially available starting materials. Trebler phosphoramidite and Cy5 phosphoramidite are from GlenResearch. First, trebler phosphoramidite is used to couple with Tetrazine to produce Tetrazine-Trebler. After DMT deprotection, coupling of Cy5 phosphoramidite with Tetrazine-Trebler will afford Cy5 labeled dendrimer A. For the synthesis of Cy5 labeled dendrimer B shown in FIG. 9C, coupling a 2nd trebler phosphoramidite to the Tetrazine-Trebler, followed by DMT deprotection and coupling with Cy5 phosphoramidite will yield the desired product.

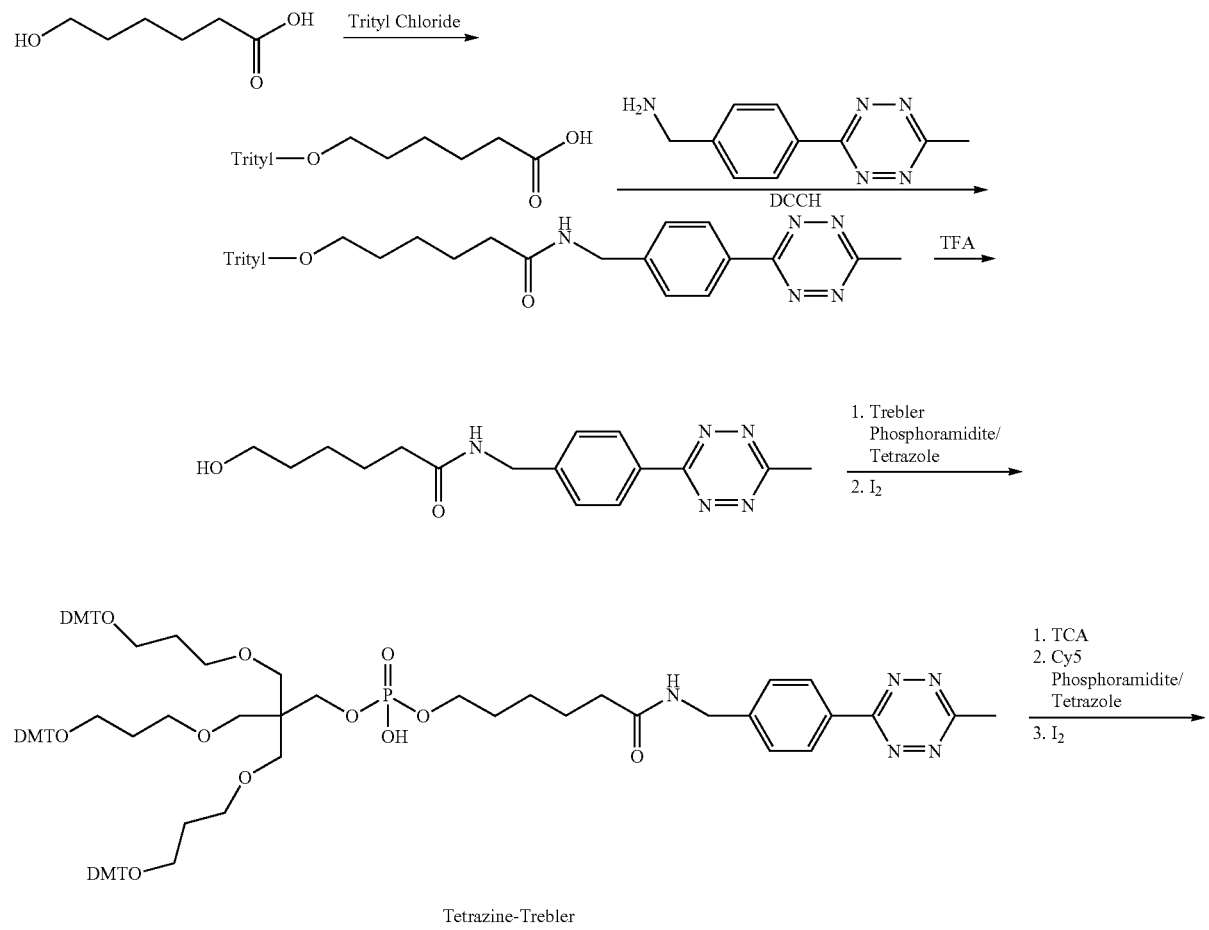
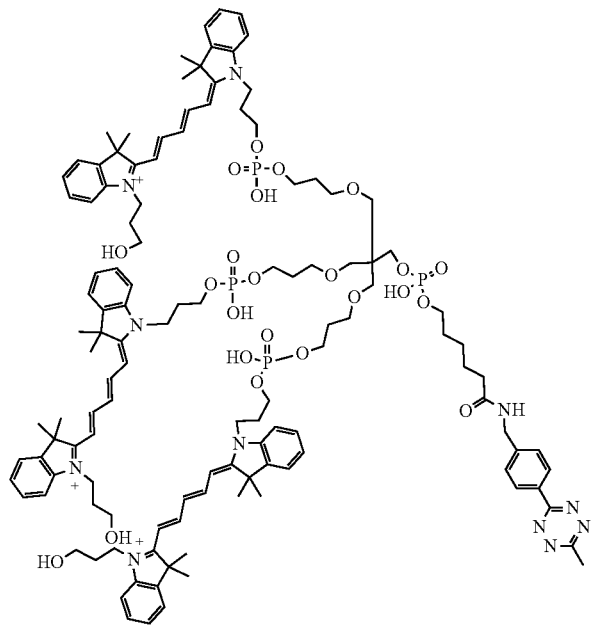
Tetrazine-Trebler
A

Scheme 25. Synthesis of Peptide-Based Flouorescent (Cy5) Dendrimer conjugated with Tetrazine (molecule A in FIG. 10).
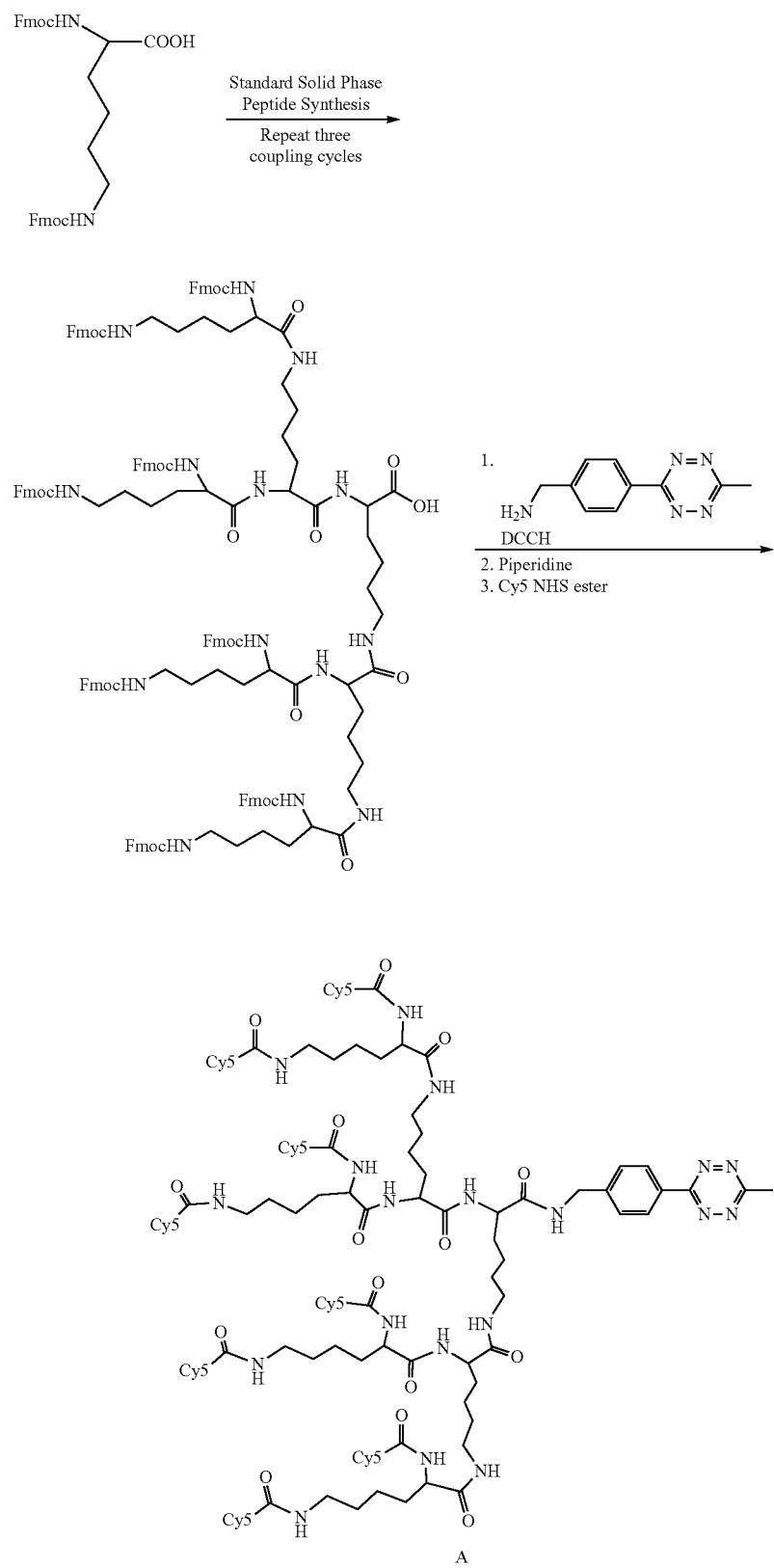

Scheme 26. Synthesis of Peptide-Based Multi-Flouorescent Dye (Cy5) Conjugated Tetrazine (molecule B in FIG. 10).

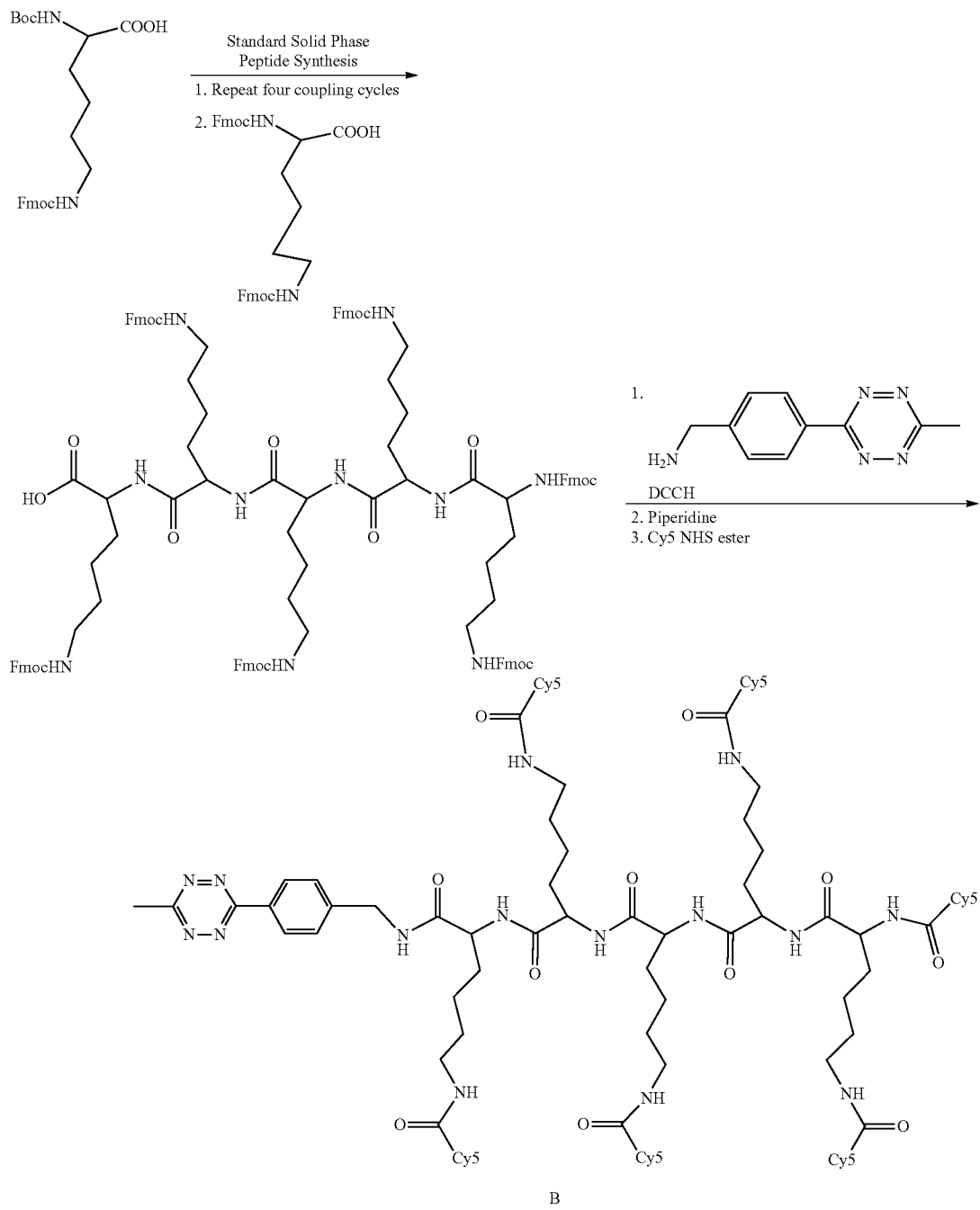

B

Figure 11A:
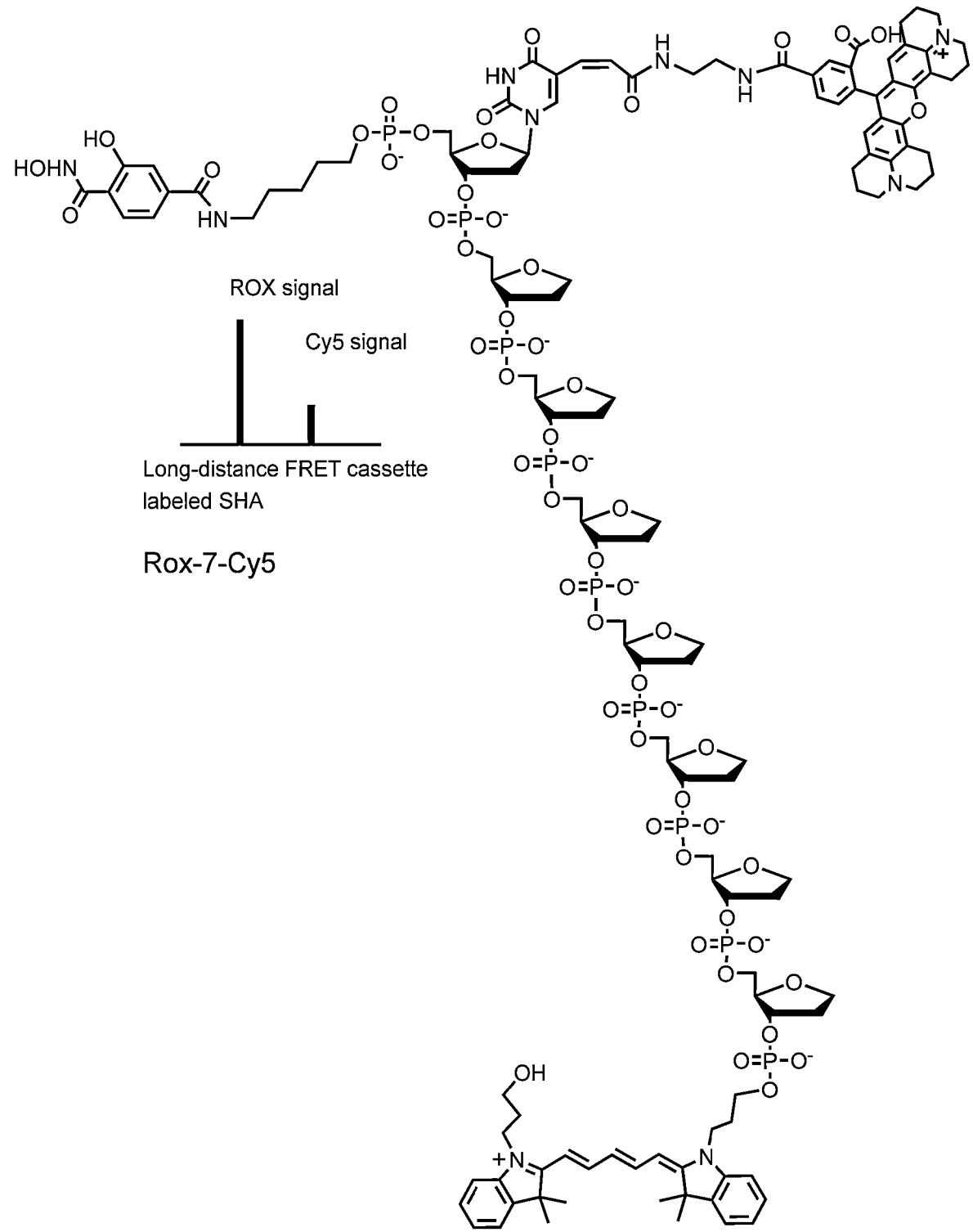
FIGS. 11A-11D. Examples of FRET Cassette Labeled Binding Molecules. The FRET cassette strategy provides numerous distinct FRET signal signatures by altering the distance between donor and acceptor fluorophores. Binding molecules conjugated to such FRET cassettes with four unique FRET signal signatures enables the coupling of such FRET cassettes to the DNA extension product using an "anchor" moiety coupling reaction; this allows for the use of two different fluorescent dyes with distinct emissions through FRET to perform scarless 2-color SBS to identify the four DNA bases. In the set of FRET cassette labeled binding molecules shown above, Rox and Cy5, serving as donor and acceptor respectively, are attached with 7 or 3 dSpacer monomers to yield two different FRET cassettes: FRET Cassette A (Rox-7-Cy5 attached to SHA), which has a long separation distance of 7 dSpacer monomers between Rox and Cy5, will have a less efficient energy transfer from the donor (Rox) to the accepter (Cy5), thereby generating a weak Cy5 emission signal and a strong Rox emission signal. FRET Cassette B (Rox-3-Cy5 attached to trans-cyclooctene TCO), which has a short separation distance of 3 dSpacer monomers between Rox and Cy5, will have a more efficient energy transfer from the donor (Rox) to the accepter (Cy5), thereby generating a strong Cy5 signal and a weak Rox signal. In Labeling Molecule C, where the single Rox is attached to Tetrazine, only the Rox signal is detectable. In Labeling Molecule D (FIG. 11D), where the single Cy5 is attached to Streptavidin, only the Cy5 signal is detectible. A scheme similar to the one indicated in FIG. 8 (four color) is followed to perform SBS by carrying out the following steps to sequence DNA: Addition of the DNA polymerase and the four 3'-O-SS(DTM)-dNTP-SS-"anchor" (3'-O-DTM-dATP-7-SS-TCO, 3'-O-DTM-dCTP-5-SS-PBA, 3'-O-DTM-dGTP-7-SS-Biotin and 3'-O-DTM-dTTP-5-SS-N$_3$) to the immobilized primed DNA template enables the incorporation of the complementary nucleotide analogue to the growing DNA strand to terminate DNA synthesis. After washing away the unincorporated nucleotide analogues, addition of the dye labeled binding molecules (A, B, C, D), which will specifically connect with each of the four unique "anchor" moieties on each DNA extension product, enables the labeling of each DNA product terminated with each of the four nucleotide analogues (A, C, G, T) with four distinct fluorescent signatures. Detection of the unique fluorescent signatures from the labeled DNA products allows for the identification of the incorporated nucleotide. Next, treatment of the DNA products with THP cleaves the SS linker, leading to the removal of the fluorescent label and the regeneration of a free 3'-OH group on the DNA extension product, which is ready for the next cycle of the DNA sequencing reaction.

Synthesis of Rox-7-Cy5 labeled SHA (shown in FIG. 11A). Cy5 labeled CPG (Glen Research) is used to start solid phase oligonucleotide synthesis on a DNA synthesizer. dSpacer phosphoramidite is used as the building block for seven consecutive coupling cycles, then Rox labeled dT phosphoramidite is used in the next coupling cycle. C5 amino modifier phosphoramidite is used in the last coupling cycle. After cleavage under mild conditions following the GlenResearch protocol, the amino modified Rox-7-Cy5 product is produced and purified by HPLC. Coupling of SHA NHS ester with amino modified Rox-7-Cy5 in DMSO/ NaCO₃, NaHCO₃ buffer (pH 8.9) will afford Rox-7-Cy5 labeled SHA.

Figure 11B:
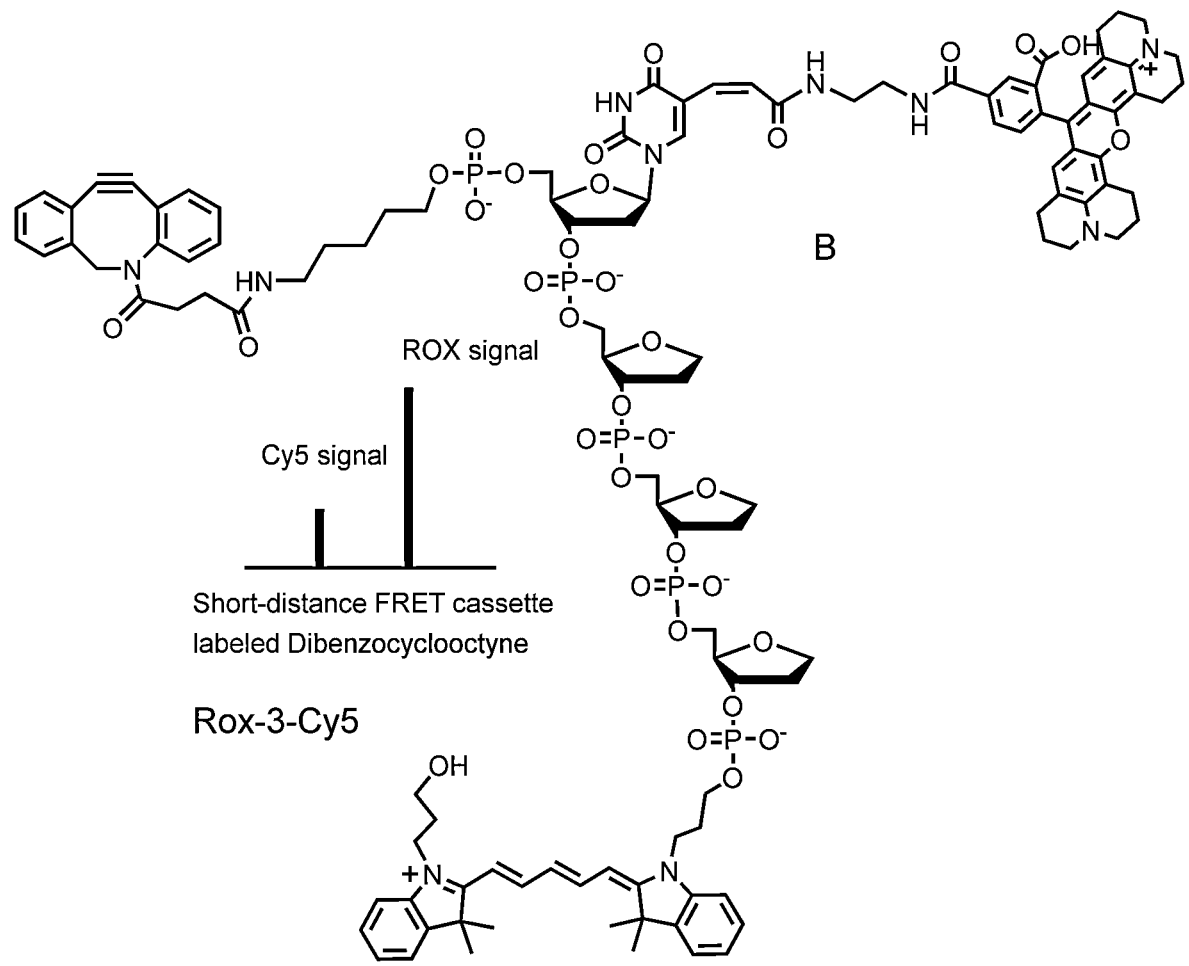
Figure 11C:
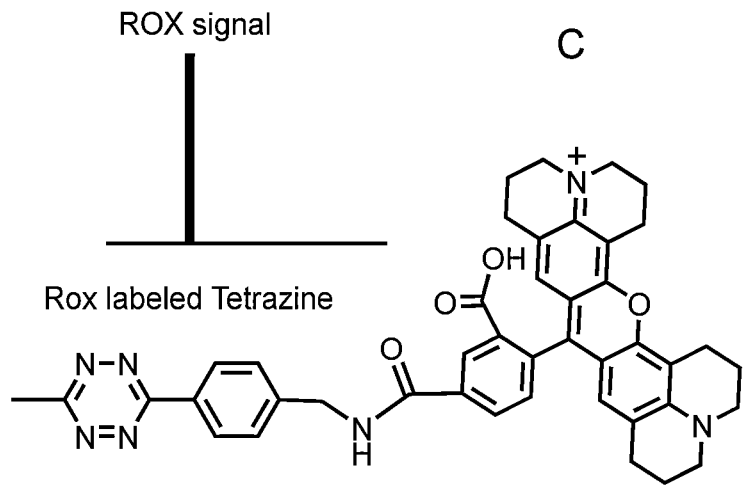
Figure 11D:
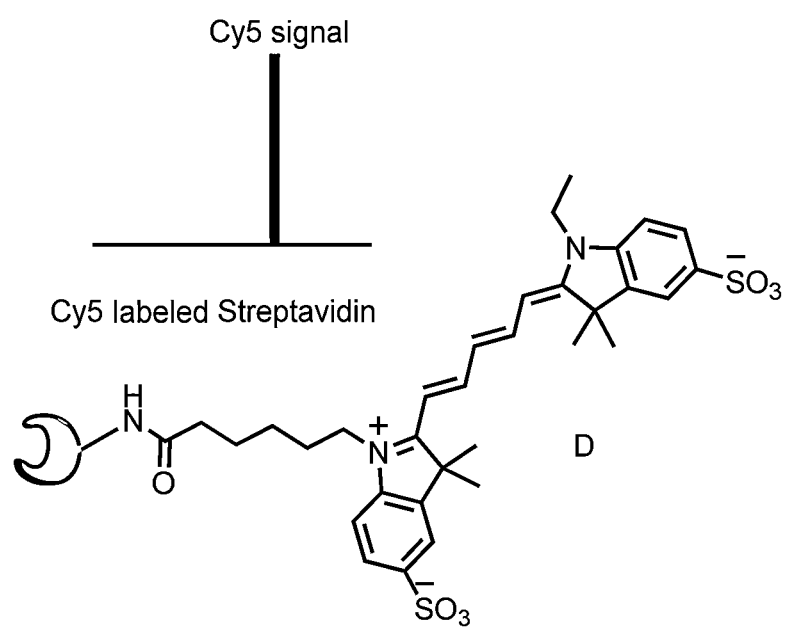
Figure 12:
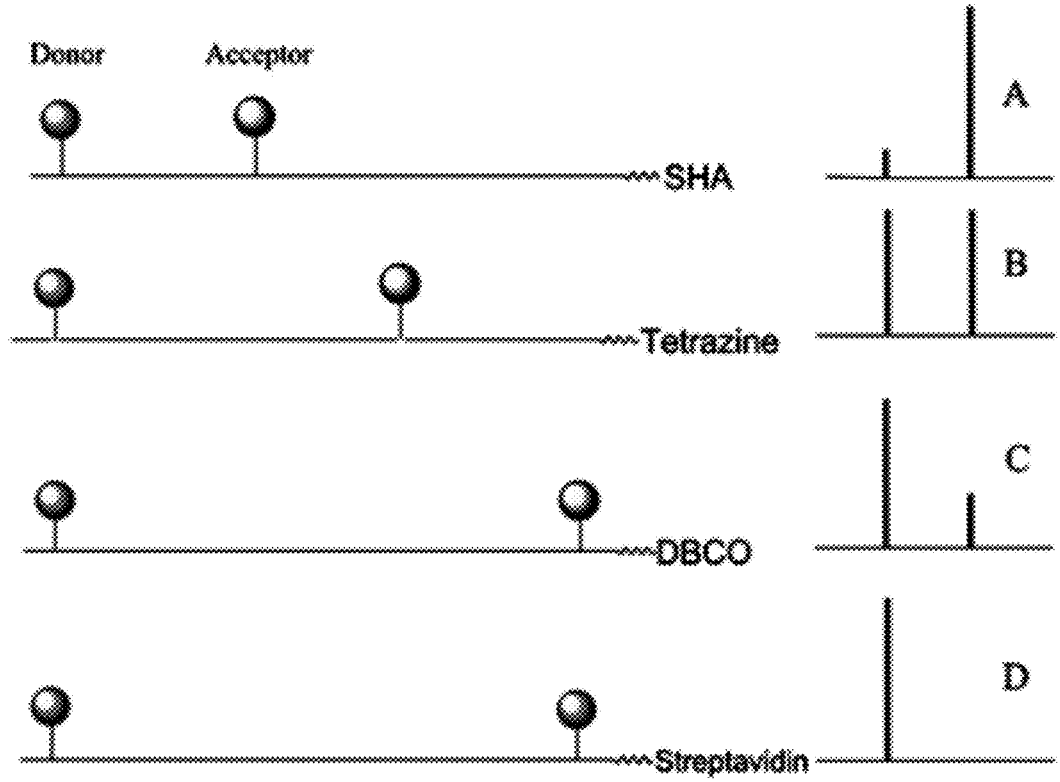
FIG. 12. General Scheme of FRET Cassette Labeled Binding Molecules (e.g., SHA, Tetrazine, DBCO, Streptavidin, etc.). The use of FRET cassettes provides numerous distinct FRET signal signatures (A, B, C, D) by altering the distance between the donor and the acceptor fluorophores. A scheme similar to the one indicated in FIG. 8 is followed to perform SBS by carrying out the following steps to sequence DNA: Addition of the DNA polymerase and the four 3'-O-SS(DTM)-dNTP-SS-"anchor" (3'-O-DTM-dATP-7-SS-TCO, 3'-O-DTM-dCTP-5-SS-PBA, 3'-O-DTM-dGTP-7-SS-Biotin and 3'-O-DTM-dUTP-5-SS-N$_3$) to the immobilized primed DNA template enables the incorporation of the complementary nucleotide analogue to the growing DNA strand to terminate DNA synthesis. After washing away the unincorporated nucleotide analogues, addition of the dye labeled binding molecules (A, B, C, D), which will specifically connect with each of the four unique "anchor" moieties on each DNA extension product, enable the labeling of each DNA product terminated with each of the four nucleotide analogues (A, C, G, T) with four distinct fluorescent signatures. Detection of the unique fluorescent signatures from the labeled DNA products allows for the identification of the incorporated nucleotide. Next, treatment of the DNA products with THP cleaves the SS linker, leading to the removal of the fluorescent label and the regeneration of a free 3'-OH group on the DNA extension product, which is ready for the next cycle of the DNA sequencing reaction.
Figure 13A:
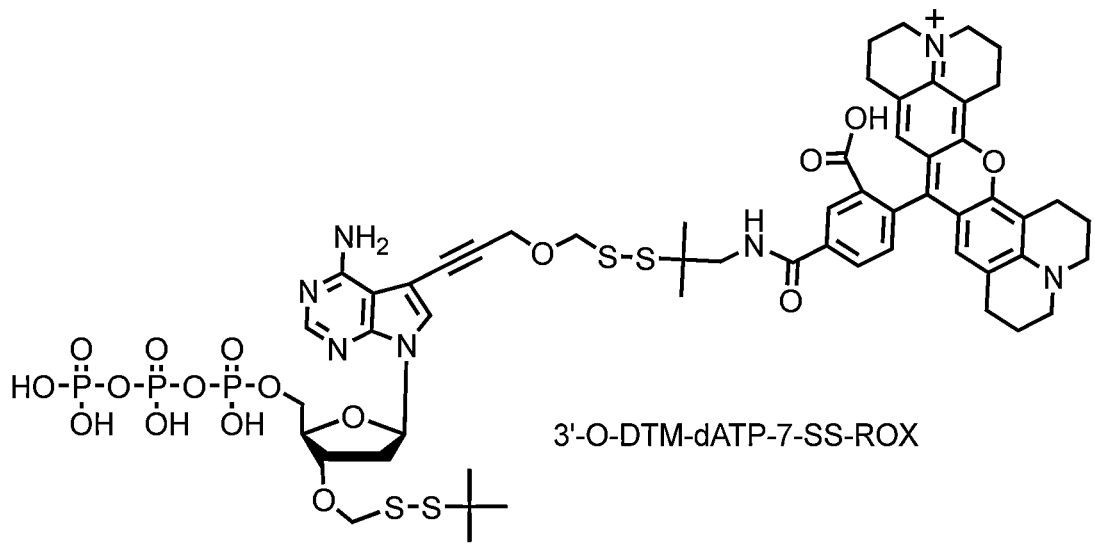
FIGS. 13A-13J. Example structures of 3'-O-DTM-dNTP-SS-Dyes Rox, 3'-O-DTM-dCTP-5-SS-Alexa488); 3'-O-SS (DTM)-dNTP-SS-"anchors" (3'-O-DTM-dGTP-7-SS-TCO and 3'-O-DTM-dUTP-5-SS-N$_3$), with their corresponding Dye Labeled Binding Molecules (Rox Labeled Tetrazine and Alexa488 Labeled Dibenzocyclooctyne).
Figure 13B:
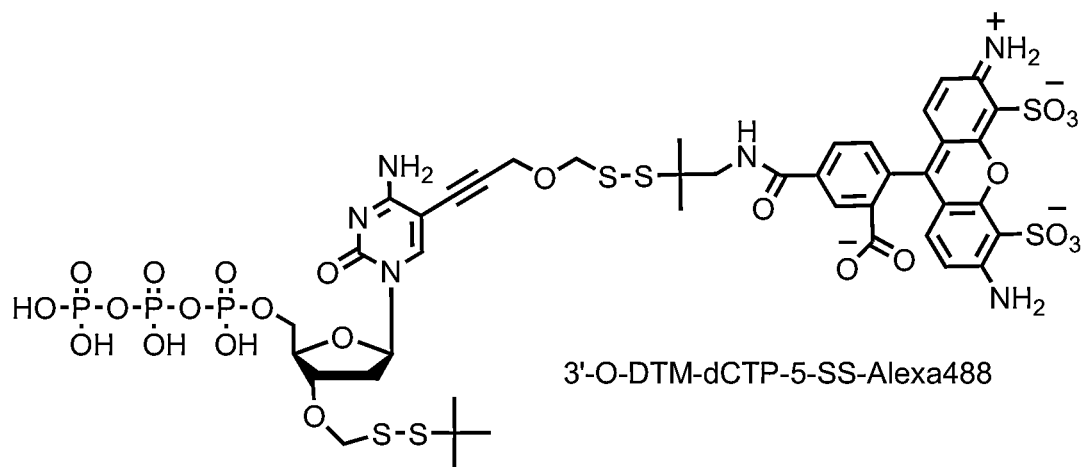
Figure 13C:
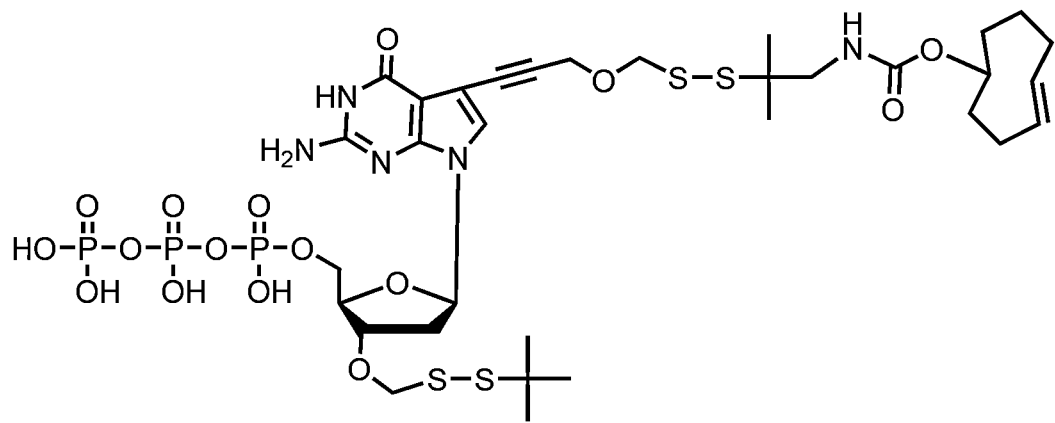
Figure 13D:
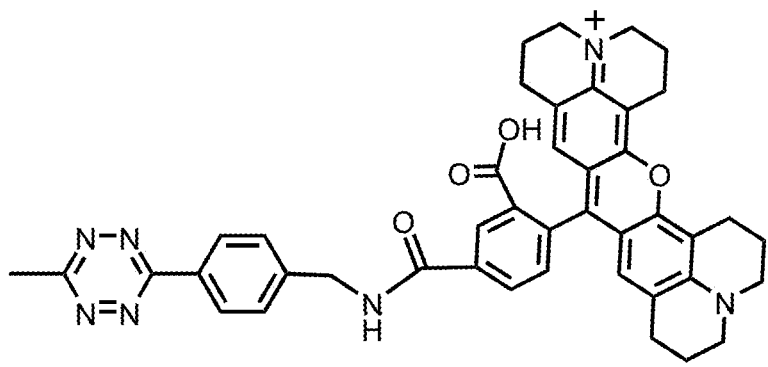
Figure 13E:
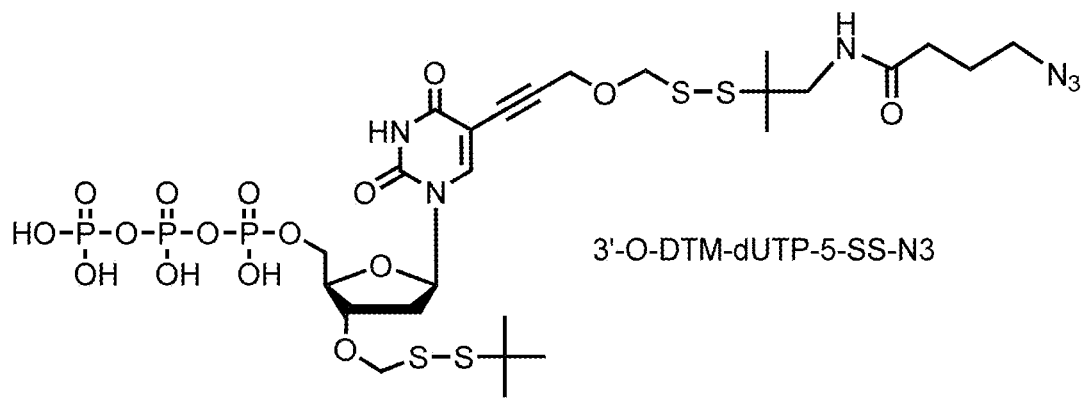
Figure 13F:
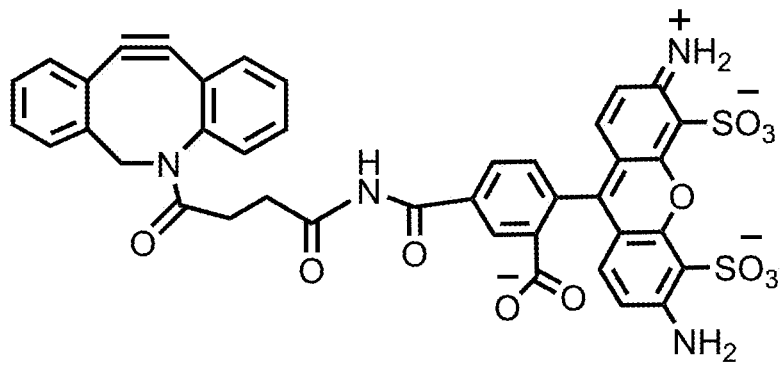
Figure 13G:
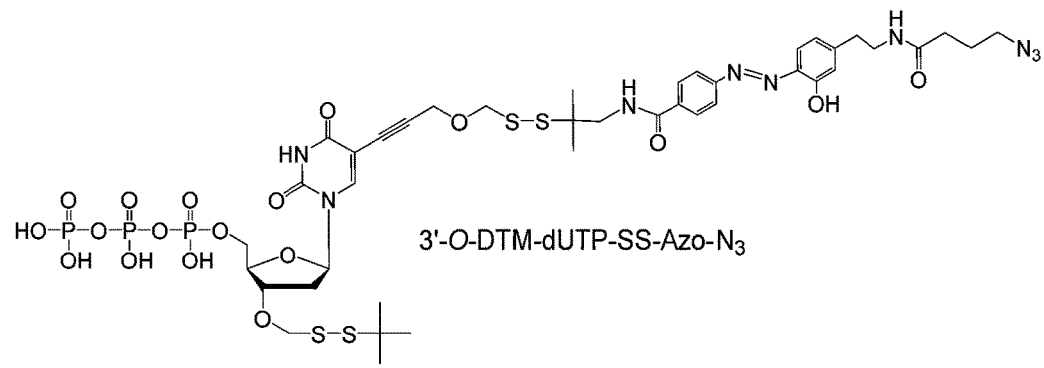
Figure 13H:
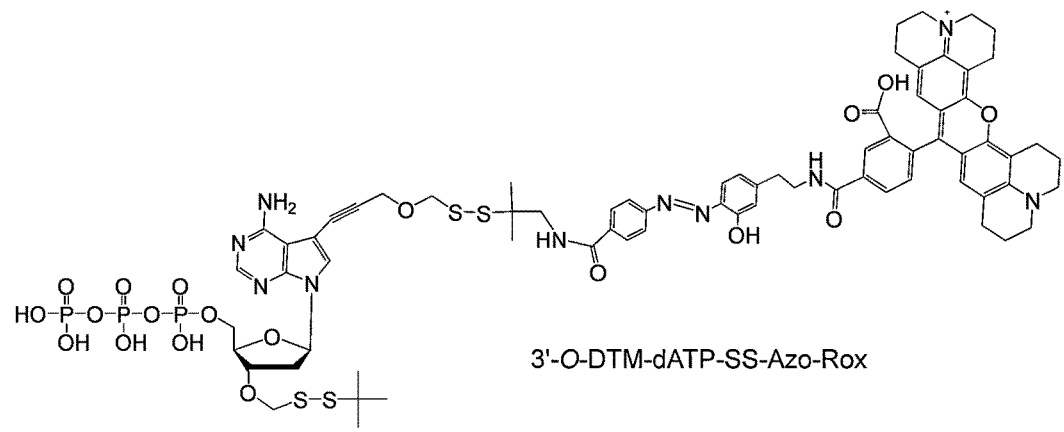
Figure 13I:
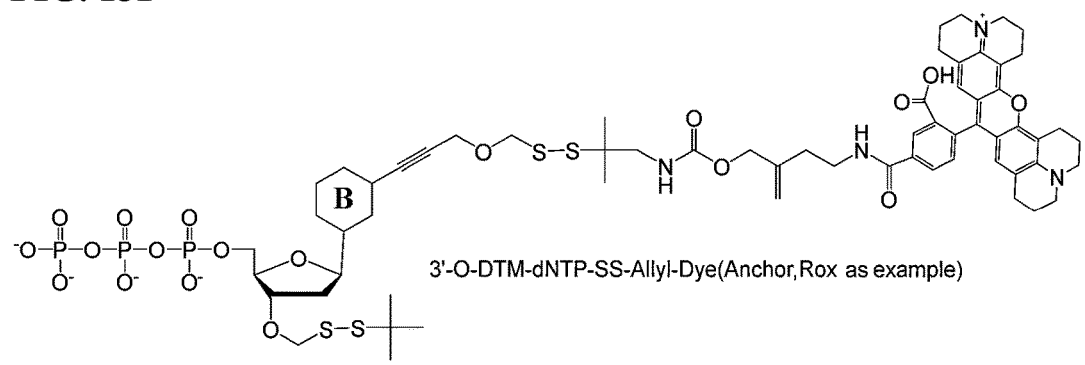
Figure 13J:
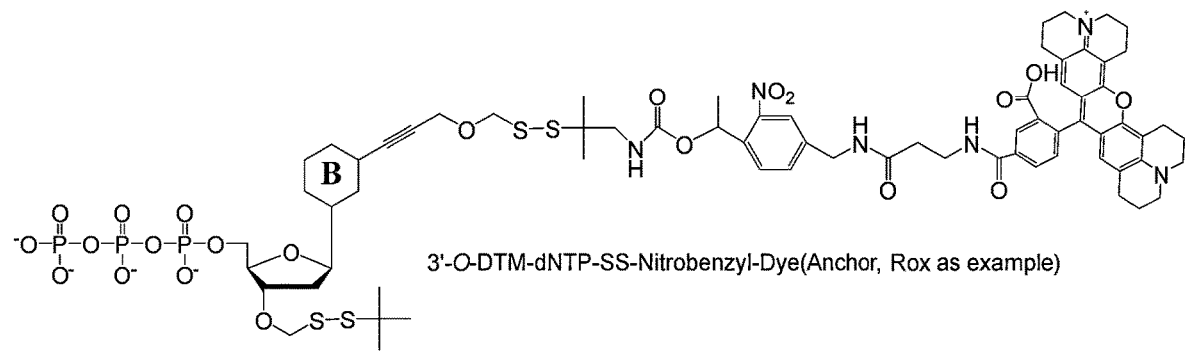

Synthesis of Rox-3-Cy5 labeled DBCO (shown in FIG. 11B). Cy5 labeled CPG (Glen Research) is used to start solid phase oligonucleotide synthesis on a DNA synthesizer. dSpacer phosphoramidite is used as the building block for three consecutive coupling cycles, then Rox labeled dT phosphoramidite is used in the next coupling cycle. C5 amino modifier phosphoramidite is used in the last coupling cycle. After cleavage under mild conditions following the GlenResearch protocol, the amino modified Rox-3-Cy5 product is produced and purified by HPLC. Coupling of DBCO NHS ester with amino modified Rox-3-Cy5 in DMSO/NaCO₃, NaHCO₃ buffer (pH 8.9) will afford Rox Cy5 labeled DBCO.

Syntheses of labeled binding molecules conjugated with fluorescent dyes via different cleavable linkers (the structures of these molecules are shown in FIG. 15) are shown in FIGS. 59-65. Synthesis of these compounds is achieved by coupling commercially available activated dyes with binding molecules containing cleavable linkage moieties, which are synthesized using commercially available materials.

Scheme 27 synthesis of SHA-2-Nitrobenzyl (linker)-ATTO647N is shown.

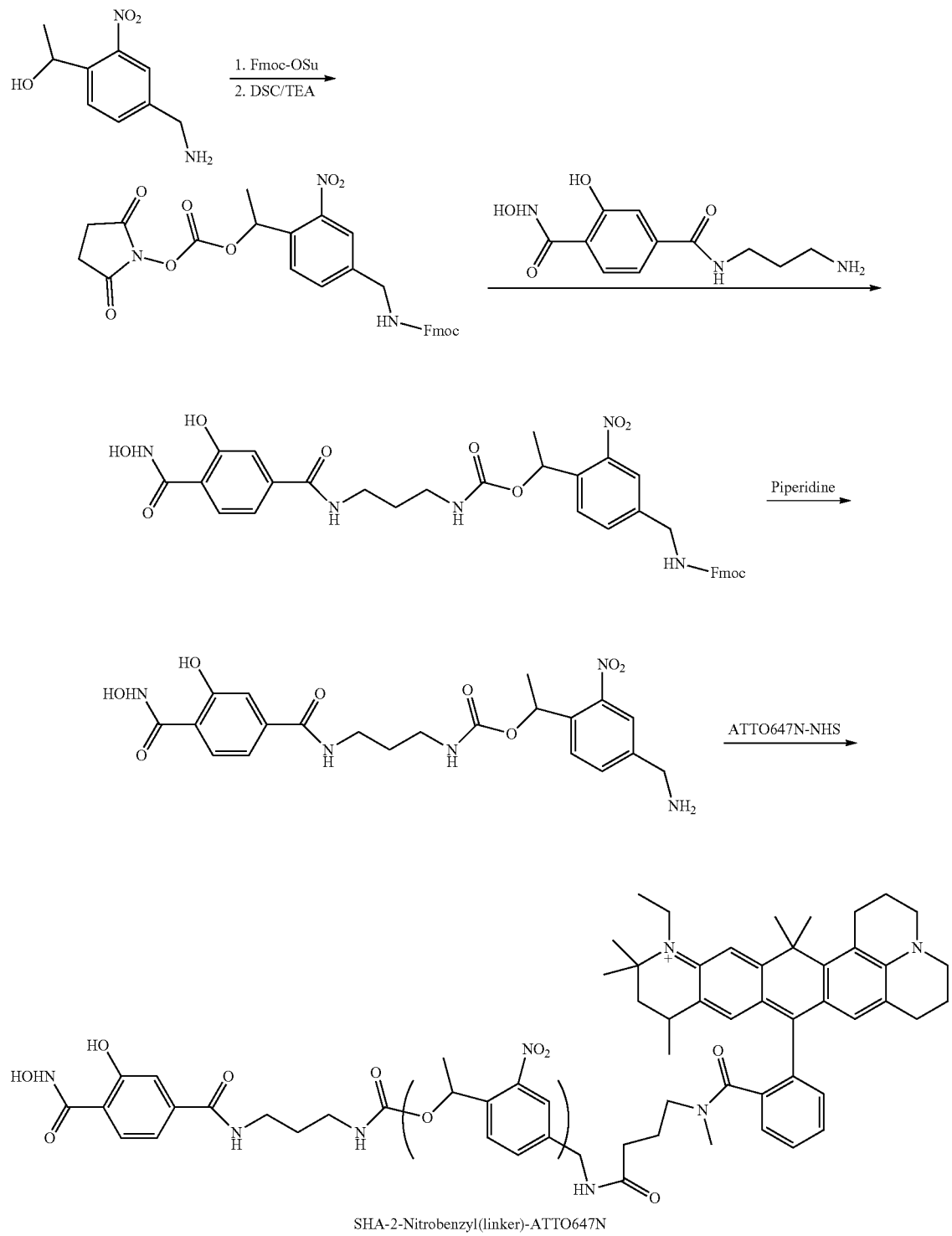

SHA-2-Nitrobenzyl(linker)-ATTO647N

Scheme 28. The synthesis of Tetrazine-Azo(linker)-ATTO647N. The synthesis of N3-Azo-NHS ester, Rox-Azo-NHS ester and the construction of the Azo linker moiety is accomplished using a literature method.
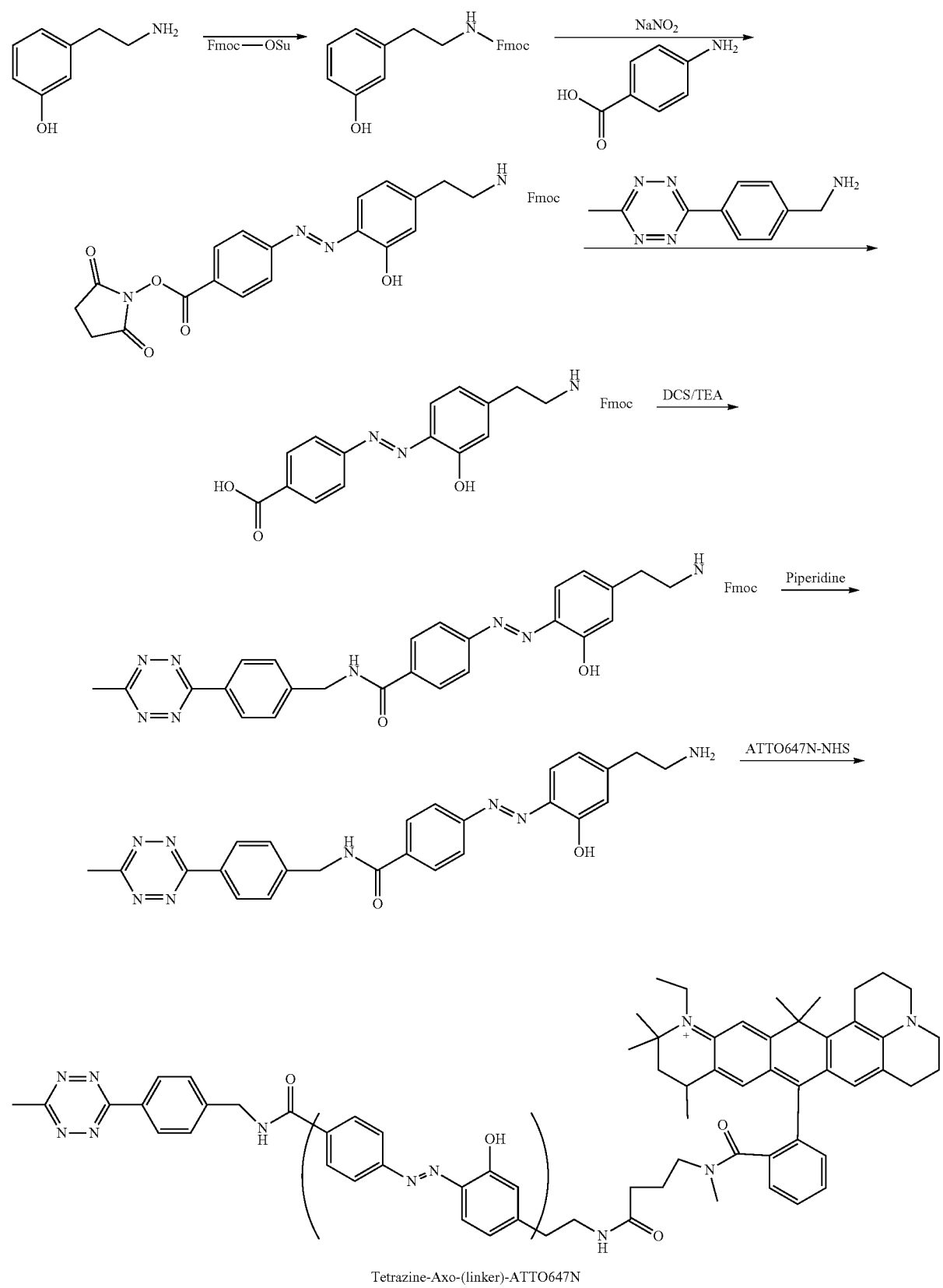
Tetrazine-Axo-(linker)-ATTO647N 597                                                   598
-continued
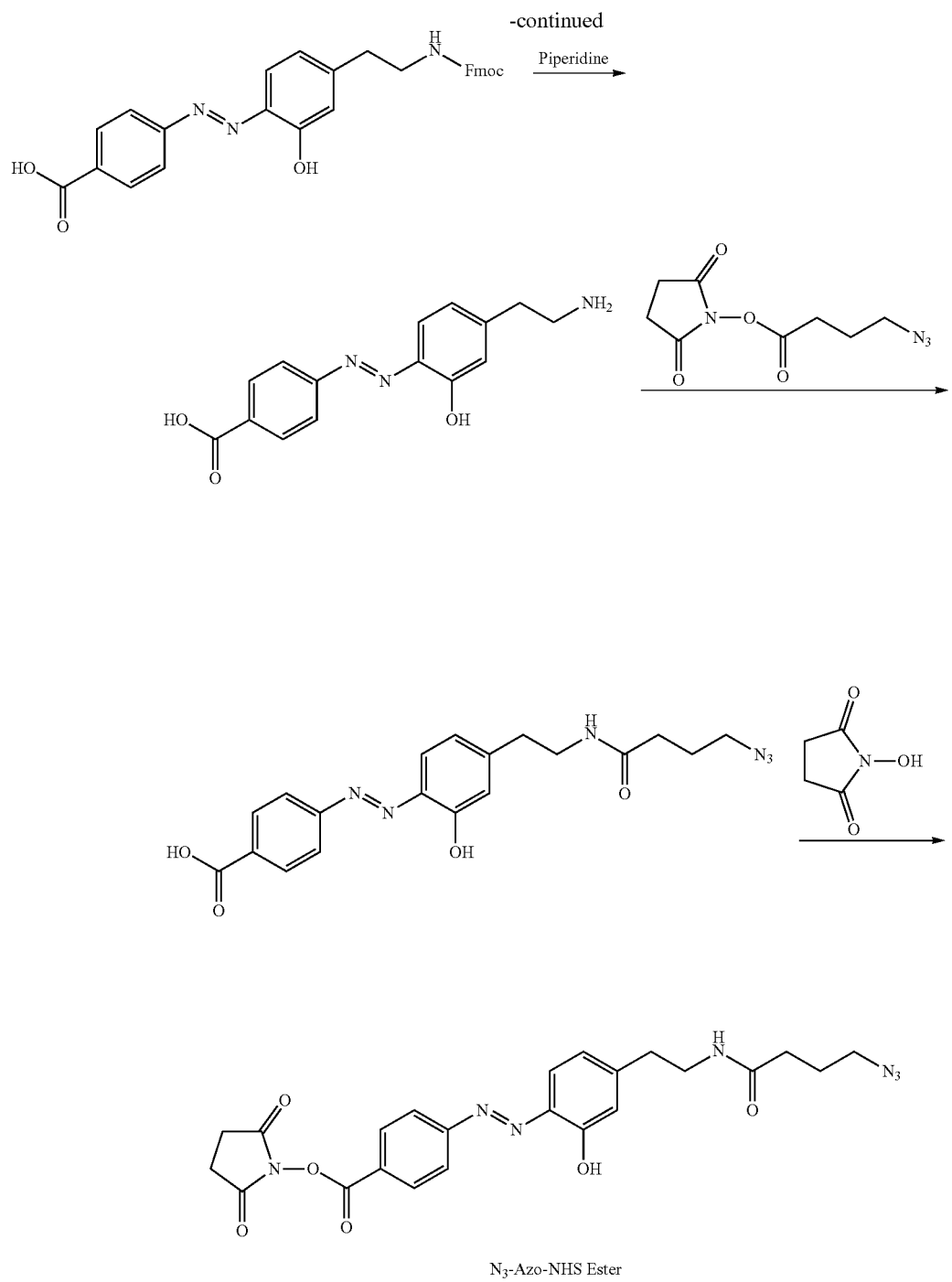
N₃-Azo-NHS Ester

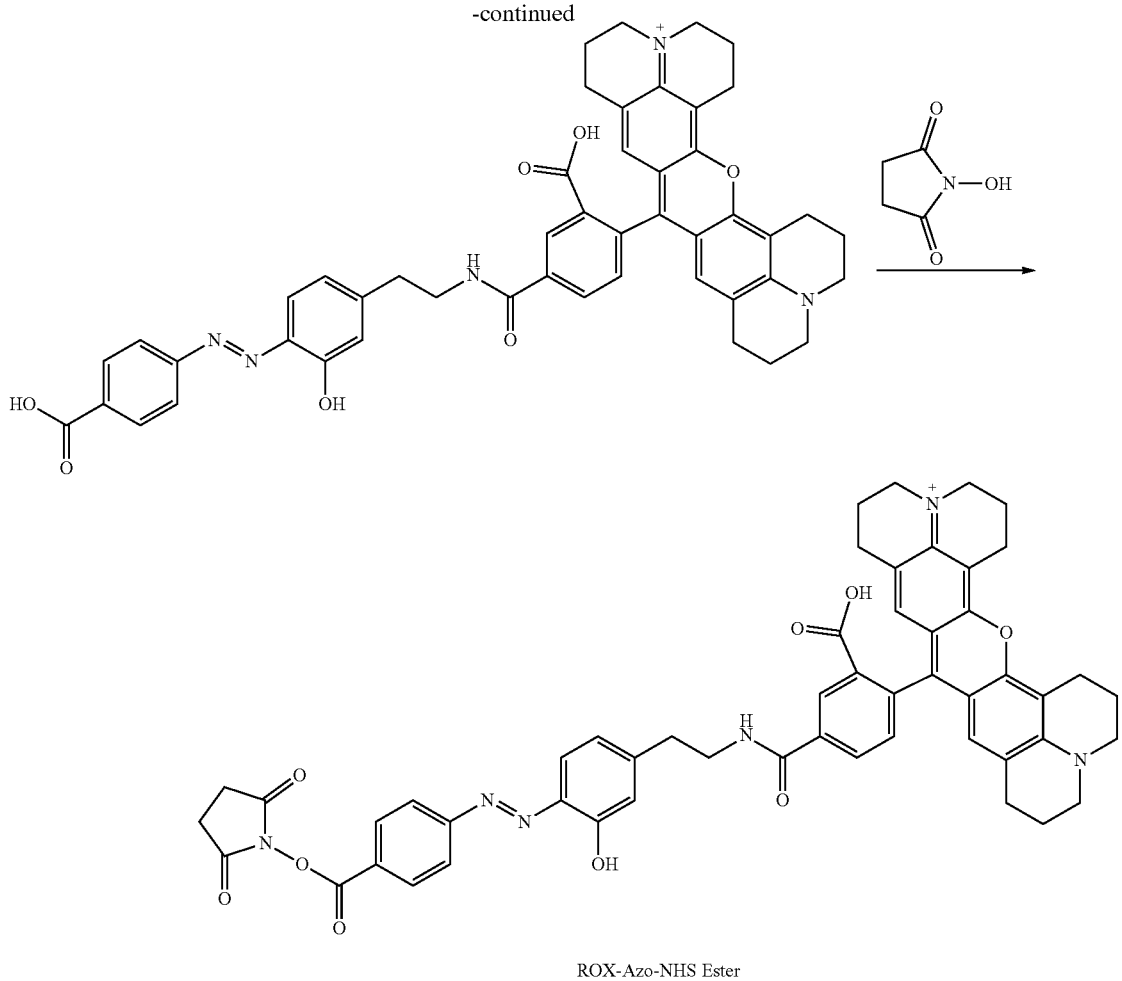
ROX-Azo-NHS Ester
The example synthesis of Streptavidin-Dimethylketal (linker)-ATTO647N is shown and the construction of the Dimethylketal linker moiety is accomplished using a literature method. Streptavidin is shown as the dark semi-circle (i.e. ☽)
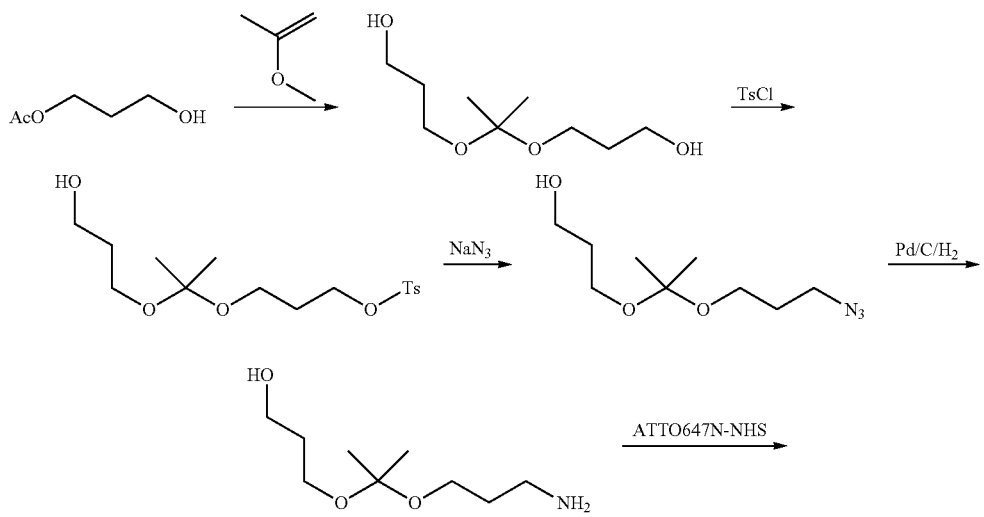

-continued
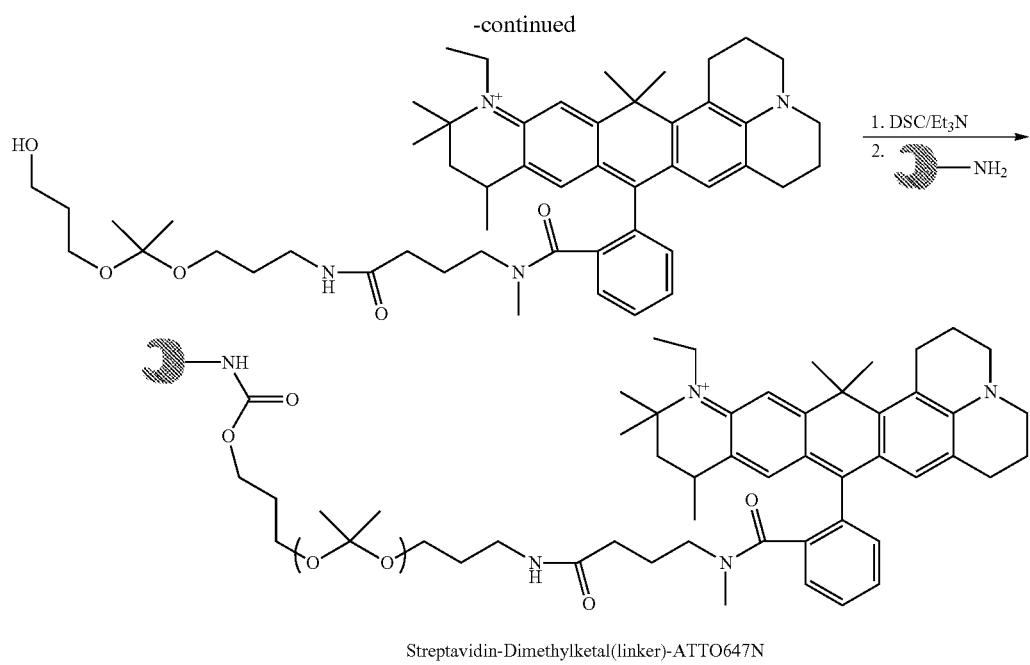
Streptavidin-Dimethylketal(linker)-ATTO647N
Scheme 29. The example synthesis of Dibenzocyclooctyne(DBCO)-Allyl(linker)-ATTO647N is shown.
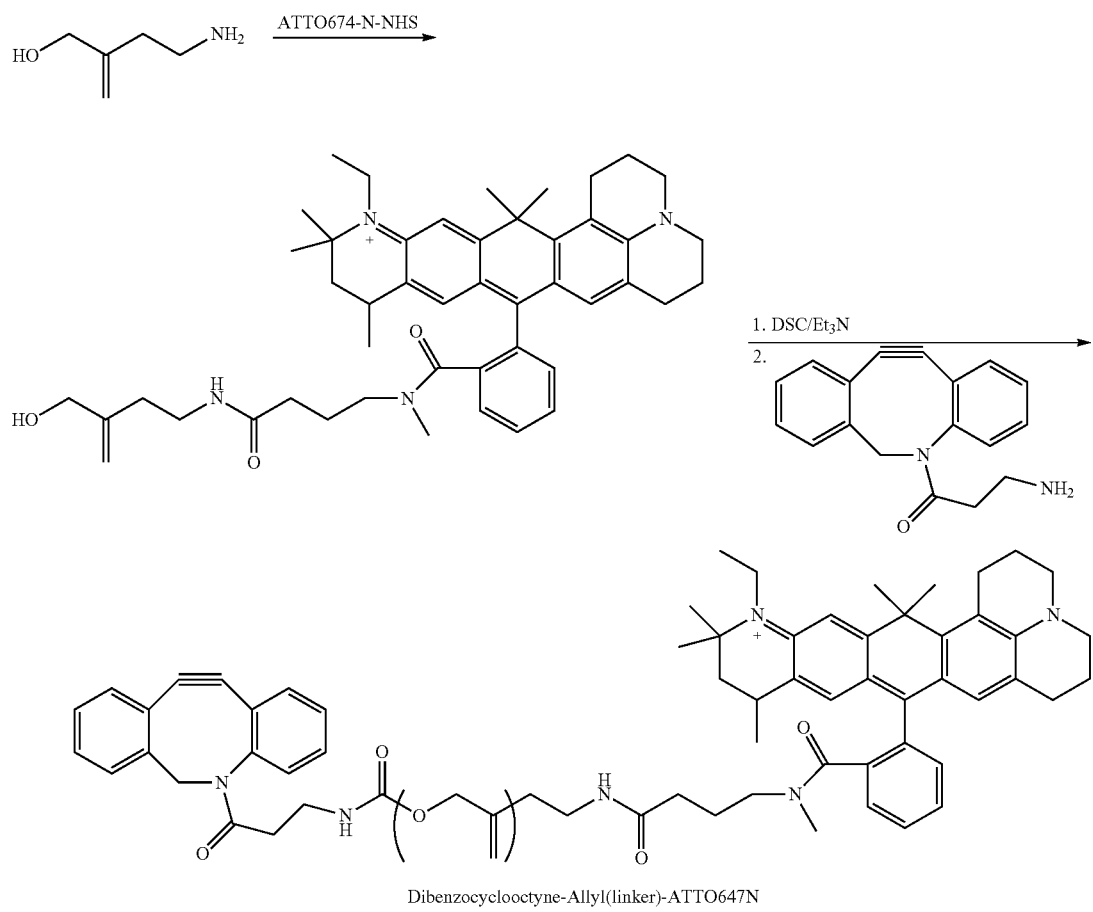
Dibenzocyclooctyne-Allyl(linker)-ATTO647N Scheme 30. The example synthesis of Dibenzocyclooc-tyne(DBCO)-Dde(linker)-ATTO647N is shown and the construction of the Dde linker moiety is accomplished using a literature method.[42]
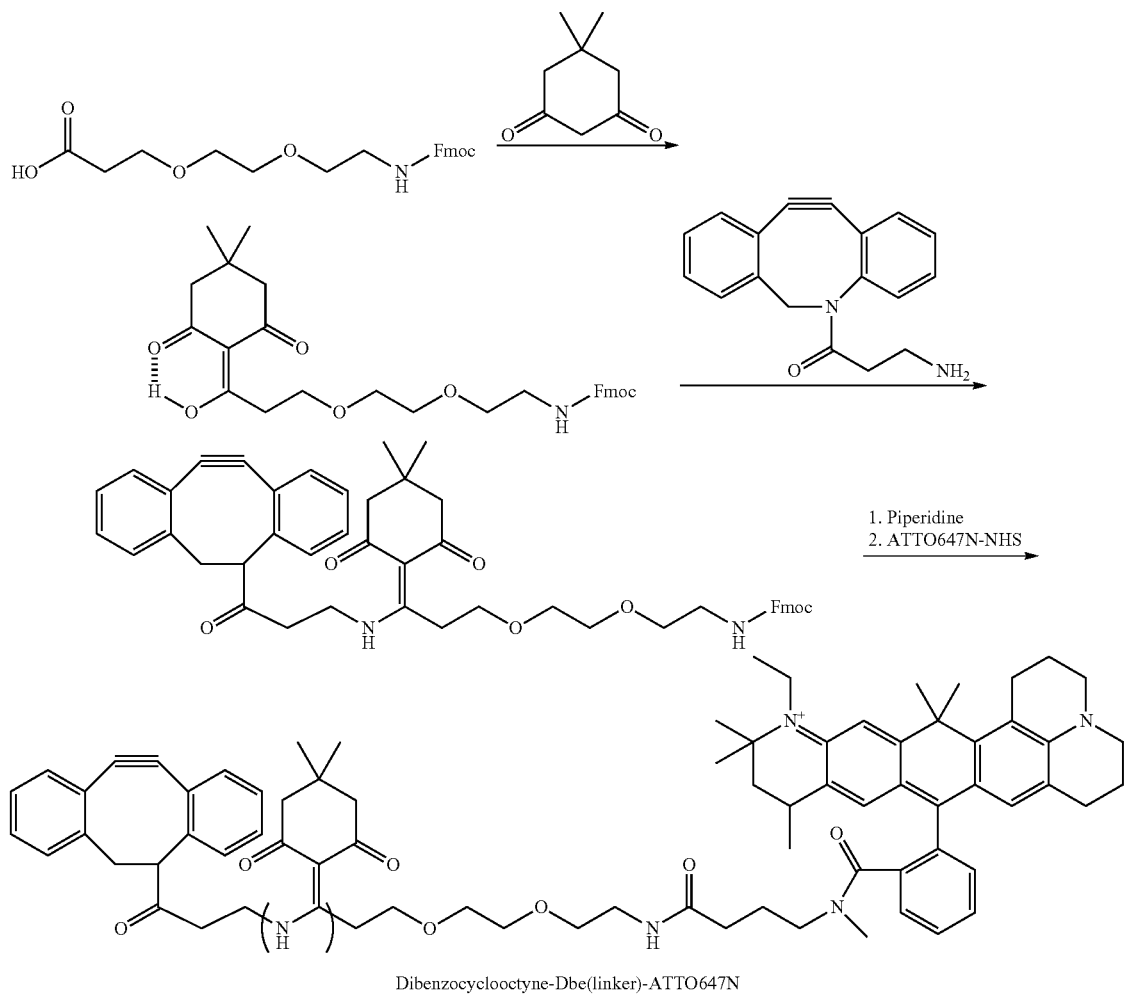
Scheme 31. The example synthesis of Tetrazine-Dde (linker)-ATTO647N and Tetrazine-Dde(linker)-ROX is shown.
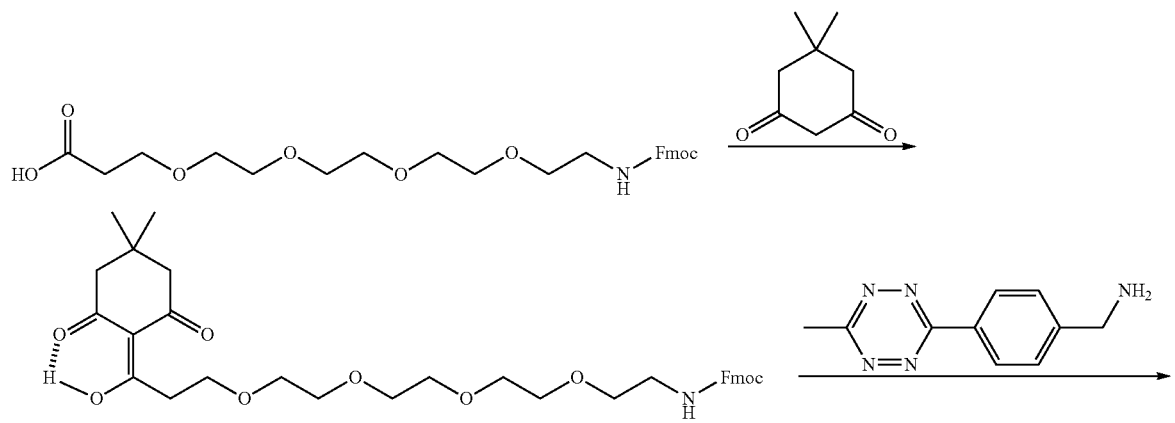

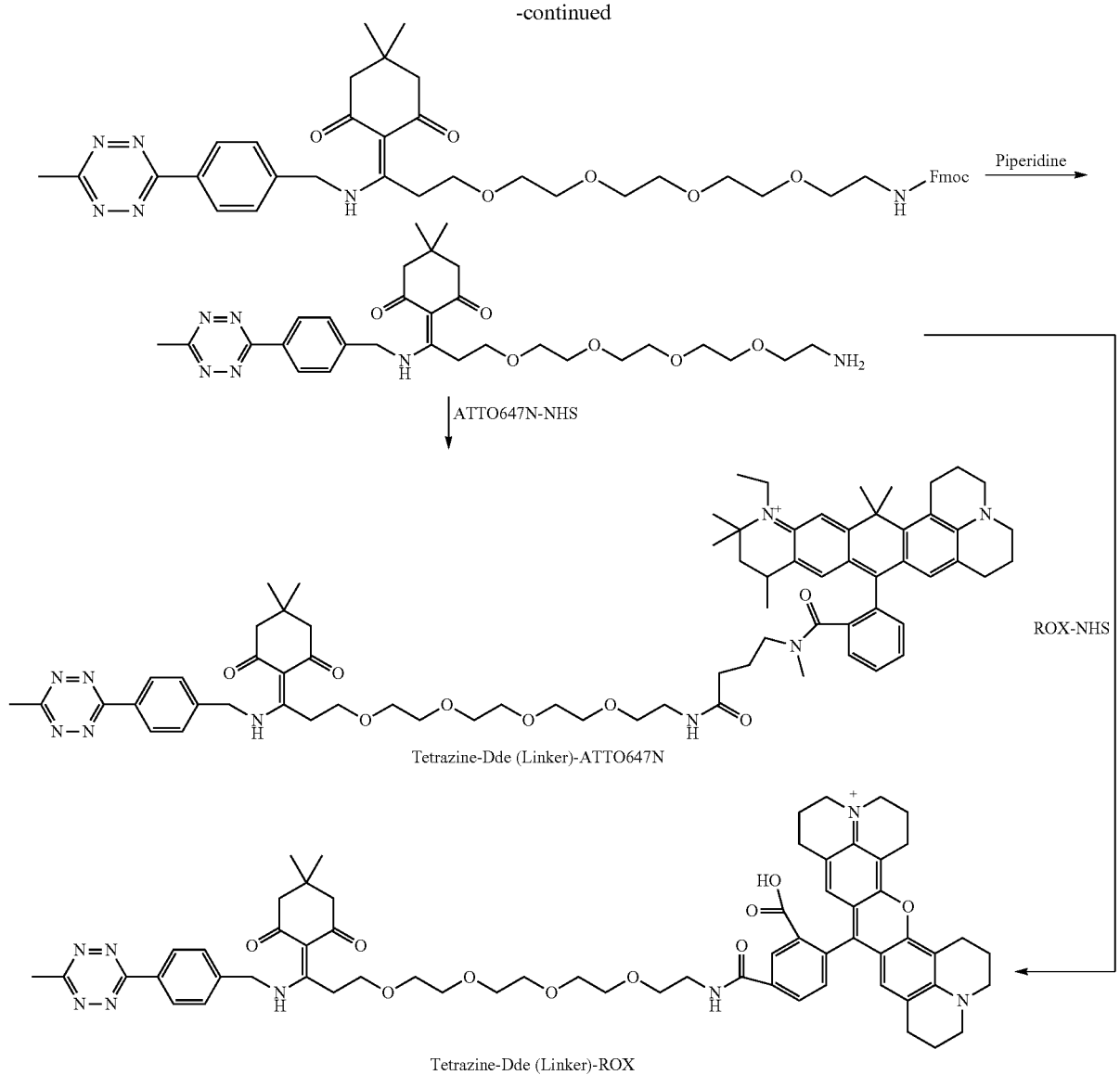
Scheme 32. The example synthesis of DBCO-Azo(—N=N-Linker)-ATTO647N and DBCO-Azo(-N=N-Linker)-ROX is shown.

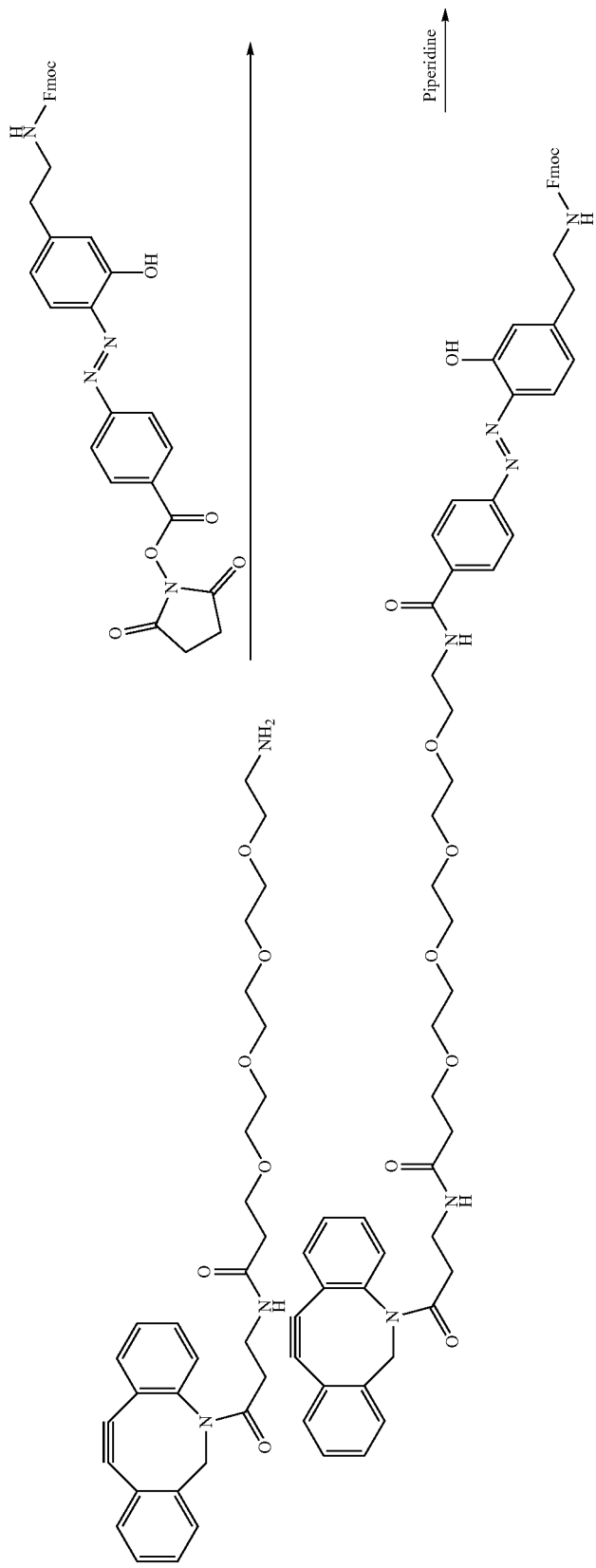

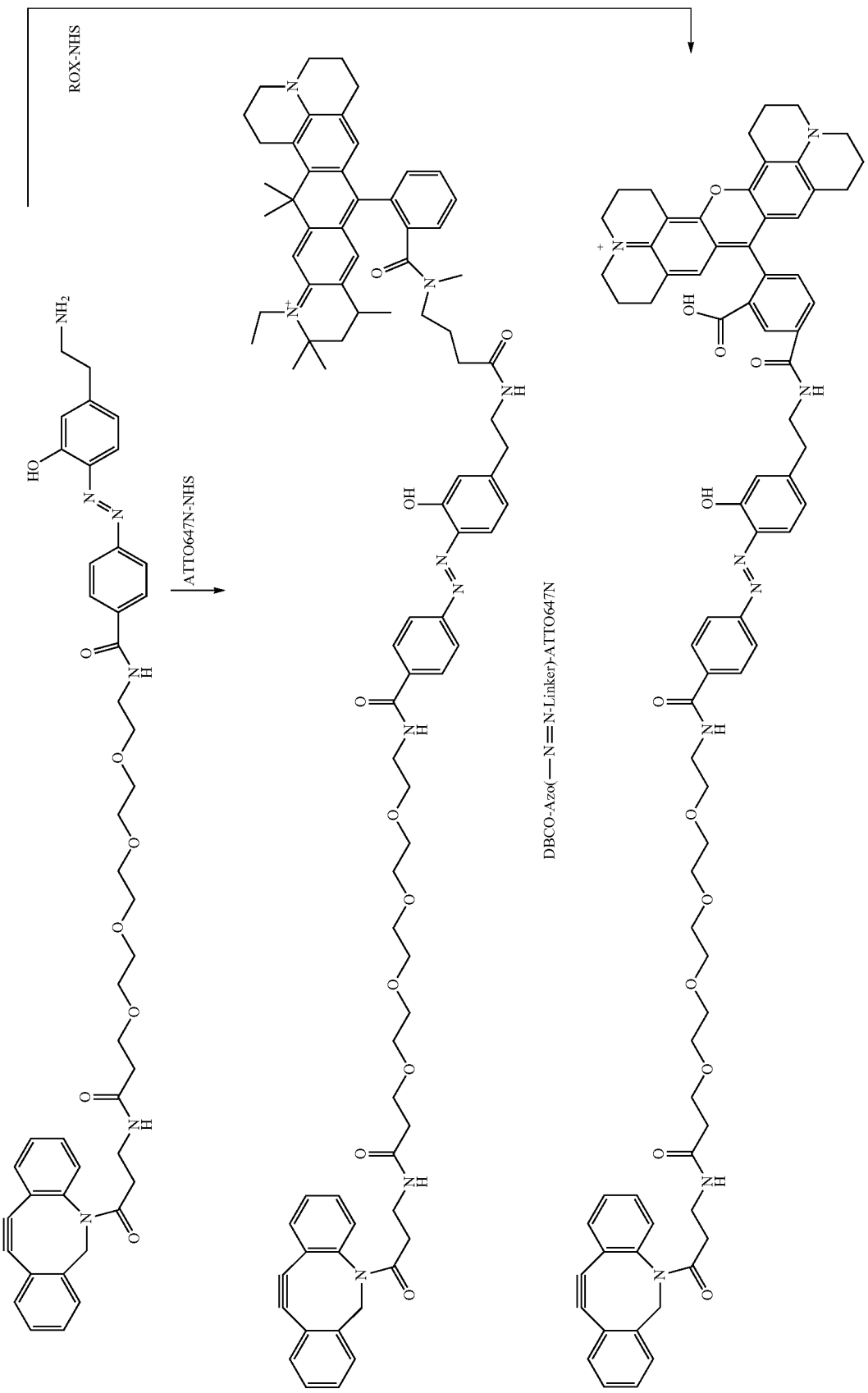

Scheme 33. The detailed cleavage reaction and the cleaved products using linkers constructed from Azo, Dimethylketal and Dde under mild conditions (using $N_2S_2O_4$, Citric acid and $N_2H_4$ respectively) are shown using Tetrazine-Azo(linker)-ATTO647N, Streptavidin-Dimethylketal(linker)-ATTO647N) and Dibenzocyclooctyne-Dde(linker)-ATTO647N described above as examples.
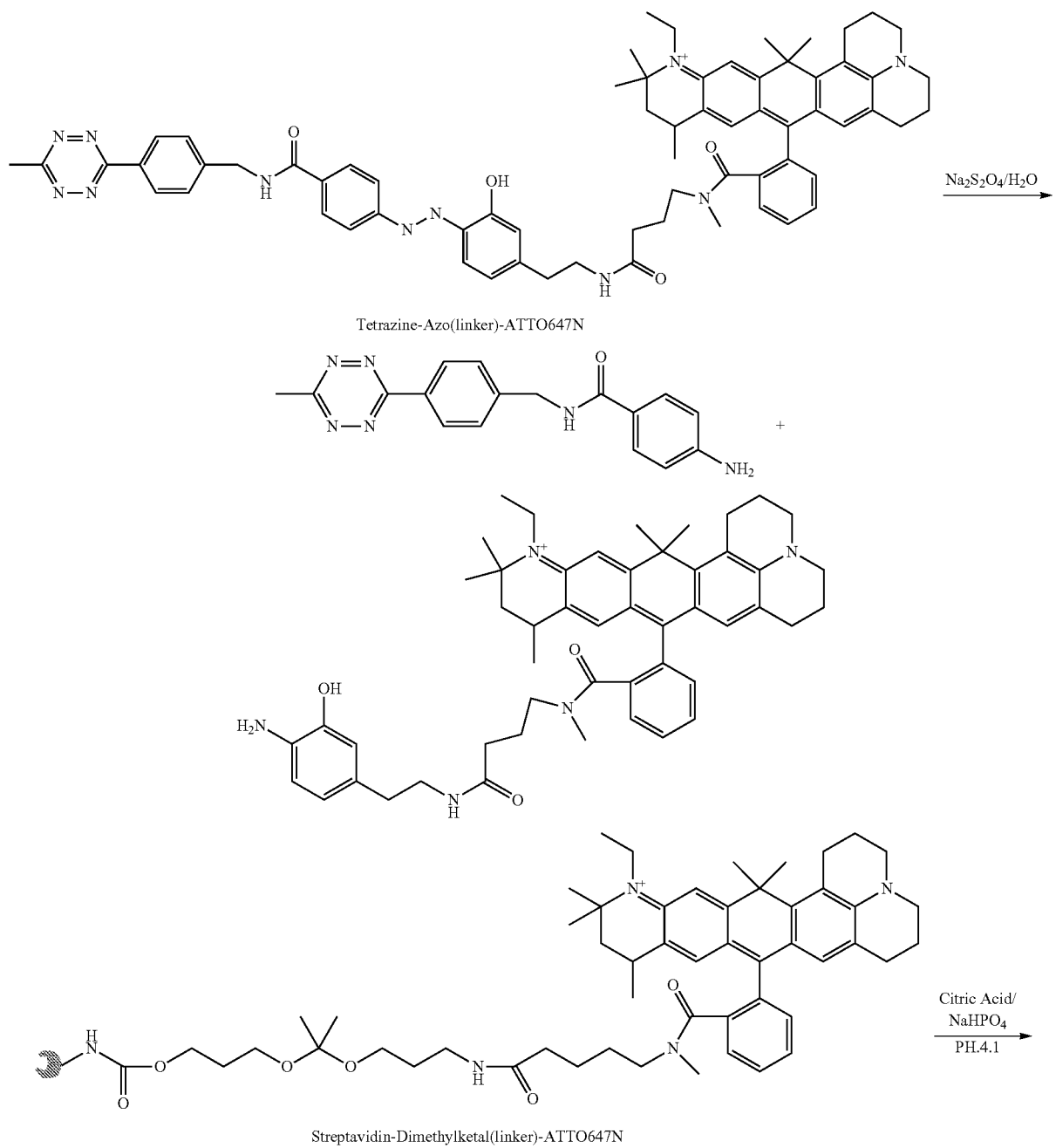
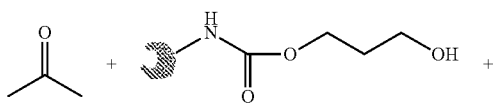

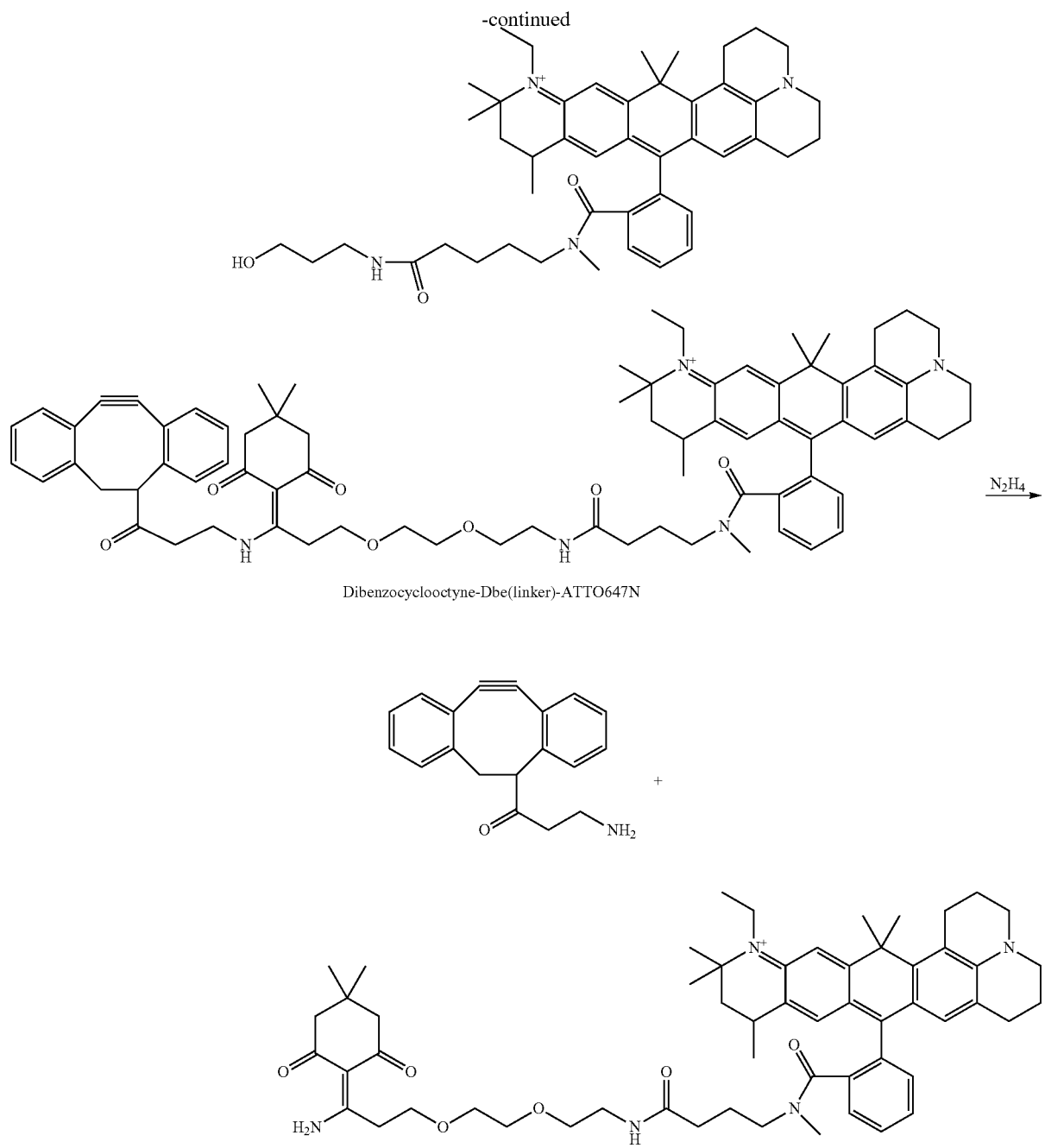

Example Syntheses of 3'-O-DTM(SS)-dNTP-Linker-Dye-or-"Anchor" (FIGS. 67 and 68) are shown in the Schemes below. Instead of using (TFA)NH-DTM(SS)-Alkyne linker, a variety of (TFA)NH-Linker-Alkyne are used to couple with 3'-O-DTM(SS)-5(7)-iodo nucleosides yielding 5(7)-linker modified nucleosides, which can then be converted to 5(7)-linker-NH$_2$ modified dNTPs via triphosphorylation at the 5'-OH. Lastly, either dye NHS esters or "anchor"-NHS esters can be used to couple with 3'-O-DTM (SS)-5(7)-linker-NH$_2$ modified dNTPs affording a variety of 3. DTM(SS)-dNTP-Linker-Dye or -"Anchor".

Scheme 34. Synthesis of 3'-O-DTM-dCTP-5-Nitrobenzyl-Rox is shown in FIG. 37.

Scheme 35. Synthesis of 3'-O-DTM-dUTP-5-Allyl-Rox is shown in FIG. 38.

Scheme 36. More generally, synthesis of 3'-O-DTM-dNTP-Nitrobenzyl-R, in which R is either a dye or an anchor, is shown in FIG. 39.

Scheme 37. Synthesis of 3'-O-DTM-dNTP-Allyl-R is shown in FIG. 40.

Schemes 38 and 39. The synthesis of either dye or anchor labeled 3'-O-DTM(SS)-dNTPs via Azo and Dde linkers respectively in FIGS. 41 and 42.

Example 4. Long DNA synthesis using 3'-O-alkyl-dithiomethyl-dNTPs

Scheme 40. Scheme for the synthesis of Long DNA using 3'-O-alkyl-dithiomethyl-dNTPs and terminal deoxynucleotidyl transferase.

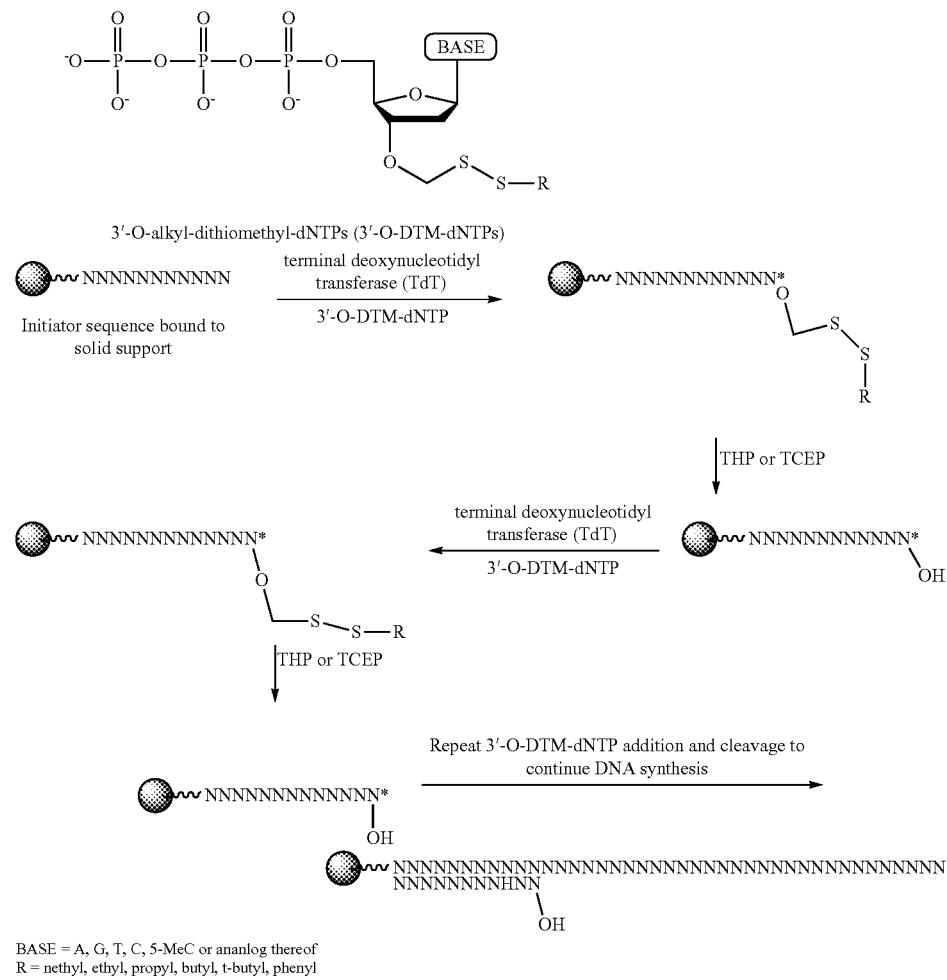

BASE = A, G, T, C, 5-MeC or ananlog thereof
R = nethyl, ethyl, propyl, butyl, t-butyl, phenyl DNA synthesis using nucleoside phosphoramidite chemistry is a standard process and used for most of the custom DNA synthesis needs. However, the synthesis is limited to short length (<120 nucleotides) and it is impractical to synthesize DNA of >200 nucleotides in length. The synthesis also involves the use and generation of toxic by-products and the disposal of such toxic waste increase the cost of DNA synthesis (LeProust et al., Nucleic Acids Res. (2010) 38(8), 2522-2540).

The invention provides improved methods for DNA synthesis using 3'-O-DTM-dNTPs nucleotides of the present invention as described below and systematically in the above scheme. These nucleotides can be used in both template-dependent (using DNA polymerase) and template-independent synthesis of polynucleotides (DNA) by using a terminal deoxynucleotidyl transferase enzyme. These nucleotides carry a chemically cleavable disulfide linkage at the 3'-O-position which pause the synthesis after single nucleotide addition. After mild treatment with THP or TCEP, the 3'-blocking group is cleaved and the generation of free 3'-OH group results in the addition of next nucleotide.

Terminal deoxynucleotidyl transferase enzyme is known to incorporate natural and modified nucleotides at the 3'-end of the polynucleotides in template independent manner. Various attempts have been made to use TdT for controlled de novo single-stranded DNA synthesis (Ud-Dean S.M.M. Syst. Synth Biol. (2009) 2, 67-73, U.S. Pat. Nos. 5,763,594 and 8,808,989). A reversible nucleoside triphosphate is necessary to prevent uncontrolled addition of dNTPs to the 3'-end of a growing DNA strand. However the efficiency of TdT to incorporate 3'-O-modified nucleotides is very limited (WO 2016/128731 A1). A mutant TdT enzyme may also be used to incorporate 3'-O-reversibly terminated nucleotides of this invention.

Thus, present invention provides the method of making long DNA comprises the steps of:
 a) an initiator sequence bound to solid support;
 b) adding a 3'-O-alkyl-dithiomethyl dNTP (3'-O-DTM-dNTP) to said initiator sequence in the presence of terminal deoxynucleotidyl transferase (TdT);
 c) removal of reagents from the initiator sequence;
 d) cleavage of the 3'-O-blocking group from the extended sequence in the presence of cleaving agent such as THP or TCEP;
 e) removal of cleaving reagents;
 f) repeat the sequence b-e.

The present method also provides the kit for nucleic acid synthesis comprises a mutant TdT, an initiator sequence and a set of four or more 3'-O-reversibly blocked dNTPs, buffers, cleaving agent, and instructions for the use of the kit for DNA synthesis.

The DNA synthesis can also be carried out using a template/primer, DNA polymerase and four 3'-O-reversibly blocked dNTPs of this invention. This will result in the formation of double stranded DNA of defined length which can be denatured and separated as single stranded DNA.

Example 5. Synthetic Methods

General synthetic methods for analogues of 3'-O-CleavableGroup-dNTP-SS-Label is shown. Starting from 5(7) iodide substituted nucleosides, the 5'-OH and amino groups on the base are protected. Then the 3'-OH is converted to 3'-O—R$^6$ using various established synthetic methods. The resulting compounds are coupled with a (TFA)NH-DTM (SS)-alkyne building block via Sonogashira coupling yielding 5(7)-(TFA)NH—SS-nucleosides. After removal of the 5'-O protecting group, the 3'-0-R$^6$-5(7)-SS-nucleosides are converted to 3'-O—R$^6$-5(7)-SS-dNTPs using the established triphosphorylation method. Further deprotection of the amino group affords 3'-O—R$^6$-5(7)-NH$_2$—SS-dNTPs. The resulting 3'-O—R$^6$-5(7)-NH$_2$—SS-dNTP precursors are then reacted with Label (Anchor or Dye)-NHS esters to produce 3'-O-CleavableGroup(R$^6$)-dNTP-SS-Label (R), where R refers to Dye or Anchor molecules.

Scheme 41: Synthesis of 3'-O-R-dUTP-DTM(SS)-Label (R), R=Dye or Anchor molecule.

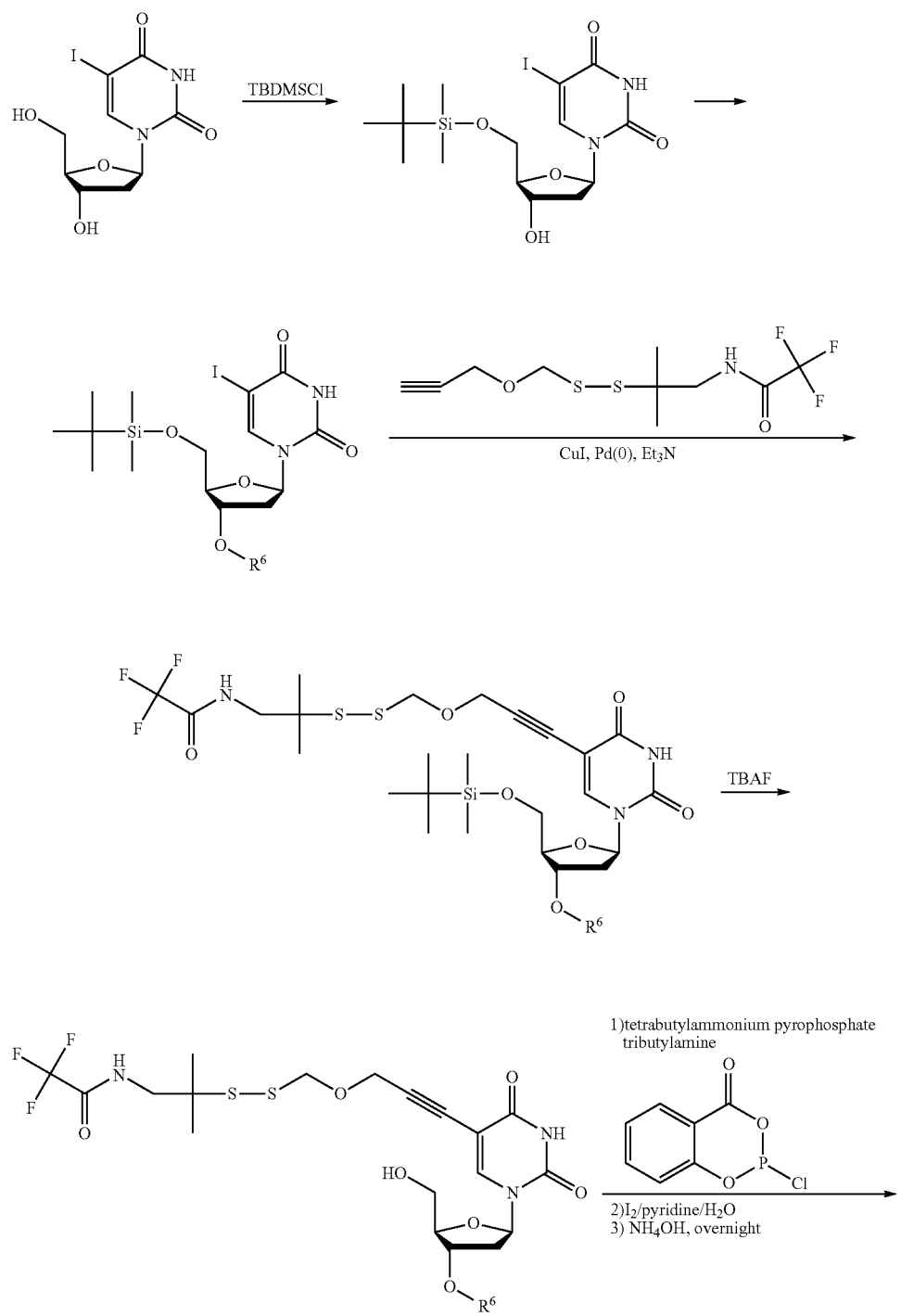

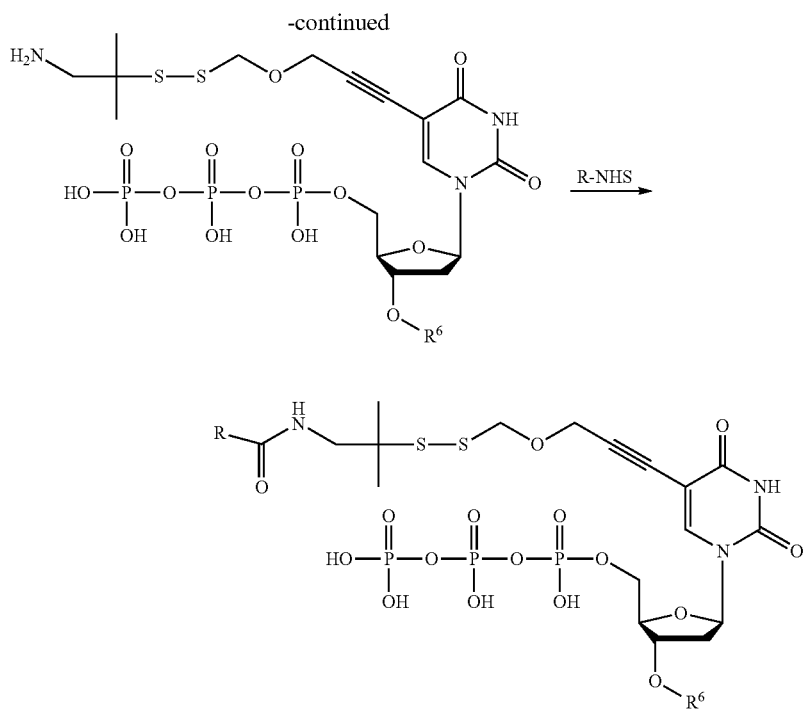
R = Dye or Anchor molecule.
Scheme 42: Synthesis of 3'-O-R$^6$-dCTP-DTM(SS)-Label (R), R$^6$=Dye or Anchor molecule.
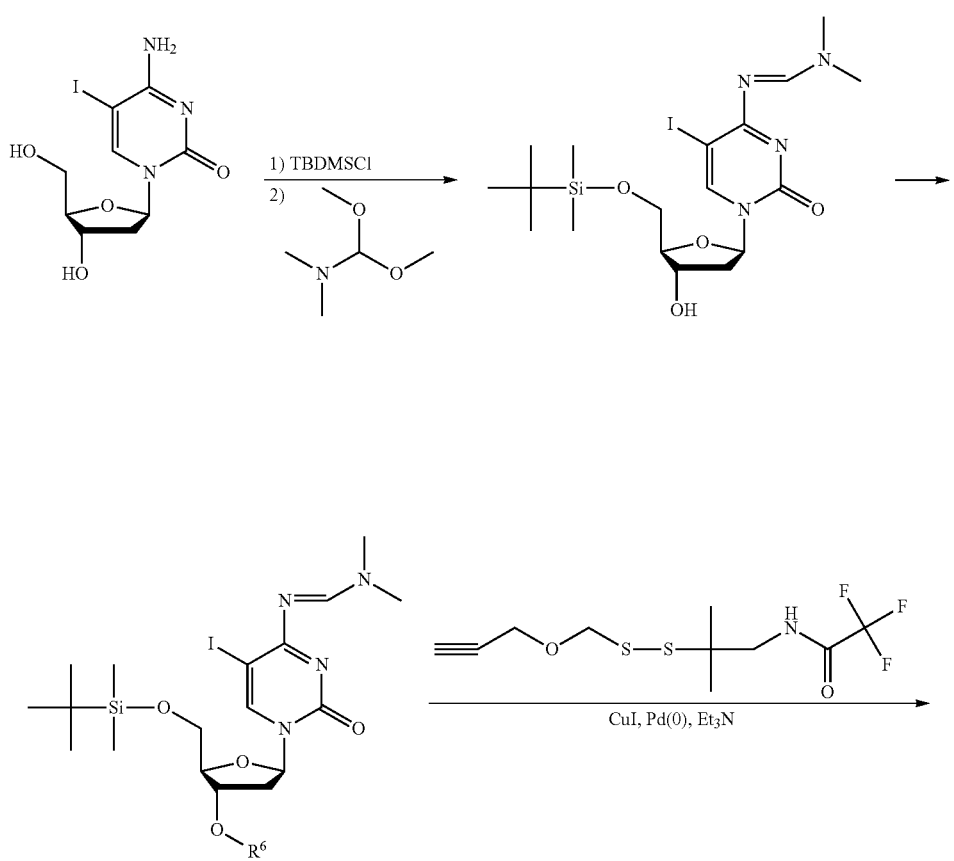

-continued
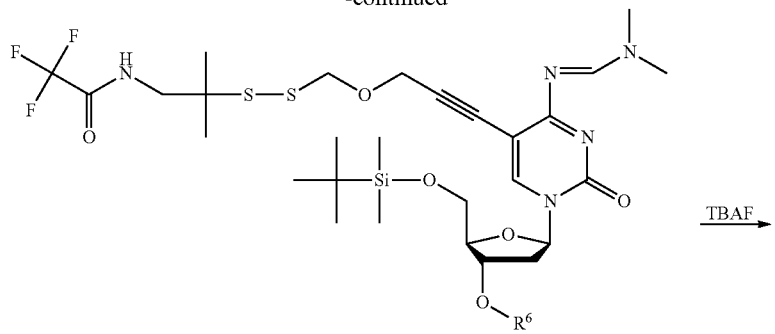
TBAF →
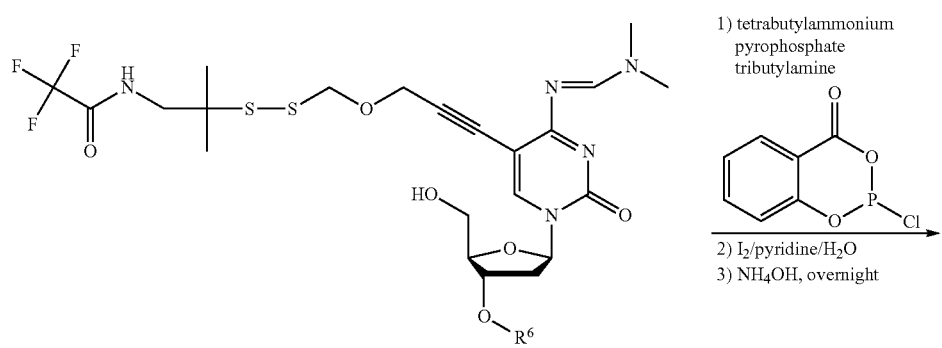
1) tetrabutylammonium pyrophosphate tributylamine
2) I₂/pyridine/H₂O
3) NH₄OH, overnight
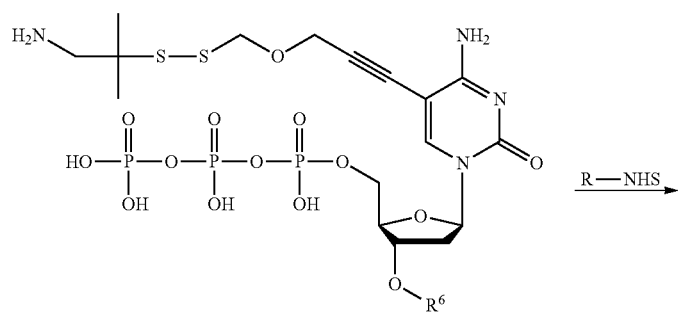
R—NHS →
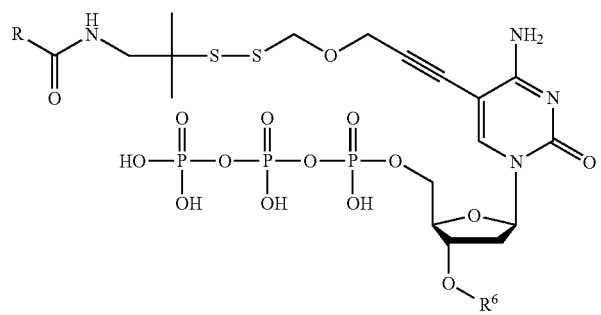

Scheme 43: Synthesis of 3'-O-R⁶-dATP-DTM(SS)-Label (R), R⁶=Dye or Anchor molecule.
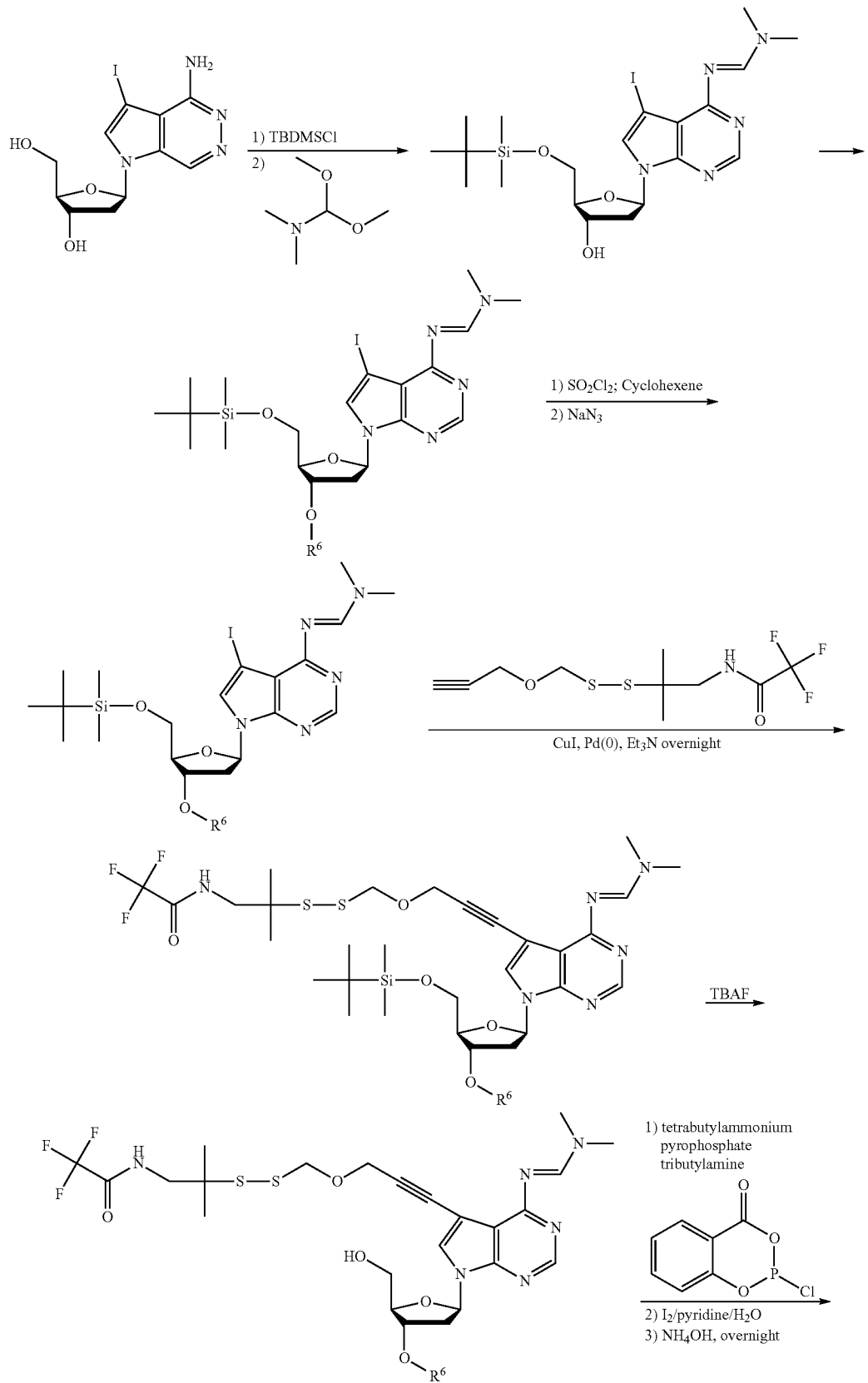

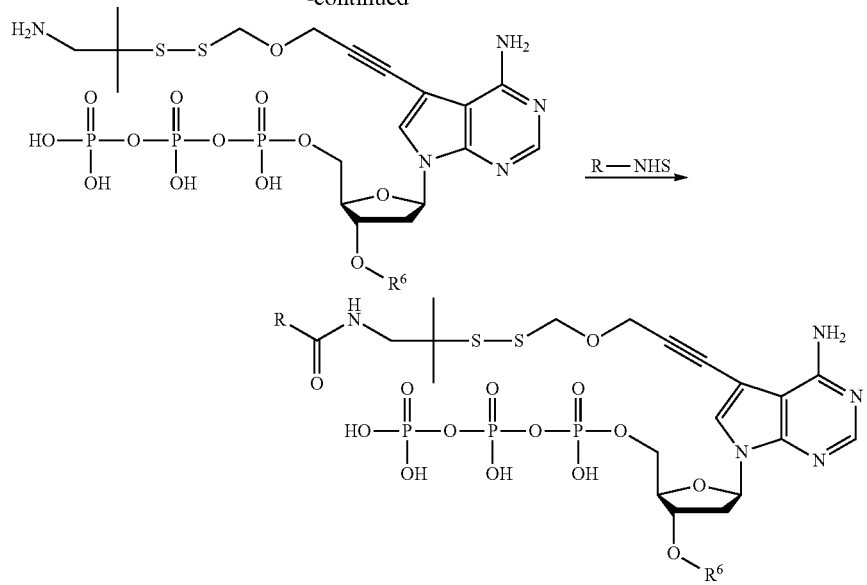
Scheme 44: Synthesis of 3'-O-R$^6$-dGTP-DTM(SS)-Label (R), R$^6$=Dye or Anchor molecule.
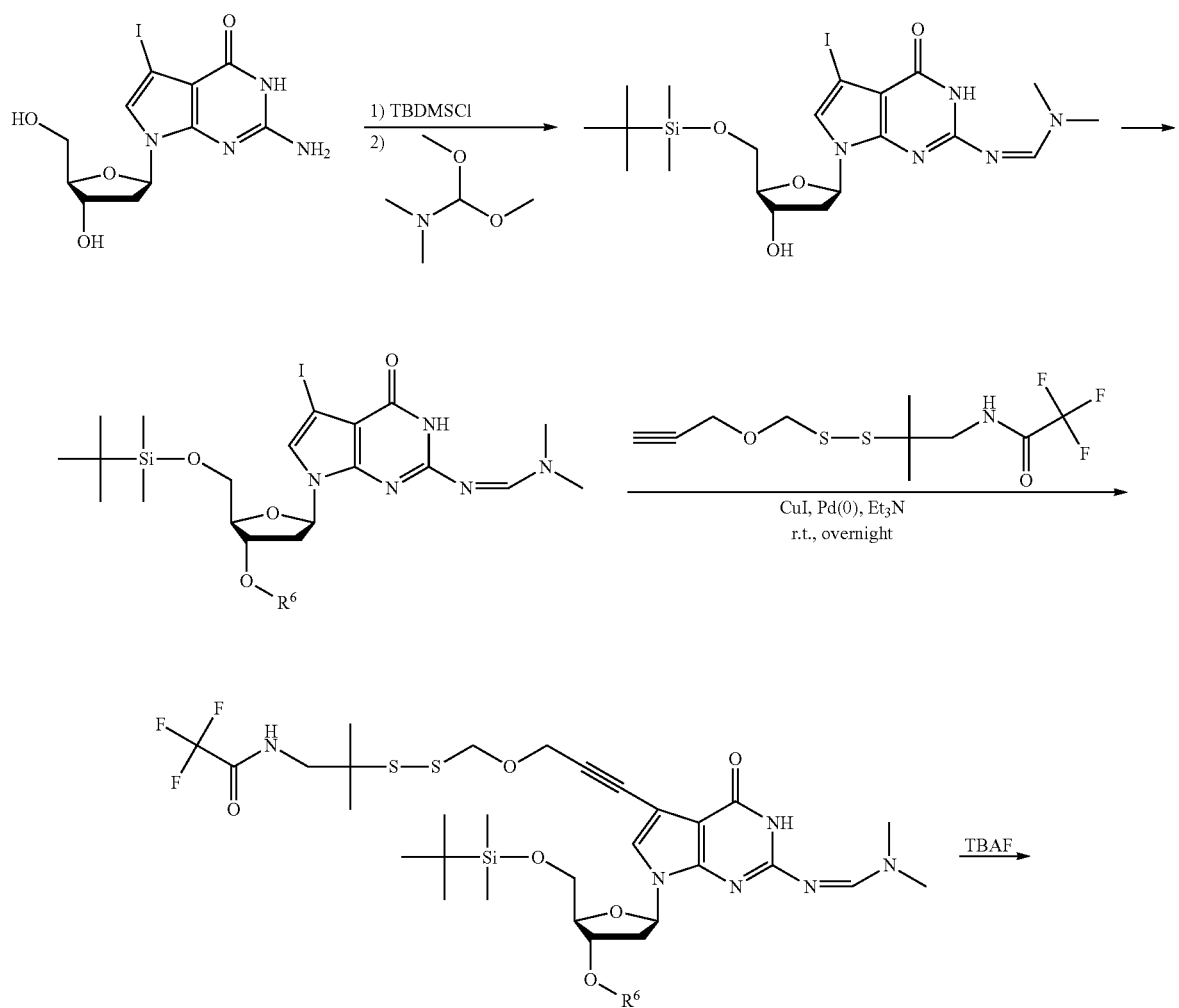

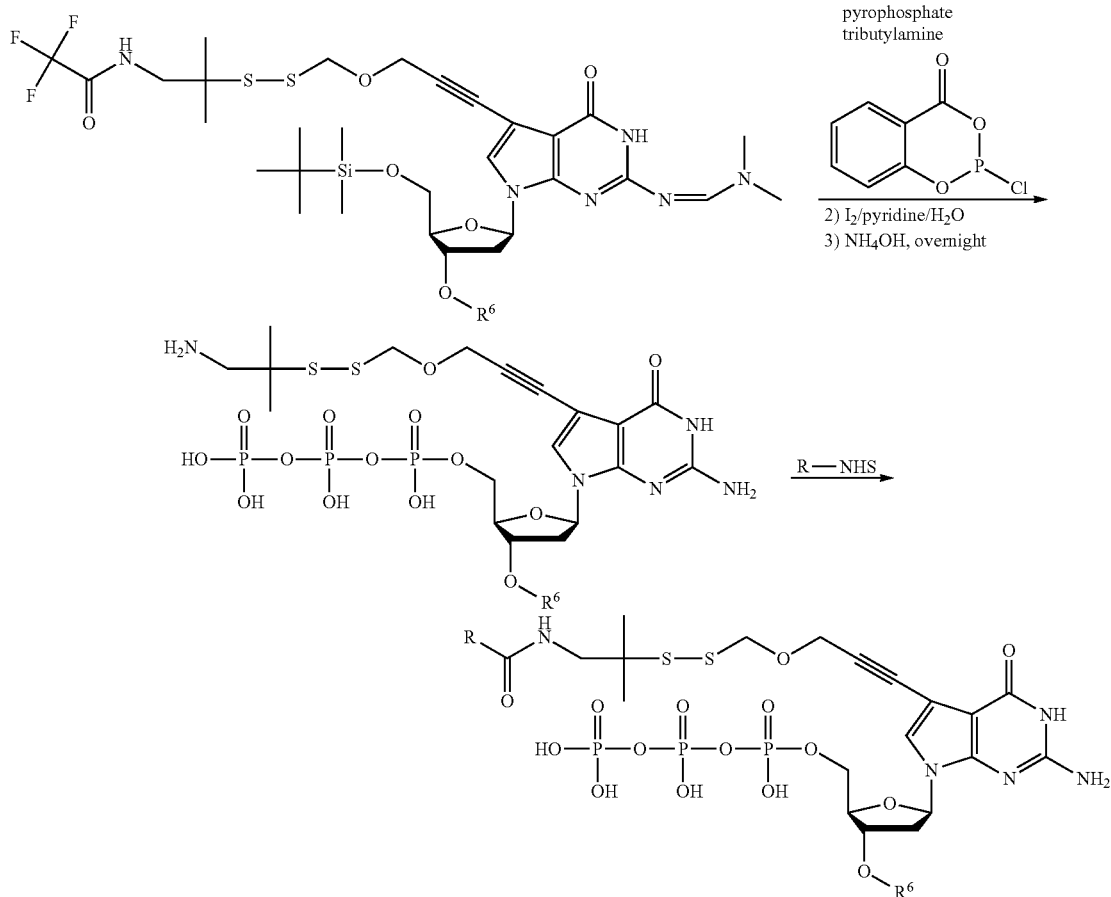
Scheme 45: Synthesis of 3'-O-Allyl-dUTP-SS-R6G.
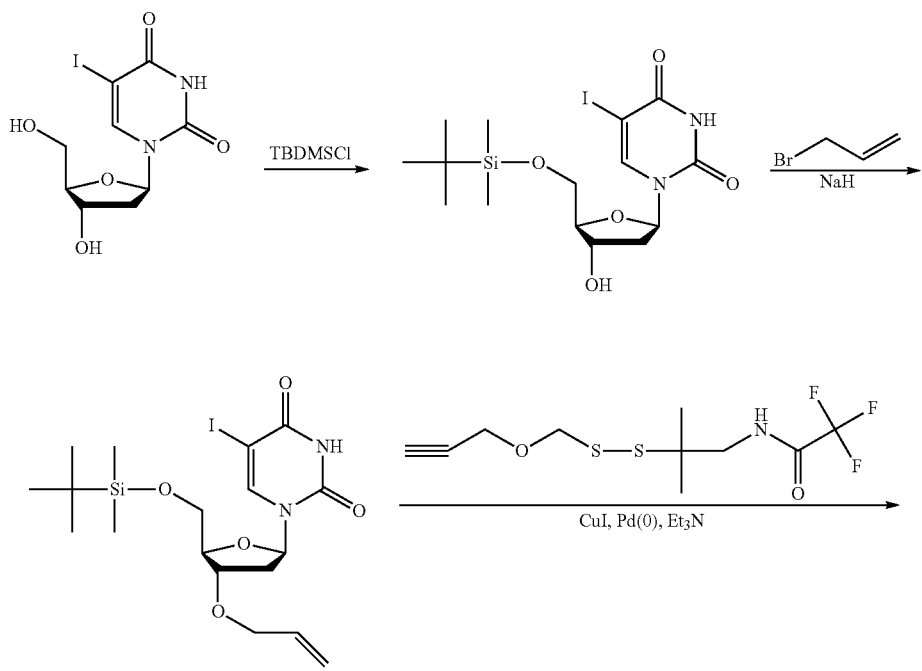

-continued
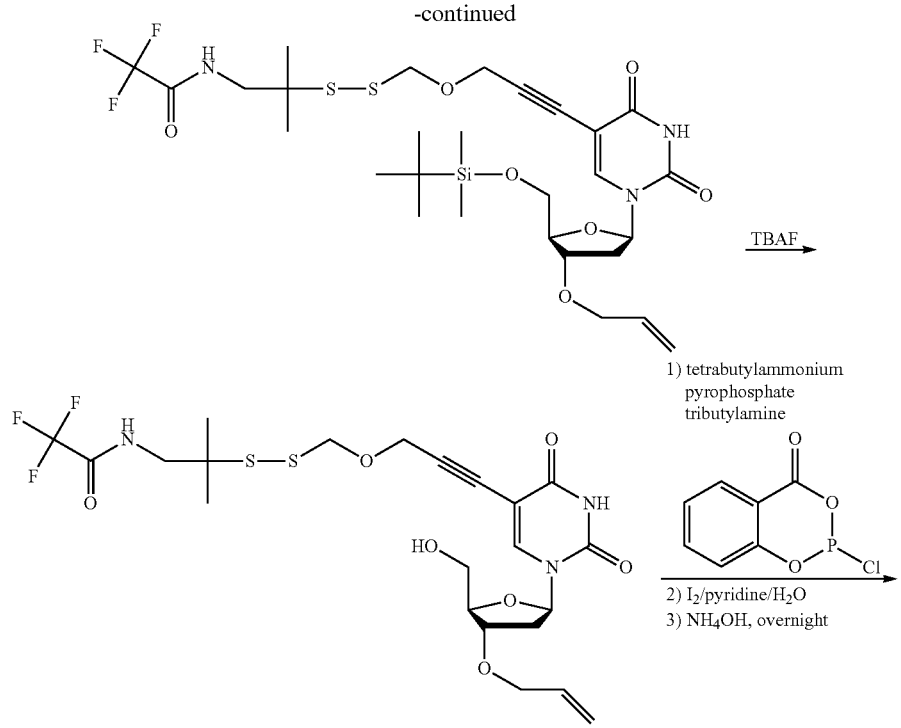
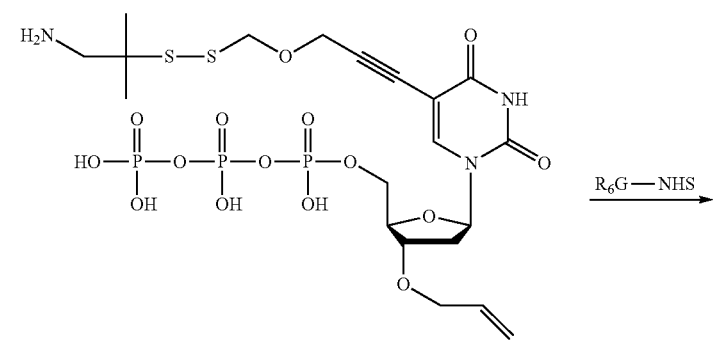
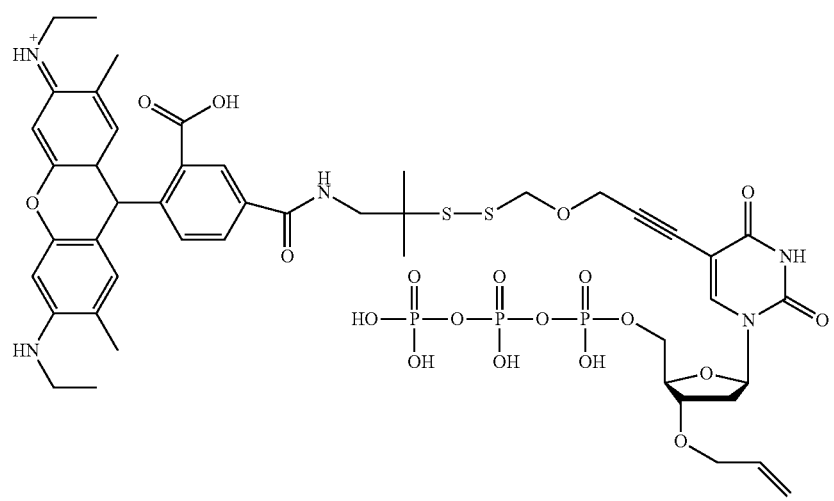

Scheme 46. Synthesis of 3'-O-Allyl-dCTP-SS-Alexa488.
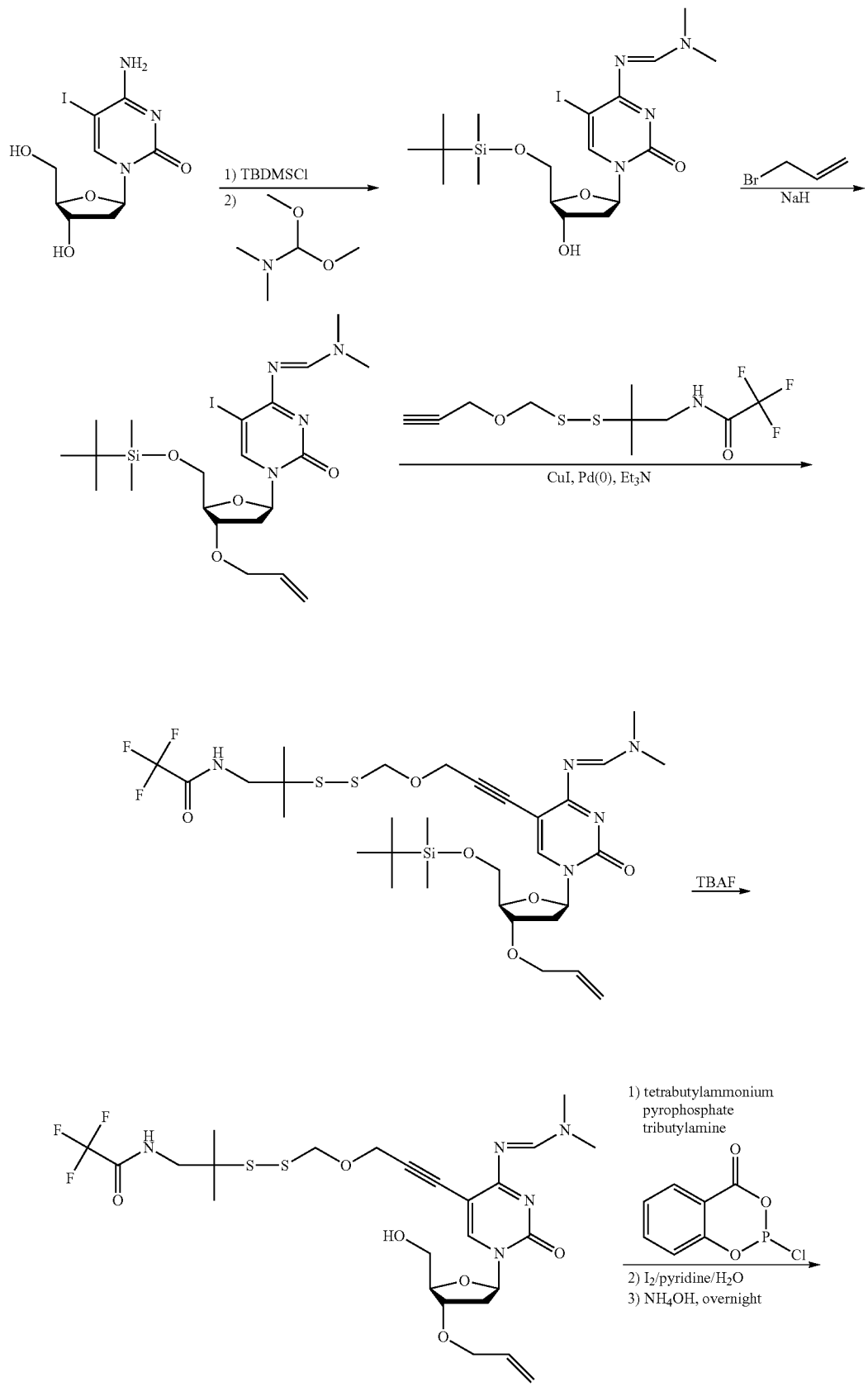

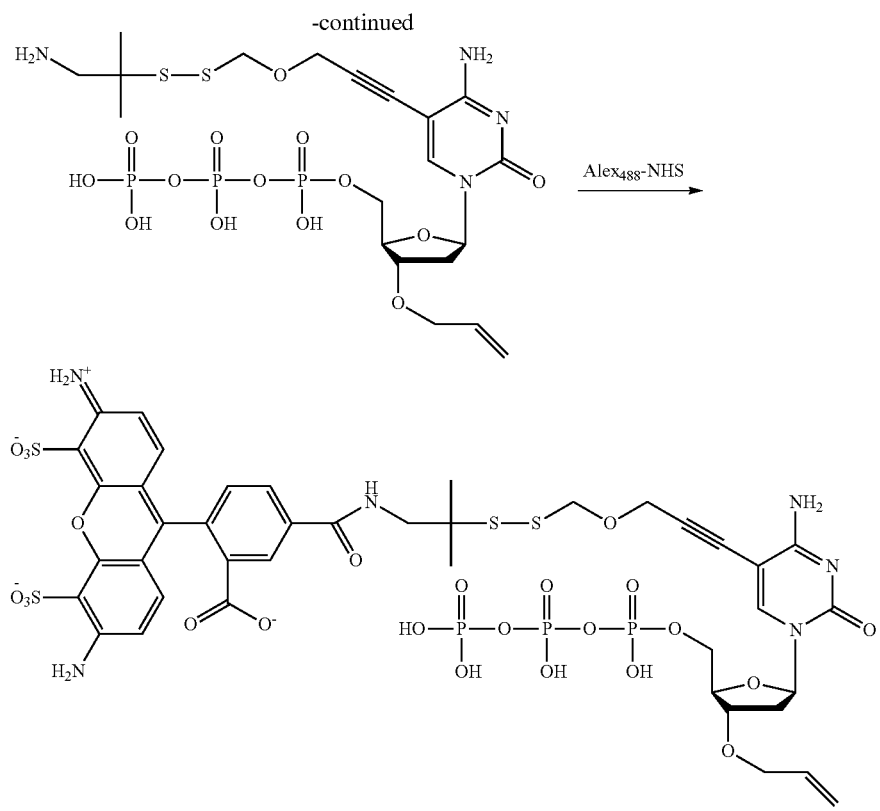
Scheme 47. Synthesis of 3'-O-Allyl-dATP-SS-Rox.
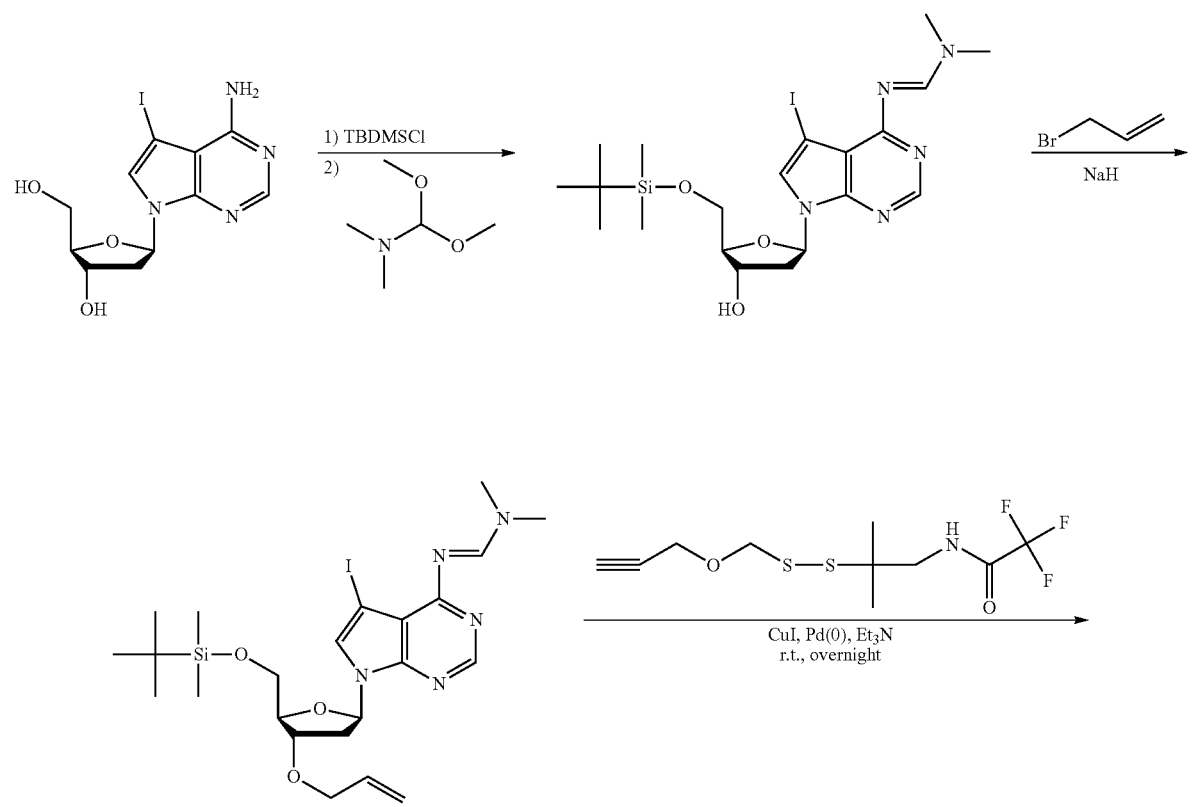

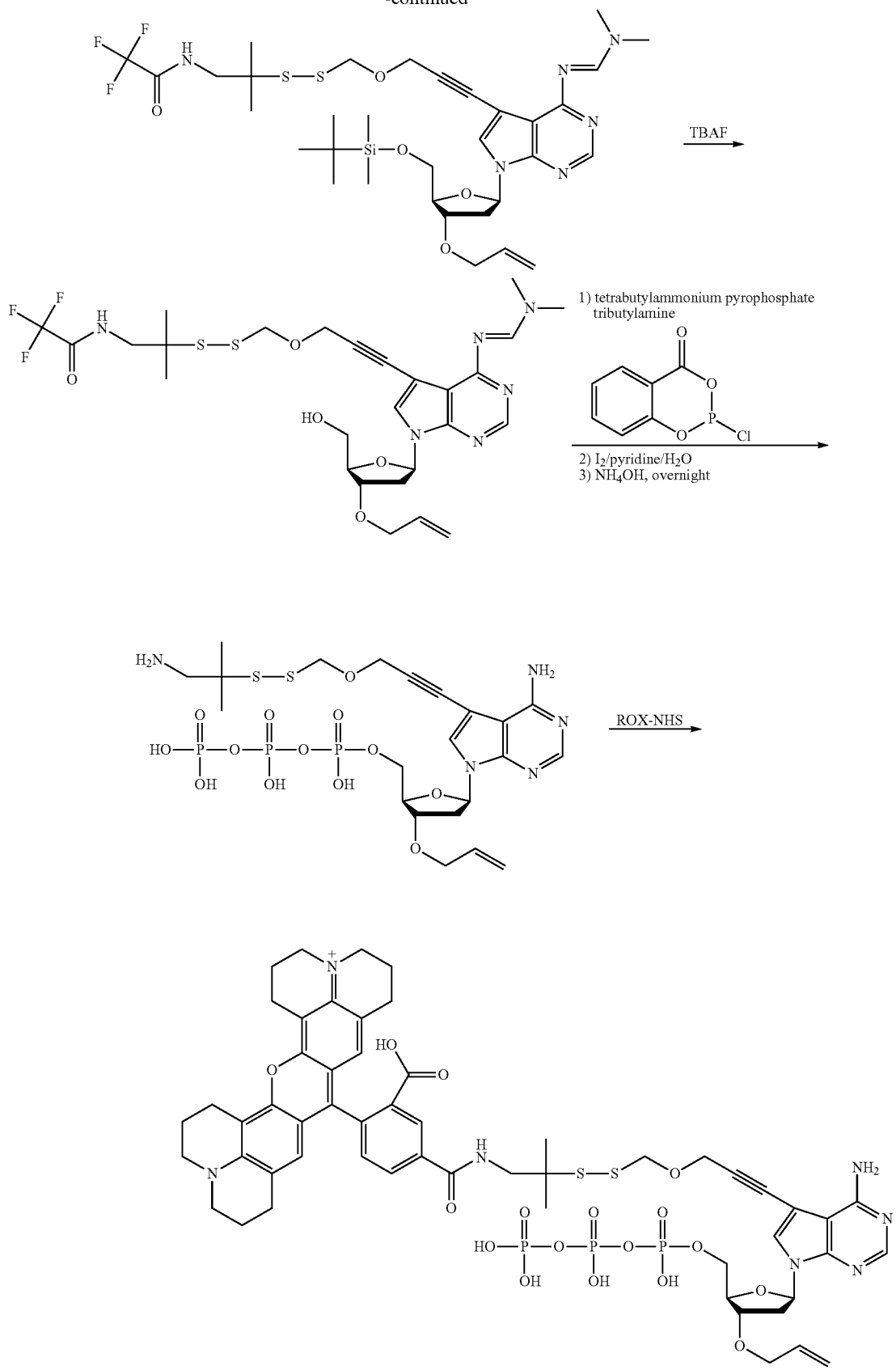

Scheme 48. Synthesis of 3'-O-Allyl-dATP-SS-Cy5.
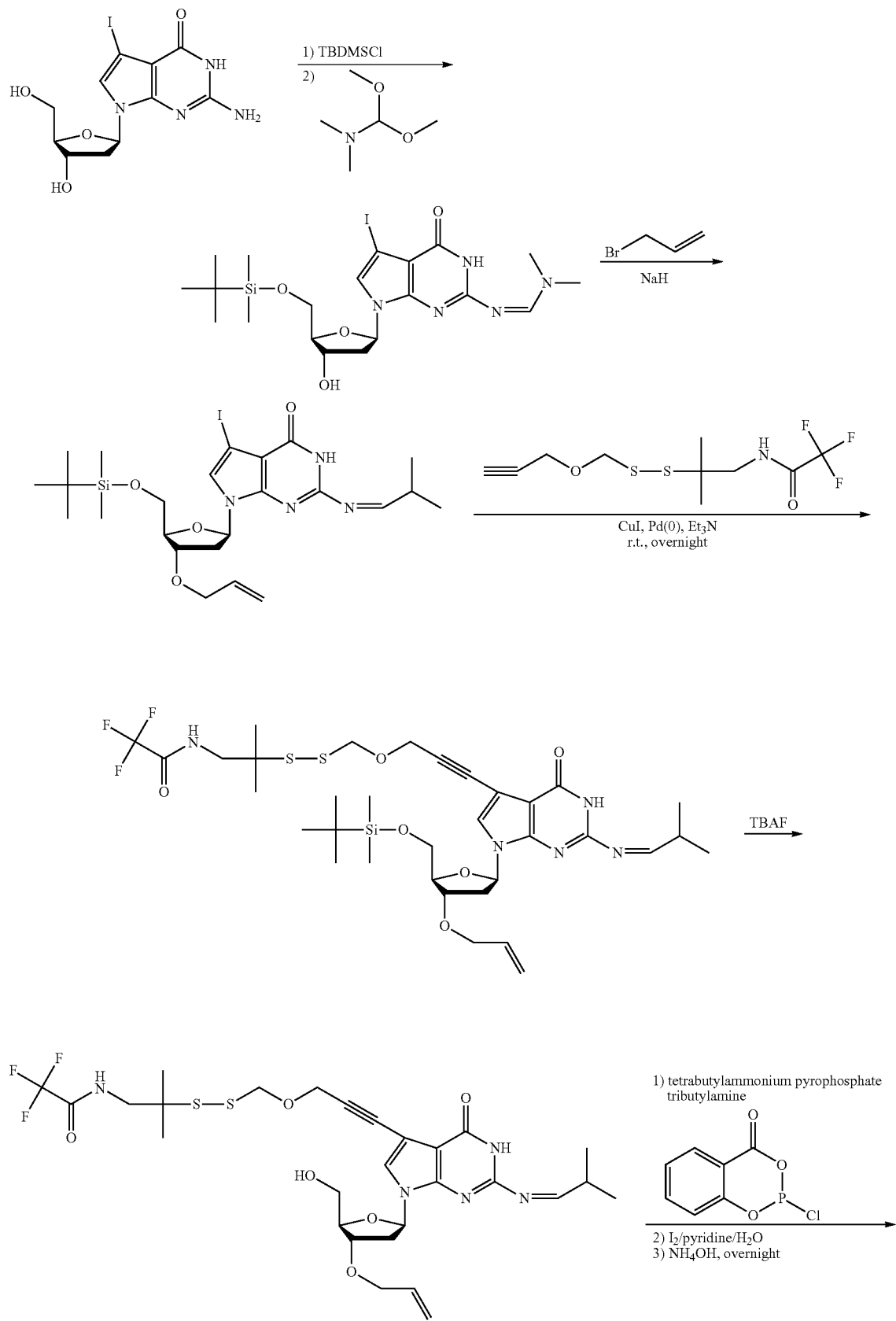

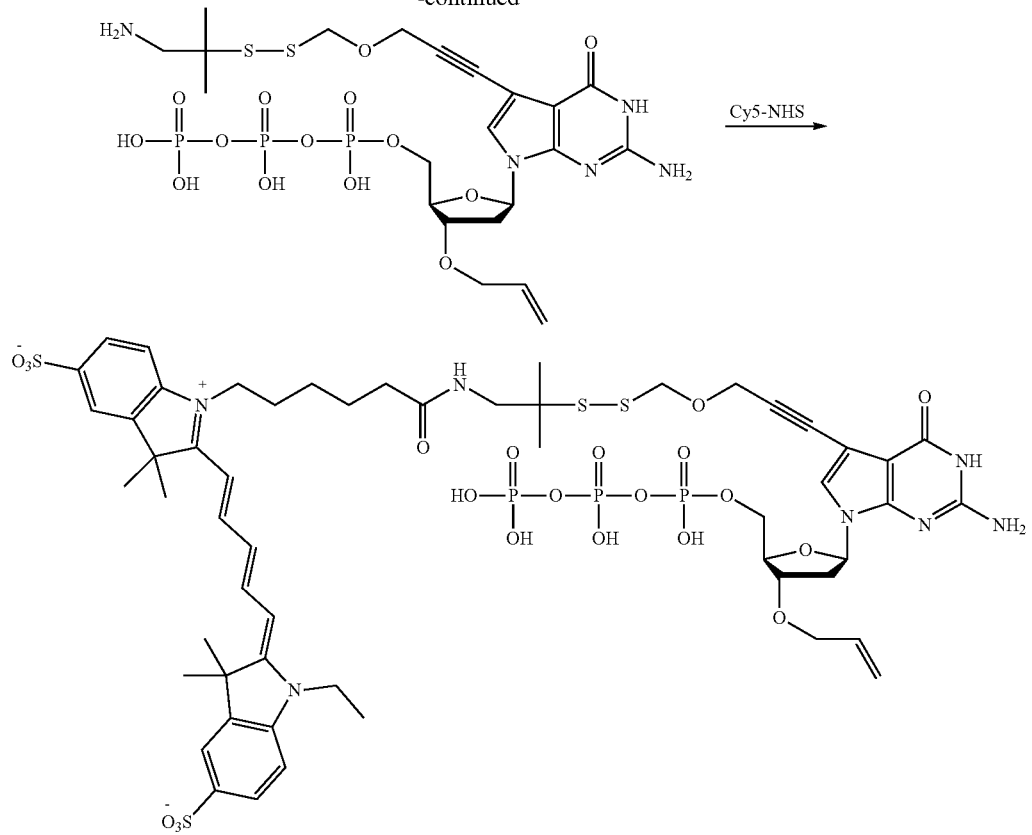
Scheme 49. Synthesis of 3'-O-N$_3$-dUTP-SS-R6G.
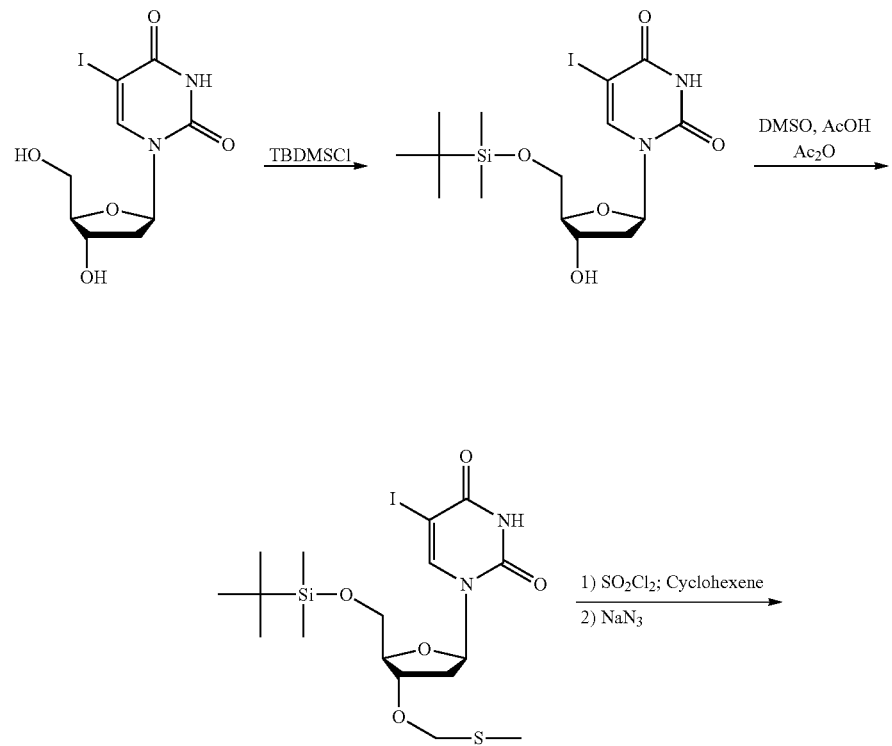

-continued
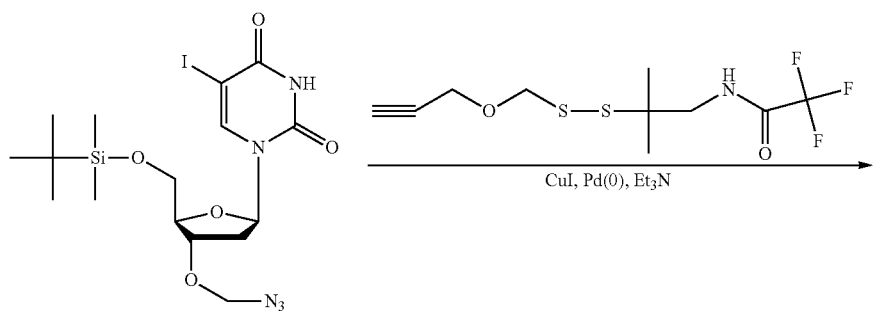
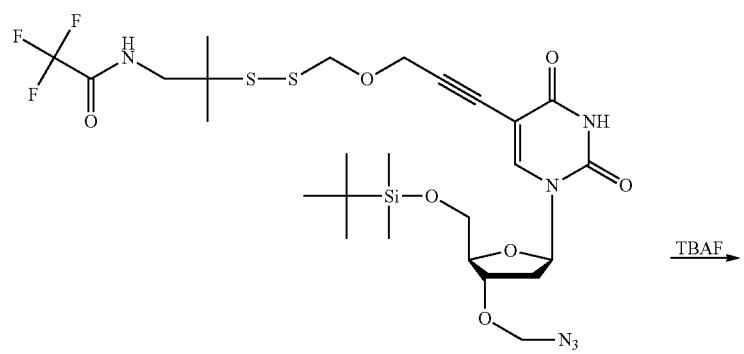
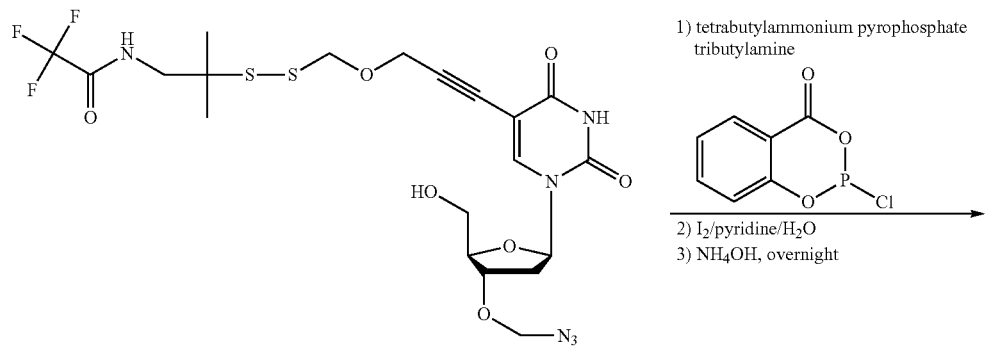
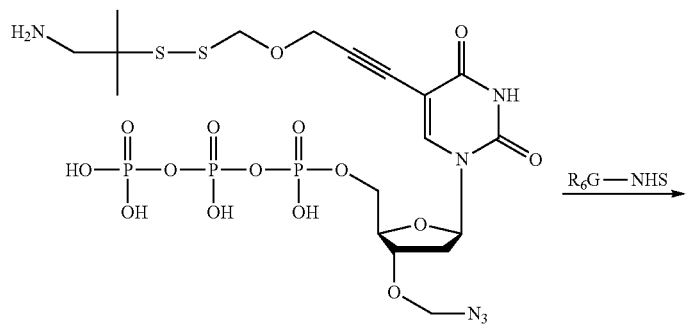

-continued
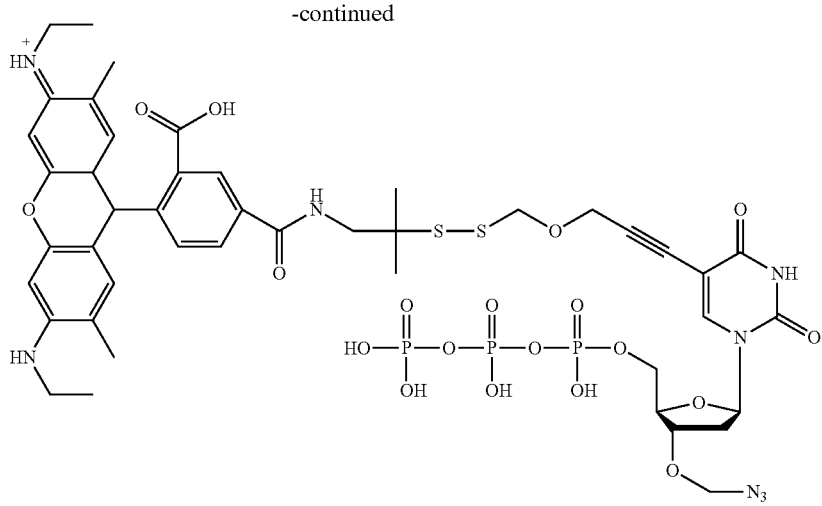
Scheme 50. Synthesis of 3'-O-N₃-dCTP-SS-Alexa488.
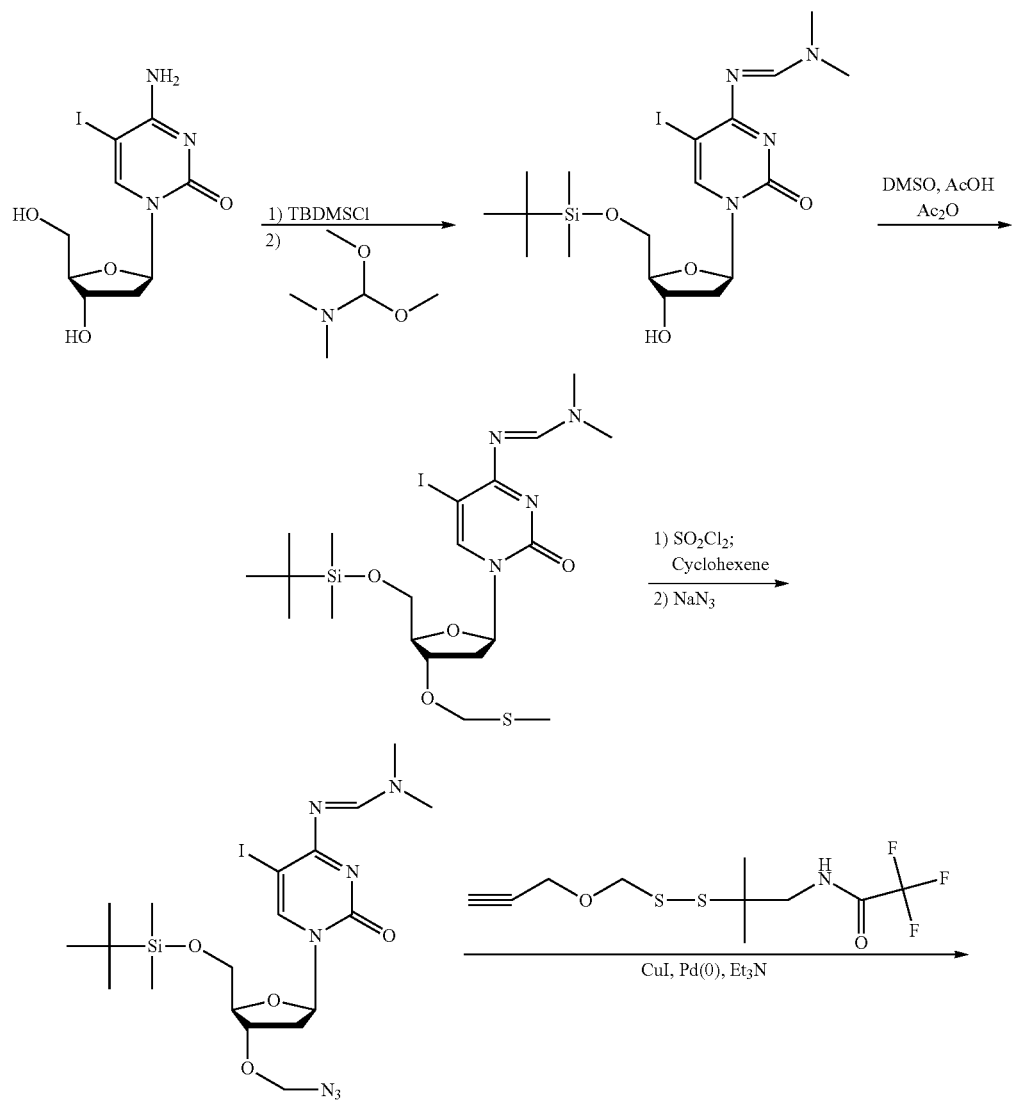

645
-continued
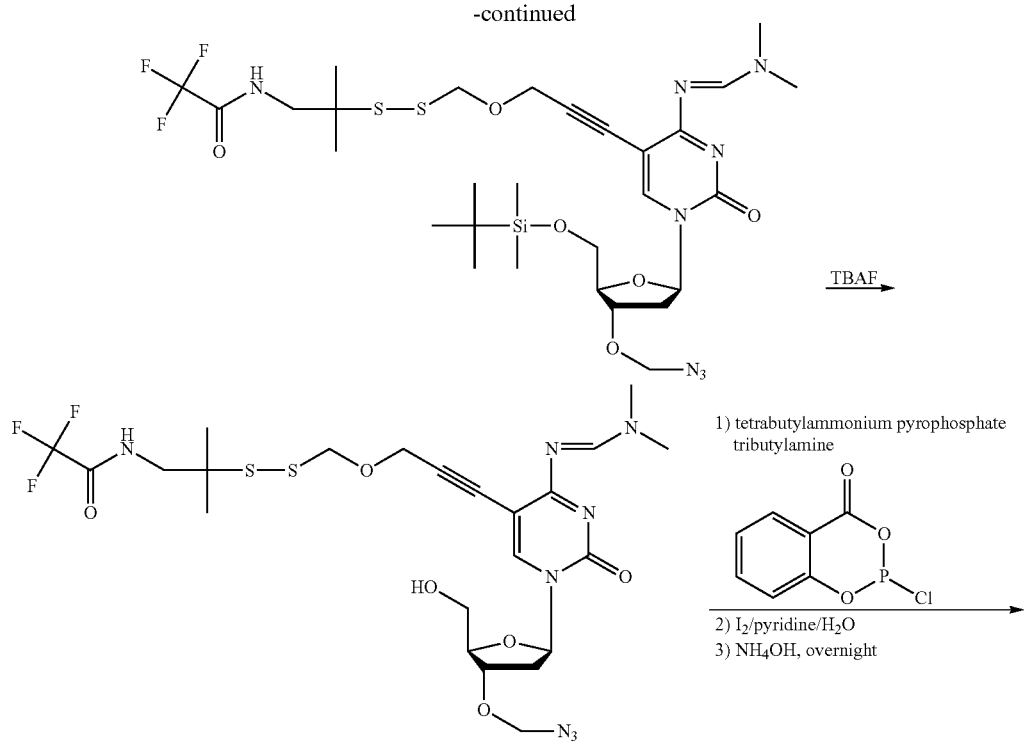
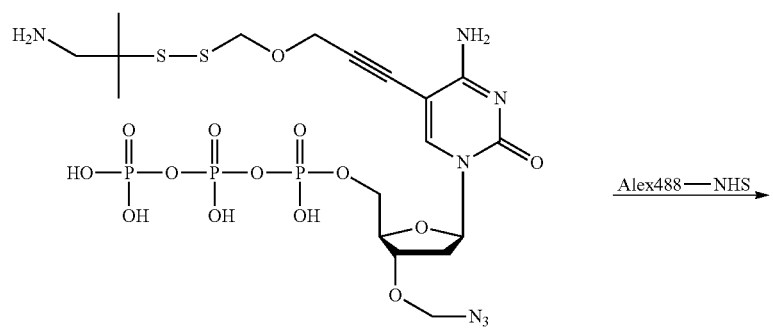
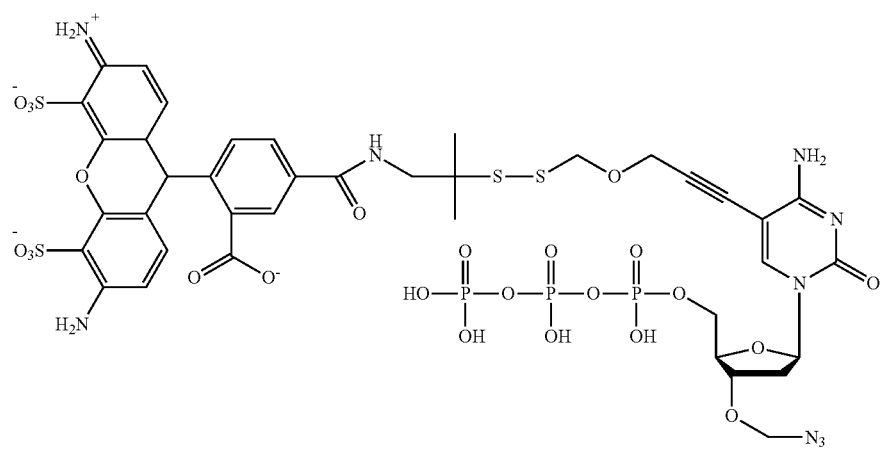
646

Scheme 51. Synthesis of 3'-O-N₃-dATP-SS-Rox.
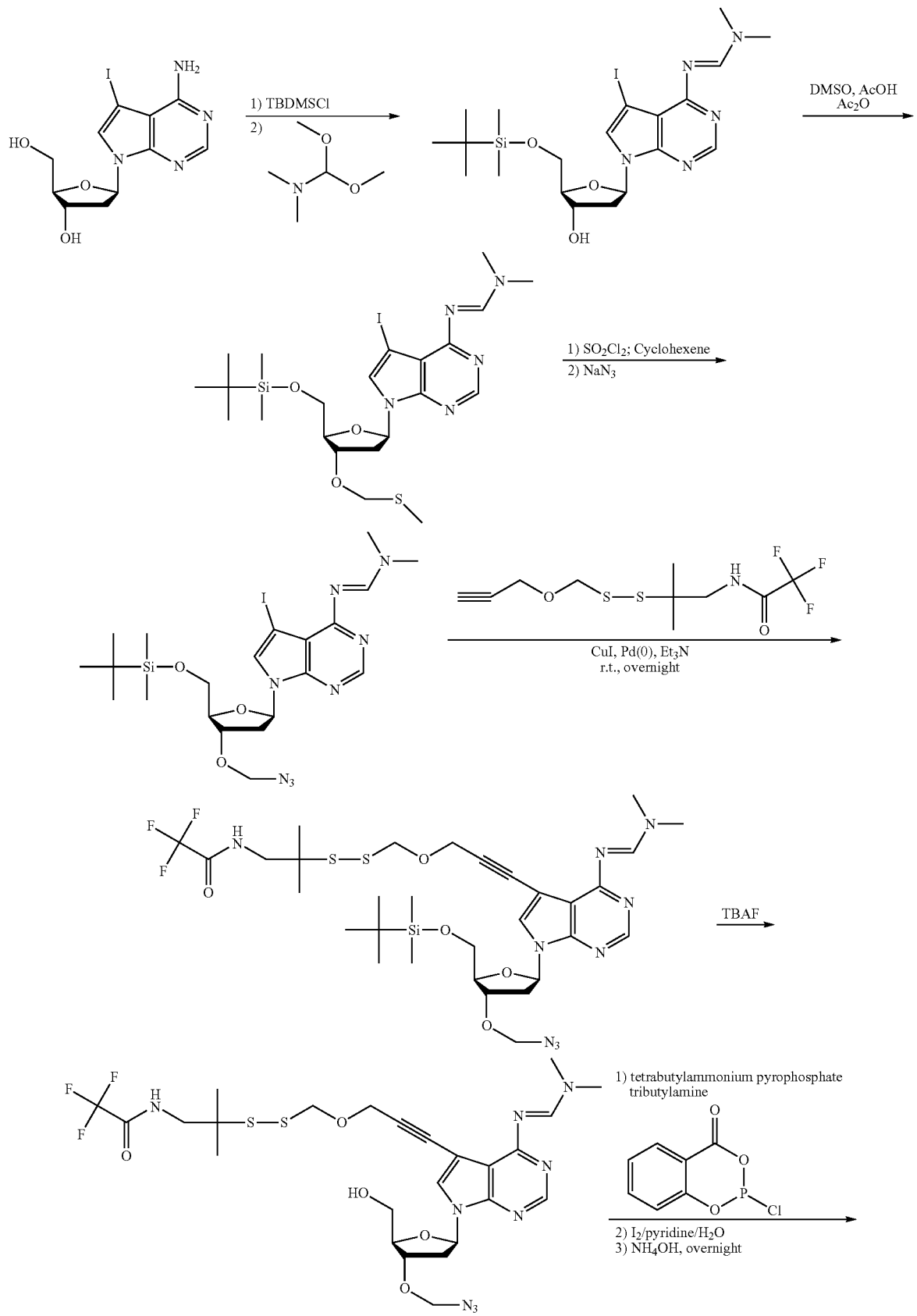

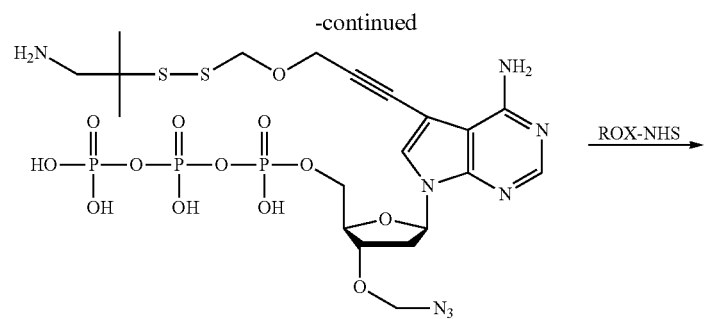
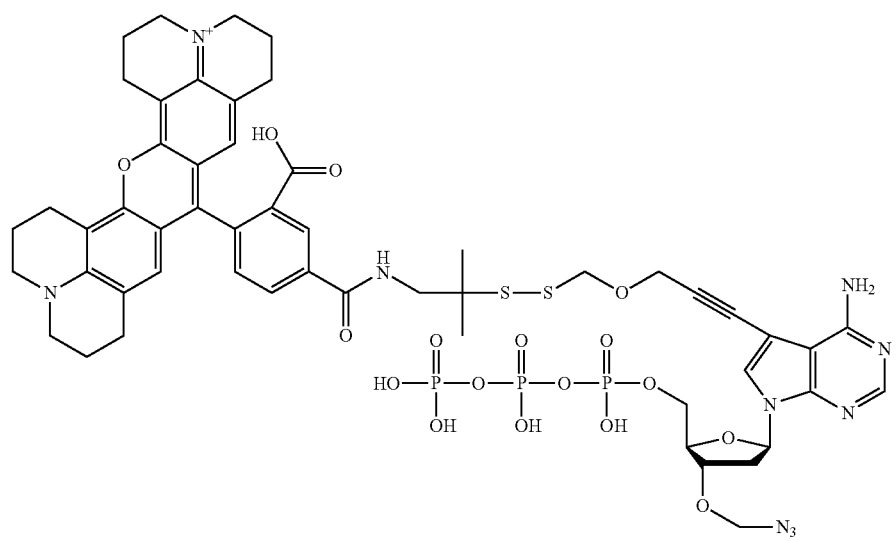
Scheme 52. Synthesis of 3'-O-N₃-dGTP-SS-Cy5.
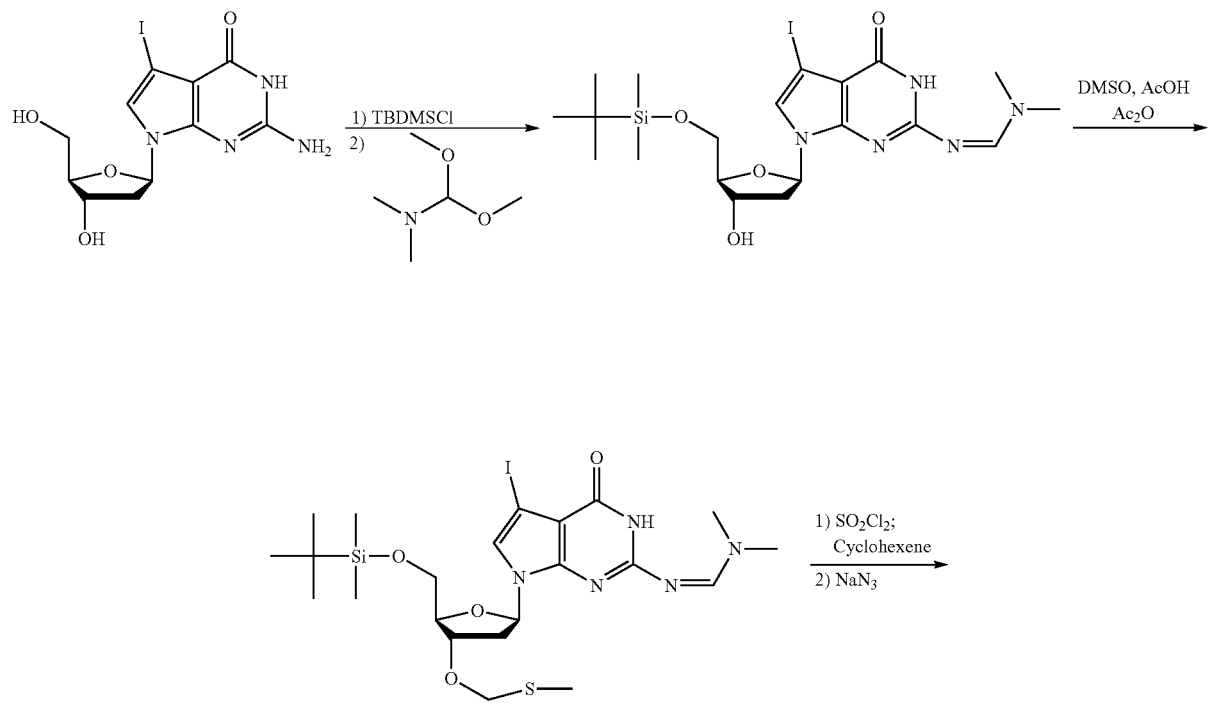

651
652
-continued
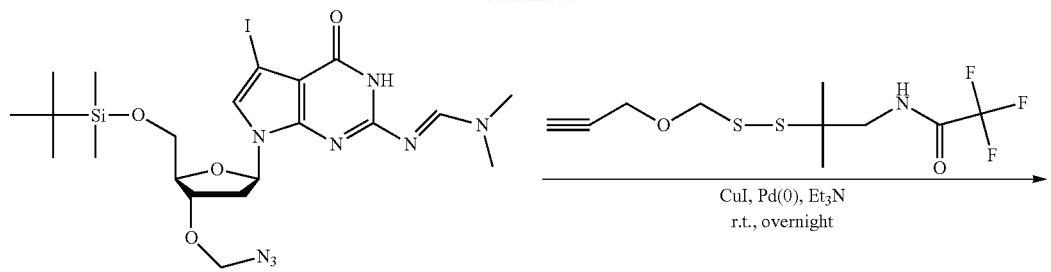
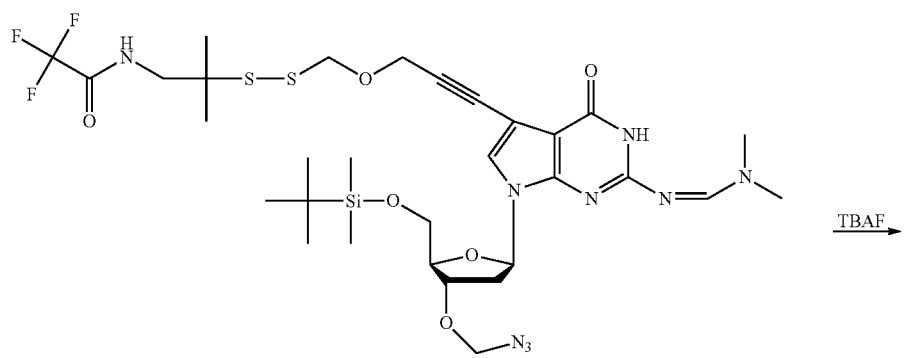
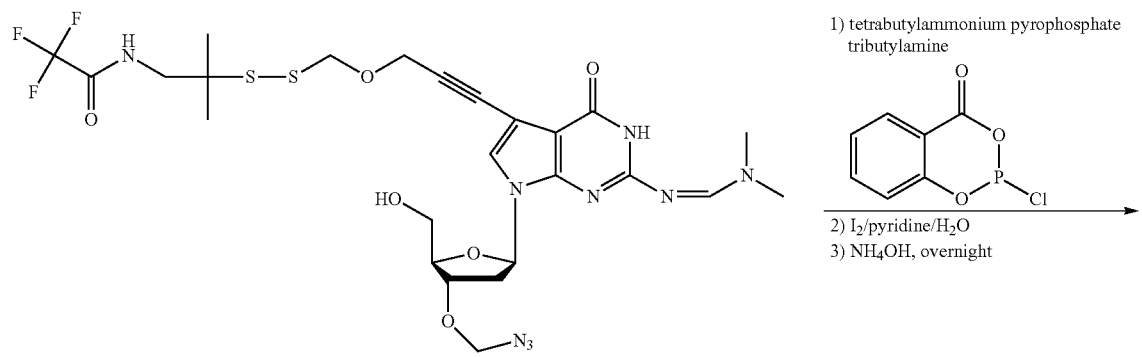
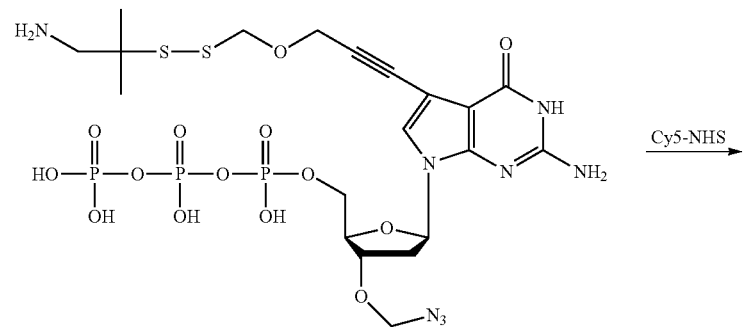

653 654
-continued
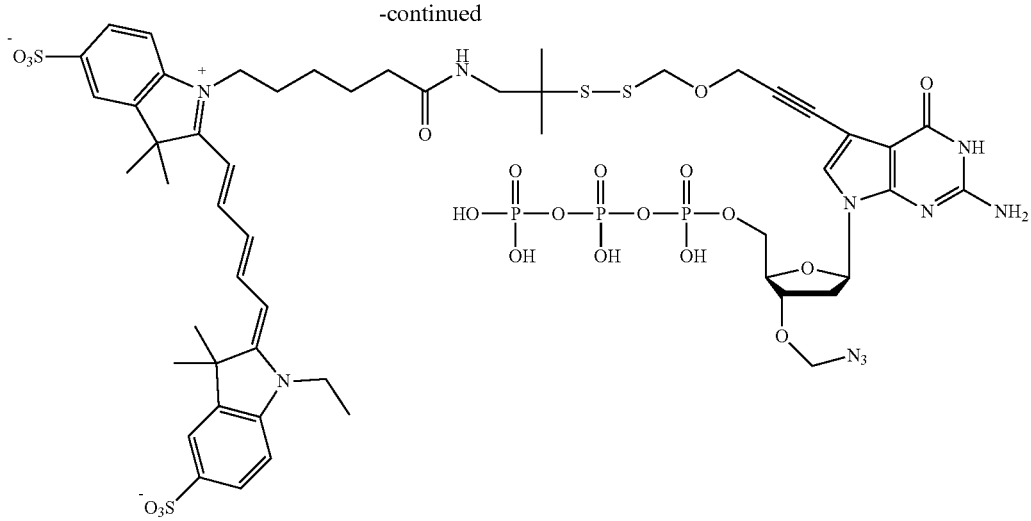
Scheme 53. Synthesis of 3'-O-Nitrobenzyl-dUTP-SS-R6G.
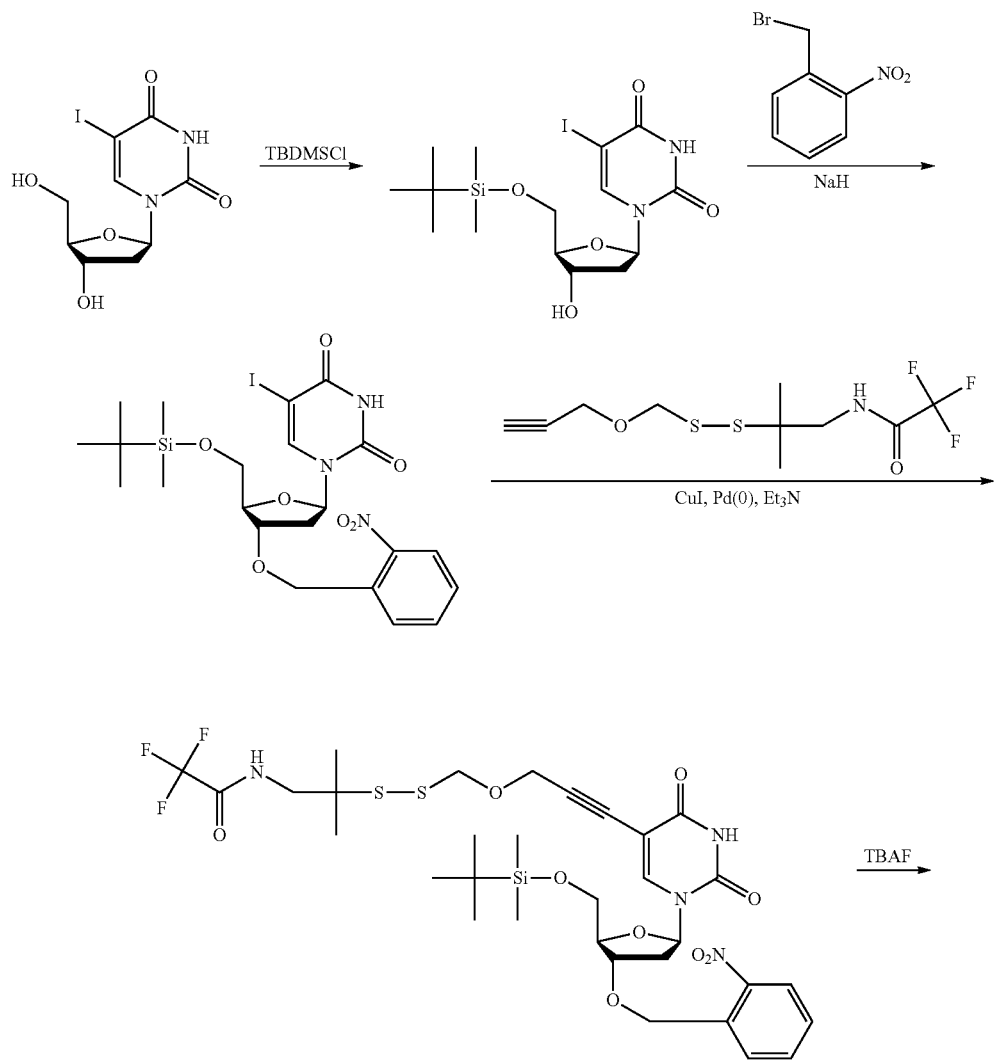

655 656
-continued
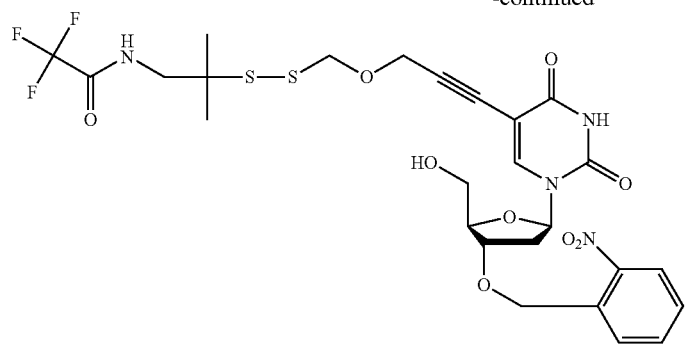
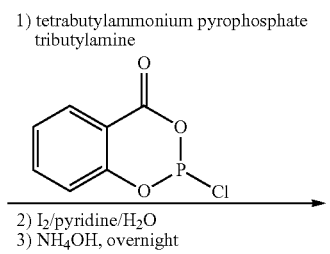
1) tetrabutylammonium pyrophosphate tributylamine
2) I₂/pyridine/H₂O
3) NH₄OH, overnight
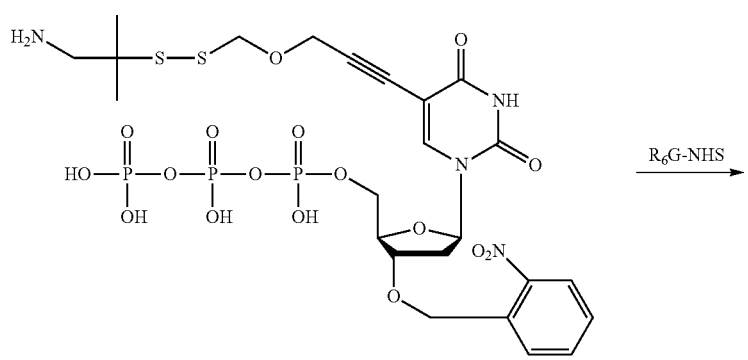
R₆G-NHS →
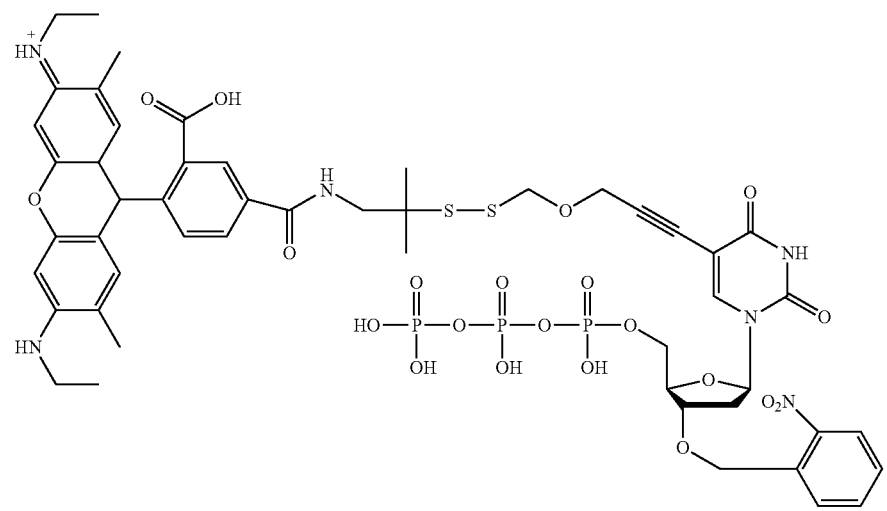
Scheme 54. Synthesis of 3'-O-nitrobenzyl-dCTP-SS-Alexa488.
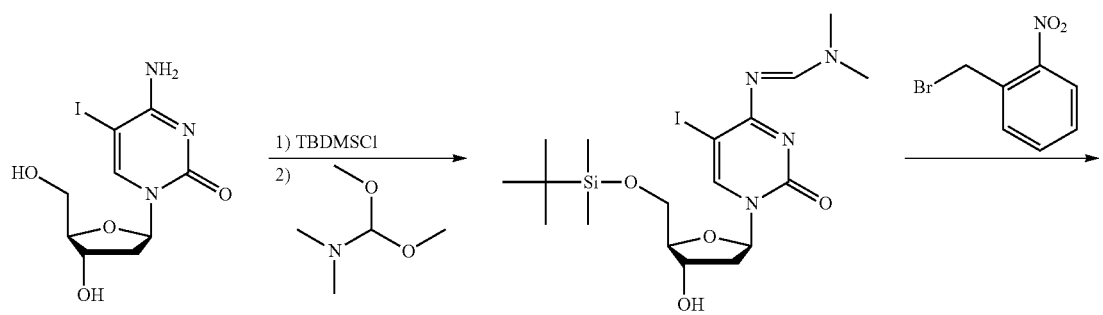

-continued
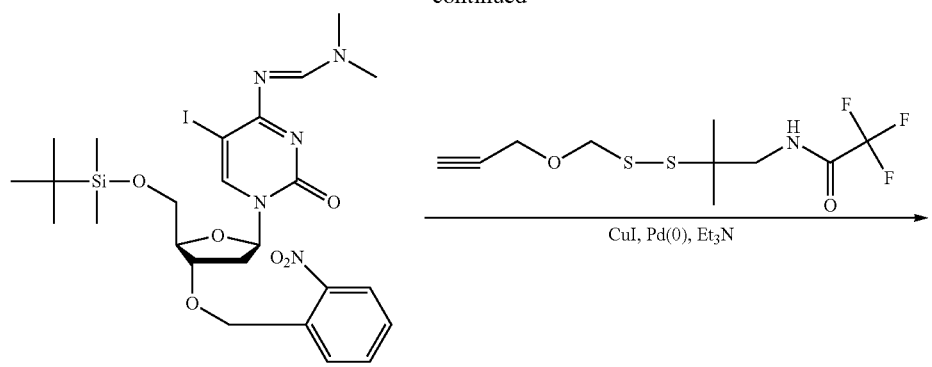
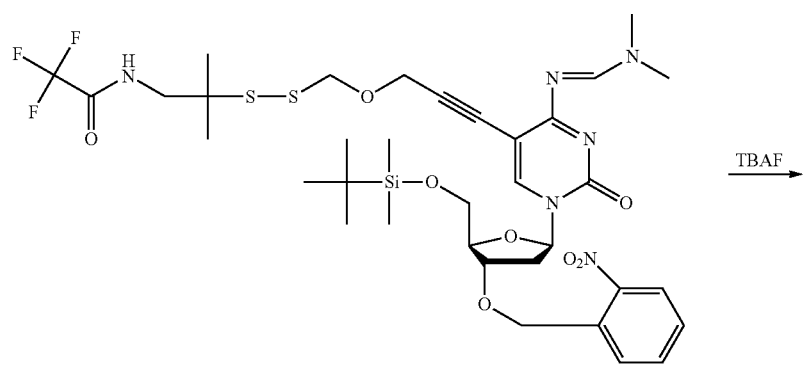
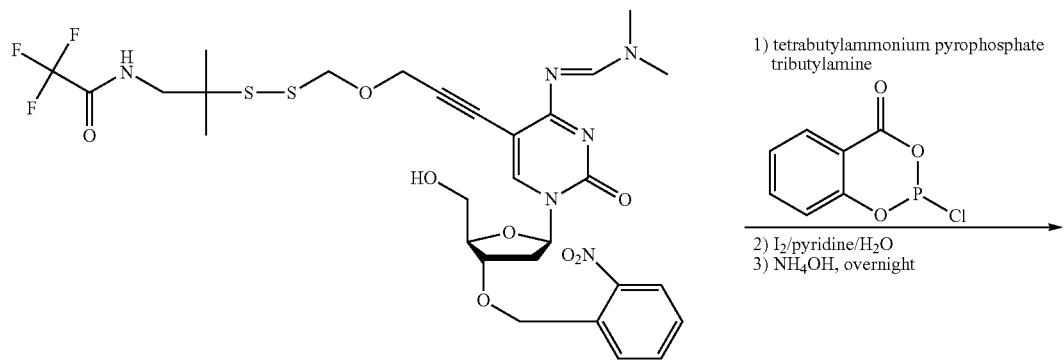
1) tetrabutylammonium pyrophosphate tributylamine
2) I₂/pyridine/H₂O
3) NH₄OH, overnight
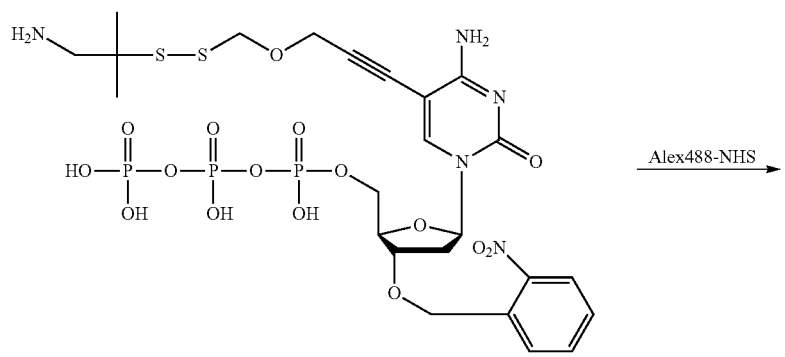
Alex488-NHS

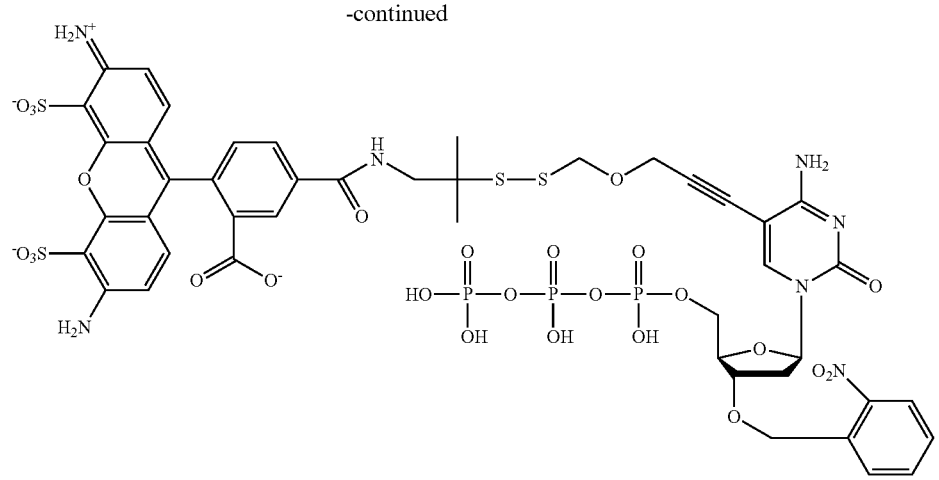
Scheme 55. Synthesis of 3'-O-nitrobenzyl-dATP-SS-Rox.
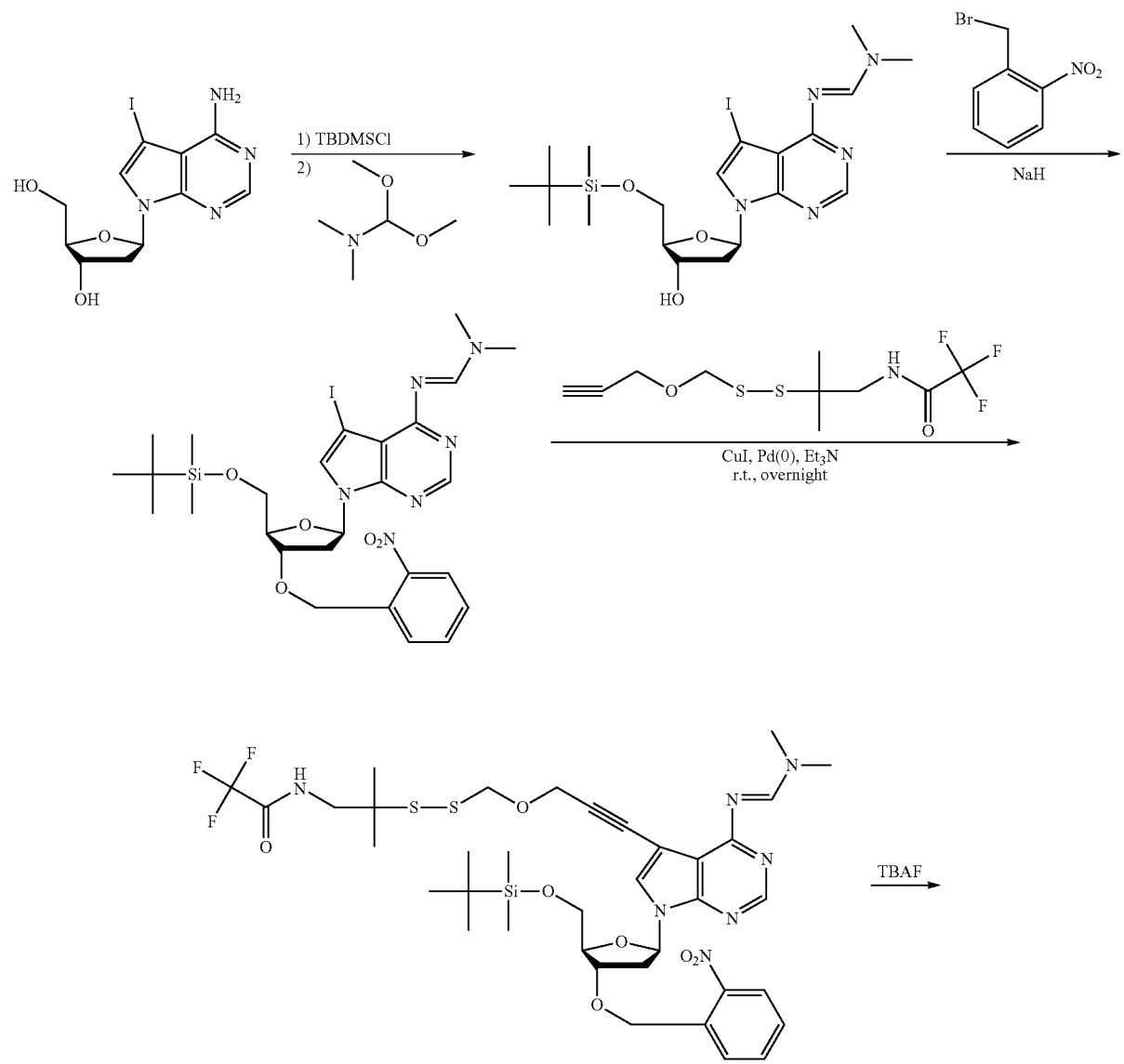

661
662
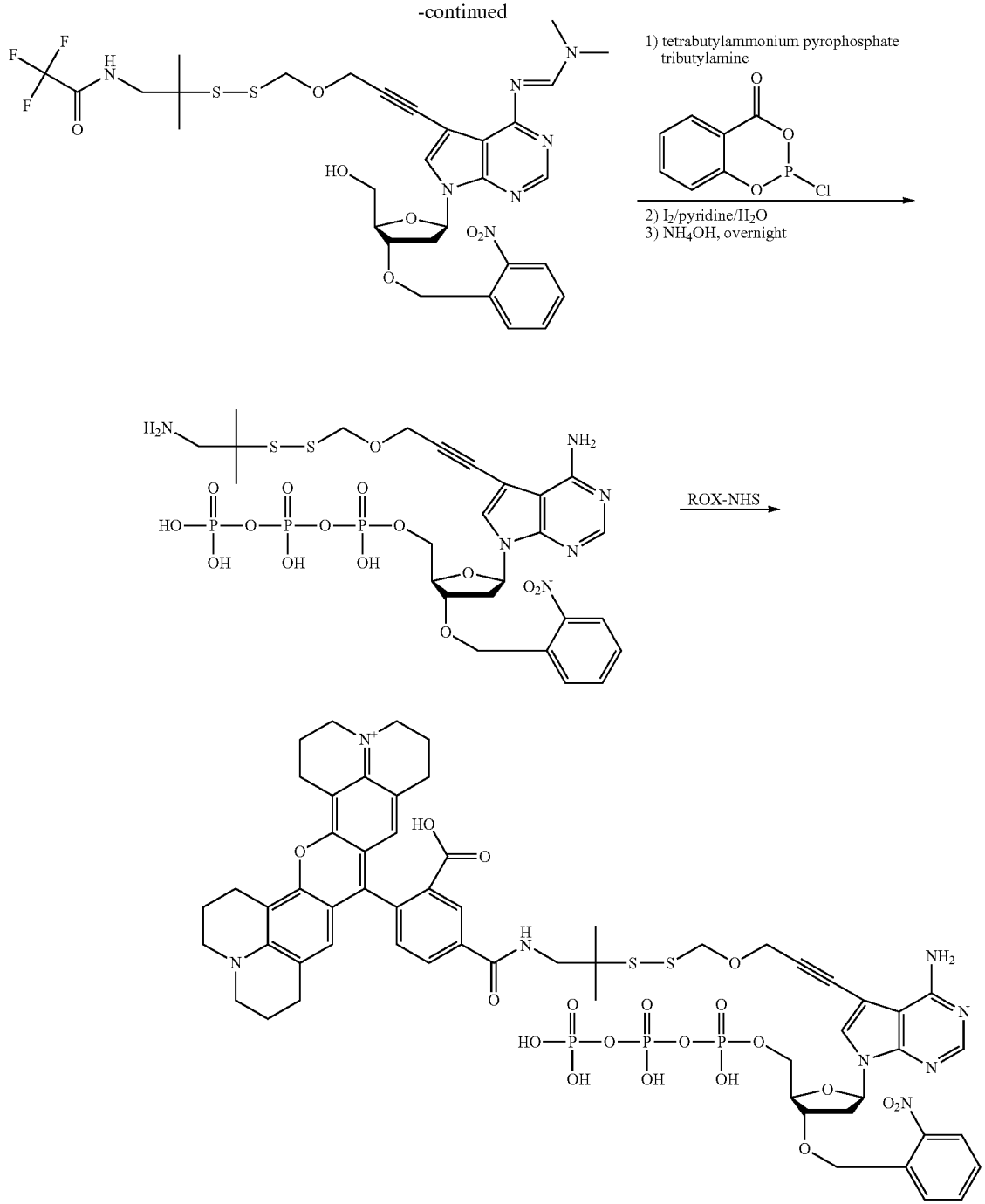
Scheme 56. Synthesis of 3'-O-nitrobenzyl-dGTP-SS-Cy5.
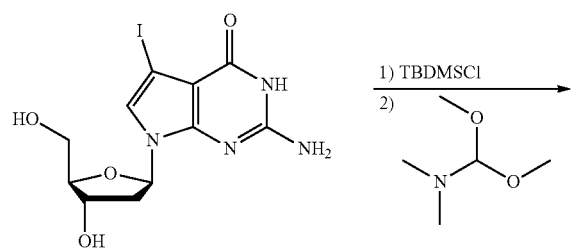

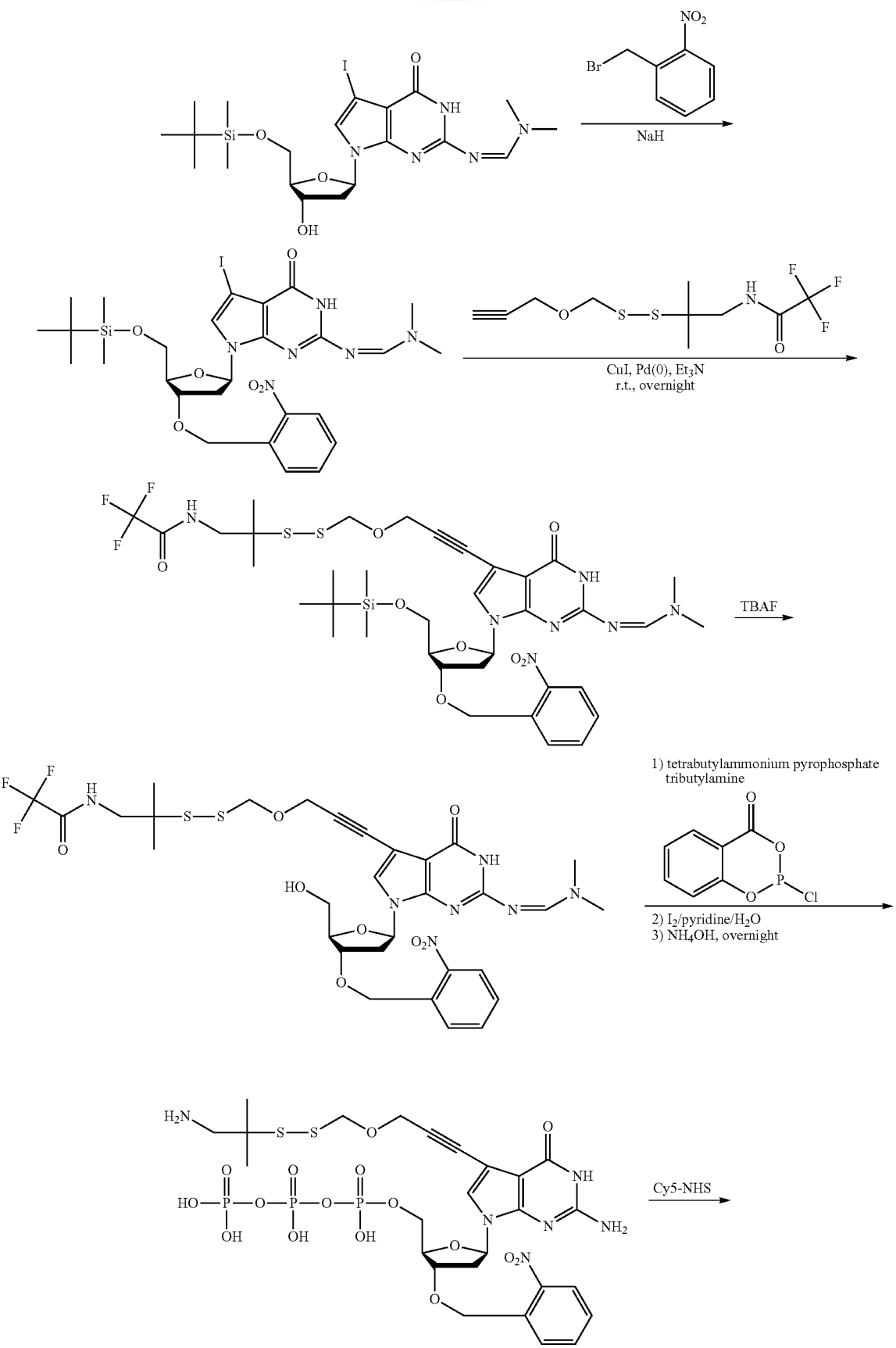

665
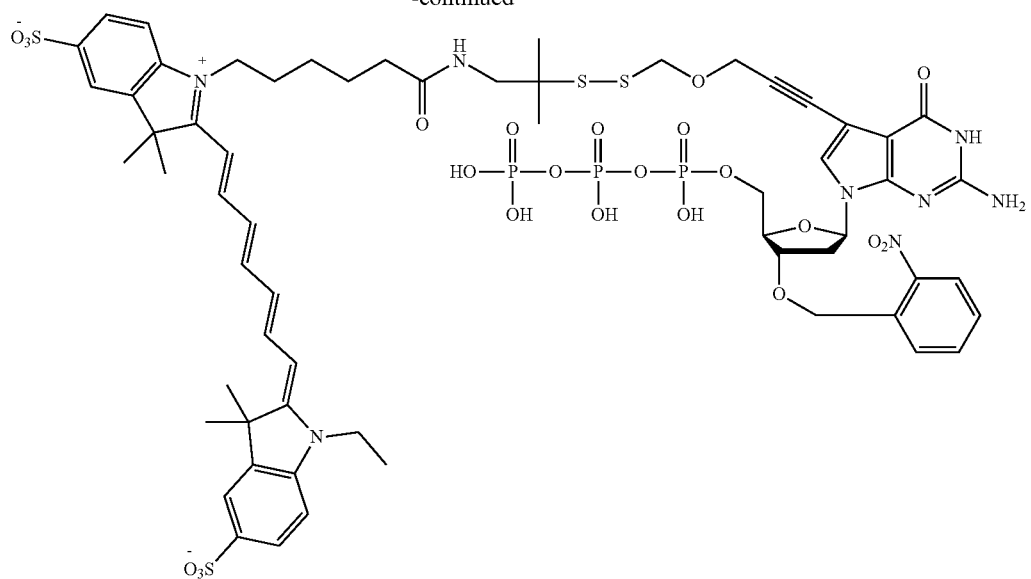
-continued
666
Scheme 57. Synthesis of 3'-O-Mom-dUTP-SS-R6G.
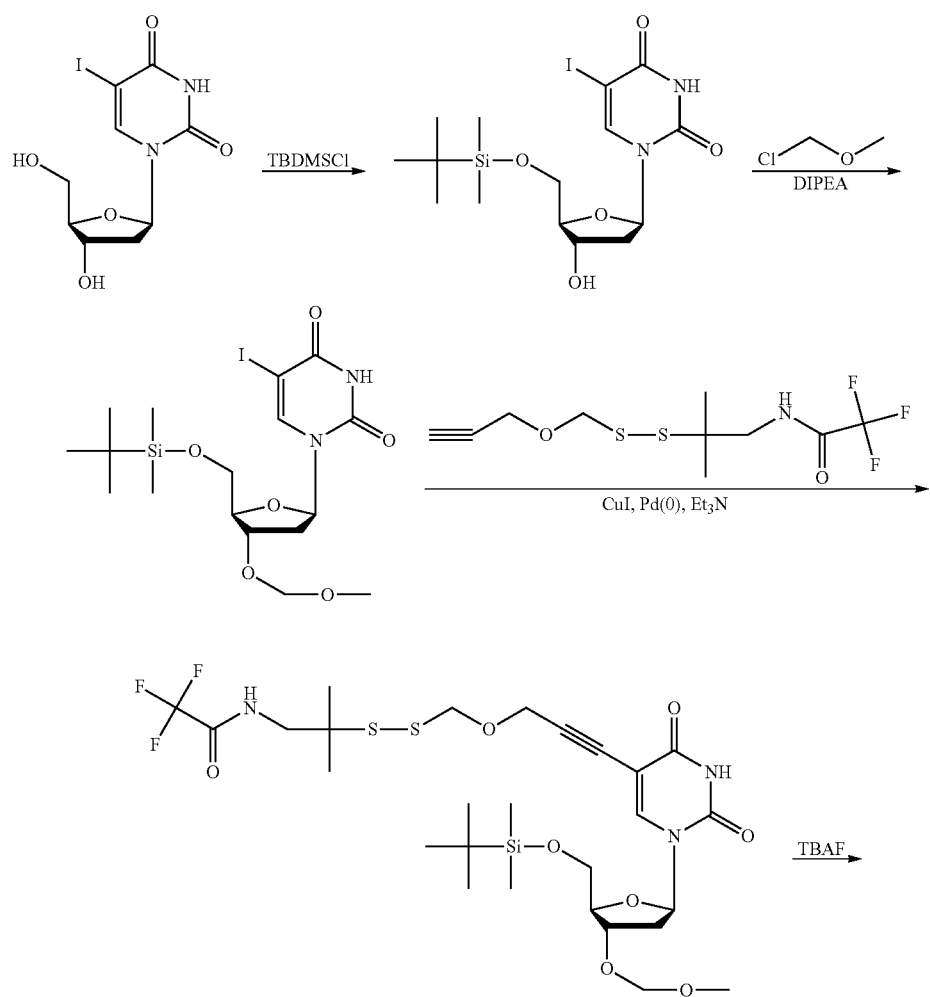

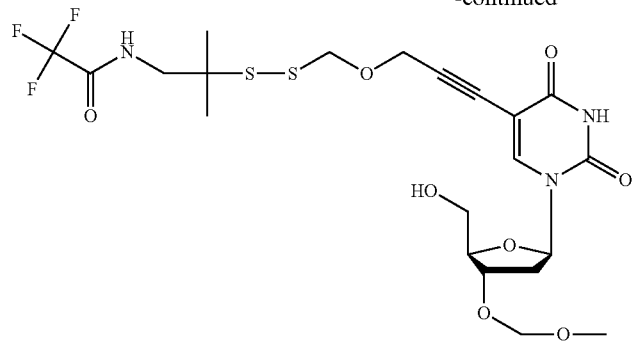
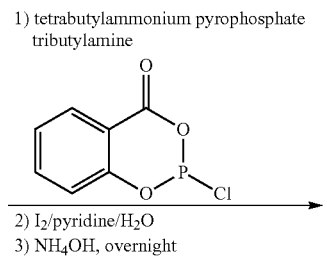
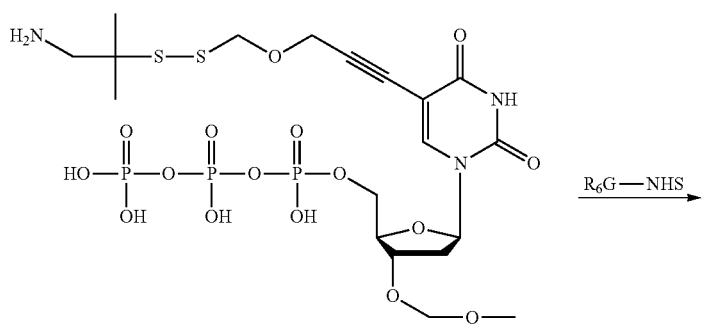
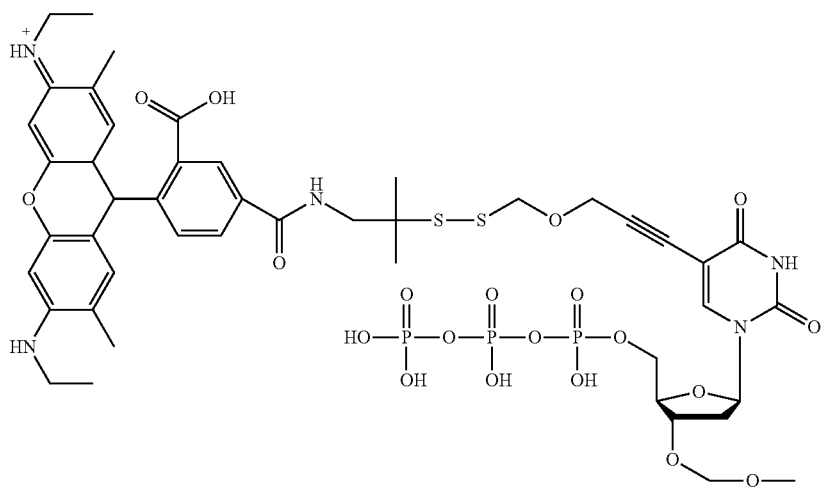
Scheme 58. Synthesis of 3'-O-Mom-dCTP-SS-Alexa488.
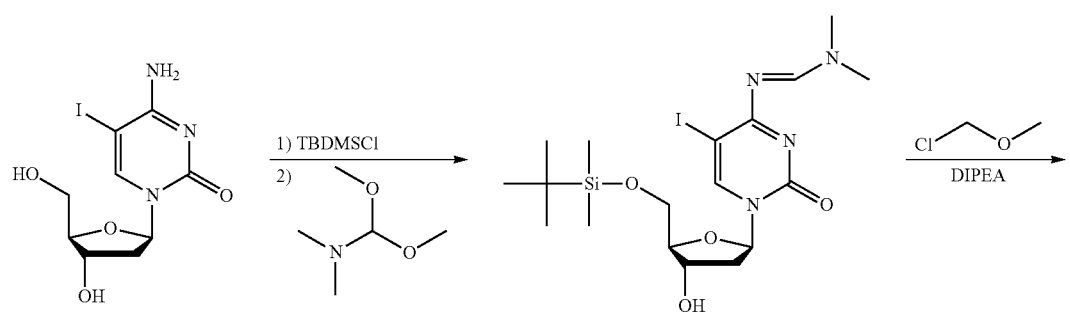

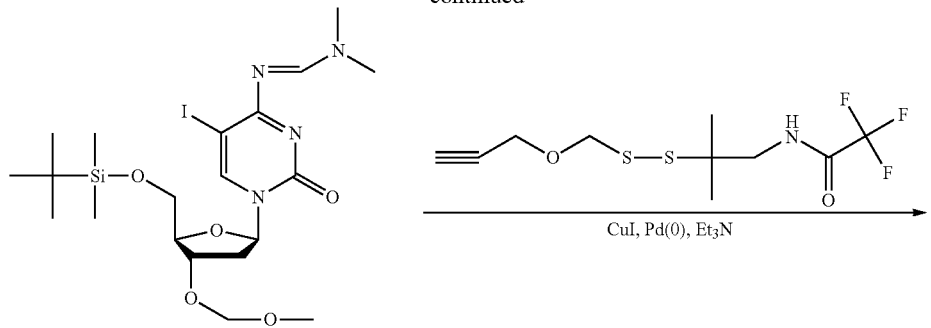
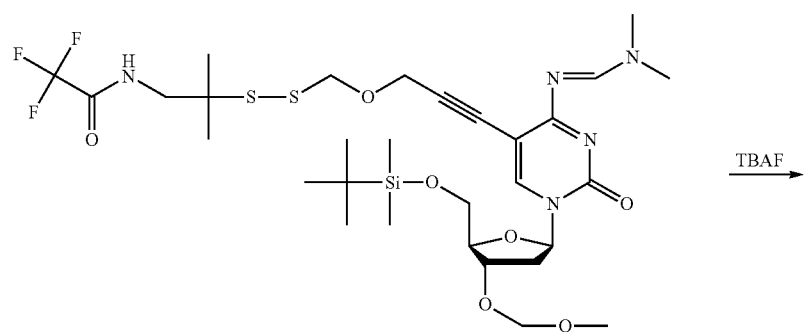
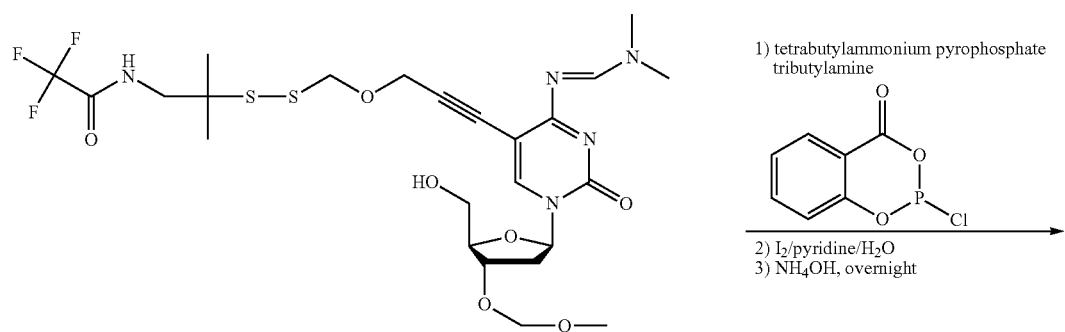
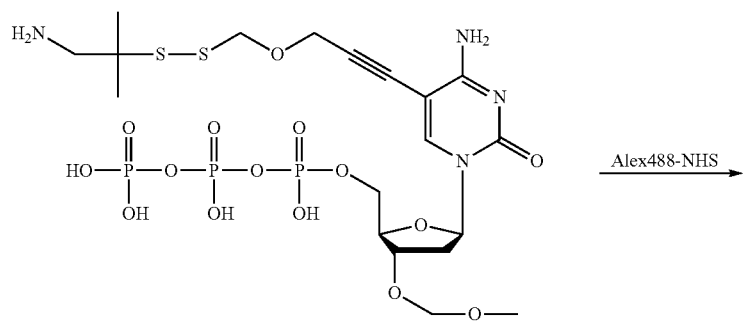

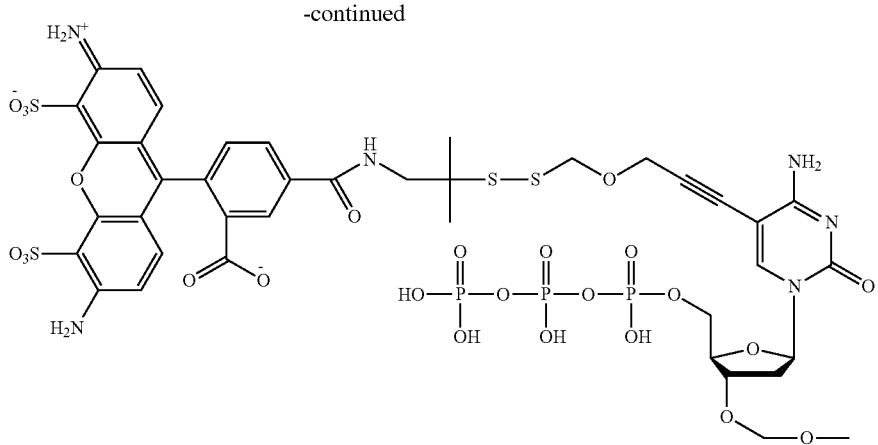
Scheme 59. Synthesis of 3'-O-Mom-dUTP-SS-Rox.
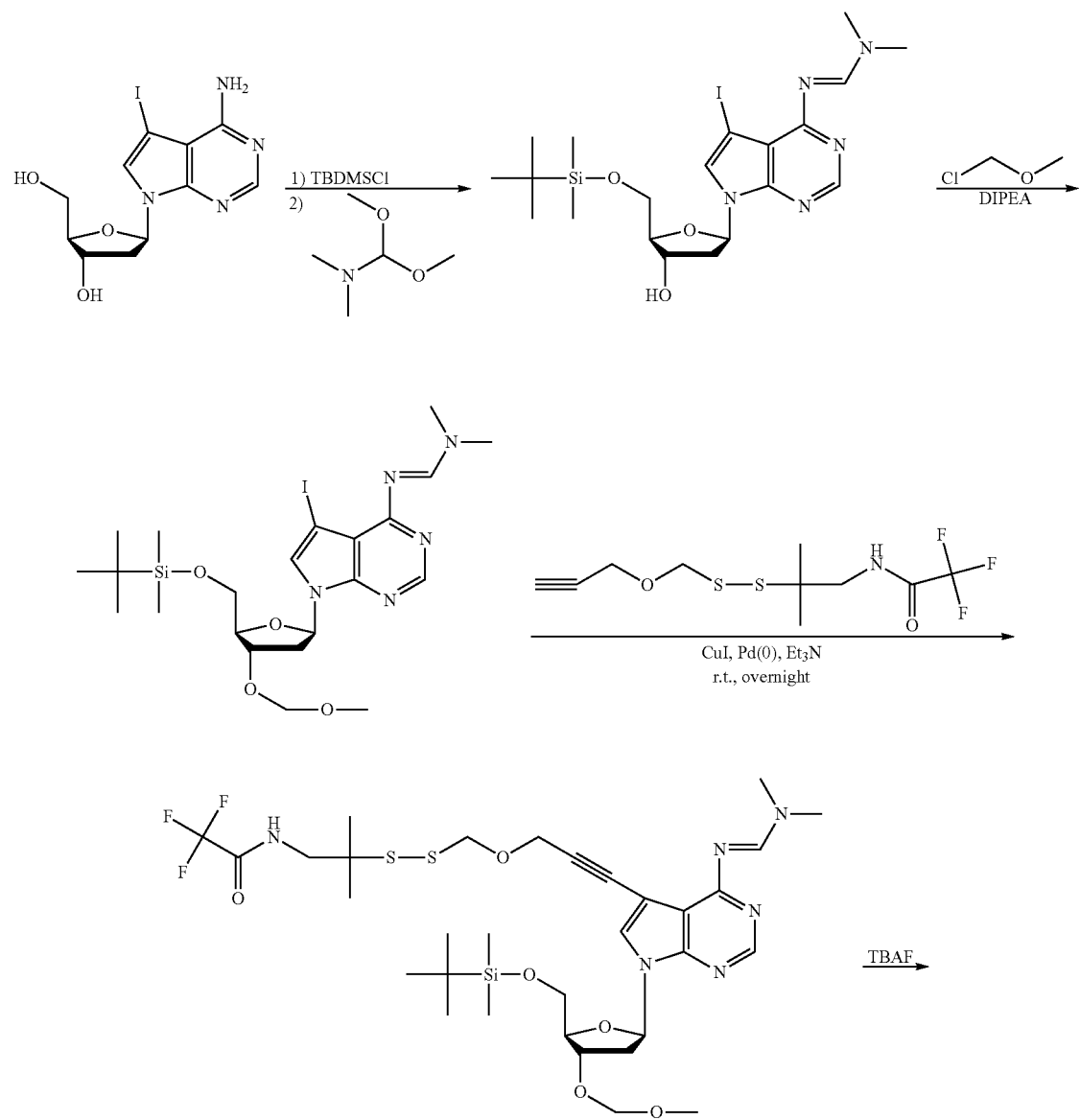

673
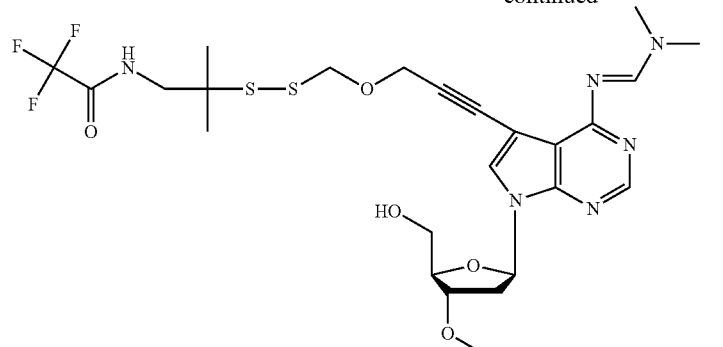
-continued
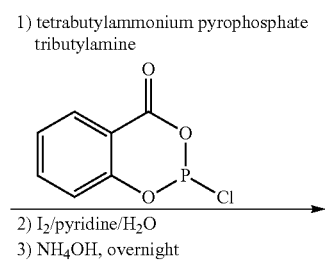
1) tetrabutylammonium pyrophosphate tributylamine
2) I₂/pyridine/H₂O
3) NH₄OH, overnight
674
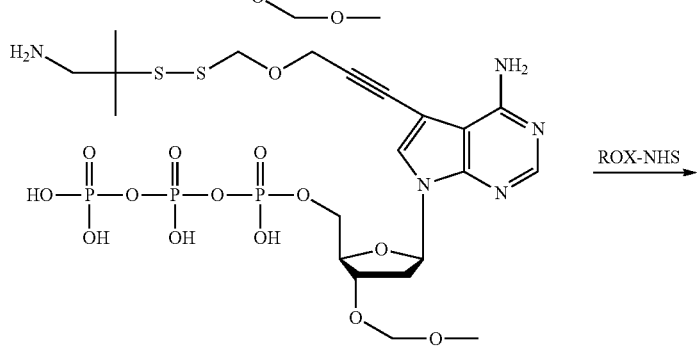
ROX-NHS →
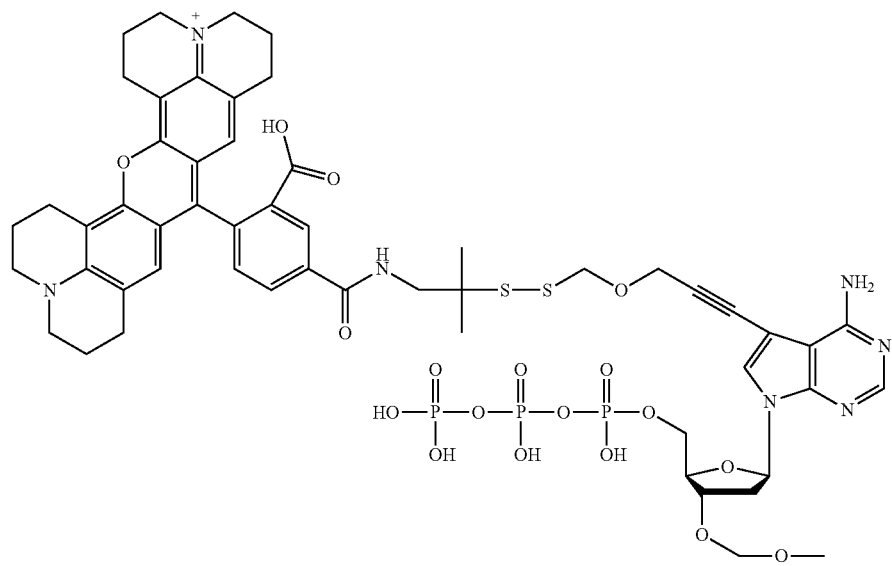
Scheme 60. Synthesis of 3'-O-Mom-dGTP-SS-Cy5.
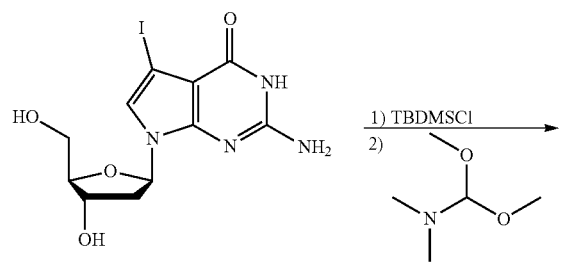
1) TBDMSCl
2)

-continued
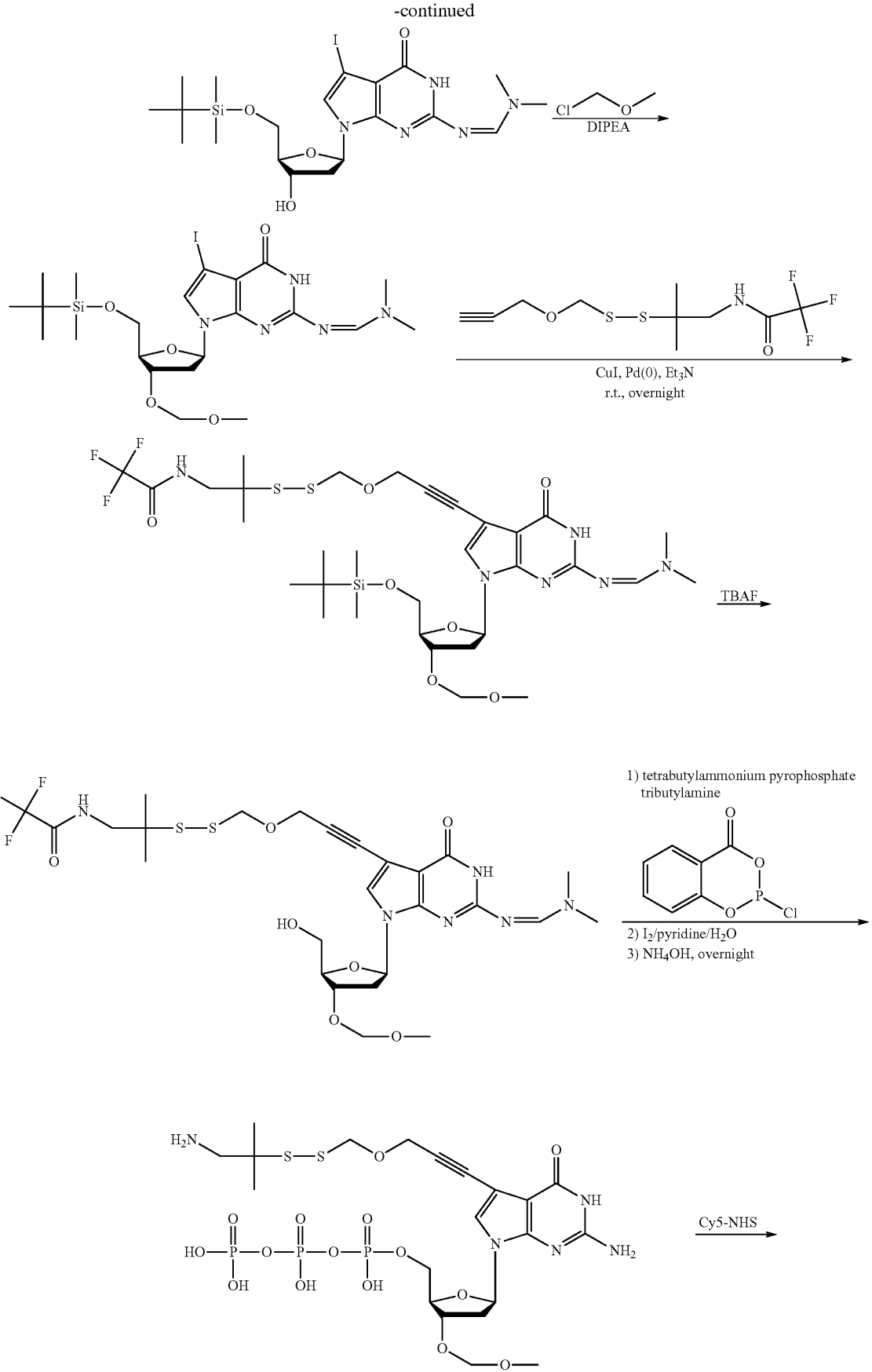

677
678
-continued
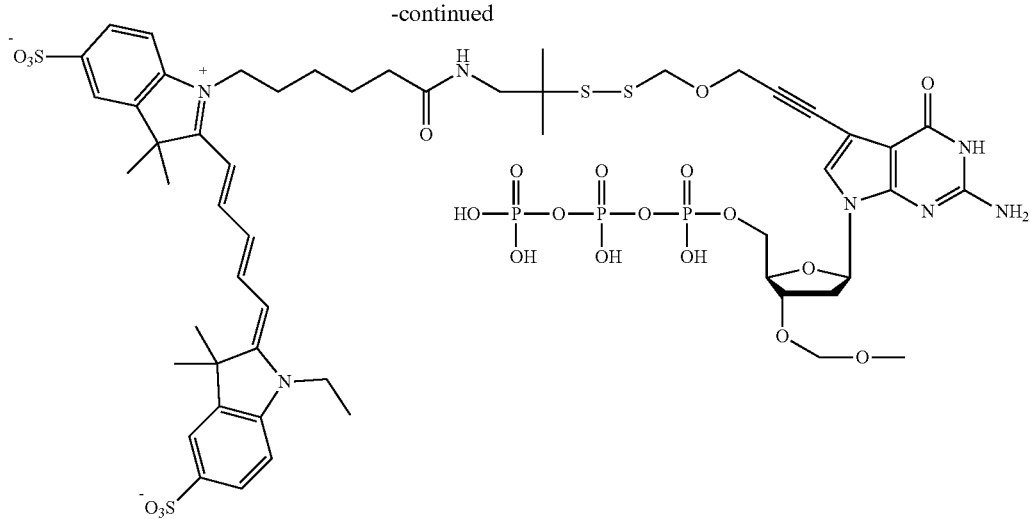
Scheme 61. Synthesis of 3'-O-Amino-dUTP-SS-R6G.
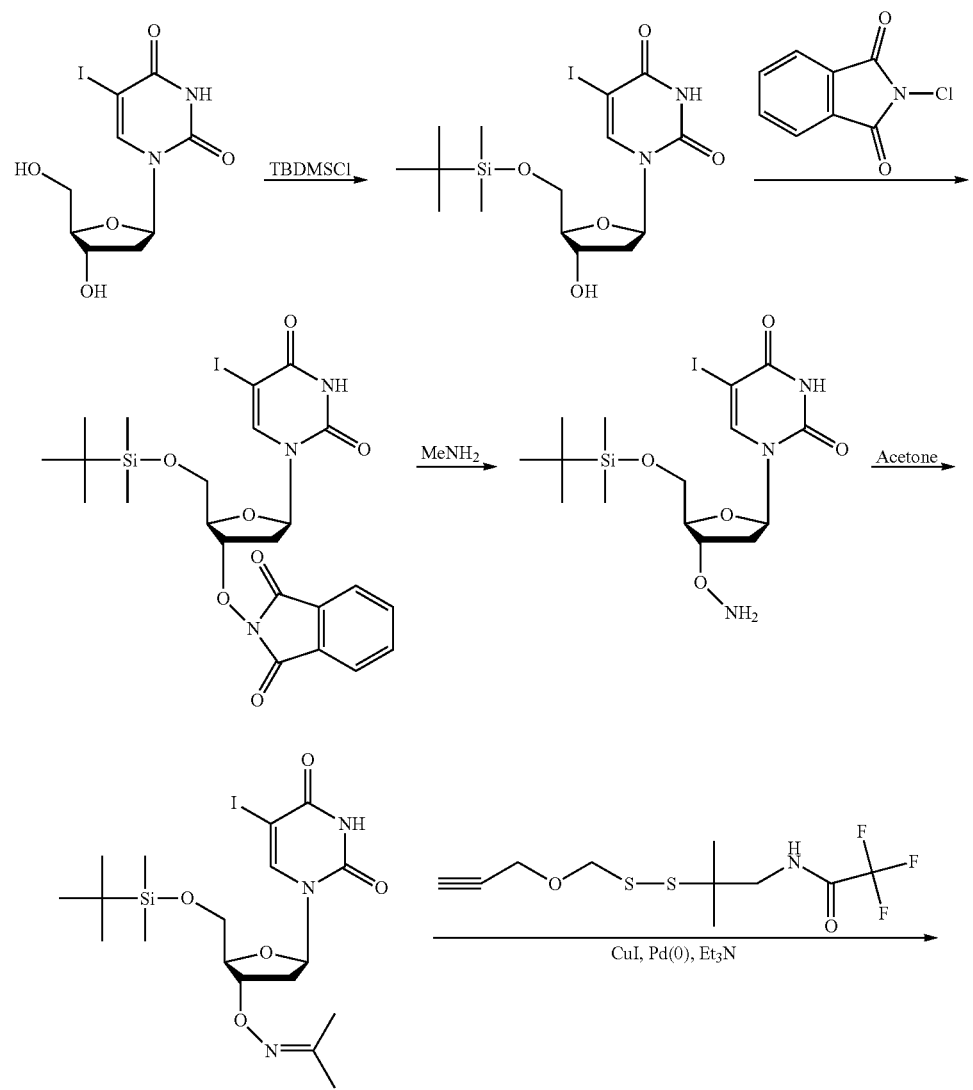

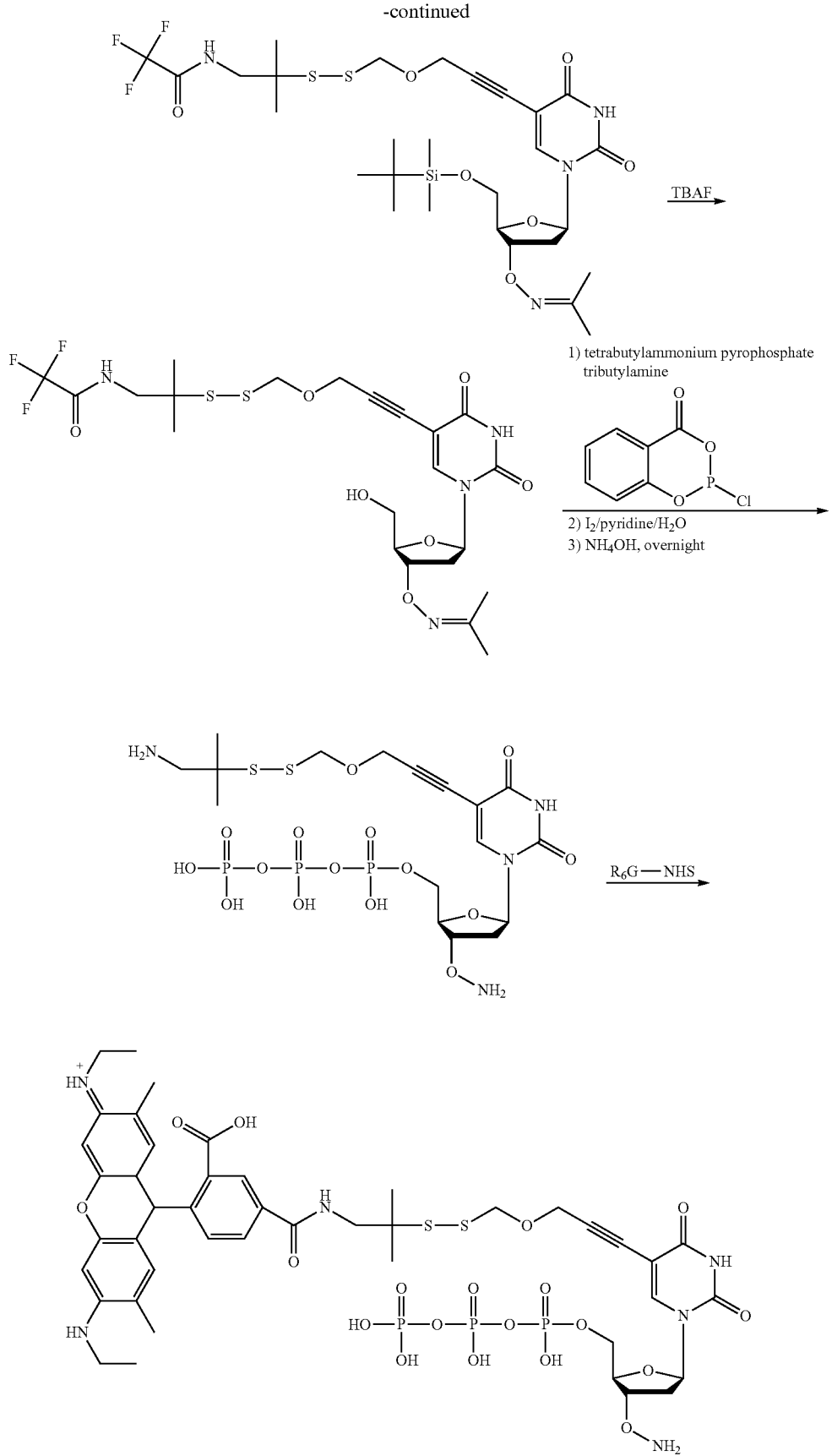

Scheme 62. Synthesis of 3'-O-amino-dCTP-SS-Alexa488.
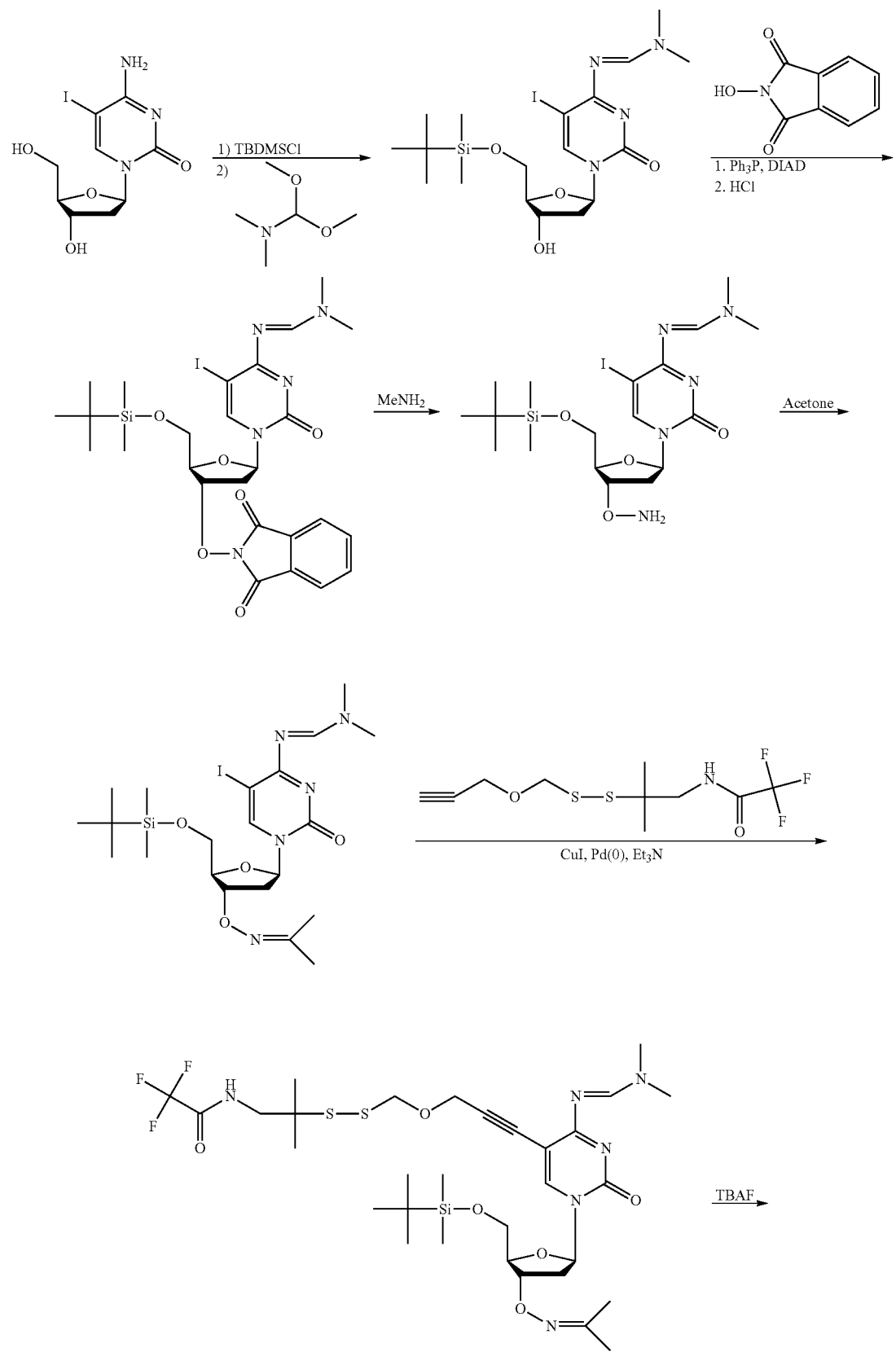

683 684
-continued
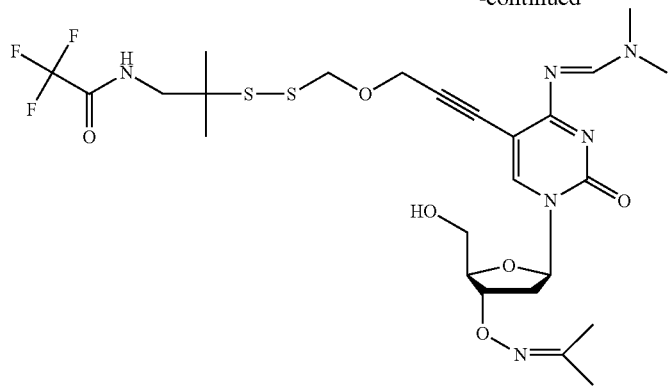
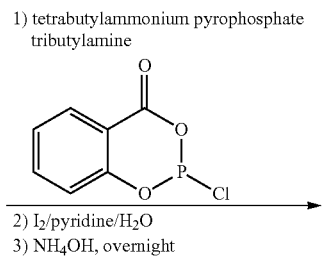
1) tetrabutylammonium pyrophosphate tributylamine
2) I$_2$/pyridine/H$_2$O
3) NH$_4$OH, overnight
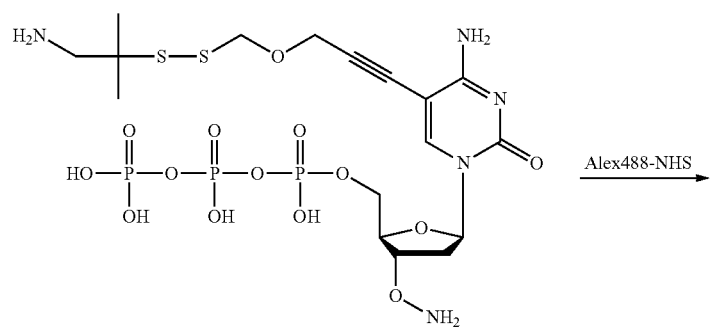
Alex488-NHS
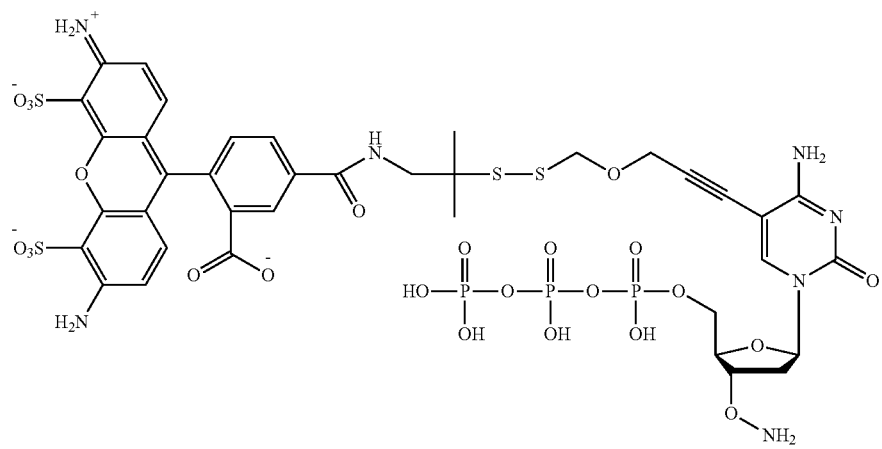
Scheme 63. Synthesis of 3'-O-Amino-dATP-SS-Rox.
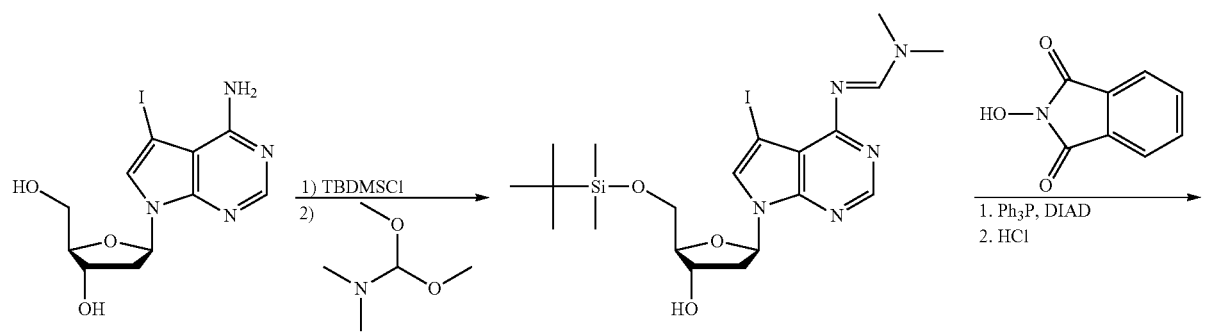
1) TBDMSCl
2)
1. Ph$_3$P, DIAD
2. HCl 685                                      686
-continued
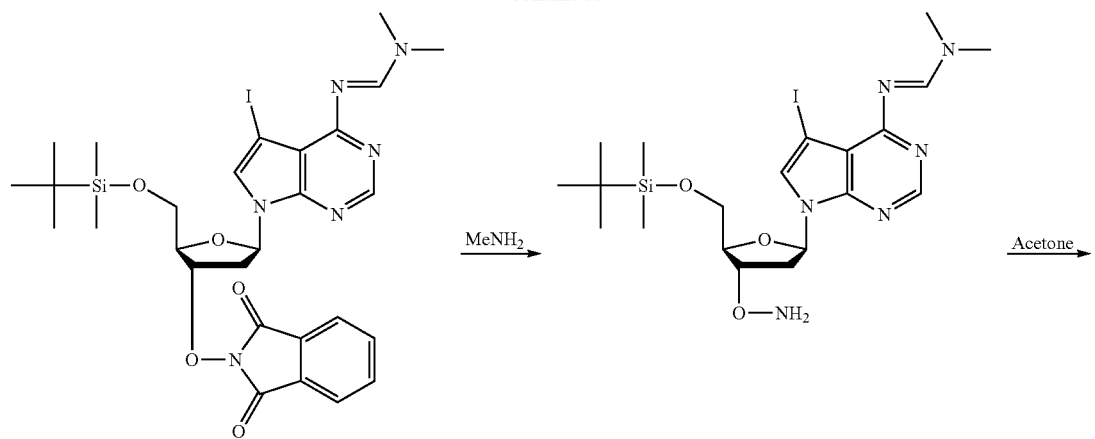
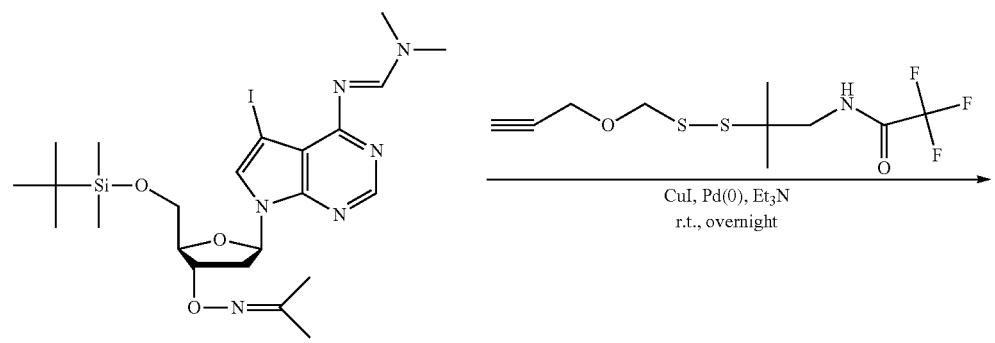
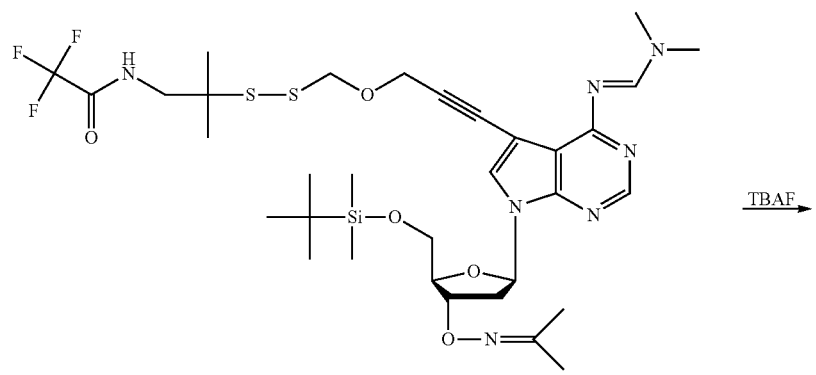
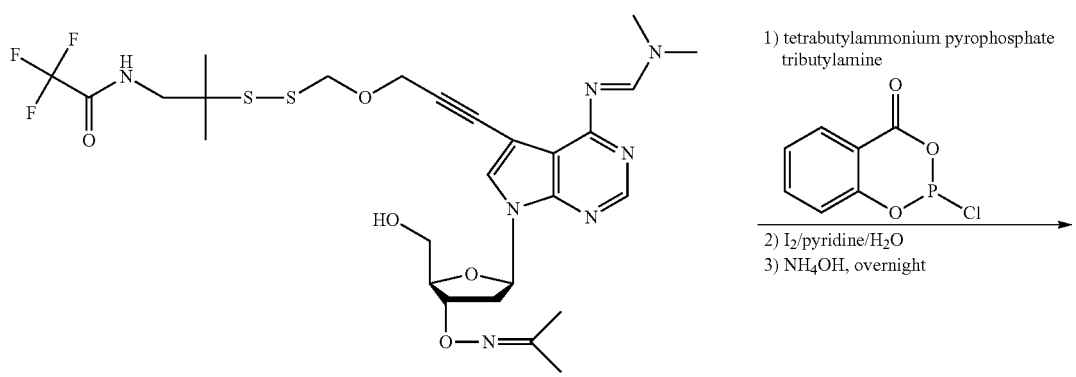

-continued
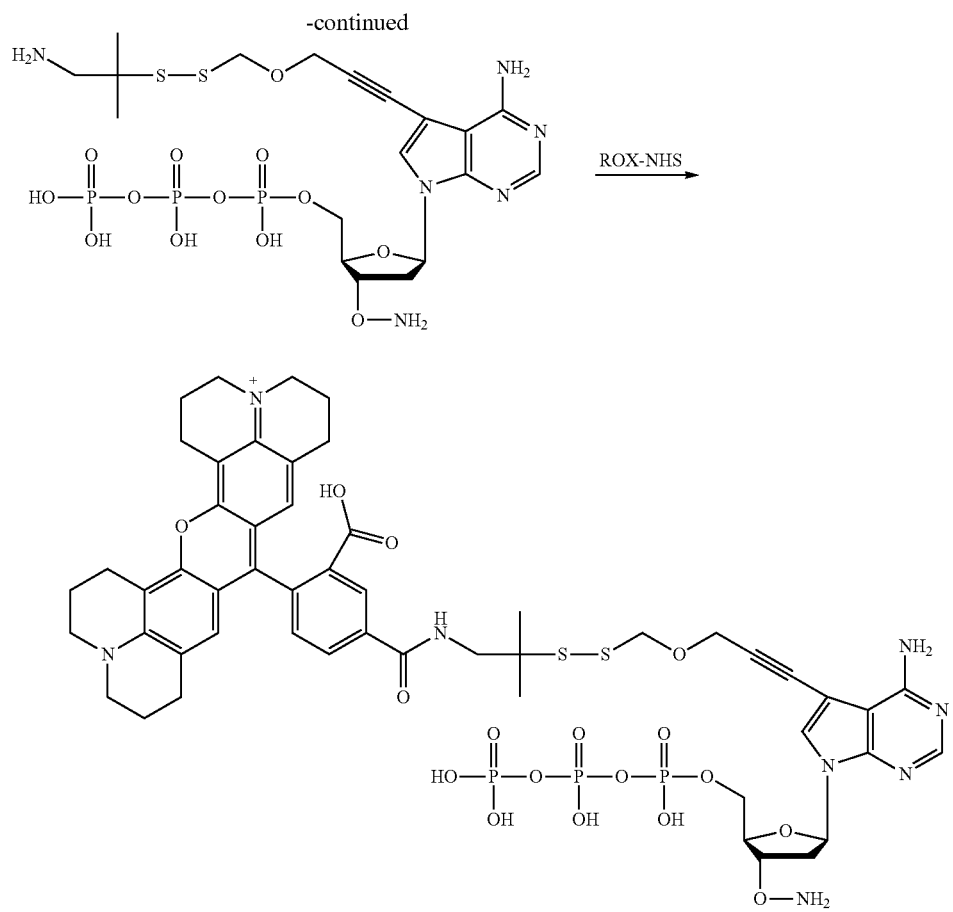
Scheme 64. Synthesis of 3'-O-Amino-dGTP-SS-Cy5.
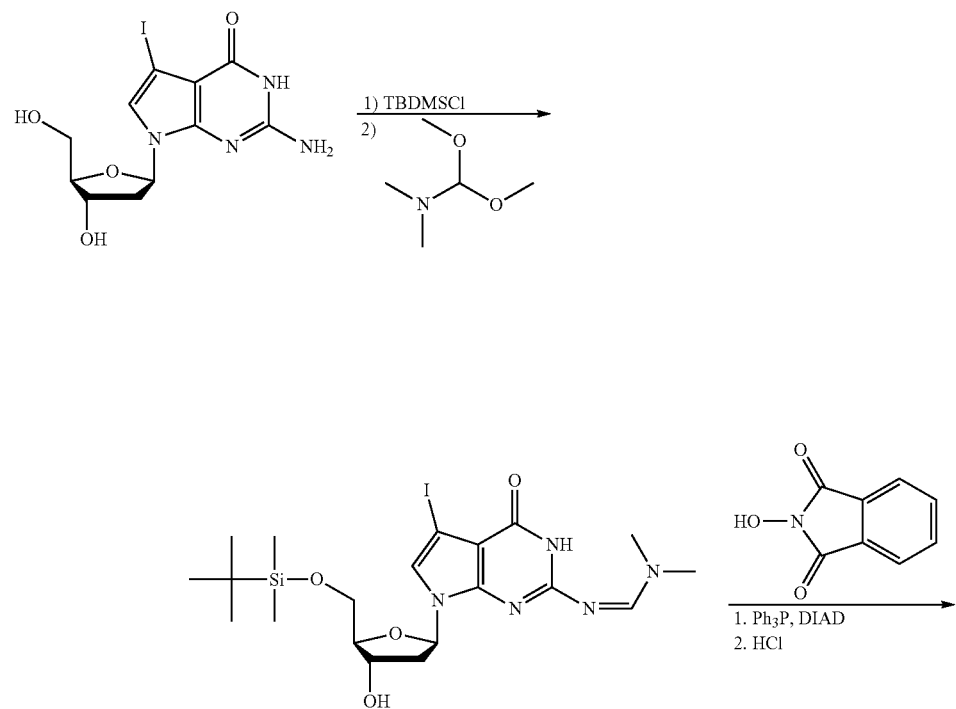

-continued
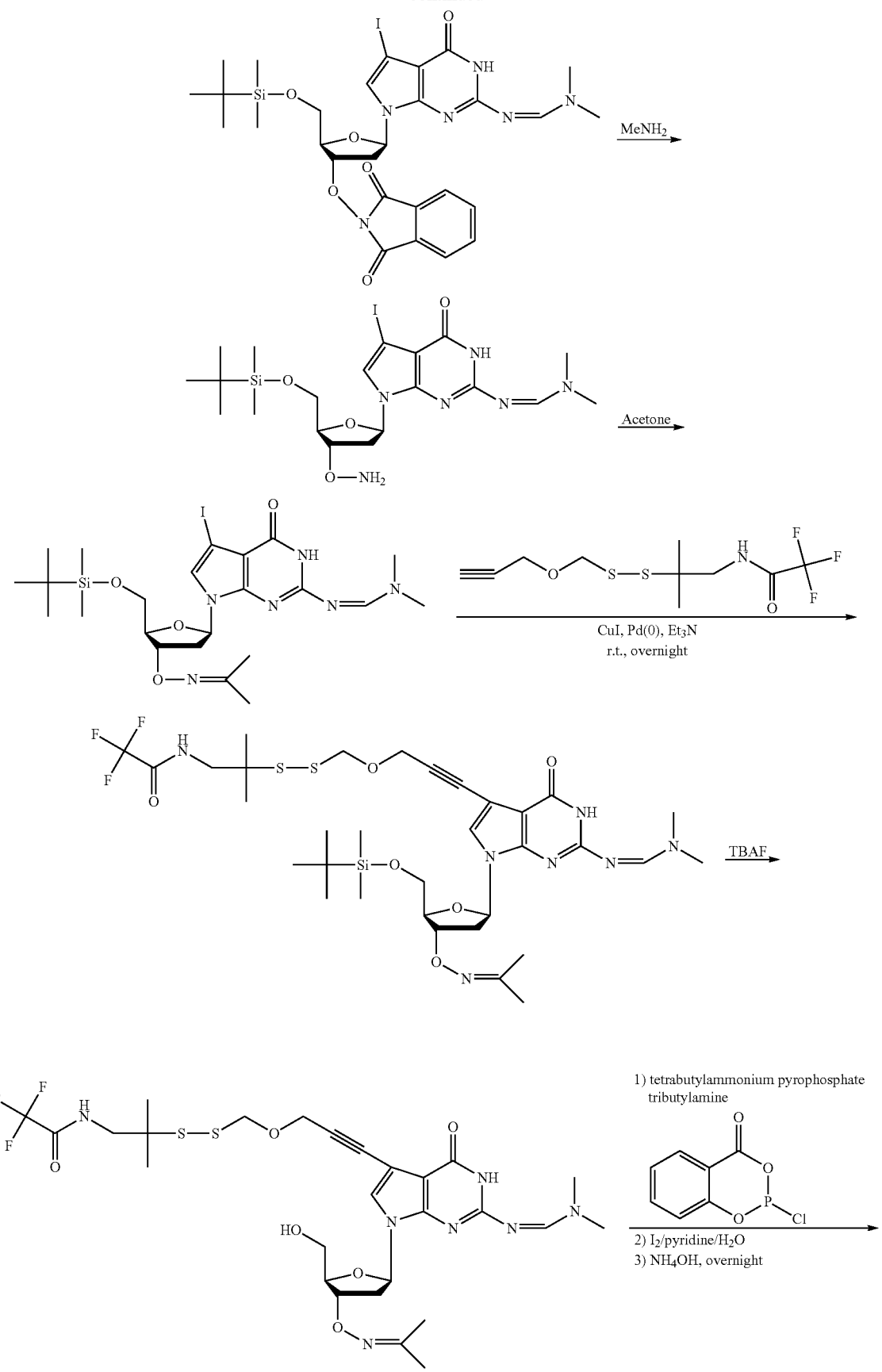

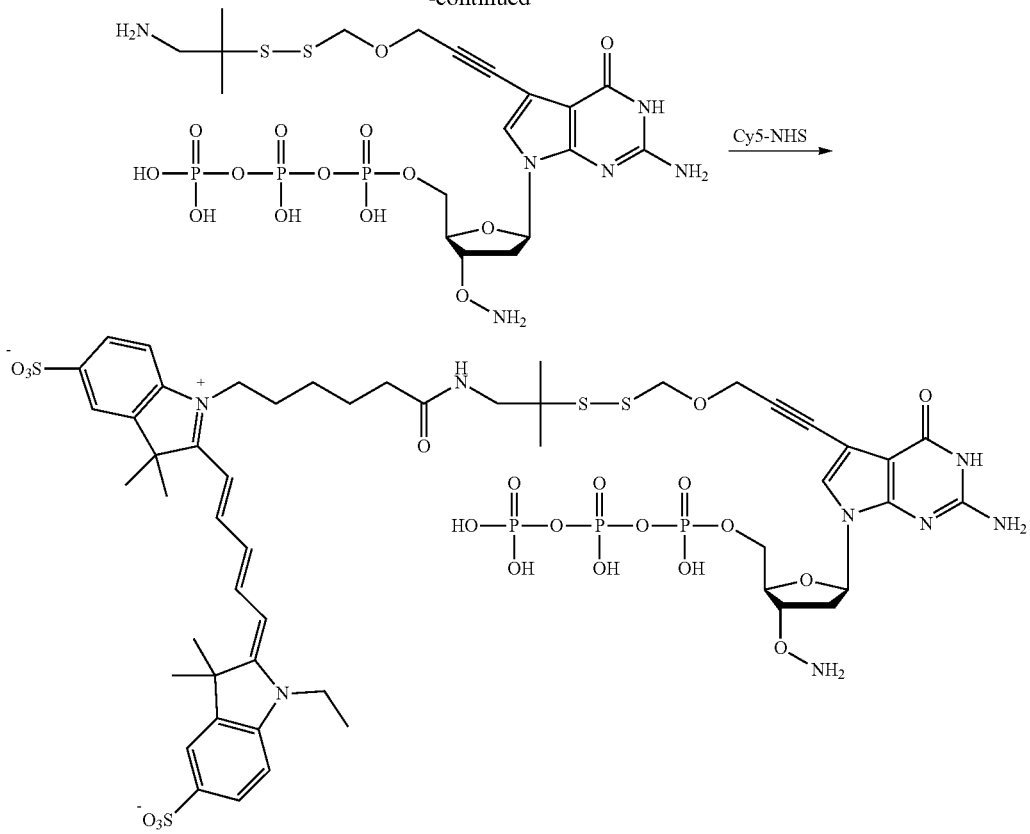
Scheme 65. Synthesis of 3'-O-Azomethyl-dATP-SS-Lebel.
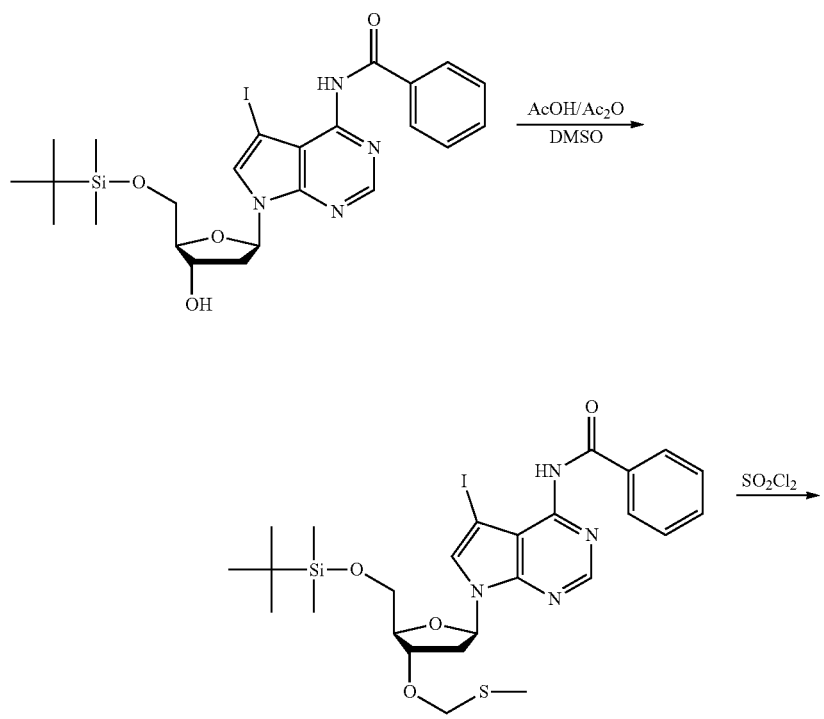

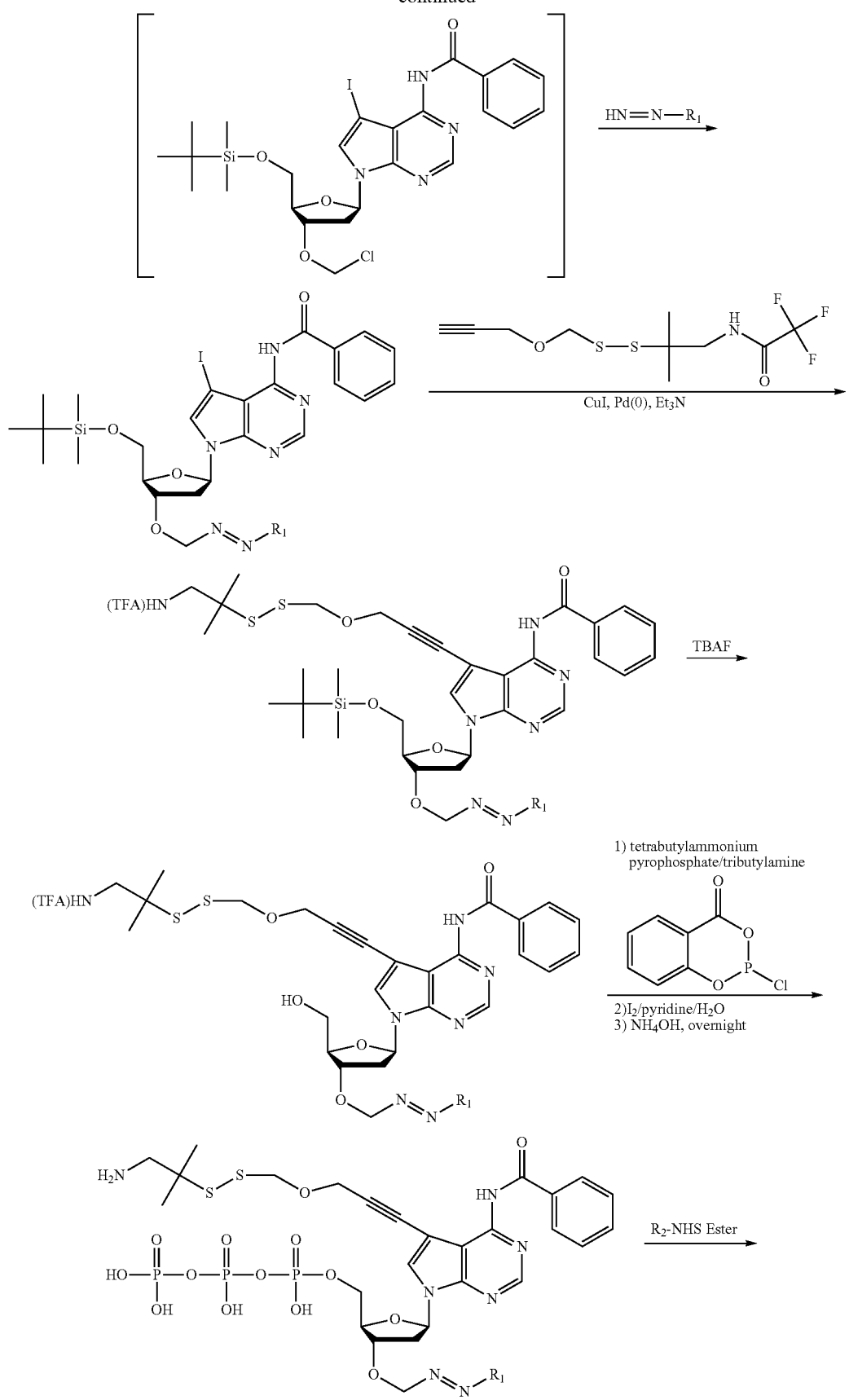

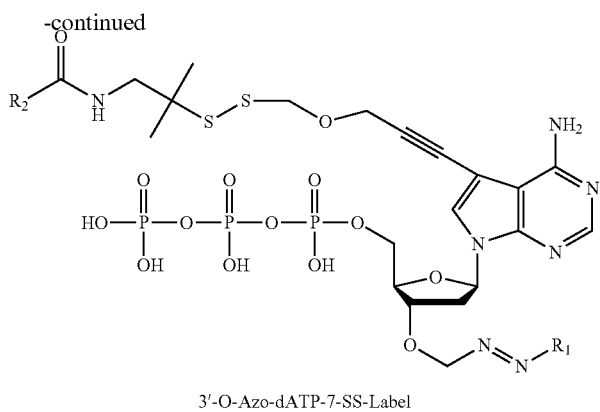

3'-O-Azo-dATP-7-SS-Label

R1 = hydrogen, alkyl and aryl
R2 = Label (Dye or Anchor moiety)

Scheme 66. Synthesis of 3'-O-Azomethyl-dATP

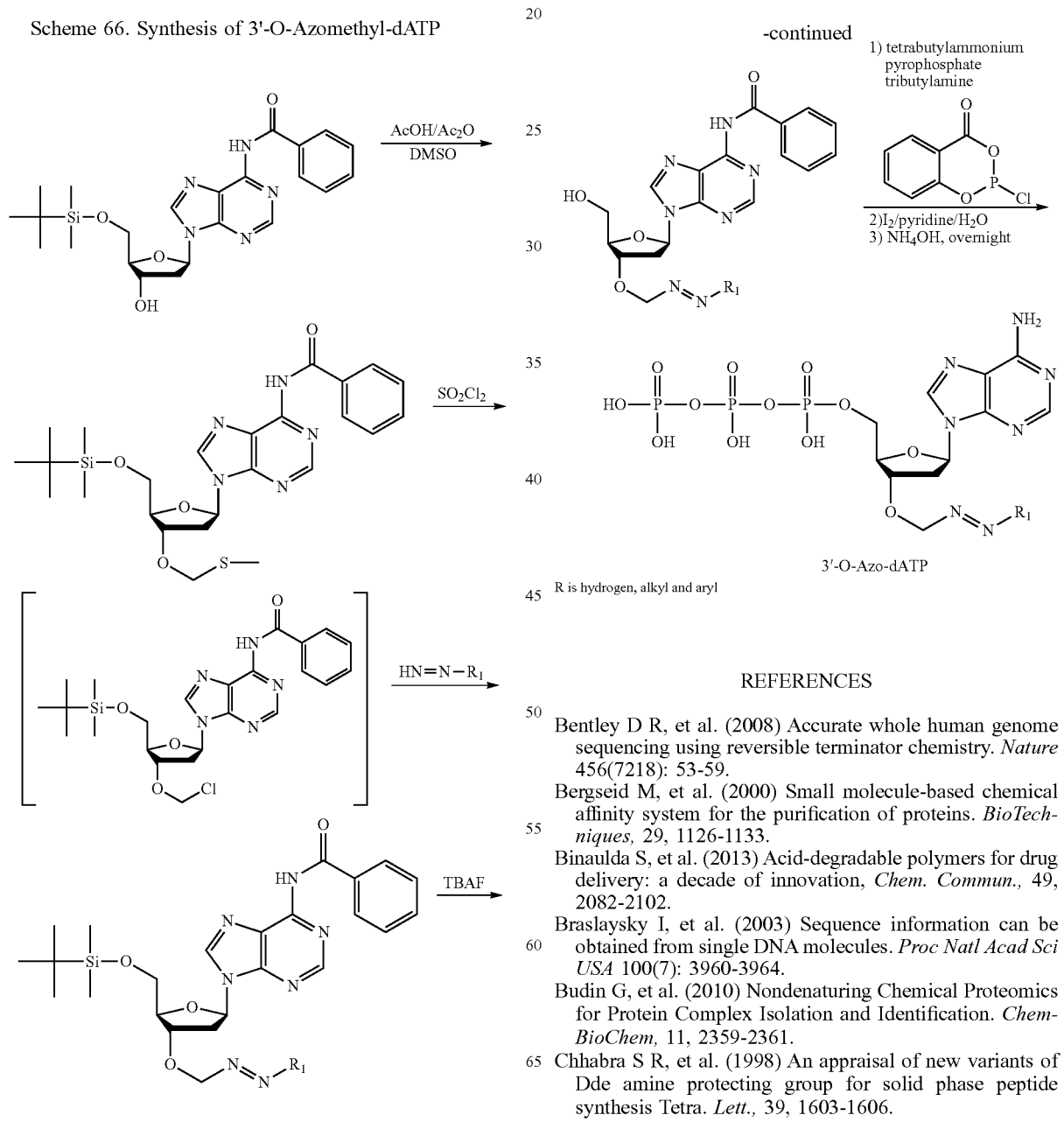

R is hydrogen, alkyl and aryl

REFERENCES

Bentley D R, et al. (2008) Accurate whole human genome sequencing using reversible terminator chemistry. *Nature* 456(7218): 53-59.

Bergseid M, et al. (2000) Small molecule-based chemical affinity system for the purification of proteins. *BioTechniques*, 29, 1126-1133.

Binaulda S, et al. (2013) Acid-degradable polymers for drug delivery: a decade of innovation, *Chem. Commun.*, 49, 2082-2102.

Braslaysky I, et al. (2003) Sequence information can be obtained from single DNA molecules. *Proc Natl Acad Sci USA* 100(7): 3960-3964.

Budin G, et al. (2010) Nondenaturing Chemical Proteomics for Protein Complex Isolation and Identification. *ChemBioChem*, 11, 2359-2361.

Chhabra S R, et al. (1998) An appraisal of new variants of Dde amine protecting group for solid phase peptide synthesis Tetra. *Lett.*, 39, 1603-1606.

Eid J. et al. (2009) Real-time DNA sequencing from single polymerase molecules. *Science* 323(5910): 133-138.

Chen F, et al. (2010) Reconstructed evolutionary adaptive pathways give polymerases accepting reversible terminators for sequencing and SNP detection. *Proc. Natl. Acad. Sci. USA,* 107, 1948-1953.

Diana C, et al. (2011) Fluoride-Cleavable, Fluorescently Labelled Reversible Terminators: Synthesis and Use in Primer Extension. *Chem. Eur. J,* 17, 2903-2915.

Fuller C W, et al (2016) Real-time single-molecule electronic DNA sequencing by synthesis using polymer-tagged nucleotides on a nanopore array. *Proc Natl Acad Sci USA* 113:5233-5238.

Guo J, et al. (2008) Four-color DNA sequencing with 3'-O-modified nucleotide reversible terminators and chemically cleavable fluorescent dideoxynucleotides. *Proc Natl Acad Sci USA* 105(27): 9145-9150.

Harris T D, et al. (2008) Single-molecule DNA sequencing of a viral genome. *Science* 320(5872): 106-109.

Hutter D, et al. (2010) Labeled nucleoside triphosphates with reversibly terminating aminoalkoxy groups. *Nucleosides Nucleotides & Nucleic Acids* 29:879-895.

Hyman E D, (1988) A new method of sequencing DNA. *Anal. Biochem.* 174(2):423-436.

Jewett J C and Bertozzi C R (2010). Rapid Cu-Free Click Chemistry with Readily Synthesized Biarylazacyclooctynones. *J. Am. Chem. Soc.,* 132, 3688-3690.

Ju J. (1999) Sets of labeled energy transfer fluorescent primers and their use in multi component analysis. U.S. Pat. No. 5,952,180.

Ju J, et al. (2003) Massive Parallel Method For Decoding DNA and RNA, U.S. Pat. No. 6,664,079.

Ju J, et al. (2006) Four-color DNA sequencing by synthesis using cleavable fluorescent nucleotide reversible terminators. *Proc Natl Acad Sci USA* 103(52): 19635-19640.

Ju J, et al. (2015) DNA sequence with non-fluorescent nucleotide reversible terminators and cleavable label modified nucleotide terminators. U.S. Pat. No. 9,115,163.

Knapp D C, et al. (2011) Fluoride-Cleavable, Fluorescently Labelled Reversible Terminators: Synthesis and Use in Primer Extension. *Chem. Eur. J.,* 17, 2903-2915.

Kumar S, et al (2012) PEG-labeled nucleotides and nanopore detection for single molecule DNA sequencing by synthesis. *Scientific Reports* 2:684.

Kwiatkowski M. (2007) Compounds for protecting hydroxyls and methods for their use, U.S. Pat. No. 7,279,563.

Leriche G, et al. (2010) Optimization of the Azobenzene Scaffold for Reductive Cleavage by Dithionite; Development of an Azobenzene Cleavable Linker for Proteomic Applications, *Eur. Org. Chem.,* 23, 4360-64.

Ellis R A, et al. (2003) Chemical constructs, EP 1119529 B1

Li Z, et al. (2003) A photocleavable fluorescent nucleotide for DNA sequencing and analysis. *Proc Natl Acad Sci USA,* 100(2): 414-419.

Lu G, et al. (2006) A diversity oriented synthesis of 3'-O-modified nucleoside triphosphates for DNA sequencing by synthesis. *Bioorg. Med. Chem. Lett.,* 16, 3902-3905.

Marjokc F, et al. (2013) Bioorthogonal labelling of biomolecules: new functional handles and ligation methods. *Org. Biomol. Chem.,* 11, 6439-6455.

Margulies M, et al. (2005) Genome sequencing in microfabricated high-density picolitre reactors. *Nature* 437 (7057):376-380.

Melissa L, et al. (2008) Tetrazine Ligation: Fast Bioconjugation Based on Inverse-Electron-Demand Diels-Alder Reactivity. *J. Am. Chem. Soc.,* 130, 13518-13519.

Metzker M L, et al. (1994) Termination of DNA synthesis by novel 3'-modified-deoxyribonucleoside 5'-triphosphates. *Nucleic Acids Res.* 22, 4259-4267.

Metzker M L. (2005) Emerging technologies in DNA sequencing. *Genome Res.,* 15, 1767-1776.

Mitra R D, et al. (2003) Fluorescent in situ sequencing on polymerase colonies. *Anal. Biochem.* 320:55-65.

Muller S, et al. (2011) Method for producing trinucleotides. PCT International Patent Application Publication No. WO 2011/061114, published May 26, 2011.

Pelletier 14, et al. (1994) Structures of ternary complexes of rat DNA polymerase beta, a DNA template-primer, and ddCTP. *Science* 264:1891-1903.

Rathod, K M, et al. (2013) Synthesis and antimicrobial activity of azo compounds containing m-cresol moiety. *Chem. Sci. Tran.,* 2, 25-28.

Ronaghi M, et al. (1998) A sequencing method based on real-time pyrophosphate. *Science* 281(5375): 363-365.

Rosenblum B B, et al. (1997) New dye-labeled terminators for improved DNA sequencing patterns. *Nucleic Acids Res,* 25:4500-4504, Rothberg J M, et al. (2011) An integrated semiconductor device enabling non-optical genome sequencing. *Nature* 475(7356): 348-352.

Ruparel H, et al. (2005) Design and synthesis of a 3'-O-allyl photocleavable fluorescent nucleotide as a reversible terminator for DNA sequencing by synthesis. *Proc Natl Acad Sci USA* 102(17): 5932-5937.

Semenyuk A. (2006) Synthesis of RNA using 2'-O-DTM protection. *JAGS,* 128, 12356-12357.

Shenoi R A, et al. (2012) Branched Multifunctional Polyether Polyketals: Variation of Ketal Group Structure Enables Unprecedented Control over Polymer Degradation in Solution and within Cells. *J. Am. Chem. Soc.,* 134, 14945-14957.

Shieha P, et al. (2014) Design strategies for bioorthogonal smart probes, *Org. Biomol. Chem.,* 12, 9307-9320.

Tong A K, et al. (2001) Triple Fluorescence Energy Transfer in Covalently Trichromophore-Labeled DNA, *J. Am. Chem. Soc.,* 123, 12923-12924.

Turcatti G, et al. (2008) A new class of reversible fluorescent nucleotides: synthesis and optimization as reversible terminators for DNA sequencing by synthesis. *Nucleic Acids Res.* 36(4), e25.

Wu J, et al. (2007) 3'-O-modified nucleotides as reversible terminators for pyrosequencing. *Proc Natl Acad Sci USA* 104:16462-16467.

Zhu Z, et al. (1994) Directly labeled DNA probes using fluorescent nucleotides with different length linkers. *Nucleic Acids Res,* 22, 3418-3422.

What is claimed is:

1. A method of sequencing, said method comprising:
contacting a double stranded nucleic acid molecule comprising a primer oligonucleotide hybridized to a template polynucleotide with a first nucleotide analogue and a first polymerase thereby binding said first nucleotide analogue to a complementary nucleotide of said double-stranded nucleic acid molecule, wherein said first nucleotide analogue comprises multiple detectable moieties and wherein said first nucleotide analogue is not incorporated into the primer oligonucleotide;
detecting the detectable moiety; and
contacting the primer oligonucleotide with a second nucleotide analogue and a second polymerase thereby binding said second nucleotide analogue to a complementary nucleotide of said template polynucleotide and incorporating said second nucleotide analogue into the primer oligonucleotide, wherein the second nucleotide analogue is not associated with a detectable moiety;
further comprising removing the first nucleotide analogue before contacting the primer oligonucleotide with the second nucleotide analogue.

2. The method of claim 1, wherein the first nucleotide analogue comprises multiple detectable moieties of the same type.

3. The method of claim 1, wherein the first nucleotide analogue is coupled to a plurality of fluorophores.

4. The method of claim 3, wherein the first nucleotide analogue is coupled to a plurality of fluorophores via a dendrimer.

5. The method of claim 3, wherein the first nucleotide analogue is coupled to a plurality of fluorophores via a polymer.

6. The method of claim 3, wherein the first nucleotide analogue is coupled to a plurality of fluorophores via a bioconjugate linker.

7. The method of claim 1, wherein the first nucleotide analogue comprises a moiety capable of preventing the first polymerase from catalyzing a polymerase reaction.

8. The method of claim 1, wherein the first polymerase is not capable of catalyzing a polymerase reaction.

9. The method of claim 1, further comprising contacting the primer oligonucleotide with a third nucleotide analogue and a third polymerase thereby binding said third nucleotide analogue to a complementary nucleotide of said double-stranded nucleic acid molecule, wherein said third nucleotide analogue is associated with a detectable moiety, wherein the third nucleotide analogue comprises multiple detectable moieties.

10. The method of claim 1, wherein the second nucleotide analogue comprises a reversible terminator.

11. The method of claim 1, wherein the first nucleotide analogue and the second nucleotide analogue both comprise the same nucleobase.

12. The method of claim 9, wherein the third nucleotide analogue is coupled to a plurality of fluorophores.

13. A method of sequencing a template polynucleotide, said method comprising:
(i) contacting a primer hybridized to the template polynucleotide with a first nucleotide analogue comprising a first reversible terminator and extending said primer with a first polymerase by incorporating the first nucleotide analogue to form an extended primer;
(ii) contacting the extended primer with a second nucleotide analogue capable of forming at least one hydrogen bond with a complementary nucleotide of the template polynucleotide, wherein the second nucleotide analogue is associated with a detectable moiety; detecting the detectable moiety; wherein the second nucleotide analogue is not incorporated into the extended primer;
(iii) and contacting the extended primer with a third nucleotide analogue comprising a second reversible terminator and extending said extended primer with a polymerase by incorporating the third nucleotide analogue, wherein said first reversible terminator and said second nucleotide analogue are removed prior to step (iii); and
(iv) repeating steps (i), (ii), and (iii), thereby sequencing the template polynucleotide.

14. The method of claim 13, wherein said first reversible terminator is removed from the first nucleotide analogue prior to step (ii).

15. The method of claim 13, wherein said first reversible terminator is removed from the first nucleotide analogue after step (ii).

16. The method of claim 1, wherein incorporating said second nucleotide analogue into the primer oligonucleotide comprises forming a phosphodiester bond between the nucleotide analogue and the primer oligonucleotide.

17. The method of claim 1, wherein incorporating said first and third nucleotide analogue into the primer oligonucleotide comprises forming a phosphodiester bond between the nucleotide analogue and the primer.

18. A method of sequencing, said method comprising:
contacting a primer oligonucleotide hybridized to a template polynucleotide with a first nucleotide analogue and a first polymerase thereby binding said first nucleotide analogue to a complementary nucleotide of said template polynucleotide, wherein said first nucleotide analogue is associated with a detectable moiety and comprises a moiety capable of preventing the first polymerase from catalyzing a polymerase reaction, and is not incorporated into the primer oligonucleotide;
detecting the detectable moiety;
removing the first nucleotide analogue; followed by
contacting the primer oligonucleotide with a second nucleotide analogue and a second polymerase thereby binding said second nucleotide analogue to a complementary nucleotide of said template polynucleotide and incorporating said second nucleotide analogue into the primer oligonucleotide, wherein the second nucleotide analogue is not associated with a detectable moiety.

19. The method of claim 18, wherein said first nucleotide analogue is coupled to a plurality of fluorophores.

20. A method of sequencing, said method comprising:
contacting a primer oligonucleotide hybridized to a template polynucleotide with a first nucleotide analogue and a first polymerase thereby binding said first nucleotide analogue to a complementary nucleotide of template polynucleotide, wherein said first nucleotide analogue is associated with a detectable moiety and does not form a phosphodiester bond with the primer oligonucleotide;
detecting the detectable moiety;
removing the first nucleotide analogue; followed by
contacting the primer oligonucleotide with a second nucleotide analogue and a second polymerase thereby binding said second nucleotide analogue to a complementary nucleotide of said template polynucleotide and incorporating said second nucleotide analogue into the primer oligonucleotide, wherein the second nucleotide analogue is not associated with a detectable moiety, and wherein the first nucleotide analogue and the second nucleotide analogue comprise the same nucleobase type.

* * * * *

SEQUENCE LISTING

```
Sequence total quantity: 10
SEQ ID NO: 1            moltype = DNA  length = 51
FEATURE                 Location/Qualifiers
misc_feature            1..51
                        note = Synthetic polynucleotide
```

```
                   source              1..51
                                       mol_type = other DNA
                                       organism = synthetic construct
SEQUENCE: 1
gaggccaagt acggcgggta cgtccttgac aatgtgtaca tcaacatcac c            51

SEQ ID NO: 2           moltype = DNA   length = 13
FEATURE                Location/Qualifiers
misc_feature           1..13
                       note = Synthetic polynucleotide
source                 1..13
                       mol_type = other DNA
                       organism = synthetic construct
SEQUENCE: 2
cacattgtca agg                                                       13

SEQ ID NO: 3           moltype = DNA   length = 17
FEATURE                Location/Qualifiers
misc_feature           1..17
                       note = Synthetic polynucleotide
source                 1..17
                       mol_type = other DNA
                       organism = synthetic construct
SEQUENCE: 3
tctctggccg cgtgtct                                                   17

SEQ ID NO: 4           moltype = DNA   length = 108
FEATURE                Location/Qualifiers
misc_feature           1..108
                       note = Synthetic polynucleotide
source                 1..108
                       mol_type = other DNA
                       organism = synthetic construct
SEQUENCE: 4
aaggagacac gcggccagag agggtcctgt ccgtgtttgt gcgtggagtt cgacaaggca    60
gggtcatcta atggtgatga gtcctatcct tttctcttcg ttctccgt               108

SEQ ID NO: 5           moltype = DNA   length = 100
FEATURE                Location/Qualifiers
misc_feature           1..100
                       note = Synthetic polynucleotide
source                 1..100
                       mol_type = other DNA
                       organism = synthetic construct
SEQUENCE: 5
tacccggagg ccaagtacgg cgggtacgtc cttgacaatg tgtacatcaa catcacctac    60
caccatgtca gtctcggttg gatcctctat tgtgtccggg                        100

SEQ ID NO: 6           moltype = DNA   length = 20
FEATURE                Location/Qualifiers
misc_feature           1..20
                       note = Synthetic polynucleotide
source                 1..20
                       mol_type = other DNA
                       organism = synthetic construct
SEQUENCE: 6
tagatgaccc tgccttgtcg                                                20

SEQ ID NO: 7           moltype = DNA   length = 17
FEATURE                Location/Qualifiers
misc_feature           1..17
                       note = Synthetic polynucleotide
source                 1..17
                       mol_type = other DNA
                       organism = synthetic construct
SEQUENCE: 7
gataggactc atcacca                                                   17

SEQ ID NO: 8           moltype = DNA   length = 20
FEATURE                Location/Qualifiers
misc_feature           1..20
                       note = Synthetic polynucleotide
source                 1..20
                       mol_type = other DNA
                       organism = synthetic construct
SEQUENCE: 8
gttgatgtac acattgtcaa                                                20

SEQ ID NO: 9           moltype = DNA   length = 51
```

-continued

```
FEATURE              Location/Qualifiers
misc_feature         1..51
                     note = Synthetic polynucleotide
source               1..51
                     mol_type = other DNA
                     organism = synthetic construct
SEQUENCE: 9
gaggccaagt acggcgggta cgtccttgac aatgtgtaca tcaacatcac c        51

SEQ ID NO: 10        moltype = DNA  length = 49
FEATURE              Location/Qualifiers
misc_feature         1..49
                     note = Synthetic polynucleotide
source               1..49
                     mol_type = other DNA
                     organism = synthetic construct
SEQUENCE: 10
cagcttaagc aatggtacat gccttgacaa tgtgtacatc aacatcacc           49
```